United States Patent
Bartberger et al.

(10) Patent No.: US 9,376,425 B2
(45) Date of Patent: Jun. 28, 2016

(54) HETEROCYCLIC COMPOUNDS AS MDM2 INHIBITORS FOR THE TREATMENT OF CANCER

(71) Applicant: AMGEN INC., Thousand Oaks, CA (US)

(72) Inventors: Michael D. Bartberger, Sherman Oaks, CA (US); Hilary Plake Beck, San Carlos, CA (US); Xiaoqi Chen, Palo Alto, CA (US); Richard Victor Connors, Pacifica, CA (US); Jeffrey Deignan, San Francisco, CA (US); Jason A. Duquette, South San Francisco, CA (US); John Eksterowicz, San Francisco, CA (US); Brian M. Fox, Brisbane, CA (US); Jiasheng Fu, Foster City, CA (US); Ana Gonzalez Buenrostro, San Mateo, CA (US); Felix Gonzalez Lopez De Turiso, San Mateo, CA (US); Darin J. Gustin, Half Moon Bay, CA (US); Julie A. Heath, Orlinda, CA (US); Michael G. Johnson, San Francisco, CA (US); Frank Kayser, San Francisco, CA (US); David John Kopecky, San Francisco, CA (US); Yihong Li, Millbrae, CA (US); Zhihong Li, Millbrae, CA (US); Zhihua Ma, Foster City, CA (US); Joel McIntosh, Pacifica, CA (US); Julio C. Medina, San Carlos, CA (US); Jeffrey Thomas Mihalic, San Francisco, CA (US); Steven H. Olson, Millbrae, CA (US); Yosup Rew, Foster City, CA (US); Philip M. Roveto, San Francisco, CA (US); Michael J. Schmitt, McLean, VA (US); Daqing Sun, Foster City, CA (US); Xiaodong Wang, Millbrae, CA (US); Malgorzata Wanska, Oak Park, CA (US); Christine Weathers, Katy, TX (US); Xuelei Yan, Foster City, CA (US)

(73) Assignee: Amgen, Inc., Thousand Oaks, CA (US)

( * ) Notice: Subject to any disclaimer, the term of this patent is extended or adjusted under 35 U.S.C. 154(b) by 0 days.

(21) Appl. No.: 14/347,628

(22) PCT Filed: Sep. 26, 2012

(86) PCT No.: PCT/US2012/057389
§ 371 (c)(1),
(2) Date: Mar. 26, 2014

(87) PCT Pub. No.: WO2013/049250
PCT Pub. Date: Apr. 4, 2013

(65) Prior Publication Data
US 2014/0235629 A1 Aug. 21, 2014

Related U.S. Application Data

(60) Provisional application No. 61/566,449, filed on Dec. 2, 2011, provisional application No. 61/539,715, filed on Sep. 27, 2011.

(51) Int. Cl.
C07D 265/06 (2006.01)
C07D 413/04 (2006.01)
(Continued)

(52) U.S. Cl.
CPC ............ C07D 413/04 (2013.01); C07D 265/06 (2013.01); C07D 265/32 (2013.01); C07D 413/10 (2013.01); C07D 413/12 (2013.01); C07D 417/04 (2013.01)

(58) Field of Classification Search
CPC .. C07D 265/16; C07D 413/04; C07D 413/10; C07D 417/04; C07D 413/12
USPC ........................................ 544/175; 514/231.2
See application file for complete search history.

(56) References Cited

U.S. PATENT DOCUMENTS 3,308,121 A 3/1967 Gannon et al.
5,334,720 A 8/1994 Schmiesing et al.
(Continued)

FOREIGN PATENT DOCUMENTS

CN 102153557 A1 8/2011
DE 3246148 A1 6/1984
(Continued)

OTHER PUBLICATIONS

Stefanovskii et al. (Chemische Berichte (1969), 102(3), 717-27). Abstract.*

(Continued)

Primary Examiner — Bruck Kifle
(74) Attorney, Agent, or Firm — Markus Bergauer; Elsa D. Lemoine

(57) ABSTRACT

The present invention provides MDM2 inhibitor compounds of Formula I or II, or the pharmaceutically acceptable salts thereof,

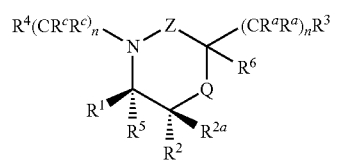

I or

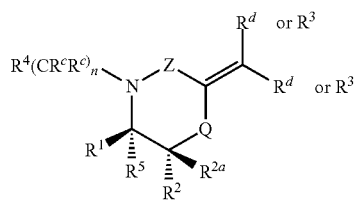

II wherein the variables are defined above, which compounds are useful as therapeutic agents, particularly for the treatment of cancers. The present invention also relates to pharmaceutical compositions that contain an MDM2 inhibitor.

37 Claims, No Drawings

(51) Int. Cl.
*C07D 413/10* (2006.01)
*C07D 417/04* (2006.01)
*C07D 413/12* (2006.01)
*C07D 265/32* (2006.01)

(56) References Cited

U.S. PATENT DOCUMENTS

| | | | |
|---|---|---|---|
| 6,620,815 | B1 | 9/2003 | Lagu et al. |
| 6,860,940 | B2 | 3/2005 | Segelke et al. |
| 7,015,041 | B2 | 3/2006 | Santarsiero et al. |
| 7,052,545 | B2 | 5/2006 | Quake et al. |
| 7,195,670 | B2 | 3/2007 | Hansen et al. |
| 7,214,540 | B2 | 5/2007 | DeLucas et al. |
| 7,229,500 | B2 | 6/2007 | Haushalter et al. |
| 7,425,638 | B2 | 9/2008 | Haley et al. |
| 7,776,875 | B2 | 8/2010 | Chen et al. |
| 8,569,341 | B2 | 10/2013 | Gribble, Jr. et al. |
| 8,952,036 | B2 | 2/2015 | Rew |
| 2004/0186134 | A1 | 9/2004 | O'Connor et al. |
| 2007/0129416 | A1 | 6/2007 | Ding et al. |
| 2008/0280769 | A1 | 11/2008 | Doemling |
| 2009/0143364 | A1 | 6/2009 | Fotouhi et al. |
| 2009/0163512 | A1 | 6/2009 | Chen et al. |
| 2011/0319378 | A1 | 12/2011 | Bartberger et al. |
| 2014/0315895 | A1 | 10/2014 | Bartberger et al. |
| 2014/0364455 | A1 | 12/2014 | Bio et al. |
| 2016/0002185 | A1 | 1/2016 | Bartberger et al. |

FOREIGN PATENT DOCUMENTS

| | | |
|---|---|---|
| TW | 200801000 A | 1/2008 |
| TW | 200808781 A | 2/2008 |
| WO | WO95/23135 A1 | 8/1995 |
| WO | WO96/06095 A1 | 2/1996 |
| WO | WO97/30045 A1 | 8/1997 |
| WO | WO99/06397 A2 | 2/1999 |
| WO | WO99/31507 A1 | 6/1999 |
| WO | WO02/17912 A1 | 3/2002 |
| WO | WO02/089738 A2 | 11/2002 |
| WO | WO02/094787 A1 | 11/2002 |
| WO | WO03/051359 A1 | 6/2003 |
| WO | WO2004/031149 A1 | 4/2004 |
| WO | WO2005/110996 A1 | 11/2005 |
| WO | WO2005/123691 A1 | 12/2005 |
| WO | WO2006/097261 A1 | 9/2006 |
| WO | WO2006/107859 A2 | 10/2006 |
| WO | WO2006/107860 A2 | 10/2006 |
| WO | WO2007/063013 A1 | 6/2007 |
| WO | WO2007/104664 A1 | 9/2007 |
| WO | WO2008/005268 A1 | 1/2008 |
| WO | WO2008/010953 A2 | 1/2008 |
| WO | WO2008/021338 A2 | 2/2008 |
| WO | WO2008/021339 A2 | 2/2008 |
| WO | WO2008/076754 A2 | 6/2008 |
| WO | WO2008/110793 A1 | 9/2008 |
| WO | WO2008/125487 A1 | 10/2008 |
| WO | WO2008/141975 A1 | 11/2008 |
| WO | WO2009/004430 A1 | 1/2009 |
| WO | WO2009/007750 A1 | 1/2009 |
| WO | WO2009/047161 A1 | 4/2009 |
| WO | WO2009/082038 A2 | 7/2009 |
| WO | WO2009/114950 A1 | 9/2009 |
| WO | WO2009/156735 A2 | 12/2009 |
| WO | WO2010/028862 A1 | 3/2010 |
| WO | WO2010/031713 A1 | 3/2010 |
| WO | WO2010/121995 A1 | 10/2010 |
| WO | WO2010/028862 A1 | 3/2011 |
| WO | WO2011/023677 A1 | 3/2011 |
| WO | WO2011/067185 A1 | 6/2011 |
| WO | WO2011/076786 A1 | 6/2011 |
| WO | WO2011/153509 A1 | 12/2011 |
| WO | WO2013/049250 A1 | 4/2013 |
| WO | WO2014/130470 A1 | 8/2014 |
| WO | WO2014/134201 A1 | 9/2014 |
| WO | WO2014/151863 A1 | 9/2014 |
| WO | WO2014/200937 A1 | 12/2014 |
| WO | WO2015/070224 A2 | 5/2015 |

OTHER PUBLICATIONS

N. J. Anthony, Pseudo-Allylic $A_{1,3}$ Strain as a Conformational Control Element: Stereoselective Syntheses of $\psi[CH_2O]$ Pseudodipeptides, Tetrahedron Letters, vol. 36, No. 22, pp. 3821-3824, (1995).

Uli Rothweiler, Isoquinolin-1-one Inhibitors of the MDM2-p53 Interaction, ChemMedChem 2008, vol. 3, pp. 1118-1128.

International Search Report, PCT/US2011/039184, Issued Sep. 9, 2011, pp. 1-3.

Written Opinion of the International Searching Authority, PCT/US2011/039184, Issued Sep. 9, 2011, pp. 1-5.

Rew, Yosup, Structure-Based Design of Novel Inhibitors of the MDM2-p53 Interaction, Journal of Medicinal Chemistry, Jun. 14, 2012;55(11): pp. 4936-4954. E-published May 9, 2012.

Michelsen, Klaus, Ordering of the N-Terminus of Human MDM2 by Small Molecule Inhibitors, Journal American Chemical Society, Oct. 17, 2012;134(41): pp. 17059-17067. Epublished Oct. 5, 2012.

Allen, John G., Discovery and Optimization of Chromenotriazolopyrimidines as Potent Inhibitors of the Mouse Double Minute 2-Tumor Protein 53 Protein-Protein Interaction, Journal of Medicinal Chemistry, Nov. 26, 2009;52(22): pp. 7044-7053.

Haruo Nakayama et al: "Hydrates of Organic Compounds. X. The Formation of Clathrate Hydrates of Tetrabutylammonium Alkanesulfonates", Bulletin of the Chemical Society of Japan, Jan. 1, 1986, pp. 833-837, XP055133190, DOI: 10.1246/bcsj.59.833 Retrieved from the Internet: URL:https://www.jstage.jst.go.jp/article/bcsj1926/59/3/59.

Daqing Sun et al: "Discovery of AMG 232, a Potent, Selective, and Orally Bioavailable MDM2-p53 Inhibitor in Clinical Development", Journal of Medicinal Chemistry, vol. 57 No. 4, Feb. 27, 2014, pp. 1454-1472, XP055116592, ISSN: 0022-2623, DOI: 10.1021/jm401753e scheme 7; compound 2.

International Search Report, PCT/US2014/041594, Issued Aug. 18 2014, pp. 1-7.

Written Opinion of the International Searching Authority, PCT/US2014/041594, Issued Aug. 18, 2014, pp. 1-12.

International Search Report, PCT/US2014/016971, Issued May 15, 2014, pp. 1-5.

Written Opinion of the International Searching Authority, PCT/US2014/016971, Issued May 15, 2014, pp. 1-3.

Qiuxia He et al: "Novel morpholin-3-one derivatives induced apoptosis and elevated the level of P53 and Fas in A549 lung cancer cells", Bioorganic & Medicinal Chemistry, Pergamon, GB, vol. 15, No. 11, Apr. 26, 2007, pp. 3889-3895, XP022047574, ISSN: 0968-0896, DOI: 10.1016/J.BMC.2007.03.008.

International Search Report, PCT/US2014/026584, Issued Jun. 26, 2014, pp. 1-5.

Written Opinion of the International Searching Authority, PCT/US2014/026584, Issued Jun. 26, 2014, pp. 1-6.

Patani GA Etal: "Bioisosterism: A Rational Approach in Drug Design", Chemical Reviews, American Chemical Society, US, vol. 96, No. 8, Dec. 16, 1996, pp. 3147-3176, XP000652176, ISSN: 0009-2665, DOI: 10.1021/CR950066Q.

Ana Z. Gonzalez et al: "Novel Inhibitors of the MDM2-p53 Interaction Featuring Hydrogen Bond Acceptors as Carboxylic Acid Isosteres". Journal of Medicinal Chemistry, vol. 57, No. 7, Mar. 6, 2014, pp. 2963-2988, XP055116598, ISSN: 0022-2623, DOI: 10.1021/jm401911v.

International Search Report, PCT/US2014/018759, Issued Jun. 12, 2014, pp. 1-5.

Written Opinion of the International Searching Authority, PCT/US2014/018759, Issued Jun. 12, 2014, pp. 1-7.

J.L. Garcia Ruano et al: "Synthesis of 2-phenyl-, 3-phenyl-, cis-2,3-diphenyl-, and trans-2,3-diphenyl-1,4-thiazanes and derivatives (N-methyl, N-alkoxycarbonyl, S-oxides, and S,S-dioxides)", The Journal of Organic Chemistry, vol. 57, No. 15, Jul. 1, 1992, pp. 4215-4224.

(56) References Cited

OTHER PUBLICATIONS

Canon et al., The MDM2 Inhibitor AMG 232 Demonstrates Robust Antitumor Efficacy and Potentiates the Activity of p53-Inducing Cytotoxic Agents, Mol Cancer Ther; 2015.
Kojima et al., MDM2 antagonists induce p53-dependent apoptosis in AML: implications for leukemia therapy, Blood, Nov. 1, 2006, vol. 106, No. 9.
Li et al., Molecular Pathways: Targeting Mdm2 and Mdm4 in Cancer Therapy, Clin Cancer Res, 19(1) Jan. 1, 2013.
Wang et al., SAR405838: An Optimized Inhibitor of MDM2—p53 Interaction That Induces Complete and Durable Tumor Regression, Cancer Res, 74(20) Oct. 15, 2014.
U.S. Appl. No. 14/774,645, filed Sep. 10, 2015, Amgen Inc.
"Guidance for Industry ANDAs: Pharmaceutical Solid Polymorphism Chemistry Manufacturing, and Controls Information," U.S. Department of Health and Human Services, Food and Drug Administration, Center for Drug Evaluation and Research (CDER), Jul. 2007, pp. 1-13.
Gattermann, L. "The Practical Methods of Organic Chemistry," 1896, MacMillan: New York, pp. 1-14.
International Search Report, PCT/US2012/057389, Issued Jan. 18, 2013, pp. 1-4.
Lawrence, H. R. et al., "Identification of a disruptor of the MDM2-p53 protein—protein interaction facilitated by high-throughput in silico docking," Bioorganic & Medicinal Chemistry Letters 19, 3756-3759 (2009).
Morissette, S. L. et. al. "High-throughput crystallization: polymorphs, salts, co-crystals and solvates of pharmaceutical solids," Advanced Drug Delivery Reviews 56, 275-300 (2004).
Notice of Allowance mailed Oct. 29, 2015 for U.S. Appl. No. 14/316,586, filed Jun. 26, 2014.
Written Opinion of the International Searching Authority, PCT/US2012/057389, Issued Jan. 18, 2013, pp. 1-6.
Zeitler, J. A. et al. "Characterization of Temperature-Induced Phase Transitions in Five Polymorphic Forms of Sulfathiazole by Terahertz Pulsed Spectroscopy and Differential Scanning Calorimetry," Journal of Pharmaceutical Sciences 95(11), 2486-2498 (2006).
U.S. Appl. No. 15/008,342, filed Jan. 27, 2015, Amgen Inc.

\* cited by examiner

HETEROCYCLIC COMPOUNDS AS MDM2 INHIBITORS FOR THE TREATMENT OF CANCER

CROSS-REFERENCE TO RELATED APPLICATIONS

This application is a 35 U.S.C. §371 filing of PCT Application No. PCT/US2012/57389, filed Sep. 26, 2012, which claims priority of U.S. Provisional Application No. 61/566,449, filed Dec. 2, 2011, which claims priority of U.S. Provisional Application No. 61/539,715, filed Sep. 27, 2011, the contents of which are incorporated by reference herein in their entirety.

FIELD OF THE INVENTION

The present invention relates to compounds that are MDM2 inhibitors that are useful as therapeutic agents, particularly for the treatment of cancers. The invention also relates to pharmaceutical compositions that contain a MDM2 inhibitor.

BACKGROUND OF THE INVENTION p53 is a tumor suppressor and transcription factor that responds to cellular stress by activating the transcription of numerous genes involved in cell cycle arrest, apoptosis, senescence, and DNA repair. Unlike normal cells, which have infrequent cause for p53 activation, tumor cells are under constant cellular stress from various insults including hypoxia and pro-apoptotic oncogene activation. Thus, there is a strong selective advantage for inactivation of the p53 pathway in tumors, and it has been proposed that eliminating p53 function may be a prerequisite for tumor survival. In support of this notion, three groups of investigators have used mouse models to demonstrate that absence of p53 function is a continuous requirement for the maintenance of established tumors. When the investigators restored p53 function to tumors with inactivated p53, the tumors regressed.

p53 is inactivated by mutation and/or loss in 50% of solid tumors and 10% of liquid tumors. Other key members of the p53 pathway are also genetically or epigenetically altered in cancer. MDM2, an oncoprotein, inhibits p53 function, and it is activated by gene amplification at incidence rates that are reported to be as high as 10%. MDM2, in turn, is inhibited by another tumor suppressor, p14ARF. It has been suggested that alterations downstream of p53 may be responsible for at least partially inactivating the p53 pathway in $p53^{WT}$ tumors (p53 wildtype). In support of this concept, some $p53^{WT}$ tumors appear to exhibit reduced apoptotic capacity, although their capacity to undergo cell cycle arrest remains intact. One cancer treatment strategy involves the use of small molecules that bind MDM2 and neutralize its interaction with p53. MDM2 inhibits p53 activity by three mechanisms: 1) acting as an E3 ubiquitin ligase to promote p53 degradation; 2) binding to and blocking the p53 transcriptional activation domain; and 3) exporting p53 from the nucleus to the cytoplasm. All three of these mechanisms would be blocked by neutralizing the MDM2-p53 interaction. In particular, this therapeutic strategy could be applied to tumors that are $p53^{WT}$, and studies with small molecule MDM2 inhibitors have yielded promising reductions in tumor growth both in vitro and in vivo. Further, in patients with p53-inactivated tumors, stabilization of wildtype p53 in normal tissues by MDM2 inhibition might allow selective protection of normal tissues from mitotic poisons.

The present invention relates to compounds capable of inhibiting the interaction between p53 and MDM2 and activating p53 downstream effector genes. As such, compounds of the present invention would be useful in the treatment of cancers, bacterial infections, viral infections, ulcers and inflammation. In particular, the compounds of the present invention are useful to treat solid tumors such as: breast, colon, lung and prostate tumors; and liquid tumors such as lymphomas and leukemias. As used herein, MDM2 means a human MDM2 protein and p53 means a human p53 protein. It is noted that human MDM2 can also be referred to as HDM2 or hMDM2.

SUMMARY OF THE INVENTION

In embodiment 1, the present invention provides compounds of Formula I or II, or pharmaceutically acceptable salts thereof,

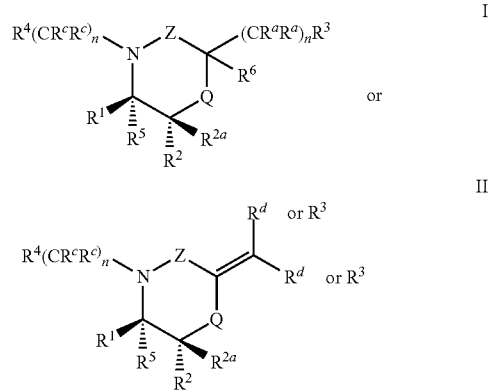

wherein:
Q is O, S, —S(=O)—, —S(=O)$_2$—, or —NR$^e$;
Z is —C(=O)— or —S(=O)$_2$—;
R$^1$ is a 5 to 10 membered aryl or heteroaryl group, which heteroaryl group can contain from one to three heteroatoms independently selected from O, N or S, and the aryl or heteroaryl group can be unsubstituted or substituted with from one to three substituents independently selected from halo, —C$_{1-6}$alkyl, —OH, —NO$_2$, —NHC(=O)C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, —(CH$_2$)$_n$C(=O)R$^f$, —(CH$_2$)$_n$C(=O)NR$^f$R$^f$, —CN, —NR$^g$R$^g$ or A,
or R$^1$ and R$^5$ together with the carbon atom to which they are attached can form a 3 to 6 membered cycloalkyl or heterocycloalkyl group, optionally containing a —(C=O)— group, which heterocycloalkyl group can contain from one to two heteroatoms independently selected from O, N or S, and the cycloalkyl or heterocycloalkyl group can be unsubstituted or substituted with from one to three substituents independently selected from halo, —C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, —(CH$_2$)$_n$C(=O)R$^f$, —(CH$_2$)$_n$C(=O)NR$^f$R$^f$ or —CN, and substituents on two adjacent carbons atoms of the cycloalkyl or heterocycloalkyl group can join together to form a five or six membered ring, including the two carbon atoms, fused to the cycloalkyl or heterocycloalkyl group,
or when R$^1$ is substituted with —NR$^g$R$^g$, then R$^g$ and R$^g$ together with the nitrogen atom to which they are attached can form a 3 to 6 membered heterocycloalkyl group, which heterocycloalkyl group can contain from one to two additional heteroatoms independently selected from O, N or S, and the heterocycloalkyl group can be unsubstituted or substituted with from one to three substituents independently selected from halo, —$C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$ or —CN;

each A is independently a 5 or 6 membered aryl or heteroaryl group, which heteroaryl group can contain from one to three heteroatoms independently selected from O, N or S, and the aryl or heteroaryl group can be unsubstituted or substituted with from one to three substituents independently selected from halo, —$C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN;

$R^2$ is a 5 to 10 membered aryl or heteroaryl group, which heteroaryl group can contain from one to three heteroatoms independently selected from O, N or S, and the aryl or heteroaryl group can be unsubstituted or substituted with from one to three substituents independently selected from halo, —$C_{1-6}$alkyl, —OH, —$NO_2$, —$NHC(=O)C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, —$(CH_2)_nC(=O)R^f$, —$(CH_2)_nC(=O)NR^fR^f$, —CN, —$NR^gR^g$ or B, or when $R^2$ is substituted with —$NR^gR^g$, then $R^g$ and $R^g$ together with the nitrogen atom to which they are attached can form a 3 to 6 membered heterocycloalkyl group, which heterocycloalkyl group can contain from one to two additional heteroatoms independently selected from O, N or S, and the heterocycloalkyl group can be unsubstituted or substituted with from one to three substituents independently selected from halo, —$C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN;

each B is independently a 5 or 6 membered aryl or heteroaryl group, which heteroaryl group can contain from one to three heteroatoms independently selected from O, N or S, and the aryl or heteroaryl groups group can be unsubstituted or substituted with from one to three substituents independently selected from halo, —$C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN;

$R^{2a}$ is hydrogen or —$C_{1-3}$alkyl;

$R^3$ is hydrogen, —$C_{1-6}$alkyl, —$C(=O)OR^f$, —$C(=O)C_{1-6}$alkyl, —$S(=O)_2R^f$, —$S(=O)R^f$, —$OR^f$, —$C(=O)NR^fN(R^f)_2$, —$C(=O)NR^fS(=O)_2R^f$, —$S(=O)_2NR^fC(=O)R^f$, —$S(=O)_2NR^fR^f$, —$N(R^f)C(=O)NR^fR^f$, —$NR^fC(=O)_2R^f$, —$C(=O)NR^fR^f$, —$NR^fS(=O)_2R^f$, —CN, —$NR^fR^f$, —$C(=O)NOH$, —$NR^fC(=O)OR^f$, —$NR^fC(=O)R^f$, —$C_{1-6}$alkyl substituted with from 1 to 3 hydroyl groups, —$C_{1-6}$alkenyl, or a 5 or 6 membered aryl or heteroaryl group, which heteroaryl group can contain from one to four heteroatoms independently selected from O, N or S, and the aryl or heteroaryl group can be unsubstituted or substituted with from one to three substituents independently selected from halo, —$C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN, and any $C_{1-6}$alkyl group can be unsubstituted or substituted with from one to three substituents independently selected from halo, —OH, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN;

$R^4$ is hydrogen, —$C_{1-6}$alkyl, —$C_{2-6}$alkenyl, —$CF_3$, —$CH_2F$, —$CHF_2$, —$S(=O)_2R^f$, —$SR^f$, —$S(=O)R^f$, —$S(=O)_2NR^fR^f$, —$NR^fS(=O)_2NR^fR^f$, —$C(=O)NR^fR^f$, —$NR^fS(=O)_2R^f$, —$C(=O)_2R^f$, —$OR^f$, a 3 to 7 membered cycloalkyl or heterocycloalkyl, optionally containing a —(C=O)— group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halo, —$C_{1-6}$alkyl-OH, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN, and the —$C_{1-6}$alkyl or —$C_{2-6}$alkenyl group can be unsubstituted or substituted with from one to three substituents independently selected from halo, —$NR^fR^f$, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN;

$R^5$ is hydrogen or —$C_{1-6}$alkyl;

$R^6$ is hydrogen, —$C_{1-6}$alkyl, —$(CH_2)NR^fR^f$, or —$(CH_2)_nC(=O)NR^fR^f$;

each $R^a$ is independently hydrogen, halo or —$C_{1-6}$alkyl, or two $R^a$ groups that are attached to the same carbon atom can form an (=O) group or a 3 to 6 membered cycloalkyl or heterocycloalkyl group, or an $R^a$ group and $R^6$ along with the atoms to which they are attached can form a 3 to 6 membered cycloalkyl or heterocycloalkyl group, which heterocycloalkyl group can contain from one to two heteroatoms independently selected from O, N or S, and the cycloalkyl or heterocycloalkyl group can be unsubstituted or substituted with from one to three substituents independently selected from halo, —$C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN;

each $R^c$ is independently hydrogen, —$C_{1-6}$alkyl, —$C_{1-6}$alkyl-$CF_3$, —$CF_3$, a 3 to 6 membered cycloalkyl or heterocycloalkyl group, which heterocycloalkyl group can contain from one to two heteroatoms independently selected from O, N or S, and the cycloalkyl or heterocycloalkyl group can be unsubstituted or substituted with from one to three substituents independently selected from halo, $C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN;

or two $R^c$ groups that are attached to the same or adjacent carbon atoms can together with the carbon atom or atoms to which they are attached form or a 3 to 6 membered cycloalkyl or heterocycloalkyl group, which heterocycloalkyl group can contain from one to two heteroatoms independently selected from O, N or S, and the cycloalkyl or heterocycloalkyl group can be unsubstituted or substituted with from one to three substituents independently selected from halo, —$C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN;

each $R^d$ is independently hydrogen or —$C_{1-6}$alkyl;

each $R^e$ is independently hydrogen or —$C_{1-6}$alkyl;

each $R^f$ is independently hydrogen, —CN, —$C_{1-6}$alkyl, —$C_{1-6}$alkyl-CN, —$C_{1-6}$alkyl-$CF_3$, hydroxy$C_{1-6}$alkyl, —$C_{1-6}$alkylNR$^e$R$^e$, or a 5 to 6 membered aryl, —$C_{1-6}$alkylaryl, heteroaryl, or —$C_{1-6}$alkylheteroaryl, or a 3 to 9 membered cycloalkyl —$C_{1-6}$alkylcycloalkyl, heterocycloalkyl or —$C_{1-6}$alkylheterocycloalkyl group, which heteroaryl, alkylheteroaryl, heterocycloalkyl, or alkylheterocycloalkyl group can contain from one to three heteroatoms independently selected from O, N or S, and the alkyl, aryl, alkylaryl, heteroaryl, alkylheteroaryl, cycloalkyl, alkylcycloalkyl, heterocycloalkyl, or alkylheterocycloalkyl group can be unsubstituted or substituted with from one to three substituents independently selected from halo, —$C_{1-6}$alkyl, —$S(=O)_2C_{1-6}$alkyl, —$S(=O)C_{1-6}$alkyl. —$OC_{1-6}$alkyl, —$CF_3$, —$OCF_3$, —$OCHF_2$, —$OCH_2F$, or —CN;

or when R$^f$ and R$^f$ are part of an NR$^f$R$^f$ or CR$^f$R$^f$ moiety in a group, then R$^f$ and R$^f$ together with the nitrogen or carbon atom to which they are attached can form a 3 to 7 membered heterocycloalkyl or cycloalkyl group, which heterocycloalkyl group can contain from one to two additional heteroatoms independently selected from O, N or S, and the heterocycloalkyl or cycloalkyl group can be unsubstituted or substituted with from one to three substituents independently selected from halo, —C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, or —CN;

each R$^g$ is independently hydrogen, or —C$_{1-6}$alkyl; and each n is independently 0, 1, 2, 3 or 4, provided that the compound is not 2-((2R,5R,6R)-6-(3-Chlorophenyl)-5-(4-chlorophenyl)-4-((1S,2S)-2-(isopropylsulfonyl)cyclopentyl)-3-oxomorpholin-2-yl)acetic acid; 2-((2S,5R,6R)-6-(3-chlorophenyl)-5-(4-chlorophenyl)-4-((1S,2S)-2-(isopropylsulfonyl)cyclopentyl)-3-oxomorpholin-2-yl) acetic acid; 2-((2R,5R,6R)-6-(3-chlorophenyl)-5-(4-chlorophenyl)-4-((1R,2R)-2-(isopropylsulfonyl)cyclopentyl)-3-oxomorpholin-2-yl)acetic acid; or 2-((2S,5R,6R)-6-(3-chlorophenyl)-5-(4-chlorophenyl)-4-((1R,2R)-2-(isopropylsulfonyl)cyclopentyl)-3-oxomorpholin-2-yl) acetic acid.

In embodiment 1A, the present invention provides compounds of Formula I or II, or pharmaceutically acceptable salts thereof,

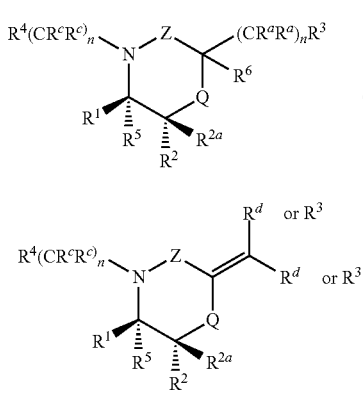

wherein:

Q is O, S, —S(=O)—, —S(=O)$_2$—, or —NR$^e$;

Z is —C(=O)— or —S(=O)$_2$—;

R$^1$ is a 5 to 10 membered aryl or heteroaryl group, which heteroaryl group can contain from one to three heteroatoms independently selected from O, N or S, and the aryl or heteroaryl group can be unsubstituted or substituted with from one to three substituents independently selected from halo, —C$_{1-6}$alkyl, —OH, —NO$_2$, —NHC(=O)C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, —(CH$_2$)$_n$C(=O)R$^f$, —(CH$_2$)$_n$C(=O)NR$^f$R$^f$, —CN, —NR$^g$R$^g$ or A, or R$^1$ and R$^5$ together with the carbon atom to which they are attached can form a 3 to 6 membered cycloalkyl or heterocycloalkyl group, optionally containing a —(C=O)— group, which heterocycloalkyl group can contain from one to two heteroatoms independently selected from O, N or S, and the cycloalkyl or heterocycloalkyl group can be unsubstituted or substituted with from one to three substituents independently selected from halo, —C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, —(CH$_2$)$_n$C(=O)R$^f$, —(CH$_2$)$_n$C(=O)NR$^f$R$^f$ or —CN, and substituents on two adjacent carbons atoms of the cycloalkyl or heterocycloalkyl group can join together to form a five or six membered ring, including the two carbon atoms, fused to the cycloalkyl or heterocycloalkyl group, or when R$^1$ is substituted with —NR$^g$R$^g$, then R$^g$ and R$^g$ together with the nitrogen atom to which they are attached can form a 3 to 6 membered heterocycloalkyl group, which heterocycloalkyl group can contain from one to two additional heteroatoms independently selected from O, N or S, and the heterocycloalkyl group can be unsubstituted or substituted with from one to three substituents independently selected from halo, —C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F or —CN;

each A is independently a 5 or 6 membered aryl or heteroaryl group, which heteroaryl group can contain from one to three heteroatoms independently selected from O, N or S, and the aryl or heteroaryl group can be unsubstituted or substituted with from one to three substituents independently selected from halo, —C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, or —CN;

R$^2$ is a 5 to 10 membered aryl or heteroaryl group, which heteroaryl group can contain from one to three heteroatoms independently selected from O, N or S, and the aryl or heteroaryl group can be unsubstituted or substituted with from one to three substituents independently selected from halo, —C$_{1-6}$alkyl, —OH, —NO$_2$, —NHC(=O)C$_{1-6}$alkyl, —S(=O)$_2$C$_{1-6}$alkyl, —S(=O)C$_{1-6}$alkyl, —OC$_{1-6}$alkyl, —CF$_3$—OCF$_3$, —OCHF$_2$, —OCH$_2$F, —(CH$_2$)$_n$C(=O)R$^f$, —(CH$_2$)$_n$C(=O)NR$^f$R$^f$, —CN, —NR$^g$R$^g$ or B, or when R$^2$ is substituted with —NR$^g$R$^g$, then R$^g$ and R$^g$ together with the nitrogen atom to which they are attached can form a 3 to 6 membered heterocycloalkyl group, which heterocycloalkyl group can contain from one to two additional heteroatoms independently selected from O, N or S, and the heterocycloalkyl group can be unsubstituted or substituted with from one to three substituents independently selected from halo, —C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, or —CN;

each B is independently a 5 or 6 membered aryl or heteroaryl group, which heteroaryl group can contain from one to three heteroatoms independently selected from O, N or S, and the aryl or heteroaryl groups group can be unsubstituted or substituted with from one to three substituents independently selected from halo, —C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, or —CN;

R$^{2a}$ is hydrogen or —C$_{1-3}$alkyl;

R$^3$ is hydrogen, —C$_{1-6}$alkyl, —C(=O)OR$^f$, —C(=O)C$_{1-6}$alkyl, —S(=O)$_2$R$^f$, —S(=O)R$^f$, —OR$^f$, —C(=O)NR$^f$N(R$^f$)$_2$, —C(=O)NR$^f$S(=O)$_2$R$^f$, —S(=O)$_2$NR$^f$C(=O)R$^f$, —S(=O)$_2$NR$^f$R$^f$, —N(R$^f$)C(=O)NR$^f$R$^f$, —NR$^f$C(=O)$_2$R$^f$, —C(=O)NR$^f$R$^f$, —NR$^f$S(=O)$_2$R$^f$, —CN, —NR$^f$R$^f$, —C(=O)NOH, —C$_{1-6}$alkenyl, or a 5 or 6 membered aryl or heteroaryl group, which heteroaryl group can contain from one to four heteroatoms independently selected from O, N or S, and the aryl or heteroaryl group can be unsubstituted or substituted with from one to three substituents independently selected from halo, —C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, or —CN, and any C$_{1-6}$alkyl group can be unsubstituted or substituted with from one to three substituents independently selected from halo, —OH, —S(=O)₂C₁₋₆alkyl, —S(=O)C₁₋₆alkyl, —OC₁₋₆alkyl, —CF₃, —OCF₃, —OCHF₂, —OCH₂F, or —CN;

R⁴ is hydrogen, —C₁₋₆alkyl, —C₂₋₆alkenyl, —CF₃, —CH₂F, —CHF₂, —S(=O)₂alkyl, —SR^f, —S(=O)R^f, —S(=O)₂NR^fR^f, —NR^fS(=O)₂NR^fR^f, —C(=O)NR^fR^f, —NR^fS(=O)₂R^f, —C(=O)₂R^f, —OR^f, a 3 to 7 membered cycloalkyl or heterocycloalkyl, optionally containing a —(C=O)— group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halo, —C₁₋₆alkyl-OH, —S(=O)₂C₁₋₆alkyl, —S(=O)C₁₋₆alkyl, —OC₁₋₆alkyl, —CF₃, —OCF₃, —OCHF₂, —OCH₂F, or —CN, and the —C₁₋₆alkyl or —C₂₋₆alkenyl group can be unsubstituted or substituted with from one to three substituents independently selected from halo, —NR^fR^f, —S(=O)₂C₁₋₆alkyl, —S(=O)C₁₋₆alkyl, —OC₁₋₆alkyl, —CF₃, —OCF₃, —OCHF₂, —OCH₂F, or —CN;

R⁵ is hydrogen or —C₁₋₆alkyl;

R⁶ is hydrogen, —C₁₋₆alkyl, —(CH₂)NR^fR^f, or —(CH₂)ₙC(=O)NR^fR^f;

each R^a is independently hydrogen, halo or —C₁₋₆alkyl, or two R^a groups that are attached to the same carbon atom can form an (=O) group or a 3 to 6 membered cycloalkyl or heterocycloalkyl group, or an R^a group and R⁶ along with the atoms to which they are attached can form a 3 to 6 membered cycloalkyl or heterocycloalkyl group, which heterocycloalkyl group can contain from one to two heteroatoms independently selected from O, N or S, and the cycloalkyl or heterocycloalkyl group can be unsubstituted or substituted with from one to three substituents independently selected from halo, —C₁₋₆alkyl, —S(=O)₂C₁₋₆alkyl, —S(=O)C₁₋₆alkyl, —OC₁₋₆alkyl, —CF₃, —OCF₃, —OCHF₂, —OCH₂F, or —CN;

each R^c is independently hydrogen, —C₁₋₆alkyl, a 3 to 6 membered cycloalkyl or heterocycloalkyl group, which heterocycloalkyl group can contain from one to two heteroatoms independently selected from O, N or S, and the cycloalkyl or heterocycloalkyl group can be unsubstituted or substituted with from one to three substituents independently selected from halo, C₁₋₆alkyl, —S(=O)₂C₁₋₆alkyl, —S(=O)C₁₋₆alkyl, —OC₁₋₆alkyl, —CF₃, —OCF₃, —OCHF₂, —OCH₂F, or —CN;

or two R^c groups that are attached to the same or adjacent carbon atoms can together with the carbon atom or atoms to which they are attached form or a 3 to 6 membered cycloalkyl or heterocycloalkyl group, which heterocycloalkyl group can contain from one to two heteroatoms independently selected from O, N or S, and the cycloalkyl or heterocycloalkyl group can be unsubstituted or substituted with from one to three substituents independently selected from halo, —C₁₋₆alkyl, —S(=O)₂C₁₋₆alkyl, —S(=O)C₁₋₆alkyl, —OC₁₋₆alkyl, —CF₃, —OCF₃, —OCHF₂, —OCH₂F, or —CN;

each R^d is independently hydrogen or —C₁₋₆alkyl;
each R^e is independently hydrogen or —C₁₋₆alkyl;
each R^f is independently hydrogen, —C₁₋₆alkyl, hydroxyC₁₋₆alkyl, —C₁₋₆alkylNR^eR^e, or a 5 to 6 membered aryl, —C₁₋₆alkylaryl, heteroaryl, or —C₁₋₆alkylheteroaryl, or a 3 to 7 membered cycloalkyl, —C₁₋₆alkylcycloalkyl, heterocycloalkyl or —C₁₋₆alkylheterocycloalkyl group, which heteroaryl, alkylheteroaryl, heterocycloalkyl, or alkylheterocycloalkyl group can contain from one to three heteroatoms independently selected from O, N or S, and the aryl, alkylaryl, heteroaryl, alkylheteroaryl, cycloalkyl, alkylcycloalkyl, heterocycloalkyl, or alkylheterocycloalkyl group can be unsubstituted or substituted with from one to three substituents independently selected from halo, —C₁₋₆alkyl, —S(=O)₂C₁₋₆alkyl, —S(=O)C₁₋₆alkyl. —OC₁₋₆alkyl, —CF₃, —OCF₃, —OCHF₂, —OCH₂F, or —CN;

or when R^f and R^f are part of an NR^fR^f or CR^fR^f moiety in a group, then R^f and R^f together with the nitrogen or carbon atom to which they are attached can form a 3 to 7 membered heterocycloalkyl or cycloalkyl group, which heterocycloalkyl group can contain from one to two additional heteroatoms independently selected from O, N or S, and the heterocycloalkyl or cycloalkyl group can be unsubstituted or substituted with from one to three substituents independently selected from halo, —C₁₋₆alkyl, —S(=O)₂C₁₋₆alkyl, —S(=O)C₁₋₆alkyl, —OC₁₋₆alkyl, —CF₃, —OCF₃, —OCHF₂, —OCH₂F, or —CN;

each R^g is independently hydrogen, or —C₁₋₆alkyl; and
each n is independently 0, 1, 2, 3 or 4, provided that the compound is not 2-((2R,5R,6R)-6-(3-Chlorophenyl)-5-(4-chlorophenyl)-4-((1S,2S)-2-(isopropylsulfonyl)cyclopentyl)-3-oxomorpholin-2-yl)acetic acid; 2-((2S,5R,6R)-6-(3-chlorophenyl)-5-(4-chlorophenyl)-4-((1S,2S)-2-(isopropylsulfonyl)cyclopentyl)-3-oxomorpholin-2-yl) acetic acid; 2-((2R,5R,6R)-6-(3-chlorophenyl)-5-(4-chlorophenyl)-4-((1R,2R)-2-(isopropylsulfonyl)cyclopentyl)-3-oxomorpholin-2-yl)acetic acid; or 2-((2S,5R,6R)-6-(3-chlorophenyl)-5-(4-chlorophenyl)-4-((1R,2R)-2-(isopropylsulfonyl)cyclopentyl)-3-oxomorpholin-2-yl) acetic acid.

In embodiment 1a, the present invention provides compounds of Formula I or II, or pharmaceutically acceptable salts thereof,

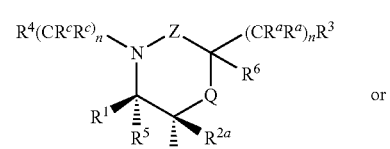

I

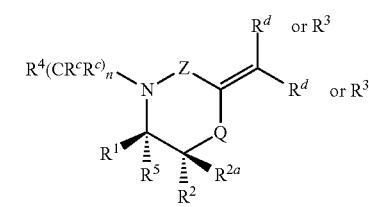

II wherein:
Q is O, S, —S(=O)—, —S(=O)₂—, or —NR^e;
Z is —C(=O)— or —S(=O)₂—;
R¹ is a 5 to 10 membered aryl or heteroaryl group, which heteroaryl group can contain from one to three heteroatoms independently selected from O, N or S, and the aryl or heteroaryl group can be unsubstituted or substituted with from one to three substituents independently selected from halo, —C₁₋₆alkyl, —OH, —NO₂, —NHC(=O)C₁₋₆alkyl, —S(=O)₂C₁₋₆alkyl, —S(=O)C₁₋₆alkyl, —OC₁₋₆alkyl, —CF₃, —OCF₃, —OCHF₂, —OCH₂F, —(CH₂)ₙC(=O)R^f, —(CH₂)ₙC(=O)NR^fR^f, —CN, —NR^gR^g or A, or R¹ and R⁵ together with the carbon atom to which they are attached can form a 3 to 6 membered cycloalkyl or heterocycloalkyl group, optionally containing a —(C=O)— group, which heterocycloalkyl group can contain from one to two heteroatoms independently selected from O, N or S, and the cycloalkyl or heterocycloalkyl group can be unsubstituted or substituted with from one to three substituents independently selected from halo, —$C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, —$(CH_2)_nC(=O)R^f$, —$(CH_2)_nC(=O)NR^fR^f$ or —CN, and substituents on two adjacent carbons atoms of the cycloalkyl or heterocycloalkyl group can join together to form a five or six membered ring, including the two carbon atoms, fused to the cycloalkyl or heterocycloalkyl group, or when $R^1$ is substituted with —$NR^gR^g$, then $R^g$ and $R^g$ together with the nitrogen atom to which they are attached can form a 3 to 6 membered heterocycloalkyl group, which heterocycloalkyl group can contain from one to two additional heteroatoms independently selected from O, N or S, and the heterocycloalkyl group can be unsubstituted or substituted with from one to three substituents independently selected from halo, —$C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$ or —CN;

each A is independently a 5 or 6 membered aryl or heteroaryl group, which heteroaryl group can contain from one to three heteroatoms independently selected from O, N or S, and the aryl or heteroaryl group can be unsubstituted or substituted with from one to three substituents independently selected from halo, —$C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN;

$R^2$ is a 5 to 10 membered aryl or heteroaryl group, which heteroaryl group can contain from one to three heteroatoms independently selected from O, N or S, and the aryl or heteroaryl group can be unsubstituted or substituted with from one to three substituents independently selected from halo, —$C_{1-6}$alkyl, —OH, —$NO_2$, —$NHC(=O)C_{1-6}$alkyl, —$S(=O)_2C_{1-6}$alkyl, —$S(=O)C_{1-6}$alkyl, —$OC_{1-6}$alkyl, —$CF_3$—$OCF_3$, —$OCHF_2$, —$OCH_2F$, —$(CH_2)_nC(=O)R^f$, —$(CH_2)_nC(=O)NR^fR^f$, —CN, —$NR^gR^g$ or B, or when $R^2$ is substituted with —$NR^gR^g$, then $R^g$ and $R^g$ together with the nitrogen atom to which they are attached can form a 3 to 6 membered heterocycloalkyl group, which heterocycloalkyl group can contain from one to two additional heteroatoms independently selected from O, N or S, and the heterocycloalkyl group can be unsubstituted or substituted with from one to three substituents independently selected from halo, —$C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN;

each B is independently a 5 or 6 membered aryl or heteroaryl group, which heteroaryl group can contain from one to three heteroatoms independently selected from O, N or S, and the aryl or heteroaryl groups group can be unsubstituted or substituted with from one to three substituents independently selected from halo, —$C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN;

$R^{2a}$ is hydrogen or —$C_{1-3}$alkyl;

$R^3$ is hydrogen, —$C_{1-6}$alkyl, —$C(=O)OR^f$, —$C(=O)C_{1-6}$alkyl, —$S(=O)_2R^f$, —$S(=O)R^f$, —$OR^f$, —$C(=O)NR^fN(R^f)_2$, —$C(=O)NR^fS(=O)_2R^f$, —$S(=O)_2NR^fC(=O)R^f$, —$S(=O)_2NR^fR^f$, —$N(R^f)C(=O)NR^fR^f$, —$NR^fC(=O)_2R^f$, —$C(=O)NR^fR^f$, —$NR^fS(=O)_2R^f$, —CN, —$NR^fR^f$, or a 5 or 6 membered aryl or heteroaryl group, which heteroaryl group can contain from one to four heteroatoms independently selected from O, N or S, and the aryl or heteroaryl group can be unsubstituted or substituted with from one to three substituents independently selected from halo, —$C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN, and any $C_{1-6}$alkyl group can be unsubstituted or substituted with from one to three substituents independently selected from halo, —OH, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN;

$R^4$ is hydrogen, —$C_{1-6}$alkyl, —$C_{2-6}$alkenyl, —$CF_3$, —$CH_2F$, —$CHF_2$, —$S(=O)_2R^f$, —$SR^f$, —$S(=O)R^f$, —$S(=O)_2NR^fR^f$, —$NR^fS(=O)_2NR^fR^f$, —$C(=O)NR^fR^f$, —$NR^fS(=O)_2R^f$, —$C(=O)_2R^f$, —$OR^f$, a 3 to 7 membered cycloalkyl or heterocycloalkyl, optionally containing a —(C=O)— group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halo, —$C_{1-6}$alkyl-OH, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or CN, and the —$C_{1-6}$alkyl or —$C_{2-6}$alkenyl group can be unsubstituted or substituted with from one to three substituents independently selected from halo, —$NR^fR^f$, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN;

$R^5$ is hydrogen or —$C_{1-6}$alkyl;

$R^6$ is hydrogen, —$C_{1-6}$alkyl, —$(CH_2)NR^fR^f$, or —$(CH_2)_nC(=O)NR^fR^f$;

each $R^a$ is independently hydrogen, halo or —$C_{1-6}$alkyl, or two $R^a$ groups that are attached to the same carbon atom can form an (=O) group or a 3 to 6 membered cycloalkyl or heterocycloalkyl group, or an $R^a$ group and $R^6$ along with the atoms to which they are attached can form a 3 to 6 membered cycloalkyl or heterocycloalkyl group, which heterocycloalkyl group can contain from one to two heteroatoms independently selected from O, N or S, and the cycloalkyl or heterocycloalkyl group can be unsubstituted or substituted with from one to three substituents independently selected from halo, —$C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN;

each $R^c$ is independently hydrogen, —$C_{1-6}$alkyl, a 3 to 6 membered cycloalkyl or heterocycloalkyl group, which heterocycloalkyl group can contain from one to two heteroatoms independently selected from O, N or S, and the cycloalkyl or heterocycloalkyl group can be unsubstituted or substituted with from one to three substituents independently selected from halo, $C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN;

or two $R^c$ groups that are attached to the same or adjacent carbon atoms can together with the carbon atom or atoms to which they are attached form or a 3 to 6 membered cycloalkyl or heterocycloalkyl group, which heterocycloalkyl group can contain from one to two heteroatoms independently selected from O, N or S, and the cycloalkyl or heterocycloalkyl group can be unsubstituted or substituted with from one to three substituents independently selected from halo, —$C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN;

each $R^d$ is independently hydrogen or —$C_{1-6}$alkyl;

each $R^e$ is independently hydrogen or —$C_{1-6}$alkyl;

each $R^f$ is independently hydrogen, —$C_{1-6}$alkyl or a 5 to 6 membered aryl, —$C_{1-6}$alkylaryl, heteroaryl, or —$C_{1-6}$alkylheteroaryl, or a 3 to 7 membered cycloalkyl —$C_{1-6}$alkylcycloalkyl, heterocycloalkyl or —$C_{1-6}$alkylheterocycloalkyl group, which heteroaryl alkylheteroaryl, heterocycloalkyl, or alkylheterocycloalkyl group can contain from one to three heteroatoms independently selected from O, N or S, and the aryl, alkylaryl, heteroaryl, alkylheteroaryl, cycloalkyl, alkylcycloalkyl, heterocycloalkyl, or alkylheterocycloalkyl group can be unsubstituted or substituted with from one to three substituents independently selected from halo, —$C_{1-6}$alkyl, —S(=O)$_2C_{1-6}$alkyl, —S(=O)$C_{1-6}$alkyl. —O$C_{1-6}$alkyl, —$CF_3$, —$OCF_3$, —$OCHF_2$, —$OCH_2F$, or —CN;

or when $R^f$ and $R^f$ are part of an $NR^fR^f$ or $CR^fR^f$ moiety in a group, then $R^f$ and $R^f$ together with the nitrogen or carbon atom to which they are attached can form a 3 to 7 membered heterocycloalkyl or cycloalkyl group, which heterocycloalkyl group can contain from one to two additional heteroatoms independently selected from O, N or S, and the heterocycloalkyl or cycloalkyl group can be unsubstituted or substituted with from one to three substituents independently selected from halo, —$C_{1-6}$alkyl, —S(=O)$_2C_{1-6}$alkyl, —S(=O)$C_{1-6}$alkyl, —O$C_{1-6}$alkyl, —$CF_3$, —$OCF_3$, —$OCHF_2$, —$OCH_2F$, or —CN;

each $R^g$ is independently hydrogen, or —$C_{1-6}$alkyl; and each n is independently 0, 1, 2, 3 or 4, provided that the compound is not 2-((2R,5R,6R)-6-(3-Chlorophenyl)-5-(4-chlorophenyl)-4-((1S,2S)-2-(isopropylsulfonyl)cyclopentyl)-3-oxomorpholin-2-yl)acetic acid; 2-((2S,5R,6R)-6-(3-chlorophenyl)-5-(4-chlorophenyl)-4-((1S,2S)-2-(isopropylsulfonyl)cyclopentyl)-3-oxomorpholin-2-yl) acetic acid; 2-((2R,5R,6R)-6-(3-chlorophenyl)-5-(4-chlorophenyl)-4-((1R,2R)-2-(isopropylsulfonyl) cyclopentyl)-3-oxomorpholin-2-yl)acetic acid; or 2-((2S,5R,6R)-6-(3-chlorophenyl)-5-(4-chlorophenyl)-4-((1R,2R)-2-(isopropylsulfonyl)cyclopentyl)-3-oxomorpholin-2-yl) acetic acid.

In embodiment 2, the present invention provides compounds in accordance with embodiment 1, 1A or 1a, or pharmaceutically acceptable salts thereof, wherein:

Q is O;

Z is —C(=O)—;

$R^1$ is a 5 to 10 membered aryl or heteroaryl group, which heteroaryl group can contain from one to three heteroatoms independently selected from O, N or S, and the aryl or heteroaryl group can be unsubstituted or substituted with from one to three substituents independently selected from halo, —$C_{1-6}$alkyl, —S(=O)$_2C_{1-6}$alkyl, —S(=O)$C_{1-6}$alkyl, —O$C_{1-6}$alkyl, —$CF_3$—$OCF_3$, —$OCHF_2$, —$OCH_2F$, —CN, or A;

each A is independently a 5 or 6 membered aryl or heteroaryl group, which heteroaryl group can contain from one to three heteroatoms independently selected from O, N or S, and the aryl or heteroaryl group can be unsubstituted or substituted with from one to three substituents independently selected from halo, —$C_{1-6}$alkyl, —S(=O)$_2C_{1-6}$alkyl, —S(=O)$C_{1-6}$alkyl, —O$C_{1-6}$alkyl, —$CF_3$, —$OCF_3$, —$OCHF_2$, —$OCH_2F$, or —CN;

$R^2$ is a 5 to 10 membered aryl or heteroaryl group, which heteroaryl group can contain from one to three heteroatoms independently selected from O, N or S, and the aryl or heteroaryl group can be unsubstituted or substituted with from one to three substituents independently selected from halo, —$C_{1-6}$alkyl, —$SO_2C_{1-6}$alkyl, —S(=O)$C_{1-6}$alkyl, —O$C_{1-6}$alkyl, —$CF_3$, —$OCF_3$, —$OCHF_2$, —$OCH_2F$, —CN, or B;

each B is independently a 5 or 6 membered aryl or heteroaryl group, which heteroaryl group can contain from one to three heteroatoms independently selected from O, N or S, and the aryl or heteroaryl group can be unsubstituted or substituted with from one to three substituents independently selected from halo, —$C_{1-6}$alkyl, —S(=O)$_2C_{1-6}$alkyl, —S(=O)$C_{1-6}$alkyl, —O$C_{1-6}$alkyl, —$CF_3$, —$OCF_3$, —$OCHF_2$, —$OCH_2F$, or —CN;

$R^3$ is hydrogen, —$C_{1-6}$alkyl, —C(=O)$OR^f$, —C(=O)$C_{1-6}$alkyl, —S(=O)$_2R^f$, —S(=O)$R^f$, —$OR^f$, —C(=O)$NR^fN(R^f)_2$, —C(=O)$NR^fS(=O)_2R^f$, —S(=O)$_2NR^fC(=O)R^f$, —S(=O)$_2NR^fR^f$, —N($R^f$)C(=O)$NR^fR^f$, —$NR^f$C(=O)$_2R^f$, —C(=O)$NR^fR^f$, —$NR^fS(=O)_2R^f$, —CN, —$NR^fR^f$, or a 5 or 6 membered aryl or heteroaryl group, which heteroaryl group can contain from one to four heteroatoms independently selected from O, N or S, and the aryl or heteroaryl group can be unsubstituted or substituted with from one to three substituents independently selected from halo, —$C_{1-6}$alkyl, —S(=O)$_2C_{1-6}$alkyl, —S(=O)$C_{1-6}$alkyl, —O$C_{1-6}$alkyl, —$CF_3$, —$OCF_3$, —$OCHF_2$, —$OCH_2F$, or —CN, and any $C_{1-6}$alkyl group can be unsubstituted or substituted with from one to three substituents independently selected from halo, —OH, —S(=O)$_2C_{1-6}$alkyl, —S(=O)$C_{1-6}$alkyl, —O$C_{1-6}$alkyl, —$CF_3$, —$OCF_3$, —$OCHF_2$, —$OCH_2F$, or —CN;

$R^4$ is hydrogen, —$C_{1-6}$alkyl, —$C_{2-6}$alkenyl, —$CF_3$, —$CH_2F$, —$CHF_2$, —S(=O)$_2R^f$, —$SR^f$, —S(=O)$R^f$, —S(=O)$_2NR^fR^f$, —$NR^fS(=O)_2NR^fR^f$, —C(=O)$NR^fR^f$, —$NR^fS(=O)_2R^f$, —C(=O)$_2R^f$, —$OR^f$, a 3 to 7 membered cycloalkyl or heterocycloalkyl, optionally containing a —(C=O)— group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halo, —$C_{1-6}$alkyl-OH, —S(=O)$_2C_{1-6}$alkyl, —S(=O)$C_{1-6}$alkyl, —O$C_{1-6}$alkyl, —$CF_3$, —$OCF_3$, —$OCHF_2$, —$OCH_2F$, or —CN, and the —$C_{1-6}$alkyl or —$C_{2-6}$alkenyl group can be unsubstituted or substituted with from one to three substituents independently selected from halo, —$NR^fR^f$, —S(=O)$_2C_{1-6}$alkyl, —S(=O)$C_{1-6}$alkyl, —O$C_{1-6}$alkyl, —$CF_3$, —$OCF_3$, —$OCHF_2$, —$OCH_2F$, or —CN;

$R^6$ is hydrogen or —$C_{1-6}$alkyl;

each $R^a$ is independently hydrogen or —$C_{1-6}$alkyl; and each $R^e$ is independently hydrogen or —$C_{1-6}$alkyl.

In embodiment 3, the present invention provides compounds in accordance with embodiment 1, 1A or 1a, or pharmaceutically acceptable salts thereof, wherein:

Q is O;

Z is —C(=O)—;

$R^1$ is a 5 to 10 membered aryl or heteroaryl group, which heteroaryl group can contain from one to three heteroatoms independently selected from O, N or S, and the aryl or heteroaryl group can be unsubstituted or substituted with from one to three substituents independently selected from halo, —$C_{1-6}$alkyl, —S(=O)$_2C_{1-6}$alkyl, —S(=O)$C_{1-6}$alkyl, —O$C_{1-6}$alkyl, —$CF_3$—$OCF_3$, —$OCHF_2$, —$OCH_2F$, —CN, or A;

each A is independently a 5 or 6 membered aryl or heteroaryl group, which heteroaryl group can contain from one to three heteroatoms independently selected from O, N or S, and the aryl or heteroaryl group can be unsubstituted or substituted with from one to three substituents independently selected from halo, —$C_{1-6}$alkyl, —S(=O)$_2C_{1-6}$alkyl, —S(=O)$C_{1-6}$alkyl, —O$C_{1-6}$alkyl, —$CF_3$, —$OCF_3$, —$OCHF_2$, —$OCH_2F$, or —CN;

$R^2$ is a 5 to 10 membered aryl or heteroaryl group, which heteroaryl group can contain from one to three heteroatoms independently selected from O, N or S, and the aryl or heteroaryl group can be unsubstituted or substituted with from one to three substituents independently selected from halo, —$C_{1-6}$alkyl, —$SO_2C_{1-6}$alkyl, —S(=O)$C_{1-6}$alkyl, —O$C_{1-6}$alkyl, —$CF_3$, —$OCF_3$, —$OCHF_2$, —$OCH_2F$, —CN, or B;

each B is independently a 5 or 6 membered aryl or heteroaryl group, which heteroaryl group can contain from one to three heteroatoms independently selected from O, N or S, and the aryl or heteroaryl group can be unsubstituted or substituted with from one to three substituents independently selected from halo, —$C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN;

$R^3$ is hydrogen, —C(=O)OH, —C(=O)O$C_{1-6}$alkyl, —$S(=O)_2C_{1-6}$alkyl, —$S(=O)C_{1-6}$alkyl, —OH, or a 5 or 6 membered aryl or heteroaryl group, which heteroaryl group can contain from one to four heteroatoms independently selected from O, N or S, and the aryl or heteroaryl group can be unsubstituted or substituted with from one to three substituents independently selected from halo, —$C_{1-6}$alkyl, —$S(=O)_2C_{1-6}$alkyl, —$S(=O)C_{1-6}$alkyl, —$OC_{1-6}$alkyl, —$CF_3$, —$OCF_3$, —$OCHF_2$, —$OCH_2F$, or —CN;

$R^4$ is hydrogen, —$C_{1-6}$alkyl, —$C_{2-6}$alkenyl, —$CF_3$, —$CH_2F$, —$CHF_2$, —$S(=O)_2C_{1-6}$alkyl, —$S(=O)C_{1-6}$alkyl, —C(=O)$C_{1-6}$alkyl, —$OR^f$, —$S(=O)R^f$, —$S(=O)_2R^f$, —$NR^fS(=O)_2R^f$, a 3 to 6 membered cycloalkyl or heterocycloalkyl, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halo, —$C_{1-6}$ alkyl, —$S(=O)_2C_{1-6}$ alkyl, —$S(=O)C_{1-6}$ alkyl, —$OC_{1-6}$alkyl, —$CF_3$, —$OCF_3$, —$OCHF_2$, —$OCH_2F$, or —CN;

$R^6$ is hydrogen or —$C_{1-6}$alkyl;

each $R^a$ is independently hydrogen or —$C_{1-6}$alkyl; and each $R^c$ is independently hydrogen or —$C_{1-6}$alkyl.

In embodiment 4, the present invention provides compounds in accordance with embodiment 1, 1A or 1a, or pharmaceutically acceptable salts thereof, wherein Q is O.

In embodiment 5, the present invention provides compounds in accordance with embodiment 1, 1A or 1a, or pharmaceutically acceptable salts thereof, wherein Z is —C(=O)—.

In embodiment 6, the present invention provides compounds in accordance with any one of embodiments 1A, 1a or 1 to 3, or pharmaceutically acceptable salts thereof, wherein —$(CR^aR^a)_n$— is —$CH_2$—.

In embodiment 7, the present invention provides compounds in accordance with any one of embodiments 1A, 1a or 1 to 3, or pharmaceutically acceptable salts thereof, wherein $R^3$ is —$CO_2R^f$ or tetrazolyl.

In embodiment 8, the present invention provides compounds in accordance with any one of embodiments 1A, 1a or 1 to 3, or pharmaceutically acceptable salts thereof, wherein $R^3$ is —$CO_2H$ or tetrazolyl.

In embodiment 9, the present invention provides compounds in accordance with any one of embodiments 1A, 1a or 1 to 3, or pharmaceutically acceptable salts thereof, wherein —$(CR^aR^a)_n$— is —$CH_2$— and $R^3$ is —$CO_2H$ or tetrazolyl.

In embodiment 10, the present invention provides compounds in accordance with any one of embodiments 1A, 1a or 1 to 9, or pharmaceutically acceptable salts thereof, wherein —$(CR^cR^c)_n$— is absent, —$CH_2$—, —$CH(CH_2CH_3)$—, —$CH_2CH_2$—, —$CH_2CH_2CH_2$—, —$CH(CH_3)$—, —$CH(CH_2CH_3)CH_2$—, —$CH(CHCH_3CH_3)CH_2$—, or —$C(CCH_3CH_3CH_3)CH_2$—.

In embodiment 11, the present invention provides compounds in accordance with embodiment 10, or pharmaceutically acceptable salts thereof, wherein —$(CR^cR^c)_n$— is absent.

In embodiment 12, the present invention provides compounds in accordance with embodiment 10, or pharmaceutically acceptable salts thereof, wherein —$(CR^cR^c)_n$— is —$CH_2$—.

In embodiment 13, the present invention provides compounds in accordance with embodiment 10, or pharmaceutically acceptable salts thereof, wherein —$(CR^cR^c)_n$— is —$CH(CH_2CH_3)$—.

In embodiment 14, the present invention provides compounds in accordance with embodiment 10, or pharmaceutically acceptable salts thereof, wherein —$(CR^cR^c)_n$— is —$CH(CH_3)$—.

In embodiment 15, the present invention provides compounds in accordance with embodiment 10, or pharmaceutically acceptable salts thereof, wherein —$(CR^cR^c)_n$— is —$CH(CH_2CH_3)CH_2$—.

In embodiment 16, the present invention provides compounds in accordance with any one of embodiments 1A, 1a or 1 to 15, or pharmaceutically acceptable salts thereof, wherein $R^4$ is hydrogen, cyclopropyl, —C(=O)$_2C_{1-6}$alkyl, cyclopentyl, cyclobutyl, cyclohexyl, phenyl, oxazolyl, —$CF_3$, —$C_{1-6}$alkyl, —$C_{2-6}$alkenyl, —$S(=O)_2C_{1-6}$alkyl, —OH, —$S(=O)_2$phenyl, or —N(phenyl)$S(=O)_2$-cyclopropyl.

In embodiment 17, the present invention provides compounds in accordance with embodiment 16, or pharmaceutically acceptable salts thereof, wherein $R^4$ is cyclopropyl.

In embodiment 18, the present invention provides compounds in accordance with embodiment 16, or pharmaceutically acceptable salts thereof, wherein $R^4$ is —C(=O)$_2C_{1-6}$alkyl.

In embodiment 19, the present invention provides compounds in accordance with embodiment 16, or pharmaceutically acceptable salts thereof, wherein $R^4$ is —$C_{1-6}$alkyl.

In embodiment 20, the present invention provides compounds in accordance with embodiment 16, or pharmaceutically acceptable salts thereof, wherein $R^4$ is —$S(=O)_2C_{1-6}$alkyl.

In embodiment 21, the present invention provides compounds in accordance with embodiment 16, or pharmaceutically acceptable salts thereof, wherein $R^4$ is —OH.

In embodiment 22, the present invention provides compounds in accordance with embodiment 16, or pharmaceutically acceptable salts thereof, wherein $R^4$ is —$S(=O)_2$phenyl.

In embodiment 23, the present invention provides compounds in accordance with embodiment 16, or pharmaceutically acceptable salts thereof, wherein $R^4$ is —N(phenyl)$S(=O)_2$-cyclopropyl.

In embodiment 24, the present invention provides compounds in accordance with any one of embodiments 1A, 1a or 1 to 9, or pharmaceutically acceptable salts thereof, wherein $R^4(CR^cR^c)_n$— is hydrogen, —$CH_2$-cyclopropyl, —$CH(CH_2CH_3)CH_2S(=O)_2C_{1-6}$alkyl, —$CH_2$-cyclopentyl, —$CH_2$-cyclobutyl, —$CH_2$-cyclohexyl, cyclopropyl, cyclobutyl, cyclohexyl or —$C_{1-6}$alkyl.

In embodiment 25, the present invention provides compounds in accordance with any one of embodiments 1A, 1a or 1 to 24, or pharmaceutically acceptable salts thereof, wherein $R^1$ is substituted phenyl, indolyl, substituted benzimidazolyl, benzthiazolyl, substituted pyridyl, or substituted thiophenyl.

In embodiment 26, the present invention provides compounds in accordance with embodiment 25, or pharmaceutically acceptable salts thereof, wherein $R^1$ is 4-chlorophenyl.

In embodiment 27, the present invention provides compounds in accordance with embodiment 25, or pharmaceutically acceptable salts thereof, wherein $R^1$ is 3-chlorophenyl.

In embodiment 28, the present invention provides compounds in accordance with any one of embodiments 1A, 1a or 1 to 27, or pharmaceutically acceptable salts thereof, wherein $R^2$ is substituted phenyl or substituted pyridyl.

In embodiment 29, the present invention provides compounds in accordance with embodiment 28, or pharmaceutically acceptable salts thereof, wherein $R^2$ is 3-chlorophenyl.

In embodiment 30, the present invention provides compounds in accordance with any one of embodiments 1A, 1a or 1 to 29, or pharmaceutically acceptable salts thereof, wherein $R^6$ is hydrogen or —$CH_3$.

In embodiment 31, the present invention provides compounds in accordance with embodiment 30, or pharmaceutically acceptable salts thereof, wherein $R^6$ is hydrogen.

In embodiment 32, the present invention provides compounds in accordance with any one of embodiments 1A, 1a or 1 to 31, or pharmaceutically acceptable salts thereof, wherein $R^5$ is hydrogen or —$CH_3$.

In embodiment 33, the present invention provides compounds in accordance with embodiment 32, or pharmaceutically acceptable salts thereof, wherein $R^5$ is hydrogen.

In embodiment 34, the present invention provides compounds in accordance with any one of embodiments 1A, 1a or 1 to 33, or pharmaceutically acceptable salts thereof, wherein $R^d$ is hydrogen.

In embodiment 35, the present invention provides compounds in accordance with embodiment 1A, 1a or 1, or pharmaceutically acceptable salts thereof, wherein:
  Q is O;
  Z is —C(=O)—;
  —$(CR^aR^a)_n$— is —$CH_2$—;
  $R^3$ is —C(=O)$_2$H or tetrazolyl;
  —$(CR^cR^c)_n$— is absent, —$CH_2$—, —CH($CH_2CH_3$)—, —$CH_2CH_2$—, —$CH_2CH_2CH_2$—, —CH($CH_3$)—, —CH($CH_2CH_3$)$CH_2$—, —CH($CHCH_3CH_3$)$CH_2$—, or —C($CCH_3CH_3CH_3$)$CH_2$—;
  $R^4$ is hydrogen, cyclopropyl, —C(=O)$_2C_{1-6}$alkyl, cyclopentyl, cyclobutyl, cyclohexyl, phenyl, oxazolyl, —$CF_3$, —$C_{1-6}$alkyl, —$C_{2-6}$alkenyl, —S(=O)$_2C_{1-6}$alkyl, —OH, —S(=O)$_2$phenyl, or —N(phenyl)S(=O)$_2$-cyclopropyl;
  $R^1$ is substituted phenyl, indolyl, substituted benzimidazolyl, benzthiazolyl, substituted pyridyl, or substituted thiophenyl; and
  $R^2$ is substituted phenyl or substituted pyridyl.

In embodiment 36, the present invention provides compounds, or pharmaceutically acceptable salts thereof, selected from:

2-((2R,5R,6R)-6-(3-chlorophenyl)-4-(cyclopropylmethyl)-5-(1H-indol-2-yl)-3-oxomorpholin-2-yl)acetic acid;
2-((2S,5R,6R)-6-(3-chlorophenyl)-4-(cyclopropylmethyl)-5-(1H-indol-2-yl)-3-oxomorpholin-2-yl)acetic acid;
2-((2R,5R,6S)-5-(benzo[d]thiazol-2-yl)-6-(3-chlorophenyl)-4-(cyclopropylmethyl)-3-oxomorpholin-2-yl)acetic acid;
2-((2S,5R,6S)-5-(benzo[d]thiazol-2-yl)-6-(3-chlorophenyl)-4-(cyclopropylmethyl)-3-oxomorpholin-2-yl)acetic acid;
2-((2S,5R,6R)-6-(3-chlorophenyl)-4-(cyclopropylmethyl)-5-(1-methyl-1H-benzo[d]imidazol-2-yl)-3-oxomorpholin-2-yl)acetic acid;
2-((2S,5S,6S)-6-(3-chlorophenyl)-4-(cyclopropylmethyl)-5-(1-methyl-1H-benzo[d]imidazol-2-yl)-3-oxomorpholin-2-yl)acetic acid;
2-((2R,5R,6R)-6-(3-chlorophenyl)-4-(cyclopropylmethyl)-5-(1-methyl-1H-benzo[d]imidazol-2-yl)-3-oxomorpholin-2-yl)acetic acid;
2-((2S,5S,6S)-6-(3-chlorophenyl)-4-(cyclopropylmethyl)-5-(1-methyl-1H-benzo[d]imidazol-2-yl)-3-oxomorpholin-2-yl)acetic acid;
2-((2S,5R,6R)-6-(3-chlorophenyl)-5-(5-chloropyridin-2-yl)-4-(cyclopropylmethyl)-3-oxomorpholin-2-yl)acetic acid;
2-((2R,5R,6R)-6-(3-chlorophenyl)-5-(5-chloropyridin-2-yl)-4-(cyclopropylmethyl)-3-oxomorpholin-2-yl)acetic acid;
2-((2R,5R,6R)-6-(3-chlorophenyl)-5-(4-chlorophenyl)-4-(cyclopropylmethyl)-3-oxomorpholin-2-yl)acetic acid;
2-((2S,5R,6R)-6-(3-chlorophenyl)-5-(4-chlorophenyl)-4-(cyclopropylmethyl)-3-oxomorpholin-2-yl)acetic acid;
2-((2S,5R,6R)-6-(3-chlorophenyl)-5-(4-chlorophenyl)-3-oxo-4-(3,3,3-trifluoropropyl)morpholin-2-yl)acetic acid;
2-((2S,5R,6R)-6-(3-chlorophenyl)-5-(4-chlorophenyl)-4-cyclobutyl-3-oxomorpholin-2-yl)acetic acid;
2-((2R,5R,6R)-6-(3-chlorophenyl)-5-(4-chlorophenyl)-4-cyclobutyl-3-oxomorpholin-2-yl)acetic acid;
2-((2R,5R,6R)-6-(3-chlorophenyl)-5-(4-chlorophenyl)-4-cyclopentyl-3-oxomorpholin-2-yl)acetic acid;
2-((2R,5R,6R)-6-(3-chlorophenyl)-5-(4-chlorophenyl)-4-cyclopentyl-3-oxomorpholin-2-yl)acetic acid;
2-((2S,5R,6R)-6-(3-chlorophenyl)-5-(4-chlorophenyl)-4-cyclohexyl-3-oxomorpholin-2-yl)acetic acid;
2-((2R,5R,6R)-6-(3-chlorophenyl)-5-(4-chlorophenyl)-4-cyclohexyl-3-oxomorpholin-2-yl)acetic acid;
2-((2S,5R,6R)-6-(3-chlorophenyl)-5-(4-chlorophenyl)-4-((R)-1-cyclohexylethyl)-3-oxomorpholin-2-yl)acetic acid;
2-((2S,5R,6R)-6-(3-chlorophenyl)-5-(4-chlorophenyl)-4-((S)-1-cyclohexylethyl)-3-oxomorpholin-2-yl)acetic acid;
2-((2R,5R,6R)-6-(3-chlorophenyl)-5-(4-chlorophenyl)-4-((R)-1-cyclobutylethyl)-3-oxomorpholin-2-yl)acetic acid;
2-((2S,5R,6R)-6-(3-chlorophenyl)-5-(4-chlorophenyl)-4-((R)-1-cyclobutylethyl)-3-oxomorpholin-2-yl)acetic acid;
2-((2R,5R,6R)-6-(3-chlorophenyl)-5-(4-chlorophenyl)-4-((S)-1-cyclobutylethyl)-3-oxomorpholin-2-yl)acetic acid;
2-((2S,5R,6R)-6-(3-chlorophenyl)-5-(4-chlorophenyl)-4-((S)-1-cyclobutylethyl)-3-oxomorpholin-2-yl)acetic acid;
2-((2R,5R,6R)-6-(3-chlorophenyl)-5-(4-chlorophenyl)-3-oxo-4-((R)-1-phenylethyl)morpholin-2-yl)acetic acid;
2-((2S,5R,6R)-6-(3-chlorophenyl)-5-(4-chlorophenyl)-3-oxo-4-((R)-1-phenylethyl)morpholin-2-yl)acetic acid;
2-((2R,5R,6R)-6-(3-chlorophenyl)-5-(4-chlorophenyl)-3-oxo-4-((S)-1-phenylethyl)morpholin-2-yl)acetic acid;
2-((2S,5R,6R)-6-(3-chlorophenyl)-5-(4-chlorophenyl)-3-oxo-4-((S)-1-phenylethyl)morpholin-2-yl)acetic acid;
2-((2R,5R,6R)-6-(3-chlorophenyl)-5-(4-chlorophenyl)-4-(cyclopentylmethyl)-3-oxomorpholin-2-yl)acetic acid;
2-((2S,5R,6R)-6-(3-chlorophenyl)-5-(4-chlorophenyl)-4-(cyclopentylmethyl)-3-oxomorpholin-2-yl)acetic acid;
2-((2S,5R,6R)-4-((R)-1-(tert-butoxy)-1-oxobutan-2-yl)-6-(3-chlorophenyl)-5-(4-chlorophenyl)-3-oxomorpholin-2-yl)acetic acid;
2-((2S,5R,6R)-4-((S)-1-(tert-butoxy)-1-oxobutan-2-yl)-6-(3-chlorophenyl)-5-(4-chlorophenyl)-3-oxomorpholin-2-yl)acetic acid;
2-((2R,5R,6R)-4-((S)-1-(tert-butoxy)-1-oxobutan-2-yl)-6-(3-chlorophenyl)-5-(4-chlorophenyl)-3-oxomorpholin-2-yl)acetic acid;
2-((2R,5R,6R)-4-((R)-1-(tert-butoxy)-1-oxobutan-2-yl)-6-(3-chlorophenyl)-5-(4-chlorophenyl)-3-oxomorpholin-2-yl)acetic acid;
2-((2S,5R,6R)-6-(3-chlorophenyl)-5-(4-chlorophenyl)-3-oxomorpholin-2-yl)acetic acid;

2-((2R,5R,6R)-6-(3-chlorophenyl)-5-(4-chlorophenyl)-3-oxomorpholin-2-yl)acetic acid;

2-((2R,5R,6R)-6-(3-chlorophenyl)-5-(4-chlorophenyl)-4-isobutyl-3-oxomorpholin-2-yl)acetic acid;

2-((2S,5R,6R)-6-(3-chlorophenyl)-5-(4-chlorophenyl)-4-isobutyl-3-oxomorpholin-2-yl)acetic acid;

2-((2R,5R,6R)-6-(3-chlorophenyl)-5-(4-chlorophenyl)-4-(cyclobutylmethyl)-3-oxomorpholin-2-yl)acetic acid;

2-((2S,5R,6R)-6-(3-chlorophenyl)-5-(4-chlorophenyl)-4-(cyclobutylmethyl)-3-oxomorpholin-2-yl)acetic acid;

2-((2S,5R,6R)-4-butyl-6-(3-chlorophenyl)-5-(4-chlorophenyl)-3-oxomorpholin-2-yl)acetic acid;

2-((2S,5R,6R)-6-(3-chlorophenyl)-5-(4-chlorophenyl)-4-(cyclohexylmethyl)-3-oxomorpholin-2-yl)acetic acid;

2-((2S,5R,6R)-4-benzyl-6-(3-chlorophenyl)-5-(4-chlorophenyl)-3-oxomorpholin-2-yl)acetic acid;

2-((2S,5R,6R)-6-(3-chlorophenyl)-5-(4-chlorophenyl)-4-(oxazol-2-ylmethyl)-3-oxomorpholin-2-yl)acetic acid;

2-((2R,5R,6R)-6-(3-chlorophenyl)-5-(4-chlorophenyl)-4-ethyl-3-oxomorpholin-2-yl)acetic acid;

2-((2S,5R,6R)-6-(3-chlorophenyl)-5-(4-chlorophenyl)-4-ethyl-3-oxomorpholin-2-yl)acetic acid;

2-((2R,5R,6R)-4-allyl-6-(3-chlorophenyl)-5-(4-chlorophenyl)-3-oxomorpholin-2-yl)acetic acid;

2-((2S,5R,6R)-4-allyl-6-(3-chlorophenyl)-5-(4-chlorophenyl)-3-oxomorpholin-2-yl)acetic acid;

2-((2R,5R,6R)-6-(3-chlorophenyl)-5-(4-chlorophenyl)-3-oxo-4-propylmorpholin-2-yl)acetic acid;

2-((2S,5R,6R)-6-(3-chlorophenyl)-5-(4-chlorophenyl)-3-oxo-4-propylmorpholin-2-yl)acetic acid;

(2S,5R,6R)-6-(3-chlorophenyl)-5-(4-chlorophenyl)-4-(cyclopropylmethyl)-2-((tetrazol-5-yl)methyl)morpholin-3-one;

(2R,5R,6R)-6-(3-chlorophenyl)-5-(4-chlorophenyl)-4-(cyclopropylmethyl)-2-((tetrazol-5-yl)methyl)morpholin-3-one;

(Z)-2-((5R,6R)-6-(3-chlorophenyl)-5-(4-chlorophenyl)-4-(cyclopropylmethyl)-3-oxomorpholin-2-ylidene)acetic acid;

(E)-2-((5R,6R)-6-(3-chlorophenyl)-5-(4-chlorophenyl)-4-(cyclopropylmethyl)-3-oxomorpholin-2-ylidene)acetic acid 2-((2S,5R,6R)-6-(3-chlorophenyl)-5-(4-chlorophenyl)-3-oxo-4-(pentan-3-yl)morpholin-2-yl)acetic acid;

2-((2S,5R,6R)-5-(4-chloro-2-fluorophenyl)-6-(3-chlorophenyl)-4-(cyclopropylmethyl)-3-oxomorpholin-2-yl)acetic acid;

2-((2S,5R,6R)-6-(3-chlorophenyl)-4-(cyclopropylmethyl)-3-oxo-5-phenylmorpholin-2-yl)acetic acid;

2-((2S,5R,6R)-6-(3-chlorophenyl)-4-(cyclopropylmethyl)-5-(4-fluorophenyl)-3-oxomorpholin-2-yl)acetic acid;

2-((2S,5R,6R)-6-(3-chlorophenyl)-4-(cyclopropylmethyl)-3-oxo-5-(4-(trifluoromethyl)phenyl)morpholin-2-yl)acetic acid;

2-((2S,5R,6R)-6-(3-chlorophenyl)-4-(cyclopropylmethyl)-5-(4-ethylphenyl)-3-oxomorpholin-2-yl)acetic acid;

2-((2S,5R,6R)-6-(3-chlorophenyl)-4-(cyclopropylmethyl)-3-oxo-5-(4-(trifluoromethoxy)phenyl)morpholin-2-yl)acetic acid;

2-((2S,5R,6R)-6-(3-chlorophenyl)-4-(cyclopropylmethyl)-3-oxo-5-(p-tolyl)morpholin-2-yl)acetic acid;

2-((2R,5R,6R)-6-(3-chlorophenyl)-4-(cyclopropylmethyl)-3-oxo-5-(p-tolyl)morpholin-2-yl)acetic acid;

2-((2R,5R,6R)-5-(4-chloro-2-fluorophenyl)-6-(3-chlorophenyl)-4-(cyclopropylmethyl)-3-oxomorpholin-2-yl)acetic acid;

2-((2R,5R,6R)-6-(3-chlorophenyl)-4-(cyclopropylmethyl)-3-oxo-5-phenylmorpholin-2-yl)acetic acid;

2-((2R,5R,6R)-6-(3-chlorophenyl)-4-(cyclopropylmethyl)-5-(4-fluorophenyl)-3-oxomorpholin-2-yl)acetic acid;

2-((2R,5R,6R)-6-(3-chlorophenyl)-4-(cyclopropylmethyl)-3-oxo-5-(4-(trifluoromethoxy)phenyl)morpholin-2-yl)acetic acid;

2-((2R,5R,6R)-6-(3-chlorophenyl)-4-(cyclopropylmethyl)-5-(4-isopropylphenyl)-3-oxomorpholin-2-yl)acetic acid;

2-((2R,5R,6R)-5-(4-bromophenyl)-6-(3-chlorophenyl)-4-(cyclopropylmethyl)-3-oxomorpholin-2-yl)acetic acid;

2-((2S,5R,6R)-5-(4-bromophenyl)-6-(3-chlorophenyl)-4-(cyclopropylmethyl)-3-oxomorpholin-2-yl)acetic acid;

2-((2R,5S,6R)-6-(3-chlorophenyl)-4-(cyclopropylmethyl)-3-oxo-5-(thiophen-2-yl)morpholin-2-yl)acetic acid;

2-((2S,5S,6R)-6-(3-chlorophenyl)-4-(cyclopropylmethyl)-3-oxo-5-(thiophen-2-yl)morpholin-2-yl)acetic acid;

2-((2S,5R,6R)-6-(3-chlorophenyl)-5-(6-chloropyridin-3-yl)-4-(cyclopropylmethyl)-3-oxomorpholin-2-yl)acetic acid;

2-((2R,5R,6R)-6-(3-chlorophenyl)-5-(6-chloropyridin-3-yl)-4-(cyclopropylmethyl)-3-oxomorpholin-2-yl)acetic acid;

2-((2R,5R,6R)-6-(3-chlorophenyl)-4-(cyclopropylmethyl)-5-(6-methoxypyridin-3-yl)-3-oxomorpholin-2-yl)acetic acid;

2-((2S,5R,6R)-6-(3-chlorophenyl)-4-(cyclopropylmethyl)-5-(6-methoxypyridin-3-yl)-3-oxomorpholin-2-yl)acetic acid;

2-((2R,5R,6R)-6-(3-chlorophenyl)-4-(cyclopropylmethyl)-5-(4-methoxyphenyl)-3-oxomorpholin-2-yl)acetic acid;

2-((2S,5R,6R)-6-(3-chlorophenyl)-4-(cyclopropylmethyl)-5-(4-methoxyphenyl)-3-oxomorpholin-2-yl)acetic acid;

2-((2R,5R,6R)-5-(4-chloro-3-fluorophenyl)-6-(3-chlorophenyl)-4-(cyclopropylmethyl)-3-oxomorpholin-2-yl)acetic acid;

2-((2S,5R,6R)-5-(4-chloro-3-fluorophenyl)-6-(3-chlorophenyl)-4-(cyclopropylmethyl)-3-oxomorpholin-2-yl)acetic acid;

2-((2R,5R,6R)-5-(2-bromo-4-chlorophenyl)-6-(3-chlorophenyl)-4-(cyclopropylmethyl)-3-oxomorpholin-2-yl)acetic acid;

2-((2S,5R,6R)-5-(2-bromo-4-chlorophenyl)-6-(3-chlorophenyl)-4-(cyclopropylmethyl)-3-oxomorpholin-2-yl)acetic acid;

2-((2R,5R,6R)-6-(3-chlorophenyl)-4-(cyclopropylmethyl)-3-oxo-5-(6-(trifluoromethyl)pyridin-3-yl)morpholin-2-yl)acetic acid;

2-((2S,5R,6R)-6-(3-chlorophenyl)-4-(cyclopropylmethyl)-3-oxo-5-(6-(trifluoromethyl)pyridin-3-yl)morpholin-2-yl)acetic acid;

2-((2R,5R,6R)-6-(3-chloro-5-fluorophenyl)-5-(4-chlorophenyl)-4-(cyclopropylmethyl)-3-oxomorpholin-2-yl)acetic acid;

2-((2S,5R,6R)-6-(3-chloro-5-fluorophenyl)-5-(4-chlorophenyl)-4-(cyclopropylmethyl)-3-oxomorpholin-2-yl)acetic acid;

2-((2R,5R,6R)-5-(4-chlorophenyl)-4-(cyclopropylmethyl)-6-(3-fluorophenyl)-3-oxomorpholin-2-yl)acetic acid;

2-((2S,5R,6R)-5-(4-chlorophenyl)-4-(cyclopropylmethyl)-6-(3-fluorophenyl)-3-oxomorpholin-2-yl)acetic acid;

2-((2R,5R,6R)-5-(4-chlorophenyl)-6-(5-chloropyridin-3-yl)-4-(cyclopropylmethyl)-3-oxomorpholin-2-yl)acetic acid;

2-((2S,5R,6R)-5-(4-chlorophenyl)-6-(5-chloropyridin-3-yl)-4-(cyclopropylmethyl)-3-oxomorpholin-2-yl)acetic acid;

2-((2R,5R,6R)-5-(4-chlorophenyl)-4-(cyclopropylmethyl)-6-(3-methoxyphenyl)-3-oxomorpholin-2-yl)acetic acid;

2-((2S,5R,6R)-5-(4-chlorophenyl)-4-(cyclopropylmethyl)-6-(3-methoxyphenyl)-3-oxomorpholin-2-yl)acetic acid;

2-((2S,5R,6R)-5-(4-chlorophenyl)-6-(2-chloropyridin-4-yl)-4-(cyclopropylmethyl)-3-oxomorpholin-2-yl)acetic acid;

2-((2S,5R,6R)-5-(4-chlorophenyl)-4-(cyclopropylmethyl)-6-(5-methoxypyridin-3-yl)-3-oxomorpholin-2-yl)acetic acid;

2-((2S,5R,6R)-5-(4-chlorophenyl)-4-(cyclopropylmethyl)-6-(3,5-dichlorophenyl)-3-oxomorpholin-2-yl)acetic acid;

2-((2S,5R,6R)-6-(3-chloro-4-fluorophenyl)-5-(4-chlorophenyl)-4-(cyclopropylmethyl)-3-oxomorpholin-2-yl)acetic acid;

2-((2S,5R,6R)-5-(4-chlorophenyl)-4-(cyclopropylmethyl)-3-oxo-6-(3-(trifluoromethoxy)phenyl)morpholin-2-yl)acetic acid;

2-((2R,5R,6R)-5-(4-chlorophenyl)-4-(cyclopropylmethyl)-6-(3,5-difluorophenyl)-3-oxomorpholin-2-yl)acetic acid;

2-((2S,5R,6R)-5-(4-chlorophenyl)-4-(cyclopropylmethyl)-6-(3,5-difluorophenyl)-3-oxomorpholin-2-yl)acetic acid;

2-((2R,5R,6R)-5-(4-chlorophenyl)-6-(3-cyano-5-fluorophenyl)-4-(cyclopropylmethyl)-3-oxomorpholin-2-yl)acetic acid;

2-((2S,5R,6R)-5-(4-chlorophenyl)-6-(3-cyano-5-fluorophenyl)-4-(cyclopropylmethyl)-3-oxomorpholin-2-yl)acetic acid;

2-((2R,5R,6R)-6-(5-chloro-2-fluorophenyl)-5-(4-chlorophenyl)-4-(cyclopropylmethyl)-3-oxomorpholin-2-yl)acetic acid;

2-((2S,5R,6R)-6-(5-chloro-2-fluorophenyl)-5-(4-chlorophenyl)-4-(cyclopropylmethyl)-3-oxomorpholin-2-yl)acetic acid;

2-((2R,5R,6R)-5-(4-chlorophenyl)-4-(cyclopropylmethyl)-3-oxo-6-(m-tolyl)morpholin-2-yl)acetic acid;

2-((2S,5R,6R)-5-(4-chlorophenyl)-4-(cyclopropylmethyl)-3-oxo-6-(m-tolyl)morpholin-2-yl)acetic acid;

2-((2R,5R,6R)-6-(3-bromo-5-chlorophenyl)-5-(4-chlorophenyl)-4-(cyclopropylmethyl)-3-oxomorpholin-2-yl)acetic acid;

2-((2S,5R,6R)-6-(3-bromo-5-chlorophenyl)-5-(4-chlorophenyl)-4-(cyclopropylmethyl)-3-oxomorpholin-2-yl)acetic acid;

2-((2R,5R,6R)-6-(3-chloro-5-(1H-pyrazol-4-yl)phenyl)-5-(4-chlorophenyl)-4-(cyclopropylmethyl)-3-oxomorpholin-2-yl)acetic acid;

2-((2S,5R,6R)-6-(3-chloro-5-(1H-pyrazol-4-yl)phenyl)-5-(4-chlorophenyl)-4-(cyclopropylmethyl)-3-oxomorpholin-2-yl)acetic acid;

2-((2R,5R,6R)-6-(3-chloro-5-(pyrimidin-5-yl)phenyl)-5-(4-chlorophenyl)-4-(cyclopropylmethyl)-3-oxomorpholin-2-yl)acetic acid;

2-((2S,5R,6R)-6-(3-chloro-5-(pyrimidin-5-yl)phenyl)-5-(4-chlorophenyl)-4-(cyclopropylmethyl)-3-oxomorpholin-2-yl)acetic acid;

2-((2R,5R,6R)-6-(3-chloro-5-(methylsulfonyl)phenyl)-5-(4-chlorophenyl)-4-(cyclopropylmethyl)-3-oxomorpholin-2-yl)acetic acid;

2-((2S,5R,6R)-6-(3-chloro-5-(methylsulfonyl)phenyl)-5-(4-chlorophenyl)-4-(cyclopropylmethyl)-3-oxomorpholin-2-yl)acetic acid;

2-((2S,5R,6R)-6-(3-chlorophenyl)-5-(4-chlorophenyl)-4-((S)-1-(ethylsulfonyl)butan-2-yl)-3-oxomorpholin-2-yl)acetic acid;

2-((2R,5R,6R)-6-(3-chlorophenyl)-5-(4-chlorophenyl)-4-((S)-1-(ethylsulfonyl)butan-2-yl)-3-oxomorpholin-2-yl)acetic acid;

2-((2R,5R,6R)-6-(3-chlorophenyl)-5-(4-chlorophenyl)-4-((S)-1-hydroxybutan-2-yl)-3-oxomorpholin-2-yl)acetic acid;

2-((2S,5R,6R)-6-(3-chlorophenyl)-5-(4-chlorophenyl)-4-((S)-1-hydroxybutan-2-yl)-3-oxomorpholin-2-yl)acetic acid;

2-((2R,5R,6R)-6-(3-chlorophenyl)-5-(4-chlorophenyl)-3-oxo-4-((S)-1-(phenylsulfonyl) butan-2-yl)morpholin-2-yl)acetic acid;

2-((2S,5R,6R)-6-(3-chlorophenyl)-5-(4-chlorophenyl)-3-oxo-4-((S)-1-(phenylsulfonyl) butan-2-yl)morpholin-2-yl)acetic acid;

2-((2R,5R,6R)-6-(3-chlorophenyl)-5-(4-chlorophenyl)-4-((S)-1-(isopropylsulfonyl)butan-2-yl)-3-oxomorpholin-2-yl)acetic acid;

2-((2S,5R,6R)-6-(3-chlorophenyl)-5-(4-chlorophenyl)-4-((S)-1-(isopropylsulfonyl)butan-2-yl)-3-oxomorpholin-2-yl)acetic acid;

2-((2R,5R,6R)-4-((S)-1-(tert-butylsulfonyl)butan-2-yl)-6-(3-chlorophenyl)-5-(4-chlorophenyl)-3-oxomorpholin-2-yl)acetic acid;

2-((2S,5R,6R)-4-((S)-1-(tert-butylsulfonyl)butan-2-yl)-6-(3-chlorophenyl)-5-(4-chlorophenyl)-3-oxomorpholin-2-yl)acetic acid;

2-((2R,5R,6R)-6-(3-chlorophenyl)-5-(4-chlorophenyl)-3-oxo-4-((S)-1-(tert-pentylsulfonyl)butan-2-yl)morpholin-2-yl)acetic acid;

2-((2S,5R,6R)-6-(3-chlorophenyl)-5-(4-chlorophenyl)-3-oxo-4-((S)-1-(tert-pentylsulfonyl)butan-2-yl)morpholin-2-yl)acetic acid;

2-((2R,5R,6R)-6-(3-chloro-5-fluorophenyl)-5-(4-chlorophenyl)-4-((S)-1-(isopropylsulfonyl)butan-2-yl)-3-oxomorpholin-2-yl)acetic acid;

2-((2S,5R,6R)-6-(3-chloro-5-fluorophenyl)-5-(4-chlorophenyl)-4-((S)-1-(isopropylsulfonyl)butan-2-yl)-3-oxomorpholin-2-yl)acetic acid;

2-((2R,5R,6R)-6-(3-chlorophenyl)-5-(4-chlorophenyl)-4-((3S,5S)-5-hydroxyhexan-3-yl)-3-oxomorpholin-2-yl)acetic acid;

2-((2R,5R,6R)-6-(3-chlorophenyl)-5-(4-chlorophenyl)-4-((3S,5R)-5-hydroxyhexan-3-yl)-3-oxomorpholin-2-yl)acetic acid;

2-((2R,5R,6R)-6-(3-chlorophenyl)-5-(4-chlorophenyl)-3-oxo-4-((S)-1-(N-phenylcyclopropanesulfonamido)butan-2-yl)morpholin-2-yl)acetic acid;

2-((2S,5R,6R)-6-(3-chlorophenyl)-5-(4-chlorophenyl)-3-oxo-4-((S)-1-(N-phenylcyclopropanesulfonamido)butan-2-yl)morpholin-2-yl)acetic acid;

2-((2R,5R,6R)-4-((S)-1-(tert-butylsulfonyl)butan-2-yl)-6-(3-chlorophenyl)-5-(4-chlorophenyl)-2-methyl-3-oxomorpholin-2-yl)acetic acid;

2-((2S,5R,6R)-4-((S)-1-(tert-butylsulfonyl)butan-2-yl)-6-(3-chlorophenyl)-5-(4-chlorophenyl)-2-methyl-3-oxomorpholin-2-yl)acetic acid;

2-((2R,5R,6R)-6-(3-Chlorophenyl)-5-(4-chlorophenyl)-4-(cyclopropylmethyl)-5-methyl-3-oxomorpholin-2-yl)acetic acid; or 2-((2S,5R,6R)-6-(3-Chlorophenyl)-5-(4-chlorophenyl)-4-(cyclopropylmethyl)-5-methyl-3-oxomorpholin-2-yl)acetic acid.

In embodiment 37, the present invention provides compounds, or pharmaceutically acceptable salts thereof, selected from:

2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)acetic acid;

2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)acetic acid;

2-((2R,5R,6R)-6-(3-chlorophenyl)-5-(4-chlorophenyl)-4-((S)-1-(N-(4-fluorophenyl)cyclopropanesulfonamido)butan-2-yl)-3-oxomorpholin-2-yl)acetic acid;

2-((2S,5R,6R)-6-(3-chlorophenyl)-5-(4-chlorophenyl)-4-((S)-1-(N-(4-fluorophenyl)cyclopropanesulfonamido)butan-2-yl)-3-oxomorpholin-2-yl)acetic acid;

2-((2R,5R,6R)-6-(3-chlorophenyl)-5-(4-chlorophenyl)-4-((S)-1-((2-chlorophenyl)sulfonyl)butan-2-yl)-3-oxomorpholin-2-yl)acetic acid;

2-((2S,5R,6R)-6-(3-chlorophenyl)-5-(4-chlorophenyl)-4-((S)-1-((2-chlorophenyl)sulfonyl)butan-2-yl)-3-oxomorpholin-2-yl)acetic acid;

2-((2R,5R,6R)-6-(3-chlorophenyl)-5-(4-chlorophenyl)-4-((S)-1-(cyclopentylsulfonyl)butan-2-yl)-3-oxomorpholin-2-yl)acetic acid;

2-((2S,5R,6R)-6-(3-chlorophenyl)-5-(4-chlorophenyl)-4-((S)-1-(cyclopentylsulfonyl)butan-2-yl)-3-oxomorpholin-2-yl)acetic acid;

2-((2R,5R,6R)-6-(3-chlorophenyl)-5-(4-chlorophenyl)-4-((S)-1-(cyclobutylsulfonyl)butan-2-yl)-3-oxomorpholin-2-yl)acetic acid;

2-((2S,5R,6R)-6-(3-chlorophenyl)-5-(4-chlorophenyl)-4-((S)-1-(cyclobutylsulfonyl)butan-2-yl)-3-oxomorpholin-2-yl)acetic acid;

2-((2R,5R,6R)-6-(3-chlorophenyl)-5-(4-chlorophenyl)-4-((S)-1-(neopentylsulfonyl)butan-2-yl)-3-oxomorpholin-2-yl)acetic acid;

2-((2S,5R,6R)-6-(3-chlorophenyl)-5-(4-chlorophenyl)-4-((S)-1-(neopentylsulfonyl)butan-2-yl)-3-oxomorpholin-2-yl)acetic acid;

2-((2R,5R,6R)-5-(4-chlorophenyl)-6-(3,5-dichlorophenyl)-4-((S)-1-(isopropylsulfonyl)butan-2-yl)-3-oxomorpholin-2-yl)acetic acid;

2-((2S,5R,6R)-5-(4-chlorophenyl)-6-(3,5-dichlorophenyl)-4-((S)-1-(isopropylsulfonyl)butan-2-yl)-3-oxomorpholin-2-yl)acetic acid;

2-((2R,5R,6R)-5-(4-chlorophenyl)-6-(3,5-dichlorophenyl)-4-((S)-1-(tert-butylsulfonyl)butan-2-yl)-3-oxomorpholin-2-yl)acetic acid;

2-((2S,5R,6R)-5-(4-chlorophenyl)-6-(3,5-dichlorophenyl)-4-((S)-1-(tert-butylsulfonyl)butan-2-yl)-3-oxomorpholin-2-yl)acetic acid;

methyl 2-((2R,5R,6R)-4-((S)-1-(tert-butylsulfonyl)butan-2-yl)-6-(3-chlorophenyl)-5-(4-chlorophenyl)-3-oxomorpholin-2-yl)acetate;

methyl 2-((2S,5R,6R)-4-((S)-1-(tert-butylsulfonyl)butan-2-yl)-6-(3-chlorophenyl)-5-(4-chlorophenyl)-3-oxomorpholin-2-yl)acetate;

(2S,5R,6R)-4-((S)-1-(tert-butylsulfonyl)butan-2-yl)-6-(3-chlorophenyl)-5-(4-chlorophenyl)-2-(2-hydroxyethyl)morpholin-3-one;

(2R,5R,6R)-4-((S)-1-(tert-butylsulfonyl)butan-2-yl)-6-(3-chlorophenyl)-5-(4-chlorophenyl)-2-(2-hydroxyethyl)morpholin-3-one;

(2R,5R,6R)-4-((S)-1-(tert-butylsulfonyl)butan-2-yl)-6-(3-chlorophenyl)-5-(4-chlorophenyl)-2-(2-methoxyethyl)morpholin-3-one;

2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid;

2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid;

2-((2R,5R,6R)-6-(3-chlorophenyl)-5-(4-chlorophenyl)-4-((S)-1-cyclopropyl-2-(isopropylsulfonyl)ethyl)-3-oxomorpholin-2-yl)acetic acid;

2-((2S,5R,6R)-6-(3-chlorophenyl)-5-(4-chlorophenyl)-4-((S)-1-cyclopropyl-2-(isopropylsulfonyl)ethyl)-3-oxomorpholin-2-yl)acetic acid (Isomer 2);

2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid;

2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid;

2-((2R,5R,6R)-6-(3-chlorophenyl)-5-(4-chlorophenyl)-4-((S)-1-(N-methylcyclopropanesulfonamido)butan-2-yl)-3-oxomorpholin-2-yl)acetic acid;

2-((2S,5R,6R)-6-(3-chlorophenyl)-5-(4-chlorophenyl)-4-((S)-1-(N-methylcyclopropanesulfonamido)butan-2-yl)-3-oxomorpholin-2-yl)acetic acid;

2-((2R,5R,6R)-4-((S)-1-(tert-butylsulfonyl)butan-2-yl)-6-(3-chlorophenyl)-5-(4-chlorophenyl)-5-methyl-3-oxomorpholin-2-yl)acetic acid;

2-((2S,5R,6R)-4-((S)-1-(tert-butylsulfonyl)butan-2-yl)-6-(3-chlorophenyl)-5-(4-chlorophenyl)-5-methyl-3-oxomorpholin-2-yl)acetic acid;

2-((2R,5R,6R)-4-((S)-1-(tert-butylsulfonyl)-3-methylbutan-2-yl)-6-(3-chlorophenyl)-5-(4-chlorophenyl)-3-oxomorpholin-2-yl)acetic acid;

2-((2S,5R,6R)-4-((S)-1-(tert-butylsulfonyl)-3-methylbutan-2-yl)-6-(3-chlorophenyl)-5-(4-chlorophenyl)-3-oxomorpholin-2-yl)acetic acid;

2-((2R,5R,6R)-4-((R)-1-(tert-butylsulfonyl)-3-methylbutan-2-yl)-6-(3-chlorophenyl)-5-(4-chlorophenyl)-3-oxomorpholin-2-yl)acetic acid;

2-((2S,5R,6R)-4-((R)-1-(tert-butylsulfonyl)-3-methylbutan-2-yl)-6-(3-chlorophenyl)-5-(4-chlorophenyl)-3-oxomorpholin-2-yl)acetic acid;

2-((2R,5R,6R)-4-((S)-1-(tert-butylsulfonyl)-3,3-dimethylbutan-2-yl)-6-(3-chlorophenyl)-5-(4-chlorophenyl)-3-oxomorpholin-2-yl)acetic acid;

2-((2S,5R,6R)-4-((S)-1-(tert-butylsulfonyl)-3,3-dimethylbutan-2-yl)-6-(3-chlorophenyl)-5-(4-chlorophenyl)-3-oxomorpholin-2-yl)acetic acid;

2-((2R,5R,6R)-6-(3-chlorophenyl)-5-(4-chlorophenyl)-4-((S)-1-(N-(2-fluorophenyl)methylsulfonamido)butan-2-yl)-3-oxomorpholin-2-yl)acetic;

2-((2S,5R,6R)-6-(3-chlorophenyl)-5-(4-chlorophenyl)-4-((S)-1-(N-(2-fluorophenyl)methylsulfonamido)butan-2-yl)-3-oxomorpholin-2-yl)acetic acid;

2-((2R,5R,6R)-6-(3-chlorophenyl)-5-(4-chlorophenyl)-4-((S)-1-(N-(2-fluorophenyl)propan-2-ylsulfonamido)butan-2-yl)-3-oxomorpholin-2-yl)acetic acid;

2-((2S,5R,6R)-6-(3-chlorophenyl)-5-(4-chlorophenyl)-4-((S)-1-(N-(2-fluorophenyl)propan-2-ylsulfonamido)butan-2-yl)-3-oxomorpholin-2-yl)acetic acid;

2-((2R,5R,6R)-6-(3-chlorophenyl)-5-(4-chlorophenyl)-4-((S)-1-(N-(2-fluorophenyl)-1-methylcyclopropanesulfonamido)butan-2-yl)-3-oxomorpholin-2-yl)acetic acid;

2-((2S,5R,6R)-6-(3-chlorophenyl)-5-(4-chlorophenyl)-4-((S)-1-(N-(2-fluorophenyl)-1-methylcyclopropanesulfonamido)butan-2-yl)-3-oxomorpholin-2-yl)acetic acid;

2-((2R,5R,6R)-6-(3-chlorophenyl)-5-(4-chlorophenyl)-4-((S)-1-(N-(3-fluoropyridin-2-yl)cyclopropanesulfonamido)butan-2-yl)-3-oxomorpholin-2-yl)acetic;

2-((2S,5R,6R)-6-(3-chlorophenyl)-5-(4-chlorophenyl)-4-((S)-1-(N-(3-fluoropyridin-2-yl)cyclopropanesulfonamido)butan-2-yl)-3-oxomorpholin-2-yl)acetic acid;

N-((S)-2-((2S,5R,6R)-2-allyl-6-(3-chlorophenyl)-5-(4-chlorophenyl)-3-oxomorpholino)butyl)-N-(pyridin-2-yl)cyclopropanesulfonamide;

N-((S)-2-((2R,5R,6R)-2-allyl-6-(3-chlorophenyl)-5-(4-chlorophenyl)-3-oxomorpholino)butyl)-N-(pyridin-2-yl)cyclopropanesulfonamide;

2-((2S,5R,6R)-6-(3-chlorophenyl)-5-(4-chlorophenyl)-3-oxo-4-((S)-1-(N-(pyridin-2-yl)cyclopropanesulfonamido)butan-2-yl)morpholin-2-yl)acetic acid;

2-((2R,5R,6R)-6-(3-chlorophenyl)-5-(4-chlorophenyl)-3-oxo-4-((S)-1-(N-(pyridin-2-yl)cyclopropanesulfonamido)butan-2-yl)morpholin-2-yl)acetic acid;

2-((2R,5R,6R)-4-((S)-1-(tert-butylsulfonyl)butan-2-yl)-5-(4-chloro-3-fluorophenyl)-6-(3-chlorophenyl)-3-oxomorpholin-2-yl)acetic acid;

2-((2S,5R,6R)-4-((S)-1-(tert-butylsulfonyl)butan-2-yl)-5-(4-chloro-3-fluorophenyl)-6-(3-chlorophenyl)-3-oxomorpholin-2-yl)acetic acid;

2-((2R,5R,6R)-6-(3-chlorophenyl)-5-(4-chlorophenyl)-4-((S)-1-(oxetan-3-ylsulfonyl)butan-2-yl)-3-oxomorpholin-2-yl)acetic acid;

2-((2S,5R,6R)-6-(3-chlorophenyl)-5-(4-chlorophenyl)-4-((S)-1-(oxetan-3-ylsulfonyl)butan-2-yl)-3-oxomorpholin-2-yl)acetic acid;

2-((2R,5R,6R)-6-(3-chlorophenyl)-5-(4-chlorophenyl)-3-oxo-4-((S)-1-((tetrahydro-2H-pyran-4-yl)sulfonyl)butan-2-yl)morpholin-2-yl)acetic acid;

2-((2S,5R,6R)-6-(3-chlorophenyl)-5-(4-chlorophenyl)-3-oxo-4-((S)-1-((tetrahydro-2H-pyran-4-yl)sulfonyl)butan-2-yl)morpholin-2-yl)acetic acid;

2-((2R,5R,6R)-6-(3-chlorophenyl)-5-(4-chlorophenyl)-4-((S)-1-cyclopropyl-2-(N-(3-fluoropyridin-2-yl)cyclopropanesulfonamido)ethyl)-3-oxomorpholin-2-yl)acetic acid;

2-((2S,5R,6R)-6-(3-chlorophenyl)-5-(4-chlorophenyl)-4-((S)-1-cyclopropyl-2-(N-(3-fluoropyridin-2-yl)cyclopropanesulfonamido)ethyl)-3-oxomorpholin-2-yl)acetic acid;

2-((2R,5R,6R)-6-(3-chlorophenyl)-5-(4-chlorophenyl)-4-((S)-1-((cyclopropylmethyl)sulfonyl)butan-2-yl)-3-oxomorpholin-2-yl)acetic acid;

2-((2S,5R,6R)-6-(3-chlorophenyl)-5-(4-chlorophenyl)-4-((S)-1-((cyclopropylmethyl)sulfonyl)butan-2-yl)-3-oxomorpholin-2-yl)acetic acid;

2-((2R,5R,6R)-6-(3-chlorophenyl)-5-(4-chlorophenyl)-4-((S)-3-methyl-1-(N-phenylcyclopropanesulfonamido)butan-2-yl)-3-oxomorpholin-2-yl)acetic acid;

2-((2R,5R,6R)-6-(3-chlorophenyl)-5-(4-chlorophenyl)-4-((R)-3-methyl-1-(N-phenylcyclopropanesulfonamido)butan-2-yl)-3-oxomorpholin-2-yl)acetic acid;

2-((2R,5R,6R)-4-((S)-1-(tert-butylsulfonyl)pentan-2-yl)-6-(3-chlorophenyl)-5-(4-chlorophenyl)-3-oxomorpholin-2-yl)acetic acid;

2-((2S,5R,6R)-4-((S)-1-(tert-butylsulfonyl)pentan-2-yl)-6-(3-chlorophenyl)-5-(4-chlorophenyl)-3-oxomorpholin-2-yl)acetic acid;

2-((2R,5R,6R)-6-(3-chlorophenyl)-5-(4-chlorophenyl)-4-((S)-1-(N-(2-fluorophenyl)cyclopropanesulfonamido)-3-methylbutan-2-yl)-3-oxomorpholin-2-yl)acetic acid;

2-((2S,5R,6R)-6-(3-chlorophenyl)-5-(4-chlorophenyl)-4-((S)-1-(N-(2-fluorophenyl)cyclopropanesulfonamido)-3-methylbutan-2-yl)-3-oxomorpholin-2-yl)acetic acid;

2-((2R,5R,6R)-6-(3-chlorophenyl)-5-(4-chlorophenyl)-4-((S)-1-(N-(2-fluorophenyl)propan-2-ylsulfonamido)-3-methylbutan-2-yl)-3-oxomorpholin-2-yl)acetic acid;

2-((2S,5R,6R)-6-(3-chlorophenyl)-5-(4-chlorophenyl)-4-((S)-1-(N-(2-fluorophenyl)propan-2-ylsulfonamido)-3-methylbutan-2-yl)-3-oxomorpholin-2-yl)acetic acid;

2-((2R,5R,6R)-6-(3-chlorophenyl)-5-(4-chlorophenyl)-4-((S)-1-(N-(2-fluorophenyl)-2-methylpropan-2-ylsulfonamido)-3-methylbutan-2-yl)-3-oxomorpholin-2-yl)acetic acid;

2-((2S,5R,6R)-6-(3-chlorophenyl)-5-(4-chlorophenyl)-4-((S)-1-(N-(2-fluorophenyl)-2-methylpropan-2-ylsulfonamido)-3-methylbutan-2-yl)-3-oxomorpholin-2-yl)acetic acid;

2-((2R,5R,6R)-6-(3-chlorophenyl)-5-(4-chlorophenyl)-3-oxo-4-((S)-1-(pyridin-2-ylsulfonyl)butan-2-yl)morpholin-2-yl)acetic acid;

2-((2S,5R,6R)-6-(3-chlorophenyl)-5-(4-chlorophenyl)-3-oxo-4-((S)-1-(pyridin-2-ylsulfonyl)butan-2-yl)morpholin-2-yl)acetic acid;

2-((2R,5R,6R)-6-(3-chlorophenyl)-5-(4-chlorophenyl)-4-((S)-1-(N-(2,4-difluorophenyl)cyclopropanesulfonamido)butan-2-yl)-3-oxomorpholin-2-yl)acetic acid;

2-((2S,5R,6R)-6-(3-chlorophenyl)-5-(4-chlorophenyl)-4-((S)-1-(N-(2,4-difluorophenyl)cyclopropanesulfonamido)butan-2-yl)-3-oxomorpholin-2-yl)acetic acid;

2-((2R,5R,6R)-6-(3-chlorophenyl)-5-(4-chlorophenyl)-4-((S)-1-(N-(2-cyanophenyl)cyclopropanesulfonamido)butan-2-yl)-3-oxomorpholin-2-yl)acetic acid;

2-((2S,5R,6R)-6-(3-chlorophenyl)-5-(4-chlorophenyl)-4-((S)-1-(N-(2-cyanophenyl)cyclopropanesulfonamido)butan-2-yl)-3-oxomorpholin-2-yl)acetic acid;

2-((2R,5R,6R)-6-(3-chlorophenyl)-5-(4-chlorophenyl)-4-((S)-1-(((S)-2-methylpyrrolidin-1-yl)sulfonyl)butan-2-yl)-3-oxomorpholin-2-yl)acetic acid;

2-((2S,5R,6R)-6-(3-chlorophenyl)-5-(4-chlorophenyl)-4-((S)-1-(((S)-2-methylpyrrolidin-1-yl)sulfonyl)butan-2-yl)-3-oxomorpholin-2-yl)acetic acid;

2-((2R,5R,6R)-6-(3-chlorophenyl)-5-(4-chlorophenyl)-4-((S)-1-(((R)-2-methylpyrrolidin-1-yl)sulfonyl)butan-2-yl)-3-oxomorpholin-2-yl)acetic;

2-((2S,5R,6R)-6-(3-chlorophenyl)-5-(4-chlorophenyl)-4-((S)-1-(((R)-2-methylpyrrolidin-1-yl)sulfonyl)butan-2-yl)-3-oxomorpholin-2-yl)acetic acid;

2-((2R,5R,6R)-6-(3-chlorophenyl)-5-(4-chlorophenyl)-4-((S)-1-(cyclopropylsulfonyl)butan-2-yl)-3-oxomorpholin-2-yl)acetic acid;

2-((2S,5R,6R)-6-(3-chlorophenyl)-5-(4-chlorophenyl)-4-((S)-1-(cyclopropylsulfonyl)butan-2-yl)-3-oxomorpholin-2-yl)acetic acid;

2-((2R,5R,6R)-6-(3-chlorophenyl)-5-(4-chlorophenyl)-4-((S)-1-(N,N-dimethylsulfamoyl)butan-2-yl)-3-oxomorpholin-2-yl)acetic acid;

2-((2S,5R,6R)-6-(3-chlorophenyl)-5-(4-chlorophenyl)-4-((S)-1-(N,N-dimethylsulfamoyl)butan-2-yl)-3-oxomorpholin-2-yl)acetic acid;

2-((2R,5S,6R)-6-(3-chlorophenyl)-5-(5-chlorothiophen-2-yl)-4-((S)-1-(N-(2-fluorophenyl)cyclopropanesulfonamido)butan-2-yl)-3-oxomorpholin-2-yl)acetic acid;

2-((2S,5S,6R)-6-(3-chlorophenyl)-5-(5-chlorothiophen-2-yl)-4-((S)-1-(N-(2-fluorophenyl)cyclopropanesulfonamido)butan-2-yl)-3-oxomorpholin-2-yl)acetic acid;

2-((2R,5S,6R)-4-((S)-1-(tert-butylsulfonyl)butan-2-yl)-6-(3-chlorophenyl)-5-(5-chlorothiophen-2-yl)-3-oxomorpholin-2-yl)acetic acid;

2-((2S,5S,6R)-4-((S)-1-(tert-butylsulfonyl)butan-2-yl)-6-(3-chlorophenyl)-5-(5-chlorothiophen-2-yl)-3-oxomorpholin-2-yl)acetic acid;

2-((2R,5R,6R)-4-((S)-1-(tert-butylsulfonyl)pentan-3-yl)-6-(3-chlorophenyl)-5-(4-chlorophenyl)-3-oxomorpholin-2-yl)acetic acid;

2-((2S,5R,6R)-4-((S)-1-(tert-butylsulfonyl)pentan-3-yl)-6-(3-chlorophenyl)-5-(4-chlorophenyl)-3-oxomorpholin-2-yl)acetic acid;

(5R,6R)-4-((S)-1-(tert-butylthio)propan-2-yl)-6-(3-chlorophenyl)-5-(4-chlorophenyl)morpholin-3-one;

2-((2S,5R,6R)-4-((S)-1-(tert-butylsulfonyl)propan-2-yl)-6-(3-chlorophenyl)-5-(4-chlorophenyl)-3-oxomorpholin-2-yl)acetic acid;

2-((2R,5R,6R)-4-((S)-1-(tert-butylsulfonyl)propan-2-yl)-6-(3-chlorophenyl)-5-(4-chlorophenyl)-3-oxomorpholin-2-yl)acetic acid;

2-((2R,5R,6R)-4-((S)-1-(tert-butylsulfonyl)propan-2-yl)-6-(3-chlorophenyl)-5-(4-chlorophenyl)-3-oxomorpholin-2-yl)acetamide;

2-((2S,5R,6R)-4-((S)-1-(tert-butylsulfonyl)propan-2-yl)-6-(3-chlorophenyl)-5-(4-chlorophenyl)-3-oxomorpholin-2-yl)acetamide;

2-((2S,5R,6R)-4-((S)-1-(tert-butylsulfonyl)propan-2-yl)-6-(3-chlorophenyl)-5-(4-chlorophenyl)-3-oxomorpholin-2-yl)-N-methylacetamide;

2-((2R,5R,6R)-4-((S)-1-(tert-butylsulfonyl)propan-2-yl)-6-(3-chlorophenyl)-5-(4-chlorophenyl)-3-oxomorpholin-2-yl)-N-methylacetamide;

2-((2S,5R,6R)-4-((S)-1-(tert-butylsulfonyl)propan-2-yl)-6-(3-chlorophenyl)-5-(4-chlorophenyl)-3-oxomorpholin-2-yl)-N-hydroxyacetamide;

2-((2R,5R,6R)-4-((S)-1-(tert-butylsulfonyl)propan-2-yl)-6-(3-chlorophenyl)-5-(4-chlorophenyl)-3-oxomorpholin-2-yl)-N-hydroxyacetamide;

2-((2S,5R,6R)-4-((S)-1-(tert-butylsulfonyl)propan-2-yl)-6-(3-chlorophenyl)-5-(4-chlorophenyl)-3-oxomorpholin-2-yl)-N,N-dimethylacetamide;

2-((2R,5R,6R)-4-((S)-1-(tert-butylsulfonyl)propan-2-yl)-6-(3-chlorophenyl)-5-(4-chlorophenyl)-3-oxomorpholin-2-yl)-N,N-dimethylacetamide;

2-((2S,5R,6R)-4-((S)-1-(tert-butylsulfonyl)propan-2-yl)-6-(3-chlorophenyl)-5-(4-chlorophenyl)-3-oxomorpholin-2-yl)-N-(2-hydroxyethyl)acetamide;

2-((2R,5R,6R)-4-((S)-1-(tert-butylsulfonyl)propan-2-yl)-6-(3-chlorophenyl)-5-(4-chlorophenyl)-3-oxomorpholin-2-yl)-N-(2-hydroxyethyl)acetamide;

(2S,5R,6R)-4-((S)-1-(tert-butylsulfonyl)propan-2-yl)-6-(3-chlorophenyl)-5-(4-chlorophenyl)-2-(2-morpholino-2-oxo ethyl)morpholin-3-one;

(2R,5R,6R)-4-((S)-1-(tert-butylsulfonyl)propan-2-yl)-6-(3-chlorophenyl)-5-(4-chlorophenyl)-2-(2-morpholino-2-oxo ethyl)morpholin-3-one;

2-((2S,5R,6R)-4-((S)-1-(tert-butylsulfonyl)propan-2-yl)-6-(3-chlorophenyl)-5-(4-chlorophenyl)-3-oxomorpholin-2-yl)-N-(methylsulfonyl)acetamide;

2-((2R,5R,6R)-4-((S)-1-(tert-butylsulfonyl)propan-2-yl)-6-(3-chlorophenyl)-5-(4-chlorophenyl)-3-oxomorpholin-2-yl)-N-(methylsulfonyl)acetamide;

2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)-N-(methylsulfonyl)acetamide;

2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)-N-(methylsulfonyl)acetamide;

2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)acetamide;

2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)acetamide;

N-((S)-2-((2R,5R,6R)-2-((1H-tetrazol-5-yl)methyl)-6-(3-chlorophenyl)-5-(4-chlorophenyl)-3-oxomorpholino)butyl)-N-methylcyclopropanesulfonamide;

N-((S)-2-((2S,5R,6R)-2-((1H-tetrazol-5-yl)methyl)-6-(3-chlorophenyl)-5-(4-chlorophenyl)-3-oxomorpholino)butyl)-N-methylcyclopropanesulfonamide;

(2R,5R,6R)-4-((S)-1-(tert-butylsulfonyl)butan-2-yl)-6-(3-chlorophenyl)-5-(4-chlorophenyl)-2-(3-hydroxy-2-oxopropyl)morpholin-3-one;

(2S,5R,6R)-4-((S)-1-(tert-butylsulfonyl)butan-2-yl)-6-(3-chlorophenyl)-5-(4-chlorophenyl)-2-(3-hydroxy-2-oxopropyl)morpholin-3-one;

methyl 2-((2R,5R,6R)-6-(3-chlorophenyl)-5-(4-chlorophenyl)-4-((S)-1-((2-(dimethylamino)ethyl)sulfonyl)butan-2-yl)-3-oxomorpholin-2-yl)acetate;

methyl 2-((2S,5R,6R)-6-(3-chlorophenyl)-5-(4-chlorophenyl)-4-((S)-1-((2-(dimethylamino)ethyl)sulfonyl)butan-2-yl)-3-oxomorpholin-2-yl)acetate;

2-((2R,5R,6R)-6-(3-chlorophenyl)-5-(4-chlorophenyl)-4-((S)-1-((2-(dimethylamino)ethyl)sulfonyl)butan-2-yl)-3-oxomorpholin-2-yl)acetic acid;

2-((2S,5R,6R)-6-(3-chlorophenyl)-5-(4-chlorophenyl)-4-((S)-1-((2-(dimethylamino)ethyl)sulfonyl)butan-2-yl)-3-oxomorpholin-2-yl)acetic acid;

2-((2R,5R,6R)-4-((1S,2S)-2-(tert-butylsulfonyl)cyclohexyl)-6-(3-chlorophenyl)-5-(4-chlorophenyl)-3-oxomorpholin-2-yl)acetic acid;

2-((2R,5R,6R)-6-(3-chlorophenyl)-5-(4-chlorophenyl)-4-((S)-1-cyclopropyl-2-(N-(2,6-difluorophenyl)cyclopropanesulfonamido)ethyl)-3-oxomorpholin-2-yl)acetic acid;

2-((2S,5R,6R)-6-(3-chlorophenyl)-5-(4-chlorophenyl)-4-((S)-1-cyclopropyl-2-(N-(2,6-difluorophenyl)cyclopropanesulfonamido)ethyl)-3-oxomorpholin-2-yl)acetic acid;

(R)-2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid;

(S)-2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid;

(R)-2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid;

(S)-2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid;

2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetamide;

2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetamide;

2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)-N-(isopropylsulfonyl)acetamide;

2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)-N-(isopropylsulfonyl)acetamide;

2-((2S,5R,6R)-4-((S)-1-(tert-butylsulfonyl)butan-2-yl)-6-(3-chlorophenyl)-5-(4-chlorophenyl)-3-oxomorpholin-2-yl)acetamide;

2-((2R,5R,6R)-4-((S)-1-(tert-butylsulfonyl)butan-2-yl)-6-(3-chlorophenyl)-5-(4-chlorophenyl)-3-oxomorpholin-2-yl)acetamide;

3-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid;

3-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid;

2-((2R,5R,6R)-6-(3-chlorophenyl)-5-(4-chlorophenyl)-4-((S)-1-(N-(2-chlorophenyl)cyclopropanesulfonamido)butan-2-yl)-3-oxomorpholin-2-yl)acetic acid; or 2-((2S,5R,6R)-6-(3-chlorophenyl)-5-(4-chlorophenyl)-4-((S)-1-(N-(2-chlorophenyl)cyclopropanesulfonamido)butan-2-yl)-3-oxomorpholin-2-yl)acetic acid.

In embodiment 38, the present invention provides compounds, or pharmaceutically acceptable salts thereof, selected from:

2-((2R,5R,6R)-4-((S)-1-(tert-butylsulfonyl)-4,4,4-trifluorobutan-2-yl)-6-(3-chlorophenyl)-5-(4-chlorophenyl)-3-oxomorpholin-2-yl)acetic acid;

2-((2S,5R,6R)-4-((S)-1-(tert-butylsulfonyl)-4,4,4-trifluorobutan-2-yl)-6-(3-chlorophenyl)-5-(4-chlorophenyl)-3-oxomorpholin-2-yl)acetic acid;

2-((2R,5R,6R)-4-((R)-1-(tert-butylsulfonyl)-4,4,4-trifluorobutan-2-yl)-6-(3-chlorophenyl)-5-(4-chlorophenyl)-3-oxomorpholin-2-yl)acetic acid;

2-((2S,5R,6R)-4-((R)-1-(tert-butylsulfonyl)-4,4,4-trifluorobutan-2-yl)-6-(3-chlorophenyl)-5-(4-chlorophenyl)-3-oxomorpholin-2-yl)acetic acid;

2-((2R,5R,6R)-4-((S)-2-(tert-butylsulfonyl)-1-cyclobutylethyl)-6-(3-chlorophenyl)-5-(4-chlorophenyl)-3-oxomorpholin-2-yl)acetic acid;

2-((2S,5R,6R)-4-((S)-2-(tert-butylsulfonyl)-1-cyclobutylethyl)-6-(3-chlorophenyl)-5-(4-chlorophenyl)-3-oxomorpholin-2-yl)acetic acid;

2-((2R,5R,6R)-4-((R)-2-(tert-butylsulfonyl)-1-cyclobutylethyl)-6-(3-chlorophenyl)-5-(4-chlorophenyl)-3-oxomorpholin-2-yl)acetic acid;

2-((2S,5R,6R)-4-((R)-2-(tert-butylsulfonyl)-1-cyclobutylethyl)-6-(3-chlorophenyl)-5-(4-chlorophenyl)-3-oxomorpholin-2-yl)acetic acid;

2-((2R,5R,6R)-6-(3-chlorophenyl)-5-(4-chlorophenyl)-3-oxo-4-((R)-1,1,1-trifluoro-3-(N-(2-fluorophenyl)cyclopropanesulfonamido)propan-2-yl)morpholin-2-yl)acetic acid;

2-((2S,5R,6R)-6-(3-chlorophenyl)-5-(4-chlorophenyl)-3-oxo-4-((R)-1,1,1-trifluoro-3-(N-(2-fluorophenyl)cyclopropanesulfonamido)propan-2-yl)morpholin-2-yl)acetic acid;

2-((2R,5R,6R)-6-(3-chlorophenyl)-5-(4-chlorophenyl)-3-oxo-4-((S)-1,1,1-trifluoro-3-(N-(2-fluorophenyl)cyclopropanesulfonamido)propan-2-yl)morpholin-2-yl)acetic acid;

2-((2S,5R,6R)-6-(3-chlorophenyl)-5-(4-chlorophenyl)-3-oxo-4-((S)-1,1,1-trifluoro-3-(N-(2-fluorophenyl)cyclopropanesulfonamido)propan-2-yl)morpholin-2-yl)acetic acid;

2-((2R,5R,6R)-6-(3-chlorophenyl)-5-(4-chlorophenyl)-4-((S)-1-cyclopropyl-2-(N-(2,5-difluorophenyl)cyclopropanesulfonamido)ethyl)-3-oxomorpholin-2-yl)acetic acid 2-((2S,5R,6R)-6-(3-chlorophenyl)-5-(4-chlorophenyl)-4-((S)-1-cyclopropyl-2-(N-(2,5-difluorophenyl)cyclopropanesulfonamido)ethyl)-3-oxomorpholin-2-yl)acetic acid;

2-((2R,5R,6R)-6-(3-chlorophenyl)-5-(4-chlorophenyl)-3-oxo-4-((S)-4,4,4-trifluoro-1-(N-(2-fluorophenyl)cyclopropanesulfonamido)butan-2-yl)morpholin-2-yl)acetic acid;

2-((2S,5R,6R)-6-(3-chlorophenyl)-5-(4-chlorophenyl)-3-oxo-4-((S)-4,4,4-trifluoro-1-(N-(2-fluorophenyl)cyclopropanesulfonamido)butan-2-yl)morpholin-2-yl)acetic acid;

2-((2S,5R,6R)-6-(3-chlorophenyl)-5-(4-chlorophenyl)-3-oxo-4-((R)-4,4,4-trifluoro-1-(N-(2-fluorophenyl)cyclopropanesulfonamido)butan-2-yl)morpholin-2-yl)acetic acid;

2-((2R,5R,6R)-6-(3-chlorophenyl)-5-(4-chlorophenyl)-3-oxo-4-((R)-4,4,4-trifluoro-1-(N-(2-fluorophenyl)cyclopropanesulfonamido)butan-2-yl)morpholin-2-yl)acetic acid;

2-((2R,5R,6R)-4-((S)-1-((S)-sec-butylsulfonyl)butan-2-yl)-6-(3-chlorophenyl)-5-(4-chlorophenyl)-3-oxomorpholin-2-yl)acetic acid;

2-((2R,5R,6R)-4-((S)-1-((R)-sec-butylsulfonyl)butan-2-yl)-6-(3-chlorophenyl)-5-(4-chlorophenyl)-3-oxomorpholin-2-yl)acetic acid;

2-((2S,5R,6R)-4-((S)-1-((S)-sec-butylsulfonyl)butan-2-yl)-6-(3-chlorophenyl)-5-(4-chlorophenyl)-3-oxomorpholin-2-yl)acetic acid;

2-((2S,5R,6R)-4-((S)-1-((R)-sec-butylsulfonyl)butan-2-yl)-6-(3-chlorophenyl)-5-(4-chlorophenyl)-3-oxomorpholin-2-yl)acetic acid;

2-((2S,5R,6R)-6-(3-chlorophenyl)-5-(4-chlorophenyl)-4-((S)-1-(((R)-3-methylbutan-2-yl)sulfonyl)butan-2-yl)-3-oxomorpholin-2-yl)acetic acid;

2-((2S,5R,6R)-6-(3-chlorophenyl)-5-(4-chlorophenyl)-4-((S)-1-(((S)-3-methylbutan-2-yl)sulfonyl)butan-2-yl)-3-oxomorpholin-2-yl)acetic acid;

2-((2R,5R,6R)-6-(3-chlorophenyl)-5-(4-chlorophenyl)-4-((S)-1-(((R)-3-methylbutan-2-yl)sulfonyl)butan-2-yl)-3-oxomorpholin-2-yl)acetic acid;

2-((2R,5R,6R)-6-(3-chlorophenyl)-5-(4-chlorophenyl)-4-((S)-1-(((S)-3-methylbutan-2-yl)sulfonyl)butan-2-yl)-3-oxomorpholin-2-yl)acetic acid;

2-((2R,5R,6R)-6-(3-chlorophenyl)-5-(4-chlorophenyl)-4-((S)-1-cyclopropyl-2-(pyridin-4-ylsulfonyl)ethyl)-3-oxomorpholin-2-yl)acetic acid;

2-((2S,5R,6R)-6-(3-chlorophenyl)-5-(4-chlorophenyl)-4-((S)-1-cyclopropyl-2-(pyridin-4-ylsulfonyl)ethyl)-3-oxomorpholin-2-yl)acetic acid;

2-((2R,5R,6R)-6-(3-chlorophenyl)-5-(4-chlorophenyl)-4-((S)-1-cyclopropyl-2-((2-hydroxy-2-methylpropyl)sulfonyl)ethyl)-3-oxomorpholin-2-yl)acetic acid;

2-((2S,5R,6R)-6-(3-chlorophenyl)-5-(4-chlorophenyl)-4-((S)-1-cyclopropyl-2-((2-hydroxy-2-methylpropyl)sulfonyl)ethyl)-3-oxomorpholin-2-yl)acetic acid;

2-((2R,5R,6R)-6-(3-chlorophenyl)-5-(4-chlorophenyl)-4-((S)-2-((2-cyanopropan-2-yl)sulfonyl)-1-cyclopropylethyl)-3-oxomorpholin-2-yl)acetic acid;

2-((2S,5R,6R)-6-(3-chlorophenyl)-5-(4-chlorophenyl)-4-((S)-2-((2-cyanopropan-2-yl)sulfonyl)-1-cyclopropylethyl)-3-oxomorpholin-2-yl)acetic acid;

2-((2R,5R,6R)-4-((S)-2-(N-(tert-butyl)sulfamoyl)-1-cyclopropylethyl)-6-(3-chlorophenyl)-5-(4-chlorophenyl)-3-oxomorpholin-2-yl)acetic acid;

2-((2S,5R,6R)-4-((S)-2-(N-(tert-butyl)sulfamoyl)-1-cyclopropylethyl)-6-(3-chlorophenyl)-5-(4-chlorophenyl)-3-oxomorpholin-2-yl)acetic acid;

2-((2R,5R,6R)-6-(3-chlorophenyl)-5-(4-chlorophenyl)-4-((S)-1-cyclopropyl-2-(N-(2-fluorophenyl)sulfamoyl)ethyl)-3-oxomorpholin-2-yl)acetic acid;

2-((2S,5R,6R)-6-(3-chlorophenyl)-5-(4-chlorophenyl)-4-((S)-1-cyclopropyl-2-(N-(2-fluorophenyl)sulfamoyl)ethyl)-3-oxomorpholin-2-yl)acetic acid;

2-((2R,5R,6R)-6-(3-chlorophenyl)-5-(4-chlorophenyl)-4-((S)-1-cyclopropyl-2-(((S)-2-methylpyrrolidin-1-yl)sulfonyl)ethyl)-3-oxomorpholin-2-yl)acetic acid;

2-((2S,5R,6R)-6-(3-chlorophenyl)-5-(4-chlorophenyl)-4-((S)-1-cyclopropyl-2-(((S)-2-methylpyrrolidin-1-yl)sulfonyl)ethyl)-3-oxomorpholin-2-yl)acetic acid;

2-((2R,5R,6R)-6-(3-chlorophenyl)-5-(4-chlorophenyl)-4-((S)-1-cyclopropyl-2-((5-fluoroindolin-1-yl)sulfonyl)ethyl)-3-oxomorpholin-2-yl)acetic acid;

2-((2S,5R,6R)-6-(3-chlorophenyl)-5-(4-chlorophenyl)-4-((S)-1-cyclopropyl-2-((5-fluoroindolin-1-yl)sulfonyl)ethyl)-3-oxomorpholin-2-yl)acetic acid;

2-((2R,5R,6R)-4-((S)-2-(N-(tert-butyl)-N-methylsulfamoyl)-1-cyclopropylethyl)-6-(3-chlorophenyl)-5-(4-chlorophenyl)-3-oxomorpholin-2-yl)acetic acid;

2-((2S,5R,6R)-4-((S)-2-(N-(tert-butyl)-N-methylsulfamoyl)-1-cyclopropylethyl)-6-(3-chlorophenyl)-5-(4-chlorophenyl)-3-oxomorpholin-2-yl)acetic acid;

2-((2R,5R,6R)-6-(3-chlorophenyl)-5-(4-chlorophenyl)-4-((S)-1-cyclopropyl-2-(morpholinosulfonyl)ethyl)-3-oxomorpholin-2-yl)acetic acid;

2-((2S,5R,6R)-6-(3-chlorophenyl)-5-(4-chlorophenyl)-4-((S)-1-cyclopropyl-2-(morpholinosulfonyl)ethyl)-3-oxomorpholin-2-yl)acetic acid;

2-((2R,5R,6R)-6-(3-chlorophenyl)-5-(4-chlorophenyl)-4-((S)-1-cyclopropyl-2-(((R)-2-methylpyrrolidin-1-yl)sulfonyl)ethyl)-3-oxomorpholin-2-yl)acetic acid;

2-((2S,5R,6R)-6-(3-chlorophenyl)-5-(4-chlorophenyl)-4-((S)-1-cyclopropyl-2-(((R)-2-methylpyrrolidin-1-yl)sulfonyl)ethyl)-3-oxomorpholin-2-yl)acetic acid;

2-((2R,5R,6R)-6-(3-chlorophenyl)-5-(4-chlorophenyl)-4-((S)-1-cyclopropyl-2-((2,2-dimethylpyrrolidin-1-yl)sulfonyl)ethyl)-3-oxomorpholin-2-yl)acetic acid;

2-((2R,5R,6R)-6-(3-chlorophenyl)-5-(4-chlorophenyl)-4-((S)-1-cyclopropyl-2-((2,2-dimethylpyrrolidin-1-yl)sulfonyl)ethyl)-3-oxomorpholin-2-yl)acetic acid;

2-((2R,5R,6R)-4-((S)-2-(tert-butylsulfonyl)-1-cyclopropylethyl)-5-(4-chloro-3-fluorophenyl)-6-(3-chlorophenyl)-3-oxomorpholin-2-yl)acetic acid;

2-((2S,5R,6R)-4-((S)-2-(tert-butylsulfonyl)-1-cyclopropylethyl)-5-(4-chloro-3-fluorophenyl)-6-(3-chlorophenyl)-3-oxomorpholin-2-yl)acetic acid;

2-((2R,5R,6R)-4-((S)-1-(tert-butylsulfonyl)-3-methylbutan-2-yl)-5-(4-chloro-3-fluorophenyl)-6-(3-chlorophenyl)-3-oxomorpholin-2-yl)acetic acid;

2-((2S,5R,6R)-4-((S)-1-(tert-butylsulfonyl)-3-methylbutan-2-yl)-5-(4-chloro-3-fluorophenyl)-6-(3-chlorophenyl)-3-oxomorpholin-2-yl)acetic acid;

2-((2R,5R,6R)-4-((R)-1-(tert-butylsulfonyl)-3-methylbutan-2-yl)-5-(4-chloro-3-fluorophenyl)-6-(3-chlorophenyl)-3-oxomorpholin-2-yl)acetic acid;

2-((2S,5R,6R)-4-((R)-1-(tert-butylsulfonyl)-3-methylbutan-2-yl)-5-(4-chloro-3-fluorophenyl)-6-(3-chlorophenyl)-3-oxomorpholin-2-yl)acetic acid;

2-((2R,5R,6R)-5-(4-chloro-3-fluorophenyl)-6-(3-chlorophenyl)-4-((S)-1-cyclopropyl-2-(N-(2-fluorophenyl)cyclopropanesulfonamido)ethyl)-3-oxomorpholin-2-yl)acetic acid;

2-((2S,5R,6R)-5-(4-chloro-3-fluorophenyl)-6-(3-chlorophenyl)-4-((S)-1-cyclopropyl-2-(N-(2-fluorophenyl)cyclopropanesulfonamido)ethyl)-3-oxomorpholin-2-yl)acetic acid;

2-((2R,5R,6R)-4-((S)-1-(tert-butylsulfonyl)butan-2-yl)-5-(4-chloro-2-fluorophenyl)-6-(3-chlorophenyl)-3-oxomorpholin-2-yl)acetic acid;

2-((2S,5R,6R)-4-((S)-1-(tert-butylsulfonyl)butan-2-yl)-5-(4-chloro-2-fluorophenyl)-6-(3-chlorophenyl)-3-oxomorpholin-2-yl)acetic acid;

2-((2R,5R,6R)-4-((S)-2-(tert-butylsulfonyl)-1-cyclopropylethyl)-5-(4-chlorophenyl)-6-(3,4-dichlorophenyl)-3-oxomorpholin-2-yl)acetic acid;

2-((2S,5R,6R)-4-((S)-2-(tert-butylsulfonyl)-1-cyclopropylethyl)-5-(4-chlorophenyl)-6-(3,4-dichlorophenyl)-3-oxomorpholin-2-yl)acetic acid;

2-((2R,5R,6R)-4-((S)-2-(tert-butylsulfonyl)-1-cyclopropylethyl)-6-(3-chloro-4-fluorophenyl)-5-(4-chlorophenyl)-3-oxomorpholin-2-yl)acetic acid;

2-((2S,5R,6R)-4-((S)-2-(tert-butylsulfonyl)-1-cyclopropylethyl)-6-(3-chloro-4-fluorophenyl)-5-(4-chlorophenyl)-3-oxomorpholin-2-yl)acetic acid;

2-((2R,5R,6R)-6-(4-bromo-3-chlorophenyl)-4-((S)-2-(tert-butylthio)-1-cyclopropylethyl)-5-(4-chlorophenyl)-3-oxomorpholin-2-yl)acetic acid;

2-((2S,5R,6R)-6-(4-bromo-3-chlorophenyl)-4-((S)-2-(tert-butylthio)-1-cyclopropylethyl)-5-(4-chlorophenyl)-3-oxomorpholin-2-yl)acetic acid;

2-((2R,5R,6R)-4-((S)-2-(tert-butylsulfonyl)-1-cyclopropylethyl)-6-(3-chloro-4-cyanophenyl)-5-(4-chlorophenyl)-3-oxomorpholin-2-yl)acetic acid;

2-((2S,5R,6R)-4-((S)-2-(tert-butylsulfonyl)-1-cyclopropylethyl)-6-(3-chloro-4-cyanophenyl)-5-(4-chlorophenyl)-3-oxomorpholin-2-yl)acetic acid;

2-((2R,5R,6R)-4-((S)-2-(tert-butylsulfonyl)-1-cyclopropylethyl)-6-(3-chloro-2-fluorophenyl)-5-(4-chlorophenyl)-3-oxomorpholin-2-yl)acetic acid;

2-((2S,5R,6R)-4-((S)-2-(tert-butylsulfonyl)-1-cyclopropylethyl)-6-(3-chloro-2-fluorophenyl)-5-(4-chlorophenyl)-3-oxomorpholin-2-yl)acetic acid;

2-((2R,5R,6R)-4-((S)-2-(tert-butylsulfonyl)-1-cyclopropylethyl)-6-(3-chloro-4-methylphenyl)-5-(4-chlorophenyl)-3-oxomorpholin-2-yl)acetic acid;

2-((2R,5R,6R)-4-((S)-2-(tert-butylthio)-1-cyclopropylethyl)-6-(3-chloro-4-methoxyphenyl)-5-(4-chlorophenyl)-3-oxomorpholin-2-yl)acetic acid;

2-((2S,5R,6R)-4-((S)-2-(tert-butylthio)-1-cyclopropylethyl)-6-(3-chloro-4-methoxyphenyl)-5-(4-chlorophenyl)-3-oxomorpholin-2-yl)acetic acid;

2-((2R,5R,6R)-6-(3-chlorophenyl)-5-(4-chlorophenyl)-4-((S)-1-(N-(2-fluorophenyl)cyclopropanesulfonamido)butan-2-yl)-2-methyl-3-oxomorpholin-2-yl)acetic acid;

2-((2S,5R,6R)-6-(3-chlorophenyl)-5-(4-chlorophenyl)-4-((S)-1-(N-(2-fluorophenyl)cyclopropanesulfonamido)butan-2-yl)-2-methyl-3-oxomorpholin-2-yl)acetic acid;

2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-2-methyl-3-oxomorpholin-2-yl)acetic acid;

2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-2-methyl-3-oxomorpholin-2-yl)acetic acid;

2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxo-2-(2,2,2-trifluoroethyl)morpholin-2-yl)acetic acid;
2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxo-2-(2,2,2-trifluoroethyl)morpholin-2-yl)acetic acid;
2-((2R,5R,6R)-4-((S)-2-(tert-butylsulfonyl)-1-cyclopropylethyl)-6-(3-chlorophenyl)-5-(4-chlorophenyl)-2-methyl-3-oxomorpholin-2-yl)acetic acid;
2-((2S,5R,6R)-4-((S)-2-(tert-butylsulfonyl)-1-cyclopropylethyl)-6-(3-chlorophenyl)-5-(4-chlorophenyl)-2-methyl-3-oxomorpholin-2-yl)acetic acid;
2-((2R,5R,6R)-6-(3-chlorophenyl)-5-(4-chlorophenyl)-4-((S)-1-cyclopropyl-2-(((S)-2-methylpyrrolidin-1-yl)sulfonyl)ethyl)-2-methyl-3-oxomorpholin-2-yl)acetic acid;
2-((2S,5R,6R)-6-(3-chlorophenyl)-5-(4-chlorophenyl)-4-((S)-1-cyclopropyl-2-(((S)-2-methylpyrrolidin-1-yl)sulfonyl)ethyl)-2-methyl-3-oxomorpholin-2-yl)acetic acid;
2-((2R,5R,6R)-4-((S)-1-(tert-butylsulfonyl)butan-2-yl)-6-(3-chlorophenyl)-5-(4-chlorophenyl)-2-methyl-3-oxomorpholin-2-yl)acetic acid;
2-((2S,5R,6R)-4-((S)-1-(tert-butylsulfonyl)butan-2-yl)-6-(3-chlorophenyl)-5-(4-chlorophenyl)-2-methyl-3-oxomorpholin-2-yl)acetic acid;
2-((2R,5R,6R)-4-((S)-1-(tert-butylsulfonyl)-4,4,4-trifluorobutan-2-yl)-6-(3-chlorophenyl)-5-(4-chlorophenyl)-2-methyl-3-oxomorpholin-2-yl)acetic acid;
2-((2S,5R,6R)-4-((S)-1-(tert-butylsulfonyl)-4,4,4-trifluorobutan-2-yl)-6-(3-chlorophenyl)-5-(4-chlorophenyl)-2-methyl-3-oxomorpholin-2-yl)acetic acid;
2-((2R,5R,6R)-4-((S)-1-(tert-butylsulfonyl)-4,4,4-trifluorobutan-2-yl)-6-(3-chlorophenyl)-5-(4-chlorophenyl)-2-ethyl-3-oxomorpholin-2-yl)acetic acid;
2-((2S,5R,6R)-4-((S)-1-(tert-butylsulfonyl)-4,4,4-trifluorobutan-2-yl)-6-(3-chlorophenyl)-5-(4-chlorophenyl)-2-ethyl-3-oxomorpholin-2-yl)acetic acid;
2-((2S,5R,6R)-4-((S)-1-(tert-butylsulfonyl)butan-2-yl)-6-(3-chlorophenyl)-5-(4-chlorophenyl)-3-oxomorpholin-2-yl)-N-cyanoacetamide;
2-((2R,5R,6R)-4-((S)-1-(tert-butylsulfonyl)butan-2-yl)-6-(3-chlorophenyl)-5-(4-chlorophenyl)-3-oxomorpholin-2-yl)-N-cyanoacetamide;
2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)-N-(2,2,2-trifluoroethyl)acetamide;
2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)-N-(2,2,2-trifluoroethyl)acetamide;
2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)-N-(cyanomethyl)acetamide;
2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)-N-(cyanomethyl)acetamide;
2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)-N-phenylacetamide;
2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)-N-phenylacetamide;
2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)-N-(2-fluorophenyl)acetamide;
2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)-N-(2-fluorophenyl)acetamide;
2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)-N-(pyridin-2-yl)acetamide;
2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)-N-(pyridin-2-yl)acetamide;
2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)acetamide;
2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetamide;
2-((2R,5R,6R)-6-(3-chlorophenyl)-5-(4-chlorophenyl)-4-((S)-1-cyclopropyl-2-(N-(2,6-difluorophenyl)cyclopropanesulfonamido)ethyl)-3-oxomorpholin-2-yl)acetamide;
2-((2S,5R,6R)-6-(3-chlorophenyl)-5-(4-chlorophenyl)-4-((S)-1-cyclopropyl-2-(N-(2,6-difluorophenyl)cyclopropanesulfonamido)ethyl)-3-oxomorpholin-2-yl)acetamide;
2-((2R,5R,6R)-6-(3-chlorophenyl)-5-(4-chlorophenyl)-4-((S)-1-cyclopropyl-2-(N-phenylcyclopropanesulfonamido)ethyl)-3-oxomorpholin-2-yl)acetamide;
2-((2S,5R,6R)-6-(3-chlorophenyl)-5-(4-chlorophenyl)-4-((S)-1-cyclopropyl-2-(N-phenylcyclopropanesulfonamido)ethyl)-3-oxomorpholin-2-yl)acetamide;
2-((2R,5R,6R)-4-((S)-1-(tert-butylsulfonyl)-4,4,4-trifluorobutan-2-yl)-6-(3-chlorophenyl)-5-(4-chlorophenyl)-3-oxomorpholin-2-yl)acetamide;
2-((2S,5R,6R)-4-((S)-1-(tert-butylsulfonyl)-4,4,4-trifluorobutan-2-yl)-6-(3-chlorophenyl)-5-(4-chlorophenyl)-3-oxomorpholin-2-yl)acetamide;
2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)-N-methylacetamide;
2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)-N-methylacetamide;
2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)-N,N-dimethylacetamide;
2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)-N,N-dimethylacetamide;
2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)-N-(pyridin-2-yl)acetamide;
2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)-N-(pyridin-2-yl)acetamide;
(2R,5R,6R)-4-((S)-2-(tert-butylsulfonyl)-1-cyclopropylethyl)-6-(3-chlorophenyl)-5-(4-chlorophenyl)-2-(2-hydroxyethyl)morpholin-3-one;
(2S,5R,6R)-4-((S)-2-(tert-butylsulfonyl)-1-cyclopropylethyl)-6-(3-chlorophenyl)-5-(4-chlorophenyl)-2-(2-hydroxyethyl)morpholin-3-one;
(2R,5R,6R)-4-((S)-1-(tert-butylsulfonyl)butan-2-yl)-6-(3-chlorophenyl)-5-(4-chlorophenyl)-2-((R)-2,3-dihydroxypropyl)morpholin-3-one;

(2R,5R,6R)-4-((S)-1-(tert-butylsulfonyl)butan-2-yl)-6-(3-chlorophenyl)-5-(4-chlorophenyl)-2-((S)-2,3-dihydroxypropyl)morpholin-3-one;
(2S,5R,6R)-4-((S)-1-(tert-butylsulfonyl)butan-2-yl)-6-(3-chlorophenyl)-5-(4-chlorophenyl)-2-((R)-2,3-dihydroxypropyl)morpholin-3-one;
(2S,5R,6R)-4-((S)-1-(tert-butylsulfonyl)butan-2-yl)-6-(3-chlorophenyl)-5-(4-chlorophenyl)-2-((S)-2,3-dihydroxypropyl)morpholin-3-one;
3-(((2R,5R,6R)-4-((S)-1-(tert-butylsulfonyl)butan-2-yl)-6-(3-chlorophenyl)-5-(4-chlorophenyl)-3-oxomorpholin-2-yl)methyl)-1,1-diethylurea;
3-(((2S,5R,6R)-4-((S)-1-(tert-butylsulfonyl)butan-2-yl)-6-(3-chlorophenyl)-5-(4-chlorophenyl)-3-oxomorpholin-2-yl)methyl)-1,1-diethylurea;
tert-butyl (((2R,5R,6R)-4-((S)-1-(tert-utylsulfonyl)butan-2-yl)-6-(3-chlorophenyl)-5-(4-chlorophenyl)-3-oxomorpholin-2-yl)methyl)carbamate;
tert-butyl (((2S,5R,6R)-4-((S)-1-(tert-butylsulfonyl)butan-2-yl)-6-(3-chlorophenyl)-5-(4-chlorophenyl)-3-oxomorpholin-2-yl)methyl)carbamate;
(2R,5R,6R)-2-(aminomethyl)-4-((S)-1-(tert-butylsulfonyl)butan-2-yl)-6-(3-chlorophenyl)-5-(4-chlorophenyl)morpholin-3-one;
and (2S,5R,6R)-2-(aminomethyl)-4-((S)-1-(tert-butylsulfonyl)butan-2-yl)-6-(3-chlorophenyl)-5-(4-chlorophenyl)morpholin-3-one;
N-(((2R,5R,6R)-4-((S)-1-(tert-butylsulfonyl)butan-2-yl)-6-(3-chlorophenyl)-5-(4-chlorophenyl)-3-oxomorpholin-2-yl)methyl)acetamide;
N-(((2S,5R,6R)-4-((S)-1-(tert-butylsulfonyl)butan-2-yl)-6-(3-chlorophenyl)-5-(4-chlorophenyl)-3-oxomorpholin-2-yl)methyl)acetamide;
2-((2R,5R,6R)-4-((S)-1-(tert-butylsulfonyl)butan-2-yl)-6-(3-chlorophenyl)-5-(4-chlorophenyl)-3-oxomorpholin-2-yl)acetonitrile;
(2R,5R,6R)-2-((1H-tetrazol-5-yl)methyl)-4-((S)-1-(tert-butylsulfonyl)butan-2-yl)-6-(3-chlorophenyl)-5-(4-chlorophenyl)morpholin-3-one;
(2S,5R,6R)-2-((1H-tetrazol-5-yl)methyl)-4-((S)-1-(tert-butylsulfonyl)butan-2-yl)-6-(3-chlorophenyl)-5-(4-chlorophenyl)morpholin-3-one;
(2S,5R,6R)-4-((S)-2-(tert-butylsulfonyl)-1-cyclopropylethyl)-6-(3-chlorophenyl)-5-(4-chlorophenyl)-2-(isoxazol-5-ylmethyl)morpholin-3-one;
(2R,5R,6R)-2-((1H-1,2,3-triazol-5-yl)methyl)-4-((S)-2-(tert-butylsulfonyl)-1-cyclopropylethyl)-6-(3-chlorophenyl)-5-(4-chlorophenyl)morpholin-3-one;
(2S,5R,6R)-2-((1H-1,2,3-triazol-5-yl)methyl)-4-((S)-2-(tert-butylsulfonyl)-1-cyclopropylethyl)-6-(3-chlorophenyl)-5-(4-chlorophenyl)morpholin-3-one;
2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)acetonitrile;
2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetonitrile;
(2R,5R,6R)-2-((1H-1,2,4-triazol-5-yl)methyl)-4-((S)-2-(tert-butylsulfonyl)-1-cyclopropylethyl)-6-(3-chlorophenyl)-5-(4-chlorophenyl)morpholin-3-one;
(2S,5R,6R)-2-((1H-1,2,4-triazol-5-yl)methyl)-4-((S)-2-(tert-butylsulfonyl)-1-cyclopropylethyl)-6-(3-chlorophenyl)-5-(4-chlorophenyl)morpholin-3-one;
(2R,5R,6R)-4-((S)-2-(tert-butylsulfonyl)-1-cyclopropylethyl)-6-(3-chlorophenyl)-5-(4-chlorophenyl)-2-((3-methyl-1H-1,2,4-triazol-5-yl)methyl)morpholin-3-one;
(2S,5R,6R)-4-((S)-2-(tert-butylsulfonyl)-1-cyclopropylethyl)-6-(3-chlorophenyl)-5-(4-chlorophenyl)-2-((3-methyl-1H-1,2,4-triazol-5-yl)methyl)morpholin-3-one;
N-((S)-2-((2R,3R,6R)-2-(3-chlorophenyl)-3-(4-chlorophenyl)-6-((3-methyl-1H-1,2,4-triazol-5-yl)methyl)-5-oxomorpholino)-2-cyclopropylethyl)-N-(2-fluorophenyl)cyclopropanesulfonamide;
N-((S)-2-((2S,3R,6R)-2-(3-chlorophenyl)-3-(4-chlorophenyl)-6-((3-methyl-1H-1,2,4-triazol-5-yl)methyl)-5-oxomorpholino)-2-cyclopropylethyl)-N-(2-fluorophenyl)cyclopropanesulfonamide;
N-((S)-2-((2R,5R,6R)-2-((1H-1,2,3-triazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide;
N-((S)-2-((2S,5R,6R)-2-((1H-1,2,3-triazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide;
N-((S)-2-((2R,5R,6R)-2-((1H-1,2,4-triazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide;
N-((S)-2-((2S,5R,6R)-2-((1H-1,2,4-triazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide;
N-((S)-2-((2R,5R,6R)-2-((1H-tetrazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide;
N-((S)-2-((2S,5R,6R)-2-((1H-tetrazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide;
(2R,5R,6R)-4-((S)-1-(tert-butylsulfonyl)butan-2-yl)-6-(3-chlorophenyl)-5-(4-chlorophenyl)-2-((1-methyl-1H-tetrazol-5-yl)methyl)morpholin-3-one;
(2R,5R,6R)-4-((S)-1-(tert-butylsulfonyl)butan-2-yl)-6-(3-chlorophenyl)-5-(4-chlorophenyl)-2-((2-methyl-2H-tetrazol-5-yl)methyl)morpholin-3-one;
(2R,5R,6R)-4-((S)-2-(tert-butylsulfonyl)-1-cyclopropylethyl)-6-(3-chlorophenyl)-5-(4-chlorophenyl)-2-((1-methyl-1H-imidazol-2-yl)methyl)morpholin-3-one;
N-((S)-2-((2R,3R,6R)-2-(3-chlorophenyl)-3-(4-chlorophenyl)-6-((5-methyl-1,3,4-oxadiazol-2-yl)methyl)-5-oxomorpholino)-2-cyclopropylethyl)-N-(2-fluorophenyl)cyclopropanesulfonamide;
N-((S)-2-((2S,3R,6R)-2-(3-chlorophenyl)-3-(4-chlorophenyl)-6-((5-methyl-1,3,4-oxadiazol-2-yl)methyl)-5-oxomorpholino)-2-cyclopropylethyl)-N-(2-fluorophenyl)cyclopropanesulfonamide;
N-((S)-2-((2R,3R,6R)-2-(3-chlorophenyl)-3-(4-chlorophenyl)-6-((1-methyl-1H-tetrazol-5-yl)methyl)-5-oxomorpholino)-2-cyclopropylethyl)-N-(2-fluorophenyl)cyclopropanesulfonamide;
N-((S)-2-((2S,3R,6R)-2-(3-chlorophenyl)-3-(4-chlorophenyl)-6-((1-methyl-1H-tetrazol-5-yl)methyl)-5-oxomorpholino)-2-cyclopropylethyl)-N-(2-fluorophenyl)cyclopropanesulfonamide;
N-((S)-2-((2R,3R,6R)-2-(3-chlorophenyl)-3-(4-chlorophenyl)-6-((2-methyl-2H-tetrazol-5-yl)methyl)-5-oxomorpholino)-2-cyclopropylethyl)-N-(2-fluorophenyl)cyclopropanesulfonamide;

N-((S)-2-((2R,3R,6R)-2-(3-chlorophenyl)-3-(4-chlorophenyl)-6-((2-methyl-2H-tetrazol-5-yl)methyl)-5-oxomorpholino)-2-cyclopropylethyl)-N-(2-fluorophenyl)cyclopropanesulfonamide;

N-((S)-2-((2R,3R,6S)-2-(3-chlorophenyl)-3-(4-chlorophenyl)-5-oxo-6-(sulfamoylmethyl)morpholino)-2-cyclopropylethyl)-N-(2-fluorophenyl)cyclopropanesulfonamide;

N-((S)-2-((2S,3R,6S)-2-(3-chlorophenyl)-3-(4-chlorophenyl)-5-oxo-6-(sulfamoylmethyl)morpholino)-2-cyclopropylethyl)-N-(2-fluorophenyl)cyclopropanesulfonamide;

2-((2R,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)acetic acid;

2-((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)acetic acid;

2-((2R,5R,6R)-6-(3-chlorophenyl)-5-(4-chlorophenyl)-4-((2S,3S)-2-(isopropylsulfonyl)pentan-3-yl)-3-oxomorpholin-2-yl)acetic acid;

2-((2S,5R,6R)-6-(3-chlorophenyl)-5-(4-chlorophenyl)-4-((2S,3S)-2-(isopropylsulfonyl)pentan-3-yl)-3-oxomorpholin-2-yl)acetic acid;

2-((2R,5R,6R)-6-(3-chlorophenyl)-5-(4-chlorophenyl)-4-((2R,3S)-2-(isopropylsulfonyl)pentan-3-yl)-3-oxomorpholin-2-yl)acetic acid;

2-((2S,5R,6R)-6-(3-chlorophenyl)-5-(4-chlorophenyl)-4-((2R,3S)-2-(isopropylsulfonyl)pentan-3-yl)-3-oxomorpholin-2-yl)acetic acid;

2-((2R,5R,6R)-6-(3-chlorophenyl)-5-(4-chlorophenyl)-4-((1S,2S)-1-cyclopropyl-2-(isopropylsulfonyl)propyl)-3-oxomorpholin-2-yl)acetic acid;

2-((2S,5R,6R)-6-(3-chlorophenyl)-5-(4-chlorophenyl)-4-((1S,2S)-1-cyclopropyl-2-(isopropylsulfonyl)propyl)-3-oxomorpholin-2-yl)acetic acid;

2-((2R,5R,6R)-6-(3-chlorophenyl)-5-(4-chlorophenyl)-4-((1S,2R)-1-cyclopropyl-2-(isopropylsulfonyl)propyl)-3-oxomorpholin-2-yl)acetic acid;

2-((2S,5R,6R)-6-(3-chlorophenyl)-5-(4-chlorophenyl)-4-((1S,2R)-1-cyclopropyl-2-(isopropylsulfonyl)propyl)-3-oxomorpholin-2-yl)acetic acid;

2-((2R,5R,6R)-4-((2S,3S)-2-(tert-butylsulfonyl)pentan-3-yl)-6-(3-chlorophenyl)-5-(4-chlorophenyl)-3-oxomorpholin-2-yl)acetic acid;

2-((2S,5R,6R)-4-((2S,3S)-2-(tert-butylsulfonyl)pentan-3-yl)-6-(3-chlorophenyl)-5-(4-chlorophenyl)-3-oxomorpholin-2-yl)acetic acid;

2-((2R,5R,6R)-4-((2R,3S)-2-(tert-butylsulfonyl)pentan-3-yl)-6-(3-chlorophenyl)-5-(4-chlorophenyl)-3-oxomorpholin-2-yl)acetic acid;

2-((2S,5R,6R)-4-((2R,3S)-2-(tert-butylsulfonyl)pentan-3-yl)-6-(3-chlorophenyl)-5-(4-chlorophenyl)-3-oxomorpholin-2-yl)acetic acid;

2-((2R,5R,6R)-4-((2S,3R)-2-(tert-butylsulfonyl)pentan-3-yl)-6-(3-chlorophenyl)-5-(4-chlorophenyl)-3-oxomorpholin-2-yl)acetic acid;

2-((2S,5R,6R)-4-((2S,3R)-2-(tert-butylsulfonyl)pentan-3-yl)-6-(3-chlorophenyl)-5-(4-chlorophenyl)-3-oxomorpholin-2-yl)acetic acid;

2-((2R,5R,6R)-4-((2R,3R)-2-(tert-butylsulfonyl)pentan-3-yl)-6-(3-chlorophenyl)-5-(4-chlorophenyl)-3-oxomorpholin-2-yl)acetic acid;

2-((2S,5R,6R)-4-((2R,3R)-2-(tert-butylsulfonyl)pentan-3-yl)-6-(3-chlorophenyl)-5-(4-chlorophenyl)-3-oxomorpholin-2-yl)acetic acid;

2-((2R,5R,6R)-4-((S)-1-(tert-butylsulfonyl)propan-2-yl)-5-(4-chloro-3-fluorophenyl)-6-(3-chloro-5-fluorophenyl)-3-oxomorpholin-2-yl)acetic acid;

2-((2S,5R,6R)-4-((S)-1-(tert-butylsulfonyl)propan-2-yl)-5-(4-chloro-3-fluorophenyl)-6-(3-chloro-5-fluorophenyl)-3-oxomorpholin-2-yl)acetic acid;

2-((2R,5R,6R)-4-((S)-1-(tert-butylsulfonyl)butan-2-yl)-5-(4-chloro-3-fluorophenyl)-6-(3-chloro-5-fluorophenyl)-3-oxomorpholin-2-yl)acetic acid; or 2-((2S,5R,6R)-4-((S)-1-(tert-butylsulfonyl)butan-2-yl)-5-(4-chloro-3-fluorophenyl)-6-(3-chloro-5-fluorophenyl)-3-oxomorpholin-2-yl)acetic acid.

In embodiment 39, the present invention provides pharmaceutical compositions comprising a compound of any one of embodiments 1A, 1a or 1 to 38, or a pharmaceutically acceptable salt thereof, and a pharmaceutically acceptable excipient.

In embodiment 40, the present invention provides methods of treating cancer in a subject in need thereof, the methods comprising administering to the subject an effective dosage amount of a compound according to any one of embodiments 1A, 1a or 1 to 38, or a pharmaceutically acceptable salt thereof.

In embodiment 41, the present invention provides methods of treating cancer in accordance with embodiment 40, wherein the cancer is selected from bladder, breast, colon, rectum, kidney, liver, small cell lung cancer, non-small-cell lung cancer, esophagus, gall-bladder, ovary, pancreas, stomach, cervix, thyroid, prostate, skin, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma, Burkett's lymphoma, acute and chronic myelogenous leukemia, melanoma, endometrial cancer, head and neck cancer, glioblastoma, or osteosarcoma.

DETAILED DESCRIPTION OF THE INVENTION

The present invention provides compounds of Formula I or II, as defined above, or pharmaceutically acceptable salts thereof. The present invention also provides pharmaceutical compositions comprising a compound of Formula I or II, or pharmaceutically acceptable salts thereof, and methods of treating diseases and/or conditions, such as diabetes, using compounds of Formula I or II, or pharmaceutically acceptable salts thereof.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$alkyl.

The term "alkoxy" means an alkyl group bonded to an oxygen atom. Representative examples of alkoxy groups include methoxy, ethoxy, tert-butoxy, propoxy and isobutoxy. Common alkoxy groups are $C_{1-8}$alkoxy.

The term "halogen" or "halo" means chlorine, fluorine, bromine or iodine.

The term "alkenyl" means a branched or straight chain hydrocarbon having one or more carbon-carbon double bonds. Representative examples alkenyl groups include ethenyl, propenyl, allyl, butenyl and 4-methylbutenyl. Common alkenyl groups are $C_{2-8}$alkenyl.

The term "alkynyl" means a branched or straight chain hydrocarbon having one or more carbon-carbon triple bonds. Representative examples of alkynyl groups include ethynyl, propynyl (propargyl) and butynyl. Common alkynyl groups are $C_{2-8}$ alkynyl.

The term "cycloalkyl" means a cyclic, nonaromatic hydrocarbon. Examples of cycloalkyl groups include cyclopropyl, cyclobutyl, cyclopentyl, cyclohexyl and cycloheptyl. A cycloalkyl group can contain one or more double bond. Examples of cycloalkyl groups that contain double bonds include cyclopentenyl, cyclohexenyl, cyclohexadienyl and cyclobutadienyl. Common cycloalkyl groups are $C_{3-8}$ cycloalkyl groups. A cycloalkyl group can also be a bicyclic group comprising a cycloalkyl ring fused to an aryl or heteroaryl ring. An example of such a fused bicyclic group is tetrahydronapthalene.

The term "perfluoroalkyl" means an alkyl group in which all of the hydrogen atoms have been replaced with fluorine atoms. Common perfluoroalkyl groups are $C_{1-8}$perfluoroalkyl. An example of a common perfluoroalkyl group is —$CF_3$.

The term "acyl" means a group derived from an organic acid by removal of the hydroxy group (—OH). For example, the acyl group $CH_3C(=O)$— is formed by the removal of the hydroxy group from $CH_3C(=O)OH$.

The term "aryl" means a cyclic, aromatic hydrocarbon. Examples of aryl groups include phenyl and naphthyl. Common aryl groups are six to thirteen membered rings.

The term "heteroatom" as used herein means an oxygen, nitrogen or sulfur atom.

The term "heteroaryl" means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heterotaoms are particularly common.

The term "heterocycloalkyl" means a cycloalkyl group in which one or more of the carbon atoms has been replaced with a heteroatom. If the heterocycloalkyl group contains more than one heteroatom, the heteroatoms may be the same or different. Examples of heterocycloalkyl groups include tetrahydrofuryl, morpholinyl, piperazinyl, piperidinyl and pyrrolidinyl. It is also possible for the heterocycloalkyl group to have one or more double bonds, but is not aromatic. Examples of heterocycloalkyl groups containing double bonds include dihydrofuran. Common heterocycloalkyl groups are three to ten membered rings containing from 1 to 4 heteroatoms. Heterocycloalkyl groups that are five and six membered rings that contain 1 to 2 heterotaoms are particularly common. A heterocycloalkyl group can also be a bicyclic group comprising a heterocycloalkyl ring fused to an aryl or heteroaryl ring. Examples of such fused bicyclic ring include tetrahydroquinoline or tetrahydroisoquinoline.

It is also noted that the cyclic ring groups, i.e., aryl, heteroaryl, cycloalkyl, and heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyndazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b)pyridinyl, pyrano(3,4-b)pyrrolyl, benzofuryl, isobenzofuryl, benzo[b]thienyl, benzo[c]thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule or group is replaced with a group or atom. Typical substitutents include: halogen, $C_{1-8}$alkyl, hydroxyl, $C_{1-8}$alkoxy, $NR^xR^x$, nitro, cyano, halo or perhalo$C_{1-8}$alkyl, $C_{2-8}$alkenyl, $C_{2-8}$alkynyl, $SR^x$, $S(=O)_2R^x$, $C(=O)OR^x$, $C(=O)R^x$, wherein each $R^x$ is independently hydrogen or $C_1$-$C_8$ alkyl. It is noted that when the substituent is $NR^xR^x$, the $R^x$ groups may be joined together with the nitrogen atom to form a ring.

The term "oxo", when used as a substituent, means the =O group, which is typically attached to a carbon atom.

A group or atom that replaces a hydrogen atom is also called a substituent.

Any particular molecule or group can have one or more substituent depending on the number of hydrogen atoms that can be replaced.

The symbol "—" represents a covalent bond and can also be used in a radical group to indicate the point of attachment to another group. In chemical structures, the symbol is commonly used to represent a methyl group in a molecule.

The term "comprising" is meant to be open ended, including the indicated component but not excluding other elements.

A group or atom that replaces a hydrogen atom is also called a substituent.

Any particular molecule or group can have one or more substituent depending on the number of hydrogen atoms that can be replaced.

The symbol "—" represents a covalent bond and can also be used in a radical group to indicate the point of attachment to another group. In chemical structures, the symbol is commonly used to represent a methyl group in a molecule.

The term "therapeutically effective amount" means an amount of a compound that ameliorates, attenuates or eliminates one or more symptom of a particular disease or condition, or prevents or delays the onset of one of more symptom of a particular disease or condition.

The terms "patient" and "subject" may be used interchangeably and mean animals, such as dogs, cats, cows, horses, sheep and humans. Particular patients are mammals. The term patient includes males and females.

The term "pharmaceutically acceptable" means that the referenced substance, such as a compound of Formula I or II, or a salt of a compound of Formula I or II, or a formulation containing a compound of Formula I or II, or a particular excipient, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

The term "cancer" means a physiological condition in mammals that is characterized by unregulated cell growth. General classes of cancers include carcinomas, lymphomas, sarcomas, and blastomas.

The compounds of the present invention can be used to treat cancer. The methods of treating a cancer comprise administering to a patient in need thereof a therapeutically effective amount of a compound of Formula I or II, or a pharmaceutically acceptable salt thereof.

The compounds of the present invention can be used to treat tumors. The methods of treating a tumor comprise administering to a patient in need thereof a therapeutically effective amount of a compound of Formula I or II, or a pharmaceutically acceptable salt thereof.

The invention also concerns the use of a compound of the present invention in the manufacture of a medicament for the treatment of a condition such as a cancer.

Cancers which may be treated with compounds of the present invention include, without limitation, carcinomas such as cancer of the bladder, breast, colon, rectum, kidney, liver, lung (small cell lung cancer, and non-small-cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). Other cancers that can be treated with a compound of the present invention include endometrial cancer, head and neck cancer, glioblastoma, malignant ascites, and hematopoietic cancers.

Particular cancers that can be treated by the compounds of the present invention include soft tissue sarcomas, bone cancers such as osteosarcoma, breast tumors, bladder cancer, Li-Fraumeni syndrome, brain tumors, rhabdomyosarcoma, adrenocortical carcinoma, colorectal cancer, non-small cell lung cancer, and acute myeleogenous leukemia (AML).

In a particular embodiment of the invention that relates to the treatment of cancers, the cancer is identified as p53wildtype ($p53^{WT}$). In another particular embodiment, the cancer is identified as $p53^{WT}$ and CDKN2A mutant. In another aspect, the present invention provides a diagnostic for determining which patients should be administered a compound of the present invention. For example, a sample of a patient's cancer cells may be taken and analyzed to determine the status of the cancer cells with respect to p53 and/or CDKN2A. In one aspect, a patient having a cancer that is $p53^{WT}$ will be selected for treatment over patients having a cancer that is mutated with respect to p53. In another aspect, a patient having a cancer that is both $p53^{WT}$ and has a mutant CDNK2A protein is selected over a patient that does not have these characteristics. The taking of a cancer cells for analyses is well known to those skilled in the art. The term "$p53^{WT}$" means a protein encoded by genomic DNA sequence no. NC_000017 version 9 (7512445.7531642) (GenBank); a protein encoded by cDNA sequence no. NM_000546 (GenBank); or a protein having the GenBank sequence no. NP_000537.3. The term "CDNK2A mutant" means a CDNK2A protein that in not wildtype. The term "CDKN2A wildtype" means a protein encoded by genomic DNA sequence no. 9:21957751-21984490 (Ensembl ID); a protein encoded by cDNA sequence no. NM_000077 (GenBank) or NM_058195 9GenBank) or; or a protein having the GenBank sequence no. NP_000068 or NP_478102.

The compounds of the present invention can also be used to treat hyperproliferative disorders such as thyroid hyperplasia (especially Grave's disease), and cysts (such as hypervascularity of ovarian stroma, characteristic of polycystic ovarian syndrome (Stein-Leventhal syndrome)).

The compounds of the present invention can also be used to treat the following diseases or conditions: asthma, chronic obstructive pulmonary disease (COPD), emphysema, psoriasis, contact dermatitis, conjunctivitis, allergic rhinitis, systemic lupus erythematosus (SLE), ulcerative colitis, Crohn's disease, multiple sclerosis, rheumatoid arthritis, inflammatory bowel disease, Alzheimer's disease, atherosclerosis and Huntington's disease.

The compounds of the present invention can also be used to treat inflammatory diseases, hypoxia, ulcers, viral infections, bacterial infections, and bacterial sepsis.

The compounds of Formula I, or the pharmaceutically acceptable salts thereof, may also be administered in combination with one or more additional pharmaceutically active compounds/agents. In a particular embodiment, the additional pharmaceutically active agent is an agent that can be used to treat a cancer. For example, an additional pharmaceutically active agent can be selected from antineoplastic agents, anti-angiogenic agents, chemotherapeutic agents and peptidal cancer therapy agents. In yet another embodiment, the antineoplastic agents are selected from antibiotic-type agents, alkylating agents, antimetabolite agents, hormonal agents, immunological agents, interferon-type agents, kinase inhibitors, miscellaneous agents and combinations thereof. It is noted that the additional pharmaceutically active compounds/agents may be a traditional small organic chemical molecules or can be macromolecules such as a proteins, antibodies, peptibodies, DNA, RNA or fragments of such macromolecules.

Examples of specific pharmaceutically active agents that can be used in the treatment of cancers and that can be used in combination with one or more compound of the present invention include: methotrexate; tamoxifen; fluorouracil; 5-fluorouracil; hydroxyurea; mercaptopurine; cisplatin; carboplatin; daunorubicin; doxorubicin; etoposide; vinblastine; vincristine; pacitaxel; thioguanine; idarubicin; dactinomycin; imatinib; gemcitabine; altretamine; asparaginase; bleomycin; capecitabine; carmustine; cladisat. aq. NaCl solution; cyclophosphamine; cytarabine; decarazine; docetaxel; idarubicin; ifosfamide; irinotecan; fludarabine; mitosmycin; mitoxane; mitoxantrone; topotecan; vinorelbine; adriamycin; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; vorinostat; capecitabine; zoledronic acid; anastrozole; sunitinib; aprepitant and nelarabine, or a pharmaceutically acceptable salt thereof.

Additional pharmaceutically active agents that can be used in the treatment of cancers and that can be used in combination with one or more compound of the present invention include: vascular endothelial growth factor (VEGF) inhibitors, hepatocyte growth factor/scatter factor (HGF/SF) inhibitors, angiopoietin 1 and/or 2 inhibitors, tumor necrosis factor-related apoptosis-inducing ligand (TRAIL) agonists, recombinant human apo2 ligand (TRAIL), insulin-like growth factor 1 receptor (IGFR-1) inhibitors, cFMS inhibitors, HER 2 inhibitors, c-met inhibitors, aurora kinase inhibitors, CDK 4 and/or 6 inhibitors, and B-raf inhibitors.

Further additional pharmaceutically active agents that can be used in the treatment of cancers and that can be used in combination with one or more compound of the present invention include antibody drug conjugates (ADCs) whereby an antibody that binds to a protein, preferably on a cancer cell, is conjugated using a linker with a chemical compound that is detrimental to the cancer cell. Examples of chemical compounds that are detrimental to a cancer cell include maytansinoids derivatives and auristatin derivatives.

Still further additional pharmaceutically active agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 319; AMG 386; AMG 479 (Ganitumab); AMG 511, AMG 900, AMG 655 (Conatumumab); AMG 745; AMG 951; and AMG 706 (Motesanib), or a pharmaceutically acceptable salt thereof.

In another aspect, the present invention relates to the use of the compounds of the present invention in combination with one or more pharmaceutical agent that is an inhibitor of a protein in the phosphatidylinositol 3-kinase (PI3K) pathway. Combinations of compounds of the present invention along with inhibitors of proteins in the PI3K pathway have shown synergy in cancer cell growth assays, including enhanced apoptosis and cell killing. Examples of proteins in the PI3K pathway include PI3K, mTOR and PKB (also known as Akt). The PI3K protein exists in several isoforms including $\alpha$, $\beta$, $\delta$, or $\gamma$. It is contemplated that a PI3K inhibitor that can be used in combination with a compound of the present invention can be selective for one or more isoform. By selective it is meant that the compounds inhibit one or more isoform more that other isoforms. Selectivity is a concept well known to those is the art and can be measured with well known activity in vitro or cell-based assays. Preferred selectivity includes greater than 2 fold, preferably 10 fold, or more preferably 100 fold greater selectivity for one or more isoform over the other isoforms. In one aspect, the PI3K inhibitors that can be used in combination with compounds of the present invention is a PI3K $\alpha$ selective inhibitor. In another aspect the compound is a PI3K $\delta$ selective inhibitor.

Examples of PI3K inhibitors that can be used in combination with one or more compounds of the present invention include those disclosed in the following: PCT published application no. WO2010/151791; PCT published application no. WO2010/151737;

PCT published application no. WO2010/151735; PCT published application no. WO2010151740; PCT published application no. WO2008/118455; PCT published application no. WO2008/118454; PCT published application no. WO2008/118468; U.S. published application no. US20100331293; U.S. published application no. US20100331306; U.S. published application no. US20090023761; U.S. published application no. US20090030002; U.S. published application no. US20090137581; U.S. published application no. US2009/0054405; U.S. published application no. U.S. 2009/0163489; U.S. published application no. US 2010/0273764; U.S. published application no. U.S. 2011/0092504; or PCT published application no. WO2010/108074.

Preferred PI3K inhibitors for use in combination with compounds of the present invention include:

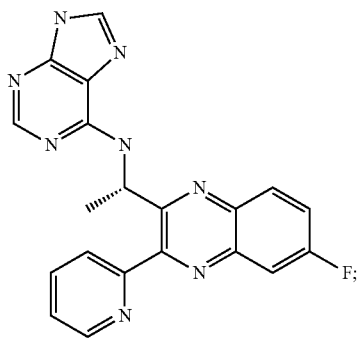

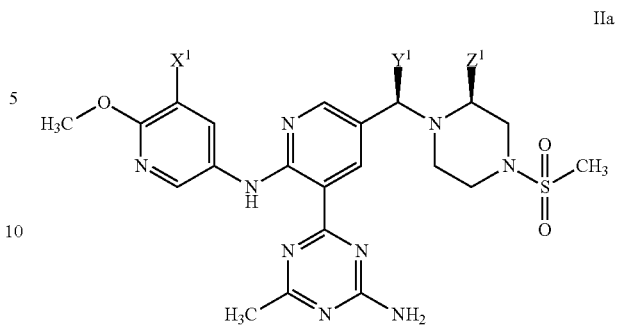

or a pharmaceutically acceptable salt thereof.

Also preferred is a compound of Formula IIa below, or a pharmaceutically acceptable salt thereof, wherein $X^1$ is fluorine or hydrogen; $Y^1$ is hydrogen or methyl; and $Z^1$ is hydrogen or methyl.

Compounds that inhibit both PI3K and mTOR (dual inhibitors) are known. In still another aspect, the present invention provides the use of dual PI3K and mTOR inhibitors for use in combination with a compound of the present invention.

mTOR is a protein in the PI3K pathway. It is another aspect of the present invention to use an mTOR inhibitor in combination with one or more compounds of the present invention. mTOR inhibitors that can be used in combination with compounds of the present invention include those disclosed in the following documents: PCT published application no. WO2010/132598 or PCT published application no. WO2010/096314.

PKB (Akt) is also a protein in the PI3K pathway. It is another aspect of the present invention to use an mTOR inhibitor in combination with one or more compounds of the present invention. PKB inhibitors that can be used in combination with compounds of the present invention include those disclosed in the following documents: U.S. Pat. Nos. 7,354,944; 7,700,636; 7,919,514; 7,514,566; U.S. patent application publication no. US 2009/0270445 A1; U.S. Pat. Nos. 7,919,504; 7,897,619; or PCT published application no. WO 2010/083246 A1.

The compounds of the present invention can be used in combination with CDK4 and/or 6 inhibitors. CDK 4 and/or 6 inhibitors that can be used in combination with compounds of the present invention include those disclosed in the following documents: PCT published application no. WO 2009/085185 or U.S. patent application publication no. US2011/0097305.

The compounds of the present invention can also be used in combination with pharmaceutically active agents that treat nausea. Examples of agents that can be used to treat nausea include: dronabinol; granisetron; metoclopramide; ondansetron; and prochlorperazine; or a pharmaceutically acceptable salt thereof.

In addition, the compounds of the present invention can be used in combination with other agents that can be used to treat cancer such as acemannan; aclarubicin; aldesleukin; alitretinoin; amifostine; amrubicin; amsacrine; anagrelide; arglabin; arsenic trioxide; BAM 002 (Novelos); bicalutamide; broxuridine; celmoleukin; cetrorelix; cladribine; clotrimazole; DA 3030 (Dong-A); daclizumab; denileukin diftitox; deslorelin; dilazep; docosanol; doxercalciferol; doxifluridine; bromocriptine; cytarabine; HIT diclofenac; interferon alfa; tretinoin; edelfosine; edrecolomab; eflornithine; emitefur; epirubicin; epoetin beta; etoposide phosphate; exisulind; fadrozole; finasteride; fludarabine phosphate; formestane; fotemustine; gallium nitrate; gemtuzumab zogamicin; gimeracil/oteracil/tegafur combination; glycopine; goserelin; heptaplatin; human chorionic gonadotropin; human fetal alpha fetoprotein; ibandronic acid; interferon alfa; interferon alfa natural; interferon alfa-2; interferon alfa-2a; interferon alfa-2b; interferon alfa-N1; interferon alfa-n3; interferon alfacon-1; interferon alpha natural; interferon beta; interferon beta-1a; interferon beta-1b; interferon gamma natural; interferon gamma-1a; interferon gamma-1b; interleukin-1 beta; iobenguane; irsogladine; lanreotide; LC 9018 (Yakult); leflunomide; lenograstim; lentinan sulfate; letrozole; leukocyte alpha interferon; leuprorelin; levamisole+fluorouracil; liarozole; lobaplatin; lonidamine; lovastatin; masoprocol; melarsoprol; metoclopramide; mifepristone; miltefosine; mirimostim; mismatched double stranded RNA; mitoguazone; mitolactol; mitoxantrone; molgramostim; nafarelin; naloxone+pentazocine; nartograstim; nedaplatin; nilutamide; noscapine; novel erythropoiesis stimulating protein; NSC 631570 octreotide; oprelvekin; osaterone; paclitaxel; pamidronic acid; peginterferon alfa-2b; pentosan polysulfate sodium; pentostatin; picibanil; pirarubicin; rabbit antithymocyte polyclonal antibody; polyethylene glycol interferon alfa-2a; porfimer sodium; raltitrexed; rasburicase; rhenium Re 186 etidronate; RH retinamide; romurtide; samarium (153 Sm) lexidronam; sargramostim; sizofuran; sobuzoxane; sonermin; strontium-89 chloride; suramin; tasonermin; tazarotene; tegafur; temoporfin; teniposide; tetrachlorodecaoxide; thymalfasin; thyrotropin alfa; toremifene; tositumomab-iodine 131; treosulfan; tretinoin; trilostane; trimetrexate; triptorelin; tumor necrosis factor alpha natural; ubenimex; bladder cancer vaccine; Maruyama vaccine; melanoma lysate vaccine; valrubicin; verteporfin; virulizin; zinostatin stimalamer; abarelix; AE 941 (Aeterna); ambamustine; antisense oligonucleotide; bcl-2 (Genta); APC 8015 (Dendreon); dexaminoglutethimide; diaziquone; EL 532 (Elan); EM 800 (Endorecherche); eniluracil; etanidazole; fenretinide; filgrastim SDO1 (Amgen); galocitabine; gastrin 17 immunogen; HLA-B7 gene therapy (Vical); granulocyte macrophage colony stimulating factor; histamine dihydrochloride; ibritumomab tiuxetan; ilomastat; IM 862 (Cytran); interleukin-2; iproxifene; LDI 200 (Milkhaus); leridistim; lintuzumab; CA 125 monoclonal antibody (MAb) (Biomira); cancer MAb (Japan Pharmaceutical Development); HER-2 and Fc MAb (Medarex); idiotypic 105AD7 MAb (CRC Technology); idiotypic CEA MAb (Trilex); LYM-1-iodine 131 MAb (Techniclone); polymorphic epithelial mucin-yttrium 90 MAb (Antisoma); marimastat; menogaril; mitumomab; motexafin gadolinium; MX 6 (Galderma); nolatrexed; P 30 protein; pegvisomant; porfiromycin; prinomastat; RL 0903 (Shire); rubitecan; satraplatin; sodium phenylacetate; sparfosic acid; SRL 172 (SR Pharma); SU 5416 (Pfizer); TA 077 (Tanabe); tetrathiomolybdate; thaliblastine; thrombopoietin; tin ethyl etiopurpurin; tirapazamine; cancer vaccine (Biomira); melanoma vaccine (New York University); melanoma vaccine (Sloan Kettering Institute); melanoma oncolysate vaccine (New York Medical College); viral melanoma cell lysates vaccine (Royal Newcastle Hospital); or valspodar. It is noted that the agents recited above may also be administered as pharmaceutically acceptable salts when appropriate.

The compounds of the present invention may also be used in combination with radiation therapy, hormone therapy, surgery and immunotherapy, which therapies are well known to those skilled in the art.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$)alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N, N-($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$) alkanoyloxy)ethyl, 1-methyl-1-(($C_1$-$C_6$)alkanoyloxy)ethyl, ($C_1$-$C_6$)alkoxycarbonyloxymethyl, N-($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as Z and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diastereomeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the tetrazole moiety are included in this invention. Also, for example, all keto-enol or imine-enamine forms of the compounds are included in this invention.

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{16}$O, $^{17}$O, $^{18}$O, $^{31}$P, $^{32}$P, $^{35}$S, $^{18}$F, and $^{36}$Cl. In one aspect, the present invention relates to compounds wherein one or more hydrogen atom is replaced with deuterium ($^2$H) atoms.

Compounds of the present invention that contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., SCH$_3$), N-hydroxsuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents, published patent applications and other publications recited herein are hereby incorporated by reference.

The examples presented below illustrate specific embodiments of the present invention. These examples are meant to be representative and are not intended to limit the scope of the claims in any manner. Unless otherwise noted, when a percent is used herein with respect to a solid, the percent is by weight with respect to the referenced solid composition. When a percent is used herein with respect to a liquid, the percent is by volume with respect to the referenced solution.

$^1$H-NMR spectra were typically acquired on a Bruker Avance III 500 spectrometer system (Bruker, Bilerica, Mass.) operating at a $^1$H frequency of 500.13 MHz, equipped with a Bruker 5 mm PABBI probe with a z-axis gradient; or on a Bruker Avance II or Avance III 400 spectrometer operating at a $^1$H frequency of 400.23 MHz, equipped with a Bruker 5 mm PABBO probe with a z-axis gradient. Samples were typically dissolved in 500 μL of either DMSO-d$_6$ or CD$_3$OD for NMR analysis. $^1$H chemical shifts are referenced to the residual solvent signals from DMSO-d$_6$ at δ 2.50 and CD$_3$OD at δ 3.30.

Significant peaks are tabulated and typically include: number of protons, multiplicity (s, singlet; d, doublet; dd, doublet of doublets; t, triplet; q, quartet; m, multiplet; br s, broad singlet) and coupling constant(s) in Hertz.

Electron Ionization (EI) mass spectra were typically recorded on an Agilent Technologies 6140 Quadrupole LC/MS mass spectrometer. Mass spectrometry results are reported as the ratio of mass over charge, sometimes followed by the relative abundance of each ion (in parentheses). Starting materials in the Examples below are typically either available from commercial sources such as Sigma-Aldrich, St. Louis, Mo., or via literature procedures.

The following abbreviations may be used herein:
~ about
+ve or pos. ion positive ion
Δ heat
Ac acetyl
Ac$_2$O acetic anhydride
aq aqueous
AcOH acetic acid
Bn benzyl
Boc tert-butyloxycarbonyl
BSA bovine serum albumin
Bu butyl
Bz benzoyl
Calcd or Calc'd calculated
Conc. concentrated
CSA camphor-10-sulfonic acid
d day(s)
DBU 1,8-diazabicyclo[5.4.0]undec-7-ene
DCE dichloroethane
DCM dichloromethane
DDQ 2,3-dichloro-5,6-dicyano-1,4-benzoquinone
DEA diethylamine
Dess-Martin periodinane;
1,1,1-triacetoxy-1,1-dihydro-1,2-benziodoxol-3-(1H)-one
Dess-Martin reagent
DIEA or DIPEA diisopropylethylamine
DMAP 4-dimethylaminopyridine
DME 1,2-dimethoxyethane
DMF N,N-dimethylformamide
DMSO dimethyl sulfoxide
DPPA diphenylphosphoryl azide
dr diastereomeric ratio
DTT dithiothreitol
DVB divinylbenzene
EDC N-ethyl-N'-(3-dimethylaminopropyl)carbodiimide
ee or e.e. enantiomeric excess
eq equivalent
ESI or ES electrospray ionization
Et ethyl
Et$_2$O diethyl ether
Et$_3$N triethylamine
EtOAc ethyl acetate
EtOH ethyl alcohol
g gram(s)
h hour(s)
HATU O-(7-azabenzotriazol-1-yl)-N,N,N',N'-tetramethyluronium hexafluorophosphate
HBTU O-benzotriazole-N,N,N',N'-tetramethyl-uronium-hexafluorophosphate
Hex hexanes
HMPA hexamethylphosphoramide
HOAt 1-hydroxy-7-azabenzotriazole
HOBt hydroxybenzotriazole
HPLC high pressure liquid chromatography
IPA or iPrOH isopropyl alcohol
Jones reagent solution of chromium(IV)oxide and sulfuric acid in water
KHMDS potassium hexamethyldisilazide
KOAc potassium acetate
LCMS, LC-MS or LC/MS liquid chromatography mass spectrometry
LDA lithium diisopropylamide
LHMDS or LiHMDS lithium hexamethyldisilazide
L-Selectride® lithium tri-sec-butylborohydride (Sigma-Aldrich, St. Louis)
M molar (mol L$^{-1}$)
mCPBA m-chloroperoxybenzoic acid
Me methyl
MeCN acetonitrile
MeI iodomethane
MeOH methyl alcohol
mg milligram(s)
min minute(s)
mL milliliter(s)
M mole(s)
MS mass spectrometry
MsCl methanesulfonyl chloride
MTBE or MtBE methyl tert-butyl ether
m/z mass-to-charge ratio
NaHMDS sodium hexamethyldisilazide
NaOtBu sodium tert-butoxide
NBS N-bromosuccinimide
nBuLi n-butyl lithium
NMO N-methylmorpholine-N-oxide
NMP 1-methyl-2-pyrrolidinone
NMR nuclear magnetic resonance
N-Selectride® sodium tri-sec-butylborohydride (Sigma-Aldrich, St. Louis)
PBS phosphate buffered saline
PMB paramethoxybenzyl Pr propyl
ppm parts per million
PTFE polytetrafluoroethylene
p-tol para-toluoyl
rac racemic
RP-HPLC or RPHPLC reversed phase high pressure liquid chromatography
RT or rt or r.t. room temperature
sat. or sat'd or satd saturated
SFC supercritical fluid chromatography
TBAF tetrabutylammonium fluoride
TBDMS tert-butyldimethylsilyl
TBDMS-Cl tert-butyldimethylsilyl chloride
TBDPS tert-butyldiphenylsilyl
TEMPO (2,2,6,6-tetramethylpiperidin-1-yl)oxidanyl
tert or t tertiary
TFA trifluoroacetic acid
THF tetrahydrofuran
TIPS triisopropylsilyl
TLC thin layer chromatography
TMS trimethylsilyl or trimethylsilane
TPAP tetrapropylammonium perruthenate
$t_R$ retention time
tBuOH tert-butyl alcohol
v/v volume per volume

EXAMPLES

General Synthetic Schemes

Compounds of the present invention generally can be prepared beginning with commercially available starting materials and using synthetic techniques known to those of skill in the art. Outlined below are some reaction schemes suitable for preparing compounds of the present invention. Further exemplification is found in the specific examples provided.

General Procedure 1

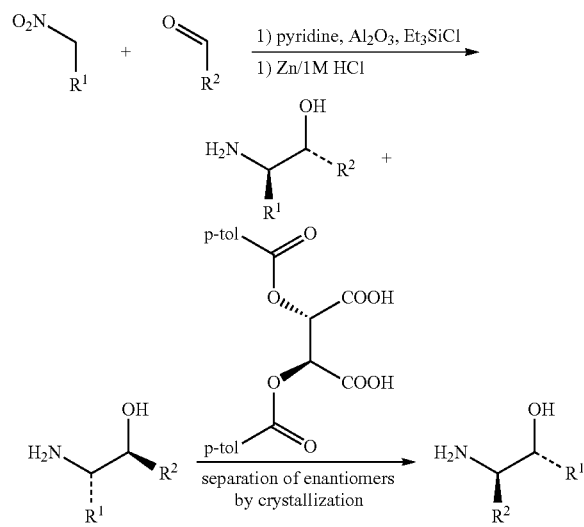

Intermediate A1

(1R,2R)-2-Amino-1-(3-chlorophenyl)-2-(4-chlorophenyl)ethanol and (1S,2S)-2-Amino-1-(3-chlorophenyl)-2-(4-chlorophenyl)ethanol

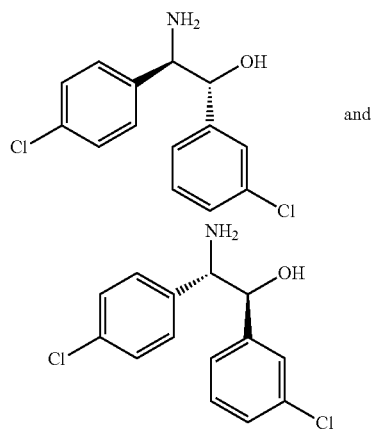

Step A. 1-Chloro-4-(nitromethyl)benzene

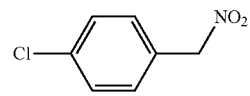 [SMILES: O=[N+]([O-])Cc1ccc(Cl)cc1]

A suspension of AgNO$_2$ (392 g) in diethylether (1.6 L) was cooled to 0° C. and a solution of 4-chlorobenzylbromide (395 g, 1.92 mol) in diethylether (1.6 L) was added dropwise over 1 h (temperature maintained below 3° C. during addition). The reaction mixture was stirred for 16 h at 0° C. in the dark. Then the mixture was filtered and the solids were washed with diethylether (3×). The combined filtrates were concentrated under reduced pressure. The residue was purified by column chromatography on silica gel (eluent: 0 to 10% EtOAc in heptane; gradient elution) to give the title compound.

Step B. (1R,2R)-2-Amino-1-(3-chlorophenyl)-2-(4-chlorophenyl)ethanol hydrochloride and (1S,2S)-2-Amino-1-(3-chlorophenyl)-2-(4-chlorophenyl)ethanol hydrochloride To a flask containing 3-chlorobenzaldehyde (135 mL, 168 g, 1.19 mol) was added 1-chloro-4-(nitromethyl)-benzene (205 g, 1.19 mol, Step A), alumina (135 g), pyridine (96 mL, 1.19 mol) and chlorotriethylsilane (200 mL, 180 g, 1.19 mol). The flask was covered in aluminum foil and spun for 16 h in the dark at room temperature on a rotary evaporator. The resulting thick paste was then filtered and washed with isopropanol. The filtrate was divided into two equal portions and used in the next step. Procedure for each portion: To each solution was added 1 M HCl (7 L, 7 mol) and then Zn powder (800 g, 12.3 mol) was added in several portions. The reaction mixture was stirred until the observed exothermic reaction (to 35° C.) was complete (90 mins). Then the mixture was cooled to 0° C. and basified with 30% NaOH to a pH of about 10. The suspension was filtered through a pad of Celite® (J. T. Baker, Phillipsberg, N.J., diatomaceous earth) and washed with DCM. The filtrate was transferred to a separatory funnel and the layers were separated. The aqueous layer was extracted with DCM. The combined organic layers were dried over $Na_2SO_4$, filtered and the filtrate was concentrated under reduced pressure. The residue was dissolved in MTBE (1.5 L) and cooled to 0° C. Then 4 N HCl in dioxane (375 mL, 1.5 mol) was added dropwise. The solid was collected by filtration. The solid was purified by crystallization from dioxane/ ethanol to give a racemic mixture of the title compounds.

Step C. (1R,2R)-2-Amino-1-(3-chlorophenyl)-2-(4-chlorophenyl)ethanol and (1S,2S)-2-Amino-1-(3-chlorophenyl)-2-(4-chlorophenyl)ethanol To a racemic mixture of (1R,2R)-2-amino-1-(3-chlorophenyl)-2-(4-chlorophenyl)ethanol hydrochloride and (1S,2S)-2-amino-1-(3-chlorophenyl)-2-(4-chlorophenyl)ethanol hydrochloride (65.5 g, 0.205 mol, Step B) in EtOAc (500 mL) was added 2 N aq. NaOH (500 mL, 1 mol). The layers were separated and the aqueous layer was extracted with EtOAc. The combined organic layers were washed with brine, dried over $Na_2SO_4$ and concentrated under reduced pressure to give a racemic mixture of the title compounds as a white solid. Mass Spectrum (ESI) m/z=282.0 (M+H).

Alternatively, Intermediate A1 can also be prepared by the following General Procedure 2:

General Procedure 2

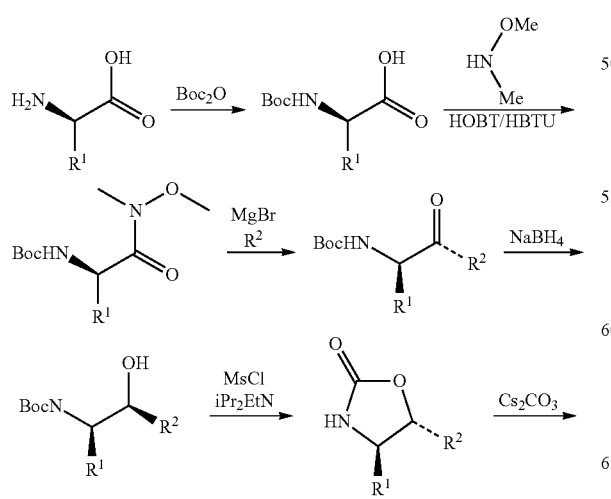

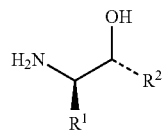

Intermediate A1

(1R,2R)-2-Amino-1-(3-chlorophenyl)-2-(4-chlorophenyl)ethanol and (1S,2S)-2-Amino-1-(3-chlorophenyl)-2-(4-chlorophenyl)ethanol Step A. (R)-2-((tert-Butoxycarbonyl)amino)-2-(4-chlorophenyl)acetic acid and (S)-2-((tert-Butoxycarbonyl)amino)-2-(4-chlorophenyl)acetic acid

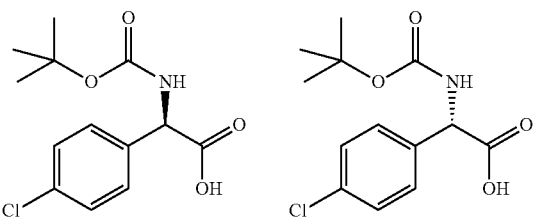 [SMILES: CC(C)(C)OC(=O)N[C@@H](C(=O)O)c1ccc(Cl)cc1 ; CC(C)(C)OC(=O)N[C@H](C(=O)O)c1ccc(Cl)cc1]

To a stirred solution of racemic 2-amino-2-(4-chlorophenyl)acetic acid (20 g, 108 mmol) in dioxane:water (200 mL:100 mL) at 0° C. was added sodium hydroxide (1N aqueous solution, 100 mL, 100 mmol). The reaction was stirred for 5 minutes and then di-tert-butyl dicarbonate (35 g, 162 mmol) and sodium hydrogen carbonate (9.08 g, 108 mmol) were added in one portion. The reaction was stirred at r.t. for 24 hours. After this time the reaction was evaporated under a vacuum and then acidified to a pH of about 4 with saturated aqueous $KHSO_4$ solution. The separated organic layer was extracted with EtOAc (300 mL), dried over $MgSO_4$, filtered and the filtrate was evaporated under reduced pressure to give the title compound. Mass Spectrum (ESI) m/z=229.9 (M−tBu+H).

Step B. (R)-tert-Butyl 1-(4-chlorophenyl)-2-(methoxy(methyl)amino)-2-oxoethylcarbamate and (S)-tert-Butyl 1-(4-chlorophenyl)-2-(methoxy(methyl)amino)-2-oxoethylcarbamate

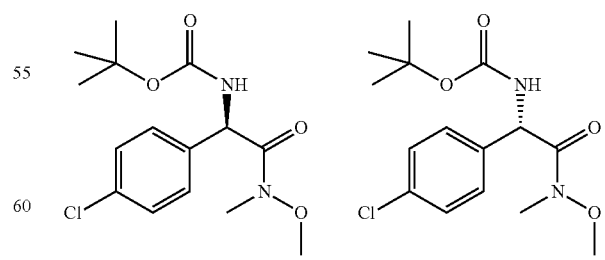

To a stirred solution of 2-((tert-butoxycarbonyl)amino)-2-(4-chlorophenyl)acetic acid (14 g, 49 mmol, Step A), HBTU (19 g, 49 mmol), HOBT (7.5 g, 49 mmol) and DIEA (8.5 mL, 49 mmol) at 0° C. in DCM (200 mL) was added a solution of N,O-dimethylhydroxylamine hydrochloride (4.8 g, 49 mmol) and DIEA (8.5 mL, 49 mmol) in DCM (40 mL) dropwise over 10 minutes. The reaction was allowed to warm to r.t. overnight. After this time the solvent was evaporated under a vacuum and the resulting oil was dissolved in EtOAc (400 mL) and NH₄Cl (100 mL, sat. aq. solution). The separated organic layer was washed with NaCl (saturated aqueous solution, 100 mL), dried over MgSO₄, filtered and evaporated under a vacuum. Column chromatography on silica gel (80 g, hexanes/EtOAc, 1:0 to 1:1, gradient elution) gave the title compound as a white solid. Mass Spectrum (ESI) m/z=351.1 (M+23).

Step C. (R)-tert-Butyl (2-(3-chlorophenyl)-1-(4-chlorophenyl)-2-oxoethyl)carbamate and (S)-tert-Butyl (2-(3-chlorophenyl)-1-(4-chlorophenyl)-2-oxoethyl) carbamate

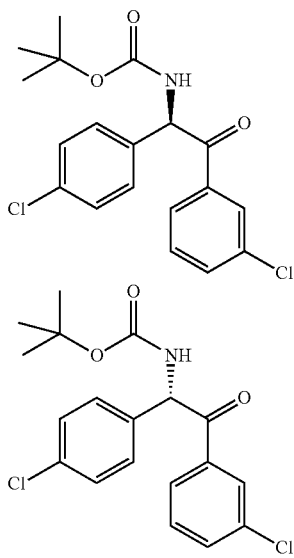

To a stirred solution of tert-butyl 1-(4-chlorophenyl)-2-(methoxy(methyl)amino)-2-oxoethylcarbamate (3.2 g, 10 mmol, Step B) in THF (50 mL) at −10° C. was added (3-chlorophenyl)magnesium bromide (49 mL, 24 mmol, 0.5 M in THF) dropwise over 5 minutes. The reaction was stirred at r.t. for 6 hours and then it was quenched by the addition of a saturated aqueous solution of NH₄Cl (40 mL). The mixture was then partitioned between EtOAc (200 mL) and water (50 mL). The separated aqueous layer was extracted with EtOAc (100 mL) and the combined organic extracts were washed with NaCl (50 mL, saturated aqueous solution), dried over MgSO₄, filtered and the filtrate was evaporated under a vacuum. Column chromatography on silica gel (80 g, hexanes/EtOAc 1:0 to 2:1, gradient elution) gave a racemic mixture of the title compounds as a white solid.

Step D. tert-Butyl ((1R,2S)-2-(3-chlorophenyl)-1-(4-chlorophenyl)-2-hydroxyethyl)carbamate and tert-Butyl ((1S,2R)-2-(3-chlorophenyl)-1-(4-chlorophenyl)-2-hydroxyethyl)carbamate

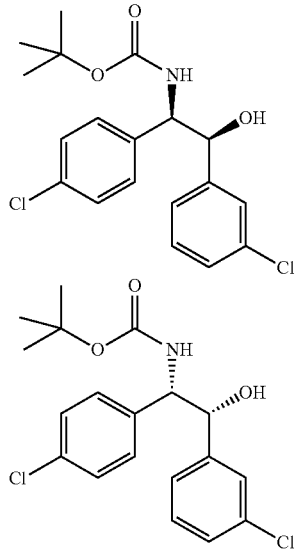

To a stirred solution of tert-butyl (2-(3-chlorophenyl)-1-(4-chlorophenyl)-2-oxoethyl)carbamate (8.2 g, 22 mmol, Step C) in THF (100 mL) at 0° C. was added a suspension of sodium borohydride (0.82 g, 22 mmol) in THF (30 mL). The reaction was allowed to warm to r.t. for 3 hours. After this time the reaction was treated with EtOAc (300 mL) and NaHCO₃ (50 mL, sat. aq. solution). The separated organic layer was washed with NaCl (saturated aqueous solution, 50 mL), dried over MgSO₄, filtered and the filtrate was evaporated under a vacuum to give a mixture of the title compounds as a white solid.

Step E. (4R,5R)-5-(3-Chlorophenyl)-4-(4-chlorophenyl)oxazolidin-2-one and (4S,5S)-5-(3-Chlorophenyl)-4-(4-chlorophenyl)oxazolidin-2-one

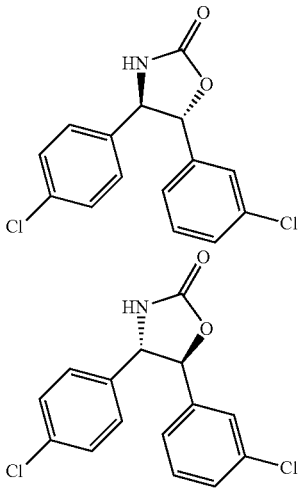

To a stirred solution of tert-butyl ((1R,2S)-2-(3-chlorophenyl)-1-(4-chlorophenyl)-2-hydroxyethyl)carbamate and tert-butyl ((1S,2R)-2-(3-chlorophenyl)-1-(4-chlorophenyl)-2-hydroxyethyl)carbamate (2.5 g, 6.54 mmol, Step D) in DCM (25 mL) at r.t. was added methane sulfonyl chloride (1.01 mL, 13.08 mmol) and DIEA (4.56 mL, 26.16 mmol) and the reaction was heated at 80° C. for 48 hours. After this time the reaction was cooled to r.t. and diluted with DCM (80 mL). The organic layer was washed with NaHCO$_3$ (saturated aqueous solution, 30 mL), NaCl (saturated aqueous solution, 30 mL), dried over MgSO$_4$, filtered and evaporated in vacuo. Column chromatography (40 g SiO$_2$, hexanes/EtOAc, 1:0 to 1:1, gradient elution) gave the title compounds as a white solid.

Step F. (1R,2R)-2-Amino-1-(3-chlorophenyl)-2-(4-chlorophenyl)ethanol and (1S,2S)-2-Amino-1-(3-chlorophenyl)-2-(4-chlorophenyl)ethanol (4R,5R)-5-(3-chlorophenyl)-4-(4-chlorophenyl)oxazolidin-2-one and (4S,5S)-5-(3-chlorophenyl)-4-(4-chlorophenyl)oxazolidin-2-one (400 mg, 1.30 mmol, Step E) in water (10 mL) and acetone (10 mL) was treated with Cs$_2$CO$_3$ (4.23 g, 12.98 mmol) in a microwave vessel. The reaction was heated in a microwave reactor for 50 minutes to 200° C. After this time the reaction mixture was concentrated and diluted with DCM (40 mL) and water (20 mL). The layers were separated and the organic layer was dried over MgSO$_4$, filtered and the filtrate was concentrated in vacuo. Column chromatography (12 g SiO$_2$, EtOAc/hexanes, 1:0 to 1:1, gradient elution) gave the title compounds as a white solid. Mass Spectrum (ESI) m/z=282.0 (M+H).

Intermediate A2

(1R,2R)-2-Amino-1-(3-chlorophenyl)-2-(4-chlorophenyl)ethanol

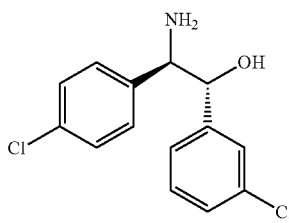

A racemic mixture of (1R,2R)-2-amino-1-(3-chlorophenyl)-2-(4-chlorophenyl)ethanol and (1S,2S)-2-amino-1-(3-chlorophenyl)-2-(4-chlorophenyl)ethanol (57 g, 0.2 mol; Intermediate A1) was dissolved in ethanol (2.65 L) and (+)-di-p-toluoyl-D-tartaric acid (68.4 g, 0.169 mol) was added. The mixture was heated to reflux and water was added until the solution became clear (175 mL). The mixture was seeded with seeding crystals (ee 95%) and allowed to cool to rt over a period of 16 h. The mixture was filtered and the solid was washed with ethanol and dried to give the salt, ee. 75%. This salt was recrystallized twice from 12.5:1 EtOH/water (36 mL/gram of salt) using seed crystals to initialize crystallization to provide the salt with 97.6% ee. The salt was dissolved in 1:1 EtOAc/2 N aq. NaOH. The layers were separated and the aqueous layer was extracted with EtOAc. The combined organic layers were washed with brine, dried over Na$_2$SO$_4$, filtered and the filtrate was concentrated under reduced pressure to give the title compound with 97.8% ee. Enantiomeric excess was determined by HPLC using a Chiralpak® AD-H column (Chiral Technologies, Inc., West Chester, Pa.) and eluting with 5% IPA/hexanes.

R$_t$=20.1 min. [α]$_D^{23.5}$=+92.7° (c=0.385, in MeOH).

(1S,2S)-2-amino-1-(3-chlorophenyl)-2-(4-chlorophenyl) ethanol: R$_t$=21.7 min.

General Procedure 3

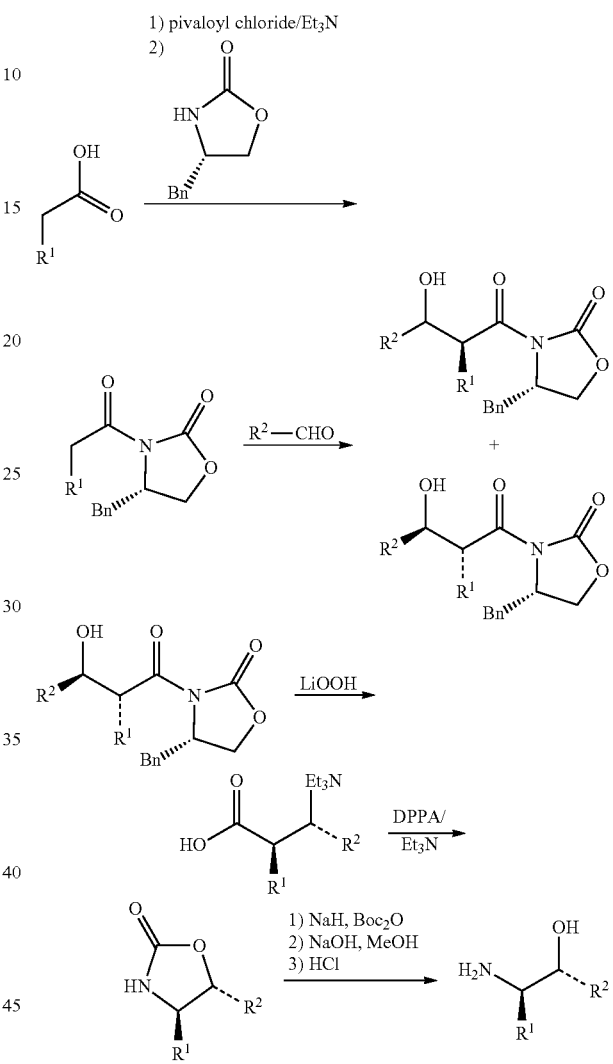

Intermediate B1

(1R,2R)-2-Amino-2-(4-chloro-2-fluorophenyl)-1-(3-chlorophenyl)ethanol

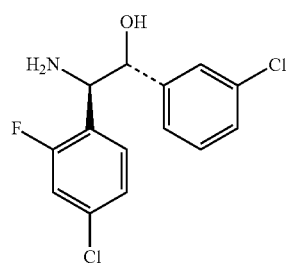 [SMILES: N[C@H](c1ccc(Cl)cc1F)[C@H](O)c1cccc(Cl)c1]

Step A. (S)-4-Benzyl-3-(2-(4-chloro-2-fluorophenyl)acetyl)oxazolidin-2-one

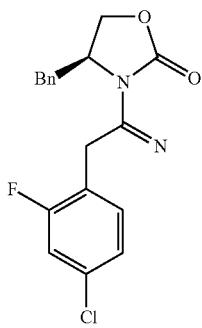 [SMILES: N=C(Cc1ccc(Cl)cc1F)N1C(=O)OC[C@@H]1Cc1ccccc1]

(S)-4-Benzyloxazolidin-2-one (4.68 g, 26.4 mmol), 2-(4-chloro-2-fluorophenyl)acetic acid (7.47 g, 39.6 mmol), and triethylamine (11.04 mL, 79 mmol) were dissolved in 50 mL of toluene and the mixture was heated to 80° C. Then pivaloyl chloride (4.9 mL, 39.6 mmol) in 10 mL of toluene was added while the internal temp was maintained between 80° C. and 85° C. The reaction mixture was heated to reflux for 18 h, cooled to room temperature and was washed with 2 N hydrochloric acid, 5% aqueous sodium carbonate, and brine. The organic layer was concentrated and the crude product was triturated with hexane. The title compound was filtered off as a white solid.

$^1$H NMR (400 MHz, CDCl$_3$) δ ppm 2.77-2.86 (m, 1 H) 3.31 (dd, J=13.30, 3.13 Hz, 1 H) 4.21-4.37 (m, 4 H) 4.66-4.74 (m, 1 H) 7.13-7.23 (m, 5 H) 7.28-7.37 (m, 3 H).

Step B. (S)-4-Benzyl-3-((2R,3S)-2-(4-chloro-2-fluorophenyl)-3-(3-chlorophenyl)-3-hydroxypropanoyl)oxazolidin-2-one

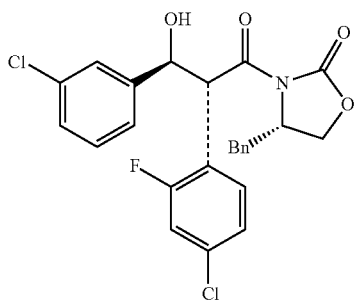 [SMILES: O=C1OC[C@H](Cc2ccccc2)N1C(=O)[C@H](c1ccc(Cl)cc1F)[C@H](O)c1cccc(Cl)c1]

To a stirred solution of (S)-4-benzyl-3-(2-(4-chloro-2-fluorophenyl)acetyl)oxazolidin-2-one (12 g, 35 mmol, Step A), 3-chlorobenzaldehyde (7.8 g, 55 mmol), chlorotrimethylsilane (11 g, 104 mmol) and magnesium chloride (0.66 g, 6.9 mmol) in 80 mL of EtOAc under nitrogen, was added dropwise a solution of triethylamine (14 g, 138 mmol) in 20 mL of EtOAc. The reaction mixture was stirred overnight and then 200 mL of sat. aq. NH$_4$Cl solution and 100 mL of EtOAc were added. The organic layer was washed with brine, dried over MgSO$_4$ and concentrated. Next, the crude product was dissolved in 100 mL of DCM, and 15 mL of 4N HCl/dioxane, diluted to 50 mL with DCM, was added dropwise. After the removal of the silyl group was complete (less than 2 h), the reaction mixture was quenched by portionwise addition of 200 mL of a sat. aq. NaHCO$_3$ solution. The organic layer was separated, washed with brine, dried over MgSO$_4$, filtered and the filtrate was concentrated in vacuo to give the crude product. Purification via silica gel chromatography employing a gradient of ethyl acetate in hexane yielded the desired product in the slower-eluting fraction. $^1$H NMR (400 MHz, CDCl$_3$) δ ppm 2.81 (dd, J=13.50, 9.00 Hz, 1 H) 3.27 (dd, J=13.60, 3.42 Hz, 1 H) 3.36 (d, J=6.46 Hz, 1 H) 4.13 (d, J=7.04 Hz, 1 H) 4.65-4.73 (m, 1 H) 5.19-5.26 (m, 1 H) 5.65 (d, J=8.02 Hz, 1 H) 6.96 (dd, J=9.78, 2.15 Hz, 1 H), 7.00-7.04 (m, 11 H). Mass Spectrum (ESI) m/z=470.0 (M−18).

Step C. (2R,3S)-2-(4-Chloro-2-fluorophenyl)-3-(3-chlorophenyl)-3-hydroxypropanoic acid

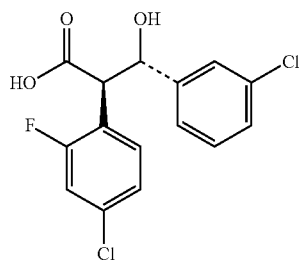 [SMILES: O=C(O)[C@H](c1ccc(Cl)cc1F)[C@H](O)c1cccc(Cl)c1]

(S)-4-Benzyl-3-((2R,3S)-2-(4-chloro-2-fluorophenyl)-3-(3-chlorophenyl)-3-hydroxypropanoyl)oxazolidin-2-one (7.19 g, 15 mmol, Step B) and hydrogen peroxide (8.6 g, 88 mmol) were combined in 125 mL of THF and cooled in an ice bath. A solution of LiOH (0.71 g, 15 mmol) in 10 mL of water was added dropwise over 10 minutes. After 25 minutes the reaction mixture was removed from the ice bath, concentrated and redissolved in 200 mL of DCM and 200 mL of a citric acid/sodium sulfite solution. The organic layer was separated and the aqueous phase was extracted with 200 mL of DCM. The combined organic layers were dried over MgSO$_4$, filtered and the filtrate was concentrated. The crude product was purified by chromatography on silica gel (gradient ranging from 0 to 40% ethyl acetate in hexane, 0.1% v/v AcOH in all solvents). $^1$H NMR (400 MHz, CDCl$_3$) δ ppm 4.20 (d, J=9.19 Hz, 1 H) 5.18 (d, J=9.00 Hz, 1 H) 6.95-7.00 (m, 2 H) 7.04 (dd, J=8.41, 1.96 Hz, 1 H) 7.10-7.24 (m, 4 H). Mass Spectrum (ESI) m/z=346.0 (M+18).

Step D. (4R,5R)-4-(4-Chloro-2-fluorophenyl)-5-(3-chlorophenyl)oxazolidin-2-one

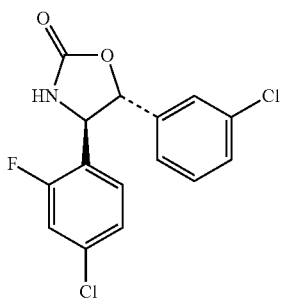 [SMILES: O=C1N[C@H](c2ccc(Cl)cc2F)[C@@H](c2cccc(Cl)c2)O1]

To a solution of (2R,3S)-2-(4-chloro-2-fluorophenyl)-3-(3-chlorophenyl)-3-hydroxypropanoic acid (1.24 g, 3.8 mmol, Step C) in 50 mL of toluene was added triethylamine (0.42 g, 4.1 mmol). The reaction mixture was heated to 40° C. in an oil bath, after which DPPA (diphenylphosphoryl azide, 1.1 g, 4.1 mmol) was added. The reaction was then heated to 85° C. overnight to give the product which was used in the next step without further purification. $^1$H NMR (400 MHz, CDCl$_3$) δ ppm 5.04 (d, J=5.7 Hz, 1 H) 5.32 (d, J=5.7 Hz, 1 H) 5.89 (s, 1 H) 7.18 (dd, J=10.1, 2.1 Hz, 2 H) 7.21-7.26 (m, 1 H) 7.36 (s, 1 H) 7.38-7.41 (m, 3 H) 7.42-7.50 (m, 2 H) 7.46 (t, J=8.1 Hz, 5 H). Mass Spectrum (ESI) m/z=326.0 (M+1).

Step E. (4R,5R)-tert-Butyl 4-(4-chloro-2-fluorophenyl)-5-(3-chlorophenyl)-2-oxooxazolidine-3-carboxylate

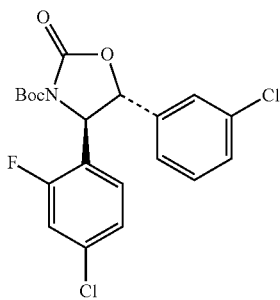 [SMILES: CC(C)(C)OC(=O)N1C(=O)O[C@H](c2cccc(Cl)c2)[C@H]1c1ccc(Cl)cc1F]

To (4R,5R)-4-(4-chloro-2-fluorophenyl)-5-(3-chlorophenyl)oxazolidin-2-one (0.38 g, 1.2 mmol, Step D) was added 8 mL of THF followed by sodium hydride (60% dispersion in mineral oil, 0.23 g, 5.9 mmol). The reaction mixture was stirred for one hour at room temperature, then di-tert-butyl dicarbonate (0.31 g, 1.4 mmol) was added. After the reaction mixture was stirred at room temperature for an additional hour, the mixture was quenched with 20% aq. citric acid solution. The organic layers were extracted with EtOAc and the combined organic layers were dried over MgSO$_4$, filtered and the filtrate was concentrated under reduced pressure.
Mass Spectrum (ESI) m/z=450.0 (M+23).

Step F. tert-Butyl ((1R,2R)-1-(4-chloro-2-fluorophenyl)-2-(3-chlorophenyl)-2-hydroxyethyl)carbamate

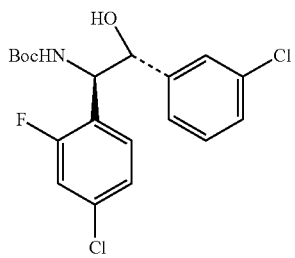 [SMILES: CC(C)(C)OC(=O)N[C@H](c1ccc(Cl)cc1F)[C@H](O)c1cccc(Cl)c1]

To (4R,5R)-tert-butyl 4-(4-chloro-2-fluorophenyl)-5-(3-chlorophenyl)-2-oxooxazolidine-3-carboxylate (0.38 g, 1.2 mmol) from Step E above was added 10 mL MeOH followed by NaOH (0.23 g, 5.9 mmol, dissolved in 5 mL of H$_2$O) and the reaction was left to stir at room temperature for 2 hours. The reraction mixture was transferred to a reparatory funnel, the mixture was extracted with DCM (3×100 mL), the organic layers were combined, dried over MgSO$_4$, filtered and the filtrate was concentrated under reduced pressure to give the title compound which was used in the next step without further purification.

Step G. (1R,2R)-2-Amino-2-(4-chloro-2-fluorophenyl)-1-(3-chlorophenyl)ethanol

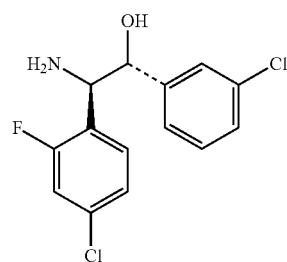 [SMILES: N[C@H](c1ccc(Cl)cc1F)[C@H](O)c1cccc(Cl)c1]

tert-Butyl (1R,2R)-1-(4-chloro-2-fluorophenyl)-2-(3-chlorophenyl)-2-hydroxyethylcarbamate (0.165 g, 0.41 mmol) from Step E above was dissolved in 6 mL of 4.0 M HCl in dioxane. The reaction mixture was stirred at room temperature for 30 minutes. The reaction mixture was concentrated under reduced pressure. To the residue was added saturated aq. sodium bicarbonate solution followed by EtOAc. The mixture was filtered through an unbuffered 5 mL Chem Elut™ cartridge (Agilent technologies, Santa Clara, Calif.) and washed with ethyl acetate. Concentration of the organic filtrate under reduced pressure gave the title compound as a white solid. Mass Spectrum (ESI) m/z=300.1 (M+1).

The following intermediates B2-B8 were also prepared by a procedure analogous to the one described above, substituting 2-(4-chloro-2-fluorophenyl)acetic acid in Step A for the appropriate carboxylic acid:

| Intermediate | Structure | Name | Characterization |
|---|---|---|---|
| B2 | H₂N, OH, Cl, phenyl | (1R,2R)-2-Amino-1-(3-chlorophenyl)-2-phenylethanol | MS 248.1 (M + 1). ¹H NMR (400 MHz, CDCl₃) δ ppm 2.74 (3 H, br. s.), 3.97 (1 H, d, J = 6.8 Hz), 4.65 (1 H, d, J = 6.6 Hz) 6.99 (1 H, d, J = 7.6 Hz), 7.10-7.33 (8 H, m). |
| B3 | H₂N, OH, Cl, 4-F-phenyl | (1R,2R)-2-Amino-1-(3-chlorophenyl)-2-(4-fluorophenyl)ethanol | MS 266.0 (M + 1). ¹H NMR (400 MHz, CDCl₃) δ ppm 2.60 (3 H, br. s.), 3.98 (1 H, d, J = 6.6 Hz), 4.60 (1 H, d, J = 6.6 Hz) 6.93-7.00 (3 H, m), 7.12-7.29 (5 H, m). |
| B4 | H₂N, OH, Cl, 4-CF₃-phenyl | (1R,2R)-2-Amino-1-(3-chlorophenyl)-2-(4-(trifluoromethyl)phenyl)ethanol | MS 316.0 (M + 1). ¹H NMR (400 MHz, DMSO D₆) δ ppm 2.11 (3 H, br. s.), 4.58 (1 H, d, J = 4.6 Hz), 5.64 (1 H, br. s.) 7.07-7.11 (1 H, m), 7.18-7.24 (3 H, m), 7.43 (2 H, d, J = 8.1 Hz), 7.56 (2 H, d, J = 8.3 Hz). |
| B5 | H₂N, OH, Cl, 4-Et-phenyl | (1R,2R)-2-Amino-1-(3-chlorophenyl)-2-(4-ethylphenyl)ethanol | MS 276.1 (M + 1). ¹H NMR (400 MHz, CDCl₃) δ ppm 1.37 (3 H, t, J = 7.6 Hz), 2.77 (2 H, q, J = 7.6 Hz), 3.62 (3 H, br. s.), 4.17 (1 H, d, J = 6.8 Hz), 4.86 (1 H, d, J = 6.8 Hz) 7.16 (1 H, d, J = 7.3 Hz), 7.25-7.55 (7 H, m). |
| B6 | H₂N, OH, Cl, 4-OCF₃-phenyl | (1R,2R)-2-Amino-1-(3-chlorophenyl)-2-(4-(trifluoromethoxy)phenyl)ethanol | MS 332.0 (M + 1). ¹H NMR (400 MHz, CDCl₃) δ ppm 2.84 (3 H, br. s.), 3.99 (1 H, d, J = 6.4 Hz), 4.60 (1 H, d, J = 6.6 Hz) 6.95 (1 H, d, J = 7.3), 7.10-7.40 (7 H, m). |
| B7 | H₂N, OH, Cl, 4-Me-phenyl | (1R,2R)-2-Amino-1-(3-chlorophenyl)-2-(p-tolyl)ethanol | MS 262.1 (M + 1). ¹H NMR (400 MHz, DMSO-D₆) δ ppm 1.98 (2 H, br. s.), 2.22 (3 H, s.), 3.81 (1 H, d, J = 6.8 Hz), 4.47 (1 H, d, J = 6.3 Hz) 5.56 (1 H, br. s.), 6.96-7.06 (5 H, m), 7.13-7.20 (3 H, m). |

| Intermediate | Structure | Name | Characterization |
|---|---|---|---|
| B8 | 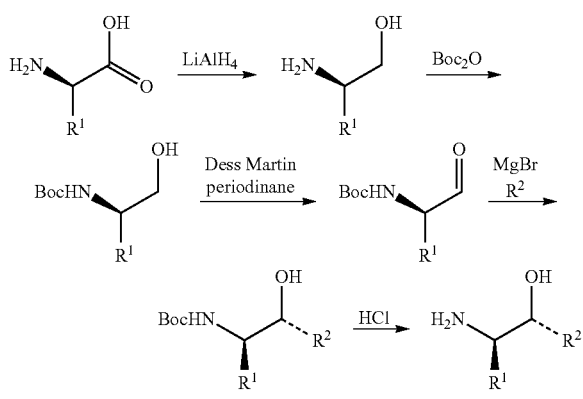 | (1R,2R)-2-Amino-1-(3-chlorophenyl)-2-(4-isopropylphenyl)ethanol | MS 290.0 (M + 1). $^1$H NMR (400 MHz, CDCl$_3$) δ ppm 1.23 (6 H, d, J = 6.8 Hz), 2.88 (1 H, m), 4.00 (1 H, d, J = 6.6 Hz), 4.68 (1 H, d, J = 6.6 Hz), 7.04 (1 H, d, J = 7.1 Hz), 7.10-7.39 (7 H, m). |

General Procedure 4

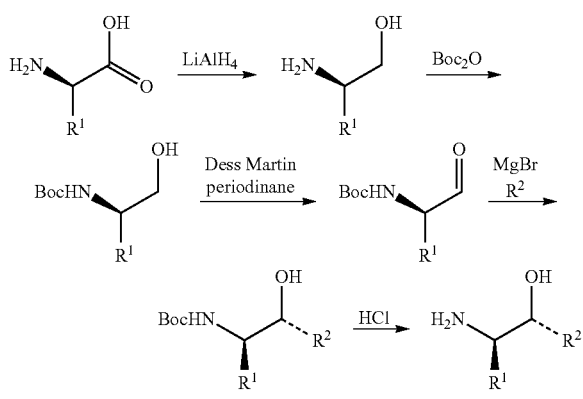

Intermediate C1

(1R,2R)-2-Amino-1-(3-chloro-5-fluorophenyl)-2-(4-chlorophenyl)ethanol

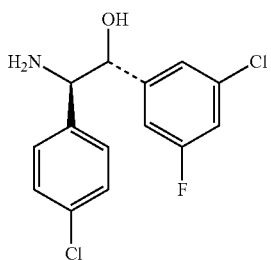 [SMILES: N[C@H](c1ccc(Cl)cc1)[C@H](O)c1cc(F)cc(Cl)c1]

Step A. (R)-2-Amino-2-(4-chlorophenyl)ethanol

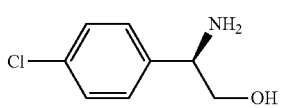 [SMILES: N[C@@H](CO)c1ccc(Cl)cc1]

A solution of 1.0M LiAlH$_4$ in THF was diluted with 460 mL anhydrous THF and was heated to 75° C. under a nitrogen atmosphere. (R)-2-Amino-2-(4-chlorophenyl)acetic acid (25.0 g, 135 mmol; Asta Tech, Inc., Bristol, Pa.) was added in several portions. The reaction mixture was heated to reflux for about 3 hours, cooled to room temperature and quenched by adding water (8.0 mL), aq. 15% NaOH (8.0 mL) and water (25.6 mL), successively. The mixture was stirred vigorously for 30 minutes. The solids were filtered off, rinsed with THF and the combined organics were concentrated in vacuo to provide the desired product as a yellow solid. $^1$H NMR (400 MHz, CDCl$_3$) δ ppm 1.59 (br. s., 2 H) 2.48 (br. s., 1 H) 3.53 (dd, J=10.56, 8.02 Hz, 1 H) 3.69-3.78 (m, 1 H) 4.05 (br. s., 1 H) 7.29 (m, 2 H) 7.31-7.35 (m, 2 H). Mass Spectrum (CI$^+$) m/z=172.0 (M+1).

Step B. (R)-tert-Butyl 1-(4-chlorophenyl)-2-hydroxyethylcarbamate

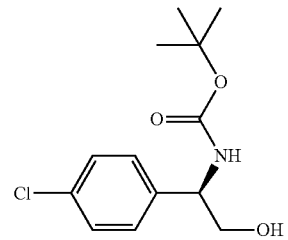 [SMILES: CC(C)(C)OC(=O)N[C@@H](CO)c1ccc(Cl)cc1]

A solution of di-tert-butyl dicarbonate (36.6 g, 168 mmol) in DCM (50 mL) was added dropwise to a solution of (R)-2-amino-2-(4-chlorophenyl)ethanol (23.01 g, 134 mmol, Step A) in DCM (200 mL) at 0° C. After the addition was completed, the ice bath was removed and the reaction mixture was stirred at room temperature for 1.5 h. The reaction mixture was concentrated in vacuo and the crude material was triturated with 10% DCM/hexane (850 mL) to provide the title compound as a white powder.

$^1$H NMR (400 MHz, DMSO-d$_6$) δ ppm 1.36 (s, 9 H) 3.41-3.52 (m, 2 H) 4.43-4.56 (m, 1 H) 4.75-4.84 (m, 1 H) 7.24 (d, J=8.02 Hz, 1 H) 7.27-7.32 (m, 2 H) 7.33-7.39 (m, 2H). Mass Spectrum (CI+) m/e=565.0 (2M$^+$+23).

Step C. (R)-tert-Butyl 1-(4-chlorophenyl)-2-oxoethylcarbamate

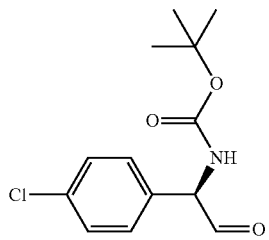 [SMILES: CC(C)(C)OC(=O)N[C@@H](C=O)c1ccc(Cl)cc1]

1,1,1,-Tris(acetoxy)-1,1-dihydro-1,2-benziodoxol-3-(1H) one ("Dess Martin periodinane") (17.42 g, 41.1 mmol) was added in several portions to a stirred suspension of (R)-tert-butyl 1-(4-chlorophenyl)-2-hydroxyethylcarbamate (5.58 g, 20.53 mmol) in wet DCM (40 mL DCM/40 µl water) at room temperature. The reaction was stirred for 2 hours, diluted with diethyl ether (40 mL) and quenched by adding a solution of $Na_2S_2O_3$ (10 eq) in sat. aq. $NaHCO_3$ solution (80 mL) at rt. The mixture was stirred vigorously for 10 minutes and the layers were separated. The aqueous layer was extracted with ether (40 mL). The organics were pooled, washed with sat. aq. $NaHCO_3$ solution and brine, dried over $MgSO_4$, filtered and the filtrate was concentrated. The crude material was used in the next step without further purification.

Step D. tert-Butyl (1R,2R)-2-(3-chloro-5-fluorophenyl)-1-(4-chlorophenyl)-2-hydroxyethylcarbamate and tert-Butyl (1R,2S)-2-(3-chloro-5-fluorophenyl)-1-(4-chlorophenyl)-2-hydroxyethylcarbamate

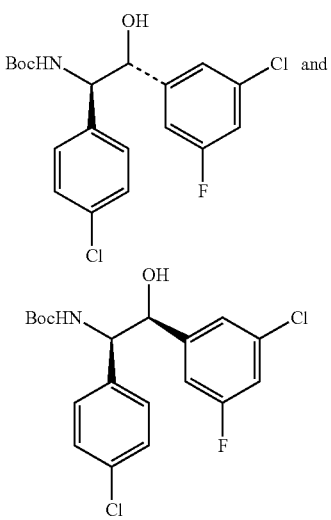

A 500 mL 3-neck flask was charged with a magnetic stirring bar, magnesium (2.163 g, 89 mmol), a crystal of iodine and anhydrous ethyl ether (100 mL). The flask was equipped with an addition funnel and a reflux condenser. The addition funnel was charged with a solution of 1-bromo-3-chloro-5-fluorobenzene (18.64 g, 89 mmol) in anhydrous ether. 15 mL of this solution was added dropwise into the flask under vigorous stirring. Then the reaction mixture was heated to reflux for about 5 minutes until the color of the iodine was no longer visible. The heating source was removed and the remainder of the 1-bromo-3-chloro-5-fluorobenzene solution was added dropwise at a rate to maintain gentle reflux. After the addition had completed, the reaction mixture was maintained at reflux temperature for another 30 min. The reaction mixture turned light brown during the heating. The oil-bath was removed and, without cooling, a solution of (R)-tert-butyl 1-(4-chlorophenyl)-2-oxoethylcarbamate (4.80 g, 17.80 mmol) in anhydrous ethyl ether (66 mL) was added over a period of 30 min. The reaction was stirred for 2 more hours at rt. The reaction mixture was poured into 200 mL of a cold sat. aq. $NH_4Cl$ solution. The two layers were separated and the aqueous layer was extracted with more ethyl acetate (2×100 mL). The combined organic layers were washed with water and then brine, dried over $Na_2SO_4$, filtered and the filtrate was concentrated. The residue was washed with 100 mL hexanes, filtered and dried to provide the title compounds as a mixture of two diastereomers (anti:syn=10:1 by NMR). The crude material was used in the next step without further purification.

Step E. (1R,2R)-2-Amino-1-(3-chloro-5-fluorophenyl)-2-(4-chlorophenyl)ethanol and (1S,2R)-2-Amino-1-(3-chloro-5-fluorophenyl)-2-(4-chlorophenyl)ethanol

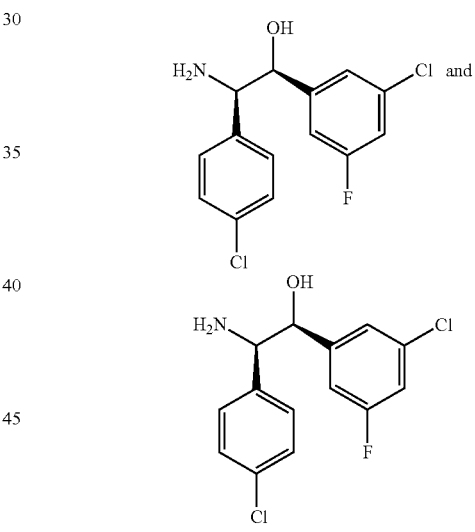

The material obtained in general procedure 4, Step D (3.0 g, 7.49 mmol) was treated with 20 mL 4N HCl in dioxane at room temperature for 2 hours. The solvent was evaporated. The residue was triturated with ethyl ether, filtered, washed with ether and dried under vacuum. The crude material was purified by preparative HPLC (Gemini™ 10 µµ 250×30 mm $C_{18}$ column 110A, Phenomenex, Torrance, Calif.; 10 to 19% MeCN/water with 0.1% TFA) to give the title compounds as a mixture of two diastereomers (anti:syn=18:1 by NMR).

$^1$H NMR (400 MHz, DMSO-$d_6$) δ ppm 4.51 (d, J=7.83 Hz, 1 H) 4.85 (dd, J=8.22, 3.91 Hz, 1 H) 6.70 (d, J=3.91 Hz, 1 H) 7.05-7.11 (m, 1 H) 7.16 (s, 1 H) 7.30 (dt, J=8.75, 2.08 Hz, 1 H) 7.39 (d, J=8.61 Hz, 2 H) 7.44 (d, J=8.61 Hz, 2 H) 8.47 (br. s., 3 H). [α]$_D$=+96° (c=0.11, MeOH, 23.4° C.).

The following intermediates C2-C15 were also prepared by a procedure analogous to the one described above, substituting the Grignard reagent prepared from 1-bromo-3-chloro-5-fluorobenzene in Step D for the appropriate Grignard reagent that was either commercially available or was prepared from the appropriate halide as described in Step D.

| Intermediate | Structure | Name | Characterization |
|---|---|---|---|
| C2 | (structure: H$_2$N, OH, 4-Cl-phenyl, 3-F-phenyl) TFA salt | (1R,2R)-2-Amino-2-(4-chlorophenyl)-1-(3-fluorophenyl) ethanol | MS 266.0 (M + 1). $^1$H NMR (400 MHz, DMSO-d$_6$) δ ppm 4.45 (d, J = 8.80 Hz, 1 H) 4.83 (dd, J = 9.00, 3.52 Hz, 1 H) 6.61 (d, J = 3.72 Hz, 1 H) 6.94 (d, J = 7.63 Hz, 1 H) 7.00-7.11 (m, 2 H) 7.22-7.30 (m, 1 H) 7.33 (m, J = 8.61 Hz, 2 H) 7.39 (m, J = 8.41 Hz, 2 H) 8.48 (br. s., 3 H). [α]$_D$ = +79° (c = 0.252 g/100 mL, MeOH, 25.1° C.). |
| C3 | (structure: H$_2$N, OH, 4-Cl-phenyl, 5-chloropyridin-3-yl) TFA salt | (1R,2R)-2-Amino-2-(4-chlorophenyl)-1-(5-chloropyridin-3-yl) ethanol | MS 283.0 (M + 1). $^1$H NMR (400 MHz, DMSO-d$_6$) δ ppm 4.59 (dd, J = 7.63, 4.89 Hz, 1 H) 4.94 (d, J = 8.61 Hz, 1 H) 6.75 (br. s., 1 H) 7.37-7.41 (m, 2 H) 7.41-7.46 (m, 2 H) 7.85 (t, J = 1.96 Hz, 1 H) 8.26 (d, J = 1.76 Hz, 1 H) 8.48 (d, J = 2.35 Hz, 1 H) 8.55 (br. s., 3 H). [α]$_D$ = +89° (c = 0.133 g/100 mL, MeOH, 22.4° C.). |
| C4 | (structure: H$_2$N, OH, 4-Cl-phenyl, 3-OMe-phenyl) TFA salt | (1R,2R)-2-Amino-2-(4-chlorophenyl)-1-(3-methoxyphenyl) ethanol | MS 278.0 (M + 1). $^1$H NMR (400 MHz, DMSO-d$_6$) δ ppm 3.66 (s, 3 H) 4.39 (d, J = 5.67 Hz, 1 H) 4.80 (dd, J = 9.19, 3.52 Hz, 1 H) 6.47 (d, J = 3.72 Hz, 1 H) 6.68 (d, J = 7.63 Hz, 1 H) 6.72-6.79 (m, 2 H) 7.12 (t, J = 7.73 Hz, 1 H) 7.31-7.41 (m, 4 H) 8.53 (br. s., 3 H). [α]$_D$ = +124° (c = 0.148 g/100 mL, MeOH, 24.0° C.). |
| C5 | (structure: H$_2$N, OH, 4-Cl-phenyl, 2-chloropyridin-4-yl) TFA salt | (1R,2R)-2-Amino-2-(4-chlorophenyl)-1-(2-chloropyridin-4-yl) ethanol | MS 283.0 (M + 1). $^1$H NMR (400 MHz, DMSO-d$_6$) δ ppm 8.50 (3 H, br. s.), 8.30 (1 H, d, J = 5.1 Hz), 7.37-7.49 (5 H, m), 7.22 (1 H, dd, J = 5.1, 1.2 Hz), 6.81 (1 H, br. s.), 4.88 (1 H, d, J = 7.8 Hz), 4.54 (1 H, br. s.). [α]$_D$ = +93° (c = 0.134 g/100 mL, MeOH, 24.0° C.). |
| C6 | (structure: H$_2$N, OH, 4-Cl-phenyl, 5-methoxypyridin-3-yl) TFA salt | (1R,2R)-2-Amino-2-(4-chlorophenyl)-1-(5-methoxypyridin-3-yl) ethanol | MS 279.1 (M + 1). MS 279.1 (M + 1). $^1$H NMR (400 MHz, DMSO-d$_6$) δ ppm 3.79 (s, 3 H) 4.56 (dd, J = 8.41, 5.28 Hz, 1 H) 4.90 (d, J = 8.80 Hz, 1 H) 6.68 (br. s., 1 H) 7.32-7.35 (m, 1 H) 7.35-7.39 (m, 2 H) 7.39-7.44 (m, 2 H) 7.92 (d, J = 1.57 Hz, 1 H) 8.17 (d, J = 2.74 Hz, 1 H) 8.54 (br. s., 3 H). [α]$_D$ = +84° (c = 0.149 g/100 mL, MeOH, 23.6° C.). MS 279.1 (M + 1) |

-continued

| Intermediate | Structure | Name | Characterization |
|---|---|---|---|
| C7 | (HCl salt) | ((1R,2R)-2-Amino-2-(4-chlorophenyl)-1-(3,5-dichlorophenyl) ethanol | MS 316 (M + 1). MS 316.0 (M + 1). $^1$H NMR (400 MHz, DMSO-d$_6$) δ ppm 4.51 (d, J = 8.02 Hz, 1 H) 4.90 (dd, J = 8.12, 4.01 Hz, 1 H) 6.71 (d, J = 4.11 Hz, 1 H) 7.25 (d, J = 1.96 Hz, 2 H) 7.43 (s, 4 H) 7.47 (t, J = 1.96 Hz, 1 H) 8.58 (br. s., 3 H). MS 316 (M + 1) [α]$_D$ = +105° (c = 0.252 g/100 mL, MeOH, 23.2° C.). |
| C8 | (TFA salt) | (1R,2R)-2-Amino-1-(3-chloro-4-fluorophenyl)-2-(4-chlorophenyl) ethanol | MS 300.0 (M + 1). $^1$H NMR (400 MHz, DMSO-d$_6$) δ ppm 4.43-4.51 (m, 1 H) 4.80-4.86 (m, 1 H) 6.63 (d, J = 3.52 Hz, 1 H) 7.14 (ddd, J = 8.61, 4.69, 2.15 Hz, 1 H) 7.26-7.31 (m, 1 H) 7.33-7.37 (m, 2 H) 7.40-7.44 (m, 2 H) 7.46 (dd, J = 7.24, 1.96 Hz, 1 H) 8.47 (br. s., 3 H). [α]$_D$ = +88° (c = 0.151 g/100 mL, MeOH, 23.8° C.). |
| C9 | 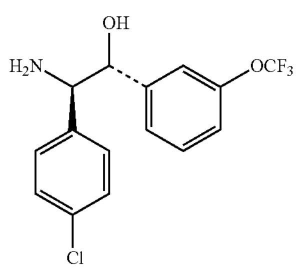 [SMILES: N[C@H](c1ccc(Cl)cc1)[C@H](O)c1cccc(OC(F)(F)F)c1] | (1R,2R)-2-Amino-2-(4-chlorophenyl)-1-(3-(trifluoromethoxy)phenyl) ethanol | MS 332.0 (M + 1). $^1$H NMR (400 MHz, CHLOROFORM-d) δ ppm 3.00 (br. s., 2 H) 4.06 (d, J = 7.04 Hz, 1 H) 4.71 (d, J = 7.43 Hz, 1 H) 7.05-7.18 (m, 6 H) 7.28-7.33 (m, 3 H). |
| C10 | 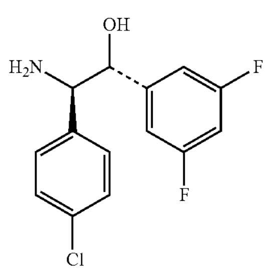 [SMILES: N[C@H](c1ccc(Cl)cc1)[C@H](O)c1cc(F)cc(F)c1] | (1R,2R)-2-Amino-2-(4-chlorophenyl)-1-(3,5-difluorophenyl) ethanol | MS 284.0 (M + 1). $^1$H NMR (400 MHz, CHLOROFORM-d) δ ppm 2.47 (br. s., 3 H) 3.94 (d, J = 6.46 Hz, 1 H) 4.59 (d, J = 6.65 Hz, 1 H) 6.66-6.76 (m, 3 H) 7.11-7.17 (m, 2 H) 7.25-7.31 (m, 2 H). |
| C11 | (TFA salt) | 3-((1R,2R)-2-Amino-2-(4-chlorophenyl)-1-hydroxyethyl)-5-chlorobenzonitrile | MS 307.0 (M + 1). $^1$H NMR (400 MHz, DMSO-d$_6$) δ ppm 4.77 (dd, J = 8.51, 4.99 Hz, 1 H) 4.86 (t, J = 5.09 Hz, 1 H) 5.63 (d, J = 5.48 Hz, 1 H) 7.19 (d, J = 8.80 Hz, 1 H) 7.30-7.37 (m, 4 H) 7.46-7.52 (m, 1 H) 7.52-7.57 (m, 1 H) 7.58-7.64 (m, 2 H). [α]$_D$ = +58° (c = 0.228 g/100 mL, MeOH, 22.4° C.). |

-continued

| Intermediate | Structure | Name | Characterization |
|---|---|---|---|
| C12 | 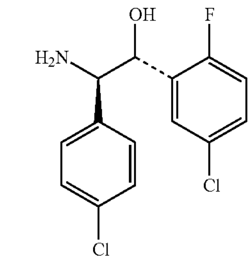 [SMILES: N[C@H](c1ccc(Cl)cc1)[C@H](O)c1cc(Cl)ccc1F] | (1R,2R)-2-Amino-1-(5-chloro-2-fluorophenyl)-2-(4-chlorophenyl)ethanol | MS 300.0 (M + 1). ¹H NMR (400 MHz, CHLOROFORM-d) δ ppm 2.79 (br. s., 3 H) 4.14 (d, J = 5.67 Hz, 1 H) 4.98 (d, J = 5.67 Hz, 1 H) 6.87 (dd, J = 9.39, 8.80 Hz, 1 H) 7.19 (ddd, J = 6.55, 4.40, 2.15 Hz, 1 H) 7.21-7.25 (m, 2 H) 7.26-7.29 (m, 2 H) 7.50 (dd, J = 6.06, 2.74 Hz, 1 H). |
| C13 | 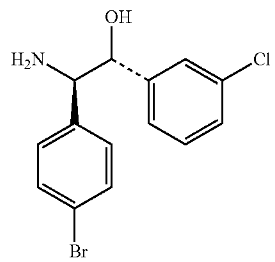 [SMILES: N[C@H](c1ccc(Br)cc1)[C@H](O)c1cccc(Cl)c1] | (1R,2R)-2-Amino-2-(4-bromophenyl)-1-(3-chlorophenyl)ethanol | MS 328.0 (M + 1). ¹H NMR (400 MHz, CHLOROFORM-d) δ ppm 4.27 (d, J = 10.17 Hz, 1 H) 4.93 (d, J = 9.98 Hz, 1 H) 6.77 (d, J = 7.63 Hz, 1 H) 6.99 (m, J = 8.61 Hz, 2 H) 7.07-7.13 (m, 2 H) 7.19-7.23 (m, 1 H) 7.38 (m, J = 8.41 Hz, 2 H). |
| C14 | 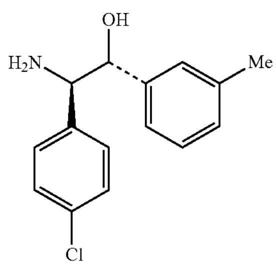 [SMILES: Cc1cccc([C@@H](O)[C@H](N)c2ccc(Cl)cc2)c1] | (1R,2R)-2-Amino-2-(4-chlorophenyl)-1-(m-tolyl)ethanol | MS 262.1 (M + 1). ¹H NMR (400 MHz, CHLOROFORM-d) δ ppm 2.30 (s, 3 H) 2.58 (br. s., 3 H) 4.08 (d, J = 6.46 Hz, 1 H) 4.63 (d, J = 6.65 Hz, 1 H) 6.95 (d, J = 7.63 Hz, 1 H) 7.04 (d, J = 7.04 Hz, 2 H) 7.12-7.20 (m, 3 H) 7.22-7.26 (m, 2 H). |
| C15 | 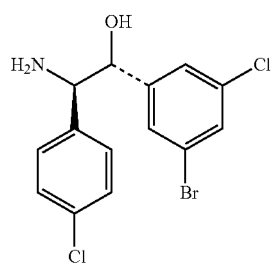 [SMILES: N[C@H](c1ccc(Cl)cc1)[C@H](O)c1cc(Cl)cc(Br)c1] | (1R,2R)-2-Amino-1-(3-bromo-5-chlorophenyl)-2-(4-chlorophenyl)ethanol | MS 360.0 (M + 1). ¹H NMR (400 MHz, CHLOROFORM-d) δ ppm 1.60 (br. s., 2 H) 3.99 (d, J = 6.46 Hz, 1 H) 4.59 (d, J = 6.46 Hz, 1 H) 7.11 (s, 1 H) 7.16 (d, J = 8.22 Hz, 2 H) 7.22 (s, 1 H) 7.28-7.32 (m, 3 H) 7.38 (t, J = 1.66 Hz, 1 H). |

General Procedure 5

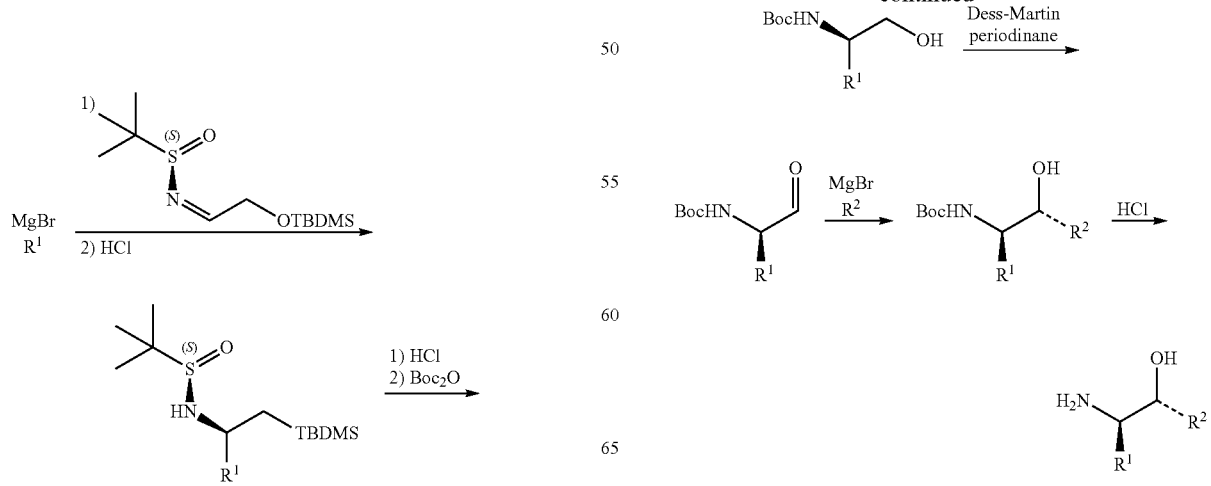

Intermediate D1

(1R,2S)-2-Amino-1-(3-chlorophenyl)-2-(5-chlorothiophen-2-yl)ethanol

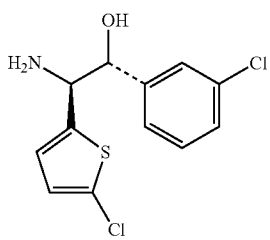

Step A. (S)-N-(2-(tert-Butyldimethylsilyloxy)ethylidene)-2-methylpropane-2-sulfinamide

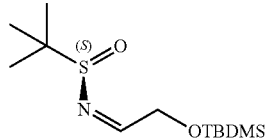

Copper(II) sulfate (30.3 g, 190 mmol) was added to a mixture of (tert-butyldimethylsilyloxy)acetaldehyde (16.55 g, 95 mmol) and (S)-(−)-2-methyl-2-propanesulfinamide (9.59 g, 79 mmol) in DCM (150 mL). The mixture was stirred at room temperature for 17 h. The mixture was filtered through a pad of Celite® (J. T. Baker, Phillipsberg, N.J., diatomaceous earth) followed by a rinse with 500 mL of DCM. The filtrate was concentrated and the crude product was purified by chromatography on silica gel (eluent: 0 to 30% EtOAc in hexane, gradient) to afford the title compound. Mass Spectrum (CI+) m/z=278.1 (M+1).

Step B. (S)-N-((S)-2-(tert-Butyldimethylsilyloxy)-1-(5-chlorothiophen-2-yl)ethyl)-2-methylpropane-2-sulfinamide

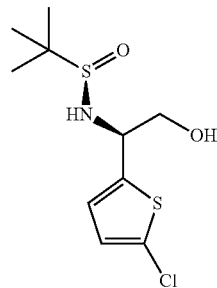 [SMILES: CC(C)(C)[S@@](=O)N[C@@H](CO)c1ccc(Cl)s1]

To a solution of (S)-N-(2-(tert-butyldimethylsilyloxy)ethylidene)-2-methylpropane-2-sulfinamide (6.02 g, 21.69 mmol) in DCM (120 mL) at −78° C. was added a 0.5M solution of 5-chloro-2-thienylmagnesium bromide in THF (87 mL, 43.4 mmol) over a period of 30 min via syringe. After 10 minutes at −78° C., the reaction mixture was warmed to 0° C. The reaction mixture was stirred at 0° C. for 3 h., then quenched by addition of 30 mL of a sat. aq. NH$_4$Cl solution and extracted with EtOAc. The combined organics were washed with 100 mL of brine, dried over Na$_2$SO$_4$, filtered and concentrated in vacuo. The residue was purified by chromatography on silica gel (linear gradient 0 to 70% EtOAc w/0.1% AcOH:hexane) to give the title compound. $^1$H NMR (400 MHz, DMSO-d$_6$) δ ppm 0.02 (s, 6 H) 0.85 (s, 9 H) 1.12 (s, 9 H) 3.31 (s, 1H) 3.62-3.89 (m, 2 H) 4.31-4.53 (m, 1 H) 5.73 (d, J=7.83 Hz, 1 H) 6.98 (s, 2 H). Mass Spectrum (CI+) m/z=419.0 (M+23).

Step C. (S)-2-Amino-2-(5-chlorothiophen-2-yl)ethanol hydrochloride

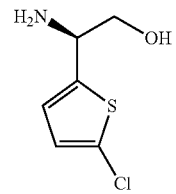

To a solution of (S)-N-((S)-2-(tert-butyldimethylsilyloxy)-1-(5-chlorothiophen-2-yl)ethyl)-2-methylpropane-2-sulfinamide (4.60 g, 11.61 mmol) in MeOH (20 mL) at 0° C. was slowly added a 4.0M solution of HCl in 1,4-dioxane (14.5 mL, 58.1 mmol). After 45 min at 0° C. the reaction mixture was concentrated in vacuo to afford the title compound. $^1$H NMR (400 MHz, DMSO-d$_6$) δ ppm 3.04-3.09 (m, 2 H) 3.13 (d, J=4.30 Hz, 1 H) 3.88 (d, J=5.09 Hz, 1 H) 6.38 (d, J=3.52 Hz, 1 H) 6.50 (d, J=3.91 Hz, 1 H) 7.99 (br. s., 2 H).

Step D. (S)-tert-Butyl 1-(5-chlorothiophen-2-yl)-2-hydroxyethylcarbamate

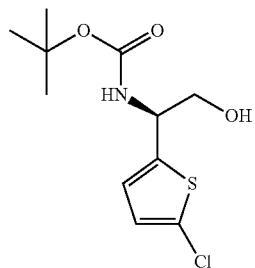 [SMILES: CC(C)(C)OC(=O)N[C@@H](CO)c1ccc(Cl)s1]

A solution of di-tert-butyl dicarbonate (3.05 g, 13.96 mmol) in DCM (10 mL) was added over a period of 30 min to a solution of (S)-2-amino-2-(5-chlorothiophen-2-yl)ethanol hydrochloride (2.48 g, 13.96 mmol) and triethylamine (3.89 mL, 27.9 mmol) in dry DCM (50 mL). The ice bath was removed after addition went to completion and the mixture was stirred at rt for 3 h. The mixture was washed with water, concentrated in vacuo and the crude product was purified by chromatography on silica gel (0 to 100% EtOAc in hexane, gradient elution) to afford the title compound along with a small amount of (S)-tert-butyl 2-(tert-butoxycarbonyloxy)-1-(5-chlorothiophen-2-yl)ethylcarbamate. $^1$H NMR (400 MHz, CDCl$_3$) δ ppm 1.46 (s, 9 H) 1.92 (br. s., 1 H) 3.89 (dd, J=8.61, 4.30 Hz, 2 H) 4.94 (br. s., 1 H) 5.18 (br. s., 1 H) 6.76-6.82 (m, 2 H). Mass Spectrum (CI+) m/z=300.0 (M+23).

Step E. (S)-tert-Butyl 1-(5-chlorothiophen-2-yl)-2-oxoethylcarbamate

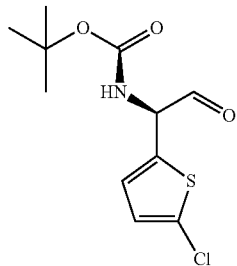

Dess-Martin periodinane (7.39 g, 17.42 mmol) was added to a solution of (S)-tert-butyl 1-(5-chlorothiophen-2-yl)-2-hydroxyethylcarbamate (2.420 g, 8.71 mmol) in wet (1 μL water/1 mL DCM) DCM (18 mL) at rt. The reaction mixture was stirred at rt for 1.5 hours. The reaction mixture was diluted with diethyl ether (20 mL) and a solution of $Na_2S_2O_3$ (10 equiv) in saturated aqueous $NaHCO_3$ (40 mL) was added. The mixture was stirred vigorously for 10 minutes and the layers were separated. The aqueous layer was extracted with diethyl ether. The organics were combined, washed with sat. aq. $NaHCO_3$ solution, water, and brine, dried over $MgSO_4$, filtered and the filtrate was concentrated to provide the title compound which was used without further purification.

Step F. tert-Butyl (1S,2R)-2-(3-chlorophenyl)-1-(5-chlorothiophen-2-yl)-2-hydroxyethylcarbamate

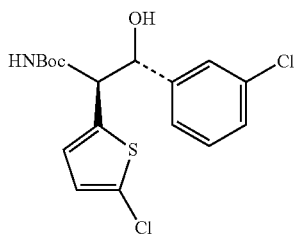

The (S)-tert-butyl 1-(5-chlorothiophen-2-yl)-2-oxoethylcarbamate (2.170 g, 7.87 mmol) dissolved in THF (40 mL) was added to 3-chlorophenylmagnesium bromide, 0.5M in THF (79 mL, 39.3 mmol) via syringe over 15 minutes at room temperature with stirring. After the addition was completed, the reaction mixture was stirred at rt for 2 hours and then quenched by addition of a sat. aq. $NH_4Cl$ solution at 0° C. The aqueous layer was extracted with EtOAc. The organic layers were combined, washed with brine, dried with $MgSO_4$, filtered and concentrated in vacuo to provide crude material. The product was purified via chromatography on silica gel (0 to 80% EtOAc w/0.1% AcOH in hexane, gradient elution) and via prep HPLC chromatography (50 to 95% gradient MeCN in water, with 0.1% TFA) to afford the title compound.

$^1$H NMR (400 MHz, $CDCl_3$) δ ppm 1.33 (br. s., 9 H) 4.97 (d, J=3.3 Hz, 1 H) 5.03 (br. s., 1 H) 5.33 (br. s., 1 H) 6.71-6.75 (m, 1 H) 6.75-6.80 (m, 1 H) 7.17-7.24 (m, 1 H) 7.24-7.31 (m, 2 H) 7.39 (s, 1 H). Mass Spectrum (CI+) m/z=410.0 (M+23).

Step G. (1R,2S)-2-Amino-1-(3-chlorophenyl)-2-(5-chlorothiophen-2-yl)ethanol tert-Butyl (1S,2R)-2-(3-chlorophenyl)-1-(5-chlorothiophen-2-yl)-2-hydroxyethylcarbamate (0.32 g, 0.824 mmol) was dissolved in 40 mL HCl (4.0 M in dioxane). The reaction mixture was stirred at room temperature for 3 hours. The reaction mixture was concentrated under reduced pressure. To the residue was added saturated aq. sodium bicarbonate solution followed by EtOAc. The layers were separated, the aq. layer was extracted with more EtOAc and the combined organic layers were dried over $MgSO_4$, filtered and the filtrate was concentrated under reduced pressure. $^1$H NMR (400 MHz, $CDCl_3$) δ ppm 3.61-3.68 (m, 1 H) 3.75-3.81 (m, 2 H) 4.19 (d, J=6.06 Hz, 1 H) 4.65 (d, J=6.06 Hz, 1 H) 6.52 (d, J=3.91 Hz, 1 H) 6.70 (d, J=3.72 Hz, 1 H) 7.11 (d, J=6.46 Hz, 1 H) 7.19-7.26 (m, 2 H) 7.33 (s, 1 H). Mass Spectrum (CI+) m/z=288.0 (M+1).

The following intermediates D2 to D5 were also prepared by a procedure analogous to the one described above, substituting 5-chloro-2-thienylmagnesium bromide in Step A for the appropriate Grignard reagent that was either commercially available or was prepared from the appropriate halide as described in Step D.

| Intermediate | Structure | Name | Characterization |
|---|---|---|---|
| D2 | 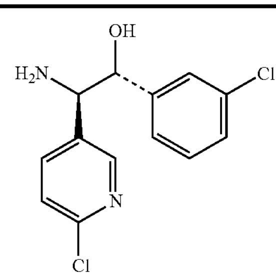 | (1R,2R)-2-Amino-1-(3-chlorophenyl)-2-(6-chloropyridin-3-yl)ethanol | $^1$H NMR (400 MHz, $CDCl_3$) δ ppm 2.60 (3 H, br. s.), 3.98 (1 H, d, J = 6.6 Hz), 4.60 (1 H, d, J = 6.6 Hz) 6.93-7.00 (3 H, m), 7.12-7.29 (5 H, m). Mass Spectrum (CI+) m/z = 283.0 (M + 1). |

-continued

| Intermediate | Structure | Name | Characterization |
|---|---|---|---|
| D3 | 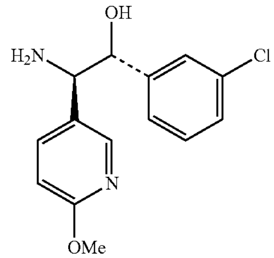 [SMILES: COc1ccc([C@@H](N)[C@H](O)c2cccc(Cl)c2)cn1] | (1R,2R)-2-Amino-1-(3-chlorophenyl)-2-(6-methoxypyridin-3-yl)ethanol | $^1$H NMR (400 MHz, DMSO-$d_6$) δ ppm 3.79 (s, 3 H) 4.46 (dd, J = 9.00, 5.09 Hz, 1 H) 4.88 (d, J = 9.19 Hz, 1 H) 6.63 (br. s., 1 H) 6.78-6.85 (m, 1 H) 7.11-7.18 (m, 1 H) 7.21-7.32 (m, 2 H) 7.35 (s, 1 H) 7.73 (dd, J = 8.71, 2.45 Hz, 1 H) 8.04 (d, J = 2.15 Hz, 1 H) 8.45 (br. s., 3 H) (TFA salt). Mass Spectrum (CI+) m/z = 279.1 (M + 1) |
| D4 | 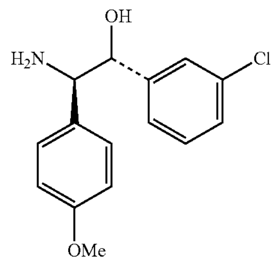 [SMILES: COc1ccc([C@@H](N)[C@H](O)c2cccc(Cl)c2)cc1] | (1R,2R)-2-Amino-1-(3-chlorophenyl)-2-(4-methoxyphenyl)ethanol | $^1$H NMR (400 MHz, CDCl$_3$) δ ppm 3.79 (s, 3 H) 3.91 (d, J = 6.46 Hz, 1 H) 4.59 (d, J = 6.65 Hz, 1 H) 6.76-6.88 (m, 2 H) 6.98 (d, J = 7.24 Hz, 1 H) 7.03-7.33 (m, 5 H). Mass Spectrum (CI+) m/z = 278.0 (M + 1). |
| D5 | 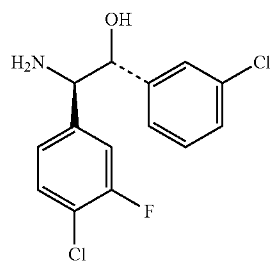 [SMILES: N[C@H](c1ccc(Cl)c(F)c1)[C@H](O)c1cccc(Cl)c1] | (1R,2R)-2-Amino-2-(4-chloro-3-fluorophenyl)-1-(3-chlorophenyl)ethanol | Mass Spectrum (CI+) m/z = 300.0 (M + 1). |

General Procedure 6

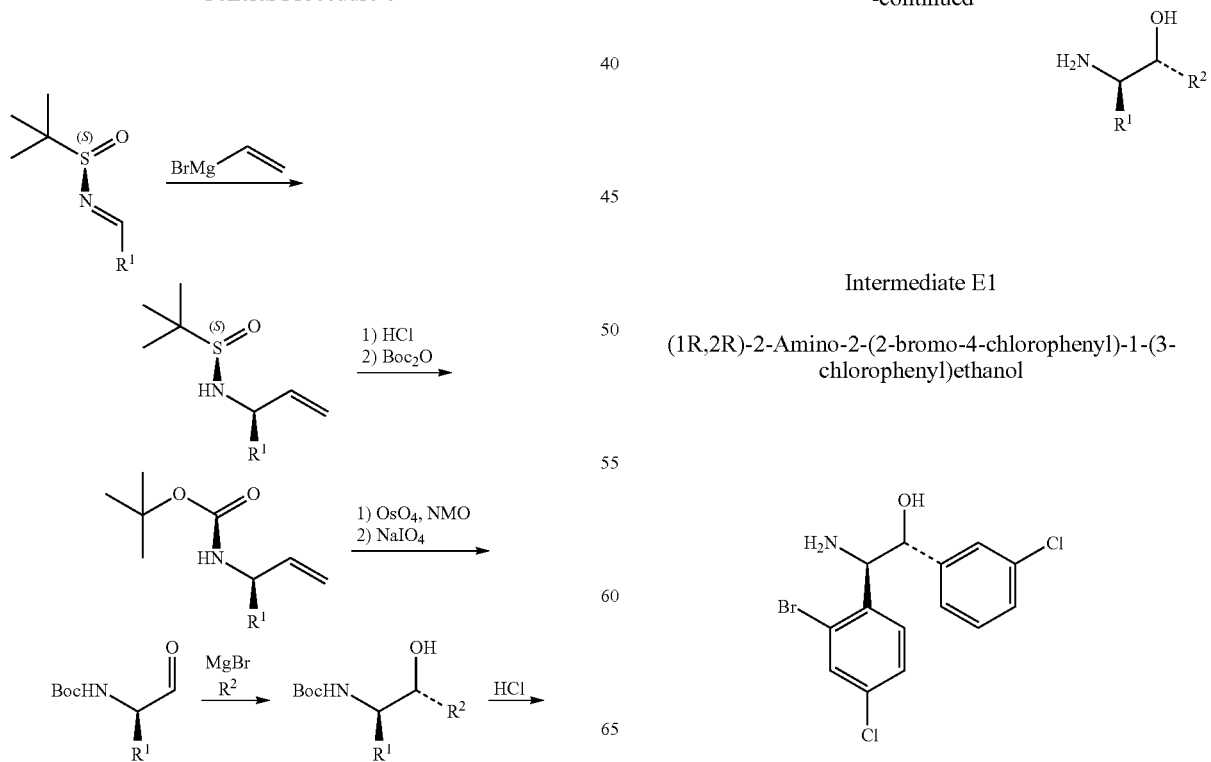

Intermediate E1

(1R,2R)-2-Amino-2-(2-bromo-4-chlorophenyl)-1-(3-chlorophenyl)ethanol

Step A. (2-Bromo-4-chlorophenyl)methanol

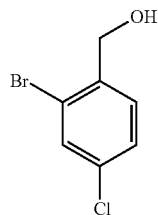

To a solution of 2-bromo-4-chlorobenzoic acid (25.2 g, 107 mmol) in THF (100 mL) at 0° C. was added borane tetrahydrofuran complex, 1.0M in THF (214 mL, 214 mmol). The reaction mixture was stirred at 0° C. for 9 h. The reaction was quenched by adding 1M aq. NaOH solution at 0° C. with stirring. The mixture was concentrated and then extracted with DCM. The combined DCM fractions were washed with 100 mL of brine, dried over $Na_2SO_4$, filtered and the filtrate was concentrated in vacuo. The crude product was purified by chromatography on silica gel (220 g silica gel, linear gradient 0 to 50% EtOAc:hexane) to give the title compound as a white solid. $^1$H NMR (400 MHz, $CDCl_3$) δ ppm 1.96 (s, 1 H), 4.72 (s, 2 H), 7.33 (dd, J=8.22, 2.15 Hz, 1 H), 7.44 (d, J=8.22 Hz, 1 H), 7.57 (d, J=2.15 Hz, 1 H).

Step B. 2-Bromo-4-chlorobenzaldehyde

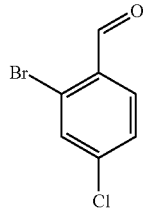

To a solution of (2-bromo-4-chlorophenyl)methanol (10.33 g, 46.6 mmol) in $CHCl_3$ (100 mL) was added manganese (IV) oxide (40.5 g, 466 mmol) with stirring. The reaction mixture was heated to reflux for 4 h under $N_2$. Then the reaction mixture was filtered and concentrated in vacuo. The crude was purified by flash chromatography on silica gel (220 g silica gel, linear gradient 0 to 50% EtOAc:hexane) to give the title compound as an off-white solid. $^1$H NMR (400 MHz, $CDCl_3$) δ ppm 7.43 (ddd, J=8.36, 1.91, 0.88 Hz, 1 H) 7.69 (d, J=1.96 Hz, 1 H) 7.87 (d, J=8.22 Hz, 1 H) 10.31 (d, J=0.78 Hz, 1 H).

Step C. (R)-N-(2-Bromo-4-chlorobenzylidene)-2-methylpropane-2-sulfinamide

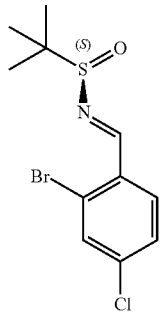

2-Bromo-4-chlorobenzaldehyde (8.72 g, 39.8 mmol) and (R)-(+)-t-butylsulfinamide (4.38 g, 36.1 mmol) were dissolved in 100 mL of THF and titanium (IV) isopropoxide (22.6 g, 80.0 mmol) was added dropwise. The reaction mixture was stirred at 65° C. for 17 hours. Then 120 mL of brine was added and the mixture was stirred vigorously for 20 minutes and filtered through a pad of Celite® (J. T. Baker, Phillipsberg, N.J., diatomaceous earth), washing with additional EtOAc. After filtration the layers were separated and the organic layer was dried over $MgSO_4$, filtered and the filtrate was concentrated. The resulting material was purified by chromatography on silica gel (220 g silica gel, linear gradient 0 to 60% EtOAc:hexane) to give the title compound. $^1$H NMR (400 MHz, $CDCl_3$) δ ppm 1.28 (s, 9 H) 7.39 (ddd, J=8.46, 2.01, 0.68 Hz, 1 H) 7.68 (d, J=2.15 Hz, 1 H) 8.00 (d, J=8.61 Hz, 1 H) 8.91-8.94 (m, 1 H). Mass Spectrum (ESI) m/z=322.0 (M+1), 645.2 (2M+1).

Step D. (S)-N-((S)-1-(2-Bromo-4-chlorophenyl)allyl)-2-methylpropane-2-sulfinamide

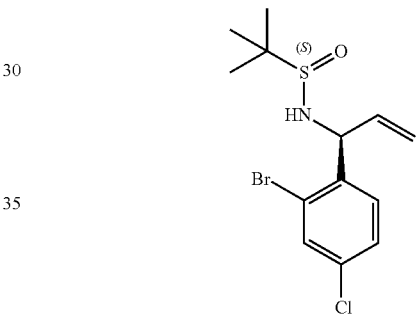

A solution of (S)-N-(2-bromo-4-chlorobenzylidene)-2-methylpropane-2-sulfinamide (5.85 g, 18.13 mmol) in DCM (50 mL) was cooled to −78° C. and vinylmagnesium bromide (1.0 M in THF, 36.3 mL, 36.3 mmol) was added dropwise over a period of 25 minutes. The reaction mixture was stirred at −78° C. for 5 h, then 40 mL of sat. aq. $NH_4Cl$ solution was added at −78° C. The reaction mixture was removed from the cooling bath and allowed to come to rt. The reaction mixture was concentrated under reduced pressure. Water and EtOAc was added and the layers were separated. The aqueous layer was extracted with EtOAc. The combined organic layers were dried over $MgSO_4$, filtered and the filtrate was concentrated. The residue was purified by chromatography on silica gel (220 g silica gel column, RediSep® Rf, Teledyne Isco, Lincoln, Nebr.; eluent: ethyl acetate/DCM=0:1 to 1:1, gradient elution over 50 min, maintaining 1:1 over 10 min; flow rate 100 mL/min) to give the title compound.

$^1$H NMR (400 MHz, $CDCl_3$) δ ppm 1.23 (s, 9 H) 3.52 (d, J=3.91 Hz, 1 H) 5.21-5.34 (m, 2 H) 5.44 (dd, J=5.87, 4.50 Hz, 1 H) 6.00 (ddd, J=16.92, 10.47, 6.26 Hz, 1 H) 7.29-7.39 (m, 2 H) 7.59 (d, J=1.96 Hz, 1 H) Mass Spectrum (ESI) m/z=352.0 (M+1), 703.0 (2M+1).

Step E. (S)-tert-Butyl 1-(2-bromo-4-chlorophenyl)allylcarbamate

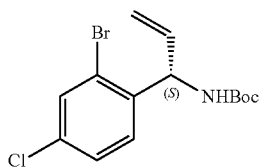

A 4.0M solution of hydrogen chloride in dioxane (11.4 mL, 45.5 mmol) was added to a solution of (S)-N-((S)-1-(2-bromo-4-chlorophenyl)allyl)-2-methylpropane-2-sulfinamide (4.56 g, 13.00 mmol) in MeOH (12 mL). The mixture was stirred at rt for 30 minutes and concentrated under reduced pressure. The residue was triturated with ether and filtered. The filter cake was washed with ether and dried in vacuo to give (S)-1-(2-bromo-4-chlorophenyl)prop-2-en-1-amine as the hydrochloride salt. Di-t-butyl dicarbonate (3.05 g, 13.99 mmol) was added dropwise to a stirred solution of triethylamine (3.54 mL, 25.4 mmol) and the product from above in DCM (50 mL) at 0° C. The reaction mixture was stirred at 0° C. for 30 minutes and then at rt for 18 h. The reaction mixture was diluted with DCM and washed with water. The combined organic layers were concentrated in vacuo. The residue was absorbed onto a plug of silica gel and purified by chromatography on silica gel (120 g silica gel column, RediSep® Rf, Teledyne Isco, Lincoln, Nebr.; eluent: ethyl acetate in hexane 0% to 40%, gradient elution) to give the title compound as a colorless oil. $^1$H NMR (400 MHz, CDCl$_3$) δ ppm 1.43 (br. s., 9 H) 4.96 (br. s., 1 H) 5.08-5.19 (m, 1 H) 5.19-5.29 (m, 1 H) 5.58 (br. s., 1 H) 5.86-6.06 (m, 1 H) 7.16-7.34 (m, 2 H) 7.59 (d, J=1.96 Hz, 1 H). Mass Spectrum (ESI) m/z=695.0 (2M+1).

Step F. (R)-tert-Butyl (1-(2-bromo-4-chlorophenyl)-2-oxoethyl)carbamate

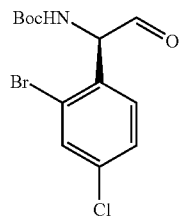

Osmium tetroxide (4 wt. % in water, 8.20 mL, 158 mmol) was added dropwise to a mixture of (S)-tert-butyl 1-(2-bromo-4-chlorophenyl)allylcarbamate (4.06 g, 11.71 mmol) and 4-methylmorpholine 4-oxide hydrate (3.17 g, 23.42 mmol) in 120 mL of 2:1 t-BuOH (80 mL) and water (40.0 mL) The reaction mixture was stirred overnight at room temperature, quenched with 30 mL of sat. aq. sodium thiosulfate solution and extracted with 4×80 mL of CHCl$_3$. The combined CHCl$_3$ extracts were dried over MgSO$_4$, filtered and the filtrate was concentrated in vacuo. The residue was purified by chromatography on silica gel (120 g silica gel column, RediSep® Rf, Teledyne Isco, Lincoln, Nebr.; eluent: ethyl acetate/hexanes 0% to 100%, gradient elution over 40 min, maintaining 100% over 10 min; flow rate 80 mL/min) to give the diol, tert-butyl ((1R)-1-(2-bromo-4-chlorophenyl)-2,3-dihydroxypropyl)carbamate. This material was dissolved in a mixture of Et$_2$O (70.0 mL) and water (35 mL), then sodium periodate (4.59 g, 21.44 mmol) was added. The reaction mixture was stirred at rt for 3 hours, diluted with ether (50 mL) and was quenched with 40 mL of sat. aq. Na$_2$S$_2$O$_3$ solution. The layers were separated and the aqueous layer was extracted with 3×60 mL of ether. The combined organic layers were washed with brine, then were dried over MgSO$_4$, filtered and the filtrate was concentrated to give the title compound. $^1$H NMR (500 MHz, CDCl$_3$) δ ppm 1.44 (br. s., 9 H) 5.77 (d, J=5.38 Hz, 1 H) 5.90 (br. s., 1 H) 7.22 (d, J=8.31 Hz, 1 H) 7.35 (dd, J=8.31, 1.96 Hz, 1 H) 7.66 (d, J=1.71 Hz, 1 H) 9.58 (br. s., 1 H).

Step G: tert-Butyl ((1R,2R)-1-(2-bromo-4-chlorophenyl)-2-(3-chlorophenyl)-2-hydroxyethyl)carbamate

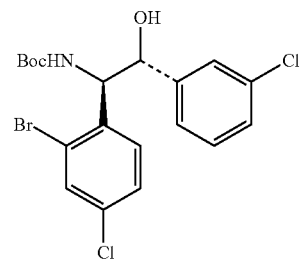 [SMILES: CC(C)(C)OC(=O)N[C@H](c1ccc(Cl)cc1Br)[C@H](O)c1cccc(Cl)c1]

A solution of (R)-tert-butyl 1-(2-bromo-4-chlorophenyl)-2-oxoethylcarbamate (3.74 g, 10.73 mmol; general procedure 6, step F) in 40 mL of THF was added to a 0.5M solution of 3-chlorophenylmagnesium bromide in THF (107 mL, 53.6 mmol) dropwise over a period of 40 minutes at room temperature. The reaction mixture was then stirred at room temperature for another 1.5 hours and quenched with 40 mL of sat. aq. NH$_4$Cl solution. The layers were separated and the aqueous layer was extracted with 3×100 mL of EtOAc. The combined organic layers were washed with sat. aq. NaCl solution, then were dried over MgSO$_4$, filtered and the filtrate was concentrated. The residue was purified by chromatography on silica gel (120 g silica gel column, RediSep® Rf, Teledyne Isco, Lincoln, Nebr.; eluent: ethyl acetate/hexanes 0% to 100%, gradient elution) to give the title compound as a white crystalline solid. $^1$H NMR (400 MHz, DMSO-d$_6$) δ ppm 1.31 (s, 9 H) 4.92 (br. s., 1 H) 5.20 (br. s., 1 H) 7.20-7.35 (m, 2 H) 7.39 (d, J=8.22 Hz, 2 H) 7.45-7.57 (m, 2 H) 7.62 (d, J=2.15 Hz, 1 H).

Step H. (1R,2R)-2-Amino-2-(2-bromo-4-chlorophenyl)-1-(3-chlorophenyl)ethanol hydrochloride A solution of 4.0M HCl in 1,4-dioxane (12.68 mL, 50.7 mmol) was added to tert-butyl (1R,2R)-1-(2-bromo-4-chlorophenyl)-2-(3-chlorophenyl)-2-hydroxyethylcarbamate (2.34 g, 5.07 mmol, Step G) in DCM (20 mL) and the reaction mixture was stirred at rt for 1.5 h and concentrated in vacuo to afford a semi-solid that was triturated with ether. The solids were separated by filtration to afford the title compound. The product was used in the next step without further purification. Mass Spectrum (ESI) m/z=360.0 (M+1).

The following intermediate E2 was prepared by a procedure analogous to the one described above.

| Intermediate | Structure | Name | Characterization |
|---|---|---|---|
| E2 | 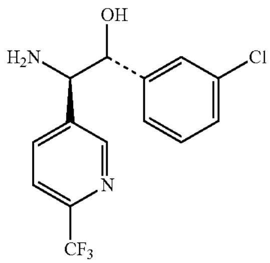 [SMILES: N[C@H](c1ccc(C(F)(F)F)nc1)[C@H](O)c1cccc(Cl)c1] | (1R,2R)-2-amino-1-(3-chlorophenyl)-2-(6-(trifluoromethyl)pyridin-3-yl) ethanol | ¹H NMR (500 MHz, CD₃OD) δ ppm 4.68 (d, J = 7.83 Hz, 1 H) 5.02 (d, J = 7.83 Hz, 1 H) 7.16-7.22 (m, 1 H) 7.27-7.30 (m, 2 H) 7.40 (s, 1 H) 7.86 (d, J = 8.07 Hz, 1 H) 8.11 (dd, J = 8.19, 2.08 Hz, 1 H) 8.61 (d, J = 1.71 Hz, 1 H). Mass Spectrum (ESI) m/z = 317.0 (M + 1). |

General Procedure 7

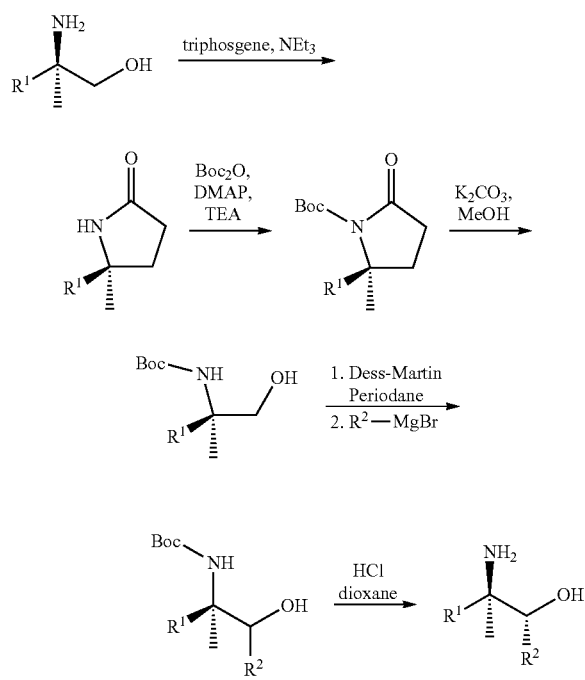

Intermediate F1

(1R,2R)-2-Amino-1-(3-chlorophenyl)-2-(4-chlorophenyl)propan-1-ol

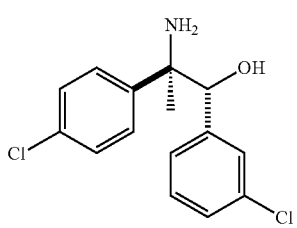

Step A. (R)-4-(4-Chlorophenyl)-4-methyloxazolidin-2-one

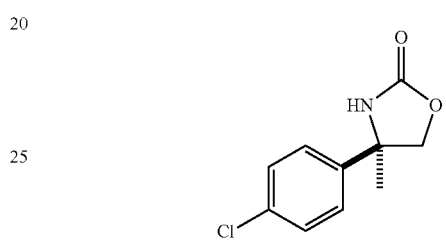

To a 100-mL round-bottomed flask equipped with an addition funnel was added (2R)-2-amino-2-(4-chlorophenyl))propan-1-ol HCl salt (5 g, 22.51 mmol) and triethylamine (9.4 mL, 67.5 mmol) in CH₂Cl₂ (45.0 mL) at 0° C. To this mixture a solution of triphosgene (1.670 mL, 11.26 mmol) in DCM (20 mL) was added dropwise over a period of 1 h at 0° C. The reaction was stirred for an additional 2 h at 0° C. The reaction was then allowed to stir at rt overnight. After this period, the reaction was quenched with a saturated sodium bicarbonate solution (30 mL) and allowed to stir for 1 hour. The crude biphasic mixture was then separated. The aqueous layer was washed with DCM (3×30 mL). The organic extract was dried over MgSO₄. The solution was filtered and concentrated in vacuo to give the crude material as a light-yellow oil. The crude material was purified by chromatography on silica gel, eluting with isocratic 3 step gradient of 10% to 30% acetone in hexanes, to provide the title compound as a light-yellow oil. ¹H NMR (400 MHz, CDCl₃) δ 7.40 (t, J=2.50 Hz, 1H), 7.37 (t, J=2.50 Hz, 2H), 7.34 (t, J=2.35 Hz, 2H), 7.31 (t, J=2.20 Hz, 1H), 5.77-5.97 (m, 1H), 4.38 (d, J=8.41 Hz, 1H), 4.31 (d, J=8.61 Hz, 1H), 1.76 (s, 3H). Mass Spectrum (ESI) m/z=212.2 [M]⁺.

Step B. (R)-tert-Butyl 4-(4-chlorophenyl)-4-methyl-2-oxooxazolidine-3-carboxylate

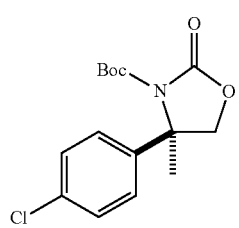

To a 100-mL round-bottomed flask was added (R)-4-(4-chlorophenyl)-4-methyloxazolidin-2-one (4.6 g, 21.73 mmol, Step A), DMAP (0.266 g, 2.173 mmol) and triethylamine (4.53 mL, 32.6 mmol) in THF (43.5 mL). To this solution at 0° C., di-tert-butyl dicarbonate (6.98 mL, 32.6 mmol) was added. The reaction was allowed to stir at room temperature overnight. The reaction mixture was diluted with saturated sodium bicarbonate (30 mL) and extracted with diethyl ether (3×30 mL). The combined organic extracts were dried over MgSO$_4$, filtered and the filtrate was concentrated under reduced pressure. The residue was absorbed onto a plug of silica gel and purified by chromatography on a silica gel column (120 g, RediSep® Rf, Teledyne Isco, Lincoln, Nebr.), eluting with a gradient of 0% to 30% acetone in hexanes, to provide the title compound. $^1$H NMR (400 MHz, CDCl$_3$) δ 7.28-7.35 (m, 2H), 7.21-7.28 (m, 2H), 4.10 (s, 2H), 1.89 (s, 3H), 1.21 (s, 9H). Mass Spectrum (ESI) m/z=256.2 [M−tBu]$^+$.

Step C: (R)-tert-Butyl (2-(4-chlorophenyl)-1-hydroxypropan-2-yl)carbamate

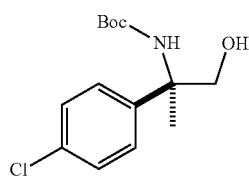

To a 250-mL round-bottomed flask was added (R)-tert-butyl 4-(4-chlorophenyl)-4-methyl-2-oxooxazolidine-3-carboxylate (5.7 g, 18.28 mmol, Step B) and potassium carbonate (2.76 g, 45.7 mmol) in methanol (73 mL). The reaction was stirred at this temperature overnight. The reaction mixture was diluted with dichloromethane (80 mL) and extracted with brine (3×30 mL). The organic extract was washed with water (30 mL) and dried over MgSO$_4$. The solution was filtered and concentrated in vacuo to give the crude material as a light yellow solid. The crude material was absorbed onto a plug of silica gel and purified by chromatography on a silica gel column (120 g, RediSep® Rf, Teledyne Isco, Lincoln, Nebr.), eluting with a gradient of 5% to 35% acetone in hexanes, to provide the title compound as white solid.

$^1$H NMR (400 MHz, CDCl$_3$) δ 7.33 (d, J=0.78 Hz, 4H), 5.13-5.26 (m, 1H), 3.85-3.97 (m, 1H), 3.73 (s, 1H), 1.60 (s, 3H), 1.43 (br. s., 9H). Mass Spectrum (ESI) m/z=308.2 [M+Na]$^+$.

Step D. (R)-tert-Butyl (2-(4-chlorophenyl)-1-oxopropan-2-yl)carbamate

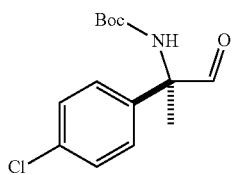

Dess-martin periodinane (13.36 g, 31.5 mmol) was added to a suspension of (R)-tert-butyl (2-(4-chlorophenyl)-1-hydroxypropan-2-yl)carbamate (4.5 g, 15.75 mmol, Step C) in wet DCM (1 µL water/1 mL DCM) at rt. The mixture was stirred at 25° C. for 2 h. After this time the reaction mixture was diluted with ether (40 mL) and a solution of Na$_2$S$_2$O$_3$ (10 equiv) in saturated aq. NaHCO$_3$ solution (40 mL) was added. The mixture was stirred vigorously for 10 minutes and the layers were separated. The aq. layer was extracted with diethyl ether. The organics were pooled, dried over MgSO$_4$, filtered and concentrated in vacuo to provide an off-white solid. The product was used in the following step without further purification.

(Note: The reaction requires the use of wet DCM. This is prepared by stirring vigorously 1 µL water/1 mL DCM until no water dropplets are observed. The resulting aldehyde is prone to the formation of hemiacetals so avoid the use of ethanol-stabilized diethyl ether). $^1$H NMR (400 MHz, CDCl$_3$) δ 9.28 (s, 1H), 7.29-7.42 (m, 4H), 5.60-5.85 (m, 1H), 1.82 (s, 3H), 1.42 (d, J=8.80 Hz, 9H). Mass Spectrum (ESI) m/z=306.1 [M+Na]$^+$.

Step E. tert-Butyl ((1S,2R)-1-(3-chlorophenyl)-2-(4-chlorophenyl)-1-hydroxypropan-2-yl)carbamate and tert-Butyl ((1R,2R)-1-(3-chlorophenyl)-2-(4-chlorophenyl)-1-hydroxypropan-2-yl)carbamate

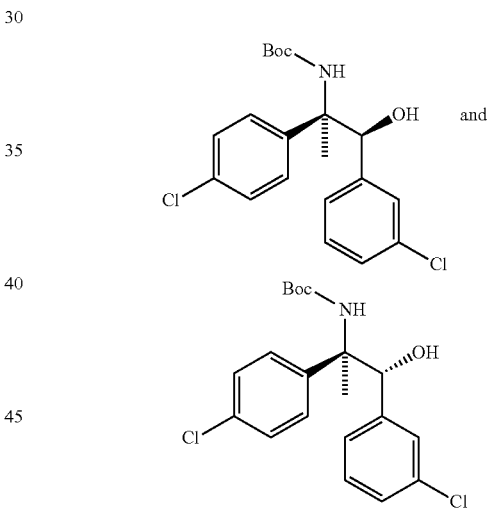

To a solution of (3-chlorophenyl)magnesium bromide (1M, 40 mmols) in diethyl ether was added a solution of (R)-tert-butyl (2-(4-chlorophenyl)-1-oxopropan-2-yl)carbamate (5.66 g, 19.95 mmol, Step D) in Et$_2$O (20 mL). After stirring overnight, the reaction mixture was quenched by addition of sat. aq. NH$_4$Cl solution (20 mL) and extracted with EtOAc (3×30 mL). The combined organic extracts were pooled and dried over MgSO$_4$. The solution was filtered and concentrated. The crude material was absorbed onto a plug of silica gel and purified by chromatography on a silica gel column (330 g, RediSep® Rf, Teledyne Isco, Lincoln, Nebr.), eluting with a gradient of 0% to 40% EtOAc in hexane, to provide the title compounds as a 3:1 mixture of isomers. Mass Spectrum (ESI) m/z=418.2 [M+Na]$^+$.

91

Step F. (1R,2R)-2-Amino-1-(3-chlorophenyl)-2-(4-chlorophenyl)propan-1-ol

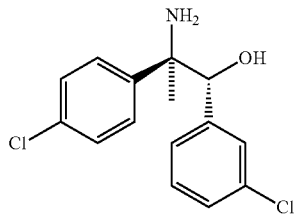 [SMILES: C[C@@](N)(c1ccc(Cl)cc1)[C@H](O)c1cccc(Cl)c1]

The mixture of tert-butyl ((1S,2R)-1-(3-chlorophenyl)-2-(4-chlorophenyl)-1-hydroxypropan-2-yl)carbamate and tert-butyl ((1R,2R)-1-(3-chlorophenyl)-2-(4-chlorophenyl)-1-hydroxypropan-2-yl)carbamate (3.0 g, 7.57 mmol, Step E) was treated with a 4.0M solution oh HCl in 1,4-dioxane (34.1 mL, 136 mmol) at rt for 2 h. The crude mixture was basified with a saturated solution of sodium bicarbonate. The biphasic solution was separated and the aqueous layer was washed with dichloromethane (3×30 mL). The combined organic layers were dried over $MgSO_4$, filtered and the filtrate was concentrated. The residue was absorbed onto a plug of silica gel and purified by chromatography on silica gel column (120 g, RediSep® Rf, Teledyne Isco, Lincoln, Nebr.), eluting with isocratic 70/25/5 DCM/Acetone/MeOH with 0.1% of triethylamine to provide the title compound as the first (faster) eluting isomer. $^1$H NMR (400 MHz, $CDCl_3$) δ 7.21-7.25 (m, 3H), 7.11-7.16 (m, 1H), 7.03-7.10 (m, 2H), 6.79 (d, J=7.63 Hz, 1H), 4.61 (s, 1H), 2.07 (s, 2H), 1.18 (s, 3H). Mass Spectrum (ESI) m/z=296.2 $[M]^+$.

Further elution provided:

Intermediate F2

(1S,2R)-2-Amino-1-(3-chlorophenyl)-2-(4-chlorophenyl)propan-1-ol

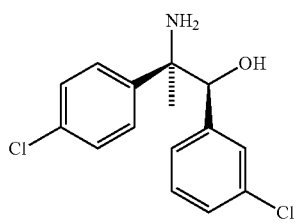 [SMILES: C[C@@](N)(c1ccc(Cl)cc1)[C@@H](O)c1cccc(Cl)c1]

$^1$H NMR (400 MHz, $CDCl_3$) δ 7.10-7.18 (m, 2H), 7.02-7.09 (m, 2H), 6.97 (d, J=15.65 Hz, 1H), 6.87 (t, J=1.86 Hz, 1H), 6.64 (d, J=7.83 Hz, 1H), 4.54 (s, 1H), 2.01-2.10 (m, 2H), 1.46 (s, 3H). Mass Spectrum (ESI) m/z=296.2 $[M]^+$.

92

Intermediate G (R)-1-((3,4-Dimethoxybenzyl)oxy)butan-2-yl-4-bromobenzenesulfonate

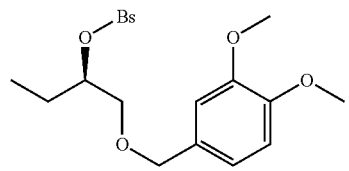

Step A. (R)-1-((3,4-Dimethoxybenzyl)oxy)butan-2-ol

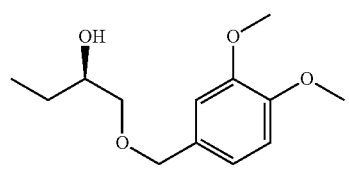 [SMILES: CC[C@@H](O)COCc1ccc(OC)c(OC)c1]

Over a period of 30 min, to a suspension of sodium hydride (60% dispersion in mineral oil, 8.91 g, 223 mmol) in DMF (300 mL) at 60° C. was added dropwise a solution of 3,4-dimethoxybenzyl alcohol (29.4 mL, 202 mmol) in DMF (100 mL). The reaction was stirred at 60° C. for 0.5 h until $H_2$ evolution ceased. The reaction was cooled to 45° C., and then (R)-2-ethyloxirane (17.61 mL, 202 mmol) was added dropwise. The reaction was allowed to stir at 45° C. overnight. The reaction mixture was diluted with sat aq. $NaHCO_3$ solution (300 mL) and extracted with diethyl ether (3×300 mL). The organic extract was washed with water (3×300 mL) and dried over $MgSO_4$. The solution was filtered and concentrated under reduced pressure. The residue was absorbed onto a plug of silica gel and purified by chromatography through a silica gel column (330 g, RediSep® Rf, Teledyne Isco, Lincoln, Nebr.), eluting with a gradient of 10% to 40% acetone in hexanes, to provide the title compound as an off-white oil. $^1$H NMR (400 MHz, $CDCl_3$) δ 6.81-6.93 (m, 3H), 4.51 (s, 2H), 3.91 (d, J=1.00 Hz, 6H), 3.69-3.82 (m, 1H), 3.52 (dd, J=3.03, 9.49 Hz, 1H), 3.33 (dd, J=8.02, 9.39 Hz, 1H), 1.44-1.58 (m, 2H), 0.98 (t, J=7.53 Hz, 3H). MS (ESI) 263.2 $[M+Na]^+$.

Step B. (R)-1-((3,4-Dimethoxybenzyl)oxy)butan-2-yl 4-bromobenzenesulfonate

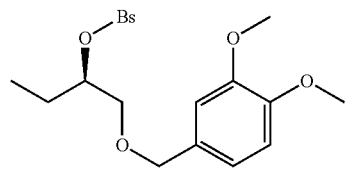

To DMAP (14.54 g, 119 mmol) and (R)-1-((3,4-dimethoxybenzyl)oxy)butan-2-ol (13.0 g, 54.1 mmol) in CH$_2$Cl$_2$ (180 mL) was added 4-bromobenzene-1-sulfonyl chloride (20.74 g, 81 mmol). The reaction was stirred at room temperature overnight. The crude material was partitioned between ethyl acetate (50 mL) and saturated sodium bicarbonate (100 mL). The organics were sequestered and the aqueous was extracted further with ethyl acetate (50 mL). The organics were combined and washed with 0.1 M HCl (2×50 mL). The organics were then washed with brine (50 mL), dried over MgSO$_4$, and concentrated in vacuo. The residue was absorbed onto a plug of silica gel and purified by chromatography through a silica gel column (330 g, RediSep® Rf, Teledyne Isco, Lincoln, Nebr.), eluting with a 3 step gradient of 10% to 30% acetone in hexanes which afforded the title compound. $^1$H NMR (400 MHz, CDCl$_3$) δ 7.75 (d, J=8.56 Hz, 2H), 7.59 (d, J=8.31 Hz, 2H), 6.66-6.89 (m, 3H), 4.67 (quin, J=5.62 Hz, 1H), 4.25-4.45 (m, 2H), 3.90 (s, 3H), 3.89 (s, 3H), 3.42-3.58 (m, 2H), 1.64-1.82 (m, 2H), 0.88 (t, J=7.46 Hz, 3H). MS (ESI) 481.0 [M+Na]$^+$.

Example 1

2-((2R,5R,6R)-6-(3-Chlorophenyl)-4-(cyclopropylmethyl)-5-(1H-indol-2-yl)-3-oxomorpholin-2-yl)acetic acid or 2-((2S,5R,6R)-6-(3-Chlorophenyl)-4-(cyclopropylmethyl)-5-(1H-indol-2-yl)-3-oxomorpholin-2-yl)acetic acid

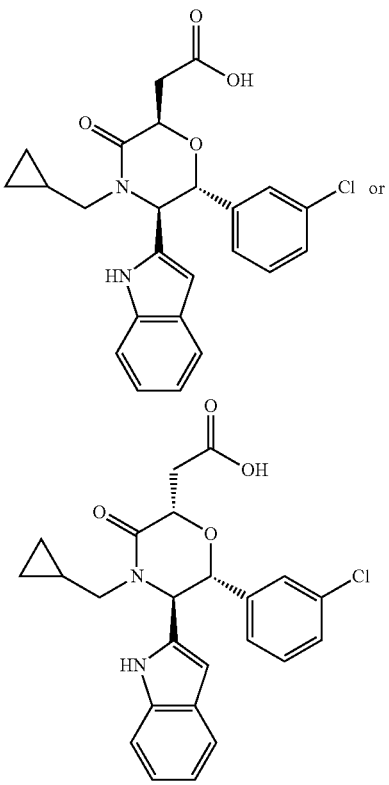

Step A. 1-(Phenylsulfonyl)-1H-indole

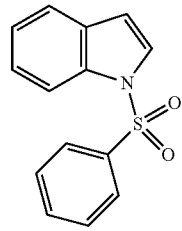 [SMILES: O=S(=O)(c1ccccc1)n1ccc2ccccc21]

Indole (10.00 g, 85 mmol) was added slowly to a suspension of NaH (60% in mineral oil, 4.27 g, 107 mmol) in anhydrous DMF (213 mL) at 0° C. under argon. After 20 minutes the ice bath was removed. After 1 hour the reaction mixture was recooled to 0° C., benzenesulfonyl chloride (12.1 mL, 94 mmol) was added slowly and the reaction mixture was allowed to warm to rt. After 16 hours the reaction mixture was poured into ice-cold water (500 mL) and extracted with diethyl ether (3×300 mL). The organics were pooled, washed with brine, dried over MgSO$_4$, filtered and the filtrate was concentrated to provide an off-white solid. Purification by chromatography on silica gel (300 g silica gel column, RediSep® Rf, Teledyne Isco, Lincoln, Nebr.; eluent: ethyl acetate in hexane 0% to 10%, gradient elution) provided the title compound as a white crystalline solid. $^1$H NMR (400 MHz, CDCl$_3$) δ ppm 6.70 (d, J=3.6 Hz, 1H), 7.26 (t, J=7.5 Hz, 1H), 7.34 (t, J=7.8 Hz, 1H), 7.46 (m, 2H), 7.55 (m, 2H), 7.60 (d, J=3.6 Hz, 1H), 7.90 (m, 2H), 8.03 (d, J=8.3 Hz, 1H).

Step B. (R)-Methyl 2-(3-chlorophenyl)-2-hydroxyacetate

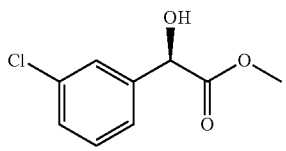

Sulfuric acid (1.43 mL, 26.8 mmol) was added to a solution of (R)-2-(3-chlorophenyl)-2-hydroxyacetic acid (50.00 g, 268 mmol) in MeOH (536 mL) at rt. The reaction mixture was heated to reflux for 5 hours. Most of the MeOH was removed in vacuo and the remaining solution was partitioned between EtOAc (200 mL) and sat. aq. NaHCO$_3$ solution (300 mL). The layers were separated and the aqueous layer was extracted with EtOAc (2×200 mL). The organics were pooled, washed with brine, dried over MgSO$_4$, filtered and the filtrate was concentrated to provide a colorless liquid.

$^1$H NMR (400 MHz, CDCl$_3$) δ ppm 3.74 (s, 3H), 5.11 (s, 1H), 7.26 (m, 3 H), 7.45 (s, 1H).

Step C. (R)-Methyl 2-(tert-butyldimethylsilyloxy)-2-(3-chlorophenyl)acetate

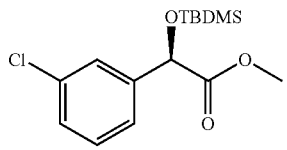 [SMILES: COC(=O)[C@H](O[Si](C)(C)C(C)(C)C)c1cccc(Cl)c1]

TBDMS-Cl (59.8 g, 397 mmol) was added to a solution of (R)-methyl 2-(3-chlorophenyl)-2-hydroxyacetate (53.10 g, 265 mmol; Example 1, step B) and imidazole (45.0 g, 662 mmol) in anhydrous DMF (265 mL) at rt under argon. After 9 hours the reaction mixture was poured into water (1 L) and extracted with $Et_2O$ (3×500 mL). The organics were pooled, washed with brine, dried over $MgSO_4$, filtered and the filtrate was concentrated to provide a colorless liquid. Purification by chromatography on silica gel (2 stacked 330 g silica gel columns, RediSep® Rf, Teledyne Isco, Lincoln, Nebr.; eluent: ethyl acetate in hexane 0% to 25%, gradient elution) provided the title compound as a colorless liquid. $^1$H NMR (400 MHz, $CDCl_3$) δ ppm 0.03 (s, 3H), 0.10 (s, 3H), 0.91 (s, 9H), 3.68 (s, 3H), 5.08 (s, 1H), 7.24 (m, 2H), 7.34 (m, 1H), 7.46 (m, 1H).

Step D. (R)-2-(tert-Butyldimethylsilyloxy)-2-(3-chlorophenyl)acetaldehyde

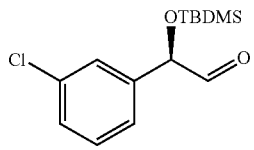 [SMILES: CC(C)(C)[Si](C)(C)O[C@@H](C=O)c1cccc(Cl)c1]

DIBAL-H (1.5 M in toluene, Aldrich) (249 mL, 374 mmol) was added dropwise over 1.5 hours to a solution of (R)-methyl 2-(tert-butyldimethylsilyloxy)-2-(3-chlorophenyl) acetate (78.50 g, 249 mmol, Step C) in anhydrous diethyl ether (499 mL) at −78° C. under argon. After 1 hour the reaction was quenched by the addition of methanol (45 mL). The reaction mixture was poured into a sat. aq. solution of potassium sodium tartrate (Rochelle salt) and stirred at rt overnight. The layers were separated and the aqueous layer was extracted with diethyl ether (2×500 mL). The organics were pooled, washed with brine, dried ($MgSO_4$), filtered and the filtrate was concentrated in vacuo to provide a colorless liquid. Purification by chromatography on silica gel (2 stacked 330 g silica gel columns, RediSep® Rf, Teledyne Isco, Lincoln, Nebr.; eluent: ethyl acetate in hexane 0% to 25%, gradient elution) provided the title compound. $^1$H NMR (400 MHz, $CDCl_3$) δ ppm 0.07 (s, 3H), 0.14 (s, 3H), 0.96 (s, 9H), 4.98 (d, J=2.2 Hz, 1H), 7.31 (m, 3H), 7.41 (m, 1H), 9.51 (d, J=2.1 Hz, 1H).

Step E. (R)-N-((R)-2-(tert-Butyldimethylsilyloxy)-2-(3-chlorophenyl)ethylidene)-2-methylpropane-2-sulfinamide

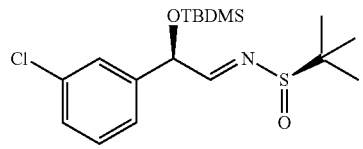

Copper(II)sulfate (14.64 g, 92 mmol) was added to a solution of (R)-2-(tert-butyldimethylsilyloxy)-2-(3-chlorophenyl)acetaldehyde (11.88 g, 41.7 mmol, Step D) and (R)-2-methylpropane-2-sulfinamide (5.56 g, 45.9 mmol) in anhydrous dichloromethane (83 mL) at rt. After 68 hours the reaction mixture was filtered through a pad of Celite® (J. T. Baker, Phillipsberg, N.J., diatomaceous earth), washed with DCM and the combined filtrates were concentrated in vacuo to provide an orange oil. Purification by chromatography on silica gel (330 g silica gel column, RediSep® Rf, Teledyne Isco, Lincoln, Nebr.; eluent: ethyl acetate in hexane 0% to 25%, gradient elution) provided the title compound as a colorless oil. $^1$H NMR (500 MHz, $CDCl_3$) δ ppm 0.05 (s, 3H), 0.11 (s, 3H), 0.93 (s, 9H), 1.23 (s, 9H), 5.44 (d, J=5.1 Hz, 1H), 7.30 (m, 3H), 7.42 (m, 1H), 7.93 (d, J=5.4 Hz, 1H).

Step F. (R)-N-((1R,2R)-2-(tert-Butyldimethylsilyloxy)-2-(3-chlorophenyl)-1-(1-(phenylsulfonyl)-1H-indol-2-yl)ethyl)-2-methylpropane-2-sulfinamide

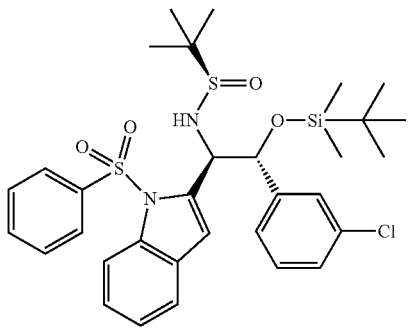 [SMILES: CC(C)(C)[S@@](=O)N[C@H](c1cc2ccccc2n1S(=O)(=O)c1ccccc1)[C@H](O[Si](C)(C)C(C)(C)C)c1cccc(Cl)c1]

n-BuLi (2.5 M in hexanes) (8.02 mL, 20.04 mmol) was added over 30 minutes to a solution of 1-(phenylsulfonyl)-1H-indole (5.50 g, 21.38 mmol, Step A) in anhydrous THF (25 mL) at −78° C. under argon. The reaction mixture was slowly warmed to 0° C. over a period of 1.5 hours. This solution was added via cannula to a solution of (R)-N-((R)-2-(tert-butyldimethylsilyloxy)-2-(3-chlorophenyl)ethylidene)-2-methylpropane-2-sulfinamide (5.18 g, 13.36 mmol, Step E) in anhydrous THF (25 mL) at −78° C. under argon. The reaction mixture was allowed to warm to rt as the bath warmed. After 14 hours the reaction was quenched by the addition of sat. aq. $NH_4Cl$ solution and the layers were separated. The aqueous layer was extracted with EtOAc (3×) and the organics were pooled, washed with brine, dried ($MgSO_4$), filtered and the filtrate was concentrated to provide a brown oil. Purification by chromatography on silica gel (330 g silica gel column, RediSep® Rf, Teledyne Isco, Lincoln, Nebr.; eluent: ethyl acetate in hexane 10% to 35%, gradient elution)

provided the title compound as a yellow oil. ¹H NMR (500 MHz, CDCl₃) δ ppm −0.53 (s, 3H), −0.29 (s, 3H), 0.81 (s, 9H), 1.10 (s, 9H), 4.09 (d, J=5.9 Hz, 1H), 5.40 (s, 1H), 5.41 (d, J=6.4 Hz, 1H), 6.70 (s, 1H), 7.25 (m, 1H), 7.30-7.40 (m, 5H), 7.43-7.52 (m, 3H), 7.61 (m, 1H), 7.79 (m, 2H), 8.19 (d, J=8.0 Hz, 1H). Mass spectrum (ESI) m/z 645.2 [M+H]⁺.

Step G. (1R,2R)-2-(tert-Butyldimethylsilyloxy)-2-(3-chlorophenyl)-1-(1-(phenylsulfonyl)-1H-indol-2-yl) ethanamine

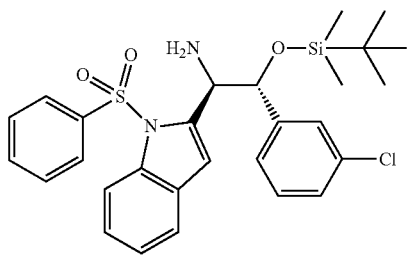 [SMILES: CC(C)(C)[Si](C)(C)O[C@H](c1cccc(Cl)c1)[C@H](N)c1cc2ccccc2n1S(=O)(=O)c1ccccc1]

4M HCl in dioxane (10.38 mL, 41.5 mmol) was added to a solution of (R)-N-((1R,2R)-2-(tert-butyldimethylsilyloxy)-2-(3-chlorophenyl)-1-(1-(phenylsulfonyl)-1H-indol-2-yl)ethyl)-2-methylpropane-2-sulfinamide (5.36 g, 8.31 mmol) in MeOH (83 mL) at rt. After 45 minutes the reaction mixture was diluted with water (200 mL), adjusted to a pH of about 8 with sat. aq. NaHCO₃ solution and extracted with EtOAc (3×150 mL). The organics were pooled, washed with brine, dried over MgSO₄, filtered and the filtrate was concentrated in vacuo to provide the crude title compound as an oil, which was used without further purification. ¹H NMR (400 MHz, CDCl₃) δ ppm −0.54 (s, 3H), −0.31 (s, 3H), 0.77 (s, 9H), 4.72 (s, 1H), 5.42 (s, 1H), 6.72 (s, 1H), 7.23 (m, 1H), 7.26-7.36 (m, 5H), 7.43 (m, 1H), 7.47 (m, 1H), 7.54 (d, J=7.6 Hz, 1H), 7.63 (m, 1H), 7.66 (m, 2H), 8.17 (d, J=8.4 Hz, 1H). Mass spectrum (ESI) m/z 541.2 [M+H]⁺.

Step H. (1R,2R)-2-(tert-Butyldimethylsilyloxy)-2-(3-chlorophenyl)-N-(cyclopropylmethyl)-1-(1-(phenylsulfonyl)-1H-indol-2-yl)ethanamine

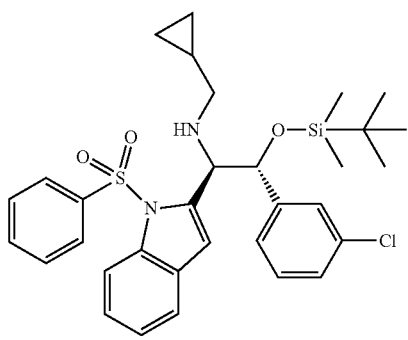 [SMILES: CC(C)(C)[Si](C)(C)O[C@H](c1cccc(Cl)c1)[C@H](NCC1CC1)c1cc2ccccc2n1S(=O)(=O)c1ccccc1]

Cyclopropanecarbaldehyde (0.456 mL, 6.10 mmol) was added to a solution of (1R,2R)-2-(tert-butyldimethylsilyloxy)-2-(3-chlorophenyl)-1-(1-(phenylsulfonyl)-1H-indol-2-yl)ethanamine (3.00 g, 5.54 mmol) in MeOH (27.7 mL) at rt. After 1 h sodium borohydride (0.252 g, 6.65 mmol) was added and the reaction mixture was stirred for 15 minutes before it was quenched with sat. aq. NH₄Cl solution. Water (50 mL) was added and the mixture was extracted with EtOAc (2×). The organics were pooled, washed with brine, dried over MgSO₄, filtered and the filtrate was concentrated to provide a yellow oil. Purification by chromatography on silica gel (330 g silica gel column, RediSep® Rf, Teledyne Isco, Lincoln, Nebr.; eluent: ethyl acetate in hexane 0% to 20%, gradient elution) provided the title compound as a colorless oil. ¹H NMR (500 MHz, CDCl₃) δ ppm −0.50 (s, 3H), −0.34 (s, 3H), −0.14 (m, 2H), 0.29 (m, 2H), 0.67 (m, 1H), 0.79 (s, 9H), 1.96 (dd, J=6.3 and 11.7 Hz, 1H), 2.12 (dd, J=6.9 and 11.8 Hz, 1H), 4.52 (s, 1H), 5.23 (s, 1H), 6.72 (s, 1H), 7.24-7.31 (m, 4H), 7.35 (m, 2H), 7.45-7.52 (m, 3H), 7.65 (m, 3H), 8.20 (d, J=8.3 Hz, 1H). Mass spectrum (ESI) m/z 595.2 [M+H]⁺.

Step I. (E)-tert-butyl 4-(((1R,2R)-2-(tert-butyldimethylsilyloxy)-2-(3-chlorophenyl)-1-(1-(phenylsulfonyl)-1H-indol-2-yl)ethyl)(cyclopropylmethyl) amino)-4-oxobut-2-enoate

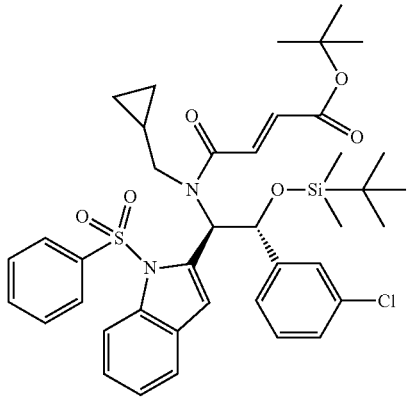 [SMILES: CC(C)(C)OC(=O)/C=C/C(=O)N(CC1CC1)[C@H](c1cc2ccccc2n1S(=O)(=O)c1ccccc1)[C@H](O[Si](C)(C)C(C)(C)C)c1cccc(Cl)c1]

One drop of DMF was added to a solution of (E)-4-tert-butoxy-4-oxobut-2-enoic acid (1.952 g, 11.34 mmol) and oxalyl chloride (1.588 mL, 18.14 mmol) in DCM (23 mL) at rt. After 2 hours the reaction mixture was concentrated in vacuo, diluted with DCM and concentrated in vacuo again (this was repeated twice) to provide a brown oil. This oil was dissolved in DCM (20 mL) and added to a solution of (1R,2R)-2-(tert-butyldimethylsilyloxy)-2-(3-chlorophenyl)-N-(cyclopropylmethyl)-1-(1-(phenylsulfonyl)-1H-indol-2-yl)ethanamine (2.70 g, 4.54 mmol, Step H) in DCM (20 mL) at rt. DIPEA (2.97 mL, 17.01 mmol) was then added to the reaction mixture. After 2 hours the reaction mixture was diluted with water and the layers were separated. The aqueous layer was extracted with DCM (2×) and the organics were pooled, washed with brine, dried over MgSO₄, filtered and the filtrate was concentrated in vacuo to provide a dark brown oil. Purification by chromatography on silica gel (330 g silica gel column, RediSep® Rf, Teledyne Isco, Lincoln, Nebr.; eluent: ethyl acetate in hexane 10% to 35%, gradient elution) provided the title compound as an off-white foam. Mass spectrum (ESI) m/z 749.2 [M+H]⁺.

Step J. tert-Butyl 2-((2R,5R,6R)-6-(3-chlorophenyl)-4-(cyclopropylmethyl)-3-oxo-5-(1-(phenylsulfonyl)-1H-indol-2-yl)morpholin-2-yl)acetate or tert-Butyl 2-((2S,5R,6R)-6-(3-chlorophenyl)-4-(cyclopropylmethyl)-3-oxo-5-(1-(phenylsulfonyl)-1H-indol-2-yl)morpholin-2-yl)acetate

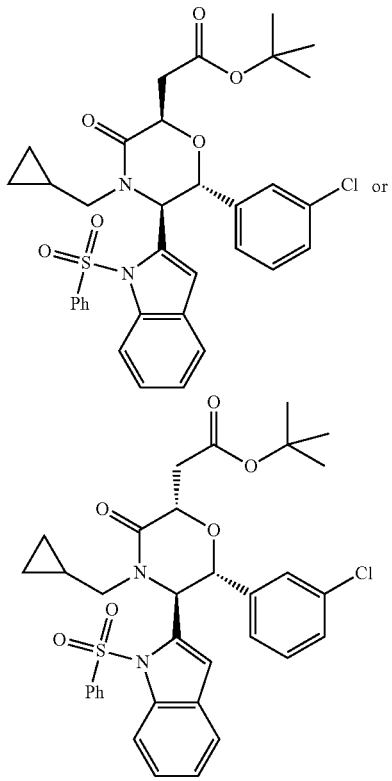

TBAF (1 M in THF) (3.83 mL, 3.83 mmol) was added to a solution of (E)-tert-butyl 4-(((1R,2R)-2-(tert-butyldimethylsilyloxy)-2-(3-chlorophenyl)-1-(1-(phenylsulfonyl)-1H-indol-2-yl)ethyl)(cyclopropylmethyl)amino)-4-oxobut-2-enoate (2.61 g, 3.48 mmol, Step I) in THF (34.8 mL) at rt. After 1 h the reaction mixture was diluted with sat. aq. NH$_4$Cl solution and the layers were separated. The aqueous layer was extracted with EtOAc (2×) and the organics were pooled, washed with brine, dried (MgSO$_4$), filtered and concentrated in vacuo to provide a yellow oil. NMR indicated an approximate 3.3:1 mixture of isomers. Purification by chromatography on silica gel (330 g silica gel column, RediSep® Rf, Teledyne Isco, Lincoln, Nebr.; eluent: 2.5% MTBE/20% hexanes in DCM) provided one of the title compounds as the first eluting, major isomer. $^1$H NMR (400 MHz, CDCl$_3$) δ ppm 0.16 (m, 1H), 0.24 (m, 1H), 0.55 (m, 1H), 0.66 (m, 1H), 1.01 (m, 1H), 1.43 (s, 9H), 2.35 (dd, J=7.6 and 14.3 Hz, 1H), 2.65 (dd, J=8.8 and 16.0 Hz, 1H), 3.00 (dd, J=3.3 and 16.0 Hz, 1H), 4.03 (dd, J=6.9 and 14.1 Hz, 1H), 4.33 (dd, J=3.3 and 8.8 Hz, 1H), 5.26 (s, 1H), 5.95 (s, 1H), 6.75 (s, 1H), 7.32 (m, 1H), 7.35-7.44 (m, 5H), 7.56 (m, 3H), 7.65 (m, 3H), 8.19 (d, J=8.0 Hz, 1H). Mass spectrum (ESI) m/z 657.2 [M+Na]$^+$.

Further elution provided another one of the title compounds as the second eluting, minor isomer. $^1$H NMR (400 MHz, CDCl$_3$) δ ppm 0.00 (m, 1H), 0.12 (m, 1H), 0.28 (m, 1H), 0.36 (m, 1H), 0.82 (m, 1H), 1.36 (s, 9H), 2.45 (m, 1H), 2.68 (m, 1H), 2.85 (m, 1H), 3.47 (m, 1H), 4.74 (m, 1H), 5.02 (m, 1H), 5.90 (m, 1H), 6.76 (bs, 1H), 7.10-7.22 (m, 8H), 7.25-7.45 (m, 4H), 7.85 (m, 1H). Mass spectrum (ESI) m/z 657.2 [M+Na]$^+$.

Step K. 2-((2R,5R,6R)-6-(3-Chlorophenyl)-4-(cyclopropylmethyl)-3-oxo-5-(1-(phenylsulfonyl)-1H-indol-2-yl)morpholin-2-yl)acetic acid or 2-((2S,5R,6R)-6-(3-Chlorophenyl)-4-(cyclopropylmethyl)-3-oxo-5-(1-(phenylsulfonyl)-1H-indol-2-yl)morpholin-2-yl)acetic acid

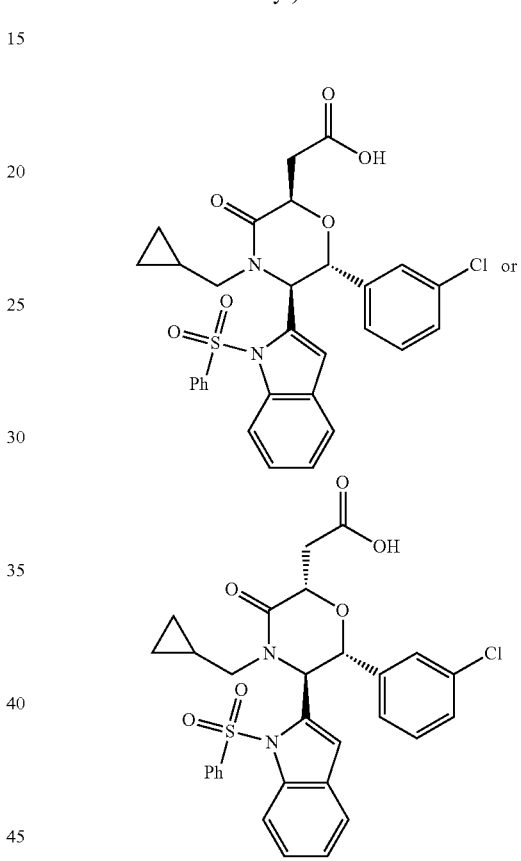

TFA (5.00 mL, 64.9 mmol) was added to a solution of tert-butyl 2-((2R,5R,6R)-6-(3-chlorophenyl)-4-(cyclopropylmethyl)-3-oxo-5-(1-(phenylsulfonyl)-1H-indol-2-yl)morpholin-2-yl)acetate or tert-butyl 2-((2S,5R,6R)-6-(3-chlorophenyl)-4-(cyclopropylmethyl)-3-oxo-5-(1-(phenylsulfonyl)-1H-indol-2-yl)morpholin-2-yl)acetate (1.19 g, 1.874 mmol, Step J; first eluting, major isomer) in DCM (15.00 mL) at rt. After 2 hours the reaction mixture was concentrated in vacuo, a few mL of hexanes were added and the solvent was removed under reduced pressure on a rotary evaporator. This procedure was repeated twice to provide one of the title compounds as a foam. $^1$H NMR (400 MHz, CDCl$_3$) δ ppm 0.17 (m, 1H), 0.27 (m, 1H), 0.60 (m, 1H), 0.70 (m, 1H), 1.03 (m, 1H), 2.41 (dd, J=7.7 and 14.1 Hz, 1H), 2.90 (dd, J=6.6 and 16.6 Hz, 1H), 3.08 (dd, J=5.4 and 16.4 Hz, 1H), 4.06 (dd, J=6.8 and 14.0 Hz, 1H), 4.30 (t, J=5.9 Hz, 1H), 5.29 (s, 1H), 5.99 (s, 1H), 6.71 (s, 1H), 7.34 (m, 1H), 7.36-7.44 (m, 5H), 7.49 (s, 1H), 7.56-7.66 (m, 5H), 8.19 (dd, J=0.7 and 8.4 Hz, 1H). Mass spectrum (ESI) m/z 579.2 [M+H]$^+$.

Step L. 2-((2R,5R,6R)-6-(3-Chlorophenyl)-4-(cyclopropylmethyl)-5-(1H-indol-2-yl)-3-oxomorpholin-2-yl)acetic acid or 2-((2S,5R,6R)-6-(3-Chlorophenyl)-4-(cyclopropylmethyl)-5-(1H-indol-2-yl)-3-oxomorpholin-2-yl)acetic acid A solution of 2-((2R,5R,6R)-6-(3-chlorophenyl)-4-(cyclopropylmethyl)-3-oxo-5-(1-(phenylsulfonyl)-1H-indol-2-yl)morpholin-2-yl)acetic acid or 2-((2S,5R,6R)-6-(3-chlorophenyl)-4-(cyclopropylmethyl)-3-oxo-5-(1-(phenylsulfonyl)-1H-indol-2-yl)morpholin-2-yl)acetic acid (1.09 g, 1.882 mmol, Step K) in TBAF (18.82 mL, 18.82 mmol; 1M in THF) was heated to reflux. After 1.5 hours the reaction mixture was cooled to rt, diluted with sat. aq. NH$_4$Cl solution and the layers were separated. The aqueous layer was extracted with EtOAc (2×) and the organics were pooled, washed with brine, dried over MgSO$_4$, filtered and the filtrate was concentrated in vacuo to provide a yellow oil. Purification by chromatography on silica gel (120 g silica gel column, RediSep® Rf, Teledyne Isco, Lincoln, Nebr.; eluent: 0 to 5% MeOH/DCM with 0.5% AcOH as additive; gradient elution) provided one of the title compounds as an off-white foam. $^1$H NMR (500 MHz, CDCl$_3$) δ ppm 0.02 (m, 1H), 0.23 (m, 1H), 0.37 (m, 1H), 0.52 (m, 1H), 0.96 (m, 1H), 2.36 (dd, J=8.0 and 14.1 Hz, 1H), 2.65 (dd, J=3.9 and 18.1 Hz, 1H), 3.20 (dd, J=4.2 and 18.1 Hz, 1H), 3.81 (m, 1H), 3.88 (dd, J=6.3 and 14.2 Hz, 1H), 4.96 (s, 1H), 5.12 (s, 1H), 6.22 (d, J=1.5 Hz, 1H), 6.87 (dt, J=1.0 and 7.6 Hz, 1H), 6.96 (dt, J=1.2 and 7.7 Hz, 1H), 7.15-7.23 (m, 4H), 7.35 (d, J=7.8 Hz, 1H), 7.41 (bs, 1H), 10.13 (s, 1H). Mass spectrum (ESI) m/z 439.2 [M+H]$^+$.

Example 2

2-((2S,5R,6R)-6-(3-Chlorophenyl)-4-(cyclopropylmethyl)-5-(1H-indol-2-yl)-3-oxomorpholin-2-yl)acetic acid or 2-((2R,5R,6R)-6-(3-Chlorophenyl)-4-(cyclopropylmethyl)-5-(1H-indol-2-yl)-3-oxomorpholin-2-yl)acetic acid

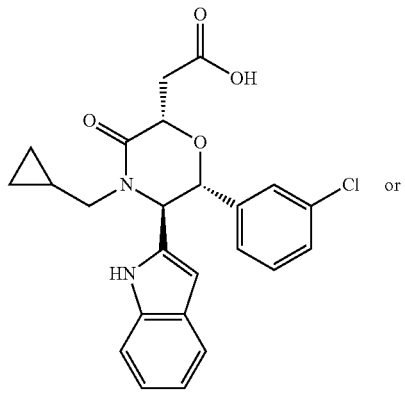

or

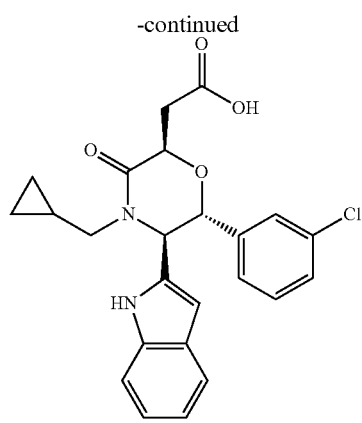

Step A. 2-((2S,5R,6R)-6-(3-Chlorophenyl)-4-(cyclopropylmethyl)-3-oxo-5-(1-(phenylsulfonyl)-1H-indol-2-yl)morpholin-2-yl)acetic acid or 2-((2R,5R,6R)-6-(3-Chlorophenyl)-4-(cyclopropylmethyl)-3-oxo-5-(1-(phenylsulfonyl)-1H-indol-2-yl)morpholin-2-yl)acetic acid

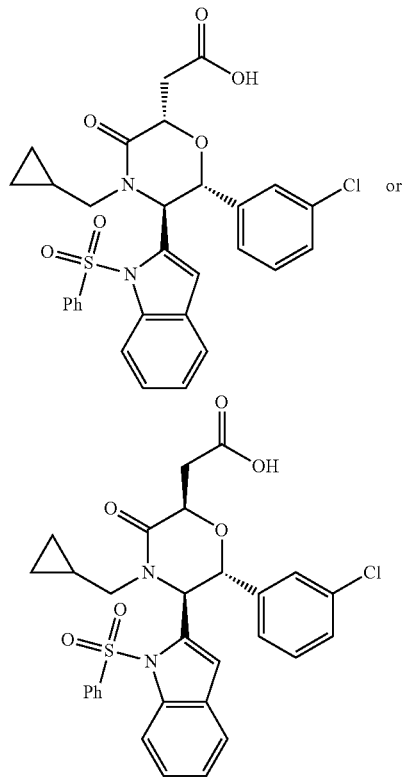

TFA (1.00 mL, 12.98 mmol) was added to a solution of tert-butyl 2-((2S,5R,6R)-6-(3-chlorophenyl)-4-(cyclopropylmethyl)-3-oxo-5-(1-(phenylsulfonyl)-1H-indol-2-yl)morpholin-2-yl)acetate or tert-butyl 2-((2S,5R,6R)-6-(3-chlorophenyl)-4-(cyclopropylmethyl)-3-oxo-5-(1-(phenylsulfonyl)-1H-indol-2-yl)morpholin-2-yl)acetate (0.254 g, 0.399 mmol; Example 1, step J; second eluting, minor isomer) in DCM (3 mL) at rt. After 2 h the reaction mixture was concentrated in vacuo, a few mL of hexanes were added and the solvent was removed under reduced pressure on a rotary evaporator. This procedure was repeated twice to provide the title compound as a foam. Mass spectrum (ESI) m/z 579.2 [M+H]⁺.

Step B. 2-((2S,5R,6R)-6-(3-Chlorophenyl)-4-(cyclopropylmethyl)-5-(1H-indol-2-yl)-3-oxomorpholin-2-yl)acetic acid or 2-((2R,5R,6R)-6-(3-Chlorophenyl)-4-(cyclopropylmethyl)-5-(1H-indol-2-yl)-3-oxomorpholin-2-yl)acetic acid TBAF (1 M solution in THF) (3.99 mL, 3.99 mmol) was added to a solution of 2-((2S,5R,6R)-6-(3-chlorophenyl)-4-(cyclopropylmethyl)-3-oxo-5-(1-(phenylsulfonyl)-1H-indol-2-yl)morpholin-2-yl)acetic acid or 2-((2R,5R,6R)-6-(3-chlorophenyl)-4-(cyclopropylmethyl)-3-oxo-5-(1-(phenylsulfonyl)-1H-indol-2-yl)morpholin-2-yl)acetic acid (0.231 g, 0.399 mmol; Example 2, Step A) in THF (3.0 mL) at rt. The reaction mixture was heated to reflux. After 1.5 h the reaction mixture was cooled to rt, diluted with sat. aq. NH₄Cl and extracted with EtOAc (3×). The organics were pooled, washed with brine, dried over MgSO₄, filtered and the filtrate was concentrated to provide a yellow oil. Purification by chromatography on silica gel (24 g silica gel column, RediSep® Rf, Teledyne Isco, Lincoln, Nebr.; eluent: 0 to 5% MeOH/DCM with 0.5% AcOH as additive; gradient elution) provided the title compound as an off-white foam. ¹H NMR (400 MHz, CDCl₃) δ ppm 0.02 (m, 1H), 0.16 (m, 1H), 0.44 (m, 1H), 0.52 (m, 1H), 1.00 (m, 1H), 2.27 (dd, J=7.8 and 14.0 Hz, 1H), 3.03 (dd, J=6.5 and 16.8 Hz, 1H), 3.33 (dd, J=5.1 and 16.8 Hz, 1H), 3.92 (dd, J=6.4 and 14.1 Hz, 1H), 4.89 (m, 1H), 4.94 (d, J=9.8 Hz, 1H), 4.99 (d, J=9.8 Hz, 1H), 6.13 (d, J=1.4 Hz, 1H), 6.70 (d, J=7.8 Hz, 1H), 7.05 (d, J=7.7 Hz, 1H), 7.09 (m, 1H), 7.18-7.25 (m, 3H), 7.40 (d, J=8.2 Hz, 1H), 7.48 (d, J=8.0 Hz, 1H), 9.52 (bs, 1H). Mass spectrum (ESI) m/z 439.2 [M+H]⁺.

Example 3

2-((2S,5S,6R)-5-(Benzo[d]thiazol-2-yl)-6-(3-chlorophenyl)-4-(cyclopropylmethyl)-3-oxomorpholin-2-yl)acetic acid and 2-((2R,5R,6S)-5-(Benzo[d]thiazol-2-yl)-6-(3-chlorophenyl)-4-(cyclopropylmethyl)-3-oxomorpholin-2-yl)acetic acid

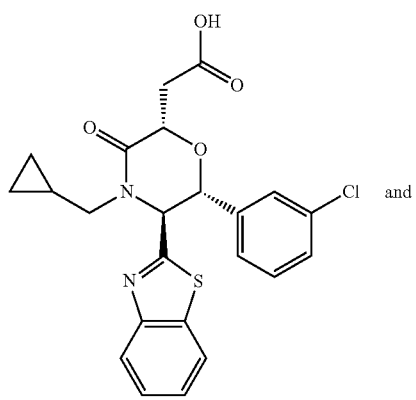 and

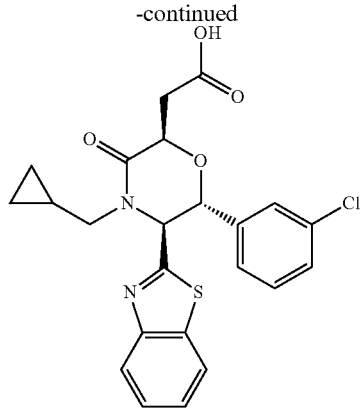

Step A. 2-(Chloromethyl)benzo[d]thiazole

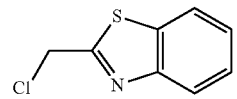

A solution of 2-aminothiophenol (2.29 g, 18.33 mmol) in 2-chloro-1,1,1-triethoxyethane (7.00 mL, 36.7 mmol) was heated to 65° C. for 2 hours. The reaction mixture was diluted with sat. NaHCO₃/brine and extracted with ethyl acetate. The organics were washed with water, dried over MgSO₄, filtered and the filtrate was concentrated under reduced pressure. Purification of the residue by flash chromatography on silica gel (eluent: 0 to 10% EtOAc/hexane, gradient elution) provided the title compound. Mass Spectrum (ESI) m/z=168 (M+1).

Step B. tert-Butyl benzo[d]thiazol-2-ylmethyl(cyclopropylmethyl)carbamate

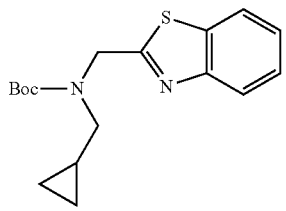 [SMILES: CC(C)(C)OC(=O)N(Cc1nc2ccccc2s1)CC1CC1]

To a solution of cyclopropylmethanamine (0.820 mL, 19.75 mmol) and caesium carbonate (19.80 g, 60.8 mmol) in DMF (76 mL) was added slowly 2-(chloromethyl)benzo[d]thiazole (2.79 g, 15.19 mmol; Example 3, Step A). When the reaction was judged complete by LCMS, di-tert-butyl dicarbonate (7.63 g, 34.9 mmol) was added. The reaction mixture was stirred at ambient temperature overnight, then diluted with sat. aq. NaHCO$_3$/brine solution and extracted with ethyl acetate. The organics were washed with sat. NaCl solution, then dried over MgSO$_4$, filtered and the filtrate was concentrated under reduced pressure. Purification of the residue by flash chromatography on silica gel (eluent: 0 to 20% EtOAc/hexane, gradient elution) provided the title compound. Mass Spectrum (ESI) m/z=219 (M+1-Boc), 263 (M+1-tbutyl), 319 (M+1), 341 (M+Na).

reduced pressure. Purification of the residue by flash chromatography on silica gel (eluent: 10 to 20% EtOAc/hexanes, gradient elution) provided the title compounds as the faster eluting, major product peak.

$^1$H NMR (400 MHz, CDCl$_3$) δ ppm −0.07 (br. s., 1 H), 0.08 (br. s., 1 H), 0.26 (br. s., 2 H), 0.67 (br. s., 1 H), 1.47 (br. s., 9 H), 2.91 (br. s., 1 H), 3.15 (br. s., 1 H), 5.51 (br. s., 1 H), 5.71 (d, J=4.89 Hz, 1 H), 7.21-7.31 (m, 2 H), 7.39 (br. s., 1 H), 7.41-7.49 (m, 1 H), 7.49-7.60 (m, 2 H), 7.90 (d, J=8.02 Hz, 1 H), 8.08 (d, J=8.22 Hz, 1 H). Mass Spectrum (ESI) m/z=403 (M+1-tbutyl), 459 (M+1), 481 (M+Na).

Step C. tert-Butyl ((1S,2R)-1-(benzo[d]thiazol-2-yl)-2-(3-chlorophenyl)-2-hydroxyethyl)(cyclopropylmethyl)carbamate and tert-Butyl ((1R,2S)-1-(benzo[d]thiazol-2-yl)-2-(3-chlorophenyl)-2-hydroxyethyl)(cyclopropylmethyl)carbamate Step D. (1R,2S)-2-(Benzo[d]thiazol-2-yl)-1-(3-chlorophenyl)-2-((cyclopropylmethyl)amino)ethanol and (1S,2R)-2-(Benzo[d]thiazol-2-yl)-1-(3-chlorophenyl)-2-((cyclopropylmethyl)amino)ethanol

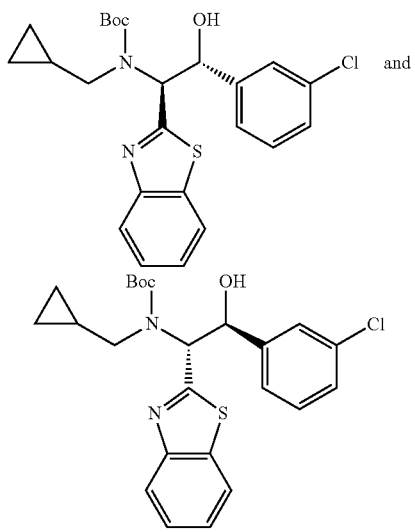 and

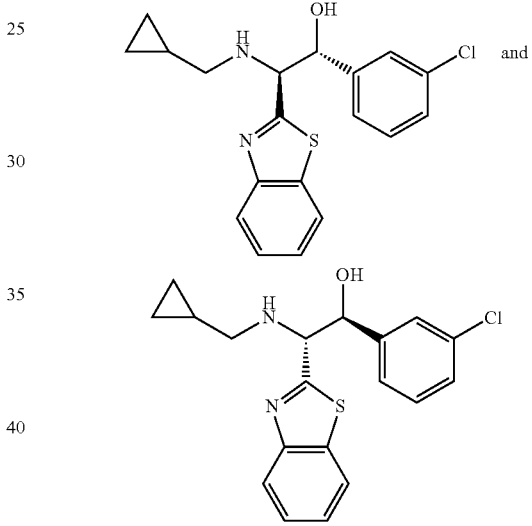 and

To a solution of tert-butyl benzo[d]thiazol-2-ylmethyl(cyclopropylmethyl)carbamate (3.15 g, 9.89 mmol; Example 3, Step B) and methyl 3-chlorobenzoate (1.375 mL, 9.89 mmol) in anhydrous THF (19.78 mL) was added LiHMDS, 1M in THF (24.73 mL, 24.73 mmol). The reaction was monitored by LCMS, with additions of LiHMDS reagent until ketone formation was complete. The reaction mixture was cooled to 0° C., neutralized with NaHCO$_3$ and extracted with EtOAc. The combined organic layers were washed with brine, dried over MgSO$_4$, filtered and the filtrate was concentrated under reduced pressure. The residue was dissolved in 30 mL of EtOH, cooled to 0° C. and reduced with sodium borohydride (0.748 g, 19.78 mmol). Still at 0° C., the reaction mixture was quenched carefully with about 5 mL of sat'd aq. NaHCO$_3$ solution and concentrated under reduced pressure to remove the ethanol. The mixture was extracted with EtOAc and washed with brine. The combined organics were dried over Na$_2$SO$_4$, filtered and the filtrate was concentrated under The racemic mixture of tert-butyl ((1S,2R)-1-(benzo[d]thiazol-2-yl)-2-(3-chlorophenyl)-2-hydroxyethyl)(cyclopropylmethyl)carbamate and tert-butyl ((1R,2S)-1-(benzo[d]thiazol-2-yl)-2-(3-chlorophenyl)-2-hydroxyethyl)(cyclopropylmethyl)carbamate (875 mg, 1.906 mmol; Example 3, Step C) was dissolved in a solution of 4N HCl in dioxane (10 mL, 40.0 mmol). The reaction mixture was stirred for 1 h at ambient temperature and then concentrated under reduced pressure. The residue was diluted in EtOAc and washed with NaHCO$_3$ to neutralize. Purification of the residue by flash chromatography on silica gel (eluent: 0 to 100% EtOAc/hexane, gradient elution) provided the title compound as a yellow oil. $^1$H NMR (400 MHz, CDCl$_3$) δ ppm 0.00-0.20 (m, 2 H), 0.40-0.57 (m, 2 H), 0.89-1.03 (m, 1 H), 2.50 (dd, J=12.13, 7.24 Hz, 1 H), 2.64 (dd, J=12.13, 6.46 Hz, 1 H), 4.19 (d, J=7.43 Hz, 1 H), 4.70 (s, 1 H), 4.98 (d, J=7.43 Hz, 1 H), 7.03-7.11 (m, 1 H), 7.15 (t, J=7.73 Hz, 1 H), 7.20-7.25 (m, 1 H), 7.27-7.30 (m, 1 H), 7.35-7.43 (m, 2 H), 7.49 (ddd, J=8.22, 7.14, 1.27 Hz, 1 H), 7.82 (d, J=8.02 Hz, 1 H), 8.00 (d, J=8.22 Hz, 1 H). Mass Spectrum (ESI) m/z=359 (M+1).

Step E. (E)-Methyl 4-(((1S,2R)-1-(benzo[d]thiazol-2-yl)-2-(3-chlorophenyl)-2-hydroxyethyl)(cyclopropylmethyl)amino)-4-oxobut-2-enoate and (E)-Methyl 4-(((1R,2S)-1-(benzo[d]thiazol-2-yl)-2-(3-chlorophenyl)-2-hydroxyethyl)(cyclopropylmethyl)amino)-4-oxobut-2-enoate Step F. Methyl 2-((2R,5S,6R)-5-(benzo[d]thiazol-2-yl)-6-(3-chlorophenyl)-4-(cyclopropylmethyl)-3-oxomorpholin-2-yl)acetate and Methyl 2-((2S,5R,6S)-5-(benzo[d]thiazol-2-yl)-6-(3-chlorophenyl)-4-(cyclopropylmethyl)-3-oxomorpholin-2-yl)acetate and Methyl 2-((2S,5S,6R)-5-(benzo[d]thiazol-2-yl)-6-(3-chlorophenyl)-4-(cyclopropylmethyl)-3-oxomorpholin-2-yl)acetate and Methyl 2-((2R,5R,6S)-5-(benzo[d]thiazol-2-yl)-6-(3-chlorophenyl)-4-(cyclopropylmethyl)-3-oxomorpholin-2-yl)acetate

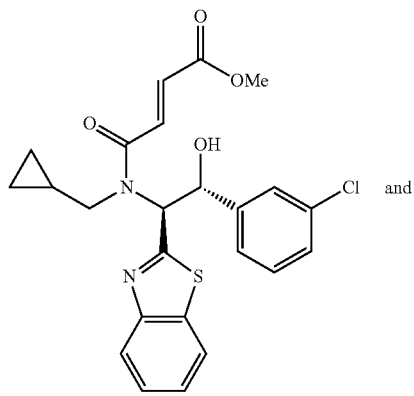 and

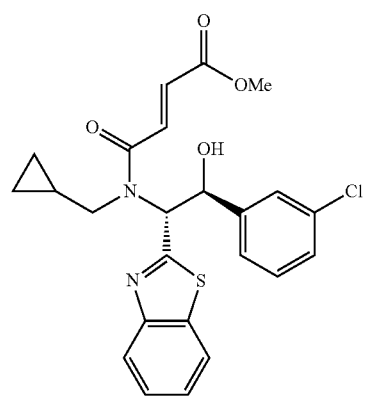

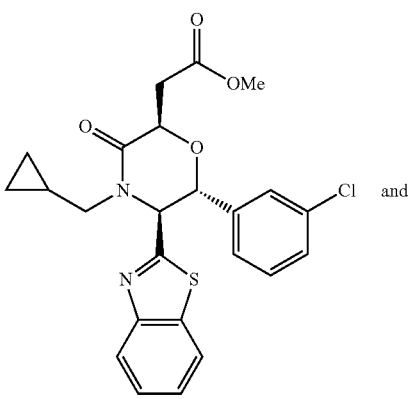 and

 and

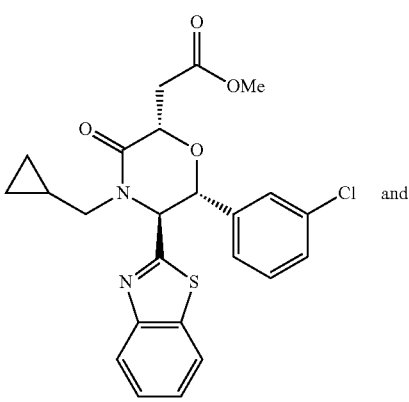 and

To a solution of the racemic mixture of (1R,2S)-2-(benzo[d]thiazol-2-yl)-1-(3-chlorophenyl)-2-((cyclopropylmethyl)amino)ethanol and (1S,2R)-2-(benzo[d]thiazol-2-yl)-1-(3-chlorophenyl)-2-((cyclopropylmethyl)amino)ethanol (310 mg, 0.864 mmol; Example 3, Step D) and triethylamine (0.60 mL, 4.32 mmol) in DMF (4 mL) was added monomethyl fumarate (112 mg, 0.864 mmol) followed by HATU (328 mg, 0.864 mmol). The reaction was monitored by LCMS, adding additional reagents until complete. Purification of the filtered reaction mixture was done by preparatory RP-HPLC (Sunfire™ Prep $C_{18}$ OBD 10 μm column; Waters, Milford, Mass.; eluent: 55 to 75% acetonitrile, water, 0.1% TFA, gradient elution). The pooled fractions were neutralized by addition of sat. aq. $NaHCO_3$ solution, concentrated under reduced pressure, and extracted with DCM. Then the combined organic layers were dried ($Na_2SO_4$), filtered and the filtrate was concentrated under reduced pressure to provide the title compounds as a yellow oil.

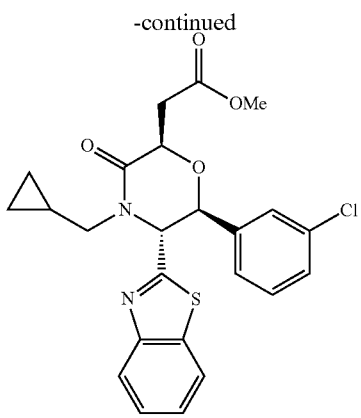

To a solution of (E)-methyl 4-(((1S,2R)-1-(benzo[d]thiazol-2-yl)-2-(3-chlorophenyl)-2-hydroxyethyl) (cyclopropylmethyl)amino)-4-oxobut-2-enoate and (E)-methyl 4-(((1R,2S)-1-(benzo[d]thiazol-2-yl)-2-(3-chlorophenyl)-2-hydroxyethyl) (cyclopropylmethyl)amino)-4-oxobut-2-enoate (203 mg, 0.43 mmol; Example 3, step E) in DMSO (2.1 mL) at ambient temperature was added caesium carbonate (281 mg, 0.86 mmol). The reaction was stirred for 2 h. It was diluted with sat. aq. NaHCO₃ solution and extracted with DCM. The combined organic layers were washed with water, dried over MgSO₄, filtered and the filtrate was concentrated under reduced pressure. Purification of the residue by preparatory RP-HPLC (eluent: 50% acetonitrile, water, 0.1% TFA, isocratic) provided the title compounds in two separately eluting fractions as racemic mixtures. The pooled HPLC fractions were neutralized by sat. aq. NaHCO₃ solution, concentrated under reduced pressure, and extracted with DCM. The combined organic layers were dried (Na₂SO₄), filtered and the filtrate was concentrated under reduced pressure to provide the title compounds.

Methyl 2-((2R,5S,6R)-5-(benzo[d]thiazol-2-yl)-6-(3-chlorophenyl)-4-(cyclopropylmethyl)-3-oxomorpholin-2-yl)acetate and methyl 2-((2S,5R,6S)-5-(benzo[d]thiazol-2-yl)-6-(3-chlorophenyl)-4-(cyclopropylmethyl)-3-oxomorpholin-2-yl)acetate (first two eluting compounds). ¹H NMR (400 MHz, CDCl₃) δ ppm 0.24 (dq, J=10.42, 4.81 Hz, 1 H), 0.46 (dq, J=9.78, 4.83 Hz, 1 H), 0.52-0.67 (m, 1 H), 0.70-0.82 (m, 1 H), 1.16 (dddd, J=9.63, 6.41, 4.70, 3.52 Hz, 1 H), 2.66 (dd, J=14.28, 7.83 Hz, 1 H), 2.91 (dd, J=16.24, 9.39 Hz, 1 H), 3.20 (dd, J=16.24, 3.52 Hz, 1 H), 3.74 (s, 3 H), 4.20 (dd, J=14.28, 6.46 Hz, 1 H), 4.55 (dd, J=9.39, 3.52 Hz, 1 H), 5.38 (s, 1 H), 5.73 (d, J=1.37 Hz, 1 H), 7.34-7.61 (m, 5 H), 7.66 (s, 1 H), 7.88-7.99 (m, 1 H), 7.99-8.07 (m, 1 H). Mass Spectrum (ESI) m/z=471 (M+1), 493 (M+Na).

Methyl 2-((2S,5S,6R)-5-(benzo[d]thiazol-2-yl)-6-(3-chlorophenyl)-4-(cyclopropylmethyl)-3-oxomorpholin-2-yl)acetate and methyl 2-((2R,5R,6S)-5-(benzo[d]thiazol-2-yl)-6-(3-chlorophenyl)-4-(cyclopropylmethyl)-3-oxomorpholin-2-yl)acetate (later two eluting compounds) Mass Spectrum (ESI) m/z=471 (M+1), 493 (M+Na).

Step G. 2-((2S,5S,6R)-5-(Benzo[d]thiazol-2-yl)-6-(3-chlorophenyl)-4-(cyclopropylmethyl)-3-oxomorpholin-2-yl)acetic acid and 2-((2R,5R,6S)-5-(Benzo[d]thiazol-2-yl)-6-(3-chlorophenyl)-4-(cyclopropylmethyl)-3-oxomorpholin-2-yl)acetic acid To a solution of the racemic mixture of methyl 2-((2R,5S,6R)-5-(benzo[d]thiazol-2-yl)-6-(3-chlorophenyl)-4-(cyclopropylmethyl)-3-oxomorpholin-2-yl)acetate and methyl 2-((2S,5R,6S)-5-(benzo[d]thiazol-2-yl)-6-(3-chlorophenyl)-4-(cyclopropylmethyl)-3-oxomorpholin-2-yl)acetate (20 mg, 0.042 mmol; first eluting compounds from Example 3, Step F) in dioxane (425 µL) at ambient temperature was added 1M aq. LiOH solution (425 µL, 0.425 mmol). The reaction mixture was stirred for 1 h, acidified with acetic acid (28.1 mg, 0.467 mmol) and concentrated under reduced pressure. Purification of the residue by preparatory RP-HPLC (Sunfire™ Prep C₁₈ OBD 10 µm column; Waters, Milford, Mass.; eluent: 40 to 60% acetonitrile, water, 0.1% TFA, gradient elution) gave the title compounds as the first eluting set of compounds (Note: Racemization occurred at C2 during treatment with base). The pooled fractions were neutralized with sat. aq. NaHCO₃ solution, concentrated under reduced pressure, acidified (1N aq. HCl), and extracted (3×DCM). Then the combined organic layers were dried (Na₂SO₄), filtered and the filtrate was concentrated under reduced pressure. ¹H NMR (400 MHz, CDCl₃) δ ppm 0.09-0.22 (m, 1 H), 0.24-0.48 (m, 2 H), 0.48-0.63 (m, 1 H), 0.95-1.07 (m, 1 H), 2.98 (dd, J=14.18, 7.34 Hz, 1 H), 3.06-3.19 (m, 1 H), 3.19-3.30 (m, 1 H), 3.80 (dd, J=14.09, 6.65 Hz, 1 H), 5.28 (dd, J=7.83, 4.69 Hz, 1 H), 5.41 (d, J=2.93 Hz, 1 H), 5.53 (d, J=2.74 Hz, 1 H), 7.01-7.20 (m, 3 H), 7.24 (s, 1 H), 7.33-7.51 (m, 2 H), 7.80-7.94 (m, 2 H); Mass Spectrum (ESI) m/z=457 (M+1).

Further elution provided:

Example 4

2-((2R,5S,6R)-5-(Benzo[d]thiazol-2-yl)-6-(3-chlorophenyl)-4-(cyclopropylmethyl)-3-oxomorpholin-2-yl)acetic acid and 2-((2S,5R,6S)-5-(Benzo[d]thiazol-2-yl)-6-(3-chlorophenyl)-4-(cyclopropylmethyl)-3-oxomorpholin-2-yl)acetic acid

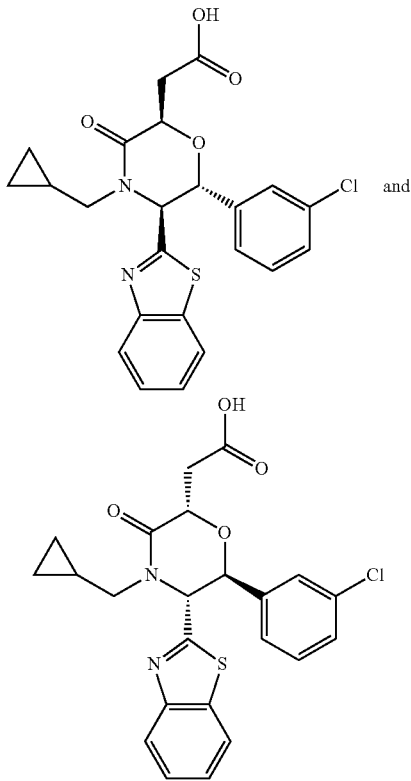

and

The title compounds were obtained from Example 3, Step G as the later eluting set of compounds (Note: Racemization occurred at C2 during treatment with base). The pooled fractions were neutralized with sat. aq. NaHCO₃ solution, concentrated under reduced pressure, acidified (1N aq. HCl), and extracted (3×DCM). Then the combined organic layers were dried (Na₂SO₄), filtered and the filtrate was concentrated under reduced pressure. ¹H NMR (400 MHz, CDCl₃) δ ppm 0.22-0.33 (m, 1 H), 0.48 (td, J=9.73, 4.60 Hz, 1 H), 0.58-0.68 (m, 1 H), 0.74-0.84 (m, 1 H), 1.12-1.24 (m, 1 H), 2.02 (s, 1 H), 2.72 (dd, J=14.28, 7.82 Hz, 1 H), 2.94 (dd, J=16.33, 6.94 Hz, 1 H), 3.25 (dd, J=16.33, 5.77 Hz, 1 H), 4.20 (dd, J=14.38, 6.55 Hz, 1 H), 4.45 (t, J=6.46 Hz, 1 H), 5.39 (s, 1 H), 5.76 (d, J=0.98 Hz, 1 H), 7.37-7.44 (m, 2 H), 7.44-7.52 (m, 2 H), 7.55 (ddd, J=8.22, 7.14, 1.27 Hz, 1 H), 7.65 (s, 1 H), 7.95 (d, J=7.43 Hz, 1 H), 8.04 (d, J=7.63 Hz, 1 H); Mass Spectrum (ESI) m/z=457 (M+1).

Example 5

2-((2S,5R,6R)-6-(3-Chlorophenyl)-4-(cyclopropylmethyl)-5-(1-methyl-1H-benzo[d]imidazol-2-yl)-3-oxomorpholin-2-yl)acetic acid and 2-((2R,5S,6S)-6-(3-Chlorophenyl)-4-(cyclopropylmethyl)-5-(1-methyl-1H-benzo[d]imidazol-2-yl)-3-oxomorpholin-2-yl)acetic acid

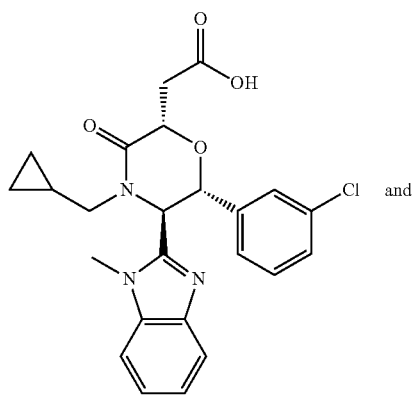

and

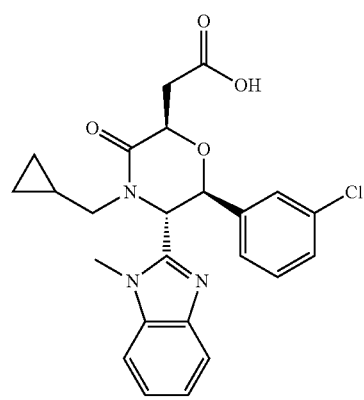

Step A. tert-Butyl cyclopropylmethyl((1-methyl-1H-benzo[d]imidazol-2-yl)methyl)carbamate

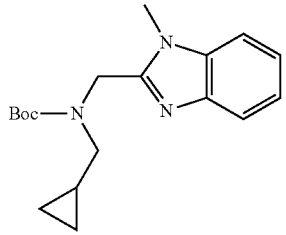 [SMILES: Cn1c(CN(CC2CC2)C(=O)OC(C)(C)C)nc2ccccc21]

To a mixture of [1-methyl-1H-benzo[d]imidazole-2-carbaldehyde (1.78 g, 11.11 mmol) and cyclopropylmethanamine (0.790 g, 11.11 mmol) was added a 2 mL of anhydrous acetonitrile and the solvent was removed under reduced pressure on a rotary evaporator. This precedure was repeated several times until a chalky solid was obtained. This was then dissolved in 100 mL of DCM, cooled to 0° C., and NaBH(OAc)₃ (3.53 g, 16.67 mmol) was added in one portion. After 30 min, the mixture was re-cooled to 0° C. and then triethylamine (4.65 mL, 33.3 mmol) and di-tert-butyl dicarbonate (2.91 g, 13.34 mmol) were added. The reaction mixture was allowed to warm to ambient temperature overnight, at which time it was quenched by addition of 100 mL of water and extracted with DCM (100 mL×2). The combined organic layers were dried over Na₂SO₄, filtered and the filtrate was concentrated under reduced pressure. The residue was suspended in acetonitrile and filtered to remove insoluble impurities. The filtrate was concentrated under reduced pressure. Purification of the residue by flash chromatography on silica gel (eluent: 0 to 25% EtOAc/hexane) provided the title compound. Mass Spectrum (ESI) m/z=316 (M+1).

Step B. tert-Butyl ((1R,2R)-2-(3-chlorophenyl)-2-hydroxy-1-(1-methyl-1H-benzo[d]imidazol-2-yl)ethyl)(cyclopropylmethyl)carbamate and tert-Butyl ((1S,2S)-2-(3-chlorophenyl)-2-hydroxy-1-(1-methyl-1H-benzo[d]imidazol-2-yl)ethyl)(cyclopropylmethyl)carbamate

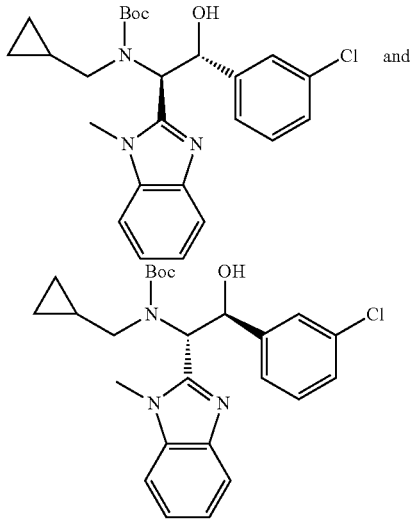

The title compound was prepared from tert-butyl cyclopropylmethyl((1-methyl-1H-benzo[d]imidazol-2-yl)methyl)

carbamate (Example 5, Step A) and methyl 3-chlorobenzoate by a procedure similar to the one described in Example 3, Step C. Purification of the residue by flash chromatography on silica gel (eluent: 10 to 20% EtOAc/Hexane) provided the title compounds as a racemic mixture as the faster eluting major stereoisomers Mass Spectrum (ESI) m/z=456 (M+1).

Step C. (1R,2R)-1-(3-Chlorophenyl)-2-((cyclopropylmethyl)amino)-2-(1-methyl-1H-benzo[d]imidazol-2-yl)ethanol and (1S,2S)-1-(3-Chlorophenyl)-2-((cyclopropylmethyl)amino)-2-(1-methyl-1H-benzo[d]imidazol-2-yl)ethanol

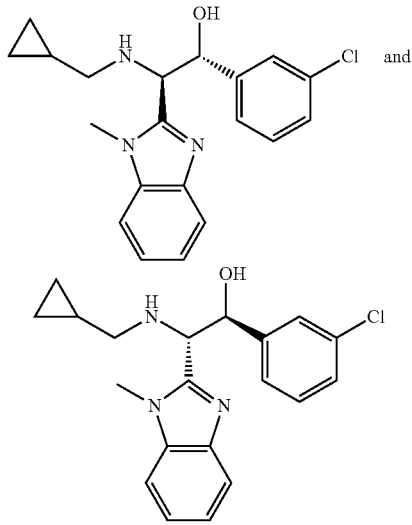

The title compounds were prepared from tert-Butyl ((1R, 2R)-2-(3-chlorophenyl)-2-hydroxy-1-(1-methyl-1H-benzo[d]imidazol-2-yl)ethyl)(cyclopropylmethyl)carbamate and tert-Butyl ((1S,2S)-2-(3-chlorophenyl)-2-hydroxy-1-(1-methyl-1H-benzo[d]imidazol-2-yl)ethyl)(cyclopropylmethyl) carbamate (Example 5, Step B) by a procedure analogous to the one described in Example 3, Step D. The crude material was carried forward without further purification to the next step. Mass Spectrum (ESI) m/z=356 (M+1).

Step D. (E)-Methyl 4-(((1R,2R)-2-(3-chlorophenyl)-2-hydroxy-1-(1-methyl-1H-benzo[d]imidazol-2-yl)ethyl)(cyclopropylmethyl)amino)-4-oxobut-2-enoate and (E)-Methyl 4-(((1S,2S)-2-(3-chlorophenyl)-2-hydroxy-1-(1-methyl-1H-benzo[d]imidazol-2-yl)ethyl)(cyclopropylmethyl)amino)-4-oxobut-2-enoate

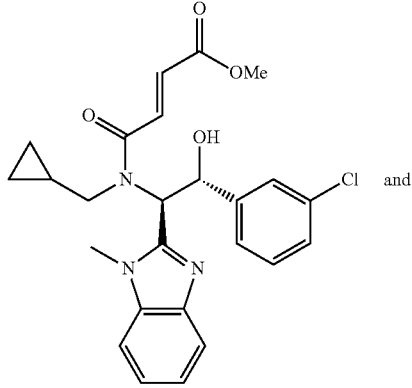

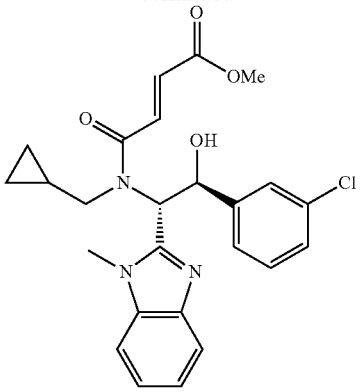

The title compound was prepared from (1R,2R)-1-(3-chlorophenyl)-2-((cyclopropylmethyl)amino)-2-(1-methyl-1H-benzo[d]imidazol-2-yl)ethanol and (1S,2S)-1-(3-chlorophenyl)-2-((cyclopropylmethyl)amino)-2-(1-methyl-1H-benzo[d]imidazol-2-yl)ethanol (Example 5, Step C) by a procedure analogous to the one described in Example 3, Step E. When complete, the reaction mixture was diluted with diethyl ether, rinsed with $NaHCO_3$/brine, washed with water, dried over $MgSO_4$, filtered and eluted through a small $SiO_2$ plug. The filtrate was concentrated under reduced pressure to provide crude product which was carried forward without further purification to the next step. Mass Spectrum (ESI) m/z=468 (M+1), 490 (M+Na).

Step E. 2-((2S,5R,6R)-6-(3-Chlorophenyl)-4-(cyclopropylmethyl)-5-(1-methyl-1H-benzo[d]imidazol-2-yl)-3-oxomorpholin-2-yl)acetic acid and 2-((2R,5S, 6S)-6-(3-chlorophenyl)-4-(cyclopropylmethyl)-5-(1-methyl-1H-benzo[d]imidazol-2-yl)-3-oxomorpholin-2-yl)acetic acid To a solution of (E)-methyl 4-(((1R,2R)-2-(3-chlorophenyl)-2-hydroxy-1-(1-methyl-1H-benzo[d]imidazol-2-yl)ethyl)(cyclopropylmethyl)amino)-4-oxobut-2-enoate and (E)-methyl 4-(((1S,2S)-2-(3-chlorophenyl)-2-hydroxy-1-(1-methyl-1H-benzo[d]imidazol-2-yl)ethyl)(cyclopropylmethyl)amino)-4-oxobut-2-enoate (323 mg, 0.690 mmol; Example 5, Step D) in dioxane (3.5 mL) was added aq. 1M LiOH solution (2071 µL, 2.07 mmol). The reaction was stirred until LCMS analysis indicated complete consumption of starting material and a single product peak was apparent. The reaction mixture was neutralized with AcOH and the solvents were removed. Purification of the residue by preparatory RP-HPLC (Sunfire™ Prep $C_{18}$ OBD 10 µm column; Waters, Milford, Mass.; eluent: 35 to 55% acetonitrile, water, 0.1% TFA, gradient elution) followed by lyophilization provided mixed fractions in which both cyclized and uncyclized acid products were observed. The combined fractions were dissolved in dioxane (3451 µL) and a 55% NaH supension in mineral oil (90 mg, 2.071 mmol) was added. After 30 minutes at ambient temperature, the reaction was neutralized by addition of AcOH and the mixture was concentrated under reduced pressure. Purification of the residue by preparatory RP-HPLC (Sunfire™ Prep $C_{18}$ OBD 10 µm column; Waters, Milford, Mass.; eluent: 26% acetonitrile, water, 0.1% TFA, isocratic elution) provided the title compounds as the faster eluting, major products, which were white solids after lyophilization. $^1$H NMR (400 MHz, $CDCl_3$) δ ppm −0.27 to −0.20 (m, 1 H), −0.03 (dq, J=9.83, 5.14 Hz, 1 H), 0.33-0.50 (m, 2 H), 0.72-0.81 (m, 1 H), 2.34-2.43 (m, 1 H), 3.05-3.16

(m, 1 H), 3.16-3.27 (m, 4 H), 4.16 (dd, J=14.97, 6.16 Hz, 1 H), 4.93 (t, J=4.89 Hz, 1 H), 5.40 (q, J=9.52 Hz, 2 H), 6.77-6.83 (m, 1 H), 7.07-7.18 (m, 2 H), 7.26-7.31 (m, 1 H), 7.34-7.39 (m, 1 H), 7.46-7.54 (m, 2 H), 7.93-7.99 (m, 1 H). Mass Spectrum (ESI) m/z=454 (M+1).

Further elution provided:

Example 6

2-((2R,5R,6R)-6-(3-Chlorophenyl)-4-(cyclopropylmethyl)-5-(1-methyl-1H-benzo[d]imidazol-2-yl)-3-oxomorpholin-2-yl)acetic acid and 2-((2S,5S,6S)-6-(3-Chlorophenyl)-4-(cyclopropylmethyl)-5-(1-methyl-1H-benzo[d]imidazol-2-yl)-3-oxomorpholin-2-yl)acetic acid

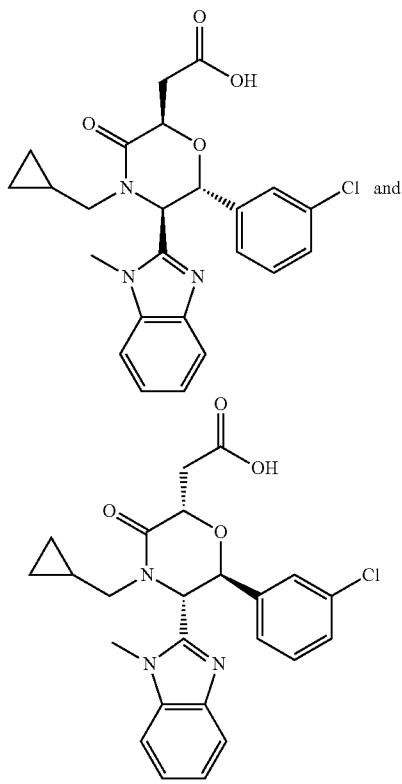

The title compounds were obtained from Example 5, Step E as the later eluting set of compounds (minor products). $^1$H NMR (400 MHz, CDCl$_3$) δ ppm –0.26 to –0.14 (m, 1H), 0.03 (dq, J=9.68, 4.99 Hz, 1 H), 0.33-0.54 (m, 2 H), 0.71-0.85 (m, 1 H), 2.37 (dd, J=14.77, 7.73 Hz, 1 H), 3.05-3.32 (m, 5 H), 4.21 (dd, J=14.77, 6.16 Hz, 1 H), 4.92 (t, J=4.79 Hz, 1 H), 5.33-5.44 (m, 2 H), 6.76 (d, J=7.83 Hz, 1 H), 7.10 (t, J=7.83 Hz, 1 H), 7.18 (t, J=1.76 Hz, 1 H), 7.28-7.38 (m, 2 H), 7.44-7.55 (m, 2 H), 7.98 (dd, J=6.55, 2.25 Hz, 1 H). Mass Spectrum (ESI) m/z=454 (M+1).

Example 7

2-((2S,5R,6R)-6-(3-Chlorophenyl)-5-(5-chloropyridin-2-yl)-4-(cyclopropylmethyl)-3-oxomorpholin-2-yl)acetic acid

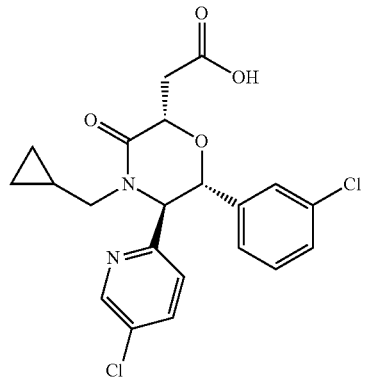 [SMILES: O=C(O)C[C@@H]1O[C@H](c2cccc(Cl)c2)[C@@H](c2ccc(Cl)cn2)N(CC2CC2)C1=O]

Step A. tert-Butyl ((5-chloropyridin-2-yl)methyl)(cyclopropylmethyl)carbamate

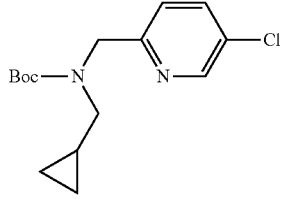 [SMILES: CC(C)(C)OC(=O)N(Cc1ccc(Cl)cn1)CC1CC1]

The title compound was prepared from 5-chloropicolinaldehyde, cyclopropylmethanamine, and di-tert-butyl dicarbonate as described in Example 5, Step A. Purification of the residue by flash chromatography on silica gel (eluent: 0 to 25% EtOAc/Hexane, gradient elution) provided the title compound as a yellow oil.

$^1$H NMR (400 MHz, CDCl$_3$) δ ppm 0.17 (br. s., 2 H) 0.25-0.55 (m, 2 H) 0.94 (br. s., 1 H) 1.08-1.78 (m, 9 H) 3.07-3.37 (m, 2 H) 4.62 (br. s., 2 H) 7.23 (br. s., 1 H) 7.63 (d, J=7.04 Hz, 1 H) 8.48 (br. s., 1 H). Mass Spectrum (ESI) m/z=197 (M+H-Boc), 241 (M+H-tbutyl), 297 (M+1), 319 (M+Na).

Step B. tert-Butyl (1R,2R)-(2-(3-chlorophenyl)-1-(5-chloropyridin-2-yl)-2-hydroxyethyl)(cyclopropylmethyl)carbamate and tert-Butyl (1S,2S)-(2-(3-chlorophenyl)-1-(5-chloropyridin-2-yl)-2-hydroxyethyl)(cyclopropylmethyl)carbamate

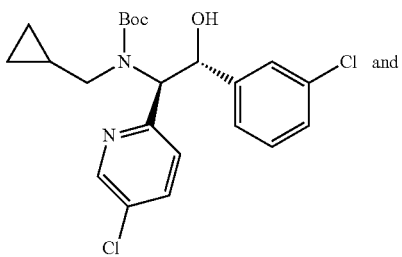

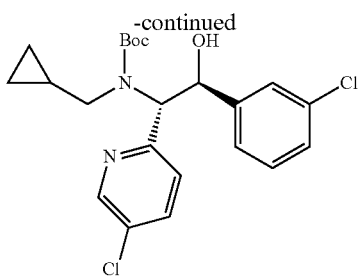

The title compound was prepared from tert-butyl ((5-chloropyridin-2-yl)methyl)(cyclopropylmethyl)carbamate (Example 7, Step A) and methyl 3-chlorobenzoate as described in Example 3, Step C. Purification of the residue by flash chromatography on silica gel (eluent: 7 to 10% EtOAc/hexane, solvents purged with $NH_3$ gas; gradient elution) provided the title compounds as a racemic mixture. Individual steroisomers were separated by chiral HPLC over several runs (flow-rate: 100 mL/min on a Chiralcel AD-H 10 cm I.D.×50 cm, 20 μm column (Daicel Chemical Industries LTD), using 15% isopropyl alcohol/hexane as the eluent) to give tert-butyl ((1R,2R)-2-(3-chlorophenyl)-1-(5-chloropyridin-2-yl)-2-hydroxyethyl)(cyclopropylmethyl)carbamate ($t_R$=16-20 min) as a white solid.

$^1$H NMR (400 MHz, $CDCl_3$) δ ppm −0.67 to −0.32 (m, 1 H) −0.31 to −0.07 (m, 1 H) 0.00 (br. s., 2 H) 0.24-0.50 (m, 1 H) 1.19 (br. s., 9 H) 2.59-3.16 (m, 2 H) 4.88-5.16 (m, 1 H) 5.36 (d, J=4.70 Hz, 1 H) 5.54-6.03 (m, 1 H) 6.90-7.34 (m, 5 H) 7.46 (dd, J=8.41, 2.54 Hz, 1 H) 8.33 (d, 1 H). Mass Spectrum (ESI) m/z=437 (M+H) and 459 (M+Na), $t_R$=6.09 min on Chiralpak® AD-H analytical HPLC column, Daicel Chemical Industries LTD, 15% iPrOH/hexanes, isocratic elution.

Further elution using 50% iPrOH/hexanes yielded the other enantiomer, tert-butyl (1S,2S)-(2-(3-chlorophenyl)-1-(5-chloropyridin-2-yl)-2-hydroxyethyl)(cyclopropylmethyl)carbamate.

Mass Spectrum (ESI) m/z=381 (M+1-tbutyl), 437 (M+Na), $t_R$=17.5 min on AD-H analytical HPLC column, Daicel Chemical Industries LTD, 15% iPrOH/hexanes, isocratic elution.

Step D. (1R,2R)-1-(3-Chlorophenyl)-2-(5-chloropyridin-2-yl)-2-((cyclopropylmethyl)amino)ethanol

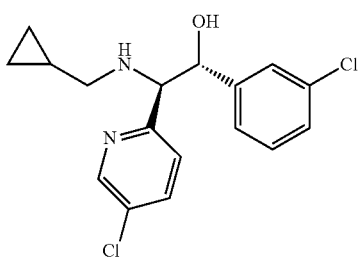 [SMILES: O[C@H](c1cccc(Cl)c1)[C@H](NCC1CC1)c1ccc(Cl)cn1]

The title compound was prepared from tert-butyl (1R,2R)-(2-(3-chlorophenyl)-1-(5-chloropyridin-2-yl)-2-hydroxyethyl)(cyclopropylmethyl)carbamate (Example 7, Step C) as described in Example 3, Step D, except that the reaction was run at 50° C. for 1.5 h. The product was used without further purification in the next step. Mass Spectrum (ESI) m/z=337 (M+1).

Step E. 2-((2S,5R,6R)-6-(3-Chlorophenyl)-5-(5-chloropyridin-2-yl)-4-(cyclopropylmethyl)-3-oxomorpholin-2-yl)acetic acid To a solution of monomethyl fumarate (42.4 mg, 0.326 mmol) and 3 equiv. triethylamine (0.123 mL, 0.890 mmol) in anhydrous DMF (1 mL) was added HATU (118 mg, 0.311 mmol). The solution was stirred for 10 minutes at ambient temperature, then it was added slowly to a vigorously stirring solution of (1R,2R)-1-(3-chlorophenyl)-2-(5-chloropyridin-2-yl)-2-(cyclopropylmethylamino)ethanol (100 mg, 0.297 mmol; Example 7, Step D) in anhydrous DMF (2 mL). The reaction was monitored by LCMS until it was judged complete, (additional activated ester was added if required). The reaction mixture was cooled to 0° C. and a 55% NaH supension in mineral oil (39 mg, 0.890 mmol) was added. The crude product was filtered. Purification of the filtrate by preparatory RP-HPLC (Sunfire™ Prep $C_{18}$ OBD 10 μm column, Waters, Milford, Mass.; eluent: 40-70% acetonitrile, water, 0.1% TFA, gradient elution) provided a cyclized ester mixture. This material was dissolved in dioxane (2 mL) and a solution of 1M LiOH in water (0.89 mL, 0.89 mmol) was added. The reaction mixture was stirred at ambient temperature overnight, then filtered. Purification of the residue by preparatory RP-HPLC (Sunfire™ Prep $C_{18}$ OBD 10 μm column, Waters, Milford, Mass.; eluent: 40-70% acetonitrile, water, 0.1% TFA, gradient elution over 30 min) provided the title compound as the first eluting compound. $^1$H NMR (400 MHz, $CDCl_3$) δ ppm −0.06-0.12 (m, 2 H) 0.34-0.54 (m, 2 H) 0.73-0.89 (m, 1 H) 2.28 (dd, J=14.38, 7.14 Hz, 1 H) 3.01-3.22 (m, 2 H) 3.93 (dd, J=14.48, 6.85 Hz, 1 H) 4.80 (t, J=5.38 Hz, 1 H) 4.86-4.99 (m, 2 H) 6.78 (d, J=7.63 Hz, 1 H) 6.87 (d, J=8.41 Hz, 1 H) 7.06-7.17 (m, 2H) 7.20-7.26 (m, 1 H) 7.58 (dd, J=8.22, 2.35 Hz, 1 H) 8.61 (d, J=2.35 Hz, 1 H). Mass Spectrum (ESI) m/z=435 (M+1).

Further elution provided:

Example 8

2-((2R,5R,6R)-6-(3-chlorophenyl)-5-(5-chloropyridin-2-yl)-4-(cyclopropylmethyl)-3-oxomorpholin-2-yl)acetic acid

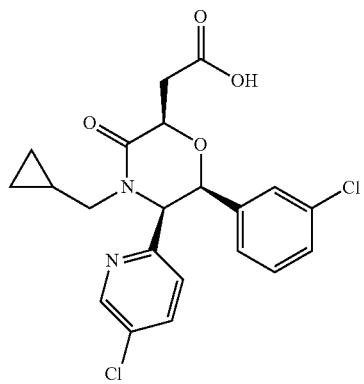 [SMILES: O=C(O)C[C@H]1O[C@@H](c2cccc(Cl)c2)[C@@H](c2ccc(Cl)cn2)N(CC2CC2)C1=O]

The title compound was obtained from Example 7, Step E as the later eluting compound. $^1$H NMR (400 MHz, $CDCl_3$) δ ppm 0.20 (dq, J=9.85, 4.87 Hz, 1 H), 0.32 (dq, J=9.66, 4.80 Hz, 1 H), 0.49-0.63 (m, 1 H), 0.63-0.76 (m, 1 H), 0.98-1.16 (m, 1 H), 2.49 (dd, J=14.18, 7.73 Hz, 1 H), 2.85-3.00 (m, 1 H), 3.00-3.15 (m, 1 H), 4.12 (dd, J=14.09, 6.65 Hz, 1 H), 4.38 (dd, J=6.65, 5.09 Hz, 1 H), 5.17 (d, J=1.57 Hz, 1 H), 5.32 (d, J=1.96 Hz, 1 H), 7.30-7.43 (m, 4 H), 7.58 (s, 1 H), 7.73 (dd, J=8.41, 2.54 Hz, 1 H), 8.57 (d, J=1.96 Hz, 1 H). Mass Spectrum (ESI) m/z=435 (M+1).

Example 9

2-((2R,5R,6R)-6-(3-Chlorophenyl)-5-(4-chlorophenyl)-4-(cyclopropylmethyl)-3-oxomorpholin-2-yl)acetic acid

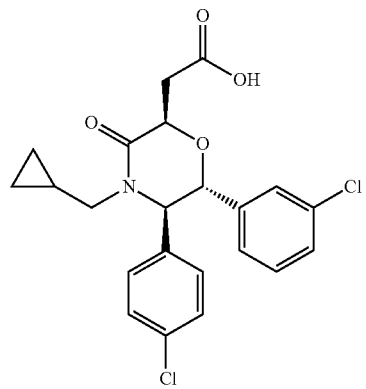 [SMILES: O=C(O)C[C@H]1O[C@H](c2cccc(Cl)c2)[C@@H](c2ccc(Cl)cc2)N(CC2CC2)C1=O]

Step A. (S)-2-bromo-4-tert-butoxy-4-oxobutanoic acid

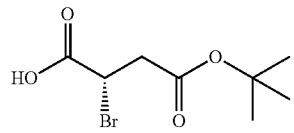

To a solution of sodium bromide (10.1 g, 97.8 mmol) in 0.75 M aq. HBr (50 mL, 37.5 mmol) at −15° C. was added sodium nitrite (2.37 g, 34.4 mmol). The reaction mixture color turned yellowish brown then light blue. Then (S)-2-amino-4-tert-butoxy-4-oxobutanoic acid (5.0 g, 26.4 mmol) was added. The slurry was stirred at −15° C. for 30 min. A gummy white solid formed. The mixture was extracted with pre-cooled EtOAc (0° C.) (3×). The organic layers were dried over $Na_2SO_4$ and concentrated under reduced pressure to give a colorless oil. The residue was purified by flash chromatography on silica gel (eluent: 0 to 100% EtOAc in hexanes) to give the title compound (4.07 g, 61%).

Step B. (1R,2R)-1-(3-Chlorophenyl)-2-(4-chlorophenyl)-2-(cyclopropylmethylamino)ethanol

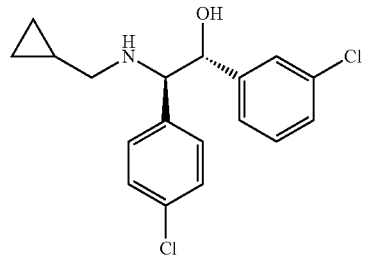 [SMILES: O[C@H](c1cccc(Cl)c1)[C@H](NCC1CC1)c1ccc(Cl)cc1]

To a solution of (1R,2R)-2-amino-1-(3-chlorophenyl)-2-(4-chlorophenyl)ethanol (890 mg, 2681 μmol; Intermediate A2) in EtOH (25 mL) was added cyclopropanecarboxaldehyde (200 μl, 2681 μmol). The reaction mixture was stirred at rt for 1 h then sodium borohydride (162 mg, 4290 μmol) was added. The cloudy reaction mixture was stirred at rt for 10 min. Then the reaction mixture was quenched with 1 M aq. HCl. Evolution of gas was observed and the cloudy reaction mixture became clear. The reaction mixture was concentrated under reduced pressure. The residue was diluted with sat. aq. $Na_2CO_3$ solution and extracted with DCM (2×). The organic layers were combined, dried over $Na_2SO_4$, filtered and the filtrate was concentrated under reduced pressure. The residue was purified by flash chromatography on silica gel {eluent: 0 to 50% [10% (2 M $NH_3$ in MeOH) in DCM]/DCM} to give the title compound.

Step C. (E)-tert-Butyl 4-(((1R,2R)-2-(3-chlorophenyl)-1-(4-chlorophenyl)-2-hydroxyethyl)(cyclopropylmethyl)amino)-4-oxobut-2-enoate

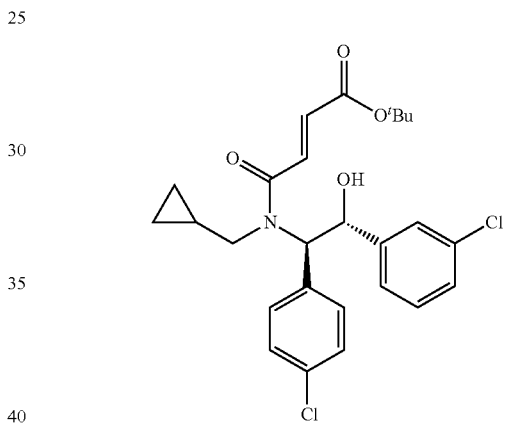

To a solution of (S)-2-bromo-4-tert-butoxy-4-oxobutanoic acid (35 mg, 140 μmol; Example 9, Step A) in DCM (1 mL) at rt was added DIEA (49 μl, 280 μmol), 1H-benzo[d][1,2,3]triazol-1-ol hydrate (21 mg, 140 μmol) and EDC hydrochloride (27 mg, 140 μmol). The reaction mixture was stirred at rt for 30 min, then (1R,2R)-1-(3-chlorophenyl)-2-(4-chlorophenyl)-2-(cyclopropylmethylamino)ethanol (47 mg, 140 mmol; Example 9, step B) in DCM (1 mL) was added. The reaction mixture was stirred at 0° C. for 2 h. Then the reaction mixture was warmed to rt and stirred at rt for 16 h. More DIEA (49 μl, 280 μmol) was added and the reaction mixture was stirred at rt for 24 h. The reaction mixture was concentrated under reduced pressure to 1 mL and diluted with EtOAc. The mixture was washed with 1 M HCl, sat. aq. $NaHCO_3$ solution, and brine. The organic layer was dried over $Na_2SO_4$, filtered and the filtrate was concentrated under reduced pressure. The residue was purified by flash chromatography on silica gel (eluent: 25-100% EtOAc in hexanes, gradient elution) to give the title compound.

Step D. tert-Butyl 2-((2R,5R,6R)-6-(3-chlorophenyl)-5-(4-chlorophenyl)-4-(cyclopropylmethyl)-3-oxomorpholin-2-yl)acetate and tert-Butyl 2-((2S,5R,6R)-6-(3-chlorophenyl)-5-(4-chlorophenyl)-4-(cyclopropylmethyl)-3-oxomorpholin-2-yl)acetate

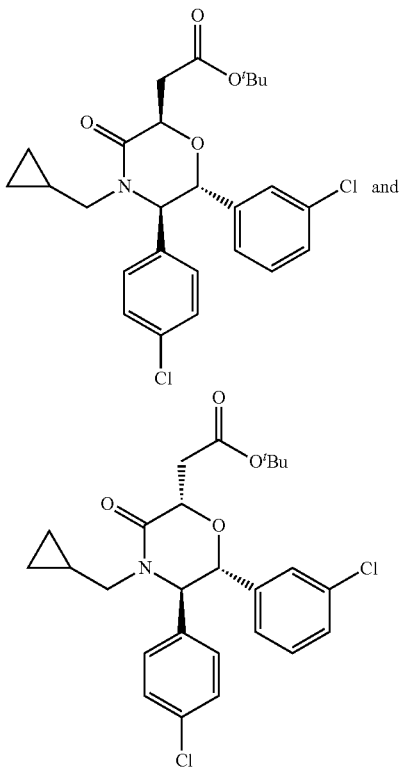

To a solution of (E)-tert-butyl 4-(((1R,2R)-2-(3-chlorophenyl)-1-(4-chlorophenyl)-2-hydroxyethyl)(cyclopropylmethyl)amino)-4-oxobut-2-enoate (20 mg, 41 mmol; Example 9, step C) in THF (1 mL) at rt was added a dispersion of 60% sodium hydride in mineral oil (2.4 mg, 61 μmol). Evolution of gas was observed and the reaction mixture turned light yellow in color. The reaction mixture was stirred at rt for 1 h. The reaction mixture was quenched with sat. NH$_4$Cl solution and evolution of gas was observed. The reaction mixture was diluted with DCM and the layers were separated. The organic layer was washed with brine, dried over Na$_2$SO$_4$, filtered and the filtrate was concentrated under reduced pressure. Purification by flash chromatography on silica gel (eluent: 30% MTBE in hexanes) provided tert-butyl 2-((2R,5R,6R)-6-(3-chlorophenyl)-5-(4-chlorophenyl)-4-(cyclopropylmethyl)-3-oxomorpholin-2-yl)acetate as the first eluting isomer and tert-butyl 2-((2S,5R,6R)-6-(3-chlorophenyl)-5-(4-chlorophenyl)-4-(cyclopropylmethyl)-3-oxomorpholin-2-yl)acetate as the second eluting isomer.

Step E. 2-((2R,5R,6R)-6-(3-Chlorophenyl)-5-(4-chlorophenyl)-4-(cyclopropylmethyl)-3-oxomorpholin-2-yl)acetic acid To a solution of tert-butyl 2-((2R,5R,6R)-6-(3-chlorophenyl)-5-(4-chlorophenyl)-4-(cyclopropylmethyl)-3-oxomorpholin-2-yl)acetate (68 mg, 139 μmol; Example 9, Step D, faster eluting isomer) in DCM (1.5 mL) was added TFA (214 μL, 2.8 μmol). The reaction mixture was stirred at rt for 60 min and then concentrated under reduced pressure. The residue was purified by reverse phase preparatory HPLC (Gemini™ Prep C$_{18}$ 5 μm column; Phenomenex, Torrance, Calif.; eluent: 0 to 100% MeCN in water, 0.1% TFA, gradient elution over 20 minutes) to give the title compound. $^1$H NMR (400 MHz, CDCl$_3$) δ ppm 0.15-0.21 (m, 1 H), 0.23-0.29 (m, 1 H), 0.54-0.61 (m, 1 H), 0.62-0.74 (m, 1 H), 0.96-1.10 (m, 1 H), 2.45 (dd, J=14.18, 7.73 Hz, 1 H), 3.04 (dd, J=16.2, 7.24 Hz, 1 H), 3.15 (dd, J=16.24, 4.89 Hz, 1 H), 4.08 (dd, J=14.18, 6.55 Hz, 1 H), 4.55-4.62 (m, 1 H), 4.90 (d, J=3.72 Hz, 1 H), 5.05 (d, J=3.91 Hz, 1 H), 7.08-7.21 (m, 3 H), 7.29-7.39 (m, 4 H), 7.44 (s, 1 H), 8.94 (brs, 1 H). Mass Spectrum (ESI) m/z=434 (M+1).

Example 10

2-((2S,5R,6R)-6-(3-Chlorophenyl)-5-(4-chlorophenyl)-4-(cyclopropylmethyl)-3-oxomorpholin-2-yl)acetic acid

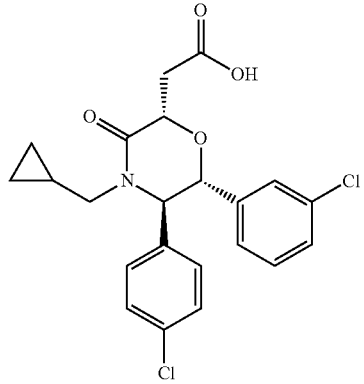 [SMILES: O=C(O)C[C@@H]1O[C@H](c2cccc(Cl)c2)[C@@H](c2ccc(Cl)cc2)N(CC2CC2)C1=O]

The title compound was prepared from tert-butyl 2-((2S,5R,6R)-6-(3-chlorophenyl)-5-(4-chlorophenyl)-4-(cyclopropylmethyl)-3-oxomorpholin-2-yl)acetate (Example 9, Step D, slower eluting isomer) as described in Example 9, Step E.

$^1$H NMR (400 MHz, CDCl$_3$) δ ppm −0.03-0.09 (m, 2 H) 0.38-0.53 (m, 2 H) 0.80-0.92 (m, 1 H) 2.32 (dd, J=14.28, 7.43 Hz, 1 H) 3.08-3.20 (m, 2 H) 4.01 (dd, J=14.18, 6.55 Hz, 1 H) 4.60 (d, J=9.6 Hz, 1 H) 4.73-4.81 (m, 2 H) 6.71 (d, J=7.83 Hz, 1 H) 6.91 (d, J=8.41 Hz, 2 H) 7.07-7.16 (m, 2 H) 7.21-7.31 (m, 3 H). Mass Spectrum (ESI) m/z=434 (M+1).

Examples 11 to 29 were also prepared from (1R,2R)-2-amino-1-(3-chlorophenyl)-2-(4-chlorophenyl)ethanol (890 mg, 2681 μmol; Intermediate A2) by a procedure analogous to the one described in Example 9, replacing cyclopropanecarboxaldehyde and sodiumborohydride in Step B with the reagents designated in the table below.

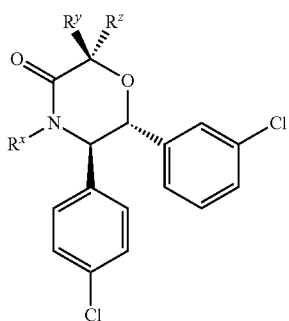

| Example | R$^x$ | R$^y$ | R$^z$ | Reagents used |
|---|---|---|---|---|
| 11 | F$_3$C~~~ | H | ~~~COOH | 3,3,3-trifluoropropanal, NaB(OAc)$_3$H |
| 12 | cyclobutyl-CH$_2$~ | H | ~~~COOH | cyclobutanone, NaBH$_3$CN |
| 13 | cyclobutyl-CH$_2$~ | ~~~COOH | H | cyclobutanone, NaBH$_3$CN |
| 14 | cyclopentyl-CH$_2$~ | H | ~~~COOH | cyclopentanone, NaBH$_3$CN |
| 15 | cyclopentyl-CH$_2$~ | ~~~COOH | H | cyclopentanone, NaBH$_3$CN |
| 16 | cyclohexyl-CH$_2$~ | H | ~~~COOH | cyclohexanone, NaBH$_3$CN |
| 17 | cyclohexyl-CH$_2$~ | ~~~COOH | H | cyclohexanone, NaBH$_3$CN |
| 18 | 1-cyclohexylethyl (or epimer) | H | ~~~COOH | 1-cyclohexylethanone, NaBH$_3$CN |

-continued

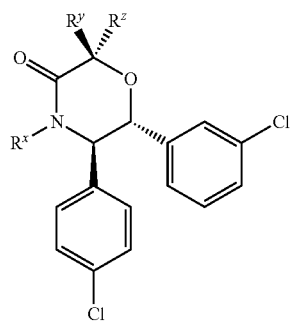

| Example | R<sup>x</sup> | R<sup>y</sup> | R<sup>z</sup> | Reagents used |
|---|---|---|---|---|
| 19 | cyclohexyl-CH(CH₃)– (either epimer) | –CH₂C(O)OH | H | 1-cyclohexylethanone, NaBH₃CN |
| 20 | cyclobutyl-CH(CH₃)– | –CH₂C(O)OH | H | 1-cyclobutylethanone, NaBH₃CN |
| 21 | cyclobutyl-CH(CH₃)– | H | –CH₂C(O)OH | 1-cyclobutylethanone, NaBH₃CN |
| 22 | cyclobutyl-CH(CH₃)– | –CH₂C(O)OH | H | 1-cyclobutylethanone, NaBH₃CN |
| 23 | cyclobutyl-CH(CH₃)– | H | –CH₂C(O)OH | 1-cyclobutylethanone, NaBH₃CN |
| 24 | Ph-CH(CH₃)– | –CH₂C(O)OH | H | acetophenone, NaBH₃CN |
| 25 | Ph-CH(CH₃)– | H | –CH₂C(O)OH | acetophenone, NaBH₃CN |
| 26 | Ph-CH(CH₃)– | –CH₂C(O)OH | H | acetophenone, NaBH₃CN |

-continued

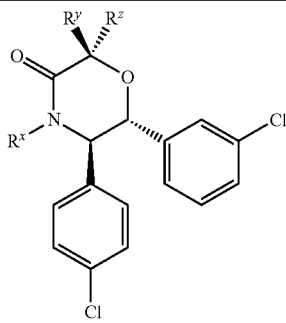

| Example | $R^x$ | $R^y$ | $R^z$ | Reagents used |
|---|---|---|---|---|
| 27 | CH(Ph)CH₃ | H | CH₂C(=O)OH | acetophenone, NaBH₃CN |
| 28 | CH₂-cyclopentyl | CH₂C(=O)OH | H | cyclopentanecarbaldehyde, NaBH₄ |
| 29 | CH₂-cyclopentyl | H | CH₂C(=O)OH | cyclopentanecarbaldehyde, NaBH₄ |

Example 11

2-((2S,5R,6R)-6-(3-Chlorophenyl)-5-(4-chlorophenyl)-3-oxo-4-(3,3,3-trifluoropropyl)morpholin-2-yl)acetic acid $^1$H NMR (500 MHz, CDCl$_3$) δ ppm 2.26-2.38 (m, 1 H), 2.40-2.54 (m, 1 H), 2.77-2.87 (m, 1 H), 3.06-3.13 (m, 1 H), 3.14-3.21 (m, 1 H), 3.96 (ddd, J=14.18, 8.44, 5.50 Hz, 1 H), 4.58-4.61 (m, 1 H), 4.61-4.65 (m, 1 H), 4.73 (t, J=4.89 Hz, 1 H), 6.73 (dt, J=7.83, 1.22 Hz, 1 H), 6.93 (d, J=8.31 Hz, 2 H), 7.06 (t, J=1.83 Hz, 1 H), 7.12 (t, J=7.83 Hz, 1 H), 7.24 (ddd, J=8.07, 2.20, 0.98 Hz, 1 H), 7.28-7.34 (m, 2 H); MS (ESI) m/z=476.1 [M+H]$^+$.

Example 12

2-((2S,5R,6R)-6-(3-Chlorophenyl)-5-(4-chlorophenyl)-4-cyclobutyl-3-oxomorpholin-2-yl)acetic acid $^1$H NMR (500 MHz, CDCl$_3$) δ ppm 1.40-1.47 (m, 2 H), 1.59-1.67 (m, 1 H), 2.16 (t, J=9.54 Hz, 1 H), 2.22-2.29 (m, 1 H), 2.31-2.37 (m, 1 H), 2.99-3.08 (m, 1 H), 3.09-3.18 (m, 1 H), 3.72-3.83 (m, 1 H), 4.42 (d, J=9.54 Hz, 1 H), 4.61-4.70 (m, 2 H), 6.71 (d, J=7.58 Hz, 1 H), 6.83 (d, J=8.31 Hz, 2 H), 7.11 (s, 1 H), 7.14 (t, J=7.95 Hz, 1 H), 7.24-7.27 (m, 3 H); MS (ESI) m/z=434.2 [M+H]$^+$.

Example 13

2-((2R,5R,6R)-6-(3-Chlorophenyl)-5-(4-chlorophenyl)-4-cyclobutyl-3-oxomorpholin-2-yl)acetic acid $^1$H NMR (500 MHz, CDCl$_3$) δ ppm 1.54-1.62 (m, 1 H), 1.63-1.68 (m, 1 H), 1.69-1.75 (m, 1 H), 1.98-2.06 (m, 1 H), 2.25 (quin, J=10.09 Hz, 1 H), 2.31-2.39 (m, 1 H), 2.89 (dd, J=16.26, 7.46 Hz, 1 H), 3.14 (dd, J=16.26, 5.26 Hz, 1 H), 4.25-4.35 (m, 1 H), 4.49 (dd, J=7.46, 5.26 Hz, 1 H), 4.81 (d, J=3.67 Hz, 1 H), 4.94 (d, J=3.67 Hz, 1 H), 7.08 (d, J=8.56 Hz, 2 H), 7.12 (d, J=7.58 Hz, 1 H), 7.28-7.32 (m, 1 H), 7.32-7.38 (m, 4 H); MS (ESI) m/z=434.1 [M+H]$^+$.

Example 14

2-((2S,5R,6R)-6-(3-Chlorophenyl)-5-(4-chlorophenyl)-4-cyclopentyl-3-oxomorpholin-2-yl)acetic acid $^1$H NMR (500 MHz, CDCl$_3$) δ ppm 1.31-1.34 (m, 1 H), 1.37-1.46 (m, 2 H), 1.67-1.74 (m, 1 H), 1.75-1.83 (m, 2 H), 1.94-2.04 (m, 1 H), 2.06-2.17 (m, 1 H), 2.99-3.07 (m, 1 H), 3.08-3.18 (m, 1 H), 3.25 (t, J=8.60 Hz, 1 H), 4.52-4.60 (m, 2 H), 4.67 (t, J=5.38 Hz, 1 H), 6.71 (d, J=7.58 Hz, 1 H), 6.94 (d, J=8.31 Hz, 2 H), 7.09 (s, 1 H), 7.12 (t, J=7.83 Hz, 1 H), 7.24 (dt, J=8.07, 0.98 Hz, 1 H), 7.28 (d, J=6.85 Hz, 2 H); MS (ESI) m/z=448.2 [M+H]$^+$.

Example 15

2-((2R,5R,6R)-6-(3-chlorophenyl)-5-(4-chlorophenyl)-4-cyclopentyl-3-oxomorpholin-2-yl)acetic acid $^1$H NMR (500 MHz, CDCl$_3$) δ ppm 1.45-1.54 (m, 2 H), 1.67-1.84 (m, 5 H), 1.89-2.00 (m, 1 H), 2.91 (dd, J=16.14, 6.85 Hz, 1 H), 3.14 (dd, J=16.14, 5.62 Hz, 1 H), 3.84-3.94 (m, 1 H), 4.39 (t, J=6.24 Hz, 1 H), 4.83-4.93 (m, 2 H), 7.19 (d, J=8.31 Hz, 3 7.42 (m, 4 H); MS (ESI) m/z=448.1 [M+H]$^+$.

Example 16

2-((2S,5R,6R)-6-(3-Chlorophenyl)-5-(4-chlorophenyl)-4-cyclohexyl-3-oxomorpholin-2-yl)acetic acid $^1$H NMR (400 MHz, CDCl$_3$) δ ppm 0.83-1.00 (m, 1 H), 1.00-1.16 (m, 1 H), 1.29-1.37 (m, 1 H), 1.38-1.52 (m, 1 H), 1.53-1.63 (m, 1 H), 1.63-1.73 (m, 2 H), 1.74-1.84 (m, 1 H), 1.95-2.15 (m, 2 H), 2.96-3.09 (m, 1 H), 3.09-3.16 (m, 1 H), 3.16-3.32 (m, 1 H), 4.50-4.56 (m, 1 H), 4.56-4.63 (m, 1 H), 4.65-4.75 (m, 1 H), 6.72 (d, J=7.63 Hz, 1 H), 6.95 (d, J=8.41 Hz, 1 H), 7.00 (d, J=8.41 Hz, 1 H), 7.08 (br. s., 1 H), 7.12 (dd, J=7.80 Hz, 1 H), 7.24 (d, J=8.22 Hz, 1 H), 7.26-7.32 (m, 2 H); MS (ESI) m/z=462.2 [M+H]$^+$.

Example 17

2-((2R,5R,6R)-6-(3-Chlorophenyl)-5-(4-chlorophenyl)-4-cyclohexyl-3-oxomorpholin-2-yl)acetic acid $^1$H NMR (500 MHz, CDCl$_3$) δ ppm 0.96-1.06 (m, 1 H), 1.18-1.24 (m, 2 H), 1.39-1.50 (m, 1 H), 1.54-1.62 (m, 2 H), 1.64-1.70 (m, 1 H), 1.72-1.76 (m, 1 H), 1.77-1.84 (m, 2 H), 2.92 (dd, J=16.26, 7.21 Hz, 1 H), 3.19 (dd, J=16.14, 5.38 Hz, 1 H), 3.98 (ddd, J=11.25, 7.83, 3.67 Hz, 1 H), 4.41 (dd, J=7.09, 5.38 Hz, 1 H), 4.83 (s, 1 H), 4.92 (d, J=1.47 Hz, 1 H), 7.25 (d, J=8.31 Hz, 2 H), 7.27-7.30 (m, 1 H), 7.33-7.36 (m, 2 H), 7.38 (d, J=8.31 Hz, 2 H), 7.41 (s, 1 H); MS (ESI) m/z=462.1 [M+H]$^+$.

Example 18

2-((2S,5R,6R)-6-(3-chlorophenyl)-5-(4-chlorophenyl)-4-((R)-1-cyclohexylethyl)-3-oxomorpholin-2-yl)acetic acid or 2-((2S,5R,6R)-6-(3-Chlorophenyl)-5-(4-chlorophenyl)-4-((S)-1-cyclohexylethyl)-3-oxomorpholin-2-yl)acetic acid $^1$H NMR (500 MHz, CDCl$_3$) δ ppm 0.54-0.66 (m, 1 H), 0.85-0.95 (m, 1 H), 1.03-1.13 (m, 1 H), 1.14-1.20 (m, 1 H), 1.23 (d, J=6.60 Hz, 3 H), 1.24-1.27 (m, 1 H), 1.62-1.71 (m, 3 H), 1.80 (d, J=12.72 Hz, 1 H), 1.95 (d, J=11.49 Hz, 1 H), 2.07-2.14 (m, 1 H), 2.45-2.57 (m, 1 H), 2.93 (dd, J=16.38, 5.87 Hz, 1 H), 3.20 (dd, J=16.38, 5.62 Hz, 1 H), 4.42 (d, J=9.78 Hz, 1 H), 4.60 (d, J=9.54 Hz, 1 H), 4.75 (t, J=5.75 Hz, 1 H), 6.68 (d, J=7.82 Hz, 1 H), 6.99 (d, J=8.31 Hz, 2 H), 7.04 (s, 1 H), 7.10 (t, J=7.90 Hz, 1 H), 7.22 (dd, J=7.83, 1.22 Hz, 1 H), 7.29 (d, J=8.31 Hz, 2 H); MS (ESI) m/z=490.1 [M+H]$^+$.

Example 19

2-((2S,5R,6R)-6-(3-chlorophenyl)-5-(4-chlorophenyl)-4-((S)-1-cyclohexylethyl)-3-oxomorpholin-2-yl)acetic acid or 2-((2S,5R,6R)-6-(3-chlorophenyl)-5-(4-chlorophenyl)-4-((R)-1-cyclohexylethyl)-3-oxomorpholin-2-yl)acetic acid $^1$H NMR (500 MHz, CDCl$_3$) δ ppm 0.66-0.73 (m, 1 H), 0.92-0.98 (m, 1 H), 1.07-1.15 (m, 2 H), 1.24 (d, J=6.85 Hz, 3 H), 1.66 (m, 4 H), 1.77 (m, 2 H), 1.92-2.00 (m, 1 H), 2.75-2.83 (m, 1 H), 3.04 (dd, J=15.89, 7.09 Hz, 1 H), 3.21 (dd, J=16.02, 5.50 Hz, 1 H), 4.58 (d, J=6.36 Hz, 1 H), 4.76-4.83 (m, 2 H), 6.93 (d, J=7.58 Hz, 1 H), 7.15 (d, J=8.07 Hz, 2 H), 7.19 (t, J=7.80 Hz, 1 H), 7.24 (s, 1 H), 7.25-7.29 (m, 1 H), 7.34 (d, J=8.07 Hz, 2 H); MS (ESI) m/z=490.1 [M+H]$^+$.

Example 20

2-((2R,5R,6R)-6-(3-Chlorophenyl)-5-(4-chlorophenyl)-4-((R)-1-cyclobutylethyl)-3-oxomorpholin-2-yl)acetic acid $^1$H NMR (500 MHz, CDCl$_3$) δ ppm 1.11 (d, J=6.85 Hz, 3 H), 1.48-1.56 (m, 1 H), 1.68-1.80 (m, 4 H), 1.82-1.93 (m, 1 H), 2.45-2.58 (m, 1 H), 2.98 (dd, J=16.14, 7.58 Hz, 1 H), 3.16 (dd, J=16.14, 5.14 Hz, 1 H), 3.69-3.85 (m, 1 H), 4.56 (dd, J=6.97, 5.26 Hz, 1 H), 4.74 (d, J=3.42 Hz, 1 H), 4.79 (d, J=3.42 Hz, 1 H), 7.11 (d, J=7.58 Hz, 1 H), 7.22 (d, J=8.31 Hz, 2 H), 7.24-7.28 (m, 1 H), 7.28-7.31 (m, 1 H), 7.32 (s, 1 H), 7.36 (d, J=8.31 Hz, 2 H); MS (ESI) m/z=462.2 [M+H]$^+$.

Example 21

2-((2S,5R,6R)-6-(3-Chlorophenyl)-5-(4-chlorophenyl)-4-((R)-1-cyclobutylethyl)-3-oxomorpholin-2-yl)acetic acid $^1$H NMR (500 MHz, CDCl$_3$) δ ppm 1.11 (d, J=6.85 Hz, 3 H), 1.42-1.48 (m, 1 H), 1.71-1.79 (m, 2 H), 1.80-1.87 (m, 1 H), 1.88-1.97 (m, 1 H), 1.99-2.07 (m, 1 H), 2.81 (m, 1 H), 2.95 (dd, J=16.02, 4.77 Hz, 1 H), 3.10-3.22 (m, 2 H), 4.47-4.53 (m, 1 H), 4.54-4.60 (m, 1 H), 4.69 (dd, J=6.97, 4.77 Hz, 1 H), 6.67 (d, J=7.83 Hz, 1 H), 7.00 (d, J=8.31 Hz, 2 H), 7.05 (dd, J=1.70 Hz, 1 H), 7.11 (t, J=7.80 Hz, 1 H), 7.21-7.26 (m, 1 H), 7.32 (d, J=8.56 Hz, 2 H); MS (ESI) m/z=462.2 [M+H]$^+$.

Example 22

2-((2R,5R,6R)-6-(3-Chlorophenyl)-5-(4-chlorophenyl)-4-((S)-1-cyclobutylethyl)-3-oxomorpholin-2-yl)acetic acid $^1$H NMR (500 MHz, CDCl$_3$) δ ppm 0.84 (d, J=7.09 Hz, 3 H), 1.52-1.58 (m, 1 H), 1.59-1.65 (m, 1 H), 1.69-1.75 (m, 1 H), 1.79-1.86 (m, 2 H), 1.96-2.06 (m, 1 H), 2.61-2.73 (m, 1 H), 2.92 (dd, J=16.14, 6.11 Hz, 1 H), 3.20 (dd, J=16.14, 6.36 Hz, 1 H), 4.21-4.34 (m, 1 H), 4.48 (t, J=6.24 Hz, 1 H), 4.76 (s, 1 H), 4.85 (d, J=1.22 Hz, 1 H), 7.25 (d, J=8.56 Hz, 3 H), 7.32-7.37 (m, 2 H), 7.37-7.42 (m, 3 H); MS (ESI) m/z=462.2 [M+H]$^+$.

Example 23

2-((2S,5R,6R)-6-(3-Chlorophenyl)-5-(4-chlorophenyl)-4-((S)-1-cyclobutylethyl)-3-oxomorpholin-2-yl)acetic acid $^1$H NMR (500 MHz, CDCl$_3$) δ ppm 0.78 (d, J=6.85 Hz, 3 H), 1.44-1.52 (m, 1 H), 1.54-1.63 (m, 1 H), 1.66-1.74 (m, 1 H), 1.75-1.84 (m, 1 H), 1.87-2.01 (m, 2 H), 2.57-2.65 (m, 1 H), 2.96 (dd, J=16.26, 5.75 Hz, 1 H), 3.15 (dd, J=16.38, 5.87 Hz, 1 H), 3.87-3.98 (m, 1 H), 4.35 (d, J=9.29 Hz, 1 H), 4.60 (d, J=9.29 Hz, 1 H), 4.74 (t, J=5.62 Hz, 1 H), 6.70 (d, J=7.83 Hz, 1 H), 7.00 (d, J=8.31 Hz, 2 H), 7.04 (t, J=1.70 Hz, 1 H), 7.11 (t, J=7.80 Hz, 1 H), 7.21-7.25 (m, 1 H), 7.28 (d, J=8.31 Hz, 2 H); MS (ESI) m/z=462.2 [M+H]$^+$.

Example 24

2-((2R,5R,6R)-6-(3-Chlorophenyl)-5-(4-chlorophenyl)-3-oxo-4-((R)-1-phenylethyl)morpholin-2-yl)acetic acid $^1$H NMR (400 MHz, CDCl$_3$) δ ppm 1.71 (d, J=6.85 Hz, 3 H), 2.94 (dd, J=15.45, 7.24 Hz, 1 H), 3.14 (dd, J=16.53, 5.38

Hz, 1 H), 4.44-4.54 (m, 1 H), 4.80 (s, 2 H), 4.89-4.99 (m, 1 H), 6.93 (d, J=7.43 Hz, 1 H), 7.01 (d, J=8.22 Hz, 2 H), 7.11-7.22 (m, 7 H), 7.23-7.27 (m, 3 H); MS (ESI) m/z=484.1 [M+H]$^+$.

Example 25

2-((2S,5R,6R)-6-(3-Chlorophenyl)-5-(4-chlorophenyl)-3-oxo-4-((R)-1-phenylethyl)morpholin-2-yl)acetic acid $^1$H NMR (400 MHz, CDCl$_3$) δ ppm 1.64 (d, J=7.04 Hz, 3 H), 2.97 (dd, J=16.43, 5.28 Hz, 1 H), 3.13 (dd, J=16.43, 5.87 Hz, 1 H), 4.59-4.71 (m, 2 H), 4.81 (t, J=5.50 Hz, 1 H), 5.10-5.18 (m, 1 H), 6.65 (d, J=7.83 Hz, 1 H), 6.76 (d, J=8.41 Hz, 2 H), 6.99-7.14 (m, 6 H), 7.14-7.19 (m, 3 H), 7.21 (d, J=8.02 Hz, 1 H); MS (ESI) m/z=484.1 [M+H]$^+$.

Example 26

2-((2R,5R,6R)-6-(3-Chlorophenyl)-5-(4-chlorophenyl)-3-oxo-4-((S)-1-phenylethyl)morpholin-2-yl)acetic acid $^1$H NMR (500 MHz, CDCl$_3$) δ ppm 1.16 (d, J=7.24 Hz, 3 H), 2.96 (dd, J=16.24, 7.24 Hz, 1 H), 3.26 (dd, J=15.85, 4.89 Hz, 1 H), 4.51 (t, J=6.16 Hz, 1 H), 4.55 (s, 1 H), 4.65 (s, 1 H), 6.05-6.17 (m, 1 H), 6.75 (d, J=7.83 Hz, 1 H), 6.87 (s, 1 H), 7.07-7.14 (m, 1 H), 7.15-7.23 (m, 3 H), 7.23-7.27 (m, 2 H), 7.39 (d, J=8.41 Hz, 2 H), 7.41-7.47 (m, 3 H); MS (ESI) m/z=484.1 [M+H]$^+$.

Example 27

2-((2S,5R,6R)-6-(3-Chlorophenyl)-5-(4-chlorophenyl)-3-oxo-4-((S)-1-phenylethyl)morpholin-2-yl)acetic acid $^1$H NMR (500 MHz, CDCl$_3$) δ ppm 1.21 (d, J=7.06 Hz, 3 H), 2.98-3.10 (m, 1 H), 3.13-3.24 (m, 1 H), 4.26 (d, J=8.61 Hz, 1 H), 4.62 (d, J=8.80 Hz, 1 H), 4.82 (br. s., 1 H), 5.54 (d, J=6.65 Hz, 1 H), 6.59 (d, J=7.24 Hz, 1 H), 6.68 (d, J=7.82 Hz, 2 H), 6.91 (br. s., 1 H), 7.01 (t, J=7.70 Hz, 1 H), 7.07 (d, J=6.26 Hz, 2 H), 7.15 (d, J=7.82 Hz, 3 H), 7.22-7.27 (m, 3 H); MS (ESI) m/z=484.1 [M+H]$^+$.

Example 28

2-((2R,5R,6R)-6-(3-Chlorophenyl)-5-(4-chlorophenyl)-4-(cyclopentylmethyl)-3-oxomorpholin-2-yl)acetic acid $^1$H NMR (400 MHz, CDCl$_3$) δ ppm 1.07-1.14 (m, 1 H), 1.20-1.27 (m, 1 H), 1.53-1.73 (m, 6 H), 2.12-2.22 (m, 1 H), 2.52 (dd, J=13.7, 6.1 Hz, 1 H), 3.02 (dd, J=16.4, 8.8 Hz, 1 H), 3.18 (dd, J=16.2, 5.1 Hz, 1 H), 4.04 (dd, J=13.7, 9.3 Hz, 1 H), 4.75-4.78 (m, 1 H), 4.79 (d, J=5.4 Hz, 1 H), 4.84 (d, J=5.5 Hz, 1 H), 6.99-7.07 (m, 4 H), 7.22-7.36 (m, 5 H). Mass Spectrum (ESI) m/z=462 (M+1).

Example 29

2-((2S,5R,6R)-6-(3-Chlorophenyl)-5-(4-chlorophenyl)-4-(cyclopentylmethyl)-3-oxomorpholin-2-yl)acetic acid $^1$H NMR (400 MHz, CDCl$_3$) δ ppm 0.96-1.05 (m, 1 H), 1.10-1.16 (m, 1 H), 1.48-1.75 (m, 6 H), 2.04-2.13 (m, 1 H), 2.38 (dd, J=13.7, 6.8 Hz, 1 H), 3.08 (dd, J=16.7, 5.3 Hz, 1 H), 3.18 (dd, J=16.8, 5.6 Hz, 1 H), 4.04 (dd, J=13.9, 8.5 Hz, 1 H), 4.58 (d, J=9.6 Hz, 1 H), 4.62 (d, J=9.6 Hz, 1 H), 4.76-4.79 (m, 1 H), 6.19 (brs, 1 H), 6.70 (d, J=7.8 Hz, 1 H), 6.90 (d, J=8.4 Hz, 2 H), 7.07-7.08 (m, 1 H), 7.12 (t, J=8.0 Hz, 1 H), 7.24-7.30 (m, 3 H). Mass Spectrum (ESI) m/z=462 (M+1).

Example 30

2-((2S,5R,6R)-4-((R)-1-(tert-butoxy)-1-oxobutan-2-yl)-6-(3-chlorophenyl)-5-(4-chlorophenyl)-3-oxomorpholin-2-yl)acetic acid

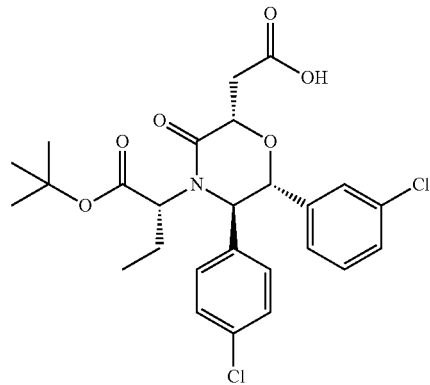 [SMILES: CC[C@H](C(=O)OC(C)(C)C)N1C(=O)[C@H](CC(=O)O)O[C@H](c2cccc(Cl)c2)[C@H]1c1ccc(Cl)cc1]

Step A. (E)-Methyl 4-((1R,2R)-2-(3-chlorophenyl)-1-(4-chlorophenyl)-2-hydroxyethylamino)-4-oxobut-2-enoate

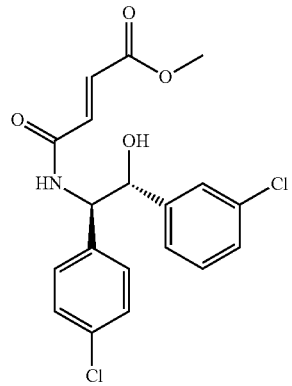 [SMILES: COC(=O)/C=C/C(=O)N[C@H](c1ccc(Cl)cc1)[C@H](O)c1cccc(Cl)c1]

To a solution of (E)-4-methoxy-4-oxobut-2-enoic acid (91 mg, 0.702 mmol) in DCM (7 mL) at 0° C. was added 1H-benzo[d][1,2,3]triazol-1-ol hydrate (107 mg, 0.702 mmol) and DCC (145 mg, 0.702 mmol). The reaction mixture was stirred at 0° C. for 60 min then a solution of (1R,2R)-2-amino-1-(3-chlorophenyl)-2-(4-chlorophenyl)ethanol (198 mg, 0.702 mmol; Intermediate A2) in DCM (7 mL) was added. The reaction mixture was stirred at 0° C. for 2 h and then warmed to rt for 2 h and then concentrated under reduced pressure. The residue was purified by flash column chromatography on silica gel (eluent: 0 to 100% EtOAc in hexanes) to give the title compound as a colorless film.

Step B. Methyl 2-((2R,5R,6R)-6-(3-chlorophenyl)-5-(4-chlorophenyl)-3-oxomorpholin-2-yl)acetate and Methyl 2-((2S,5R,6R)-6-(3-chlorophenyl)-5-(4-chlorophenyl)-3-oxomorpholin-2-yl)acetate

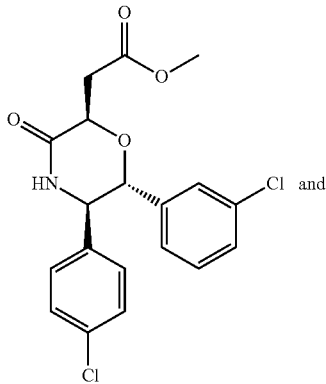

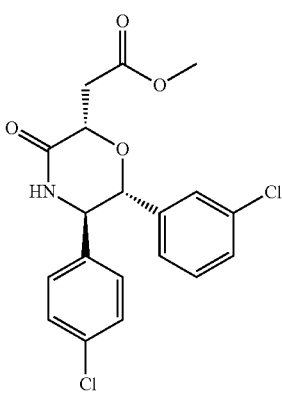

To a solution of (E)-methyl 4-((1R,2R)-2-(3-chlorophenyl)-1-(4-chlorophenyl)-2-hydroxyethylamino)-4-oxobut-2-enoate (220 mg, 0.558 mmol; Example 28, Step A) in THF (6 mL) was added a dispersion of 60% sodium hydride in mineral oil (33 mg, 0.837 mmol). The reaction mixture was stirred at rt for 16 h. The reaction mixture was quenched with sat. NH₄Cl solution and extracted with DCM. The organic layer was dried over Na₂SO₄, filtered and the filtrate was concentrated under reduced pressure. The residue was purified by flash chromatography on silica gel (eluent: 0 to 50% EtOAc in hexanes) to give the title compounds as a mixture of two diastereomers (129 mg, 57% yield).

Step C. (R)-tert-Butyl 2-((2R,3R,6R)-2-(3-chlorophenyl)-3-(4-chlorophenyl)-6-(2-methoxy-2-oxoethyl)-5-oxomorpholino)butanoate and (R)-tert-Butyl 2-((2R,3R,6S)-2-(3-chlorophenyl)-3-(4-chlorophenyl)-6-(2-methoxy-2-oxo ethyl)-5-oxomorpholino)butanoate and (S)-tert-Butyl 2-((2R,3R,6R)-2-(3-chlorophenyl)-3-(4-chlorophenyl)-6-(2-methoxy-2-oxoethyl)-5-oxomorpholino)butanoate and (S)-tert-Butyl 2-((2R,3R,6S)-2-(3-chlorophenyl)-3-(4-chlorophenyl)-6-(2-methoxy-2-oxo ethyl)-5-oxomorpholino)butanoate

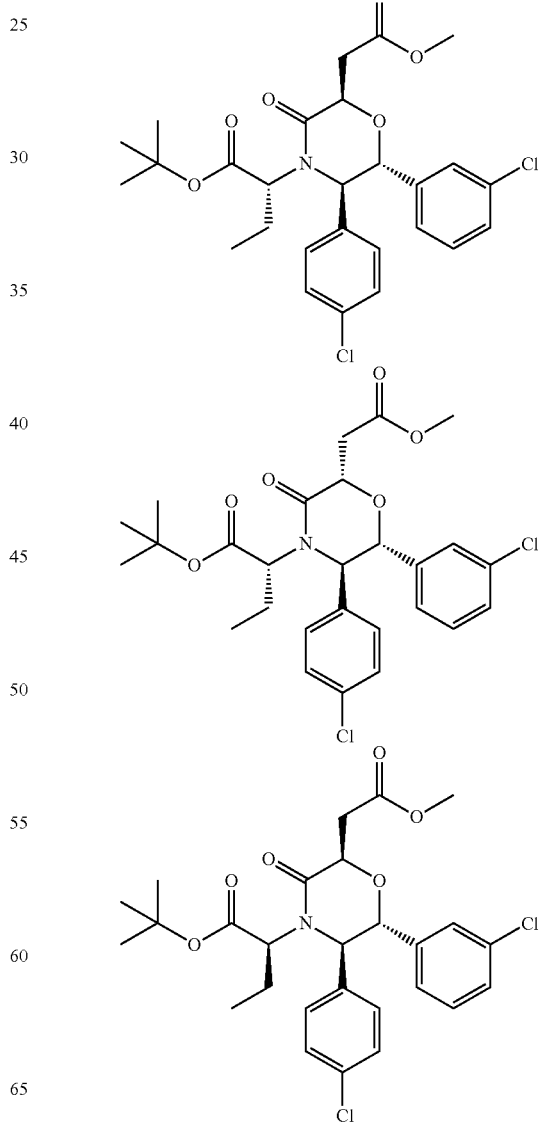

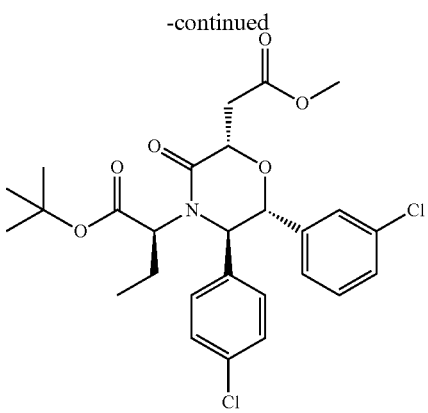

To a solution of methyl 2-((2R,5R,6R)-6-(3-chlorophenyl)-5-(4-chlorophenyl)-3-oxomorpholin-2-yl)acetate and methyl 2-((2S,5R,6R)-6-(3-chlorophenyl)-5-(4-chlorophenyl)-3-oxomorpholin-2-yl)acetate (129 mg, 0.327 mmol; Example 28, Step B) in DMF (3 mL) at 0° C. was added a dispersion of 60% sodium hydride in mineral oil (31.4 mg, 1.309 mmol). The reaction mixture was stirred at rt for 20 min and then cooled to 0° C. tert-Butyl 2-bromobutanoate (304 µL, 1.636 mmol) was added and the reaction mixture was warmed to rt and stirred at rt for 4 h. The reaction mixture was quenched with sat. aq. $NH_4Cl$ solution and extracted with DCM (3×). The organic layers were combined, dried over $Na_2SO_4$, filtered and the filtrate was concentrated under reduced pressure. The residue was diluted with EtOAc and washed with 1 M LiCl solution (3×). The organic layer was dried over $Na_2SO_4$, filtered and the filtrate was concentrated under reduced pressure. The residue was purified by flash chromatography on silica gel (eluent: 0 to 50% DCM in hexanes and then 30% EtOAc in hexanes) to give the title compounds as a mixture of four diastereomers.

Step D. 2-((2R,5R,6R)-4-((R)-1-tert-Butoxy-1-oxobutan-2-yl)-6-(3-chlorophenyl)-5-(4-chlorophenyl)-3-oxomorpholin-2-yl)acetic acid and 2-((2S,5R,6R)-4-((R)-1-tert-Butoxy-1-oxobutan-2-yl)-6-(3-chlorophenyl)-5-(4-chlorophenyl)-3-oxomorpholin-2-yl)acetic acid and 2-((2R,5R,6R)-4-((S)-1-tert-Butoxy-1-oxobutan-2-yl)-6-(3-chlorophenyl)-5-(4-chlorophenyl)-3-oxomorpholin-2-yl)acetic acid and 2-((2S,5R,6R)-4-((S)-1-tert-Butoxy-1-oxobutan-2-yl)-6-(3-chlorophenyl)-5-(4-chlorophenyl)-3-oxomorpholin-2-yl)acetic acid To a mixture of (R)-tert-butyl 2-((2R,3R,6R)-2-(3-chlorophenyl)-3-(4-chlorophenyl)-6-(2-methoxy-2-oxoethyl)-5-oxomorpholino)butanoate, (R)-tert-butyl 2-((2R,3R,6S)-2-(3-chlorophenyl)-3-(4-chlorophenyl)-6-(2-methoxy-2-oxoethyl)-5-oxomorpholino)butanoate, (S)-tert-butyl 2-((2R,3R,6R)-2-(3-chlorophenyl)-3-(4-chlorophenyl)-6-(2-methoxy-2-oxoethyl)-5-oxomorpholino)butanoate, and (S)-tert-butyl 2-((2R,3R,6S)-2-(3-chlorophenyl)-3-(4-chlorophenyl)-6-(2-methoxy-2-oxoethyl)-5-oxomorpholino)butanoate (100 mg, 0.186 mmol; Example 28, Step C) in water and THF (1:1, 3 mL total) at rt was added 3 M aq. LiOH solution (311 µL, 0.932 mmol). The reaction mixture was stirred at rt for 4 h and diluted with EtOAc. The aqueous layer was acidified with 1 M HCl and extracted with EtOAc (3×). The organic layers were combined, dried over $Na_2SO_4$, filtered and the filtrate was concentrated under reduced pressure. Purification by chiral SFC (flowrate: 24 mL/min on a Lux Cellulose-2 21×250 mm column, Phenomenex, Torrance, Calif.; using methanol (0.2% DEA)/$CO_2$ as the eluent) provided the title compound as the first eluting isomer that was then further purified by flash chromatography on silica gel (eluent: 7:3:0.1 EtOAc:Hex:AcOH) to provide the title compound. $^1$H NMR (400 MHz, $CDCl_3$) δ ppm 0.99 (t, J=7.53 Hz, 3 H) 1.46 (s, 9 H) 1.95-2.08 (m, 2 H) 3.13-3.20 (m, 3 H) 4.63-4.75 (m, 3 H) 6.70 (d, J=7.63 Hz, 1 H) 7.02-7.15 (m, 4 H) 7.21-7.23 (m, 1 H) 7.27 (d, J=8.6 Hz, 2 H). Mass Spectrum (ESI) m/z=466 (M-58+1).

Example 31

2-((2S,5R,6R)-4-((S)-1-(tert-Butoxy)-1-oxobutan-2-yl)-6-(3-chlorophenyl)-5-(4-chlorophenyl)-3-oxomorpholin-2-yl)acetic acid

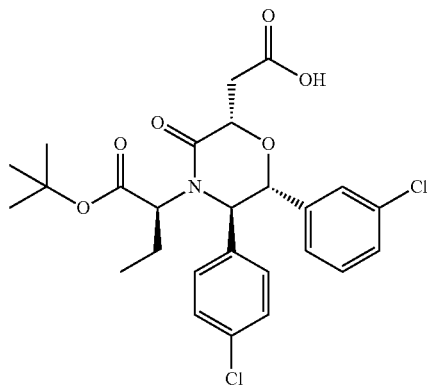 [SMILES: CC[C@@H](C(=O)OC(C)(C)C)N1C(=O)[C@H](CC(=O)O)O[C@H](c2cccc(Cl)c2)[C@H]1c1ccc(Cl)cc1]

The second eluting isomer from Example 28, Step D was further purified by flash chromatography on silica gel (eluent: 7:3:0.1 EtOAc:Hex:AcOH) to provide the title compound. $^1$H NMR (400 MHz, $CDCl_3$) δ ppm 0.67 (t, J=7.53 Hz, 3 H) 1.49 (s, 9 H) 1.63-1.75 (m, 1 H) 2.26 (dt, J=14.38, 7.48 Hz, 1 H) 2.83 (dd, J=16.33, 6.55 Hz, 1 H) 3.12 (dd, J=7.73, 5.18 Hz, 1 H) 3.27 (dd, J=16.33, 5.97 Hz, 1 H) 4.63 (d, J=9.78 Hz, 1 H) 4.76 (d, J=9.78 Hz, 1 H) 4.86 (t, J=6.26 Hz, 1 H) 6.72 (d, J=7.6 Hz, 1 H) 7.03 (d, J=8.41 Hz, 1 H) 7.08-7.12 (m, 2 H) 7.21-7.24 (m, 1 H) 7.30 (d, J=8.61 Hz, 3 H). Mass Spectrum (ESI) m/z=466 (M-58+1).

Example 32

2-((2R,5R,6R)-4-((S)-1-(tert-Butoxy)-1-oxobutan-2-yl)-6-(3-chlorophenyl)-5-(4-chlorophenyl)-3-oxomorpholin-2-yl)acetic acid

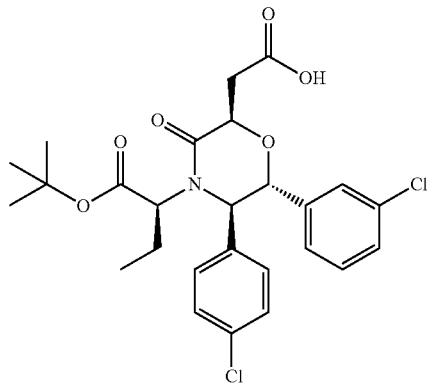 [SMILES: CC[C@@H](C(=O)OC(C)(C)C)N1C(=O)[C@@H](CC(=O)O)O[C@H](c2cccc(Cl)c2)[C@H]1c1ccc(Cl)cc1]

The third eluting isomer from Example 28, Step D was further purified by flash chromatography on silica gel (eluent: EtOAc/Hex/AcOH=7:3:0.1) to provide the title compound. $^1$H NMR (400 MHz, CDCl$_3$) δ ppm 0.69 (t, J=7.53 Hz, 3 H) 1.42 (s, 9 H) 1.63-1.70 (m, 1 H) 2.14-2.24 (m, 1 H) 3.07 (d, J=6.06 Hz, 2 H) 3.45 (dd, J=8.12, 4.99 Hz, 1 H) 4.65 (t, J=6.16 Hz, 1 H) 4.82 (d, J=5.48 Hz, 1 H) 4.97 (d, J=5.48 Hz, 1 H) 7.10-7.15 (m, 1 H) 7.18-7.25 (m, 3 H) 7.28-7.30 (m, 1 H) 7.34 (d, J=8.41 Hz, 2 H) 7.37 (brs, 1 H). Mass Spectrum (ESI) m/z=466 (M-58+1).

Example 33

2-((2R,5R,6R)-4-((R)-1-(tert-Butoxy)-1-oxobutan-2-yl)-6-(3-chlorophenyl)-5-(4-chlorophenyl)-3-oxomorpholin-2-yl)acetic acid

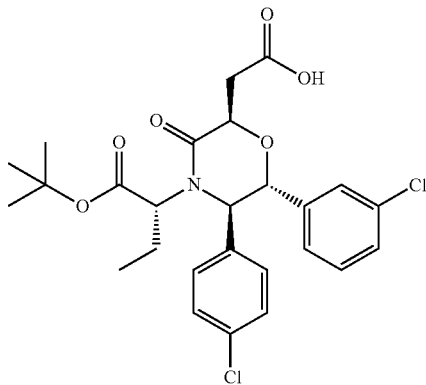 [SMILES: CC[C@H](C(=O)OC(C)(C)C)N1C(=O)[C@@H](CC(=O)O)O[C@H](c2cccc(Cl)c2)[C@H]1c1ccc(Cl)cc1]

The fourth eluting isomer from Example 28, Step D was further purified by flash chromatography on silica gel (eluent: EtOAc/Hex/AcOH=7:3:0.1) to provide the title compound. $^1$H NMR (400 MHz, CDCl$_3$) δ ppm 0.96 (t, J=7.43 Hz, 3 H) 1.46 (s, 9 H) 1.84-2.02 (m, 2 H) 3.04 (dd, J=16.0, 8.0 Hz, 1 H) 3.14 (dd, J=16.0, 5.3 Hz, 1 H) 3.47 (t, J=7.14 Hz, 1 H) 4.76 (d, J=7.04 Hz, 1 H) 4.82-4.90 (m, 2 H) 6.90 (d, J=7.63 Hz, 1 H) 7.12-7.25 (m, 5 H) 7.30 (d, J=8.41 Hz, 2 H). Mass Spectrum (ESI) m/z=466 (M-58+1).

Example 34

2-((2S,5R,6R)-6-(3-Chlorophenyl)-5-(4-chlorophenyl)-3-oxomorpholin-2-yl)acetic acid

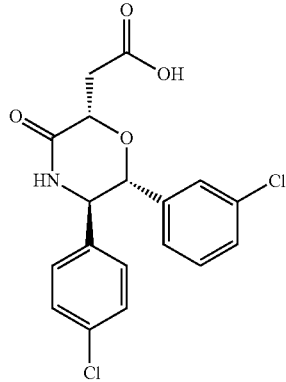 [SMILES: O=C(O)C[C@@H]1O[C@H](c2cccc(Cl)c2)[C@@H](c2ccc(Cl)cc2)NC1=O]

Step A. (R)-2-Bromo-4-tert-butoxy-4-oxobutanoic acid

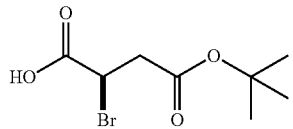

The title compound was prepared from (R)-2-amino-4-tert-butoxy-4-oxobutanoic acid (Bachem Americas, Inc., Torrance, Calif.) using the procedures described in Example 9, Step A.

Step B. (R)-tert-Butyl 3-bromo-4-((1R,2R)-2-(3-chlorophenyl)-1-(4-chlorophenyl)-2-hydroxyethylamino)-4-oxobutanoate

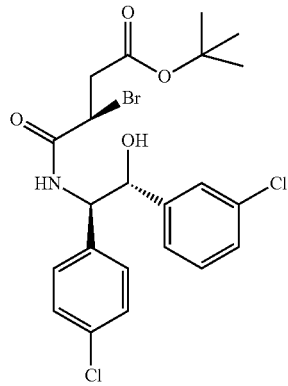 [SMILES: CC(C)(C)OC(=O)C[C@@H](Br)C(=O)N[C@H](c1ccc(Cl)cc1)[C@H](O)c1cccc(Cl)c1]

To a solution of (R)-2-bromo-4-tert-butoxy-4-oxobutanoic acid (0.806 g, 3.19 mmol; Example 34, Step A) in DCM (30 mL) at 0° C. was added 1-hydroxybenzotriazole hydrate (0.488 g, 3.19 mmol) and DCC (0.657 g, 3.19 mmol). The reaction mixture was stirred at 0° C. for 60 min, then ((1R,2R)-2-amino-1-(3-chlorophenyl)-2-(4-chlorophenyl)ethanol and (1S,2S)-2-amino-1-(3-chlorophenyl)-2-(4-chlorophenyl)ethanol (899 mg, 3.19 mmol; Intermediate A2) in DCM (10 mL) was added. The reaction mixture was stirred at 0° C. for 2 h. Then the reaction mixture was warmed to rt and stirred at rt for 16 h. The reaction mixture was concentrated to 5 mL and filtered. The filtrate was concentrated under reduced pressure. Purification by flash chromatography on silica gel (eluent: 25 to 100% EtOAc in hexanes) provided the title compound as the second eluting isomer.

Step C. tert-Butyl 2-((2S,5R,6R)-6-(3-chlorophenyl)-5-(4-chlorophenyl)-3-oxomorpholin-2-yl)acetate and tert-Butyl 2-((2R,5R,6R)-6-(3-chlorophenyl)-5-(4-chlorophenyl)-3-oxomorpholin-2-yl)acetate

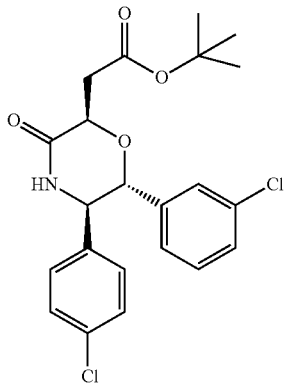 [SMILES: O=C(O)C[C@H]1O[C@H](c2cccc(Cl)c2)[C@@H](c2ccc(Cl)cc2)NC1=O]

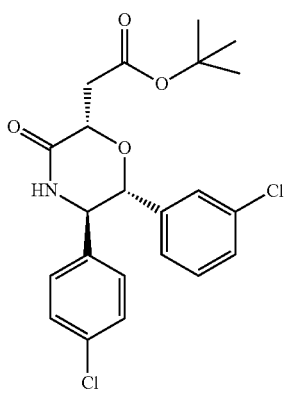

To a solution of (R)-tert-butyl 3-bromo-4-((1R,2R)-2-(3-chlorophenyl)-1-(4-chlorophenyl)-2-hydroxyethylamino)-4-oxobutanoate (352 mg, 681 μmol; Example 34, Step B) in DMF (7 mL) at 0° C. was added a dispersion of 60% sodium hydride in mineral oil (33 mg, 817 μmol). Evolution of gas was observed and the reaction mixture was stirred at 0° C. for 30 min. The reaction mixture was quenched with water. Evolution of gas was observed. The reaction mixture was diluted with EtOAc and the layers were separated. The organic layer was washed with 1 M LiCl and brine. The organic layer was dried over Na₂SO₄, filtered and the filtrate was concentrated under reduced pressure. The residue was purified by flash chromatography on silica gel (eluent: 0 to 50% EtOAc in hexanes) to give a residue. The residue was dissolved in THF (1.5 mL) and a dispersion of 60% sodium hydride in mineral oil (26 mg, 639 μmol) was added at rt. The reaction mixture was stirred at rt for 30 min. The reaction mixture was quenched with water and diluted with EtOAc. The layers were separated and the organic layer was washed with brine. The organic layer was dried over Na₂SO₄, filtered and the filtrate was concentrated under reduced pressure. Purification by flash chromatography on silica gel (eluent: 5% MTBE in DCM) (2×) provided tert-butyl 2-((2S,5R,6R)-6-(3-chlorophenyl)-5-(4-chlorophenyl)-3-oxomorpholin-2-yl)acetate as the first eluting diastereomer and tert-butyl 2-((2R,5R,6R)-6-(3-chlorophenyl)-5-(4-chlorophenyl)-3-oxomorpholin-2-yl)acetate as the second eluting diastereomer.

Step D. 2-((2S,5R,6R)-6-(3-chlorophenyl)-5-(4-chlorophenyl)-3-oxomorpholin-2-yl)acetic acid To tert-butyl 2-((2S,5R,6R)-6-(3-chlorophenyl)-5-(4-chlorophenyl)-3-oxomorpholin-2-yl)acetate (26 mg, 60 μmol; Example 34, Step C, first eluting isomer) in DCM (2 mL) at rt was added TFA (0.5 mL). The reaction mixture was stirred at rt for 90 min. The reaction mixture was concentrated under reduced pressure and the residue was purified by reverse phase preparatory HPLC (Gemini™ Prep C₁₈, 5 μm column; Phenomenex, Torrance, Calif.; eluent: 0 to 100% MeCN in water, 0.1% TFA, gradient elution over 20 minutes) to give the title compound. ¹H NMR (400 MHz, CDCl₃) δ ppm 3.09-3.25 (m, 2 H) 4.53 (d, J=9.4 Hz, 1 H) 4.65 (d, J=9.2 Hz, 1 H) 4.77 (t, J=4.9 Hz, 1 H) 6.74 (dt, J=7.8, 1.37 Hz, 1 H) 6.89-6.96 (m, 2 H) 7.09 (t, J=1.9 Hz, 1 H) 7.15 (t, J=7.8 Hz, 1 H) 7.25-7.30 (m, 3 H) 7.98 (br. s, 1 H) 10.53 (br. s, 1 H). Mass Spectrum (ESI) m/z=380 (M+1).

Example 35

2-((2R,5R,6R)-6-(3-Chlorophenyl)-5-(4-chlorophenyl)-3-oxomorpholin-2-yl)acetic acid

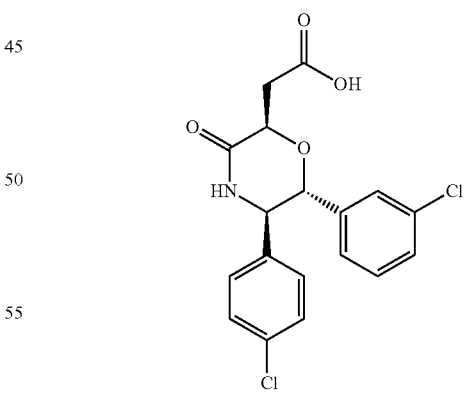

Using tert-butyl 2-((2R,5R,6R)-6-(3-chlorophenyl)-5-(4-chlorophenyl)-3-oxomorpholin-2-yl)acetate (Example 34, Step C; second eluting diastereomer) in the previous procedure provided the title compound. ¹H NMR (400 MHz, CDCl₃) δ ppm 3.06-3.19 (m, 2 H) 4.65-4.74 (m, 2 H) 4.96-5.02 (m, 1 H) 6.80 (dt, J=7.78, 1.39 Hz, 1 H) 6.94-7.00 (m, 2 H) 7.13-7.20 (m, 2 H) 7.25-7.32 (m, 3 H) 8.06 (br. s, 1 H) 9.87 (br. s, 1 H). Mass Spectrum (ESI) m/z=380 (M+1).

Example 36

2-((2R,5R,6R)-6-(3-Chlorophenyl)-5-(4-chlorophenyl)-4-isobutyl-3-oxomorpholin-2-yl)acetic acid

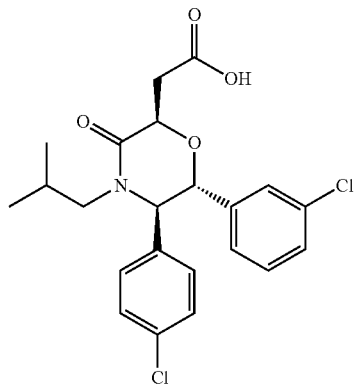 [SMILES: CC(C)CN1C(=O)[C@@H](CC(=O)O)O[C@H](c2cccc(Cl)c2)[C@H]1c1ccc(Cl)cc1]

Step A. Methyl 2-((2R,5R,6R)-6-(3-chlorophenyl)-5-(4-chlorophenyl)-4-isobutyl-3-oxomorpholin-2-yl) acetate

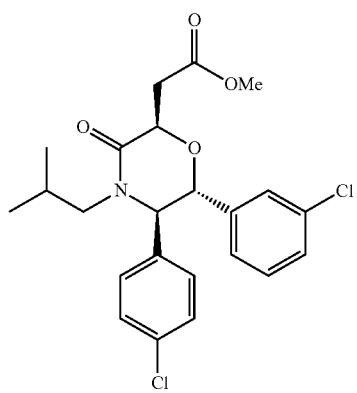 [SMILES: COC(=O)C[C@H]1O[C@H](c2cccc(Cl)c2)[C@@H](c2ccc(Cl)cc2)N(CC(C)C)C1=O]

The title compound was prepared from methyl 2-((2R,5R,6R)-6-(3-chlorophenyl)-5-(4-chlorophenyl)-3-oxomorpholin-2-yl)acetate and methyl 2-((2S,5R,6R)-6-(3-chlorophenyl)-5-(4-chlorophenyl)-3-oxomorpholin-2-yl)acetate (Example 30, Step B) by a procedure similar to the one described in Example 30, Step C, replacing sodium hydride and tert-butyl 2-bromobutanoate with isobutyl bromide and Cs$_2$CO$_3$. The mixture of steroisomers obtained was separated by reversed phase preparatory HPLC (Sunfire™ Prep C$_{18}$ OBD 10 μm column; Waters, Milford, Mass.; eluent: acetonitrile, water, 0.1% TFA, gradient elution) to provide the title compound as the first eluting isomer.

Step B. 2-((2R,5R,6R)-6-(3-Chlorophenyl)-5-(4-chlorophenyl)-4-isobutyl-3-oxomorpholin-2-yl)acetic acid To a solution of methyl 2-((2R,5R,6R)-6-(3-chlorophenyl)-5-(4-chlorophenyl)-4-isobutyl-3-oxomorpholin-2-yl) acetate (5.3 mg, 0.012 mmol; Example 36, Step B) in THF (0.26 mL) was added a 1N solution of lithium hydroxide in water (7.41 mg in 0.177 mL). The mixture was stirred at room temperature for 4.5 hours, then acidified to about pH 4 using 1 N HCl, and then concentrated in vacuo. The residue was taken up in EtOAc and the organics were washed with water, dried over MgSO$_4$, filtered and the filtrate was concentrated to give the title compound. $^1$H NMR (400 MHz, CDCl$_3$) δ ppm 0.76 (ddd, J=18.10, 6.60, 3.18 Hz, 6 H), 1.82 (dt, J=6.17, 3.39 Hz, 1 H) 2.13-2.30 (m, 1 H) 2.81-3.06 (m, 2 H) 3.68-3.88 (m, 1 H) 4.41-4.68 (m, 1 H) 4.70-4.89 (m, 2 H) 6.86 (d, J=7.09 Hz, 1 H) 6.94-7.03 (m, 2 H) 7.04-7.16 (m, 1 H) 7.16-7.38 (m, 5 H). Mass Spectrum (ESI) m/z=436 (M+1).

Example 37

2-((2S,5R,6R)-6-(3-Chlorophenyl)-5-(4-chlorophenyl)-4-isobutyl-3-oxomorpholin-2-yl)acetic acid

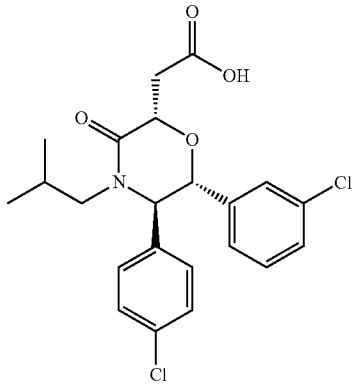 [SMILES: CC(C)CN1C(=O)[C@H](CC(=O)O)O[C@H](c2cccc(Cl)c2)[C@H]1c1ccc(Cl)cc1]

Step A. Methyl 2-((2S,5R,6R)-6-(3-chlorophenyl)-5-(4-chlorophenyl)-4-isobutyl-3-oxomorpholin-2-yl) acetate

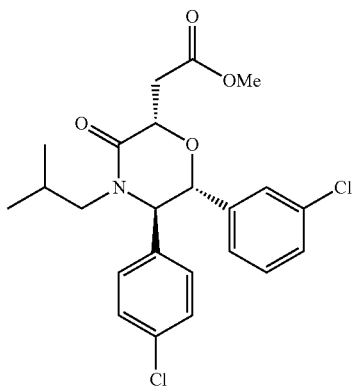 [SMILES: COC(=O)C[C@@H]1O[C@H](c2cccc(Cl)c2)[C@@H](c2ccc(Cl)cc2)N(CC(C)C)C1=O]

The title compound was obtained as the second eluting isomer in Example 36, Step A.

Step B. 2-((2S,5R,6R)-6-(3-Chlorophenyl)-5-(4-chlorophenyl)-4-isobutyl-3-oxomorpholin-2-yl)acetic acid The title compound was obtained from methyl 2-((2S,5R,6R)-6-(3-chlorophenyl)-5-(4-chlorophenyl)-4-isobutyl-3-oxomorpholin-2-yl)acetate (Example 37, Step A) by a procedure analogous to the one described in Example 36, Step B. $^1$H NMR (400 MHz, CDCl$_3$) δ ppm 0.79 (d, J=8 Hz, 3H), 0.86 (d, J=8 Hz, 3H), 1.82-1.90 (m, 1 H), 2.23 (dd, J=12, 8 Hz, 1H), 2.98 (dd, J=16, 4 Hz, 1H), 3.19 (dd, J=16, 4 Hz, 1H), 3.88 (dd, J=16, 8 Hz, 1H), 4.54 (d, J=8 Hz, 1 H), 4.58 (d, J=8 Hz, 1 H), 4.79 (t, J=6 Hz, 1 H), 6.69 (d, J=8 Hz, 1H), 6.89 (d, J=8 Hz, 2H), 7.08-7.12 (m, 2H), 7.22-7.29 (m, 3 H). Mass Spectrum (ESI) m/z=436 (M+1).

Example 38

2-((2R,5R,6R)-6-(3-Chlorophenyl)-5-(4-chlorophenyl)-4-(cyclobutylmethyl)-3-oxomorpholin-2-yl)acetic acid

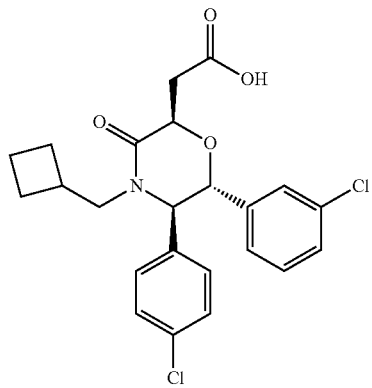 [SMILES: O=C(O)C[C@H]1O[C@H](c2cccc(Cl)c2)[C@@H](c2ccc(Cl)cc2)N(CC2CCC2)C1=O]

Step A. Methyl 2-((2R,5R,6R)-6-(3-chlorophenyl)-5-(4-chlorophenyl)-4-(cyclobutylmethyl)-3-oxomorpholin-2-yl)acetate and Methyl 2-((2S,5R,6R)-6-(3-chlorophenyl)-5-(4-chlorophenyl)-4-(cyclobutylmethyl)-3-oxomorpholin-2-yl)acetate

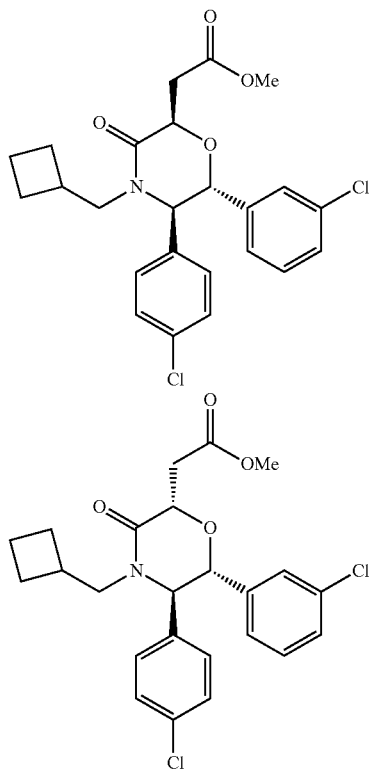

The title compounds were prepared as a mixture of stereoisomers from methyl 2-((2R,5R,6R)-6-(3-chlorophenyl)-5-(4-chlorophenyl)-3-oxomorpholin-2-yl)acetate and methyl 2-((2S,5R,6R)-6-(3-chlorophenyl)-5-(4-chlorophenyl)-3-oxomorpholin-2-yl)acetate (Example 30, Step B) by a procedure analogous to the one described in Example 30, Step C, replacing sodium hydride and tert-butyl 2-bromobutanoate with bromomethyl cyclobutane and $Cs_2CO_3$.

Step B. 2-((2R,5R,6R)-6-(3-Chlorophenyl)-5-(4-chlorophenyl)-4-(cyclobutylmethyl)-3-oxomorpholin-2-yl)acetic acid The title compound was obtained from methyl 2-((2R,5R,6R)-6-(3-chlorophenyl)-5-(4-chlorophenyl)-4-(cyclobutylmethyl)-3-oxomorpholin-2-yl)acetate and methyl 2-((2S,5R,6R)-6-(3-chlorophenyl)-5-(4-chlorophenyl)-4-(cyclobutylmethyl)-3-oxomorpholin-2-yl)acetate (Example 38, Step A) by a procedure similar to the one described in Example 36, Step B. Individual stereoisomers were separated by chiral HPLC (250×30 mm Chiralpak® IC column (Chiral Technologies, Inc., West Chester, Pa., USA) with 46 g/min ispropylamine+(20 µM $NH_3$)+84 g/min $CO_2$ on a Thar 350 SFC (Thar Technologies, Inc., Pittsburg, Pa.)) to give the title compound as the first eluting isomer. $^1$H NMR (400 MHz, $CDCl_3$) δ ppm 0.84-0.94 (m, 1 H), 1.50-1.96 (m, 2 H), 2.02-2.15 (m, 1 H), 2.59-2.68 (m, 1 H), 2.94 (dd, J=16.1, 6.7 Hz, 1 H), 3.00 (dd, J=16.0, 6.8 Hz, 1 H), 3.16 (dd, J=16.0, 6.0 Hz, 1 H), 4.04 (dd, J=13.9, 8.5 Hz, 1 H), 4.58 (d, J=9.6 Hz, 1 H), 3.39-3.51 (m, 1 H), 4.12-4.18 (m, 1 H), 4.55 (t, J=6.5 Hz, 1 H), 4.75 (d, J=4.1 Hz, 1H), 4.83 (d, J=4.1 Hz, 1H), 7.05-7.13 (m, 3 H), 7.27-7.36 (m, 5 H), 9.43 (brs, 1 H). Mass Spectrum (ESI) m/z=448 (M+1).

Example 39

2-((2S,5R,6R)-6-(3-chlorophenyl)-5-(4-chlorophenyl)-4-(cyclobutylmethyl)-3-oxomorpholin-2-yl)acetic acid

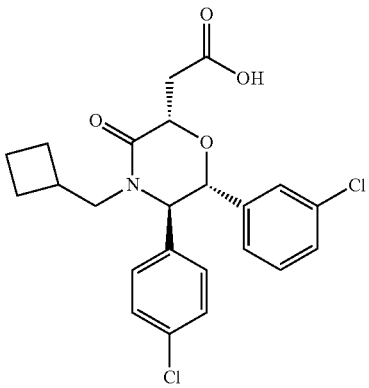 [SMILES: O=C(O)C[C@@H]1O[C@H](c2cccc(Cl)c2)[C@@H](c2ccc(Cl)cc2)N(CC2CCC2)C1=O]

The title compound was obtained as the second eluting isomer from Example 38, Step B.

$^1$H NMR (400 MHz, $CDCl_3$) δ ppm 1.50-1.66 (m, 2 H), 1.73-1.88 (m, 2 H), 1.96 (brs, 1 H), 2.42-2.51 (m, 2 H), 2.81-2.86 (m, 2 H), 3.10-3.16 (m, 1 H), 4.10-4.13 (m, 1 H), 4.46 (d, J=9.4 Hz, 1 H), 4.53 (d, J=9.4 Hz, 1 H), 4.81 (brs, 1 H), 6.63 (d, J=7.6 Hz, 1H), 6.89 (d, J=8.4 Hz, 1H), 7.07 (t, J=7.8 Hz, 1H), 7.11 (brs, 1 H), 7.07-7.08 (m, 1 H), 7.20-7.23 (m, 1H), 7.26-7.28 (m, 3 H). Mass Spectrum (ESI) m/z=448 (M+1).

Example 40

2-((2S,5R,6R)-4-Butyl-6-(3-chlorophenyl)-5-(4-chlorophenyl)-3-oxomorpholin-2-yl)acetic acid

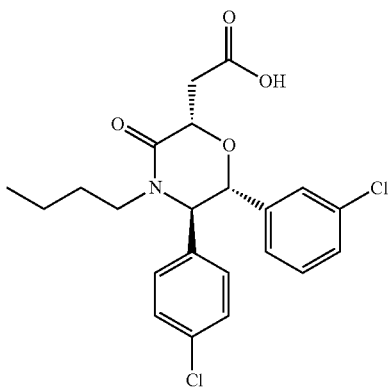 [SMILES: CCCCN1C(=O)[C@H](CC(=O)O)O[C@H](c2cccc(Cl)c2)[C@H]1c1ccc(Cl)cc1]

Step A. tert-Butyl 2-((2S,5R,6R)-4-butyl-6-(3-chlorophenyl)-5-(4-chlorophenyl)-3-oxomorpholin-2-yl)acetate

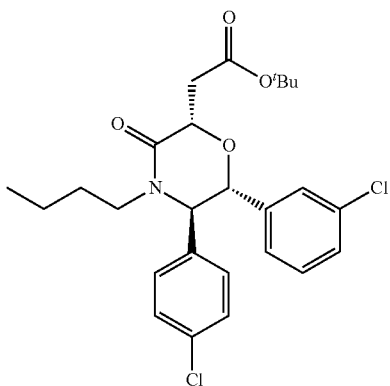 [SMILES: CCCCN1C(=O)[C@H](CC(=O)OC(C)(C)C)O[C@H](c2cccc(Cl)c2)[C@H]1c1ccc(Cl)cc1]

To a stirring solution of tert-butyl 2-((2S,5R,6R)-6-(3-chlorophenyl)-5-(4-chlorophenyl)-3-oxomorpholin-2-yl)acetate (75.0 mg, 0.172 mmol; Example 34, Step C) dissolved in 430 µL of DMF was added caesium carbonate (280 mg, 0.859 mmol) at rt. The reaction was stirred at rt for another 15 min and was then treated with 1-iodobutane (157 µL, 1.375 mmol). After being stirred at rt for 14 h, the reaction was quenched with sat. aq. NaHCO$_3$ solution and extracted with EtOAc (2×). The combined organic layers were washed with sat. aq. NaCl solution, dried over Na$_2$SO$_4$, filtered and the filtrate was concentrated under reduced pressure. Purification of the residue by flash chromatography on silica gel (eluent: 0 to 40% EtOAc in hexanes, gradient elution) provided the title compound as a colorless solid.

Step B. 2-((2S,5R,6R)-4-Butyl-6-(3-chlorophenyl)-5-(4-chlorophenyl)-3-oxomorpholin-2-yl)acetic acid To a stirring solution of tert-butyl 2-((2S,5R,6R)-4-butyl-6-(3-chlorophenyl)-5-(4-chlorophenyl)-3-oxomorpholin-2-yl)acetate (45.0 mg, 0.091 mmol; Example 40, Step A) dissolved in 920 µL of dichloromethane at rt was added 2,2,2-trifluoroacetic acid (305 µL, 0.091 mmol). After being stirred at rt for 4 h, the reaction was quenched (water) and extracted with EtOAc (2×). The combined organic layers were washed with sat. aq. NaCl solution, dried over Na$_2$SO$_4$, filtered and the filtrate was concentrated under reduced pressure. Purification of the residue by silica gel prep. plate (5% MeOH/DCM) provided the title compound as a white solid. $^1$H NMR (400 MHz, CDCl$_3$) δ ppm 0.82 (t, J=1.00 Hz, 3 H), 1.10-1.25 (m, 2 H), 1.36-1.48 (m, 2 H), 2.47 (ddd, J=13.99, 8.31, 6.06 Hz, 1 H), 2.98-3.10 (m, 1 H), 3.10-3.21 (m, 1 H), 3.86-3.98 (m, 1 H), 4.50-4.57 (m, 1 H), 4.58-4.64 (m, 1 H), 4.76 (t, J=5.38 Hz, 1 H), 6.70 (d, J=7.63 Hz, 1 H), 6.92 (d, J=8.41 Hz, 2 H), 7.08 (m, 1 H), 7.09-7.13 (m, 1 H), 7.20-7.25 (m, 1 H), 7.28 (d, J=8.41 Hz, 2 H). MS (ESI) m/z=436.1 [M+1].

EXAMPLES 41-49 were also prepared from tert-butyl 2-((2S,5R,6R)-6-(3-chlorophenyl)-5-(4-chlorophenyl)-3-oxomorpholin-2-yl)acetate (Example 34, Step C) by a procedure analogous to the one described in Example 40, replacing 1-iodobutane in Step A with the appropriate reagent.

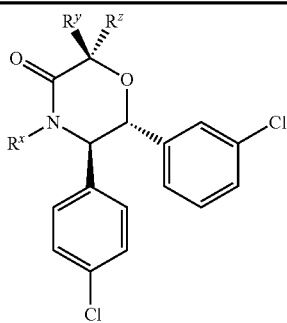

| Example | R$^x$ | R$^y$ | R$^z$ | Reagent used in step A |
|---|---|---|---|---|
| 41 | cyclohexylmethyl | H | CH$_2$COOH | (iodomethyl)cyclohexane |

-continued

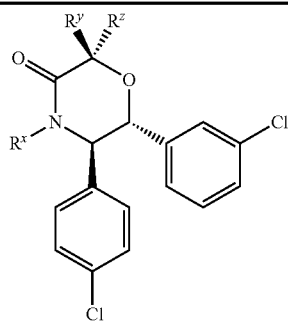

| Example | R$^x$ | R$^y$ | R$^z$ | Reagent used in step A |
|---|---|---|---|---|
| 42 | benzyl | H | CH$_2$COOH | benzylbromide |
| 43 | oxazol-2-ylmethyl | H | CH$_2$COOH | 2-chloromethyloxazole |
| 44 | Et | CH$_2$COOH | H | iodoethane |
| 45 | Et | H | CH$_2$COOH | iodoethane |
| 46 | allyl | CH$_2$COOH | H | allylbromide |
| 47 | allyl | H | CH$_2$COOH | allylbromide |
| 48 | n-propyl | CH$_2$COOH | H | 1-bromopropane |
| 49 | n-propyl | H | CH$_2$COOH | 1-bromopropane |

Example 41

2-((2S,5R,6R)-6-(3-Chlorophenyl)-5-(4-chlorophenyl)-4-(cyclohexylmethyl)-3-oxomorpholin-2-yl)acetic acid $^1$H NMR (500 MHz, CDCl$_3$) δ ppm 0.79-0.90 (m, 2 H), 1.10-1.26 (m, 3 H), 1.51 (d, J=13.94 Hz, 1 H), 1.57 (ddd, J=11.07, 6.42, 3.06 Hz, 1 H), 1.65 (m, 3 H), 1.70-1.76 (m, 1 H), 2.24 (dd, J=13.94, 6.36 Hz, 1 H), 3.00 (dd, J=16.26, 5.26 Hz, 1 H), 3.19 (dd, J=16.26, 6.24 Hz, 1 H), 3.90 (dd, J=13.94, 8.31 Hz, 1 H), 4.49-4.55 (m, 1 H), 4.56-4.61 (m, 1 H), 4.76 (t, J=5.87 Hz, 1 H), 6.69 (d, J=7.83 Hz, 1 H), 6.90 (d, J=8.31 Hz, 2 H), 7.09 (s, 1 H), 7.12 (t, J=7.83 Hz, 1 H), 7.23-7.26 (m, 1 H), 7.29 (d, J=8.56 Hz, 2 H). MS (ESI) m/z=476.1 [M+H]$^+$.

Example 42

2-((2S,5R,6R)-4-Benzyl-6-(3-chlorophenyl)-5-(4-chlorophenyl)-3-oxomorpholin-2-yl)acetic acid $^1$H NMR (400 MHz, CDCl$_3$) δ ppm 3.08-3.18 (m, 1 H), 3.20-3.29 (m, 1 H), 3.50 (d, J=14.67 Hz, 1 H), 4.36 (d, J=9.78 Hz, 1 H), 4.66 (d, J=9.78 Hz, 1 H), 4.86 (t, J=5.48 Hz, 1 H), 5.48 (d, J=14.67 Hz, 1 H), 6.63 (d, J=7.82 Hz, 1 H), 6.80 (d, J=8.41 Hz, 2 H), 6.98 (t, J=1.76 Hz, 1 H), 6.99-7.02 (m, 2 H), 7.05 (dd, J=7.92 Hz, 1 H), 7.18 (ddd, J=8.02, 1.96, 0.98 Hz, 1 H), 7.26 (d, J=5.09 Hz, 2 H), 7.27-7.30 (m, 3 H). MS (ESI) m/z=492.1 [M+Na].

Example 43

2-((2S,5R,6R)-6-(3-Chlorophenyl)-5-(4-chlorophenyl)-4-(oxazol-2-ylmethyl)-3-oxomorpholin-2-yl)acetic acid $^1$H NMR (400 MHz, CDCl$_3$) δ ppm 3.03-3.13 (m, 1 H), 3.15-3.24 (m, 1 H), 3.94 (d, J=16.04 Hz, 1 H), 4.69-4.78 (m, 2 H), 4.88 (t, J=5.38 Hz, 1 H), 5.13 (d, J=16.04 Hz, 1 H), 6.72 (d, J=7.63 Hz, 1 H), 6.92 (d, J=8.22 Hz, 2 H), 7.03 (s, 1 H), 7.05-7.09 (m, 1 H), 7.10 (s, 1 H), 7.18-7.22 (m, 1 H), 7.25 (d, J=8.41 Hz, 2 H), 7.56 (s, 1 H). MS (ESI) m/z=483.1 [M+Na].

Example 44

2-((2R,5R,6R)-6-(3-Chlorophenyl)-5-(4-chlorophenyl)-4-ethyl-3-oxomorpholin-2-yl)acetic acid $^1$H NMR (400 MHz, CDCl$_3$) δ ppm 1.15 (t, J=6.97 Hz, 3 H) 2.79 (dd, J=13.69, 6.85 Hz, 1 H) 2.90-3.09 (m, 1 H) 3.09-3.20 (m, 1 H) 3.99 (dd, J=13.69, 7.09 Hz, 1 H) 4.56-4.71 (m, 1 H) 4.77 (d, J=4.65 Hz, 1 H) 4.87 (d, J=4.65 Hz, 1 H) 7.03 (d, J=7.09 Hz, 1 H) 7.12 (d, J=8.07 Hz, 2 H) 7.20-7.39 (m, 5 H) 7.66 (br. s., 1 H). Mass Spectrum (ESI) m/z=408 (M+1).

Example 45

2-((2S,5R,6R)-6-(3-Chlorophenyl)-5-(4-chlorophenyl)-4-ethyl-3-oxomorpholin-2-yl)acetic acid $^1$H NMR (400 MHz, CDCl$_3$) δ ppm 1.03 (t, J=7.09 Hz, 3 H) 2.68 (dq, J=13.88, 6.79 Hz, 1 H) 3.06-3.27 (m, 2 H) 3.86-4.02 (m, 1 H) 4.54-4.72 (m, 2 H) 4.78 (t, J=4.65 Hz, 1 H) 6.64-6.79 (m, 1 H) 6.95 (d, J=8.31 Hz, 2 H) 7.03-7.17 (m, 2 H) 7.20-7.36 (m, 3 H) 10.33 (br. s., 1 H). Mass Spectrum (ESI) m/z=408 (M+1).

Example 46

2-((2R,5R,6R)-4-Allyl-6-(3-chlorophenyl)-5-(4-chlorophenyl)-3-oxomorpholin-2-yl)acetic acid $^1$H NMR (400 MHz, CDCl$_3$) δ ppm 2.90-3.12 (m, 3 H) 4.54 (t, J=5.87 Hz, 1 H) 4.63-4.75 (m, 2 H) 4.80 (d, J=4.40 Hz, 1 H) 4.99 (d, J=16.87 Hz, 1 H) 5.20 (d, J=10.03 Hz, 1 H) 5.63-5.75 (m, 1 H) 6.94 (d, J=7.58 Hz, 1 H) 7.01 (d, J=8.31 Hz, 2 H) 7.12-7.32 (m, 5 H) 9.15 (br. s., 1 H). Mass Spectrum (ESI) m/z=420 (M+1).

Example 47

2-((2S,5R,6R)-4-Allyl-6-(3-chlorophenyl)-5-(4-chlorophenyl)-3-oxomorpholin-2-yl)acetic acid $^1$H NMR (400 MHz, CDCl$_3$) δ ppm 3.02-3.23 (m, 3 H) 4.55-4.75 (m, 3 H) 4.82 (t, J=4.77 Hz, 1 H) 4.93 (d, J=20 Hz, 1 H) 5.17 (d, J=10.27 Hz, 1 H) 5.58-5.79 (m, 1 H) 6.64-6.80 (m, 1 H) 6.92 (d, J=8.31 Hz, 2 H) 7.02-7.18 (m, 2 H) 7.20-7.37 (m, 3 H) 10.11 (br. s., 1 H). Mass Spectrum (ESI) m/z=420 (M+1).

Example 48

2-((2R,5R,6R)-6-(3-Chlorophenyl)-5-(4-chlorophenyl)-3-oxo-4-propylmorpholin-2-yl)acetic acid $^1$H NMR (400 MHz, CDCl$_3$) δ ppm 0.78 (t, J=7.34 Hz, 3 H) 1.43-1.56 (m, 2 H) 2.54 (ddd, J=13.84, 8.85, 5.48 Hz, 1 H) 2.90 (dd, J=16.04, 7.24 Hz, 1 H) 3.08 (dd, J=16.24, 5.48 Hz, 1 H) 3.83 (ddd, J=13.55, 9.34, 7.04 Hz, 1 H) 4.56 (dd, J=6.94, 5.77 Hz, 1 H) 4.67 (d, J=4.89 Hz, 1 H) 4.77 (d, J=4.89 Hz, 1 H) 6.93-7.04 (m, 3 H) 7.15-7.29 (m, 5 H). Mass Spectrum (ESI) m/z=422 (M+1).

Example 49

2-((2S,5R,6R)-6-(3-Chlorophenyl)-5-(4-chlorophenyl)-3-oxo-4-propylmorpholin-2-yl)acetic acid $^1$H NMR (400 MHz, CDCl$_3$) δ ppm 0.71 (t, J=7.34 Hz, 3 H) 1.28-1.47 (m, 2 H) 2.39 (ddd, J=13.79, 8.90, 5.28 Hz, 1 H) 3.03 (qd, J=16.82, 5.28 Hz, 2 H) 3.80 (ddd, J=13.74, 9.15, 6.85 Hz, 1 H) 4.44-4.57 (m, 2 H) 4.68 (t, J=5.38 Hz, 1 H) 6.63 (d, J=7.63 Hz, 1 H) 6.84 (d, J=8.41 Hz, 2 H) 6.94-7.10 (m, 2 H) 7.10-7.31 (m, 3 H). Mass Spectrum (ESI) m/z=422 (M+1).

Example 50

(2S,5R,6R)-6-(3-Chlorophenyl)-5-(4-chlorophenyl)-4-(cyclopropylmethyl)-2-((tetrazol-5-yl)methyl)morpholin-3-one and (2R,5R,6R)-6-(3-Chlorophenyl)-5-(4-chlorophenyl)-4-(cyclopropylmethyl)-2-((tetrazol-5-yl)methyl)morpholin-3-one

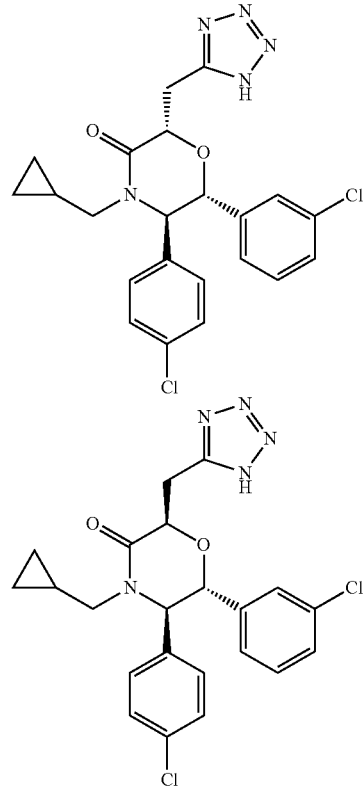

Step A. (1R,2R)-1-(3-Chlorophenyl)-2-(4-chlorophenyl)-2-(cyclopropylmethylamino)ethanol and (1S,2S)-1-(3-Chlorophenyl)-2-(4-chlorophenyl)-2-(cyclopropylmethylamino)ethanol

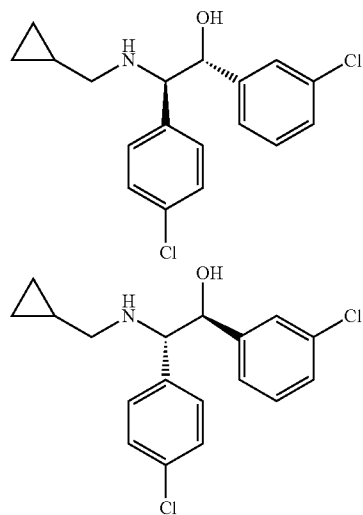

The title compounds were prepared from the racemic mixture of (1R,2R)-2-amino-1-(3-chlorophenyl)-2-(4-chlorophenyl)ethanol and (1S,2S)-2-amino-1-(3-chlorophenyl)-2-(4-chlorophenyl)ethanol (Intermediate A1) using a procedure analogous to the one described in Example 9, Step B.

Step B. tert-Butyl 2-((2R,5R,6R)-6-(3-chlorophenyl)-5-(4-chlorophenyl)-4-(cyclopropylmethyl)-3-oxomorpholin-2-yl)acetate and tert-Butyl 2-((2S,5R,6R)-6-(3-chlorophenyl)-5-(4-chlorophenyl)-4-(cyclopropylmethyl)-3-oxomorpholin-2-yl)acetate and tert-Butyl 2-((2R,5S,6S)-6-(3-chlorophenyl)-5-(4-chlorophenyl)-4-(cyclopropylmethyl)-3-oxomorpholin-2-yl)acetate and tert-Butyl 2-((2S,5S,6S)-6-(3-chlorophenyl)-5-(4-chlorophenyl)-4-(cyclopropylmethyl)-3-oxomorpholin-2-yl)acetate

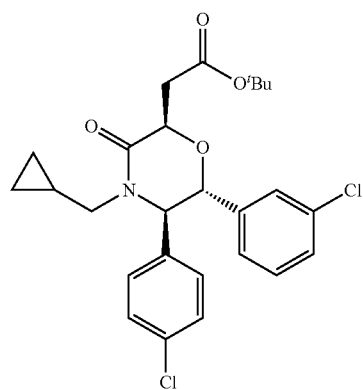

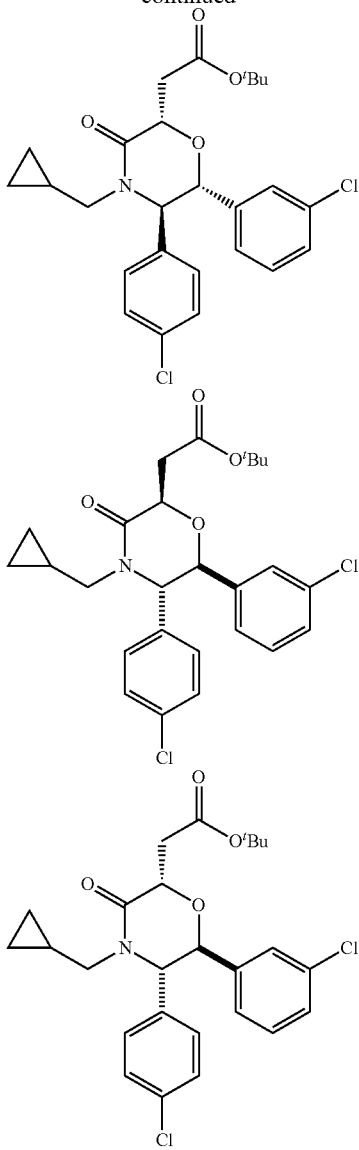

To a solution of (1R,2R)-1-(3-chlorophenyl)-2-(4-chlorophenyl)-2-(cyclopropylmethylamino)ethanol and (1S,2S)-1-(3-chlorophenyl)-2-(4-chlorophenyl)-2-(cyclopropylmethylamino)ethanol (82 mg, 0.244 mmol; Example 50, Step A) in THF (2 mL) at rt was added a dispersion of 60% sodium hydride in mineral oil (10 mg, 268 μmol). Evolution of gas was observed and the reaction mixture turned light yellow in color. The reaction mixture was stirred at rt for 0.5 h Then a solution of (S)-4-tert-butyl-1-methyl-2-bromosuccinate (65 mg, 0.244 mmol; Example 9, Step A) in THF (1 mL) was added dropwise over 5 min. The orange slurry was stirred at rt overnight. The mixture was quenched with water and extracted with EtOAc (3×). The combined organic layers were dried over Na$_2$SO$_4$ and concentrated. The residue was purified by flash chromatography on silica gel (4 g column; eluent: 0 to 25% EtOAc in hexanes) to provide the title compounds Step C. 2-((2R,5R,6R)-6-(3-chlorophenyl)-5-(4-chlorophenyl)-4-(cyclopropylmethyl)-3-oxomorpholin-2-yl)acetic acid and 2-((2S,5R,6R)-6-(3-chlorophenyl)-5-(4-chlorophenyl)-4-(cyclopropylmethyl)-3-oxomorpholin-2-yl)acetic acid and 2-((2R,5S,6S)-6-(3-chlorophenyl)-5-(4-chlorophenyl)-4-(cyclopropylmethyl)-3-oxomorpholin-2-yl)acetic acid and 2-((2S,5S,6S)-6-(3-chlorophenyl)-5-(4-chlorophenyl)-4-(cyclopropylmethyl)-3-oxomorpholin-2-yl)acetic acid

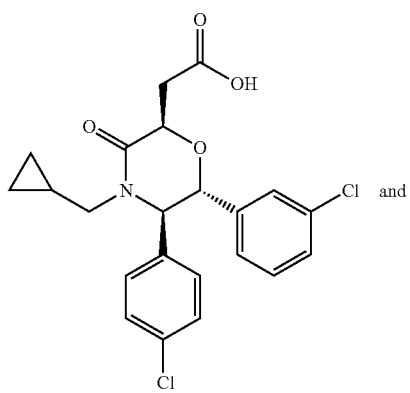 and

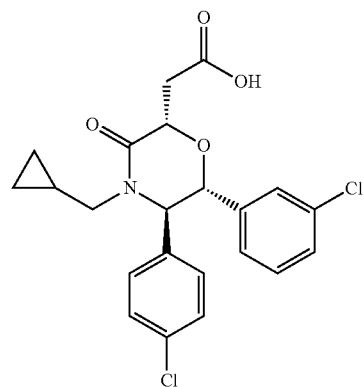

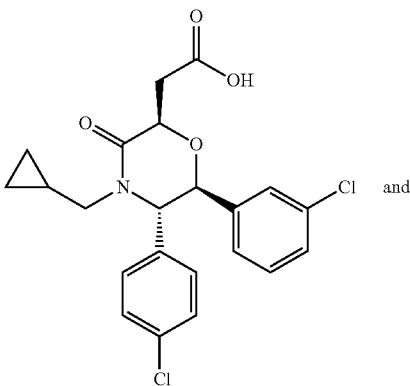 and

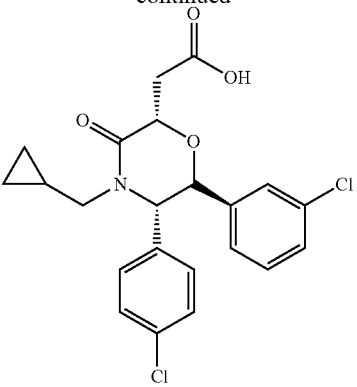

The title compounds were prepared from tert-Butyl 2-((2R,5R,6R)-6-(3-chlorophenyl)-5-(4-chlorophenyl)-4-(cyclopropylmethyl)-3-oxomorpholin-2-yl)acetate and tert-Butyl 2-((2S,5R,6R)-6-(3-chlorophenyl)-5-(4-chlorophenyl)-4-(cyclopropylmethyl)-3-oxomorpholin-2-yl)acetate and tert-Butyl 2-((2R,5S,6S)-6-(3-chlorophenyl)-5-(4-chlorophenyl)-4-(cyclopropylmethyl)-3-oxomorpholin-2-yl)acetate and tert-Butyl 2-((2S,5S,6S)-6-(3-chlorophenyl)-5-(4-chlorophenyl)-4-(cyclopropylmethyl)-3-oxomorpholin-2-yl)acetate (Example 46, step B) by a procedure analogous to the one described in Example 9, Step E.

Step D. Methyl 2-((2S,5R,6R)-6-(3-chlorophenyl)-5-(4-chlorophenyl)-4-(cyclopropylmethyl)-3-oxomorpholin-2-yl)acetate and methyl 2-((2R,5R,6R)-6-(3-chlorophenyl)-5-(4-chlorophenyl)-4-(cyclopropylmethyl)-3-oxomorpholin-2-yl)acetate and methyl 2-((2S,5S,6S)-6-(3-chlorophenyl)-5-(4-chlorophenyl)-4-(cyclopropylmethyl)-3-oxomorpholin-2-yl)acetate and methyl 2-((2R,5S,6S)-6-(3-chlorophenyl)-5-(4-chlorophenyl)-4-(cyclopropylmethyl)-3-oxomorpholin-2-yl)acetate

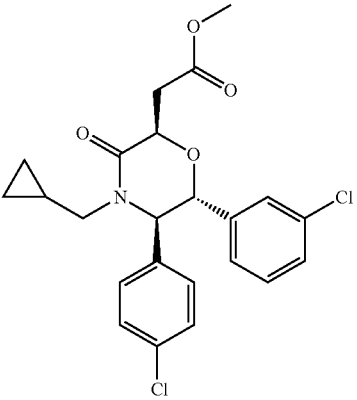

-continued

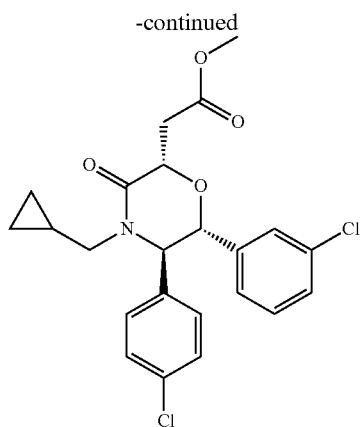

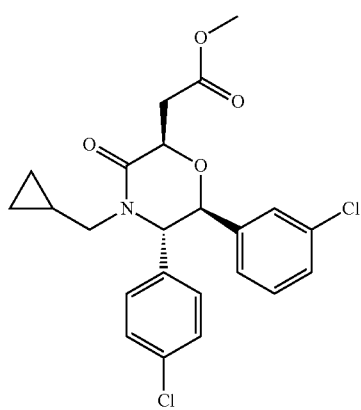

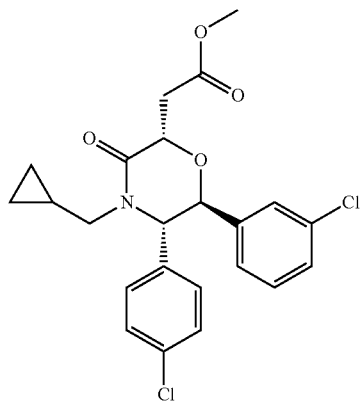

To a solution of 2-((2S,5S,6S)-6-(3-chlorophenyl)-5-(4-chlorophenyl)-4-(cyclopropylmethyl)-3-oxomorpholin-2-yl)acetic acid and 2-((2R,5S,6S)-6-(3-chlorophenyl)-5-(4-chlorophenyl)-4-(cyclopropylmethyl)-3-oxomorpholin-2-yl)acetic acid and 2-((2R,5R,6R)-6-(3-chlorophenyl)-5-(4-chlorophenyl)-4-(cyclopropylmethyl)-3-oxomorpholin-2-yl)acetic acid and 2-((2S,5R,6R)-6-(3-chlorophenyl)-5-(4-chlorophenyl)-4-(cyclopropylmethyl)-3-oxomorpholin-2-yl)acetic acid (81 mg, 187 µmol; Example 50, Step C) in 1 mL of MeOH and 2 mL of DCM at 0° C. was added (trimethylsilyl)diazomethane (2.0 M in diethyl ether (187 µl, 373 µmol)) dropwise. Evolution of gas was observed. The yellow reaction mixture was stirred at 0° C. for 15 min. The reaction mixture was warmed to rt and concentrated under reduced pressure. The residue was purified by flash chromatography on silica gel (eluent: 0 to 20% EtOAc in hexanes, gradient elution) to give the title compounds as a mixture of stereoisomers.

Step E. 2-((2S,5R,6R)-6-(3-chlorophenyl)-5-(4-chlorophenyl)-4-(cyclopropylmethyl)-3-oxomorpholin-2-yl)acetamide and 2-((2R,5R,6R)-6-(3-chlorophenyl)-5-(4-chlorophenyl)-4-(cyclopropylmethyl)-3-oxomorpholin-2-yl)acetamide and 2-((2R,5S,6S)-6-(3-chlorophenyl)-5-(4-chlorophenyl)-4-(cyclopropylmethyl)-3-oxomorpholin-2-yl)acetamide and 2-((2S,5S,6S)-6-(3-chlorophenyl)-5-(4-chlorophenyl)-4-(cyclopropylmethyl)-3-oxomorpholin-2-yl)acetamide

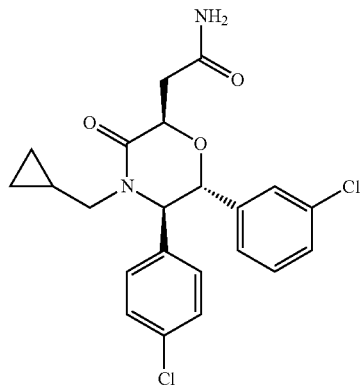

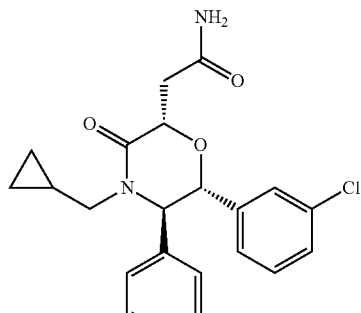

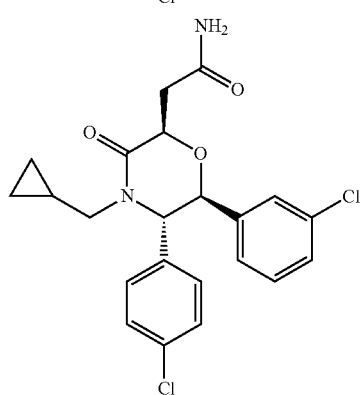

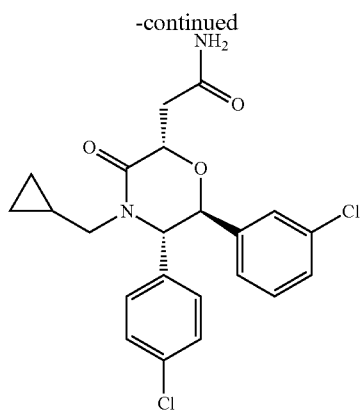

To a solution of methyl 2-((2S,5S,6S)-6-(3-chlorophenyl)-5-(4-chlorophenyl)-4-(cyclopropylmethyl)-3-oxomorpholin-2-yl)acetate and methyl 2-((2R,5S,6S)-6-(3-chlorophenyl)-5-(4-chlorophenyl)-4-(cyclopropylmethyl)-3-oxomorpholin-2-yl)acetate and methyl 2-((2R,5R,6R)-6-(3-chlorophenyl)-5-(4-chlorophenyl)-4-(cyclopropylmethyl)-3-oxomorpholin-2-yl)acetate and methyl 2-((2S,5R,6R)-6-(3-chlorophenyl)-5-(4-chlorophenyl)-4-(cyclopropylmethyl)-3-oxomorpholin-2-yl)acetate (56 mg, 125 μmol; Example 50, Step D) in 2M $NH_3$ in MeOH (1 mL) was added sodium cyanide (0.61 mg, 12 μmol). The reaction mixture was capped and heated to 50° C. for 7 h. The reaction mixture was cooled to rt and saturated with $NH_3$ (g) for 1 min. The reaction mixture was capped and heated to 50° C. for 16 h. Again, the reaction mixture was cooled to rt and saturated with $NH_3$ (g) for 1 min. This process was repeated (3×). Then the reaction was concentrated under reduced pressure and the crude product was used without further purification.

Step F. 2-((2S,5R,6R)-6-(3-chlorophenyl)-5-(4-chlorophenyl)-4-(cyclopropylmethyl)-3-oxomorpholin-2-yl)acetonitrile and 2-((2R,5R,6R)-6-(3-chlorophenyl)-5-(4-chlorophenyl)-4-(cyclopropylmethyl)-3-oxomorpholin-2-yl)acetonitrile and 2-((2R,5S,6S)-6-(3-chlorophenyl)-5-(4-chlorophenyl)-4-(cyclopropylmethyl)-3-oxomorpholin-2-yl)acetonitrile and 2-((2S,5S,6S)-6-(3-chlorophenyl)-5-(4-chlorophenyl)-4-(cyclopropylmethyl)-3-oxomorpholin-2-yl)acetonitrile

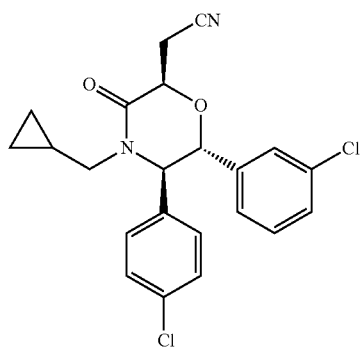

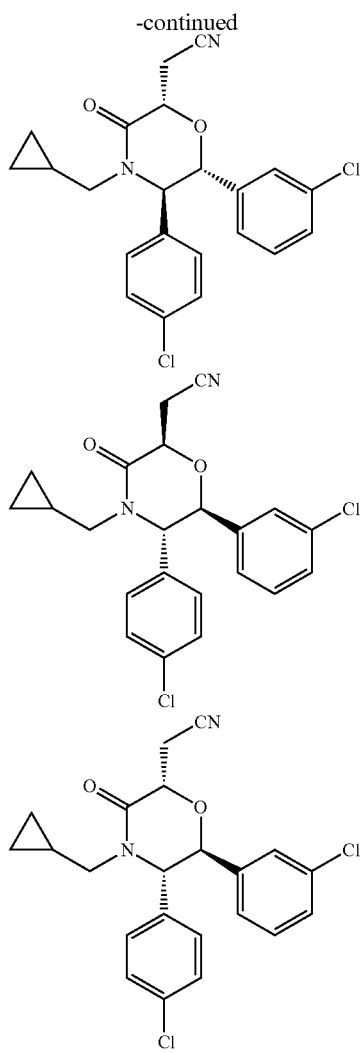

To a solution of 2-((2S,5S,6S)-6-(3-chlorophenyl)-5-(4-chlorophenyl)-4-(cyclopropylmethyl)-3-oxomorpholin-2-yl)acetamide and 2-((2R,5S,6S)-6-(3-chlorophenyl)-5-(4-chlorophenyl)-4-(cyclopropylmethyl)-3-oxomorpholin-2-yl)acetamide and 2-((2R,5R,6R)-6-(3-chlorophenyl)-5-(4-chlorophenyl)-4-(cyclopropylmethyl)-3-oxomorpholin-2-yl)acetamide and 2-((2S,5R,6R)-6-(3-chlorophenyl)-5-(4-chlorophenyl)-4-(cyclopropylmethyl)-3-oxomorpholin-2-yl)acetamide (54 mg, 125 μmol; Example 50, Step E) in THF (1 mL) at 0° C. was added triethylamine (87 μl, 623 μmol) followed by trifluoroacetic acid anhydride (44 μl, 312 μmol). The light orange reaction mixture was stirred at 0° C. for 90 min. The reaction mixture was quenched with 10% aq. citric acid solution and extracted with EtOAc (2×). The organic layers were combined and washed with brine. The organic layers were dried over $Na_2SO_4$ and concentrated under reduced pressure. The crude residue was used without further purification.

Step G. (2S,5R,6R)-2-((2H-Tetrazol-5-yl)methyl)-6-(3-chlorophenyl)-5-(4-chlorophenyl)-4-(cyclopropylmethyl)morpholin-3-one and (2R,5R,6R)-2-((2H-Tetrazol-5-yl)methyl)-6-(3-chlorophenyl)-5-(4-chlorophenyl)-4-(cyclopropylmethyl)morpholin-3-one To a solution of 2-((2R,5S,6S)-6-(3-chlorophenyl)-5-(4-chlorophenyl)-4-(cyclopropylmethyl)-3-oxomorpholin-2- yl)acetonitrile and 2-((2S,5S,6S)-6-(3-chlorophenyl)-5-(4-chlorophenyl)-4-(cyclopropylmethyl)-3-oxomorpholin-2-yl)acetonitrile and 2-((2S,5R,6R)-6-(3-chlorophenyl)-5-(4-chlorophenyl)-4-(cyclopropylmethyl)-3-oxomorpholin-2-yl)acetonitrile and 2-((2R,5R,6R)-6-(3-chlorophenyl)-5-(4-chlorophenyl)-4-(cyclopropylmethyl)-3-oxomorpholin-2-yl)acetonitrile (21 mg, 51 µmol; Example 50, Step F) in dioxane (1 mL) at rt was added azidotributyltin (139 µl, 506 µmol). The reaction mixture was heated to 100° C. for 2 d, cooled to rt and diluted with 3 mL of 10% aq. citric acid solution. The reaction mixture was stirred at rt for 10 min then extracted with EtOAc (3×). The organic layers were combined, dried over Na$_2$SO$_4$, filtered and the filtrate was concentrated under reduced pressure. The residue was purified by reverse phase preparatory HPLC (Gemini™ Prep C$_{18}$ 5 µm column; Phenomenex, Torrance, Calif.; eluent: (0 to 100% MeCN+0.1% TFA) in (water+0.1% TFA), gradient elution over 20 minutes). The residue was then purified on silica gel (eluent: EtOAc/hexanes/AcOH 7:3:0.1). Individual stereoisomers were separated by chiral SFC (flow rate: 12 mL/min; 250×30 mm Chiralpak® AD-H column (Chiral Technologies, Inc., West Chester, Pa., USA) using methanol (0.2% DEA)/CO$_2$ as the eluent on a Thar 350 SFC, Thar Technologies, Inc., Pittsburg, Pa.). The enantiopure material obtained was then further purified by flash chromatography on silica gel (eluent: EtOAc/hexanes/AcOH 7:3:0.1) to give the title compound. $^1$H NMR (400 MHz, CDCl$_3$) δ ppm –0.07 to –0.01 (m, 1 H), 0.00-0.10 (m, 1 H), 0.37-0.54 (m, 2 H), 0.69-0.80 (m, 1 H), 2.35 (dd, J=14.18, 7.34 Hz, 1 H), 3.61-3.77 (m, 2 H), 3.93 (dd, J=14.18, 6.75 Hz, 1 H), 4.61 (d, J=9.8 Hz, 1 H), 4.69-4.73 (m, 2 H), 6.76 (d, J=7.83 Hz, 1 H), 6.89 (d, J=8.41 Hz, 2 H), 7.09 (s, 1 H), 7.15 (t, J=7.83 Hz, 1 H), 7.24-7.33 (m, 3 H). Mass Spectrum (ESI) m/z=458 (M+1).

Example 51

(Z)-2-((5R,6R)-6-(3-Chlorophenyl)-5-(4-chlorophenyl)-4-(cyclopropylmethyl)-3-oxomorpholin-2-ylidene)acetic acid or (E)-2-((5R,6R)-6-(3-Chlorophenyl)-5-(4-chlorophenyl)-4-(cyclopropylmethyl)-3-oxomorpholin-2-ylidene)acetic acid (Isomer 1)

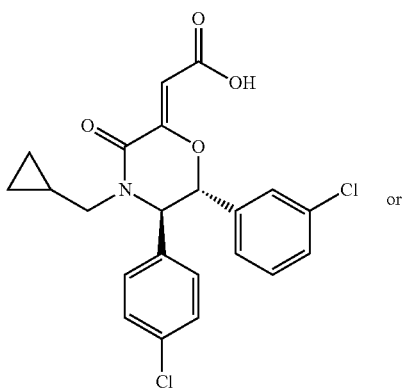

or

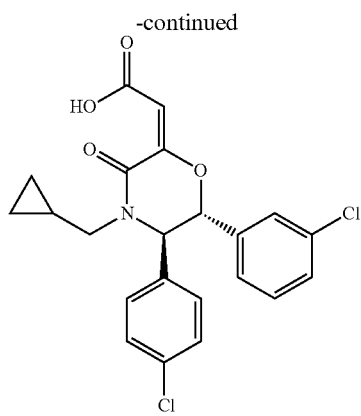

Step A. (5R,6R)-6-(3-Chlorophenyl)-5-(4-chlorophenyl)-4-(cyclopropylmethyl)morpholine-2,3-dione

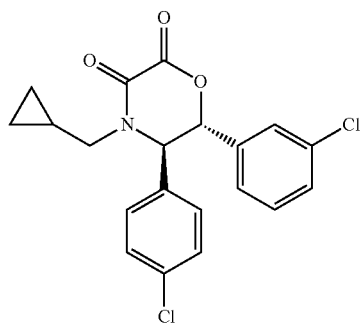 [SMILES: O=C1O[C@H](c2cccc(Cl)c2)[C@@H](c2ccc(Cl)cc2)N(CC2CC2)C1=O]

(1R,2R)-1-(3-chlorophenyl)-2-(4-chlorophenyl)-2-(cyclopropylmethylamino)ethanol (146 mg, 434 µmol; Example 9 step B) was dissolved in benzene (8684 µl, 434 µmol) then oxalyl chloride (110 µl, 1303 µmol) was added, followed by pyridine (106 µl, 1303 µmol). The reaction was stirred for 2 h. Then the reaction mixture was concentrated under reduced pressure. The residue was dissolved in DMF/MeOH and purified by reverse phase preparatory HPLC (Gemini™ Prep C18 5 µm column; Phenomenex, Torrance, Calif.; eluent: (0 to 100% MeCN in water, both containing 0.1% TFA, gradient elution over 20 minutes). The fractions containing the desired product were combined and concentrated to afford the title compound as a white solid. $^1$H NMR (400 MHz, CDCl$_3$) δ –0.07 (dt, J=9.68, 4.94 Hz, 0 H), 0.01 (dq, J=9.56, 4.77 Hz, 0 H), 0.15-0.24 (m, 1 H), 0.32 (s, 1 H), 0.53 (ddd, J=12.23, 7.43, 4.60 Hz, 0 H), 2.59 (dd, J=14.18, 7.53 Hz, 0 H), 5.01 (d, J=3.91 Hz, 1 H), 5.49 (d, J=3.72 Hz, 1 H), 6.98-7.12 (m, 3 H), 7.18-7.39 (m, 5 H). Mass Spectrum (ESI) m/z=390.1 (M+1).

161

Step B. (E)-tert-Butyl 2-((5R,6R)-6-(3-chlorophenyl)-5-(4-chlorophenyl)-4-(cyclopropylmethyl)-3-oxomorpholin-2-ylidene)acetate and (Z)-tert-Butyl 2-((5R,6R)-6-(3-chlorophenyl)-5-(4-chlorophenyl)-4-(cyclopropylmethyl)-3-oxomorpholin-2-ylidene)acetate

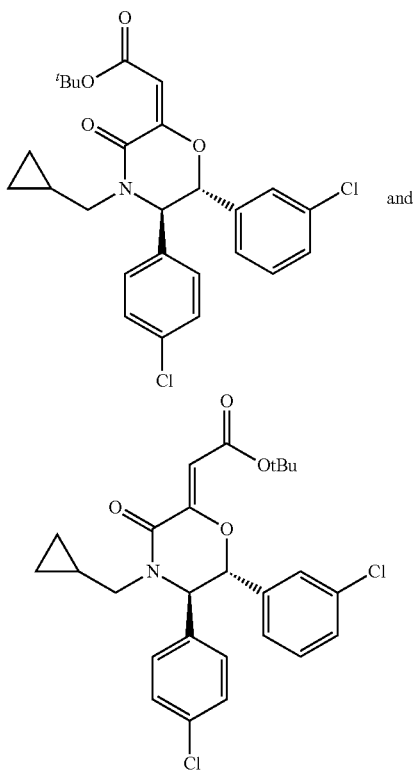

and (5R,6R)-6-(3-chlorophenyl)-5-(4-chlorophenyl)-4-(cyclopropylmethyl)morpholine-2,3-dione (50 mg, 129 μmol; Example 51, step A) was dissolved in 1 mL of DCM, then (tert-butoxycarbonylmethylene)triphenylphosphorane (68 mg, 181 μmol) was added. After 2 d the reaction mixture was concentrtaed and the residue was purified by flash chromatography on silica gel (eluent: linear gradient of 5% to 100% EtOAc/hexanes). The fractions containing the desired product were combined and concentrated to afford a mixture of the title compounds.

Step C. (Z)-2-((5R,6R)-6-(3-Chlorophenyl)-5-(4-chlorophenyl)-4-(cyclopropylmethyl)-3-oxomorpholin-2-ylidene)acetic acid or (E)-2-((5R,6R)-6-(3-Chlorophenyl)-5-(4-chlorophenyl)-4-(cyclopropylmethyl)-3-oxomorpholin-2-ylidene)acetic acid (Isomer 1)

To a solution of (E) and (Z)-tert-butyl 2-((5R,6R)-6-(3-chlorophenyl)-5-(4-chlorophenyl)-4-(cyclopropylmethyl)-3-oxomorpholin-2-ylidene)acetate (10 mg, 20 μmol; Example 51, Step B) in 1 mL of DCM was added 0.5 mL of TFA. After 2 h the reaction mixture was concentrated. The residue was dissolved in DMF and purified by reverse phase preparatory HPLC (Gemini™ Prep $C_{18}$ 5 μm column; Phe-

162 nomenex, Torrance, Calif.; eluent: (0 to 100% MeCN in water, both containing 0.1% TFA, gradient elution over 20 minutes). The fractions containing the desired product were combined and concentrated to afford one of the title compounds as the first eluting isomer. $^1$H NMR (400 MHz, CDCl$_3$) δ −0.08-0.03 (m, 1 H), 0.04-0.15 (m, 1 H), 0.24-0.33 (m, 1 H), 0.38-0.48 (m, 1 H), 0.60-0.72 (m, 1 H), 2.54 (dd, J=14.28, 7.63 Hz, 1 H), 3.85 (dd, J=14.09, 7.24 Hz, 1 H), 5.06 (d, J=3.52 Hz, 1 H), 5.33 (d, J=3.33 Hz, 1 H), 6.33 (s, 1 H), 7.03-7.39 (m, 8 H). Mass Spectrum (ESI) m/z=432.1 (M+1).

Example 52

(E)-2-((5R,6R)-6-(3-Chlorophenyl)-5-(4-chlorophenyl)-4-(cyclopropylmethyl)-3-oxomorpholin-2-ylidene)acetic acid or (Z)-2-((5R,6R)-6-(3-Chlorophenyl)-5-(4-chlorophenyl)-4-(cyclopropylmethyl)-3-oxomorpholin-2-ylidene)acetic acid (Isomer 2)

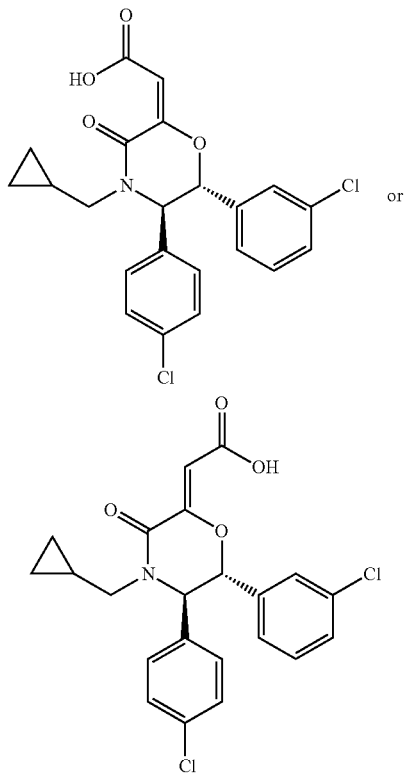

One of the title compounds was obtained as the second (slower) eluting isomer from Example 51, Step C. $^1$H NMR (400 MHz, CDCl$_3$) δ −0.13-0.07 (m, 2 H), 0.20-0.44 (m, 2 H), 0.57-0.77 (m, 1 H), 2.48 (dd, J=14.08, 7.63 Hz, 1 H), 3.78 (dd, J=14.18, 6.75 Hz, 1 H), 4.85 (s, 1 H), 4.98 (d, J=5.28 Hz, 1 H), 5.98 (s, 1 H), 6.81-6.98 (m, 2 H), 7.04-7.32 (m, 6 H). Mass Spectrum (ESI) m/z=432.1 (M+1).

Example 53

2-((2S,5R,6R)-6-(3-Chlorophenyl)-5-(4-chlorophenyl)-3-oxo-4-(pentan-3-yl)morpholin-2-yl)acetic acid

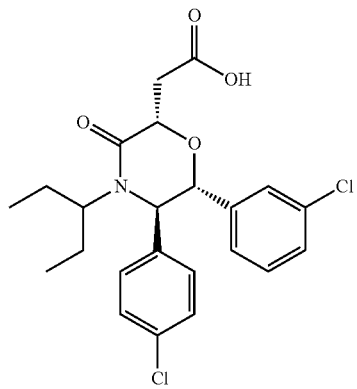 [SMILES: CCC(CC)N1C(=O)[C@H](CC(=O)O)O[C@H](c2cccc(Cl)c2)[C@H]1c1ccc(Cl)cc1]

Step A. (1R,2R)-1-(3-Chlorophenyl)-2-(4-chlorophenyl)-2-(pentan-3-ylamino)ethanol

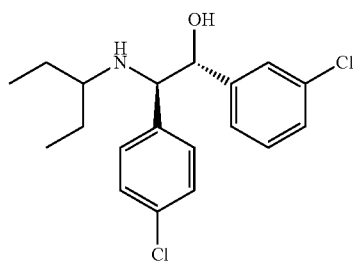 [SMILES: CCC(CC)N[C@H](c1ccc(Cl)cc1)[C@H](O)c1cccc(Cl)c1]

The title compound was prepared as described in Example 9, Step B, substituting cyclopropanecarboxaldehyde with pentan-3-one.

Step B. tert-Butyl 2-((5R,6R)-6-(3-chlorophenyl)-5-(4-chlorophenyl)-3-oxo-4-(pentan-3-yl)morpholin-2-ylidene)acetate and (Z)-2-((5R,6R)-6-(3-Chlorophenyl)-5-(4-chlorophenyl)-3-oxo-4-(pentan-3-yl)morpholin-2-ylidene)acetic acid

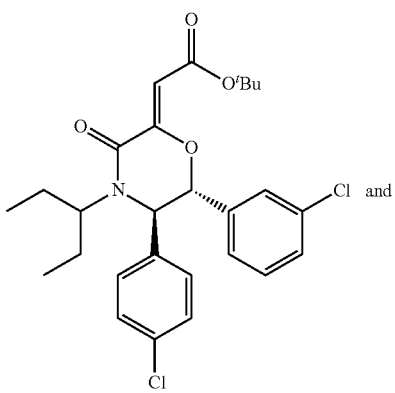 and 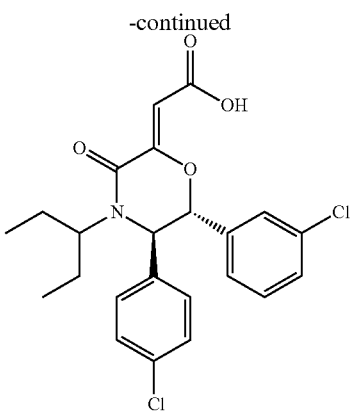

The title compound was obtained from (1R,2R)-1-(3-chlorophenyl)-2-(4-chlorophenyl)-2-(pentan-3-ylamino)ethanol (Example 53, Step A) by a procedure analogous to the one described in Example 51, Step A. Purification by chromatography on silica gel (eluent: 5 to 95% EtOAc in hexanes, gradient elution) provided a mixture of the title compounds. Mass Spectrum (ESI) m/z=504 (M+1, $^t$butyl ester) and m/z=448 (M+1, acid).

Step C. 2-((2S,5R,6R)-6-(3-Chlorophenyl)-5-(4-chlorophenyl)-3-oxo-4-(pentan-3-yl)morpholin-2-yl)acetic acid To a solution of 620 mg (1.23 mmol) of tert-butyl 2-((5R,6R)-6-(3-chlorophenyl)-5-(4-chlorophenyl)-3-oxo-4-(pentan-3-yl)morpholin-2-ylidene)acetate in 10 mL of methanol was added 70 mg of $PtO_2$. The reaction vessel was purged with hydrogen (g) and the reaction mixture was stirred under an atmosphere of $H_2$. After 24 h the reaction mixture was filtered through a 0.45 μm PTFE membrane and then concentrated under reduced pressure. To the residue was added 3 mL DCM followed by 1.0 mL TFA. The reaction was then stirred at room temperature for one hour and concentrated under reduced pressure. The residue was purified by HPLC (Gemini™ Prep $C_{18}$ 5 μm column; Phenomenex, Torrance, Calif.; 5 to 95% $CH_3CN$ (0.1% TFA): $H_2O$ (0.1% TFA) gradient) to give the title compound. $^1$H NMR (400 MHz, $CDCl_3$) δ ppm 0.66 (t, J=7.53 Hz, 3 H) 0.88-0.97 (m, 3 H) 1.36-1.46 (m, 1 H) 1.57-1.66 (m, 1 H) 1.75-1.92 (m, 2 H) 2.94-3.03 (m, 2 H) 3.19 (dd, J=16.14, 6.94 Hz, 1 H) 4.46 (d, J=9.59 Hz, 1 H) 4.66 (d, J=9.59 Hz, 1 H) 4.74 (dd, J=6.85, 4.70 Hz, 1 H) 6.70 (d, J=7.63 Hz, 1 H) 7.01-7.15 (m, 4 H) 7.23-7.34 (m, 3 H). Mass Spectrum (ESI) m/z=450 (M+1).

Examples 54 to 61 were also prepared by a procedure analogous to the one described in Example 9, Step B and Example 53, replacing (1R,2R)-2-amino-1-(3-chlorophenyl)-2-(4-chlorophenyl)ethanol (Intermediate A2) with the designated intermediates.

[Structure: morpholinone core with N-CH2-cyclopropyl, C=O, substituents R^y, R^z at one carbon, R^x at another, and 3-chlorophenyl group]

| Example | R^x | R^y | R^z | Intermediate used |
|---|---|---|---|---|
| 54 | 2-F,4-Cl-phenyl | H | -CH2-C(=O)OH | B1 |
| 55 | phenyl | H | -CH2-C(=O)OH | B2 |
| 56 | 4-F-phenyl | H | -CH2-C(=O)OH | B3 |
| 57 | 4-CF3-phenyl | H | -CH2-C(=O)OH | B4 |
| 58 | 4-Et-phenyl | H | -CH2-C(=O)OH | B5 |
| 59 | 4-OCF3-phenyl | H | -CH2-C(=O)OH | B6 |
| 60 | 4-CH3-phenyl | H | -CH2-C(=O)OH | B7 |

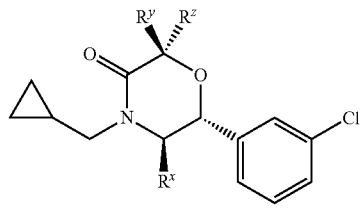

| Example | $R^x$ | $R^y$ | $R^z$ | Intermediate used |
|---|---|---|---|---|
| 61 | 4-methylphenyl | -CH₂C(O)OH | H | B7 |

Example 54

2-((2S,5R,6R)-5-(4-Chloro-2-fluorophenyl)-6-(3-chlorophenyl)-4-(cyclopropylmethyl)-3-oxomorpholin-2-yl)acetic acid $^1$H NMR (400 MHz, CDCl$_3$) δ ppm 0.03-0.09 (m, 2 H) 0.47 (dd, J=17.85, 8.07 Hz, 2 H) 0.85 (t, J=7.34 Hz, 1 H) 2.34 (dd, J=14.67, 7.34 Hz, 1 H) 3.06-3.20 (m, 2 H) 3.98 (dd, J=14.43, 6.60 Hz, 1 H) 4.70 (d, J=9.78 Hz, 1 H) 4.75 (t, J=5.14 Hz, 1 H) 5.10 (d, J=9.29 Hz, 1 H) 7.06-7.19 (m, 4 H) 7.25 (s, 1 H) 7.27 (s, 1 H). Mass Spectrum (CI$^+$) m/z=452.0 (M+1), 926.2 (2M+23).

Example 55

2-((2S,5R,6R)-6-(3-Chlorophenyl)-4-(cyclopropylmethyl)-3-oxo-5-phenylmorpholin-2-yl)acetic acid $^1$H NMR (400 MHz, CDCl$_3$) δ ppm −0.06-0.11 (m, 2 H) 0.34-0.53 (m, 2 H) 0.87 (d, J=7.34 Hz, 1 H) 1.04-1.21 (m, 1 H) 1.06-1.21 (m, 1 H) 1.21-1.30 (m, 1 H) 1.36 (t, J=6.85 Hz, 2 H) 1.59 (d, J=10.27 Hz, 1 H) 1.76 (d, J=7.34 Hz, 1 H) 2.28-2.40 (m, 1 H) 3.06 (dd, J=16.38, 5.14 Hz, 2 H) 3.11-3.24 (m, 1 H) 3.98 (dd, J=14.18, 6.36 Hz, 1 H) 4.60-4.77 (m, 2 H) 4.79 (t, J=5.38 Hz, 1 H) 6.72 (d, J=7.83 Hz, 1 H) 6.96 (d, J=7.83 Hz, 2 H) 7.02 (s, 1 H) 7.09 (t, J=7.83 Hz, 1 H) 7.21 (d, J=7.82 Hz, 1 H) 7.25-7.34 (m, 4 H) 7.74 (br. s., 1 H). Mass Spectrum (CI$^+$) m/z=400.1 (M+1), 823.3 (2M+23).

Example 56

2-((2S,5R,6R)-6-(3-Chlorophenyl)-4-(cyclopropylmethyl)-5-(4-fluorophenyl)-3-oxomorpholin-2-yl)acetic acid $^1$H NMR (400 MHz, CDCl$_3$) δ ppm −0.07-0.06 (m, 2 H) 0.34-0.48 (m, 2 H) 0.79-0.89 (m, 1 H) 1.13 (t, J=7.09 Hz, 1 H) 1.24 (d, J=7.34 Hz, 1 H) 2.28 (dd, J=14.18, 7.34 Hz, 1 H) 2.93-3.03 (m, 1 H) 3.07-3.16 (m, 1 H) 3.96 (dd, J=14.18, 6.36 Hz, 1 H) 4.59 (d, J=9.78 Hz, 1 H) 4.72 (d, J=9.29 Hz, 1 H) 4.79 (t, J=5.38 Hz, 1 H) 6.69 (d, J=7.83 Hz, 1 H) 6.89-7.02 (m, 4 H) 7.03-7.11 (m, 2 H) 7.20 (d, 1 H). Mass Spectrum (CI$^+$) m/z=418.1 (M+1), 859.2 (2M+23).

Example 57

2-((2S,5R,6R)-6-(3-Chlorophenyl)-4-(cyclopropylmethyl)-3-oxo-5-(4-(trifluoromethyl)phenyl)morpholin-2-yl)acetic acid 1H NMR (400 MHz, CDCl$_3$) δ ppm −0.03 (br. s., 2 H) 0.32-0.47 (m, 2 H) 0.79-0.94 (m, 2 H) 2.21 (dd, J=12.47, 7.09 Hz, 1 H) 2.89 (dd, J=13.69, 1.96 Hz, 1 H) 2.98-3.13 (m, 1 H) 3.94-4.05 (m, 1 H) 4.13 (q, 1 H) 4.61 (d, J=10.27 Hz, 1 H) 4.79 (d, J=9.78 Hz, 1 H) 4.89 (br. s., 1 H) 6.64 (d, J=7.34 Hz, 1 H) 7.00-7.13 (m, 3 H) 7.19 (d, J=7.83 Hz, 1 H) 7.53 (d, J=7.83 Hz, 2 H). Mass Spectrum (CI$^+$) m/z=468.1 (M+1), 959.3 (2M+23).

Example 58

2-((2S,5R,6R)-6-(3-Chlorophenyl)-4-(cyclopropylmethyl)-5-(4-ethylphenyl)-3-oxomorpholin-2-yl)acetic acid $^1$H NMR (400 MHz, CDCl$_3$) δ ppm −0.05-0.11 (m, 2 H) 0.31-0.50 (m, 2 H) 0.82-0.93 (m, 1 H) 1.14 (t, J=7.34 Hz, 1 H) 1.19-1.26 (m, 3 H) 2.34 (dd, J=14.18, 7.34 Hz, 1 H) 2.63 (q, J=7.83 Hz, 2 H) 2.82 (q, J=7.34 Hz, 1 H) 2.94 (dd, J=16.14, 5.38 Hz, 1 H) 3.14 (dd, J=16.14, 5.87 Hz, 1 H) 3.96 (dd, J=13.94, 6.60 Hz, 1 H) 4.59-4.72 (m, 2 H) 4.81 (t, J=5.62 Hz, 1 H) 6.74 (d, J=7.34 Hz, 1 H) 6.86 (d, J=7.82 Hz, 2 H) 6.99 (s, 1 H) 7.07-7.13 (m, 2 H) 7.19 (d, 1 H). Mass Spectrum (CI$^+$) m/z=428.2 (M+1), 879.3 (2M+23).

Example 59

2-((2S,5R,6R)-6-(3-Chlorophenyl)-4-(cyclopropylmethyl)-3-oxo-5-(4-(trifluoromethoxy)phenyl)morpholin-2-yl)acetic acid $^1$H NMR (400 MHz, CDCl$_3$) δ ppm −0.03-0.06 (m, 2 H) 0.35-0.51 (m, 2 H) 0.86 (dd, J=13.69, 6.85 Hz, 1 H) 1.16 (t, J=7.34 Hz, 1 H) 2.31 (dd, J=14.18, 7.34 Hz, 1 H) 2.83 (q, J=7.01 Hz, 1 H) 2.93 (dd, J=16.14, 5.87 Hz, 1 H) 3.06-3.18 (m, 1 H) 3.98 (dd, J=14.18, 6.36 Hz, 1 H) 4.59 (d, J=9.78 Hz, 1 H) 4.76 (d, J=9.78 Hz, 1 H) 4.82 (t, J=5.62 Hz, 1 H) 6.69 (d, J=7.83 Hz, 1 H) 7.00 (d, J=8.80 Hz, 2 H) 7.03-7.07 (m, 1 H)

7.05-7.10 (m, 1H) 7.14 (d, J=7.82 Hz, 2 H) 7.22 (d, 1 H). Mass Spectrum (CI⁺) m/z=484.1 (M+1), 991.2 (2M+23).

Example 60

2-((2S,5R,6R)-6-(3-Chlorophenyl)-4-(cyclopropylmethyl)-3-oxo-5-(p-tolyl)morpholin-2-yl)acetic acid ¹H NMR (400 MHz, CDCl₃) δ ppm −0.08-0.11 (m, 2 H) 0.31-0.51 (m, 2 H) 0.78-0.94 (m, 1 H) 1.13 (t, J=7.34 Hz, 1 H) 1.21-1.32 (m, 1 H) 2.26-2.41 (m, 4 H) 2.81 (q, J=7.34 Hz, 1 H) 2.96 (dd, J=16.14, 5.38 Hz, 1 H) 3.14 (dd, J=16.14, 5.87 Hz, 1 H) 3.96 (dd, J=14.18, 6.36 Hz, 1 H) 4.58-4.74 (m, 2 H) 4.80 (t, J=5.38 Hz, 1 H) 6.72 (d, J=7.83 Hz, 1 H) 6.84 (d, J=7.82 Hz, 2 H) 6.98-7.13 (m, 2 H) 7.16-7.24 (m, 1 H). Mass Spectrum (CI⁺) m/z=414.1 (M+1), 851.2 (2M+23).

Example 61

2-((2R,5R,6R)-6-(3-Chlorophenyl)-4-(cyclopropylmethyl)-3-oxo-5-(p-tolyl)morpholin-2-yl)acetic acid ¹H NMR (400 MHz, CDCl₃) δ ppm 0.08 (s, 1 H) 0.13 (br. s., 1 H) 0.42 (br. s., 1 H) 0.52 (br. s., 1 H) 0.56 (d, J=6.36 Hz, 1 H) 0.71 (d, J=6.36 Hz, 1 H) 0.81-1.02 (m, 2 H) 1.11 (t, J=7.34 Hz, 1 H) 1.27 (s, 3 H) 2.24-2.38 (m, 4 H) 2.69-2.78 (m, 1 H) 2.79-2.87 (m, 1 H) 3.05 (br. s., 1 H) 4.02 (br. s., 1 H) 4.76 (d, J=3.42 Hz, 1 H) 4.83 (br. s., 2 H) 6.96 (br. s., 2 H) 7.02-7.25 (m, 5 H) 7.25-7.33 (m, 4 H). Mass Spectrum (CI⁺) m/z=414.1 (M+1), 851.2 (2M+23).

Example 62

2-((2R,5R,6R)-5-(4-Chloro-2-fluorophenyl)-6-(3-chlorophenyl)-4-(cyclopropylmethyl)-3-oxomorpholin-2-yl)acetic acid

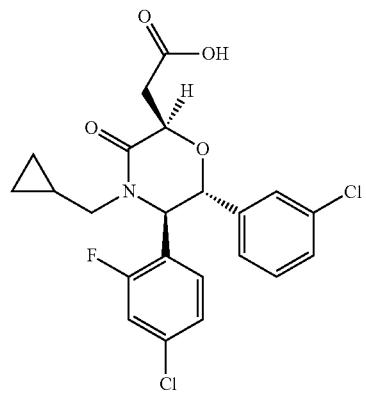 [SMILES: O=C(O)C[C@H]1O[C@H](c2cccc(Cl)c2)[C@@H](c2ccc(Cl)cc2F)N(CC2CC2)C1=O]

Step A. (E)-tert-Butyl 4-(((1R,2R)-1-(4-chloro-2-fluorophenyl)-2-(3-chlorophenyl)-2-hydroxyethyl)amino)-4-oxobut-2-enoate

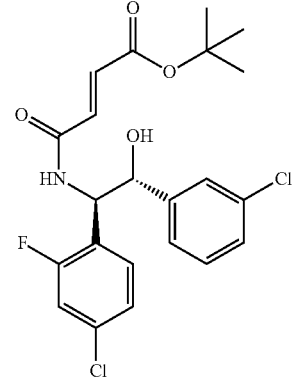 [SMILES: CC(C)(C)OC(=O)/C=C/C(=O)N[C@H](c1ccc(Cl)cc1F)[C@H](O)c1cccc(Cl)c1]

To (E)-4-tert-butoxy-4-oxobut-2-enoic acid (0.90 g, 0.525 mmol; AMRI, Albany, N.Y.) and HBTU (0.2 g, 0.525 mmol) was added dry DMF (858 uL) followed by DIEA (0.12 g, 0.913 mmol). The reaction mixture was stirred at rt for about 20 min. after which (1R,2R)-2-amino-2-(4-chloro-2-fluorophenyl)-1-(3-chlorophenyl)ethanol (0.137 g, 0.456 mmol, Intermediate B1) was added. The reaction mixture was stirred at rt for 22 h. The mixture was diluted with EtOAc, washed with water, then saturated aq. NaHCO₃ solution. The organic layers were extracted with EtOAc, combined, dried over MgSO₄, filtered and the filtrate was concentrated under reduced pressure. The crude residue was purified by chromatography on silica gel (eluent: 5 to 95% EtOAc:hexanes, gradient elution). ¹H NMR (400 MHz, CDCl₃) δ ppm 1.13-1.21 (m, 6 H) 1.13-1.21 (m, 2 H) 1.34-1.46 (m, 12 H) 1.95 (s, 1 H) 4.03 (d, J=7.34 Hz, 1 H) 4.89 (d, J=4.40 Hz, 1 H) 5.35 (dd, J=8.31, 4.40 Hz, 1 H) 6.47-6.57 (m, 1 H) 6.71-6.80 (m, 1 H) 6.92 (s, 1 H) 6.93-6.96 (m, 1 H) 6.97 (s, 1 H) 6.98-7.04 (m, 2 H) 7.04-7.09 (m, 2 H) 7.13 (d, J=6.36 Hz, 2 H) 7.25 (s, 1 H). Mass Spectrum (CI⁺) m/z=454.1 (M+1), 909.2 (2M+1).

Step B. tert-Butyl 2-((2R,5R,6R)-5-(4-chloro-2-fluorophenyl)-6-(3-chlorophenyl)-3-oxomorpholin-2-yl)acetate and tert-Butyl 2-((2S,5R,6R)-5-(4-chloro-2-fluorophenyl)-6-(3-chlorophenyl)-3-oxomorpholin-2-yl)acetate

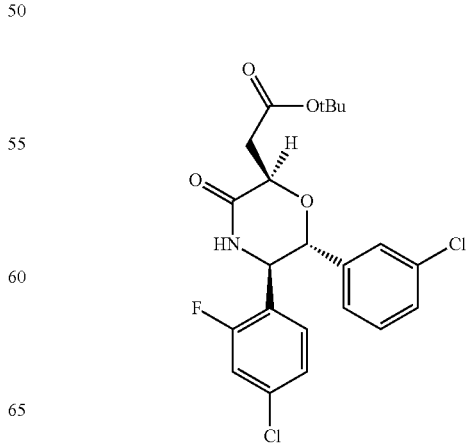

-continued

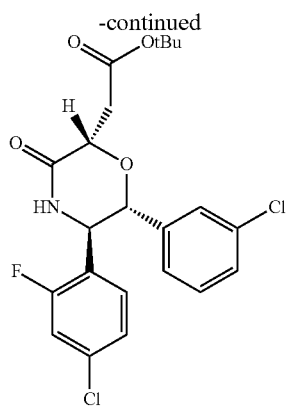

A solution of (E)-tert-butyl 4-((1R,2R)-1-(4-chloro-2-fluorophenyl)-2-(3-chlorophenyl)-2-hydroxyethylamino)-4-oxobut-2-enoate (0.73 g, 0.161 mmol) in dry THF (2 mL) was cooled to 0° C. in an ice/water bath. To the cooled solution was added sodium hydride (60% in mineral oil, 0.02 g, 0.482 mmol). The reaction mixture was stirred at 0° C. for 2 h. The reaction mixture was quenched with saturated aq. NH$_4$Cl solution; after which EtOAc was added. The organic layer was extracted with EtOAc, dried over MgSO$_4$, then concentrated under reduced pressure. The crude residue was purified by silica gel column chromatography (eluent: 5 to 95% EtOAc:hexanes, gradient elution). Mass Spectrum (CI$^+$) m/z=454.1 (M+1), 909.2 (2M+1), 931.2 (2M+23).

Step C. 2-((2R,5R,6R)-5-(4-Chloro-2-fluorophenyl)-6-(3-chlorophenyl)-4-(cyclopropylmethyl)-3-oxo-morpholin-2-yl)acetic acid To a mixture of tert-butyl 2-((2R,5R,6R)-5-(4-chloro-2-fluorophenyl)-6-(3-chlorophenyl)-3-oxomorpholin-2-yl)acetate and tert-butyl 2-((2S,5R,6R)-5-(4-chloro-2-fluorophenyl)-6-(3-chlorophenyl)-3-oxomorpholin-2-yl)acetate (0.054 g, 0.120 mmol; Example 62, Step B) in 3 mL of dry DMF was added caesium carbonate (0.195 g, 0.595 mmol). The mixture was stirred at room temperature for approximately 10 minutes, then (bromomethyl)cyclopropane (0.128 g, 0.951 mmol, Oakwood Products, Inc., West Columbia, S.C.) was added. The reaction mixture was stirred at rt for 22 h. The reaction mixture was diluted with EtOAc and the combined organics were washed with water, saturated aq. NaHCO$_3$ solution and concentrated under reduced pressure.

To the crude diastereomeric mixture of tert-butyl 2-((2R,5R,6R)-5-(4-chloro-2-fluorophenyl)-6-(3-chlorophenyl)-4-(cyclopropylmethyl)-3-oxomorpholin-2-yl)acetate and tert-butyl 2-((2S,5R,6R)-5-(4-chloro-2-fluorophenyl)-6-(3-chlorophenyl)-4-(cyclopropylmethyl)-3-oxomorpholin-2-yl)acetate thus obtained was added 2 mL DCM followed by 1.0 mL trifluoroacetic acid (0.014 g, 0.120 mmol). The mixture was stirred at rt for 2 hours and then concentrated under reduced pressure. The residue was purified by SFC (Method: 250×21.2 mm IC-H column w/20 g/min MeOH (0.2% DEA)+60 g/min CO$_2$ on a Thar 80 SFC. Outlet pressure 100 bar; Temp. 20° C.; Wavelength 220 nm). The title compound was obtained as the first eluting stereoisomer. The pooled fractions containing the title compound were concentrated, then diluted with toluene and concentrated followed by repeating this procedure with ethanol in order to azeotrope off diethylamine employed as co-solvent during SFC. $^1$H NMR (400 MHz, CDCl$_3$) δ ppm 0.13-0.38 (m, 2 H) 0.55-0.79 (m, 2 H) 1.07 (br. s., 1 H) 2.43 (dd, J=14.28, 7.63 Hz, 1 H) 2.76 (br. s., 1 H) 2.85-3.00 (m, 2 H) 3.03 (s, 1 H) 3.11 (dd, J=16.24, 5.67 Hz, 1 H) 4.11 (dd, J=14.18, 6.75 Hz, 1 H) 4.43 (t, J=6.16 Hz, 1 H) 4.98 (d, J=1.76 Hz, 2 H) 5.49 (d, J=2.15 Hz, 1 H) 7.15 (dd, J=10.17, 1.57 Hz, 1 H) 7.32-7.39 (m, 3 H) 7.55 (s, 1 H). Mass Spectrum (CI$^+$) m/z=453.1 (M+1), 927.3 (2M+23).

Examples 63 to 82 were also prepared by procedures similar to the one described in Example 62, replacing (1R,2R)-2-amino-2-(4-chloro-2-fluorophenyl)-1-(3-chlorophenyl)ethanol (Intermediate B1) in Step A with the designated intermediates.

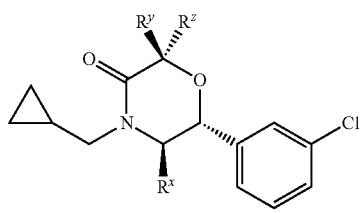

| Example | R$^x$ | R$^y$ | R$^z$ | Intermediate used |
|---------|-------|-------|-------|-------------------|
| 63 | phenyl | CH$_2$C(O)OH | H | B2 |
| 64 | 4-fluorophenyl | CH$_2$C(O)OH | H | B3 |

-continued
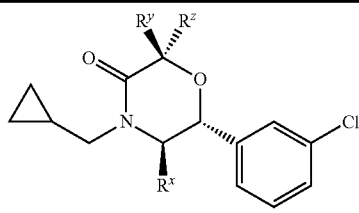
| Example | R$^x$ | R$^y$ | R$^z$ | Intermediate used |
|---|---|---|---|---|
| 65 | 4-(OCF$_3$)phenyl | CH$_2$COOH | H | B6 |
| 66 | 4-isopropylphenyl | CH$_2$COOH | H | B8 |
| 67 | 4-Br-phenyl | CH$_2$COOH | H | C13 |
| 68 | 4-Br-phenyl | H | CH$_2$COOH | C13 |
| 69 | 5-Cl-thiophen-2-yl | CH$_2$COOH | H | D1 |
| 70 | 5-Cl-thiophen-2-yl | H | CH$_2$COOH | D1 |
| 71 | 6-Cl-pyridin-3-yl | H | CH$_2$COOH | D2 |

-continued
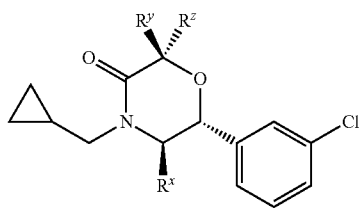
| Example | R$^x$ | R$^y$ | R$^z$ | Intermediate used |
|---|---|---|---|---|
| 72 | | | H | D2 |
| 73 | | | H | D3 |
| 74 | | H | | D3 |
| 75 | | | H | D4 |
| 76 | | H | | D4 |
| 77 | | | H | D5 |
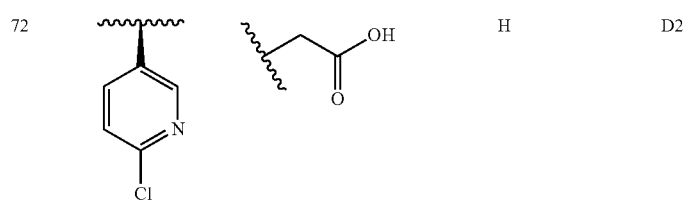
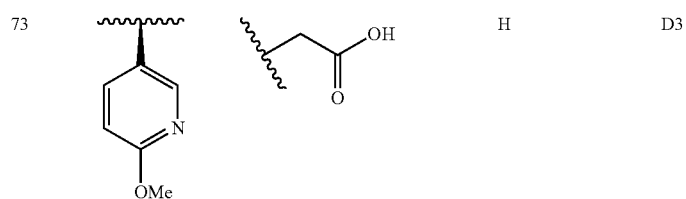
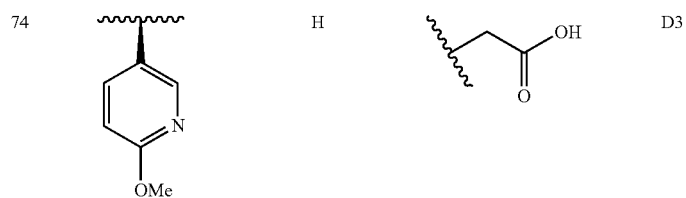
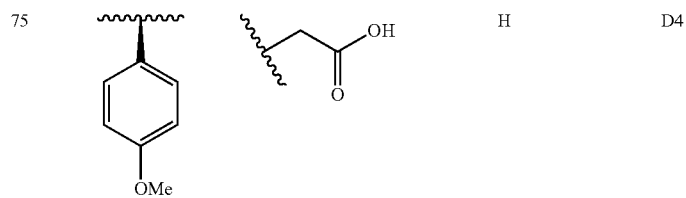
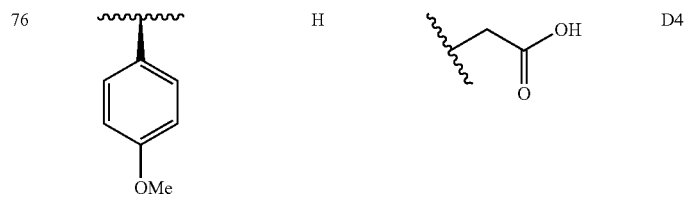
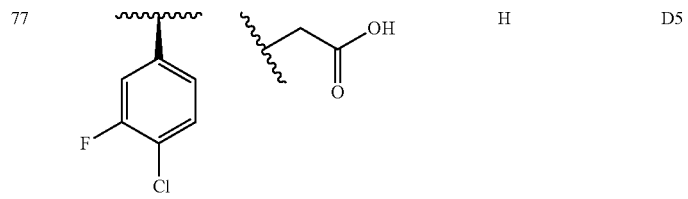

-continued

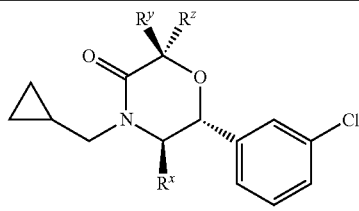

| Example | Rˣ | Rʸ | Rᶻ | Intermediate used |
|---|---|---|---|---|
| 78 | 3-F,4-Cl-phenyl | H | CH₂COOH | D5 |
| 79 | 2-Br,4-Cl-phenyl | CH₂COOH | H | E1 |
| 80 | 2-Br,4-Cl-phenyl | H | CH₂COOH | E1 |
| 81 | 6-CF₃-pyridin-3-yl | CH₂COOH | H | E2 |
| 82 | 6-CF₃-pyridin-3-yl | H | CH₂COOH | E2 |

Example 63

2-((2R,5R,6R)-6-(3-Chlorophenyl)-4-(cyclopropyl-methyl)-3-oxo-5-phenylmorpholin-2-yl)acetic acid ¹H NMR (400 MHz, CDCl₃) δ ppm 0.03-0.21 (m, 2 H) 0.38-0.60 (m, 2 H) 0.89-1.04 (m, 1 H) 2.33 (dd, J=14.18, 7.73 Hz, 1 H) 2.85 (dd, J=16.04, 7.43 Hz, 1 H) 3.07 (dd, J=16.04, 5.48 Hz, 1 H) 4.00 (dd, J=14.18, 6.55 Hz, 2 H) 4.47 (dd, J=7.24, 5.67 Hz, 2 H) 4.82 (d, J=3.72 Hz, 1 H) 4.95 (d, J=3.91 Hz, 1 H) 7.03-7.13 (m, 3 H) 7.14-7.27 (m, 3 H) 7.35 (s, 1 H). Mass Spectrum (CI⁺) m/z=400.1 (M+1), 823.2 (2M+23).

Example 64

2-((2R,5R,6R)-6-(3-Chlorophenyl)-4-(cyclopropyl-methyl)-5-(4-fluorophenyl)-3-oxomorpholin-2-yl) acetic acid ¹H NMR (400 MHz, CDCl₃) δ ppm 0.17-0.33 (m, 2 H) 0.53-0.73 (m, 2 H) 1.01-1.14 (m, 1 H) 2.46 (dd, J=13.82, 7.70 Hz, 1 H) 2.94 (dd, J=16.14, 6.11 Hz, 2 H) 3.17 (dd, J=16.14, 6.85 Hz, 2 H) 4.09 (dd, J=13.45, 7.34 Hz, 1 H) 4.44-4.51 (m, 1 H) 4.90 (br. s., 1 H) 4.89-4.90 (m, 1 H) 5.06 (d, J=3.42 Hz, 1 H) 5.00-5.10 (m, 1 H) 7.06-7.14 (m, 2 H) 7.28-7.40 (m, 2 H) 7.48 (s, 1 H). Mass Spectrum (CI⁺) m/z=418.1 (M+1), 859.2 (2M+23).

Example 65

2-((2R,5R,6R)-6-(3-Chlorophenyl)-4-(cyclopropylmethyl)-3-oxo-5-(4-(trifluoromethoxy)phenyl)morpholin-2-yl)acetic acid $^1$H NMR (400 MHz, CDCl$_3$) δ ppm 0.15-0.36 (m, 2 H) 0.48-0.76 (m, 2 H) 1.00-1.17 (m, 1 H) 2.45 (dd, J=14.18, 7.53 Hz, 1 H) 2.88-3.00 (m, 2 H) 3.03 (s, 1 H) 3.15 (dd, J=16.24, 6.06 Hz, 1 H) 4.10 (dd, J=13.99, 6.75 Hz, 1 H) 4.47 (t, J=6.36 Hz, 1 H) 4.92 (d, J=2.93 Hz, 1 H) 5.11 (d, J=3.33 Hz, 2 H) 7.20-7.28 (m, 3 H) 7.30-7.41 (m, 2 H) 7.48 (s, 1 H). Mass Spectrum (CI$^+$) m/z=484.1 (M+1), 991.3 (2M+23).

Example 66

2-((2R,5R,6R)-6-(3-Chlorophenyl)-4-(cyclopropylmethyl)-5-(4-isopropylphenyl)-3-oxomorpholin-2-yl)acetic acid $^1$H NMR (400 MHz, CDCl$_3$) δ ppm −0.08-0.14 (m, 2 H) 0.28-0.55 (m, 2 H) 0.77-0.95 (m, 1 H) 1.06 (d, J=7.04 Hz, 6 H) 2.27 (dd, J=14.09, 7.83 Hz, 1 H) 2.67-2.85 (m, 2 H) 2.99 (dd, J=16.14, 5.77 Hz, 1 H) 3.89 (dd, J=14.08, 6.65 Hz, 1 H) 4.35 (t, J=6.46 Hz, 1 H) 4.71 (d, J=3.52 Hz, 1 H) 4.83 (d, J=3.52 Hz, 1 H) 6.88 (d, J=8.02 Hz, 2 H) 7.00-7.06 (m, 3 H) 7.06-7.17 (m, 3 H) 7.20 (s, 1 H). Mass Spectrum (CI$^+$) m/z=442.1 (M+1), 907.3 (2M+23).

Example 67

2-((2R,5R,6R)-5-(4-Bromophenyl)-6-(3-chlorophenyl)-4-(cyclopropylmethyl)-3-oxomorpholin-2-yl)acetic acid First eluting isomer using chiral SFC separation as described in Example 62.

$^1$H NMR (400 MHz, CDCl$_3$) δ ppm 0.05-0.23 (m, 2 H) 0.40-0.65 (m, 2 H) 0.93 (d, J=7.24 Hz, 1 H) 0.96 (br. s., 1 H) 1.27 (t, J=6.85 Hz, 1 H) 2.26-2.39 (m, 1 H) 2.87 (d, J=14.09 Hz, 1 H) 3.08 (d, J=11.54 Hz, 1 H) 4.05 (dd, J=13.79, 5.97 Hz, 1 H) 4.13 (q, J=7.17 Hz, 1 H) 4.65 (br. s., 1 H) 4.84 (br. s., 1 H) 4.93 (br. s., 1 H) 7.04 (t, J=7.63 Hz, 2 H) 7.06-7.13 (m, 1 H) 7.18-7.25 (m, 1 H) 7.39 (br. s., 1 H) 7.47 (d, 2 H). Mass Spectrum (CI$^+$) m/z=478.0 (M+1), 977.1 (2M+23).

Example 68

2-((2S,5R,6R)-5-(4-Bromophenyl)-6-(3-chlorophenyl)-4-(cyclopropylmethyl)-3-oxomorpholin-2-yl)acetic acid Second eluting isomer using chiral SFC separation as described in Example 62.

$^1$H NMR (400 MHz, CDCl$_3$) δ ppm 0.00 (d, J=4.30 Hz, 2 H) 0.35-0.51 (m, 2 H) 0.77-0.86 (m, 1 H) 1.19-1.29 (m, 2 H) 2.29 (dd, J=14.18, 7.53 Hz, 1 H) 3.00-3.22 (m, 2 H) 3.97 (dd, J=14.18, 6.55 Hz, 1 H) 4.57 (d, J=9.59 Hz, 1 H) 4.69-4.78 (m, 2 H) 6.68 (d, J=7.63 Hz, 1 H) 6.81 (d, J=8.41 Hz, 2 H) 7.01-7.15 (m, 2 H) 7.21 (dd, J=8.02, 0.98 Hz, 1 H) 7.39 (d, J=8.41 Hz, 2 H) 10.47 (br. s., 1 H). Mass Spectrum (CI$^+$) m/z=478.0 (M+1), 977.1 (2M+23).

Example 69

2-((2R,5S,6R)-6-(3-Chlorophenyl)-4-(cyclopropylmethyl)-3-oxo-5-(thiophen-2-yl)morpholin-2-yl)acetic acid First eluting isomer using chiral SFC separation as described in Example 62.

$^1$H NMR (400 MHz, CDCl$_3$) δ ppm 0.03-0.28 (m, 2 H) 0.38-0.62 (m, 2 H) 0.94 (br. s., 1 H) 1.16-1.32 (m, 1 H) 2.58 (dd, J=14.38, 7.53 Hz, 1 H) 3.00-3.23 (m, 1 H) 3.92-4.12 (m, 1 H) 4.62-4.78 (m, 2 H) 4.93 (d, J=9.59 Hz, 1 H) 6.45 (d, J=3.72 Hz, 1 H) 6.70 (d, J=3.72 Hz, 1 H) 6.84-6.96 (m, 1 H) 7.12-7.23 (m, 2 H) 7.30 (d, 1 H). Mass Spectrum (CI$^+$) m/e=440.0 (M+1), 903.0 (2M+23).

Example 70

2-((2S,5S,6R)-6-(3-Chlorophenyl)-4-(cyclopropylmethyl)-3-oxo-5-(thiophen-2-yl)morpholin-2-yl)acetic acid Second eluting isomer using chiral SFC separation as described in Example 62.

$^1$H NMR (400 MHz, CDCl$_3$) δ ppm 0.06-0.23 (m, J=19.76, 9.15, 4.72, 4.72 Hz, 2 H) 0.41-0.59 (m, 2 H) 0.84-1.00 (m, 1 H) 1.26 (s, 1 H) 2.57 (dd, J=14.38, 7.53 Hz, 1 H) 3.13 (d, J=4.89 Hz, 2 H) 4.02 (dd, J=14.28, 6.65 Hz, 1 H) 4.63-4.77 (m, 2 H) 4.93 (d, J=9.39 Hz, 1 H) 6.45 (d, J=3.72 Hz, 1 H) 6.70 (d, J=3.72 Hz, 1 H) 6.92 (d, J=7.82 Hz, 1 H) 7.10-7.23 (m, 2 H) 8.54 (br. s., 1 H). Mass Spectrum (CI$^+$) m/e=440.0 (M+1), 903.1 (2M+23).

Example 71

2-((2S,5R,6R)-6-(3-Chlorophenyl)-5-(6-chloropyridin-3-yl)-4-(cyclopropylmethyl)-3-oxomorpholin-2-yl)acetic acid First eluting isomer using chiral SFC separation as described in Example 62.

$^1$H NMR (400 MHz, CDCl$_3$) δ ppm −0.01 (br. s., 2 H) 0.32-0.53 (m, 2 H) 0.74-0.87 (m, 1 H) 2.26 (dd, J=14.18, 7.34 Hz, 1 H) 2.81 (q, J=7.17 Hz, 2 H) 2.88 (d, J=6.26 Hz, 1 H) 3.08 (d, J=15.26 Hz, 1 H) 3.97 (dd, J=14.08, 6.26 Hz, 1 H) 4.59 (d, J=9.59 Hz, 1 H) 4.83 (d, J=9.19 Hz, 1 H) 6.69 (d, J=7.63 Hz, 1 H) 7.11 (t, J=7.83 Hz, 1 H) 7.19 (s, 1 H) 7.24 (d, J=8.22 Hz, 1 H) 7.30 (d, J=8.02 Hz, 1 H) 7.39 (dd, J=8.02, 1.56 Hz, 1 H) 7.92 (s, 1 H). Mass Spectrum (CI$^+$) m/z=435.1 (M+1), 871.1 (2M+1).

Example 72

2-((2R,5R,6R)-6-(3-Chlorophenyl)-5-(6-chloropyridin-3-yl)-4-(cyclopropylmethyl)-3-oxomorpholin-2-yl)acetic acid Second eluting isomer using chiral SFC separation as described in Example 62.

$^1$H NMR (400 MHz, CDCl$_3$) δ ppm 0.11-0.32 (m, 2 H) 0.48-0.74 (m, 2 H) 0.78-0.97 (m, 3 H) 1.02 (br. s., 2 H) 1.16 (t, J=7.04 Hz, 2 H) 2.39 (dd, J=8.22, 2.54 Hz, 1 H) 2.83-3.08 (m, 3 H) 3.91-4.13 (m, 2 H) 4.49 (br. s., 2 H) 4.92 (br. s., 1 H) 5.08 (br. s., 1 H) 7.21 (d, 1 H) 7.29-7.35 (m, 2 H) 7.39 (br. s., 1 H) 7.49 (br. s., 1 H) 7.73 (br. s., 1 H) 8.25 (br. s., 1 H). Mass Spectrum (CI$^+$) m/z=435.1 (M+1), 871.2 (2M+1).

Example 73

2-((2R,5R,6R)-6-(3-Chlorophenyl)-4-(cyclopropylmethyl)-5-(6-methoxypyridin-3-yl)-3-oxomorpholin-2-yl)acetic acid First eluting isomer using chiral SFC separation as described in Example 62.
$^1$H NMR (400 MHz, CDCl$_3$) δ ppm 0.16-0.38 (m, 2 H) 0.54-0.80 (m, 2 H) 1.03-1.17 (m, 1 H) 2.51 (dd, J=13.99, 7.73 Hz, 1 H) 3.05 (dd, J=13.79, 5.97 Hz, 2 H) 4.01-4.11 (m, 3 H) 4.37 (t, J=5.67 Hz, 1 H) 4.92 (d, J=2.35 Hz, 1 H) 5.10 (d, J=2.35 Hz, 1 H) 6.92 (d, J=8.61 Hz, 1 H) 7.25-7.32 (m, 5 H) 7.33-7.43 (m, 2 H) 7.53 (s, 1 H) 7.73 (dd, J=8.71, 2.45 Hz, 1 H) 8.17 (d, J=2.15 Hz, 1 H). Mass Spectrum (CI$^+$) m/z=431.1 (M+1).

Example 74

2-((2S,5R,6R)-6-(3-Chlorophenyl)-4-(cyclopropylmethyl)-5-(6-methoxypyridin-3-yl)-3-oxomorpholin-2-yl)acetic acid Second eluting isomer using chiral SFC separation as described in Example 62.
$^1$H NMR (400 MHz, CDCl$_3$) δ ppm 0.07 (q, J=4.24 Hz, 2 H) 0.49 (dd, J=15.65, 8.22 Hz, 2 H) 0.80-0.93 (m, 1 H) 2.41 (dd, J=14.28, 7.24 Hz, 1 H) 3.04-3.24 (m, 2 H) 3.90-4.01 (m, 4 H) 4.62 (d, J=9.78 Hz, 1 H) 4.71-4.88 (m, 2 H) 6.80 (t, J=8.41 Hz, 2 H) 7.09-7.20 (m, 2 H) 7.25-7.27 (m, 1 H) 7.28 (dd, J=2.15, 1.17 Hz, 1 H) 7.39 (dd, J=8.71, 2.45 Hz, 1 H) 7.72 (d, J=2.35 Hz, 1 H). Mass Spectrum (CI$^+$) m/z=431.1 (M+1), 861.3 (2M+1).

Example 75

2-((2R,5R,6R)-6-(3-Chlorophenyl)-4-(cyclopropylmethyl)-5-(4-methoxyphenyl)-3-oxomorpholin-2-yl)acetic acid First eluting isomer using chiral SFC separation as described in Example 62.
$^1$H NMR (400 MHz, CDCl$_3$) δ ppm 0.16-0.34 (m, 2 H) 0.55-0.72 (m, 2 H) 1.05-1.11 (m, 1 H) 2.48 (dd, J=13.89, 7.83 Hz, 1 H) 2.93 (dd, J=15.85, 5.48 Hz, 1 H) 3.19 (dd, J=15.94, 7.34 Hz, 1 H) 3.83 (s, 3 H) 4.07 (dd, J=14.48, 6.65 Hz, 1 H) 4.47-4.53 (m, 1 H) 4.89 (d, J=3.91 Hz, 1 H) 4.99 (d, J=3.72 Hz, 1 H) 6.92 (d, J=8.80 Hz, 2 H) 7.09 (d, J=8.61 Hz, 2 H) 7.19 (d, J=7.43 Hz, 1 H) 7.29-7.38 (m, 3 H) 7.45 (s, 1 H). Mass Spectrum (CI$^+$) m/z=430.1 (M+1), 883.3 (2M+23).

Example 76

2-((2S,5R,6R)-6-(3-Chlorophenyl)-4-(cyclopropylmethyl)-5-(4-methoxyphenyl)-3-oxomorpholin-2-yl)acetic acid Second eluting isomer using chiral SFC separation as described in Example 62.
$^1$H NMR (400 MHz, CDCl$_3$) δ ppm −0.04-0.13 (m, 2 H) 0.33-0.53 (m, 2 H) 0.81-0.94 (m, 1 H) 2.37 (dd, J=14.18, 7.53 Hz, 1 H) 3.04-3.23 (m, J=16.95, 16.95, 16.58, 5.48 Hz, 2 H) 3.80 (s, 3 H) 3.97 (dd, J=14.18, 6.55 Hz, 1 H) 4.59-4.72 (m, 2 H) 4.76 (t, J=5.48 Hz, 1 H) 6.73 (d, J=7.63 Hz, 1 H) 6.78-6.84 (m, 2 H) 6.85-6.91 (m, 2 H) 7.06 (t, J=1.76 Hz, 1 H) 7.10 (t, J=7.83 Hz, 1 H) 7.22 (ddd, 1 H). Mass Spectrum (CI$^+$) m/z=430.1 (M+1), 883.3 (2M+23).

Example 77

2-((2R,5R,6R)-5-(4-Chloro-3-fluorophenyl)-6-(3-chlorophenyl)-4-(cyclopropylmethyl)-3-oxomorpholin-2-yl)acetic acid First eluting isomer using chiral SFC separation as described in Example 62.
$^1$H NMR (400 MHz, CDCl$_3$) δ ppm −0.10-0.07 (m, 2 H) 0.28-0.49 (m, 2 H) 0.76-0.87 (m, 1 H) 2.15 (dd, J=14.09, 7.63 Hz, 1 H) 2.67 (q, J=7.17 Hz, 3 H) 3.89 (dd, J=14.18, 6.55 Hz, 1 H) 4.47 (dd, J=7.83, 4.50 Hz, 1 H) 4.67-4.80 (m, 2 H) 6.73 (d, J=8.22 Hz, 1 H) 6.87-6.94 (m, 2 H) 7.03 (t, J=7.83 Hz, 1 H) 7.11 (s, 1 H) 7.20 (t, J=7.73 Hz, 1 H) 8.24 (br. s., 1 H). Mass Spectrum (CI$^+$) m/z=452.0 (M+1), 928.2 (2M+23).

Example 78

2-((2S,5R,6R)-5-(4-chloro-3-fluorophenyl)-6-(3-chlorophenyl)-4-(cyclopropylmethyl)-3-oxomorpholin-2-yl)acetic acid Second eluting isomer using chiral SFC separation as described in Example 62.
$^1$H NMR (400 MHz, CDCl$_3$) δ ppm −0.01 (d, J=4.30 Hz, 2 H) 0.34-0.53 (m, 2 H) 0.71-0.91 (m, 1 H) 2.26 (dd, J=14.18, 7.53 Hz, 1 H) 2.97 (d, J=4.50 Hz, 2 H) 3.99 (dd, J=14.28, 6.46 Hz, 1 H) 4.56 (d, J=9.59 Hz, 1 H) 4.67-4.83 (m, 2 H) 6.68 (dd, J=17.90, 7.92 Hz, 2 H) 6.80 (dd, J=9.19, 1.37 Hz, 1 H) 7.06-7.15 (m, 2 H) 7.20-7.25 (m, 1 H) 7.28 (t, J=7.83 Hz, 1 H) 9.00 (br. s., 1 H). Mass Spectrum (CI$^+$) m/z=452.0 (M+1), 928.2 (2M+23).

Example 79

2-((2R,5R,6R)-5-(2-Bromo-4-chlorophenyl)-6-(3-chlorophenyl)-4-(cyclopropylmethyl)-3-oxomorpholin-2-yl)acetic acid First eluting isomer using chiral SFC separation as described in Example 62.
$^1$H NMR (400 MHz, CDCl$_3$) δ ppm 0.21 (dt, J=9.63, 4.87 Hz, 1 H) 0.33 (dd, J=9.10, 4.60 Hz, 1 H) 0.52-0.68 (m, 1 H) 0.68-0.84 (m, 1 H) 1.00-1.17 (m, 1 H) 2.33 (dd, J=14.08, 8.02 Hz, 1 H) 2.84-3.02 (m, 1 H) 3.02-3.21 (m, 1 H) 4.04-4.26 (m, 1 H) 4.38 (br. s., 1 H) 5.02 (s, 1 H) 5.71 (br. s., 1 H) 7.21-7.50 (m, 4 H) 7.55-7.72 (m, 2 H) 9.43 (br. s., 1 H). Mass Spectrum (CI$^+$) m/z=514.0 (M+1).

Example 80

2-((2S,5R,6R)-5-(2-Bromo-4-chlorophenyl)-6-(3-chlorophenyl)-4-(cyclopropylmethyl)-3-oxomorpholin-2-yl)acetic acid Second eluting isomer using chiral SFC separation as described in Example 62.

$^1$H NMR (400 MHz, CDCl$_3$) δ ppm ppm −0.07-0.16 (m, 2 H) 0.28-0.54 (m, 2 H) 0.69-0.92 (m, 1 H) 2.27 (dd, J=14.18, 6.94 Hz, 1 H) 3.07 (d, J=4.89 Hz, 2 H) 3.73-3.86 (m, 1 H) 4.51-4.68 (m, 1 H) 4.74 (t, J=4.21 Hz, 1 H) 5.26 (br. s., 1 H) 6.67 (d, J=7.63 Hz, 1 H) 6.97-7.13 (m, 2 H) 7.17-7.26 (m, 2 H) 7.32 (br. s., 1 H) 7.41 (br. s., 1 H) 9.04 (br. s., 1 H). Mass Spectrum (CI$^+$) m/z=514.0 (M+1).

Example 81

2-((2R,5R,6R)-6-(3-Chlorophenyl)-4-(cyclopropylmethyl)-3-oxo-5-(6-(trifluoromethyl)pyridin-3-yl)morpholin-2-yl)acetic acid First eluting isomer using chiral SFC separation as described in Example 62.

$^1$H NMR (400 MHz, CDCl$_3$) δ ppm 0.11-0.31 (m, 2 H) 0.49-0.74 (m, 2 H) 0.96-1.08 (m, 1 H) 2.29-2.45 (m, 1 H) 2.99 (br. s., 2 H) 4.07 (d, J=10.17 Hz, 1 H) 4.09-4.18 (m, 1 H) 4.42 (br. s., 1 H) 4.93 (br. s., 1 H) 5.23 (br. s., 1 H) 7.30-7.39 (m, 2 H) 7.52 (br. s., 1 H) 7.76 (br. s., 2 H) 7.95 (d, J=4.89 Hz, 1 H) 8.62 (br. s., 1 H). Mass Spectrum (CI$^+$) m/z=469.1 (M+1), 959.2 (2M+23).

Example 82

2-((2S,5R,6R)-6-(3-Chlorophenyl)-4-(cyclopropylmethyl)-3-oxo-5-(6-(trifluoromethyl)pyridin-3-yl)morpholin-2-yl)acetic acid Second eluting isomer using chiral SFC separation as described in Example 62.

$^1$H NMR (400 MHz, CDCl$_3$) δ ppm −0.04 (br. s., 2 H) 0.33-0.49 (m, 2 H) 0.75-0.83 (m, 1 H) 2.18-2.30 (m, 1 H) 2.89-3.14 (m, 2 H) 3.96 (d, J=9.98 Hz, 1 H) 4.64 (br. s., 1 H) 4.91 (d, J=9.19 Hz, 2 H) 6.68 (d, J=6.46 Hz, 1 H) 7.02-7.14 (m, 2 H) 7.22 (d, J=7.24 Hz, 2 H) 7.63 (br. s., 2 H) 8.25 (br. s., 1 H). Mass Spectrum (CI$^+$) m/z=469.1 (M+1), 959.2 (2M+23).

Examples 83 to 105 were also prepared by a procedure analogous to the one described in Example 9, Step B and Example 53, replacing (1R,2R)-2-amino-1-(3-chlorophenyl)-2-(4-chlorophenyl)ethanol (Intermediate A2) with the designated intermediates.

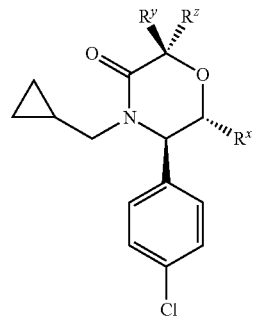

| Example | R$^x$ | R$^y$ | R$^z$ | Intermediate used |
|---|---|---|---|---|
| 83 | 3-Cl, 5-F phenyl | CH$_2$COOH | H | C1 |
| 84 | 3-Cl, 5-F phenyl | H | CH$_2$COOH | C1 |
| 85 | 3-F phenyl | CH$_2$COOH | H | C2 |
| 86 | 3-F phenyl | H | CH$_2$COOH | C2 |

-continued
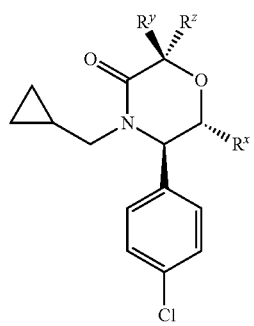
| Example | R<sup>x</sup> | R<sup>y</sup> | R<sup>z</sup> | Intermediate used |
|---|---|---|---|---|
| 87 | 5-chloropyridin-3-yl | -CH₂COOH | H | C3 |
| 88 | 5-chloropyridin-3-yl | H | -CH₂COOH | C3 |
| 89 | 3-methoxyphenyl | -CH₂COOH | H | C4 |
| 90 | 3-methoxyphenyl | H | -CH₂COOH | C4 |
| 91 | 2-chloropyridin-4-yl | H | -CH₂COOH | C5 |
| 92 | 5-methoxypyridin-3-yl | H | -CH₂COOH | C6 |
| 93 | 3,5-dichlorophenyl | H | -CH₂COOH | C7 |

-continued
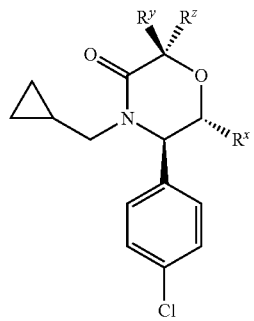
| Example | R$^x$ | R$^y$ | R$^z$ | Intermediate used |
|---|---|---|---|---|
| 94 | 3-Cl-4-F-phenyl | H | CH$_2$COOH | C8 |
| 95 | 3-OCF$_3$-phenyl | H | CH$_2$COOH | C9 |
| 96 | 3,5-diF-phenyl | CH$_2$COOH | H | C10 |
| 97 | 3,5-diF-phenyl | H | CH$_2$COOH | C10 |
| 98 | 3-CN-5-F-phenyl | CH$_2$COOH | H | C11 |
| 99 | 3-CN-5-F-phenyl | H | CH$_2$COOH | C11 |
| 100 | 2-F-5-Cl-phenyl | CH$_2$COOH | H | C12 |

-continued

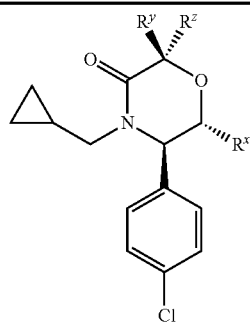

| Example | R$^x$ | R$^y$ | R$^z$ | Intermediate used |
|---|---|---|---|---|
| 101 | 2-F, 5-Cl phenyl | H | CH$_2$COOH | C12 |
| 102 | 3-Me phenyl | CH$_2$COOH | H | C14 |
| 103 | 3-Me phenyl | H | CH$_2$COOH | C14 |
| 104 | 3-Cl, 5-Br phenyl | CH$_2$COOH | H | C15 |
| 105 | 3-Cl, 5-Br phenyl | H | CH$_2$COOH | C15 |

Example 83

2-((2R,5R,6R)-6-(3-Chloro-5-fluorophenyl)-5-(4-chlorophenyl)-4-(cyclopropylmethyl)-3-oxomorpholin-2-yl)acetic acid First eluting isomer using chiral SFC separation as described in Example 62.

$^1$H NMR (400 MHz, CDCl$_3$) δ ppm 0.13-0.30 (m, 2 H) 0.58 (d, J=8.22 Hz, 1 H) 0.67 (d, J=4.30 Hz, 1 H) 0.96-1.08 (m, 1 H) 2.41 (dd, J=13.99, 7.53 Hz, 1 H) 2.95-3.04 (m, 1 H) 3.09-3.21 (m, 1 H) 4.09 (dd, J=13.89, 6.85 Hz, 1 H) 4.57 (br. s., 1 H) 4.88 (d, J=3.33 Hz, 1 H) 5.00 (d, J=3.52 Hz, 1 H) 6.28-6.38 (m, 1 H) 7.00 (d, J=8.61 Hz, 1 H) 7.07-7.17 (m, 3 H) 7.20 (s, 1 H) 7.38 (d, J=8.22 Hz, 2 H). Mass Spectrum (CI$^+$) m/z=451.0 (M+1), 927.1 (2M+23).

Example 84

2-((2S,5R,6R)-6-(3-Chloro-5-fluorophenyl)-5-(4-chlorophenyl)-4-(cyclopropylmethyl)-3-oxomorpholin-2-yl)acetic acid Second eluting isomer using chiral SFC separation as described in Example 62.

$^1$H NMR (400 MHz, CDCl$_3$) δ ppm 0.00 (d, J=3.91 Hz, 2 H) 0.43 (dd, J=15.06, 8.22 Hz, 2 H) 0.73-0.88 (m, 1 H) 1.20-1.25 (m, 1 H) 2.29 (dd, J=14.18, 7.53 Hz, 1 H) 3.12 (br. s., 2 H) 3.95 (dd, J=14.18, 6.36 Hz, 1 H) 4.57 (d, J=9.59 Hz, 1 H) 4.65-4.80 (m, 2 H) 6.54 (d, J=8.61 Hz, 1 H) 6.71 (s, 1 H) 6.90 (d, J=8.41 Hz, 2 H) 6.97 (dt, J=8.36, 1.98 Hz, 1 H) 7.28 (d, J=8.41 Hz, 2 H) 8.71 (br. s., 1 H). Mass Spectrum (CI$^+$) m/z=451.0 (M+1), 927.1 (2M+23).

Example 85

2-((2R,5R,6R)-5-(4-Chlorophenyl)-4-(cyclopropylmethyl)-6-(3-fluorophenyl)-3-oxomorpholin-2-yl)acetic acid First eluting isomer using chiral SFC separation as described in Example 62.
$^1$H NMR (400 MHz, CDCl$_3$) δ ppm 0.12-0.28 (m, 2 H) 0.54 (dd, J=8.12, 4.21 Hz, 1 H) 0.60-0.68 (m, 1 H) 1.01 (br. s., 1 H) 2.44 (dd, J=14.09, 7.63 Hz, 1 H) 2.96-3.05 (m, 1 H) 3.08-3.18 (m, 1 H) 4.06 (dd, J=13.99, 6.16 Hz, 1 H) 4.61 (d, J=7.63 Hz, 1 H) 4.90 (d, J=3.91 Hz, 1 H) 5.03 (d, J=3.91 Hz, 1 H) 7.07 (d, J=7.63 Hz, 2 H) 7.12 (d, J=8.02 Hz, 3 H) 7.32-7.39 (m, 3 H) 7.66 (br. s., 1 H). Mass Spectrum (CI$^+$) m/z=418.1 (M+1), 859.2 (2M+23).

Example 86

2-((2S,5R,6R)-5-(4-Chlorophenyl)-4-(cyclopropylmethyl)-6-(3-fluorophenyl)-3-oxomorpholin-2-yl)acetic acid Second eluting isomer using chiral SFC separation as described in Example 62.
$^1$H NMR (400 MHz, CDCl$_3$) δ ppm 0.00 (d, J=4.11 Hz, 2 H) 0.42 (dd, J=14.67, 8.02 Hz, 2 H) 0.77-0.89 (m, 1 H) 1.21-1.25 (m, 1 H) 2.29 (dd, J=14.18, 7.53 Hz, 1 H) 3.12 (t, J=4.40 Hz, 2 H) 3.96 (dd, J=14.09, 6.46 Hz, 1 H) 4.60 (d, J=9.59 Hz, 1 H) 4.71-4.80 (m, 2 H) 6.60 (d, J=7.63 Hz, 1 H) 6.78 (d, J=9.39 Hz, 1 H) 6.88 (d, J=8.22 Hz, 2 H) 6.93 (td, J=8.41, 2.54 Hz, 1 H) 7.13 (td, J=7.92, 6.06 Hz, 1 H) 7.25 (s, 1 H) 8.76 (br. s., 1 H). Mass Spectrum (CI$^+$) m/z=418.1 (M+1), 859.2 (2M+23).

Example 87

2-((2R,5R,6R)-5-(4-Chlorophenyl)-6-(5-chloropyridin-3-yl)-4-(cyclopropylmethyl)-3-oxomorpholin-2-yl)acetic acid First eluting isomer using chiral SFC separation as described in Example 62.
$^1$H NMR (400 MHz, CDCl$_3$) δ ppm ppm −0.10-0.10 (m, 2 H) 0.30-0.49 (m, 2 H) 0.62-0.83 (m, 4 H) 2.24 (dd, J=14.18, 7.53 Hz, 1 H) 2.81-3.09 (m, 2 H) 3.89 (dd, J=14.38, 6.94 Hz, 1 H) 4.47-4.62 (m, 1 H) 4.55 (br. s., 1 H) 4.74-4.91 (m, 4.75-4.92 (m, 2 H) 4.93-4.94 (m, 0 H) 6.93 (d, J=8.22 Hz, 2 H) 7.22 (d, J=8.22 Hz, 2 H) 7.72 (s, 1 H) 8.27 (br. s., 1 H) 8.45 (br. s., 1 H). Mass Spectrum (CI$^+$) m/z=435.1 (M+1), 891.1 (2M+23).

Example 88

2-((2S,5R,6R)-5-(4-Chlorophenyl)-6-(5-chloropyridin-3-yl)-4-(cyclopropylmethyl)-3-oxomorpholin-2-yl)acetic acid Second eluting isomer using chiral SFC separation as described in Example 62.
$^1$H NMR (400 MHz, CDCl$_3$) δ ppm 0.35-0.56 (m, 2 H) 0.83 (dd, J=10.96, 7.24 Hz, 2 H) 1.25 (s, 2 H) 2.33 (dd, J=14.18, 7.53 Hz, 1 H) 3.05-3.30 (m, 2 H) 4.00 (dd, J=14.09, 6.46 Hz, 1 H) 4.70-4.79 (m, 1 H) 4.80-4.88 (m, 2 H) 6.98 (d, J=8.22 Hz, 2 H) 7.36 (d, J=8.02 Hz, 2 H) 7.51 (s, 1 H) 8.23 (br. s., 1 H) 8.62 (br. s., 1 H) 10.09 (br. s., 1 H). Mass Spectrum (CI+) m/z=435.1 (M+1), 891.1 (2M+23).

Example 89

2-((2R,5R,6R)-5-(4-Chlorophenyl)-4-(cyclopropylmethyl)-6-(3-methoxyphenyl)-3-oxomorpholin-2-yl)acetic acid First eluting isomer using chiral SFC separation as described in Example 62.
$^1$H NMR (400 MHz, CDCl$_3$) δ ppm −0.05-0.11 (m, 2 H) 0.30-0.51 (m, 2 H) 0.67-0.77 (m, 1 H) 0.81-0.91 (m, 1 H) 1.00 (t, J=7.24 Hz, 1 H) 1.05-1.17 (m, 3 H) 2.25 (dd, J=14.08, 7.83 Hz, 1 H) 2.67 (d, J=7.43 Hz, 1 H) 2.75 (dd, J=15.85, 7.04 Hz, 1 H) 2.95 (dd, J=15.65, 5.87 Hz, 1 H) 3.62 (s, 3 H) 3.91 (dd, J=14.09, 6.46 Hz, 1 H) 4.38 (t, J=6.46 Hz, 1 H) 4.72 (d, J=3.52 Hz, 1 H) 4.91 (d, J=3.52 Hz, 1 H) 6.72 (dd, J=8.12, 2.05 Hz, 1 H) 6.75-6.81 (m, 2 H) 6.99 (d, J=8.61 Hz, 2 H) 7.06-7.14 (m, 2 H) 7.19 (d, 2 H). Mass Spectrum (CI$^+$) m/z=430.1 (M+1), 883.3 (2M+23).

Example 90

2-((2S,5R,6R)-5-(4-Chlorophenyl)-4-(cyclopropylmethyl)-6-(3-methoxyphenyl)-3-oxomorpholin-2-yl)acetic acid Second eluting isomer using chiral SFC separation as described in Example 62.
$^1$H NMR (400 MHz, CDCl$_3$) δ ppm 0.00 (d, J=4.11 Hz, 2 H) 0.41 (dd, J=16.43, 8.22 Hz, 2 H) 0.81-0.86 (m, 1 H) 1.22 (d, 1 H) 2.26 (dd, J=14.09, 7.63 Hz, 1 H) 2.82-2.90 (m, 1 H) 2.97-3.06 (m, 1 H) 3.08-3.17 (m, 1 H) 3.67 (s, 3 H) 3.97 (dd, J=14.18, 6.36 Hz, 1 H) 4.55 (d, J=9.59 Hz, 1 H) 4.70-4.81 (m, 2 H) 6.46-6.54 (m, 2 H) 6.76 (dd, J=8.12, 2.25 Hz, 1 H) 6.88 (d, J=8.41 Hz, 2 H) 7.09 (t, J=7.92 Hz, 1 H) 7.21 (s, 1 H). Mass Spectrum (CI$^+$) m/z=430.1 (M+1), 883.3 (2M+23).

Example 91

2-((2S,5R,6R)-5-(4-Chlorophenyl)-6-(2-chloropyridin-4-yl)-4-(cyclopropylmethyl)-3-oxomorpholin-2-yl)acetic acid Second eluting isomer using chiral SFC separation as described in Example 62.
$^1$H NMR (400 MHz, CDCl$_3$) δ ppm −0.03-0.08 (m, 2 H) 0.37-0.56 (m, 2 H) 0.77-0.90 (m, 1 H) 2.31 (dd, J=14.18, 7.53 Hz, 1 H) 3.17 (dd, J=5.09, 2.93 Hz, 2 H) 4.00 (dd, J=14.28, 6.46 Hz, 1 H) 4.63-4.73 (m, 2 H) 4.78 (t, J=5.18 Hz, 1 H) 6.66 (dd, J=5.18, 1.27 Hz, 1 H) 6.96 (d, J=8.22 Hz, 2 H) 7.05 (s, 1 H) 7.35 (d, J=8.02 Hz, 2 H) 8.26 (d, J=5.09 Hz, 1 H) 8.59 (br. s., 1 H). Mass Spectrum (CI$^+$) m/z=435.1 (M+1), 893.2 (2M+23).

Example 92

2-((2S,5R,6R)-5-(4-Chlorophenyl)-4-(cyclopropylmethyl)-6-(5-methoxypyridin-3-yl)-3-oxomorpholin-2-yl)acetic acid First eluting isomer using chiral SFC separation as described in Example 62.
$^1$H NMR (400 MHz, CDCl$_3$) δ ppm −0.01 (br. s., 2 H) 0.46 (br. s., 2 H) 0.77-0.90 (m, 1 H) 1.18-1.31 (m, 2 H) 2.36 (d, J=7.04 Hz, 1 H) 3.04-3.25 (m, 2 H) 3.98 (br. s., 1 H) 4.77-4.91 (m, 2 H) 4.96 (d, J=7.83 Hz, 1 H) 6.96-7.16 (m, 3 H) 7.39 (d, J=7.43 Hz, 2 H) 8.31-8.45 (m, 1 H). Mass Spectrum (CI$^+$) m/z=431.2 (M+1), 863.2 (2M+1).

Example 93

2-((2S,5R,6R)-5-(4-Chlorophenyl)-4-(cyclopropylmethyl)-6-(3,5-dichlorophenyl)-3-oxomorpholin-2-yl)acetic acid Second eluting isomer using chiral SFC separation as described in Example 62.
$^1$H NMR (400 MHz, CDCl$_3$) δ ppm 0.04 (ddd, J=3.23, 1.47, 1.17 Hz, 2 H) 0.38-0.53 (m, 2 H) 0.78-0.90 (m, 1 H) 2.31 (dd, J=14.18, 7.53 Hz, 1 H) 3.04-3.14 (m, 1 H) 3.14-3.23 (m, 1 H) 4.01 (dd, J=14.18, 6.55 Hz, 1 H) 4.57 (d, J=9.59 Hz, 1 H) 4.68-4.80 (m, 2 H) 6.83 (d, J=1.96 Hz, 2 H) 6.89-6.97 (m, 2 H) 7.22-7.29 (m, 2 H) 7.32 (d, J=8.61 Hz, 2 H). Mass Spectrum (CI$^+$) m/z=468.1 (M+1), 961.0 (2M+23).

Example 94

2-((2S,5R,6R)-6-(3-Chloro-4-fluorophenyl)-5-(4-chlorophenyl)-4-(cyclopropylmethyl)-3-oxomorpholin-2-yl)acetic acid Second eluting isomer using chiral SFC separation as described in Example 62.
$^1$H NMR (400 MHz, CDCl$_3$) δ ppm 0.00 (d, J=2.35 Hz, 2 H) 0.43 (dd, J=16.24, 8.02 Hz, 2 H) 0.83 (br. s., 1 H) 2.28 (dd, J=13.89, 7.24 Hz, 1 H) 3.10 (br. s., 2 H) 3.93-4.03 (m, 1 H) 4.57 (d, J=9.59 Hz, 1 H) 4.70 (d, J=9.59 Hz, 2 H) 4.74 (d, J=2.74 Hz, 2 H) 6.62-6.72 (m, 1 H) 6.84-7.00 (m, 3 H) 7.14 (d, J=6.06 Hz, 1 H) 7.21-7.33 (m, 1 H). Mass Spectrum (CI$^+$) m/z=452.0 (M+1), 925.2 (2M+23).

Example 95

2-((2S,5R,6R)-5-(4-Chlorophenyl)-4-(cyclopropylmethyl)-3-oxo-6-(3-(trifluoromethoxy)phenyl)morpholin-2-yl)acetic acid Second eluting isomer using chiral SFC separation as described in Example 62.
$^1$H NMR (400 MHz, CDCl$_3$) δ ppm 0.02 (d, J=3.33 Hz, 2 H) 0.37-0.52 (m, 2 H) 0.79-0.90 (m, 1 H) 1.19-1.28 (m, 1 H) 2.30 (dd, J=14.09, 7.63 Hz, 1 H) 3.03-3.20 (m, 2 H) 4.00 (dd, J=14.18, 6.36 Hz, 1 H) 4.60-4.69 (m, 1 H) 4.70-4.75 (m, 1 H) 4.79 (br. s., 1 H) 6.78 (s, 1 H) 6.89 (d, J=8.41 Hz, 2 H) 6.94 (d, J=7.82 Hz, 1 H) 7.12 (d, J=8.22 Hz, 1 H) 7.23-7.26 (m, 2 H) 7.27 (s, 1 H). Mass Spectrum (CI$^+$) m/z=483.1 (M+1), 991.2 (2M+23).

Example 96

2-((2R,5R,6R)-5-(4-Chlorophenyl)-4-(cyclopropylmethyl)-6-(3,5-difluorophenyl)-3-oxomorpholin-2-yl)acetic acid First eluting isomer using chiral SFC separation as described in Example 62.
$^1$H NMR (400 MHz, CDCl$_3$) δ ppm −0.04-0.12 (m, 2 H) 0.30-0.51 (m, 2 H) 0.80-0.88 (m, 2 H) 2.22 (dd, J=14.18, 7.73 Hz, 1 H) 2.76 (dd, J=16.24, 7.24 Hz, 1 H) 2.96 (dd, J=16.24, 5.28 Hz, 1 H) 3.86-3.93 (m, 1 H) 4.34 (dd, J=7.14, 5.38 Hz, 1 H) 4.69 (d, J=3.72 Hz, 1 H) 4.82 (d, J=3.52 Hz, 1 H) 6.59-6.67 (m, 1 H) 6.76 (d, J=6.06 Hz, 2 H) 6.95 (d, J=8.41 Hz, 2 H) 7.19 (d, 2 H). Mass Spectrum (CI$^+$) m/z=436.1 (M+1), 895.2 (2M+23).

Example 97

2-((2S,5R,6R)-5-(4-Chlorophenyl)-4-(cyclopropylmethyl)-6-(3,5-difluorophenyl)-3-oxomorpholin-2-yl)acetic acid Second eluting isomer using chiral SFC separation as described in Example 62.
$^1$H NMR (400 MHz, CDCl$_3$) δ ppm 0.00 (br. s., 2 H) 0.42 (dd, J=19.56, 8.22 Hz, 2 H) 0.80-0.90 (m, 2 H) 2.27 (dd, J=13.79, 7.34 Hz, 1 H) 2.97-3.15 (m, 2 H) 3.97 (dd, J=13.79, 5.77 Hz, 1 H) 4.57-4.66 (m, 1 H) 4.71 (d, J=9.39 Hz, 1 H) 4.81 (br. s., 1 H) 6.50 (d, J=5.87 Hz, 2 H) 6.69 (t, J=8.61 Hz, 1 H) 6.94 (d, J=7.83 Hz, 2 H) 7.28 (d, 1 H) 7.30 (s, 1 H). Mass Spectrum (CI$^+$) m/z=436.1 (M+1), 895.2 (2M+23).

Example 98

2-((2R,5R,6R)-5-(4-Chlorophenyl)-6-(3-cyano-5-fluorophenyl)-4-(cyclopropylmethyl)-3-oxomorpholin-2-yl)acetic acid First eluting isomer using chiral SFC separation as described in Example 62.
$^1$H NMR (400 MHz, CDCl$_3$) δ ppm −0.05-0.11 (m, 2 H) 0.35-0.53 (m, 2 H) 0.76-0.88 (m, 1 H) 2.24 (dd, J=14.28, 7.63 Hz, 1 H) 2.86 (dd, J=16.53, 8.12 Hz, 1 H) 2.93-3.06 (m, 1 H) 3.90 (dd, J=14.28, 6.65 Hz, 1 H) 4.50 (dd, J=8.12, 4.01 Hz, 1 H) 4.76 (q, J=4.89 Hz, 2 H) 6.93 (d, J=8.22 Hz, 2 H) 7.10 (s, 1 H) 7.22 (d, J=8.41 Hz, 2 H) 7.34 (d, J=15.45 Hz, 2 H) 7.46 (s, 1 H). Mass Spectrum (CI$^+$) m/z=459.1 (M+1), 941.0 (2M+23).

Example 99

2-((2S,5R,6R)-5-(4-Chlorophenyl)-6-(3-cyano-5-fluorophenyl)-4-(cyclopropylmethyl)-3-oxomorpholin-2-yl)acetic acid Second eluting isomer using chiral SFC separation as described in Example 62.
$^1$H NMR (400 MHz, CDCl$_3$) δ ppm −0.02-0.03 (m, 2 H) 0.36-0.52 (m, 2 H) 0.76-0.88 (m, 1 H) 2.30 (dd, J=14.28, 7.63 Hz, 1 H) 3.16 (dd, J=9.19, 5.09 Hz, 2 H) 3.53 (s, 1 H) 3.93-4.03 (m, 2 H) 4.63-4.74 (m, 2 H) 4.77 (t, J=4.79 Hz, 1 H) 6.88-6.95 (m, 2 H) 7.09-7.16 (m, 2 H) 7.32 (d, J=8.41 Hz, 2 H) 7.52 (t, J=1.76 Hz, 1 H). Mass Spectrum (CI$^+$) m/z=459.1 (M+1), 941.1 (2M+23).

Example 100

2-((2R,5R,6R)-6-(5-Chloro-2-fluorophenyl)-5-(4-chlorophenyl)-4-(cyclopropylmethyl)-3-oxomorpholin-2-yl)acetic acid First eluting isomer using chiral SFC separation as described in Example 62.
$^1$H NMR (400 MHz, CDCl$_3$) δ ppm 0.00 (br. s., 2 H) 0.42 (dd, J=14.57, 8.71 Hz, 2 H) 0.78-0.96 (m, 2 H) 2.28 (dd, J=13.50, 7.43 Hz, 1 H) 2.95-3.17 (m, 2 H) 3.99 (dd, J=13.79, 5.18 Hz, 1 H) 4.72-4.88 (m, 2 H) 4.97 (d, J=9.19 Hz, 1 H) 6.72 (t, J=8.51 Hz, 1 H) 6.94 (d, J=7.24 Hz, 2 H) 7.13-7.33 (m, 3 H) 7.51 (br. s., 1 H). Mass Spectrum (CI$^+$) m/z=452.0 (M+1), 927.1 (2M+23).

Example 101

2-((2S,5R,6R)-6-(5-Chloro-2-fluorophenyl)-5-(4-chlorophenyl)-4-(cyclopropylmethyl)-3-oxomorpholin-2-yl)acetic acid Second eluting isomer using chiral SFC separation as described in Example 62.

$^1$H NMR (400 MHz, CDCl$_3$) δ ppm 0.01 (d, J=3.72 Hz, 2 H) 0.40 (dd, J=17.80, 8.02 Hz, 2 H) 0.79-0.88 (m, 1 H) 0.92 (t, J=7.24 Hz, 1 H) 1.06-1.13 (m, 2 H) 2.21 (dd, J=14.09, 7.43 Hz, 1 H) 2.64 (q, J=7.11 Hz, 1 H) 2.76-2.86 (m, 1 H) 2.88-2.96 (m, 1 H) 3.89 (dd, J=13.89, 6.65 Hz, 1 H) 3.92-4.01 (m, 1 H) 4.51 (br. s., 1 H) 4.73 (d, J=5.28 Hz, 1 H) 5.00 (d, J=5.09 Hz, 1 H) 6.74 (t, J=9.10 Hz, 1 H) 6.94 (d, J=8.22 Hz, 2 H) 7.12-7.20 (m, 3 H) 7.48 (dd, 1 H). Mass Spectrum (CI$^+$) m/z=452.0 (M+1), 927.1 (2M+23).

Example 102

2-((2R,5R,6R)-5-(4-Chlorophenyl)-4-(cyclopropylmethyl)-3-oxo-6-(m-tolyl)morpholin-2-yl)acetic acid First eluting isomer using chiral SFC separation as described in Example 62.

$^1$H NMR (400 MHz, CDCl$_3$) δ ppm 0.17-0.35 (m, 2 H) 0.48-0.75 (m, 2 H) 1.02-1.16 (m, 1 H) 2.37 (s, 3 H) 2.43-2.53 (m, 1 H) 2.90 (dd, J=15.94, 4.99 Hz, 1 H) 3.15 (dd, J=16.04, 8.02 Hz, 1 H) 4.02-4.15 (m, 1 H) 4.37 (d, J=14.08 Hz, 1 H) 4.37 (s, 1 H) 4.90 (d, J=2.35 Hz, 1 H) 5.13 (d, J=2.54 Hz, 1 H) 7.13-7.23 (m, 3 H) 7.27 (s, 3 H) 7.31 (br. s., 1 H) 7.34-7.42 (m, 1 H). Mass Spectrum (CI$^+$) m/z=414.1 (M+1), 851.2 (2M+23).

Example 103

2-((2S,5R,6R)-5-(4-Chlorophenyl)-4-(cyclopropylmethyl)-3-oxo-6-(m-tolyl)morpholin-2-yl)acetic acid Second eluting isomer using chiral SFC separation as described in Example 62.

$^1$H NMR (400 MHz, CDCl$_3$) δ ppm 0.05 (d, J=3.72 Hz, 2 H) 0.38-0.54 (m, 2 H) 0.84-0.94 (m, 1 H) 1.25-1.30 (m, 1 H) 2.28 (s, 3 H) 2.31-2.42 (m, 1 H) 3.16 (br. s., 2 H) 4.00 (dd, J=14.18, 6.36 Hz, 1 H) 4.59 (d, J=9.39 Hz, 1 H) 4.79 (br. s., 1 H) 4.84 (d, J=9.59 Hz, 1 H) 6.73 (d, J=6.65 Hz, 1 H) 6.85 (s, 1 H) 6.90 (d, J=8.41 Hz, 2 H) 7.06-7.12 (m, 2 H) 7.27 (d, J=3.13 Hz, 1 H) 9.44 (br. s., 1 H). Mass Spectrum (CI$^+$) m/z=414.1 (M+1), 851.2 (2M+23).

Example 104

2-((2R,5R,6R)-6-(3-Bromo-5-chlorophenyl)-5-(4-chlorophenyl)-4-(cyclopropylmethyl)-3-oxomorpholin-2-yl)acetic acid First eluting isomer using chiral SFC separation as described in Example 62.

$^1$H NMR (400 MHz, CDCl$_3$) δ ppm −0.01 (dd, J=3.03, 1.66 Hz, 2 H) 0.35-0.48 (m, 2 H) 0.73-0.88 (m, 1 H) 2.27 (dd, J=14.28, 7.43 Hz, 1 H) 3.00-3.22 (m, 2 H) 3.97 (dd, J=14.28, 6.65 Hz, 1 H) 4.53 (d, J=9.59 Hz, 1 H) 4.67 (d, J=9.59 Hz, 1 H) 4.72 (t, J=5.18 Hz, 1 H) 6.83 (t, J=1.47 Hz, 1 H) 6.88 (s, 1 H) 6.91 (d, J=3.13 Hz, 2 H) 7.29 (d, J=8.41 Hz, 2 H) 7.38 (t, J=1.76 Hz, 1 H) 7.59 (br. s., 1 H). Mass Spectrum (CI$^+$) m/z=514.0 (M+1).

Example 105

2-((2S,5R,6R)-6-(3-Bromo-5-chlorophenyl)-5-(4-chlorophenyl)-4-(cyclopropylmethyl)-3-oxomorpholin-2-yl)acetic acid Second eluting isomer using chiral SFC separation as described in Example 62.

$^1$H NMR (400 MHz, CDCl$_3$) δ ppm −0.02 (d, J=19.76 Hz, 2 H) 0.24-0.51 (m, 2 H) 0.79 (br. s., 1 H) 0.91-1.02 (m, 2 H) 1.02-1.14 (m, 1 H) 2.02-2.22 (m, 1 H) 2.59-2.77 (m, 2 H) 2.85 (d, J=11.54 Hz, 1 H) 3.78-3.97 (m, 1 H) 4.43 (br. s., 1 H) 4.59-4.76 (m, 2 H) 6.91 (d, J=7.24 Hz, 2 H) 7.01-7.11 (m, 3 H) 7.11-7.22 (m, 3 H). Mass Spectrum (CI$^+$) m/e=514.0 (M+1).

Example 106

2-((2R,5R,6R)-6-(3-Chloro-5-(1H-pyrazol-4-yl)phenyl)-5-(4-chlorophenyl)-4-(cyclopropylmethyl)-3-oxomorpholin-2-yl)acetic acid

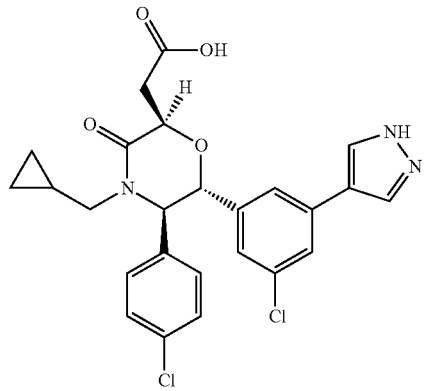 [SMILES: O=C(O)C[C@H]1O[C@H](c2cc(Cl)cc(-c3cn[nH]c3)c2)[C@@H](c2ccc(Cl)cc2)N(CC2CC2)C1=O]

Step A. tert-Butyl 2-((2R,5R,6R)-6-(3-bromo-5-chlorophenyl)-5-(4-chlorophenyl)-4-(cyclopropylmethyl)-3-oxomorpholin-2-yl)acetate and tert-Butyl 2-((2S,5R,6R)-6-(3-bromo-5-chlorophenyl)-5-(4-chlorophenyl)-4-(cyclopropylmethyl)-3-oxomorpholin-2-yl)acetate

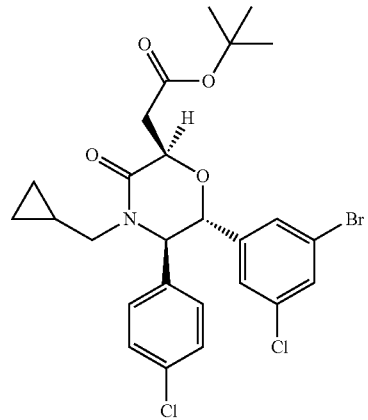

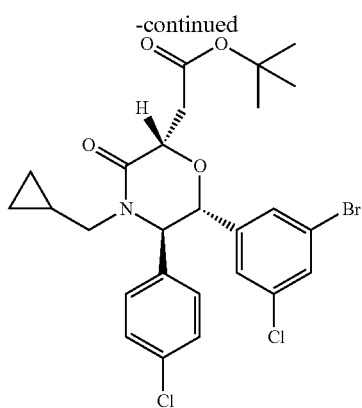

The title compound was prepared by a procedure analogous to the one described in Example 9, step A to ttep D, replacing (1R,2R)-2-amino-1-(3-chlorophenyl)-2-(4-chlorophenyl)ethanol (Intermediate A2) with (1R,2R)-2-amino-1-(3-bromo-5-chlorophenyl)-2-(4-chlorophenyl)ethanol (Intermediate C15).

Step B. tert-Butyl 2-((2R,5R,6R)-6-(3-chloro-5-(1H-pyrazol-4-yl)phenyl)-5-(4-chlorophenyl)-4-(cyclopropylmethyl)-3-oxomorpholin-2-yl)acetate and tert-Butyl 2-((2S,5R,6R)-6-(3-chloro-5-(1H-pyrazol-4-yl)phenyl)-5-(4-chlorophenyl)-4-(cyclopropylmethyl)-3-oxomorpholin-2-yl)acetate

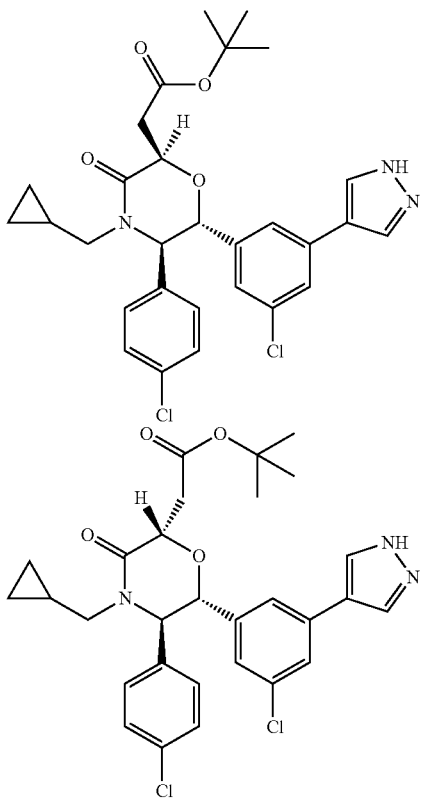

A mixture of tert-Butyl 2-((2R,5R,6R)-6-(3-bromo-5-chlorophenyl)-5-(4-chlorophenyl)-4-(cyclopropylmethyl)-3-oxomorpholin-2-yl)acetate and tert-butyl 2-((2S,5R,6R)-6-(3-bromo-5-chlorophenyl)-5-(4-chlorophenyl)-4-(cyclopropylmethyl)-3-oxomorpholin-2-yl)acetate (100 mg, 0.176 mmol, Example 106, Step A), tert-butyl 4-(4,4,5,5-tetramethyl-1,3,2-dioxaborolan-2-yl)-1H-pyrazole-1-carboxylate (155 mg, 0.527 mmol; Acros Organics, Belgium), 1,1'-bis(diphenylphosphino)ferrocene-palladium dichloride (7.17 mg, 8.78 μmol; Strem Chemicals, Inc., Newburyport, Mass.) and sodium carbonate (0.314 mL, 0.878 mmol) in 1 mL of water were mixed in 1 mL of dioxane. The reaction mixture was purged with nitrogen for a few minutes. The mixture was heated to 100° C. for 16 hours. After cooling to rt, the reaction mixture was filtered through a Chem Elut™ cartridge (Agilent technologies, Santa Clara, Calif.), washed with 50 mL of DCM and concentrated in vacuo. The crude material was purified by chromatography on silica gel (0 to 100% EtOAc/Hexane, gradient elution) to provide the title compounds as a mixture of two diastereomers, which was used in the next step without further purification or separation.

Mass Spectrum (ESI) m/z=556.2 (M+1).

Step C. 2-((2R,5R,6R)-6-(3-Chloro-5-(1H-pyrazol-4-yl)phenyl)-5-(4-chlorophenyl)-4-(cyclopropylmethyl)-3-oxomorpholin-2-yl)acetic acid A mixture of tert-butyl 2-((2R,5R,6R)-6-(3-chloro-5-(1H-pyrazol-4-yl)phenyl)-5-(4-chlorophenyl)-4-(cyclopropylmethyl)-3-oxomorpholin-2-yl)acetate and tert-butyl 2-((2S,5R,6R)-6-(3-chloro-5-(1H-pyrazol-4-yl)phenyl)-5-(4-chlorophenyl)-4-(cyclopropylmethyl)-3-oxomorpholin-2-yl)acetate (59 mg, 0.106 mmol, Example 106, Step B) in 2 mL of DCM was treated with 1 mL of TFA at rt for 2 h. The reaction mixture was evaporated to dryness and purified on a 12 g silica gel column (0 to 100% EtOAc/hexanes, gradient elution) to provide 17 mg of white solid as a mixture of two diastereomers. The mixture was concentrated under reduced pressure. Chiral purification was carried out via SFC using MeOH (0.2% DEA)+60 g/min $CO_2$ on a Thar 80 SFC. Outlet pressure 100 bar; Temp. 20° C.; Wavelength 220 nm. Toluene followed by ethanol was used to azeotrope off the diethylamine employed as co-solvent during SFC. The title compound was obtained as the first eluting isomer. $^1$H NMR (400 MHz, $CDCl_3$) δ ppm 0.06-0.24 (m, 2 H) 0.49 (tt, J=8.71, 4.60 Hz, 1 H) 0.59 (tt, J=8.51, 4.50 Hz, 1 H) 0.91-1.03 (m, 1 H) 1.14 (t, J=7.24 Hz, 6 H) 2.33 (dd, J=14.18, 7.73 Hz, 1 H) 2.77 (q, J=7.24 Hz, 4 H) 2.94 (dd, J=15.06, 10.56 Hz, 1 H) 3.10 (dd, J=15.26, 3.13 Hz, 1 H) 4.08 (dd, J=14.09, 6.46 Hz, 1 H) 4.89 (dd, J=10.56, 3.13 Hz, 1 H) 4.92-5.01 (m, 2 H) 7.06-7.13 (m, 3 H) 7.22 (s, 1 H) 7.29-7.35 (m, 3 H) 7.55 (s, 2 H). Mass Spectrum (CI$^+$) m/z=500.0 (M+1).

Example 107

2-((2S,5R,6R)-6-(3-Chloro-5-(1H-pyrazol-4-yl)phenyl)-5-(4-chlorophenyl)-4-(cyclopropylmethyl)-3-oxomorpholin-2-yl)acetic acid

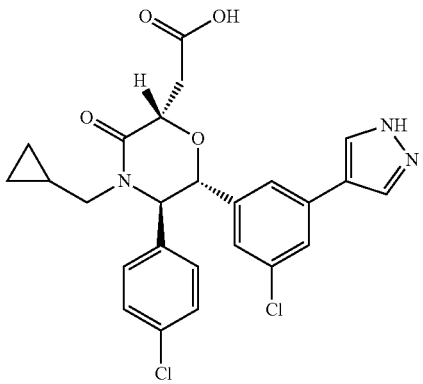 [SMILES: O=C(O)C[C@@H]1O[C@H](c2cc(Cl)cc(-c3cn[nH]c3)c2)[C@@H](c2ccc(Cl)cc2)N(CC2CC2)C1=O]

The title compound was obtained as the second eluting isomer from Example 106, Step C. ¹H NMR (400 MHz, CDCl₃) δ ppm −0.02-0.07 (m, 2 H) 0.32-0.49 (m, 2 H) 0.79-0.88 (m, 1 H) 1.22 (t, J=7.24 Hz, 6 H) 2.30 (dd, J=14.28, 7.63 Hz, 1 H) 2.73-2.93 (m, 5 H) 3.24 (dd, J=15.85, 3.33 Hz, 1 H) 4.01 (dd, J=14.18, 6.36 Hz, 1 H) 4.49 (d, J=9.59 Hz, 1 H) 4.68 (d, J=9.59 Hz, 1 H) 4.92 (dd, J=8.71, 3.42 Hz, 1 H) 6.51 (s, 1 H) 6.86 (s, 1 H) 6.95 (d, J=8.22 Hz, 2 H) 7.16 (s, 1 H) 7.30 (s, 2 H) 7.37 (s, 2 H). Mass Spectrum (CI⁺) m/z=500.0 (M+1).

Example 108

2-((2R,5R,6R)-6-(3-Chloro-5-(pyrimidin-5-yl)phenyl)-5-(4-chlorophenyl)-4-(cyclopropylmethyl)-3-oxomorpholin-2-yl)acetic acid

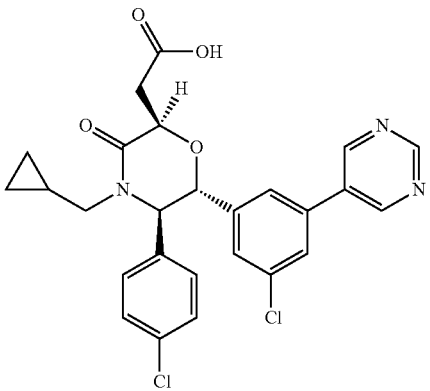 [SMILES: O=C(O)C[C@H]1O[C@H](c2cc(Cl)cc(-c3cncnc3)c2)[C@@H](c2ccc(Cl)cc2)N(CC2CC2)C1=O]

The title compound was obtained by a procedure analogous to the one described in Example 106 Step B and Step C, replacing tert-butyl 4-(4,4,5,5-tetramethyl-1,3,2-dioxaborolan-2-yl)-1H-pyrazole-1-carboxylate with pyrimidin-5-ylboronic acid (Combi-Blocks Inc., San Diego, Calif.), as the first eluting isomer using chiral SFC separation as described in Example 106, Step C. ¹H NMR (400 MHz, CDCl₃) δ ppm 0.13 (dq, J=9.51, 4.85 Hz, 1 H) 0.21 (dq, J=9.44, 4.68 Hz, 1 H) 0.50 (tt, J=8.73, 4.57 Hz, 1 H) 0.56-0.65 (m, 1 H) 0.80-1.04 (m, 2 H) 1.20 (t, J=7.34 Hz, 6 H) 2.34 (dd, J=14.08, 7.63 Hz, 1 H) 2.89 (q, J=7.37 Hz, 4 H) 3.07 (dd, J=15.75, 3.42 Hz, 1 H) 4.08 (dd, J=14.09, 6.46 Hz, 1 H) 4.78 (dd, J=9.10, 3.42 Hz, 1 H) 5.00 (s, 2 H) 7.15 (d, J=8.22 Hz, 2 H) 7.33-7.39 (m, 3 H) 7.47-7.53 (m, 2 H) 8.89 (s, 2 H) 9.21 (s, 1 H). Mass Spectrum (CI⁺) m/z=512.0 (M+1).

Example 109

2-((2S,5R,6R)-6-(3-Chloro-5-(pyrimidin-5-yl)phenyl)-5-(4-chlorophenyl)-4-(cyclopropylmethyl)-3-oxomorpholin-2-yl)acetic acid

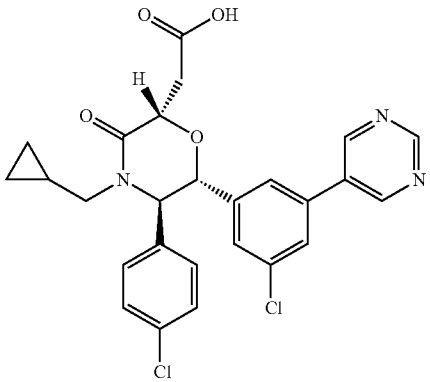 [SMILES: O=C(O)C[C@@H]1O[C@H](c2cc(Cl)cc(-c3cncnc3)c2)[C@@H](c2ccc(Cl)cc2)N(CC2CC2)C1=O]

The title compound was obtained by a procedure analogous to the one described in Example 106 Step B and Step C, replacing tert-butyl 4-(4,4,5,5-tetramethyl-1,3,2-dioxaborolan-2-yl)-1H-pyrazole-1-carboxylate with pyrimidin-5-ylboronic acid (Combi-Blocks Inc., San Diego, Calif.), as the second eluting isomer using chiral SFC separation as described in Example 106, Step C. ¹H NMR (400 MHz, CDCl₃) δ ppm −0.03-0.07 (m, 2H) 0.35-0.43 (m, 1 H) 0.43-0.51 (m, 1 H) 0.81-0.90 (m, 1 H) 1.19-1.26 (m, 6 H) 2.31 (dd, J=14.08, 7.63 Hz, 1 H) 2.86 (q, J=7.30 Hz, 4 H) 3.13 (dd, J=16.04, 4.50 Hz, 1 H) 3.49 (q, J=7.04 Hz, 1 H) 4.01 (dd, J=14.28, 6.26 Hz, 1 H) 4.68-4.78 (m, 2 H) 4.87 (dd, J=6.94, 4.60 Hz, 1 H) 6.79 (t, J=1.37 Hz, 1 H) 6.98 (d, J=8.41 Hz, 2 H) 7.25 (t, J=1.57 Hz, 1 H) 7.32 (d, J=8.41 Hz, 2 H) 7.44 (t, J=1.86 Hz, 1 H) 8.69 (s, 2 H) 9.22 (s, 1 H). Mass Spectrum (CI⁺) m/z=512.0 (M+1).

Example 110

2-((2R,5R,6R)-6-(3-Chloro-5-(methylsulfonyl)phenyl)-5-(4-chlorophenyl)-4-(cyclopropylmethyl)-3-oxomorpholin-2-yl)acetic acid

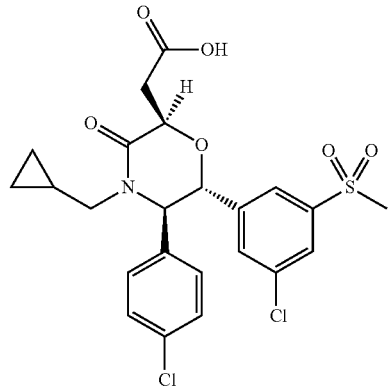 [SMILES: CS(=O)(=O)c1cc(Cl)cc([C@H]2O[C@H](CC(=O)O)C(=O)N(CC3CC3)[C@@H]2c2ccc(Cl)cc2)c1]

A mixture of tert-Butyl 2-((2R,5R,6R)-6-(3-bromo-5-chlorophenyl)-5-(4-chlorophenyl)-4-(cyclopropylmethyl)-3-oxomorpholin-2-yl)acetate and tert-butyl 2-((2S,5R,6R)-

6-(3-bromo-5-chlorophenyl)-5-(4-chlorophenyl)-4-(cyclopropylmethyl)-3-oxomorpholin-2-yl)acetate (51 mg, 0.090 mmol, Example 106, Step A), copper (I) iodide (4.55 mg, 0.134 mmol) and methanesulphinic acid, sodium salt (36.6 mg, 0.358 mmol) were mixed in DMF. N,N'-dimethyl-ethylenediamine (0.048 mL, 0.448 mmol) was injected. The reaction mixture was purged with nitrogen for 1 minute, then heated to 125° C. for 16 hours. After cooling to rt, the reaction mixture was partitioned between EtOAc and water and the layers were separated. The organic layer was washed with brine, dried over MgSO$_4$, filtered and the filtrate was concentrated in vacuo. The crude material was purified by chromatography on silica gel (0 to 100%, EtOAc/hexane, gradient elution) to provide 103 mg of product as a mixture of two diastereomers. Chiral purification was carried out via SFC using MeOH (0.2% DEA)+60 g/min CO$_2$ on a Thar 80 SFC. Outlet pressure 100 bar; Temp. 20° C.; Wavelength 220 nm. The pooled fractions containing the first eluting isomer were treated with 1 mL TFA/DCM (1:2) at room temperature for 2 hours, concentrated in vacuo, and purified by reverse phase HPLC on a 250×30 mm 10 μm C$_{18}$ column (Phenomenex, Torrance, Calif.; 10 to 90% MeCN/water with 0.1% TFA) to provide the title compound. $^1$H NMR (400 MHz, CDCl$_3$) δ ppm 0.11-0.29 (m, 2 H) 0.52-0.63 (m, 1 H) 0.65-0.76 (m, 1 H) 0.94-1.08 (m, 1 H) 2.37-2.39 (m, J=13.89 Hz, 1 H) 2.96 (dd, J=16.63, 8.02 Hz, 1 H) 3.04 (s, 3 H) 3.21 (dd, J=16.53, 4.60 Hz, 1 H) 4.12 (dd, J=13.99, 6.55 Hz, 1 H) 4.60 (dd, J=7.83, 4.30 Hz, 1 H) 4.97 (d, J=4.11 Hz, 1 H) 5.04 (d, J=4.11 Hz, 1 H) 7.12 (d, J=8.22 Hz, 2 H) 7.40 (d, J=8.41 Hz, 2 H) 7.67 (s, 1 H) 7.76 (s, 1 H) 7.92 (s, 1 H). Mass Spectrum (CI$^+$) m/z=512.0 (M+1).

Example 111

2-((2S,5R,6R)-6-(3-Chloro-5-(methylsulfonyl)phenyl)-5-(4-chlorophenyl)-4-(cyclopropylmethyl)-3-oxomorpholin-2-yl)acetic acid

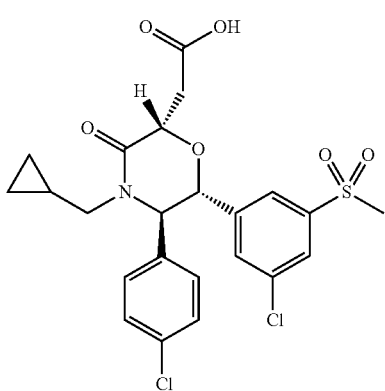 [SMILES: CS(=O)(=O)c1cc(Cl)cc([C@H]2O[C@@H](CC(=O)O)C(=O)N(CC3CC3)[C@@H]2c2ccc(Cl)cc2)c1]

The title compound was obtained in Example 110. The pooled fractions containing the second eluting isomer after chiral SFC separation were treated with 1 mL TFA/DCM (1:2) at room temperature for 2 hours, concentrated in vacuo, and purified by reverse phase HPLC on a 250×30 mm 10 μm C$_{18}$ column (Phenomenex, Torrance, Calif.; 10 to 90% MeCN/water with 0.1% TFA) to provide the title compound. $^1$H NMR (400 MHz, CDCl$_3$) δ ppm −0.01-0.08 (m, 2 H) 0.39-0.54 (m, 2 H) 0.77-0.93 (m, 1 H) 2.34 (dd, J=14.18, 7.53 Hz, 1 H) 2.93 (s, 3 H) 3.10-3.24 (m, 2 H) 4.02 (dd, J=14.28, 6.46 Hz, 1 H) 4.72 (s, 2 H) 4.80 (t, J=5.28 Hz, 1 H) 6.94 (d, J=8.41 Hz, 2 H) 7.24-7.26 (m, 1 H) 7.28 (s, 1 H) 7.33 (d, J=8.41 Hz, 2 H) 7.84 (t, J=1.76 Hz, 1 H). Mass Spectrum (CI$^+$) m/z=512.0 (M+1)

Example 112

2-((2R,5R,6R)-6-(3-Chlorophenyl)-5-(4-chlorophenyl)-4-((S)-1-(ethylsulfonyl)butan-2-yl)-3-oxomorpholin-2-yl)acetic acid or 2-((2S,5R,6R)-6-(3-Chlorophenyl)-5-(4-chlorophenyl)-4-((S)-1-(ethylsulfonyl)butan-2-yl)-3-oxomorpholin-2-yl) acetic acid (Isomer 1)

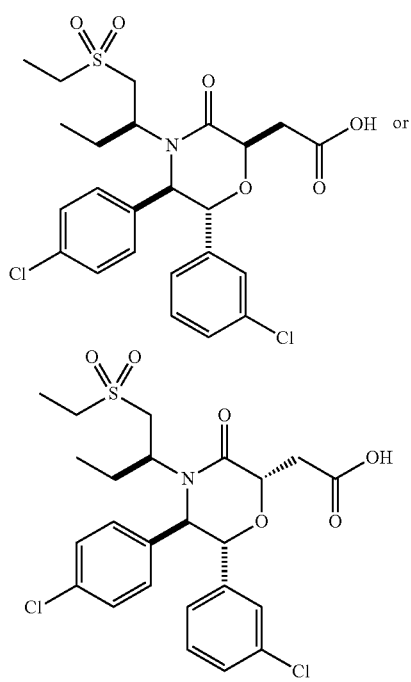

Step A. (5R,6R)-6-(3-Chlorophenyl)-5-(4-chlorophenyl)morpholin-3-one

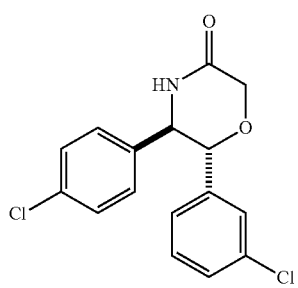 [SMILES: O=C1CO[C@H](c2cccc(Cl)c2)[C@@H](c2ccc(Cl)cc2)N1]

To a solution of (1R,2R)-2-amino-1-(3-chlorophenyl)-2-(4-chlorophenyl)ethanol (0.47 g, 1.666 mmol; Intermediate A2) and triethylamine (0.349 mL, 2.499 mmol) in THF at 0° C. was added chloracetyl chloride (0.16 mL, 2.0 mmol). The reaction mixture was stirred at 0° C. for 1 h. After this time sat aq. NH$_4$Cl solution and ethyl acetate was added. The layers were separated and the combined organic layers were washed with water (3×10 mL) dried over MgSO₄, filtered and the filtrate was concentrated in vacuo to give 2-chloro-N-((1R,2R)-2-(3-chlorophenyl)-1-(4-chlorophenyl)-2-hydroxyethyl)acetamide as a light yellow oil which was taken to the next step without further purification. MS (ESI) 380.0 [M+Na]⁺.

The product from above was dissolved in THF (15 mL) and treated with several portions of sodium hydride (60% dispersion in mineral oil, 0.167 g, 4.16 mmol) over a period of 5 minutes. The reaction was stirred at rt for 5 h. After this time sat aq. NH₄Cl solution and ethyl acetate was added. The layers were separated and the combined organic layers were washed with water (3×10 mL) dried over MgSO₄, filtered and the filtrate was concentrated in vacuo to give the crude material as a yellow oil. This was absorbed onto a plug of silica gel and purified by chromatography on silica gel, eluting with a gradient of 0% to 30% acetone in hexanes, to provide the title compound as yellow oil. ¹H NMR (400 MHz, CDCl₃) δ 7.47-7.54 (m, 1H), 7.46-7.54 (m, 1H), 7.34-7.42 (m, 2H), 7.29-7.32 (m, 2H), 7.26-7.29 (m, 1H), 7.13-7.25 (m, 1H), 6.98 (d, J=8.41 Hz, 1H), 4.57-4.65 (m, 1H), 4.45 (d, J=9.98 Hz, 1H), 4.00 (d, J=5.67 Hz, 2H). Mass Spectrum (ESI) m/z=322.2 (M⁺).

Step B. (5R,6R)-6-(3-Chlorophenyl)-5-(4-chlorophenyl)-4-((S)-1-((3,4-dimethoxybenzyl)oxy)butan-2-yl)morpholin-3-one

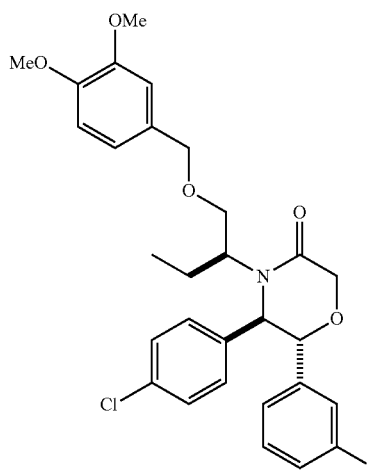

A solution of (5R,6R)-6-(3-chlorophenyl)-5-(4-chlorophenyl)morpholin-3-one (260 mg, 0.807 mmol, Example 112, Step A), (R)-1-((3,4-dimethoxybenzyl)oxy)butan-2-yl 4-bromobenzenesulfonate (556 mg, 1.210 mmol, Intermediate G), and sodium 2-methylpropan-2-olate (116 mg, 1.210 mmol) in 1,4-dioxane (2 mL) was stirred at 85° C. overnight. After this period the reaction contents were poured into sat. aq. NaHCO₃ solution (10 mL) and brine (10 mL) and extracted with 2.5% MeOH in CH₂Cl₂ (3×30 mL). The combined organics were dried over sodium sulfate, filtered and the filtrate was concentrated in vacuo. Silica gel chromatography (gradient elution with 10 to 40% acetone in hexanes) afforded the title compound as the second eluting major fraction.

¹H NMR (400 MHz, CDCl₃) δ 7.29 (s, 3H), 7.21-7.25 (m, 1H), 7.18 (t, J=1.66 Hz, 1H), 7.11 (t, J=7.92 Hz, 1H), 7.06 (d, J=8.41 Hz, 1H), 6.78-6.92 (m, 3H), 4.77 (d, J=7.83 Hz, 1H), 4.58 (d, J=7.83 Hz, 1H), 4.45 (s, 2H), 3.96 (t, J=9.49 Hz, 1H), 3.91 (s, 3H), 3.89 (s, 3H), 1.80-1.95 (m, J=7.14, 14.77 Hz, 1H), 1.61-1.72 (m, 1H), 0.63 (t, J=7.53 Hz, 3H). Mass Spectrum (ESI) m/z=566.2 [M+Na]⁺.

Step C. (5R,6R)-6-(3-Chlorophenyl)-5-(4-chlorophenyl)-4-((S)-1-hydroxybutan-2-yl)morpholin-3-one

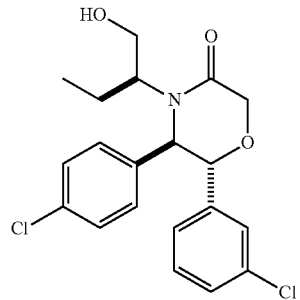 [SMILES: CC[C@@H](CO)N1C(=O)CO[C@H](c2cccc(Cl)c2)[C@H]1c1ccc(Cl)cc1]

To a 0° C. solution of (5R,6R)-6-(3-chlorophenyl)-5-(4-chlorophenyl)-4-((S)-1-((3,4-dimethoxybenzyl)oxy)butan-2-yl)morpholin-3-one (140 mg, 0.257 mmol; Example 112, Step B) in CH₂Cl₂ (2443 µl) and water (129 µl) was added DDQ (Fluka, Buchs, Switzerland) (70.0 mg, 0.309 mmol). The reaction was stirred at 0° C. After 2 h the reaction contents were poured into sat. aq. NaHCO₃ solution (50 mL) and CH₂Cl₂ (30 mL). The layers were separated and the aqueous layer was extracted further with CH₂Cl₂ (2×20 mL). The combined organics were dried over sodium sulfate, filtered and the filtrate was concentrated in vacuo. Silica gel chromatography (gradient elution 10 to 40% acetone in hexanes) afforded the title compound. ¹H NMR (400 MHz, CDCl₃) δ 7.22-7.26 (m, 2H), 7.17-7.21 (m, 1H), 7.01-7.13 (m, 4H), 6.75 (d, J=7.83 Hz, 1H), 4.54 (d, J=4.70 Hz, 2H), 4.35 (d, J=2.74 Hz, 2H), 3.53-3.62 (m, 2H), 3.41 (q, J=7.04 Hz, 1H), 3.26-3.37 (m, 1H), 1.76-1.92 (m, 1H), 1.41 (ddd, J=6.06, 7.53, 13.79 Hz, 1H), 1.14 (t, J=6.94 Hz, 1H), 0.62-0.70 (m, 3H). Mass Spectrum (ESI) m/z=394.2 [M]⁺.

Step D. (5R,6R)-6-(3-Chlorophenyl)-5-(4-chlorophenyl)-4-((S)-1-(ethylthio)butan-2-yl)morpholin-3-one

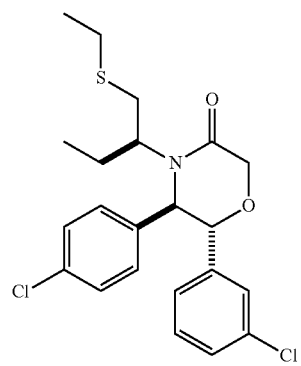 [SMILES: CCSC[C@H](CC)N1C(=O)CO[C@H](c2cccc(Cl)c2)[C@H]1c1ccc(Cl)cc1]

To a solution of (5R,6R)-6-(3-chlorophenyl)-5-(4-chlorophenyl)-4-((S)-1-hydroxybutan-2-yl)morpholin-3-one (300 mg, 0.761 mmol; Example 112, Step C) and ethanethiol (0.225 mL, 3.04 mmol) in 0.2 mL of toluene was added cyanomethylenetributylphosphorane (TCI America, Portland, Oreg.) (0.735 mL, 3.04 mmol). The resulting solution was stirred at 110° C. overnight. After this period, the mixture was concentrated, the crude material absorved onto a plug of silica gel and purified by chromatography on silica gel, eluting with 20% acetone in hexanes to provide the title compound as a light yellow oil. $^1$H NMR (400 MHz, CDCl$_3$) δ 7.21-7.34 (m, 3H), 7.11-7.18 (m, 2H), 7.07 (d, J=8.41 Hz, 2H), 6.79 (d, J=7.83 Hz, 1H), 4.77 (d, J=9.00 Hz, 1H), 4.56 (d, J=9.00 Hz, 1H), 4.44 (q, J=16.43 Hz, 2H), 3.06-3.15 (m, 2H), 2.44-2.62 (m, 3H), 2.04 (td, J=7.36, 14.43 Hz, 1H), 1.56-1.68 (m, 1H), 1.23-1.31 (m, 3H), 0.66 (t, J=7.43 Hz, 3H). Mass Spectrum (ESI) m/z=438.2 [M]$^+$.

Step E. (5R,6R)-2Allyl-6-(3-chlorophenyl)-5-(4-chlorophenyl)-4-((S)-1-(ethylthio)butan-2-yl)morpholin-3-one

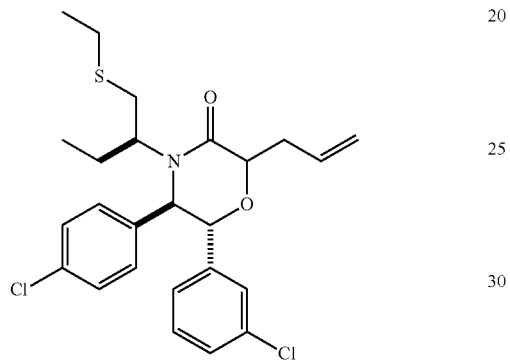

To a 5-mL round-bottomed flask was added (5R,6R)-6-(3-chlorophenyl)-5-(4-chlorophenyl)-4-((S)-1-(ethylthio)butan-2-yl)morpholin-3-one (40 mg, 0.091 mmol; Example 112, Step D) and lithium bis(trimethylsilyl)amide (1.0M solution in tetrahydrofuran, 137 μl, 0.137 mmol) in THF (456 μl) at −78° C. The reaction mixture was stirred for 15 minutes. After this period allyl bromide (11.84 μl, 0.137 mmol) was added at −78° C. The reaction was allowed to stir for 3 h. After this period it was quenched by addition of a sat. aq. NH$_4$Cl solution (3 mL), then extracted with diethyl ether (3×10 mL). The combined organic extracts were dried over MgSO$_4$. The solution was filtered and concentrated in vacuo to give the crude material as a light yellow oil. The crude material was purified by chromatography on silica gel, eluting with a gradient of 0% to 20% acetone in hexanes, to provide the title compound as a 2:1 mixture of epimers at C2. Mass Spectrum (ESI) m/z=478.0 [M]$^+$.

Step F. 2-((2R,5R,6R)-6-(3-Chlorophenyl)-5-(4-chlorophenyl)-4-((S)-1-(ethylsulfonyl)butan-2-yl)-3-oxomorpholin-2-yl)acetic acid or 2-((2S,5R,6R)-6-(3-Chlorophenyl)-5-(4-chlorophenyl)-4-((S)-1-(ethylsulfonyl)butan-2-yl)-3-oxomorpholin-2-yl)acetic acid (Isomer 1)

To a rapidly stirring solution of (5R,6R)-2-allyl-6-(3-chlorophenyl)-5-(4-chlorophenyl)-4-((S)-1-(ethylthio)butan-2-yl)morpholin-3-one (25 mg, 0.052 mmol; Example 112, Step E) in a mixture of water (280 μl), acetonitrile (187 μl) and CCl$_4$ (187 μl) was added sodium periodate (67 mg, 0.31 mmol), followed by ruthenium(III) chloride hydrate (1.2 mg, 5.2 μmol). The biphasic mixture was stirred vigorously at rt for 5 h, and then was acidified with 10% citric acid. The mixture was diluted with EtOAc and filtered through a pad of Celite® (diatomaceous earth) to remove. The filtrate was extracted (2×EtOAc) and the combined organic layers were washed with brine (10 mL), dried (Na$_2$SO$_4$), and concentrated under reduced pressure. Purification of the residue by RP-HPLC (Gemini™ Prep C$_{18}$ 5 μm column; Phenomenex, Torrance, Calif.; 30 to 60% MeCN/H$_2$O in 30 min) provided one of the title compounds as the faster eluting isomer (t$_R$=17.51 min). $^1$H NMR (400 MHz, CDCl$_3$) δ 7.33-7.38 (m, 2H), 7.25 (td, J=2.15, 3.91 Hz, 4H), 7.14-7.21 (m, 1H), 7.02 (d, J=7.63 Hz, 1H), 5.09 (d, J=7.04 Hz, 1H), 4.95 (d, J=7.04 Hz, 1H), 4.79 (t, J=5.87 Hz, 1H), 4.05 (br. s., 1H), 3.44 (br. s., 1H), 3.01-3.16 (m, 4H), 2.97 (d, J=12.91 Hz, 1H), 2.14 (ddd, J=7.34, 9.44, 14.13 Hz, 1H), 1.60 (ddd, J=4.21, 7.53, 13.89 Hz, 1H), 1.38-1.50 (m, 3H), 0.57 (t, J=7.43 Hz, 3H). Mass Spectrum (ESI) m/z=528.0 [M]$^+$.

Example 113

2-((2S,5R,6R)-6-(3-Chlorophenyl)-5-(4-chlorophenyl)-4-((S)-1-(ethylsulfonyl)butan-2-yl)-3-oxomorpholin-2-yl)acetic acid or 2-((2R,5R,6R)-6-(3-Chlorophenyl)-5-(4-chlorophenyl)-4-((S)-1-(ethylsulfonyl)butan-2-yl)-3-oxomorpholin-2-yl)acetic acid (Isomer 2)

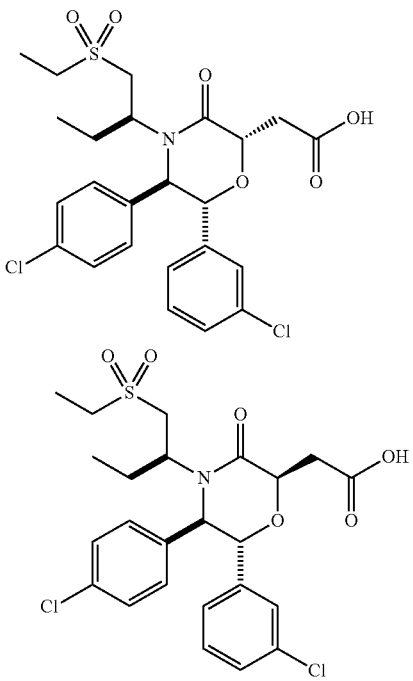

One of the title compounds was obtained as the second (slower) eluting isomer in Example 112, Step F (t$_R$=18.56 min). $^1$H NMR (400 MHz, CDCl$_3$) δ 7.23 (d, J=7.82 Hz, 9H), 7.13 (d, J=8.02 Hz, 4H), 6.93-7.09 (m, 15H), 6.75 (d, J=7.63 Hz, 3H), 4.94 (d, J=9.39 Hz, 3H), 4.56-4.71 (m, 7H), 3.09 (d, J=6.46 Hz, 3H), 2.92-3.03 (m, 10H), 2.88-2.92 (m, 1H), 2.78-2.88 (m, 3H), 2.00-2.16 (m, 3H), 1.49-1.61 (m, 1H), 1.36 (t, J=7.53 Hz, 3H), 0.49 (t, J=7.34 Hz, 3H). Mass Spectrum (ESI) m/z=528.0 [M]$^+$.

Example 114

2-((2R,5R,6R)-6-(3-Chlorophenyl)-5-(4-chlorophenyl)-4-((S)-1-hydroxybutan-2-yl)-3-oxomorpholin-2-yl)acetic acid

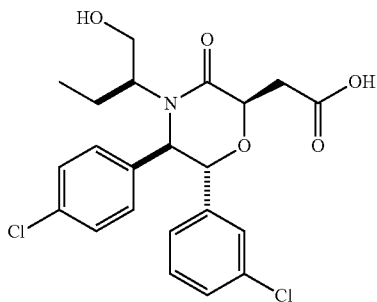 [SMILES: CC[C@@H](CO)N1C(=O)[C@@H](CC(=O)O)O[C@H](c2cccc(Cl)c2)[C@H]1c1ccc(Cl)cc1]

Step A: tert-Butyl 2-((2R,5R,6R)-6-(3-chlorophenyl)-5-(4-chlorophenyl)-4-((S)-1-((3,4-dimethoxybenzyl)oxy)butan-2-yl)-3-oxomorpholin-2-yl)acetate

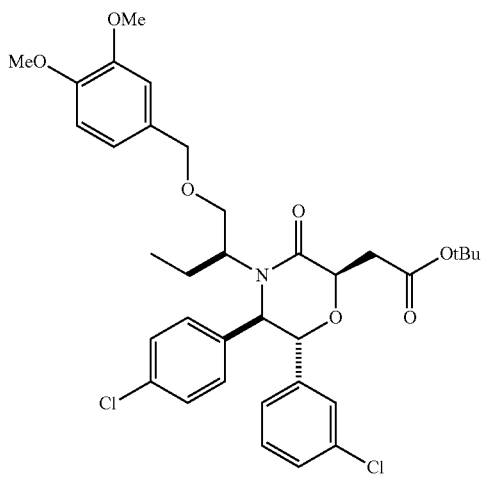 [SMILES: CC[C@@H](COCc1ccc(OC)c(OC)c1)N1C(=O)[C@@H](CC(=O)OC(C)(C)C)O[C@H](c2cccc(Cl)c2)[C@H]1c1ccc(Cl)cc1]

To a solution of tert-butyl 2-((2R,5R,6R)-6-(3-chlorophenyl)-5-(4-chlorophenyl)-3-oxomorpholin-2-yl)acetate (0.34 g, 0.779 mmol; Example 32, Step C, second eluting isomer) and (R)-1-((3,4-dimethoxybenzyl)oxy)butan-2-yl 4-bromobenzenesulfonate (0.394 g, 0.857 mmol, Intermediate G) in 2 mL of 1,4-dioxane sodium 2-methylpropan-2-olate (0.082 g, 0.857 mmol) was added. The reaction mixture was stirred at 85° C. overnight. The reaction contents were poured into a mixture of water (50 mL) and brine (10 mL) and extracted against 2.5% MeOH in $CH_2Cl_2$ (3×30 mL). The combined organic extracts were dried over $MgSO_4$, filtered and the filtrate was concentrated under reduced pressure. The residue was purified by silica gel chromatography (gradient elution 10 to 40% acetone in hexanes) to afford the title compound. Mass Spectrum (ESI) m/z=480.2 $[M+2]^+$.

Step B. tert-Butyl 2-((2R,5R,6R)-6-(3-chlorophenyl)-5-(4-chlorophenyl)-4-((S)-1-hydroxybutan-2-yl)-3-oxomorpholin-2-yl)acetate

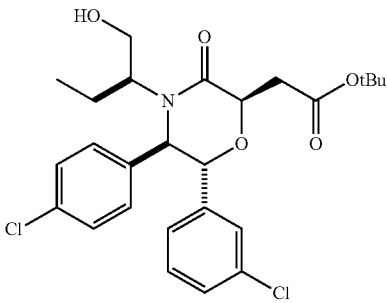 [SMILES: CC[C@@H](CO)N1C(=O)[C@@H](CC(=O)OC(C)(C)C)O[C@H](c2cccc(Cl)c2)[C@H]1c1ccc(Cl)cc1]

To a solution of tert-butyl 2-((2R,5R,6R)-6-(3-chlorophenyl)-5-(4-chlorophenyl)-4-((S)-1-((3,4-dimethoxybenzyl)oxy)butan-2-yl)-3-oxomorpholin-2-yl)acetate (140 mg, 0.213 mmol; Example 114, Step A) in a mixture of $CH_2Cl_2$ (2019 µl) and water (106 µl) at 0° C. was added DDQ (Fluka, Buchs, Switzerland) (57.9 mg, 0.255 mmol). The reaction was stirred at 0° C. After 2 h the reaction contents were poured into saturated aq. sodium bicarbonate (50 mL) and $CH_2Cl_2$ (30 mL). Organics were sequestered and the aquoues was extracted further with $CH_2Cl_2$ (2×20 mL). The combined organics were dried over sodium sulfate, filtered and the filtrate was concentrated in vacuo. Silica gel chromatography (gradient elution 10% to 30% acetone in hexanes) afforded the title compound. $^1$H NMR (400 MHz, $CDCl_3$) δ 7.28 (s, 2H), 7.20-7.24 (m, 1H), 7.00-7.12 (m, 4H), 6.68 (d, J=7.63 Hz, 1H), 4.81 (d, J=9.78 Hz, 1H), 4.61 (d, J=9.59 Hz, 1H), 4.52 (dd, J=3.13, 4.11 Hz, 1H), 4.29 (dd, J=10.66, 11.84 Hz, 1H), 3.53 (dd, J=4.11, 12.13 Hz, 1H), 3.35 (dd, J=2.93, 17.02 Hz, 1H), 2.75-2.94 (m, 2H), 1.89-2.07 (m, 1H), 1.61 (ddd, J=4.11, 7.83, 14.09 Hz, 1H), 1.55 (s, 9H), 0.58 (t, J=7.63 Hz, 3H). Mass Spectrum (ESI) m/z=530.1 $[M+Na]^+$.

Step C. 2-((2R,5R,6R)-6-(3-Chlorophenyl)-5-(4-chlorophenyl)-4-((S)-1-hydroxybutan-2-yl)-3-oxomorpholin-2-yl)acetic acid To a solution of tert-butyl 2-((2R,5R,6R)-6-(3-chlorophenyl)-5-(4-chlorophenyl)-4-((S)-1-hydroxybutan-2-yl)-3-oxomorpholin-2-yl)acetate (20 mg, 0.039 mmol; Example 114, Step B) in DCM (1.0 mL) was added 0.1% trifluoroacetic acid in 98/2 acetonitrile/water (0.974 µL, 0.013 mmol). The reaction mixture was stirred at 25° C. for 30 minutes. The crude product was concentrated and purified by reversed phase preparatory HPLC (Gemini™ Prep $C_{18}$ 5 µm column; Phenomenex, Torrance, Calif.; gradient elution of 25% to 75% MeCN in water, where both solvents contain 0.1% TFA, 30 min method) to provide the title compound as a white foam ($t_R$=15.5 min).

$^1$H NMR (400 MHz, $CDCl_3$) δ 7.25-7.36 (m, 3H), 7.21 (dd, J=1.08, 7.92 Hz, 1H), 7.03-7.16 (m, 4H), 6.75 (d, J=7.63 Hz, 1H), 4.79 (d, J=9.39 Hz, 1H), 4.64 (d, J=9.78 Hz, 1H), 4.55 (t, J=3.52 Hz, 1H), 4.35 (t, J=11.15 Hz, 1H), 3.55 (dd, J=3.91, 11.93 Hz, 1H), 3.41 (dd, J=3.03, 17.70 Hz, 1H), 2.80-3.01 (m, 2H), 1.99 (dt, J=1.96, 7.14 Hz, 1H), 1.48-1.67 (m, 1H), 0.56 (t, J=7.53 Hz, 3H). Mass Spectrum (ESI) m/z=452.0 $[M]^+$.

Example 115

2-((2S,5R,6R)-6-(3-Chlorophenyl)-5-(4-chlorophenyl)-4-((S)-1-hydroxybutan-2-yl)-3-oxomorpholin-2-yl)acetic acid

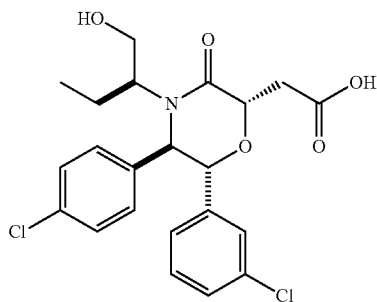 [SMILES: CC[C@@H](CO)N1C(=O)[C@H](CC(=O)O)O[C@H](c2cccc(Cl)c2)[C@H]1c1ccc(Cl)cc1]

The title compound was prepared from tert-butyl 2-((2S,5R,6R)-6-(3-chlorophenyl)-5-(4-chlorophenyl)-4-((S)-1-hydroxybutan-2-yl)-3-oxomorpholin-2-yl)acetate (Example 32, Step C, first eluting isomer) by a procedure analogous to that described in Example 114. The crude product was purified by reversed phase preparatory HPLC (Gemini™ Prep $C_{18}$ 5 μm column; Phenomenex, Torrance, Calif.; gradient elution of 25% to 75% MeCN in water, where both solvents contain 0.1% TFA, 30 min method) to provide the title compound as a white foam ($t_R$=14.3 min). $^1$H NMR (400 MHz, CDCl$_3$) δ 7.48 (s, 1H), 7.29-7.42 (m, 6H), 7.22 (s, 1H), 4.80-4.96 (m, 2H), 4.41-4.53 (m, 1H), 3.82-3.94 (m, 1H), 3.65-3.79 (m, 1H), 2.98-3.17 (m, 2H), 1.83-1.99 (m, 1H), 1.43-1.58 (m, 1H), 0.71 (t, J=7.43 Hz, 3H). Mass Spectrum (ESI) m/z=452.0 [M]$^+$.

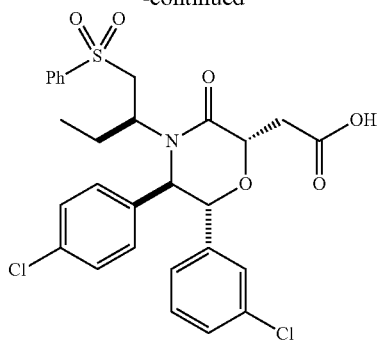

One of the title compounds was prepared from (5R,6R)-6-(3-Chlorophenyl)-5-(4-chlorophenyl)-4-((S)-1-hydroxybutan-2-yl)morpholin-3-one (Example 112, Step C) by a procedure analogous to that described in Example 112, Steps D through F, replacing ethanethiol in step D with thiophenol. The crude product was purified by reversed phase preparatory HPLC (Gemini™ Prep $C_{18}$ 5 μm column; Phenomenex, Torrance, Calif.; gradient elution of 25% to 75% MeCN in water, where both solvents contain 0.1% TFA, 30 min method) to provide one of the title compounds as the faster eluting isomer as a white foam ($t_R$=18.82 min). $^1$H NMR (400 MHz, CDCl$_3$) δ 7.96 (d, J=7.24 Hz, 2H), 7.56-7.77 (m, 3H), 7.14-7.46 (m, 9H), 7.02 (d, J=7.63 Hz, 1H), 4.88-5.12 (m, 2H), 4.63 (dd, J=4.89, 6.85 Hz, 1H), 4.21 (dd, J=9.39, 14.28 Hz, 1H), 3.42 (br. s., 1H), 2.98-3.21 (m, 3H), 2.09 (ddd, J=7.43, 9.44, 14.23 Hz, 1H), 1.57 (ddd, J=4.11, 7.58, 13.94 Hz, 1H), 0.48 (t, J=7.43 Hz, 3H). Mass Spectrum (ESI) m/z=576.0 [M]$^+$.

Example 116

2-((2R,5R,6R)-6-(3-Chlorophenyl)-5-(4-chlorophenyl)-3-oxo-4-((S)-1-(phenylsulfonyl) butan-2-yl)morpholin-2-yl)acetic acid or 2-((2S,5R,6R)-6-(3-Chlorophenyl)-5-(4-chlorophenyl)-3-oxo-4-((S)-1-(phenylsulfonyl)butan-2-yl)morpholin-2-yl)acetic acid (Isomer 1)

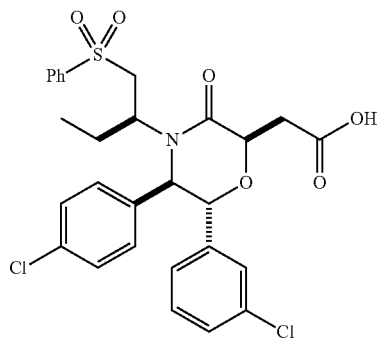 or

Example 117

2-((2S,5R,6R)-6-(3-Chlorophenyl)-5-(4-chlorophenyl)-3-oxo-4-((S)-1-(phenylsulfonyl) butan-2-yl)morpholin-2-yl)acetic acid or 2-((2R,5R,6R)-6-(3-Chlorophenyl)-5-(4-chlorophenyl)-3-oxo-4-((S)-1-(phenylsulfonyl)butan-2-yl)morpholin-2-yl)acetic acid (Isomer 2)

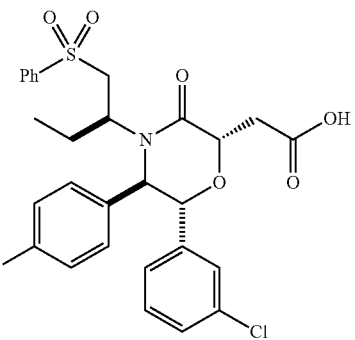 or

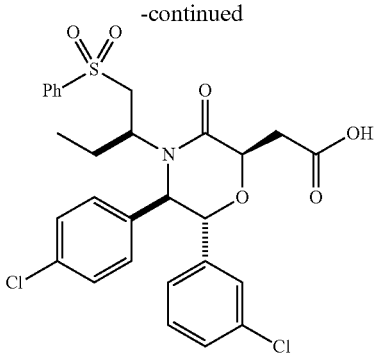

One of the title compounds was obtained as the second (slower) eluting isomer in Example 116 as a white foam ($t_R$=19.61 min). $^1$H NMR (400 MHz, CDCl$_3$) δ 7.83-8.06 (m, 2H), 7.50-7.78 (m, 3H), 7.03-7.46 (m, 8H), 6.85 (d, J=7.83 Hz, 1H), 5.04 (d, J=9.78 Hz, 1H), 4.64-4.87 (m, 2H), 4.24 (dd, J=9.29, 13.79 Hz, 1H), 2.90-3.40 (m, 4H), 2.06-2.23 (m, 1H), 1.46-1.72 (m, 1H), 0.47 (t, J=7.43 Hz, 3H). Mass Spectrum (ESI) m/z=576.0 [M]$^+$.

Example 118

2-((2R,5R,6R)-6-(3-Chlorophenyl)-5-(4-chlorophenyl)-4-((S)-1-(isopropylsulfonyl)butan-2-yl)-3-oxomorpholin-2-yl)acetic acid or 2-((2S,5R,6R)-6-(3-Chlorophenyl)-5-(4-chlorophenyl)-4-((S)-1-(isopropylsulfonyl)butan-2-yl)-3-oxomorpholin-2-yl) acetic acid (Isomer 1)

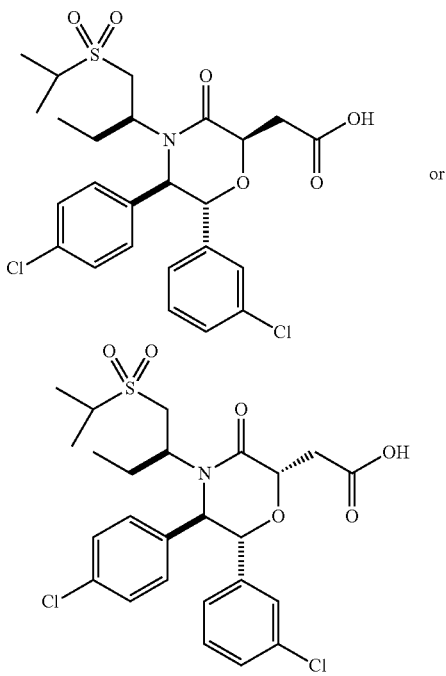

One of the title compound was prepared from (5R,6R)-6-(3-Chlorophenyl)-5-(4-chlorophenyl)-4-((S)-1-hydroxybutan-2-yl)morpholin-3-one (Example 112, Step C) by a procedure analgous to that described in Example 112, Steps D though F, replacing ethanethiol in step D with propane-2-thiol. The crude product was purified by reversed phase preparatory HPLC (Gemini™ Prep C$_{18}$ 5 μm column; Phenomenex, Torrance, Calif.; gradient elution of 25% to 75% MeCN in water, where both solvents contain 0.1% TFA, 30 min method) to provide one of the title compounds as a white foam ($t_R$=17.16 min). $^1$H NMR (400 MHz, CDCl$_3$) δ 7.32-7.39 (m, 3H), 7.30 (s, 2H), 7.21-7.27 (m, 2H), 7.17 (s, 1H), 6.99-7.07 (m, 1H), 5.07-5.17 (m, 1H), 4.95 (s, 1H), 4.74 (s, 1H), 3.11 (d, J=6.06 Hz, 3H), 2.86-2.98 (m, 1H), 2.05-2.21 (m, 1H), 1.55-1.69 (m, 1H), 1.43 (dd, J=4.30, 6.85 Hz, 6H), 0.56 (t, J=7.53 Hz, 3H). Mass Spectrum (ESI) m/z=542.0 [M]$^+$.

Example 119

2-((2S,5R,6R)-6-(3-Chlorophenyl)-5-(4-chlorophenyl)-4-((S)-1-(isopropylsulfonyl)butan-2-yl)-3-oxomorpholin-2-yl)acetic acid or 2-((2R,5R,6R)-6-(3-Chlorophenyl)-5-(4-chlorophenyl)-4-((S)-1-(isopropylsulfonyl)butan-2-yl)-3-oxomorpholin-2-yl) acetic acid (Isomer 2)

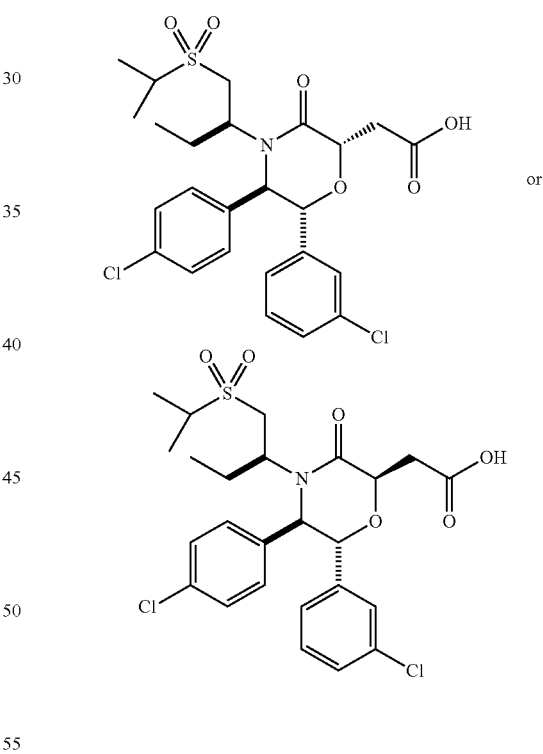

One of the title compounds was obtained as the second (slower) eluting isomer in Example 118 as a white foam ($t_R$=17.7 min). $^1$H NMR (400 MHz, CDCl$_3$) δ 7.31 (d, J=8.61 Hz, 3H), 7.17-7.24 (m, 1H), 7.14 (s, 5H), 6.83 (d, J=7.82 Hz, 1H), 5.06 (d, J=9.98 Hz, 1H), 4.75 (dd, J=5.09, 6.46 Hz, 1H), 4.69 (d, J=9.59 Hz, 1H), 3.22 (dd, J=6.65, 16.43 Hz, 1H), 3.07-3.16 (m, 1H), 2.99 (dd, J=4.79, 16.33 Hz, 1H), 2.86 (d, J=13.50 Hz, 1H), 2.12-2.25 (m, 1H), 1.56-1.70 (m, 1H), 1.44 (dt, J=1.57, 4.89 Hz, 6H), 0.56 (t, J=7.63 Hz, 3H). Mass Spectrum (ESI) m/z=542.0 [M]$^+$.

Example 120

2-((2R,5R,6R)-4-((S)-1-(tert-Butylsulfonyl)butan-2-yl)-6-(3-chlorophenyl)-5-(4-chlorophenyl)-3-oxo-morpholin-2-yl)acetic acid

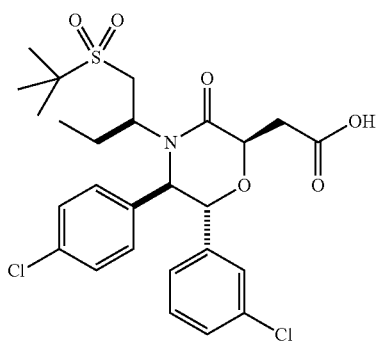 [SMILES: CC[C@@H](CS(=O)(=O)C(C)(C)C)N1C(=O)[C@@H](CC(=O)O)O[C@H](c2cccc(Cl)c2)[C@H]1c1ccc(Cl)cc1]

The title compound was prepared from (5R,6R)-6-(3-Chlorophenyl)-5-(4-chlorophenyl)-4-((S)-1-hydroxybutan-2-yl)morpholin-3-one (Example 112, Step C) by a procedure analogous to that described in Example 112, Steps D though F, replacing ethanethiol in Step D with 2-methylpropane-2-thiol. The crude product was purified by reversed phase preparatory HPLC (Gemini™ Prep $C_{18}$ 5 mm column; Phenomenex, Torrance, Calif.; gradient elution of 25% to 75% MeCN in water, where both solvents contain 0.1% TFA, 30 min method), which provided the title compound as the faster eluting isomer as a white foam ($t_R$=16.7 min). The stereochemistry was confirmed by examination of the co-crystal structure of the compound in complex with MDM2.

$^1$H NMR (400 MHz, CDCl$_3$) δ 7.18-7.27 (m, 5H), 7.11-7.17 (m, 1H), 7.07 (t, J=7.82 Hz, 1H), 6.97 (d, J=7.63 Hz, 1H), 5.06 (d, J=6.46 Hz, 1H), 4.86 (d, J=6.65 Hz, 1H), 4.63 (t, J=5.97 Hz, 1H), 3.85 (dd, J=9.00, 13.69 Hz, 1H), 3.23-3.39 (m, 1H), 3.00 (s, 2H), 2.87 (d, J=13.69 Hz, 1H), 1.97-2.17 (m, 1H), 1.45-1.64 (m, 1H), 1.31-1.40 (m, 9H), 0.45 (t, J=7.53 Hz, 3H). Mass Spectrum (ESI) m/z=556.0 [M]$^+$.

Example 121

2-((2S,5R,6R)-4-((S)-1-(tert-butylsulfonyl)butan-2-yl)-6-(3-chlorophenyl)-5-(4-chlorophenyl)-3-oxo-morpholin-2-yl)acetic acid

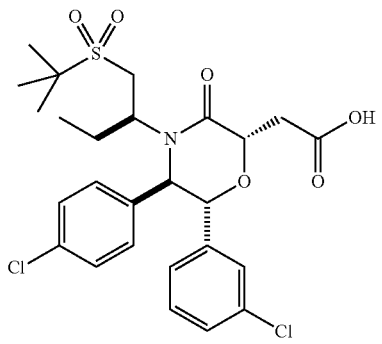 [SMILES: CC[C@@H](CS(=O)(=O)C(C)(C)C)N1C(=O)[C@H](CC(=O)O)O[C@H](c2cccc(Cl)c2)[C@H]1c1ccc(Cl)cc1]

The title compound was obtained as the second (slower) eluting isomer in Example 120 as a white foam ($t_R$=17.4 min).

$^1$H NMR (400 MHz, CDCl$_3$) d 7.30 (d, J=8.61 Hz, 2H), 7.17-7.22 (m, 1H), 7.03-7.16 (m, 4H), 6.85 (d, J=7.63 Hz, 1H), 5.07 (d, J=9.78 Hz, 1H), 4.75 (t, J=5.77 Hz, 1H), 4.69 (d, J=9.78 Hz, 1H), 3.95-4.08 (m, 1H), 3.26-3.37 (m, 1H), 3.16-3.26 (m, J=6.46 Hz, 1H), 2.82-3.02 (m, 2H), 2.11-2.27 (m, 1H), 1.52-1.71 (m, 1H), 1.43 (s, 9H), 0.55 (t, J=7.53 Hz, 3H). Mass Spectrum (ESI) m/z=556.0 [M]$^+$.

Example 122

2-((2R,5R,6R)-6-(3-Chlorophenyl)-5-(4-chlorophenyl)-3-oxo-4-((S)-1-(tert-pentylsulfonyl)butan-2-yl)morpholin-2-yl)acetic acid or 2-((2S,5R,6R)-6-(3-Chlorophenyl)-5-(4-chlorophenyl)-3-oxo-4-((S)-1-(tert-pentylsulfonyl)butan-2-yl)morpholin-2-yl)acetic acid (Isomer 1)

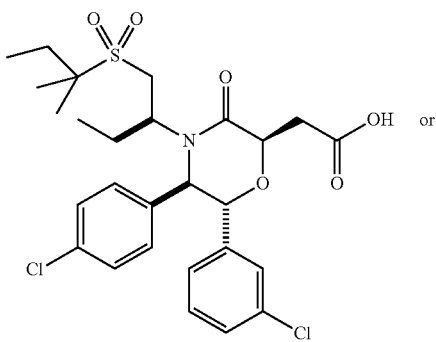

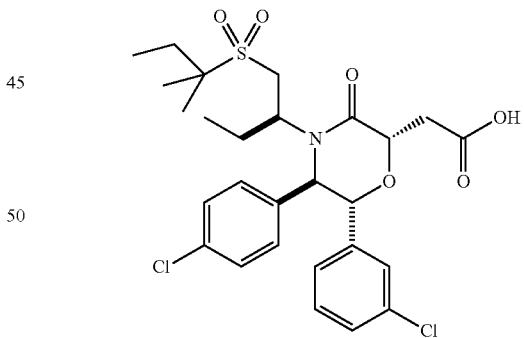

One of the title compound was prepared from (5R,6R)-6-(3-Chlorophenyl)-5-(4-chlorophenyl)-4-((S)-1-hydroxybutan-2-yl)morpholin-3-one (Example 112, Step C) by a procedure analogous to that described in Example 112, Steps D though F, replacing ethanethiol in Step D with 2-methylbutane-2-thiol. The crude product was purified by reversed phase preparatory HPLC (Gemini™ Prep C$_{18}$ 5 µm column; Phenomenex, Torrance, Calif.) (gradient elution of 25% to 75% MeCN in water, where both solvents contain 0.1% TFA, 30 min method) to provide one of the title compounds as the faster eluting isomer as a white foam (t$_R$=19.5 min). $^1$H NMR (400 MHz, CDCl$_3$) δ 7.34 (s, 5H), 7.21-7.26 (m, 1H), 7.14-7.21 (m, 1H), 7.03-7.12 (m, 1H), 5.16 (d, J=6.26 Hz, 1H), 4.94 (d, J=6.46 Hz, 1H), 4.68 (t, J=6.06 Hz, 1H), 3.86-3.98 (m, 1H), 3.10 (dd, J=3.91, 6.06 Hz, 1H), 2.95 (dd, J=2.25, 13.60 Hz, 1H), 2.08-2.21 (m, 1H), 1.84 (dd, J=2.35, 7.63 Hz, 1H), 1.56-1.70 (m, 1H), 1.38 (s, 6H), 1.03 (t, J=7.53 Hz, 3H), 0.54 (t, J=7.43 Hz, 3H). Mass Spectrum (ESI) m/z=570.0 [M]$^+$.

Example 123

2-((2S,5R,6R)-6-(3-Chlorophenyl)-5-(4-chlorophenyl)-3-oxo-4-((S)-1-(tert-pentylsulfonyl)butan-2-yl)morpholin-2-yl)acetic acid or 2-((2R,5R,6R)-6-(3-Chlorophenyl)-5-(4-chlorophenyl)-3-oxo-4-((S)-1-(tert-pentylsulfonyl)butan-2-yl)morpholin-2-yl)acetic acid (Isomer 2)

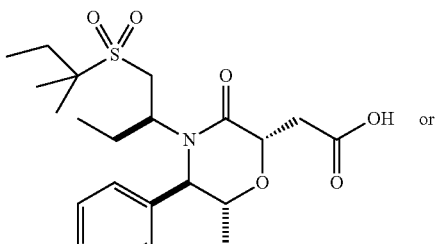

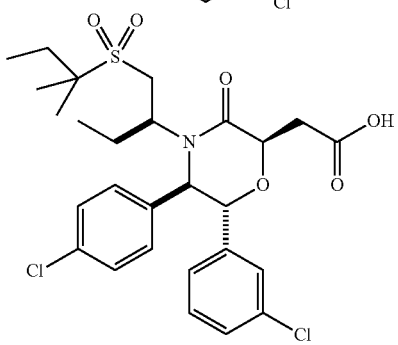

The title compound was obtained as the second (slower) eluting isomer in Example 122 as a white foam (t$_R$=20.04 min). $^1$H NMR (400 MHz, CDCl$_3$) δ 7.27-7.35 (m, J=8.41 Hz, 3H), 7.03-7.24 (m, 5H), 6.85 (d, J=7.63 Hz, 1H), 5.08 (d, J=9.78 Hz, 1H), 4.64-4.79 (m, 2H), 3.94-4.09 (m, 1H), 3.23 (dd, J=7.04, 16.24 Hz, 1H), 2.97 (dd, J=4.79, 16.33 Hz, 1H), 2.89 (dd, J=2.45, 13.40 Hz, 1H), 2.12-2.24 (m, 1H), 1.77-1.90 (m, 2H), 1.56-1.71 (m, 1H), 1.32-1.41 (m, 6H), 1.03 (t, J=7.53 Hz, 3H), 0.54 (t, J=7.53 Hz, 3H). Mass Spectrum (ESI) m/z=570.0 [M]$^+$.

Example 124

2-((2R,5R,6R)-6-(3-Chloro-5-fluorophenyl)-5-(4-chlorophenyl)-4-((S)-1-(isopropylsulfonyl)butan-2-yl)-3-oxomorpholin-2-yl)acetic acid or 2-((2S,5R,6R)-6-(3-Chloro-5-fluorophenyl)-5-(4-chlorophenyl)-4-((S)-1-(isopropylsulfonyl)butan-2-yl)-3-oxomorpholin-2-yl)acetic acid (Isomer 1)

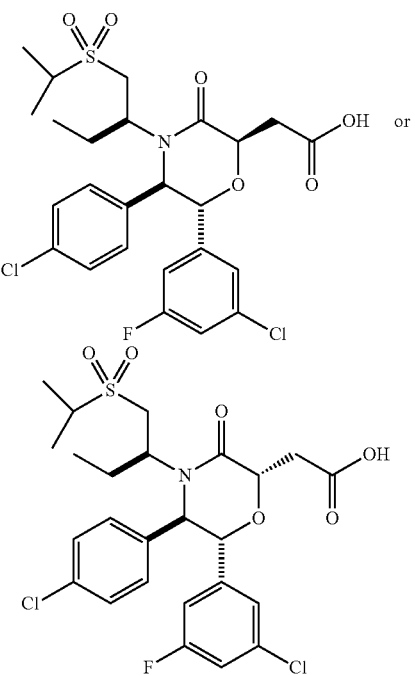

Step A. (5R,6R)-6-(3-Chloro-5-fluorophenyl)-5-(4-chlorophenyl)morpholin-3-one

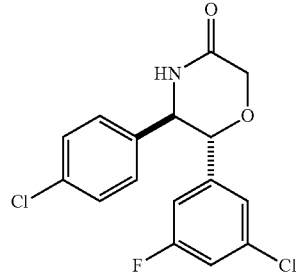

The above compound was prepared from (1R,2R)-2-amino-1-(3-chloro-5-fluorophenyl)-2-(4-chlorophenyl)ethanol (Intermediate C1) by a procedure analogous to that described in Example 112, Step A. The crude material was absorbed onto a plug of silica gel and purified by chromatography on silica gel, eluting with a gradient of 0% to 30% acetone in hexanes, to provide the title compound as a solid. $^1$H NMR (400 MHz, CDCl$_3$) δ 7.29-7.35 (m, 2H), 6.94-7.06 (m, 3H), 6.83 (s, 1H), 6.57-6.65 (m, 1H), 6.04-6.11 (m, 1H), 4.53-4.62 (m, 2H), 4.37-4.48 (m, 2H). Mass Spectrum (ESI) m/z=340.0 [M]$^+$.

Step B. (5R,6R)-6-(3-Chloro-5-fluorophenyl)-5-(4-chlorophenyl)-4-(1-((3,4-dimethoxybenzyl)oxy)butan-2-yl)morpholin-3-one

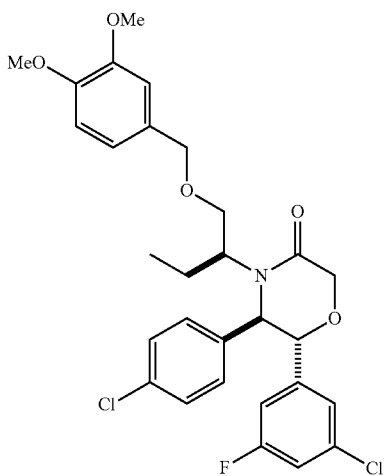

The above compound was prepared from (5R,6R)-6-(3-chloro-5-fluorophenyl)-5-(4-chlorophenyl)morpholin-3-one (Example 124, Step A) by a procedure analogous to that described in Example 112, Step B. The crude material was absorbed onto a plug of silica gel and purified by chromatography on silica gel, eluting with a gradient of 0% to 30% acetone in hexanes, to provide the title compound. $^1$H NMR (400 MHz, CDCl$_3$) δ 7.31 (d, J=8.61 Hz, 2H), 7.08 (d, J=8.41 Hz, 2H), 7.00 (d, J=8.22 Hz, 1H), 6.87-6.92 (m, 3H), 6.85 (s, 1H), 6.67-6.75 (m, 1H), 4.75 (d, J=7.63 Hz, 1H), 4.57 (d, J=7.63 Hz, 1H), 4.41 (d, J=17.22 Hz, 1H), 4.34-4.37 (m, 2H), 3.96 (s, 1H), 3.87-3.93 (m, 6H), 3.38 (s, 1H), 3.17-3.27 (m, 1H), 1.79-1.94 (m, 1H), 1.60-1.73 (m, 1H), 0.62 (t, J=7.53 Hz, 3H). Mass Spectrum (ESI) m/z=562.0 [M]$^+$.

Step C. (5R,6R)-6-(3-Chloro-5-fluorophenyl)-5-(4-chlorophenyl)-4-(1-hydroxybutan-2-yl)morpholin-3-one

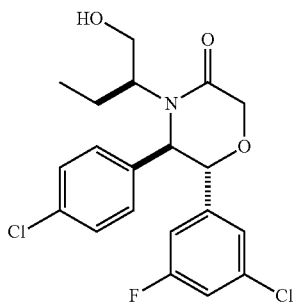

The above compound was prepared from ((5R,6R)-6-(3-chloro-5-fluorophenyl)-5-(4-chlorophenyl)-4-(1-((3,4-dimethoxybenzyl)oxy)butan-2-yl)morpholin-3-one (Example 124, Step B) by a procedure analogous to that described in Example 112, Step C. The crude material was purified by chromatography on silica gel, eluting with a gradient of 0% to 30% acetone in hexanes (left in a isocratic 15% acetone/hexanes mixture for 15 minutes before increasing the gradient, the aldehyde comes out first), to provide the title compound as an off-white solid. $^1$H NMR (400 MHz, CDCl$_3$) δ 7.32-7.40 (m, 2H), 7.11-7.18 (m, 2H), 7.02 (td, J=2.10, 8.31 Hz, 1H), 6.89 (s, 1H), 6.69 (td, J=1.86, 9.00 Hz, 1H), 4.60 (s, 2H), 4.42 (d, J=2.54 Hz, 2H), 3.59-3.72 (m, 2H), 3.32-3.44 (m, 1H), 1.83-1.98 (m, 1H), 1.49 (s, 1H), 0.73 (t, J=7.43 Hz, 3H). Mass Spectrum (ESI) m/z=412.0 [M]$^+$.

Step D. (5R,6R)-6-(3-chloro-5-fluorophenyl)-5-(4-chlorophenyl)-4-(1-(isopropylthio)butan-2-yl)morpholin-3-one

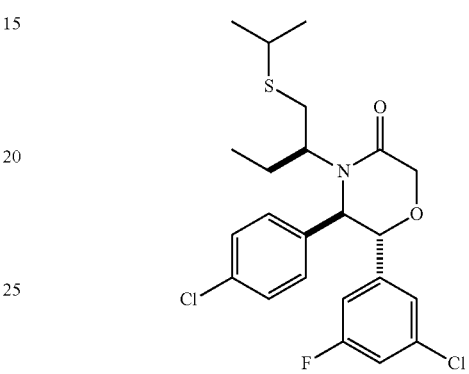

The above compound was prepared from (5R,6R)-6-(3-chloro-5-fluorophenyl)-5-(4-chlorophenyl)-4-(1-hydroxybutan-2-yl)morpholin-3-one (Example 124, Step C) by a procedure analogus to that described in Example 112, Step D. The crude mixture was concentrated and purified by chromatography on silica gel, eluting with isocratic 20% acetones in hexanes, to provide the title compound. $^1$H NMR (400 MHz, CDCl$_3$) δ 7.35 (d, J=8.61 Hz, 2H), 6.97-7.15 (m, 3H), 6.85 (s, 1H), 6.67 (d, J=8.80 Hz, 1H), 4.77 (d, J=9.00 Hz, 1H), 4.37-4.61 (m, 3H), 3.12-3.26 (m, 1H), 2.99-3.12 (m, 1H), 2.84-2.99 (m, 1H), 2.49-2.61 (m, 1H), 1.98-2.16 (m, 1H), 1.53-1.73 (m, 1H), 1.30 (d, J=6.65 Hz, 6H), 0.65 (t, J=7.53 Hz, 3H). Mass Spectrum (ESI) m/z=470.2 [M]$^+$.

Step E. (5R,6R)-2-allyl-6-(3-chloro-5-fluorophenyl)-5-(4-chlorophenyl)-4-((S)-1-(isopropylthio)butan-2-yl)morpholin-3-one

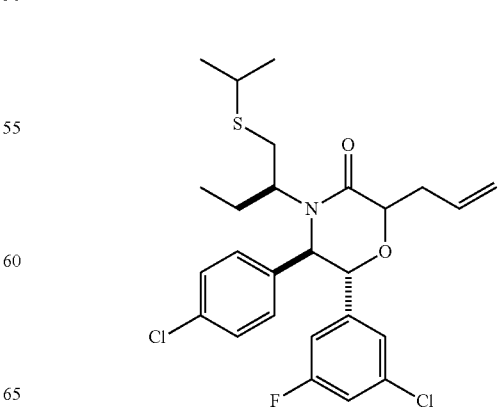

The above compound was prepared from (5R,6R)-6-(3-chloro-5-fluorophenyl)-5-(4-chlorophenyl)-4-((S)-1-(isopropylthio)butan-2-yl)morpholin-3-one (Example 124, Step D) by a procedure analogous to that described in Example 112, Step E. The crude material was purified by chromatography on silica gel, eluting with 3 step isocratic 0% to 30% acetone in hexanes, to provide the title compound. Mass Spectrum (ESI) m/z=510.2 [M]+.

Step F. 2-((2R,5R,6R)-6-(3-chloro-5-fluorophenyl)-5-(4-chlorophenyl)-4-((S)-1-(isopropylsulfonyl)butan-2-yl)-3-oxomorpholin-2-yl)acetic acid or 2-((2S,5R,6R)-6-(3-chloro-5-fluorophenyl)-5-(4-chlorophenyl)-4-((S)-1-(isopropylsulfonyl)butan-2-yl)-3-oxomorpholin-2-yl)acetic acid One of the title compounds was prepared from (5R,6R)-2-allyl-6-(3-chloro-5-fluorophenyl)-5-(4-chlorophenyl)-4-((S)-1-(isopropylthio)butan-2-yl)morpholin-3-one (Example 124, Step E) by a procedure analogous to that described in Example 112, Step F. The crude product was purified by reversed phase preparatory HPLC (Gemini™ Prep C$_{18}$ 5 μm column; Phenomenex, Torrance, Calif.; gradient elution of 25% to 75% MeCN in water, where both solvents contain 0.1% TFA, 30 min method), to provide one of the title compounds as the faster eluting isomer (t$_R$=17.9 min). $^1$H NMR (400 MHz, CDCl$_3$) δ 7.31-7.44 (m, 6H), 6.97-7.10 (m, 2H), 6.90 (d, J=8.80 Hz, 1H), 5.12 (s, 1H), 4.97 (d, J=6.46 Hz, 1H), 4.68-4.77 (m, 1H), 4.42 (s, 1H), 4.27-4.35 (m, 1H), 3.12 (d, J=5.87 Hz, 2H), 2.94 (d, J=13.50 Hz, 1H), 1.78 (s, 2H), 1.45 (dd, J=3.42, 6.75 Hz, 6H), 0.57 (t, J=7.24 Hz, 3H). Mass Spectrum (ESI) m/z=560.0 [M]+, 582.0 [M+Na]+.

Example 125

2-((2S,5R,6R)-6-(3-Chloro-5-fluorophenyl)-5-(4-chlorophenyl)-4-((S)-1-(isopropylsulfonyl)butan-2-yl)-3-oxomorpholin-2-yl)acetic acid or 2-((2R,5R,6R)-6-(3-Chloro-5-fluorophenyl)-5-(4-chlorophenyl)-4-((S)-1-(isopropylsulfonyl)butan-2-yl)-3-oxomorpholin-2-yl)acetic acid (Isomer 2)

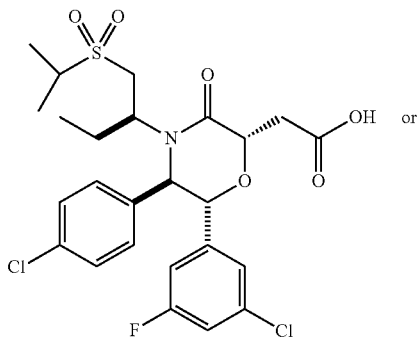

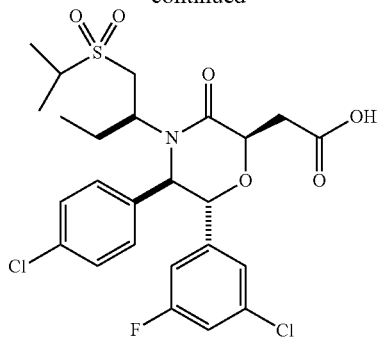

One of the title compounds was obtained as the second (slower) eluting isomer in Example 124 (t$_R$=18.37 min) as a white foam. $^1$H NMR (400 MHz, CDCl$_3$) δ 7.29-7.41 (m, 3H), 7.12-7.20 (m, 2H), 6.90-6.99 (m, 1H), 6.73-6.80 (m, 1H), 6.61-6.69 (m, 1H), 4.98-5.07 (m, 1H), 4.63-4.79 (m, 3H), 3.19-3.29 (m, 1H), 3.06-3.17 (m, 1H), 2.93-3.03 (m, 1H), 2.79-2.92 (m, 1H), 2.10-2.26 (m, 1H), 1.94-2.10 (m, 1H), 1.43 (s, 8H), 0.49-0.62 (m, 3H). Mass Spectrum (ESI) m/z=560.0 [M]+, 582.0 [M+Na]+.

Example 126

2-((2R,5R,6R)-6-(3-Chlorophenyl)-5-(4-chlorophenyl)-4-((3S,5S)-5-hydroxyhexan-3-yl)-3-oxomorpholin-2-yl)acetic acid or 2-((2R,5R,6R)-6-(3-Chlorophenyl)-5-(4-chlorophenyl)-4-((3S,5R)-5-hydroxyhexan-3-yl)-3-oxomorpholin-2-yl)acetic acid (Isomer 1)

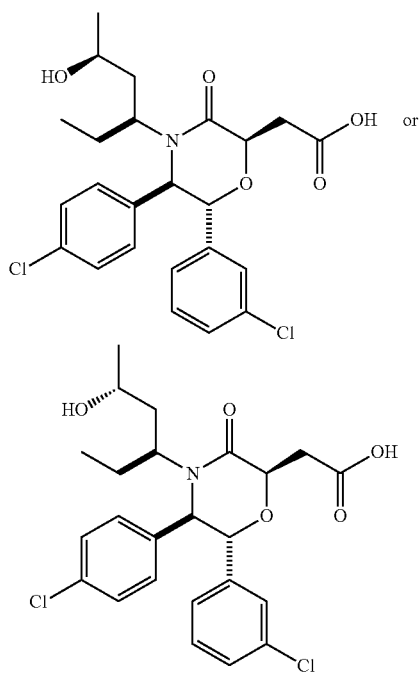

Step A. tert-Butyl 2-((2R,5R,6R)-6-(3-chlorophenyl)-5-(4-chlorophenyl)-4-((3S)-2-hydroxypentan-3-yl)-3-oxomorpholin-2-yl)acetate

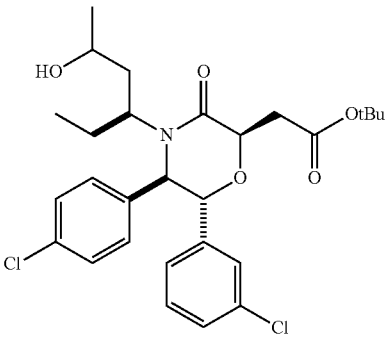

To a solution of oxalyl chloride (13.13 µl, 0.150 mmol) in DCM (295 µl) at −60° C. was added a solution of (methylsulfinyl)methane (21.4 µl, 0.301 mmol) in DCM (295 µl) under N₂. After being stirred for 2 min, a solution of tert-butyl 2-((2R,5R,6R)-6-(3-chlorophenyl)-5-(4-chlorophenyl)-4-((S)-1-hydroxybutan-2-yl)-3-oxomorpholin-2-yl)acetate (50 mg, 0.100 mmol; Example 114, Step B) in DCM (295 µl) was added, and the resulting mixture was stirred for 15 min. To this mixture was added triethylamine (70.0 µl, 0.502 mmol). After being stirred at −60° C. for 5 min, the reaction was allowed to warm to room temperature, and quenched (H₂O, 10 mL). The solution was extracted (3×20 mL DCM) and the organics were washed with H₂O and brine. The combined organic layers were dried (MgSO₄), filtered and the filtrate was concentrated under reduced pressure to give tert-butyl 2-((2R,5R,6R)-6-(3-chlorophenyl)-5-(4-chlorophenyl)-3-oxo-4-((S)-1-oxobutan-2-yl)morpholin-2-yl)acetate that was used immediately without further purification. To a 25-mL round-bottomed flask was added tert-butyl 2-((2R,5R,6R)-6-(3-chlorophenyl)-5-(4-chlorophenyl)-3-oxo-4-((S)-1-oxobutan-2-yl)morpholin-2-yl)acetate from above (0.051 g, 0.1 mmol) and methylmagnesium bromide, 1.4M solution in toluene/THF (75:25) (0.079 mL, 0.110 mmol) in THF (0.500 mL) at −78° C. The reaction mixture was stirred at −78° C. for 2 h and allowed to reach room temperature overnight. After this period, LCMS analysis showed what seemed to be left over starting material (3 peaks: Mass Spectrum (ESI) m/z=544.2 [M+Na]⁺, 528.1 [M+Na]⁺, and 544.2 [M+Na]⁺). As a result, an additional 0.2 equiv of methylmagnesium bromide, 1.4M solution in toluene/THF (75:25) was added and stirred for 1 h at room temperature. The reaction mixture was diluted with water (10 mL) and extracted with diethyl ether (3×10 mL). The crude mixture was used without further purification in the next reaction assuming 100% yield.

Step B. 2-((2R,5R,6R)-6-(3-Chlorophenyl)-5-(4-chlorophenyl)-4-((3S,5S)-5-hydroxyhexan-3-yl)-3-oxomorpholin-2-yl)acetic acid or 2-((2R,5R,6R)-6-(3-Chlorophenyl)-5-(4-chlorophenyl)-4-((3S,5R)-5-hydroxyhexan-3-yl)-3-oxomorpholin-2-yl)acetic acid (Isomer 1)

One of the title compounds was prepared from tert-butyl 2-((2R,5R,6R)-6-(3-chlorophenyl)-5-(4-chlorophenyl)-4-((3S)-2-hydroxypentan-3-yl)-3-oxomorpholin-2-yl)acetate (Example 126, Step A) by a procedure analogous to that described in Example 114, Step C. The crude product was purified by reversed phase preparatory HPLC (Gemini™ Prep C₁₈ 5 mm column; Phenomenex, Torrance, Calif.; gradient elution of 25% to 75% MeCN in water, where both solvents contain 0.1% TFA, 30 min method) to provide one of the title compounds as the faster eluting isomer (t_R=15.2 min).

¹H NMR (400 MHz, CDCl₃) δ 7.33 (d, J=8.41 Hz, 2H), 7.20-7.27 (m, 1H), 7.08-7.16 (m, 2H), 7.04 (d, J=8.41 Hz, 2H), 6.75 (d, J=7.83 Hz, 1H), 4.72-4.79 (m, 1H), 4.69 (t, J=4.50 Hz, 1H), 4.58-4.66 (m, 1H), 4.29-4.43 (m, 1H), 3.19 (d, J=4.30 Hz, 1H), 3.07 (d, J=4.89 Hz, 1H), 2.67-2.80 (m, 1H), 1.89-2.11 (m, 2H), 1.19 (d, J=6.65 Hz, 3H), 0.71 (t, J=7.53 Hz, 3H). Mass Spectrum (ESI) m/z=466.2 [M]⁺.

Example 127

2-((2R,5R,6R)-6-(3-Chlorophenyl)-5-(4-chlorophenyl)-4-((3S,5R)-5-hydroxyhexan-3-yl)-3-oxomorpholin-2-yl)acetic acid or 2-((2R,5R,6R)-6-(3-Chlorophenyl)-5-(4-chlorophenyl)-4-((3S,5S)-5-hydroxyhexan-3-yl)-3-oxomorpholin-2-yl)acetic acid (Isomer 2)

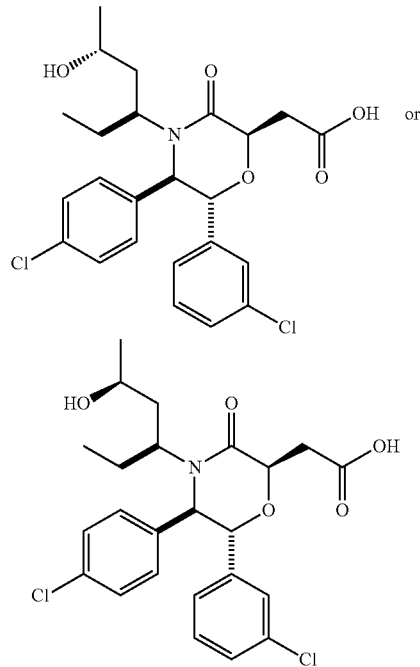

One of the title compounds was obtained as the second (slower) eluting isomer in Example 126 (t_R=16.9 min) as a white foam. ¹H NMR (400 MHz, CDCl₃) δ 9.53 (s, 1H), 7.32 (d, J=8.61 Hz, 2H), 7.24 (s, 1H), 7.04-7.15 (m, 4H), 6.77 (d, J=9.00 Hz, 2H), 4.85 (d, J=10.17 Hz, 2H), 4.68 (s, 2H), 3.55-3.62 (m, 1H), 3.15 (dd, J=2.35, 5.09 Hz, 2H), 2.95-3.05 (m, 1H), 2.13-2.32 (m, 1H), 1.54-1.72 (m, 1H), 1.16 (d, J=6.26 Hz, 3H), 0.82 (t, J=7.53 Hz, 3H). Mass Spectrum (ESI) m/z=466.2 [M]⁺.

Example 128

2-((2R,5R,6R)-6-(3-Chlorophenyl)-5-(4-chlorophenyl)-3-oxo-4-((S)-1-(N-phenylcyclopropanesulfonamido)butan-2-yl)morpholin-2-yl)acetic acid or 2-((2S,5R,6R)-6-(3-Chlorophenyl)-5-(4-chlorophenyl)-3-oxo-4-((S)-1-(N-phenylcyclopropanesulfonamido)butan-2-yl)morpholin-2-yl)acetic acid (Isomer 1)

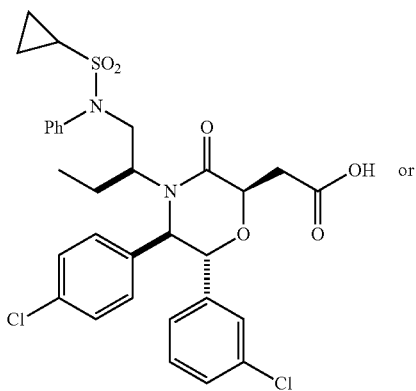

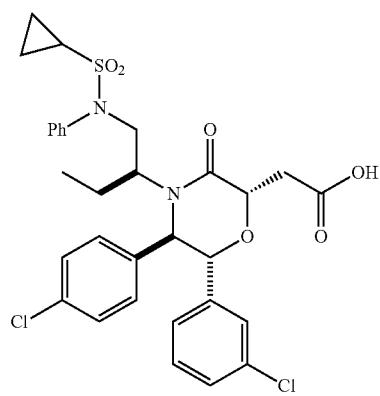

One of the title compound was prepared from (5R,6R)-6-(3-Chlorophenyl)-5-(4-chlorophenyl)-4-((S)-1-hydroxybutan-2-yl)morpholin-3-one (Example 112, Step C) by a procedure analogous to that described in Example 112, Steps D though F, replacing ethanethiol in Step D with N-phenylcyclopropanesulfonamide. The crude product was purified by reversed phase preparatory HPLC (Gemini™ Prep C$_{18}$ 5 μm column; Phenomenex, Torrance, Calif.; gradient elution of 25% to 75% MeCN in water, where both solvents contain 0.1% TFA, 30 min method) which provided one of the title compounds as the faster eluting isomer ($t_R$=20.2 min). $^1$H NMR (400 MHz, CDCl$_3$) δ 7.43-7.54 (m, 4H), 7.33-7.43 (m, 2H), 7.31 (d, J=1.37 Hz, 1H), 7.16-7.27 (m, 2H), 6.95-7.14 (m, 3H), 4.79 (d, J=12.52 Hz, 2H), 4.44-4.62 (m, 1H), 4.33 (s, 1H), 3.72-3.92 (m, 1H), 2.91-3.16 (m, 3H), 2.30-2.47 (m, 1H), 1.83-2.07 (m, 1H), 1.45-1.67 (m, 1H), 1.06 (d, J=4.70 Hz, 2H), 0.93 (d, J=6.46 Hz, 2H), 0.51 (t, J=7.53 Hz, 3H). Mass Spectrum (ESI) m/z=631.1 [M]$^+$.

Example 129

2-((2S,5R,6R)-6-(3-Chlorophenyl)-5-(4-chlorophenyl)-3-oxo-4-((S)-1-(N-phenylcyclopropanesulfonamido)butan-2-yl)morpholin-2-yl)acetic acid or 2-((2R,5R,6R)-6-(3-Chlorophenyl)-5-(4-chlorophenyl)-3-oxo-4-((S)-1-(N-phenylcyclopropanesulfonamido)butan-2-yl)morpholin-2-yl)acetic acid (Isomer 2)

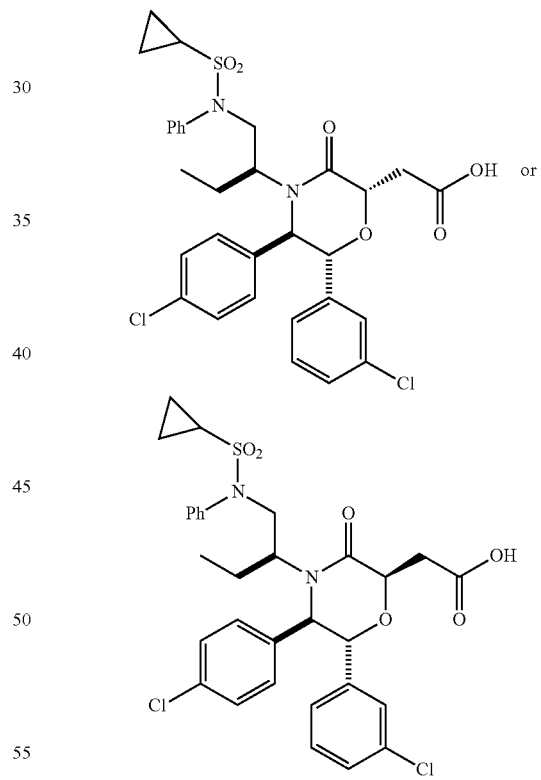

One of the title compounds was obtained as the second (slower) eluting isomer in Example 128 ($t_R$=20.8 min). $^1$H NMR (400 MHz, CDCl$_3$) δ 7.35-7.57 (m, 5H), 7.25-7.29 (m, 3H), 7.14-7.24 (m, 1H), 7.09 (d, J=1.56 Hz, 1H), 6.97 (d, J=8.22 Hz, 2H), 6.83 (d, J=7.82 Hz, 1H), 4.77 (d, J=9.98 Hz, 1H), 4.50-4.69 (m, 3H), 3.74-3.88 (m, 1H), 2.89-3.07 (m, 1H), 2.72 (d, J=7.43 Hz, 1H), 2.51 (d, J=5.09 Hz, 1H), 2.28-2.42 (m, 1H), 1.90-2.06 (m, 1H), 1.47-1.66 (m, 1H), 0.82-1.13 (m, 4H), 0.54 (t, J=7.53 Hz, 3H). Mass Spectrum (ESI) m/z=631.1 [M]$^+$.

Example 130

2-((2R,5R,6R)-4-((S)-1-(tert-Butylsulfonyl)butan-2-yl)-6-(3-chlorophenyl)-5-(4-chlorophenyl)-2-methyl-3-oxomorpholin-2-yl)acetic acid or 2-((2S,5R,6R)-4-((S)-1-(tert-Butylsulfonyl)butan-2-yl)-6-(3-chlorophenyl)-5-(4-chlorophenyl)-2-methyl-3-oxomorpholin-2-yl)acetic acid (Isomer 1)

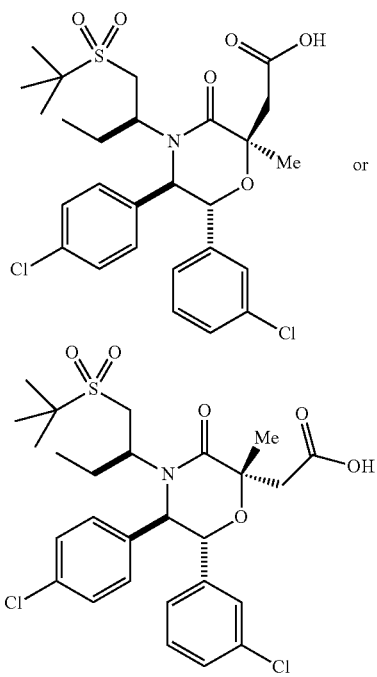

or

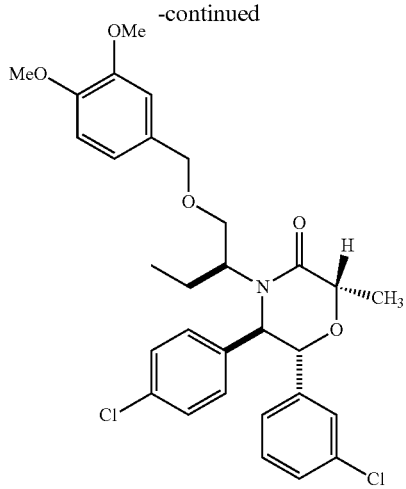

To a solution of (5R,6R)-6-(3-chlorophenyl)-5-(4-chlorophenyl)-4-(1-((3,4-dimethoxybenzyl)oxy)butan-2-yl)morpholin-3-one (1.0 g, 1.837 mmol) (Example 112, Step B) in THF (4.59 mL) at −78° C. was added a 1.0M solution of lithium bis(trimethylsilyl)amide in THF (2.2 mL, 2.204 mmol, Fluka, Buchs, Switzerland). To this mixture was added iodomethane (Fluka, Buchs, Switzerland) (0.125 mL, 2.02 mmol) at this temperature and the reaction was stirred for 30 minutes. After this period, the reaction mixture was diluted with sat. aq. NH$_4$Cl solution (10 mL) and extracted with diethyl ether (3×30 mL). The organic layers were dried over MgSO$_4$, filtered and the filtrate was concentrated under reduced pressure. The residue was purified by chromatography on silica gel, eluting with of 10% to 30% acetone in hexanes (gradient), to provide the title compounds as a 2:1 mixture of epimers at C2. Mass Spectrum (ESI) m/z=580.1 [M+Na]$^+$.

Step A. (2R,5R,6R)-6-(3-Chlorophenyl)-5-(4-chlorophenyl)-4-((S)-1-((3,4-dimethoxybenzyl)oxy)butan-2-yl)-2-methylmorpholin-3-one and (2R,5S,6R)-6-(3-Chlorophenyl)-5-(4-chlorophenyl)-4-((S)-1-((3,4-dimethoxybenzyl)oxy)butan-2-yl)-2-methylmorpholin-3-one Step B. (2S,5R,6R)-2-Allyl-6-(3-chlorophenyl)-5-(4-chlorophenyl)-4-((S)-1-((3,4-dimethoxybenzyl)oxy)butan-2-yl)-2-methylmorpholin-3-one and (2S,5R,6R)-2-Allyl-6-(3-chlorophenyl)-5-(4-chlorophenyl)-4-((S)-1-((3,4-dimethoxybenzyl)oxy)butan-2-yl)-2-methylmorpholin-3-one

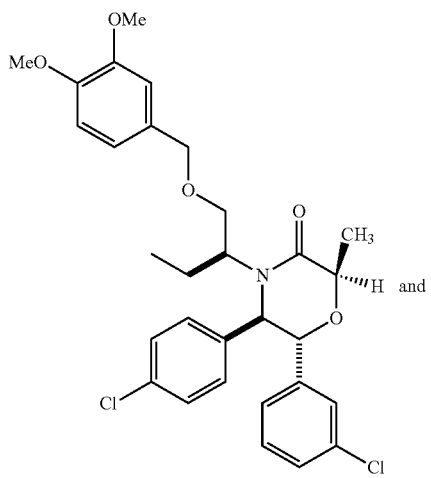 and

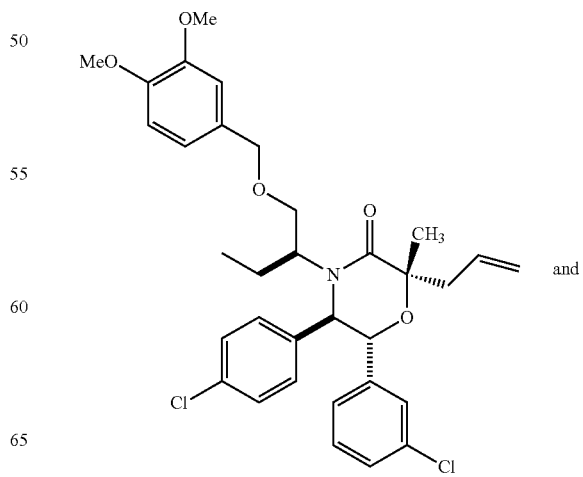 and

-continued

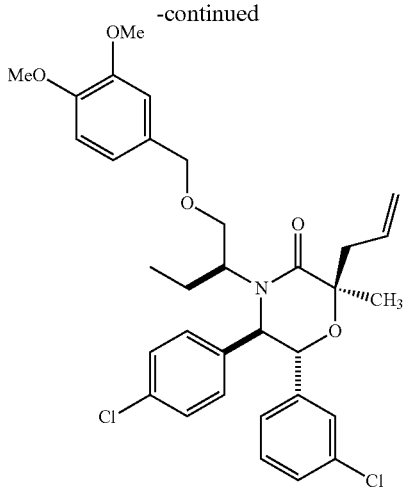

To a mixture of (2R,5R,6R)-6-(3-chlorophenyl)-5-(4-chlorophenyl)-4-((S)-1-((3,4-dimethoxybenzyl)oxy)butan-2-yl)-2-methylmorpholin-3-one and (2R,5S,6R)-6-(3-chlorophenyl)-5-(4-chlorophenyl)-4-((S)-1-((3,4-dimethoxybenzyl)oxy)butan-2-yl)-2-methylmorpholin-3-one (620 mg, 1.110 mmol; Example 130, Step A) in THF (2775 μl) at −78° C. was added a 1.0M solution of lithium bis(trimethylsilyl)amide in THF (1332 μl, 1.332 mmol). To this mixture allyl bromide (106 μl, 1.221 mmol) was added and the resulting mixture was stirred for 2 h at −78° C., 1 h at −60° C., and 2 h at −42° C. After this time the reaction mixture was diluted with water (5 mL) and extracted with diethyl ether (3×10 mL). The organic extract was dried over MgSO$_4$. The solution was filtered and concentrated in vacuo to give the crude material as a light yellow oil which was purified by chromatography on silica gel, eluting with a 5% to 25% acetone in hexanes (gradient), to provide the title compounds as a 3:1 mixture of diastereomers. $^1$H NMR (400 MHz, CDCl$_3$) δ 7.24 (d, J=7.24 Hz, 2H), 7.17-7.22 (m, 1H), 7.10 (d, J=1.96 Hz, 1H), 7.01-7.08 (m, 1H), 6.84-7.01 (m, 5H), 6.62 (d, J=7.63 Hz, 1H), 5.80-6.09 (m, 1H), 5.08-5.27 (m, 2H), 4.72 (d, J=19.37 Hz, 2H), 4.29-4.55 (m, 2H), 3.98 (s, 1H), 3.85-3.94 (m, 6H), 3.27-3.42 (m, 1H), 2.93-3.09 (m, 1H), 2.81-2.93 (m, 1H), 2.44-2.70 (m, 1H), 1.81-1.99 (m, 1H), 1.65-1.80 (m, 1H), 1.63 (s, 3H), 0.56-0.69 (m, 3H). Mass Spectrum (ESI) m/z=620.2 [M+Na]$^+$.

Step C. (2R,5R,6R)-2-Allyl-6-(3-chlorophenyl)-5-(4-chlorophenyl)-4-((S)-1-hydroxybutan-2-yl)-2-methylmorpholin-3-one or (2S,5R,6R)-2-Allyl-6-(3-chlorophenyl)-5-(4-chlorophenyl)-4-((S)-1-hydroxybutan-2-yl)-2-methylmorpholin-3-one

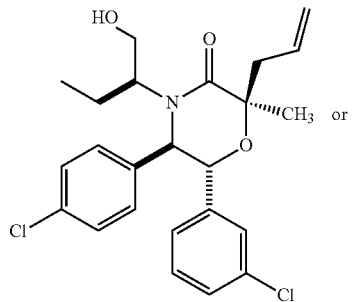 or

-continued

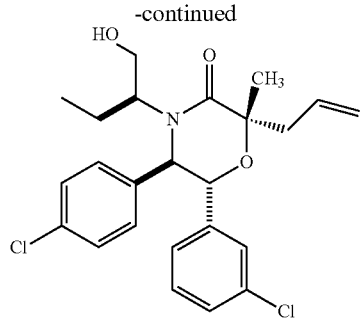

One of the title compound was prepared from ((2S,5R,6R)-2-allyl-6-(3-chlorophenyl)-5-(4-chlorophenyl)-4-((S)-1-((3,4-dimethoxybenzyl)oxy)butan-2-yl)-2-methylmorpholin-3-one and (2S,5R,6R)-2-allyl-6-(3-chlorophenyl)-5-(4-chlorophenyl)-4-((S)-1-((3,4-dimethoxybenzyl)oxy)butan-2-yl)-2-methylmorpholin-3-one (Example 130, Step B) by a procedure analogous to that described in Example 112, Step C. The crude material was purified by chromatography on silica gel, eluting with a gradient of 0% to 30% acetone in hexanes (left in a isocratic 10% acetone/hexanes mixture for 15 minutes before increasing the gradient, the aldehyde comes out first, the desired product comes at 15% acetone in hexanes), to provide one of the title compounds as the faster eluting isomer. $^1$H NMR (400 MHz, CDCl$_3$) δ 7.08-7.25 (m, 3H), 6.87-7.06 (m, 4H), 6.61 (d, J=7.83 Hz, 1H), 5.92-6.12 (m, 1H), 5.11-5.28 (m, 2H), 4.66 (d, J=9.39 Hz, 1H), 4.45 (d, J=9.59 Hz, 1H), 3.56 (t, J=12.70 Hz, 1H), 3.36-3.49 (m, 1H), 3.07-3.23 (m, 1H), 2.87-3.03 (m, 1H), 2.78 (dd, J=8.22, 13.69 Hz, 1H), 2.44 (dd, J=6.26, 13.69 Hz, 1H), 1.70-1.88 (m, 1H), 1.57 (s, 3H), 1.28-1.46 (m, 3H), 0.60 (t, J=7.53 Hz, 3H). Mass Spectrum (ESI) m/z=448.2 [M]$^+$.

Further elution provided another one of the title compounds as the second (slower) eluting isomer. $^1$H NMR (400 MHz, CDCl$_3$) δ 7.17-7.24 (m, 2H), 6.88-7.08 (m, 4H), 6.59 (d, J=7.63 Hz, 1H), 5.69-5.86 (m, 1H), 5.03-5.19 (m, 2H), 4.77 (d, J=9.59 Hz, 2H), 4.49 (d, J=9.59 Hz, 1H), 3.38-3.57 (m, 2H), 3.25-3.38 (m, 1H), 2.93 (dd, J=6.36, 14.57 Hz, 1H), 2.50-2.64 (m, 1H), 1.70-1.90 (m, 1H), 1.38-1.46 (m, 1H), 1.31-1.37 (m, 2H), 1.19 (s, 3H), 0.68 (t, J=7.43 Hz, 2H). Mass Spectrum (ESI) m/z=448.2 [M]$^+$.

Step D. (2R,5R,6R)-2-Allyl-4-((S)-1-(tert-butylthio)butan-2-yl)-6-(3-chlorophenyl)-5-(4-chlorophenyl)-2-methylmorpholin-3-one and (2S,5R,6R)-2-Allyl-4-((S)-1-(tert-butylthio)butan-2-yl)-6-(3-chlorophenyl)-5-(4-chlorophenyl)-2-methylmorpholin-3-one

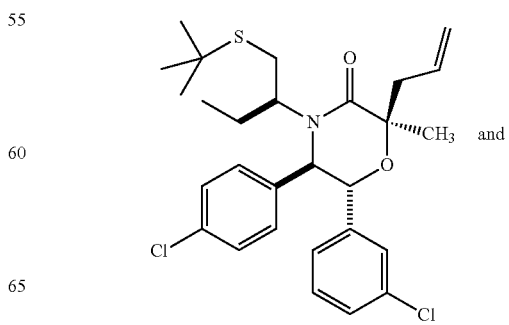 and

229

-continued

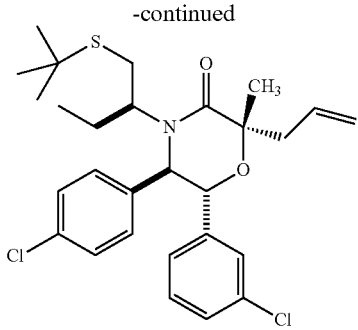

The title compounds were prepared from (2R,5R,6R)-2-allyl-6-(3-chlorophenyl)-5-(4-chlorophenyl)-4-((S)-1-hydroxybutan-2-yl)-2-methylmorpholin-3-one and (2S,5R,6R)-2-allyl-6-(3-chlorophenyl)-5-(4-chlorophenyl)-4-((S)-1-hydroxybutan-2-yl)-2-methylmorpholin-3-one (mixture of isomers from Example 130, Step C) by a procedure analgous to that described in Example 112, Step D. The crude mixture was concentrated and purified by chromatography on silica gel, eluting with 0% and 15% acetones in hexanes (two step isocratic), to provide the title compounds as a 3:1 mixture of epimers at C2. $^1$H NMR (400 MHz, CDCl$_3$) δ 7.27 (s, 2H), 7.15-7.23 (m, 1H), 7.09 (d, J=3.91 Hz, 2H), 6.66-6.76 (m, 1H), 5.95-6.13 (m, 1H), 5.13-5.28 (m, 1H), 4.72 (d, J=9.19 Hz, 2H), 3.18-3.31 (m, 1H), 2.80-2.97 (m, 2H), 2.49-2.66 (m, 1H), 2.39-2.50 (m, 1H), 2.01-2.16 (m, 1H), 1.58-1.75 (m, 5H), 1.28-1.32 (m, 9H), 0.64 (t, J=7.53 Hz, 3H). Mass Spectrum (ESI) m/z=520.2.

Step E. 2-((2R,5R,6R)-4-((S)-1-(tert-Butylsulfonyl)butan-2-yl)-6-(3-chlorophenyl)-5-(4-chlorophenyl)-2-methyl-3-oxomorpholin-2-yl)acetic acid or 2-((2S,5R,6R)-4-((S)-1-(tert-Butylsulfonyl)butan-2-yl)-6-(3-chlorophenyl)-5-(4-chlorophenyl)-2-methyl-3-oxomorpholin-2-yl)acetic acid (Isomer 1)

One of the title compounds was prepared from (2R,5R,6R)-2-allyl-4-((S)-1-(tert-butylthio)butan-2-yl)-6-(3-chlorophenyl)-5-(4-chlorophenyl)-2-methylmorpholin-3-one and (2S,5R,6R)-2-allyl-4-((S)-1-(tert-butylthio)butan-2-yl)-6-(3-chlorophenyl)-5-(4-chlorophenyl)-2-methylmorpholin-3-one (mixture of isomers from Example 130, Step D) by a procedure analogous to the one described in Example 112, Step F. The crude product was purified by reversed phase preparatory HPLC (Gemini™ Prep C$_{18}$ 5 μm column; Phenomenex, Torrance, Calif.; gradient elution of 25% to 75% MeCN in water, where both solvents contain 0.1% TFA, 30 min method), to provide one of the title compounds as the faster eluting isomer (t$_R$=19.03 min). $^1$H NMR (400 MHz, CDCl$_3$) δ 7.27 (s, 3H), 7.17-7.22 (m, 1H), 7.11 (s, 1H), 6.99 (s, 1H), 6.85 (d, J=8.02 Hz, 2H), 5.01 (d, J=9.78 Hz, 1H), 4.88 (d, J=9.78 Hz, 1H), 3.98 (dd, J=7.73, 13.79 Hz, 1H), 3.27-3.43 (m, 1H), 3.10-3.21 (m, 1H), 2.93-3.09 (m, J=16.04 Hz, 2H), 2.10-2.25 (m, J=7.04, 16.43 Hz, 1H), 1.69-1.83 (m, 4H), 1.79 (s, 4H), 1.42 (s, 9H), 0.61 (t, J=7.53 Hz, 3H). Mass Spectrum (ESI) m/z=570.0 [M]$^+$.

230

Example 131

2-((2S,5R,6R)-4-((S)-1-(tert-Butylsulfonyl)butan-2-yl)-6-(3-chlorophenyl)-5-(4-chlorophenyl)-2-methyl-3-oxomorpholin-2-yl)acetic acid or 2-((2R,5R,6R)-4-((S)-1-(tert-Butylsulfonyl)butan-2-yl)-6-(3-chlorophenyl)-5-(4-chlorophenyl)-2-methyl-3-oxomorpholin-2-yl)acetic acid (Isomer 2)

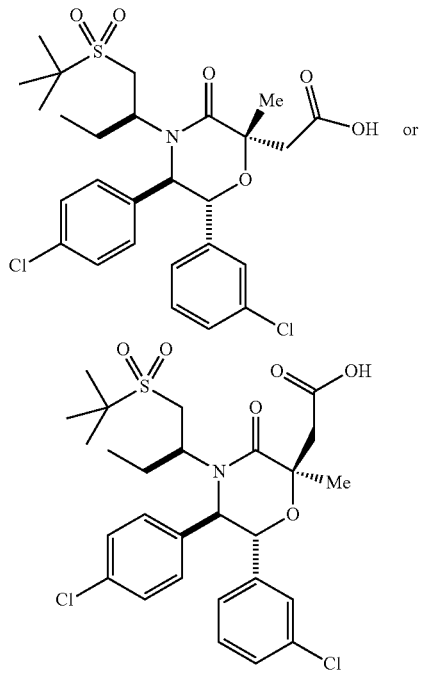

One of the title compounds was obtained as the second (slower) eluting isomer in Example 130 (t$_R$=20.2 min) as a white foam. $^1$H NMR (400 MHz, CDCl$_3$) δ 7.27-7.40 (m, 2H), 7.13-7.18 (m, 1H), 6.99-7.10 (m, 2H), 6.89-6.98 (m, 1H), 6.81-6.88 (m, 1H), 6.55-6.66 (m, 1H), 5.31-5.43 (m, 1H), 5.07 (s, 1H), 3.63-3.75 (m, 1H), 3.44-3.57 (m, 1H), 3.28 (s, 2H), 2.85 (s, 1H), 1.93-2.07 (m, 1H), 1.79-1.92 (m, 1H), 1.61 (s, 3H), 1.31 (s, 9H), 0.64 (t, J=7.63 Hz, 3H). Mass Spectrum (ESI) m/z=570.0 [M]$^+$.

Example 132

2-((2R,5R,6R)-6-(3-Chlorophenyl)-5-(4-chlorophenyl)-4-(cyclopropylmethyl)-5-methyl-3-oxomorpholin-2-yl)acetic acid or 2-((2S,5R,6R)-6-(3-Chlorophenyl)-5-(4-chlorophenyl)-4-(cyclopropylmethyl)-5-methyl-3-oxomorpholin-2-yl)acetic acid

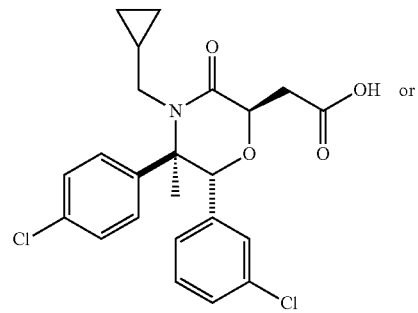

-continued

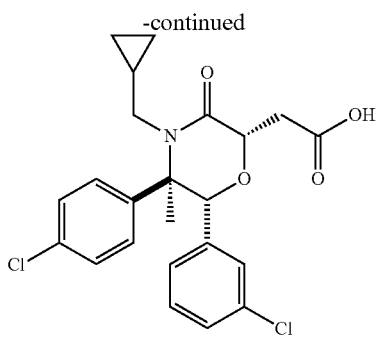

Step A. (1R,2R)-1-(3-chlorophenyl)-2-(4-chlorophenyl)-2-((cyclopropylmethyl)amino) propan-1-ol

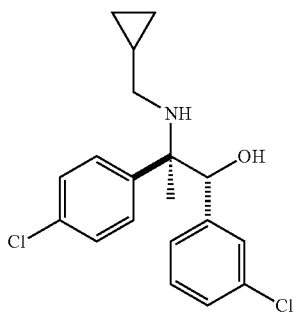 [SMILES: C[C@@](NCC1CC1)(c1ccc(Cl)cc1)[C@H](O)c1cccc(Cl)c1]

To a stirred solution of (1R,2R)-2-amino-1-(3-chlorophenyl)-2-(4-chlorophenyl)propan-1-ol (340 mg, 1.148 mmol; Intermediate F1) in methanol (3 mL) was added cyclopropanecarboxaldehyde (87 μl, 1.15 mmol) and the reaction was stirred at rt overnight under a $N_2$ atmosphere. After this time $NaBH_4$ (76 mg, 2.01 mmol) was added and the reaction was stirred for 10 minutes. The reaction was acidified to pH 2 with HCl (1M aqueous solution) and then it was concentrated under a vacuum. The resulting residue was partitioned between DCM and $NaHCO_3$. The separated aqueous layer was extracted with DCM (3×20 mL) and the combined organic extracts were dried over $MgSO_4$, filtered and the filtrate was concentrated under reduced pressure to give the title compound which was used in the next step without further purification. Mass Spectrum (ESI) m/z=350.2 $[M]^+$.

Step B. (5R,6R)-6-(3-Chlorophenyl)-5-(4-chlorophenyl)-4-(cyclopropylmethyl)-5-methylmorpholin-3-one

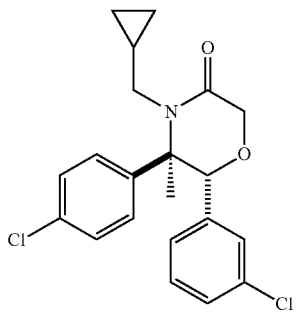 [SMILES: C[C@@]1(c2ccc(Cl)cc2)[C@@H](c2cccc(Cl)c2)OCC(=O)N1CC1CC1]

The above compound was prepared from (1R,2R)-1-(3-chlorophenyl)-2-(4-chlorophenyl)-2-((cyclopropylmethyl)amino)propan-1-ol (Example 132, Step A) by a procedure similar to the one described in Example 112, Step A. The crude material was absorbed onto a plug of silica gel and purified by chromatography on silica gel, eluting with a gradient of 0% to 40% acetone in hexanes, to provide the title compound. $^1$H NMR (400 MHz, CDCl$_3$) δ 7.32 (d, J=8.80 Hz, 2H), 7.14 (ddd, J=0.88, 2.05, 8.02 Hz, 1H), 6.94-7.12 (m, 3H), 6.78 (t, J=1.66 Hz, 1H), 6.33 (d, J=7.82 Hz, 1H), 4.74 (s, 1H), 4.37-4.63 (m, 2H), 3.34 (dd, J=5.97, 14.18 Hz, 1H), 2.42 (dd, J=6.85, 14.28 Hz, 1H), 1.55 (s, 3H), 0.37-0.45 (m, 2H), −0.15-0.09 (m, 2H). Mass Spectrum (ESI) m/z=390.2 $[M]^+$.

Step C. (2R,5R,6R)-2-Allyl-6-(3-chlorophenyl)-5-(4-chlorophenyl)-4-(cyclopropylmethyl)-5-methylmorpholin-3-one and (2R,5R,6R)-2-Allyl-6-(3-chlorophenyl)-5-(4-chlorophenyl)-4-(cyclopropylmethyl)-5-methylmorpholin-3-one

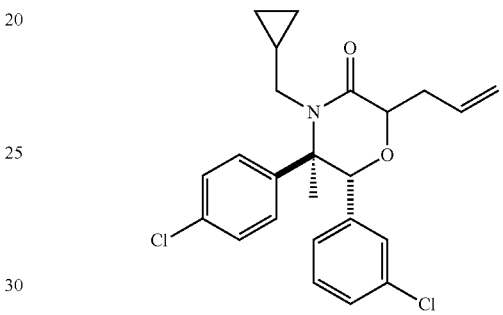

The title compounds were prepared from (5R,6R)-6-(3-chlorophenyl)-5-(4-chlorophenyl)-4-(cyclopropylmethyl)-5-methylmorpholin-3-one (Example 132, Step B) by a procedure analogous to that described in Example 112, Step E. The crude material was absorbed onto a plug of silica gel and purified by chromatography on a silica gel column (120 g), eluting with a gradient of 5% to 15% acetone in hexanes, to provide the title compounds as a 2:1 mixture of diastereomers. NMR for the 2:1 mixture of diastereomers: $^1$H NMR (400 MHz, CDCl$_3$) δ 7.28-7.37 (m, 4H), 7.15 (td, J=0.98, 8.02 Hz, 2H), 7.06 (d, J=8.02 Hz, 4H), 6.96-7.02 (m, 2H), 6.76-6.83 (m, 2H), 6.30-6.41 (m, 2H), 5.80-6.08 (m, 2H), 5.27 (dd, J=1.86, 17.12 Hz, 1H), 5.02-5.19 (m, 3H), 4.76 (s, 1H), 4.59-4.67 (m, 2H), 4.51 (t, J=4.99 Hz, 1H), 3.46 (dd, J=5.77, 14.18 Hz, 1H), 3.32 (dd, J=5.97, 14.18 Hz, 2H), 2.74-2.86 (m, 4H), 2.47 (dd, J=6.75, 14.18 Hz, 2H), 2.24 (dd, J=7.14, 14.18 Hz, 1H), 1.52-1.57 (m, 6H), 0.96-1.05 (m, 2H), 0.35-0.48 (m, 4H), −0.09-0.06 (m, 4H). Mass Spectrum (ESI) m/z=430.2 $[M]^+$.

Step D. 2-((2S,5R,6R)-4-((S)-1-(tert-Butylsulfonyl)butan-2-yl)-6-(3-chlorophenyl)-5-(4-chlorophenyl)-2-methyl-3-oxomorpholin-2-yl)acetic acid or 2-((2R,5R,6R)-4-((S)-1-(tert-Butylsulfonyl)butan-2-yl)-6-(3-chlorophenyl)-5-(4-chlorophenyl)-2-methyl-3-oxomorpholin-2-yl)acetic acid The title compound was prepared from a mixture of (2R,5R,6R)-2-allyl-6-(3-chlorophenyl)-5-(4-chlorophenyl)-4-(cyclopropylmethyl)-5-methylmorpholin-3-one and (2R,5R,6R)-2-allyl-6-(3-chlorophenyl)-5-(4-chlorophenyl)-4-(cyclopropylmethyl)-5-methylmorpholin-3-one (Example 132, Step C) by a procedure analogous to that described in Example 112, Step F. The crude product was purified by reversed phase preparatory HPLC (Gemini™ Prep C$_{18}$ 5 μm column; Phenomenex, Torrance, Calif.; gradient elution of 25% to 75% MeCN in water, where both solvents contain 0.1% TFA, 30 min method) to provide one of the title compounds as a white foam ($t_R$=19.13 min). $^1$H NMR (400 MHz, CDCl$_3$) δ 7.37 (d, J=8.80 Hz, 2H), 7.18 (dd, J=1.17, 8.02 Hz, 1H), 6.96-7.14 (m, 3H), 6.81 (s, 1H), 6.38 (d, J=7.83 Hz, 1H), 5.11 (t, J=6.16 Hz, 1H), 4.98 (s, 1H), 3.50 (dd, J=5.87, 14.28 Hz, 1H), 3.20 (d, J=5.48 Hz, 1H), 2.98-3.11 (m, 1H), 2.42 (dd, J=7.04, 14.28 Hz, 1H), 1.62 (s, 3H), 0.94-1.13 (m, 1H), 0.40-0.55 (m, 2H), 0.03 (d, J=4.70 Hz, 2H). Mass Spectrum (ESI) m/z=448.0 [M]$^+$.

Example 133

2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)acetic acid N-(2-fluorophenyl)cyclopropanesulfonamide

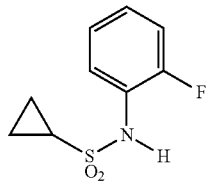

The above compound was synthesized by the following procedure:

To a solution of cyclopropanesulfonyl chloride (1.010 mL, 9.92 mmol) and pyridine (2 mL) in DCM (2 mL) was added 2-fluoroaniline (0.956 mL, 9.92 mmol) at room temperature and the reaction was stirred at 50° C. for 5 hours, then at room temperature overnight. Diethyl ether was added to the reaction (20 mL), and the mixture was washed with H$_2$O (2×20 mL) and brine (20 mL). The organic layer was dried with Na$_2$SO$_4$. Upon concentration, the crude material was adsorbed onto a plug of silica gel and purified by flash chromatography through a silica gel column (80 g), eluting through a two-step isocratic method of 10% and 20% acetone in hexanes, to provide N-(2-fluorophenyl)propane-2-sulfonamide as an off-white solid. $^1$H NMR (400 MHz, CDCl$_3$) δ 7.56-7.68 (m, 1H), 7.06-7.24 (m, 3H), 6.56 (br. s., 1H), 2.51 (tt, J=4.89, 8.02 Hz, 1H), 1.15-1.22 (m, 2H), 0.93-1.03 (m, 2H). Mass spectrum (ESI) m/z=216.2 [M+H]$^+$.

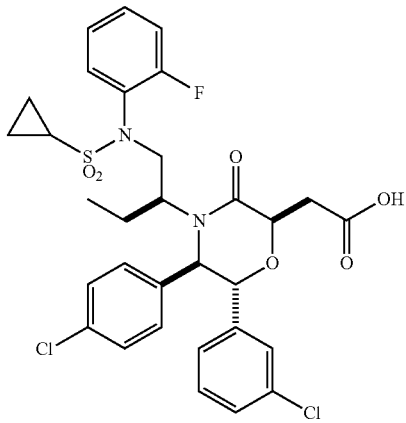

The title compound was prepared from (5R,6R)-6-(3-chlorophenyl)-5-(4-chlorophenyl)-4-((S)-1-hydroxybutan-2-yl)morpholin-3-one (Example 112, Step C) by procedures similar to those described in Example 112, Steps D though F, replacing ethanethiol in Step D with N-(2-fluorophenyl)cyclopropanesulfonamide. The crude product was purified by reverse phase preparatory HPLC (Gemini™ Prep C$_{18}$ 5 µm column; Phenomenex, Torrance, Calif.; gradient elution of 25% to 75% MeCN in water, where both solvents contain 0.1% TFA, 30 min method) to provide the title compound as the faster eluting isomer as a white foam ($t_R$=20.0 min). The stereochemistry was confirmed by examination of the co-crystal structure of the compound in complex with MDM2. $^1$H NMR (400 MHz, CDCl$_3$) δ 7.52 (dt, J=1.56, 7.82 Hz, 1H), 7.35-7.43 (m, 1H), 7.29-7.34 (m, 2H), 7.26-7.28 (m, 1H), 7.25 (s, 1H), 7.14-7.24 (m, 5H), 7.07 (d, J=7.43 Hz, 1H), 4.90-4.98 (m, 1H), 4.82-4.89 (m, 1H), 4.44 (t, J=6.36 Hz, 1H), 4.34 (dd, J=8.90, 14.77 Hz, 1H), 3.81 (dd, J=4.60, 14.77 Hz, 1H), 3.15 (br. s., 1H), 3.04 (d, J=6.46 Hz, 2H), 2.41-2.55 (m, 1H), 1.83-2.00 (m, J=7.04, 8.22 Hz, 1H), 1.47-1.65 (m, J=2.25, 7.14 Hz, 1H), 0.87-1.12 (m, 4H), 0.49 (t, J=7.53 Hz, 3H). Mass spectrum (ESI) m/z=649.0 [M]$^+$.

Example 134

2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)acetic acid

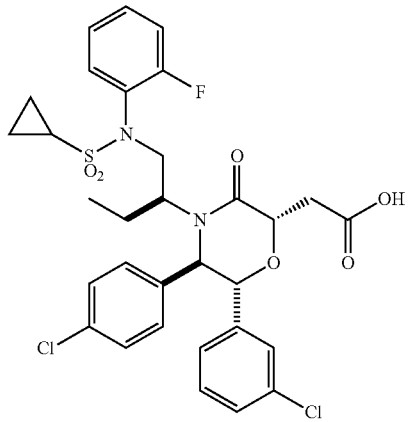

The title compounds was obtained as the second (slower) eluting isomer in Example 133 as a white foam ($t_R$=20.5 min). The stereochemistry was confirmed by examination of the co-crystal structure of the compound complexed to MDM2. $^1$H NMR (400 MHz, CDCl$_3$) δ 7.54 (t, J=7.83 Hz, 1H), 7.35-7.44 (m, 1H), 7.30 (s, 2H), 7.12-7.26 (m, 4H), 7.00-7.11 (m, 3H), 6.87 (d, J=7.63 Hz, 1H), 4.88 (d, J=9.78 Hz, 1H), 4.59-4.72 (m, 2H), 4.39 (dd, J=10.37, 14.48 Hz, 1H), 3.76 (d, J=12.32 Hz, 1H), 2.96 (bs, 1H), 2.81 (dd, J=7.04, 16.04 Hz, 1H), 2.38-2.58 (m, 2H), 1.95 (td, J=7.51, 14.92 Hz, 1H), 1.43-1.61 (m, 1H), 0.83-1.12 (m, 4H), 0.50 (t, J=7.43 Hz, 3H). Mass spectrum (ESI) m/z=649.0 [M]$^+$.

Example 135

2-((2R,5R,6R)-6-(3-chlorophenyl)-5-(4-chlorophenyl)-4-((S)-1-(N-(4-fluorophenyl)cyclopropanesulfonamido)butan-2-yl)-3-oxomorpholin-2-yl)acetic acid or 2-((2S,5R,6R)-6-(3-chlorophenyl)-5-(4-chlorophenyl)-4-((S)-1-(N-(4-fluorophenyl)cyclopropanesulfonamido)butan-2-yl)-3-oxomorpholin-2-yl)acetic acid

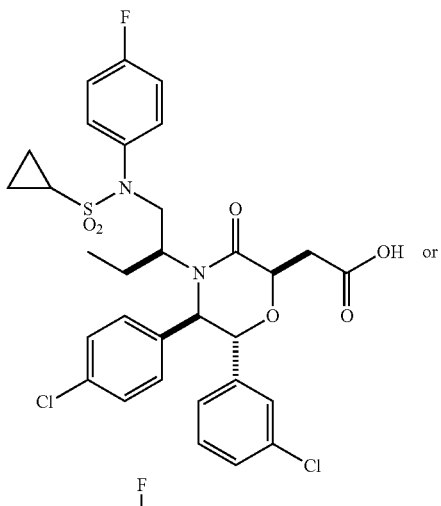

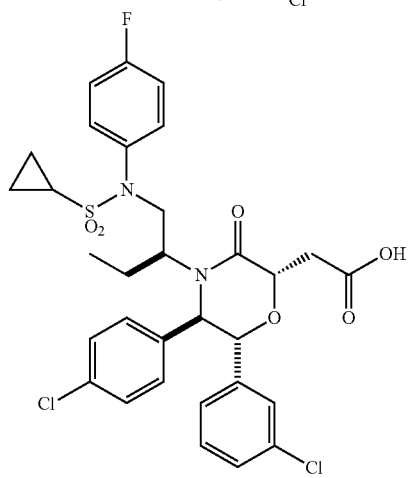

N-(4-fluorophenyl)cyclopropanesulfonamide

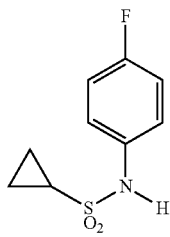

The above compound was synthesized by the following procedure:

To a solution of cyclopropanesulfonyl chloride (697 mg, 4.96 mmol) in dichloromethane (1 mL) and pyridine (1 mL) was added 4-fluoroaniline (0.476 mL, 4.96 mmol) at room temperature, and the reaction was stirred at 50° C. for 5 hours, then at room temperature overnight. EtOAc was added to the reaction and the mixture was washed with $H_2O$ and brine. The organic layer was dried with $Na_2SO_4$. Upon concentration the crude was purified by flash chromatography (Combiflash; Ethyl acetate/Hexanes). $^1$H NMR (400 MHz, CDCl$_3$) δ 7.30-7.33 (m, 2H), 7.06-7.12 (m, 2H), 3.34 (s, 1H), 2.48-2.55 (m, 1H), 0.93-1.04 (m, 4H).

One of the title compounds was prepared from (5R,6R)-6-(3-chlorophenyl)-5-(4-chlorophenyl)-4-((S)-1-hydroxybutan-2-yl)morpholin-3-one (Example 112, Step C) by procedures similar to those described in Example 112, Steps D though F, replacing ethanethiol in Step D with N-(4-fluorophenyl)cyclopropanesulfonamide. The crude product was purified by reverse phase preparatory HPLC (Gemini™ Prep $C_{18}$ 5 µm column; Phenomenex, Torrance, Calif.; gradient elution of 25% to 75% MeCN in water, where both solvents contain 0.1% TFA, 30 min method) to provide one of the title compounds as the faster eluting isomer as a white foam ($t_R$=20.3 min). $^1$H NMR (400 MHz, CDCl$_3$) δ 7.39-7.46 (m, 2H), 7.32 (d, J=8.61 Hz, 2H), 7.19-7.28 (m, 3H), 7.10-7.18 (m, 4H), 7.06 (d, J=7.43 Hz, 1H), 4.84 (td, J=7.43, 9.19 Hz, 2H), 4.33-4.48 (m, J=8.80 Hz, 2H), 3.80 (dd, J=4.79, 14.38 Hz, 2H), 2.95-3.14 (m, 2H), 2.31-2.42 (m, 1H), 1.84-2.00 (m, 1H), 1.51-1.65 (m, 1H), 1.00-1.10 (m, 2H), 0.89-1.00 (m, 2H), 0.50 (t, J=7.53 Hz, 3H). Mass spectrum (ESI) m/z=649.0 [M]$^+$.

Example 136

2-((2R,5R,6R)-6-(3-chlorophenyl)-5-(4-chlorophenyl)-4-((S)-1-(N-(4-fluorophenyl)cyclopropanesulfonamido)butan-2-yl)-3-oxomorpholin-2-yl)acetic acid or 2-((2S,5R,6R)-6-(3-chlorophenyl)-5-(4-chlorophenyl)-4-((S)-1-(N-(4-fluorophenyl)cyclopropanesulfonamido)butan-2-yl)-3-oxomorpholin-2-yl)acetic acid

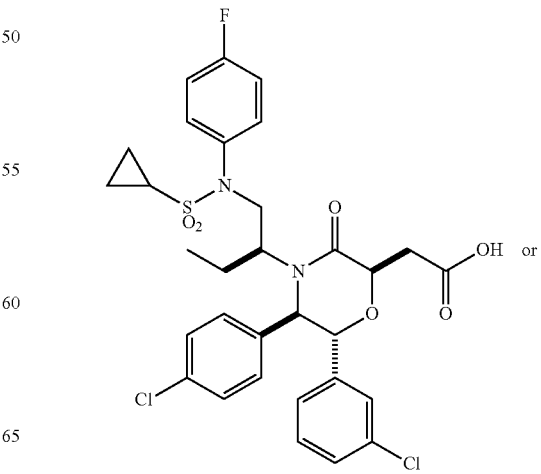

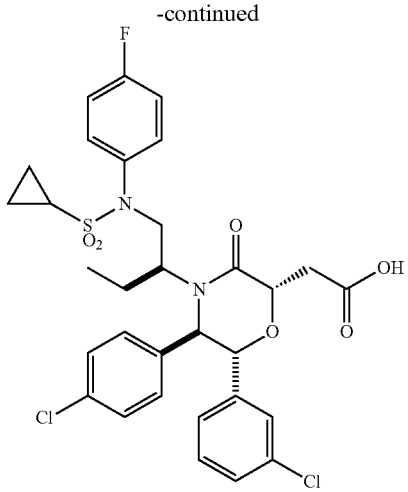

One of the title compounds was obtained as the second (slower) eluting isomer in Example 135 as a white foam ($t_R$=20.7 min). $^1$H NMR (400 MHz, CDCl$_3$) δ 7.39-7.49 (m, 2H), 7.30 (s, 1H), 7.23-7.28 (m, 2H), 7.04-7.22 (m, 4H), 6.98 (d, J=8.22 Hz, 2H), 6.83 (d, J=7.63 Hz, 1H), 4.61-4.79 (m, 3H), 4.49 (dd, J=9.49, 14.18 Hz, 1H), 3.74 (dd, J=3.62, 14.38 Hz, 2H), 2.89 (dd, J=6.65, 16.24 Hz, 1H), 2.59 (dd, J=5.48, 16.24 Hz, 1H), 2.27-2.40 (m, 1H), 1.95 (dd, J=7.04, 8.61 Hz, 1H), 1.50-1.66 (m, 1H), 0.85-1.09 (m, 4H), 0.53 (t, J=7.53 Hz, 3H). Mass spectrum (ESI) m/z=649.0 [M]$^+$.

Example 137

2-((2R,5R,6R)-6-(3-chlorophenyl)-5-(4-chlorophenyl)-4-((S)-1-((2-chlorophenyl)sulfonyl)butan-2-O-3-oxomorpholin-2-yl)acetic acid or 2-((2S,5R,6R)-6-(3-chlorophenyl)-5-(4-chlorophenyl)-4-((S)-1-((2-chlorophenyl)sulfonyl)butan-2-yl)-3-oxomorpholin-2-yl)acetic acid

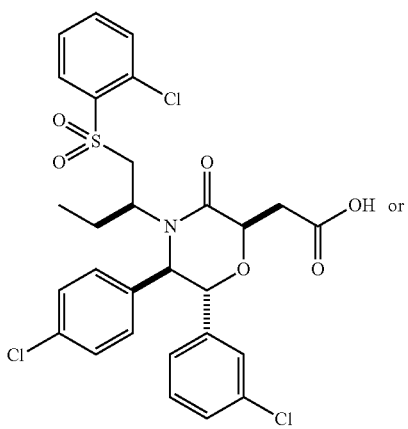

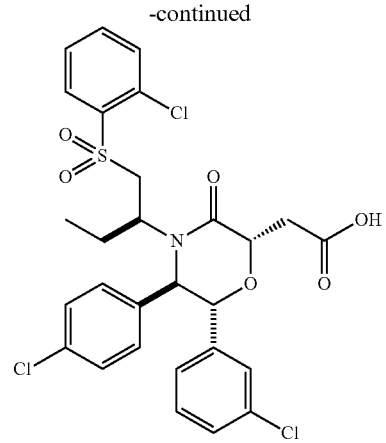

One of the title compounds was prepared from (5R,6R)-6-(3-chlorophenyl)-5-(4-chlorophenyl)-4-((S)-1-hydroxybutan-2-yl)morpholin-3-one (Example 112, Step C) by procedures similar to those described in Example 112, Steps D though F, replacing ethanethiol in Step D with 2-chlorothiophenol. The crude product was purified by reverse phase preparatory HPLC (Gemini™ Prep C$_{18}$ 5 μm column; Phenomenex, Torrance, Calif.; gradient elution of 25% to 75% MeCN in water, where both solvents contain 0.1% TFA, 30 min method) to provide one of the title compounds as the faster eluting isomer as a white foam ($t_R$=19.7 min). $^1$H NMR (400 MHz, CDCl$_3$) δ 8.20 (dd, J=1.27, 7.92 Hz, 1H), 7.50-7.66 (m, 3H), 7.31-7.39 (m, 2H), 7.28 (s, 1H), 7.21-7.26 (m, 3H), 7.13-7.20 (m, 1H), 7.00 (d, J=7.63 Hz, 1H), 5.04 (d, J=7.24 Hz, 1H), 4.92 (d, J=7.04 Hz, 1H), 4.57 (dd, J=5.28, 6.65 Hz, 1H), 4.47 (dd, J=9.00, 14.48 Hz, 1H), 3.35-3.50 (m, 2H), 2.97-3.17 (m, 2H), 2.06-2.23 (m, 1H), 1.45-1.64 (m, 1H), 0.52 (t, J=7.53 Hz, 3H). Mass spectrum (ESI) m/z=610.8 [M]$^+$.

Example 138

2-((2R,5R,6R)-6-(3-chlorophenyl)-5-(4-chlorophenyl)-4-((S)-1-((2-chlorophenyl)sulfonyl)butan-2-yl)-3-oxomorpholin-2-yl)acetic acid or 2-((2S,5R,6R)-6-(3-chlorophenyl)-5-(4-chlorophenyl)-4-((S)-1-((2-chlorophenyl)sulfonyl)butan-2-yl)-3-oxomorpholin-2-yl)acetic acid

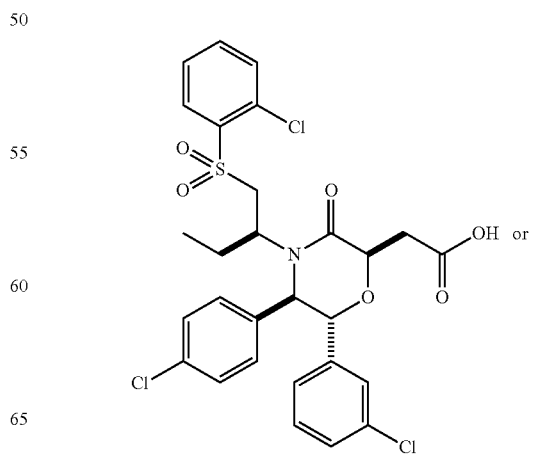

239

-continued

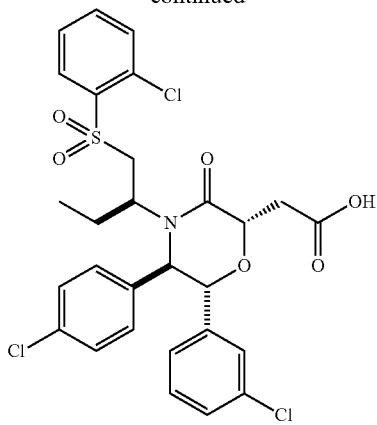

One of the title compounds was obtained as the second (slower) eluting isomer in Example 137 as a white foam ($t_R$=20.6 min). $^1$H NMR (400 MHz, CDCl$_3$) δ 8.15 (dd, J=1.56, 7.83 Hz, 1H), 7.48-7.65 (m, 3H), 7.32 (d, J=8.41 Hz, 2H), 7.21 (td, J=0.98, 8.02 Hz, 1H), 7.04-7.15 (m, 4H), 6.82 (d, J=7.63 Hz, 1H), 5.01 (d, J=9.78 Hz, 1H), 4.78 (t, J=5.87 Hz, 1H), 4.70 (d, J=9.78 Hz, 1H), 4.47 (dd, J=9.59, 14.28 Hz, 1H), 3.41 (dd, J=2.54, 14.28 Hz, 1H), 3.32 (br. s., 1H), 3.21 (dd, J=5.97, 16.53 Hz, 1H), 2.90 (dd, J=5.87, 16.43 Hz, 1H), 2.10-2.25 (m, 1H), 1.50-1.65 (m, 1H), 0.50 (t, J=7.53 Hz, 3H). Mass spectrum (ESI) m/z=610.8 [M]$^+$.

Example 139

2-((2R,5R,6R)-6-(3-chlorophenyl)-5-(4-chlorophenyl)-4-((S)-1-(cyclopentylsulfonyl)butan-2-yl)-3-oxomorpholin-2-yl)acetic acid or 2-((2S,5R,6R)-6-(3-chlorophenyl)-5-(4-chlorophenyl)-4-((S)-1-(cyclopentylsulfonyl)butan-2-yl)-3-oxomorpholin-2-yl)acetic acid

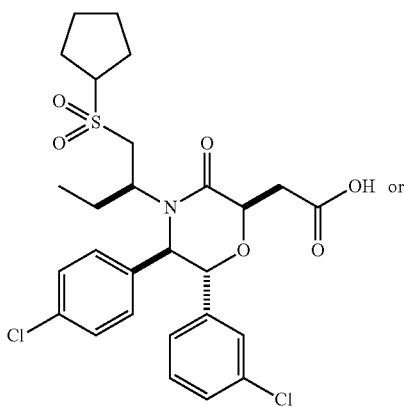

240

-continued

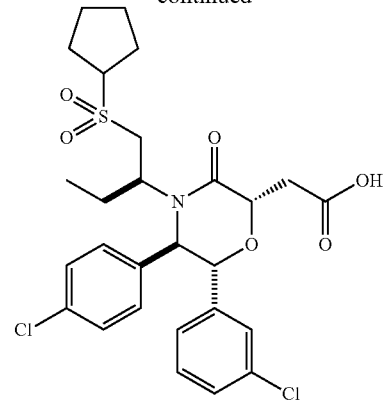

One of the title compounds was prepared from (5R,6R)-6-(3-chlorophenyl)-5-(4-chlorophenyl)-4-((S)-1-hydroxybutan-2-yl)morpholin-3-one (Example 112, Step C) by procedures similar to those described in Example 112, Steps D though F, replacing ethanethiol in Step D with cyclopentyl mercaptan. The crude product was purified by reverse phase preparatory HPLC (Gemini™ Prep C$_{18}$ 5 µm column; Phenomenex, Torrance, Calif.; gradient elution of 25% to 75% MeCN in water, where both solvents contain 0.1% TFA, 30 min method) to provide one of the title compounds as the faster eluting isomer as a white foam ($t_R$=18.5 min). $^1$H NMR (400 MHz, CDCl$_3$) δ 7.22 (ddd, J=6.46, 8.61, 12.52 Hz, 5H), 7.12-7.17 (m, J=1.17, 1.96 Hz, 1H), 7.08 (t, J=7.82 Hz, 1H), 6.95 (d, J=7.63 Hz, 1H), 5.02 (d, J=6.65 Hz, 1H), 4.85 (d, J=6.65 Hz, 1H), 4.62 (t, J=6.06 Hz, 1H), 3.89 (dd, J=9.00, 13.50 Hz, 1H), 3.19-3.39 (m, 2H), 2.98-3.04 (m, 2H), 2.84 (dd, J=2.64, 13.99 Hz, 1H), 1.87-2.12 (m, 5H), 1.75 (br. s., 2H), 1.60 (d, J=4.11 Hz, 3H), 0.46 (t, J=7.53 Hz, 3H). Mass spectrum (ESI) m/z=568.1 [M]$^+$.

Example 140

2-((2R,5R,6R)-6-(3-chlorophenyl)-5-(4-chlorophenyl)-4-((S)-1-(cyclopentylsulfonyl)butan-2-yl)-3-oxomorpholin-2-yl)acetic acid or 2-((2S,5R,6R)-6-(3-chlorophenyl)-5-(4-chlorophenyl)-4-((S)-1-(cyclopentylsulfonyl)butan-2-yl)-3-oxomorpholin-2-yl)acetic acid

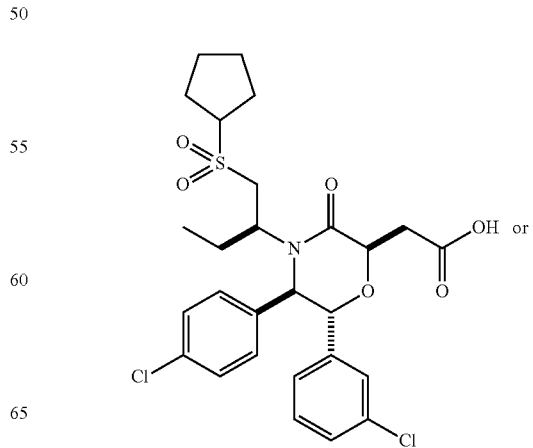

-continued

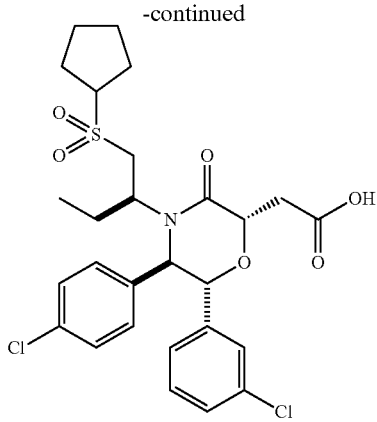

One of the title compounds was obtained as the second (slower) eluting isomer in Example 139 as a white foam ($t_R$=19.2 min). $^1$H NMR (400 MHz, CDCl$_3$) δ 7.32 (d, J=8.61 Hz, 2H), 7.21 (dd, J=1.08, 2.05 Hz, 1H), 7.05-7.18 (m, 4H), 6.85 (d, J=7.63 Hz, 1H), 5.07 (d, J=9.78 Hz, 1H), 4.77 (t, J=5.77 Hz, 1H), 4.71 (d, J=9.78 Hz, 1H), 4.07 (t, J=10.86 Hz, 1H), 3.40 (quin, J=8.12 Hz, 1H), 3.23 (dd, J=6.46, 16.43 Hz, 1H), 3.00 (dd, J=4.99, 16.33 Hz, 1H), 2.89 (d, J=12.32 Hz, 1H), 2.07 (d, J=7.43 Hz, 5H), 1.81-1.94 (m, 2H), 1.53-1.79 (m, 3H), 0.57 (t, J=7.53 Hz, 3H). Mass spectrum (ESI) m/z=568.1 [M]$^+$.

Example 141

2-((2R,5R,6R)-6-(3-chlorophenyl)-5-(4-chlorophenyl)-4-((S)-1-(cyclobutylsulfonyl)butan-2-yl)-3-oxomorpholin-2-yl)acetic acid or 2-((2S,5R,6R)-6-(3-chlorophenyl)-5-(4-chlorophenyl)-4-((S)-1-(cyclobutylsulfonyl)butan-2-yl)-3-oxomorpholin-2-yl)acetic acid

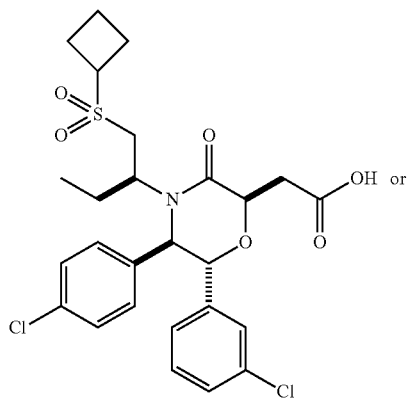

-continued

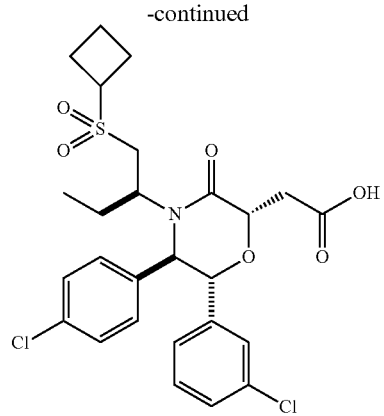

One of the title compounds was prepared from (5R,6R)-6-(3-chlorophenyl)-5-(4-chlorophenyl)-4-((S)-1-hydroxybutan-2-yl)morpholin-3-one (Example 112, Step C) by procedures similar to those described in Example 112, Steps D though F, replacing ethanethiol in Step D with cyclobutanethiol (prepared from the corresponding alkylmagnesium bromide and sulfure in a manner analogous to that described in Example 212, Step A). The crude product was purified by reverse phase preparatory HPLC (Gemini™ Prep C$_{18}$ 5 μm column; Phenomenex, Torrance, Calif.; gradient elution of 25% to 75% MeCN in water, where both solvents contain 0.1% TFA, 30 min method) to provide one of the title compounds as the faster eluting isomer as a white foam ($t_R$=17.8 min). $^1$H NMR (400 MHz, CDCl$_3$) δ 7.23-7.28 (m, 2H), 7.21 (s, 2H), 7.16 (d, J=9.39 Hz, 2H), 7.06-7.12 (m, 1H), 6.95 (d, J=7.63 Hz, 1H), 5.02 (d, J=6.65 Hz, 1H), 4.86 (d, J=6.85 Hz, 1H), 4.63 (t, J=6.06 Hz, 1H), 3.66 (quin, J=8.17 Hz, 1H), 3.02 (d, J=6.26 Hz, 2H), 2.72 (dd, J=2.64, 14.18 Hz, 2H), 2.38-2.62 (m, 3H), 2.17-2.30 (m, 2H), 1.93-2.10 (m, 3H), 1.44-1.59 (m, 1H), 0.46 (t, J=7.53 Hz, 3H). Mass spectrum (ESI) m/z=554.2 [M]$^+$.

Example 142

2-((2R,5R,6R)-6-(3-chlorophenyl)-5-(4-chlorophenyl)-4-((S)-1-(cyclobutylsulfonyl)butan-2-yl)-3-oxomorpholin-2-yl)acetic acid or 2-((2S,5R,6R)-6-(3-chlorophenyl)-5-(4-chlorophenyl)-4-((S)-1-(cyclobutylsulfonyl)butan-2-yl)-3-oxomorpholin-2-yl)acetic acid

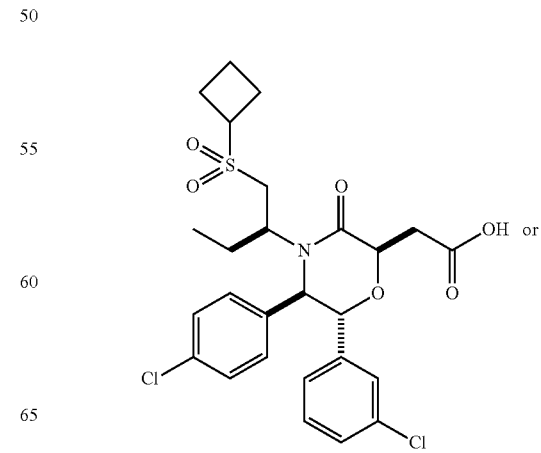

243

-continued

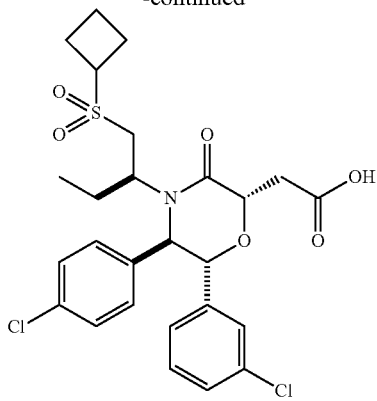

One of the title compounds was obtained as the second (slower) eluting isomer in Example 141 as a white foam ($t_R$=18.3 min). $^1$H NMR (400 MHz, CDCl$_3$) δ 7.33 (d, J=8.61 Hz, 3H), 7.20-7.26 (m, 1H), 7.06-7.18 (m, 3H), 6.83-6.90 (m, 1H), 5.02-5.13 (m, 1H), 4.63-4.79 (m, 2H), 3.88-4.05 (m, 1H), 3.70-3.86 (m, 1H), 3.17-3.40 (m, 2H), 2.95-3.08 (m, 1H), 2.50-2.82 (m, 3H), 2.26-2.44 (m, 3H), 2.15-2.24 (m, 2H), 1.54-1.73 (m, 1H), 0.57 (t, J=7.53 Hz, 3H). Mass spectrum (ESI) m/z=554.0 [M]$^+$.

Example 143

2-((2R,5R,6R)-6-(3-chlorophenyl)-5-(4-chlorophenyl)-4-((S)-1-(neopentylsulfonyl)butan-2-yl)-3-oxomorpholin-2-yl)acetic acid or 2-((2S,5R,6R)-6-(3-chlorophenyl)-5-(4-chlorophenyl)-4-((S)-1-(neopentylsulfonyl)butan-2-yl)-3-oxomorpholin-2-yl)acetic acid

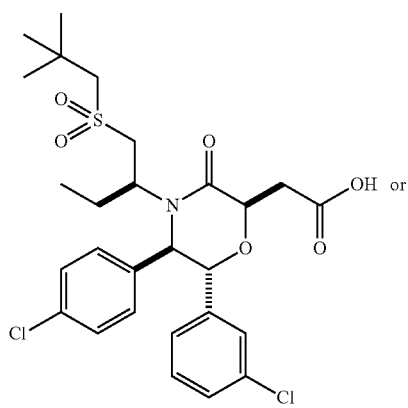

244

-continued

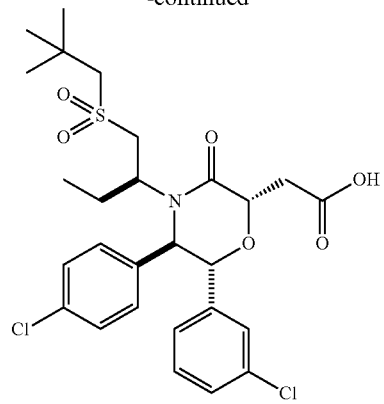

One of the title compounds was prepared from (5R,6R)-6-(3-chlorophenyl)-5-(4-chlorophenyl)-4-((S)-1-hydroxybutan-2-yl)morpholin-3-one (Example 112, Step C) by procedures similar to those described in Example 112, Steps D though F, replacing ethanethiol in Step D with neopentylthiol (prepared from the corresponding alkylmagnesium bromide and sulfure in a manner analogous to that described in Example 212, Step A). The crude product was purified by reverse phase preparatory HPLC (Gemini™ Prep C$_{18}$ 5 μm column; Phenomenex, Torrance, Calif.; gradient elution of 25% to 75% MeCN in water, where both solvents contain 0.1% TFA, 30 min method) to provide one of the title compounds as the faster eluting isomer as a white foam ($t_R$=21.1 min). $^1$H NMR (400 MHz, CDCl$_3$) δ 7.23-7.28 (m, 2H), 7.21 (s, 3H), 7.14-7.17 (m, 1H), 7.05-7.12 (m, 1H), 6.95 (d, J=7.63 Hz, 1H), 5.00 (d, J=6.46 Hz, 1H), 4.85 (d, J=6.65 Hz, 1H), 4.60 (t, J=6.06 Hz, 1H), 3.82-3.97 (m, 1H), 3.01 (d, J=6.46 Hz, 2H), 2.77-2.95 (m, 3H), 1.95-2.10 (m, 1H), 1.41-1.56 (m, 1H), 1.16 (s, 10H), 0.38-0.52 (m, 3H). Mass spectrum (ESI) m/z=570.2 [M]$^+$.

Example 144

2-((2R,5R,6R)-6-(3-chlorophenyl)-5-(4-chlorophenyl)-4-((S)-1-(neopentylsulfonyl)butan-2-yl)-3-oxomorpholin-2-yl)acetic acid or 2-((2S,5R,6R)-6-(3-chlorophenyl)-5-(4-chlorophenyl)-4-((S)-1-(neopentylsulfonyl)butan-2-yl)-3-oxomorpholin-2-yl)acetic acid

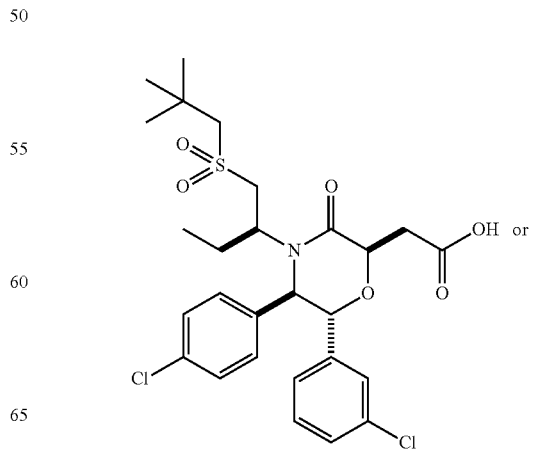

-continued

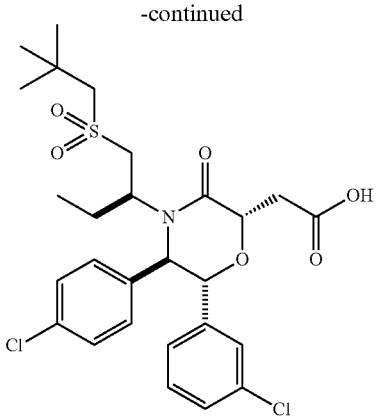

One of the title compounds was obtained as the second (slower) eluting isomer in Example 143 as a white foam ($t_R$=20.6 min). $^1$H NMR (400 MHz, CDCl$_3$) δ 7.33 (d, J=8.61 Hz, 2H), 7.21-7.26 (m, 1H), 7.12-7.18 (m, J=6.26 Hz, 3H), 7.10 (t, J=1.86 Hz, 1H), 6.83 (d, J=7.82 Hz, 1H), 5.04 (d, J=9.78 Hz, 1H), 4.76 (dd, J=4.89, 6.85 Hz, 1H), 4.71 (d, J=9.78 Hz, 1H), 3.26 (dd, J=6.94, 16.33 Hz, 1H), 2.87-3.07 (m, 5H), 2.07-2.26 (m, 1H), 1.48-1.71 (m, 1H), 1.27 (s, 10H), 0.56 (t, J=7.43 Hz, 3H). Mass spectrum (ESI) m/z=570.2 [M]$^+$.

Example 145

2-((2R,5R,6R)-5-(4-chlorophenyl)-6-(3,5-dichlorophenyl)-4-((S)-1-(isopropylsulfonyl)butan-2-yl)-3-oxomorpholin-2-yl)acetic acid or 2-((2S,5R,6R)-5-(4-chlorophenyl)-6-(3,5-dichlorophenyl)-4-((S)-1-(isopropylsulfonyl)butan-2-yl)-3-oxomorpholin-2-yl) acetic acid

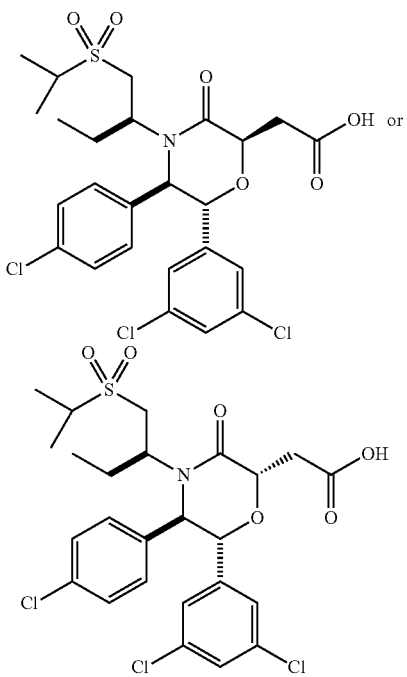

Step A. (5R,6R)-5-(4-chlorophenyl)-6-(3,5-dichlorophenyl)morpholin-3-one

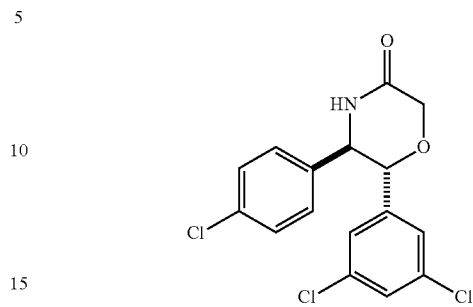

The above compound was prepared from (1R,2R)-2-amino-2-(4-chlorophenyl)-1-(3,5-dichlorophenyl)ethanol (Intermediate C7) by a procedure similar to that described in Example 112, Step A. The crude material was adsorbed onto a plug of silica gel and purified by flash chromatography on silica gel, eluting with a gradient of 0% to 30% acetone in hexanes, to provide the title compound as a solid. $^1$H NMR (400 MHz, CDCl$_3$) δ 7.29-7.36 (m, 3H), 6.96-7.06 (m, 2H), 6.91 (d, J=1.96 Hz, 2H), 6.20 (s, 1H), 4.54-4.63 (m, 2H), 4.38-4.48 (m, 2H). Mass spectrum (ESI) m/z=355.4 [M–H]$^+$.

Step B. (5R,6R)-5-(4-chlorophenyl)-6-(3,5-dichlorophenyl)-4-((S)-1-((3,4-dimethoxybenzyl)oxy)butan-2-yl)morpholin-3-one

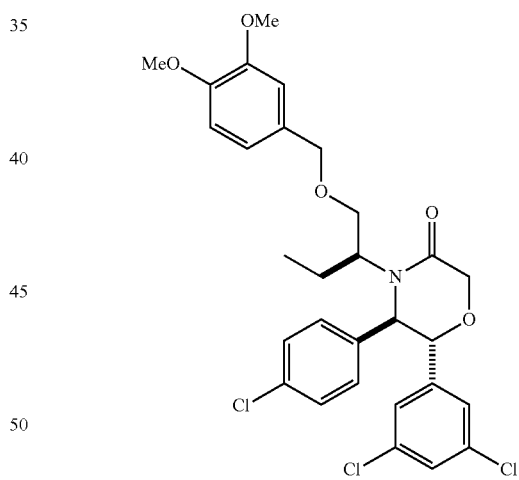

The above compound was prepared from (5R,6R)-5-(4-chlorophenyl)-6-(3,5-dichlorophenyl)morpholin-3-one (Example 145, Step A) by a procedure similar to that described in Example 112, Step B. The crude material was adsorbed onto a plug of silica gel and purified by flash chromatography on silica gel, eluting with a gradient of 0% to 30% acetone in hexanes, to provide the title compound. $^1$H NMR (400 MHz, CDCl$_3$) δ 7.34 (d, J=8.41 Hz, 2H), 7.27-7.29 (m, 1H), 7.10 (d, J=8.41 Hz, 2H), 6.98 (d, J=1.56 Hz, 2H), 6.92 (d, J=0.78 Hz, 2H), 6.87 (s, 1H), 4.76 (d, J=7.63 Hz, 1H), 4.58 (d, J=7.63 Hz, 1H), 4.35-4.51 (m, 4H), 3.98 (s, 1H), 3.92 (d, J=4.89 Hz, 6H), 3.39 (dd, J=4.11, 9.78 Hz, 1H), 3.17-3.31 (m, 1H), 1.82-1.96 (m, 1H), 1.63-1.74 (m, 1H), 0.65 (t, J=7.53 Hz, 3H). Mass spectrum (ESI) m/z=600.0 [M+Na]$^+$.

Step C. (5R,6R)-5-(4-chlorophenyl)-6-(3,5-dichlorophenyl)-4-((S)-1-hydroxybutan-2-yl)morpholin-3-one

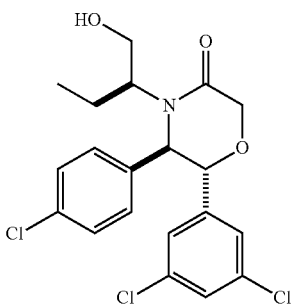

The above compound was prepared from (5R,6R)-5-(4-chlorophenyl)-6-(3,5-dichlorophenyl)-4-((S)-1-((3,4-dimethoxybenzyl)oxy)butan-2-yl)morpholin-3-one (Example 145, Step B) by a procedure similar to that described in Example 112, Step C. The crude material was purified by flash chromatography on silica gel, eluting with a gradient of 0% to 30% acetone in hexanes (eluted in an isocratic 15% acetone/hexanes mixture for 15 minutes before increasing the gradient, the aldehyde comes out first), to provide the title compound as an off-white solid. $^1$H NMR (400 MHz, CDCl$_3$) δ 7.35-7.41 (m, 2H), 7.26-7.32 (m, 2H), 7.09-7.21 (m, 2H), 6.95 (s, 1H), 4.54-4.67 (m, 2H), 4.43 (d, J=2.15 Hz, 2H), 3.58-3.81 (m, 2H), 3.39 (dd, J=3.62, 5.58 Hz, 1H), 1.93 (ddd, J=7.43, 8.51, 13.99 Hz, 1H), 1.52 (ddd, J=6.06, 7.53, 13.79 Hz, 1H), 0.75 (t, J=7.53 Hz, 3H). Mass spectrum (ESI) m/z=427.4 [M−H]$^+$.

Step D. (5R,6R)-5-(4-chlorophenyl)-6-(3,5-dichlorophenyl)-4-((S)-1-(isopropylthio)butan-2-yl)morpholin-3-one

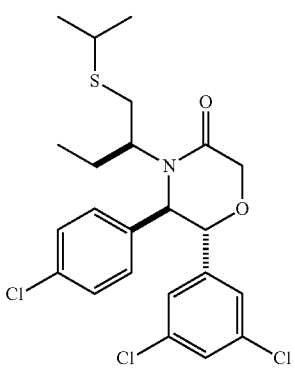

The above compound was prepared from (5R,6R)-5-(4-chlorophenyl)-6-(3,5-dichlorophenyl)-4-((S)-1-hydroxybutan-2-yl)morpholin-3-one (Example 145, Step C) by a procedure similar to that described in Example 112, Step D, replacing ethanethiol in with isopropylthiol. The crude mixture was concentrated and purified by flash chromatography on silica gel, in an isocratic elution with 5% acetones in hexanes, to provide the above compound. $^1$H NMR (400 MHz, CDCl$_3$) δ 7.33-7.40 (m, 2H), 7.31 (t, J=1.96 Hz, 1H), 7.02-7.11 (m, 2H), 6.91 (d, J=1.96 Hz, 2H), 5.22 (d, J=16.43 Hz, 1H), 4.65 (dd, J=1.17, 16.04 Hz, 1H), 4.43 (s, 2H), 4.11 (s, 1H), 3.18-3.31 (m, 1H), 2.74-2.88 (m, 2H), 1.70 (d, J=7.24 Hz, 1H), 1.37-1.51 (m, 1H), 1.18-1.27 (m, 6H), 0.75 (t, J=7.34 Hz, 3H). Mass spectrum (ESI) m/z=585.2 [M−H]$^+$.

Step E. (2R,5R,6R)-2-allyl-5-(4-chlorophenyl)-6-(3,5-dichlorophenyl)-4-((S)-1-(isopropylthio)butan-2-yl)morpholin-3-one and (2S,5R,6R)-2-allyl-5-(4-chlorophenyl)-6-(3,5-dichlorophenyl)-4-((S)-1-(isopropylthio)butan-2-yl)morpholin-3-one

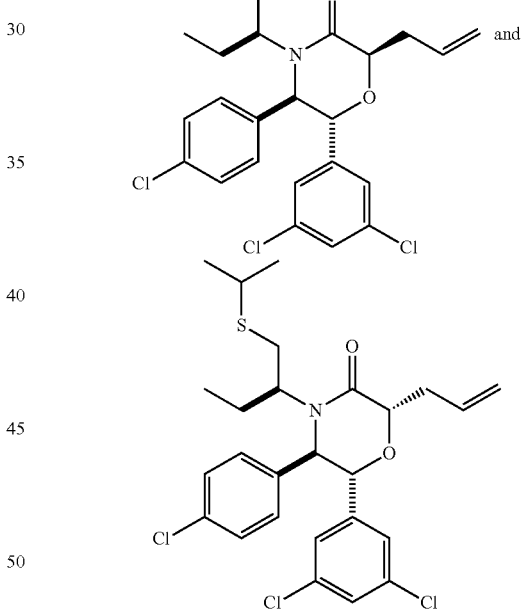

The above compounds were prepared from (5R,6R)-5-(4-chlorophenyl)-6-(3,5-dichlorophenyl)-4-((S)-1-(isopropylthio)butan-2-yl)morpholin-3-one (Example 145, Step D) by a procedure similar to that described in Example 112, Step E. The crude material was purified by flash chromatography on silica gel, eluting through a two-step isocratic method of 5% and 10% acetone in hexanes, to provide the title compounds. Mass spectrum (ESI) m/z=527.2 [M]$^+$ for both isomers.

249

Step F. 2-((2R,5R,6R)-5-(4-chlorophenyl)-6-(3,5-dichlorophenyl)-4-((S)-1-(isopropylsulfonyl)butan-2-yl)-3-oxomorpholin-2-yl)acetic acid or 2-((2S,5R,6R)-5-(4-chlorophenyl)-6-(3,5-dichlorophenyl)-4-((S)-1-(isopropylsulfonyl)butan-2-yl)-3-oxomorpholin-2-yl)acetic acid

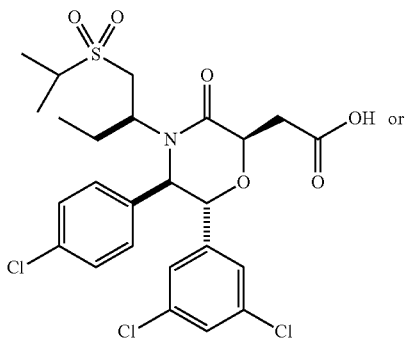

or

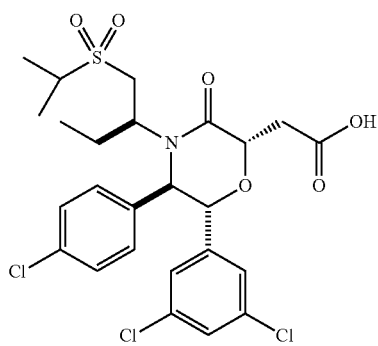

250

Example 146

2-((2R,5R,6R)-5-(4-chlorophenyl)-6-(3,5-dichlorophenyl)-4-((S)-1-(isopropylsulfonyl)butan-2-yl)-3-oxomorpholin-2-yl)acetic acid or 2-((2S,5R,6R)-5-(4-chlorophenyl)-6-(3,5-dichlorophenyl)-4-((S)-1-(isopropylsulfonyl)butan-2-yl)-3-oxomorpholin-2-yl) acetic acid

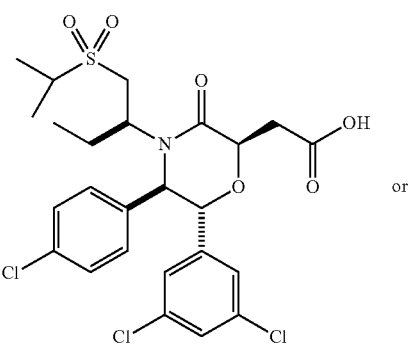

or

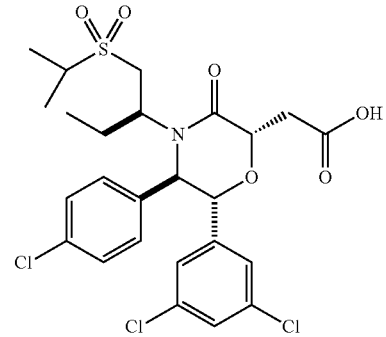

One of the title compounds was prepared from the fast eluting isomer from Example 145, Step E, by a procedure similar to that described in Example 112, Step F. The crude product was purified by reverse phase preparatory HPLC (Gemini™ Prep $C_{18}$ 5 μm column; Phenomenex, Torrance, Calif.; gradient elution of 25% to 75% MeCN in water, where both solvents contain 0.1% TFA, 30 min method), to provide one of the title compounds ($t_R$=18.7 min). $^1$H NMR (400 MHz, CDCl$_3$) δ 7.36 (dd, J=8.41, 12.91 Hz, 4H), 7.27 (t, J=1.86 Hz, 1H), 7.14 (d, J=1.76 Hz, 2H), 5.10 (d, J=6.26 Hz, 1H), 4.96 (d, J=6.46 Hz, 1H), 4.72 (dd, J=4.79, 6.94 Hz, 1H), 3.99 (d, J=4.50 Hz, 1H), 3.33-3.47 (m, 1H), 3.04-3.20 (m, 3H), 2.95 (dd, J=2.25, 13.79 Hz, 1H), 2.16 (dt, J=2.35, 7.04 Hz, 1H), 1.54-1.70 (m, 1H), 1.45 (dd, J=4.30, 6.85 Hz, 6H), 0.57 (t, J=7.53 Hz, 3H). Mass spectrum (ESI) m/z=575.0 [M−H]$^+$.

One of the title compounds was prepared from the slowest eluting isomer from Example 145, Step E) by a procedure similar to that described in Example 112, Step F. The crude product was purified by reverse phase preparatory HPLC (Gemini™ Prep $C_{18}$ 5 μm column; Phenomenex, Torrance, Calif.; gradient elution of 25% to 75% MeCN in water, where both solvents contain 0.1% TFA, 30 min method), to provide one of the title compounds ($t_R$=19.5 min). $^1$H NMR (400 MHz, CDCl$_3$) δ 7.35 (d, J=8.22 Hz, 2H), 7.23 (t, J=1.57 Hz, 1H), 7.15 (d, J=8.22 Hz, 2H), 6.86 (d, J=1.57 Hz, 2H), 4.98-5.04 (m, 1H), 4.71-4.76 (m, 1H), 4.68 (s, 1H), 3.98-4.11 (m, 1H), 3.23 (dd, J=6.55, 16.33 Hz, 1H), 3.11 (quin, J=6.90 Hz, 1H), 2.98 (dd, J=5.09, 16.43 Hz, 1H), 2.86 (dd, J=1.96, 13.50 Hz, 1H), 2.12-2.23 (m, 1H), 1.57-1.67 (m, 1H), 1.43 (dd, J=4.60, 6.75 Hz, 6H), 0.56 (t, J=7.53 Hz, 3H). Mass spectrum (ESI) m/z=575.0 [M−H]$^+$.

Example 147

2-((2R,5R,6R)-5-(4-chlorophenyl)-6-(3,5-dichlorophenyl)-4-((S)-1-(tert-butylsulfonyl)butan-2-yl)-3-oxomorpholin-2-yl)acetic acid or 2-((2S,5R,6R)-5-(4-chlorophenyl)-6-(3,5-dichlorophenyl)-4-((S)-1-(tert-butylsulfonyl)butan-2-yl)-3-oxomorpholin-2-yl)acetic acid

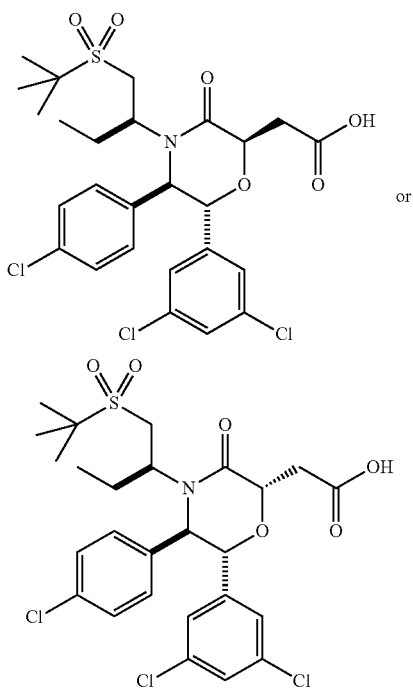

or

Step A. (2R,5R,6R)-2-allyl-5-(4-chlorophenyl)-6-(3,5-dichlorophenyl)-4-((S)-1-(tert-butylthio)butan-2-yl)morpholin-3-one and (2S,5R,6R)-2-allyl-5-(4-chlorophenyl)-6-(3,5-dichlorophenyl)-4-((S)-1-(tert-butylthio)butan-2-yl)morpholin-3-one

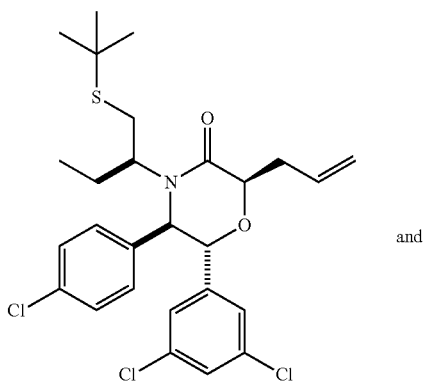

and

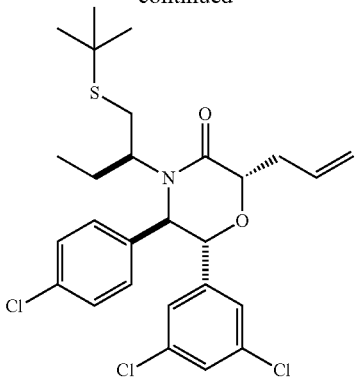

The above compounds were prepared from (5R,6R)-5-(4-chlorophenyl)-6-(3,5-dichlorophenyl)-4-((S)-1-hydroxybutan-2-yl)morpholin-3-one (Example 145, Step C) by procedures similar to those described in Example 112, Steps D and E, replacing ethanethiol in Step D with tert-butylthiol. The crude material was purified by flash chromatography on silica gel, eluting through a two-step isocratic method of 5% and 10% acetone in hexanes, to provide the above compounds. Mass spectrum (ESI) m/z=539.1 [M−H]+ for both isomers.

Step B. 2-((2R,5R,6R)-5-(4-chlorophenyl)-6-(3,5-dichlorophenyl)-4-((S)-1-(tert-butylsulfonyl)butan-2-yl)-3-oxomorpholin-2-yl)acetic acid or 2-((2S,5R,6R)-5-(4-chlorophenyl)-6-(3,5-dichlorophenyl)-4-((S)-1-(tert-butylsulfonyl)butan-2-yl)-3-oxomorpholin-2-yl)acetic acid

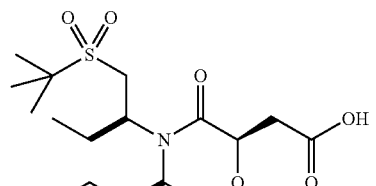

or

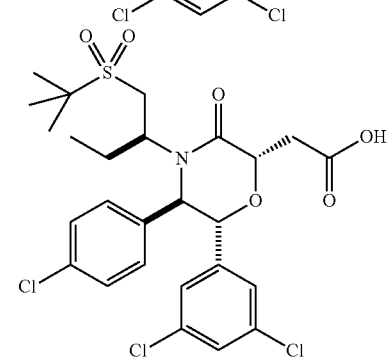

One of the title compounds was prepared from fastest eluting isomer from Example 147, Step A, by a procedure similar to that described in Example 112, Step F. The crude product was purified by reverse phase preparatory HPLC (Gemini™ Prep C$_{18}$ 5 μm column; Phenomenex, Torrance, Calif.; gradient elution of 25% to 75% MeCN in water, where both solvents contain 0.1% TFA, 30 min method), to provide one of the title compounds (t$_R$=20.0 min). $^1$H NMR (400 MHz, CDCl$_3$) δ 7.34 (td, J=8.61, 10.17 Hz, 4H), 7.25 (t, J=1.86 Hz, 1H), 7.13 (d, J=1.76 Hz, 2H), 5.11 (d, J=6.46 Hz, 1H), 4.94 (d, J=6.26 Hz, 1H), 4.71 (t, J=5.77 Hz, 1H), 3.93-3.93 (m, 1H), 3.89-4.01 (m, J=9.39 Hz, 1H), 3.02-3.16 (m, 2H), 2.94 (dd, J=2.25, 13.60 Hz, 1H), 2.07-2.23 (m, 1H), 1.54-1.70 (m, 1H), 1.44 (s, 9H), 0.54 (t, J=7.43 Hz, 3H). Mass spectrum (ESI) m/z=590.0 [M−H]$^+$.

Example 148

2-((2R,5R,6R)-5-(4-chlorophenyl)-6-(3,5-dichlorophenyl)-4-((S)-1-(tert-butylsulfonyl)butan-2-yl)-3-oxomorpholin-2-yl)acetic acid or 2-((2S,5R,6R)-5-(4-chlorophenyl)-6-(3,5-dichlorophenyl)-4-((S)-1-(tert-butylsulfonyl)butan-2-yl)-3-oxomorpholin-2-yl)acetic acid

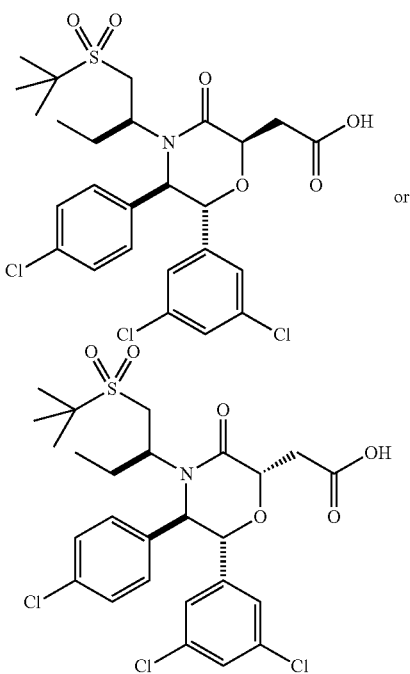

One of the title compounds was prepared from the slowest eluting isomer from Example 147, Step A, by a procedure similar to that described in Example 112, Step F. The crude product was purified by reverse phase preparatory HPLC (Gemini™ Prep C$_{18}$ 5 μm column; Phenomenex, Torrance, Calif.; gradient elution of 25% to 75% MeCN in water, where both solvents contain 0.1% TFA, 30 min method), to provide one of the title compounds (t$_R$=20.6 min). $^1$H NMR (400 MHz, CDCl$_3$) δ 7.35 (d, J=8.41 Hz, 2H), 7.22 (t, J=1.86 Hz, 1H), 7.16 (d, J=8.22 Hz, 2H), 6.87 (d, J=1.76 Hz, 2H), 5.04 (d, J=9.78 Hz, 1H), 4.71-4.76 (m, J=11.74 Hz, 1H), 4.66 (d, J=9.78 Hz, 1H), 4.02 (dtd, J=3.33, 9.88, 13.40 Hz, 1H), 3.19-3.36 (m, J=6.85, 16.24 Hz, 2H), 2.98 (dd, J=4.89, 16.43 Hz, 1H), 2.86-2.93 (m, J=2.74 Hz, 1H), 2.14-2.26 (m, 1H), 1.58-1.70 (m, 1H), 1.44 (s, 9H), 0.55 (t, J=7.53 Hz, 3H). Mass spectrum (ESI) m/z=590.0 [M−H]$^+$.

Example 149

Methyl 2-((2R,5R,6R)-4-((S)-1-(tert-butylsulfonyl)butan-2-yl)-6-(3-chlorophenyl)-5-(4-chlorophenyl)-3-oxomorpholin-2-yl)acetate

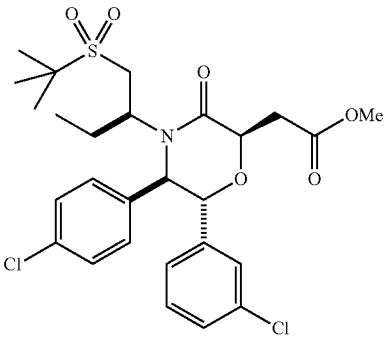

The title compound was prepared with the following procedure:

To a solution of 2-((2R,5R,6R)-4-((S)-1-(tert-butylsulfonyl)butan-2-yl)-6-(3-chlorophenyl)-5-(4-chlorophenyl)-3-oxomorpholin-2-yl)acetic acid (Example 120) (75 mg, 0.135 mmol) in MeOH (0.270 mL) and benzene (1.080 mL) was added 2.0 M (trimethylsilyl)diazomethane in hexanes (0.135 mL, 0.270 mmol) at 0° C. dropwise. After stirring for 2 hours at 0° C., the reaction was concentrated under reduced pressure. The crude material was adsorbed onto a plug of silica gel and purified by flash chromatography through a Redi-Sep pre-packed silica gel column (12 g), eluting by a step-gradient method from 5% to 25% acetone in hexanes in five increments, to provide methyl 2-((2R,5R,6R)-4-((S)-1-(tert-butylsulfonyl)butan-2-yl)-6-(3-chlorophenyl)-5-(4-chlorophenyl)-3-oxomorpholin-2-yl)acetate as a white foam. $^1$H NMR (400 MHz, CDCl$_3$) δ 7.18-7.22 (m, 4H), 7.12-7.17 (m, 1H), 7.08 (t, J=7.73 Hz, 1H), 6.99 (d, J=7.63 Hz, 1H), 5.06 (d, J=6.65 Hz, 1H), 4.90 (d, J=6.65 Hz, 1H), 4.62 (dd, J=3.91, 7.83 Hz, 1H), 3.88 (dd, J=8.80, 13.69 Hz, 1H), 3.65 (s, 3H), 3.23-3.35 (m, 1H), 2.97-3.09 (m, J=7.83 Hz, 1H), 2.82-2.96 (m, 2H), 1.98-2.16 (m, 1H), 1.54-1.67 (m, 1H), 1.36 (s, 9H), 0.47 (t, J=7.53 Hz, 3H). Mass spectrum (ESI) m/z=570.2 [M−H]$^+$.

Example 150

Methyl 2-((2S,5R,6R)-4-((S)-1-(tert-butylsulfonyl)butan-2-yl)-6-(3-chlorophenyl)-5-(4-chlorophenyl)-3-oxomorpholin-2-yl)acetate

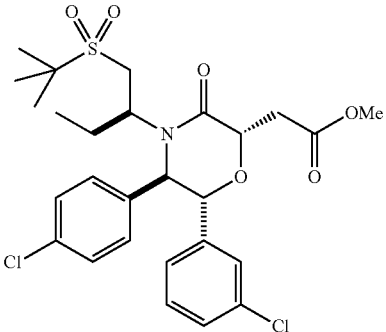

The title compound was prepared from 2-((2S,5R,6R)-4-((S)-1-(tert-butylsulfonyl)butan-2-yl)-6-(3-chlorophenyl)-5-

(4-chlorophenyl)-3-oxomorpholin-2-yl)acetic acid (Example 121) by a procedure similar to that described in Example 149. The crude product was purified by flash chromatography through a silica gel column (12 g), eluting by a step-gradient method from 5% to 25% acetone in hexanes in five increments, to provide methyl 2-((2S,5R,6R)-4-((S)-1-(tert-butylsulfonyl)butan-2-yl)-6-(3-chlorophenyl)-5-(4-chlorophenyl)-3-oxomorpholin-2-yl)acetate as a white foam. $^1$H NMR (400 MHz, CDCl$_3$) δ 7.29 (d, J=8.61 Hz, 2H), 7.16-7.21 (m, 1H), 7.05-7.16 (m, 4H), 6.82 (d, J=7.63 Hz, 1H), 5.05 (d, J=9.78 Hz, 1H), 4.77 (d, J=4.69 Hz, 1H), 4.69 (d, J=9.78 Hz, 1H), 4.05 (dd, J=8.51, 13.60 Hz, 1H), 3.72 (s, 3H), 3.22-3.35 (m, 1H), 3.05-3.16 (m, J=4.70 Hz, 1H), 2.86-3.03 (m, 2H), 2.18 (s, 1H), 1.62-1.76 (m, 1H), 1.45 (s, 9H), 0.56 (t, J=7.53 Hz, 3H). Mass spectrum (ESI) m/z=570.2 [M−H]$^+$.

Example 151

(2S,5R,6R)-4-((S)-1-(tert-butylsulfonyl)butan-2-yl)-6-(3-chlorophenyl)-5-(4-chlorophenyl)-2-(2-hydroxyethyl)morpholin-3-one

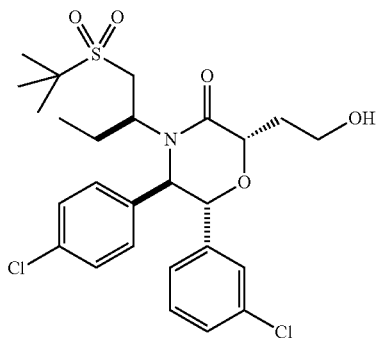

The title compound was prepared through the following procedure:

To a solution of methyl 2-((2S,5R,6R)-4-((S)-1-(tert-butylsulfonyl)butan-2-yl)-6-(3-chlorophenyl)-5-(4-chlorophenyl)-3-oxomorpholin-2-yl)acetate (65 mg, 0.114 mmol, Example 150) in THF (0.114 mL) was added super hydride (lithium triethylborohydride, 1.0 M solution in THF) (0.239 mL, 0.239 mmol). After 15 minutes LC/MS shows full conversion to desired product and MeOH (0.5 mL) was added dropwise. Then, potassium peroxomonosulfate compound (oxone) (210 mg, 0.342 mmol) in water (2 mL) was added dropwise over 1 minute. After an hour, saturated aqueous NaHSO$_3$ (1 mL) was added at room temperature. An exotherm was observed. The reaction was extracted with diethyl ether (2×20 mL). The combined organic layers were dried over MgSO$_4$, filtered and evaporated under a vacuum. The crude material was adsorbed onto a plug of silica gel and purified by flash chromatography through a silica gel column (12 g), eluting by a step-gradient method from 10% to 40% acetone in hexanes in six increments, to provide the title compound. $^1$H NMR (400 MHz, CDCl$_3$) δ 7.30 (d, J=8.61 Hz, 2H), 7.18-7.23 (m, 1H), 7.06-7.17 (m, 4H), 6.87 (d, J=7.83 Hz, 1H), 5.10 (d, J=9.98 Hz, 1H), 4.66 (d, J=9.78 Hz, 1H), 4.51 (t, J=5.48 Hz, 1H), 4.06 (dd, J=10.17, 13.50 Hz, 1H), 3.89-3.97 (m, 1H), 3.78-3.87 (m, 1H), 3.23-3.40 (m, 1H), 2.83 (d, J=13.50 Hz, 1H), 2.31 (d, J=5.48 Hz, 2H), 2.14-2.26 (m, 1H), 1.56-1.69 (m, 1H), 1.44 (s, 9H), 0.53 (t, J=7.53 Hz, 3H). Mass spectrum (ESI) m/z=542.2 [M]$^+$.

Example 152

(2R,5R,6R)-4-((S)-1-(tert-butylsulfonyl)butan-2-yl)-6-(3-chlorophenyl)-5-(4-chlorophenyl)-2-(2-hydroxyethyl)morpholin-3-one

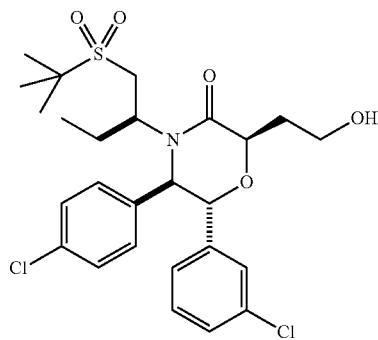

The title compound was prepared from methyl 2-((2R,5R,6R)-4-((S)-1-(tert-butylsulfonyl)butan-2-yl)-6-(3-chlorophenyl)-5-(4-chlorophenyl)-3-oxomorpholin-2-yl)acetate (Example 149) by a procedure similar to that described in Example 151. The crude product was purified by flash chromatography through a silica gel column (12 g), eluting by a step-gradient method from 10% to 30% acetone in hexanes in six increments, to provide the title compound as a white foam. $^1$H NMR (400 MHz, CDCl$_3$) δ 7.30-7.37 (m, 2H), 7.20-7.25 (m, 4H), 7.15 (t, J=8.02 Hz, 1H), 7.01 (d, J=7.63 Hz, 1H), 5.13 (d, J=7.63 Hz, 1H), 4.87 (d, J=7.63 Hz, 1H), 4.50 (t, J=6.85 Hz, 1H), 4.00 (dd, J=9.10, 13.60 Hz, 1H), 3.87 (s, 2H), 3.26-3.42 (m, 1H), 2.86-3.04 (m, J=2.54 Hz, 1H), 2.07-2.42 (m, 3H), 1.57-1.71 (m, 1H), 1.45 (s, 9H), 0.55 (t, J=7.53 Hz, 3H). Mass spectrum (ESI) m/z=570.2 [M−H]$^+$.

Example 153

(2R,5R,6R)-4-((S)-1-(tert-butylsulfonyl)butan-2-yl)-6-(3-chlorophenyl)-5-(4-chlorophenyl)-2-(2-methoxyethyl)morpholin-3-one

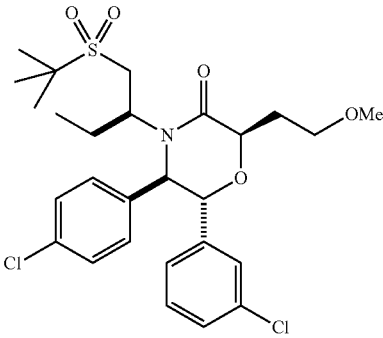

The title compound was prepared with the following procedure:

To a solution of (2R,5R,6R)-4-((S)-1-(tert-butylsulfonyl)butan-2-yl)-6-(3-chlorophenyl)-5-(4-chlorophenyl)-2-(2-hydroxyethyl)morpholin-3-one (40 mg, 0.074 mmol, Example 152) in DMF (0.737 mL) was added first sodium hydride (60% in oil; 2.95 mg, 0.074 mmol) at 0° C. and then methyl iodide (0.005 mL, 0.081 mmol). The reaction was stirred at this temperature for 2 hours, after which period the crude mixture was concentrated. Purified by reverse phase preparatory HPLC (Gemini™ Prep $C_{18}$ 5 μm column; Phenomenex, Torrance, Calif.; gradient elution of 25% to 75% MeCN in water, where both solvents contain 0.1% TFA, 30 min method) to provide the title compound as a white foam ($t_R$=21.4 min). $^1$H NMR (400 MHz, $CDCl_3$) δ 7.29-7.35 (m, 2H), 7.24 (dd, J=3.62, 4.79 Hz, 4H), 7.15 (t, J=8.02 Hz, 1H), 7.02 (d, J=7.82 Hz, 1H), 5.11 (d, J=7.43 Hz, 1H), 4.85 (d, J=7.24 Hz, 1H), 4.45 (dd, J=5.48, 7.82 Hz, 1H), 3.99 (dd, J=8.90, 13.79 Hz, 1H), 3.48-3.67 (m, 2H), 3.36 (s, 3H), 2.89-3.02 (m, 1H), 2.24-2.37 (m, 2H), 2.07-2.22 (m, 1H), 1.55-1.72 (m, 1H), 1.44 (s, 9H), 0.54 (t, J=7.53 Hz, 3H). Mass spectrum (ESI) m/z=556.2 [M]$^+$.

Example 154

2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid

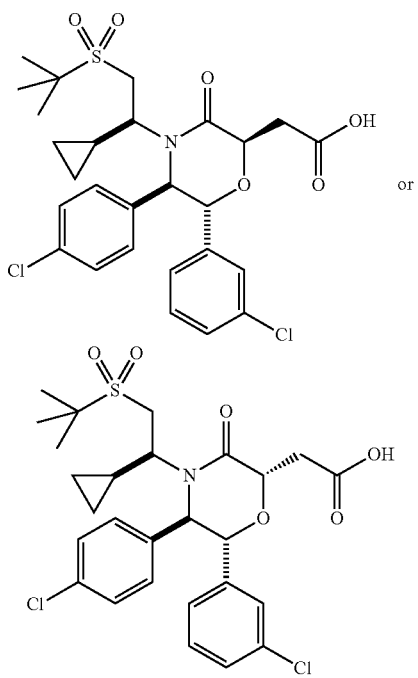

or

Racemic ethyl 2-bromo-2-cyclopropylacetate

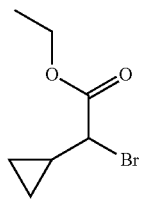

The above compound was prepared by adding a solution of 2-cyclopropylacetic acid (24.7 g, 247 mmol) in anhydrous DCE (250 mL) to thionyl chloride (22 mL, 302 mmol) dropwise over 5 minutes at 25° C. After refluxing for 2 hours, the reaction was cooled to room temperature, and N-bromosuccinimde (53.6 g, 301 mmol) and hydrogen bromide (48% aqueous solution; 0.195 mL, 1.727 mmol) were added successively at 25° C. The mixture was refluxed for 3 days, then cooled to room temperature. Absolute EtOH (200 mL) was added and the resulting dark brown solution was stirred at room temperature for one hour. The reaction mixture was concentrated under reduced pressure and the residue was suspended in carbon tetrachloride (300 mL) and filtered through a glass filter. The filtrate was concentrated under the reduced pressure. The crude product was purified by flash chromatography (silica-gel, 330 g×2, 5% ethyl acetate in hexanes) to provide ethyl 2-bromo-2-cyclopropylacetate. $^1$H NMR (400 MHz, $CDCl_3$) δ ppm 4.24 (m, 2 H), 3.58 (d, J=12.0 Hz, 1H), 1.58 (m, 1H), 0.90-0.80 (m, 2 H), 0.53 (m, 1H), 0.42 (m, 1H), 1.3 (t, J=8.0 Hz, 3 H).

Step A. Ethyl 2-((2R,3R)-2-(3-chlorophenyl)-3-(4-chlorophenyl)-5-oxomorpholino)-2-cyclopropylacetate

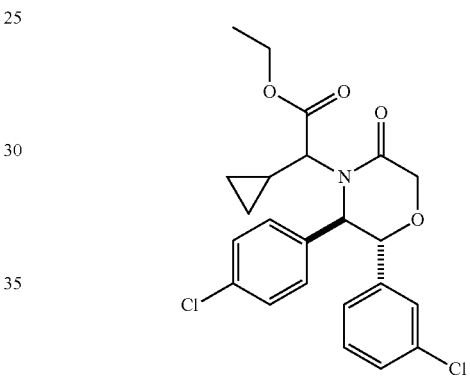

The above compound was prepared according to the following procedure:

To a solution of (5R,6R)-6-(3-chlorophenyl)-5-(4-chlorophenyl)morpholin-3-one (4.3 g, 13.35 mmol) (Example 112, Step A) in DMF (26.7 mL) was added sodium hydride (1.068 g, 26.7 mmol) at 0° C. and the mixture was stirred at this temperature for 30 minutes. To the mixture was added racemic ethyl 2-bromo-2-cyclopropylacetate (3.71 mL, 26.7 mmol) in DMF (40 mL) dropwise and the mixture was stirred at room temperature for 2 hours. The reaction was quenched with sat. $NH_4Cl$ (10 mL) and diluted with diethyl ether (10 mL). The solution was washed with 10% citric acid (10 mL), 5% $NaHCO_3$ (10 mL), water (10 mL), brine (10 mL), then dried with $MgSO_4$. The solvent was evaporated under reduced pressure and the residue was purified by flash chromatography on silica gel (120 g) eluting with 20% to 50% acetone in hexanes ethyl 2-((2R,3R)-2-(3-chlorophenyl)-3-(4-chlorophenyl)-5-oxomorpholino)-2-cyclopropylacetate as a 1.2:1 mixture of epimers which were taken into the next step as a mixture. Mass spectrum (ESI) m/z=448.0 [M−H]$^+$.

Step B. (5R,6R)-6-(3-chlorophenyl)-5-(4-chlorophenyl)-4-((R)-1-cyclopropyl-2-hydroxyethyl)morpholin-3-one and (5R,6R)-6-(3-chlorophenyl)-5-(4-chlorophenyl)-4-((S)-1-cyclopropyl-2-hydroxyethyl)morpholin-3-one

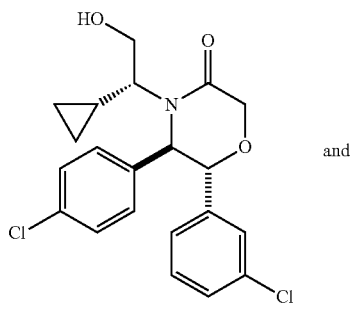

and

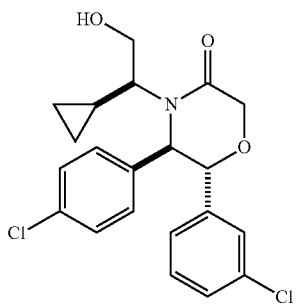

The above compounds were prepared according to the following procedure:

To a solution of methyl 2-((2R,3R)-2-(3-chlorophenyl)-3-(4-chlorophenyl)-5-oxomorpholino)-2-cyclopropylacetate (3.6 g, 8.29 mmol) (Example 154, Step A) in THF (8.29 mL) was added super hydride (lithium triethylborohydride, 1.0 M solution in THF) (17.4 mL, 17.4 mmol) at 0° C. After 15 minutes LCMS showed complete conversion to the desired product. MeOH was added (3 mL) dropwise over 1 minute. Then, potassium peroxomonosulfate compound (oxone) (15.29 g, 24.87 mmol) in water (60 mL) was added dropwise over 10 minutes. After 1 hour, saturated aqueous NaHSO$_3$ (9 mL) was added at room temperature. The reaction was extracted with diethyl ether (2×60 mL). The combined organic layers were dried over MgSO$_4$, filtered, and evaporated under a vacuum. The crude material was adsorbed onto a plug of silica gel and purified by flash chromatography through a silica gel column (330 g), eluting with isocratic 20% acetone in hexanes, to provide (5R,6R)-6-(3-chlorophenyl)-5-(4-chlorophenyl)-4-((R)-1-cyclopropyl-2-hydroxyethyl)morpholin-3-one (fast eluting isomer) and (5R,6R)-6-(3-chlorophenyl)-5-(4-chlorophenyl)-4-((S)-1-cyclopropyl-2-hydroxyethyl)morpholin-3-one (slow eluting isomer) as off-white solids.

Characterization data for fast eluting isomer, (5R,6R)-6-(3-chlorophenyl)-5-(4-chlorophenyl)-4-((R)-1-cyclopropyl-2-hydroxyethyl)morpholin-3-one:

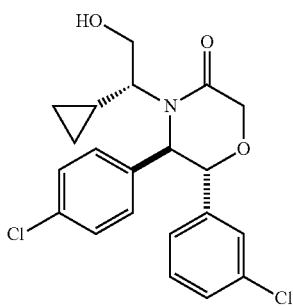 [SMILES: O=C1CO[C@H](c2cccc(Cl)c2)[C@@H](c2ccc(Cl)cc2)N1[C@@H](CO)C1CC1]

$^1$H NMR (400 MHz, CDCl$_3$) δ 7.23 (d, J=8.41 Hz, 3H), 7.12 (d, J=17.41 Hz, 3H), 6.92 (d, J=8.41 Hz, 2H), 6.73-6.79 (m, 1H), 4.49-4.63 (m, 2H), 4.42 (s, 2H), 3.52-3.69 (m, 2H), 2.28-2.39 (m, 1H), 1.31-1.46 (m, 1H), 0.55 (s, 2H), 0.22-0.31 (m, 1H), −0.04-0.05 (m, 1H). Mass spectrum (ESI) m/z=405.4 [M−H]$^+$.

Characterization data for slow eluting isomer, (5R,6R)-6-(3-chlorophenyl)-5-(4-chlorophenyl)-4-((S)-1-cyclopropyl-2-hydroxyethyl)morpholin-3-one:

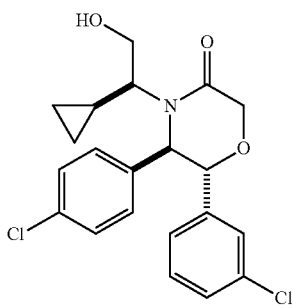

$^1$H NMR (400 MHz, CDCl$_3$) δ 7.04-7.25 (m, 7H), 6.79 (d, J=7.63 Hz, 1H), 4.87 (d, J=7.43 Hz, 1H), 4.52 (d, J=7.43 Hz, 1H), 4.26-4.42 (m, 2H), 3.50-3.59 (m, 1H), 3.13-3.36 (m, 2H), 2.88 (br. s., 1H), 0.79 (ddd, J=3.03, 4.94, 7.87 Hz, 1H), 0.40-0.57 (m, 2H), 0.11-0.23 (m, 1H), −0.10-0.06 (m, 1H). Mass spectrum (ESI) m/z=405.4 [M−H]$^+$.

Step C. (5R,6R)-4-((S)-2-(tert-butylthio)-1-cyclopropylethyl)-6-(3-chlorophenyl)-5-(4-chlorophenyl)morpholin-3-one

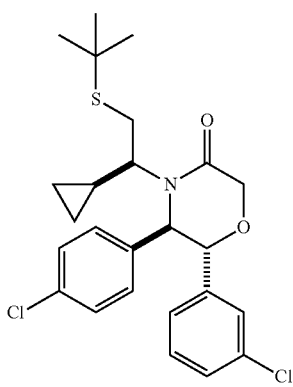 [SMILES: CC(C)(C)SC[C@H](C1CC1)N1C(=O)CO[C@H](c2cccc(Cl)c2)[C@H]1c1ccc(Cl)cc1]

The above compound was prepared from (5R,6R)-6-(3-chlorophenyl)-5-(4-chlorophenyl)-4-((S)-1-cyclopropyl-2-hydroxyethyl)morpholin-3-on (Example 154, Step B, slow eluting isomer) by a procedure similar to that described in Example 112, Step D, replacing ethanethiol with tert-butylthiol. The crude mixture was concentrated and purified by flash chromatography on silica gel, eluting through a two-step isocratic method of 5% and 10% acetone in hexanes, to provide the title compound. Mass spectrum (ESI) m/z=478.2 [M]+.

Step D. (5R,6R)-2-allyl-4-((S)-2-(tert-butylthio)-1-cyclopropylethyl)-6-(3-chlorophenyl)-5-(4-chlorophenyl)morpholin-3-one

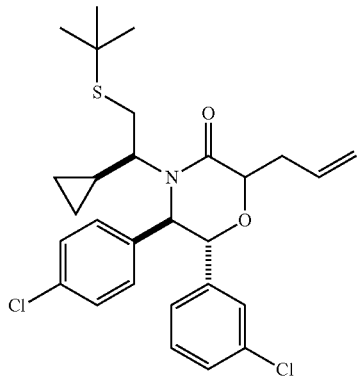 [SMILES: C=CCC1O[C@H](c2cccc(Cl)c2)[C@@H](c2ccc(Cl)cc2)N([C@H](CSC(C)(C)C)C2CC2)C1=O]

The above compound was prepared from (5R,6R)-4-((S)-2-(tert-butylthio)-1-cyclopropylethyl)-6-(3-chlorophenyl)-5-(4-chlorophenyl)morpholin-3-one (Example 154, Step C) by a procedure similar to that described in Example 112, Step E. The crude material was purified by flash chromatography on silica gel, eluting through a three-step isocratic method of 0%, 5% and 10% acetone in hexanes, to provide ((5R,6R)-2-allyl-4-((S)-2-(tert-butylthio)-1-cyclopropylethyl)-6-(3-chlorophenyl)-5-(4-chlorophenyl)morpholin-3-one as a 2:1 mixture of isomers at C2. Mass spectrum (ESI) m/z=518.2 [M]+ for both isomers.

Step E. 2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid

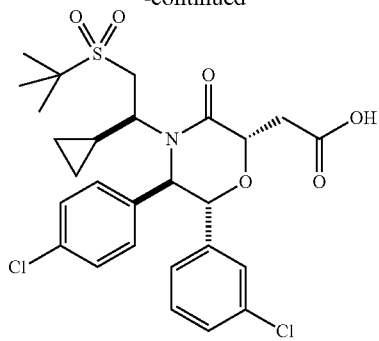

One of the title compounds was prepared from (5R,6R)-2-allyl-4-((S)-2-(tert-butylthio)-1-cyclopropylethyl)-6-(3-chlorophenyl)-5-(4-chlorophenyl)morpholin-3-one (Example 154, Step D) by a procedure similar to that described in Example 112, Step F. The crude product was purified by reverse phase preparatory HPLC (Gemini™ Prep $C_{18}$ 5 μm column; Phenomenex, Torrance, Calif.; gradient elution of 25% to 75% MeCN in water, where both solvents contain 0.1% TFA, 30 min method), to provide one of the title compounds as the faster eluting isomer ($t_R$=18.4 min). $^1$H NMR (400 MHz, CDCl$_3$) δ 7.28 (s, 5H), 7.06-7.17 (m, 3H), 5.10 (d, J=4.70 Hz, 1H), 4.86 (d, J=4.70 Hz, 1H), 4.50 (t, J=6.16 Hz, 1H), 3.74-3.98 (m, 1H), 2.90-3.16 (m, J=5.67 Hz, 2H), 2.01-2.08 (m, 1H), 1.35 (s, 9H), 1.09-1.28 (m, 1H), 0.22-0.43 (m, 2H), −0.13-0.07 (m, 1H), −0.69 to −0.66 (bs, 1H). Mass spectrum (ESI) m/z=568.1 [M]+.

Example 155

2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid

 or 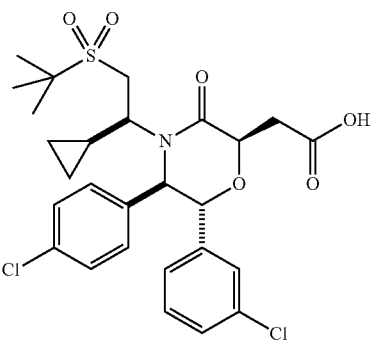 or

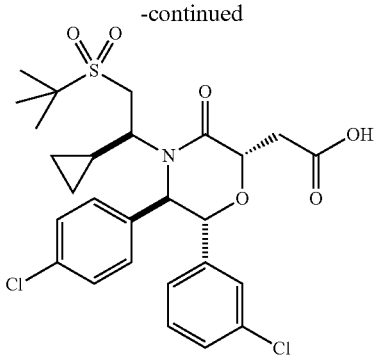

One of the title compounds was obtained as the second (slower) eluting isomer in Example 154 as a white foam ($t_R$=18.9 min). $^1$H NMR (400 MHz, CDCl$_3$) δ 7.48 (d, J=8.61 Hz, 2H), 7.21-7.40 (m, 5H), 7.04 (d, J=7.63 Hz, 1H), 5.23 (d, J=9.78 Hz, 1H), 4.85-4.98 (m, J=2.54 Hz, 2H), 4.30-4.54 (m, 1H), 3.44 (dd, J=7.24, 16.24 Hz, 1H), 3.11-3.25 (m, J=4.60, 16.14 Hz, 2H), 2.72-2.93 (m, 1H), 1.62 (s, 9H), 0.43-0.76 (m, 2H), −0.07-0.13 (m, 1H), −0.72 to −0.54 (m, 1H). Mass spectrum (ESI) m/z=569.2 [M+H]$^+$.

Example 156

2-((2R,5R,6R)-6-(3-chlorophenyl)-5-(4-chlorophenyl)-4-((S)-1-cyclopropyl-2-(isopropylsulfonyl)ethyl)-3-oxomorpholin-2-yl)acetic acid or 2-((2S,5R,6R)-6-(3-chlorophenyl)-5-(4-chlorophenyl)-4-((S)-1-cyclopropyl-2-(isopropylsulfonyl)ethyl)-3-oxomorpholin-2-yl)acetic acid

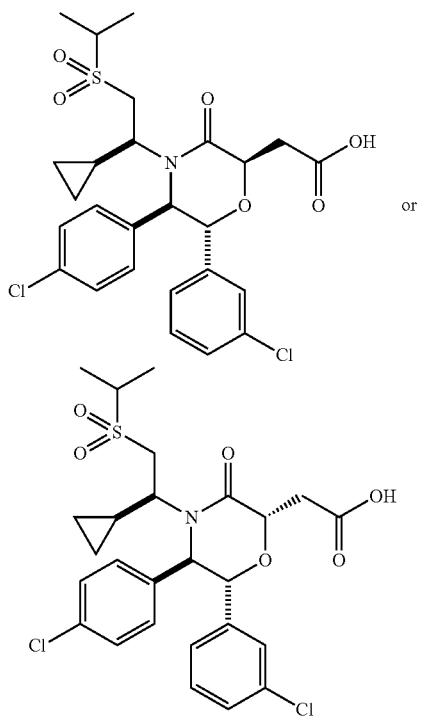

One of the title compounds was prepared from (5R,6R)-6-(3-chlorophenyl)-5-(4-chlorophenyl)-4-((S)-1-cyclopropyl-2-hydroxyethyl)morpholin-3-one (Example 154, Step B) by procedures similar to those described in Example 112, Steps D though F, replacing ethanethiol in Step D with isopropylthiol. The crude product was purified by reverse phase preparatory HPLC (Gemini™ Prep C$_{18}$ 5 μm column; Phenomenex, Torrance, Calif.; gradient elution of 25% to 75% MeCN in water, where both solvents contain 0.1% TFA, 30 min method) to provide one of the title compounds as the faster eluting isomer and a white foam ($t_R$=17.3 min). $^1$H NMR (400 MHz, CDCl$_3$) δ 7.31 (m, 2H), 7.08-7.23 (m, 6H), 5.09 (d, J=4.70 Hz, 1H), 4.88 (d, J=4.69 Hz, 1H), 4.51 (t, J=6.06 Hz, 1H), 3.72-3.98 (m, 1H), 2.95-3.22 (m, 5H), 1.56-1.80 (m, 1H), 1.34 (dd, J=4.70, 6.85 Hz, 6H), 0.20-0.52 (m, 2H), −0.12-0.08 (m, 1H), −0.86 to −0.56 (m, 1H). Mass spectrum (ESI) m/z=554.1 [M]$^+$.

Example 157

2-((2R,5R,6R)-6-(3-chlorophenyl)-5-(4-chlorophenyl)-4-((S)-1-cyclopropyl-2-(isopropylsulfonyl)ethyl)-3-oxomorpholin-2-yl)acetic acid or 2-((2S,5R,6R)-6-(3-chlorophenyl)-5-(4-chlorophenyl)-4-((S)-1-cyclopropyl-2-(isopropylsulfonyl)ethyl)-3-oxomorpholin-2-yl)acetic acid

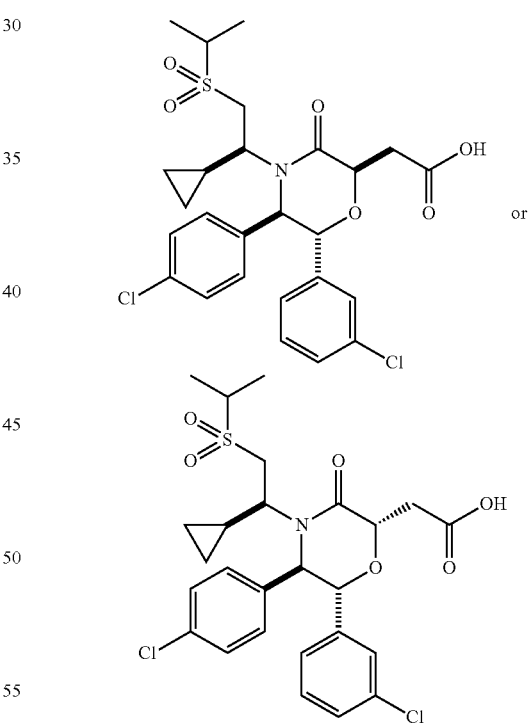

One of the title compounds was obtained as the second (slower) eluting isomer in Example 156 as a white foam ($t_R$=17.8 min). $^1$H NMR (400 MHz, CDCl$_3$) δ 7.37 (s, 1H), 7.31 (d, J=8.61 Hz, 2H), 7.02-7.24 (m, 4H), 6.85 (d, J=7.83 Hz, 1H), 5.03 (d, J=9.98 Hz, 1H), 4.69-4.81 (m, 2H), 4.16-4.38 (m, 1H), 3.20-3.34 (m, 2H), 3.05-3.19 (m, 2H), 2.92-3.04 (m, 2H), 1.37-1.49 (m, 6H), 0.24-0.58 (m, 2H), −0.26 to −0.01 (m, 1H), −0.89 to −0.69 (m, 1H). Mass spectrum (ESI) m/z=554.2 [M]$^+$.

Example 158

2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid

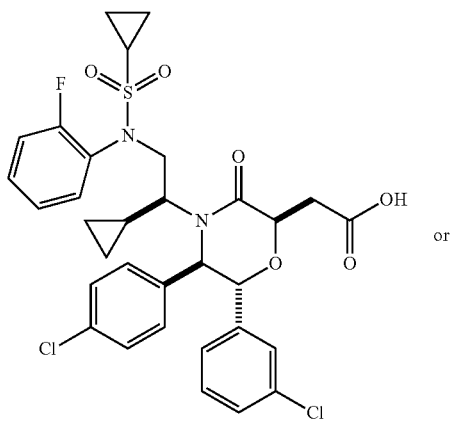

or

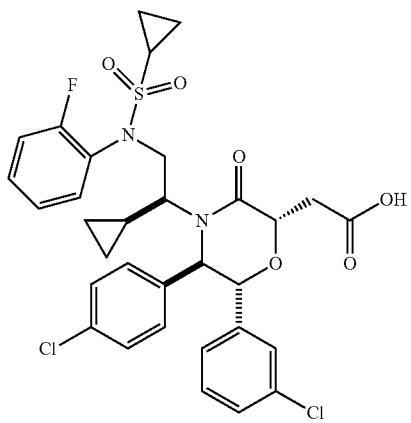

One of the title compounds was prepared from (5R,6R)-6-(3-chlorophenyl)-5-(4-chlorophenyl)-4-((S)-1-cyclopropyl-2-hydroxyethyl)morpholin-3-one (Example 154, Step B) by procedures similar to those described in Example 112, Steps D though F, replacing ethanethiol in Step D with N-(2-fluorophenyl)cyclopropanesulfonamide (from Example 133). The crude product was purified by reverse phase preparatory HPLC (Gemini™ Prep $C_{18}$ 5 μm column; Phenomenex, Torrance, Calif.; gradient elution of 25% to 75% MeCN in water, where both solvents contain 0.1% TFA, 30 min method) to provide one of the title compounds as the faster eluting isomer and a white foam ($t_R$=20.6 min). $^1$H NMR (400 MHz, CDCl$_3$) δ 7.43 (t, J=7.70 Hz, 1H), 7.23-7.34 (m, 5H), 7.06-7.21 (m, 6H), 4.93-5.06 (m, 1H), 4.82 (d, J=5.62 Hz, 1H), 4.33 (t, J=6.24 Hz, 2H), 3.69-3.90 (m, 1H), 3.06 (d, J=4.40 Hz, 1H), 2.98 (d, J=6.60 Hz, 1H), 2.40 (br. s., 2H), 1.31-1.56 (m, 1H), 0.75-1.00 (m, 5H), 0.16-0.55 (m, 2H), −0.17-0.11 (m, 1H), −0.99 to −0.59 (m, 1H). Mass spectrum (ESI) m/z=661.0 [M]$^+$.

Example 159

2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid

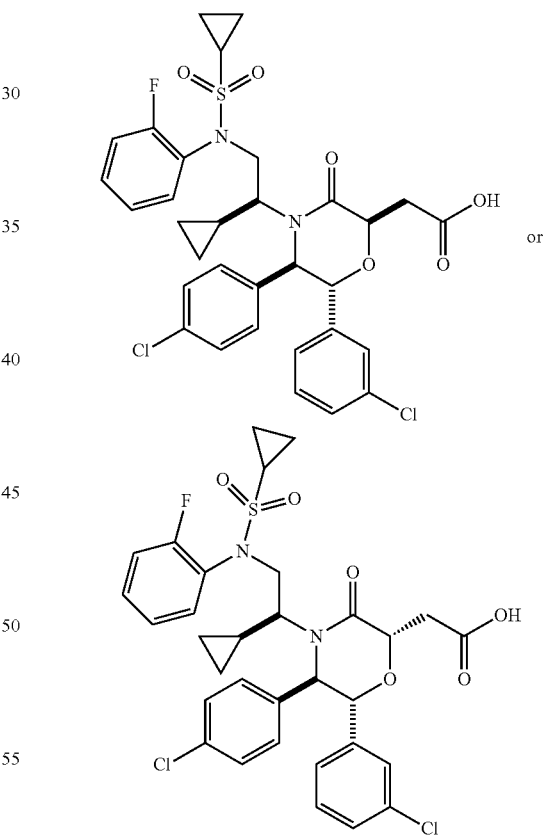

One of the title compounds was obtained as the second (slower) eluting isomer in Example 158 as a white foam ($t_R$=21.1 min). $^1$H NMR (400 MHz, CDCl$_3$) δ 7.61 (br. s., 1H), 7.36-7.46 (m, 1H), 7.31 (d, J=8.07 Hz, 2H), 7.03-7.27 (m, 7H), 6.92 (d, J=6.11 Hz, 1H), 4.93 (d, J=10.03 Hz, 1H), 4.69-4.78 (m, 2H), 4.57 (br. s., 1H), 3.84-4.07 (m, 1H), 2.77 (br. s., 1H), 2.46 (br. s., 3H), 0.81-1.16 (m, 6H), 0.14-0.50 (m, 2H), −0.19 (br. s., 1H). Mass spectrum (ESI) m/z=661.0 [M]$^+$.

Example 160

2-((2R,5R,6R)-6-(3-chlorophenyl)-5-(4-chlorophenyl)-4-((S)-1-(N-methylcyclopropanesulfonamido)butan-2-yl)-3-oxomorpholin-2-yl)acetic acid or
2-((2S,5R,6R)-6-(3-chlorophenyl)-5-(4-chlorophenyl)-4-((S)-1-(N-methylcyclopropanesulfonamido)butan-2-yl)-3-oxomorpholin-2-yl)acetic acid

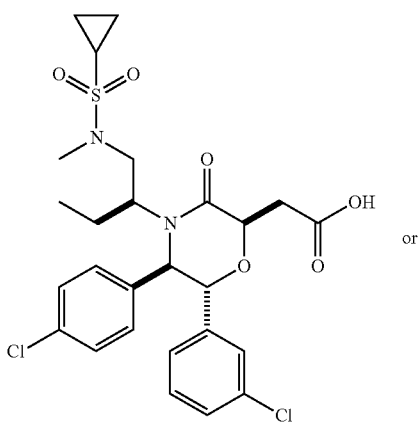

or

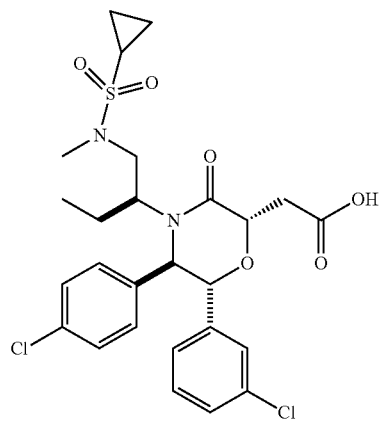

One of the title compounds was prepared from a mixture of 2-((2R,5R,6R)-6-(3-chlorophenyl)-5-(4-chlorophenyl)-4-((S)-1-(N-methylcyclopropanesulfonamido)butan-2-yl)-3-oxomorpholin-2-yl)acetic acid and 2-((2S,5R,6R)-6-(3-chlorophenyl)-5-(4-chlorophenyl)-4-((S)-1-(N-methylcyclopropanesulfonamido)butan-2-yl)-3-oxomorpholin-2-yl)acetic acid which was prepared in Example 243 Step E. The compounds were purified by reverse phase preparatory HPLC (Gemini™ Prep C$_{18}$ 5 µm column; Phenomenex, Torrance, Calif.; gradient elution of 25% to 75% MeCN in water, where both solvents contain 0.1% TFA, 30 min method) to provide one of the title compounds as the faster eluting isomer as a white foam (t$_R$=17.0 min). $^1$H NMR (400 MHz, CDCl$_3$) δ 7.28-7.38 (m, 4H), 7.14-7.27 (m, 4H), 4.82-4.98 (m, 2H), 4.71 (t, J=6.16 Hz, 1H), 3.11 (dd, J=6.26, 9.00 Hz, 3H), 2.88 (s, 3H), 2.33 (s, 1H), 1.77-1.96 (m, 1H), 1.53-1.73 (m, 1H), 1.08-1.29 (m, 2H), 0.85-1.07 (m, 4H), 0.57 (t, J=7.53 Hz, 3H). Mass spectrum (ESI) m/z=569.2 [M]$^+$.

Example 161

2-((2R,5R,6R)-6-(3-chlorophenyl)-5-(4-chlorophenyl)-4-((S)-1-(N-methylcyclopropanesulfonamido)butan-2-yl)-3-oxomorpholin-2-yl)acetic acid or
2-((2S,5R,6R)-6-(3-chlorophenyl)-5-(4-chlorophenyl)-4-((S)-1-(N-methylcyclopropanesulfonamido)butan-2-yl)-3-oxomorpholin-2-yl)acetic acid

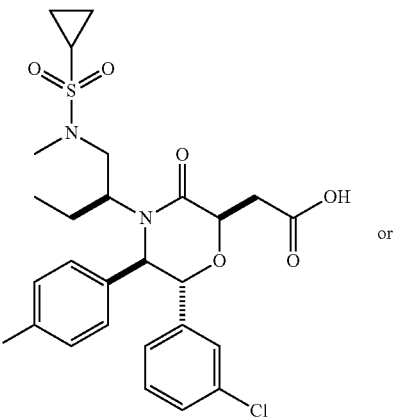

or

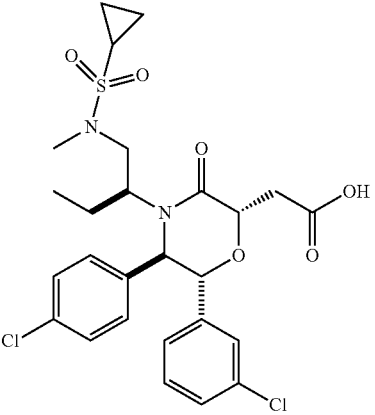

One of the title compounds was obtained as the second (slower) eluting isomer in Example 160 as a white foam (t$_R$=18.3 min). $^1$H NMR (400 MHz, CDCl$_3$) δ 77.32 (d, J=8.41 Hz, 2H), 7.12-7.28 (m, 2H), 7.06 (td, J=2.01, 3.81 Hz, 2H), 6.81-6.96 (m, 2H), 4.55-4.88 (m, 3H), 3.36 (dd, J=7.04, 16.24 Hz, 1H), 3.18 (dd, J=2.74, 4.89 Hz, 1H), 2.86-2.99 (m, 5H), 2.34 (br. s., 1H), 1.93 (s, 1H), 1.64-1.81 (m, 1H), 1.22 (d, J=3.33 Hz, 2H), 0.97-1.11 (m, 3H), 0.63 (t, J=7.53 Hz, 3H). Mass spectrum (ESI) m/z=569.2 [M]$^+$.

Example 162

2-((2R,5R,6R)-4-((S)-1-(tert-butylsulfonyl)butan-2-yl)-6-(3-chlorophenyl)-5-(4-chlorophenyl)-5-methyl-3-oxomorpholin-2-yl)acetic acid or 2-((2S,5R,6R)-4-((S)-1-(tert-butylsulfonyl)butan-2-yl)-6-(3-chlorophenyl)-5-(4-chlorophenyl)-5-methyl-3-oxomorpholin-2-yl)acetic acid

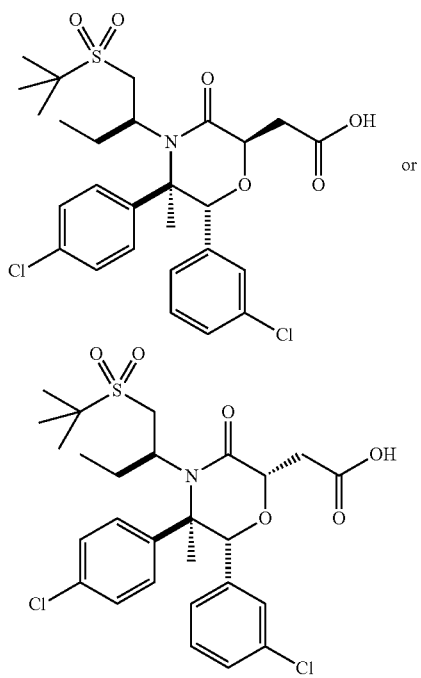

Step A. (2R)-1-((tert-butyldimethylsilyl)oxy)-1-(3-chlorophenyl)-2-(4-chlorophenyl)propan-2-amine

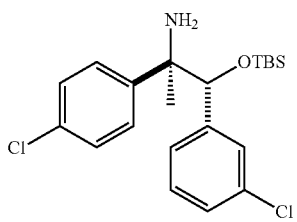

The above compound was prepared according to the following procedure:

To a solution of (2R)-2-amino-1-(3-chlorophenyl)-2-(4-chlorophenyl)propan-1-ol (Intermediate F2, 300 mg, 1.013 mmol) and imidazole, 99+%, crystalline (138 mg, 2.026 mmol) in DMF (1 mL) was added tert-butyldimethylchlorosilane (168 mg, 1.114 mmol) at room temperature. The mixture was stirred overnight at 45° C. After this period the mixture was diluted with water (10 mL) and extracted with DCM (3×20 mL). The organic extract was dried over MgSO$_4$. The solution was filtered and concentrated under a vacuum to give the crude material as a light-yellow oil. The crude material was adsorbed onto a plug of silica gel and purified by flash chromatography through a Redi-Sep pre-packed silica gel column (120 g), eluting with isocratic 70/25/5 DCM/Acetone/MeOH with 0.1% of triethylamine to provide (2R)-1-((tert-butyldimethylsilyl)oxy)-1-(3-chlorophenyl)-2-(4-chlorophenyl)propan-2-amine as light-yellow oil (second mayor fraction out of the column). $^1$H NMR (400 MHz, CDCl$_3$) δ 7.30-7.39 (m, 2H), 7.26-7.29 (m, 2H), 7.22-7.26 (m, 1H), 7.13-7.20 (m, 2H), 6.89-7.02 (m, 1H), 4.66 (s, 1H), 2.18 (s, 1H), 1.27 (d, J=2.15 Hz, 3H), 0.77-0.81 (m, 9H), −0.26 (s, 3H), −0.42 to −0.36 (m, 3H). Mass spectrum (ESI) m/z=410.2 [M]$^+$.

Step B. (R)-1-(((1R,2R)-1-((tert-butyldimethylsilyl)oxy)-1-(3-chlorophenyl)-2-(4-chlorophenyl)propan-2-yl)amino)butan-2-ol

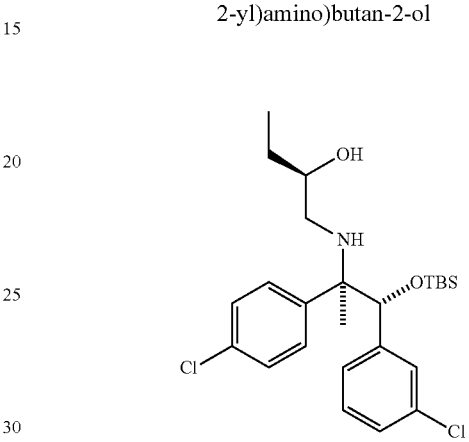

The above compound was prepared according to the following procedure:

A mixture of (1R,2R)-1-((tert-butyldimethylsilyl)oxy)-1-(3-chlorophenyl)-2-(4-chlorophenyl)propan-2-amine (380 mg, 0.926 mmol) (Example 162, Step A), ytterbium (III) trifluoromethanesulfonate (40.2 mg, 0.065 mmol) and (R)-(+)-1,2-epoxybutane, 98% (0.334 mL, 4.63 mmol) in acetonitrile (3.086 mL) was heated in a microwave at 130° C. for 8 hours. The reaction solution was concentrated under reduced pressure then partitioned between ethyl acetate (3×30 mL) and water (30 mL). The combined organic layers were stirred over anhydrous magnesium sulfate and filtered. The filtrate was concentrated under reduced pressure to afford a yellow oil. The crude mixture was taken to the next step without further purification. Mass spectrum (ESI) m/z=482.2 [M]$^+$.

Step C. (S)-1-((1R,2R)-1-((tert-butyldimethylsilyl)oxy)-1-(3-chlorophenyl)-2-(4-chlorophenyl)propan-2-yl)-2-ethylaziridine

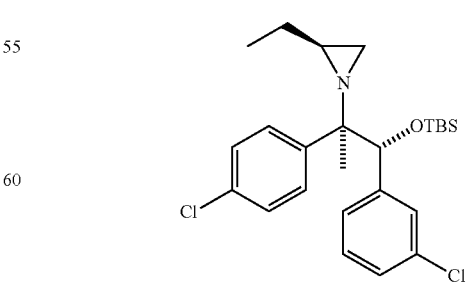

The above compound was prepared according to the following procedure:

To a room temperature solution of triphenylphosphine (303 mg, 1.154 mmol) and (R)-1-(((1R,2R)-1-((tert-butyldimethylsilyl)oxy)-1-(3-chlorophenyl)-2-(4-chlorophenyl)propan-2-yl)amino)butan-2-ol (464 mg, 0.962 mmol, Example 162, Step B) dissolved in THF (1.9 mL) was added diethyl azodicarboxylate, 40 wt. % solution in toluene (454 µL, 1.154 mmol). The reaction was stirred at room temperature for 48 hours. The crude mixture was concentrated, adsorbed onto a plug of silica gel and purified by flash chromatography through a silica gel column (80 g), eluting with isocratic 5% acetone in hexanes, to provide (S)-1-((1R,2R)-1-((tert-butyldimethylsilyl)oxy)-1-(3-chlorophenyl)-2-(4-chlorophenyl)propan-2-yl)-2-ethylaziridine as light-yellow oil. $^1$H NMR (400 MHz, CDCl$_3$) δ 7.12-7.17 (m, 2H), 7.04-7.09 (m, 2H), 6.95-7.01 (m, 1H), 6.84 (t, J=7.82 Hz, 1H), 6.76 (s, 1H), 6.49 (d, J=7.83 Hz, 1H), 4.48 (s, 1H), 1.96-2.06 (m, 1H), 1.80-1.92 (m, 1H), 1.25-1.34 (m, 1H), 1.22 (d, J=2.93 Hz, 1H), 1.10-1.17 (m, 2H), 1.08 (s, 3H), 0.93 (t, J=7.43 Hz, 3H), 0.81-0.86 (m, 9H), 0.01 (s, 3H) −0.43 (s, 3H). Mass spectrum (ESI) m/z=464.2 [M]$^+$.

Step D. (S)-N-((1R,2R)-1-((tert-butyldimethylsilyl)oxy)-1-(3-chlorophenyl)-2-(4-chlorophenyl)propan-2-yl)-1-(tert-butylthio)butan-2-amine

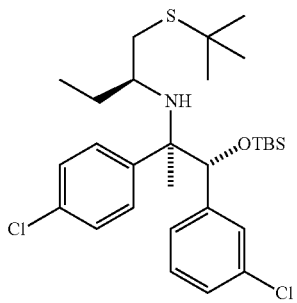 [SMILES: CC[C@@H](CSC(C)(C)C)N[C@](C)(c1ccc(Cl)cc1)[C@H](O[Si](C)(C)C(C)(C)C)c1cccc(Cl)c1]

The above compound was prepared according to the following procedure:

To a round-bottomed flask was added (S)-1-((1R,2R)-1-((tert-butyldimethylsilyl)oxy)-1-(3-chlorophenyl)-2-(4-chlorophenyl)propan-2-yl)-2-ethylaziridine (200 mg, 0.431 mmol, Example 162, Step C), tert-butanethiol (0.097 mL, 0.861 mmol) and indium (III) chloride (0.275 µL, 4.31 µmol) in DCM (2.153 mL). The reaction was stirred at room temperature overnight, and then concentrated. A $^1$H NMR of the crude mixture was taken to confirm the reaction was complete, and this product was taken to the next step without further purification. $^1$H NMR (400 MHz, CDCl$_3$) d 7.26 (d, J=1.17 Hz, 2H), 7.16 (d, J=8.61 Hz, 2H), 7.02 (d, J=9.00 Hz, 1H), 6.88 (t, J=7.83 Hz, 1H), 6.75-6.83 (m, 1H), 6.43 (d, J=7.43 Hz, 1H), 4.57 (s, 1H), 2.43-2.64 (m, 1H), 2.11-2.27 (m, 2H), 1.97-2.09 (m, 1H), 1.50-1.64 (m, 1H), 1.40-1.48 (m, 1H), 1.38 (s, 3H), 1.32 (s, 3H), 1.04 (s, 9H), 0.90 (s, 9H), 0.05 (s, 3H), −0.32 (s, 3H). Mass spectrum (ESI) m/z=554.2 [M]$^+$.

Step E. (1R,2R)-2-(((S)-1-(tert-butylthio)butan-2-yl)amino)-1-(3-chlorophenyl)-2-(4-chlorophenyl)propan-1-ol

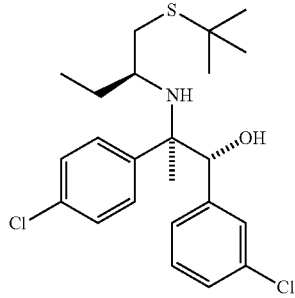 [SMILES: CC[C@@H](CSC(C)(C)C)N[C@](C)(c1ccc(Cl)cc1)[C@H](O)c1cccc(Cl)c1]

The above compound was prepared according to the following procedure:

To a 25 mL round-bottomed flask was added (S)-N-((1R,2R)-1-((tert-butyldimethylsilyl)oxy)-1-(3-chlorophenyl)-2-(4-chlorophenyl)propan-2-yl)-1-(tert-butylthio)butan-2-amine (540 mg, 0.973 mmol, Example 162, Step D) and tetrabutylammonium fluoride, 1.0 M solution in tetrahydrofuran (2.434 mL, 2.434 mmol) in THF (1.261 mL) at room temperature. The reaction was stirred for 1 hour at this temperature. After this time the reaction was quenched with water (10 mL) washed with diethyl ether (3×10 mL) and dried over MgSO$_4$. The solution was filtered and concentrated under a vacuum to give the crude material as a light-yellow oil. The crude material was adsorbed onto a plug of silica gel and purified by flash chromatography through a silica gel column (40 g), eluting through a three-step isocratic method of 0%, 5%, and 10% acetone in hexanes, to provide (1R,2R)-2-(((S)-1-(tert-butylthio)butan-2-yl)amino)-1-(3-chlorophenyl)-2-(4-chlorophenyl)propan-1-ol as light-yellow oil.

$^1$H NMR (400 MHz, CDCl$_3$) d 7.30 (s, 2H), 7.22-7.27 (m, 2H), 7.09-7.15 (m, 1H), 6.98 (s, 2H), 6.45-6.52 (m, 1H), 4.66-4.76 (m, 1H), 2.69-2.82 (m, 1H), 2.27-2.38 (m, 1H), 2.13-2.25 (m, 1H), 1.59-1.72 (m, 1H), 1.40-1.51 (m, 1H), 1.32 (s, 3H), 1.12 (s, 9H), 0.96 (t, J=7.43 Hz, 3H). Mass spectrum (ESI) m/z=440.2 [M]$^+$.

Step F. 2-((1R,2R)-2-(((S)-1-(tert-butylthio)butan-2-yl)amino)-1-(3-chlorophenyl)-2-(4-chlorophenyl)propoxy)acetic acid

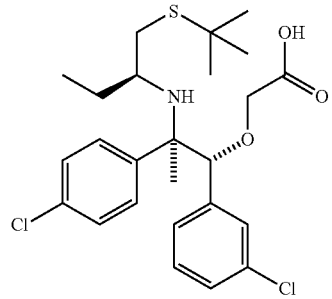 [SMILES: CC[C@@H](CSC(C)(C)C)N[C@](C)(c1ccc(Cl)cc1)[C@H](OCC(=O)O)c1cccc(Cl)c1]

The above compound was prepared according to the following procedure:

To a round-bottomed flask was added (1R,2R)-2-(((S)-1-(tert-butylthio)butan-2-yl)amino)-1-(3-chlorophenyl)-2-(4- chlorophenyl)propan-1-ol (270 mg, 0.613 mmol, Example 162, Step E) and bromoacetic acid (102 mg, 0.736 mmol) in THF (2.043 mL). To this solution, sodium hydride (60% in oil; 73.6 mg, 1.839 mmol) was added in portions over 5 minutes. The reaction was allowed to stir at room temperature overnight, whereupon the crude mixture was diluted in water (10 mL) and extracted with diethy ether (3×20 mL). The combined organic layers were dried over MgSO$_4$, filtered and concentrated. The crude material was taken to the next step without further purification. Mass spectrum (ESI) m/z=498.2 [M]$^+$.

Step G. (5R,6R)-4-((S)-1-(tert-butylthio)butan-2-yl)-6-(3-chlorophenyl)-5-(4-chlorophenyl)-5-methyl-morpholin-3-one

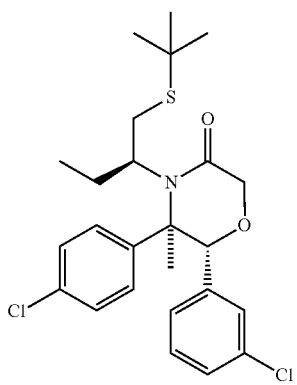 [SMILES: CC[C@@H](CSC(C)(C)C)N1C(=O)CO[C@H](c2cccc(Cl)c2)[C@@]1(C)c1ccc(Cl)cc1]

The above compound was prepared according to the following procedure:

To a solution of 2-((1R,2R)-2-(((S)-1-(tert-butylthio)butan-2-yl)amino)-1-(3-chlorophenyl)-2-(4-chlorophenyl)propoxy)acetic acid (306 mg, 0.614 mmol, Example 162, Step F) and N,N-diethylpropan-2-amine (0.405 mL, 2.60 mmol) in DMF (2.0 mL) was added HATU (280 mg, 0.737 mmol). The reaction was stirred for 2 hours at room temperature, then quenched with water (30 mL), extracted with diethyl ether (3×30 mL), dried over MgSO$_4$, filtered, and concentrated. The crude material was adsorbed onto a plug of silica gel and purified by flash chromatography through a silica gel column (40 g), eluting through a three-step isocratic method of 5%, 10%, and 15% acetone in hexanes, to provide (5R,6R)-4-((S)-1-(tert-butylthio)butan-2-yl)-6-(3-chlorophenyl)-5-(4-chlorophenyl)-5-methylmorpholin-3-one as white solid. $^1$H NMR (400 MHz, CDCl$_3$) δ 7.37-7.44 (m, 2H), 7.31-7.38 (m, 2H), 7.14-7.21 (m, 1H), 7.00 (s, 1H), 6.79-6.86 (m, 1H), 6.30-6.38 (m, 1H), 4.92 (s, 1H), 4.33-4.62 (m, 2H), 3.26-3.38 (m, 1H), 2.49-2.64 (m, 2H), 1.95-2.14 (m, 2H), 1.51 (s, 3H), 1.08 (s, 9H), 0.94 (t, J=7.63 Hz, 3H). Mass spectrum (ESI) m/z=480.2 [M]$^+$.

Step H. 2-((2R,5R,6R)-4-((S)-1-(tert-butylsulfonyl)butan-2-yl)-6-(3-chlorophenyl)-5-(4-chlorophenyl)-5-methyl-3-oxomorpholin-2-yl)acetic acid or 2-((2S,5R,6R)-4-((S)-1-(tert-butylsulfonyl)butan-2-yl)-6-(3-chlorophenyl)-5-(4-chlorophenyl)-5-methyl-3-oxomorpholin-2-yl)acetic acid

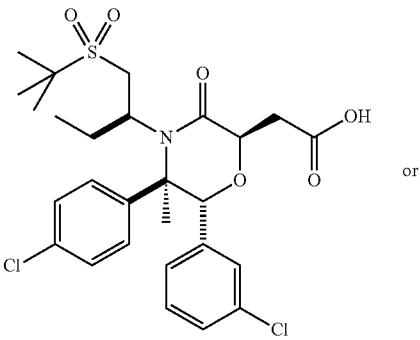

or

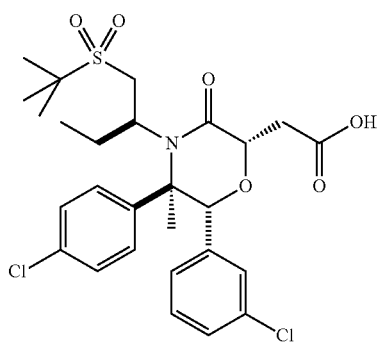

One of the title compounds was prepared from (5R,6R)-4-((S)-1-(tert-butylthio)butan-2-yl)-6-(3-chlorophenyl)-5-(4-chlorophenyl)-5-methylmorpholin-3-one (Example 162, Step G) by procedures similar to those described in Example 112, Steps E through F. The material was purified on a Thar 200 SFC (Thar Technologies, Inc., Pittsburg, Pa.) (250 mm×30 mm IA column; 2.0 mL injections of 85 mg/10 mL (8.5 mg/mL) sample solution in MeOH (17 mg/injection); run time=6 min, cycle time=5 min; 42 mL/min (20 mM ammonia in methanol)+98 g/min CO$_2$; outlet pressure=100 bar; temp.=25° C.; wavelength=220 nm), and it provided one of the title compounds as the first eluting isomer. $^1$H NMR (400 MHz, CDCl$_3$) δ 7.44 (d, J=8.61 Hz, 2H), 7.26-7.28 (m, 2H), 7.19 (dd, J=1.27, 7.92 Hz, 1H), 7.01 (t, J=7.92 Hz, 1H), 6.85-6.89 (m, 1H), 6.39 (d, J=7.83 Hz, 1H), 5.29 (s, 1H), 5.03-5.14 (m, 1H), 3.69 (dd, J=9.88, 13.01 Hz, 1H), 3.09-3.27 (m, 2H), 2.97-3.07 (m, 1H), 2.23-2.37 (m, 1H), 2.02-2.18 (m, 1H), 1.60 (s, 3H), 1.21-1.28 (m, 9H), 0.99 (t, J=7.53 Hz, 3H). Mass spectrum (ESI) m/z=570.2 [M]$^+$.

Example 163

2-((2R,5R,6R)-4-((S)-1-(tert-butylsulfonyl)butan-2-yl)-6-(3-chlorophenyl)-5-(4-chlorophenyl)-5-methyl-3-oxomorpholin-2-yl)acetic acid or 2-((2S,5R,6R)-4-((S)-1-(tert-butylsulfonyl)butan-2-yl)-6-(3-chlorophenyl)-5-(4-chlorophenyl)-5-methyl-3-oxomorpholin-2-yl)acetic acid

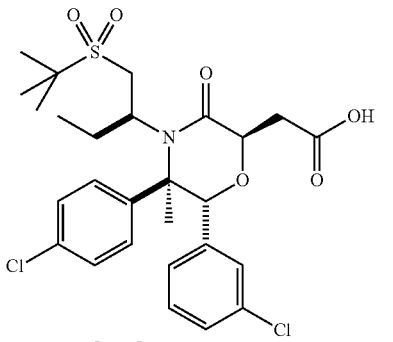

or

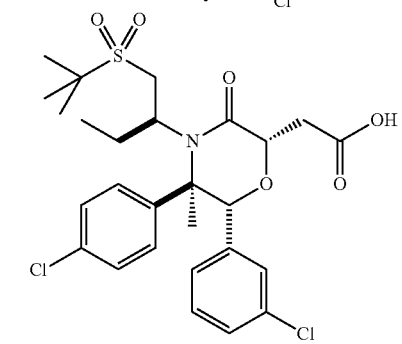

One of the title compounds was obtained as the second (slower) eluting isomer in Example 162 as a white foam. $^1$H NMR (400 MHz, CDCl$_3$) δ 7.50-7.64 (m, 1H), 7.44 (d, J=8.80 Hz, 2H), 7.32 (d, J=7.63 Hz, 1H), 7.20 (d, J=8.02 Hz, 1H), 7.03 (t, J=7.92 Hz, 1H), 6.83 (s, 1H), 6.36 (d, J=7.82 Hz, 1H), 5.09 (s, 1H), 4.78 (t, J=5.67 Hz, 1H), 3.75 (dd, J=9.98, 12.91 Hz, 1H), 3.32-3.51 (m, 1H), 2.87-3.24 (m, 3H), 2.19-2.34 (m, 1H), 2.03-2.18 (m, 1H), 1.59 (s, 3H), 1.24 (s, 9H), 1.01 (t, J=7.53 Hz, 3H). Mass spectrum (ESI) m/z=570.0 [M]$^+$.

Example 164

2-((2R,5R,6R)-4-((S)-1-(tert-butylsulfonyl)-3-methylbutan-2-yl)-6-(3-chlorophenyl)-5-(4-chlorophenyl)-3-oxomorpholin-2-yl)acetic acid or 2-((2S,5R,6R)-4-((S)-1-(tert-butylsulfonyl)-3-methylbutan-2-yl)-6-(3-chlorophenyl)-5-(4-chlorophenyl)-3-oxomorpholin-2-yl)acetic acid

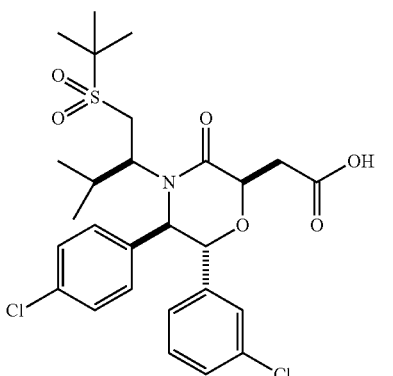

or

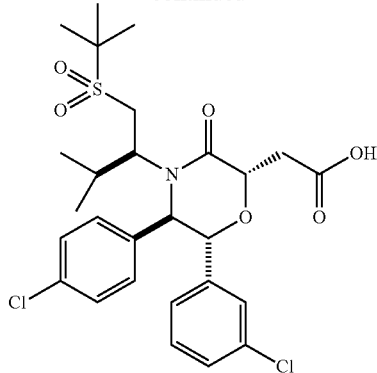

Step A. (5R,6R)-4-((R)-1-(tert-butylthio)-3-methylbutan-2-yl)-6-(3-chlorophenyl)-5-(4-chlorophenyl)morpholin-3-one or (5R,6R)-4-((S)-1-(tert-butylthio)-3-methylbutan-2-yl)-6-(3-chlorophenyl)-5-(4-chlorophenyl)morpholin-3-one

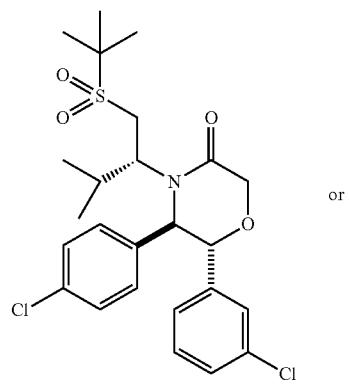

or

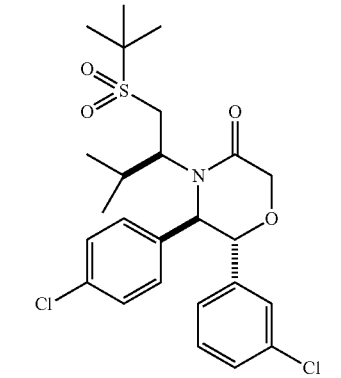

The above compounds were prepared from (1R,2R)-2-amino-1-(3-chlorophenyl)-2-(4-chlorophenyl)ethanol (Intermediate A2) by procedures similar to those described in Example 162, Steps A though F, replacing (R)-(+)-1,2-epoxybutane in Step B with racemic 1,2-epoxy-3-methylbutane. The crude product was purified by reverse phase preparatory HPLC (Gemini™ Prep C$_{18}$ 5 μm column; Phenomenex, Torrance, Calif.; gradient elution of 50% to 90% MeCN in water, where both solvents contain 0.1% TFA, 30 min method) to provide the title compounds (t$_R$=14.0 min and t$_R$=14.8 min) as white foams. Mass spectrum (ESI) m/z=480.2 [M]$^+$ for both isomers.

Step B. 2-((2R,5R,6R)-4-((S)-1-(tert-butylsulfonyl)-3-methylbutan-2-yl)-6-(3-chlorophenyl)-5-(4-chlorophenyl)-3-oxomorpholin-2-yl)acetic acid or 2-((2S,5R,6R)-4-((S)-1-(tert-butylsulfonyl)-3-methylbutan-2-yl)-6-(3-chlorophenyl)-5-(4-chlorophenyl)-3-oxomorpholin-2-yl)acetic acid

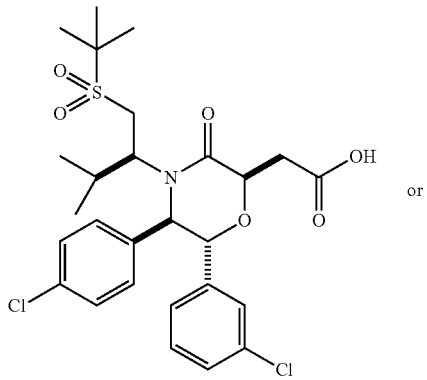

or

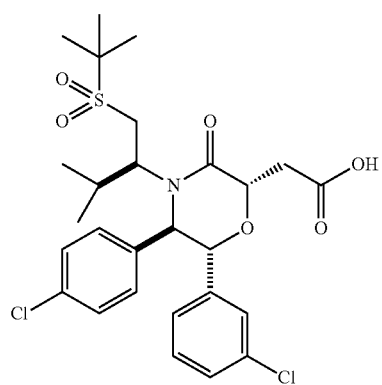

One of the title compounds was prepared from (5R,6R)-4-((S)-1-(tert-butylthio)-3-methylbutan-2-yl)-6-(3-chlorophenyl)-5-(4-chlorophenyl)morpholin-3-one (Example 164, Step A, slowest eluting isomer) by procedures similar to those described in Example 112, Steps E through F. The crude product was purified by reverse phase preparatory HPLC (Gemini™ Prep $C_{18}$ 5 μm column; Phenomenex, Torrance, Calif.; gradient elution of 25% to 75% MeCN in water, where both solvents contain 0.1% TFA, 30 min method) to provide one of the title compounds as the faster eluting isomer as a white foam ($t_R$=19.0 min). $^1$H NMR (400 MHz, CDCl$_3$) δ 7.49 (d, J=8.22 Hz, 2H), 7.33-7.42 (m, 3H), 7.22 (d, J=0.98 Hz, 3H), 5.28-5.39 (m, 1H), 5.16 (s, 1H), 4.66 (t, J=6.16 Hz, 1H), 3.77 (dd, J=7.43, 14.09 Hz, 1H), 3.30 (t, J=7.53 Hz, 1H), 3.09-3.22 (m, J=3.23, 6.16 Hz, 3H), 2.33-2.49 (m, 1H), 1.49 (s, 9H), 0.78 (d, J=6.65 Hz, 3H), 0.53 (d, J=6.85 Hz, 3H). Mass spectrum (ESI) m/z=570.0 [M]$^+$.

Example 165

2-((2R,5R,6R)-4-((S)-1-(tert-butylsulfonyl)-3-methylbutan-2-yl)-6-(3-chlorophenyl)-5-(4-chlorophenyl)-3-oxomorpholin-2-yl)acetic acid or 2-((2S,5R,6R)-4-((S)-1-(tert-butylsulfonyl)-3-methylbutan-2-yl)-6-(3-chlorophenyl)-5-(4-chlorophenyl)-3-oxomorpholin-2-yl)acetic acid

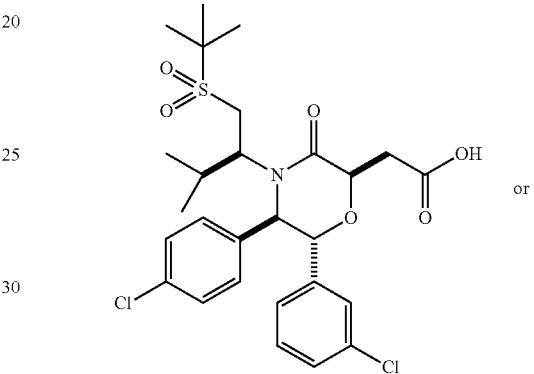

or

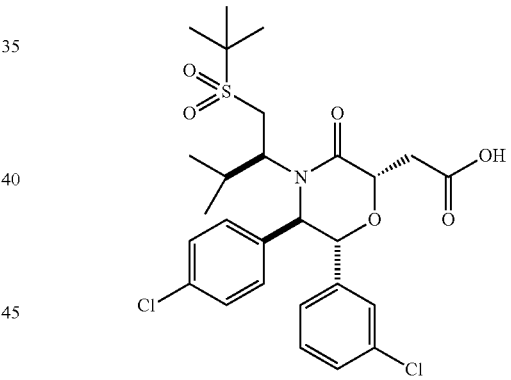

One of the title compounds was obtained as the second (slower) eluting isomer in Example 164, Step B, as a white foam ($t_R$=19.7 min). $^1$H NMR (400 MHz, CDCl$_3$) δ 7.28-7.35 (m, 2H), 7.14-7.26 (m, 3H), 7.06-7.13 (m, 2H), 6.90 (d, J=7.63 Hz, 1H), 5.22 (d, J=9.98 Hz, 1H), 4.83 (d, J=9.98 Hz, 1H), 4.74 (dd, J=4.60, 6.36 Hz, 1H), 3.94 (dd, J=8.80, 13.89 Hz, 1H), 3.18 (dd, J=6.36, 16.33 Hz, 2H), 2.96-3.08 (m, J=4.50 Hz, 2H), 2.30-2.43 (m, 1H), 1.43-1.49 (m, 9H), 0.74 (d, J=6.65 Hz, 3H), 0.64 (s, 3H). Mass spectrum (ESI) m/z=570.0 [M]$^+$.

Example 166

2-((2R,5R,6R)-4-((R)-1-(tert-butylsulfonyl)-3-methylbutan-2-yl)-6-(3-chlorophenyl)-5-(4-chlorophenyl)-3-oxomorpholin-2-yl)acetic acid or 2-((2S,5R,6R)-4-((R)-1-(tert-butylsulfonyl)-3-methylbutan-2-yl)-6-(3-chlorophenyl)-5-(4-chlorophenyl)-3-oxomorpholin-2-yl)acetic acid

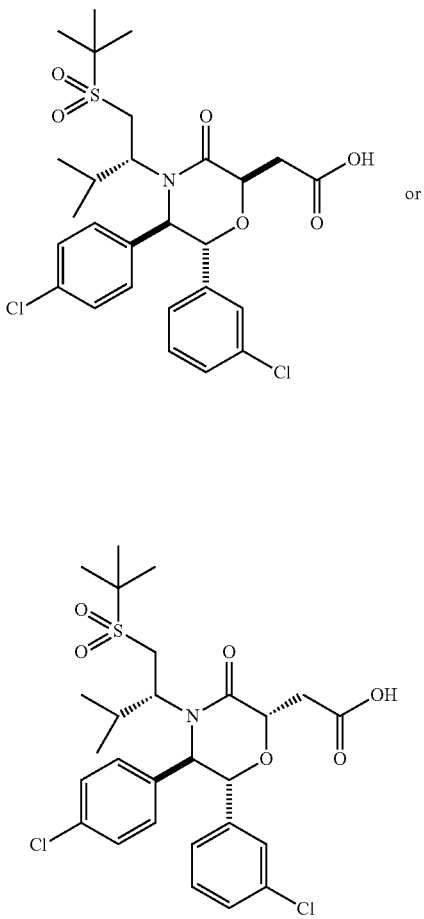

One of the title compounds was prepared from (5R,6R)-4-((R)-1-(tert-butylthio)-3-methylbutan-2-yl)-6-(3-chlorophenyl)-5-(4-chlorophenyl)morpholin-3-one (Example 164, Step A, fastest eluting isomer) by procedures similar to those described in Example 112, Steps E through F. The crude product was purified by reverse phase preparatory HPLC (Gemini™ Prep $C_{18}$ 5 µm column; Phenomenex, Torrance, Calif.; gradient elution of 25% to 75% MeCN in water, where both solvents contain 0.1% TFA, 30 min method) to provide one of the title compounds as the faster eluting isomer as a white foam ($t_R$=17.9 min). $^1$H NMR (400 MHz, CDCl$_3$) δ 7.31-7.37 (m, 2H), 7.23 (d, J=7.63 Hz, 4H), 7.14 (t, J=7.73 Hz, 1H), 6.89 (d, J=7.63 Hz, 1H), 5.01 (d, J=7.63 Hz, 1H), 4.92 (dd, J=5.38, 7.14 Hz, 1H), 4.76 (d, J=7.63 Hz, 1H), 4.00 (dd, J=6.85, 13.89 Hz, 1H), 3.57 (q, J=6.59 Hz, 1H), 3.24-3.32 (m, J=5.28 Hz, 1H), 3.14-3.20 (m, J=4.70 Hz, 2H), 2.34 (qd, J=6.77, 13.52 Hz, 1H), 1.35 (s, 9H), 1.03 (d, J=6.85 Hz, 3H), 0.98 (d, J=6.85 Hz, 3H). Mass spectrum (ESI) m/z=570.0 [M]$^+$.

Example 167

2-((2R,5R,6R)-4-((R)-1-(tert-butylsulfonyl)-3-methylbutan-2-yl)-6-(3-chlorophenyl)-5-(4-chlorophenyl)-3-oxomorpholin-2-yl)acetic acid or 2-((2S,5R,6R)-4-((R)-1-(tert-butylsulfonyl)-3-methylbutan-2-yl)-6-(3-chlorophenyl)-5-(4-chlorophenyl)-3-oxomorpholin-2-yl)acetic acid

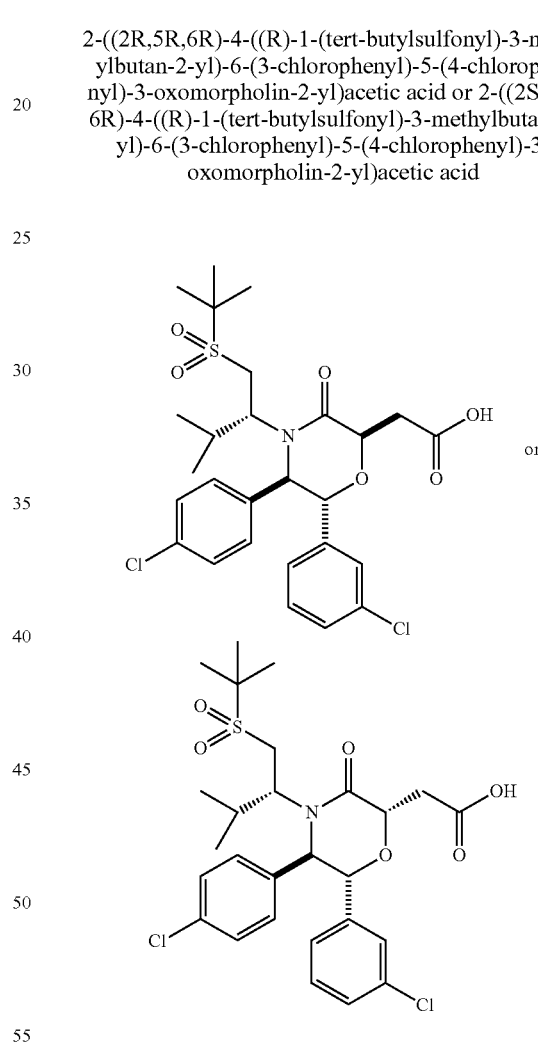

One of the title compounds was obtained as the second (slower) eluting isomer in Example 166 as a white foam ($t_R$=18.3 min). $^1$H NMR (400 MHz, CDCl$_3$) δ 7.31 (d, J=8.61 Hz, 2H), 7.18-7.25 (m, J=0.98, 2.15 Hz, 1H), 7.05-7.16 (m, 4H), 6.75 (d, J=7.82 Hz, 1H), 4.71-4.84 (m, J=1.76 Hz, 3H), 3.89 (dd, J=6.16, 13.79 Hz, 1H), 3.50-3.63 (m, 1H), 3.35 (dd, J=5.48, 14.09 Hz, 1H), 3.13 (dd, J=5.28, 11.15 Hz, 2H), 1.36 (s, 9H), 1.08 (d, J=6.65 Hz, 3H), 0.97 (s, 3H). Mass spectrum (ESI) m/z=570.0 [M]$^+$.

Example 168

2-((2R,5R,6R)-4-((S)-1-(tert-butylsulfonyl)-3,3-dimethylbutan-2-yl)-6-(3-chlorophenyl)-5-(4-chlorophenyl)-3-oxomorpholin-2-yl)acetic acid or 2-((2S,5R,6R)-4-((S)-1-(tert-butylsulfonyl)-3,3-dimethylbutan-2-yl)-6-(3-chlorophenyl)-5-(4-chlorophenyl)-3-oxomorpholin-2-yl)acetic acid Step A. (5R,6R)-4-((R)-1-(tert-butylthio)-3,3-dimethylbutan-2-yl)-6-(3-chlorophenyl)-5-(4-chlorophenyl)morpholin-3-one or (5R,6R)-4-((S)-1-(tert-butylthio)-3,3-dimethylbutan-2-yl)-6-(3-chlorophenyl)-5-(4-chlorophenyl)morpholin-3-one

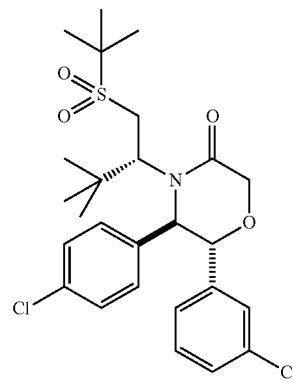

or

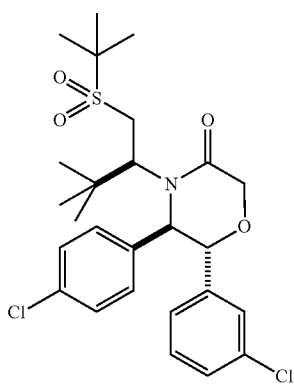

The above compounds were prepared from (1R,2R)-2-amino-1-(3-chlorophenyl)-2-(4-chlorophenyl)ethanol (Intermediate A2) by procedures similar to those described in Example 162, Steps A though F, replacing (R)-(+)-1,2-epoxybutane in Step B with racemic 3,3-dimethyl-1,2-epoxybutane. The crude product was purified by reverse phase preparatory HPLC (Gemini™ Prep C$_{18}$ 5 μm column; Phenomenex, Torrance, Calif.; gradient elution of 50% to 90% MeCN in water, where both solvents contain 0.1% TFA, 30 min method) to provide the title compounds (t$_R$=15.3 min and t$_R$=15.9 min) as white foams. Mass spectrum (ESI) m/z=494.2 [M]$^+$ for both isomers.

Step B. 2-((2R,5R,6R)-4-((S)-1-(tert-butylsulfonyl)-3,3-dimethylbutan-2-yl)-6-(3-chlorophenyl)-5-(4-chlorophenyl)-3-oxomorpholin-2-yl)acetic acid or 2-((2S,5R,6R)-4-((S)-1-(tert-butylsulfonyl)-3,3-dimethylbutan-2-yl)-6-(3-chlorophenyl)-5-(4-chlorophenyl)-3-oxomorpholin-2-yl)acetic acid

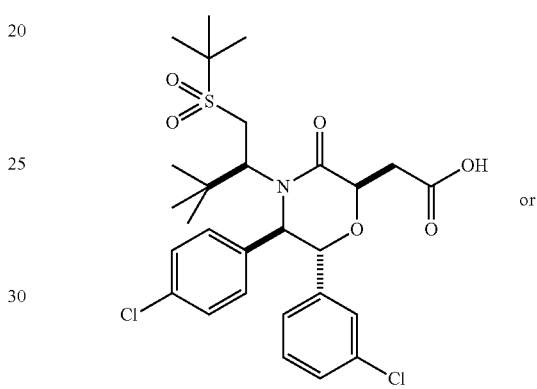

or

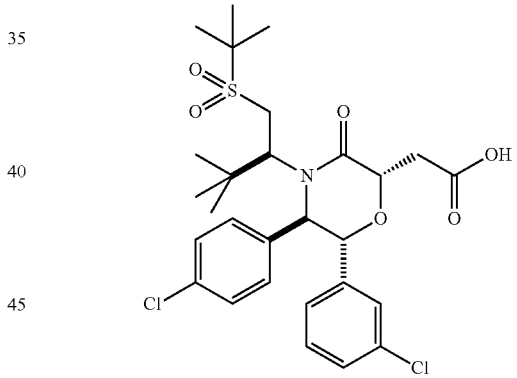

One of the title compounds was prepared from (5R,6R)-4-((S)-1-(tert-butylthio)-3-methylbutan-2-yl)-6-(3-chlorophenyl)-5-(4-chlorophenyl)morpholin-3-one (Step A, slowest eluting isomer) by procedures similar to those described in Example 112, Steps E through F. The crude product was purified by reverse phase preparatory HPLC (Gemini™ Prep C$_{18}$ 5 μm column; Phenomenex, Torrance, Calif.; gradient elution of 25% to 75% MeCN in water, where both solvents contain 0.1% TFA, 30 min method) to provide one of the title compounds as the faster eluting isomer as a white foam (t$_R$=20.5 min). $^1$H NMR (400 MHz, CDCl$_3$) δ 7.33 (d, J=8.41 Hz, 2H), 7.27-7.30 (m, 3H), 7.08-7.23 (m, 3H), 5.34 (d, J=7.24 Hz, 1H), 5.20 (d, J=7.43 Hz, 1H), 4.76 (t, J=6.26 Hz, 1H), 3.95 (dd, J=9.59, 13.69 Hz, 1H), 3.60 (d, J=2.35 Hz, 1H), 3.51 (s, 1H), 3.12 (d, J=6.26 Hz, 1H), 2.99 (dd, J=2.35, 13.69 Hz, 1H), 1.48 (s, 9H), 0.78 (s, 9H). Mass spectrum (ESI) m/z=584.0 [M]$^+$.

Example 169

2-((2R,5R,6R)-4-((S)-1-(tert-butylsulfonyl)-3,3-dimethylbutan-2-yl)-6-(3-chlorophenyl)-5-(4-chlorophenyl)-3-oxomorpholin-2-yl)acetic acid or 2-((2S,5R,6R)-4-((S)-1-(tert-butylsulfonyl)-3,3-dimethylbutan-2-yl)-6-(3-chlorophenyl)-5-(4-chlorophenyl)-3-oxomorpholin-2-yl)acetic acid

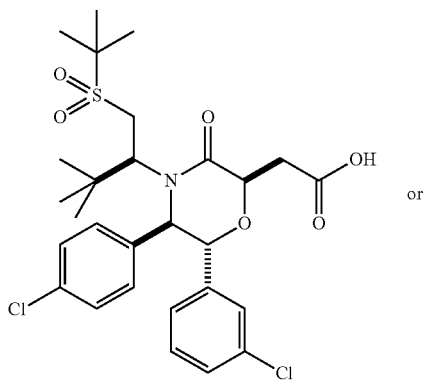

or

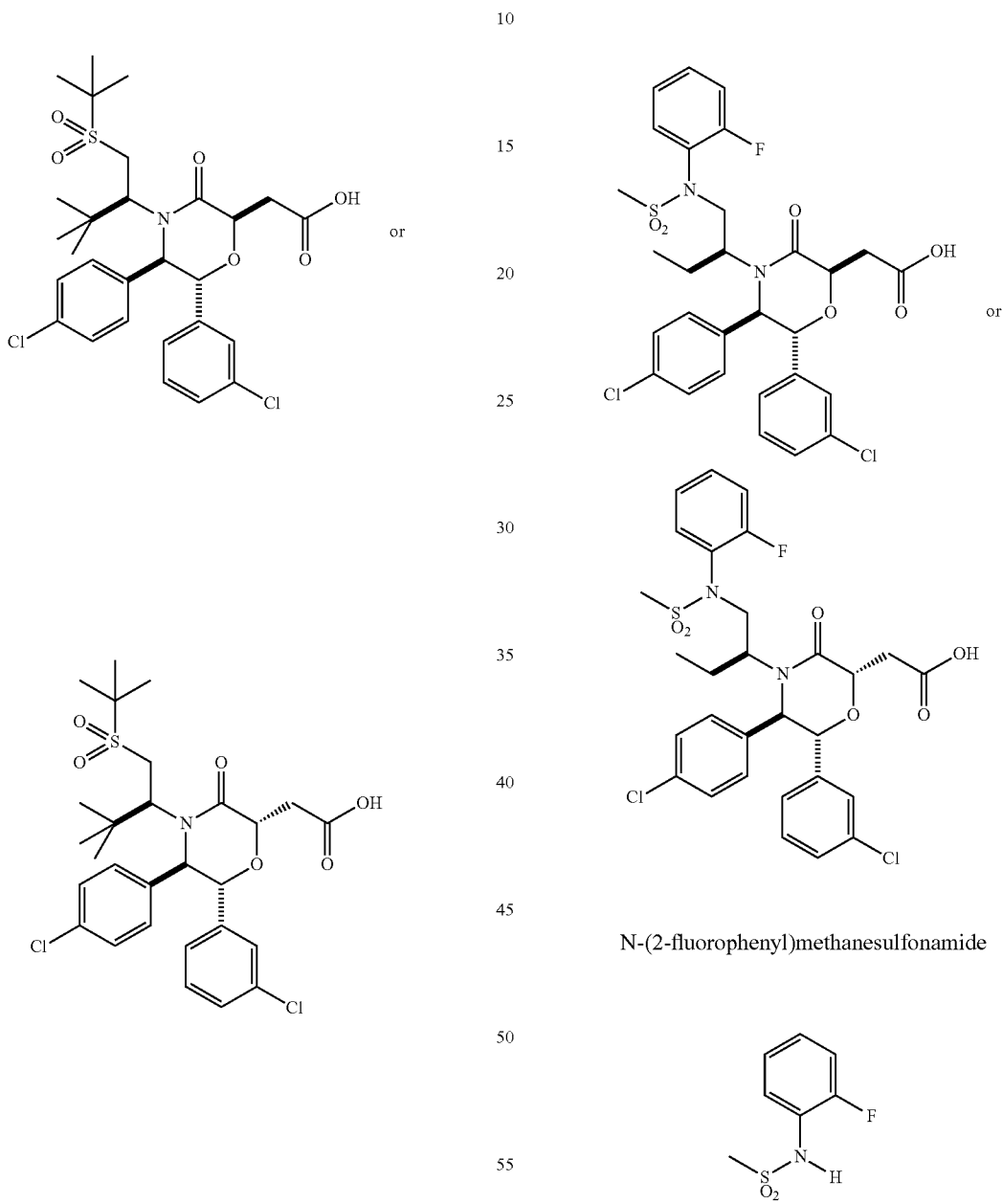

Example 170

2-((2R,5R,6R)-6-(3-chlorophenyl)-5-(4-chlorophenyl)-4-((S)-1-(N-(2-fluorophenyl)methylsulfonamido)butan-2-yl)-3-oxomorpholin-2-yl)acetic acid or 2-((2S,5R,6R)-6-(3-chlorophenyl)-5-(4-chlorophenyl)-4-((S)-1-(N-(2-fluorophenyl)methylsulfonamido)butan-2-yl)-3-oxomorpholin-2-yl)acetic acid N-(2-fluorophenyl)methanesulfonamide One of the title compounds was obtained as the second (slower) eluting isomer in Example 168 as a white foam ($t_R$=21.2 min). $^1$H NMR (400 MHz, CDCl$_3$) δ 7.27-7.48 (m, 4H), 7.06-7.21 (m, 3H), 6.98 (d, J=7.83 Hz, 1H), 5.29 (d, J=10.17 Hz, 1H), 4.94 (d, J=10.17 Hz, 1H), 4.77 (dd, J=4.89, 6.85 Hz, 1H), 3.98 (dd, J=10.37, 13.50 Hz, 1H), 3.55 (dd, J=2.15, 10.37 Hz, 1H), 3.25 (dd, J=7.04, 16.24 Hz, 1H), 2.86-3.00 (m, 1H), 1.48 (s, 9H), 0.77 (s, 9H). Mass spectrum (ESI) m/z=583.8 [M]$^+$.

The above compound was synthesized with the following procedure:

To a solution of methanesulfonyl chloride (0.696 mL, 9.00 mmol) and pyridine (2.250 mL) in DCM (2.250 mL) was added 2-fluoroaniline (0.867 mL, 9.00 mmol) at room temperature. The reaction was stirred at 50° C. for 5 hours, then cooled to room temperature and stirred overnight. Diethyl ether was added to the reaction (20 mL) and the mixture was washed with H$_2$O (2×20 mL) and brine (20 mL). The organic layer was dried with Na$_2$SO$_4$. Upon concentration the crude material was adsorbed onto a plug of silica gel and purified by flash chromatography through a silica gel column (80 g), eluting through a two-step isocratic method of 10% and 20% acetone in hexanes, to provide N-(2-fluorophenyl)propane-2-sulfonamide as an off-white solid.

$^1$H NMR (400 MHz, CDCl$_3$) δ 7.54-7.67 (m, 1H), 7.10-7.25 (m, 3H), 6.36-6.65 (m, 1H), 3.06 (s, 3H).

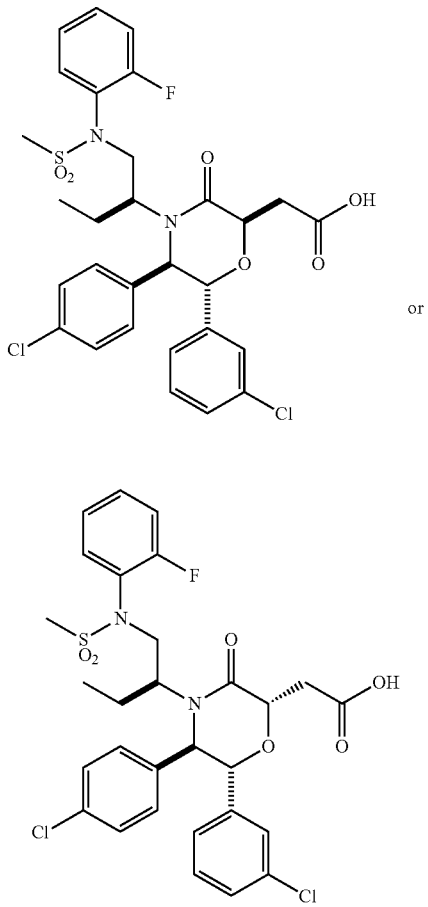

7.26 (m, 6H), 7.05 (d, J=7.63 Hz, 1H), 4.89-4.98 (m, 1H), 4.87 (s, 1H), 4.41 (d, J=12.72 Hz, 1H), 4.29 (dd, J=8.71, 14.77 Hz, 1H), 3.73 (dd, J=4.70, 14.87 Hz, 1H), 3.03 (dd, J=3.23, 6.36 Hz, 3H), 2.93 (br. s, 3H), 1.80-1.98 (m, 1H), 1.49-1.64 (m, 1H), 0.48 (t, J=7.53 Hz, 3H). Mass spectrum (ESI) m/z=623.1 [M]$^+$.

Example 171

2-((2R,5R,6R)-6-(3-chlorophenyl)-5-(4-chlorophenyl)-4-((S)-1-(N-(2-fluorophenyl)methylsulfonamido)butan-2-yl)-3-oxomorpholin-2-yl)acetic acid or
2-((2S,5R,6R)-6-(3-chlorophenyl)-5-(4-chlorophenyl)-4-((S)-1-(N-(2-fluorophenyl)methylsulfonamido)butan-2-yl)-3-oxomorpholin-2-yl)acetic acid

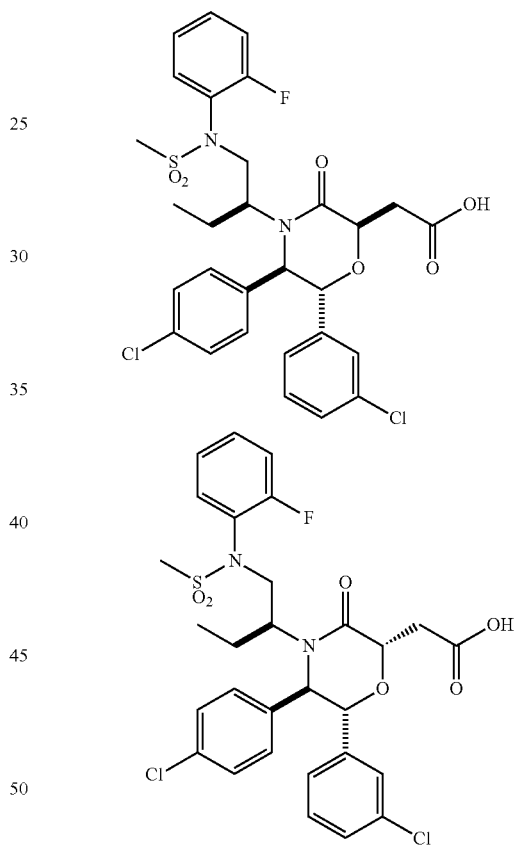

One of the title compounds was prepared from (5R,6R)-6-(3-chlorophenyl)-5-(4-chlorophenyl)-4-((S)-1-hydroxybutan-2-yl)morpholin-3-one (Example 112, Step C) by procedures similar to those described in Example 112, Steps D though F, replacing ethanethiol in Step D with N-(2-fluorophenyl)methylsulfonamide. The crude product was purified by reverse phase preparatory HPLC (Gemini™ Prep C$_{18}$ 5 μm column; Phenomenex, Torrance, Calif.; gradient elution of 25% to 75% MeCN in water, where both solvents contain 0.1% TFA, 30 min method) to provide one of the title compounds as the faster eluting isomer as a white foam (t$_R$=18.5 min). $^1$H NMR (400 MHz, CDCl$_3$) δ 7.46-7.52 (m, J=1.57 Hz, 1H), 7.35-7.44 (m, 1H), 7.32 (d, J=8.41 Hz, 3H), 7.14-

One of the title compounds was obtained as the second (slower) eluting isomer in Example 170 as a white foam (t$_R$=19.1 min). $^1$H NMR (400 MHz, CDCl$_3$) δ 7.52-7.61 (m, J=1.57 Hz, 1H), 7.40-7.49 (m, 1H), 7.32 (d, J=8.61 Hz, 2H), 7.16-7.28 (m, 4H), 7.11 (t, J=1.66 Hz, 1H), 7.06 (d, J=8.22 Hz, 2H), 6.87 (d, J=7.63 Hz, 1H), 4.88 (d, J=9.78 Hz, 1H), 4.62-4.75 (m, 2H), 4.38 (dd, J=9.59, 14.67 Hz, 1H), 3.69 (dd, J=3.72, 14.87 Hz, 1H), 2.99-3.09 (m, 1H), 2.93 (d, J=0.78 Hz, 3H), 2.82 (dd, J=7.14, 16.14 Hz, 1H), 2.58 (d, J=5.28 Hz, 1H), 1.88-2.06 (m, 1H), 1.46-1.63 (m, 1H), 0.52 (t, J=7.53 Hz, 3H). Mass spectrum (ESI) m/z=623.1 [M]$^+$.

Example 172

2-((2R,5R,6R)-6-(3-chlorophenyl)-5-(4-chlorophenyl)-4-((S)-1-(N-(2-fluorophenyl)propan-2-ylsulfonamido)butan-2-yl)-3-oxomorpholin-2-yl)acetic acid or 2-((2S,5R,6R)-6-(3-chlorophenyl)-5-(4-chlorophenyl)-4-((S)-1-(N-(2-fluorophenyl)propan-2-ylsulfonamido)butan-2-yl)-3-oxomorpholin-2-yl) acetic acid

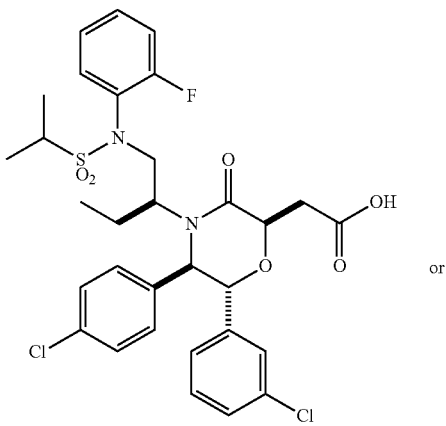

or

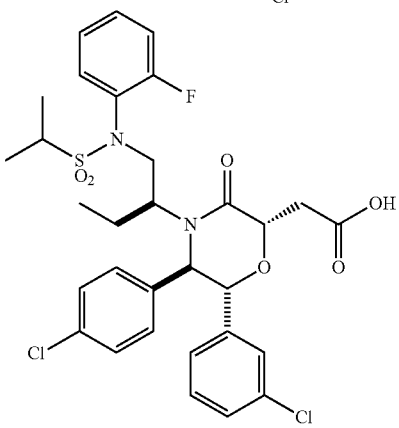

N-(2-fluorophenyl)propane-2-sulfonamide

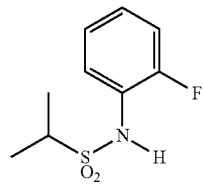

The above compound was synthesized with the following procedure:

To a solution of 2-propanesulfonyl chloride (1.011 mL, 9.00 mmol) and pyridine (2 mL) in DCM (2 mL) was added 2-fluoroaniline (0.867 mL, 9.00 mmol) at room temperature and the reaction was stirred at 50° C. for 5 hours, then at room temperature overnight. Diethyl ether was added to the reaction (20 mL) and the mixture was washed with H₂O (2×20 mL) and brine (20 mL). The organic layer was dried with Na₂SO₄. Upon concentration the crude material was adsorbed onto a plug of silica gel and purified by flash chromatography through a silica gel column (80 g), eluting through a two-step isocratic method of 10% and 20% acetone in hexanes, to provide N-(2-fluorophenyl)propane-2-sulfonamide as an off-white solid. $^1$H NMR (400 MHz, CDCl$_3$) δ 7.64-7.73 (m, 1H), 7.05-7.22 (m, 3H), 6.35-6.54 (m, 1H), 3.17-3.39 (m, 1H), 1.44 (d, J=6.85 Hz, 6H). Mass spectrum (ESI) m/z=240.2 [M+Na]$^+$.

One of the title compounds was prepared from (5R,6R)-6-(3-chlorophenyl)-5-(4-chlorophenyl)-4-((S)-1-hydroxybutan-2-yl)morpholin-3-one (Example 112, Step C) by procedures similar to those described in Example 112, Steps D though F, replacing ethanethiol in Step D with N-(2-fluorophenyl)isopropylsulfonamide. The crude product was purified by reverse phase preparatory HPLC (Gemini™ Prep C$_{18}$ 5 μm column; Phenomenex, Torrance, Calif.; gradient elution of 25% to 75% MeCN in water, where both solvents contain 0.1% TFA, 30 min method) to provide one of the title compounds as the faster eluting isomer as a white foam (t$_R$=20.5 min). $^1$H NMR (400 MHz, CDCl$_3$) δ 7.67 (dt, J=1.47, 7.97 Hz, 1H), 7.34-7.43 (m, J=1.47, 4.79 Hz, 1H), 7.31 (d, J=8.41 Hz, 2H), 7.26-7.28 (m, 1H), 7.13-7.25 (m, 6H), 7.04 (d, J=7.63 Hz, 1H), 4.89-4.98 (m, 1H), 4.77-4.87 (m, 1H), 4.37 (t, J=6.16 Hz, 2H), 3.78 (dd, J=4.50, 14.87 Hz, 1H), 2.92-3.28 (m, 4H), 1.90 (quind, J=7.53, 15.06 Hz, 1H), 1.47-1.63 (m, 1H), 1.39 (d, J=6.85 Hz, 6H), 0.45 (t, J=7.53 Hz, 3H). Mass spectrum (ESI) m/z=651.2 [M]$^+$.

Example 173

2-((2R,5R,6R)-6-(3-chlorophenyl)-5-(4-chlorophenyl)-4-((S)-1-(N-(2-fluorophenyl)propan-2-ylsulfonamido)butan-2-yl)-3-oxomorpholin-2-yl)acetic acid or 2-((2S,5R,6R)-6-(3-chlorophenyl)-5-(4-chlorophenyl)-4-((S)-1-(N-(2-fluorophenyl)propan-2-ylsulfonamido)butan-2-yl)-3-oxomorpholin-2-yl) acetic acid

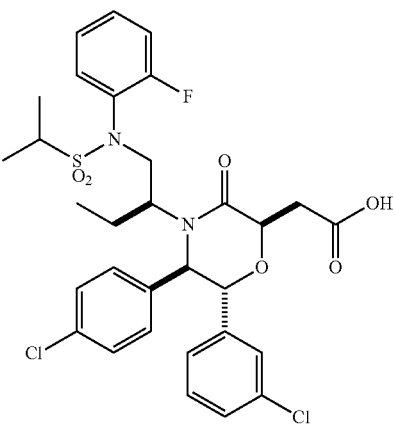

or

-continued

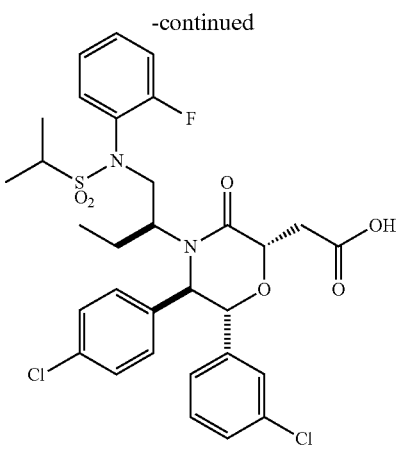

One of the title compounds was obtained as the second (slower) eluting isomer in Example 172 as a white foam ($t_R$=21.1 min). $^1$H NMR (400 MHz, CDCl$_3$) δ 7.67 (dt, J=1.47, 7.97 Hz, 1H), 7.35-7.45 (m, 1H), 7.30 (d, J=8.61 Hz, 2H), 7.15-7.27 (m, 4H), 7.10 (t, J=1.76 Hz, 1H), 7.05 (d, J=8.22 Hz, 2H), 6.88 (d, J=7.82 Hz, 1H), 4.87 (d, J=9.98 Hz, 1H), 4.58-4.73 (m, 2H), 4.40-4.56 (m, 1H), 3.65-3.80 (m, 1H), 3.18 (s, 1H), 2.76-2.92 (m, 1H), 2.53 (dd, J=4.89, 16.04 Hz, 1H), 2.03 (s, 1H), 1.43-1.60 (m, 1H), 1.38 (t, J=7.04 Hz, 6H), 0.48 (t, J=7.53 Hz, 3H). Mass spectrum (ESI) m/z=651.1 [M]$^+$.

Example 174

2-((2R,5R,6R)-6-(3-chlorophenyl)-5-(4-chlorophenyl)-4-((S)-1-(N-(2-fluorophenyl)-1-methylcyclopropanesulfonamido)butan-2-yl)-3-oxomorpholin-2-yl)acetic acid or 2-((2S,5R,6R)-6-(3-chlorophenyl)-5-(4-chlorophenyl)-4-((S)-1-(N-(2-fluorophenyl)-1-methylcyclopropanesulfonamido)butan-2-yl)-3-oxomorpholin-2-yl)acetic acid N-(2-fluorophenyl)-1-methylcyclopropane-1-sulfonamide

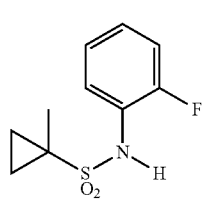

The above compound was synthesized with the following procedure:

An argon-cooled 50 mL round-bottomed flask with a stir bar was charged with (π-allyl) palladium (II) chloride dimer (0.014 g, 0.037 mmol), 2-di-t-butylphosphino-3,4,5,6-tetramethyl-2',4',6'-tri-i-isopropylbiphenyl (0.053 g, 0.111 mmol), potassium carbonate (0.714 mL, 11.84 mmol) and 1-methylcyclopropane-1-sulfonamide (1.0 g, 7.40 mmol) in the dry-box. Taken outside the box, the mixture was diluted in 2-methyltetrahydrofuran (24.7 mL), and 1-bromo-2-fluorobenzene (0.731 mL, 6.66 mmol) was added. The reaction was stirred for 15 minutes at ambient temperature and placed in a pre-heated bath at 80° C. The reaction was stirred over the weekend. The reaction was diluted in 20 mL of a sat. ammonium chloride solution and extracted with diethyl ether (3×30 mL). The combined organic layers were dried over MgSO$_4$, filtered and concentrated to give a reddish crude oil. The crude material was adsorbed onto a plug of silica gel and purified by flash chromatography through a Redi-Sep pre-packed silica gel column (80 g), eluting by a step-gradient method from 0% to 20% acetone in hexanes in four increments, to give N-(2-fluorophenyl)-1-methylcyclopropane-1-sulfonamide as light-yellow solid. $^1$H NMR (400 MHz, CDCl$_3$) δ 7.64 (dd, J=7.34, 9.10 Hz, 1H), 7.07-7.23 (m, 3H), 6.43-6.64 (m, 1H), 1.54 (s, 3H), 1.29-1.38 (m, 2H), 0.71-0.79 (m, 2H). Mass spectrum (ESI) m/z=230.2 [M+H]$^+$.

The above compound was synthesized with the following procedure:

An argon-cooled 50 mL round-bottomed flask with a stir bar was charged with (π-allyl) palladium (II) chloride dimer (0.014 g, 0.037 mmol), 2-di-t-butylphosphino-3,4,5,6-tetramethyl-2',4',6'-tri-i-isopropylbiphenyl (0.053 g, 0.111 mmol), potassium carbonate (0.714 mL, 11.84 mmol) and 1-methylcyclopropane-1-sulfonamide (1.0 g, 7.40 mmol) in the dry-box. Taken outside the box, the mixture was diluted in 2-methyltetrahydrofuran (24.7 mL), and 1-bromo-2-fluorobenzene (0.731 mL, 6.66 mmol) was added. The reaction was allowed to stir for 15 minutes at ambient temperature, then it was placed in a pre-heated bath at 80° C. The reaction was stirred over the weekend. The reaction was diluted in 20 mL of a sat. ammonium chloride solution and extracted with diethyl ether (3×30 mL). The combined organic layers were dried over MgSO$_4$, filtered and concentrated to give a reddish crude oil. The crude material was adsorbed onto a plug of silica gel and purified by flash chromatography through a Redi-Sep pre-packed silica gel column (80 g), eluting by a step-gradient method from 0% to 20% acetone in hexanes in four increments, to give N-(2-fluorophenyl)-1-methylcyclopropane-1-sulfonamide as light-yellow solid. $^1$H NMR (400 MHz, CDCl$_3$) δ 7.64 (dd, J=7.34, 9.10 Hz, 1H), 7.07-7.23 (m, 3H), 6.43-6.64 (m, 1H), 1.54 (s, 3H), 1.29-1.38 (m, 2H), 0.71-0.79 (m, 2H). Mass spectrum (ESI) m/z=230.2 [M+H]$^+$.

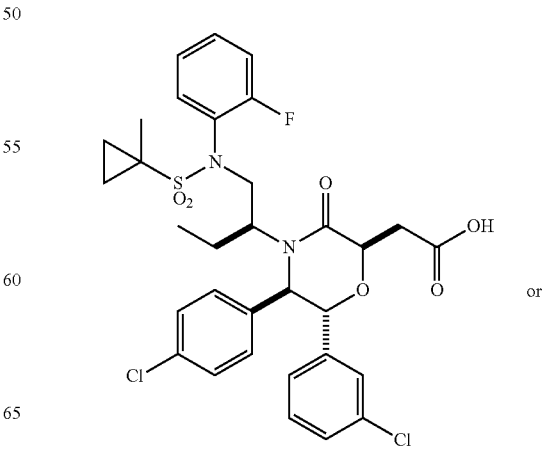

or

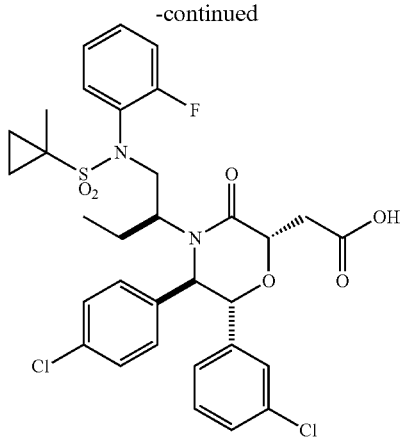

One of the title compounds was prepared from (5R,6R)-6-(3-chlorophenyl)-5-(4-chlorophenyl)-4-((S)-1-hydroxybutan-2-yl)morpholin-3-one (Example 112, Step C) by procedures similar to those described in Example 112, Steps D though F, replacing ethanethiol in Step D with N-(2-fluorophenyl)methylcyclopropanesulfonamide. The crude product was purified by reverse phase preparatory HPLC (Gemini™ Prep C$_{18}$ 5 μm column; Phenomenex, Torrance, Calif.; gradient elution of 25% to 75% MeCN in water, where both solvents contain 0.1% TFA, 30 min method) to provide one of the title compounds as the faster eluting isomer as a white foam (t$_R$=21.0 min). $^1$H NMR (400 MHz, CDCl$_3$) δ 7.60 (t, J=7.24 Hz, 1H), 7.28-7.41 (m, 3H), 7.11-7.26 (m, 7H), 7.03 (d, J=7.43 Hz, 1H), 4.92 (d, J=7.63 Hz, 1H), 4.82 (d, J=7.63 Hz, 1H), 4.31-4.51 (m, 2H), 3.84 (dd, J=4.40, 14.97 Hz, 1H), 3.03 (dd, J=6.46, 9.59 Hz, 2H), 1.82-1.97 (m, 1H), 1.54 (s, 5H), 0.99-1.19 (m, 2H), 0.66 (s, 2H), 0.46 (t, J=7.53 Hz, 3H). Mass spectrum (ESI) m/z=663.0 [M]$^+$.

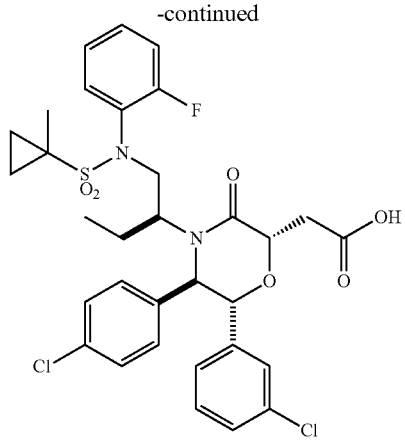

One of the title compounds was obtained as the second (slower) eluting isomer in Example 174 as a white foam (t$_R$=21.7 min). $^1$H NMR (400 MHz, CDCl$_3$) δ 7.54-7.66 (m, 1H), 7.33-7.42 (m, 1H), 7.29 (s, 1H), 7.10-7.26 (m, 5H), 6.96-7.09 (m, 3H), 6.87 (d, J=7.82 Hz, 1H), 4.86 (d, J=9.98 Hz, 1H), 4.58-4.73 (m, 2H), 4.42-4.57 (m, 1H), 3.65-3.87 (m, 1H), 2.94-3.08 (m, 1H), 2.74-2.92 (m, 1H), 2.41-2.58 (m, 1H), 2.02 (s, 1H), 1.43-1.59 (m, 4H), 0.96-1.19 (m, 2H), 0.59-0.73 (m, 2H), 0.48 (t, J=7.53 Hz, 3H). Mass spectrum (ESI) m/z=663.1 [M]$^+$.

Example 175

2-((2R,5R,6R)-6-(3-chlorophenyl)-5-(4-chlorophenyl)-4-((S)-1-(N-(2-fluorophenyl)-1-methylcyclopropanesulfonamido)butan-2-yl)-3-oxomorpholin-2-yl)acetic acid or 2-((2S,5R,6R)-6-(3-chlorophenyl)-5-(4-chlorophenyl)-4-((S)-1-(N-(2-fluorophenyl)-1-methylcyclopropanesulfonamido)butan-2-yl)-3-oxomorpholin-2-yl)acetic acid Example 176

2-((2R,5R,6R)-6-(3-chlorophenyl)-5-(4-chlorophenyl)-4-((S)-1-(N-(3-fluoropyridin-2-yl)cyclopropanesulfonamido)butan-2-yl)-3-oxomorpholin-2-yl)acetic acid or 2-((2S,5R,6R)-6-(3-chlorophenyl)-5-(4-chlorophenyl)-4-((S)-1-(N-(3-fluoropyridin-2-yl)cyclopropanesulfonamido)butan-2-yl)-3-oxomorpholin-2-yl)acetic acid

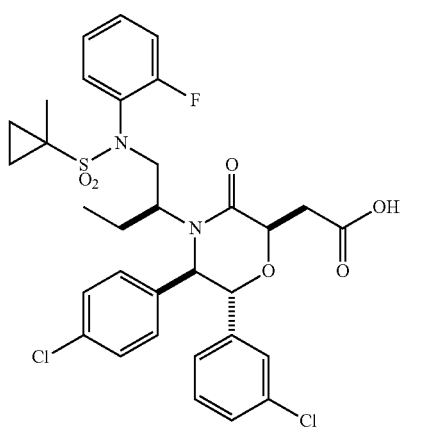 or

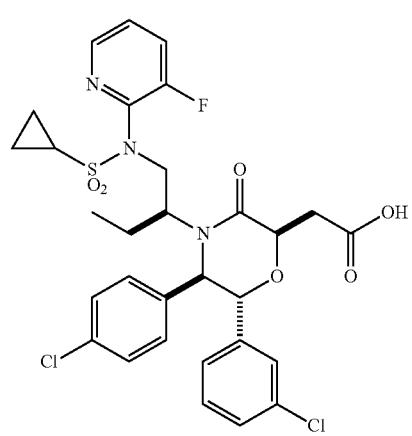 or

-continued

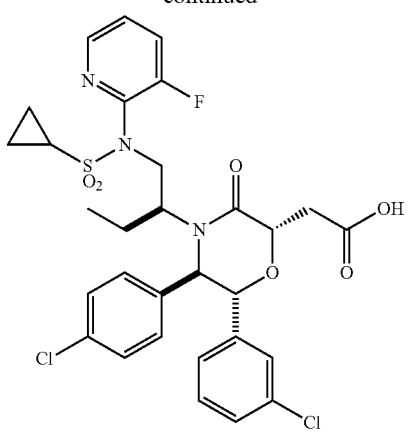

N-(3-fluoropyridin-2-yl)cyclopropanesulfonamide

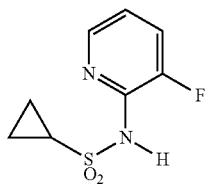 [SMILES: O=S(=O)(Nc1ncccc1F)C1CC1]

The above compound was synthesized with the following procedure:

To a solution of 2-amino-3-fluoropyridine (0.797 g, 7.11 mmol) and pyridine (1.8 mL) in DCM (1.8 mL) was added cyclopropanesulfonyl chloride (0.725 mL, 7.11 mmol) at room temperature. The reaction was stirred at 50° C. for 5 hours, then cooled to room temperature and stirred overnight. Diethyl ether was added to the reaction (20 mL) and the mixture was washed with $H_2O$ (2×20 mL) and brine (20 mL). The organic layer was dried with $Na_2SO_4$. Upon concentration, the crude material was adsorbed onto a plug of silica gel and purified by flash chromatography through a silica gel column (80 g), eluting through a three-step isocratic method of 10%, 20% and 30% acetone in hexanes, to provide N-(3-fluoropyridin-2-yl)cyclopropanesulfonamide as a white solid. $^1$H NMR (400 MHz, CDCl$_3$) δ 8.15 (bs, 1H), 7.43-7.46 (m, 2H), 7.02 (bs, 1H), 3.27 (bs, 1H), 1.45-1.48 (m, 2H), 1.12-1.14 (m, 2H). Mass spectrum (ESI) m/z=217.2 [M+H]$^+$.

-continued

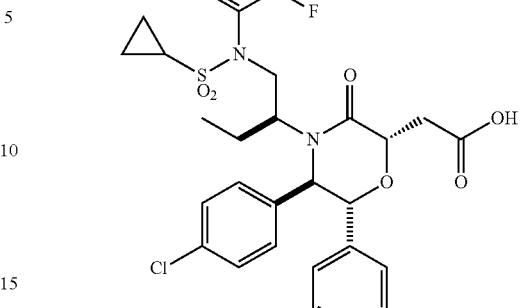

One of the title compounds was prepared from (5R,6R)-6-(3-chlorophenyl)-5-(4-chlorophenyl)-4-((S)-1-hydroxybutan-2-yl)morpholin-3-one (Example 112, Step C) by procedures similar to those described in Example 112, Steps D though F, replacing ethanethiol in Step D with N-(3-fluoropyridin-2-yl)cyclopropanesulfonamide. The crude product was purified by reverse phase preparatory HPLC (Gemini™ Prep C$_{18}$ 5 μm column; Phenomenex, Torrance, Calif.; gradient elution of 25% to 75% MeCN in water, where both solvents contain 0.1% TFA, 30 min method) to provide one of the title compounds as the faster eluting isomer as a white foam (t$_R$=18.4 min). $^1$H NMR (400 MHz, CDCl$_3$) δ 8.35 (d, J=3.72 Hz, 1H), 7.61 (t, J=8.61 Hz, 1H), 7.37 (td, J=4.11, 8.22 Hz, 1H), 7.28-7.30 (m, 1H), 7.15-7.25 (m, 4H), 7.02-7.13 (m, J=8.41 Hz, 3H), 4.99 (d, J=7.63 Hz, 1H), 4.79 (d, J=7.63 Hz, 1H), 4.41-4.63 (m, 2H), 3.81-3.97 (m, 1H), 3.00-3.12 (m, 3H), 2.49-2.65 (m, 1H), 1.93-2.08 (m, 1H), 1.50-1.64 (m, 1H), 0.95-1.17 (m, 4H), 0.50 (s, 3H). Mass spectrum (ESI) m/z=650.0 [M]$^+$.

Example 177

2-((2R,5R,6R)-6-(3-chlorophenyl)-5-(4-chlorophenyl)-4-((S)-1-(N-(3-fluoropyridin-2-yl)cyclopropanesulfonamido)butan-2-yl)-3-oxomorpholin-2-yl) acetic acid or 2-((2S,5R,6R)-6-(3-chlorophenyl)-5-(4-chlorophenyl)-4-((S)-1-(N-(3-fluoropyridin-2-yl) cyclopropanesulfonamido)butan-2-yl)-3-oxomorpholin-2-yl)acetic acid

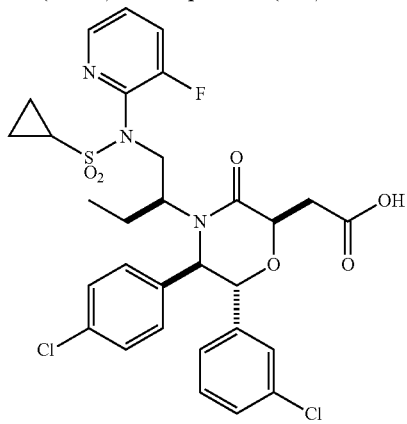 or 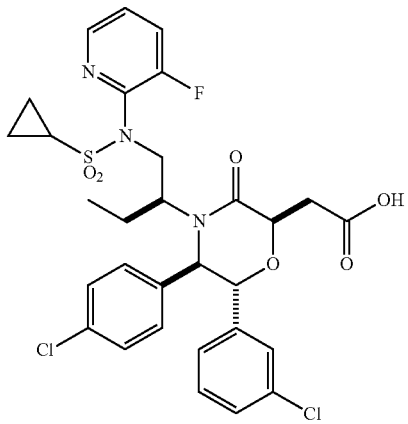 or

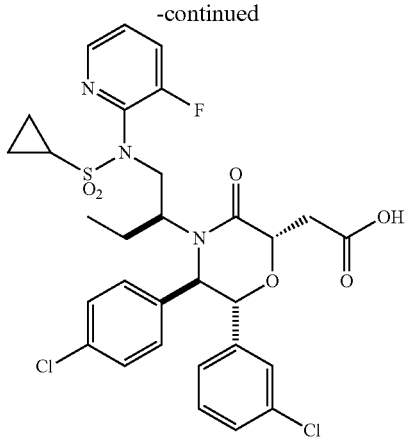

One of the title compounds was obtained as the second (slower) eluting isomer in Example 176 as a white foam ($t_R$=19.0 min). $^1$H NMR (400 MHz, CDCl$_3$) δ 8.33 (d, J=4.50 Hz, 1H), 7.55-7.65 (m, J=1.37, 17.22 Hz, 1H), 7.32-7.41 (m, J=4.50 Hz, 2H), 7.24 (m, 3H), 7.12-7.20 (m, 1H), 7.08 (s, 1H), 6.98 (d, J=7.83 Hz, 2H), 6.89 (d, J=7.63 Hz, 1H), 5.00 (d, J=9.78 Hz, 1H), 4.52-4.70 (m, 3H), 3.79-3.98 (m, 1H), 2.95-3.08 (m, 1H), 2.67 (dd, J=4.50, 15.85 Hz, 1H), 2.45-2.57 (m, 1H), 1.96-2.13 (m, 1H), 1.45-1.61 (m, 1H), 0.94-1.19 (m, 4H), 0.50 (m, 3H). Mass spectrum (ESI) m/z=650.1 [M]$^+$.

Example 178

N-((S)-2-((2S,5R,6R)-2-allyl-6-(3-chlorophenyl)-5-(4-chlorophenyl)-3-oxomorpholino)butyl)-N-(pyridin-2-yl)cyclopropanesulfonamide or N-((S)-2-((2R,5R,6R)-2-allyl-6-(3-chlorophenyl)-5-(4-chlorophenyl)-3-oxomorpholino)butyl)-N-(pyridin-2-yl)cyclopropanesulfonamide

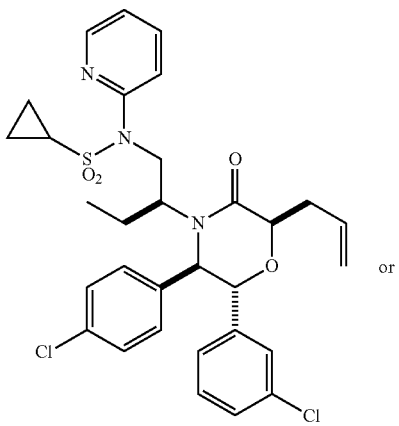

or

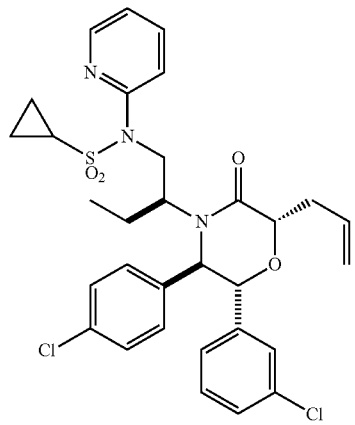

N-(pyridin-2-yl)cyclopropanesulfonamide

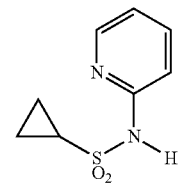 [SMILES: O=S(=O)(Nc1ccccn1)C1CC1]

The above compound was synthesized with the following procedure:

To a solution of 2-aminopyridine (0.669 g, 7.11 mmol) and pyridine (1.8 mL) in DCM (1.8 mL) was added cyclopropanesulfonyl chloride (0.725 mL, 7.11 mmol) at room temperature. The reaction was stirred at 50° C. for 5 hours, then cooled to room temperature and stirred overnight. Diethyl ether was added to the reaction (20 mL) and the mixture was washed with H$_2$O (2×20 mL) and brine (20 mL). The organic layer was dried with Na$_2$SO$_4$. Upon concentration, a precipitate was observed and the solution was filtered, rinsed with DCM (2 mL) and dried. The precipitate corresponded to the desired product and was used without further purification. $^1$H NMR (400 MHz, CDCl$_3$) δ 8.19-8.39 (m, 1H), 7.74 (ddd, J=1.86, 7.09, 8.85 Hz, 1H), 7.56 (d, J=8.61 Hz, 1H), 6.93 (ddd, J=0.98, 5.77, 6.94 Hz, 1H), 2.64 (tt, J=4.87, 8.05 Hz, 1H), 1.21-1.30 (m, 2H), 0.93-1.05 (m, 2H). Mass spectrum (ESI) m/z=199.2 [M+H]$^+$.

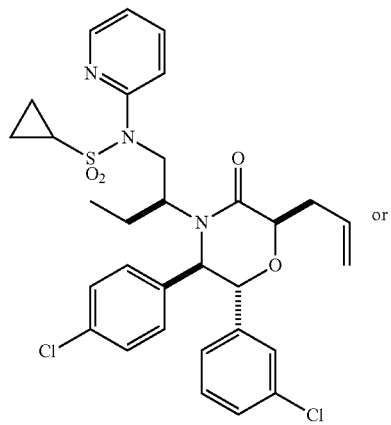

or

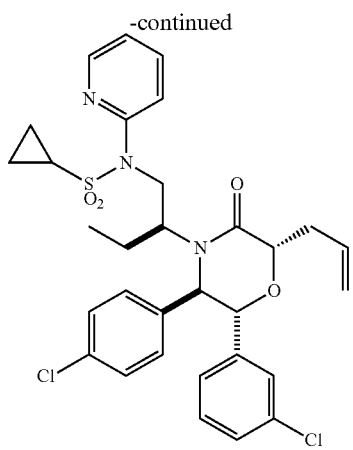

One of the title compounds was prepared from (5R,6R)-6-(3-chlorophenyl)-5-(4-chlorophenyl)-4-((S)-1-hydroxybutan-2-yl)morpholin-3-one (Example 112, Step C) by procedures similar to those described in Example 112, Steps D though E, replacing ethanethiol in Step D with N-(pyridin-2-yl)cyclopropanesulfonamide. The crude product was purified by flash chromatography through a silica gel column (40 g), eluting through a two-step isocratic method of 10% and 25% acetone in hexanes to provide one of the title compounds as the faster eluting isomer as a white foam. $^1$H NMR (400 MHz, CDCl$_3$) δ 8.46 (dd, J=1.27, 4.79 Hz, 1H), 7.74-7.86 (m, 1H), 7.67 (d, J=8.02 Hz, 1H), 7.17-7.27 (m, 5H), 7.11 (t, J=7.92 Hz, 1H), 7.06 (t, J=1.76 Hz, 1H), 6.85 (d, J=8.22 Hz, 1H), 6.72 (d, J=7.63 Hz, 1H), 5.75-5.95 (m, 1H), 5.12 (dd, J=1.76, 17.02 Hz, 1H), 5.04 (dd, J=1.96, 10.17 Hz, 1H), 4.78 (dd, J=9.00, 14.28 Hz, 1H), 4.26 (dd, J=3.72, 8.61 Hz, 1H), 3.91-4.05 (m, 1H), 2.93 (br. s., 1H), 2.71-2.84 (m, 1H), 2.40-2.50 (m, 1H), 2.28 (d, J=8.61 Hz, 1H), 2.03 (td, J=7.16, 8.36 Hz, 1H), 1.25-1.37 (m, 1H), 0.83-1.13 (m, 6H), 0.59 (t, J=7.63 Hz, 3H). Mass spectrum (ESI) m/z=636.1 [M+Na]$^+$.

Example 179

N-((S)-2-((2S,5R,6R)-2-allyl-6-(3-chlorophenyl)-5-(4-chlorophenyl)-3-oxomorpholino)butyl)-N-(pyridin-2-yl)cyclopropanesulfonamide or N-((S)-2-((2R,5R,6R)-2-allyl-6-(3-chlorophenyl)-5-(4-chlorophenyl)-3-oxomorpholino)butyl)-N-(pyridin-2-yl)cyclopropanesulfonamide

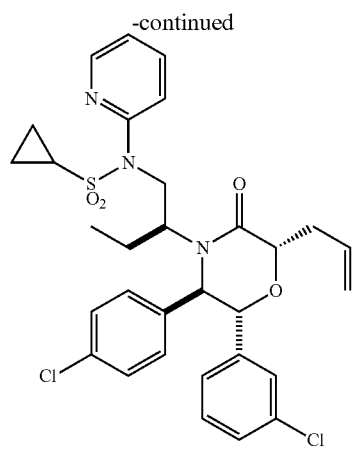

One of the title compounds was obtained as the second (slower) eluting isomer in Example 178. $^1$H NMR (400 MHz, CDCl$_3$) δ 8.38 (td, J=1.10, 3.86 Hz, 1H), 7.66-7.78 (m, 1H), 7.56 (d, J=8.02 Hz, 1H), 7.04-7.23 (m, 6H), 6.78-6.93 (m, 3H), 5.66-5.89 (m, 1H), 4.97-5.16 (m, 2H), 4.53-4.81 (m, 3H), 3.92-4.10 (m, 2H), 2.79-2.93 (m, 1H), 2.57-2.77 (m, 2H), 2.38-2.49 (m, 1H), 1.84-2.00 (m, 1H), 1.55-1.59 (m, 1H), 0.80-1.03 (m, 4H), 0.48 (t, J=7.53 Hz, 3H). Mass spectrum (ESI) m/z=636.1 [M+Na]$^+$.

Example 180

2-((2S,5R,6R)-6-(3-chlorophenyl)-5-(4-chlorophenyl)-3-oxo-4-((S)-1-(N-(pyridin-2-yl)cyclopropanesulfonamido)butan-2-yl)morpholin-2-yl)acetic acid or 2-((2R,5R,6R)-6-(3-chlorophenyl)-5-(4-chlorophenyl)-3-oxo-4-((S)-1-(N-(pyridin-2-yl)cyclopropanesulfonamido)butan-2-yl)morpholin-2-yl)acetic acid

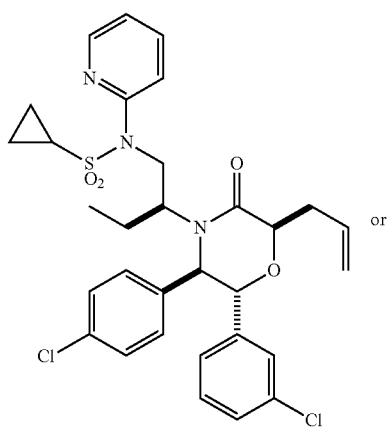 or 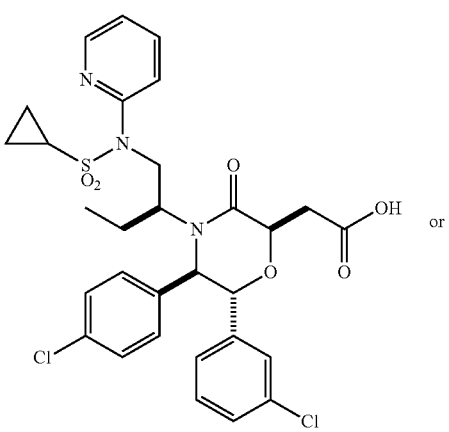

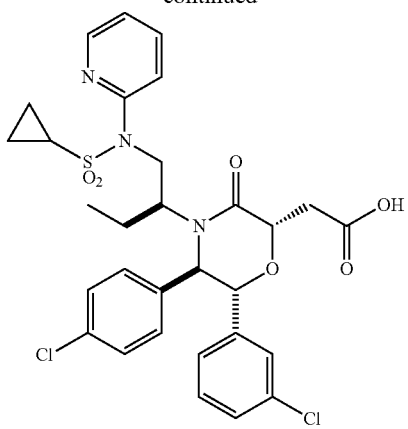

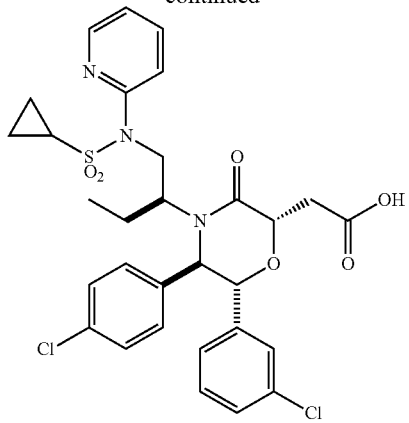

One of the title compounds was prepared from the faster eluting isomer in Example 178 by a procedure similar to that described in Example 112, Step F. The crude product was purified by reverse phase preparatory HPLC (Gemini™ Prep $C_{18}$ 5 μm column; Phenomenex, Torrance, Calif.; gradient elution of 25% to 75% MeCN in water, where both solvents contain 0.1% TFA, 30 min method) to provide one of the title compounds as a white foam ($t_R$=19.4 min). $^1$H NMR (400 MHz, CDCl$_3$) δ 8.47 (d, J=3.91 Hz, 1H), 7.80-7.89 (m, 1H), 7.73 (d, J=8.22 Hz, 1H), 7.11-7.29 (m, 5H), 7.08 (s, 1H), 6.81 (dd, J=7.92, 11.25 Hz, 3H), 4.68-4.86 (m, 2H), 4.62 (s, 2H), 4.13 (d, J=12.91 Hz, 1H), 3.06 (dd, J=7.04, 16.04 Hz, 1H), 2.93 (br. s., 1H), 2.67 (dd, J=5.18, 16.14 Hz, 1H), 2.41-2.54 (m, 1H), 1.91-2.08 (m, 1H), 1.57-1.74 (m, 1H), 0.89-1.11 (m, 4H), 0.59 (t, J=7.53 Hz, 3H). Mass spectrum (ESI) m/z=632.2 [M]$^+$.

One of the title compounds was prepared from N-((S)-2-((2S,5R,6R)-2-allyl-6-(3-chlorophenyl)-5-(4-chlorophenyl)-3-oxomorpholino)butyl)-N-(pyridin-2-yl)cyclopropanesulfonamide or N-((S)-2-((2R,5R,6R)-2-allyl-6-(3-chlorophenyl)-5-(4-chlorophenyl)-3-oxomorpholino)butyl)-N-(pyridin-2-yl)cyclopropanesulfonamide (Example 179, which is the slower eluting isomer from Example 178) by a procedure similar to that described in Example 112, Step F. The crude product was purified by reverse phase preparatory HPLC (Gemini™ Prep $C_{18}$ 5 μm column; Phenomenex, Torrance, Calif.; gradient elution of 25% to 75% MeCN in water, where both solvents contain 0.1% TFA, 30 min method) to provide one of the title compounds as a white foam ($t_R$=18.7 min). $^1$H NMR (400 MHz, CDCl$_3$) δ 8.48 (d, J=1.17 Hz, 1H), 7.80 (dt, J=1.86, 7.78 Hz, 1H), 7.65 (d, J=8.22 Hz, 1H), 7.18-7.28 (m, 6H), 6.95-7.07 (m, J=8.22 Hz, 3H), 4.66-4.88 (m, 3H), 4.49 (t, J=6.36 Hz, 1H), 4.15 (dd, J=4.30, 14.28 Hz, 1H), 2.96-3.17 (m, 3H), 2.47-2.57 (m, 1H), 1.91-2.08 (m, 1H), 1.59-1.76 (m, 1H), 1.09 (d, J=4.89 Hz, 2H), 0.91-1.02 (m, 2H), 0.58 (t, J=7.53 Hz, 3H). Mass spectrum (ESI) m/z=632.2 [M]$^+$.

Example 181

2-((2S,5R,6R)-6-(3-chlorophenyl)-5-(4-chlorophenyl)-3-oxo-4-((S)-1-(N-(pyridin-2-yl)cyclopropanesulfonamido)butan-2-yl)morpholin-2-yl)acetic acid or 2-((2R,5R,6R)-6-(3-chlorophenyl)-5-(4-chlorophenyl)-3-oxo-4-((S)-1-(N-(pyridin-2-yl)cyclopropanesulfonamido)butan-2-yl)morpholin-2-yl)acetic acid Example 182

2-((2R,5R,6R)-4-((S)-1-(tert-butylsulfonyl)butan-2-yl)-5-(4-chloro-3-fluorophenyl)-6-(3-chlorophenyl)-3-oxomorpholin-2-yl)acetic acid or 2-((2S,5R,6R)-4-((S)-1-(tert-butylsulfonyl)butan-2-yl)-5-(4-chloro-3-fluorophenyl)-6-(3-chlorophenyl)-3-oxomorpholin-2-yl)acetic acid

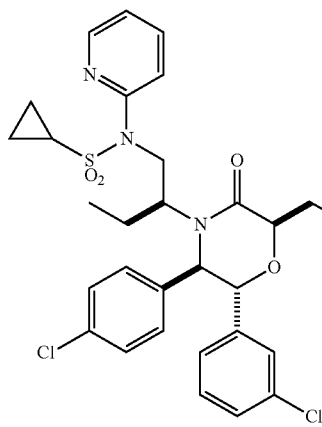 or

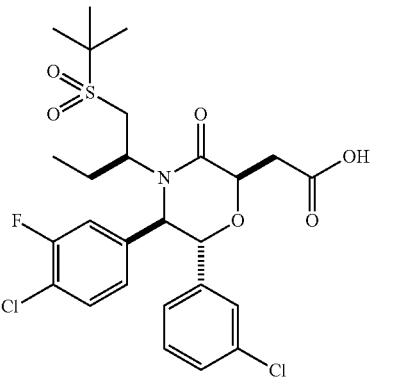 or

301
-continued

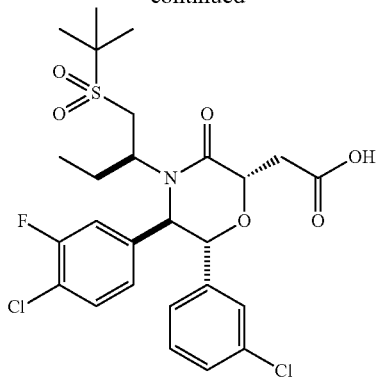

One of the title compounds was prepared from (1R,2R)-2-amino-2-(4-chloro-3-fluorophenyl)-1-(3-chlorophenyl)ethanol (Intermediate D5) by procedures similar to those described in Example 112, Steps A though F, replacing ethanethiol in Step D with tert-butylthiol. The crude product was purified by reverse phase preparatory HPLC (Gemini™ Prep $C_{18}$ 5 µm column; Phenomenex, Torrance, Calif.; gradient elution of 25% to 75% MeCN in water, where both solvents contain 0.1% TFA, 30 min method) to provide one of the title compounds as the faster eluting isomer as a white foam ($t_R$=18.4 min). $^1$H NMR (400 MHz, CDCl$_3$) δ 7.40 (t, J=7.82 Hz, 1H), 7.29-7.35 (m, 2H), 7.24-7.26 (m, 1H), 7.20 (t, J=7.83 Hz, 1H), 7.12 (td, J=1.59, 7.97 Hz, 2H), 5.19 (d, J=6.06 Hz, 1H), 4.96 (d, J=6.06 Hz, 1H), 4.63 (t, J=5.87 Hz, 1H), 3.93 (dd, J=8.71, 13.79 Hz, 1H), 3.69 (bs, 1H), 2.87-3.19 (m, 3H), 2.10-2.29 (m, 1H), 1.60-1.78 (m, 1H), 1.45 (s, 9H), 0.59 (t, J=7.53 Hz, 3H). Mass spectrum (ESI) m/z=574.0 [M]$^+$.

Example 183

2-((2R,5R,6R)-4-((S)-1-(tert-butylsulfonyl)butan-2-yl)-5-(4-chloro-3-fluorophenyl)-6-(3-chlorophenyl)-3-oxomorpholin-2-yl)acetic acid or 2-((2S,5R,6R)-4-((S)-1-(tert-butylsulfonyl)butan-2-yl)-5-(4-chloro-3-fluorophenyl)-6-(3-chlorophenyl)-3-oxomorpholin-2-yl)acetic acid

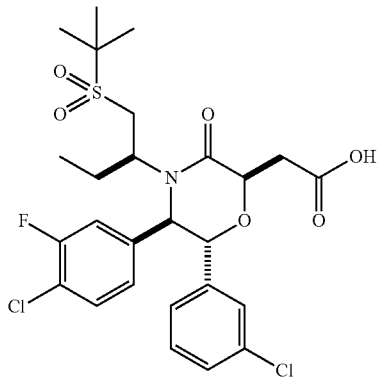

or

302
-continued

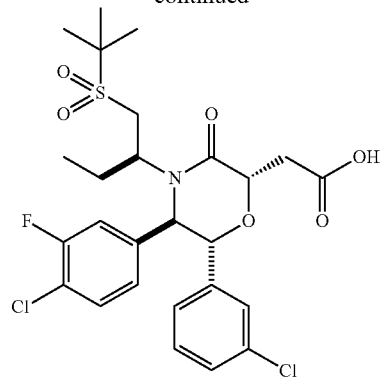

One of the title compounds was obtained as the second (slower) eluting isomer in Example 182 as a white foam ($t_R$=18.9 min). $^1$H NMR (400 MHz, CDCl$_3$) δ 7.32-7.39 (m, 1H), 7.08-7.24 (m, 3H), 7.03 (dd, J=1.57, 9.39 Hz, 1H), 6.94 (d, J=8.41 Hz, 1H), 6.86 (d, J=7.82 Hz, 1H), 5.11 (d, J=9.78 Hz, 1H), 4.75 (t, J=5.87 Hz, 1H), 4.66 (d, J=9.78 Hz, 1H), 4.02 (dd, J=9.78, 13.50 Hz, 1H), 2.88-3.27 (m, 4H), 2.13-2.28 (m, 1H), 1.61-1.74 (m, 1H), 1.41-1.47 (m, 9H), 0.59 (t, J=7.53 Hz, 3H). Mass spectrum (ESI) m/z=574.2 [M]$^+$.

Example 184

2-((2R,5R,6R)-6-(3-chlorophenyl)-5-(4-chlorophenyl)-4-((S)-1-(oxetan-3-ylsulfonyl)butan-2-yl)-3-oxomorpholin-2-yl)acetic acid or 2-((2S,5R,6R)-6-(3-chlorophenyl)-5-(4-chlorophenyl)-4-((S)-1-(oxetan-3-ylsulfonyl)butan-2-yl)-3-oxomorpholin-2-yl)acetic acid

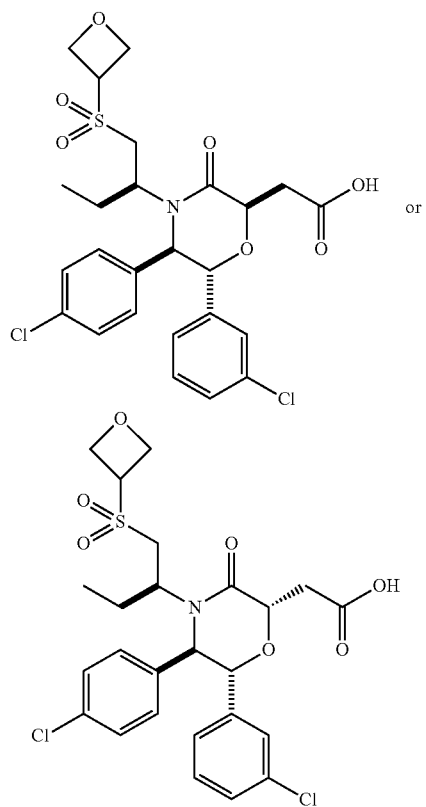

303

Oxetane-3-thiol

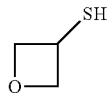

The above compound was synthesized by adding sodium hydrogen sulfide (183 mg, 3.26 mmol) to a DMF (2.72 mL) solution containing 3-iodooxetane (0.500 mL, 2.72 mmol). The mixture was stirred overnight at 50° C. under an argon atmosphere. The reaction was then cooled and partitioned between diethyl ether (3×10 mL) and water (10 mL). The organic layers were combined, dried over magnesium sulfate, decanted, and the solvents were removed under vacuum until about 1 mL of solvent remained. This product was used as a solution without further purification.

One of the title compounds was prepared from (1R,2R)-2-amino-1-(3-chlorophenyl)-2-(4-chlorophenyl)ethanol (Intermediate A2) by procedures similar to those described in Example 182, Steps A though H, replacing tert-butylthiol in Step D with oxetane-3-thiol. The crude product was purified by reverse phase preparatory HPLC (Gemini™ Prep $C_{18}$ 5 μm column; Phenomenex, Torrance, Calif.; gradient elution of 25% to 75% MeCN in water, where both solvents contain 0.1% TFA, 30 min method) to provide one of the title compounds as the faster eluting isomer as a white foam ($t_R$=15.9 min). $^1$H NMR (400 MHz, CDCl$_3$) δ 7.35 (s, 2H), 7.30 (s, 2H), 7.23-7.26 (m, 2H), 7.19 (t, J=7.82 Hz, 1H), 7.04 (d, J=7.63 Hz, 1H), 4.86-5.13 (m, 6H), 4.74 (dd, J=5.67, 6.65 Hz, 1H), 4.33-4.45 (m, 1H), 3.91-4.05 (m, 1H), 3.39-3.54 (m, 1H), 3.04-3.19 (m, 2H), 2.86 (d, J=16.43 Hz, 1H), 2.04-2.17 (m, 1H), 1.50-1.70 (m, 1H), 0.58 (t, J=7.43 Hz, 3H). Mass spectrum (ESI) m/z=556.0 [M]$^+$.

Example 185

2-((2R,5R,6R)-6-(3-chlorophenyl)-5-(4-chlorophenyl)-4-((S)-1-(oxetan-3-ylsulfonyl)butan-2-yl)-3-oxomorpholin-2-yl)acetic acid or 2-((2S,5R,6R)-6-(3-chlorophenyl)-5-(4-chlorophenyl)-4-((S)-1-(oxetan-3-ylsulfonyl)butan-2-yl)-3-oxomorpholin-2-yl)acetic acid

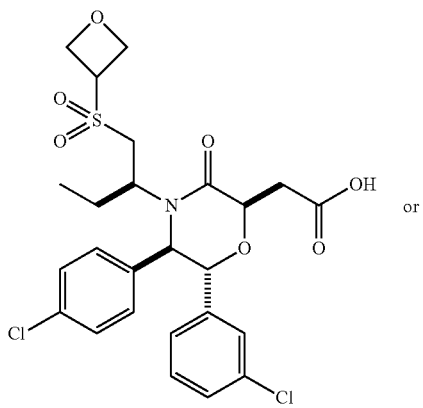

or

304

-continued

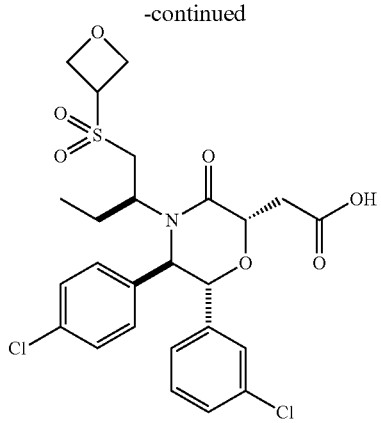

One of the title compounds was obtained as the second (slower) eluting isomer in Example 184 as a white foam ($t_R$=15.8 min). $^1$H NMR (400 MHz, CDCl$_3$) δ 7.32 (d, J=8.61 Hz, 2H), 7.19-7.24 (m, 1H), 7.08-7.16 (m, 3H), 7.06 (t, J=1.76 Hz, 1H), 6.82 (d, J=7.83 Hz, 1H), 4.88-5.11 (m, 5H), 4.72 (s, 2H), 4.31-4.49 (m, 1H), 3.91-4.13 (m, 1H), 3.26-3.43 (m, 1H), 3.01-3.23 (m, 2H), 2.78-2.90 (m, 1H), 2.09-2.23 (m, 1H), 1.55-1.75 (m, 1H), 0.58 (td, J=7.04, 14.87 Hz, 3H). Mass spectrum (ESI) m/z=556.1 [M]$^+$.

Example 186

2-((2R,5R,6R)-6-(3-chlorophenyl)-5-(4-chlorophenyl)-3-oxo-4-((S)-1-((tetrahydro-2H-pyran-4-yl)sulfonyl)butan-2-yl)morpholin-2-yl)acetic acid or 2-((2S,5R,6R)-6-(3-chlorophenyl)-5-(4-chlorophenyl)-3-oxo-4-((S)-1-((tetrahydro-2H-pyran-4-yl)sulfonyl)butan-2-yl)morpholin-2-yl)acetic acid

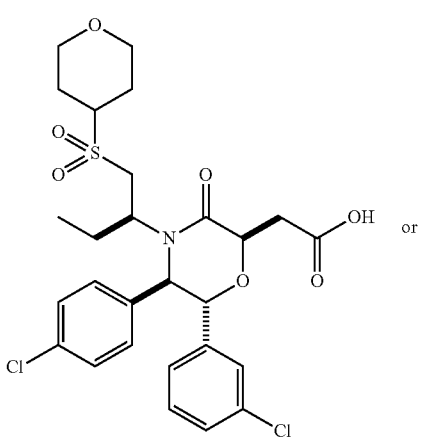

or

-continued

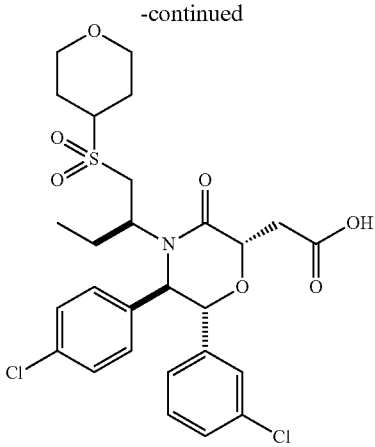

Tetrahydro-2H-pyran-4-thiol

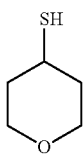

The above compound was synthesized by adding sodium hydrogen sulfide (47.6 mg, 0.849 mmol) to a DMF (0.707 mL) solution containing 4-iodotetrahydro-2h-pyran (0.150 mL, 0.707 mmol). The resulting mixture was stirred overnight at 50° C. under an argon atmosphere. The reaction was cooled and partitioned between diethyl ether (3×10 mL) and water (10 mL). The organic layers were combined, dried over magnesium sulfate, decanted, and the solvents were removed under vacuum until about 1 mL of solvent remained. This product was used as a solution without further purification.

One of the title compounds was prepared from (1R,2R)-2-amino-1-(3-chlorophenyl)-2-(4-chlorophenyl)ethanol (Intermediate A2) by procedures similar to those described in Example 162, Steps A though H, replacing tert-butylthiol in Step D with tetrahydro-2H-pyran-4-thiol. The crude product was purified by reverse phase preparatory HPLC (Gemini™ Prep $C_{18}$ 5 μm column; Phenomenex, Torrance, Calif.; gradient elution of 25% to 75% MeCN in water, where both solvents contain 0.1% TFA, 30 min method) to provide one of the title compounds as the faster eluting isomer as a white foam ($t_R$=16.0 min). $^1$H NMR (400 MHz, CDCl$_3$) δ 7.19-7.28 (m, 5H), 7.15 (d, J=0.98 Hz, 1H), 7.05-7.12 (m, 1H), 6.95 (d, J=7.83 Hz, 1H), 5.00 (d, J=6.46 Hz, 1H), 4.85 (s, 1H), 4.62 (t, J=5.97 Hz, 1H), 4.06 (d, J=9.78 Hz, 2H), 3.90 (br. s., 1H), 3.24-3.41 (m, 3H), 2.95-3.09 (m, 3H), 2.75-2.91 (m, 2H), 1.89 (d, J=11.54 Hz, 5H), 1.40-1.65 (m, 1H), 0.47 (t, J=7.53 Hz, 3H). Mass spectrum (ESI) m/z=584.0 [M]$^+$.

Example 187

2-((2R,5R,6R)-6-(3-chlorophenyl)-5-(4-chlorophenyl)-3-oxo-4-((S)-1-((tetrahydro-2H-pyran-4-yl)sulfonyl)butan-2-yl)morpholin-2-yl)acetic acid or 2-((2S,5R,6R)-6-(3-chlorophenyl)-5-(4-chlorophenyl)-3-oxo-4-((S)-1-((tetrahydro-2H-pyran-4-yl)sulfonyl)butan-2-yl)morpholin-2-yl)acetic acid

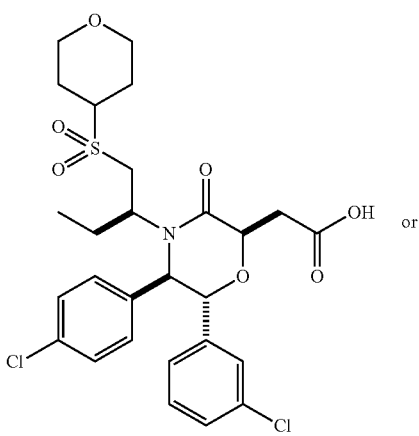

or

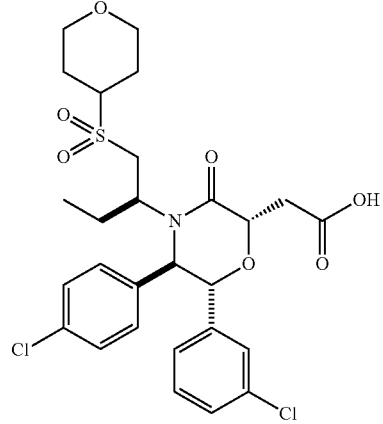

One of the title compounds was obtained as the second (slower) eluting isomer in Example 186 as a white foam ($t_R$=16.6 min). $^1$H NMR (400 MHz, CDCl$_3$) δ 7.31 (d, J=8.61 Hz, 2H), 7.18-7.24 (m, 1H), 7.04-7.17 (m, 4H), 6.82 (d, J=7.82 Hz, 1H), 5.02 (d, J=9.59 Hz, 1H), 4.70 (d, J=9.78 Hz, 2H), 4.10-4.25 (m, 2H), 3.94-4.08 (m, 1H), 3.43 (s, 3H), 2.82-3.24 (m, 4H), 1.85-2.28 (m, 5H), 1.55-1.76 (m, 1H), 0.56 (t, J=7.43 Hz, 3H). Mass spectrum (ESI) m/z=584.1 [M]$^+$.

Example 188

2-((2R,5R,6R)-6-(3-chlorophenyl)-5-(4-chlorophenyl)-4-((S)-1-cyclopropyl-2-(N-(3-fluoropyridin-2-yl)cyclopropanesulfonamido)ethyl)-3-oxomorpholin-2-yl)acetic acid or 2-((2S,5R,6R)-6-(3-chlorophenyl)-5-(4-chlorophenyl)-4-((S)-1-cyclopropyl-2-(N-(3-fluoropyridin-2-yl)cyclopropanesulfonamido)ethyl)-3-oxomorpholin-2-yl)acetic acid

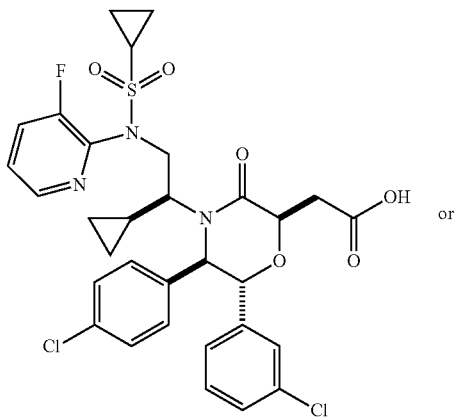

or

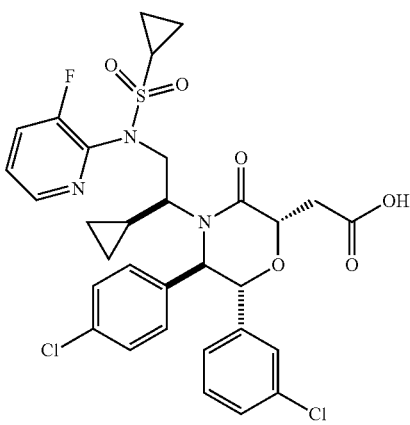

One of the title compounds was prepared from (5R,6R)-6-(3-chlorophenyl)-5-(4-chlorophenyl)-4-((S)-1-cyclopropyl-2-hydroxyethyl)morpholin-3-one (Example 154, Step B) by procedures similar to those described in Example 112, Steps D though F, replacing ethanethiol in Step D with N-(3-fluoropyridin-2-yl)cyclopropanesulfonamide (see Example 176).

The crude product was purified by reverse phase preparatory HPLC (Gemini™ Prep $C_{18}$ 5 µm column; Phenomenex, Torrance, Calif.; gradient elution of 25% to 75% MeCN in water, where both solvents contain 0.1% TFA, 30 min method) to provide one of the title compounds as the faster eluting isomer as a white foam ($t_R$=18.9 min). $^1$H NMR (400 MHz, CDCl$_3$) δ 8.14-8.31 (m, 1H), 7.46-7.58 (m, 1H), 7.20-7.31 (m, 5H), 7.07-7.18 (m, 4H), 4.93-5.11 (m, 1H), 4.69-4.87 (m, 1H), 4.25-4.41 (m, 2H), 3.66-3.94 (m, 1H), 2.86-3.18 (m, 3H), 2.48 (bs, 2H), 1.27-1.50 (m, 1H), 0.82-1.11 (m, 5H), 0.22-0.57 (m, 2H), −0.12-0.12 (m, 1H). Mass spectrum (ESI) m/z=662.0 [M]$^+$.

Example 189

2-((2R,5R,6R)-6-(3-chlorophenyl)-5-(4-chlorophenyl)-4-((S)-1-cyclopropyl-2-(N-(3-fluoropyridin-2-yl)cyclopropanesulfonamido)ethyl)-3-oxomorpholin-2-yl)acetic acid or 2-((2S,5R,6R)-6-(3-chlorophenyl)-5-(4-chlorophenyl)-4-((S)-1-cyclopropyl-2-(N-(3-fluoropyridin-2-yl)cyclopropanesulfonamido)ethyl)-3-oxomorpholin-2-yl)acetic acid

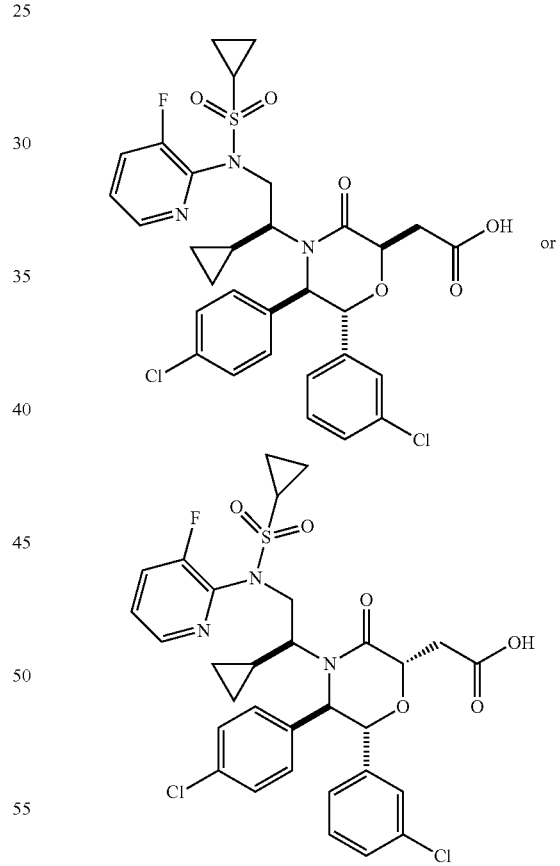

One of the title compounds was obtained as the second (slower) eluting isomer in Example 188 as a white foam ($t_R$=19.9 min). $^1$H NMR (400 MHz, CDCl$_3$) δ 8.27-8.40 (m, 1H), 7.55-7.69 (m, 1H), 7.33-7.46 (m, 1H), 7.27 (s, 8H), 4.99 (d, J=9.98 Hz, 1H), 4.58-4.75 (m, 2H), 3.90-4.19 (m, 1H), 2.88-3.06 (m, 1H), 2.49-2.73 (m, 2H), 1.98-2.09 (m, 2H), 0.96-1.14 (m, 5H), 0.21-0.51 (m, 2H), −0.36 to −0.19 (m, 1H), −0.99 to −0.80 (m, 1H). Mass spectrum (ESI) m/z=662.0 [M]$^+$.

Example 190

2-((2R,5R,6R)-6-(3-chlorophenyl)-5-(4-chlorophenyl)-4-((S)-1-((cyclopropylmethyl)sulfonyl)butan-2-yl)-3-oxomorpholin-2-yl)acetic acid or 2-((2S,5R,6R)-6-(3-chlorophenyl)-5-(4-chlorophenyl)-4-((S)-1-((cyclopropylmethyl)sulfonyl)butan-2-yl)-3-oxomorpholin-2-yl)acetic acid

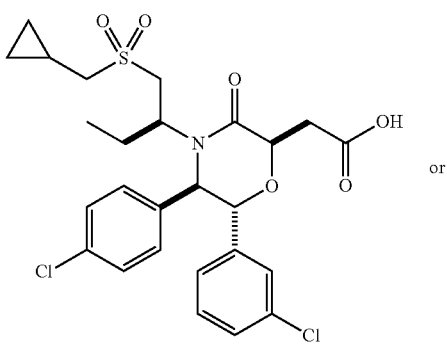

or

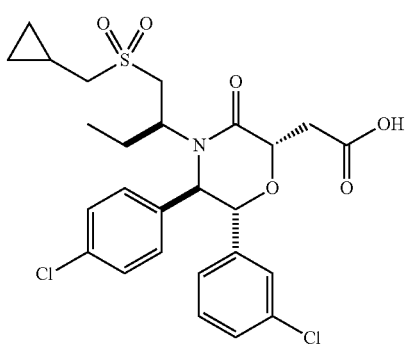

One of the title compounds was prepared from (5R,6R)-6-(3-chlorophenyl)-5-(4-chlorophenyl)-4-((S)-1-hydroxybutan-2-yl)morpholin-3-one (Example 112, Step C) by procedures similar to those described in Example 112, Steps D though F, replacing ethanethiol in Step D with cyclopropylmethanethiol (prepared from the corresponding alkylmagnesium bromide and sulfure in a manner analogous to that described in Example 212, Step A). The crude product was purified by reverse phase preparatory HPLC (Gemini™ Prep C$_{18}$ 5 μm column; Phenomenex, Torrance, Calif.; gradient elution of 45% to 65% MeCN in water, where both solvents contain 0.1% TFA, 20 min method) to provide one of the title compounds as the faster eluting isomer as a white foam. $^1$H NMR (500 MHz, CDCl$_3$) δ ppm 0.37-0.47 (m, 2 H) 0.57 (t, J=7.58 Hz, 3 H) 0.74-0.83 (m, 2H) 1.16-1.25 (m, 1 H) 1.62 (ddd, J=13.94, 7.58, 4.40 Hz, 1 H) 2.16 (ddd, J=14.18, 9.66, 7.46 Hz, 1 H) 2.91-3.08 (m, 3 H) 3.08-3.17 (m, 2 H) 3.44 (br. s., 1 H) 4.04 (br. s., 1 H) 4.72 (t, J=6.11 Hz, 1 H) 4.95 (d, J=6.85 Hz, 1 H) 5.10 (d, J=6.85 Hz, 1 H) 7.00-7.06 (m, 1 H) 7.10-7.21 (m, 1 H) 7.21-7.32 (m, 4 H) 7.35 (d, J=8.56 Hz, 2 H). Mass spectrum (ESI) m/z=554 [M+1].

Example 191

2-((2R,5R,6R)-6-(3-chlorophenyl)-5-(4-chlorophenyl)-4-((S)-1-((cyclopropylmethyl)sulfonyl)butan-2-yl)-3-oxomorpholin-2-yl)acetic acid or 2-((2S,5R,6R)-6-(3-chlorophenyl)-5-(4-chlorophenyl)-4-((S)-1-((cyclopropylmethyl)sulfonyl)butan-2-yl)-3-oxomorpholin-2-yl)acetic acid

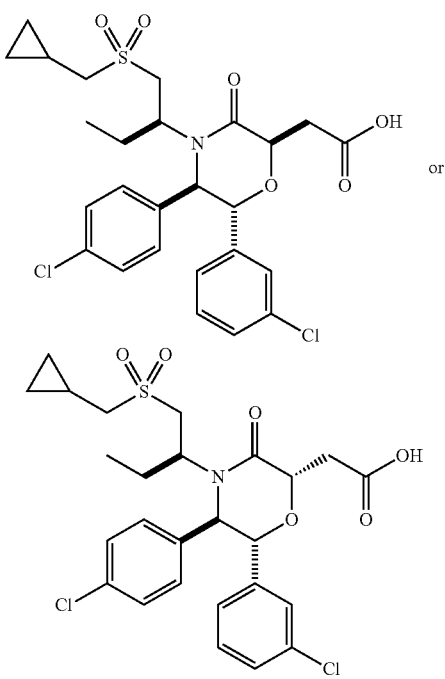

One of the title compounds was obtained as the second (slower) eluting isomer in Example 190 as a white foam. $^1$H NMR (500 MHz, CDCl$_3$) δ ppm 0.43 (d, J=4.65 Hz, 2H) 0.57 (t, J=7.34 Hz, 3 H) 0.75-0.85 (m, 2 H) 1.16-1.25 (m, 1 H) 1.54-1.69 (m, 1 H) 2.12-2.23 (m, 1 H) 2.85-3.08 (m, 4 H) 3.24 (dd, J=16.38, 6.85 Hz, 1 H) 3.34 (br. s., 1H) 4.10 (br. s., 1 H) 4.69 (d, J=9.78 Hz, 1 H) 4.74 (dd, J=6.60, 4.89 Hz, 1 H) 5.04 (d, J=9.78 Hz, 1 H) 6.83 (d, J=7.58 Hz, 1 H) 7.06 (s, 1 H) 7.08-7.16 (m, 3 H) 7.21 (d, J=8.07 Hz, 1 H) 7.29-7.37 (m, 2 H). Mass spectrum (ESI) m/z=554 [M+1].

Example 192

2-((2R,5R,6R)-6-(3-chlorophenyl)-5-(4-chlorophenyl)-4-((S)-3-methyl-1-(N-phenylcyclopropanesulfonamido)butan-2-yl)-3-oxomorpholin-2-yl)acetic acid or 2-((2S,5R,6R)-6-(3-chlorophenyl)-5-(4-chlorophenyl)-4-((S)-3-methyl-1-(N-phenylcyclopropanesulfonamido) butan-2-yl)-3-oxomorpholin-2-yl) acetic acid

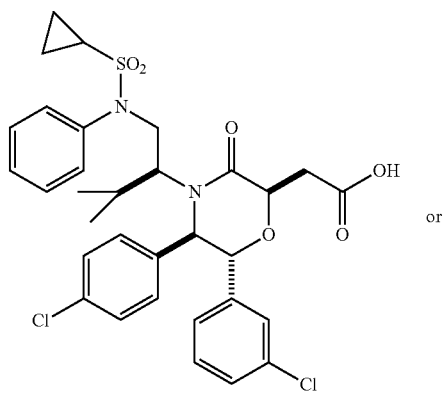

or

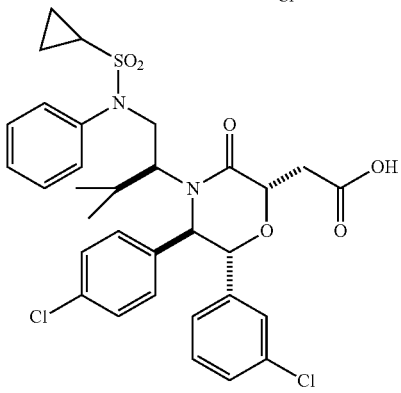

Step A. (5R,6R)-6-(3-chlorophenyl)-5-(4-chlorophenyl)-4-((S)-1-((3,4-dimethoxybenzyl)oxy)-3-methylbutan-2-yl)morpholin-3-one and (5R,6R)-6-(3-chlorophenyl)-5-(4-chlorophenyl)-4-((R)-1-((3,4-dimethoxybenzyl)oxy)-3-methylbutan-2-yl) morpholin-3-one

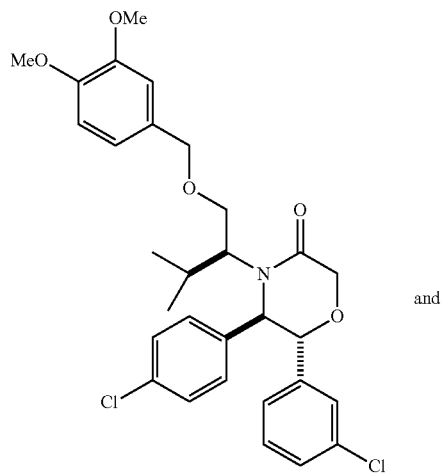

and

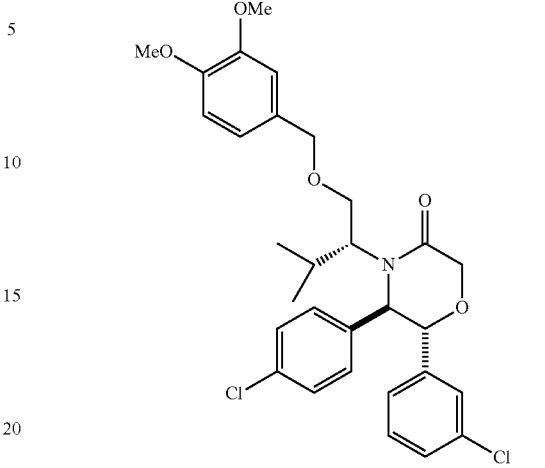

(R)-1-((3,4-dimethoxybenzyl)oxy)-3-methylbutan-2-yl-4-bromobenzenesulfonate and (S)-1-((3,4-dimethoxybenzyl)oxy)-3-methylbutan-2-yl-4-bromobenzenesulfonate

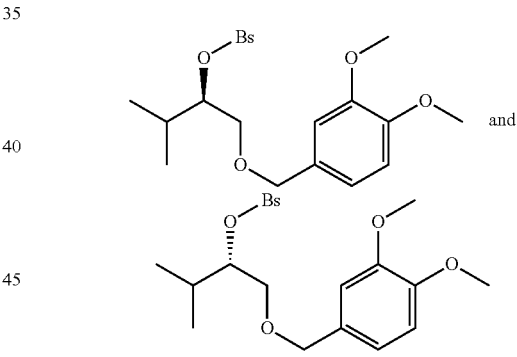

The above compounds were prepared from 3,4-dimethoxybenzyl alcohol by procedures similar to those described in general intermediate G, Steps A and B, replacing (R)-2-ethyloxirane in step A with racemic 1,2-epoxy-3-methylbutane.

The title compounds were prepared from (5R,6R)-6-(3-chlorophenyl)-5-(4-chlorophenyl) morpholin-3-one (Example 112, Step A) by a procedure similar to that described in Example 112, Step B, replacing (R)-1-((3,4-dimethoxybenzyl)oxy)butan-2-yl 4-bromobenzenesulfonate in Step B with a mixture of (R)-1-((3,4-dimethoxybenzyl)oxy)-3-methylbutan-2-yl 4-bromobenzenesulfonate and (S)-1-((3,4-dimethoxybenzyl)oxy)-3-methylbutan-2-yl 4-bromobenzenesulfonate.

313

Step B. (5R,6R)-6-(3-chlorophenyl)-5-(4-chlorophenyl)-4-((R)-1-hydroxy-3-methylbutan-2-yl)morpholin-3-one) and (5R,6R)-6-(3-chlorophenyl)-5-(4-chlorophenyl)-4-((S)-1-hydroxy-3-methylbutan-2-yl)morpholin-3-one

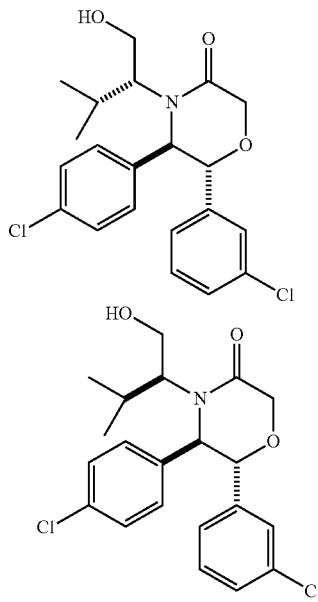

and

314

Step C. 2-((2R,5R,6R)-6-(3-chlorophenyl)-5-(4-chlorophenyl)-4-((S)-3-methyl-1-(N-phenylcyclopropanesulfonamido)butan-2-yl)-3-oxomorpholin-2-yl)acetic acid or 2-((2S,5R,6R)-6-(3-chlorophenyl)-5-(4-chlorophenyl)-4-((S)-3-methyl-1-(N-phenylcyclopropanesulfonamido) butan-2-yl)-3-oxomorpholin-2-yl)acetic acid

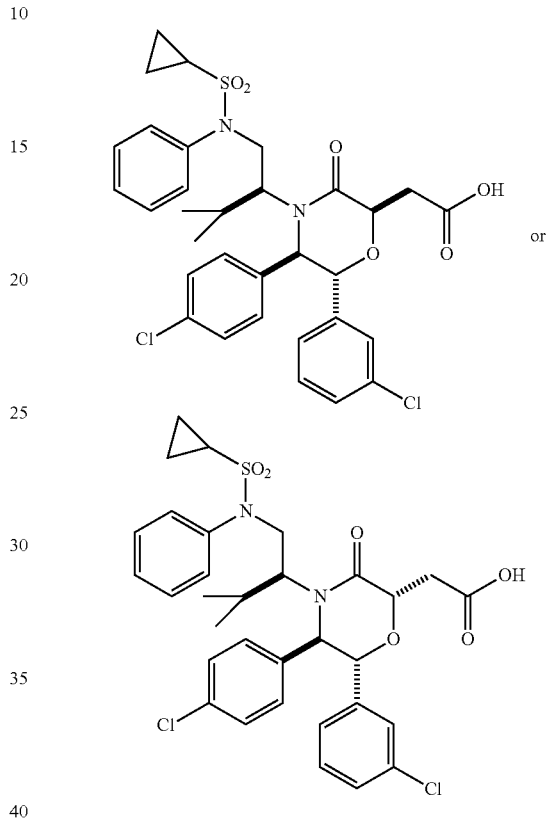

or

One title compound was prepared from (5R,6R)-6-(3-chlorophenyl)-5-(4-chlorophenyl)-4-((S)-1-((3,4-dimethoxybenzyl)oxy)-3-methylbutan-2-yl)morpholin-3-one and (5R,6R)-6-(3-chlorophenyl)-5-(4-chlorophenyl)-4-((R)-1-((3,4-dimethoxybenzyl)oxy)-3-methylbutan-2-yl)morpholin-3-one (Example 192, Step A) by a procedure similar to that described in Example 112, Steps C. Flash chromatography on silica gel (gradient elution from 30 to 40% ethyl acetate in hexanes) afforded one of the titled compounds as the first (faster) eluting peak. $^1$H NMR (500 MHz, CDCl$_3$) δ ppm 0.92 (d, J=6.60 Hz, 3 H) 1.09 (d, J=6.60 Hz, 3 H) 2.47 (dd, J=11.00, 4.16 Hz, 1 H) 2.71 (dt, J=10.94, 6.63 Hz, 1 H) 3.48 (d, J=12.47 Hz, 1 H) 3.55-3.65 (m, 1 H) 4.38-4.53 (m, 3 H) 4.62 (d, J=16.87 Hz, 1 H) 6.69 (d, J=7.83 Hz, 1 H) 6.94-7.01 (m, 4 H) 7.08 (t, J=1.71 Hz, 1 H) 7.12 (t, J=7.95 Hz, 1 H) 7.22-7.27 (m, 1 H)

The second compound was obtained as the second (slower) eluting peak. $^1$H NMR (500 MHz, CDCl$_3$) δ ppm 0.82 (d, J=6.60 Hz, 3 H) 0.80 (d, J=6.60 Hz, 3 H) 2.24 (m, 1H) 2.33-2.44 (m, 1 H) 3.44 (d, J=8.07 Hz, 1 H) 3.74 (d, J=7.58 Hz, 1 H) 3.90 (s, 1 H) 4.39-4.54 (m, 2 H) 4.60-4.75 (m, 2 H) 6.83 (dt, J=7.76, 1.38 Hz, 1 H) 7.04-7.22 (m, 4H) 7.22-7.25 (m, 1 H) 7.31 (m, 2 H)

One of the title compounds was prepared from 4S,6R)-6-(3-chlorophenyl)-5-(4-chlorophenyl)-4-((S)-1-hydroxy-3-methylbutan-2-yl)morpholin-3-one (Example 192, Step B) by procedures similar to those described in Example 112, Steps D though F, replacing ethanethiol in Step D with N-phenylcyclopropanesulfonamide which was prepared by a method analogous to that described for N-(2-fluorophenyl) cyclopropanesulfonamide in Example 133. The crude product was purified by reverse phase preparatory HPLC (Gemini™ Prep C$_{18}$ 5 µm column; Phenomenex, Torrance, Calif.; gradient elution of 45% to 65% MeCN in water, where both solvents contain 0.1% TFA, 20 min method) to provide one of the title compounds as the faster eluting peak as a white foam. $^1$H NMR (500 MHz, CDCl$_3$) δ ppm 0.58 (d, J=6.85 Hz, 3H) 0.72 (d, J=6.60 Hz, 3 H) 0.87-0.97 (m, 2 H) 0.99-1.11 (m, 2 H) 2.23 (dt, J=8.80, 6.85 Hz, 1 H) 2.33-2.39 (m, 1 H) 2.89-2.95 (m, 1 H) 3.04 (t, J=6.36 Hz, 2 H) 3.97 (dd, J=14.55, 3.30 Hz, 1 H) 4.31 (t, J=6.36 Hz, 1 H) 4.54 (dd, J=14.55, 9.66 Hz, 1 H) 4.90-4.97 (m, 2 H) 7.02-7.07 (m, 1 H) 7.07-7.14 (m, 2 H) 7.17-7.23 (m, 2 H) 7.23-7.30 (m, 3 H) 7.34-7.39 (m, 1 H) 7.43-7.49 (m, 2 H) 7.49-7.54 (m, 2 H). Mass spectrum (ESI) m/z=645 [M+1].

Example 193

2-((2R,5R,6R)-6-(3-chlorophenyl)-5-(4-chlorophenyl)-4-((R)-3-methyl-1-(N-phenylcyclopropanesulfonamido) butan-2-yl)-3-oxomorpholin-2-yl)acetic acid or 2-((2S,5R,6R)-6-(3-chlorophenyl)-5-(4-chlorophenyl)-4-((R)-3-methyl-1-(N-phenylcyclopropanesulfonamido) butan-2-yl)-3-oxomorpholin-2-yl)acetic acid

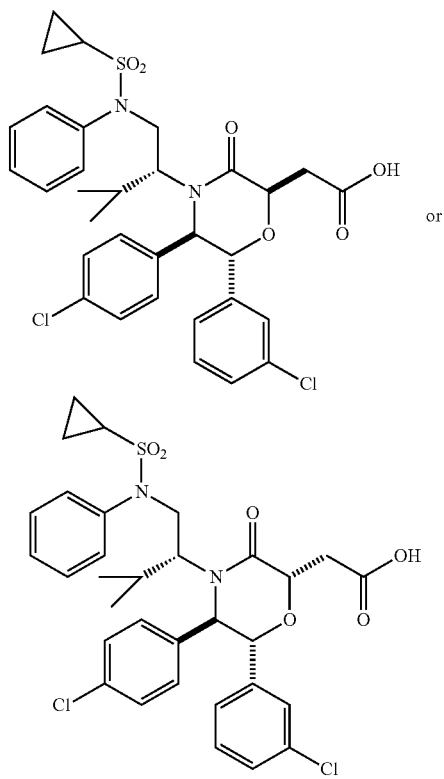

One of the title compounds was prepared from (5R,6R)-6-(3-chlorophenyl)-5-(4-chlorophenyl)-4-((R)-1-hydroxy-3-methylbutan-2-yl)morpholin-3-one (Example 192, Step B) by procedures similar to those described in Example 112, Steps D though F, replacing ethanethiol in Step D with N-phenylcyclopropanesulfonamide which was prepared by a method analogous to that described for N-(2-fluorophenyl) cyclopropanesulfonamide in Example 133. The crude product was purified by reverse phase preparatory HPLC (Gemini™ Prep $C_{18}$ 5 µm column; Phenomenex, Torrance, Calif.; gradient elution of 45% to 65% MeCN in water, where both solvents contain 0.1% TFA, 20 min method) to provide one of the title compounds as the first (faster) eluting peak. $^1$H NMR (500 MHz, CDCl$_3$) δ ppm 0.77 (br. s., 3 H) 0.87-1.05 (m, 7 H) 2.28-2.43 (m, 2 H) 2.99-3.22 (m, 3 H) 4.06 (br. s., 1 H) 4.21-4.45 (m, 1 H) 4.73-4.92 (m, 3 H) 7.01-7.35 (m, 13 H). Mass spectrum (ESI) m/z=645 [M+1].

Example 194

2-((2R,5R,6R)-4-((S)-1-(tert-butylsulfonyl)pentan-2-yl)-6-(3-chlorophenyl)-5-(4-chlorophenyl)-3-oxomorpholin-2-yl)acetic acid or 2-((2S,5R,6R)-4-((S)-1-(tert-butylsulfonyl)pentan-2-yl)-6-(3-chlorophenyl)-5-(4-chlorophenyl)-3-oxomorpholin-2-yl)acetic acid (isomer 1)

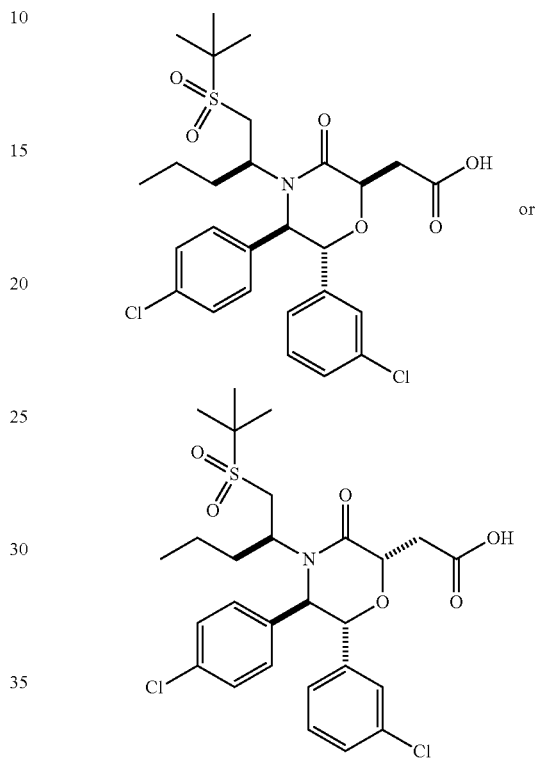

Step A. (5R,6R)-6-(3-chlorophenyl)-5-(4-chlorophenyl)-4-((S)-1-((3,4-dimethoxybenzyl)oxy)pentan-2-yl)morpholin-3-one and (5R,6R)-6-(3-chlorophenyl)-5-(4-chlorophenyl)-4-((R)-1-((3,4-dimethoxybenzyl)oxy)pentan-2-yl)morpholin-3-one

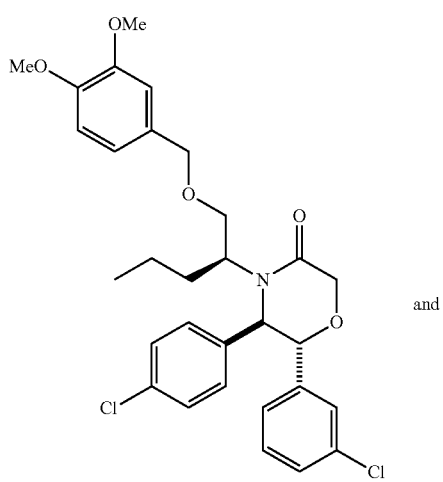

-continued

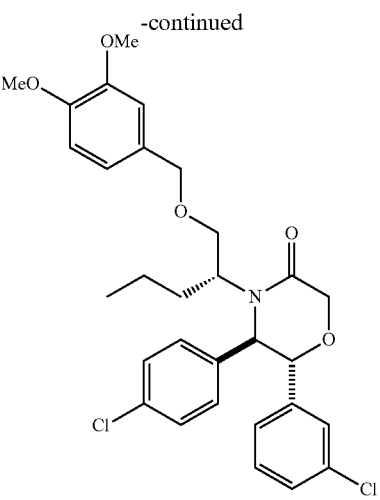

(R)-1-((3,4-dimethoxybenzyl)oxy)pentan-2-yl-4-bromobenzenesulfonate and (S)-1-((3,4-dimethoxybenzyl)oxy)pentan-2-yl 4-bromobenzenesulfonate

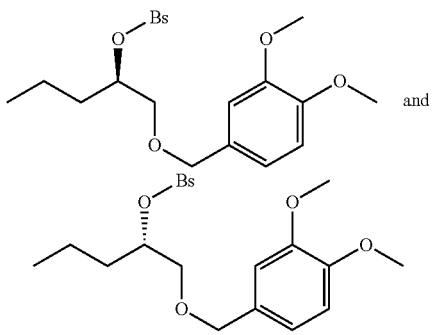

The above compounds were prepared from 3,4-dimethoxybenzyl alcohol by procedures similar to those described in general intermediate G, Steps A and B, replacing (R)-2-ethyloxirane in step A with racemic 1,2-epoxypentane. $^1$H NMR (500 MHz, CDCl$_3$) δ ppm 0.88 (t, J=7.34 Hz, 3 H) 1.27-1.41 (m, 2 H) 1.59-1.72 (m, 2 H) 3.47-3.52 (m, 2 H) 3.90 (s, 3 H) 3.88 (s, 3 H) 4.29-4.40 (m, 2 H) 4.66-4.79 (m, 1 H) 6.72-6.77 (m, 1 H) 6.79-6.86 (m, 2 H) 7.55-7.61 (m, 2 H) 7.71-7.79 (m, 2 H)

The title compounds were prepared from (5R,6R)-6-(3-chlorophenyl)-5-(4-chlorophenyl) morpholin-3-one (Example 112, Step A) by a procedure similar to that described in Example 112, Step B, replacing (R)-1-((3,4-dimethoxybenzyl)oxy)butan-2-yl 4-bromobenzenesulfonate in Step B with a mixture of (R)-1-((3,4-dimethoxybenzyl)oxy)pentan-2-yl 4-bromobenzenesulfonate and (S)-1-((3,4-dimethoxybenzyl)oxy)pentan-2-yl 4-bromobenzenesulfonate Step B. (5R,6R)-6-(3-chlorophenyl)-5-(4-chlorophenyl)-4-((R)-1-hydroxypentan-2-yl)morpholin-3-one and (5R,6R)-6-(3-chlorophenyl)-5-(4-chlorophenyl)-4-((S)-1-hydroxypentan-2-yl)morpholin-3-one Isomer 1

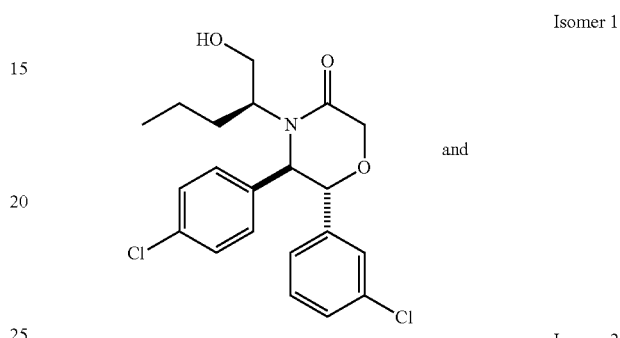

and

Isomer 2

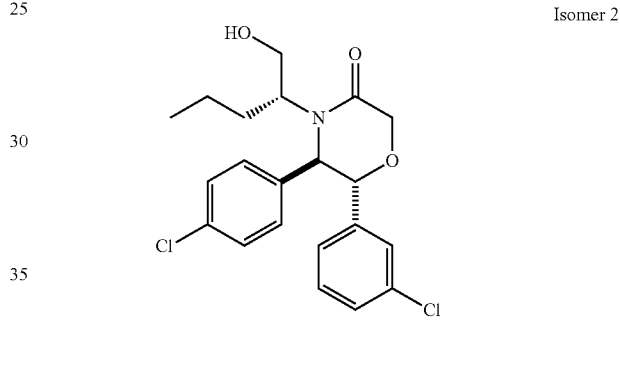

The title compounds were prepared from (5R,6R)-6-(3-chlorophenyl)-5-(4-chlorophenyl)-4-((S)-1-((3,4-dimethoxybenzyl)oxy)pentan-2-yl)morpholin-3-one and (5R,6R)-6-(3-chlorophenyl)-5-(4-chlorophenyl)-4-((R)-1-((3,4-dimethoxybenzyl)oxy)pentan-2-yl)morpholin-3-one (Example 194, Step A) by a procedure similar to that described in Example 112, Step C. Flash chromatography on silica gel (gradient elution from 30 to 40% ethyl acetate in hexanes) afforded Isomer 1 which was obtained as the faster eluting peak. $^1$H NMR (500 MHz, CDCl$_3$) δ ppm 0.95 (t, J=7.21 Hz, 3 H) 1.29-1.38 (m, 1 H) 1.38-1.50 (m, 1 H) 1.85 (q, J=7.83 Hz, 2 H) 2.93-3.01 (m, 1 H) 3.53 (m, 1 H) 3.55-3.64 (m, 1 H) 4.38-4.60 (m, 4 H) 5.03 (d, J=9.78 Hz, 1 H) 6.72 (dt, J=7.76, 1.38 Hz, 1 H) 6.92-7.01 (m, 2 H) 7.09-7.18 (m, 2 H) 7.22-7.36 (m, 3 H)

The second compound was obtained as the second (slower) eluting peak. $^1$H NMR (500 MHz, CDCl$_3$) δ ppm 0.63-0.72 (t, J=7.21 Hz, 3 H) 0.93-1.03 (m, 1 H) 1.08-1.19 (m, 1 H) 1.33-1.44 (m, 1 H) 1.81-1.91 (m, 1 H) 3.36-3.46 (m, 1 H) 3.54 (dd, J=11.37, 3.79 Hz, 1 H) 3.65-3.73 (m, 1 H) 4.36-4.41 (m, 2 H) 4.54-4.60 (m, 1 H) 4.60-4.66 (m, 1 H) 6.80 (dt, J=7.76, 1.38 Hz, 1 H) 7.04-7.17 (m, 4 H) 7.19-7.24 (m, 1 H) 7.24-7.33 (m, 2 H)

Step C. 2-((2R,5R,6R)-4-((S)-1-(tert-butylsulfonyl)pentan-2-yl)-6-(3-chlorophenyl)-5-(4-chlorophenyl)-3-oxomorpholin-2-yl)acetic acid or 2-((2S,5R,6R)-4-((S)-1-(tert-butylsulfonyl)pentan-2-yl)-6-(3-chlorophenyl)-5-(4-chlorophenyl)-3-oxomorpholin-2-yl)acetic acid

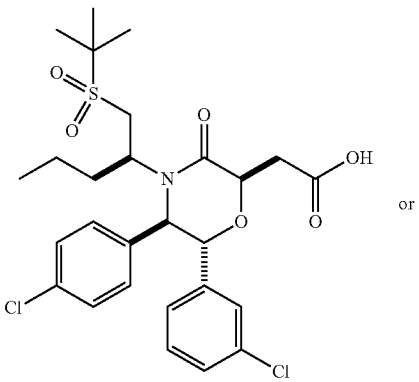

or

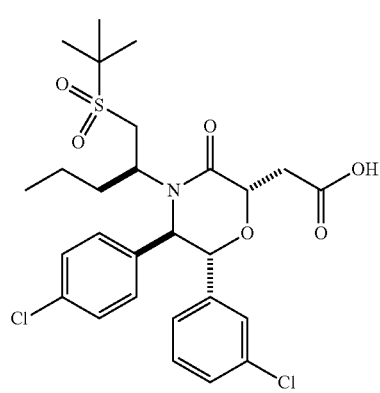

One of the title compounds was prepared from (5R,6R)-6-(3-chlorophenyl)-5-(4-chlorophenyl)-4-((S)-1-hydroxypentan-2-yl)morpholin-3-one (Example 194, Step B) by procedures similar to those described in Example 112, Steps D though F, replacing ethanethiol in Step D with 2-methylpropane-2-thiol. The crude product was purified by reverse phase preparatory HPLC (Gemini™ Prep $C_{18}$ 5 µm column; Phenomenex, Torrance, Calif.; gradient elution of 40% to 60% MeCN in water, where both solvents contain 0.1% TFA, 20 min method) to provide one of the title compounds as the first (faster) eluting peak. $^1$H NMR (500 MHz, CDCl$_3$) δ ppm 0.58 (t, J=7.83 Hz, 3 H) 0.73-0.82 (m, 1 H) 0.92-1.11 (m, 1 H) 1.37-1.54 (m, 10 H) 1.87 (br. s., 1 H) 2.21 (m, 1 H) 2.93 (m, 1 H) 3.06-3.16 (m, 2 H) 3.95 (m, 1 H) 4.70 (t, J=5.99 Hz, 1 H) 4.94 (d, J=6.60 Hz, 1 H) 5.16 (d, J=6.60 Hz, 1 H) 7.04-7.07 (m, 1 H) 7.17 (m, 1 H) 7.22-7.39 (m, 6 H). Mass spectrum (ESI) m/z=570 [M+1].

Example 195

2-((2R,5R,6R)-4-((S)-1-(tert-butylsulfonyl)pentan-2-yl)-6-(3-chlorophenyl)-5-(4-chlorophenyl)-3-oxomorpholin-2-yl)acetic acid or 2-((2S,5R,6R)-4-((S)-1-(tert-butylsulfonyl)pentan-2-yl)-6-(3-chlorophenyl)-5-(4-chlorophenyl)-3-oxomorpholin-2-yl)acetic acid

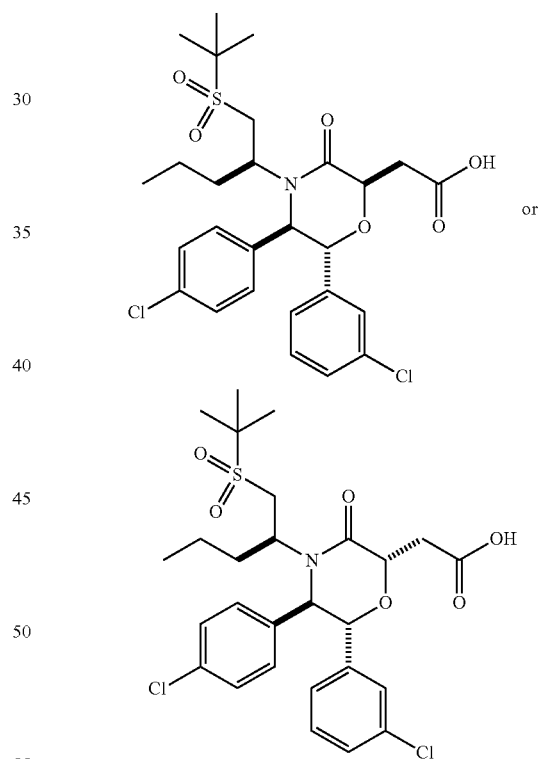

One of the title compounds was obtained as the second (slower) eluting isomer in Example 194, Step C as a white foam. $^1$H NMR (500 MHz, CDCl$_3$) δ ppm 0.57 (t, J=7.21 Hz, 3 H) 0.68-0.82 (m, 1 H) 0.97-1.09 (m, 1 H) 1.38-1.56 (m, 11 H) 2.14-2.30 (m, 1 H) 2.85-2.93 (m, 1 H) 2.98 (dd, J=16.26, 4.52 Hz, 1 H) 3.23 (dd, J=16.26, 7.21 Hz, 1 H) 3.43 (br. s., 1 H) 4.00-4.08 (m, 1 H) 4.67-4.75 (m, 2 H) 5.09 (d, J=9.78 Hz, 1 H) 6.85 (d, J=7.83 Hz, 1 H) 7.05-7.18 (m, 4 H) 7.18-7.35 (m, 3 H)

Mass spectrum (ESI) m/z=570 [M+1].

Example 196

2-((2R,5R,6R)-6-(3-chlorophenyl)-5-(4-chlorophenyl)-4-((S)-1-(N-(2-fluorophenyl)cyclopropanesulfonamido)-3-methylbutan-2-yl)-3-oxomorpholin-2-yl)acetic acid or 2-((2S,5R,6R)-6-(3-chlorophenyl)-5-(4-chlorophenyl)-4-((S)-1-(N-(2-fluorophenyl)cyclopropane sulfonamido)-3-methylbutan-2-yl)-3-oxomorpholin-2-yl)acetic acid

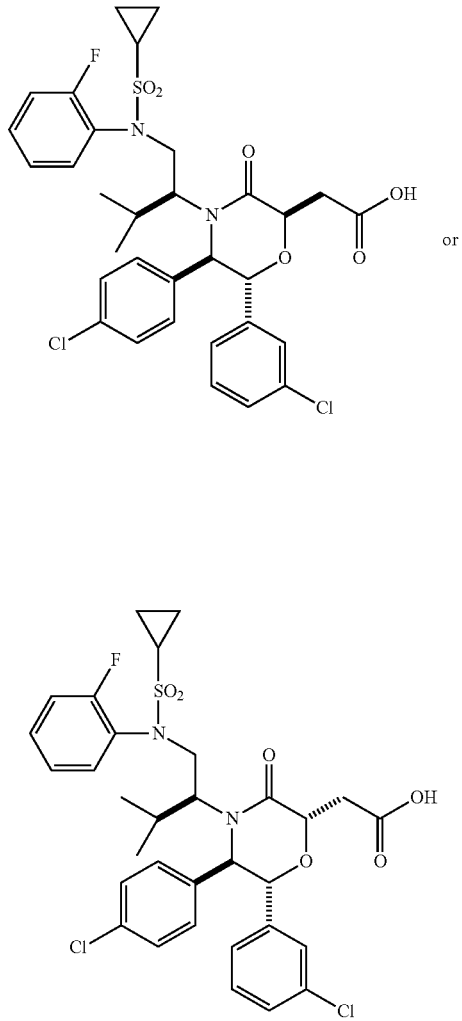

or

One of the title compounds was prepared from (5R,6R)-6-(3-chlorophenyl)-5-(4-chlorophenyl)-4-((S)-1-hydroxy-3-methylbutan-2-yl)morpholin-3-one (Example 192, Step B) by procedures similar to those described in Example 112, Steps D though F, replacing ethanethiol in Step D with N-(2-fluorophenyl)cyclopropanesulfonamide (see Example 133). The crude product was purified by reverse phase preparatory HPLC (Gemini™ Prep $C_{18}$ 5 μm column; Phenomenex, Torrance, Calif.; gradient elution of 40% to 60% MeCN in water, where both solvents contain 0.1% TFA, 20 min method) to provide one of the title compounds as the first (faster) eluting peak. $^1$H NMR (500 MHz, CDCl$_3$) δ ppm 0.58 (d, J=6.85 Hz, 3 H) 0.70 (d, J=6.60 Hz, 3 H) 0.87-1.03 (m, 3 H) 1.05-1.13 (m, 1 H) 2.10-2.21 (m, 1 H) 2.43-2.52 (m, 1 H) 3.02-3.13 (m, 3 H) 3.97 (dd, J=15.16, 3.42 Hz, 1 H) 4.33 (dd, J=14.67, 9.78 Hz, 1 H) 4.46 (t, J=6.48 Hz, 1 H) 4.99 (d, J=8.56 Hz, 1 H) 5.13 (d, J=8.31 Hz, 1 H) 7.08 (d, J=7.58 Hz, 1 H) 7.14-7.33 (m, 9 H) 7.36-7.43 (m, 1 H) 7.59 (td, J=7.82, 1.47 Hz, 1 H). Mass spectrum (ESI) m/z=664 [M+1].

Example 197

2-((2R,5R,6R)-6-(3-chlorophenyl)-5-(4-chlorophenyl)-4-((S)-1-(N-(2-fluorophenyl)cyclopropanesulfonamido)-3-methylbutan-2-yl)-3-oxomorpholin-2-yl)acetic acid or 2-((2S,5R,6R)-6-(3-chlorophenyl)-5-(4-chlorophenyl)-4-((S)-1-(N-(2-fluorophenyl)cyclopropane sulfonamido)-3-methylbutan-2-yl)-3-oxomorpholin-2-yl)acetic acid

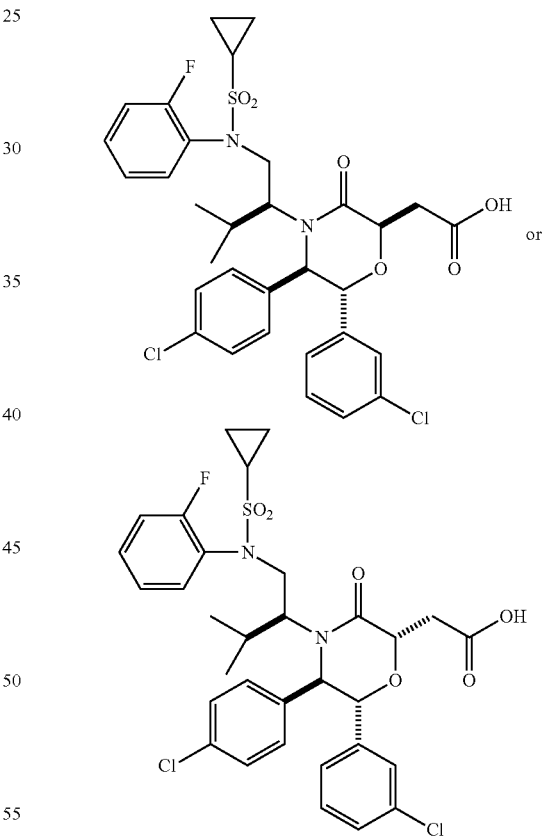

One of the title compounds was obtained as the second (slower) eluting isomer in Example 196 as a white foam. $^1$H NMR (500 MHz, CDCl$_3$) δ ppm 0.58 (d, J=6.36 Hz, 3H) 0.69 (d, J=6.60 Hz, 3 H) 0.87-1.03 (m, 4 H) 1.05-1.13 (m, 1 H) 2.12-2.23 (m, 1 H) 2.41-2.55 (m, 2 H) 2.75 (dd, J=15.77, 8.19 Hz, 1 H) 2.98 (br. s., 1 H) 3.96 (d, J=12.96 Hz, 1 H) 4.31-4.41 (m, 1 H) 4.67 (dd, J=8.07, 4.65 Hz, 1 H) 4.81 (d, J=10.03 Hz, 1 H) 5.09 (d, J=10.03 Hz, 1 H) 6.95 (d, J=7.58 Hz, 1 H) 7.11-7.35 (m, 9 H) 7.36-7.46 (m, 1H) 7.59-7.69 (m, 1 H). Mass spectrum (ESI) m/z=664 [M+1].

Example 198

2-((2R,5R,6R)-6-(3-chlorophenyl)-5-(4-chlorophenyl)-4-((S)-1-(N-(2-fluorophenyl)propan-2-ylsulfonamido)-3-methylbutan-2-yl)-3-oxomorpholin-2-yl)acetic acid or 2-((2S,5R,6R)-6-(3-chlorophenyl)-5-(4-chlorophenyl)-4-((S)-1-(N-(2-fluorophenyl)propan-2-ylsulfonamido)-3-methylbutan-2-yl)-3-oxomorpholin-2-yl)acetic acid

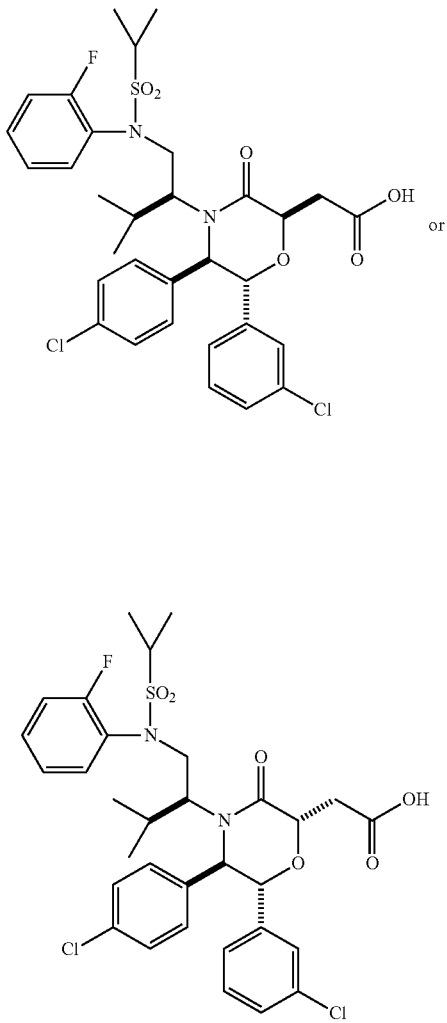

One of the title compounds was prepared from (5R,6R)-6-(3-chlorophenyl)-5-(4-chlorophenyl)-4-((S)-1-hydroxy-3-methylbutan-2-yl)morpholin-3-one (Example 192, Step B) by procedures similar to those described in Example 112, Steps D though F, replacing ethanethiol in Step D with N-(2-fluorophenyl)propane-2-sulfonamide (see Example 172). The crude product was purified by reverse phase preparatory HPLC (Gemini™ Prep $C_{18}$ 5 µm column; Phenomenex, Torrance, Calif.; gradient elution of 40% to 60% MeCN in water, where both solvents contain 0.1% TFA, 20 min method) to provide one of the title compounds as the first (faster) eluting peak. $^1$H NMR (500 MHz, CDCl$_3$) δ ppm 0.59 (d, J=6.85 Hz, 3 H) 0.65 (d, J=6.60 Hz, 3 H) 1.39 (dd, J=15.41, 6.85 Hz, 6 H) 2.06-2.16 (m, 1 H) 2.97 (br. s., 1 H) 3.02-3.12 (m, 2 H) 3.15-3.24 (m, 1 H) 3.90 (dd, J=15.28, 3.06 Hz, 1 H) 4.32-4.54 (m, 2 H) 4.96 (d, J=9.05 Hz, 1 H) 5.08 (d, J=9.05 Hz, 1 H) 7.02 (d, J=7.58 Hz, 1 H) 7.12-7.32 (m, 9 H) 7.32-7.43 (m, 1 H) 7.75 (td, J=8.07, 1.22 Hz, 1 H)

Mass spectrum (ESI) m/z=665 [M+1].

Example 199

2-((2R,5R,6R)-6-(3-chlorophenyl)-5-(4-chlorophenyl)-4-((S)-1-(N-(2-fluorophenyl)propan-2-ylsulfonamido)-3-methylbutan-2-yl)-3-oxomorpholin-2-yl)acetic acid or 2-((2S,5R,6R)-6-(3-chlorophenyl)-5-(4-chlorophenyl)-4-((S)-1-(N-(2-fluorophenyl)propan-2-ylsulfonamido)-3-methylbutan-2-yl)-3-oxomorpholin-2-yl)acetic acid One of the title compounds was obtained as the second (slower) eluting isomer in Example 198 as a white foam. $^1$H NMR (500 MHz, CDCl$_3$) δ ppm 0.53-0.68 (m, 6 H) 1.35-1.43 (m, 6 H) 2.08-2.17 (m, 1 H) 2.50 (dd, J=16.02, 4.28 Hz, 1 H) 2.75-2.82 (m, 1 H) 3.10-3.25 (m, 2 H) 3.89 (d, J=14.43 Hz, 1 H) 4.51 (br. s., 1 H) 4.65 (dd, J=8.07, 4.40 Hz, 1 H) 4.78 (d, J=10.27 Hz, 1 H) 5.03 (d, J=10.03 Hz, 1 H) 6.94 (d, J=7.58 Hz, 1 H) 7.09-7.33 (m, 9 H) 7.34-7.42 (m, 1 H) 7.74 (t, J=7.34 Hz, 1 H)

Mass spectrum (ESI) m/z=665 [M+1].

Example 200

2-((2R,5R,6R)-6-(3-chlorophenyl)-5-(4-chlorophenyl)-4-((S)-1-(N-(2-fluorophenyl)-2-methylpropan-2-ylsulfonamido)-3-methylbutan-2-yl)-3-oxomorpholin-2-yl)acetic acid or 2-((2S,5R,6R)-6-(3-chlorophenyl)-5-(4-chlorophenyl)-4-((S)-1-(N-(2-fluorophenyl)-2-methylpropan-2-ylsulfonamido)-3-methylbutan-2-yl)-3-oxomorpholin-2-yl)acetic acid

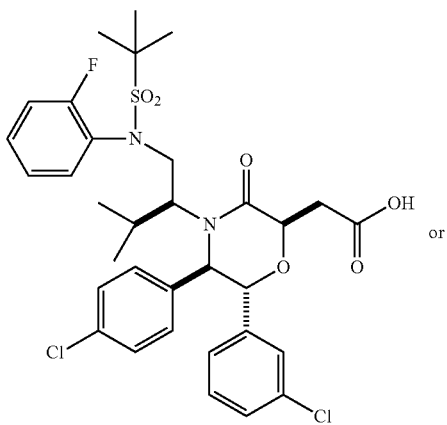

or

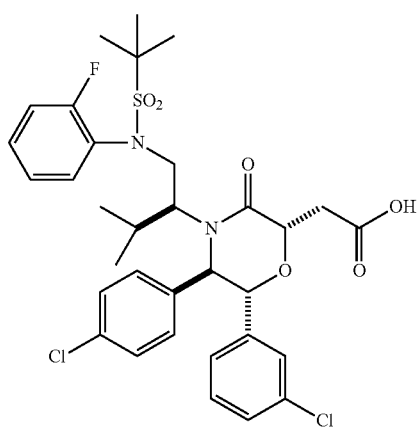

One of the title compounds was prepared from (5R,6R)-6-(3-chlorophenyl)-5-(4-chlorophenyl)-4-((S)-1-hydroxy-3-methylbutan-2-yl)morpholin-3-one (Example 192, Step B) by procedures similar to those described in Example 112, Steps D though F, replacing ethanethiol in Step D with N-(2-fluorophenyl)-2-methylpropane-2-sulfonamide
(prepared by a procedure similar to the one described for N-(2-fluorophenyl)-1-methylcyclopropane-1-sulfonamide in Example 174) The crude product was purified by reverse phase preparatory HPLC (Gemini™ Prep $C_{18}$ 5 μm column; Phenomenex, Torrance, Calif.; gradient elution of 40% to 60% MeCN in water, where both solvents contain 0.1% TFA, 20 min method) to provide one of the title compounds as the first (faster) eluting peak. $^1$H NMR (500 MHz, CDCl$_3$) δ ppm 0.50-0.74 (m, 6 H) 1.36 (s, 9 H) 2.01-2.14 (m, 1 H) 3.04 (br. s., 2 H) 3.91 (br. s., 2 H) 4.52 (br. s., 2 H) 4.92 (d, J=9.29 Hz, 1 H) 5.00 (d, J=9.29 Hz, 1 H) 7.01 (br. s., 1 H) 7.10-7.31 (m, 9 H) 7.31-7.38 (m, 1 H) 7.87 (br. s., 1 H). Mass spectrum (ESI) m/z=679 [M+1].

Example 201

2-((2R,5R,6R)-6-(3-chlorophenyl)-5-(4-chlorophenyl)-4-((S)-1-(N-(2-fluorophenyl)-2-methylpropan-2-ylsulfonamido)-3-methylbutan-2-yl)-3-oxomorpholin-2-yl)acetic acid or 2-((2S,5R,6R)-6-(3-chlorophenyl)-5-(4-chlorophenyl)-4-((S)-1-(N-(2-fluorophenyl)-2-methylpropan-2-ylsulfonamido)-3-methylbutan-2-yl)-3-oxomorpholin-2-yl)acetic acid

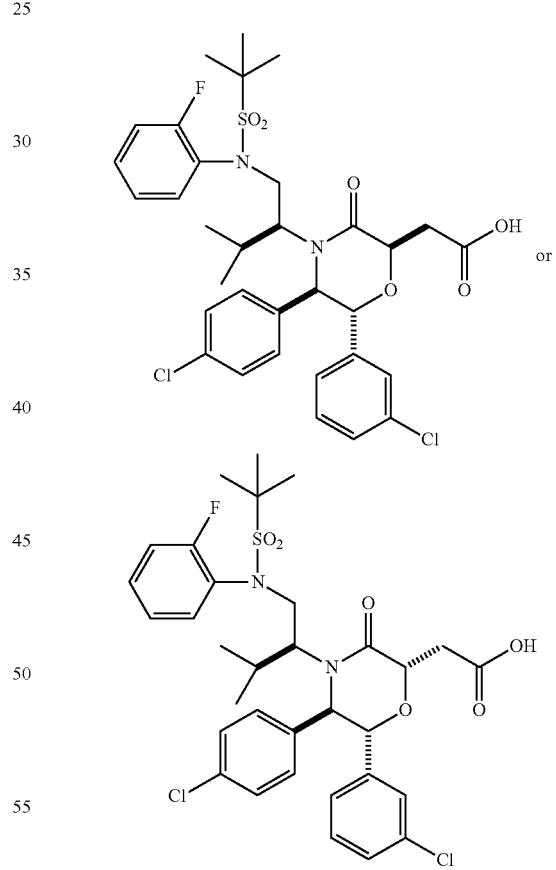

One of the title compounds was obtained as the second (slower) eluting isomer in Example 200 as a white foam. $^1$H NMR (500 MHz, CDCl$_3$) δ ppm 0.48-0.71 (m, 6 H) 1.35 (s, 9 H) 2.00-2.16 (m, 2 H) 3.01 (br. s., 3 H) 3.91 (br. s., 1 H) 4.64 (br. s., 1 H) 4.76 (d, J=9.78 Hz, 1 H) 4.92 (d, J=10.03 Hz, 1 H) 6.95 (br. s., 1 H) 7.10-7.31 (m, 9 H) 7.35 (br. s., 1 H) 7.83 (br. s., 1 H)

Mass spectrum (ESI) m/z=679 [M+1].

Example 202

2-((2R,5R,6R)-6-(3-chlorophenyl)-5-(4-chlorophenyl)-3-oxo-4-((S)-1-(pyridin-2-ylsulfonyl)butan-2-yl)morpholin-2-yl)acetic acid or 2-((2S,5R,6R)-6-(3-chlorophenyl)-5-(4-chlorophenyl)-3-oxo-4-((S)-1-(pyridin-2-ylsulfonyl)butan-2-yl)morpholin-2-yl)acetic acid

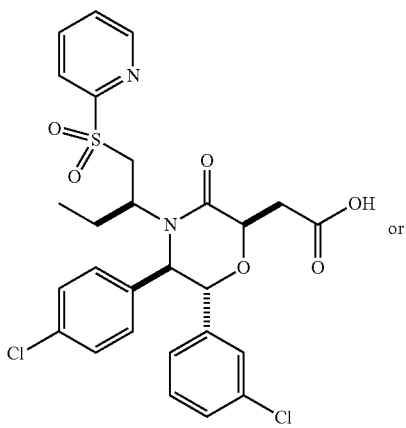

One of the title compounds was prepared from (5R,6R)-6-(3-chlorophenyl)-5-(4-chlorophenyl)-4-((S)-1-hydroxybutan-2-yl)morpholin-3-one (Example 112, Step C) by procedures similar to those described in Example 112, Steps D though F, replacing ethanethiol in Step D with 2-mercaptopyridine. The crude product was purified by reverse phase preparatory HPLC (Gemini™ Prep $C_{18}$ 5 μm column; Phenomenex, Torrance, Calif.; gradient elution of 35% to 55% MeCN in water, where both solvents contain 0.1% TFA, 20 min method) to provide one of the title compounds as the faster eluting isomer as a white foam. $^1$H NMR (400 MHz, CDCl$_3$) δ ppm 0.54 (t, J=7.53 Hz, 3H) 1.60 (ddd, J=14.09, 7.63, 3.91 Hz, 1 H) 2.11-2.23 (m, 1 H) 3.11 (d, J=6.06 Hz, 2 H) 3.44-3.55 (m, 2 H) 4.39 (dd, J=15.06, 9.78 Hz, 1 H) 4.67 (t, J=6.06 Hz, 1 H) 4.93 (d, J=7.43 Hz, 1 H) 5.10 (d, J=7.43 Hz, 1 H) 6.98 (d, J=7.82 Hz, 1 H) 7.12-7.30 (m, 5 H) 7.32-7.37 (m, 2 H) 7.62 (ddd, J=7.73, 4.70, 1.08 Hz, 1 H) 8.01-8.07 (m, 1 H) 8.16 (d, J=7.83 Hz, 1 H) 8.75-8.80 (m, 1 H). Mass spectrum (ESI) m/z=577 [M+1].

Example 203

2-((2R,5R,6R)-6-(3-chlorophenyl)-5-(4-chlorophenyl)-3-oxo-4-((S)-1-(pyridin-2-ylsulfonyl)butan-2-yl)morpholin-2-yl)acetic acid or 2-((2S,5R,6R)-6-(3-chlorophenyl)-5-(4-chlorophenyl)-3-oxo-4-((S)-1-(pyridin-2-ylsulfonyl)butan-2-yl)morpholin-2-yl)acetic acid

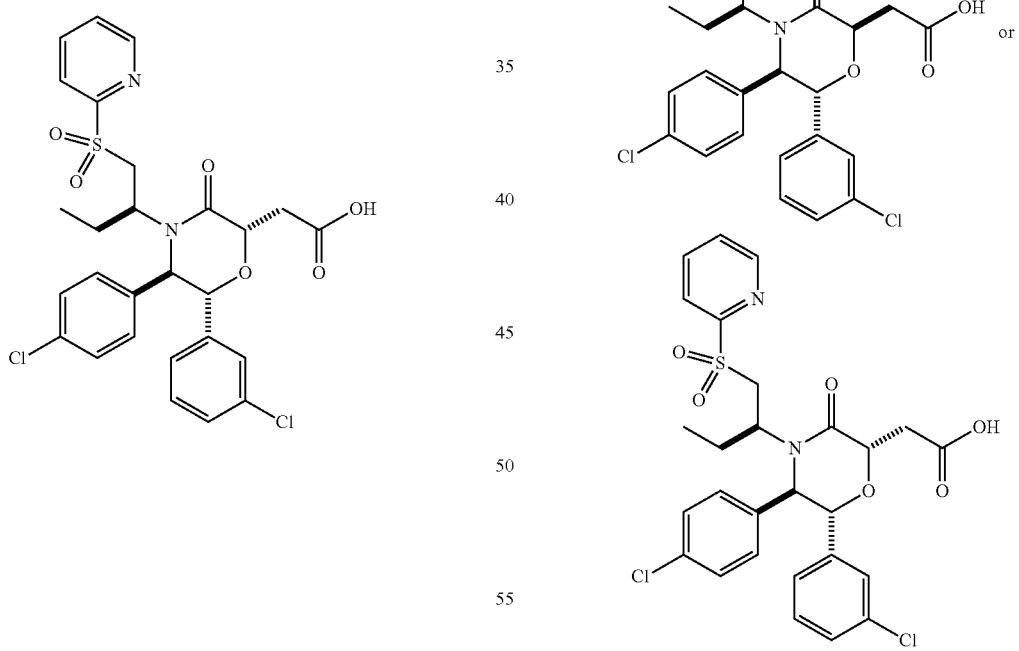

One of the title compounds was obtained as the second (slower) eluting isomer in Example 202 as a white foam. $^1$H NMR (400 MHz, CDCl$_3$) δ ppm 0.56 (t, J=7.53 Hz, 3H) 1.57-1.68 (m, 1 H) 2.12-2.29 (m, 1 H) 3.05-3.20 (m, 3 H) 3.32 (m, 1 H) 4.37 (dd, J=14.48, 9.19 Hz, 1 H) 4.69-4.74 (m, 2 H) 5.18 (d, J=9.78 Hz, 1 H) 6.86 (d, J=7.83 Hz, 1 H) 7.07-7.36 (m, 7 H) 7.65 (ddd, J=7.63, 4.79, 1.08 Hz, 1 H) 8.05 (td, J=7.78, 1.66 Hz, 1 H) 8.15 (d, J=7.82 Hz, 1 H) 8.81 (d, J=4.11 Hz, 1 H). Mass spectrum (ESI) m/z=577 [M+1].

Example 204

2-((2R,5R,6R)-6-(3-chlorophenyl)-5-(4-chlorophenyl)-4-((S)-1-(N-(2,4-difluorophenyl)cyclopropanesulfonamido)butan-2-yl)-3-oxomorpholin-2-yl)acetic acid or 2-((2S,5R,6R)-6-(3-chlorophenyl)-5-(4-chlorophenyl)-4-((S)-1-(N-(2,4-difluorophenyl)cyclopropanesulfonamido)butan-2-yl)-3-oxomorpholin-2-yl) acetic acid

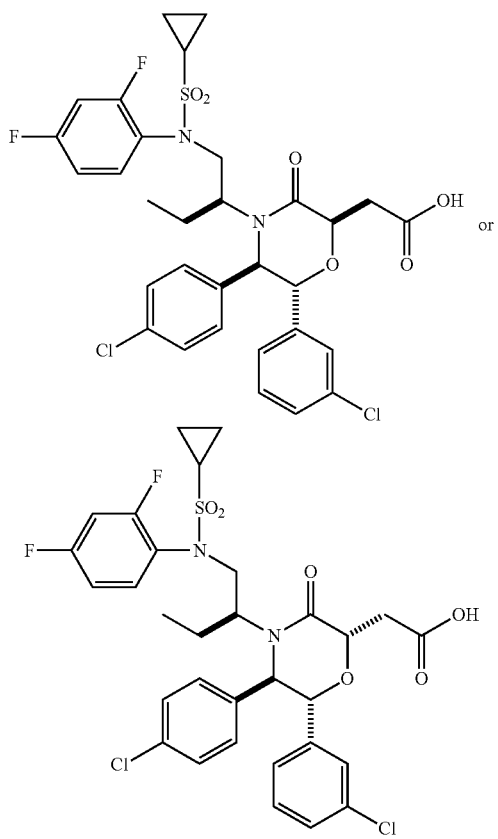

One of the title compounds was prepared from (5R,6R)-6-(3-chlorophenyl)-5-(4-chlorophenyl)-4-((S)-1-hydroxybutan-2-yl)morpholin-3-one (Example 112, Step C) by procedures similar to those described in Example 112, Steps D though F, replacing ethanethiol in Step D with N-(2,4-difluorophenyl)cyclopropanesulfonamide which was made using a procedure similar to that described for N-(2-fluorophenyl) cyclopropanesulfonamide in Example 133. The crude product was purified by reverse phase preparatory HPLC (Gemini™ Prep C$_{18}$ 5 μm column; Phenomenex, Torrance, Calif.; gradient elution of 40% to 60% MeCN in water, where both solvents contain 0.1% TFA, 20 min method) to provide one of the title compounds as the faster eluting isomer as a white foam. $^1$H NMR (500 MHz, CDCl$_3$) δ ppm 0.49 (t, J=7.46 Hz, 3 H) 0.87-1.09 (m, 4 H) 1.48-1.64 (m, 1 H) 1.85-1.94 (m, 1 H) 2.42-2.53 (m, 1 H) 2.97-3.15 (m, 2 H) 3.20 (br. s., 1 H) 3.69-3.82 (m, 1 H) 4.20-4.34 (m, 1 H) 4.48 (t, J=6.48 Hz, 1 H) 4.87 (d, J=7.34 Hz, 1 H) 4.96 (d, J=7.09 Hz, 1 H) 6.90-7.03 (m, 2 H) 7.03-7.13 (m, 1 H) 7.13-7.37 (m, 7 H) 7.38-7.54 (m, 1 H). Mass spectrum (ESI) m/z=667 [M+1].

Example 205

2-((2R,5R,6R)-6-(3-chlorophenyl)-5-(4-chlorophenyl)-4-((S)-1-(N-(2,4-difluorophenyl)cyclopropanesulfonamido)butan-2-yl)-3-oxomorpholin-2-yl)acetic acid or 2-((2S,5R,6R)-6-(3-chlorophenyl)-5-(4-chlorophenyl)-4-((S)-1-(N-(2,4-difluorophenyl)cyclopropanesulfonamido)butan-2-yl)-3-oxomorpholin-2-yl) acetic acid

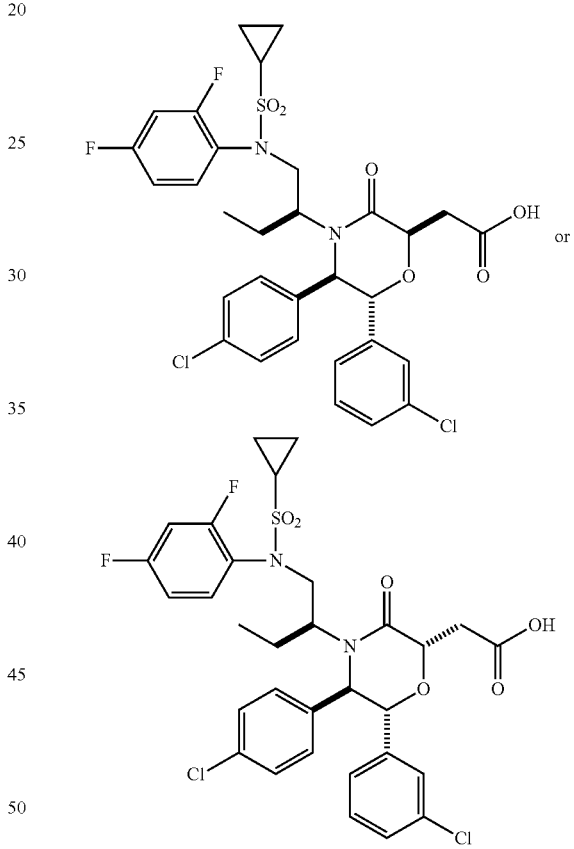

One of the title compounds was obtained as the second (slower) eluting isomer in Example 204 as a white foam. $^1$H NMR (500 MHz, CDCl$_3$) δ ppm 0.50 (t, J=7.58 Hz, 3 H) 0.90-1.10 (m, 4 H) 1.55 (ddd, J=14.31, 7.70, 4.65 Hz, 1 H) 1.94 (ddd, J=14.43, 8.68, 7.46 Hz, 1 H) 2.34-2.46 (m, 1 H) 2.66 (dd, J=16.02, 5.01 Hz, 1 H) 2.94 (dd, J=16.02, 7.46 Hz, 1 H) 3.03 (br. s., 1 H) 3.60-3.78 (m, 1 H) 4.37 (br. s., 1 H) 4.61-4.76 (m, 2 H) 4.89 (d, J=10.03 Hz, 1 H) 6.87 (d, J=7.58 Hz, 1 H) 6.92-7.01 (m, 2 H) 7.01-7.14 (m, 3 H) 7.18 (t, J=7.83 Hz, 1 H) 7.23-7.36 (m, 3 H) 7.44-7.57 (m, 1 H)

Mass spectrum (ESI) m/z=667 [M+1].

Example 206

2-((2R,5R,6R)-6-(3-chlorophenyl)-5-(4-chlorophenyl)-4-((S)-1-(N-(2-cyanophenyl)cyclopropanesulfonamido)butan-2-yl)-3-oxomorpholin-2-yl)acetic acid or 2-((2S,5R,6R)-6-(3-chlorophenyl)-5-(4-chlorophenyl)-4-((S)-1-(N-(2-cyanophenyl)cyclopropanesulfonamido)butan-2-yl)-3-oxomorpholin-2-yl)acetic acid

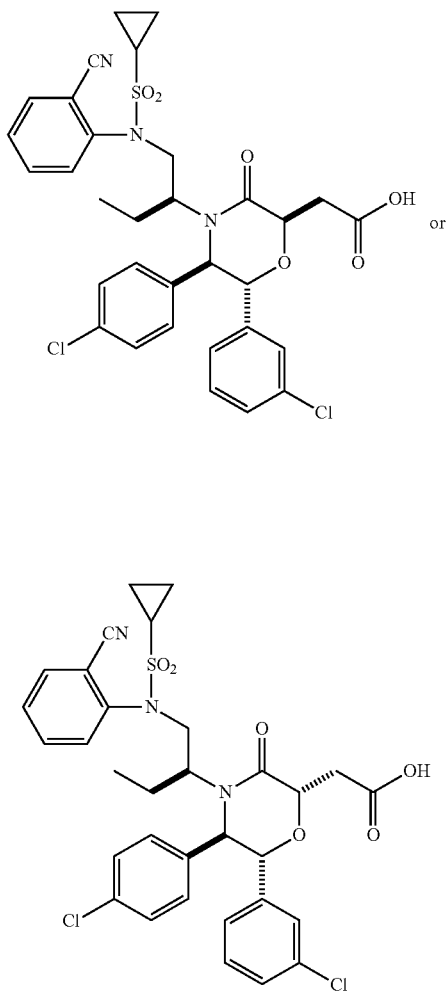

One of the title compounds was prepared from (5R,6R)-6-(3-chlorophenyl)-5-(4-chlorophenyl)-4-((S)-1-hydroxybutan-2-yl)morpholin-3-one (Example 112, Step C) by procedures similar to those described in Example 112, Steps D though F, replacing ethanethiol in Step D with N-(2-cyanophenyl)cyclopropanesulfonamide. which was made using a procedure similar to that described for N-(2-fluorophenyl)cyclopropanesulfonamide in Example 133. The crude product was purified by reverse phase preparatory HPLC (Gemini™ Prep $C_{18}$ 5 μm column; Phenomenex, Torrance, Calif.; gradient elution of 40% to 60% MeCN in water, where both solvents contain 0.1% TFA, 20 min method) to provide one of the title compounds as the faster eluting isomer as a white foam. $^1$H NMR (500 MHz, CDCl$_3$) δ ppm 0.52 (t, J=7.21 Hz, 3 H) 0.90-1.13 (m, 4 H) 1.54 (br. s., 1 H) 1.93 (dt, J=14.86, 7.61 Hz, 1 H) 2.50-2.69 (m, 1 H) 2.99-3.07 (m, 2 H) 3.30 (br. s., 1 H) 3.80-4.08 (m, 1 H) 4.28-4.54 (m, 2 H) 4.86 (d, J=7.58 Hz, 1 H) 4.98 (br. s., 1 H) 6.99-7.08 (m, 1 H) 7.14-7.29 (m, 6 H) 7.33 (d, J=8.56 Hz, 2 H) 7.45-7.56 (m, 1 H) 7.67-7.73 (m, 1 H) 7.76 (d, J=7.58 Hz, 1 H). Mass spectrum (ESI) m/z=656 [M+1].

Example 207

2-((2R,5R,6R)-6-(3-chlorophenyl)-5-(4-chlorophenyl)-4-((S)-1-(N-(2-cyanophenyl)cyclopropanesulfonamido)butan-2-yl)-3-oxomorpholin-2-yl)acetic acid or 2-((2S,5R,6R)-6-(3-chlorophenyl)-5-(4-chlorophenyl)-4-((S)-1-(N-(2-cyanophenyl)cyclopropanesulfonamido)butan-2-yl)-3-oxomorpholin-2-yl)acetic acid

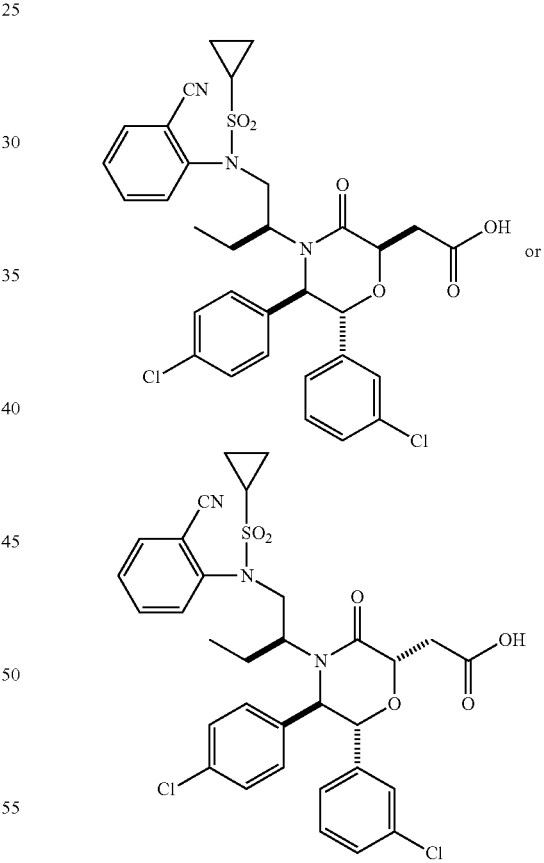

One of the title compounds was obtained as the second (slower) eluting isomer in Example 206 as a white foam. $^1$H NMR (500 MHz, CDCl$_3$) δ ppm 0.54 (t, J=7.21 Hz, 3H) 0.88-1.19 (m, 4 H) 1.55 (m., 1 H) 1.88-2.05 (m, 1 H) 2.43-2.73 (m, 3 H) 3.10-3.34 (m, 1 H) 3.81-4.03 (m., 1 H) 4.50 (m., 1 H) 4.58-4.78 (m, 2 H) 4.78-5.02 (m, 1 H) 6.85 (d, J=7.58 Hz, 1 H) 7.00-7.12 (m, 3 H) 7.12-7.35 (m, 5 H) 7.47-7.56 (m, 1 H) 7.77 (d, J=7.58 Hz, 1 H). Mass spectrum (ESI) m/z=656 [M+1].

Example 208

2-((2R,5R,6R)-6-(3-chlorophenyl)-5-(4-chlorophenyl)-4-((S)-1-(((S)-2-methylpyrrolidin-1-yl)sulfonyl)butan-2-yl)-3-oxomorpholin-2-yl)acetic acid or 2-((2S,5R,6R)-6-(3-chlorophenyl)-5-(4-chlorophenyl)-4-((S)-1-(((S)-2-methylpyrrolidin-1-yl)sulfonyl)butan-2-yl)-3-oxomorpholin-2-yl)acetic acid

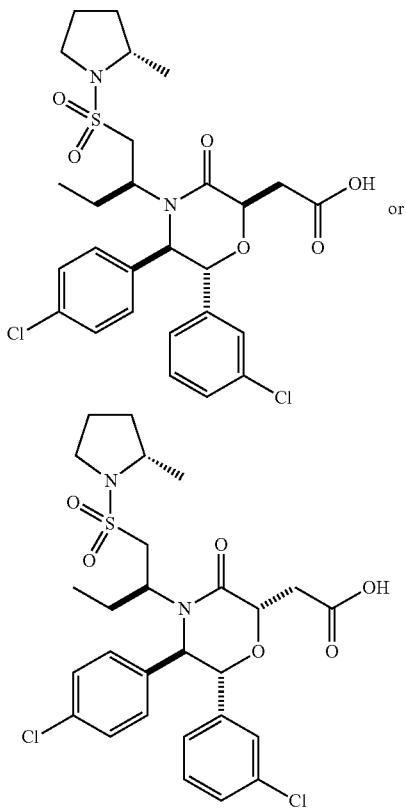

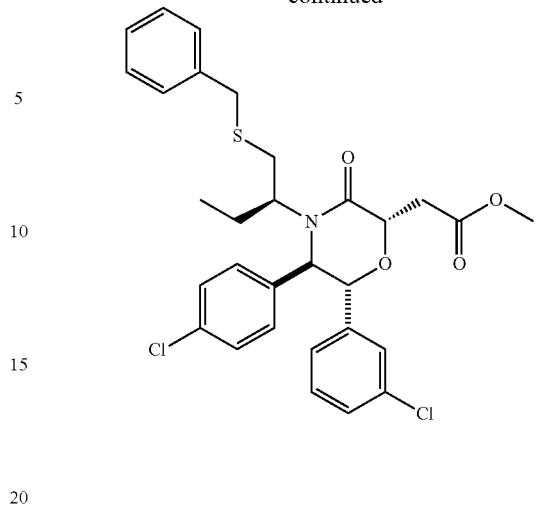

To a solution of methyl 2-((2R,5R,6R)-6-(3-chlorophenyl)-5-(4-chlorophenyl)-4-((S)-1-hydroxybutan-2-yl)-3-oxomorpholin-2-yl)acetate and methyl 2-((2S,5R,6R)-6-(3-chlorophenyl)-5-(4-chlorophenyl)-4-((S)-1-hydroxybutan-2-yl)-3-oxomorpholin-2-yl)acetate (Example 214, Step D; 0.600 g, 1.287 mmol) and benzyl mercaptan (0.755 mL, 6.43 mmol) in toluene (5 mL) was added 2-(tributylphosphoranylidene) acetonitrile (1.863 g, 7.72 mmol) and the resulting solution was heated at 105° C. for 15 hours. The reaction mixture was cooled, concentrated, and loaded onto silica gel without work-up. Purification by flash chromatography (24 g SiO₂, 10% and 20% ethyl acetate/hexanes) provided methyl 2-((2S,5R,6R)-4-((S)-1-(benzylthio)butan-2-yl)-6-(3-chlorophenyl)-5-(4-chlorophenyl)-3-oxomorpholin-2-yl)acetate and methyl 2-((2S,5R,6R)-4-((S)-1-(benzylthio)butan-2-yl)-6-(3-chlorophenyl)-5-(4-chlorophenyl)-3-oxomorpholin-2-yl)acetate as a mixture of diastereomers.

Step A. Methyl 2-((2R,5R,6R)-4-((S)-1-(benzylthio)butan-2-yl)-6-(3-chlorophenyl)-5-(4-chlorophenyl)-3-oxomorpholin-2-yl)acetate and methyl 2-((2S,5R,6R)-4-((S)-1-(benzylthio)butan-2-yl)-6-(3-chlorophenyl)-5-(4-chlorophenyl)-3-oxomorpholin-2-yl)acetate

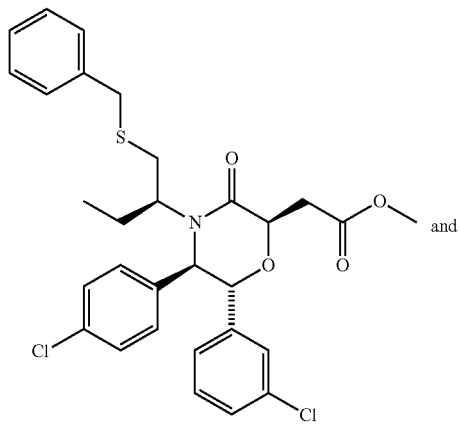

Step B. Methyl 2-((2R,5R,6R)-6-(3-chlorophenyl)-5-(4-chlorophenyl)-4-((S)-1-(chlorosulfonyl)butan-2-yl)-3-oxomorpholin-2-yl)acetate and methyl 2-((2S,5R,6R)-6-(3-chlorophenyl)-5-(4-chlorophenyl)-4-((S)-1-(chloro sulfonyl)butan-2-yl)-3-oxomorpholin-2-yl)acetate

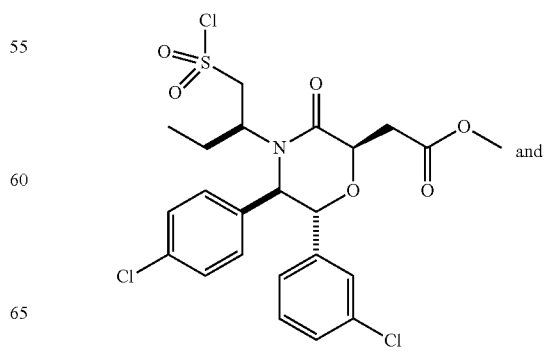

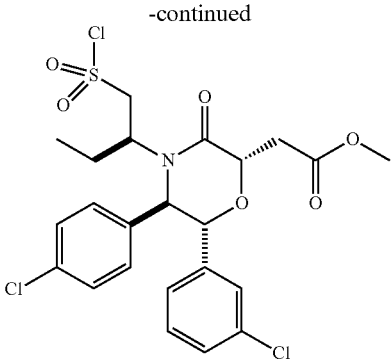

A solution of methyl 2-((2R,5R,6R)-4-((S)-1-(benzylthio)butan-2-yl)-6-(3-chlorophenyl)-5-(4-chlorophenyl)-3-oxomorpholin-2-yl)acetate and methyl 2-((2S,5R,6R)-4-((S)-1-(benzylthio)butan-2-yl)-6-(3-chlorophenyl)-5-(4-chlorophenyl)-3-oxomorpholin-2-yl)acetate (Example 208, Step A; 0.660 g, 1.153 mmol) and iodosobenzene (0.837 g, 3.80 mmol) in hydrochloric acid (4.0 M solution in 1,4-dioxane; 25.4 mL, 101 mmol) was stirred vigorously for 3 hours. The reaction was concentrated under the reduced pressure, and the residue was dried under a vacuum to give the titled products which were taken to the next step without purification.

Step C. Methyl 2-((2R,5R,6R)-6-(3-chlorophenyl)-5-(4-chlorophenyl)-4-((S)-1-(((S)-2-methylpyrrolidin-1-yl)sulfonyl)butan-2-yl)-3-oxomorpholin-2-yl)acetate and methyl 2-((2S,5R,6R)-6-(3-chlorophenyl)-5-(4-chlorophenyl)-4-((S)-1-(((S)-2-methylpyrrolidin-1-yl)sulfonyl)butan-2-yl)-3-oxomorpholin-2-yl)acetate

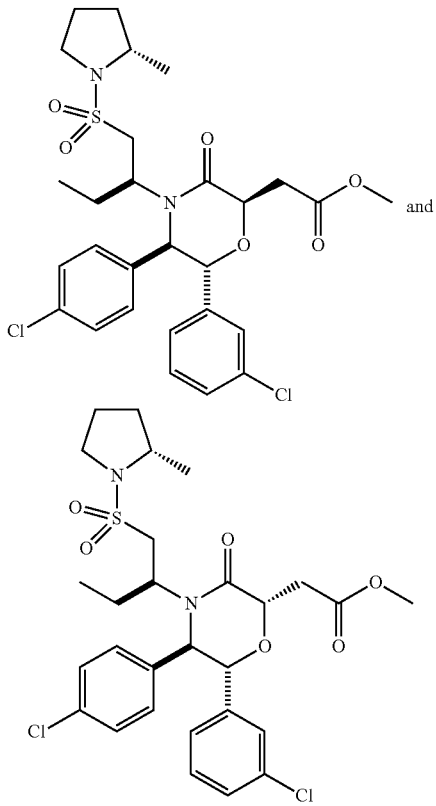

Methyl 2-((2R,5R,6R)-6-(3-chlorophenyl)-5-(4-chlorophenyl)-4-((S)-1-(chlorosulfonyl)butan-2-yl)-3-oxomorpholin-2-yl)acetate and methyl 2-((2S,5R,6R)-6-(3-chlorophenyl)-5-(4-chlorophenyl)-4-((S)-1-(chloro sulfonyl)butan-2-yl)-3-oxomorpholin-2-yl)acetate (Example 208, Step B) was dissolved in DCM (10 mL) at 0° C. and (S)-(+)-2-methylpyrrolidine (0.213 mL, 2.500 mmol) was added to the solution. The reaction was slowly warmed to room temperature and stirred overnight. The reaction was quenched with sat. aq. NH$_4$Cl, extracted with DCM (2×), washed with brine, and the combined organic layers were dried over Na$_2$SO$_4$ and concentrated under reduced pressure. Purification by flash chromatography (24 g SiO$_2$, 25% and 40% ethyl acetate in hexanes) provided methyl 2-((5R,6R)-6-(3-chlorophenyl)-5-(4-chlorophenyl)-4-((S)-1-(((S)-2-methylpyrrolidin-1-yl)sulfonyl)butan-2-yl)-3-oxomorpholin-2-yl)acetate as colorless oil.

Step D. 2-((2R,5R,6R)-6-(3-chlorophenyl)-5-(4-chlorophenyl)-4-((S)-1-(((S)-2-methylpyrrolidin-1-yl)sulfonyl)butan-2-yl)-3-oxomorpholin-2-yl)acetic acid or 2-((2S,5R,6R)-6-(3-chlorophenyl)-5-(4-chlorophenyl)-4-((S)-1-(((S)-2-methylpyrrolidin-1-yl)sulfonyl)butan-2-yl)-3-oxomorpholin-2-yl)acetic acid

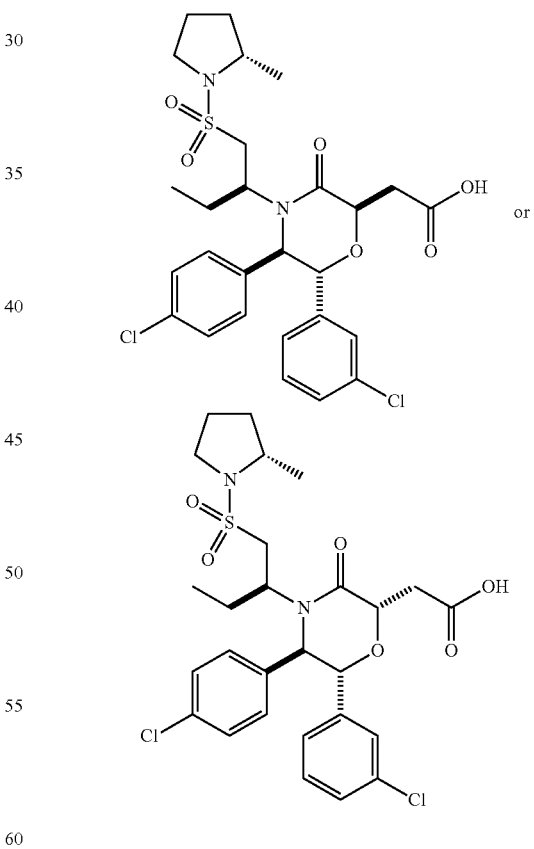

To a solution of methyl 2-((2R,5R,6R)-6-(3-chlorophenyl)-5-(4-chlorophenyl)-4-((S)-1-(((S)-2-methylpyrrolidin-1-yl)sulfonyl)butan-2-yl)-3-oxomorpholin-2-yl)acetate and methyl 2-((2S,5R,6R)-6-(3-chlorophenyl)-5-(4-chlorophenyl)-4-((S)-1-(((S)-2-methylpyrrolidin-1-yl)sulfonyl)butan-2-yl)-3-oxomorpholin-2-yl)acetate (Example 208, Step C, 0.250 g, 0.418 mmol) in THF (1 mL), methanol (1 mL), and water (2 mL) was added lithium hydroxide monohydrate (0.116 mL, 4.18 mmol) at room temperature. After stirring at room temperature for 1.5 hours, the reaction was neutralized with 10% citric acid, extracted with ethyl acetate (2×), and washed with brine. The combined organic layers were dried over Na$_2$SO$_4$ and concentrated under reduced pressure. The crude product was purified by reverse phase preparatory HPLC (Gemini™ Prep C$_{18}$ 5 μm column; Phenomenex, Torrance, Calif.) (eluent: 40-60% acetonitrile in water, where both solvents contain 0.1% TFA, gradient elution) to provide one of the title compounds as the faster eluting isomer $^1$H NMR (500 MHz, CDCl$_3$) δ ppm 0.56 (t, J=7.58 Hz, 3 H) 1.30 (d, J=6.11 Hz, 3 H) 1.55-1.68 (m, 2 H) 1.82-1.93 (m, 1 H) 1.93-2.03 (m, 1 H) 2.03-2.18 (m, 2 H) 2.88 (dd, J=13.69, 2.20 Hz, 1 H) 3.12 (d, J=5.87 Hz, 2 H) 3.32 (dt, J=9.90, 7.27 Hz, 2 H) 3.41 (dq, J=6.88, 5.13 Hz, 1 H) 3.82-3.98 (m, 2 H) 4.77 (t, J=5.99 Hz, 1 H) 4.93 (d, J=6.85 Hz, 1 H) 5.08 (d, J=6.85 Hz, 1 H) 7.05 (dt, J=7.89, 1.56 Hz, 1 H) 7.16 (t, J=7.70 Hz, 1 H) 7.20-7.31 (m, 9 H) 7.31-7.37 (m, 2 H). Mass spectrum (ESI) m/z=583 [M+1].

Example 209

2-((2R,5R,6R)-6-(3-chlorophenyl)-5-(4-chlorophenyl)-4-((S)-1-(((S)-2-methylpyrrolidin-1-yl)sulfonyl)butan-2-yl)-3-oxomorpholin-2-yl)acetic acid or
2-((2S,5R,6R)-6-(3-chlorophenyl)-5-(4-chlorophenyl)-4-((S)-1-(((S)-2-methylpyrrolidin-1-yl)sulfonyl)butan-2-yl)-3-oxomorpholin-2-yl)acetic acid

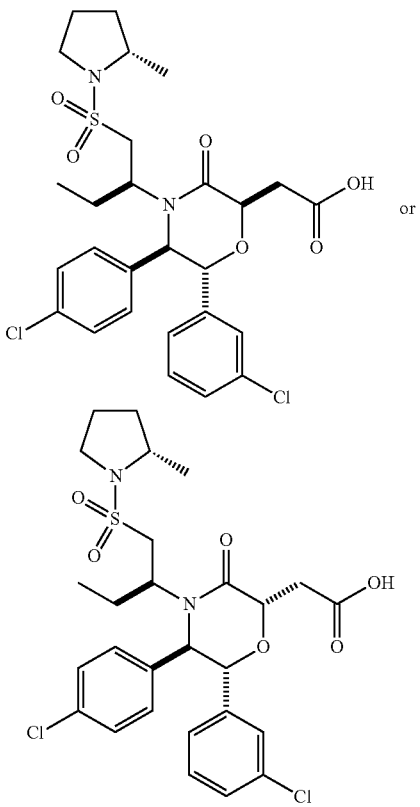

One of the title compounds was obtained as the second (slower) eluting isomer in Example 208 as a white foam. $^1$H NMR (500 MHz, CDCl$_3$) δ ppm 0.55 (t, J=7.46 Hz, 3 H) 1.29 (d, J=6.11 Hz, 3 H) 1.49-1.70 (m, 2 H) 1.80-1.93 (m, 1 H) 1.93-2.03 (m, 1 H) 2.03-2.23 (m, 2 H) 2.72-2.87 (m, 1 H) 2.98 (dd, J=16.38, 4.89 Hz, 1 H) 3.12-3.36 (m, 3 H) 3.36-3.47 (m, 1 H) 3.85-4.02 (m, 2 H) 4.69 (d, J=9.78 Hz, 1 H) 4.77 (t, J=5.99 Hz, 1 H) 5.00 (d, J=9.78 Hz, 1 H) 6.82-6.88 (m, 1 H) 7.04-7.08 (m, 1 H) 7.08-7.16 (m, 3 H) 7.18-7.23 (m, 1 H) 7.31 (d, J=8.31 Hz, 2 H)

Mass spectrum (ESI) m/z=583 [M+1].

Example 210

2-((2R,5R,6R)-6-(3-chlorophenyl)-5-(4-chlorophenyl)-4-((S)-1-(((R)-2-methylpyrrolidin-1-yl)sulfonyl)butan-2-yl)-3-oxomorpholin-2-yl)acetic acid or
2-((2S,5R,6R)-6-(3-chlorophenyl)-5-(4-chlorophenyl)-4-((S)-1-(((R)-2-methylpyrrolidin-1-yl)sulfonyl)butan-2-yl)-3-oxomorpholin-2-yl)acetic acid

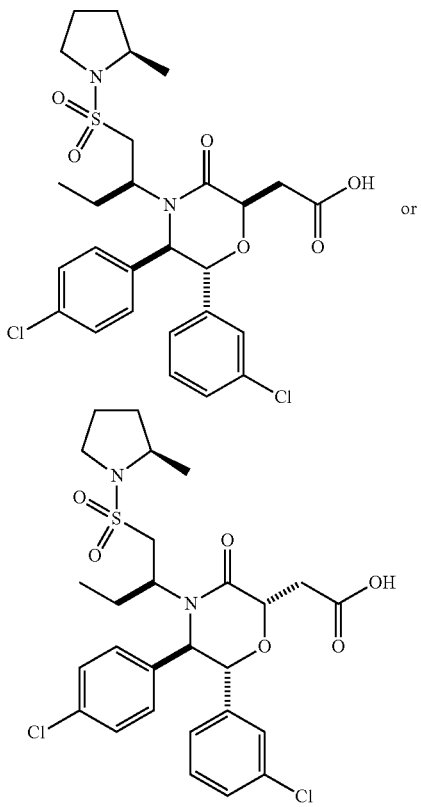

One of the title compounds was prepared from methyl 2-((5R,6R)-4-((S)-1-(benzylthio)butan-2-yl)-6-(3-chlorophenyl)-5-(4-chlorophenyl)-3-oxomorpholin-2-yl)acetate (Example 208, Step A) by procedures similar to those described in Example 208, Steps B though D, replacing (S)-(+)-2-methylpyrrolidine in Step C with (R)-(−)-2-methylpyrrolidine. The crude product was purified by reverse phase preparatory HPLC (Gemini™ Prep C$_{18}$ 5 μm column; Phenomenex, Torrance, Calif.; gradient elution of 40% to 60% MeCN in water, where both solvents contain 0.1% TFA, 20 min method) to provide one of the title compounds as the faster eluting isomer as a white foam. $^1$H NMR (500 MHz, CDCl$_3$) δ ppm 0.56 (t, J=7.21 Hz, 3 H) 1.29 (d, J=6.11 Hz, 3 H) 1.56-1.72 (m, 2 H) 1.89 (dd, J=12.10, 5.99 Hz, 1 H) 1.93-2.03 (m, 1 H) 2.03-2.20 (m, 2 H) 2.88 (d, J=12.47 Hz, 1

H) 3.13 (br. s., 2 H) 3.30 (br. s., 1 H) 3.35-3.48 (m, 2 H) 3.79-3.93 (m, 2 H) 4.80 (t, J=5.62 Hz, 1 H) 4.92 (d, J=7.09 Hz, 1 H) 5.06 (d, J=6.85 Hz, 1 H) 7.01 (d, J=7.83 Hz, 1 H) 7.09-7.19 (m, 1 H) 7.19-7.30 (m, 4 H) 7.33 (d, J=8.56 Hz, 2 H). Mass spectrum (ESI) m/z=583 [M+1].

Example 211

2-((2R,5R,6R)-6-(3-chlorophenyl)-5-(4-chlorophenyl)-4-((S)-1-(((R)-2-methylpyrrolidin-1-yl)sulfonyl)butan-2-yl)-3-oxomorpholin-2-yl)acetic acid or 2-((2S,5R,6R)-6-(3-chlorophenyl)-5-(4-chlorophenyl)-4-((S)-1-(((R)-2-methylpyrrolidin-1-yl)sulfonyl)butan-2-yl)-3-oxomorpholin-2-yl)acetic acid

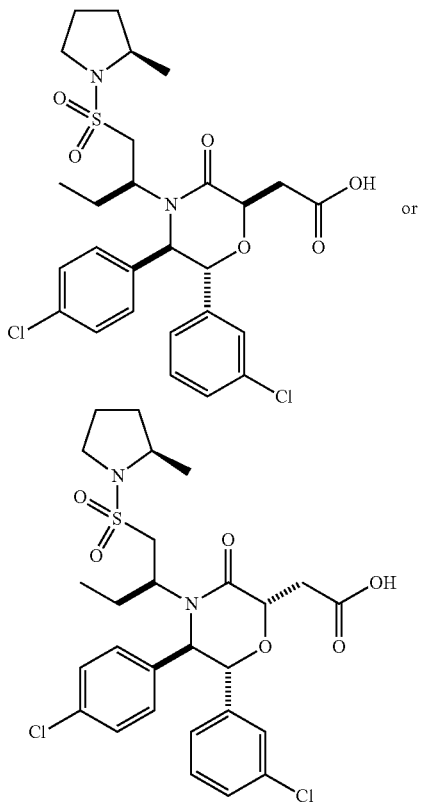

One of the title compounds was obtained as the second (slower) eluting isomer in Example 210 as a white foam. $^1$H NMR (500 MHz, CDCl$_3$) δ ppm 0.56 (t, J=6.24 Hz, 3 H) 1.30 (d, J=6.11 Hz, 3 H) 1.54-1.71 (m, 2 H) 1.83-1.94 (m, 1 H) 1.94-2.04 (m, 1 H) 2.04-2.22 (m, 2 H) 2.83 (d, J=12.47 Hz, 1 H) 2.90-3.01 (m, 1 H) 3.21 (br. s., 1 H) 3.29 (dd, J=16.14, 5.62 Hz, 1 H) 3.36-3.47 (m, 2 H) 3.78-3.89 (m, 1 H) 3.89-4.03 (m, 1 H) 4.69 (d, J=9.54 Hz, 1 H) 4.77 (br. s., 1 H) 5.00 (d, J=9.29 Hz, 1 H) 6.84 (d, J=7.58 Hz, 1 H) 7.06 (s, 1 H) 7.08-7.17 (m, 3 H) 7.17-7.24 (m, 1 H) 7.31 (d, J=7.58 Hz, 6 H). Mass spectrum (ESI) m/z=583 [M+1].

Example 212

2-((2R,5R,6R)-6-(3-chlorophenyl)-5-(4-chlorophenyl)-4-((S)-1-(cyclopropylsulfonyl)butan-2-yl)-3-oxomorpholin-2-yl)acetic acid or 2-((2S,5R,6R)-6-(3-chlorophenyl)-5-(4-chlorophenyl)-4-((S)-1-(cyclopropylsulfonyl)butan-2-yl)-3-oxomorpholin-2-yl)acetic acid

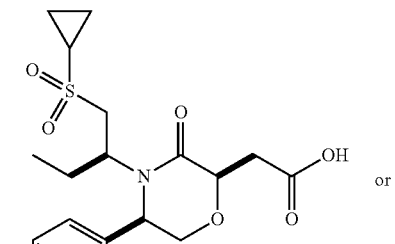

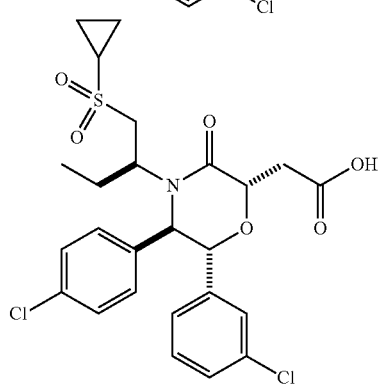

Step A. Cyclopropanethiol

To a solution of cyclopropylmagnesium bromide, 0.5 M in tetrahydrofuran (25 mL, 12.50 mmol) at 0° C. was added sulfur powder (0.401 g, 12.50 mmol) in small portions. The mixture was heated at 50° C. for 3 hours and cooled to 0° C. Lithium aluminum hydride, (1.0 M solution in diethyl ether; 10.0 mL, 10.0 mmol) was added at 0° C. The solution was heated to 65° C. for 30 minutes, and then cooled to 0° C. Water (1 mL), 5% aqueous H$_2$SO$_4$ (5 mL) and ether (10 mL) were added to the chilled solution. The layers were separated and the aqueous layer was extracted with ether (10 mL). The combined ether extract was washed with 5% aqueous H$_2$SO$_4$, 5% aqueous Na$_2$CO$_3$ (4×), and brine. After drying over MgSO$_4$, the solution was filtered and concentrated under a vacuum to approximately 15 mL and taken directly to the next step.

Step B. 2-((2R,5R,6R)-6-(3-chlorophenyl)-5-(4-chlorophenyl)-4-((S)-1-(cyclopropylsulfonyl)butan-2-yl)-3-oxomorpholin-2-yl)acetic acid or 2-((2S,5R,6R)-6-(3-chlorophenyl)-5-(4-chlorophenyl)-4-((S)-1-(cyclopropylsulfonyl)butan-2-yl)-3-oxomorpholin-2-yl)acetic acid

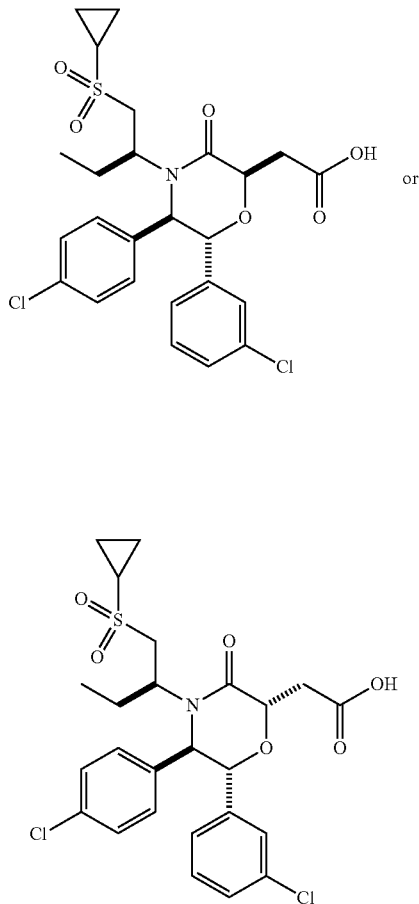

One of the title compounds was prepared from (5R,6R)-6-(3-chlorophenyl)-5-(4-chlorophenyl)-4-((S)-1-hydroxybutan-2-yl)morpholin-3-one (Example 112, Step C) by procedures similar to those described in Example 112, Steps D though F, replacing ethanethiol in Step D with cyclopropanethiol (Example 212, Step A). The crude product was purified by reverse phase preparatory HPLC (Gemini™ Prep C$_{18}$ 5 μm column; Phenomenex, Torrance, Calif.; gradient elution of 35% to 55% MeCN in water, where both solvents contain 0.1% TFA, 20 min method) to provide one of the title compounds as the faster eluting isomer as a white foam. $^1$H NMR (500 MHz, CDCl$_3$) δ ppm 0.57 (t, J=7.46 Hz, 3 H) 1.04-1.14 (m, 2 H) 1.23-1.35 (m, 2 H) 1.56-1.66 (m, 1 H) 2.09-2.20 (m, 1 H) 2.38-2.45 (m, 1 H) 2.99-3.17 (m, 3 H) 3.40 (br. s., 1 H) 4.03-4.16 (m, 1 H) 4.73 (t, J=5.99 Hz, 1 H) 4.94 (d, J=6.85 Hz, 1 H) 5.08 (d, J=6.85 Hz, 1 H) 7.02 (d, J=7.83 Hz, 1 H) 7.15-7.21 (m, 1 H) 7.22-7.30 (m, 4 H) 7.31-7.37 (m, 2 H). Mass spectrum (ESI) m/z=540 [M+1].

Example 213

2-((2R,5R,6R)-6-(3-chlorophenyl)-5-(4-chlorophenyl)-4-((S)-1-(cyclopropylsulfonyl)butan-2-yl)-3-oxomorpholin-2-yl)acetic acid or 2-((2S,5R,6R)-6-(3-chlorophenyl)-5-(4-chlorophenyl)-4-((S)-1-(cyclopropylsulfonyl)butan-2-yl)-3-oxomorpholin-2-yl)acetic acid

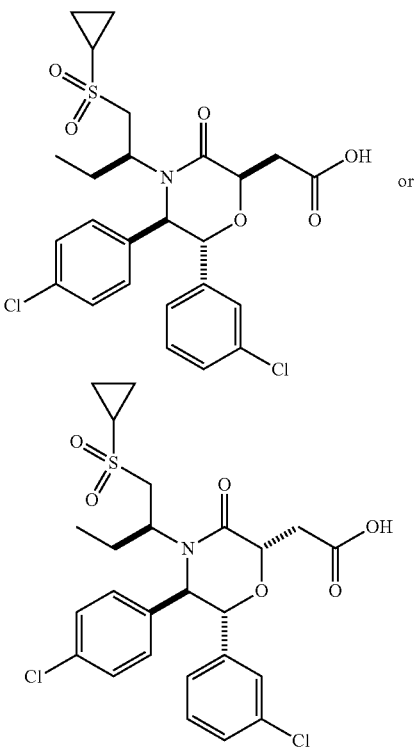

One of the title compounds was obtained as the second (slower) eluting isomer in Example 212 as a white foam. $^1$H NMR (500 MHz, CDCl$_3$) δ ppm 0.57 (t, J=7.46 Hz, 3 H) 1.04-1.13 (m, 2 H) 1.24-1.34 (m, 2 H) 1.61 (ddd, J=13.88, 7.64, 3.91 Hz, 1 H) 2.19 (ddd, J=14.18, 9.78, 7.34 Hz, 1 H) 2.39-2.47 (m, 1 H) 2.93-3.07 (m, 2 H) 3.23 (dd, J=16.26, 6.97 Hz, 1 H) 3.31 (br. s., 1 H) 4.09-4.24 (m, 1 H) 4.69 (d, J=9.78 Hz, 1 H) 4.73 (dd, J=6.97, 4.77 Hz, 1 H) 5.03 (d, J=9.78 Hz, 1 H) 6.82 (d, J=7.82 Hz, 1 H) 7.01-7.07 (m, 1 H) 7.07-7.15 (m, 3 H) 7.18-7.22 (m, 1 H) 7.31 (d, J=8.56 Hz, 2 H). Mass spectrum (ESI) m/z=540 [M+1].

Example 214

2-((2R,5R,6R)-6-(3-chlorophenyl)-5-(4-chlorophenyl)-4-((S)-1-(N,N-dimethylsulfamoyl)butan-2-yl)-3-oxomorpholin-2-yl)acetic acid

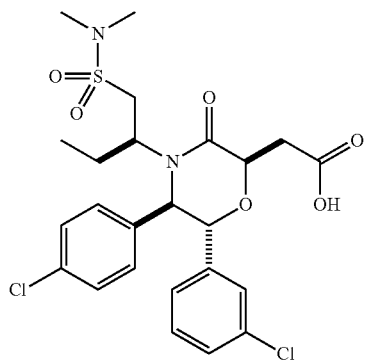 [SMILES: CC[C@@H](CS(=O)(=O)N(C)C)N1C(=O)[C@@H](CC(=O)O)O[C@H](c2cccc(Cl)c2)[C@H]1c1ccc(Cl)cc1]

Step A. (5R,6R)-4-((S)-1-((tert-butyldimethylsilyl)oxy)butan-2-yl)-6-(3-chlorophenyl)-5-(4-chlorophenyl)morpholin-3-one

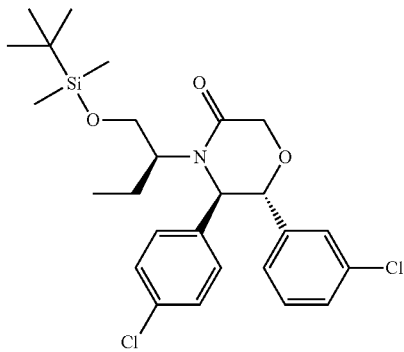 [SMILES: CC[C@@H](CO[Si](C)(C)C(C)(C)C)N1C(=O)CO[C@H](c2cccc(Cl)c2)[C@H]1c1ccc(Cl)cc1]

Following the procedure of Oriama (Oriyama, T.; Yatabe, K.; Kawada, Y.; Koga, G. *Synlett* 1995, 45), tert-butyldimethylsilyl trifluoromethanesulfonate (1.09 mL, 4.73 mmol) was added to a solution of (5R,6R)-6-(3-chlorophenyl)-5-(4-chlorophenyl)-4-((S)-1-((3,4-dimethoxybenzyl)oxy)butan-2-yl)morpholin-3-one (1.12 g, 2.06 mmol, Example 112, Step B) in DCM (21 mL) at 25° C. After stirring at 25° C. for 1 hour, triethylamine (0.774 mL, 5.55 mmol) was added. After stirring an additional 20 minutes at 25° C., the reaction was quenched with water, extracted with DCM (2×) and washed with brine. The combined organic layers were dried over Na$_2$SO$_4$ and concentrated under reduced pressure. Purification of the residue by flash chromatography on silica gel (40 g SiO$_2$, 15% and 20% ethyl acetate in hexanes) provided (5R,6R)-4-((S)-1-((tert-butyldimethylsilyl)oxy)butan-2-yl)-6-(3-chlorophenyl)-5-(4-chlorophenyl)morpholin-3-one as a colorless liquid.

Step B. (2R,5R,6R)-2-allyl-4-((S)-1-((tert-butyldimethylsilyl)oxy)butan-2-yl)-6-(3-chlorophenyl)-5-(4-chlorophenyl)morpholin-3-one and (2S,5R,6R)-2-allyl-4-((S)-1-((tert-butyldimethylsilyl)oxy)butan-2-yl)-6-(3-chlorophenyl)-5-(4-chlorophenyl)morpholin-3-one

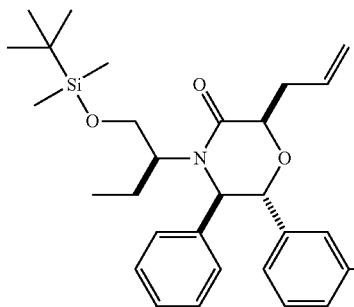

and

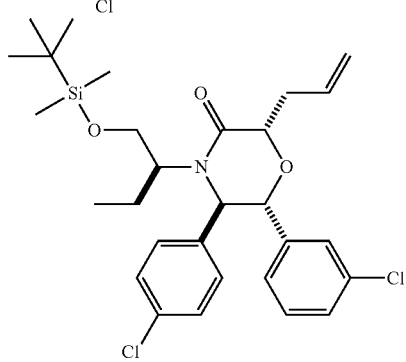

To a solution of (5R,6R)-4-((S)-1-((tert-butyldimethylsilyl)oxy)butan-2-yl)-6-(3-chlorophenyl)-5-(4-chlorophenyl)morpholin-3-one (687 mg, 1.35 mmol; Example 214, Step A) and allyl bromide (175 μL, 2.03 mmol) in THF (5.4 mL) was added lithium bis(trimethylsilyl)amide 1 M in THF (1.62 mL, 1.62 mmol) at 78° C. dropwise under Ar. After stirring at 78° C. for 5 hours, the reaction was quenched with sat. aqueous NH$_4$Cl, extracted with ethyl acetate (2×), and washed with brine. The combined organic layers were dried over Na$_2$SO$_4$ and concentrated under reduced pressure. Purification of the residue by flash chromatography on silica gel (40 g SiO$_2$, 10% and 15% ethyl acetate in hexanes) provided the title compounds as a mixture of diastereomers.

Step C. Methyl 2-((2R,5R,6R)-4-((S)-1-((tert-butyldimethylsilyl)oxy)butan-2-yl)-6-(3-chlorophenyl)-5-(4-chlorophenyl)-3-oxomorpholin-2-yl)acetate and methyl 2-((2S,5R,6R)-4-((S)-1-((tert-butyldimethylsilyl)oxy)butan-2-yl)-6-(3-chlorophenyl)-5-(4-chlorophenyl)-3-oxomorpholin-2-yl)acetate

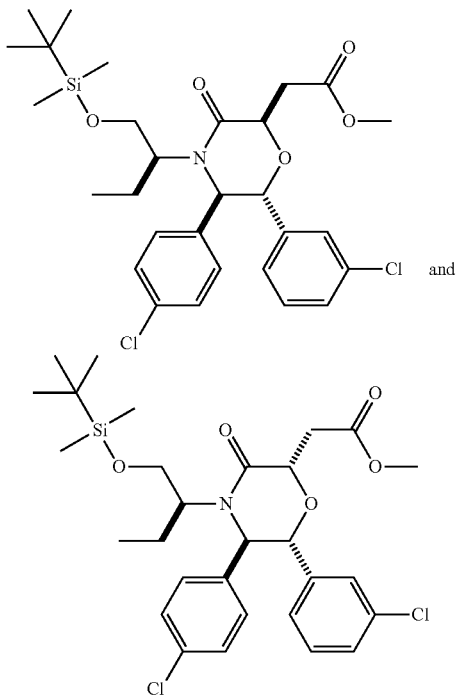

To a solution of (2R,5R,6R)-2-allyl-4-((S)-1-((tert-butyldimethylsilyl)oxy)butan-2-yl)-6-(3-chlorophenyl)-5-(4-chlorophenyl)morpholin-3-one and (2S,5R,6R)-2-allyl-4-((S)-1-((tert-butyldimethylsilyl)oxy)butan-2-yl)-6-(3-chlorophenyl)-5-(4-chlorophenyl)morpholin-3-one (673 mg, 1.23 mmol; Example 214, Step B) and sodium periodate (525 mg, 2.45 mmol) in acetonitrile (4.4 mL), $CCl_4$ (4.4 mL), and water (6.6 mL) was added ruthenium(III) chloride hydrate (28 mg, 0.12 mmol) at 25° C. After being stirred vigorously at 25° C. for 20 minutes, additional sodium periodate (525 mg, 2.45 mmol) was added. The reaction was stirred at 25° C. for 5 hours and diluted with brine and ethyl acetate. The filtrate was filtered through Celite® (diatomaceous earth), extracted with ethyl acetate (2×), and the combined organic layers were washed with brine, dried over $Na_2SO_4$, and concentrated under reduced pressure to provide a crude carboxylic acid intermediate. The crude carboxylic acid was dissolved in MeOH (2.0 mL) and DCM (8.0 mL) and cooled to 0° C. (Trimethylsilyl)diazomethane (2.0 M in diethyl ether; 1.22 mL, 2.45 mmol) was added and the reaction was slowly warmed to 25° C. After stirring at 25° C. for 22 hours, the reaction was concentrated under reduced pressure and purified by flash chromatography on silica gel (4 g $SiO_2$, 16% and 26% ethyl acetate in hexanes) to provide the title compounds as a mixture of diastereomers.

Step D. Methyl 2-((2R,5R,6R)-6-(3-chlorophenyl)-5-(4-chlorophenyl)-4-((S)-1-hydroxybutan-2-yl)-3-oxomorpholin-2-yl)acetate and methyl 2-((2S,5R,6R)-6-(3-chlorophenyl)-5-(4-chlorophenyl)-4-((S)-1-hydroxybutan-2-yl)-3-oxomorpholin-2-yl)acetate

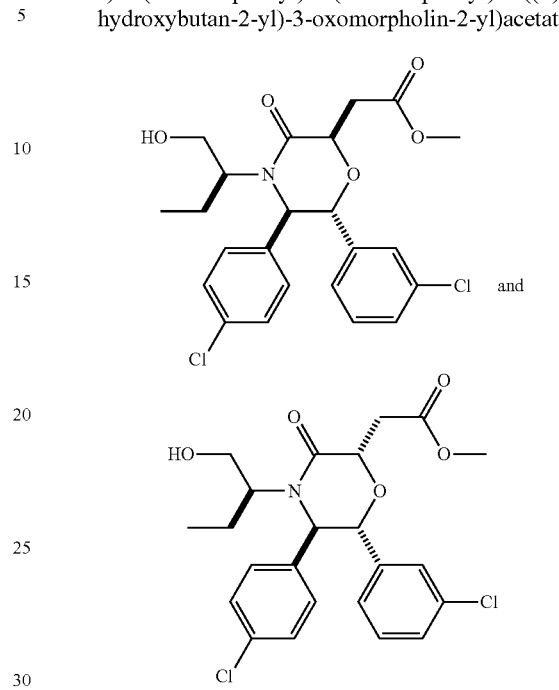

To a solution of methyl 2-((2R,5R,6R)-4-((S)-1-((tert-butyldimethylsilyl)oxy)butan-2-yl)-6-(3-chlorophenyl)-5-(4-chlorophenyl)-3-oxomorpholin-2-yl)acetate and methyl 2-((2S,5R,6R)-4-((S)-1-((tert-butyldimethylsilyl)oxy)butan-2-yl)-6-(3-chlorophenyl)-5-(4-chlorophenyl)-3-oxomorpholin-2-yl)acetate (385 mg, 0.663 mmol; Example 214, Step C) in THF (6.6 mL) was added 1 M tetrabutylammonium fluoride in THF (2.0 mL, 2.0 mmol) dropwise at 25° C. After stirring at 25° C. for 24 hours, the reaction was quenched with saturated aq. $NH_4Cl$, extracted with ethyl acetate (2×) and washed with brine. The combined organic layers were dried over $Na_2SO_4$ and concentrated under reduced pressure. Purification by flash chromatography on silica gel (24 g $SiO_2$, 37% and 47% ethyl acetate in hexanes) provided the title compounds as a mixture of diastereomers.

Step E. Methyl 2-((2R,5R,6R)-4-((S)-1-(benzylthio)butan-2-yl)-6-(3-chlorophenyl)-5-(4-chlorophenyl)-3-oxomorpholin-2-yl)acetate and methyl 2-((2S,5R,6R)-4-((S)-1-(benzylthio)butan-2-yl)-6-(3-chlorophenyl)-5-(4-chlorophenyl)-3-oxomorpholin-2-yl)acetate

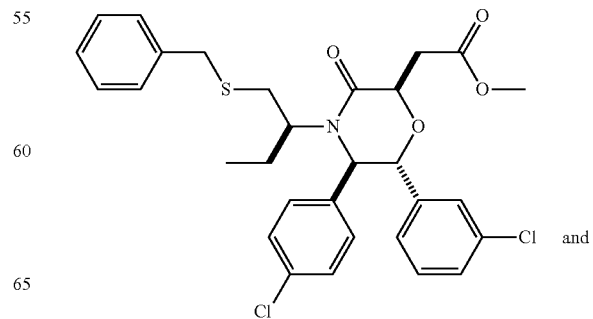

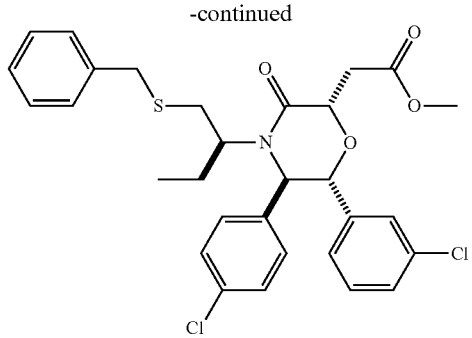

To a solution of methyl 2-((2R,5R,6R)-6-(3-chlorophenyl)-5-(4-chlorophenyl)-4-((S)-1-hydroxybutan-2-yl)-3-oxomorpholin-2-yl)acetate and methyl 2-((2S,5R,6R)-6-(3-chlorophenyl)-5-(4-chlorophenyl)-4-((S)-1-hydroxybutan-2-yl)-3-oxomorpholin-2-yl)acetate (247 mg, 0.530 mmol; Example 214, Step D) and phenylmethanethiol (312 μL, 2.65 mmol) in toluene (2.7 mL) was added 2-(tributylphosphoranylidene)acetonitrile (852 μL, 3.18 mmol) and the resulting solution was heated at 105° C. for 18 hours. The reaction was cooled and loaded directly onto a silica gel column. Purification by flash chromatography on silica gel (24 g $SiO_2$, 10% and 20% ethyl acetate in hexanes) provided the title compounds as a mixture of diastereomers.

Step F. Methyl 2-((2R,5R,6R)-6-(3-chlorophenyl)-5-(4-chlorophenyl)-4-((S)-1-(N,N-dimethylsulfamoyl)butan-2-yl)-3-oxomorpholin-2-yl)acetate and methyl 2-((2S,5R,6R)-6-(3-chlorophenyl)-5-(4-chlorophenyl)-4-((S)-1-(N,N-dimethylsulfamoyl)butan-2-yl)-3-oxomorpholin-2-yl)acetate

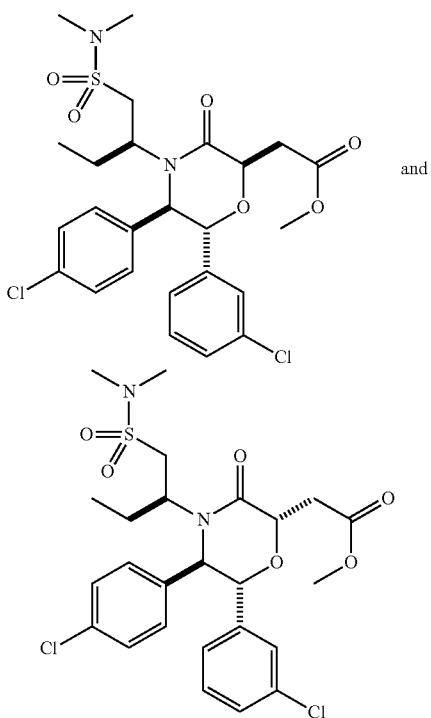

A solution of methyl 2-((2R,5R,6R)-4-((S)-1-(benzylthio)butan-2-yl)-6-(3-chlorophenyl)-5-(4-chlorophenyl)-3-oxomorpholin-2-yl)acetate and methyl 2-((2S,5R,6R)-4-((S)-1-(benzylthio)butan-2-yl)-6-(3-chlorophenyl)-5-(4-chlorophenyl)-3-oxomorpholin-2-yl)acetate (194 mg, 0.339 mmol; Example 214, Step E) and iodosobenzene (246 mg, 1.12 mmol) in hydrogen chloride (4 M in dioxane; 7.5 mL, 30 mmol) was stirred vigorously at 25° C. for 3 hours. The reaction was concentrated under reduced pressure and the residue was dried under a vacuum overnight. The residue was dissolved in DCM (6.8 mL) and dimethylamine hydrochloride (138 mg, 1.69 mmol) was added to the solution. The slurry was cooled to 0° C. and N-ethyl-N-isopropylpropan-2-amine (295 μL, 1.69 mmol) was added. The reaction was slowly warmed to 25° C. and stirred for 3 hours. The reaction was quenched with sat. aq. $NH_4Cl$, extracted with DCM (2×), and washed with brine. The combined organic layers were dried over $Na_2SO_4$ and concentrated under reduced pressure. Purification by reverse phase preparatory HPLC (Gemini™ Prep $C_{18}$ 5 μm column; Phenomenex, Torrance, Calif.; gradient elution of 45% to 70% MeCN in water, where both solvents contain 0.1% TFA, 30 minute method) provided methyl 2-((2R,5R,6R)-6-(3-chlorophenyl)-5-(4-chlorophenyl)-4-((S)-1-(N,N-dimethylsulfamoyl)butan-2-yl)-3-oxomorpholin-2-yl)acetate (more polar isomer) and methyl 2-((2S,5R,6R)-6-(3-chlorophenyl)-5-(4-chlorophenyl)-4-((S)-1-(N,N-dimethylsulfamoyl)butan-2-yl)-3-oxomorpholin-2-yl)acetate (less polar isomer) successively.

Step G. 2-((2R,5R,6R)-6-(3-chlorophenyl)-5-(4-chlorophenyl)-4-((S)-1-(N,N-dimethylsulfamoyl)butan-2-yl)-3-oxomorpholin-2-yl)acetic acid

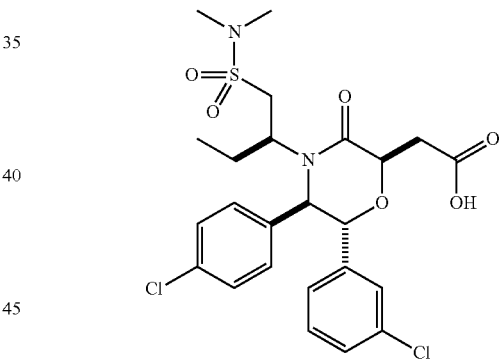

To a solution of methyl 2-((2S,5R,6R)-6-(3-chlorophenyl)-5-(4-chlorophenyl)-4-((S)-1-(N,N-dimethylsulfamoyl)butan-2-yl)-3-oxomorpholin-2-yl)acetate (17 mg, 0.030 mmol; Example 214, Step F, more polar, earlier eluting isomer) in THF (87 μL), methanol (87 μL), and water (131 μL) was added 2 M aq. lithium hydroxide (30 μL, 0.061 mmol) at 25° C. After stirring at 25° C. for 1.5 hours, the reaction was neutralized with 10% citric acid, extracted with ethyl acetate (2×), and washed with brine. The combined organic layers were dried over $Na_2SO_4$ and concentrated under reduced pressure. Purification by reverse phase preparatory HPLC (Gemini™ Prep $C_{18}$ 5 μm column; Phenomenex, Torrance, Calif.; gradient elution of 45% to 70% acetonitrile in water, where both solvents contain 0.1% TFA, 30 min method) provided the title compound as a pale yellow foam. $^1$H NMR (400 MHz, $CDCl_3$) δ ppm 7.31-7.36 (2 H, m), 7.20-7.26 (4 H, m), 7.12-7.19 (1 H, m), 7.01 (1 H, d, J=7.6 Hz), 5.03 (1 H, d, J=7.0 Hz), 4.93 (1 H, d, J=7.0 Hz), 4.77 (1 H, t, J=6.0 Hz), 3.87 (1 H, dd, J=13.7, 9.4 Hz), 3.29 (1 H, br. s.), 3.11 (2 H, d, J=6.1 Hz), 2.89 (3 H, s), 2.89 (3 H, s), 2.82-2.87 (1 H, m), 2.05-2.20 (1 H, m), 1.63 (1 H, ddd, J=13.9, 7.7, 4.2 Hz), 0.56 (3 H, t, J=7.5 Hz). MS (ESI) 543.2 [M+H]+.

Example 215

2-((2S,5R,6R)-6-(3-chlorophenyl)-5-(4-chlorophenyl)-4-((S)-1-(N,N-dimethylsulfamoyl)butan-2-yl)-3-oxomorpholin-2-yl)acetic acid

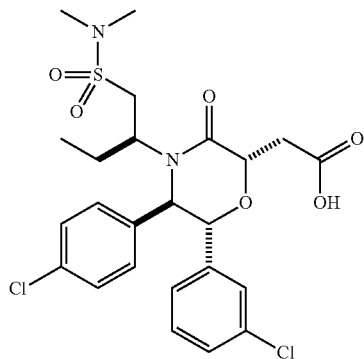

The title compound was obtained from methyl 2-((2S,5R,6R)-6-(3-chlorophenyl)-5-(4-chlorophenyl)-4-((S)-1-(N,N-dimethylsulfamoyl)butan-2-yl)-3-oxomorpholin-2-yl)acetate (Example 214, Step F, less polar isomer) by a procedure similar to that described in Example 214, Step G as a pale yellow foam. $^1$H NMR (400 MHz, CDCl$_3$) δ ppm 7.30 (2 H, d, J=8.4 Hz), 7.18-7.24 (1 H, m), 7.08-7.15 (3 H, m), 7.05 (1 H, t, J=1.7 Hz), 6.83 (1 H, d, J=7.6 Hz), 4.97 (1 H, d, J=9.8 Hz), 4.77 (1 H, t, J=5.9 Hz), 4.68 (1 H, d, J=9.8 Hz), 3.92 (1 H, dd, J=13.4, 10.3 Hz), 3.20-3.29 (1 H, m), 3.20 (1 H, br. s.), 2.97 (1 H, dd, J=16.2, 5.3 Hz), 2.88 (6 H, s), 2.88 (6 H, s), 2.80 (1 H, dd, J=13.9, 2.7 Hz), 2.14 (1 H, ddd, J=14.2, 9.5, 7.4 Hz), 1.53-1.73 (1 H, m), 0.56 (3 H, t, J=7.5 Hz); MS (ESI) 543.2 [M+H]+.

Example 216

2-((2R,5S,6R)-6-(3-chlorophenyl)-5-(5-chlorothiophen-2-yl)-4-((S)-1-(N-(2-fluorophenyl)cyclopropanesulfonamido)butan-2-yl)-3-oxomorpholin-2-yl)acetic acid or 2-((2S,5S,6R)-6-(3-chlorophenyl)-5-(5-chlorothiophen-2-yl)-4-((S)-1-(N-(2-fluorophenyl)cyclopropanesulfonamido)butan-2-yl)-3-oxomorpholin-2-yl)acetic acid

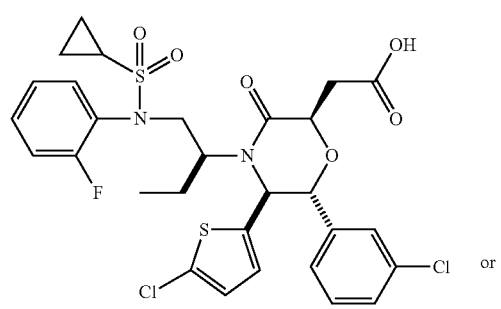

or

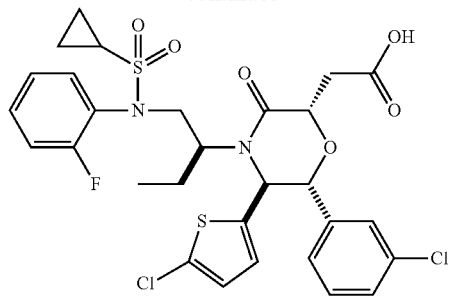

Step A. (E)-tert-butyl 4-((((1S,2R)-2-(3-chlorophenyl)-1-(5-chlorothiophen-2-yl)-2-hydroxyethyl)amino)-4-oxobut-2-enoate

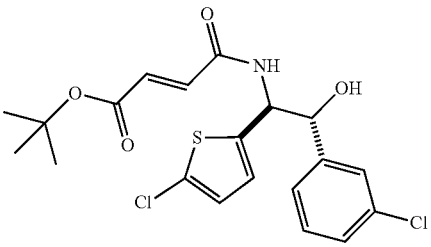

To a solution of (E)-4-(tert-butoxy)-4-oxobut-2-enoic acid (406 mg, 2.36 mmol) and (1R,2S)-2-amino-1-(3-chlorophenyl)-2-(5-chlorothiophen-2-yl)ethanol (567 mg, 1.97 mmol; Intermediate D1, page 75) in DMF (3.7 mL) was added HBTU (858 mg, 2.26 mmol) followed by DIEA (857 μL, 4.92 mmol) at 25° C. After stirring at 25° C. for 16 hours, the reaction was quenched with 10% aq. citric acid, extracted ethyl acetate (3×), and washed with sat. aq. NaHCO$_3$ and brine. The combined organic layers were dried over Na$_2$SO$_4$ and concentrated under reduced pressure. Purification by flash chromatography on silica gel (SiO$_2$, 40 g, 20% and 40% ethyl acetate in hexanes) provided the title compound as a pale yellow film.

Step B. tert-Butyl 2-((2R,5S,6R)-6-(3-chlorophenyl)-5-(5-chlorothiophen-2-yl)-3-oxomorpholin-2-yl)acetate and tert-butyl 2-((2S,5S,6R)-6-(3-chlorophenyl)-5-(5-chlorothiophen-2-yl)-3-oxomorpholin-2-yl)acetate

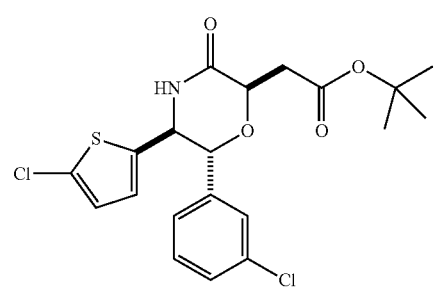

and

-continued

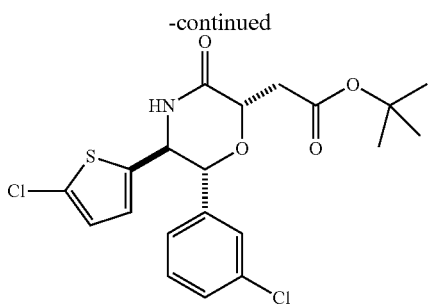

To a solution of (E)-tert-butyl 4-(((1S,2R)-2-(3-chlorophenyl)-1-(5-chlorothiophen-2-yl)-2-hydroxyethyl)amino)-4-oxobut-2-enoate (493 mg, 1.11 mmol; Example 216, Step A) in THF (12.4 mL) was added sodium hydride (60% in mineral oil; 134 mg, 3.34 mmol) at 0° C. The reaction was allowed to warm to 25° C. and stirred for 70 minutes. The reaction was quenched with sat. aq. NH$_4$Cl, extracted with ethyl acetate (2×), and washed with brine. The combined organic layers were dried (Na$_2$SO$_4$) and concentrated under reduced pressure. Purification by flash chromatography on silica gel (SiO$_2$, 40 g, 30% ethyl acetate in hexanes) provided the title compounds as a mixture of diastereomers.

Step C. tert-Butyl 2-((2R,5S,6R)-6-(3-chlorophenyl)-5-(5-chlorothiophen-2-yl)-4-((S)-1-((3,4-dimethoxybenzyl)oxy)butan-2-yl)-3-oxomorpholin-2-yl)acetate and tert-butyl 2-((2S,5S,6R)-6-(3-chlorophenyl)-5-(5-chlorothiophen-2-yl)-4-((S)-1-((3,4-dimethoxybenzyl)oxy)butan-2-yl)-3-oxomorpholin-2-yl)acetate

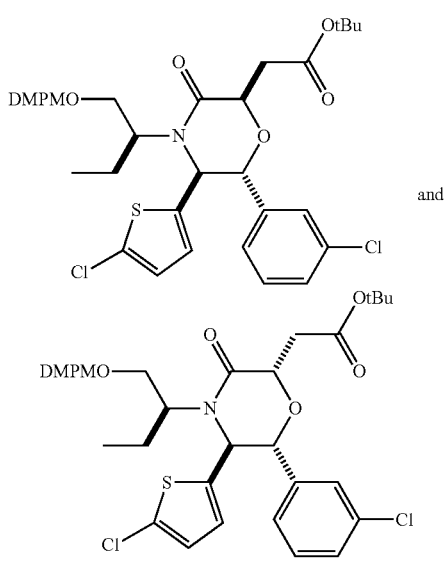

To a solution of tert-butyl 2-((2R,5S,6R)-6-(3-chlorophenyl)-5-(5-chlorothiophen-2-yl)-3-oxomorpholin-2-yl)acetate and tert-butyl 2-((2S,5S,6R)-6-(3-chlorophenyl)-5-(5-chlorothiophen-2-yl)-3-oxomorpholin-2-yl)acetate (371 mg, 0.839 mmol; Example 216, Step B) and (R)-1-((3,4-dimethoxybenzyl)oxy)butan-2-yl 4-bromobenzenesulfonate (Intermediate G; 462 mg, 1.01 mmol) in 1,4-dioxane (1.46 mL) was added sodium 2-methylpropan-2-olate (97 mg, 1.01 mmol) and the resulting solution was heated to 85° C. for 12 hours. The reaction was quenched with ice-cold aq. 10% citric acid and extracted with ethyl acetate (2×). The combined organic layers were washed with brine, dried over Na$_2$SO$_4$, and concentrated under reduced pressure. Purification by flash chromatography on silica gel (40 g SiO$_2$, 15%, 15-20%, 20%, and 35% ethyl acetate in hexanes) provided the title compounds as a mixture of diastereomers.

Step D. tert-Butyl 2-((2R,5S,6R)-6-(3-chlorophenyl)-5-(5-chlorothiophen-2-yl)-4-((S)-1-hydroxybutan-2-yl)-3-oxomorpholin-2-yl)acetate and tert-butyl 2-((2S,5S,6R)-6-(3-chlorophenyl)-5-(5-chlorothiophen-2-yl)-4-((S)-1-hydroxybutan-2-yl)-3-oxomorpholin-2-yl)acetate

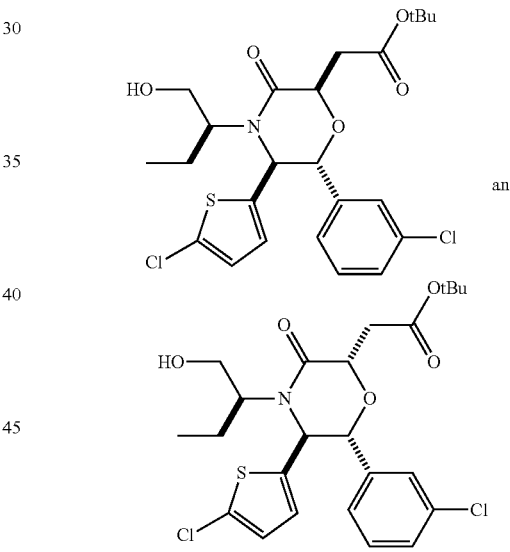

To a solution of tert-butyl 2-((2R,5S,6R)-6-(3-chlorophenyl)-5-(5-chlorothiophen-2-yl)-4-((S)-1-((3,4-dimethoxybenzyl)oxy)butan-2-yl)-3-oxomorpholin-2-yl)acetate and tert-butyl 2-((2S,5S,6R)-6-(3-chlorophenyl)-5-(5-chlorothiophen-2-yl)-4-((S)-1-((3,4-dimethoxybenzyl)oxy)butan-2-yl)-3-oxomorpholin-2-yl)acetate (151 mg, 0.227 mmol; Example 216, Step C) in DCM (3.1 mL) and water (155 µL) at 0° C. was added 2,3-dichloro-5,6-dicyano-p-benzoquinone (62 mg, 0.27 mmol). After stirring at 0° C. for 2.5 hours, the reaction was quenched with sat. aq. NaHCO$_3$, extracted with DCM (3×), and washed with brine. The combined organic layers were dried over MgSO$_4$ and concentrated under reduced pressure. Purification by flash chromatography on silica gel (24 g SiO$_2$, 20% and 30% ethyl acetate in hexanes) provided the title compounds as a mixture of diastereomers.

Step E. tert-Butyl 2-((2R,5S,6R)-6-(3-chlorophenyl)-5-(5-chlorothiophen-2-yl)-4-((S)-1-(N-(2-fluorophenyl)cyclopropanesulfonamido)butan-2-yl)-3-oxomorpholin-2-yl)acetate and tert-butyl 2-((2S,5S,6R)-6-(3-chlorophenyl)-5-(5-chlorothiophen-2-yl)-4-((S)-1-(N-(2-fluorophenyl)cyclopropanesulfonamido)butan-2-yl)-3-oxomorpholin-2-yl)acetate

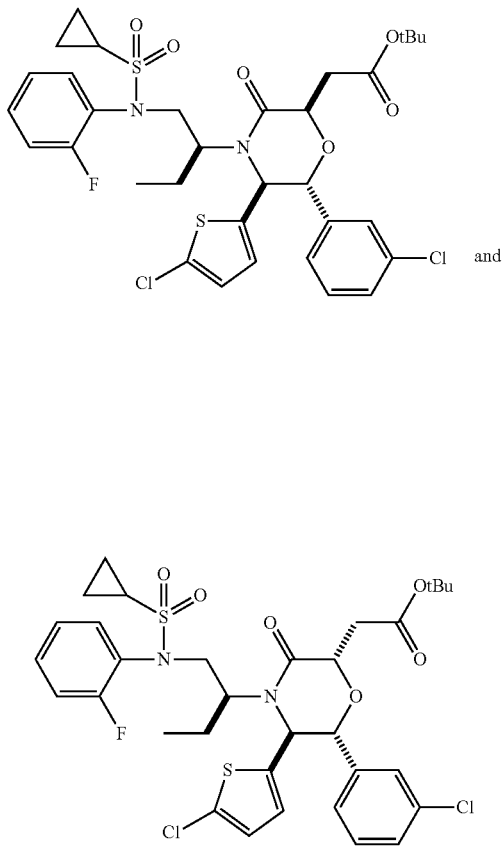

To a solution of tert-butyl 2-((2R,5S,6R)-6-(3-chlorophenyl)-5-(5-chlorothiophen-2-yl)-4-((S)-1-hydroxybutan-2-yl)-3-oxomorpholin-2-yl)acetate and tert-butyl 2-((2S,5S,6R)-6-(3-chlorophenyl)-5-(5-chlorothiophen-2-yl)-4-((S)-1-hydroxybutan-2-yl)-3-oxomorpholin-2-yl)acetate (33 mg, 0.064 mmol; Example 216, Step D) and N-(2-fluorophenyl)cyclopropanesulfonamide (Example 133; 83 mg, 0.39 mmol) in toluene (320 µL) was added 2-(tributylphosphoranylidene)acetonitrile (100 µL, 0.39 mmol), and the resulting solution was heated at 85° C. for 110 minutes. The reaction was cooled and loaded directly onto a silica gel column. Purification by flash chromatography on silica gel (12 g SiO$_2$, 10% and 20% ethyl acetate in hexanes) provided the title compounds as a mixture of diastereomers.

Step F. 2-((2R,5S,6R)-6-(3-chlorophenyl)-5-(5-chlorothiophen-2-yl)-4-((S)-1-(N-(2-fluorophenyl)cyclopropanesulfonamido)butan-2-yl)-3-oxomorpholin-2-yl)acetic acid or 2-((2S,5S,6R)-6-(3-chlorophenyl)-5-(5-chlorothiophen-2-yl)-4-((S)-1-(N-(2-fluorophenyl)cyclopropanesulfonamido)butan-2-yl)-3-oxomorpholin-2-yl)acetic acid

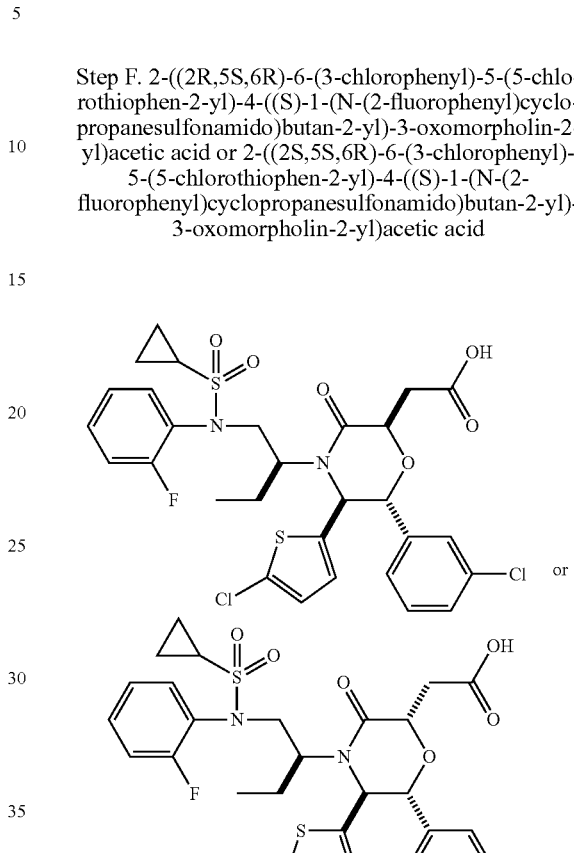

To a solution of tert-butyl 2-((2R,5S,6R)-6-(3-chlorophenyl)-5-(5-chlorothiophen-2-yl)-4-((S)-1-(N-(2-fluorophenyl)cyclopropanesulfonamido)butan-2-yl)-3-oxomorpholin-2-yl)acetate and tert-butyl 2-((2S,5S,6R)-6-(3-chlorophenyl)-5-(5-chlorothiophen-2-yl)-4-((S)-1-(N-(2-fluorophenyl)cyclopropanesulfonamido)butan-2-yl)-3-oxomorpholin-2-yl)acetate (34.0 mg, 0.048 mmol; Example 216, Step E) in DCM (0.20 mL) at 0° C. was added trifluoroacetic acid (184 µL, 2.39 mmol). The reaction was warmed to 25° C., and stirred for 55 minutes. The reaction was concentrated under reduced pressure, and purification by reverse phase preparatory HPLC (Gemini™ Prep C$_{18}$ 5 µm column; Phenomenex, Torrance, Calif.; gradient elution of 45% to 65% acetonitrile in water, where both solvents contain 0.1% TFA, 30 minute method) provided the title compound as the more polar isomer. $^1$H NMR (400 MHz, CDCl$_3$) δ ppm 7.33-7.45 (6 H, m), 7.14-7.22 (2 H, m), 6.76-6.79 (1 H, m), 6.74-6.76 (1 H, m), 5.17 (1 H, d, J=5.3 Hz), 5.01 (1 H, d, J=4.9 Hz), 4.42 (1 H, t, J=6.4 Hz), 4.29 (1 H, dd, J=14.9, 6.7 Hz), 3.85 (1 H, dd, J=14.8, 5.8 Hz), 3.40-3.48 (1 H, m), 3.02-3.09 (1 H, m), 2.92-3.01 (1 H, m), 2.46-2.59 (1 H, m), 1.87 (1 H, dt, J=14.5, 7.4 Hz), 1.60-1.73 (1 H, m), 0.92-1.11 (4 H, m), 0.56 (3 H, t, J=7.5 Hz); MS (ESI) 655.0 [M+H]$^+$.

Example 217

2-((2R,5S,6R)-6-(3-chlorophenyl)-5-(5-chlorothiophen-2-yl)-4-((S)-1-(N-(2-fluorophenyl)cyclopropanesulfonamido)butan-2-yl)-3-oxomorpholin-2-yl)acetic acid or 2-((2S,5S,6R)-6-(3-chlorophenyl)-5-(5-chlorothiophen-2-yl)-4-((S)-1-(N-(2-fluorophenyl)cyclopropanesulfonamido)butan-2-yl)-3-oxomorpholin-2-yl)acetic acid

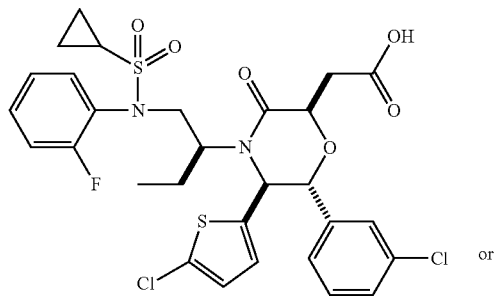

or

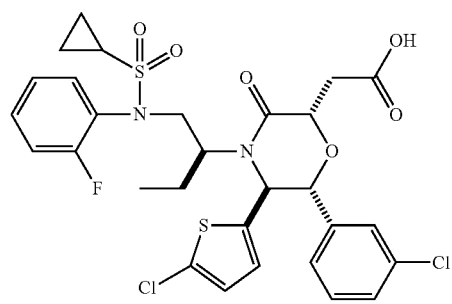

The title compound was obtained from the reverse phase HPLC purification in Example 216, Step F as the less polar isomer. $^1$H NMR (400 MHz, CDCl$_3$) δ ppm 7.51 (1 H, td, J=7.8, 1.3 Hz), 7.36-7.44 (1 H, m), 7.28-7.31 (1 H, m), 7.16-7.26 (4 H, m), 7.06 (1 H, d, J=7.6 Hz), 6.70 (1 H, d, J=3.7 Hz), 6.57 (1 H, d, J=3.7 Hz), 5.07 (1 H, d, J=9.8 Hz), 4.70 (1 H, d, J=9.8 Hz), 4.62 (1 H, dd, J=7.0, 5.5 Hz), 4.44 (1 H, dd, J=14.6, 10.1 Hz), 3.78 (1 H, dd, J=14.8, 3.4 Hz), 3.32 (1 H, br. s.), 2.83 (1 H, dd, J=16.1, 7.1 Hz), 2.55 (1 H, dd, J=16.0, 5.3 Hz), 2.40-2.50 (1 H, m), 1.86-2.06 (1 H, m), 1.57-1.73 (1 H, m), 0.88-1.10 (4 H, m), 0.62 (3 H, t, J=7.5 Hz); MS (ESI) 655.0 [M+H]$^+$.

Example 218

2-((2R,5S,6R)-4-((S)-1-(tert-butylsulfonyl)butan-2-yl)-6-(3-chlorophenyl)-5-(5-chlorothiophen-2-yl)-3-oxomorpholin-2-yl)acetic acid or 2-((2S,5S,6R)-4-((S)-1-(tert-butylsulfonyl)butan-2-yl)-6-(3-chlorophenyl)-5-(5-chlorothiophen-2-yl)-3-oxomorpholin-2-yl)acetic acid

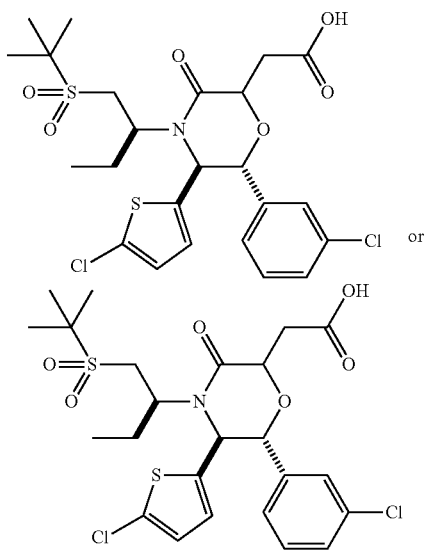

or

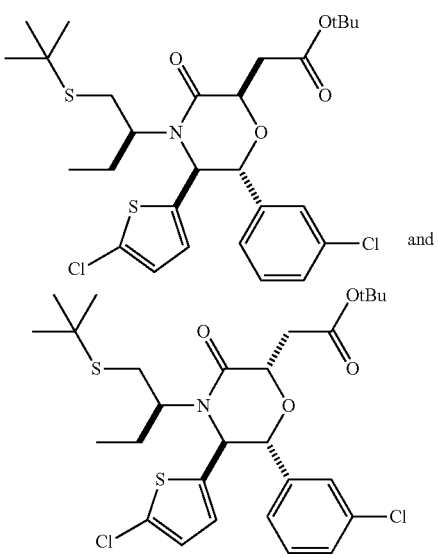

Step A. tert-Butyl 2-((2R,5S,6R)-4-((S)-1-(tert-butylthio)butan-2-yl)-6-(3-chlorophenyl)-5-(5-chlorothiophen-2-yl)-3-oxomorpholin-2-yl)acetate and tert-butyl 2-((2S,5S,6R)-4-((S)-1-(tert-butylthio)butan-2-yl)-6-(3-chlorophenyl)-5-(5-chlorothiophen-2-yl)-3-oxomorpholin-2-yl)acetate

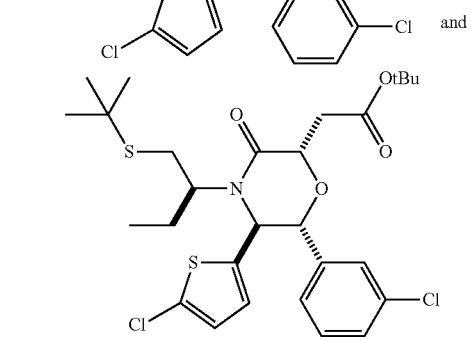

and

Step A. tert-Butyl 2-((2R,5S,6R)-4-((S)-1-(tert-butylthio)butan-2-yl)-6-(3-chlorophenyl)-5-(5-chlorothiophen-2-yl)-3-oxomorpholin-2-yl)acetate and tert-butyl 2-((2S,5S,6R)-4-((S)-1-(tert-butylthio)butan-2-yl)-6-(3-chlorophenyl)-5-(5-chlorothiophen-2-yl)-3-oxomorpholin-2-yl)acetate

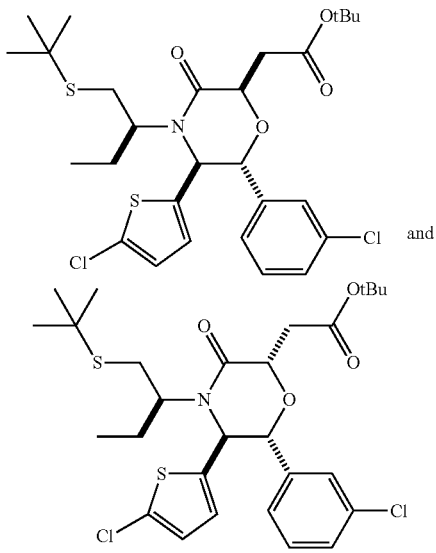

and

To a solution of tert-butyl 2-((2R,5S,6R)-6-(3-chlorophenyl)-5-(5-chlorothiophen-2-yl)-4-((S)-1-hydroxybutan-2-yl)-3-oxomorpholin-2-yl)acetate and tert-butyl 2-((2S,5S,6R)-6-(3-chlorophenyl)-5-(5-chlorothiophen-2-yl)-4-((S)-1-hydroxybutan-2-yl)-3-oxomorpholin-2-yl)acetate (47 mg, 0.091 mmol; Example 216, Step D) and 2-methyl-1-propanethiol (79 μL, 0.73 mmol) in toluene (0.50 mL) was added 2-(tributylphosphoranylidene)acetonitrile (196 μL, 0.731 mmol) and the resulting solution was heated at 85° C. for 23 hours. The reaction was cooled loaded directly onto a silica gel column. Purification by flash chromatography on silica gel (12 g SiO₂, 10% and 20% ethyl acetate in hexanes) provided the title compounds as a mixture of diastereomers.

Step B. tert-butyl 2-((2R,5S,6R)-4-((S)-1-(tert-butylsulfonyl)butan-2-yl)-6-(3-chlorophenyl)-5-(5-chlorothiophen-2-yl)-3-oxomorpholin-2-yl)acetate and tert-butyl 2-((2S,5S,6R)-4-((S)-1-(tert-butylsulfonyl)butan-2-yl)-6-(3-chlorophenyl)-5-(5-chlorothiophen-2-yl)-3-oxomorpholin-2-yl)acetate

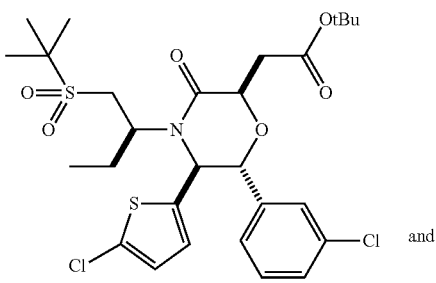

and

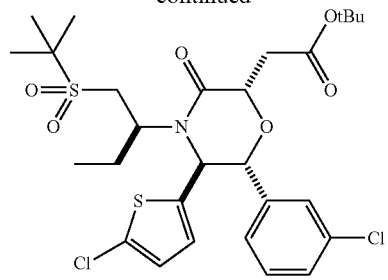

To a solution of tert-butyl 2-((2R,5S,6R)-4-((S)-1-(tert-butylthio)butan-2-yl)-6-(3-chlorophenyl)-5-(5-chlorothiophen-2-yl)-3-oxomorpholin-2-yl)acetate and tert-butyl 2-((2S,5S,6R)-4-((S)-1-(tert-butylthio)butan-2-yl)-6-(3-chlorophenyl)-5-(5-chlorothiophen-2-yl)-3-oxomorpholin-2-yl)acetate (21 mg, 0.035 mmol; Example 218, Step A) in DMF (0.44 mL) at 0° C. was added mCPBA (19 mg, 70%, 0.077 mmol). After stirring for 90 minutes at 0° C., the reaction was quenched with 1 M aq. Na₂S₂O₃, extracted with ethyl acetate (2×), and washed with 10% aq. citric acid, 1 M aq. LiOH, sat. NaHCO₃, and brine. The combined organic layers were dried over Na₂SO₄ and concentrated under reduced pressure. Purification by flash chromatography on silica gel (12 g SiO₂, 20% and 40% ethyl acetate in hexanes) provided the title compounds as a mixture of diastereomers.

Step C. 2-((2R,5S,6R)-4-((S)-1-(tert-butylsulfonyl)butan-2-yl)-6-(3-chlorophenyl)-5-(5-chlorothiophen-2-yl)-3-oxomorpholin-2-yl)acetic acid or 2-((2S,5S,6R)-4-((S)-1-(tert-butylsulfonyl)butan-2-yl)-6-(3-chlorophenyl)-5-(5-chlorothiophen-2-yl)-3-oxomorpholin-2-yl)acetic acid

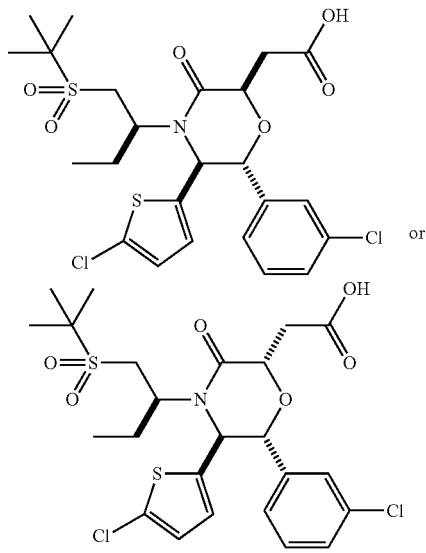

To a solution of tert-butyl 2-((2R,5S,6R)-4-((S)-1-(tert-butylsulfonyl)butan-2-yl)-6-(3-chlorophenyl)-5-(5-chlorothiophen-2-yl)-3-oxomorpholin-2-yl)acetate and tert-butyl 2-((2S,5S,6R)-4-((S)-1-(tert-butylsulfonyl)butan-2-yl)-6-(3-chlorophenyl)-5-(5-chlorothiophen-2-yl)-3-oxomorpholin-2-yl)acetate (11 mg, 0.018 mmol; Example 218, Step B) in DCM (73 μL) was added trifluoroacetic acid (70 μL, 0.91 mmol) at 0° C. The reaction was warmed to 25° C. and stirred for 1 hour. The reaction was concentrated under reduced pressure and purified by reverse phase preparatory HPLC (Gemini™ Prep $C_{18}$ 5 μm column; Phenomenex, Torrance, Calif.; gradient elution of 45% to 65% acetonitrile in water, where both solvents contain 0.1% TFA, 30 minute method) to provide the title compound as the more polar isomer. Gemini™ Prep $C_{18}$ 5 μm column; Phenomenex, Torrance, Calif.; gradient elution of 45% to 65% acetonitrile in water, where both solvents contain 0.1% TFA, 30 min method $^1$H NMR (400 MHz, CDCl$_3$) δ ppm 7.49 (1 H, s), 7.28-7.38 (3 H, m), 6.93 (1 H, d, J=3.9 Hz), 6.78 (1 H, d, J=3.9 Hz), 5.40 (1 H, d, J=4.1 Hz), 5.07 (1 H, d, J=4.1 Hz), 4.55 (1 H, t, J=6.2 Hz), 3.80 (1 H, dd, J=13.8, 7.5 Hz), 3.68 (1 H, br. s.), 2.98-3.14 (3 H, m), 2.10 (1 H, dt, J=14.9, 7.6 Hz), 1.63-1.78 (1 H, m), 1.45 (9 H, s), 0.65 (3 H, t, J=7.4 Hz); MS (ESI) 562.0 [M+H]$^+$.

Example 219

2-((2R,5S,6R)-4-((S)-1-(tert-butylsulfonyl)butan-2-yl)-6-(3-chlorophenyl)-5-(5-chlorothiophen-2-yl)-3-oxomorpholin-2-yl)acetic acid or 2-((2S,5S,6R)-4-((S)-1-(tert-butylsulfonyl)butan-2-yl)-6-(3-chlorophenyl)-5-(5-chlorothiophen-2-yl)-3-oxomorpholin-2-yl)acetic acid (less polar isomer)

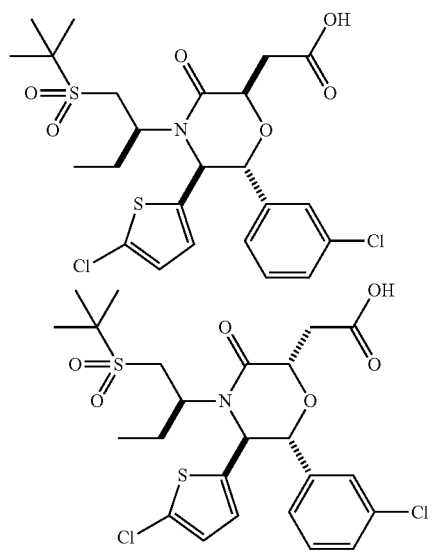

The title compound was obtained from the RP-HPLC purification in Example 218, Step C as the less polar isomer. $^1$H NMR (400 MHz, CDCl$_3$) δ ppm 7.15-7.26 (3 H, m), 7.03 (1 H, d, J=7.6 Hz), 6.70-6.72 (1 H, m), 6.67-6.69 (1 H, m), 5.29 (1 H, d, J=9.8 Hz), 4.71 (1 H, d, J=9.8 Hz), 4.66-4.71 (1 H, m), 4.02 (1 H, dd, J=13.4, 9.9 Hz), 3.62 (1 H, t, J=7.6 Hz), 3.18 (1 H, dd, J=16.3, 6.4 Hz), 2.91-3.02 (2 H, m), 2.16-2.29 (1 H, m), 1.78 (1 H, ddd, J=14.0, 7.6, 3.8 Hz), 1.44 (9 H, s), 0.68 (3 H, t, J=7.4 Hz); MS (ESI) 562.0 [M+H]$^+$.

Example 220

2-((2R,5R,6R)-4-((S)-1-(tert-butylsulfonyl)pentan-3-yl)-6-(3-chlorophenyl)-5-(4-chlorophenyl)-3-oxomorpholin-2-yl)acetic acid or 2-((2S,5R,6R)-4-((S)-1-(tert-butylsulfonyl)pentan-3-yl)-6-(3-chlorophenyl)-5-(4-chlorophenyl)-3-oxomorpholin-2-yl)acetic acid

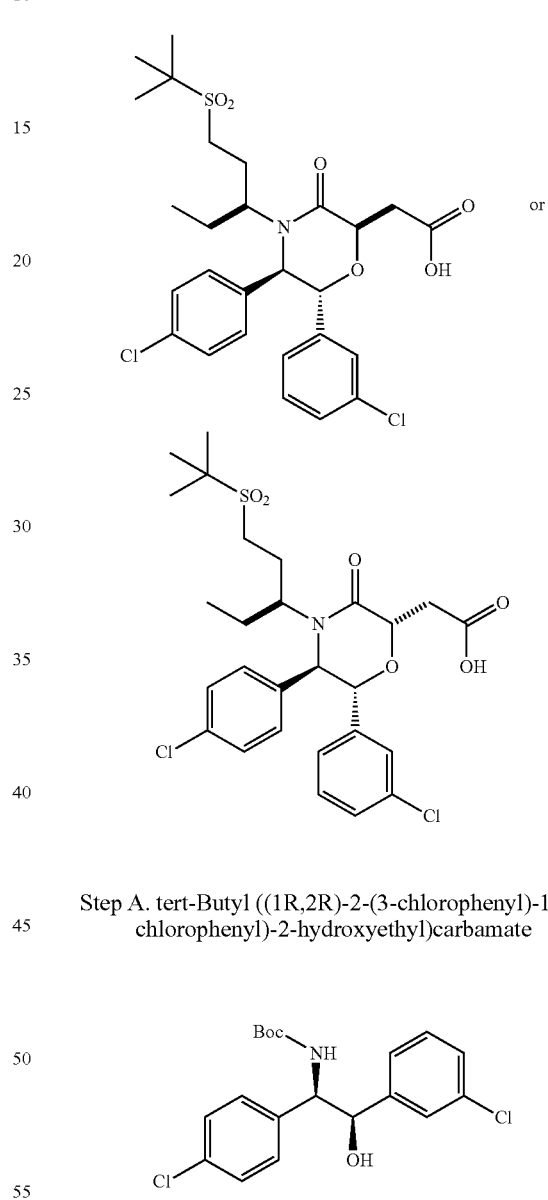

Step A. tert-Butyl ((1R,2R)-2-(3-chlorophenyl)-1-(4-chlorophenyl)-2-hydroxyethyl)carbamate

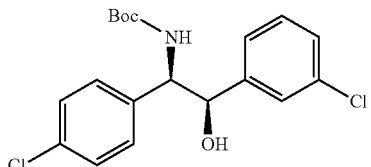

Magnesium (0.113 g, 4.63 mmol), a crystal of iodine and anhydrous ether (5 mL) were stirred at room temperature. A solution of 1-bromo-3-chlorobenzene (0.544 mL, 4.63 mmol) in anhydrous ether (5 mL) was added dropwise by addition funnel to the magnesium mixture. After adding 1 mL of the 1-bromo-3-chlorobenzene solution, addition was paused and the reaction mixture was heated to reflux. After 5 minutes, the iodine color was gone and the reaction mixture became colorless and slightly turbid. The reaction mixture was removed from the heat and the remainder of the bromide solution was added at a rate that maintained a gentle reflux.

The reaction mixture was heated at reflux for an additional 30 minutes and cooled to room temperature over 15 minutes. A solution of (R)-tert-butyl 1-(4-chlorophenyl)-2-oxoethylcarbamate (0.500 g, 1.854 mmol; Intermediate C1, Step C) in anhydrous ether (5 mL) was added. After 2 hours the reaction was quenched with sat. aq. NH₄Cl and extracted with EtOAc (3×). The organics were pooled, washed with brine, dried (MgSO₄), filtered and concentrated under a vacuum to provide a yellow oil. Flash chromatography using a Combiflash Companion with a 50 g spherical silica gel column (Supelco) and eluting with 10-30% EtOAc/hexanes provided the title compound as a yellow glass.

Step B. (1R,2R)-2-Amino-1-(3-chlorophenyl)-2-(4-chlorophenyl)ethanol hydrochloride

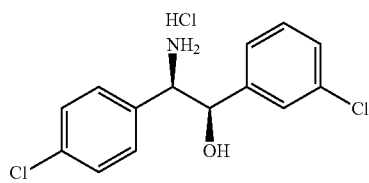 [SMILES: Cl ; N[C@H](c1ccc(Cl)cc1)[C@H](O)c1cccc(Cl)c1]

tert-Butyl ((1R,2R)-2-(3-chlorophenyl)-1-(4-chlorophenyl)-2-hydroxyethyl)carbamate (13.0 g, 0.0341 mol, Example 220, Step A) was cooled to 0° C. under N₂ atmosphere and 4 N HCl in 1,4-dioxane (130 mL) was added dropwise over 15 minutes. The reaction was stirred at room temperature for 2 hours. The solvent was evaporated under vacuum to obtain a dark brown, thick oil which was triturated with n-pentane (150 mL). The n-pentane layer was decanted, and the sticky solid was triturated again with 25% ether in n-pentane (150 mL) and the solvent was decanted. This process was repeated with 50% ether in n-pentane (150 mL) to obtain an off white solid which was stirred overnight in 75% ether in pentane (150 mL). The solvent was again decanted, and the remaining solid was finally washed with ether (150 mL) and filtered to get the titled compound as an off white solid.

Step C. (1R,2R)-2-(((S)-1-(tert-butylthio)pentan-3-yl)amino)-1-(3-chlorophenyl)-2-(4-chlorophenyl)ethanol

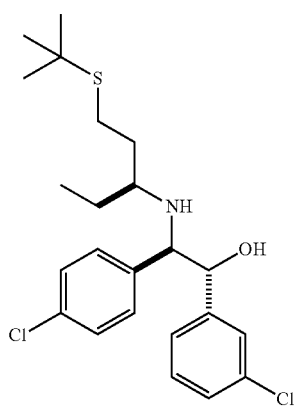

To K₃PO₄ (431 mg, 2.033 mmol) was added ethyl vinyl ketone (806 μL, 8.13 mmol) and 2-methylpropane-2-thiol (688 μL, 6.10 mmol). An exotherm was observed. The heterogenous mixture was stirred at room temperature for 15 min. Then (1R,2R)-2-amino-1-(3-chlorophenyl)-2-(4-chlorophenyl)ethanol hydrochloride (650 mg, 2.040 mmol; Example 220, Step B) and MeOH (4080 μL) were added. Then sodium cyanoborohydride (320 mg, 5.10 mmol) and AcOH (350 μL, 6.12 mmol) were added. The mixture was stirred at room temperature for 2 days. The mixture was quenched with 1 M HCl. The mixture was concentrated and diluted with DCM. The organic layer was washed with sat. NaHCO₃ and the aqueous layer was extracted with DCM (2×). The combined organic layers were dried over Na₂SO₄, filtered and the filtrate was concentrated. The residue was purified by flash chromatography on silica gel (40 g column; eluent: 0-50% EtOAc in hexanes) to give a residue. The residue was further purified by flash chromatography on silica gel (2×24 g GOLD columns (Teledyne Isco, Lincoln, Nebr.) stacked; eluent: 20-50% MTBE in hexanes). The second eluting isomer was further purified by a 2 g SCX SI bond column (Varian, Lake Forest, Calif.); eluent: 2 M NH₃ in MeOH to give (1R,2R)-2-(((S)-1-(tert-butylthio)pentan-3-yl)amino)-1-(3-chlorophenyl)-2-(4-chlorophenyl)ethanol.

Step D. 2-((2R,5R,6R)-4-((S)-1-(tert-butylsulfonyl)pentan-3-yl)-6-(3-chlorophenyl)-5-(4-chlorophenyl)-3-oxomorpholin-2-yl)acetic acid or 2-((2S,5R,6R)-4-((S)-1-(tert-butylsulfonyl)pentan-3-yl)-6-(3-chlorophenyl)-5-(4-chlorophenyl)-3-oxomorpholin-2-yl)acetic acid

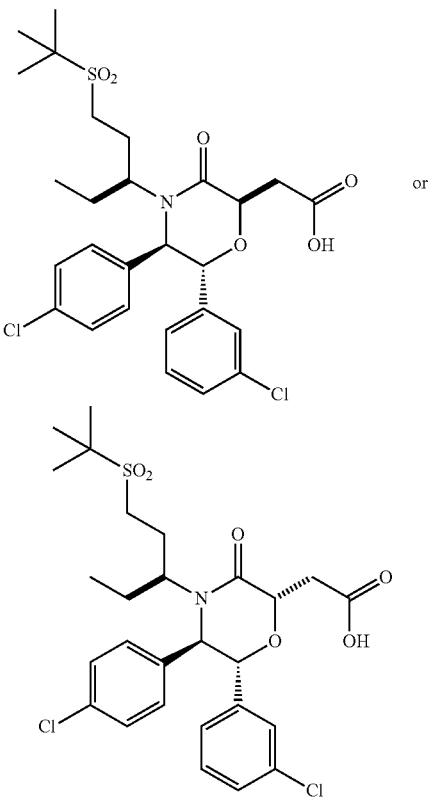

One of the title compounds was prepared from (1R,2R)-2-(((S)-1-(tert-butylthio)pentan-3-yl)amino)-1-(3-chlorophenyl)-2-(4-chlorophenyl)ethanol (Example 220, Step C) by procedures similar to those described in Example 162, Steps F through H. The residue was purified by chiral HPLC (2×250×30 mm Chiralpak® AD-H column (Chiral Technologies, Inc., West Chester, Pa., USA) with 18 g/min EtOH+(20 mM NH₃)+82 g/min CO₂ on a Thar 200 SFC (Thar Technologies, Inc., Pittsburg, Pa.)) to give one of the title compounds as the first eluting isomer. $^1$H NMR (400 MHz, chloroform-d) δ ppm 7.25-7.34 (m, 3 H) 7.19-7.24 (m, 1 H) 7.05-7.15 (m, 3 H) 6.67 (d, J=7.63 Hz, 1 H) 4.62-4.74 (m, 3 H) 3.15-3.25 (m, 2 H) 2.94-3.12 (m, 3 H) 2.43 (br. s., 1 H) 2.08-2.20 (m, 1 H) 1.85-1.96 (m, 1 H) 1.56-1.62 (m, 1 H) 1.44 (s, 9 H) 0.61 (t, J=7.53 Hz, 3 H). Mass spectrum (ESI) m/z=570 [M+1].

Example 221

2-((2R,5R,6R)-4-((S)-1-(tert-butylsulfonyl)pentan-3-yl)-6-(3-chlorophenyl)-5-(4-chlorophenyl)-3-oxomorpholin-2-yl)acetic acid or 2-((2S,5R,6R)-4-((S)-1-(tert-butylsulfonyl)pentan-3-yl)-6-(3-chlorophenyl)-5-(4-chlorophenyl)-3-oxomorpholin-2-yl)acetic acid

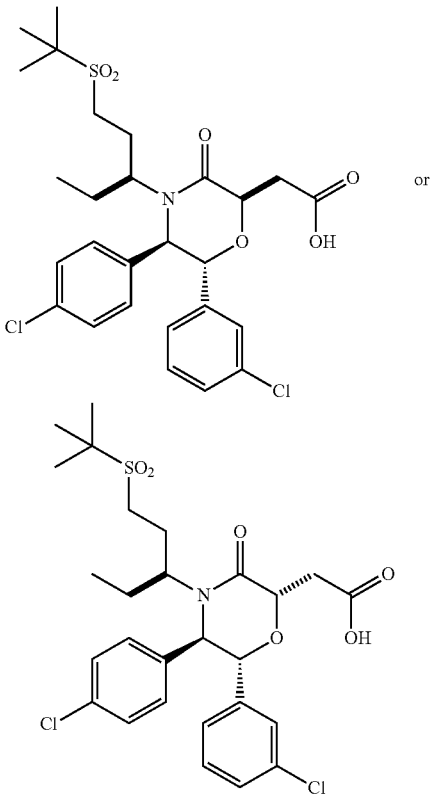

One of the title compounds was isolated as the second eluting isomer in Example 220, Step D. The residue was further purified by chiral HPLC (2×250×30 mm Chiralpak® AD-H column (Chiral Technologies, Inc., West Chester, Pa., USA) with 25 g/min IPA+(20 mM NH₃)+75 g/min CO₂ on a Thar 200 SFC (Thar Technologies, Inc., Pittsburg, Pa.)) to give one of the title compounds. $^1$H NMR (400 MHz, chloroform-d) δ ppm 7.11-7.31 (m, 7 H) 6.98 (d, J=7.63 Hz, 1 H) 4.86 (d, J=5.87 Hz, 1 H) 4.78 (d, J=5.48 Hz, 1 H) 4.69 (br. s, 1 H) 3.59 (br. s, 1 H) 3.02 (br. s, 2 H) 2.91 (t, J=7.04 Hz, 2 H) 2.00-2.21 (m, 2 H) 1.72 (dt, J=13.64, 6.97 Hz, 1 H) 1.58 (dt, J=13.01, 6.60 Hz, 1 H) 1.34 (s, 9 H) 0.59 (t, J=7.34 Hz, 3 H). Mass spectrum (ESI) m/z=570 [M+1].

Example 222

(5R,6R)-4-((S)-1-(tert-butylthio)propan-2-yl)-6-(3-chlorophenyl)-5-(4-chlorophenyl)morpholin-3-one

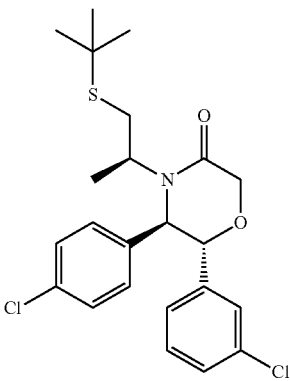 [SMILES: C[C@@H](CSC(C)(C)C)N1C(=O)CO[C@H](c2cccc(Cl)c2)[C@H]1c1ccc(Cl)cc1]

The title compound was obtained from (1R,2R)-2-amino-1-(3-chlorophenyl)-2-(4-chlorophenyl)ethanol hydrochloride (Example 220, Step B) by procedures similar to those described in Example 162, Steps A through G, replacing (R)-(+)-1,2-epoxybutane in Step B with (R)-(+)-propylene oxide. The crude residue was purified by flash chromatography on silica gel (40 g column, eluent: 0 to 35% ethyl acetate hexanes) to provide the title compound. $^1$H NMR (400 MHz, chloroform-d) δ ppm 1.29-1.38 (m, 12H) 2.58 (dd, J=12.32, 5.67 Hz, 1 H) 3.08-3.20 (m, 1 H) 3.37 (dd, J=12.32, 9.19 Hz, 1 H) 4.39 (d, J=10.95 Hz, 2 H) 4.51 (d, J=8.61 Hz, 1 H) 4.75 (d, J=8.80 Hz, 1 H) 6.81 (d, J=7.82 Hz, 1 H) 7.05 (d, J=8.41 Hz, 2 H) 7.10-7.20 (m, 2 H) 7.21-7.35 (m, 3 H). Mass spectrum (ESI) m/z=452 (M+1).

Example 223

2-((2S,5R,6R)-4-((S)-1-(tert-butylsulfonyl)propan-2-yl)-6-(3-chlorophenyl)-5-(4-chlorophenyl)-3-oxomorpholin-2-yl)acetic acid or 2-((2R,5R,6R)-4-((S)-1-(tert-butylsulfonyl)propan-2-yl)-6-(3-chlorophenyl)-5-(4-chlorophenyl)-3-oxomorpholin-2-yl)acetic acid

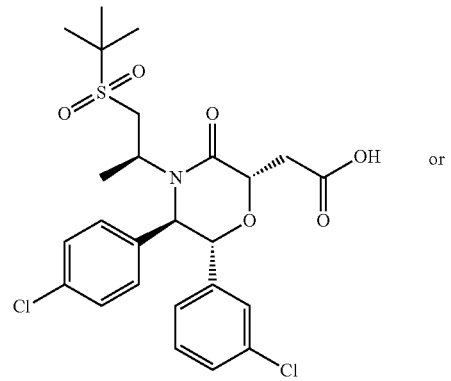

365
-continued

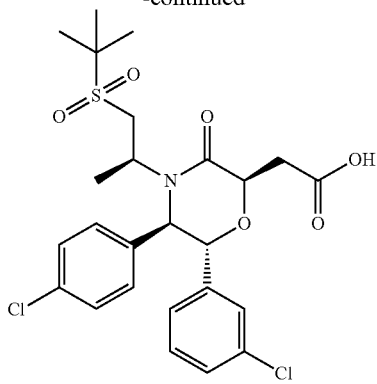

One of the title compounds was obtained from (5R,6R)-4-((S)-1-(tert-butylthio)propan-2-yl)-6-(3-chlorophenyl)-5-(4-chlorophenyl)morpholin-3-one (Example 222) by procedures similar to those described in Example 112, Steps E through F. The crude residue was purified by reverse phase HPLC on a 100×30 mm 5 μm $C_{18}$ column (Phenomenex, Torrance, Calif.; eluent: 45 to 55% MeCN/water with 0.1% TFA) followed by purification by preparative thin layer chromatography (eluent: 15% acetone/DCM) to provide one of the title compounds as the first eluting isomer. $^1$H NMR (400 MHz, chloroform-d) δ ppm 1.37 (d, J=6.85 Hz, 3 H) 1.44 (br. s., 9 H) 2.85 (dd, J=13.40, 3.42 Hz, 1 H) 2.97 (dd, J=16.24, 4.70 Hz, 1 H) 3.26 (dd, J=16.24, 7.24 Hz, 1 H) 3.57-3.71 (m, 1 H) 4.15 (dd, J=13.40, 9.68 Hz, 1 H) 4.64 (d, J=9.78 Hz, 1 H) 4.73 (dd, J=7.04, 4.69 Hz, 1 H) 5.02 (d, J=9.59 Hz, 1 H) 6.81 (d, J=7.82 Hz, 1 H) 7.04-7.16 (m, 4 H) 7.20-7.22 (m, 1 H) 7.31 (d, J=8.41 Hz, 2 H). Mass spectrum (ESI) m/z=542 (M+1).

Example 224

2-((2R,5R,6R)-4-((S)-1-(tert-butylsulfonyl)propan-2-yl)-6-(3-chlorophenyl)-5-(4-chlorophenyl)-3-oxomorpholin-2-yl)acetic acid or 2-((2S,5R,6R)-4-((S)-1-(tert-butylsulfonyl)propan-2-yl)-6-(3-chlorophenyl)-5-(4-chlorophenyl)-3-oxomorpholin-2-yl)acetic acid

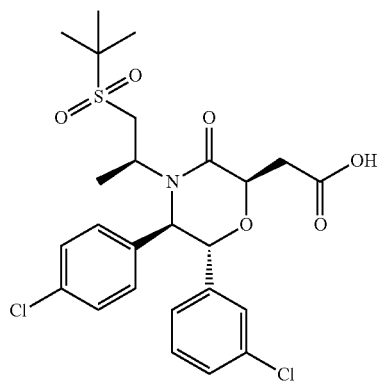 or

366
-continued

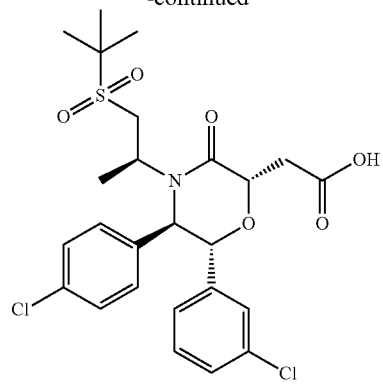

One of the title compounds was isolated as the second eluting isomer in Example 223. $^1$H NMR (400 MHz, chloroform-d) δ ppm 1.37 (d, J=6.85 Hz, 3 H) 1.43 (s, 9 H) 2.89 (dd, J=13.30, 2.54 Hz, 1 H) 3.02-3.18 (m, 2 H) 3.68-3.79 (m, 1 H) 4.06 (dd, J=13.20, 8.90 Hz, 1 H) 4.72 (t, J=4.79 Hz, 1 H) 4.88 (d, J=5.87 Hz, 1 H) 5.09 (d, J=6.46 Hz, 1 H) 7.01 (d, J=7.04 Hz, 1 H) 7.08-7.20 (m, 1 H) 7.20-7.30 (m, 4 H) 7.31-7.38 (m, 2 H). Mass spectrum (ESI) m/z=542 (M+1).

Example 225

2-((2R,5R,6R)-4-((S)-1-(tert-butylsulfonyl)propan-2-yl)-6-(3-chlorophenyl)-5-(4-chlorophenyl)-3-oxomorpholin-2-yl)acetamide or 2-((2S,5R,6R)-4-((S)-1-(tert-butylsulfonyl)propan-2-yl)-6-(3-chlorophenyl)-5-(4-chlorophenyl)-3-oxomorpholin-2-yl)acetamide

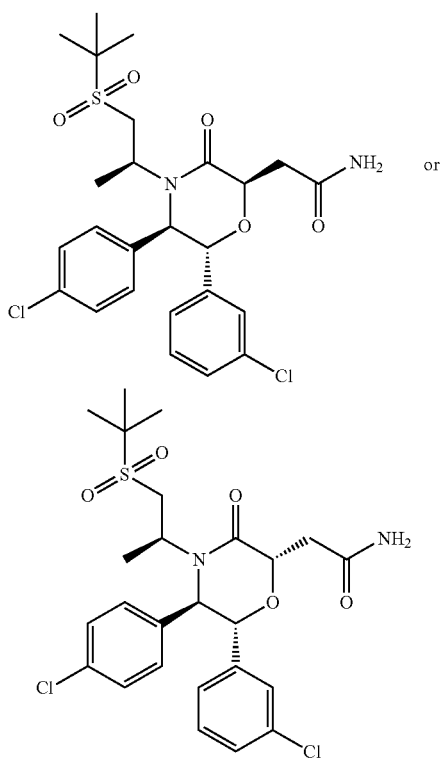

2-((2S,5R,6R)-4-((S)-1-(tert-butylsulfonyl)propan-2-yl)-6-(3-chlorophenyl)-5-(4-chlorophenyl)-3-oxomorpholin-2-yl)acetic acid or 2-((2R,5R,6R)-4-((S)-1-(tert-butylsulfonyl)propan-2-yl)-6-(3-chlorophenyl)-5-(4-chlorophenyl)-3-oxomorpholin-2-yl)acetic acid (mixture of isomers from Example 223) (50 mg, 0.092 mmol) in DMF (1 mL) was added triethylamine (0.051 mL, 0.369 mmol) and HATU (42.1 mg, 0.111 mmol). After 30 minutes, ammonia (7 N in MeOH) (0.053 mL, 0.369 mmol) was added. After 4 hours, HATU (42.1 mg, 0.111 mmol) was added. After stirring overnight, the mixture was diluted with water and extracted with ethyl acetate. The organic layer was washed with water and brine. The organic layer was dried over $Na_2SO_4$ and then concentrated. The residue was purified by reverse phase HPLC on a 100×30 mm 5 μm $C_{18}$ column (Phenomenex, Torrance, Calif.; eluent: 30 to 50% MeCN/water with 0.1% TFA) to provide one of the title compounds as the first eluting isomer. $^1$H NMR (400 MHz, chloroform-d) δ ppm 1.38 (d, J=6.85 Hz, 3 H) 1.43 (s, 9 H) 2.85 (dd, J=13.50, 3.33 Hz, 1 H) 2.97 (dd, J=16.24, 4.30 Hz, 1 H) 3.08 (dd, J=15.85, 7.24 Hz, 1 H) 3.70-3.80 (m, 1 H) 4.11 (dd, J=13.50, 9.39 Hz, 1 H) 4.71 (dd, J=7.34, 4.40 Hz, 1 H) 4.94 (d, J=7.43 Hz, 1 H) 5.09 (d, J=7.43 Hz, 1 H) 6.97 (d, J=7.63 Hz, 1 H) 7.16 (t, J=8.02 Hz, 1 H) 7.20-7.38 (m, 6 H). Mass spectrum (ESI) m/z=541 (M+1).

Example 226

2-((2S,5R,6R)-4-((S)-1-(tert-butylsulfonyl)propan-2-yl)-6-(3-chlorophenyl)-5-(4-chlorophenyl)-3-oxomorpholin-2-yl)acetamide or 2-((2R,5R,6R)-4-((S)-1-(tert-butylsulfonyl)propan-2-yl)-6-(3-chlorophenyl)-5-(4-chlorophenyl)-3-oxomorpholin-2-yl)acetamide

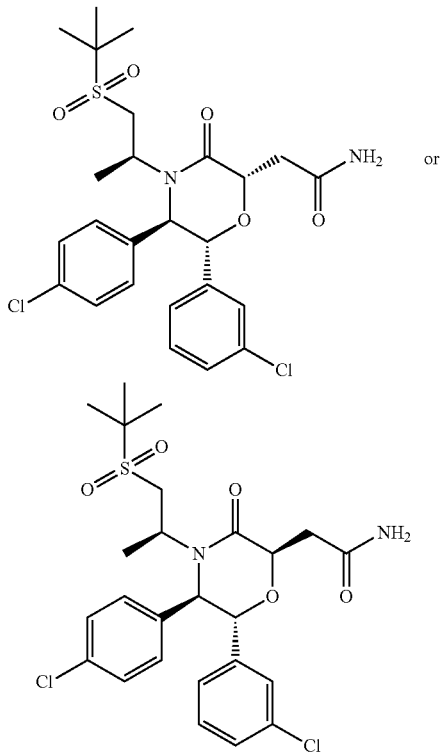

One of the title compounds was isolated as the second eluting isomer in Example 225. $^1$H NMR (400 MHz, chloroform-d) δ ppm 1.36 (d, J=7.04 Hz, 3 H) 1.42 (s, 9 H) 2.80 (dd, J=13.30, 3.13 Hz, 1 H) 2.91 (dd, J=15.75, 6.94 Hz, 1 H) 3.10 (dd, J=15.85, 4.50 Hz, 1 H) 3.58-3.68 (m, 1 H) 4.21 (dd, J=13.30, 9.98 Hz, 1 H) 4.65 (d, J=9.78 Hz, 1 H) 4.75 (dd, J=6.85, 4.50 Hz, 1 H) 5.04 (d, J=9.78 Hz, 1 H) 6.82 (d, J=7.82 Hz, 1 H) 7.04-7.15 (m, 4 H) 7.20-7.23 (m, 1 H) 7.30 (d, J=8.61 Hz, 2 H). Mass spectrum (ESI) m/z=541 (M+1).

Example 227

2-((2S,5R,6R)-4-((S)-1-(tert-butylsulfonyl)propan-2-yl)-6-(3-chlorophenyl)-5-(4-chlorophenyl)-3-oxomorpholin-2-yl)-N-methylacetamide or 2-((2R,5R,6R)-4-((S)-1-(tert-butylsulfonyl)propan-2-yl)-6-(3-chlorophenyl)-5-(4-chlorophenyl)-3-oxomorpholin-2-yl)-N-methylacetamide

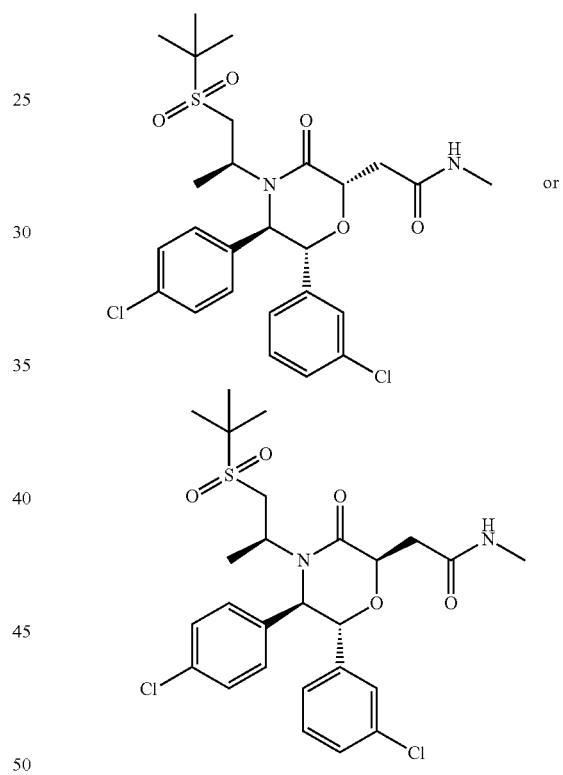

One of the title compounds was obtained following a procedure analogous to the one described in Example 225 using methylamine (2.0 M solution in THF) in place of ammonia. The crude residue was purified by reverse phase HPLC on a 100×30 mm 5 μm $C_{18}$ column (Phenomenex, Torrance, Calif.; eluent: 30 to 50% MeCN/water with 0.1% TFA) followed by preparative thin layer chromatography (eluent: 15% acetone/DCM) to provide one of the title compounds as the first eluting isomer. $^1$H NMR (400 MHz, chloroform-d) δ ppm 1.37 (d, J=6.85 Hz, 3 H) 1.43 (s, 9 H) 2.74-2.88 (m, 5 H) 3.03 (dd, J=15.26, 4.30 Hz, 1 H) 3.54-3.67 (m, 1 H) 4.23 (dd, J=13.40, 9.29 Hz, 1 H) 4.63 (d, J=9.78 Hz, 1 H) 4.76 (dd, J=7.14, 4.40 Hz, 1 H) 4.98 (d, J=9.78 Hz, 1 H) 6.77 (d, J=7.63 Hz, 1 H) 7.03-7.13 (m, 4 H) 7.20 (ddd, J=8.02, 2.15, 1.00 Hz, 1 H) 7.29 (d, J=8.61 Hz, 2 H). Mass spectrum (ESI) m/z=555 (M+1).

Example 228

2-((2R,5R,6R)-4-((S)-1-(tert-butylsulfonyl)propan-2-yl)-6-(3-chlorophenyl)-5-(4-chlorophenyl)-3-oxomorpholin-2-yl)-N-methylacetamide or 2-((2S,5R,6R)-4-((S)-1-(tert-butylsulfonyl)propan-2-yl)-6-(3-chlorophenyl)-5-(4-chlorophenyl)-3-oxomorpholin-2-yl)-N-methylacetamide

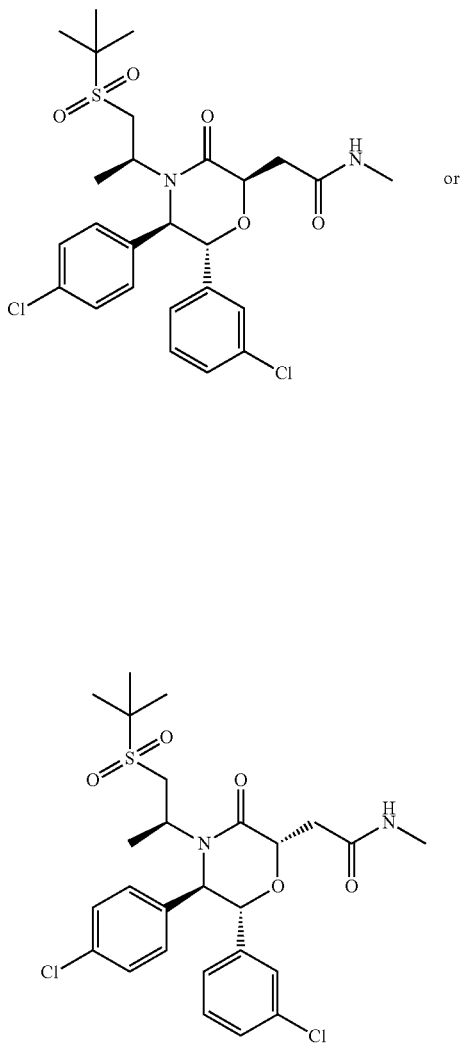

One of the title compounds was isolated as the second eluting isomer in Example 227. ¹H NMR (400 MHz, chloroform-d) δ ppm 1.39 (d, J=7.04 Hz, 3 H) 1.43 (s, 9 H) 2.77-2.93 (m, 5 H) 3.02 (dd, J=15.26, 6.85 Hz, 1 H) 3.67-3.78 (m, 1 H) 4.09 (dd, J=13.50, 8.80 Hz, 1 H) 4.64 (dd, J=6.75, 4.21 Hz, 1 H) 4.97 (d, J=7.04 Hz, 1 H) 5.06 (d, J=7.04 Hz, 1 H) 6.99 (d, J=6.26 Hz, 1 H) 7.16 (m, 1 H) 7.20-7.29 (m, 4 H) 7.33 (d, J=8.61 Hz, 2 H). Mass spectrum (ESI) m/z=555 (M+1).

Example 229

2-((2S,5R,6R)-4-((S)-1-(tert-butylsulfonyl)propan-2-yl)-6-(3-chlorophenyl)-5-(4-chlorophenyl)-3-oxomorpholin-2-yl)-N-hydroxyacetamide or 2-((2R,5R,6R)-4-((S)-1-(tert-butylsulfonyl)propan-2-yl)-6-(3-chlorophenyl)-5-(4-chlorophenyl)-3-oxomorpholin-2-yl)-N-hydroxyacetamide

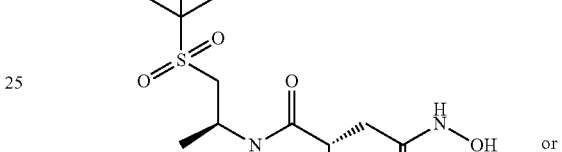

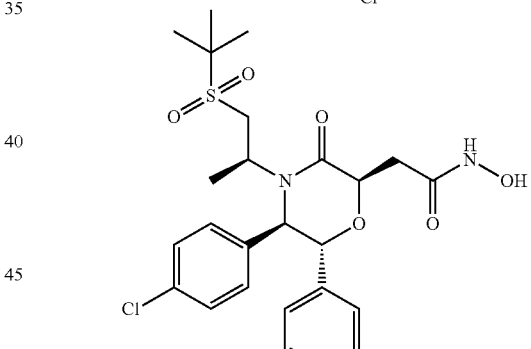

One of the title compounds was obtained following a procedure analogous to the one described in Example 225 using hydroxylamine hydrochloride in place of ammonia. The crude residue was purified by preparative thin layer chromatography (eluent: 5% methanol/DCM with 0.5% aq. NH₄OH) to provide one of the title compounds as the first eluting isomer. ¹H NMR (400 MHz, acetonitrile-d₃) δ ppm 1.29 (d, J=7.04 Hz, 3 H) 1.35 (s, 9 H) 2.48-2.62 (m, 1 H) 2.83 (dd, J=15.45, 2.74 Hz, 1 H) 3.03 (dd, J=13.60, 3.81 Hz, 1 H) 3.42-3.57 (m, 1 H) 4.03 (dd, J=13.69, 9.00 Hz, 1 H) 4.75-4.86 (m, 2 H) 4.91 (d, J=9.98 Hz, 1 H) 6.87 (d, J=7.82 Hz, 1 H) 7.06 (t, J=1.86 Hz, 1 H) 7.13-7.29 (m, 4 H) 7.34 (d, J=8.61 Hz, 2 H). Mass spectrum (ESI) m/z=557 (M+1).

Example 230

2-((2R,5R,6R)-4-((S)-1-(tert-butylsulfonyl)propan-2-yl)-6-(3-chlorophenyl)-5-(4-chlorophenyl)-3-oxomorpholin-2-yl)-N-hydroxyacetamide or 2-((2S,5R,6R)-4-((S)-1-(tert-butylsulfonyl)propan-2-yl)-6-(3-chlorophenyl)-5-(4-chlorophenyl)-3-oxomorpholin-2-yl)-N-hydroxyacetamide (5:1 mixture of diastereomers at C2)

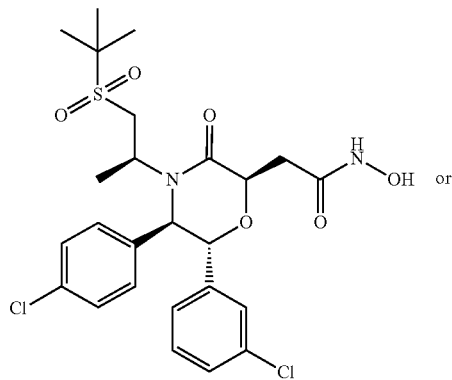

or

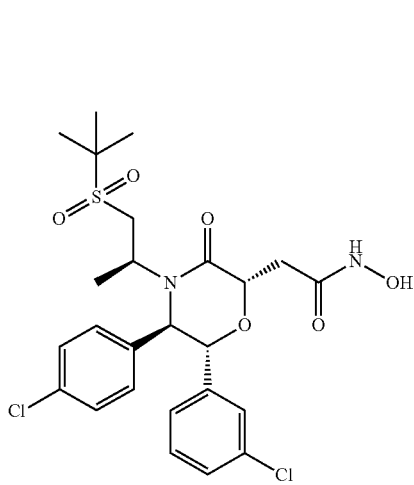

One of the title compounds was isolated as the second eluting isomer in Example 229. A small amount of the first eluting isomer from Example 229 was present in this sample (5:1 mixture of diastereomers).

$^1$H NMR (400 MHz, acetonitrile-$d_3$) δ ppm 1.30 (d, J=6.85 Hz, 3 H) 1.34 (s, 9 H) 2.63-2.72 (m, 1 H) 2.79-2.86 (m, 1 H) 3.01 (dd, J=13.50, 4.30 Hz, 1 H) 3.55-3.65 (m, 1 H) 3.95 (dd, J=13.40, 9.10 Hz, 1 H) 4.61-4.68 (m, 1 H) 4.89 (d, J=7.83 Hz, 1 H) 4.99 (d, J=8.22 Hz, 1 H) 7.03 (d, J=7.43 Hz, 1 H) 7.10 (s, 1 H) 7.22-7.30 (m, 3 H) 7.31-7.38 (m, 3 H). Mass spectrum (ESI) m/z=557 (M+1).

Example 231

2-((2S,5R,6R)-4-((S)-1-(tert-butylsulfonyl)propan-2-yl)-6-(3-chlorophenyl)-5-(4-chlorophenyl)-3-oxomorpholin-2-yl)-N,N-dimethylacetamide or 2-((2R,5R,6R)-4-((S)-1-(tert-butylsulfonyl)propan-2-yl)-6-(3-chlorophenyl)-5-(4-chlorophenyl)-3-oxomorpholin-2-yl)-N,N-dimethylacetamide

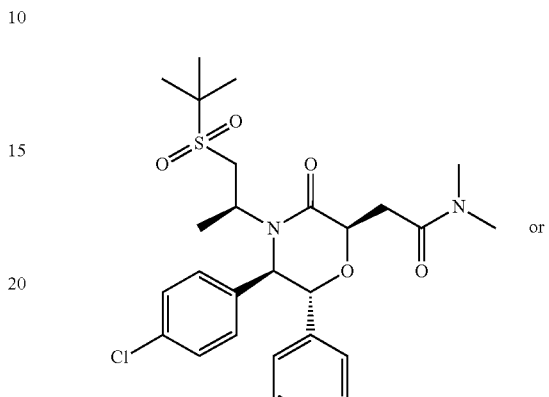

or

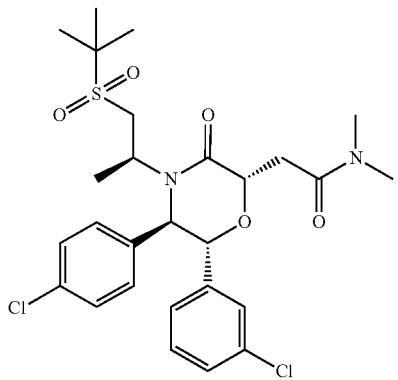

One of the title compounds was obtained following a procedure analogous to the one described in Example 225 using dimethylamine (2.0 M solution in THF) in place of ammonia. The crude residue was purified by preparative thin layer chromatography (eluent: 15% acetone/hexanes) to provide one of the title compounds as the first eluting isomer. $^1$H NMR (400 MHz, chloroform-d) δ ppm 1.42 (d, J=7.04 Hz, 3 H) 1.43 (s, 9 H) 2.92-3.08 (m, 9 H) 3.56-3.64 (m, 1 H) 4.20 (dd, J=13.60, 6.94 Hz, 1 H) 4.64 (d, J=9.59 Hz, 1 H) 4.82 (t, J=4.89 Hz, 1 H) 4.93 (d, J=9.78 Hz, 1 H) 6.74 (d, J=7.63 Hz, 1 H) 7.02-7.13 (m, 4 H) 7.18 (ddd, J=8.07, 2.20, 1.08 Hz, 1 H) 7.24-7.31 (m, 2 H). Mass spectrum (ESI) m/z=569 (M+1).

Example 232

2-((2R,5R,6R)-4-((S)-1-(tert-butylsulfonyl)propan-2-yl)-6-(3-chlorophenyl)-5-(4-chlorophenyl)-3-oxo-morpholin-2-yl)-N,N-dimethylacetamide or 2-((2S,5R,6R)-4-((S)-1-(tert-butylsulfonyl)propan-2-yl)-6-(3-chlorophenyl)-5-(4-chlorophenyl)-3-oxomorpholin-2-yl)-N,N-dimethylacetamide

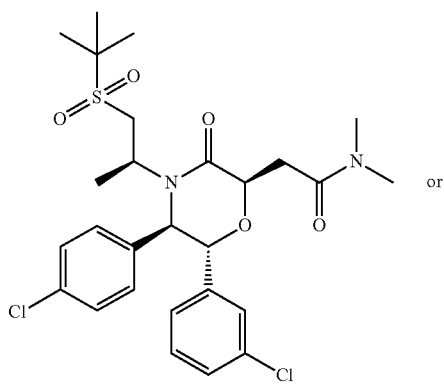

or

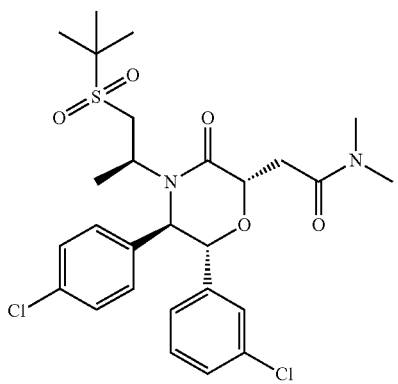

One of the title compounds was isolated as the second eluting isomer in Example 231. ¹H NMR (400 MHz, chloroform-d) δ ppm 1.39-1.47 (m, 12 H) 2.77-3.08 (m, 8 H) 3.15 (dd, J=16.14, 6.36 Hz, 1 H) 3.68-3.78 (m, 1 H) 4.08 (dd, J=13.50, 8.61 Hz, 1 H) 4.72 (dd, J=6.26, 3.52 Hz, 1 H) 5.04 (d, J=7.04 Hz, 1 H) 5.18 (d, J=7.04 Hz, 1 H) 7.01 (d, J=7.63 Hz, 1 H) 7.05-7.26 (m, 3 H) 7.32 (d, J=8.61 Hz, 2 H) 7.37 (d, J=8.61 Hz, 2H). Mass spectrum (ESI) m/z=569 (M+1).

Example 233

2-((2S,5R,6R)-4-((S)-1-(tert-butylsulfonyl)propan-2-yl)-6-(3-chlorophenyl)-5-(4-chlorophenyl)-3-oxo-morpholin-2-yl)-N-(2-hydroxyethyl)acetamide or 2-((2R,5R,6R)-4-((S)-1-(tert-butylsulfonyl)propan-2-yl)-6-(3-chlorophenyl)-5-(4-chlorophenyl)-3-oxo-morpholin-2-yl)-N-(2-hydroxyethyl)acetamide

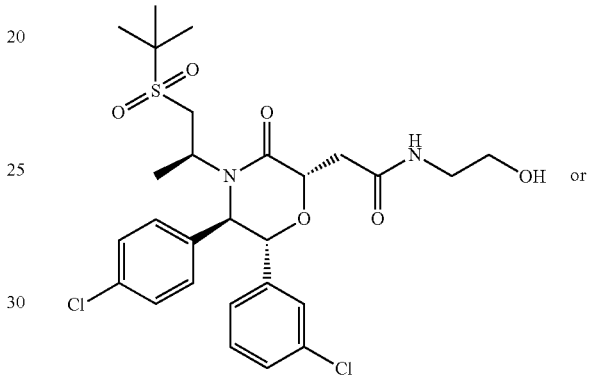

or

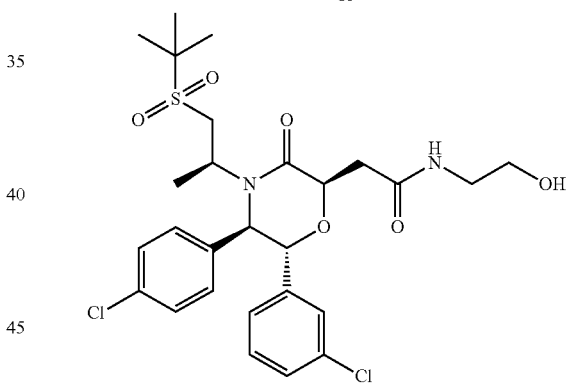

One of the title compounds was obtained following a procedure analogous to the one described in Example 225 using ethanolamine in place of ammonia. The crude residue was purified by preparative thin layer chromatography (eluent: 8% ethanol/toluene with 0.5% aq. NH₄OH) to provide one of the title compounds as the first eluting isomer. ¹H NMR (400 MHz, chloroform-d) δ ppm 1.35 (d, J=6.85 Hz, 3 H) 1.43 (s, 9 H) 2.79-2.89 (m, 2 H) 3.00 (dd, J=14.67, 5.67 Hz, 1 H) 3.30-3.40 (m, 1 H) 3.44-3.55 (m, 1 H) 3.56-3.71 (m, 2 H) 3.74-3.83 (m, 1 H) 4.19 (dd, J=13.30, 9.59 Hz, 1 H) 4.65 (d, J=9.78 Hz, 1 H) 4.77 (t, J=6.06 Hz, 1 H) 5.00 (d, J=9.59 Hz, 1 H) 6.34 (t, J=5.38 Hz, 1 H) 6.78 (d, J=7.63 Hz, 1 H) 7.05-7.15 (m, 4 H) 7.20 (ddd, J=7.97, 2.10, 1.08 Hz, 1 H) 7.30 (d, J=8.61 Hz, 2 H). Mass spectrum (ESI) m/z=585 (M+1).

Example 234

2-((2R,5R,6R)-4-((S)-1-(tert-butylsulfonyl)propan-2-yl)-6-(3-chlorophenyl)-5-(4-chlorophenyl)-3-oxo-morpholin-2-yl)-N-(2-hydroxyethyl)acetamide or 2-((2S,5R,6R)-4-((S)-1-(tert-butylsulfonyl)propan-2-yl)-6-(3-chlorophenyl)-5-(4-chlorophenyl)-3-oxo-morpholin-2-yl)-N-(2-hydroxyethyl)acetamide

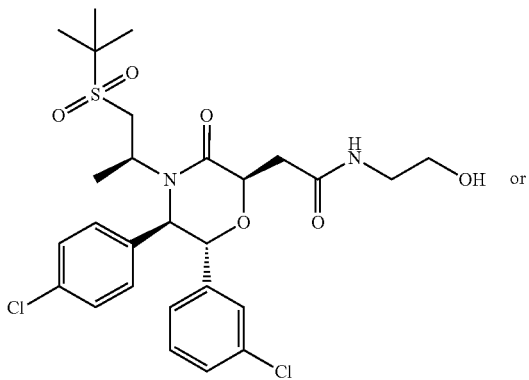

One of the title compounds was isolated as the second eluting isomer in Example 233. ¹H NMR (400 MHz, chloroform-d) δ ppm 1.38 (d, J=6.85 Hz, 3 H) 1.43 (s, 9 H) 2.81-2.91 (m, 2 H) 3.03 (dd, J=15.26, 7.04 Hz, 1 H) 3.44 (ddd, J=4.84, 3.96, 0.98 Hz, 2 H) 3.67-3.78 (m, 3 H) 4.08 (dd, J=13.50, 9.00 Hz, 1 H) 4.68 (dd, J=7.04, 4.69 Hz, 1 H) 5.00 (d, J=7.43 Hz, 1 H) 5.06 (d, J=7.04 Hz, 1 H) 6.36 (t, J=5.38 Hz, 1 H) 6.99 (d, J=7.63 Hz, 1 H) 7.08-7.19 (m, 1 H) 7.20-7.40 (m, 6 H). Mass spectrum (ESI) m/z=585 (M+1).

Example 235

(2S,5R,6R)-4-((S)-1-(tert-butylsulfonyl)propan-2-yl)-6-(3-chlorophenyl)-5-(4-chlorophenyl)-2-(2-morpholino-2-oxoethyl)morpholin-3-one or (2R,5R,6R)-4-((S)-1-(tert-butylsulfonyl)propan-2-yl)-6-(3-chlorophenyl)-5-(4-chlorophenyl)-2-(2-morpholino-2-oxoethyl)morpholin-3-one

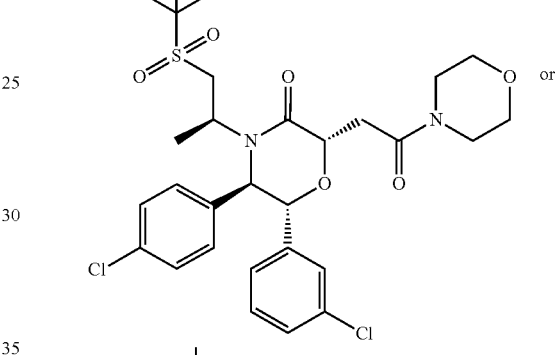

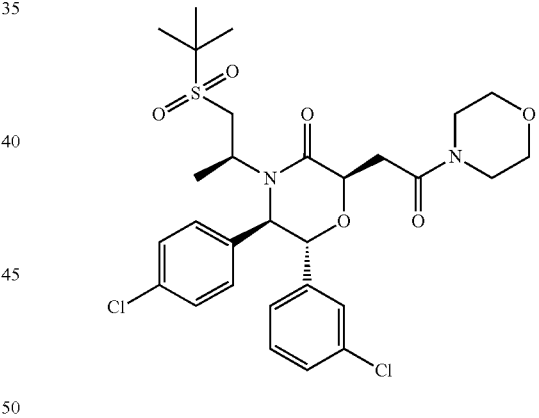

One of the title compounds was obtained following a procedure analogous to the one described in Example 225 using morpholine in place of ammonia. The crude residue was purified by preparative thin layer chromatography (eluent: 50% THF/toluene) to provide one of the title compounds as the first eluting isomer. ¹H NMR (400 MHz, chloroform-d) δ ppm 1.39 (d, J=6.85 Hz, 3 H) 1.43 (s, 9 H) 2.93 (dd, J=13.50, 4.30 Hz, 1 H) 3.00 (dd, J=16.04, 6.65 Hz, 1 H) 3.10 (dd, J=15.85, 4.11 Hz, 1 H) 3.42-3.78 (m, 9 H) 4.19 (dd, J=13.40, 8.12 Hz, 1 H) 4.63 (d, J=9.59 Hz, 1 H) 4.85 (dd, J=6.65, 4.11 Hz, 1 H) 4.96 (d, J=9.59 Hz, 1 H) 6.75 (d, J=7.82 Hz, 1 H) 7.03-7.13 (m, 4 H) 7.19 (ddd, J=8.02, 2.05, 1.08 Hz, 1 H) 7.25-7.32 (m, 2 H). Mass spectrum (ESI) m/z=611 (M+1).

Example 236

(2R,5R,6R)-4-((S)-1-(tert-butylsulfonyl)propan-2-yl)-6-(3-chlorophenyl)-5-(4-chlorophenyl)-2-(2-morpholino-2-oxoethyl)morpholin-3-one or (2S,5R,6R)-4-((S)-1-(tert-butylsulfonyl)propan-2-yl)-6-(3-chlorophenyl)-5-(4-chlorophenyl)-2-(2-morpholino-2-oxoethyl)morpholin-3-one

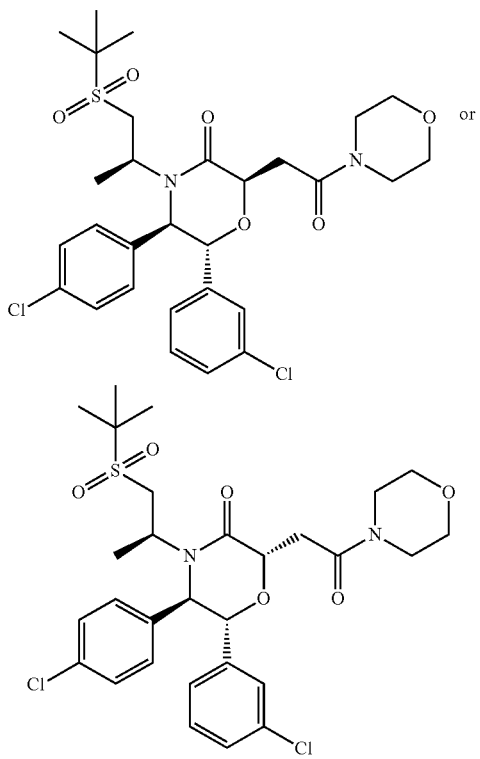

One of the title compounds was isolated as the second eluting isomer in Example 235. $^1$H NMR (400 MHz, chloroform-d) δ ppm 1.37-1.46 (m, 12 H) 2.88 (dd, J=13.50, 3.52 Hz, 1 H) 2.96 (dd, J=16.04, 3.52 Hz, 1 H) 3.14 (dd, J=16.04, 6.65 Hz, 1 H) 3.46-3.51 (m, 2 H) 3.58-3.77 (m, 7 H) 4.08 (dd, J=13.40, 8.71 Hz, 1 H) 4.73 (dd, J=6.65, 3.33 Hz, 1 H) 5.05 (d, J=7.04 Hz, 1 H) 5.14 (d, J=7.04 Hz, 1 H) 7.00 (d, J=7.63 Hz, 1 H) 7.14 (t, J=7.73 Hz, 1 H) 7.19-7.26 (m, 2 H) 7.33 (d, J=3.13 Hz, 4 H). Mass spectrum (ESI) m/z=611 (M+1).

Example 237

2-((2S,5R,6R)-4-((S)-1-(tert-butylsulfonyl)propan-2-yl)-6-(3-chlorophenyl)-5-(4-chlorophenyl)-3-oxomorpholin-2-yl)-N-(methylsulfonyl)acetamide

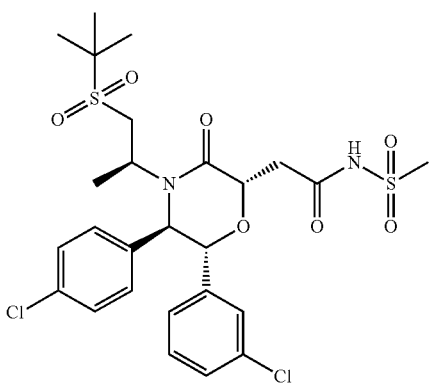 [SMILES: C[C@@H](CS(=O)(=O)C(C)(C)C)N1C(=O)[C@H](CC(=O)NS(C)(=O)=O)O[C@H](c2cccc(Cl)c2)[C@H]1c1ccc(Cl)cc1]

To a solution of 2-((2S,5R,6R)-4-((S)-1-(tert-butylsulfonyl)propan-2-yl)-6-(3-chlorophenyl)-5-(4-chlorophenyl)-3-oxomorpholin-2-yl)acetic acid and 2-((2R,5R,6R)-4-((S)-1-(tert-butylsulfonyl)propan-2-yl)-6-(3-chlorophenyl)-5-(4-chlorophenyl)-3-oxomorpholin-2-yl)acetic acid (as a mixture of isomers from Example 223) (69 mg, 0.127 mmol) in THF (2 mL) was added 1,1'-carbonyldiimidazole (82 mg, 0.509 mmol), N,N-diisopropylethylamine (0.111 mL, 0.636 mmol), and methanesulfonamide (48.4 mg, 0.509 mmol). The resulting mixture was heated at 70° C. After stirring for 24 hours, the mixture had evaporated nearly to dryness. The mixture was diluted with 2 mL THF and was cooled to room temperature. After two more days at room temperature, the mixture was acidified with 10% aq. citric acid, diluted with water, and extracted with ethyl acetate. The organic layer was washed with brine. The combined aqueous layers were extracted with DCM (2×). The combined organic layers were dried over Na$_2$SO$_4$, and concentrated. The crude residue was purified by preparative thin layer chromatography (eluent: 25% THF/toluene) to provide the title compound as the first eluting isomer.

$^1$H NMR (400 MHz, chloroform-d) δ ppm 1.34 (d, J=6.85 Hz, 3 H) 1.43 (s, 9 H) 2.81 (dd, J=13.30, 3.33 Hz, 1 H) 2.89 (dd, J=15.06, 4.70 Hz, 1 H) 3.18 (dd, J=15.16, 8.31 Hz, 1 H) 3.27 (br. s., 3 H) 3.55-3.67 (m, 1 H) 4.19 (dd, J=13.20, 10.66 Hz, 1 H) 4.64 (d, J=9.78 Hz, 1 H) 4.72-4.76 (m, 1 H) 5.03 (d, J=10.17 Hz, 1 H) 6.81 (d, J=7.82 Hz, 1 H) 7.03-7.18 (m, 4 H) 7.20 (d, J=1.57 Hz, 1 H) 7.31 (d, J=8.61 Hz, 2 H). Mass spectrum (ESI) m/z=619 (M+1).

Example 238

2-((2R,5R,6R)-4-((S)-1-(tert-butylsulfonyl)propan-2-yl)-6-(3-chlorophenyl)-5-(4-chlorophenyl)-3-oxomorpholin-2-yl)-N-(methylsulfonyl)acetamide

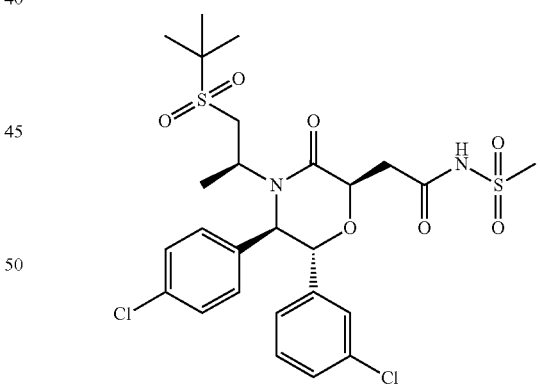

The title compound was obtained as the second eluting isomer in Example 237. $^1$H NMR (400 MHz, acetonitrile-d$_3$) δ ppm 1.30 (d, J=6.85 Hz, 3 H) 1.34 (s, 9 H) 2.90 (s, 3 H) 2.97 (s, 2 H) 3.01 (dd, J=13.40, 4.40 Hz, 1 H) 3.56-3.69 (m, 1 H) 3.93 (dd, J=13.60, 8.90 Hz, 1 H) 4.73 (dd, J=7.92, 4.99 Hz, 1 H) 4.95 (d, J=8.02 Hz, 1 H) 4.99 (d, J=8.02 Hz, 1 H) 7.04 (d, J=6.06 Hz, 1 H) 7.14 (s, 1 H) 7.18-7.31 (m, 4 H) 7.32-7.38 (m, 2 H). Mass spectrum (ESI) m/z=619 (M+1).

Example 239

2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)-N-(methylsulfonyl)acetamide or 2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)-N-(methylsulfonyl)acetamide

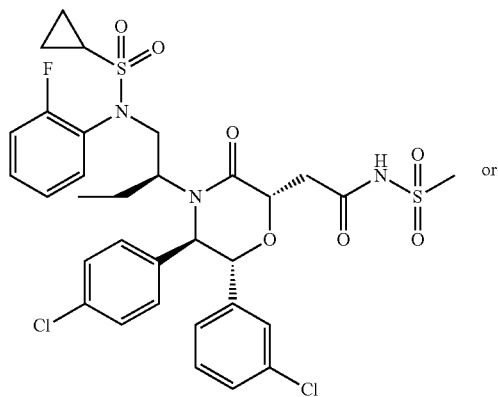

or

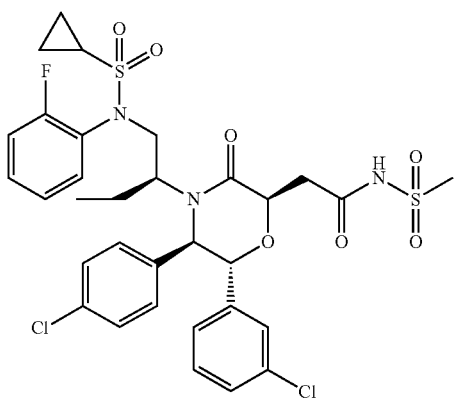

One of the title compounds was obtained from 2-((5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)acetic acid and 2-((5R,6R)-6-(3-chlorophenyl)-5-(4-chlorophenyl)-4-((R)-1-(N-(2-fluorophenyl)cyclopropanesulfonamido)butan-2-yl)-3-oxomorpholin-2-yl)acetic acid (115 mg, 0.177 mmol) (mixture of isomers from Example 133) using a procedure analogous to the one described in Example 237. The crude residue was purified by thin layer chromatography (eluent: 50% THF/toluene) to provide one of the title compounds as the first eluting isomer. $^1$H NMR (400 MHz, acetonitrile-$d_3$) δ ppm 0.47 (t, J=7.53 Hz, 3 H) 0.80-0.89 (m, 2 H) 0.97 (ddd, J=6.46, 2.74, 1.37 Hz, 2 H) 1.54-1.67 (m, 1 H) 1.81-1.89 (m, 1 H) 2.44-2.61 (m, 2 H) 2.75-2.91 (m, 2 H) 3.07 (br. s., 3 H) 3.64-3.76 (m, 1 H) 4.21-4.33 (m, 1 H) 4.64 (d, J=9.98 Hz, 1 H) 4.76-4.87 (m, 2 H) 6.92 (d, J=7.63 Hz, 1 H) 7.04 (d, J=8.22 Hz, 2 H) 7.08-7.13 (m, 1 H) 7.17-7.35 (m, 6 H) 7.39-7.49 (m, 1 H) 7.56 (t, J=7.92 Hz, 1 H). Mass spectrum (ESI) m/z=726 (M+1).

Example 240

2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)-N-(methylsulfonyl)acetamide or 2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)-N-(methylsulfonyl)acetamide

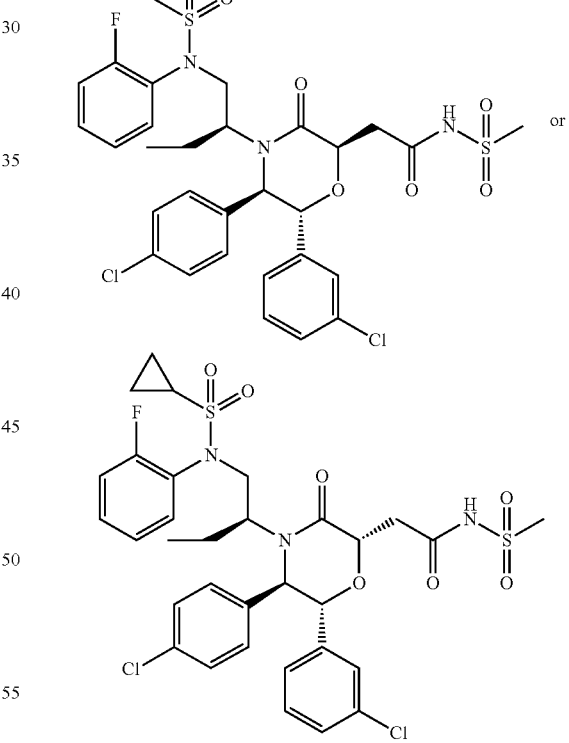

One of the title compounds was isolated as the second eluting isomer in Example 239. $^1$H NMR (400 MHz, acetonitrile-$d_3$) δ ppm 0.43 (t, J=7.24 Hz, 3 H) 0.76-1.04 (m, 4 H) 1.48-1.66 (m, 1 H) 1.83-1.91 (m, 1 H) 2.53-2.64 (m, 1 H) 2.86-3.08 (m, 6 H) 3.73 (dd, J=13.30, 3.13 Hz, 1 H) 4.20-4.38 (m, 1 H) 4.42-4.64 (m, 1 H) 4.69-4.82 (m, 1 H) 4.90 (d, J=8.61 Hz, 1 H) 7.02-7.20 (m, 4 H) 7.21-7.36 (m, 6 H) 7.43 (m, 2 H) 7.56 (t, J=7.24 Hz, 1 H). Mass spectrum (ESI) m/z=726 (M+1).

Example 241

2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)acetamide or 2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)acetamide

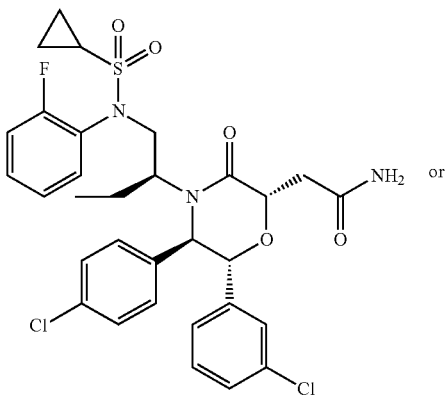

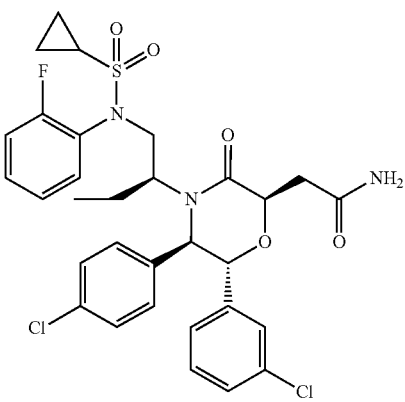

One of the title compounds was obtained from 2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)acetic acid and 2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)acetic acid (87 mg, 0.134 mmol) (mixture of isomers from Example 133) by a procedure analogous to the one described in Example 225. The crude residue was purified by thin layer chromatography (eluent: 8% ethanol/toluene with 0.5% aq. NH$_4$OH) to provide one of the title compounds as the first eluting isomer. $^1$H NMR (400 MHz, chloroform-d) δ ppm 0.48 (t, J=7.53 Hz, 3 H) 0.86-1.08 (m, 4 H) 1.47-1.55 (m, 1 H) 1.89-2.03 (m, 1 H) 2.34-2.50 (m, 2 H) 2.80 (dd, J=15.26, 5.67 Hz, 1 H) 2.88-2.98 (m, 1 H) 3.72 (dd, J=14.97, 3.62 Hz, 1 H) 4.47 (dd, J=14.77, 8.90 Hz, 1 H) 4.65 (d, J=9.98 Hz, 1 H) 4.73 (dd, J=6.85, 5.48 Hz, 1 H) 4.82 (d, J=9.98 Hz, 1 H) 6.84 (dt, J=7.73, 1.42 Hz, 1 H) 7.00 (d, J=8.22 Hz, 2 H) 7.08-7.30 (m, 7 H) 7.34-7.43 (m, 1 H) 7.56 (td, J=7.87, 1.66 Hz, 1 H). Mass spectrum (ESI) m/z=648 (M+1).

Example 242

2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)acetamide or 2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)acetamide

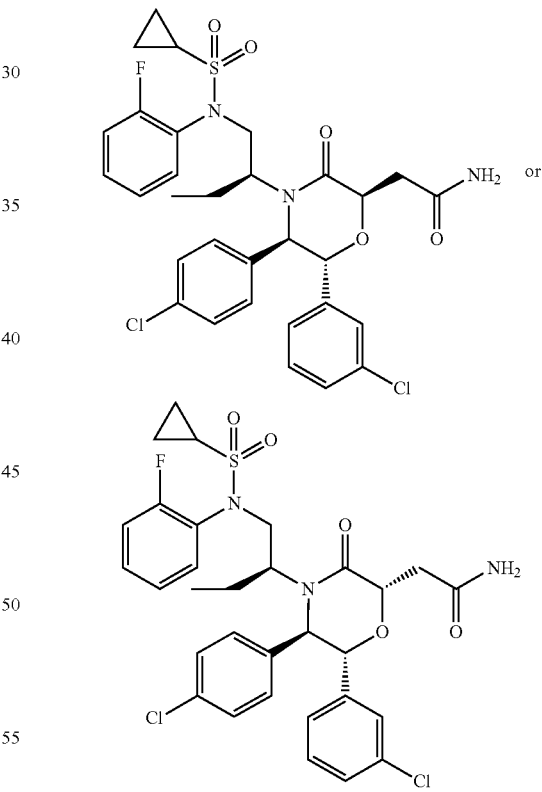

One of the title compounds was isolated as the second eluting isomer in Example 241. $^1$H NMR (400 MHz, chloroform-d) δ ppm 0.49 (t, J=7.63 Hz, 3 H) 0.87-1.11 (m, 4 H) 1.44-1.67 (m, 2 H) 1.85-2.00 (m, 1 H) 2.39-2.53 (m, 1 H) 2.84 (dd, J=15.85, 4.30 Hz, 1 H) 2.97 (dd, J=15.85, 7.43 Hz, 1 H) 3.79 (dd, J=14.67, 4.30 Hz, 1 H) 4.31-4.43 (m, 2 H) 4.91 (d, J=8.02 Hz, 1 H) 4.96 (d, J=8.02 Hz, 1 H) 7.02 (d, J=7.43 Hz, 1 H) 7.14-7.33 (m, 9 H) 7.34-7.41 (m, 1 H) 7.53 (td, J=7.82, 1.57 Hz, 1 H). Mass spectrum (ESI) m/z=648 (M+1).

Example 243

N-((S)-2-((2R,5R,6R)-2-((1H-tetrazol-5-yl)methyl)-6-(3-chlorophenyl)-5-(4-chlorophenyl)-3-oxomorpholino)butyl)-N-methylcyclopropanesulfonamide or N-((S)-2-((2S,5R,6R)-2-((1H-tetrazol-5-yl)methyl)-6-(3-chlorophenyl)-5-(4-chlorophenyl)-3-oxomorpholino)butyl)-N-methylcyclopropanesulfonamide

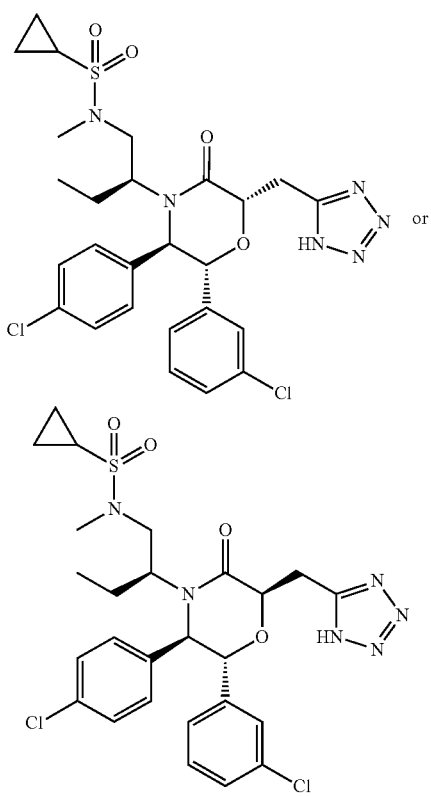

Step A. (2R,5R,6R)-2-allyl-6-(3-chlorophenyl)-5-(4-chlorophenyl)-4-((S)-1-hydroxybutan-2-yl)morpholin-3-one and (2S,5R,6R)-2-allyl-6-(3-chlorophenyl)-5-(4-chlorophenyl)-4-((S)-1-hydroxybutan-2-yl)morpholin-3-one

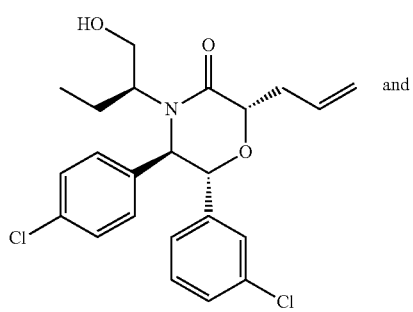

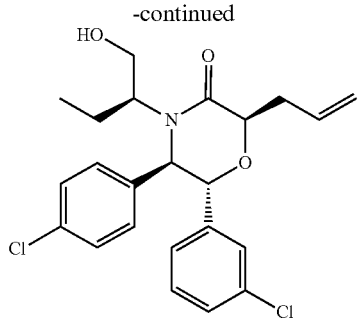

The title compounds were prepared from (5R,6R)-6-(3-chlorophenyl)-5-(4-chlorophenyl)-4-((S)-1-((3,4-dimethoxybenzyl)oxy)butan-2-yl)morpholin-3-one (Example 112, Step B) by procedures similar to those described in Example 130, Steps B and C.

Step B. (S)-2-((2R,5R,6R)-2-allyl-6-(3-chlorophenyl)-5-(4-chlorophenyl)-3-oxomorpholino)butanal and (S)-2-((2S,5R,6R)-2-allyl-6-(3-chlorophenyl)-5-(4-chlorophenyl)-3-oxomorpholino)butanal

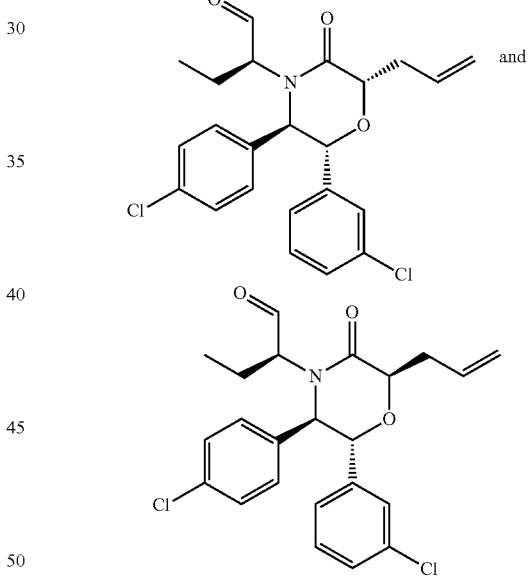

To a solution of (2R,5R,6R)-2-allyl-6-(3-chlorophenyl)-5-(4-chlorophenyl)-4-((S)-1-hydroxybutan-2-yl)morpholin-3-one and (2S,5R,6R)-2-allyl-6-(3-chlorophenyl)-5-(4-chlorophenyl)-4-((S)-1-hydroxybutan-2-yl)morpholin-3-one (163 mg, 0.375 mmol; Example 243, Step A) in DCM (1.8 mL) was added Dess-Martin periodinane (175 mg, 0.413 mmol) and water (7.44 µL, 0.413 mmol). After 30 minutes, sat. aq. sodium thiosulfate was added. The mixture was extracted with DCM (2×). The combined organic layers were washed with sat. aq. NaHCO$_3$, dried over Na$_2$SO$_4$, and concentrated to provide the title compounds.

Step C. (2R,5R,6R)-2-allyl-6-(3-chlorophenyl)-5-(4-chlorophenyl)-4-((S)-1-(methylamino)butan-2-yl)morpholin-3-one and (2S,5R,6R)-2-allyl-6-(3-chlorophenyl)-5-(4-chlorophenyl)-4-((S)-1-(methylamino)butan-2-yl)morpholin-3-one

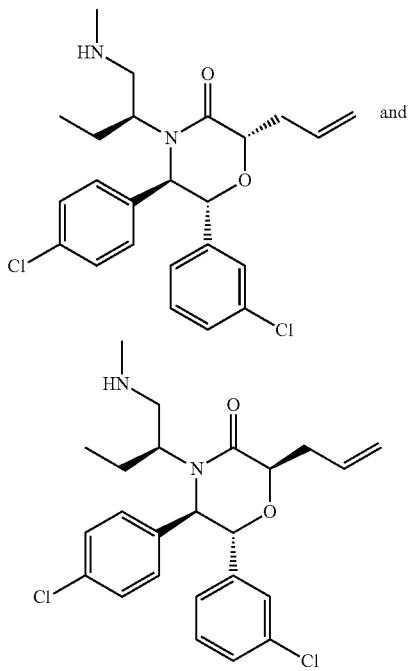

To a solution of (S)-2-((2R,5R,6R)-2-allyl-6-(3-chlorophenyl)-5-(4-chlorophenyl)-3-oxomorpholino)butanal and (S)-2-((2S,5R,6R)-2-allyl-6-(3-chlorophenyl)-5-(4-chlorophenyl)-3-oxomorpholino)butanal (188 mg, 0.435 mmol; Example 243, Step B) in DCE (4 mL) was added 2.0 M methylamine solution in THF (1.305 mL, 2.61 mmol) and sodium triacetoxyborohydride (276 mg, 1.305 mmol). Three drops of AcOH were added. After stirring overnight, the reaction was quenched with dilute aq. NaHCO₃. The mixture was extracted with ethyl acetate. The organic layer was washed with brine, dried over Na₂SO₄, and concentrated to provide the title compounds.

Step D. N-((S)-2-((2R,5R,6R)-2-allyl-6-(3-chlorophenyl)-5-(4-chlorophenyl)-3-oxomorpholino)butyl)-N-methylcyclopropanesulfonamide and N-((S)-2-((2S,5R,6R)-2-allyl-6-(3-chlorophenyl)-5-(4-chlorophenyl)-3-oxomorpholino)butyl)-N-methylcyclopropanesulfonamide

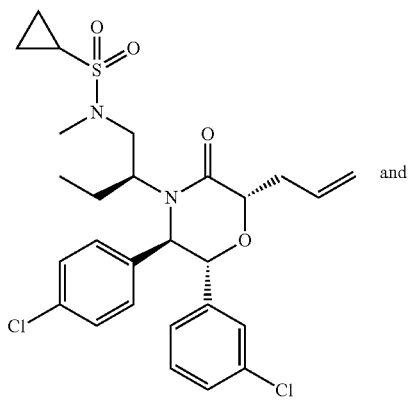

and

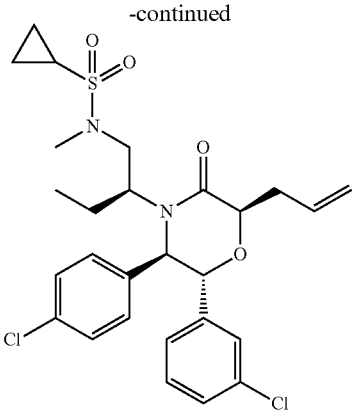

To a solution of (2R,5R,6R)-2-allyl-6-(3-chlorophenyl)-5-(4-chlorophenyl)-4-((S)-1-(methylamino)butan-2-yl)morpholin-3-one and (2S,5R,6R)-2-allyl-6-(3-chlorophenyl)-5-(4-chlorophenyl)-4-((S)-1-(methylamino)butan-2-yl)morpholin-3-one (162 mg, 0.362 mmol; Example 243, Step C) and pyridine (0.070 mL, 0.869 mmol) in DCM (4 mL) was added cyclopropanesulfonyl chloride (0.044 mL, 0.435 mmol). After 90 minutes, DMAP (5.0 mg, 0.041 mmol) was added. After one more hour, cyclopropanesulfonyl chloride (0.044 mL, 0.435 mmol) and pyridine (0.070 mL, 0.869 mmol) were added. After stirring for three days, the mixture was quenched with water and extracted with DCM (2×). Sat. aq. NH₄Cl was added. The combined organic layers were dried over Na₂SO₄, and concentrated. The crude residue was purified by flash chromatography on silica gel (12 g column, eluent: 5 to 70% ethyl acetate/hexanes) to provide the title compounds.

Step E. 2-((2R,5R,6R)-6-(3-chlorophenyl)-5-(4-chlorophenyl)-4-((S)-1-(N-methylcyclopropanesulfonamido)butan-2-yl)-3-oxomorpholin-2-yl)acetic acid and 2-((2S,5R,6R)-6-(3-chlorophenyl)-5-(4-chlorophenyl)-4-((S)-1-(N-methylcyclopropanesulfonamido)butan-2-yl)-3-oxomorpholin-2-yl)acetic acid

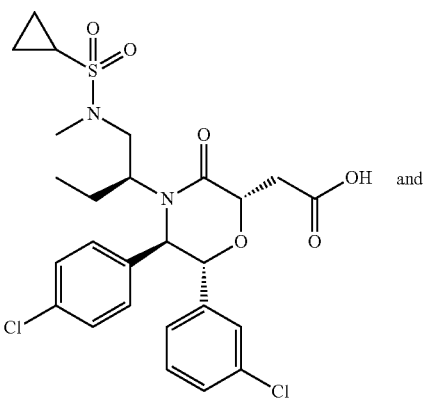

and

-continued

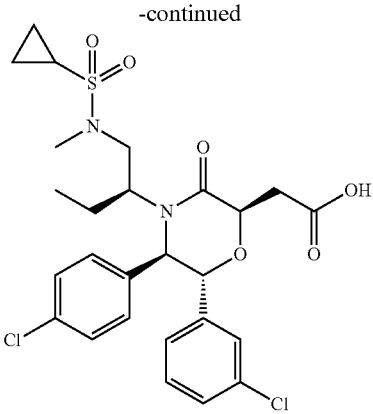

To a solution of N-((S)-2-((2R,5R,6R)-2-allyl-6-(3-chlorophenyl)-5-(4-chlorophenyl)-3-oxomorpholino)butyl)-N-methylcyclopropanesulfonamide and N-((S)-2-((2S,5R,6R)-2-allyl-6-(3-chlorophenyl)-5-(4-chlorophenyl)-3-oxomorpholino)butyl)-N-methylcyclopropanesulfonamide (77 mg, 0.140 mmol; Example 243, Step D) in acetonitrile (1.0 mL), ethyl acetate (1.0 mL), and water (1.5 mL) was added sodium periodate (179 mg, 0.838 mmol) and ruthenium(III) chloride hydrate (0.223 µL, 3.07 µmol). After 1 hour, the mixture was diluted with water and extracted with ethyl acetate. The organic layer was washed with brine, dried over Na$_2$SO$_4$, and concentrated to provide the title compounds.

Step F. 2-((2R,5R,6R)-6-(3-chlorophenyl)-5-(4-chlorophenyl)-4-((S)-1-(N-methylcyclopropanesulfonamido)butan-2-yl)-3-oxomorpholin-2-yl)acetamide and 2-((2S,5R,6R)-6-(3-chlorophenyl)-5-(4-chlorophenyl)-4-((S)-1-(N-methylcyclopropanesulfonamido)butan-2-yl)-3-oxomorpholin-2-yl)acetamide

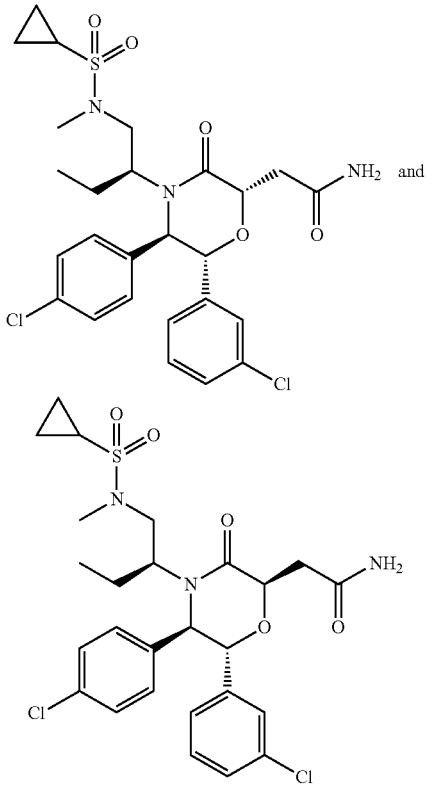

To a solution of 2-((2R,5R,6R)-6-(3-chlorophenyl)-5-(4-chlorophenyl)-4-((S)-1-(N-methylcyclopropanesulfonamido)butan-2-yl)-3-oxomorpholin-2-yl)acetic acid and 2-((2S,5R,6R)-6-(3-chlorophenyl)-5-(4-chlorophenyl)-4-((S)-1-(N-methylcyclopropanesulfonamido)butan-2-yl)-3-oxomorpholin-2-yl)acetic acid (75 mg, 0.132 mmol; Example 243, Step E) in DMF (2 mL) was added HATU (100 mg, 0.263 mmol) and triethylamine (0.055 mL, 0.395 mmol). After 30 minutes, 7 N ammonia solution in methanol (0.094 mL, 0.658 mmol) was added. After 90 minutes, the mixture was quenched with sat. aq. NaHCO$_3$ and extracted with ethyl acetate. The organic layer was washed with brine, dried over Na$_2$SO$_4$, and concentrated. The crude residue was purified by flash chromatography on silica gel (4 g column, eluent: 0 to 10% MeOH/DCM) to provide the title compounds.

Step G. N-((S)-2-((2R,3R,6R)-2-(3-chlorophenyl)-3-(4-chlorophenyl)-6-(cyanomethyl)-5-oxomorpholino)butyl)-N-methylcyclopropanesulfonamide and N-((S)-2-((2R,3R,6S)-2-(3-chlorophenyl)-3-(4-chlorophenyl)-6-(cyanomethyl)-5-oxomorpholino)butyl)-N-methylcyclopropanesulfonamide

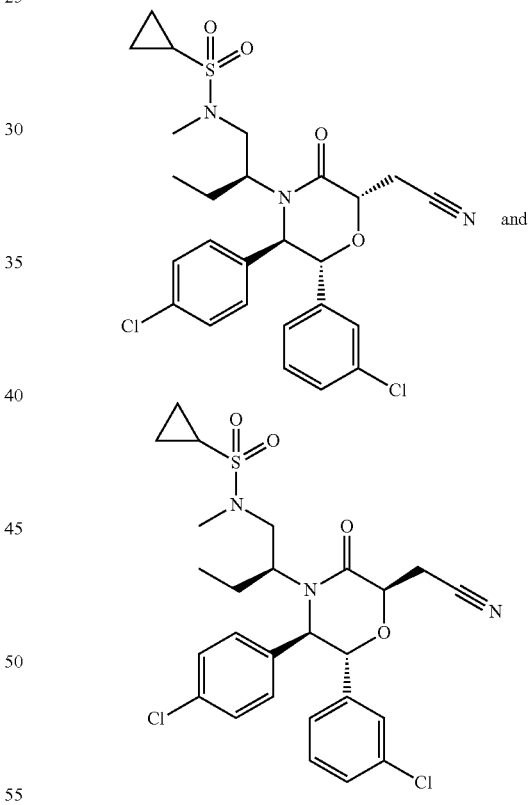

To a 0° C. solution of 2-((2R,5R,6R)-6-(3-chlorophenyl)-5-(4-chlorophenyl)-4-((S)-1-(N-methylcyclopropanesulfonamido)butan-2-yl)-3-oxomorpholin-2-yl)acetamide and 2-((2S,5R,6R)-6-(3-chlorophenyl)-5-(4-chlorophenyl)-4-((S)-1-(N-methylcyclopropanesulfonamido)butan-2-yl)-3-oxomorpholin-2-yl)acetamide (59 mg, 0.104 mmol; Example 243, Step F) in THF (1.5 mL) was added triethylamine (0.072 mL, 0.519 mmol) and trifluoroacetic anhydride (0.037 mL, 0.259 mmol). After 90 minutes, the reaction was quenched with 10% aq. citric acid. The mixture was extracted with ethyl acetate (2×). The combined organic layers were washed with brine, dried over Na₂SO₄, and concentrated. The crude residue was purified by flash chromatography on silica gel (2 stacked 4 g columns, eluent: 15 to 70% ethyl acetate/hexanes) to provide the title compounds.

Step H. N-((S)-2-((2R,5R,6R)-2-((1H-tetrazol-5-yl)methyl)-6-(3-chlorophenyl)-5-(4-chlorophenyl)-3-oxomorpholino)butyl)-N-methylcyclopropanesulfonamide or N-((S)-2-((2S,5R,6R)-2-((1H-tetrazol-5-yl)methyl)-6-(3-chlorophenyl)-5-(4-chlorophenyl)-3-oxomorpholino)butyl)-N-methylcyclopropanesulfonamide

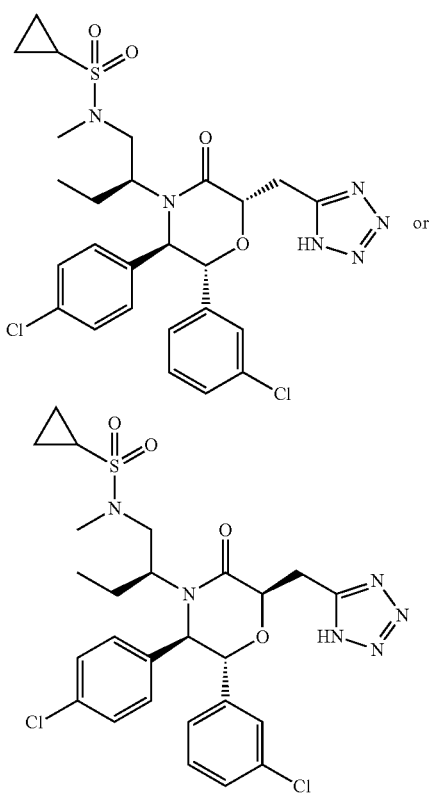

A solution of N-((S)-2-((2R,3R,6R)-2-(3-chlorophenyl)-3-(4-chlorophenyl)-6-(cyanomethyl)-5-oxomorpholino)butyl)-N-methylcyclopropanesulfonamide and N-((S)-2-((2R,3R,6S)-2-(3-chlorophenyl)-3-(4-chlorophenyl)-6-(cyanomethyl)-5-oxomorpholino)butyl)-N-methylcyclopropanesulfonamide (42 mg, 0.076 mmol; Example 243, Step G), ammonium chloride (40.8 mg, 0.763 mmol), and sodium azide (49.6 mg, 0.763 mmol) in DMF (0.5 mL) was heated at 100° C. for 2 days. The mixture was acidified with 10% aq. citric acid. The mixture was extracted with ethyl acetate (2×). The combined organic layers were washed with brine, dried over Na₂SO₄, and concentrated. The crude residue was purified by preparative reverse phase HPLC on a 100×30 mm 5 μm C₁₈ column (Phenomenex, Torrance, Calif.; eluent: 10 to 90% MeCN/water with 0.1% TFA) to provide one of the title compounds as the first eluting isomer. ¹H NMR (400 MHz, chloroform-d) δ ppm 0.58 (t, J=7.53 Hz, 3 H) 0.94-1.09 (m, 2 H) 1.12-1.25 (m, 2 H) 1.52-1.69 (m, 1 H) 1.83-1.98 (m, 1 H) 2.33 (ddd, J=7.87, 4.84, 3.13 Hz, 1 H) 2.89 (s, 3 H) 3.01 (dd, J=14.48, 4.11 Hz, 1 H) 3.07-3.19 (m, 1 H) 3.69 (dd, J=15.85, 6.85 Hz, 1 H) 3.79 (dd, J=15.85, 6.06 Hz, 1 H) 4.08 (t, J=11.64 Hz, 1 H) 4.72 (t, J=6.26 Hz, 1 H) 4.93 (dd, J=10.37, 6.65 Hz, 2 H) 7.04-7.12 (m, 3 H) 7.19-7.26 (m, 3 H) 7.33 (d, J=8.41 Hz, 2 H). Mass spectrum (ESI) m/z=593 (M+1).

Example 244

N-((S)-2-((2S,5R,6R)-2-((1H-tetrazol-5-yl)methyl)-6-(3-chlorophenyl)-5-(4-chlorophenyl)-3-oxomorpholino)butyl)-N-methylcyclopropanesulfonamide or N-((S)-2-((2R,5R,6R)-2-((1H-tetrazol-5-yl)methyl)-6-(3-chlorophenyl)-5-(4-chlorophenyl)-3-oxomorpholino)butyl)-N-methylcyclopropanesulfonamide

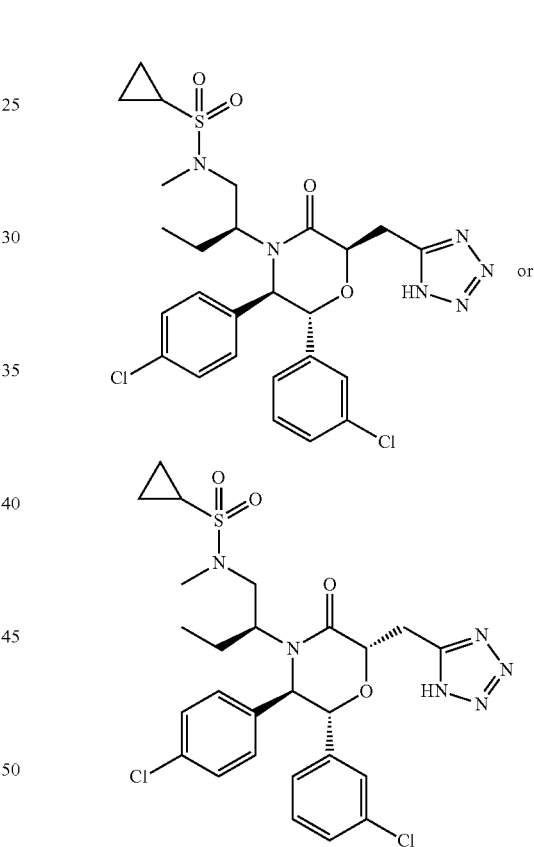

One of the title compounds was isolated as the second eluting isomer in Example 243, Step H. It was further purified by preparative TLC (eluent: 50% acetone/hexanes) to provide one of the title compounds. ¹H NMR (400 MHz, acetonitrile-d₃) δ ppm 0.56 (t, J=7.53 Hz, 3 H) 0.90-1.08 (m, 4 H) 1.64-1.84 (m, 2 H) 2.39-2.48 (m, 1 H) 2.86 (s, 3 H) 2.91-3.07 (m, 2 H) 3.29 (dd, J=15.36, 8.71 Hz, 1 H) 3.64 (dd, J=15.45, 3.91 Hz, 1 H) 3.68-3.82 (m, 1 H) 4.74 (d, J=9.78 Hz, 1 H) 4.81 (d, J=9.78 Hz, 1 H) 4.94 (dd, J=8.61, 3.91 Hz, 1 H) 6.87 (d, J=7.63 Hz, 1 H) 7.06 (t, J=1.86 Hz, 1 H) 7.11-7.26 (m, 4 H) 7.31 (d, J=8.61 Hz, 2 H). Mass spectrum (ESI) m/z=593 (M+1).

Example 245

(2R,5R,6R)-4-((S)-1-(tert-butylsulfonyl)butan-2-yl)-6-(3-chlorophenyl)-5-(4-chlorophenyl)-2-(3-hydroxy-2-oxopropyl)morpholin-3-one or (2S,5R,6R)-4-((S)-1-(tert-butylsulfonyl)butan-2-yl)-6-(3-chlorophenyl)-5-(4-chlorophenyl)-2-(3-hydroxy-2-oxopropyl)morpholin-3-one

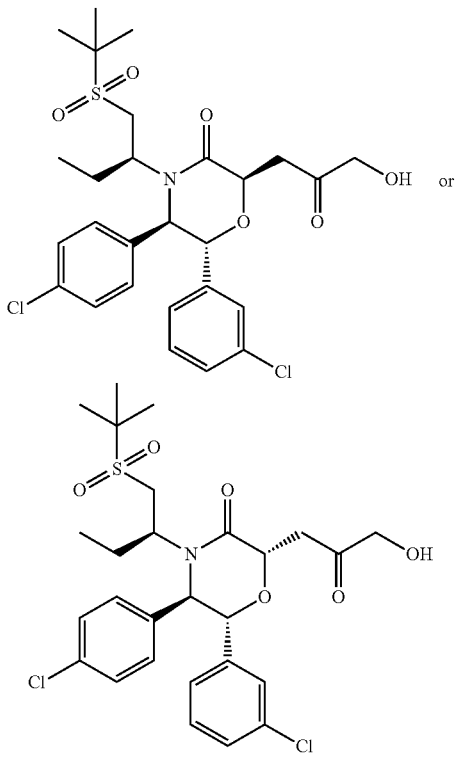

To a solution of 2-((2R,5R,6R)-4-((S)-1-(tert-butylsulfonyl)butan-2-yl)-6-(3-chlorophenyl)-5-(4-chlorophenyl)-3-oxomorpholin-2-yl)acetic acid and 2-((2S,5R,6R)-4-((S)-1-(tert-butylsulfonyl)butan-2-yl)-6-(3-chlorophenyl)-5-(4-chlorophenyl)-3-oxomorpholin-2-yl)acetic acid (99 mg, 0.178 mmol, Example 120, mixture of diastereomers) in DCM (2 mL) was added oxalyl chloride (0.098 mL, 0.196 mmol) and 2 drops DMF. Evolution of gas was observed. After 1 hour, the mixture was concentrated. To the residue was added tris(trimethylsilyloxy)ethylene (129 µL, 0.392 mmol). The mixture was heated at 90° C. for 90 minutes, then tris(trimethylsilyloxy)ethylene (129 µL, 0.392 mmol) was added. After 90 minutes, the mixture was cooled to room temperature and 1 mL THF and 1 mL 5% aq. HCl were added. The mixture was heated at reflux for 1 hour. The mixture was cooled, diluted with water, and extracted with ethyl acetate. The organic layer was washed with brine, dried over $Na_2SO_4$, and concentrated. The residue was purified by preparative reverse phase HPLC (Gemeni™ Prep $C_{18}$ 5 µm column, Phenomenex, Torrance, Calif.; eluent: 25 to 75% MeCN/water with 0.1% TFA) to afford one of the title compounds as a single isomer. $^1$H NMR (400 MHz, chloroform-d) δ ppm 0.48 (t, J=7.43 Hz, 3 H) 1.36 (s, 9 H) 1.50-1.67 (m, 1 H) 1.96-2.15 (m, 1 H) 2.87 (dd, J=13.60, 2.84 Hz, 1 H) 2.98 (dd, J=16.73, 4.01 Hz, 1 H) 3.15 (dd, J=16.63, 7.24 Hz, 1 H) 3.31 (t, J=9.00 Hz, 1 H) 3.86 (dd, J=13.60, 9.10 Hz, 1 H) 4.25 (s, 2 H) 4.68 (dd, J=7.24, 4.11 Hz, 1 H) 4.88 (d, J=6.65 Hz, 1 H) 5.06 (d, J=6.65 Hz, 1 H) 6.96 (d, J=3.13 Hz, 1 H) 7.08 (t, J=7.83 Hz, 1 H) 7.13-7.22 (m, 3 H) 7.23-7.32 (m, 3 H). Mass spectrum (ESI) m/z=570 (M+1).

Example 246

Methyl 2-((2R,5R,6R)-6-(3-chlorophenyl)-5-(4-chlorophenyl)-4-((S)-1-((2-(dimethylamino)ethyl)sulfonyl)butan-2-yl)-3-oxomorpholin-2-yl)acetate and methyl 2-((2S,5R,6R)-6-(3-chlorophenyl)-5-(4-chlorophenyl)-4-((S)-1-((2-(dimethylamino)ethyl)sulfonyl)butan-2-yl)-3-oxomorpholin-2-yl)acetate

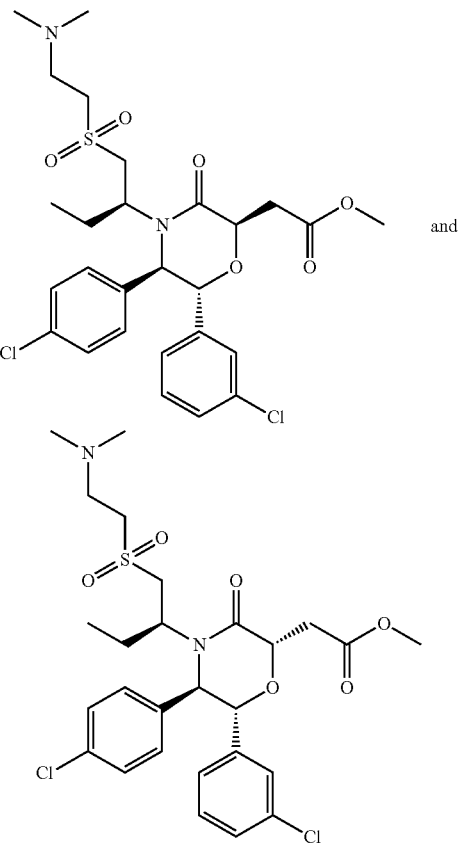

Step A. (S)-1-((1R,2R)-2-((tert-butyldimethylsilyl)oxy)-2-(3-chlorophenyl)-1-(4-chlorophenyl)ethyl)-2-ethylaziridine

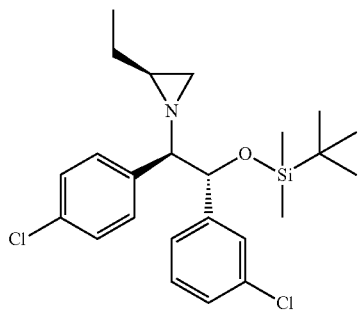 [SMILES: CC[C@H]1CN1[C@H](c1ccc(Cl)cc1)[C@H](O[Si](C)(C)C(C)(C)C)c1cccc(Cl)c1]

The title compound was prepared from (1R,2R)-2-amino-1-(3-chlorophenyl)-2-(4-chlorophenyl)ethanol (Intermediate A2) by procedures similar to those described in Example 160, Steps A through C.

Step B. (5R,6R,8S)-5-(3-chlorophenyl)-6-(4-chlorophenyl)-8-ethyl-2,2,3,3-tetramethyl-4-oxa-10-thia-7-aza-3-siladodecan-12-ol

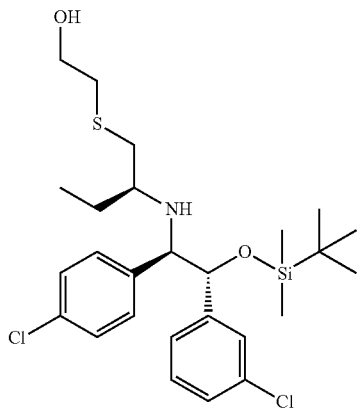 [SMILES: CC[C@@H](CSCCO)N[C@H](c1ccc(Cl)cc1)[C@H](O[Si](C)(C)C(C)(C)C)c1cccc(Cl)c1]

To a stirred solution of (S)-1-((1R,2R)-2-((tert-butyldimethylsilyl)oxy)-2-(3-chlorophenyl)-1-(4-chlorophenyl)ethyl)-2-ethylaziridine (644 mg, 1.429 mmol; Example 246, Step A) in DCM (7 mL) was added 2-mercaptoethanol (201 µL, 2.86 mmol) and indium (III) chloride (3.16 mg, 0.014 mmol). After stirring for 18 hours, the mixture was concentrated to provide the title compound.

Step C. (1R,2R)-1-(3-chlorophenyl)-2-(4-chlorophenyl)-2-(((S)-1-((2-hydroxyethyl)thio)butan-2-yl)amino)ethanol

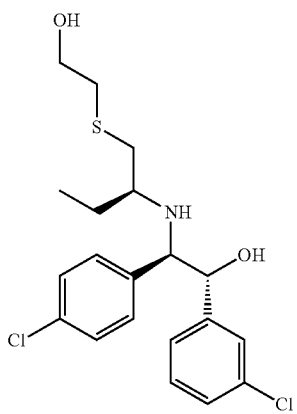 [SMILES: CC[C@@H](CSCCO)N[C@H](c1ccc(Cl)cc1)[C@H](O)c1cccc(Cl)c1]

To a solution of (5R,6R,8S)-5-(3-chlorophenyl)-6-(4-chlorophenyl)-8-ethyl-2,2,3,3-tetramethyl-4-oxa-10-thia-7-aza-3-siladodecan-12-ol (816 mg, 1.544 mmol; Example 246, Step B) in THF (7.7 mL) was added tetrabutylammonium fluoride 1.0 M solution in THF (3087 µL, 3.09 mmol). After 45 minutes, the mixture was diluted with water and extracted with ethyl acetate (2×). The combined organic layers were dried over $Na_2SO_4$ and concentrated. This was purified by flash chromatography on silica gel (40 g column, eluent: 50 to 100% ethyl acetate/hexanes) to provide the title compound.

Step D. (9S,11R,12R)-12-(3-chlorophenyl)-11-(4-chlorophenyl)-9-ethyl-2,2-dimethyl-3,3-diphenyl-4-oxa-7-thia-10-aza-3-siladodecan-12-ol

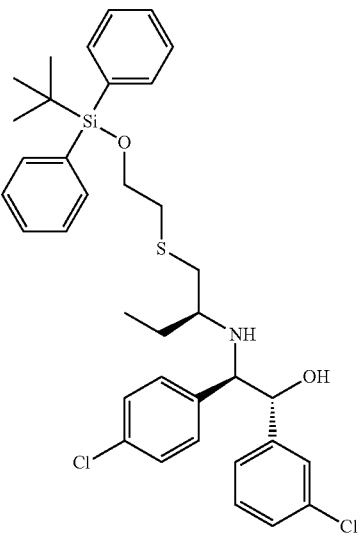 [SMILES: CC[C@@H](CSCCO[Si](c1ccccc1)(c1ccccc1)C(C)(C)C)N[C@H](c1ccc(Cl)cc1)[C@H](O)c1cccc(Cl)c1]

To a solution of (1R,2R)-1-(3-chlorophenyl)-2-(4-chlorophenyl)-2-(((S)-1-((2-hydroxyethyl)thio)butan-2-yl)amino)ethanol (522 mg, 1.260 mmol; Example 246, Step C) in DCM (12.6 mL) was added triethylamine (0.351 mL, 2.52 mmol), 4-(dimethylamino)pyridine (7.69 mg, 0.063 mmol), and tert-butyldiphenylsilyl chloride (0.328 mL, 1.260 mmol). After stirring for 3 days, the reaction was quenched with water and extracted with ethyl acetate (2×). The combined organic layers were dried over $Na_2SO_4$ and concentrated. The crude residue was purified by flash chromatography on silica gel (40 g column, eluent: 0 to 100% ethyl acetate/hexanes) to provide the title compound.

Step E. (9S,11R,12R)-12-(3-chlorophenyl)-11-(4-chlorophenyl)-9-ethyl-2,2-dimethyl-3,3-diphenyl-4,13-dioxa-7-thia-10-aza-3-silapentadecan-15-oic acid

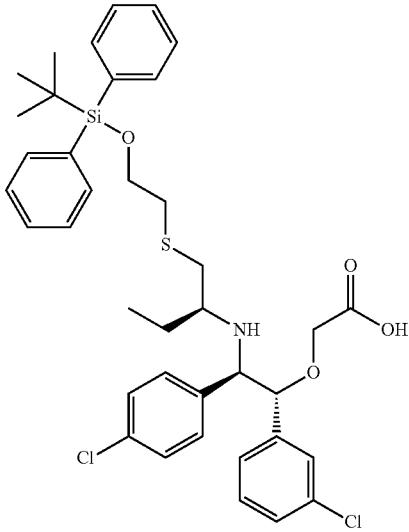 [SMILES: CC[C@@H](CSCCO[Si](c1ccccc1)(c1ccccc1)C(C)(C)C)N[C@H](c1ccc(Cl)cc1)[C@H](OCC(=O)O)c1cccc(Cl)c1]

To a solution of (9S,11R,12R)-12-(3-chlorophenyl)-11-(4-chlorophenyl)-9-ethyl-2,2-dimethyl-3,3-diphenyl-4-oxa-7-thia-10-aza-3-siladodecan-12-ol (581 mg, 0.890 mmol; Example 246, Step D) in THF (4.4 mL) was added bromoacetic acid (148 mg, 1.068 mmol) and sodium hydride (60% dispersion in mineral oil; 107 mg, 2.67 mmol). After stirring for 18 hours, additional sodium hydride (60% dispersion in mineral oil; 70 mg, 1.75 mmol) was added. After 45 minutes, the reaction was quenched with water and extracted with ethyl acetate (3×). The combined organic layers were dried over $Na_2SO_4$ and concentrated. The crude residue was purified by flash chromatography on silica gel (40 g column, eluent: 0 to 10% MeOH/DCM) to provide the title compound.

Step F. (5R,6R)-4-((S)-1-((2-((tert-butyldiphenylsilyl)oxy)ethyl)thio)butan-2-yl)-6-(3-chlorophenyl)-5-(4-chlorophenyl)morpholin-3-one

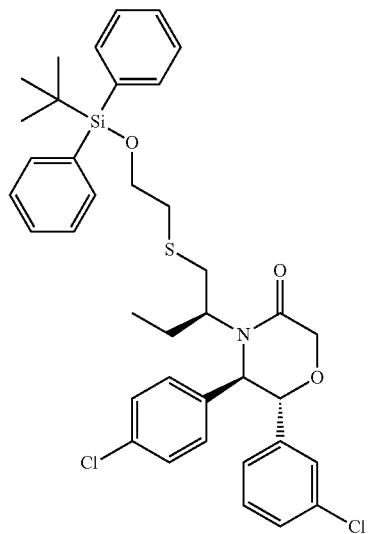 [SMILES: CC[C@@H](CSCCO[Si](c1ccccc1)(c1ccccc1)C(C)(C)C)N1C(=O)CO[C@H](c2cccc(Cl)c2)[C@H]1c1ccc(Cl)cc1]

To a solution of (9S,11R,12R)-12-(3-chlorophenyl)-11-(4-chlorophenyl)-9-ethyl-2,2-dimethyl-3,3-diphenyl-4,13-dioxa-7-thia-10-aza-3-silapentadecan-15-oic acid (225 mg, 0.317 mmol; Example 246, Step E) in DMF (2 mL) was added N,N-diisopropylethylamine (0.111 mL, 0.633 mmol) and HATU (144 mg, 0.380 mmol). After 1 hour and 15 minutes, the mixture was diluted with water, saturated aqueous $NH_4Cl$ was added and the mixture was extracted with ethyl acetate. The organic layer was washed with brine, dried over $Na_2SO_4$, and concentrated. The crude residue was purified by flash chromatography on silica gel (12 g column, eluent: 10 to 30% ethyl acetate/hexanes) to provide the title compound.

Step G. (2R,5R,6R)-2-allyl-4-((S)-1-((2-((tert-butyldiphenylsilyl)oxy)ethyl)thio)butan-2-yl)-6-(3-chlorophenyl)-5-(4-chlorophenyl)morpholin-3-one and (2S,5R,6R)-2-allyl-4-((S)-1-((2-((tert-butyldiphenylsilyl)oxy)ethyl)thio)butan-2-yl)-6-(3-chlorophenyl)-5-(4-chlorophenyl)morpholin-3-one (5R,6R)-4-((S)-1-((2-((tert-butyldiphenylsilyl)oxy)ethyl)thio)butan-2-yl)-6-(3-chlorophenyl)-5-(4-chlorophenyl)morpholin-3-one (190 mg, 0.274 mmol; Example 246, Step F) was dissolved in toluene and concentrated (3×). The resulting material was dissolved in THF (0.68 mL). Argon was bubbled through the mixture for 10 minutes. The mixture was cooled to −78° C. and lithium bis(trimethylsilyl)amide 1.0 M solution in THF (987 μL, 0.987 mmol) was added at such a rate to maintain the internal temperature below −65° C. Allyl bromide (85 μL, 0.987 mmol) was added. After 90 minutes, the reaction was quenched with water. The mixture was extracted with ethyl acetate (2×). The combined organic layers were washed with brine, dried over $Na_2SO_4$, and concentrated to provide the title compounds.

397

Step H. 2-((2R,5R,6R)-4-((S)-1-((2-((tert-butyl-diphenylsilyl)oxy)ethyl)sulfonyl)butan-2-yl)-6-(3-chlorophenyl)-5-(4-chlorophenyl)-3-oxomorpholin-2-yl)acetic acid and 2-((2S,5R,6R)-4-((S)-1-((2-((tert-butyldiphenylsilyl)oxy)ethyl)sulfonyl)butan-2-yl)-6-(3-chlorophenyl)-5-(4-chlorophenyl)-3-oxomorpholin-2-yl)acetic acid

398

Step I. Methyl 2-((2R,5R,6R)-4-((S)-1-((2-((tert-butyldiphenylsilyl)oxy)ethyl)sulfonyl)butan-2-yl)-6-(3-chlorophenyl)-5-(4-chlorophenyl)-3-oxomorpholin-2-yl)acetate and methyl 2-((2S,5R,6R)-4-((S)-1-((2-((tert-butyldiphenylsilyl)oxy)ethyl)sulfonyl)butan-2-yl)-6-(3-chlorophenyl)-5-(4-chlorophenyl)-3-oxomorpholin-2-yl)acetate

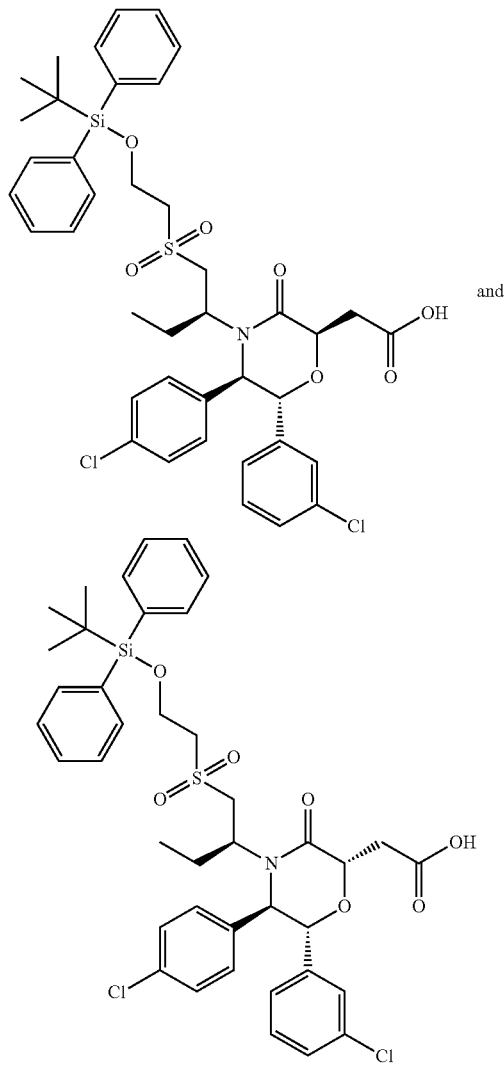

To a stirred mixture of (2R,5R,6R)-2-allyl-4-((S)-1-((2-((tert-butyldiphenylsilyl)oxy)ethyl)thio)butan-2-yl)-6-(3-chlorophenyl)-5-(4-chlorophenyl)morpholin-3-one and (2S,5R,6R)-2-allyl-4-((S)-1-((2-((tert-butyldiphenylsilyl)oxy)ethyl)thio)butan-2-yl)-6-(3-chlorophenyl)-5-(4-chlorophenyl)morpholin-3-one (183 mg, 0.250 mmol; Example 246, Step G) in acetonitrile (2 mL), ethyl acetate (2 mL), and water (3 mL) was added ruthenium(III) chloride hydrate (0.398 µL, 5.49 µmol) then sodium periodate (427 mg, 1.998 mmol) was added in 2 portions. After 90 minutes, the mixture was diluted with water and extracted with ethyl acetate. The organic layer was washed with brine, dried over Na₂SO₄, and concentrated to provide the title compounds.

To a solution of 2-((2R,5R,6R)-4-((S)-1-((2-((tert-butyl-diphenylsilyl)oxy)ethyl)sulfonyl)butan-2-yl)-6-(3-chlorophenyl)-5-(4-chlorophenyl)-3-oxomorpholin-2-yl)acetic acid and 2-((2S,5R,6R)-4-((S)-1-((2-((tert-butyldiphenylsilyl)oxy)ethyl)sulfonyl)butan-2-yl)-6-(3-chlorophenyl)-5-(4-chlorophenyl)-3-oxomorpholin-2-yl)acetic acid (199 mg, 0.254 mmol; Example 246, Step H) in DCM (2.2 mL) and MeOH (254 µL) was added (trimethylsilyl)diazomethane 2.0 M solution in diethylether (254 µL, 0.508 mmol). After 45 minutes, (trimethylsilyl)diazomethane 2.0 M solution in diethylether (200 µL, 0.400 mmol) was added. After 30 minutes, the mixture was concentrated, dissolved in toluene, and concentrated (2×) to provide the title compounds.

Step J. Methyl 2-((2R,5R,6R)-6-(3-chlorophenyl)-5-(4-chlorophenyl)-4-((S)-1-((2-hydroxyethyl)sulfonyl)butan-2-yl)-3-oxomorpholin-2-yl)acetate and methyl 2-((2S,5R,6R)-6-(3-chlorophenyl)-5-(4-chlorophenyl)-4-((S)-1-((2-hydroxyethyl)sulfonyl)butan-2-yl)-3-oxomorpholin-2-yl)acetate

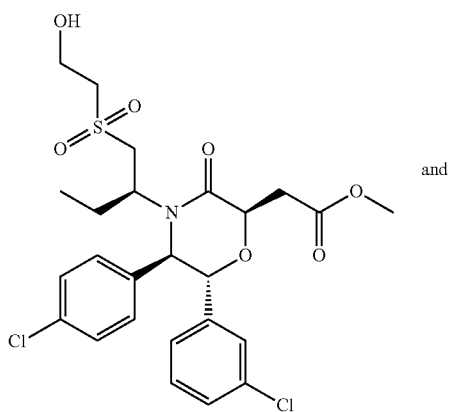

and

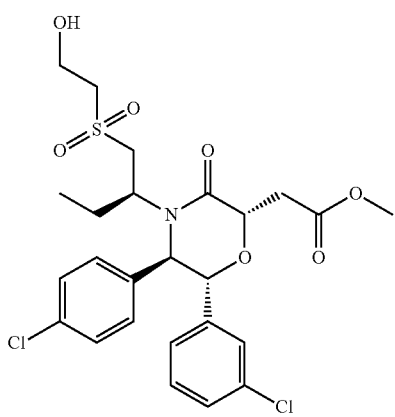

To a solution of methyl 2-((2R,5R,6R)-4-((S)-1-((2-((tert-butyldiphenylsilyl)oxy)ethyl)sulfonyl)butan-2-yl)-6-(3-chlorophenyl)-5-(4-chlorophenyl)-3-oxomorpholin-2-yl)acetate and methyl 2-((2S,5R,6R)-4-((S)-1-((2-((tert-butyldiphenylsilyl)oxy)ethyl)sulfonyl)butan-2-yl)-6-(3-chlorophenyl)-5-(4-chlorophenyl)-3-oxomorpholin-2-yl) acetate (199 mg, 0.250 mmol; Example 246, Step I) in THF (2.5 mL) was added tetrabutylammonium fluoride 1.0 M solution in THF (375 µL, 0.375 mmol). After stirring for 16 hours, the mixture was diluted with water and extracted with ethyl acetate (2×). The combined organic layers were washed with brine, dried over Na$_2$SO$_4$ and concentrated. The crude residue was purified by flash chromatography on silica gel (12 g column, eluent: 0 to 10% MeOH/DCM) to provide the title compounds.

Step K. Methyl 2-((2R,5R,6R)-6-(3-chlorophenyl)-5-(4-chlorophenyl)-3-oxo-4-((S)-1-(vinylsulfonyl)butan-2-yl)morpholin-2-yl)acetate and methyl 2-((2S,5R,6R)-6-(3-chlorophenyl)-5-(4-chlorophenyl)-3-oxo-4-((S)-1-(vinylsulfonyl)butan-2-yl)morpholin-2-yl)acetate

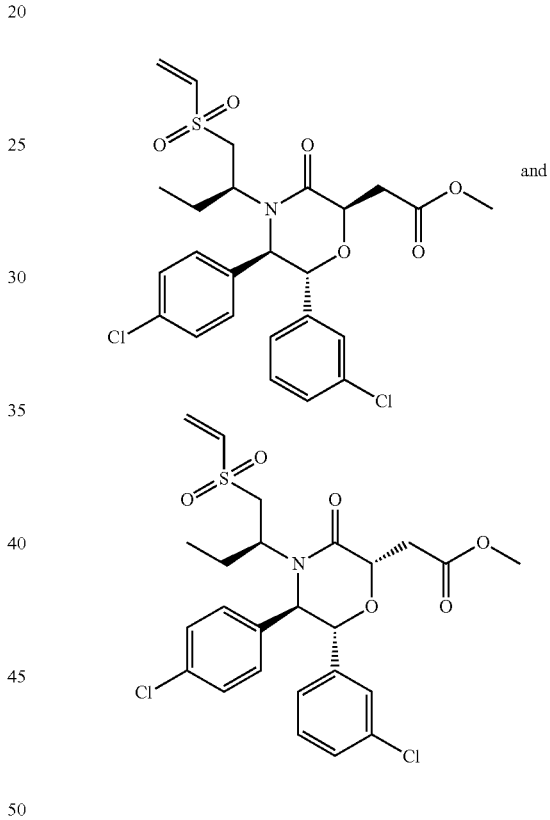

To a 0° C. solution of methyl 2-((2R,5R,6R)-6-(3-chlorophenyl)-5-(4-chlorophenyl)-4-((S)-1-((2-hydroxyethyl)sulfonyl)butan-2-yl)-3-oxomorpholin-2-yl)acetate and methyl 2-((2S,5R,6R)-6-(3-chlorophenyl)-5-(4-chlorophenyl)-4-((S)-1-((2-hydroxyethyl)sulfonyl)butan-2-yl)-3-oxomorpholin-2-yl)acetate (102 mg, 0.183 mmol; Example 246, Step J) in DCM (2 mL) was added triethylamine (0.064 mL, 0.457 mmol) and methanesulfonyl chloride (0.016 mL, 0.201 mmol). After 1 hour, triethylamine (0.064 mL, 0.457 mmol) was added. After 15 minutes, the mixture was diluted with water and extracted with DCM (2×). The combined organic layers were washed with brine, dried over Na$_2$SO$_4$, and concentrated to provide the title compounds.

401

Step L. Methyl 2-((2R,5R,6R)-6-(3-chlorophenyl)-5-(4-chlorophenyl)-4-((S)-1-((2-(dimethylamino)ethyl)sulfonyl)butan-2-yl)-3-oxomorpholin-2-yl)acetate and methyl 2-((2S,5R,6R)-6-(3-chlorophenyl)-5-(4-chlorophenyl)-4-((S)-1-((2-(dimethylamino)ethyl)sulfonyl)butan-2-yl)-3-oxomorpholin-2-yl)acetate

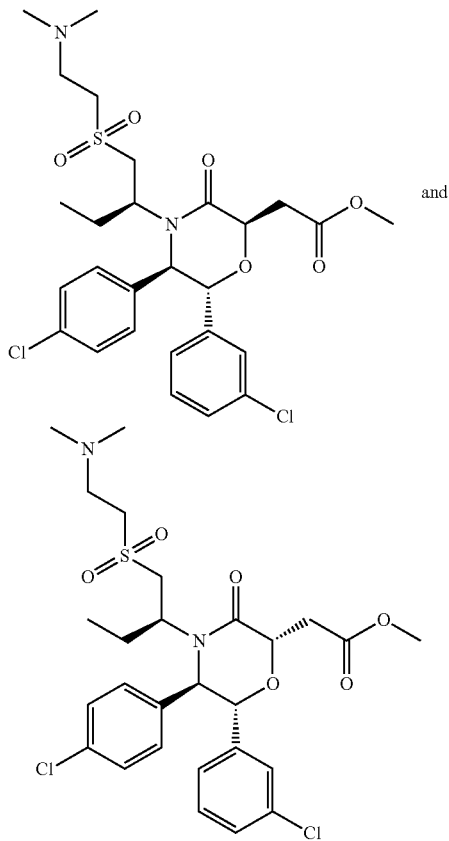

and

402

Example 247

2-((2R,5R,6R)-6-(3-chlorophenyl)-5-(4-chlorophenyl)-4-((S)-1-((2-(dimethylamino)ethyl)sulfonyl)butan-2-yl)-3-oxomorpholin-2-yl)acetic acid or 2-((2S,5R,6R)-6-(3-chlorophenyl)-5-(4-chlorophenyl)-4-((S)-1-((2-(dimethylamino)ethyl)sulfonyl)butan-2-yl)-3-oxomorpholin-2-yl)acetic acid

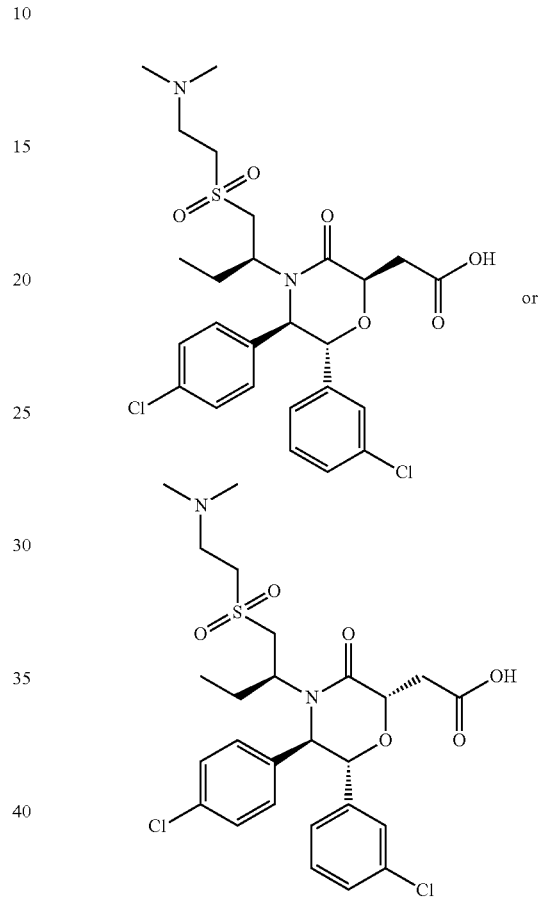

or

To a solution of methyl 2-((2R,5R,6R)-6-(3-chlorophenyl)-5-(4-chlorophenyl)-3-oxo-4-((S)-1-(vinylsulfonyl)butan-2-yl)morpholin-2-yl)acetate and methyl 2-((2S,5R,6R)-6-(3-chlorophenyl)-5-(4-chlorophenyl)-3-oxo-4-((S)-1-(vinylsulfonyl)butan-2-yl)morpholin-2-yl)acetate (53 mg, 0.098 mmol; Example 246, Step K) in EtOH (1 mL) was added dimethylamine 2.0 M solution in THF (0.147 mL, 0.294 mmol). After 1 hour, the mixture was concentrated to provide the title compounds as a 6:4 mixture of diastereomers. $^1$H NMR (400 MHz, chloroform-d) δ ppm 0.53-0.62 (m, 4.63 H) 0.87-0.91 (m, 0.48 H) 0.95-1.07 (m, 0.85 H) 1.19-1.35 (m, 3.86 H) 1.42 (t, J=7.34 Hz, 0.51H) 1.53-1.69 (m, 0.87 H) 2.03-2.21 (m, 1.65 H) 2.25-2.54 (m, 8.46 H) 2.73 (s, 1.11H) 2.79 (d, J=10.60 Hz, 0.30 H) 2.91-3.06 (m, 2.41 H) 3.06-3.21 (m, 3.02 H) 3.64-3.76 (m, 6.76 H) 4.69 (d, J=9.78 Hz, 0.63 H) 4.74-4.80 (m, 1.45 H) 4.93-4.99 (m, 1.29 H) 5.00-5.04 (m, 0.57 H) 6.78 (d, J=7.43 Hz, 0.45 H) 7.00 (d, J=8.41 Hz, 1.00 H) 7.05-7.37 (m, 32.5 H). (Proton integration was defined by setting the doublet at δ 7.00 to 1.00, other integration should be considered raw due to the complexity of the diastereomer mixture. The multiplet at δ 7.05-7.37 contains chloroform.) Mass spectrum (ESI) m/z=585 (M+1).

To a stirred solution of methyl 2-((2R,5R,6R)-6-(3-chlorophenyl)-5-(4-chlorophenyl)-4-((S)-1-((2-(dimethylamino)ethyl)sulfonyl)butan-2-yl)-3-oxomorpholin-2-yl)acetate and methyl 2-((2S,5R,6R)-6-(3-chlorophenyl)-5-(4-chlorophenyl)-4-((S)-1-((2-(dimethylamino)ethyl)sulfonyl)butan-2-yl)-3-oxomorpholin-2-yl)acetate (43 mg, 0.073 mmol; Example 246, Step L) in EtOH (1 mL) was added LiOH (1.0 M aqueous, 0.734 mL, 0.734 mmol). After 2.5 hours, the mixture was acidified with 5% aq. HCl. The mixture was basified with sat. aq. NaHCO$_3$. The mixture was diluted with water and extracted with DCM. The aqueous layer was back extracted with 10% MeOH/DCM. The aqueous layer was back extracted again with DCM. The combined organic layers were dried over Na$_2$SO$_4$ and concentrated. The crude residue was purified by preparative reverse phase HPLC on a 100×50 mm 10 μm C$_{18}$ column (Phenomenex, Torrance, Calif.; eluent: 35 to 50% MeCN/water with 0.1% TFA). Fractions containing the title compound were concentrated to 5 mL. The mixture was basified with aq. NaHCO$_3$ then extracted with DCM (3×). The combined organic layers were dried over Na$_2$SO$_4$ and concentrated to provide one of the title compounds as the first eluting isomer.

403

$^1$H NMR (400 MHz, acetonitrile-$d_3$) δ ppm 0.54 (t, J=7.34 Hz, 3 H) 0.80-0.92 (m, 1 H) 1.27 (s, 6 H) 1.47-1.72 (m, 1 H) 1.96-2.06 (m, 1 H) 2.19-3.60 (m, 8 H) 4.67-4.71 (m, 1 H) 4.97-5.01 (m, 2H) 7.07 (d, J=7.43 Hz, 1 H) 7.17 (s, 1 H) 7.20-7.31 (m, 2 H) 7.31-7.38 (m, 4 H). Mass spectrum (ESI) m/z=571 (M+1).

Example 248

2-((2S,5R,6R)-6-(3-chlorophenyl)-5-(4-chlorophenyl)-4-((S)-1-((2-(dimethylamino)ethyl)sulfonyl)butan-2-yl)-3-oxomorpholin-2-yl)acetic acid or 2-((2R,5R,6R)-6-(3-chlorophenyl)-5-(4-chlorophenyl)-4-((S)-1-((2-(dimethylamino)ethyl)sulfonyl)butan-2-yl)-3-oxomorpholin-2-yl)acetic acid

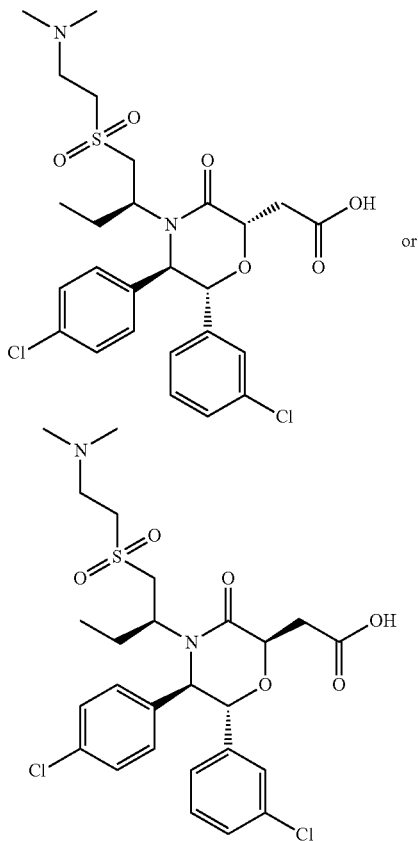

One of the title compounds was obtained as the second eluting isomer in Example 247. Fractions containing the title compound were concentrated to 5 mL. The resulting mixture was made basic with aq. NaHCO$_3$ then extracted with DCM (3×). The combined organic layers were dried over Na$_2$SO$_4$ and concentrated to provide one of the title compounds as the second eluting isomer. $^1$H NMR (400 MHz, chloroform-d) δ ppm 0.57 (t, J=7.43 Hz, 3 H) 0.82-0.93 (m, 1 H) 1.26 (s, 6 H) 1.55-1.64 (m, 1 H) 2.20-2.31 (m, 1 H) 2.79 (s, 4 H) 2.87 (dd, J=17.02, 4.11 Hz, 1 H) 3.06 (d, J=14.48 Hz, 1 H) 3.30 (dd, J=17.02, 3.13 Hz, 1 H) 3.46-3.55 (m, 1 H) 4.53 (t, J=3.62 Hz, 1 H) 4.64 (d, J=9.78 Hz, 1 H) 5.04 (d, J=9.59 Hz, 1 H) 6.73 (d, J=7.63 Hz, 1 H) 7.02-7.12 (m, 2 H) 7.20 (ddd, J=8.12, 2.05, 0.98 Hz, 1 H) 7.24-7.34 (m, 4 H). Mass spectrum (ESI) m/z=571 (M+1).

404

Example 249

2-((2R,5R,6R)-4-((1S,2S)-2-(tert-butylsulfonyl)cyclohexyl)-6-(3-chlorophenyl)-5-(4-chlorophenyl)-3-oxomorpholin-2-yl)acetic acid

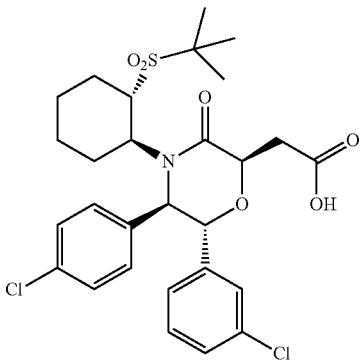 [SMILES: CC(C)(C)S(=O)(=O)[C@H]1CCCC[C@@H]1N1C(=O)[C@@H](CC(=O)O)O[C@H](c2cccc(Cl)c2)[C@H]1c1ccc(Cl)cc1]

Step A. (1R,2R)-2-(((1R,2R)-2-((tert-butyldimethylsilyl)oxy)-2-(3-chlorophenyl)-1-(4-chlorophenyl)ethyl)amino)cyclohexanol and (1S,2S)-2-(((1R,2R)-2-((tert-butyldimethylsilyl)oxy)-2-(3-chlorophenyl)-1-(4-chlorophenyl)ethyl)amino)cyclohexanol

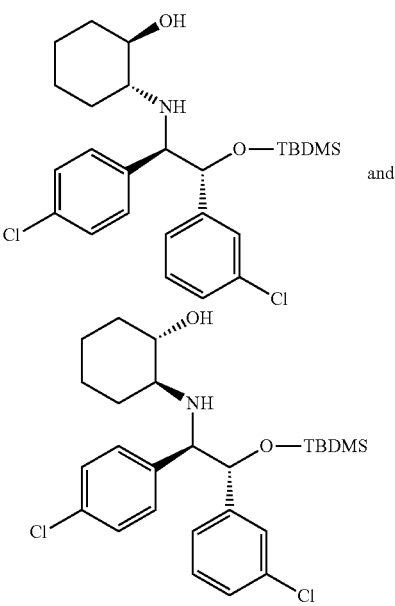

(1R,2R)-2-((tert-butyldimethylsilyl)oxy)-2-(3-chlorophenyl)-1-(4-chlorophenyl)ethanamine (1.27 g, 3.20 mmol) (prepared from Intermediate A2 following a procedure similar to the one described in Example 162, Step A), ytterbium triflate (0.139, 0.224 mmol), and 7-oxabicyclo[4.1.0]heptane (1.57 g, 16.0 mmol) were mixed in acetonitrile (11 mL) and heated in a sealed tube for 3 hours. The reaction mixture was cooled and concentrated, and the resulting residue was purified by flash chromatography on silica gel, eluting with a hexane/ethyl acetate gradient (20-100%). The fractions were pooled and concentrated to provide the title compounds. Mass spectrum (ESI) m/e=494 (M+1).

Step B. 7-((1R,2R)-2-((tert-butyldimethylsilyl)oxy)-2-(3-chlorophenyl)-1-(4-chlorophenyl)ethyl)-7-azabicyclo[4.1.0]heptane

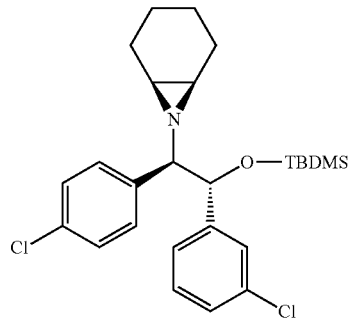

(E)-Diethyl diazene-1,2-dicarboxylate (1.78 mL, 3.91 mmol) was added to a THF (11 mL) solution containing triphenylphosphine (1.025 g, 3.91 mmol) and a mixture of (1R,2R)-2-(((1R,2R)-2-((tert-butyldimethylsilyl)oxy)-2-(3-chlorophenyl)-1-(4-chlorophenyl)ethyl)amino)cyclohexanol and (1S,2S)-2-(((1R,2R)-2-((tert-butyldimethylsilyl)oxy)-2-(3-chlorophenyl)-1-(4-chlorophenyl)ethyl)amino)cyclohexanol (1.61 g, 3.26 mmol; Example 249, Step A). The resulting mixture was stirred overnight at 23° C. The reaction was concentrated, redissolved in EtOAc, washed with water, washed with brine, dried over sodium sulfate, and concentrated. The resulting residue was purified by flash chromatography on silica gel, eluting with a hexane/ethyl acetate gradient (0-100%). The fractions were pooled and concentrated to provide the title compound. Mass spectrum (ESI) m/e=476 (M+1).

Step C. (1S,2S)-N-((1R,2R)-2-((tert-butyldimethylsilyl)oxy)-2-(3-chlorophenyl)-1-(4-chlorophenyl)ethyl)-2-(tert-butylthio)cyclohexanamine and (1R,2R)-N-((1R,2R)-2-((tert-butyldimethylsilyl)oxy)-2-(3-chlorophenyl)-1-(4-chlorophenyl)ethyl)-2-(tert-butylthio)cyclohexanamine

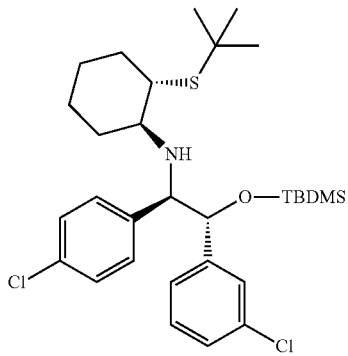

and

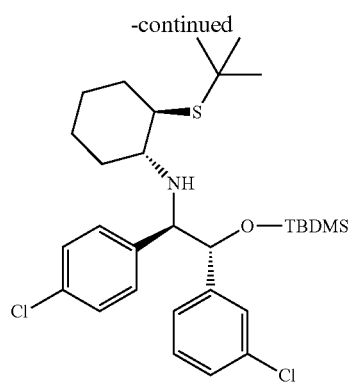

2-methyl-2-propanethiol (0.71 mL, 6.30 mmol) was added to a DCM (31.5 mL) solution containing anhydrous indium (III) chloride (2.0 µL, 0.031 mmol) and 7-((1R,2R)-2-((tert-butyldimethylsilyl)oxy)-2-(3-chlorophenyl)-1-(4-chlorophenyl)ethyl)-7-azabicyclo[4.1.0]heptane (1.5 g, 3.15 mmol; Example 249, Step B). The resulting mixture was stirred overnight at 23° C. The reaction was then concentrated, and the residue was used in the next step without further processing. Mass spectrum (ESI) m/e=566 (M+1)

Step D. (1R,2R)-2-(((1S,2S)-2-(tert-butylthio)cyclohexyl)amino)-1-(3-chlorophenyl)-2-(4-chlorophenyl)ethanol and (1R,2R)-2-(((1R,2R)-2-(tert-butylthio)cyclohexyl)amino)-1-(3-chlorophenyl)-2-(4-chlorophenyl)ethanol

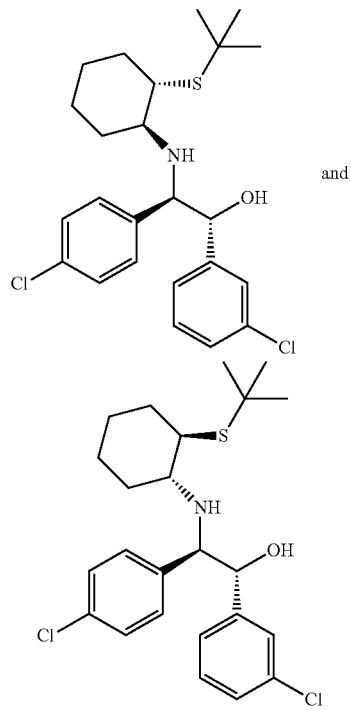

Tetra-n-butylammonium fluoride, 1M solution in THF (1.72 mL, 1.72 mmol) was added to a THF (15.60 mL) solution containing (1S,2S)-N-((1R,2R)-2-((tert-butyldimethylsilyl)oxy)-2-(3-chlorophenyl)-1-(4-chlorophenyl)ethyl)-2-(tert-butylthio)cyclohexanamine and (1R,2R)-N-((1R,2R)-

2-((tert-butyldimethylsilyl)oxy)-2-(3-chlorophenyl)-1-(4-chlorophenyl)ethyl)-2-(tert-butylthio)cyclohexanamine (0.884 g, 1.56 mmol; Example 249, Step C). The resulting mixture was stirred overnight at 23° C. The reaction was then concentrated, and the resulting residue was purified by flash chromatography on silica gel, eluting with a hexane/ethyl acetate gradient (0-100%). The fractions were pooled and concentrated to give the title compounds. Mass spectrum (ESI) m/e=452 (M+1).

Step E. 2-((1R,2R)-2-(((1S,2S)-2-(tert-butylthio)cyclohexyl)amino)-1-(3-chlorophenyl)-2-(4-chlorophenyl)ethoxy)acetic acid and 2-((1R,2R)-2-(((1R,2R)-2-(tert-butylthio)cyclohexyl)amino)-1-(3-chlorophenyl)-2-(4-chlorophenyl)ethoxy)acetic acid

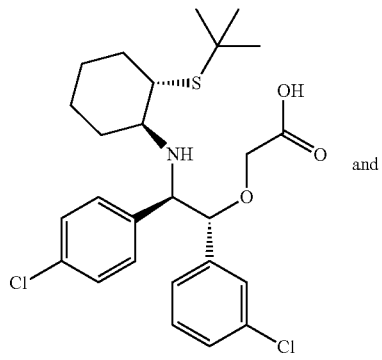
and

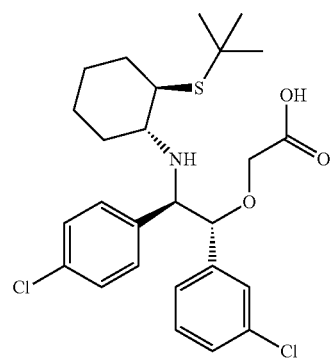

Sodium hydride (0.092 g, 2.305 mmol) was added to a THF (7.68 mL) solution containing methyl 2-bromoacetate (0.088 mL, 0.922 mmol) and (1R,2R)-2-(((1S,2S)-2-(tert-butylthio)cyclohexyl)amino)-1-(3-chlorophenyl)-2-(4-chlorophenyl)ethanol and (1R,2R)-2-(((1R,2R)-2-(tert-butylthio)cyclohexyl)amino)-1-(3-chlorophenyl)-2-(4-chlorophenyl)ethanol (0.348 g, 0.768 mmol; Example 249, Step D). The resulting solution was stirred 3 hours at 23° C. The reaction was concentrated, redissolved in EtOAc, washed with water, brine, dried over sodium sulfate, and concentrated. This material was used in the next step without further processing. Mass spectrum (ESI) m/e=510 (M+1).

Step F. (5R,6R)-4-((1S,2S)-2-(tert-butylthio)cyclohexyl)-6-(3-chlorophenyl)-5-(4-chlorophenyl)morpholin-3-one and (5R,6R)-4-((1R,2R)-2-(tert-butylthio)cyclohexyl)-6-(3-chlorophenyl)-5-(4-chlorophenyl)morpholin-3-one

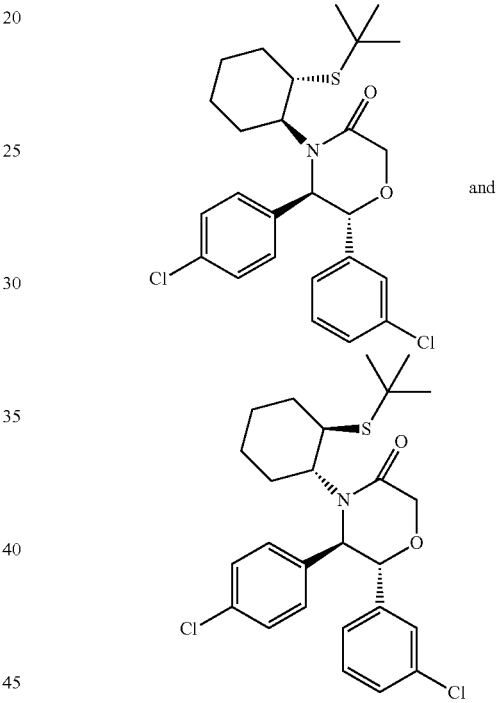

N-ethyl-N-isopropylpropan-2-amine (0.301 mL, 1.73 mmol) was added to a DMF (2.88 mL) solution containing 2-(3H-[1,2,3]triazolo[4,5-b]pyridin-3-yl)-1,1,3,3-tetramethylisouronium hexafluorophosphate(V) (0.394 g, 1.04 mmol) and a mixture of 2-((1R,2R)-2-(((1S,2S)-2-(tert-butylthio)cyclohexyl)amino)-1-(3-chlorophenyl)-2-(4-chlorophenyl)ethoxy)acetic acid and 2-((1R,2R)-2-(((1R,2R)-2-(tert-butylthio)cyclohexyl)amino)-1-(3-chlorophenyl)-2-(4-chlorophenyl)ethoxy)acetic acid (0.441 g, 0.863 mmol; Example 249, Step E). The resulting mixture was stirred overnight at 23° C. The reaction was concentrated, redissolved in EtOAc, washed with water, brine, dried over sodium sulfate, and concentrated. The reaction was purified by flash chromatography on silica gel, eluting with a hexane/ethyl acetate gradient (0-100%). The desired fractions were pooled and concentrated. Mass spectrum (ESI) m/e=492 (M+1).

Step G. (2R,5R,6R)-2-allyl-4-((1S,2S)-2-(tert-butylthio)cyclohexyl)-6-(3-chlorophenyl)-5-(4-chlorophenyl)morpholin-3-one

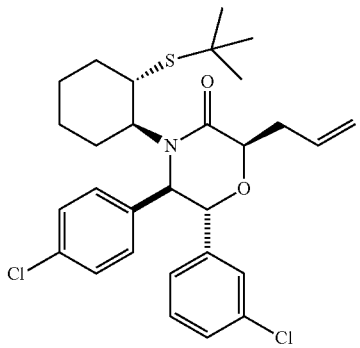

Lithium bis(trimethylsilyl)amide (1.49 mL, 1.49 mmol) was added to a dry, degassed, inhibitor free, THF (2.98 mL) solution containing a mixture of (5R,6R)-4-((1S,2S)-2-(tert-butylthio)cyclohexyl)-6-(3-chlorophenyl)-5-(4-chlorophenyl)morpholin-3-one and (5R,6R)-4-((1R,2R)-2-(tert-butylthio)cyclohexyl)-6-(3-chlorophenyl)-5-(4-chlorophenyl)morpholin-3-one (0.147 g, 0.298 mmol; Example 249, Step F) at −78° C. After 30 minutes 3-bromoprop-1-ene (0.129 mL, 1.49 mmol) was added and the reaction was allowed to stir at −78° C. for 3 hours whereupon the LCMS indicated that the reaction was complete. MeOH (1 mL) was added and the reaction was allowed to warm up to room temp. After concentrating, the mixture was directly purified by reverse phase preparatory HPLC (SB-C8 5 μm column; Agilent, Santa Clara, Calif.; gradient elution of 50% to 90% MeCN in water, where both solvents contain 0.1% TFA, 25 min. method). The fractions were pooled and lyophilized to give the titled compound. Mass spectrum (ESI) m/e=532 (M+1).

Step H. 2-((2R,5R,6R)-4-((1S,2S)-2-(tert-butylsulfonyl)cyclohexyl)-6-(3-chlorophenyl)-5-(4-chlorophenyl)-3-oxomorpholin-2-yl)acetic acid

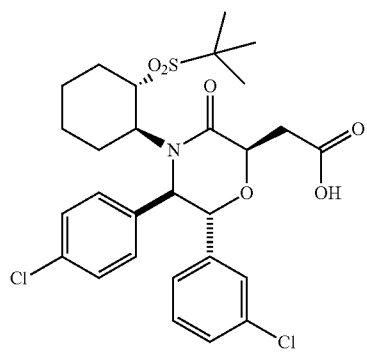

Sodium periodate (32 mg, 0.15 mmol) was added to a acetonitrile/EtOAc/water (1:1:1.5) solution (3.5 mL) containing (2R,5R,6R)-2-allyl-4-((1S,2S)-2-(tert-butylthio)cyclohexyl)-6-(3-chlorophenyl)-5-(4-chlorophenyl)morpholin-3-one (20 mg, 0.038 mmol; Example 249, Step G) and ruthenium chloride (0.85 mg, 3.76 μmol). The resulting mixture was stirred for 1 hour at 23° C. The reaction was then filtered and concentrated. The resulting residue was dissolved in MeOH and purified by reverse phase preparatory HPLC (SB-C8 5 μm column; Agilent, Santa Clara, Calif.; gradient elution of 20% to 90% MeCN in water, where both solvents contain 0.1% TFA, 25 min. method). Desired fractions were pooled and lyophilized to give the titled product.

$^1$H NMR (500 MHz, MeOH) δ ppm 0.65-0.84 (m, 1 H) 1.23-1.41 (m, 2 H) 1.41-1.53 (m, 9 H) 1.53-1.63 (m, 2 H) 1.67 (d, J=12.47 Hz, 1 H) 2.14-2.27 (m, 1 H) 2.40-2.56 (m, 1 H) 2.97 (dd, J=15.89, 3.42 Hz, 1 H) 3.02-3.14 (m, 1 H) 3.16-3.27 (m, 1 H) 4.69 (ddd, J=11.92, 10.45, 4.03 Hz, 1 H) 4.83 (dd, J=9.29, 3.42 Hz, 1 H) 5.08 (d, J=9.29 Hz, 1 H) 5.14 (d, J=9.29 Hz, 1 H) 6.98 (d, J=7.58 Hz, 1 H) 7.12-7.29 (m, 4 H) 7.29-7.50 (m, 3 H); Mass spectrum (ESI) m/e=582 (M+1).

Example 250

2-((2R,5R,6R)-6-(3-chlorophenyl)-5-(4-chlorophenyl)-4-((S)-1-cyclopropyl-2-(N-(2,6-difluorophenyl)cyclopropanesulfonamido)ethyl)-3-oxomorpholin-2-yl)acetic acid

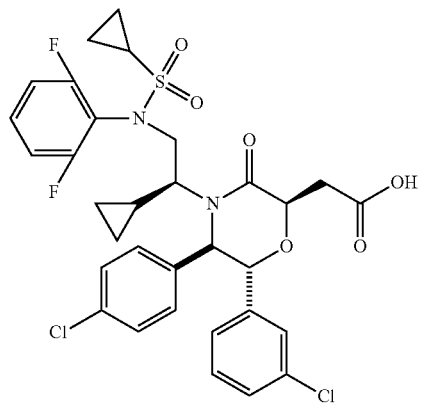

Step A. (S)-Ethyl 2-((2R,3R)-2-(3-chlorophenyl)-3-(4-chlorophenyl)-5-oxomorpholino)-2-cyclopropylacetate and (R)-ethyl 2-((2R,3R)-2-(3-chlorophenyl)-3-(4-chlorophenyl)-5-oxomorpholino)-2-cyclopropylacetate

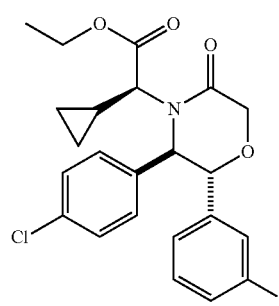

and

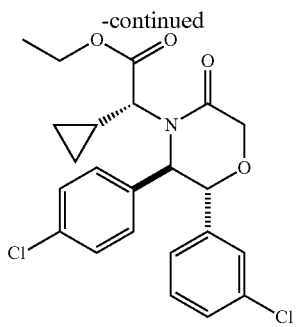

To a solution of (5R,6R)-6-(3-chlorophenyl)-5-(4-chlorophenyl)morpholin-3-one (7.98 g, 24.8 mmol; Example 112, Step A) in DMF (60 mL) was added sodium hydride (1.98 g, 49.5 mmol) on portions at 0° C. and the mixture was stirred at this temperature for 30 minutes. To the reaction mixture was added a solution of ethyl 2-bromo-2-cyclopropylacetate (from EXAMPLE 154, 6.88 mL, 49.5 mmol) in DMF (6 mL) dropwise (around 10 minutes), and the reaction was stirred overnight allowing the temperature to rise from 0° C. to room temperature. The reaction was quenched with sat. NH$_4$Cl and extracted twice with diethyl ether. The organic layers were combined, washed with brine, and dried over Mg$_2$SO$_4$. The solvent was evaporated under reduced pressure, and the crude residue was purified by flash chromatography on silica gel (eluent: 0 to 50% EtOAc in hexane) to give the title compounds as a pale yellow solid and a 1.7:1 mixture of two diastereomers.

$^1$H NMR (400 MHz, chloroform-d) δ ppm, 6.76 (1H, d, J=8 Hz), 6.70 (1H, d, J=8 Hz), 4.75 (1 H, d, J=8 Hz), 4.69 (1H, d, J=8 Hz), 4.59 (1H, d, J=8 Hz), 4.51 (d, J=8 Hz) (since the compound was isolated as a mixture of two diastereoisomers, only three sets of distinctive proton signals are reported). Mass spectrum (ESI) m/e=448.0 (M+1).

Step B. (5R,6R)-6-(3-chlorophenyl)-5-(4-chlorophenyl)-4-((S)-1-cyclopropyl-2-hydroxyethyl)morpholin-3-one

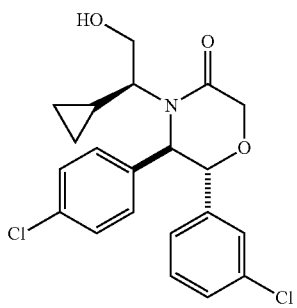

To a solution of (S)-ethyl 2-((2R,3R)-2-(3-chlorophenyl)-3-(4-chlorophenyl)-5-oxomorpholino)-2-cyclopropylacetate and (R)-ethyl 2-((2R,3R)-2-(3-chlorophenyl)-3-(4-chlorophenyl)-5-oxomorpholino)-2-cyclopropylacetate (2.30 g, 5.30 mmol; Example 250, Step A) in THF (5.30 mL) at −10° C. was added lithium triethylborohydride (1.0 M solution in THF, 11.1 mL, 11.1 mmol) dropwise. The reaction was stirred for 80 minutes between −10 to −5° C. MeOH (2 mL) was added to quench the reaction, followed by adding a solution of potassium peroxomonosulfate (9.77 g, 15.9 mmol) in water (40 mL) dropwise over 10 minutes at −10° C. To this mixture was slowly added sat Na$_2$S$_2$O$_3$ solution (9 mL) at −10° C. and the mixture was stirred for about 5 minutes. The mixture was diluted with EtOAc and washed with H$_2$O and brine. The organic layer was dried with Mg$_2$SO$_4$, filtered, and concentrated. The crude material was purified by flash chromatography (eluent: 0-50% EtOAc in hexane) to give the title compound as the second eluting isomer and as a pale white solid.

$^1$H NMR (400 MHz, methanol-d4) δ ppm 7.36 (m, 2H)), 7.2-7.29 (m, 5H), 7.03-7.06 (m, 1H), 4.91 (d, J=8 Hz, 1H), 4.86 (d, J=8 Hz, 1H), 4.51 (d, J=8 Hz, 1H), 4.33 (d, J=8 Hz, 1H), 3.90 (t, J=12 Hz, 1H), 3.48 (dd, J=8, 4 Hz, 1H), 2.69 (m, 1H), 1.32 (m, 1H), 0.46 (m, 1H), 0.37 (m, 1H), 0.01 (m, 1H), −0.48 (m, 1H). Mass spectrum (ESI) m/e=406.0 (M+1).

Step C. N-((S)-2-((2R,3R)-2-(3-chlorophenyl)-3-(4-chlorophenyl)-5-oxomorpholino)-2-cyclopropylethyl)-N-(2,6-difluorophenyl)cyclopropanesulfonamide

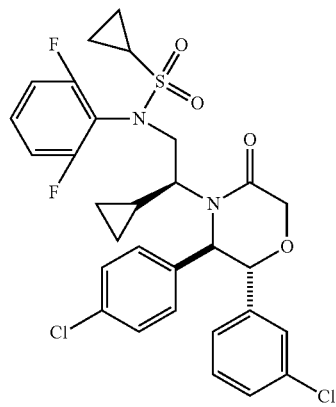

To a solution of (5R,6R)-6-(3-chlorophenyl)-5-(4-chlorophenyl)-4-((S)-1-cyclopropyl-2-hydroxyethyl)morpholin-3-one (105 mg, 0.26 mmol; Example 250, Step B) and N-(2,6-difluorophenyl)cyclopropanesulfonamide which was made using a procedure similar to that described for N-(2-fluorophenyl)cyclopropanesulfonamide in Example 133. (181 mg, 0.77 mmol) in toluene (1.5 mL) was added cyanomethylenetributylphosphorane (0.19 mL, 0.77 mmol) and the resulting solution was purged with N$_2$ for 10 minutes and then stirred at 100° C. for 3.5 hours. The reaction was cooled to room temperature and purified by flash chromatography without workup (eluent: 0-30% EtOAc in hexane) to give the title compound as a pale white solid. $^1$H NMR (400 MHz, chloroform-d) δ ppm 7.20-7.30 (m, 3H), 7.12 (m, 1H), 7.04-7.09 (m, 5H), 6.93 (m, 1H), 6.84 (m, 1H), 4.89 (d, J=12 Hz, 1H), 4.51 (d, J=8 Hz, 1H), 4.25 (d, J=16 Hz, 1H), 4.04 (d, J=8 Hz, 1H), 3.76 (s, br, 1H), 2.44 (m, 1H), 1.52 (m, 1H), 2.51 (m, 2H), 0.90-0.96 (m, 3H), 0.81 (m, 1H), 0.36 (s, br, 1H), 0.19 (s, br, 1H), −0.22 (s, br, 1H), −0.98 (s, br, 1H). Mass spectrum (ESI) m/e=621.0 (M+1).

Step D. N-((S)-2-((2R,5R,6R)-2-allyl-6-(3-chlorophenyl)-5-(4-chlorophenyl)-3-oxomorpholino)-2-cyclopropylethyl)-N-(2,6-difluorophenyl)cyclopropanesulfonamide and N-((S)-2-((2S,5R,6R)-2-allyl-6-(3-chlorophenyl)-5-(4-chlorophenyl)-3-oxomorpholino)-2-cyclopropylethyl)-N-(2,6-difluorophenyl)cyclopropanesulfonamide

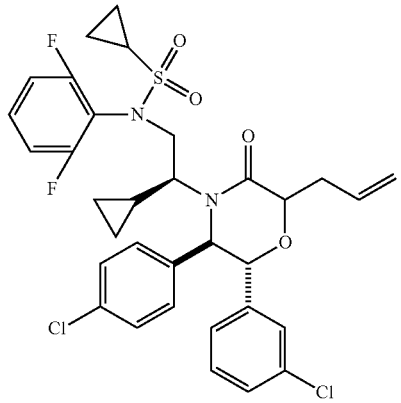

To a solution of N-((S)-2-((2R,3R)-2-(3-chlorophenyl)-3-(4-chlorophenyl)-5-oxomorpholino)-2-cyclopropylethyl)-N-(2,6-difluorophenyl)cyclopropanesulfonamide (81 mg, 0.13 mmol; Example 250, Step D) and lithium bis(trimethylsilyl)amide (1.0 M solution in THF, 0.521 mL, 0.52 mmol) in THF (0.5 mL) was added allyl bromide (0.045 mL, 0.52 mmol) at −78° C. under the atmosphere of $N_2$. The reaction was stirred at −78° C. for 1.5 hours. The reaction was quenched with $H_2O$ (2 mL) at −78° C. and then diluted with EtOAc and sat. $NH_4Cl$. The organic layer was washed with $H_2O$ and brine and concentrated. The crude was purified by flash chromatography (eluent: 0-30% EtOAc in hexane) to give the title compounds as a pale white solid and a 2:1 mixture of diastereomers. $^1H$ NMR (400 MHz, chloroform-d) δ ppm 5.65-5.76 (m, 1H), 5.54-5.63 (m, 1H), 2.63-2.67 (m, 1H), 2.52-2.56 (m, 1H) (since the compound was isolated as a mixture of two diastereoisomers, only two sets of distinctive proton signals are reported). Mass spectrum (ESI) m/e=661.0 (M+1).

Step E. 2-((2R,5R,6R)-6-(3-chlorophenyl)-5-(4-chlorophenyl)-4-((S)-1-cyclopropyl-2-(N-(2,6-difluorophenyl)cyclopropanesulfonamido)ethyl)-3-oxomorpholin-2-yl)acetic acid or 2-((2S,5R,6R)-6-(3-chlorophenyl)-5-(4-chlorophenyl)-4-((S)-1-cyclopropyl-2-(N-(2,6-difluorophenyl)cyclopropanesulfonamido)ethyl)-3-oxomorpholin-2-yl)acetic acid

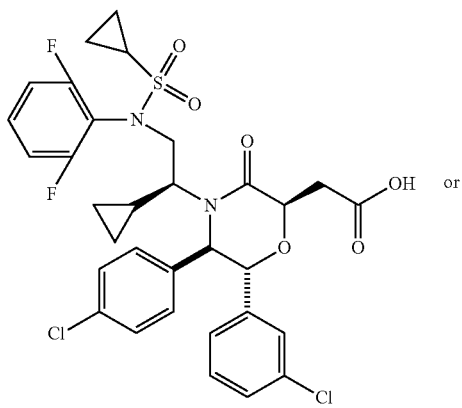

or

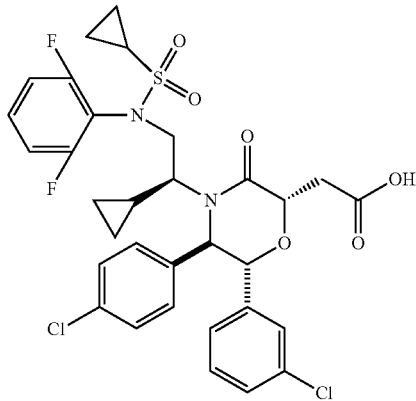

To a solution of N-((S)-2-((2R,5R,6R)-2-allyl-6-(3-chlorophenyl)-5-(4-chlorophenyl)-3-oxomorpholino)-2-cyclopropylethyl)-N-(2,6-difluorophenyl)cyclopropanesulfonamide and N-((S)-2-((2S,5R,6R)-2-allyl-6-(3-chlorophenyl)-5-(4-chlorophenyl)-3-oxomorpholino)-2-cyclopropylethyl)-N-(2,6-difluorophenyl)cyclopropanesulfonamide (64 mg, 0.097 mmol) in $H_2O$ (0.40 mL), acetonitrile (0.27 mL) and $CCl_4$ (0.27 mL) was added sodium periodate (124 mg, 0.58 mmol) followed by ruthenium(III) chloride hydrate (2.18 mg, 9.67 μmol) at room temperature and the reaction was stirred at room temperature for 1 hour. The reaction was diluted with EtOAc and washed with sat. $NH_4Cl$ and brine. The organic layer was dried with $Mg_2SO_4$ and concentrated. The crude material was purified by preparative reverse phase HPLC (eluent: 40-60% of acetonitrile in water with 0.1% of TFA gradient on Gemini™ preparative $C_{18}$ 5 5 μm column, Phenomenex, Torrance, Calif.) to give one of the title compound as the first eluting isomer and as a white solid. By analytical HPLC (15 min. method, 10-100% MeCN in water with 0.1% TFA on Agilent Eclipse $C_{18}$ column) the retention time was 10.35 minutes. $^1H$ NMR (400 MHz, chloroform-d) δ ppm 7.43 (m, 1H), 7.15-7.33 (m, 3H), 7.05-7.17 (m, 6H), 6.90-6.92 (d, J=8 Hz, 1H), 5.03 (d, J=12 Hz, 1H), 4.71-4.73 (m, 3H), 3.83 (s, br, 1H), 3.65 (s, br, 1H), 2.89-2.95 (m, 1H), 2.64 (s, br, 1H), 2.53 (s, br, 1H), 2.39 (s, br, 1H), 1.66 (s, br, 1H), 1.02-1.07 (m, 4H), 0.43 (s, br, 1H), 0.29 (s, br, 1H), −0.26 (s, br, 1H), −0.96 (s, br, 1H). Mass spectrum (ESI) m/e=679.0 (M+1).

Example 251

2-((2R,5R,6R)-6-(3-chlorophenyl)-5-(4-chlorophenyl)-4-((S)-1-cyclopropyl-2-(N-(2,6-difluorophenyl)cyclopropanesulfonamido)ethyl)-3-oxomorpholin-2-yl)acetic acid or 2-((2S,5R,6R)-6-(3-chlorophenyl)-5-(4-chlorophenyl)-4-((S)-1-cyclopropyl-2-(N-(2,6-difluorophenyl)cyclopropanesulfonamido)ethyl)-3-oxomorpholin-2-yl)acetic acid

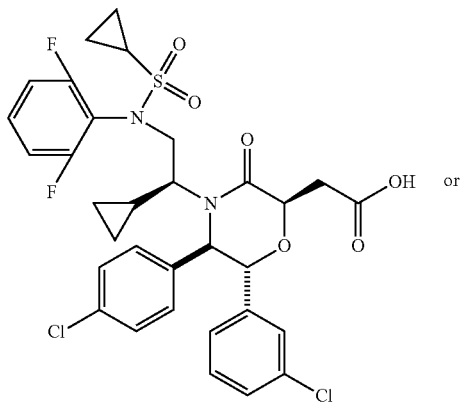

or

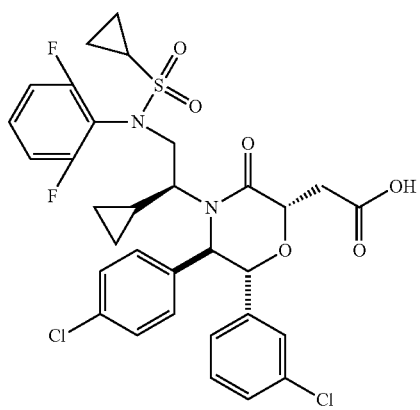

One of the title compounds was prepared as the second eluting isomer from Example 150, Step E as a white solid. By analytical HPLC (15 min. method, 10 to 100% MeCN in water with 0.1% TFA on an Agilent Eclipse $C_{18}$ column (Agilent Technologies, Santa Clara, Calif.) the $t_R$=10.54 minutes. $^1$H NMR (400 MHz, chloroform-d) δ ppm 7.20-7.34 (m, 7H), 6.98-7.11 (m, 2H), 6.66 (s, br, 1H), 5.08 (s, br, 1H), 4.86 (d, J=4 Hz, 1H), 4.49 (s, br, 1H), 3.74 (s, br, 1H), 3.08 (s, br, 2H), 2.75 (s, br, 1H), 2.68 (s, br, 1H), 2.48 (s, br, 1H), 1.42 (s, br, 1H), 0.96-1.01 (m, 4H), 0.47 (s, be, 1H), 0.33 (s, br, 1H), 0.00 (s, br, 1H), −0.17 (s, br, 1H). Mass spectrum (ESI) m/e=679.0 (M+1).

Example 252

(R)-2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl) propanoic acid or (S)-2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl) propanoic acid or (R)-2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)

propanoic acid or (S)-2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl) propanoic acid

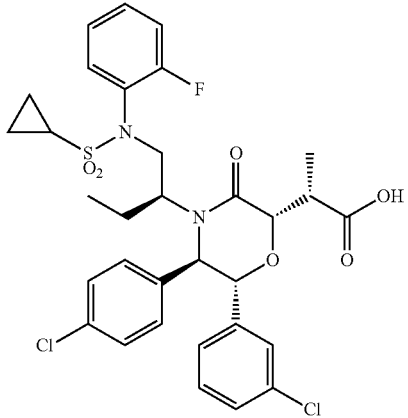

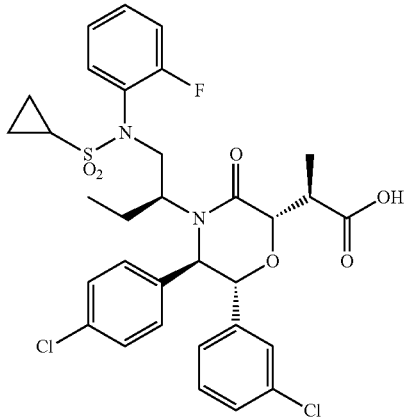

417

-continued

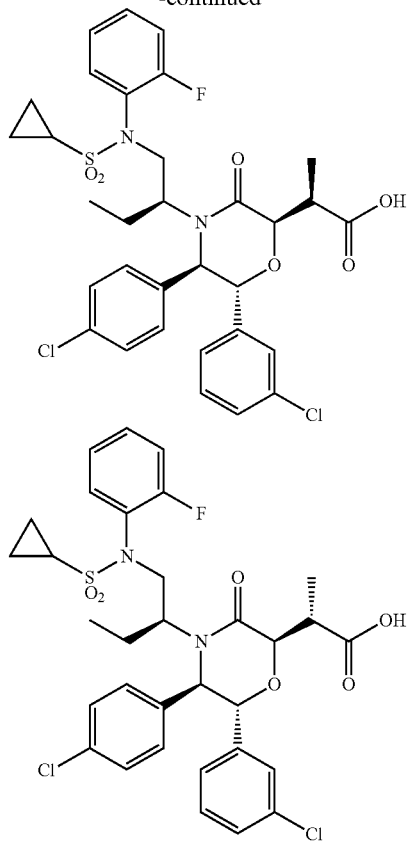

Step A. N-((S)-2-((2R,3R,6R)-2-(3-chlorophenyl)-3-(4-chlorophenyl)-5-oxo-6-((S,E)-pent-3-en-2-yl)morpholino)butyl)-N-(2-fluorophenyl)cyclopropanesulfonamide and N-((S)-2-((2R,3R,6R)-2-(3-chlorophenyl)-3-(4-chlorophenyl)-5-oxo-6-((R,E)-pent-3-en-2-yl)morpholino)butyl)-N-(2-fluorophenyl)cyclopropanesulfonamide and N-((S)-2-((2R,3R,6S)-2-(3-chlorophenyl)-3-(4-chlorophenyl)-5-oxo-6-((S,E)-pent-3-en-2-yl)morpholino)butyl)-N-(2-fluorophenyl)cyclopropanesulfonamide and N-((S)-2-((2R,3R,6S)-2-(3-chlorophenyl)-3-(4-chlorophenyl)-5-oxo-6-((R,E)-pent-3-en-2-yl)morpholino)butyl)-N-(2-fluorophenyl)cyclopropanesulfonamide

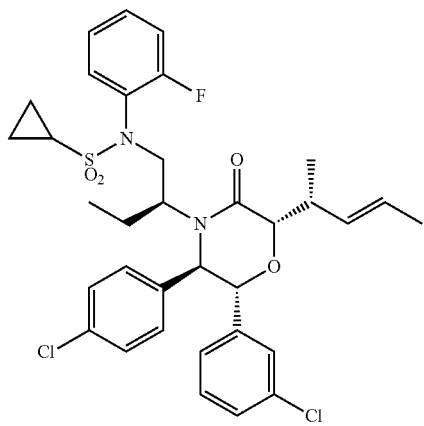

418

-continued

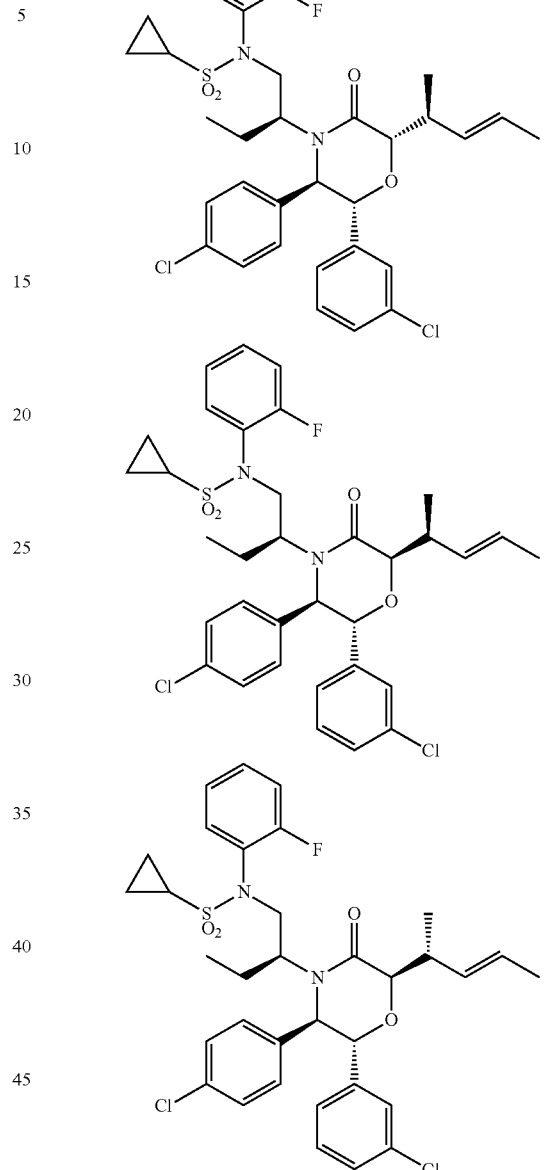

N-((S)-2-((2R,3R)-2-(3-chlorophenyl)-3-(4-chlorophenyl)-5-oxomorpholino)butyl)-N-(2-fluorophenyl)cyclopropanesulfonamide (800 mg, 1.352 mmol) (prepared from (5R,6R)-6-(3-chlorophenyl)-5-(4-chlorophenyl)-4-((S)-1-hydroxybutan-2-yl)morpholin-3-one [Example 112, Step C] by procedures similar to those described in Example 112, Steps D, replacing ethanethiol with N-(2-fluorophenyl)cyclopropanesulfonamide [described in Example 133].) was thrice dissolved in toluene and concentrated under a vacuum. The resulting residue was dissolved in THF (6762 µL) and degassed by bubbling with Ar (g) through the solution for 10 minutes. Then the mixture was cooled to −78° C. under Ar (g) and lithium bis(trimethylsilyl)amide (1.0 M in THF) (4869 µL, 4.87 mmol) was added dropwise. The mixture turned bright yellow. Then (E)-4-bromopent-2-ene (reference: *J. Org. Chem.*, 2008, 73, 5180 and *J. Am. Chem. Soc.* 1965, 1267) (726 mg, 4.87 mmol) was added neat. The mixture was stirred at −78° C. for 1 hour. The mixture was then quenched with sat. NH₄Cl and warmed to room temperature. The mixture was extracted with EtOAc (2×). The combined organic layers were dried over Na₂SO₄, filtered and the filtrate was concentrated under a vacuum. The residue was purified by flash chromatography on silica gel (100 g VersaPak® I-style silica gel column (SUPELCO, Bellefonte, Pa.); eluent: 30% MTBE in hexanes) to give the title compounds as a mixture of four isomers.

Step B. (R)-2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid or (S)-2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid or (R)-2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid or (S)-2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid

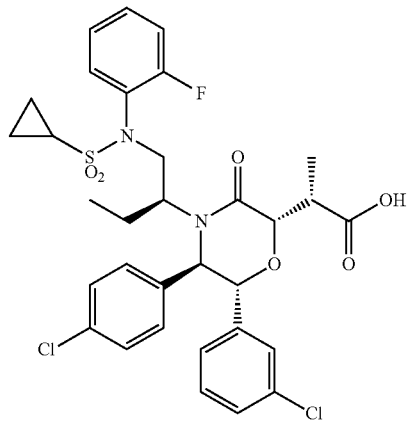

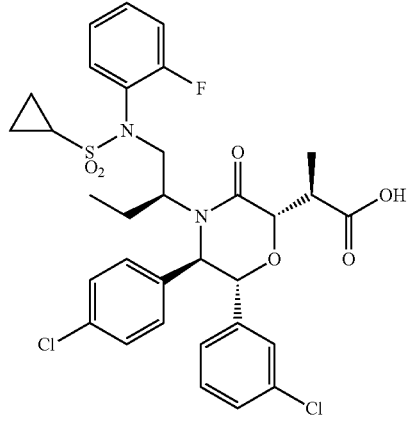

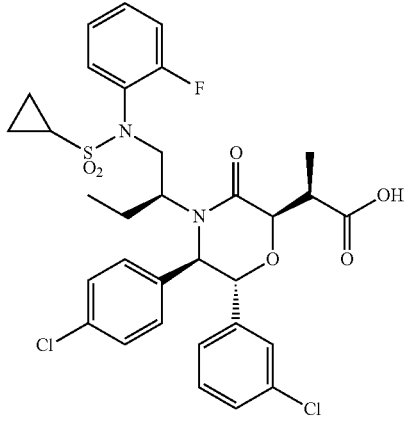

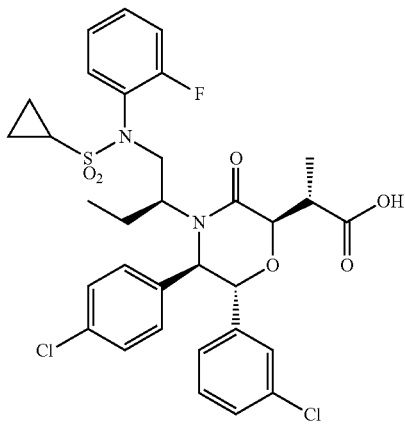

To N-((S)-2-((2R,3R,6R)-2-(3-chlorophenyl)-3-(4-chlorophenyl)-5-oxo-6-((S,E)-pent-3-en-2-yl)morpholino)butyl)-N-(2-fluorophenyl)cyclopropanesulfonamide and N-((S)-2-((2R,3R,6R)-2-(3-chlorophenyl)-3-(4-chlorophenyl)-5-oxo-6-((R,E)-pent-3-en-2-yl)morpholino)butyl)-N-(2-fluorophenyl)cyclopropanesulfonamide and N-((S)-2-((2R,3R,6S)-2-(3-chlorophenyl)-3-(4-chlorophenyl)-5-oxo-6-((S,E)-pent-3-en-2-yl)morpholino)butyl)-N-(2-fluorophenyl)cyclopropanesulfonamide and N-((S)-2-((2R,3R,6S)-2-(3-chlorophenyl)-3-(4-chlorophenyl)-5-oxo-6-((R,E)-pent-3-en-2-yl)morpholino)butyl)-N-(2-fluorophenyl) (a mixture of four isomers from Example 252, Step A) (56 mg, 0.085 mmol) in THF (424 μL) was added water dropwise until cloudy (0.5 mL) and then t-BuOH (0.05 mL) dropwise until the reaction mixture was clear. Then NMO (14.92 mg, 0.127 mmol) was added followed by osmium tetroxide (4% aq.; 3.24 μL, 0.509 μmol). The mixture was stirred at room temperature for 3 days. More osmium tetroxide (4% aq.; 3.24 μL, 0.509 μmol) was added and the mixture was stirred at room temperature for 24 hours. Then sodium periodate (50.8 mg, 0.238 mmol) was added and the cloudy reaction mixture was stirred at room temperature for 90 min. A white precipitate formed. The mixture was diluted with EtOAc. The organic layer was washed with sat. Na$_2$S$_2$O$_3$ and brine. The organic layer was dried over Na$_2$SO$_4$, filtered and the filtrate was concentrated under a vacuum. The residue was dissolved in t-BuOH (327 μL) and 2-methylbut-2-ene (327 μL) was added. Then a solution of sodium chlorite (16.13 mg, 0.178 mmol) and potassium dihydrogen phosphate (24.27 mg, 0.178 mmol) in water (0.8 mL) was added. The mixture was stirred at ambient temperature for 2 hours. The mixture was diluted with 1 M HCl and EtOAc and the layers were separated. The organic layer was dried over Na$_2$SO$_4$ and concentrated under a vacuum. The resulting residue was purified by chiral HPLC (250×21 mm Chiralpak® IA column (Chiral Technologies, Inc., West Chester, Pa., USA) with 12.5 g/min IPA+(20 mM NH$_3$)+37.8 g/min CO$_2$ on a Thar 80 SFC (Thar Technologies, Inc., Pittsburg, Pa.)) to give the title compound as the first eluting isomer. $^1$H NMR (chloroform-d, 400 MHz): δ ppm 7.48 (tt, J=7.9, 0.8 Hz, 1 H), 7.33-7.40 (m, 1 H), 7.12-7.32 (m, 10 H), 5.05 (d, J=6.5 Hz, 1 H), 4.93 (d, J=6.3 Hz, 1 H), 4.39 (dd, J=14.8, 8.1 Hz, 1 H), 4.11 (d, J=4.1 Hz, 1 H), 3.79-3.88 (m, 1 H), 3.27-3.32 (m, 1 H), 3.12-3.16 (m, 1 H), 2.43-2.54 (m, 1 H), 1.82-1.94 (m, 1 H), 1.52-1.68 (m, 1H), 1.32-1.41 (m, 3H), 0.91-1.07 (m, 4 H), 0.45 (t, J=7.5 Hz, 3 H). Mass spectrum (ESI) m/z=663 [M+1].

Example 253

(R)-2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid or (S)-2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid or (R)-2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid or (S)-2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid

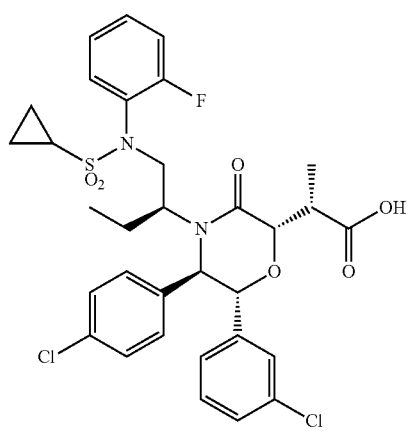

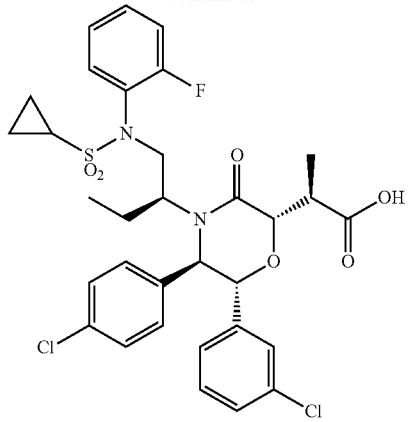

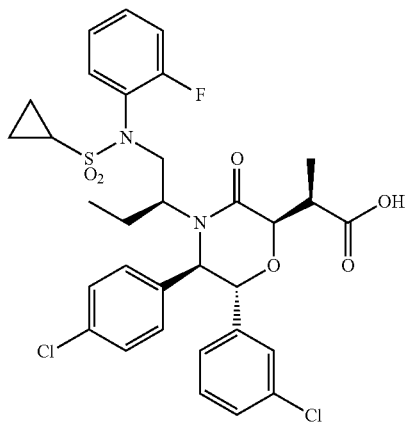

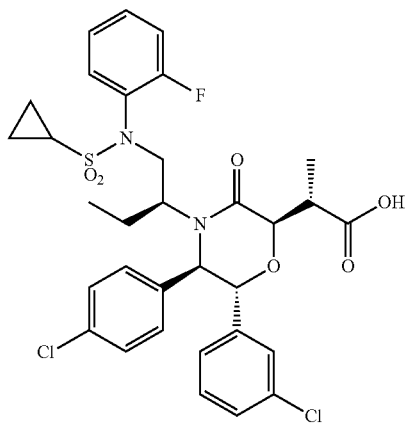

The title compound was isolated in Example 252, Step B as the second eluting isomer. $^1$H NMR (chloroform-d, 400 MHz): δ ppm 7.46 (t, J=7.5 Hz, 1 H), 7.11-7.40 (m, 11 H), 4.94 (d, J=6.5 Hz, 1 H), 4.81 (d, J=6.5 Hz, 1 H), 4.25-4.36 (m, 2 H), 3.80-3.88 (m, 1 H), 3.23 (t, J=7.1 Hz, 2 H), 2.45-2.52 (m, 1 H), 2.44-2.53 (m, 1 H), 1.81-1.94 (m, 1 H), 1.32 (d, J=7.2 Hz, 3 H), 0.81-1.06 (m, 4 H), 0.46 (t, J=7.5 Hz, 3 H). Mass spectrum (ESI) m/z=663 [M+1].

Example 254

(R)-2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid or (S)-2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid or (R)-2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid or (S)-2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid

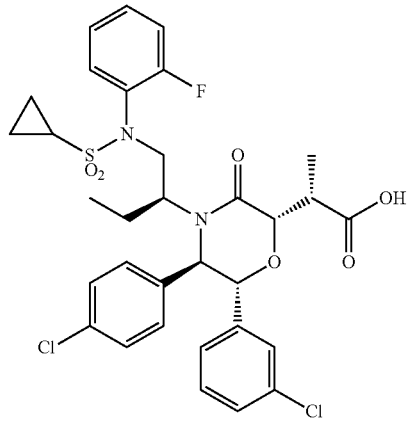

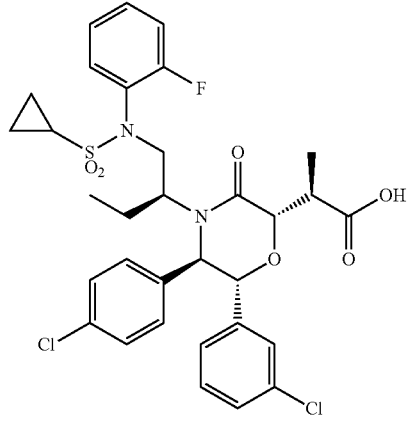

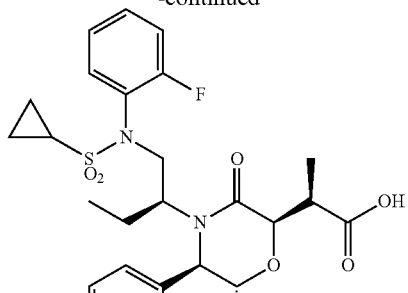

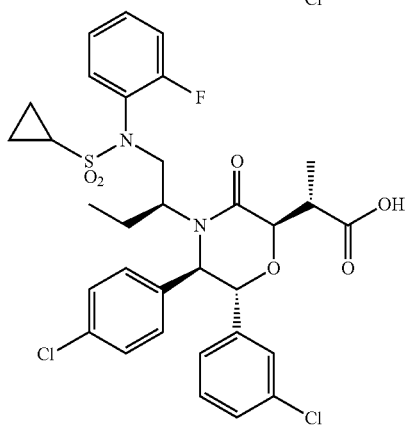

The title compound was isolated in Example 252, Step B as the third eluting isomer. $^1$H NMR (chloroform-d, 400 MHz): δ ppm 7.47-7.53 (m, 1 H), 7.32-7.41 (m, 1 H), 7.09-7.33 (m, 6 H), 6.98-7.08 (m, 3 H), 6.75 (d, J=7.8 Hz, 1 H), 4.68-4.75 (m, 1 H), 4.60-4.66 (m, 2H), 4.18-4.32 (m, 1 H), 3.68-3.79 (m, 1 H), 3.12 (br. s., 1 H), 2.83 (t, J=6.8 Hz, 1 H), 2.34-2.45 (m, 1 H), 1.87-2.03 (m, 1 H), 1.46-1.59 (m, 1 H), 1.04 (d, J=7.2 Hz, 3 H), 0.84-0.98 (m, 4 H), 0.53 (t, J=7.5 Hz, 3 H). Mass spectrum (ESI) m/z=663 [M+1].

Example 255

(R)-2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid or (S)-2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid or (R)-2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid or (S)-2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid

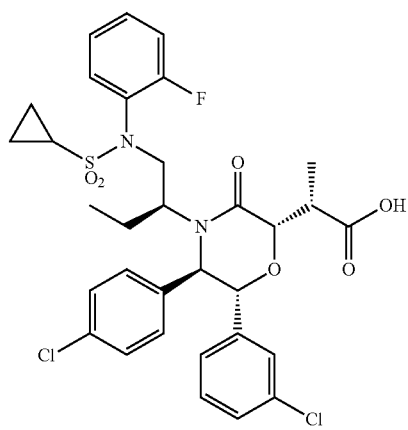

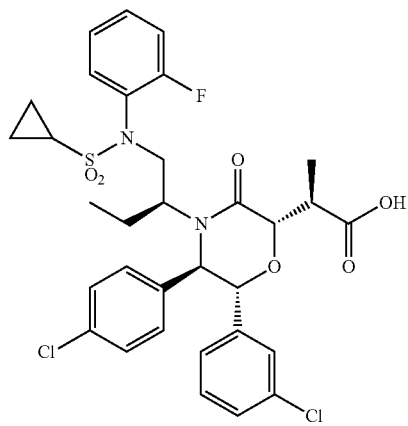

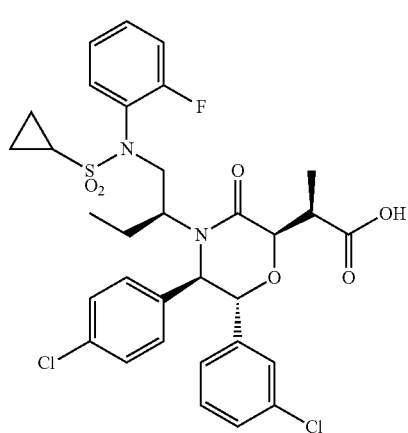

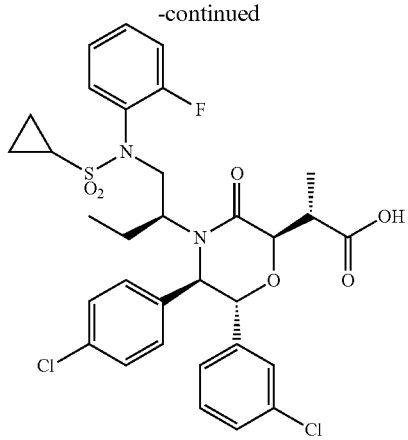

The title compound was isolated in Example 252, Step B as the fourth eluting isomer. $^1$H NMR (chloroform-d, 400 MHz): δ ppm 7.45 (t, J=7.9 Hz, 1 H), 7.33-7.40 (m, 1 H), 7.22-7.30 (m, 3 H), 7.04-7.21 (m, 4 H), 6.97 (d, J=8.2 Hz, 2 H), 6.70 (d, J=7.8 Hz, 1 H), 4.60-4.70 (m, 3 H), 4.13-4.21 (m, 1 H), 3.75-3.85 (m, 1 H), 3.05-3.15 (m, 1 H), 2.86-2.91 (m, 1 H), 2.39-2.46 (m, 1H), 1.93-2.03 (m, 1 H), 1.58-1.72 (m, 1 H), 1.09 (d, J=7.2 Hz, 3 H), 0.82-1.00 (m, 4 H), 0.58 (t, J=7.5 Hz, 3H). Mass spectrum (ESI) m/z=663 [M+1].

Example 256

2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetamide or 2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetamide

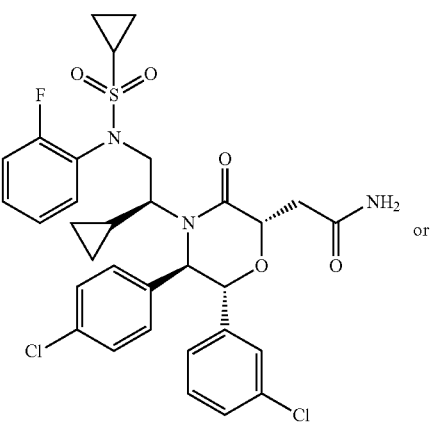 or

427

-continued

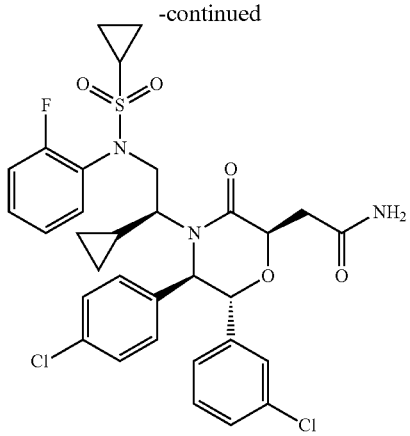

One of the title compounds was obtained from 2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid and 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl) acetic acid (mixture of isomers from Example 158) by a procedure analogous to the one described in Example 225. The crude residue was purified by preparative thin layer chromatography (eluent: 8% ethanol/toluene with 0.5% aq. NH$_4$OH) to provide one of the title compounds as the first eluting isomer. $^1$H NMR (400 MHz, CDCl$_3$) δ ppm −1.23-(−)0.78 (m, 1 H) −0.43-(−)0.06 (m, 1 H) 0.10-0.32 (m, 1 H) 0.34-0.50 (m, 1 H) 0.76-1.14 (m, 4 H) 1.21-1.38 (m, 1 H) 1.46-1.79 (m, 2 H) 2.15-2.53 (m, 2 H) 2.76 (dt, J=12.72, 2.93 Hz, 1 H) 3.75-4.05 (m, 1 H) 4.72 (d, J=9.98 Hz, 1 H) 4.77 (t, J=6.16 Hz, 1 H) 4.84 (d, J=9.78 Hz, 1 H) 5.13-5.34 (m, 1 H) 5.75-6.00 (m, 1 H) 6.87 (d, J=7.04 Hz, 1 H) 7.06 (d, J=7.63 Hz, 2H) 7.11-7.32 (m, 7 H) 7.35-7.44 (m, 1 H) 7.61 (t, J=7.63 Hz, 1 H). Mass spectrum (ESI) m/z=660 (M+1).

Example 257

2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetamide or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetamide

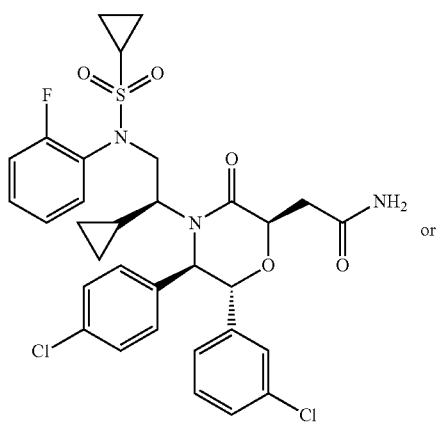

or

428

-continued

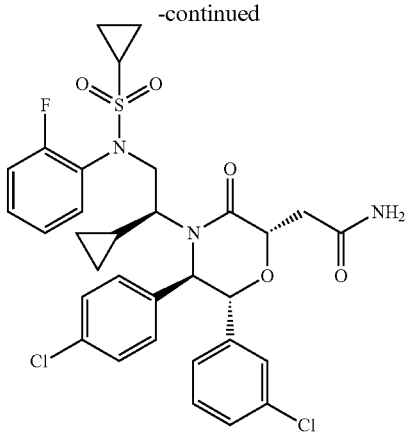

One of the title compounds was isolated as the second eluting isomer in Example 256. $^1$H NMR (400 MHz, CDCl$_3$-d) δ ppm −0.10-0.15 (m, 1 H) 0.22-0.42 (m, 1 H) 0.40-0.59 (m, 1 H) 0.87-1.05 (m, 5 H) 1.23-1.39 (m, 1 H) 1.42-1.68 (m, 2 H) 2.45 (quin, J=6.11 Hz, 1 H) 2.87-3.02 (m, 2 H) 3.75-3.96 (m, 1 H) 4.36 (dd, J=6.65, 5.28 Hz, 1 H) 4.95 (d, J=6.46 Hz, 1 H) 5.03 (d, J=7.83 Hz, 1 H) 5.32 (br. s., 1 H) 6.18 (br. s., 1 H) 7.09-7.43 (m, 11 H) 7.52 (td, J=7.78, 1.27 Hz, 1 H). Mass spectrum (ESI) m/z=660 (M+1).

Example 258

2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)-N-(isopropylsulfonyl)acetamide or 2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)-N-(isopropylsulfonyl)acetamide

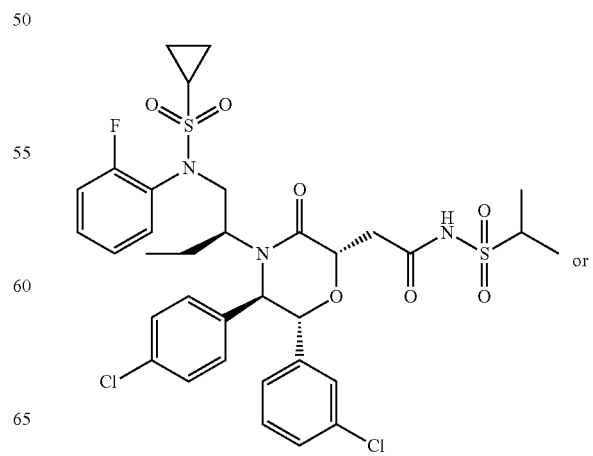

or

429

-continued

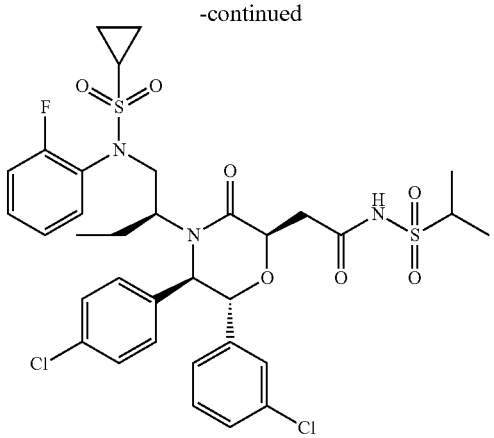

One of the title compounds was obtained from 2-((2R,5R,6R)-6-(3-chlorophenyl)-5-(4-chlorophenyl)-4-((S)-1-(N-(2-fluorophenyl)cyclopropanesulfonamido)butan-2-yl)-3-oxo-morpholin-2-yl)acetic acid and 2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)acetic acid (mixture of isomers from Example 133) using a procedure analogous to the one described in Example 237 using isopropylsulfonamide (Nanjing Pharmatechs Co., Ltd.) in place of methanesulfonamide. The crude residue was purified by preparative thin layer chromatography (eluent: 30% THF/toluene) to provide one of the title compounds as the first eluting isomer. $^1$H NMR (400 MHz, acetonitrile-$d_3$) δ ppm 0.47 (t, J=7.53 Hz, 3 H) 0.80-0.89 (m, 2 H) 0.96-1.00 (m, 2 H) 1.22 (d, J=6.85 Hz, 3 H) 1.26 (d, J=6.85 Hz, 3 H) 1.53-1.66 (m, 1 H) 1.81-1.92 (m, 1 H) 2.02-2.21 (m, 1 H) 2.44-2.60 (m, 2 H) 2.85 (dd, J=15.85, 4.89 Hz, 1H) 3.53 (dt, J=13.84, 6.87 Hz, 1 H) 3.63-3.75 (m, 1 H) 4.17-4.31 (m, 1 H) 4.64 (d, J=9.98 Hz, 1 H) 4.76-4.85 (m, 2 H) 6.90 (d, J=7.63 Hz, 1H) 7.03 (d, J=8.41 Hz, 2 H) 7.13 (t, J=1.96 Hz, 1 H) 7.17-7.32 (m, 6 H) 7.40-7.48 (m, 1 H) 7.55 (td, J=8.02, 1.76 Hz, 1 H). Mass spectrum (ESI) m/z=754 (M+1).

Example 259

2-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)-N-(isopropylsulfonyl)acetamide or 2-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)-N-(isopropylsulfonyl)acetamide

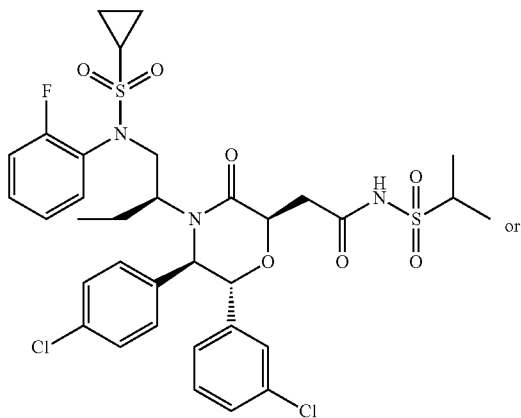

or

430

-continued

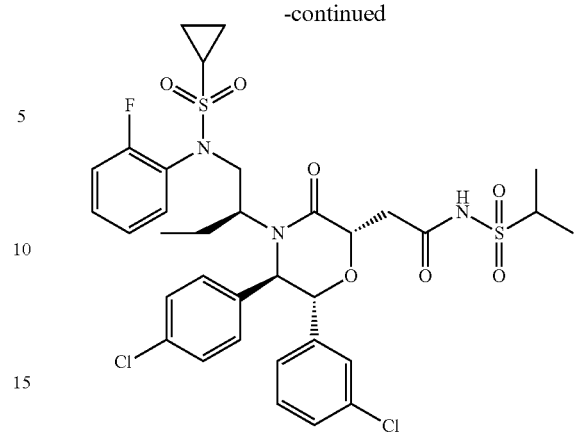

One of the title compounds was isolated as the second eluting isomer in Example 258. $^1$H NMR (400 MHz, acetonitrile-$d_3$) δ ppm 0.45 (t, J=7.53 Hz, 3 H) 0.80-1.01 (m, 4 H) 1.11 (d, J=6.85 Hz, 3 H) 1.25 (d, J=6.85 Hz, 3 H) 1.47-1.65 (m, 1 H) 1.82-1.91 (m, 1 H) 2.46-2.63 (m, 2 H) 2.90 (dd, J=15.50, 4.30 Hz, 1 H) 3.02 (dd, J=15.70, 9.20 Hz, 1 H) 3.54 (quip, J=6.94 Hz, 1 H) 3.72 (dd, J=14.48, 4.69 Hz, 1H) 4.15-4.32 (m, 1 H) 4.41 (dd, J=9.29, 4.21 Hz, 1 H) 4.81 (d, J=8.61 Hz, 1 H) 4.89 (d, J=8.61 Hz, 1 H) 7.07 (d, J=7.43 Hz, 1 H) 7.12-7.18 (m, 3 H) 7.20-7.34 (m, 6 H) 7.39-7.49 (m, 1 H) 7.56 (t, J=8.02 Hz, 1 H) 9.22 (s, 1 H). Mass spectrum (ESI) m/z=754 (M+1).

Example 260

2-((2S,5R,6R)-4-((S)-1-(tert-butylsulfonyl)butan-2-yl)-6-(3-chlorophenyl)-5-(4-chlorophenyl)-3-oxomorpholin-2-yl)acetamide or 2-((2R,5R,6R)-4-((S)-1-(tert-butylsulfonyl)butan-2-yl)-6-(3-chlorophenyl)-5-(4-chlorophenyl)-3-oxomorpholin-2-yl)

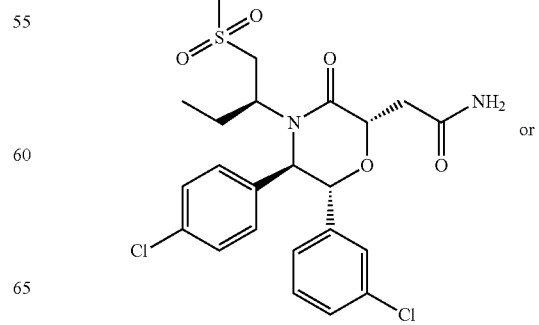

or

431
-continued

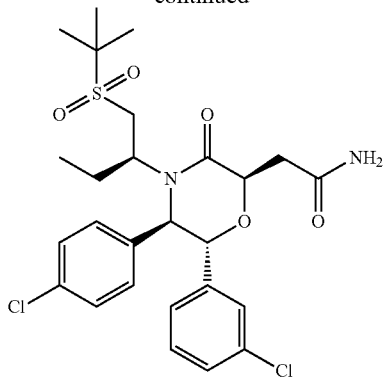

432
-continued

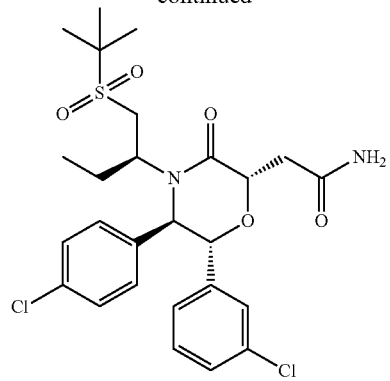

One of the title compounds was obtained from 2-((2R,5R, 6R)-4-((S)-1-(tert-butylsulfonyl)butan-2-yl)-6-(3-chlorophenyl)-5-(4-chlorophenyl)-3-oxomorpholin-2-yl)acetic acid and 2-((2S,5R,6R)-4-((S)-1-(tert-butylsulfonyl)butan-2-yl)-6-(3-chlorophenyl)-5-(4-chlorophenyl)-3-oxomorpholin-2-yl)acetic acid (mixture of isomers from Example 120) by a procedure analogous to the one described in Example 225. The crude residue was purified by thin layer chromatography (eluent: 8% ethanol/toluene with 0.5% aq. NH$_4$OH) to provide one of the title compounds as the first eluting isomer. $^1$H NMR (400 MHz, CDCl$_3$) δ ppm 0.53 (t, J=7.53 Hz, 3H) 1.43 (s, 9 H) 1.57-1.59 (m, 1 H) 2.10-2.25 (m, 1 H) 2.76-2.93 (m, 2 H) 3.06 (dd, J=15.65, 4.30 Hz, 1 H) 3.28 (t, J=9.59 Hz, 1 H) 4.07 (dd, J=13.40, 9.88 Hz, 1 H) 4.70 (d, J=9.98 Hz, 1 H) 4.77 (dd, J=7.04, 4.30 Hz, 1 H) 5.08 (d, J=9.78 Hz, 1 H) 5.40 (br. s., 1 H) 6.01 (br. s., 1 H) 6.83 (dt, J=7.78, 1.39 Hz, 1 H) 7.06-7.23 (m, 4 H) 7.25-7.33 (m, 3 H). Mass spectrum (ESI) m/z=555 (M+1).

Example 261

2-((2R,5R,6R)-4-((S)-1-(tert-butylsulfonyl)butan-2-yl)-6-(3-chlorophenyl)-5-(4-chlorophenyl)-3-oxomorpholin-2-yl)acetamide or 2-((2S,5R,6R)-4-((S)-1-(tert-butylsulfonyl)butan-2-yl)-6-(3-chlorophenyl)-5-(4-chlorophenyl)-3-oxomorpholin-2-yl)acetamide One of the title compounds was isolated as the second eluting isomer in Example 260. $^1$H NMR (400 MHz, CDCl$_3$-d) δ ppm 0.55 (t, J=7.53 Hz, 3 H) 1.44 (s, 9 H) 1.62-1.75 (m, 1 H) 2.10-2.25 (m, 1 H) 2.83-2.99 (m, 2 H) 3.07 (dd, J=15.85, 7.24 Hz, 1 H) 3.37 (t, J=7.92 Hz, 1 H) 4.00 (dd, J=13.50, 9.19 Hz, 1 H) 4.68 (dd, J=7.24, 3.91 Hz, 1 H) 5.04 (d, J=7.43 Hz, 1 H) 5.13 (d, J=7.24 Hz, 1 H) 5.34 (br. s., 1 H) 6.01 (br. s., 1 H) 7.01 (d, J=7.63 Hz, 1 H) 7.15 (t, J=7.73 Hz, 1 H) 7.21-7.24 (m, 1 H) 7.25-7.36 (m, 5 H). Mass spectrum (ESI) m/z=555 (M+1).

Example 262

3-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid or 3-((2S,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid

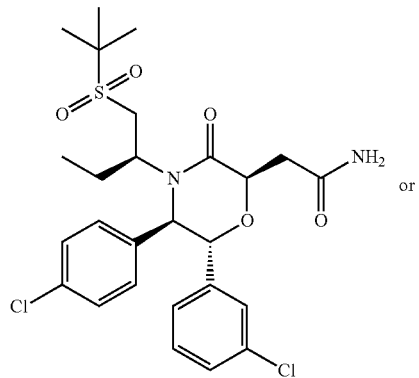

or

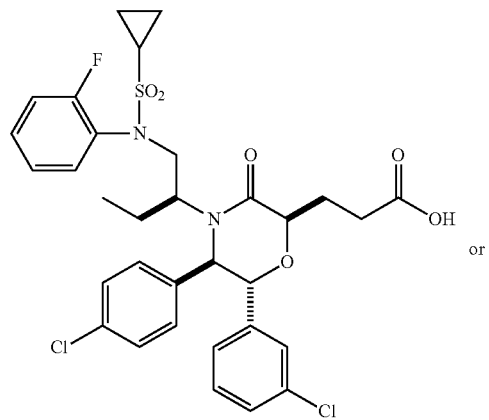

or

433

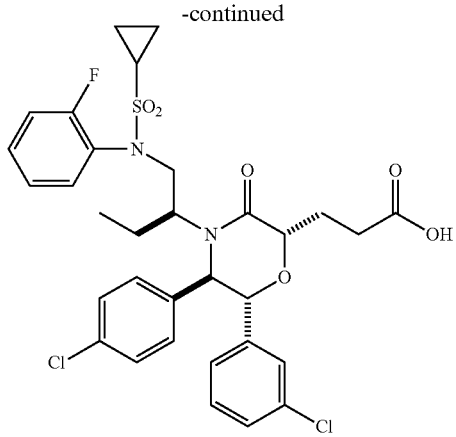

Step A. N-((S)-2-((2R,5R,6R)-2-allyl-6-(3-chlorophenyl)-5-(4-chlorophenyl)-3-oxomorpholino)butyl)-N-(2-fluorophenyl)cyclopropanesulfonamide and N-((S)-2-((2S,5R,6R)-2-allyl-6-(3-chlorophenyl)-5-(4-chlorophenyl)-3-oxomorpholino)butyl)-N-(2-fluorophenyl)cyclopropanesulfonamide The title compounds were prepared from (5R,6R)-6-(3-chlorophenyl)-5-(4-chlorophenyl)-4-((S)-1-hydroxybutan-

434

2-yl)morpholin-3-one (Example 112, Step C) by procedures similar to those described in Example 112, Steps D and E, replacing ethanethiol in Step D with N-(2-fluorophenyl)cyclopropanesulfonamide (obtained from Example 133). The crude material was purified by flash chromatography on silica gel, eluting with a gradient of 20% to 40% ethyl acetate in hexanes, to provide the title compounds as a mixture of two diastereomers.

Step B. N-((S)-2-((2R,3R,6R)-2-(3-chlorophenyl)-3-(4-chlorophenyl)-6-((S)-2,3-dihydroxypropyl)-5-oxomorpholino)butyl)-N-(2-fluorophenyl)cyclopropanesulfonamide and N-((S)-2-((2R,3R,6S)-2-(3-chlorophenyl)-3-(4-chlorophenyl)-6-((R)-2,3-dihydroxypropyl)-5-oxomorpholino)butyl)-N-(2-fluorophenyl)cyclopropanesulfonamide and N-((S)-2-((2R,3R,6R)-2-(3-chlorophenyl)-3-(4-chlorophenyl)-6-((S)-2,3-dihydroxypropyl)-5-oxomorpholino)butyl)-N-(2-fluorophenyl)cyclopropanesulfonamide and N-((S)-2-((2R,3R,6S)-2-(3-chlorophenyl)-3-(4-chlorophenyl)-6-((R)-2,3-dihydroxypropyl)-5-oxomorpholino)butyl)-N-(2-fluorophenyl)cyclopropanesulfonamide

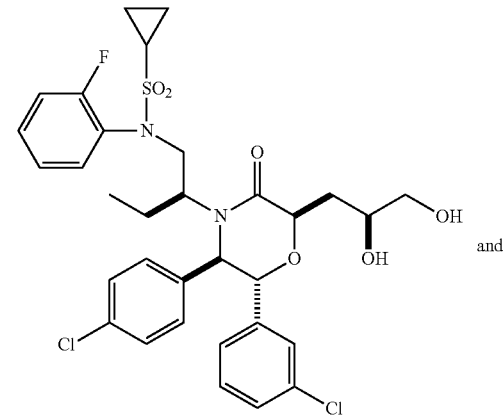

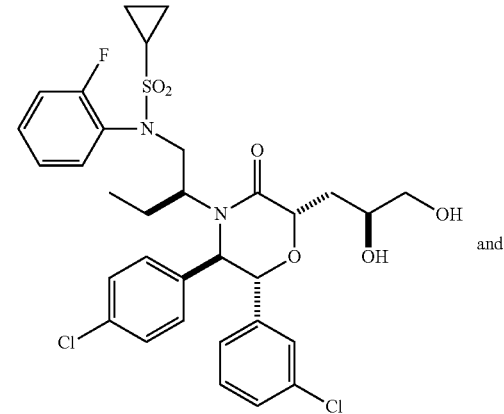

435
-continued

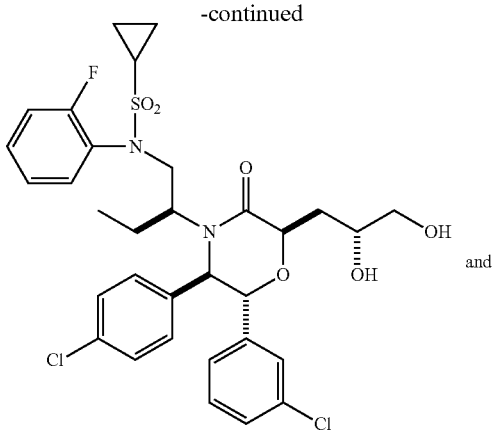
and

436

Step C. N-((S)-2-((2R,3R,6R)-2-(3-chlorophenyl)-3-(4-chlorophenyl)-5-oxo-6-(2-oxoethyl)morpholino)butyl)-N-(2-fluorophenyl)cyclopropanesulfonamide and N-((S)-2-((2R,3R,6S)-2-(3-chlorophenyl)-3-(4-chlorophenyl)-5-oxo-6-(2-oxoethyl)morpholino)butyl)-N-(2-fluorophenyl)cyclopropanesulfonamide

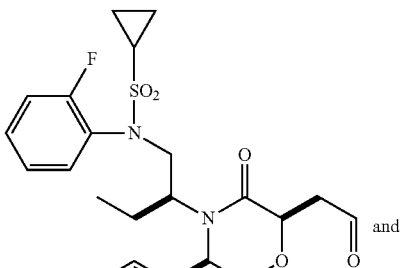
and

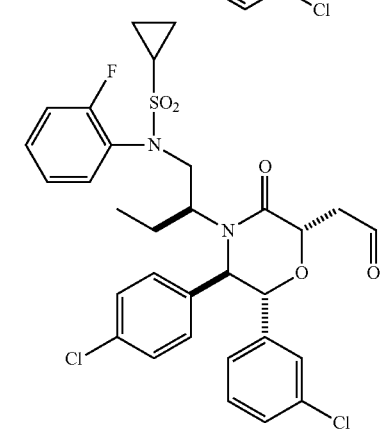

To a solution of N-((S)-2-((2R,5R,6R)-2-allyl-6-(3-chlorophenyl)-5-(4-chlorophenyl)-3-oxomorpholino) butyl)-N-(2-fluorophenyl)cyclopropanesulfonamide and N-((S)-2-((2S,5R,6R)-2-allyl-6-(3-chlorophenyl)-5-(4-chlorophenyl)-3-oxomorpholino)butyl)-N-(2-fluorophenyl) cyclopropanesulfonamide (0.670 g, 1.061 mmol, Example 262, step A) in THF (2.5 mL), water (1.5 mL) and tert-butanol (1.5 mL) was added 4-methylmorpholine 4-oxide (0.435 g, 3.71 mmol) followed by osmium tetroxide (2.5 wt. %, solution in tert-butanol; 0.259 mL, 0.027 mmol). After stirring at 25° C. for 16 hours, the reaction was diluted with water and extracted with ethyl acetate (3×). The combined organic extracts were washed with brine, dried over Na₂SO₄ and concentrated under the reduced pressure. The crude material was purified by flash chromatography on silica gel, eluting with a gradient of 60% to 100% ethyl acetate/hexanes to provide the title compounds as a mixture of four diastereomers.

To a clear solution of N-((S)-2-((2R,3R,6R)-2-(3-chlorophenyl)-3-(4-chlorophenyl)-6-((S)-2,3-dihydroxypropyl)-5-oxomorpholino)butyl)-N-(2-fluorophenyl)cyclopropanesulfonamide and N-((S)-2-((2R,3R,6S)-2-(3-chlorophenyl)-3-(4-chlorophenyl)-6-((R)-2,3-dihydroxypropyl)-5-oxomorpholino)butyl)-N-(2-fluorophenyl)cyclopropanesulfonamide and N-((S)-2-((2R,3R,6R)-2-(3-chlorophenyl)-3-(4-chlorophenyl)-6-((S)-2,3-dihydroxypropyl)-5-oxomorpholino)butyl)-N-(2-fluorophenyl)cyclopropanesulfonamide and N-((S)-2-((2R,3R,6S)-2-(3-chlorophenyl)-3-(4-chlorophenyl)-6-((R)-2,3-dihydroxypropyl)-5-oxomorpholino)butyl)-N-(2-fluorophenyl)cyclopropanesulfonamide (0.610 g, 0.916 mmol, Example 262, Step B) in water (5 mL) and THF (10 mL) was added sodium periodate (0.152 mL, 2.75 mmol). Methanol (5 mL) was added and the resulting mixture was stirred at room temperature for 30 minutes. The reaction was diluted with brine and extracted with ethyl acetate (2×). The combined organic layers were washed with brine), dried over Na₂SO₄ and concentrated under the reduced pressure to provide the title compounds as a mixture of diastereomers.

Step D. N-((S)-2-((2R,3R,6R)-2-(3-chlorophenyl)-3-(4-chlorophenyl)-5-oxo-6-(3-oxopropyl)morpholino)butyl)-N-(2-fluorophenyl)cyclopropanesulfonamide and N-((S)-2-((2R,3R,6S)-2-(3-chlorophenyl)-3-(4-chlorophenyl)-5-oxo-6-(3-oxopropyl)morpholino)butyl)-N-(2-fluorophenyl)cyclopropanesulfonamide

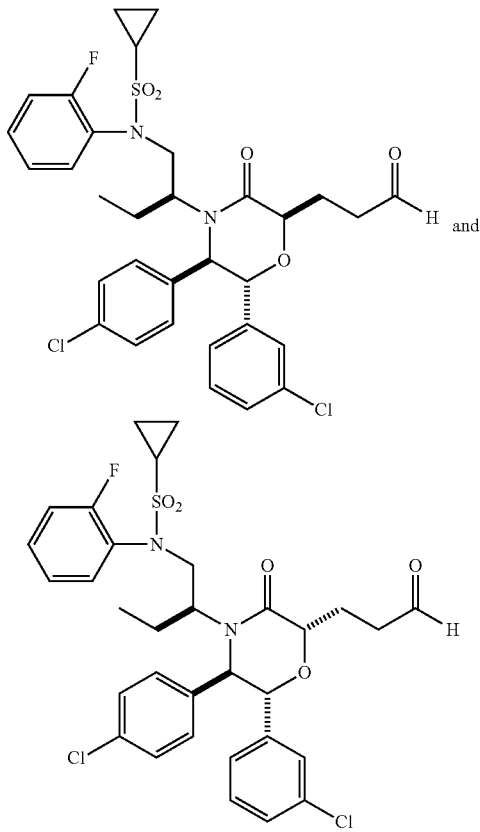

To a solution of (methoxymethyl)triphenylphosphonium chloride (1.242 g, 3.62 mmol) in THF (7 mL) was added potassium bis(trimethylsilyl)amide (0.5 M solution in toluene; 6.44 mL, 3.22 mmol) at −78° C. The solution turned a blood red color. After addition, the reaction was stirred at 0° C. for 30 minutes. Then a solution of N-((S)-2-((2R,3R,6R)-2-(3-chlorophenyl)-3-(4-chlorophenyl)-5-oxo-6-(2-oxoethyl)morpholino)butyl)-N-(2-fluorophenyl)cyclopropanesulfonamide and N-((S)-2-((2R,3R,6S)-2-(3-chlorophenyl)-3-(4-chlorophenyl)-5-oxo-6-(2-oxoethyl)morpholino)butyl)-N-(2-fluorophenyl)cyclopropanesulfonamide (0.510 g, 0.805 mmol, Example 262, step C) in THF (7 mL) was added dropwise at 0° C. The reaction was warmed to 25° C. and stirred for 90 minutes. The reaction was quenched with sat. NH₄Cl solution, extracted with ethyl acetate (2×), and washed with brine. The combined organic layers were dried over Na₂SO₄ and concentrated under reduced pressure. The crude material was purified by flash chromatography on silica gel, eluting with a gradient of 20%-40% ethyl acetate/hexanes to provide the methoxyallyl intermediates as a mixture of diastereomers. The intermediates (0.400 g, 0.605 mmol) were dissolved in acetonitrile (5 mL) and 3 N hydrochloric acid (5 mL, 4.42 mmol) was added to the solution. After stirring for 3 hours, the reaction was extracted with ethyl acetate (2×), washed with brine (2×), and the combined organic layers were dried over Na₂SO₄ and concentrated under the reduced pressure to provide the title compounds as a mixture of diastereomers.

Step E. 3-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid or 3-((2S,5R,6R)-6-(3-chlorophenyl)-5-(4-chlorophenyl)-4-((S)-1-(N-(2-fluorophenyl)cyclopropanesulfonamido) butan-2-yl)-3-oxomorpholin-2-yl)propanoic acid

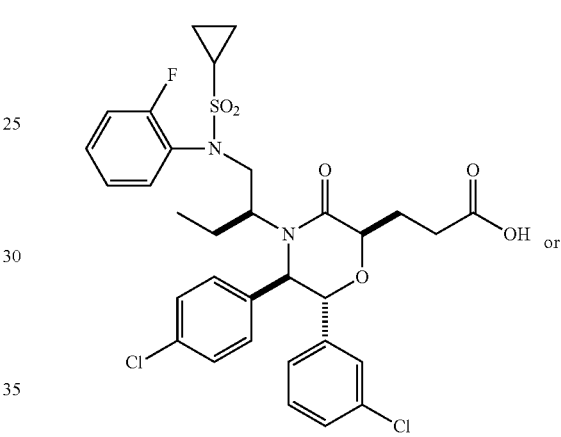

or

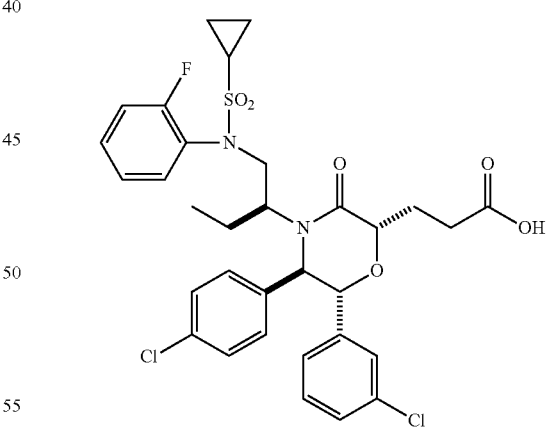

To a clear solution of N-((S)-2-((2R,3R,6R)-2-(3-chlorophenyl)-3-(4-chlorophenyl)-5-oxo-6-(3-oxopropyl)morpholino)butyl)-N-(2-fluorophenyl)cyclopropanesulfonamide and N-((S)-2-((2R,3R,6S)-2-(3-chlorophenyl)-3-(4-chlorophenyl)-5-oxo-6-(3-oxopropyl)morpholino)butyl)-N-(2-fluorophenyl)cyclopropanesulfonamide (0.380 g, 0.587 mmol, Example 262, step D) in a solution of 1.25 M potassium phosphate monobasic in water (6 mL), tert-butanol (6 mL), and 2-methyl-2-butene (2.0 M in tetrahydrofuran; 14.67 ml, 29.3 mmol) was added a solution of sodium chlorite (0.212 g, 2.347 mmol) in 1.25 M potassium phosphate monobasic in water (1.5 mL) at 0° C. After stirring at 25° C. for 90 minutes, an additional 2.0 equivalents of sodium chlorite were added to the solution. After 90 minutes, 2.0 equivalents of sodium chlorite were again added to the solution. After stirring overnight, the reaction was quenched with 1 M $Na_2S_2O_3$ solution (5 mL). After 10 minutes of stirring, the solution was acidified with 5% $H_2SO_4$, and extracted with ethyl acetate (3×). The combined organic layers were washed with brine, dried with $Na_2SO_4$, and concentrated under reduced pressure. The crude product was purified by reverse phase preparatory HPLC (Gemini™ Prep $C_{18}$ 5 µm column; Phenomenex, Torrance, Calif.; gradient elution of 40% to 60% acetonitrile in water where both solvents contain 0.1% TFA) to provide one of the title compounds as the first (faster) eluting isomer. $^1$H NMR (500 MHz, $CDCl_3$) δ ppm 0.49 (t, J=7.58 Hz, 3 H) 0.87-1.01 (m, 3 H) 1.03-1.12 (m, 1 H) 1.46-1.56 (m, 1 H) 1.87-1.98 (m, 1 H) 2.20-2.30 (m, 1 H) 2.30-2.41 (m, 1 H) 2.41-2.59 (m, 3 H) 3.10 (br. s., 1 H) 3.80 (dd, J=14.92, 4.40 Hz, 1 H) 4.09 (dd, J=10.76, 4.40 Hz, 1 H) 4.31-4.40 (m, 1 H) 4.76 (d, J=9.05 Hz, 1 H) 4.88 (d, J=9.05 Hz, 1 H) 6.94 (dt, J=7.70, 1.41 Hz, 1 H) 7.02-7.13 (m, 3 H) 7.13-7.25 (m, 4 H) 7.30 (d, J=8.56 Hz, 2H) 7.34-7.42 (m, 1 H) 7.51-7.60 (m, 1 H). Mass Spectrum (ESI) m/z=663 [M+1].

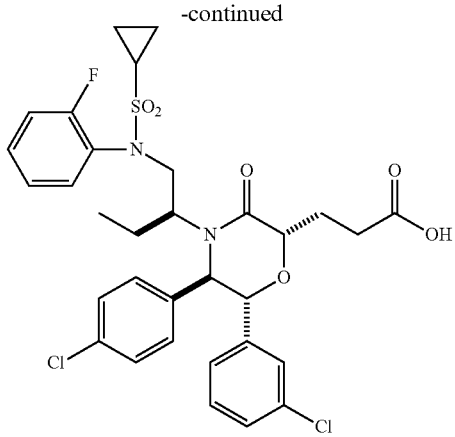

One of the title compounds was obtained as the second (slower) eluting isomer in Example 262, Step E. $^1$H NMR (500 MHz, $CDCl_3$) δ ppm 0.51 (t, J=7.46 Hz, 3 H) 0.84-1.00 (m, 3 H) 1.00-1.11 (m, 1 H) 1.47-1.57 (m, 1 H) 1.71-1.83 (m, 1 H) 1.98 (dt, J=16.02, 7.27 Hz, 1 H) 2.18-2.30 (m, 1 H) 2.35-2.51 (m, 3 H) 3.06 (br. s., 1 H) 3.74 (d, J=13.69 Hz, 1 H) 4.33 (dd, J=8.07, 3.91 Hz, 2 H) 4.60 (d, J=10.03 Hz, 1 H) 4.78 (d, J=9.78 Hz, 1H) 6.80 (dt, J=7.70, 1.41 Hz, 1 H) 6.98-7.09 (m, 3 H) 7.12-7.34 (m, 6 H) 7.34-7.43 (m, 1 H) 7.50-7.59 (m, 1 H)

Mass Spectrum (ESI) m/z=663 [M+1].

Example 263

3-((2R,5R,6R)-6-(3-chlorophenyl)-5-(4-chlorophenyl)-4-((S)-1-(N-(2-fluorophenyl)cyclopropanesulfonamido)butan-2-yl)-3-oxomorpholin-2-yl)propanoic acid or 3-((2S,5R,6R)-6-(3-chlorophenyl)-5-(4-chlorophenyl)-4-((S)-1-(N-(2-fluorophenyl)cyclopropanesulfonamido) butan-2-yl)-3-oxomorpholin-2-yl)propanoic acid Example 264

2-((2R,5R,6R)-6-(3-chlorophenyl)-5-(4-chlorophenyl)-4-((S)-1-(N-(2-chlorophenyl)cyclopropanesulfonamido)butan-2-yl)-3-oxomorpholin-2-yl)acetic acid or 2-((2S,5R,6R)-6-(3-chlorophenyl)-5-(4-chlorophenyl)-4-((S)-1-(N-(2-chlorophenyl)cyclopropanesulfonamido)butan-2-yl)-3-oxomorpholin-2-yl) acetic acid

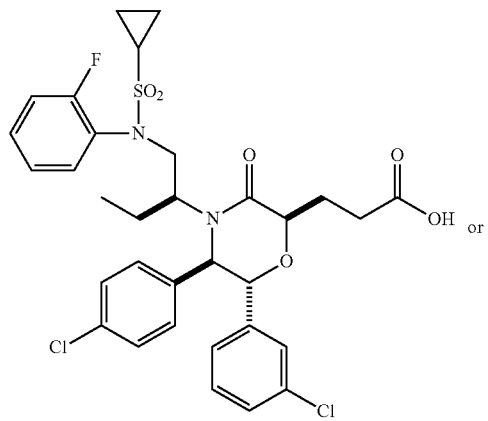 or

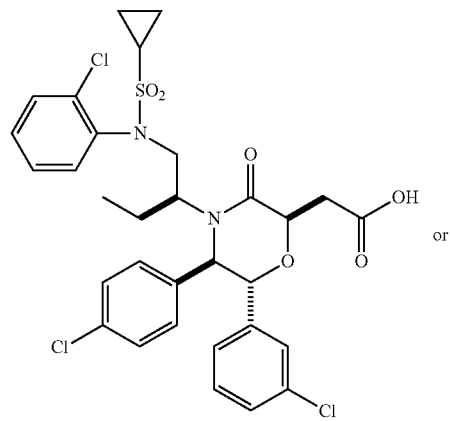 or

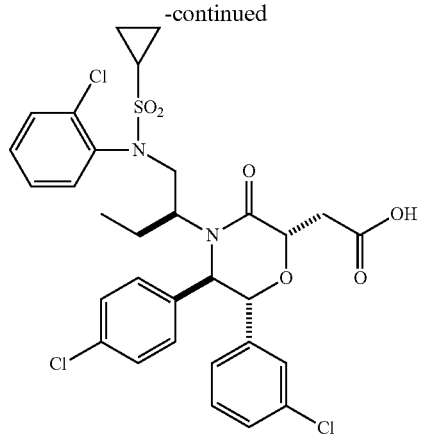

One of the title compound was prepared from (5R,6R)-6-(3-chlorophenyl)-5-(4-chlorophenyl)-4-((S)-1-hydroxybutan-2-yl)morpholin-3-one (Example 112, Step C) by procedures similar to those described in Example 112, Steps D though F, replacing ethanethiol in Step D with N-(2-chlorophenyl)cyclopropanesulfonamide which was made using a procedure similar to that described for N-(2-fluorophenyl)cyclopropanesulfonamide in Example 133. The crude product was purified by reverse phase preparatory HPLC (Gemini™ Prep $C_{18}$ 5 μm column; Phenomenex, Torrance, Calif.; gradient elution of 40% to 60% MeCN in water where both solvents contain 0.1% TFA, 20 min method) to provide one of the title compounds as the faster eluting isomer as a white foam. $t_R$=13.7 minutes. Mass Spectrum (ESI) m/z=665 [M+1].

Example 265

2-((2R,5R,6R)-6-(3-chlorophenyl)-5-(4-chlorophenyl)-4-((S)-1-(N-(2-chlorophenyl)cyclopropanesulfonamido)butan-2-yl)-3-oxomorpholin-2-yl)acetic acid or 2-((2S,5R,6R)-6-(3-chlorophenyl)-5-(4-chlorophenyl)-4-((S)-1-(N-(2-chlorophenyl)cyclopropanesulfonamido)butan-2-yl)-3-oxomorpholin-2-yl) acetic acid

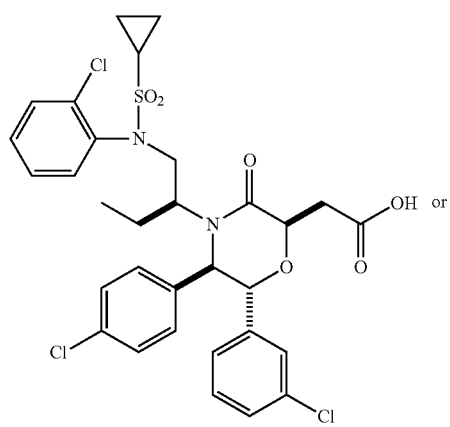

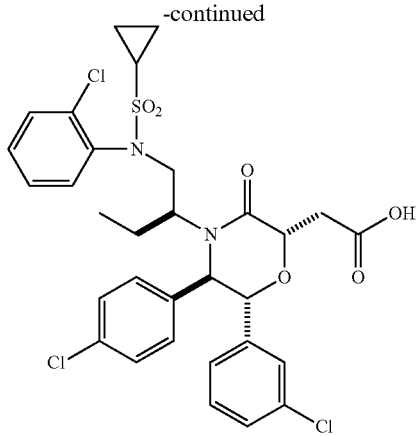

One of the title compounds was obtained as the second (slower) eluting isomer in Example 264. $t_R$=14.3 minutes. Mass Spectrum (ESI) m/z=665 [M+1].

Example 266

2-((2R,5R,6R)-4-((S)-1-(tert-butylsulfonyl)-4,4,4-trifluorobutan-2-yl)-6-(3-chlorophenyl)-5-(4-chlorophenyl)-3-oxomorpholin-2-yl)acetic acid or 2-((2S,5R,6R)-4-((S)-1-(tert-butylsulfonyl)-4,4,4-trifluorobutan-2-yl)-6-(3-chlorophenyl)-5-(4-chlorophenyl)-3-oxomorpholin-2-yl)acetic acid

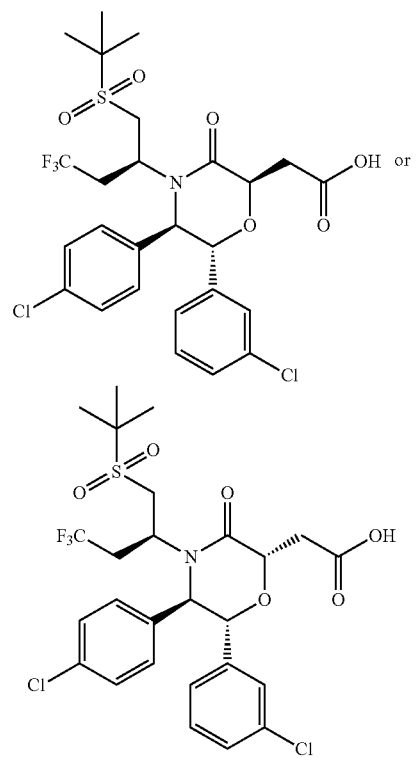

Step A. (1R,2R)-2-(((S)-1-(tert-Butylthio)-4,4,4-trifluorobutan-2-yl)amino)-1-(3-chlorophenyl)-2-(4-chlorophenyl)ethanol

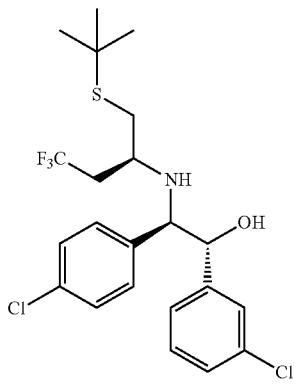 [SMILES: CC(C)(C)SC[C@H](CC(F)(F)F)N[C@H](c1ccc(Cl)cc1)[C@H](O)c1cccc(Cl)c1]

The title compound was obtained from Intermediate A2 following procedures similar to those described in Example 162, Steps A through E, replacing (R)-(+)-1,2-epoxybutane in Step B with 1,1,1-trifluoro-3,4-epoxybutane (TCI America, Portland, Oreg.). The crude residue was purified by flash chromatography on silica gel (330 g column, gradient elution of 0% to 20% ethyl acetate in hexanes) to provide the title compound as the first eluting isomer.

Step B. (5R,6R)-4-((S)-1-(tert-Butylthio)-4,4,4-trifluorobutan-2-yl)-6-(3-chlorophenyl)-5-(4-chlorophenyl)morpholin-3-one

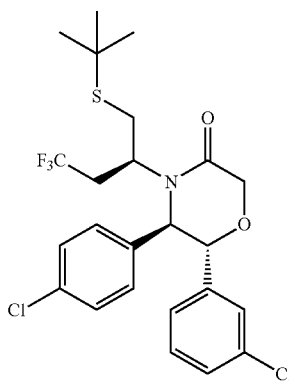

The title compound was obtained from (1R,2R)-2-(((S)-1-(tert-butylthio)-4,4,4-trifluorobutan-2-yl)amino)-1-(3-chlorophenyl)-2-(4-chlorophenyl)ethanol (Example 266, Step A) by procedures similar to those described in Example 162, Steps F and G. The crude residue was purified by flash chromatography on silica gel (80 g column, gradient elution of 0% to 20% ethyl acetate in hexanes) to provide the title compound.

Step C. (2R,5R,6R)-2-Allyl-4-((S)-1-(tert-butylthio)-4,4,4-trifluorobutan-2-yl)-6-(3-chlorophenyl)-5-(4-chlorophenyl)morpholin-3-one or (2S,5R,6R)-2-allyl-4-((S)-1-(tert-butylthio)-4,4,4-trifluorobutan-2-yl)-6-(3-chlorophenyl)-5-(4-chlorophenyl)morpholin-3-one

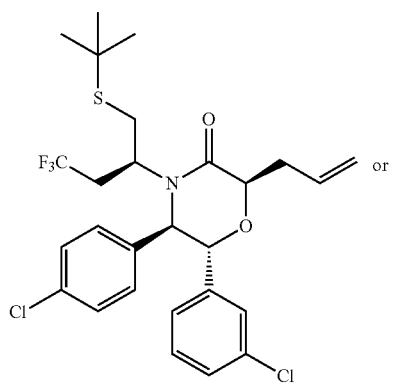 or

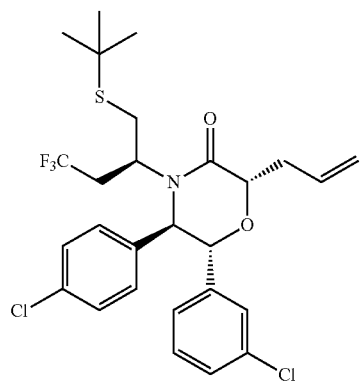

One of the title compounds was obtained from (5R,6R)-4-((S)-1-(tert-butylthio)-4,4,4-trifluorobutan-2-yl)-6-(3-chlorophenyl)-5-(4-chlorophenyl)morpholin-3-one (Example 266, Step B) by a procedure similar to that described in Step 112, Step E. The crude residue was purified by flash chromatography on silica gel (80 g column, gradient elution of 0% to 25% ethyl acetate in hexanes) to provide one of the title compounds as the first eluting isomer.

445

Step D. 2-((2R,5R,6R)-4-((S)-1-(tert-Butylsulfonyl)-4,4,4-trifluorobutan-2-yl)-6-(3-chlorophenyl)-5-(4-chlorophenyl)-3-oxomorpholin-2-yl)acetic acid or 2-((2S,5R,6R)-4-((S)-1-(tert-butylsulfonyl)-4,4,4-trifluorobutan-2-yl)-6-(3-chlorophenyl)-5-(4-chlorophenyl)-3-oxomorpholin-2-yl)acetic acid

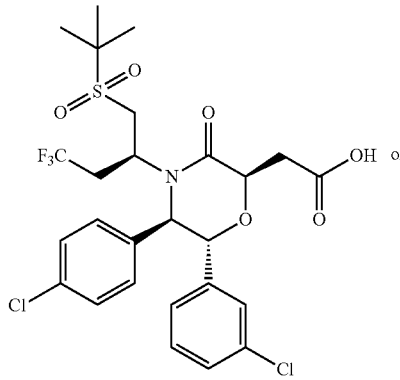

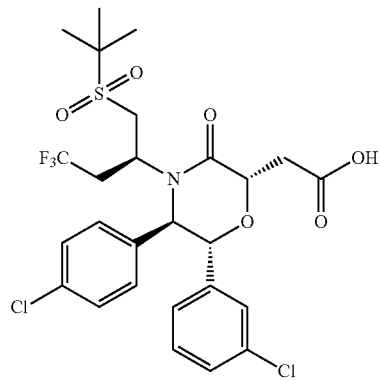

One of the title compounds was obtained from (2R,5R,6R)-2-allyl-4-((S)-1-(tert-butylthio)-4,4,4-trifluorobutan-2-yl)-6-(3-chlorophenyl)-5-(4-chlorophenyl)morpholin-3-one or (2S,5R,6R)-2-allyl-4-((S)-1-(tert-butylthio)-4,4,4-trifluorobutan-2-yl)-6-(3-chlorophenyl)-5-(4-chlorophenyl)morpholin-3-one (Example 266, Step C) by a procedure similar to that described in Step 112, Step F. The crude residue was purified by flash chromatography on silica gel (40 g column, gradient elution of 0% to 10% MeOH in dichloromethane) to provide one of the title compounds. $^1$H NMR (400 MHz, CDCl$_3$, δ ppm): 7.31-7.36 (m, 2H), 7.25-7.30 (m, 2H), 7.20-7.24 (m, 2H), 7.13 (t, J=8.12 Hz, 1H), 6.88-7.04 (m, 1H), 5.18 (d, J=7.83 Hz, 1H), 5.04 (d, J=7.83 Hz, 1H), 4.82 (dd, J=6.85, 4.11 Hz, 1H), 4.05-4.19 (m, 1H), 3.81-3.94 (m, 1H), 3.22 (dd, J=16.92, 6.94 Hz, 2H), 2.92-3.14 (m, 2H), 2.26-2.42 (m, 1H), 1.36-1.51 (m, 9H). MS (ESI) m/z=610 [M+1].

446

Example 267

2-((2R,5R,6R)-4-((S)-1-(tert-Butylsulfonyl)-4,4,4-trifluorobutan-2-yl)-6-(3-chlorophenyl)-5-(4-chlorophenyl)-3-oxomorpholin-2-yl)acetic acid or 2-((2S,5R,6R)-4-((S)-1-(tert-butylsulfonyl)-4,4,4-trifluorobutan-2-yl)-6-(3-chlorophenyl)-5-(4-chlorophenyl)-3-oxomorpholin-2-yl)acetic acid

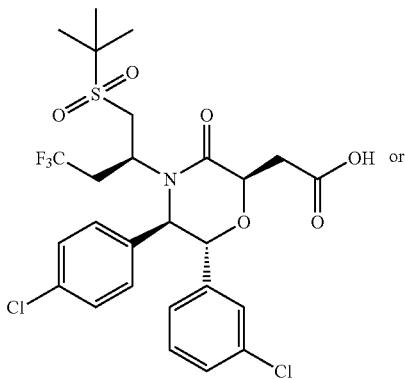

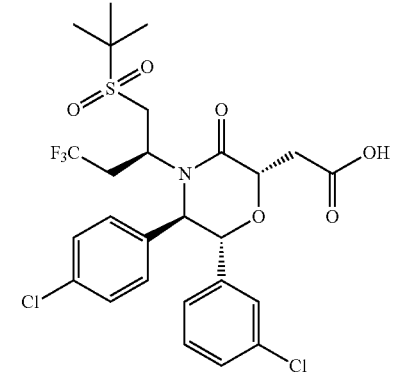

Step A. (2R,5R,6R)-2-Allyl-4-((S)-1-(tert-butylthio)-4,4,4-trifluorobutan-2-yl)-6-(3-chlorophenyl)-5-(4-chlorophenyl)morpholin-3-one or (2S,5R,6R)-2-allyl-4-((S)-1-(tert-butylthio)-4,4,4-trifluorobutan-2-yl)-6-(3-chlorophenyl)-5-(4-chlorophenyl)morpholin-3-one

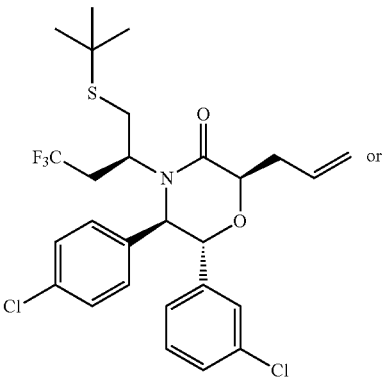

-continued

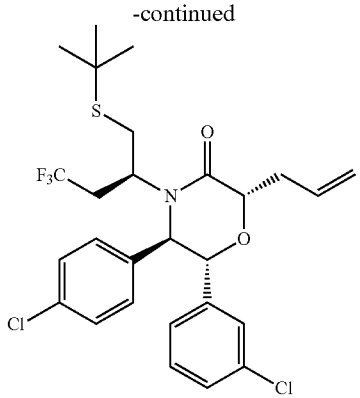

Further elution of the chromatography column described in Example 266, Step C provided one of the title compounds as the second (slower) eluting isomer.

Step B. 2-((2R,5R,6R)-4-((S)-1-(tert-Butylsulfonyl)-4,4,4-trifluorobutan-2-yl)-6-(3-chlorophenyl)-5-(4-chlorophenyl)-3-oxomorpholin-2-yl)acetic acid or 2-((2S,5R,6R)-4-((S)-1-(tert-butylsulfonyl)-4,4,4-trifluorobutan-2-yl)-6-(3-chlorophenyl)-5-(4-chlorophenyl)-3-oxomorpholin-2-yl)acetic acid One of the title compounds was obtained from (2R,5R,6R)-2-allyl-4-((S)-1-(tert-butylthio)-4,4,4-trifluorobutan-2-yl)-6-(3-chlorophenyl)-5-(4-chlorophenyl)morpholin-3-one or (2S,5R,6R)-2-allyl-4-((S)-1-(tert-butylthio)-4,4,4-trifluorobutan-2-yl)-6-(3-chlorophenyl)-5-(4-chlorophenyl)morpholin-3-one (Example 267, Step A) by a procedure similar to that described in Example 112, Step F. The crude residue was purified by preparative TLC (eluent: 5% MeOH in dichloromethane) to provide one of the title compounds. $^1$H NMR (400 MHz, CDCl$_3$, δ ppm): 7.33 (dd, J=8.71, 0.49 Hz, 2H), 7.01-7.25 (m, 5H), 6.77-6.94 (m, 1H), 5.14 (s, 1H), 4.75-4.86 (m, 1H), 4.66-4.73 (m, 1H), 3.97-4.15 (m, 1H), 3.69-3.91 (m, 1H), 3.10-3.29 (m, 2H), 2.85-3.10 (m, 2H), 2.21-2.42 (m, 1H), 1.42 (s, 9H). MS (ESI) m/z=610 [M+1].

Example 268

2-((2R,5R,6R)-4-((R)-1-(tert-Butylsulfonyl)-4,4,4-trifluorobutan-2-yl)-6-(3-chlorophenyl)-5-(4-chlorophenyl)-3-oxomorpholin-2-yl)acetic acid or 2-((2S,5R,6R)-4-((R)-1-(tert-butylsulfonyl)-4,4,4-trifluorobutan-2-yl)-6-(3-chlorophenyl)-5-(4-chlorophenyl)-3-oxomorpholin-2-yl)acetic acid

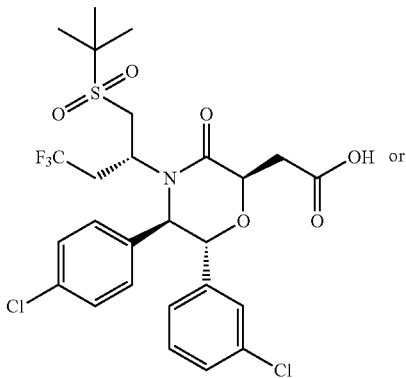

-continued

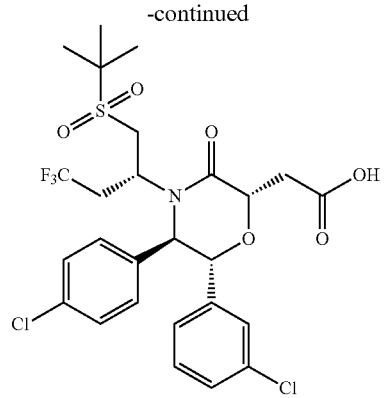

Step A. (5R,6R)-4-((R)-1-(tert-Butylthio)-4,4,4-trifluorobutan-2-yl)-6-(3-chlorophenyl)-5-(4-chlorophenyl)morpholin-3-one The title compound was obtained from a mixture of (1R,2R)-2-(((S)-1-(tert-butylthio)-4,4,4-trifluorobutan-2-yl)amino)-1-(3-chlorophenyl)-2-(4-chlorophenyl)ethanol and (1R,2R)-2-(((R)-1-(tert-butylthio)-4,4,4-trifluorobutan-2-yl)amino)-1-(3-chlorophenyl)-2-(4-chlorophenyl)ethanol (Example 266, Step A before chromatographic separation) by procedures similar to those described in Example 162, Steps F and G. The crude residue was purified by chiral SFC (250× 30 mm Chiralpak® AD column (Chiral Technologies, Inc., West Chester, Pa., USA), two columns in series, with 25 g/min MeOH+20 mM NH$_3$+75 g/min CO$_2$ on a Thar 200 SFC (Thar Technologies, Inc., Pittsburg, Pa.)) to give the title compound as the second (slower) eluting isomer.

449

Step B. (2R,5R,6R)-2-Allyl-4-((R)-1-(tert-butylthio)-4,4,4-trifluorobutan-2-yl)-6-(3-chlorophenyl)-5-(4-chlorophenyl)morpholin-3-one or (2S,5R,6R)-2-allyl-4-((R)-1-(tert-butylthio)-4,4,4-trifluorobutan-2-yl)-6-(3-chlorophenyl)-5-(4-chlorophenyl)morpholin-3-one

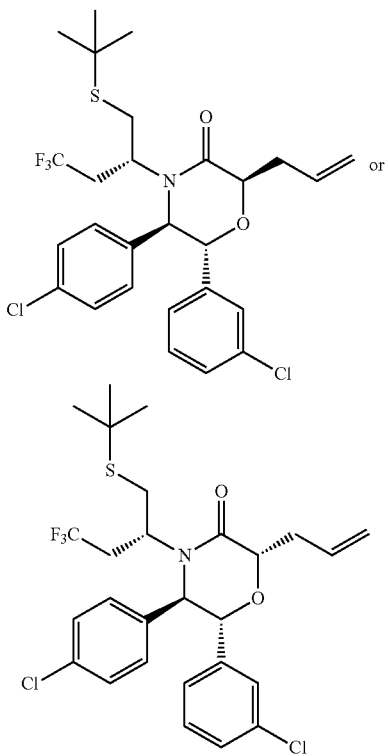

One of the title compounds was obtained from (5R,6R)-4-((R)-1-(tert-butylthio)-4,4,4-trifluorobutan-2-yl)-6-(3-chlorophenyl)-5-(4-chlorophenyl)morpholin-3-one (Example 268, Step A) by a procedure similar to that described in Step 112, Step E. The crude residue was purified by flash chromatography on silica gel (24 g column, gradient elution of 0% to 25% ethyl acetate in hexanes) to provide one of the title compounds as the first eluting isomer.

Step C. 2-((2R,5R,6R)-4-((R)-1-(tert-Butylsulfonyl)-4,4,4-trifluorobutan-2-yl)-6-(3-chlorophenyl)-5-(4-chlorophenyl)-3-oxomorpholin-2-yl)acetic acid or 2-((2S,5R,6R)-4-((R)-1-(tert-butylsulfonyl)-4,4,4-trifluorobutan-2-yl)-6-(3-chlorophenyl)-5-(4-chlorophenyl)-3-oxomorpholin-2-yl)acetic acid

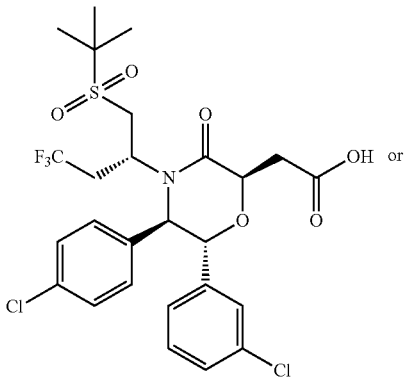

450

-continued

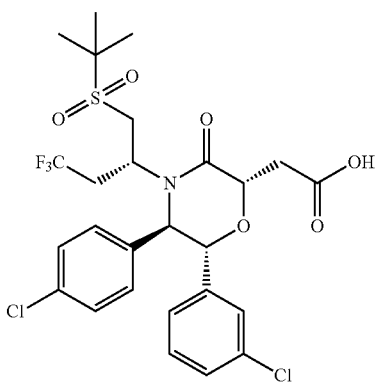

One of the title compounds was obtained from (2R,5R,6R)-2-allyl-4-((R)-1-(tert-butylthio)-4,4,4-trifluorobutan-2-yl)-6-(3-chlorophenyl)-5-(4-chlorophenyl)morpholin-3-one or (2S,5R,6R)-2-allyl-4-((R)-1-(tert-butylthio)-4,4,4-trifluorobutan-2-yl)-6-(3-chlorophenyl)-5-(4-chlorophenyl)morpholin-3-one (Example 268, Step B) by a procedure similar to that described in Step 112, Step F. The crude residue was purified by flash chromatography on silica gel (12 g column, gradient elution of 0% to 10% MeOH in dichloromethane) to provide one of the title compounds. $^1$H NMR (400 MHz, CDCl$_3$, δ ppm): 7.36 (d, J=8.61 Hz, 2H), 7.15-7.28 (m, 5H), 6.91 (d, J=7.82 Hz, 1H), 5.00 (d, J=7.24 Hz, 1H), 4.78-4.81 (m, 1H), 4.68 (d, J=7.24 Hz, 1H), 3.89-4.01 (m, 1H), 3.74-3.89 (m, 1H), 3.27-3.46 (m, 1H), 3.20 (d, J=7.24 Hz, 1H), 3.09 (d, J=4.11 Hz, 1H), 2.82-2.93 (m, 1H), 2.66-2.82 (m, 1H), 1.23 (s, 9H). MS (ESI) m/z=610 [M+1].

Example 269

2-((2R,5R,6R)-4-((R)-1-(tert-Butylsulfonyl)-4,4,4-trifluorobutan-2-yl)-6-(3-chlorophenyl)-5-(4-chlorophenyl)-3-oxomorpholin-2-yl)acetic acid or 2-((2S,5R,6R)-4-((R)-1-(tert-butylsulfonyl)-4,4,4-trifluorobutan-2-yl)-6-(3-chlorophenyl)-5-(4-chlorophenyl)-3-oxomorpholin-2-yl)acetic acid

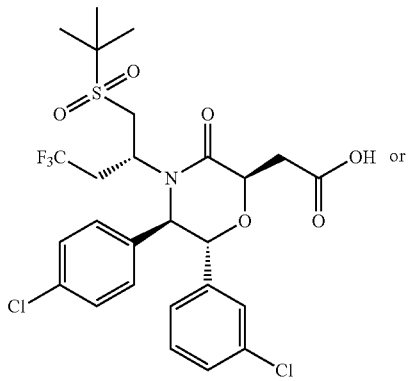

451
-continued

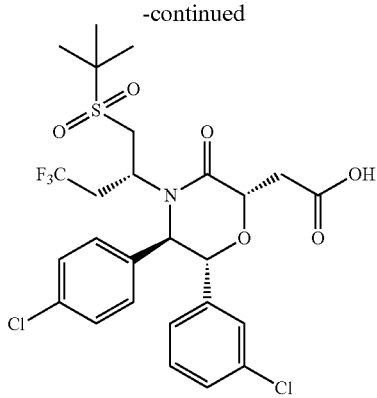

Step A. (2R,5R,6R)-2-Allyl-4-((R)-1-(tert-butylthio)-4,4,4-trifluorobutan-2-yl)-6-(3-chlorophenyl)-5-(4-chlorophenyl)morpholin-3-one or (2S,5R,6R)-2-allyl-4-((R)-1-(tert-butylthio)-4,4,4-trifluorobutan-2-yl)-6-(3-chlorophenyl)-5-(4-chlorophenyl)morpholin-3-one

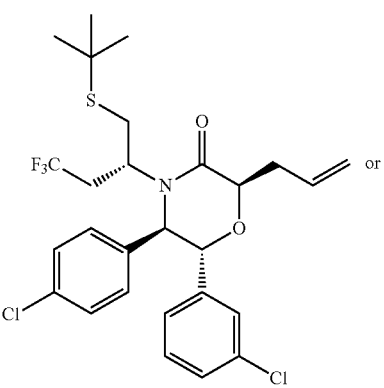

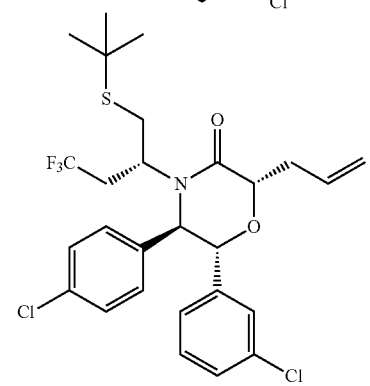

Further elution of the chromatographic separation described in Example 268, Step B provided one of the title compounds as the second (slower) eluting isomer.

452

Step B. 2-((2R,5R,6R)-4-((R)-1-(tert-Butylsulfonyl)-4,4,4-trifluorobutan-2-yl)-6-(3-chlorophenyl)-5-(4-chlorophenyl)-3-oxomorpholin-2-yl)acetic acid or 2-((2S,5R,6R)-4-((R)-1-(tert-butylsulfonyl)-4,4,4-trifluorobutan-2-yl)-6-(3-chlorophenyl)-5-(4-chlorophenyl)-3-oxomorpholin-2-yl)acetic acid

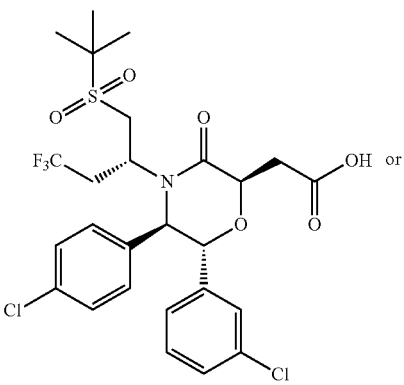

One of the title compounds was obtained from (2R,5R,6R)-2-allyl-4-((R)-1-(tert-butylthio)-4,4,4-trifluorobutan-2-yl)-6-(3-chlorophenyl)-5-(4-chlorophenyl)morpholin-3-one or (2S,5R,6R)-2-allyl-4-((R)-1-(tert-butylthio)-4,4,4-trifluorobutan-2-yl)-6-(3-chlorophenyl)-5-(4-chlorophenyl)morpholin-3-one (Example 269, Step A) by a procedure similar to that described in Step 112, Step F. The crude residue was purified by preparative TLC (eluent: 5% MeOH in dichloromethane) to provide one of the title compounds. $^1$H NMR (400 MHz, CDCl$_3$, δ ppm): 7.17-7.45 (m, 3H), 7.04 (d, J=1.96 Hz, 4H), 6.65-6.79 (m, 1H), 4.76-4.92 (m, 1H), 4.66-4.76 (m, 1H), 4.47-4.64 (m, 1H), 3.65-4.06 (m, 2H), 3.23-3.46 (m, 1H), 3.05-3.23 (m, 1H), 2.64-2.92 (m, 3H), 1.20 (s, 9H). MS (ESI) m/z=610 [M+1].

Example 270

2-((2R,5R,6R)-4-((S)-2-(tert-Butylsulfonyl)-1-cyclobutylethyl)-6-(3-chlorophenyl)-5-(4-chlorophenyl)-3-oxomorpholin-2-yl)acetic acid or 2-((2S,5R,6R)-4-((S)-2-(tert-butylsulfonyl)-1-cyclobutylethyl)-6-(3-chlorophenyl)-5-(4-chlorophenyl)-3-oxomorpholin-2-yl)acetic acid

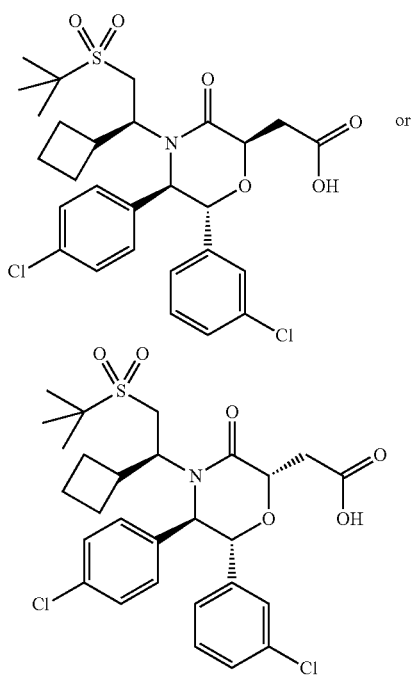

Step A. 2-((3,4-Dimethoxybenzyl)oxy)acetic acid

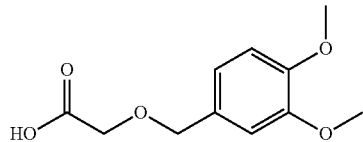 [SMILES: COc1ccc(COCC(=O)O)cc1OC]

Sodium hydride (60% dispersion in oil, 1.427 g, 35.7 mmol) was added portionwise to a solution of (3,4-dimethoxyphenyl)methanol (5.17 mL, 35.7 mmol) and bromoacetic acid (5.95 g, 42.8 mmol) in THF (71.3 mL). The mixture was stirred at room temperature overnight. The mixture was diluted with water (100 mL) and extracted with diethyl ether (3×100 mL). The combined organic layers were dried over MgSO_4, filtered, and concentrated to give the title compound. The crude residue was used without further purification.

Step B. 2-((3,4-Dimethoxybenzyl)oxy)-N-methoxy-N-methylacetamide

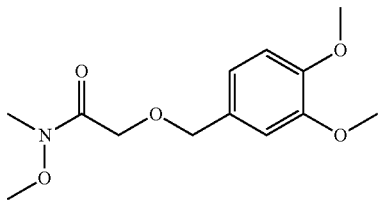

Carbonyldiimidazole (7.96 g, 49.1 mmol) was added portionwise to a solution of 2-((3,4-dimethoxybenzyl)oxy)acetic acid (7.4 g, 32.7 mmol, Example 270, Step A) in dichloromethane (65.4 mL) at 0° C. The mixture was stirred for 1 hour, then N,O-dimethylhydroxylammonium chloride (4.88 g, 49.1 mmol) was added. The mixture was warmed to room temperature and stirred at room temperature for 2 days. The mixture was poured into 100 mL 1 N HCl and washed with diethyl ether (3×100 mL). The combined organic layers were dried over MgSO_4, filtered, and concentrated. The residue was purified by flash column chromatography on silica gel (330 g column; gradient elution of 0% to 80% acetone in hexanes) to provide the title compound as a light-yellow oil.

Step C. 1-Cyclobutyl-2-((3,4-dimethoxybenzyl)oxy)ethanone

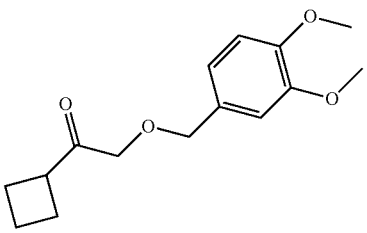 [SMILES: COc1ccc(COCC(=O)C2CCC2)cc1OC]

Bromocyclobutane (6.75 g, 50 mmol) in THF (5 mL) was added dropwise to a solution of magnesium (1.215 g, 50.0 mmol) and iodine (0.030 g, 0.117 mmol) in THF (29.2 mL) at 50° C. The mixture was stirred at 50° C. for 2 hours and cooled to room temperature. 2-((3,4-dimethoxybenzyl)oxy)-N-methoxy-N-methylacetamide (6.3 g, 23.39 mmol, Example 270, Step B) was added, and the reaction was stirred at room temperature overnight. The mixture was quenched with saturated ammonium chloride (30 mL) and extracted with diethyl ether (3×30 mL). The combined organic layers were dried over MgSO_4, filtered, and concentrated. The residue was purified by flash chromatography on silica gel (330 g, column; gradient elution of 0% to 40% acetone in hexanes) to give the title compound as light-yellow oil.

Step D. (1R,2R)-1-(3-Chlorophenyl)-2-(4-chlorophenyl)-2-(((S)-1-cyclobutyl-2-((3,4-dimethoxybenzyl)oxy)ethyl)amino)ethanol and (1R,2R)-1-(3-chlorophenyl)-2-(4-chlorophenyl)-2-((R)-1-cyclobutyl-2-((3,4-dimethoxybenzyl)oxy)ethyl)amino)ethanol

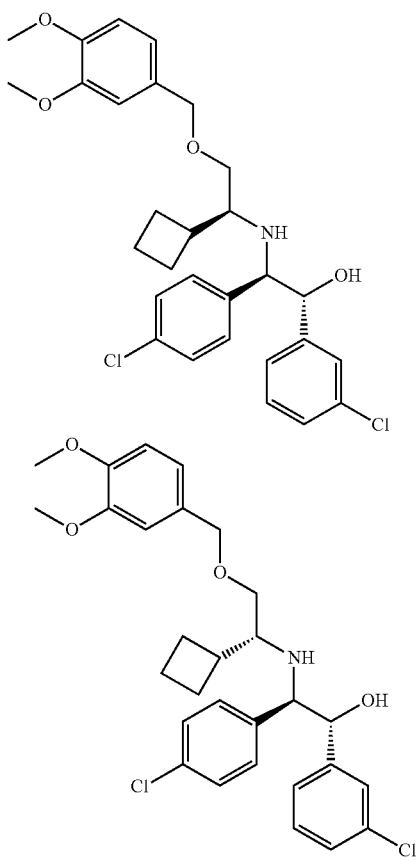

and p-Toluenesulfonic acid monohydrate (1.799 mg, 9.46 µmol) was added to a solution of (1R,2R)-2-amino-1-(3-chlorophenyl)-2-(4-chlorophenyl)ethanol (58.7 mg, 0.208 mmol, Intermediate A2) and 1-cyclobutyl-2-((3,4-dimethoxybenzyl)oxy)ethanone (50 mg, 0.189 mmol, Example 270, Step C) in toluene. The resulting solution was refluxed for 3 hours with a condenser and a Dean-Stark trap. The mixture was cooled to room temperature and concentrated. The residue was dissolved in THF and LAH (1.0 M in THF, 0.284 mL, 0.284 mmol) was added at 0° C. The mixture was warmed to room temperature and stirred for 2 hours. The mixture was quenched with saturated potassium sodium tartrate and diluted with ethyl acetate. The organic layer was collected and concentrated. The residue was purified by flash chromatography on silica gel (gradient elution of 10% to 50% ethyl acetate in hexanes) to give the title compounds as a mixture of diastereomers.

Step E. (5R,6R)-6-(3-Chlorophenyl)-5-(4-chlorophenyl)-4-((S)-1-cyclobutyl-2-((3,4-dimethoxybenzyl)oxy)ethyl)morpholin-3-one and (5R,6R)-6-(3-chlorophenyl)-5-(4-chlorophenyl)-4-((R)-1-cyclobutyl-2-((3,4-dimethoxybenzyl)oxy)ethyl)morpholin-3-one

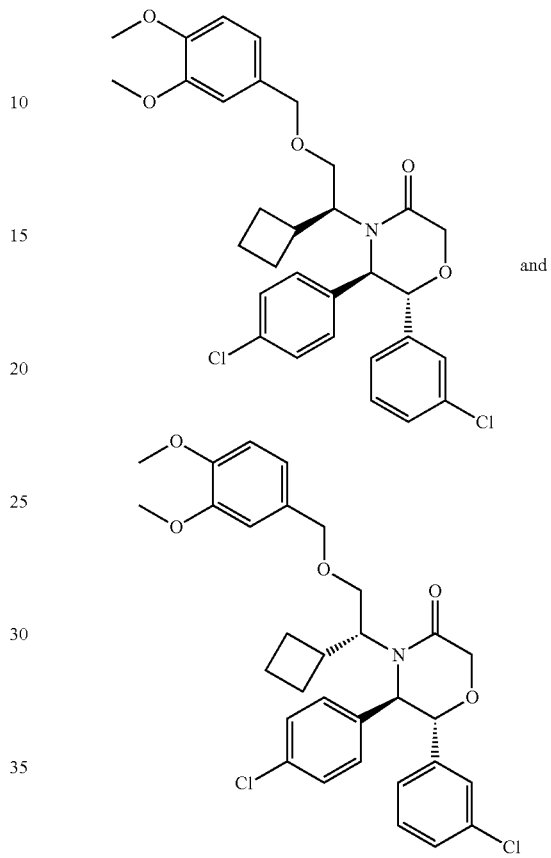

and

The title compounds were obtained from (1R,2R)-1-(3-chlorophenyl)-2-(4-chlorophenyl)-2-(((S)-1-cyclobutyl-2-((3,4-dimethoxybenzyl)oxy)ethyl)amino)ethanol and (1R,2R)-1-(3-chlorophenyl)-2-(4-chlorophenyl)-2-(((R)-1-cyclobutyl-2-((3,4-dimethoxybenzyl)oxy)ethyl)amino)ethanol (Example 270, Step D) by procedures similar to those described in Example 162, Steps F and G.

Step F. (5R,6R)-6-(3-Chlorophenyl)-5-(4-chlorophenyl)-4-((S)-1-cyclobutyl-2-hydroxyethyl)morpholin-3-one

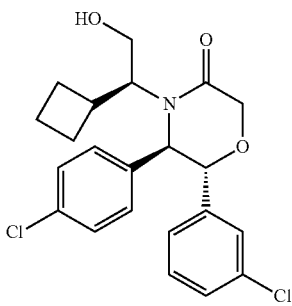 [SMILES: O=C1CO[C@H](c2cccc(Cl)c2)[C@@H](c2ccc(Cl)cc2)N1[C@H](CO)C1CCC1]

The title compound was obtained from (5R,6R)-6-(3-chlorophenyl)-5-(4-chlorophenyl)-4-((S)-1-cyclobutyl-2-((3,4-dimethoxybenzyl)oxy)ethyl)morpholin-3-one and (5R,6R)-

6-(3-chlorophenyl)-5-(4-chlorophenyl)-4-((R)-1-cyclobutyl-2-((3,4-dimethoxybenzyl)oxy)ethyl)morpholin-3-one (Example 270, Step E) by a procedure similar to that described in Example 112, Step C. The residue was purified by flash chromatography on silica gel (330 g column; gradient elution of 0% to 15% then 15% to 50% acetone in hexanes) to give the title compound as the second (slower) eluting isomer as an off-white solid.

Step G. 2-((2R,5R,6R)-4-((S)-2-(tert-Butylsulfonyl)-1-cyclobutylethyl)-6-(3-chlorophenyl)-5-(4-chlorophenyl)-3-oxomorpholin-2-yl)acetic acid or 2-((2S,5R,6R)-4-((S)-2-(tert-butylsulfonyl)-1-cyclobutylethyl)-6-(3-chlorophenyl)-5-(4-chlorophenyl)-3-oxomorpholin-2-yl)acetic acid

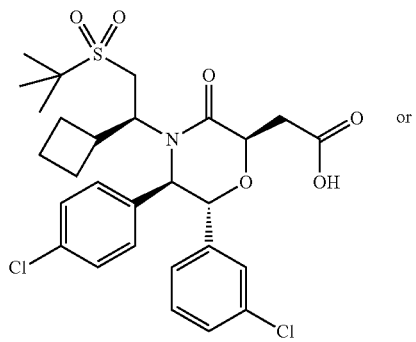

One of the title compounds was prepared from (5R,6R)-6-(3-chlorophenyl)-5-(4-chlorophenyl)-4-((S)-1-cyclobutyl-2-hydroxyethyl)morpholin-3-one (Example 270, Step F) by procedures analogous to those described in Example 112, Steps D though F, replacing ethanethiol in Step D with 2-me-thyl-2-propanethiol. The residue was purified by reverse phase preparatory HPLC (Agilient 1100, column: Gemini® 5 μm $C_{18}$, 100 mm×30 mm (Phenomenex, Torrance, Calif.), gradient elution of 25% to 75% acetonitrile in water, where both solvents contain 0.1% TFA, 30 minutes) to give one of the title compounds as the first (faster) eluting isomer. $^1$H NMR (400 MHz, CDCl$_3$, δ ppm): 10.94 (br. s., 1H), 7.29-7.49 (m, 5H), 7.03-7.27 (m, 3H), 5.20-5.29 (m, 1H), 5.03 (d, J=5.67 Hz, 1H), 4.46-4.86 (m, 1H), 3.72-3.92 (m, 1H), 3.46-3.61 (m, 1H), 2.89-3.28 (m, 5H), 1.85 (d, J=12.91 Hz, 1H), 1.55-1.69 (m, 3H), 1.38-1.53 (m, 9H), 0.74 (br. s., 1H). MS (ESI) m/z=582 [M+1].

Example 271

2-((2R,5R,6R)-4-((S)-2-(tert-Butylsulfonyl)-1-cyclobutylethyl)-6-(3-chlorophenyl)-5-(4-chlorophenyl)-3-oxomorpholin-2-yl)acetic acid or 2-((2S,5R,6R)-4-((S)-2-(tert-butylsulfonyl)-1-cyclobutylethyl)-6-(3-chlorophenyl)-5-(4-chlorophenyl)-3-oxomorpholin-2-yl)acetic acid

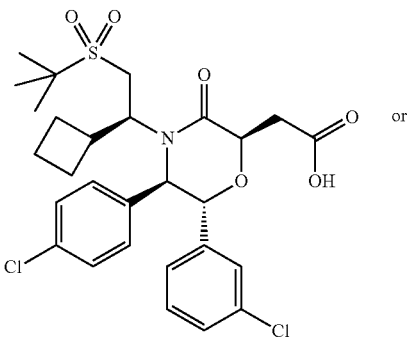

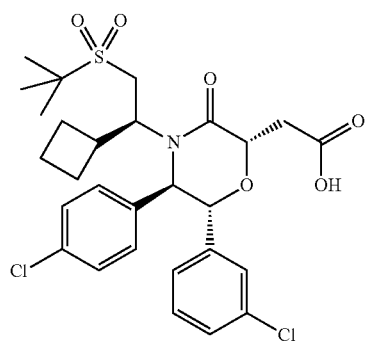

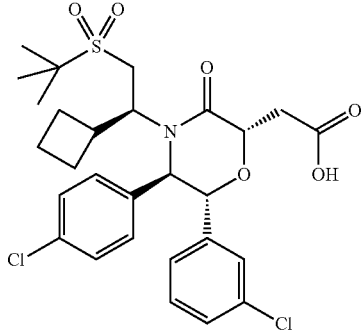

Further elution of the HPLC separation described in Example 270, Step G provided the title compound as the second (slower) eluting isomer. $^1$H NMR (400 MHz, CDCl$_3$, δ ppm): 10.79 (br. s., 1H), 7.24 (d, J=8.41 Hz, 2H), 7.10 (d, J=5.28 Hz, 3H), 6.96-7.07 (m, 2H), 6.79 (d, J=7.43 Hz, 1H), 5.05 (d, J=9.78 Hz, 1H), 4.64-4.78 (m, 2H), 3.75-3.89 (m, 1H), 3.36 (t, J=8.51 Hz, 1H), 3.00-3.20 (m, 2H), 2.92 (dd, J=16.63, 5.28 Hz, 1H), 2.78 (d, J=13.11 Hz, 1H), 1.68-1.83 (m, 1H), 1.46-1.64 (m, 2H), 1.36 (s, 11H), 0.63-0.88 (m, 1H). MS (ESI) m/z=582 [M+1].

Example 272

2-((2R,5R,6R)-4-((R)-2-(tert-Butylsulfonyl)-1-cyclobutylethyl)-6-(3-chlorophenyl)-5-(4-chlorophenyl)-3-oxomorpholin-2-yl)acetic acid or 2-((2S,5R,6R)-4-((R)-2-(tert-butylsulfonyl)-1-cyclobutylethyl)-6-(3-chlorophenyl)-5-(4-chlorophenyl)-3-oxomorpholin-2-yl)acetic acid

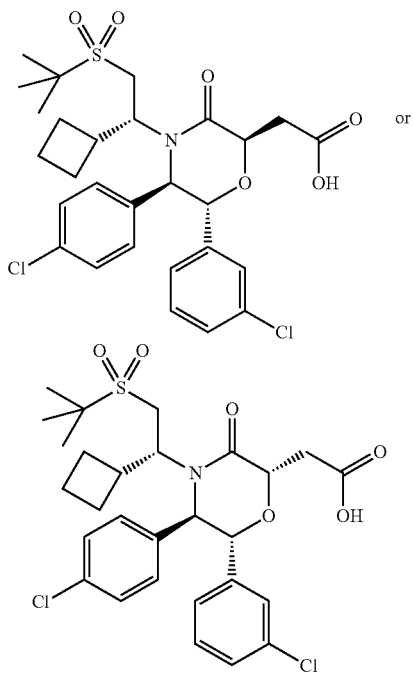

Step A. (5R,6R)-6-(3-Chlorophenyl)-5-(4-chlorophenyl)-4-((R)-1-cyclobutyl-2-hydroxyethyl)morpholin-3-one

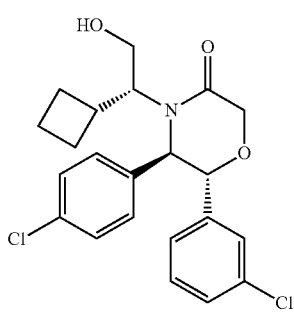 [SMILES: O=C1CO[C@H](c2cccc(Cl)c2)[C@@H](c2ccc(Cl)cc2)N1[C@@H](CO)C1CCC1]

The title compound was isolated as the first (faster) eluting isomer from the chromatographic separation described in Example 270, Step F.

Step B. 2-((2R,5R,6R)-4-((R)-2-(tert-Butylsulfonyl)-1-cyclobutylethyl)-6-(3-chlorophenyl)-5-(4-chlorophenyl)-3-oxomorpholin-2-yl)acetic acid or 2-((2S,5R,6R)-4-((R)-2-(tert-butylsulfonyl)-1-cyclobutylethyl)-6-(3-chlorophenyl)-5-(4-chlorophenyl)-3-oxomorpholin-2-yl)acetic acid

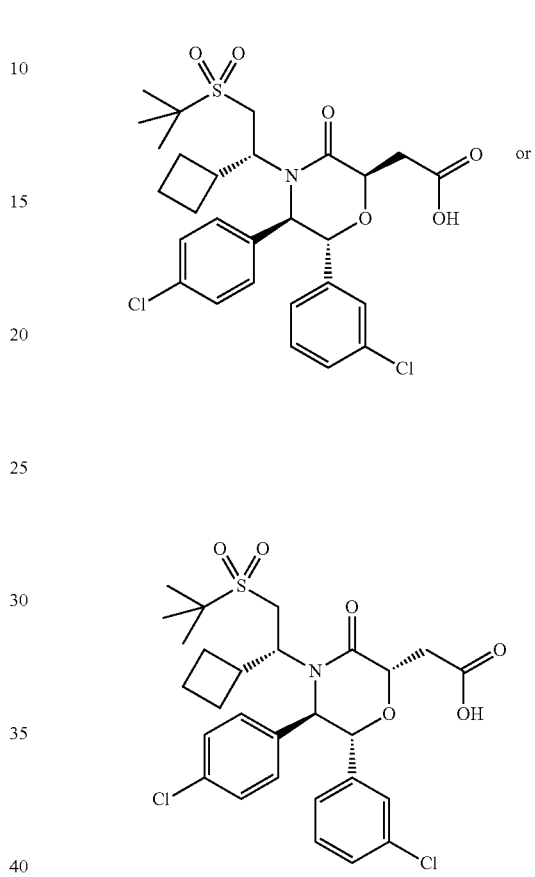

One of the title compounds was prepared from (5R,6R)-6-(3-chlorophenyl)-5-(4-chlorophenyl)-4-((R)-1-cyclobutyl-2-hydroxyethyl)morpholin-3-one (Example 272, Step A) by procedures analogous to those described in Example 112, Steps D though F, replacing ethanethiol in Step D with 2-methyl-2-propanethiol. The residue was purified by reverse phase preparatory HPLC (Agilient 1100, column: Gemini® 5 µm $C_{18}$, 100 mm×30 mm (Phenomenex, Torrance, Calif.), gradient elution of 25% to 75% acetonitrile in water, where both solvents contain 0.1% TFA, 30 minutes) to give one of the title compounds as the first (faster) eluting isomer. $^1$H NMR (400 MHz, $CDCl_3$, δ ppm): 9.02 (br. s., 1H), 7.30-7.36 (m, 2H), 7.18-7.26 (m, 4H), 7.15 (t, J=7.83 Hz, 1H), 6.99 (d, J=0.39 Hz, 1H), 6.91 (dt, J=7.83, 1.47 Hz, 1H), 4.91 (d, J=6.85 Hz, 1H), 4.82 (dd, J=6.94, 5.18 Hz, 1H), 4.72 (d, J=6.85 Hz, 1H), 3.88 (br. s., 1H), 3.45-3.53 (m, 1H), 3.07-3.21 (m, 3H), 2.90 (br. s., 1H), 1.69-2.12 (m, 6H), 1.27 (s, 9H). MS (ESI) m/z=582 [M+1].

Example 273

2-((2R,5R,6R)-4-((R)-2-(tert-Butylsulfonyl)-1-cyclobutylethyl)-6-(3-chlorophenyl)-5-(4-chlorophenyl)-3-oxomorpholin-2-yl)acetic acid or 2-((2S,5R,6R)-4-((R)-2-(tert-butylsulfonyl)-1-cyclobutylethyl)-6-(3-chlorophenyl)-5-(4-chlorophenyl)-3-oxomorpholin-2-yl)acetic acid

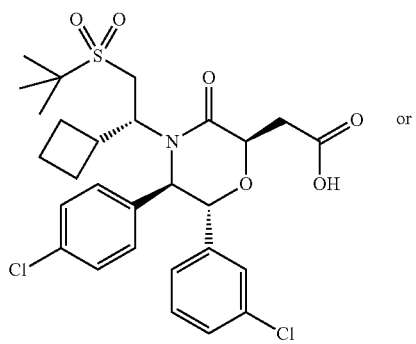

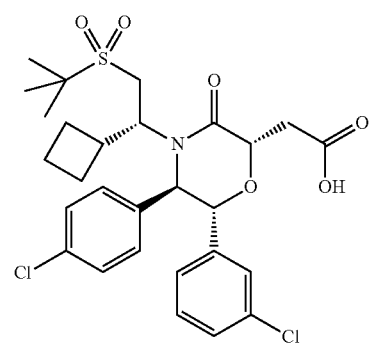

Further elution of the HPLC purification described in Example 272, Step B provided one of the title compounds as the second (slower) eluting isomer. $^1$H NMR (400 MHz, CDCl$_3$, δ ppm): 8.83 (br. s., 1H), 7.29-7.34 (m, 2H), 7.20-7.24 (m, 1H), 7.02-7.13 (m, 3H), 6.99 (d, J=0.59 Hz, 1H), 6.72 (d, J=7.63 Hz, 1H), 4.79 (t, J=4.89 Hz, 1H), 4.71 (br. s., 2H), 3.04-3.24 (m, 4H), 2.08 (br. s., 1H), 1.60-1.95 (m, 6H), 1.28-1.36 (m, 10H). MS (ESI) m/z=582 [M+1].

Example 274

2-((2R,5R,6R)-6-(3-Chlorophenyl)-5-(4-chlorophenyl)-3-oxo-4-((R)-1,1,1-trifluoro-3-(N-(2-fluorophenyl)cyclopropanesulfonamido)propan-2-yl)morpholin-2-yl)acetic acid and 2-((2S,5R,6R)-6-(3-chlorophenyl)-5-(4-chlorophenyl)-3-oxo-4-((R)-1,1,1-trifluoro-3-(N-(2-fluorophenyl)cyclopropanesulfonamido)propan-2-yl)morpholin-2-yl)acetic acid or 2-((2R,5R,6R)-6-(3-chlorophenyl)-5-(4-chlorophenyl)-3-oxo-4-((S)-1,1,1-trifluoro-3-(N-(2-fluorophenyl)cyclopropanesulfonamido)propan-2-yl)morpholin-2-yl)acetic acid and 2-((2S,5R,6R)-6-(3-chlorophenyl)-5-(4-chlorophenyl)-3-oxo-4-((S)-1,1,1-trifluoro-3-(N-(2-fluorophenyl)cyclopropanesulfonamido)propan-2-yl)morpholin-2-yl)acetic acid

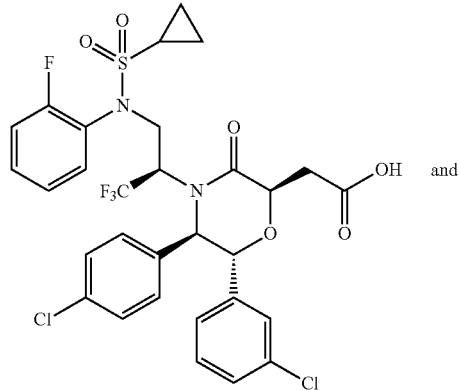

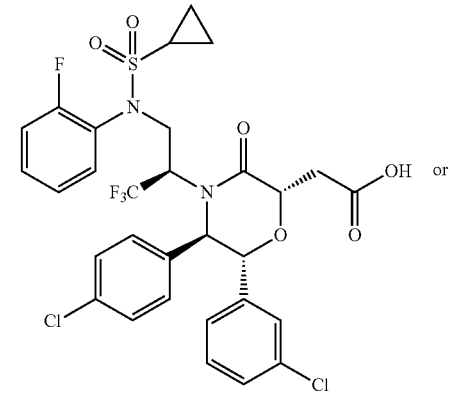

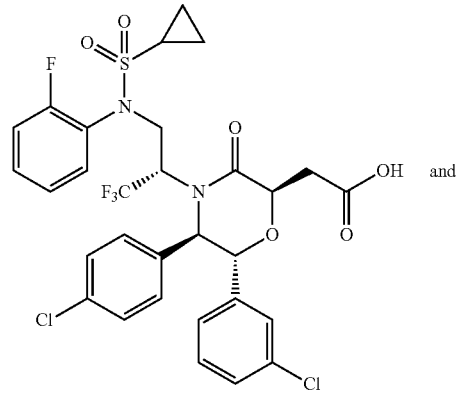

-continued

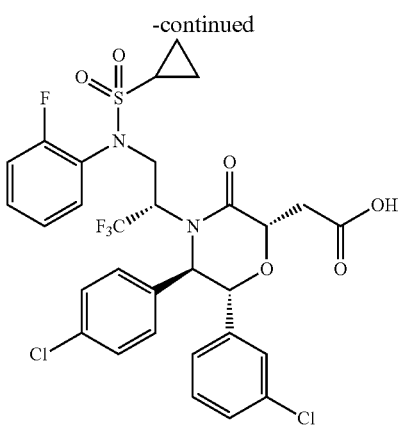

Step A. (7)-Ethyl 2-(((1R,2R)-2-((tert-butyldimethyl-silyl)oxy)-2-(3-chlorophenyl)-1-(4-chlorophenyl)ethyl)imino)-3,3,3-trifluoropropanoate

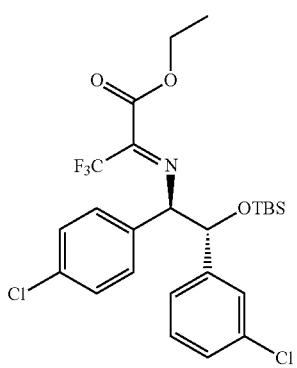 [SMILES: CCOC(=O)/C(=N/[C@H](c1ccc(Cl)cc1)[C@H](O[Si](C)(C)C(C)(C)C)c1cccc(Cl)c1)C(F)(F)F]

(1R,2R)-2-((tert-Butyldimethylsilyl)oxy)-2-(3-chlorophenyl)-1-(4-chlorophenyl)ethanamine (1.0 g, 2.52 mmol, prepared from Intermediate A2 following a procedure similar to the one described in Example 162, Step A) was added to a solution of ethyl 3,3,3-trifluoropyruvate (0.401 mL, 3.03 mmol) in toluene (25.2 mL) at room temperature. Pyridinium p-toluenesulfonate (0.063 g, 0.252 mmol) was added, and the mixture was heated to reflux with a Dean Stark apparatus for 20 hours. The mixture was concentrated and the residue was purified by flash chromatography on silica gel (120 g column; gradient elution of 0% to 30% acetone in hexanes) to give the title compound as a light-yellow oil.

Step B. (R)-2-(((1R,2R)-2-(3-Chlorophenyl)-1-(4-chlorophenyl)-2-hydroxyethyl)amino)-3,3,3-trifluoropropan-1-ol and (S)-2-(((1R,2R)-2-(3-chlorophenyl)-1-(4-chlorophenyl)-2-hydroxyethyl)amino)-3,3,3-trifluoropropan-1-ol

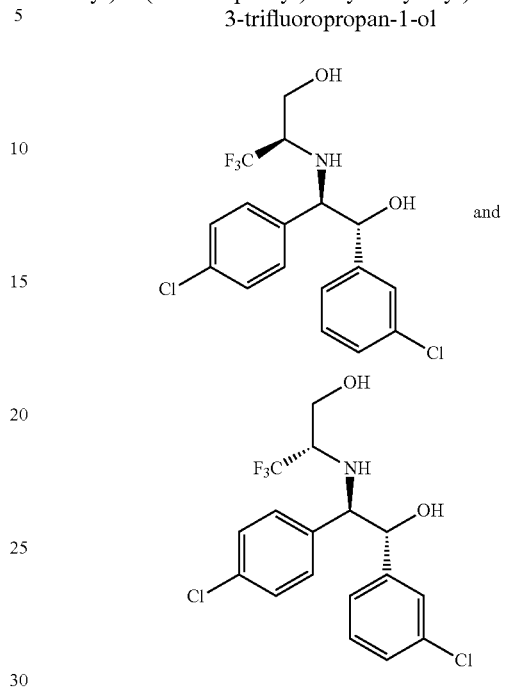

Lithium aluminum hydride (2.79 mL, 2.79 mmol) was added to a solution of (Z)-ethyl 2-(((1R,2R)-2-((tert-butyldimethylsilyl)oxy)-2-(3-chlorophenyl)-1-(4-chlorophenyl)ethyl)imino)-3,3,3-trifluoropropanoate (1.02 g, 1.860 mmol, Example 274, Step A) in diethyl ether (3.72 mL) at 0° C. The mixture was warmed to room temperature and stirred at room temperature for 1 hour. Water (2 mL) and 15% aqueous NaOH (1 mL) were added, and the mixture was stirred at room temperature for 20 minutes. The precipitate was filtered and washed with diethyl ether. The filtrate was concentrated, and the residue was purified by flash chromatography on silica gel (120 g column; gradient elution of 0% to 60% acetone in hexanes) to give the title compounds as a light-yellow oil.

Step C. (1R,2R)-2-(((R)-3-((tert-Butyldimethylsilyl)oxy)-1,1,1-trifluoropropan-2-yl)amino)-1-(3-chlorophenyl)-2-(4-chlorophenyl)ethanol and (1R,2R)-2-(((S)-3-((tert-butyldimethylsilyl)oxy)-1,1,1-trifluoropropan-2-yl)amino)-1-(3-chlorophenyl)-2-(4-chlorophenyl)ethanol

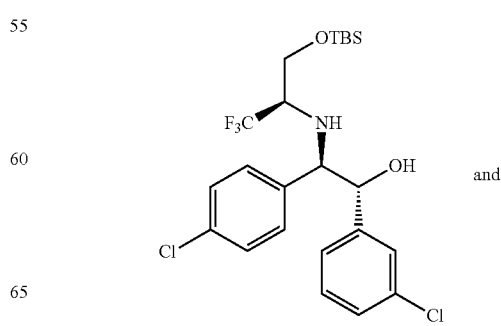

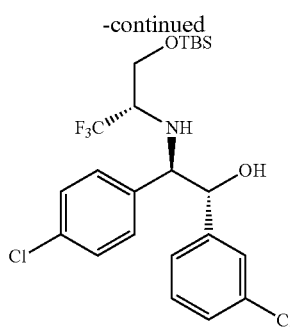

4-Dimethylaminopyridine (1.116 g, 9.13 mmol), triethylamine (1.27 mL, 9.13 mmol), and then tert-butyldimethylchlorosilane (0.674 g, 4.47 mmol) were added to a stirring solution of (R)-2-(((1R,2R)-2-(3-chlorophenyl)-1-(4-chlorophenyl)-2-hydroxyethyl)amino)-3,3,3-trifluoropropan-1-ol and (S)-2-(((1R,2R)-2-(3-chlorophenyl)-1-(4-chlorophenyl)-2-hydroxyethyl)amino)-3,3,3-trifluoropropan-1-ol (1.8 g, 4.57 mmol) in dichloromethane (22.8 ml) at 0° C. After stirring for 2 hours at 0° C., the crude mixture was diluted with saturated aqueous ammonium chloride and extracted with dichloromethane (3×). The combined organic layers were dried over magnesium sulfate, filtered and concentrated. The crude material was purified by flash chromatography on silica gel (80 g column, gradient elution of 0% to 60% acetone in hexanes) to provide the title compounds as light-yellow oil.

Step D. (5R,6R)-4-((R)-3-((tert-Butyldimethylsilyl)oxy)-1,1,1-trifluoropropan-2-yl)-6-(3-chlorophenyl)-5-(4-chlorophenyl)morpholin-3-one and (5R,6R)-4-((S)-3-((tert-butyldimethylsilyl)oxy)-1,1,1-trifluoropropan-2-yl)-6-(3-chlorophenyl)-5-(4-chlorophenyl)morpholin-3-one

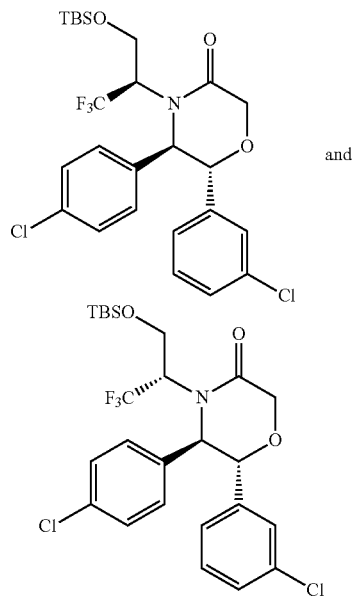

The title compounds were prepared from (1R,2R)-2-(((R)-3-((tert-butyldimethylsilyl)oxy)-1,1,1-trifluoropropan-2-yl)amino)-1-(3-chlorophenyl)-2-(4-chlorophenyl)ethanol and (1R,2R)-2-(((S)-3-((tert-butyldimethylsilyl)oxy)-1,1,1-trifluoropropan-2-yl)amino)-1-(3-chlorophenyl)-2-(4-chlorophenyl)ethanol (Example 274, Step C) by procedures analogous to those described in Example 162, Steps F and G.

Step E. (5R,6R)-6-(3-Chlorophenyl)-5-(4-chlorophenyl)-4-((R)-1,1,1-trifluoro-3-hydroxypropan-2-yl)morpholin-3-one or (5R,6R)-6-(3-chlorophenyl)-5-(4-chlorophenyl)-4-((S)-1,1,1-trifluoro-3-hydroxypropan-2-yl)morpholin-3-one

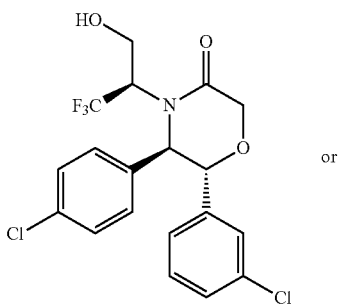

One of the title compounds was prepared from (5R,6R)-4-((R)-3-((tert-butyldimethylsilyl)oxy)-1,1,1-trifluoropropan-2-yl)-6-(3-chlorophenyl)-5-(4-chlorophenyl)morpholin-3-one and (5R,6R)-4-((S)-3-((tert-butyldimethylsilyl)oxy)-1,1,1-trifluoropropan-2-yl)-6-(3-chlorophenyl)-5-(4-chlorophenyl)morpholin-3-one (Example 274, Step D) by a procedure analogous to that described in Example 214, Step D. The residue was purified by flash chromatography on silica gel (40 g column; gradient elution of 0% to 60% acetone in hexanes) to give one of the title compounds as the first (faster) eluting isomer.

Step F. 2-((2R,5R,6R)-6-(3-Chlorophenyl)-5-(4-chlorophenyl)-3-oxo-4-((R)-1,1,1-trifluoro-3-(N-(2-fluorophenyl)cyclopropanesulfonamido)propan-2-yl)morpholin-2-yl)acetic acid and 2-((2S,5R,6R)-6-(3-chlorophenyl)-5-(4-chlorophenyl)-3-oxo-4-((R)-1,1,1-trifluoro-3-(N-(2-fluorophenyl)cyclopropanesulfonamido)propan-2-yl)morpholin-2-yl)acetic acid or 2-((2R,5R,6R)-6-(3-chlorophenyl)-5-(4-chlorophenyl)-3-oxo-4-((S)-1,1,1-trifluoro-3-(N-(2-fluorophenyl)cyclopropanesulfonamido)propan-2-yl)morpholin-2-yl)acetic acid and 2-((2S,5R,6R)-6-(3-chlorophenyl)-5-(4-chlorophenyl)-3-oxo-4-((S)-1,1,1-trifluoro-3-(N-(2-fluorophenyl)cyclopropanesulfonamido)propan-2-yl)morpholin-2-yl)acetic acid

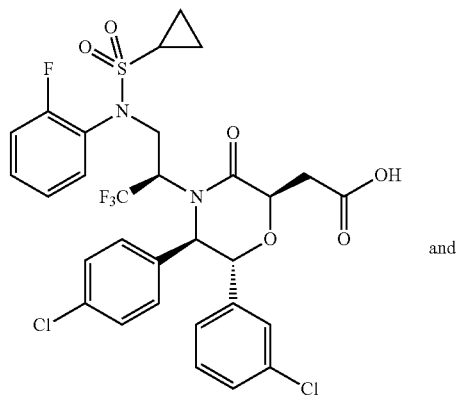

and

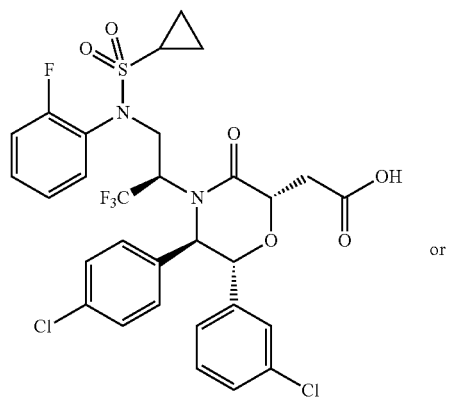

or


and

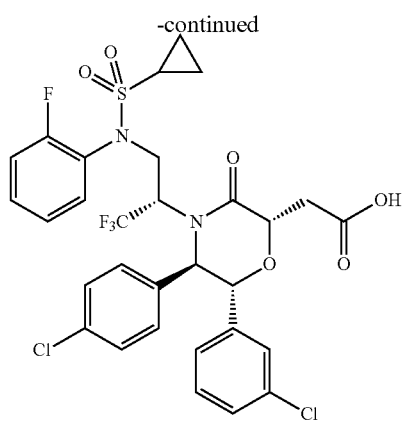

One diastereomeric pair of the title compounds was prepared from (5R,6R)-6-(3-chlorophenyl)-5-(4-chlorophenyl)-4-((R)-1,1,1-trifluoro-3-hydroxypropan-2-yl)morpholin-3-one or (5R,6R)-6-(3-chlorophenyl)-5-(4-chlorophenyl)-4-((S)-1,1,1-trifluoro-3-hydroxypropan-2-yl)morpholin-3-one (Example 274, Step E) by procedures analogous to those described in Example 112, Steps D through F, replacing ethanethiol in Step D with N-(2-fluorophenyl)cyclopropanesulfonamide (see Example 133). The residue was purified by reverse phase preparatory HPLC (Agilent 1100, column: Gemini® 5 µm $C_{18}$, 100 mm×30 mm (Phenomenex, Torrance, Calif.), gradient elution of 25% to 75% acetonitrile in water, where both solvents contain 0.1% TFA, 30 minutes) to give one pair of the title compounds as a mixture of diastereomers.

MS (ESI) m/z=689.0 [M+1].

Example 275

2-((2R,5R,6R)-6-(3-Chlorophenyl)-5-(4-chlorophenyl)-4-((S)-1-cyclopropyl-2-(N-(2,5-difluorophenyl)cyclopropanesulfonamido)ethyl)-3-oxomorpholin-2-yl)acetic acid or 2-((2S,5R,6R)-6-(3-chlorophenyl)-5-(4-chlorophenyl)-4-((S)-1-cyclopropyl-2-(N-(2,5-difluorophenyl)cyclopropanesulfonamido)ethyl)-3-oxomorpholin-2-yl)acetic acid

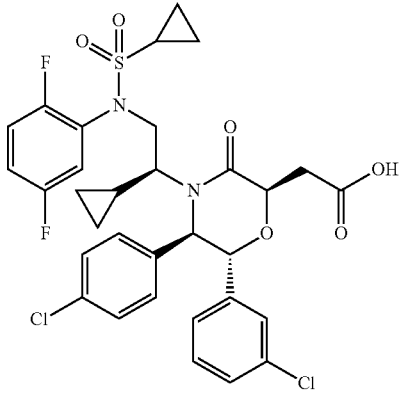

or

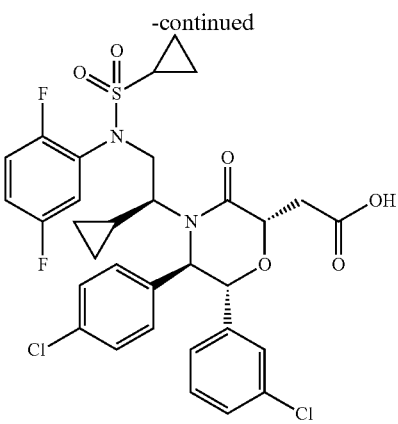

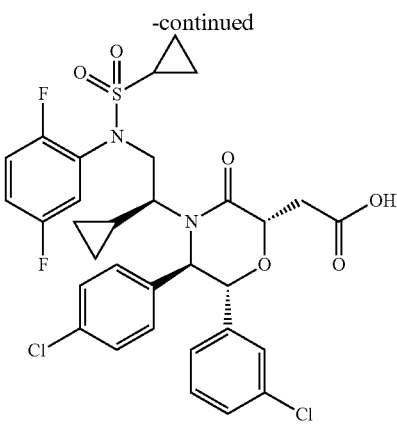

One of the title compounds was prepared from (5R,6R)-6-(3-chlorophenyl)-5-(4-chlorophenyl)-4-((S)-1-cyclopropyl-2-hydroxyethyl)morpholin-3-one (Example 154, Step B) by procedures similar to those described in Example 112, Steps D though F, replacing ethanethiol in Step D with N-(2,5-difluorophenyl)cyclopropanesulfonamide (prepared from 2,5-difluoroaniline following a procedure similar to the one described in Example 133). The residue was purified by reverse phase preparatory HPLC (Waters DeltaPrep 4000, column: Gemini-NX® 10 μm $C_{18}$, 110 Å, 100 mm×50 mm (Phenomenex, Torrance, Calif.), gradient elution of 45% to 75% acetonitrile in water, where both solvents contain 0.1% TFA, 20 minutes) to give one of the compounds as the first (faster) eluting isomer. $^1$H NMR (400 MHz, CDCl$_3$, δ ppm): 7.16-7.32 (m, 5H), 6.93-7.15 (m, 6H), 4.96 (br. s., 1H), 4.82 (d, J=5.48 Hz, 1H), 4.27-4.39 (m, 1H), 2.90-3.10 (m, 2H), 2.28-2.45 (m, 1H), 1.31 (d, J=7.04 Hz, 1H), 0.76-0.95 (m, 6H), 0.42 (br. s., 1H), 0.44 (br. s., 1H), 0.28 (br. s., 1H), 0.01 (br. s., 2H). MS (ESI) m/z=679[M+1].

Further elution of the HPLC purification described in Example 275 provided one of the title compounds as the second (slower) eluting isomer. $^1$H NMR (400 MHz, CDCl$_3$, δ ppm): 7.22-7.38 (m, 4H), 7.01-7.20 (m, 6H), 6.84-7.01 (m, 1H), 4.80-5.00 (m, 1H), 4.62-4.79 (m, 2H), 2.31-2.66 (m, 3H), 1.52-1.79 (m, 1H), 0.74-1.14 (m, 7H), 0.44 (br. s., 1H), 0.24 (br. s., 1H), −0.23 (br. s., 1H), −0.93 (br. s., 1H). MS (ESI) m/z=679 [M+1].

Example 276

2-((2R,5R,6R)-6-(3-Chlorophenyl)-5-(4-chlorophenyl)-4-((S)-1-cyclopropyl-2-(N-(2,5-difluorophenyl)cyclopropanesulfonamido)ethyl)-3-oxomorpholin-2-yl)acetic acid or 2-((2S,5R,6R)-6-(3-chlorophenyl)-5-(4-chlorophenyl)-4-((S)-1-cyclopropyl-2-(N-(2,5-difluorophenyl)cyclopropanesulfonamido)ethyl)-3-oxomorpholin-2-yl)acetic acid Example 277

2-((2R,5R,6R)-6-(3-Chlorophenyl)-5-(4-chlorophenyl)-3-oxo-4-((S)-4,4,4-trifluoro-1-(N-(2-fluorophenyl)cyclopropanesulfonamido)butan-2-yl)morpholin-2-yl)acetic acid or 2-((2S,5R,6R)-6-(3-chlorophenyl)-5-(4-chlorophenyl)-3-oxo-4-((S)-4,4,4-trifluoro-1-(N-(2-fluorophenyl)cyclopropanesulfonamido)butan-2-yl)morpholin-2-yl)acetic acid or 2-((2S,5R,6R)-6-(3-chlorophenyl)-5-(4-chlorophenyl)-3-oxo-4-((R)-4,4,4-trifluoro-1-(N-(2-fluorophenyl)cyclopropanesulfonamido)butan-2-yl)morpholin-2-yl)acetic acid or 2-((2R,5R,6R)-6-(3-chlorophenyl)-5-(4-chlorophenyl)-3-oxo-4-((R)-4,4,4-trifluoro-1-(N-(2-fluorophenyl)cyclopropanesulfonamido)butan-2-yl)morpholin-2-yl)acetic acid

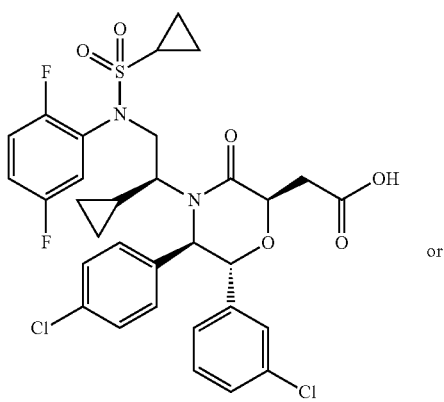

or

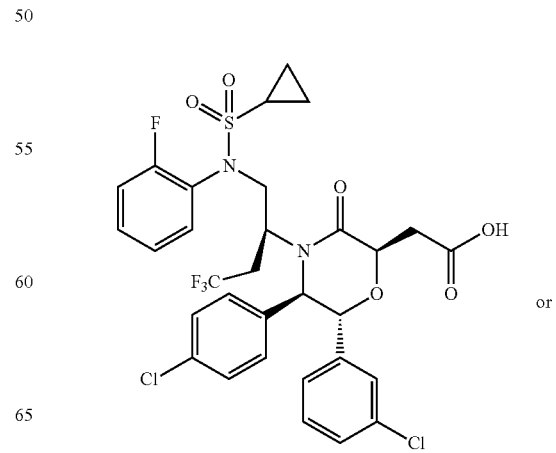

or

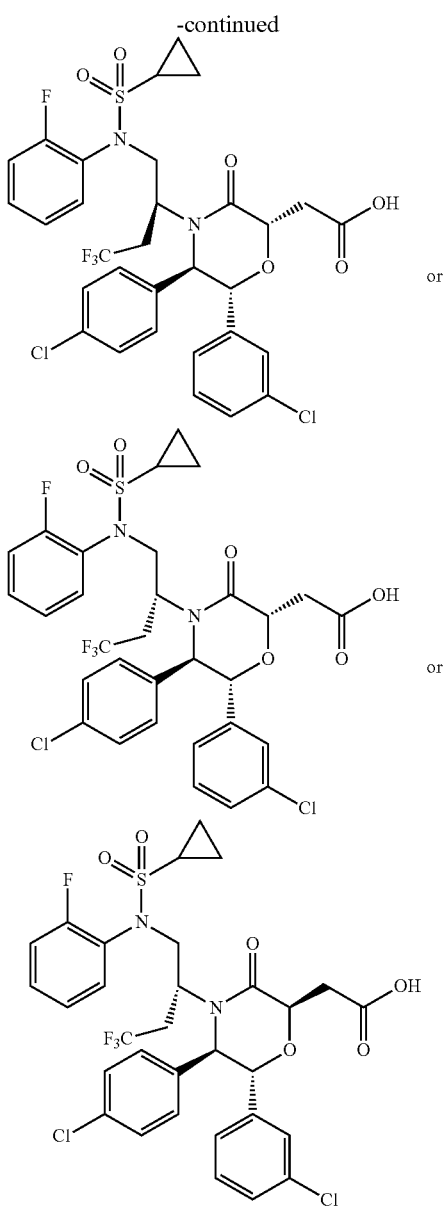

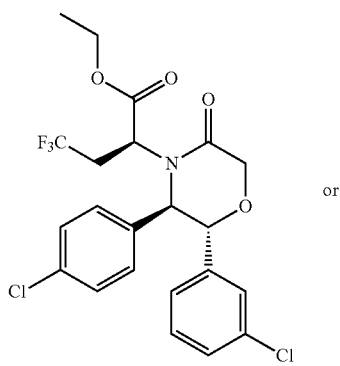

Step A. (S)-Ethyl 2-((2R,3R)-2-(3-chlorophenyl)-3-(4-chlorophenyl)-5-oxomorpholino)-4,4,4-trifluorobutanoate or (R)-ethyl 2-((2R,3R)-2-(3-chlorophenyl)-3-(4-chlorophenyl)-5-oxomorpholino)-4,4,4-trifluorobutanoate

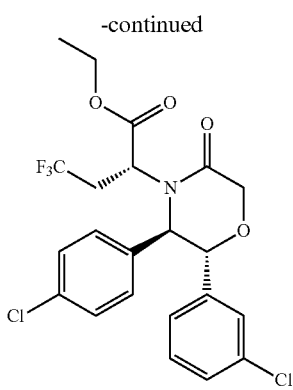

One of the title compounds was prepared from (5R,6R)-6-(3-chlorophenyl)-5-(4-chlorophenyl)morpholin-3-one (Example 112, Step A) by a procedure similar to that described in Example 154, Step A, replacing ethyl 2-bromo-2-cyclopropylacetate with 2-bromo-4,4,4-trifluorobutyric acid ethyl ester (Matrix Scientific, Columbia, S.C.). The residue was purified by flash chromatography on silica gel (24 g column, gradient elution of 0% to 20% ethyl acetate in hexanes) to give one of the title compounds as the first (faster) eluting isomer.

Step B. (5R,6R)-6-(3-Chlorophenyl)-5-(4-chlorophenyl)-4-((S)-4,4,4-trifluoro-1-hydroxybutan-2-yl)morpholin-3-one or (5R,6R)-6-(3-chlorophenyl)-5-(4-chlorophenyl)-4-((R)-4,4,4-trifluoro-1-hydroxybutan-2-yl)morpholin-3-one

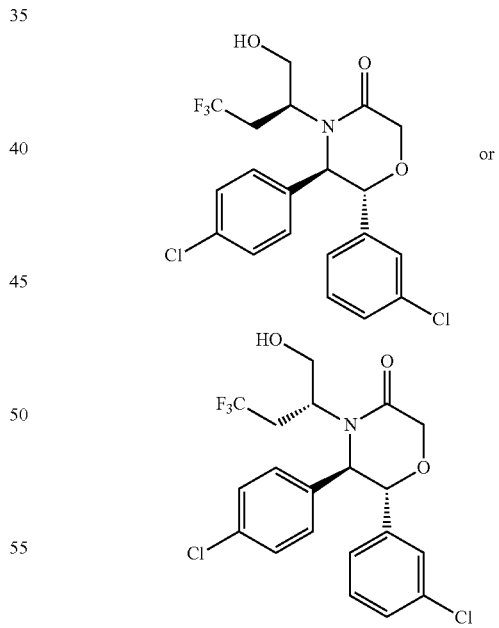

Lithium triethylborohydride (1.0 M in THF, 0.180 mL, 0.180 mmol) was added dropwise to a solution of (S)-ethyl 2-((2R,3R)-2-(3-chlorophenyl)-3-(4-chlorophenyl)-5-oxomorpholino)-4,4,4-trifluorobutanoate or (R)-ethyl 2-((2R,3R)-2-(3-chlorophenyl)-3-(4-chlorophenyl)-5-oxomorpholino)-4,4,4-trifluorobutanoate (42 mg, 0.086 mmol, Example 277, Step A) in THF (1 mL) at 0° C. After stirring at 0° C. for 90 minutes, methanol (3.47 µL, 0.086 mmol) was added followed by Oxone® (potassium peroxymonosulfate, DuPont, Wilmington, Del.) (47.4 mg, 0.077 mmol) in water (1 mL). The mixture was warmed to room temperature and stirred for 30 minutes. The mixture was diluted with water and ethyl acetate. The layers were separated and the aqueous layer was extracted with ethyl acetate. The combined organic layers were washed with brine, dried over $Na_2SO_4$, filtered, and concentrated. The residue was purified by preparative TLC (eluent: 5% MeOH in dichloromethane) to give one of the title compounds.

Step C. (2R,5R,6R)-2-Allyl-6-(3-chlorophenyl)-5-(4-chlorophenyl)-4-((S)-4,4,4-trifluoro-1-(N-(2-fluorophenyl)cyclopropanesulfonamido)butan-2-yl)morpholin-3-one or (2S,5R,6R)-2-allyl-6-(3-chlorophenyl)-5-(4-chlorophenyl)-4-((S)-4,4,4-trifluoro-1-(N-(2-fluorophenyl)cyclopropanesulfonamido)butan-2-yl)morpholin-3-one or (2S,5R,6R)-2-allyl-6-(3-chlorophenyl)-5-(4-chlorophenyl)-4-((R)-4,4,4-trifluoro-1-(N-(2-fluorophenyl)cyclopropanesulfonamido)butan-2-yl)morpholin-3-one or (2S,5R,6R)-2-allyl-6-(3-chlorophenyl)-5-(4-chlorophenyl)-4-((S)-4,4,4-trifluoro-1-(N-(2-fluorophenyl)cyclopropanesulfonamido)butan-2-yl)morpholin-3-one

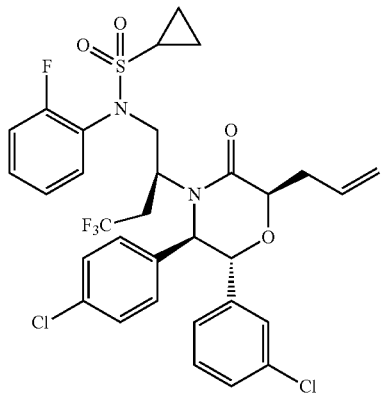

or

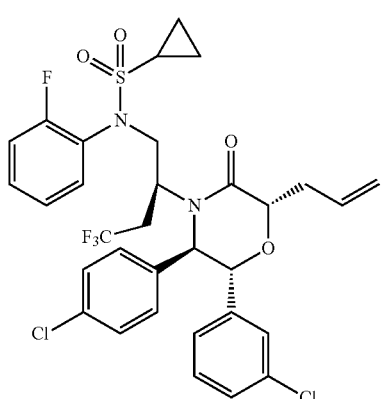

or

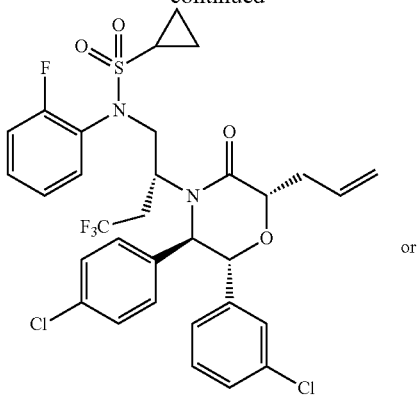

or

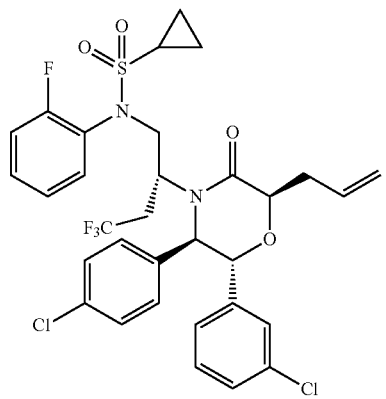

One of the title compounds was prepared from (5R,6R)-6-(3-chlorophenyl)-5-(4-chlorophenyl)-4-((S)-4,4,4-trifluoro-1-hydroxybutan-2-yl)morpholin-3-one or (5R,6R)-6-(3-chlorophenyl)-5-(4-chlorophenyl)-4-((R)-4,4,4-trifluoro-1-hydroxybutan-2-yl)morpholin-3-one (Example 277, Step B) by procedures analogous to those described in Example 112, Steps D though E, replacing ethanethiol in Step D with N-(2-fluorophenyl)cyclopropanesulfonamide (Example 133). The residue was purified by preparative TLC (eluent: 25% ethyl acetate in hexanes) to give one of the title compounds as the first (faster) eluting isomer.

Step D. 2-((2R,5R,6R)-6-(3-Chlorophenyl)-5-(4-chlorophenyl)-3-oxo-4-((S)-4,4,4-trifluoro-1-(N-(2-fluorophenyl)cyclopropanesulfonamido)butan-2-yl)morpholin-2-yl)acetic acid or 2-((2S,5R,6R)-6-(3-chlorophenyl)-5-(4-chlorophenyl)-3-oxo-4-((S)-4,4,4-trifluoro-1-(N-(2-fluorophenyl)cyclopropanesulfonamido)butan-2-yl)morpholin-2-yl)acetic acid or 2-((2S,5R,6R)-6-(3-chlorophenyl)-5-(4-chlorophenyl)-3-oxo-4-((R)-4,4,4-trifluoro-1-(N-(2-fluorophenyl)cyclopropanesulfonamido)butan-2-yl)morpholin-2-yl)acetic acid or 2-((2R,5R,6R)-6-(3-chlorophenyl)-5-(4-chlorophenyl)-3-oxo-4-((R)-4,4,4-trifluoro-1-(N-(2-fluorophenyl)cyclopropanesulfonamido)butan-2-yl)morpholin-2-yl)acetic acid

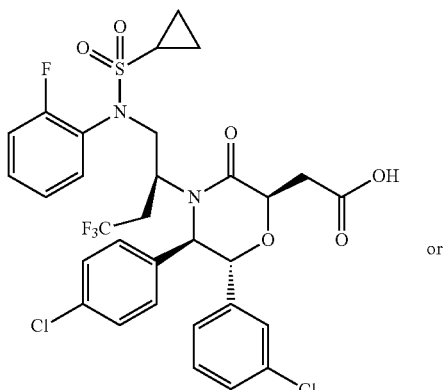 or

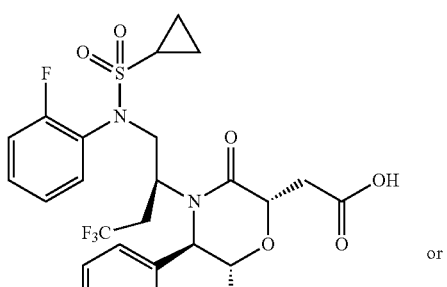 or

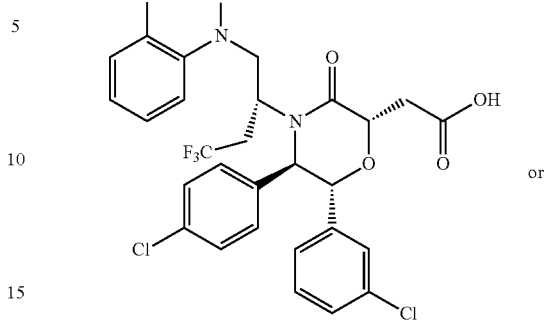

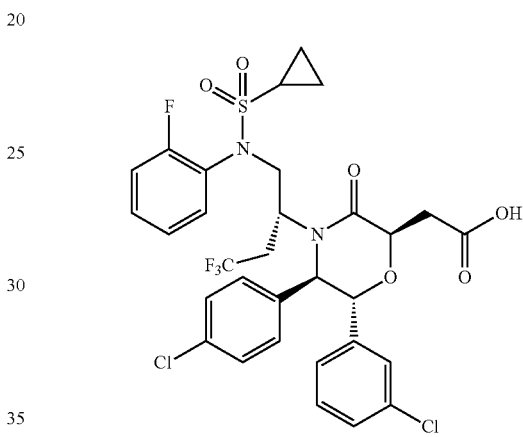

One of the title compounds was prepared from (2R,5R,6R)-2-allyl-6-(3-chlorophenyl)-5-(4-chlorophenyl)-4-((S)-4,4,4-trifluoro-1-(N-(2-fluorophenyl)cyclopropanesulfonamido)butan-2-yl)morpholin-3-one or (2S,5R,6R)-2-allyl-6-(3-chlorophenyl)-5-(4-chlorophenyl)-4-((S)-4,4,4-trifluoro-1-(N-(2-fluorophenyl)cyclopropanesulfonamido)butan-2-yl)morpholin-3-one or (2S,5R,6R)-2-allyl-6-(3-chlorophenyl)-5-(4-chlorophenyl)-4-((R)-4,4,4-trifluoro-1-(N-(2-fluorophenyl)cyclopropanesulfonamido)butan-2-yl)morpholin-3-one or (2S,5R,6R)-2-allyl-6-(3-chlorophenyl)-5-(4-chlorophenyl)-4-((S)-4,4,4-trifluoro-1-(N-(2-fluorophenyl)cyclopropanesulfonamido)butan-2-yl)morpholin-3-one (Example 277, Step C) by a procedure analogous to that described in Example 112, Step F. The residue was purified by preparative TLC (eluent: 5% MeOH in dichloromethane) to give one of the title compounds. $^1$H NMR (400 MHz, acetonitrile-$d_3$, δ ppm): 9.26 (br. s., 1H), 7.29-7.62 (m, 7H), 7.09-7.28 (m, 2H), 6.97 (d, J=7.82 Hz, 1H), 5.24 (br. s., 1H), 4.96 (d, J=9.78 Hz, 1H), 4.66-4.89 (m, 1H), 4.18-4.45 (m, 1H), 3.71-3.93 (m, 1H), 2.81-3.23 (m, 2H), 2.56-2.76 (m, 1H), 1.39-1.49 (m, 1H), 1.27-1.38 (m, 3H), 1.12-1.27 (m, 2H), 1.00-1.12 (m, 1H), 0.76-1.00 (m, 2H). MS (ESI) m/z=703 [M+1].

Example 278

2-((2R,5R,6R)-6-(3-Chlorophenyl)-5-(4-chlorophenyl)-3-oxo-4-((S)-4,4,4-trifluoro-1-(N-(2-fluorophenyl)cyclopropanesulfonamido)butan-2-yl)morpholin-2-yl)acetic acid or 2-((2S,5R,6R)-6-(3-chlorophenyl)-5-(4-chlorophenyl)-3-oxo-4-((S)-4,4,4-trifluoro-1-(N-(2-fluorophenyl)cyclopropanesulfonamido)butan-2-yl)morpholin-2-yl)acetic acid or 2-((2S,5R,6R)-6-(3-chlorophenyl)-5-(4-chlorophenyl)-3-oxo-4-((R)-4,4,4-trifluoro-1-(N-(2-fluorophenyl)cyclopropanesulfonamido)butan-2-yl)morpholin-2-yl)acetic acid or 2-((2R,5R,6R)-6-(3-chlorophenyl)-5-(4-chlorophenyl)-3-oxo-4-((R)-4,4,4-trifluoro-1-(N-(2-fluorophenyl)cyclopropanesulfonamido)butan-2-yl)morpholin-2-yl)acetic acid

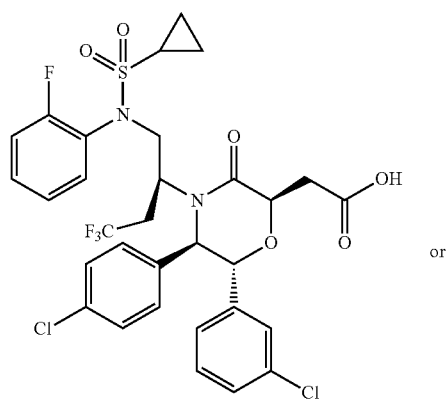

or

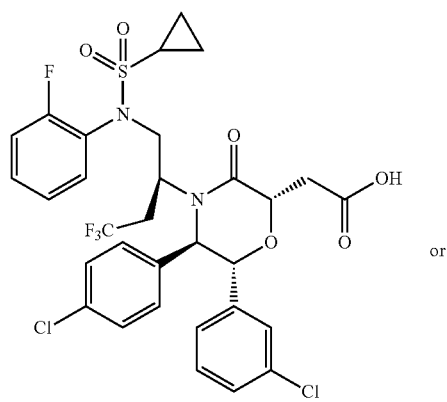

or

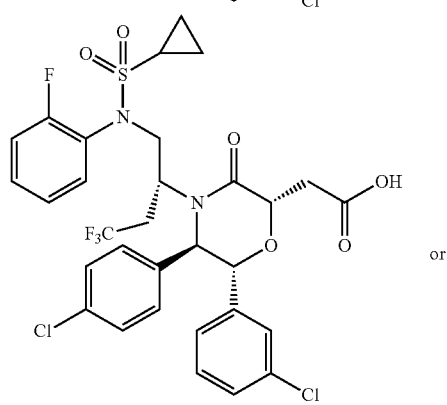

or

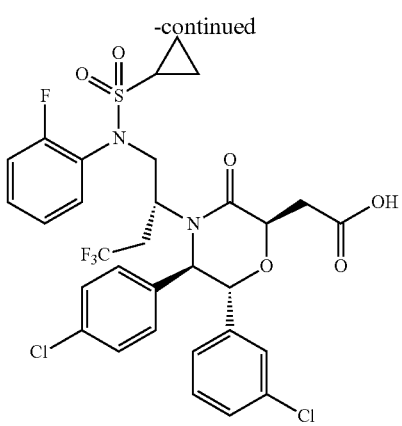

Step A. (2R,5R,6R)-2-Allyl-6-(3-chlorophenyl)-5-(4-chlorophenyl)-4-((S)-4,4,4-trifluoro-1-(N-(2-fluorophenyl)cyclopropanesulfonamido)butan-2-yl)morpholin-3-one or (2S,5R,6R)-2-allyl-6-(3-chlorophenyl)-5-(4-chlorophenyl)-4-((S)-4,4,4-trifluoro-1-(N-(2-fluorophenyl)cyclopropanesulfonamido)butan-2-yl)morpholin-3-one or (2S,5R,6R)-2-allyl-6-(3-chlorophenyl)-5-(4-chlorophenyl)-4-((R)-4,4,4-trifluoro-1-(N-(2-fluorophenyl)cyclopropanesulfonamido)butan-2-yl)morpholin-3-one or (2S,5R,6R)-2-allyl-6-(3-chlorophenyl)-5-(4-chlorophenyl)-4-((S)-4,4,4-trifluoro-1-(N-(2-fluorophenyl)cyclopropanesulfonamido)butan-2-yl)morpholin-3-one

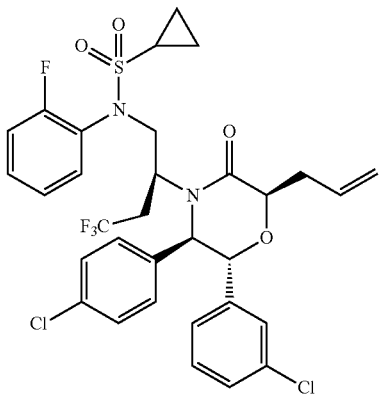

or

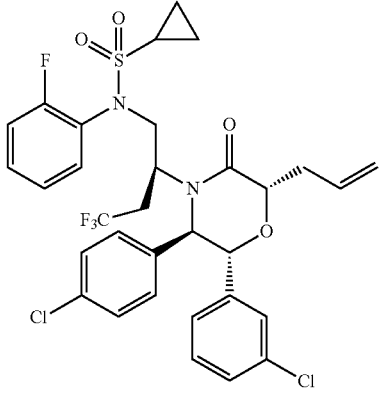

or

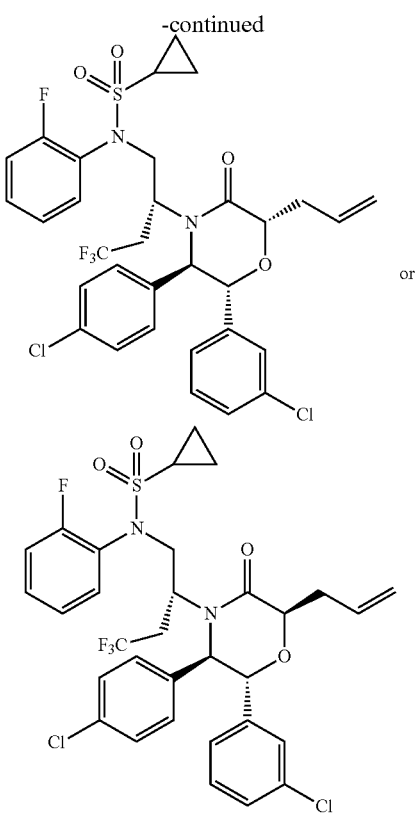

The second (slower) eluting isomer from the chromatographic separation described in Example 277, Step C was isolated to provide one of the title compounds.

Step B. 2-((2R,5R,6R)-6-(3-Chlorophenyl)-5-(4-chlorophenyl)-3-oxo-4-((S)-4,4,4-trifluoro-1-(N-(2-fluorophenyl)cyclopropanesulfonamido)butan-2-yl)morpholin-2-yl)acetic acid or 2-((2S,5R,6R)-6-(3-chlorophenyl)-5-(4-chlorophenyl)-3-oxo-4-((S)-4,4,4-trifluoro-1-(N-(2-fluorophenyl)cyclopropanesulfonamido)butan-2-yl)morpholin-2-yl)acetic acid or 2-((2S,5R,6R)-6-(3-chlorophenyl)-5-(4-chlorophenyl)-3-oxo-4-((R)-4,4,4-trifluoro-1-(N-(2-fluorophenyl)cyclopropanesulfonamido)butan-2-yl)morpholin-2-yl)acetic acid or 2-((2R,5R,6R)-6-(3-chlorophenyl)-5-(4-chlorophenyl)-3-oxo-4-((R)-4,4,4-trifluoro-1-(N-(2-fluorophenyl)cyclopropanesulfonamido)butan-2-yl)morpholin-2-yl)acetic acid One of the title compounds was prepared from (2R,5R,6R)-2-allyl-6-(3-chlorophenyl)-5-(4-chlorophenyl)-4-((S)-4,4,4-trifluoro-1-(N-(2-fluorophenyl)cyclopropanesulfonamido)butan-2-yl)morpholin-3-one or (2S,5R,6R)-2-allyl-6-(3-chlorophenyl)-5-(4-chlorophenyl)-4-((S)-4,4,4-trifluoro-1-(N-(2-fluorophenyl)cyclopropanesulfonamido)butan-2-yl)morpholin-3-one or (2S,5R,6R)-2-allyl-6-(3-chlorophenyl)-5-(4-chlorophenyl)-4-((R)-4,4,4-trifluoro-1-(N-(2-fluorophenyl)cyclopropanesulfonamido)butan-2-yl)morpholin-3-one or (2S,5R,6R)-2-allyl-6-(3-chlorophenyl)-5-(4-chlorophenyl)-4-((S)-4,4,4-trifluoro-1-(N-(2-fluorophenyl)cyclopropanesulfonamido)butan-2-yl)morpholin-3-one (Example 278, Step A) by a procedure analogous to that described in Example 112, Step F. The residue was purified by preparative TLC (eluent: 5% MeOH in dichloromethane) to give one of the title compounds. $^1$H NMR (400 MHz, CDCl$_3$, δ ppm): 7.22-7.41 (m, 7H), 7.05-7.20 (m, 5H), 5.07-5.24 (m, 1H), 4.91 (d, J=3.91 Hz, 1H), 4.58-4.86 (m, 1H), 3.02-3.27 (m, 2H), 2.42-2.55 (m, 1H), 2.36 (t, J=7.43 Hz, 1H), 1.65 (dt, J=15.21, 7.75 Hz, 2H), 1.17-1.39 (m, 2H), 0.70-1.07 (m, 4H). MS (ESI) m/z=703 [M+1].

Example 279

2-((2R,5R,6R)-6-(3-Chlorophenyl)-5-(4-chlorophenyl)-3-oxo-4-((S)-4,4,4-trifluoro-1-(N-(2-fluorophenyl)cyclopropanesulfonamido)butan-2-yl)morpholin-2-yl)acetic acid or 2-((2S,5R,6R)-6-(3-chlorophenyl)-5-(4-chlorophenyl)-3-oxo-4-((S)-4,4,4-trifluoro-1-(N-(2-fluorophenyl)cyclopropanesulfonamido)butan-2-yl)morpholin-2-yl)acetic acid or 2-((2S,5R,6R)-6-(3-chlorophenyl)-5-(4-chlorophenyl)-3-oxo-4-((R)-4,4,4-trifluoro-1-(N-(2-fluorophenyl)cyclopropanesulfonamido)butan-2-yl)morpholin-2-yl)acetic acid or 2-((2R,5R,6R)-6-(3-chlorophenyl)-5-(4-chlorophenyl)-3-oxo-4-((R)-4,4,4-trifluoro-1-(N-(2-fluorophenyl)cyclopropanesulfonamido)butan-2-yl)morpholin-2-yl)acetic acid

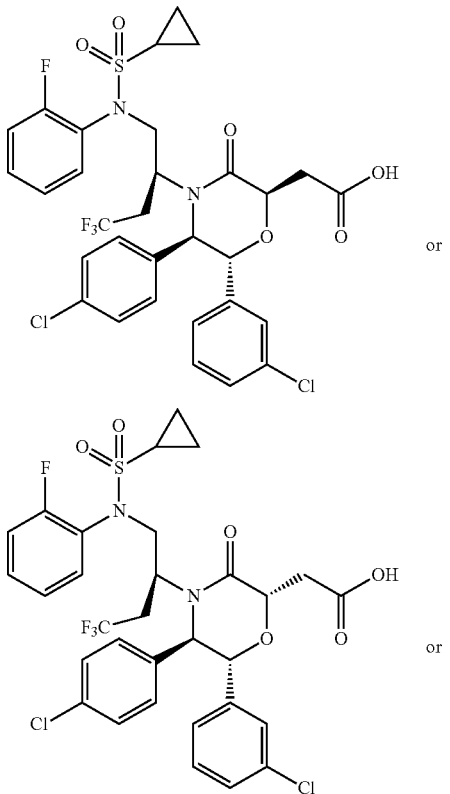

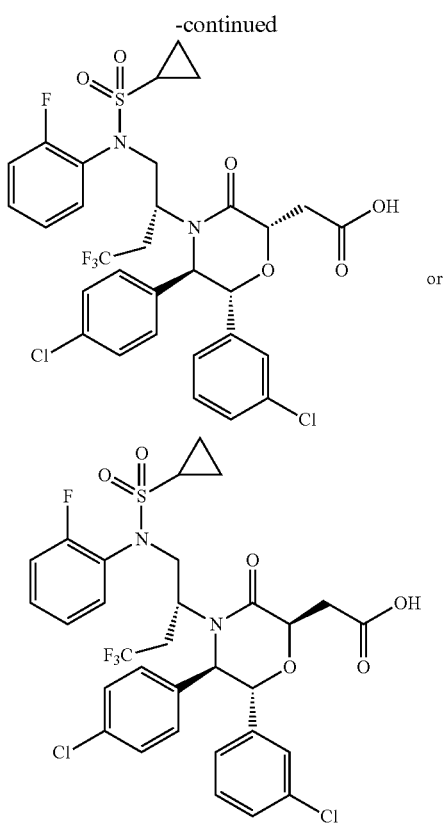

Step A. (S)-Ethyl 2-((2R,3R)-2-(3-chlorophenyl)-3-(4-chlorophenyl)-5-oxomorpholino)-4,4,4-trifluorobutanoate or (R)-ethyl 2-((2R,3R)-2-(3-chlorophenyl)-3-(4-chlorophenyl)-5-oxomorpholino)-4,4,4-trifluorobutanoate

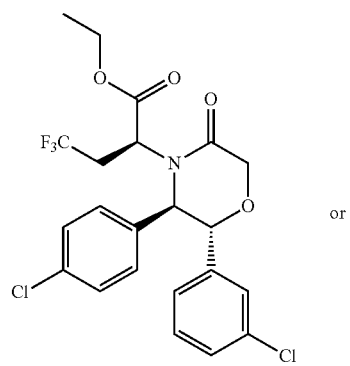

Further elution from the chromatography described in Example 277, Step A provided one of the title compounds as the second (slower) eluting isomer.

Step B. (5R,6R)-6-(3-Chlorophenyl)-5-(4-chlorophenyl)-4-((S)-4,4,4-trifluoro-1-hydroxybutan-2-yl)morpholin-3-one or (5R,6R)-6-(3-chlorophenyl)-5-(4-chlorophenyl)-4-((R)-4,4,4-trifluoro-1-hydroxybutan-2-yl)morpholin-3-one

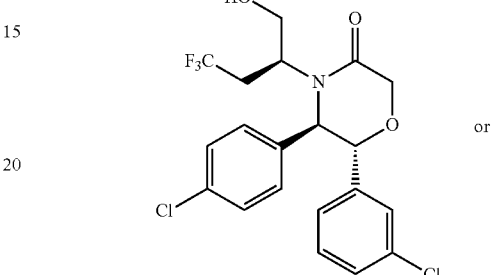

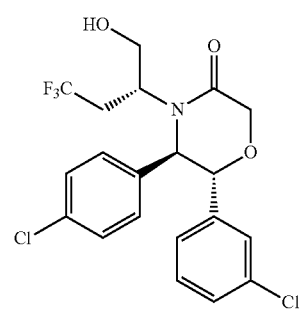

One of the title compounds was prepared from (S)-ethyl 2-((2R,3R)-2-(3-chlorophenyl)-3-(4-chlorophenyl)-5-oxomorpholino)-4,4,4-trifluorobutanoate or (R)-ethyl 2-((2R,3R)-2-(3-chlorophenyl)-3-(4-chlorophenyl)-5-oxomorpholino)-4,4,4-trifluorobutanoate (Example 279, Step A) by a procedure analogous to that described in Example 277, Step B.

Step C. 2-((2R,5R,6R)-6-(3-chlorophenyl)-5-(4-chlorophenyl)-3-oxo-4-((S)-4,4,4-trifluoro-1-(N-(2-fluorophenyl)cyclopropanesulfonamido)butan-2-yl)morpholin-2-yl)acetic acid or 2-((2S,5R,6R)-6-(3-chlorophenyl)-5-(4-chlorophenyl)-3-oxo-4-((S)-4,4,4-trifluoro-1-(N-(2-fluorophenyl)cyclopropanesulfonamido)butan-2-yl)morpholin-2-yl)acetic acid or 2-((2S,5R,6R)-6-(3-chlorophenyl)-5-(4-chlorophenyl)-3-oxo-4-((R)-4,4,4-trifluoro-1-(N-(2-fluorophenyl)cyclopropanesulfonamido)butan-2-yl)morpholin-2-yl)acetic acid 2-((2R,5R,6R)-6-(3-chlorophenyl)-5-(4-chlorophenyl)-3-oxo-4-((R)-4,4,4-trifluoro-1-(N-(2-fluorophenyl)cyclopropanesulfonamido)butan-2-yl)morpholin-2-yl)acetic acid

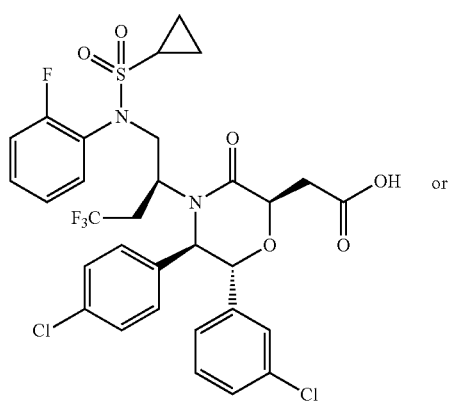 or

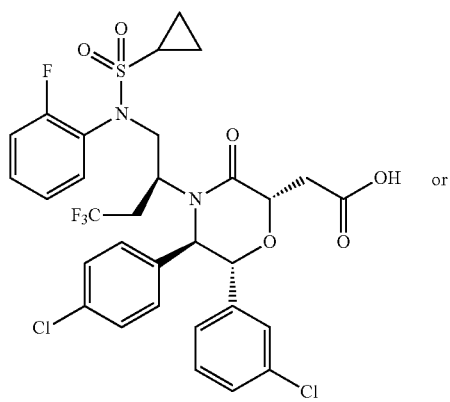 or

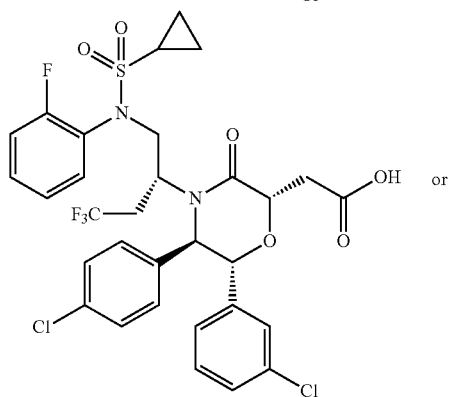 or

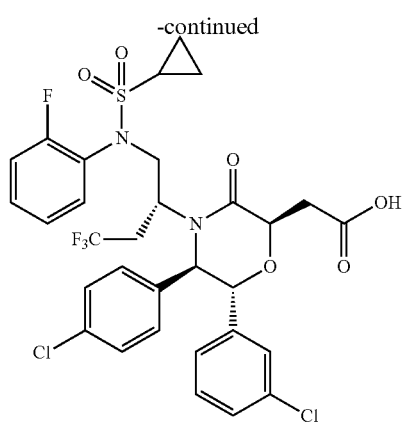

One of the title compounds was prepared from (5R,6R)-6-(3-chlorophenyl)-5-(4-chlorophenyl)-4-((S)-4,4,4-trifluoro-1-hydroxybutan-2-yl)morpholin-3-one or (5R,6R)-6-(3-chlorophenyl)-5-(4-chlorophenyl)-4-((R)-4,4,4-trifluoro-1-hydroxybutan-2-yl)morpholin-3-one (Example 279, Step B) by procedures analogous to those described in Example 112, Steps D though F, replacing ethanethiol in Step D with N-(2-fluorophenyl)cyclopropanesulfonamide (Example 133). The residue was purified by preparative TLC (eluent: 5% MeOH in dichloromethane) to give one of the title compounds. $^1$H NMR (400 MHz, CDCl$_3$, δ ppm): 6.87-7.44 (m, 12H), 4.92-5.20 (m, 1H), 4.72-4.79 (m, 2H), 3.49-3.55 (m, 1H), 3.33 (br. s., 1H), 3.01-3.24 (m, 2H), 2.30-2.73 (m, 1H), 1.54-1.76 (m, 1H), 1.18-1.40 (m, 2H), 0.74-1.13 (m, 4H). MS (ESI) m/z=703 [M+1].

Example 280

2-((2R,5R,6R)-4-((S)-1-((S)-sec-Butylsulfonyl)butan-2-yl)-6-(3-chlorophenyl)-5-(4-chlorophenyl)-3-oxomorpholin-2-yl)acetic acid and 2-((2R,5R,6R)-4-((S)-1-((R)-sec-butylsulfonyl)butan-2-yl)-6-(3-chlorophenyl)-5-(4-chlorophenyl)-3-oxomorpholin-2-yl)acetic acid or 2-((2S,5R,6R)-4-((S)-1-((S)-sec-butylsulfonyl)butan-2-yl)-6-(3-chlorophenyl)-5-(4-chlorophenyl)-3-oxomorpholin-2-yl)acetic acid and 2-((2S,5R,6R)-4-((S)-1-((R)-sec-butylsulfonyl)butan-2-yl)-6-(3-chlorophenyl)-5-(4-chlorophenyl)-3-oxomorpholin-2-yl)acetic acid

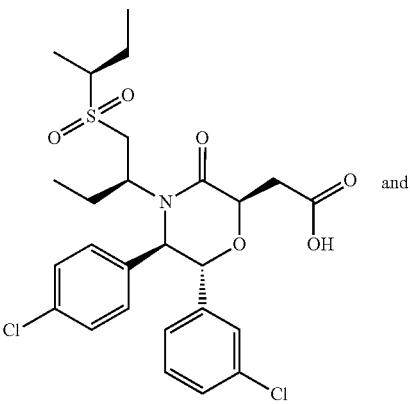 and

485

-continued

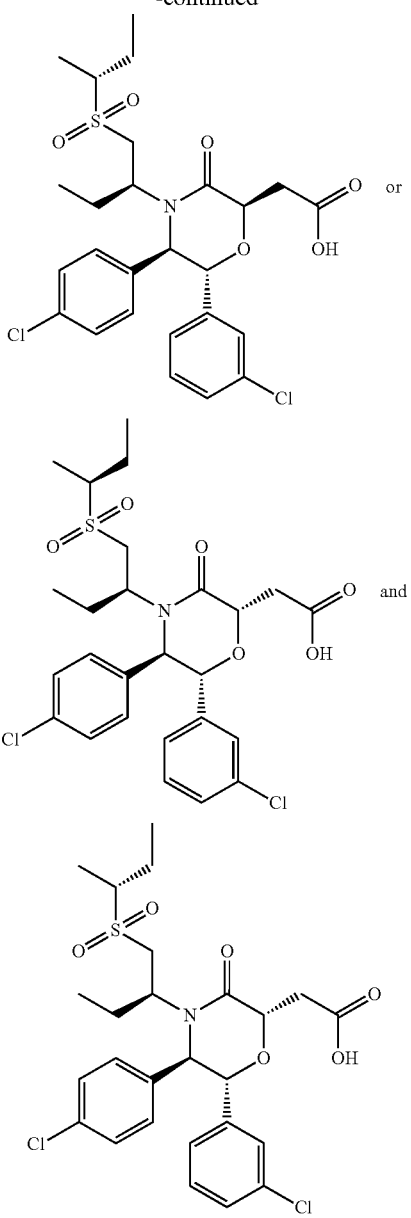

One set of the title compounds were prepared from (5R,6R)-6-(3-chlorophenyl)-5-(4-chlorophenyl)-4-((S)-1-hydroxybutan-2-yl)morpholin-3-one (Example 112, Step C) by procedures analogous to those described in Example 112, Steps D though F, replacing ethanethiol in Step D with 1-methyl-1-propanethiol. The residue was purified by chiral SFC (250×21 mm Chiralpak® OZ-H column (Chiral Technologies, Inc., West Chester, Pa., USA) with 16 g/min MeOH+64 g/min $CO_2$) to give one set of the title compounds as the first (faster) eluting isomers. MS (ESI) m/z=556 [M+1].

486

Example 281

2-((2R,5R,6R)-4-((S)-1-((S)-sec-Butylsulfonyl)butan-2-yl)-6-(3-chlorophenyl)-5-(4-chlorophenyl)-3-oxomorpholin-2-yl)acetic acid and 2-((2R,5R,6R)-4-((S)-1-((R)-sec-butylsulfonyl)butan-2-yl)-6-(3-chlorophenyl)-5-(4-chlorophenyl)-3-oxomorpholin-2-yl)acetic acid or 2-((2S,5R,6R)-4-((S)-1-((S)-sec-butylsulfonyl)butan-2-yl)-6-(3-chlorophenyl)-5-(4-chlorophenyl)-3-oxomorpholin-2-yl)acetic acid and 2-((2S,5R,6R)-4-((S)-1-((R)-sec-butylsulfonyl)butan-2-yl)-6-(3-chlorophenyl)-5-(4-chlorophenyl)-3-oxomorpholin-2-yl)acetic acid

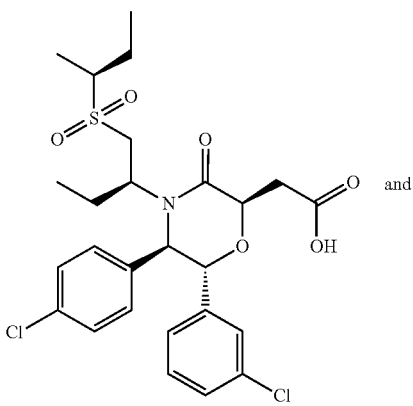

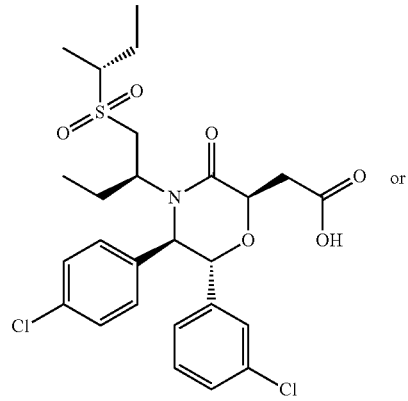

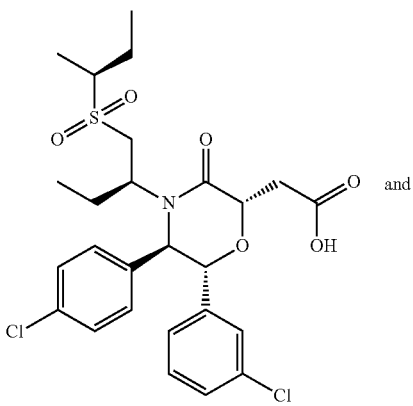

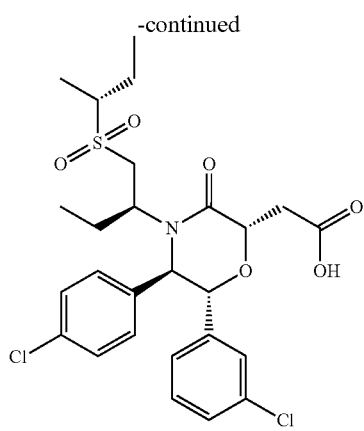

Further elution of the chromatographic purification described in Example 280 provided one set of the title compounds as the second (slower) eluting isomers. Spectrum (ESI) m/z=556 [M+1].

Example 282

2-((2S,5R,6R)-6-(3-Chlorophenyl)-5-(4-chlorophenyl)-4-((S)-1-(((R)-3-methylbutan-2-yl)sulfonyl)butan-2-yl)-3-oxomorpholin-2-yl)acetic acid or
2-((2S,5R,6R)-6-(3-Chlorophenyl)-5-(4-chlorophenyl)-4-((S)-1-(((S)-3-methylbutan-2-yl)sulfonyl)butan-2-yl)-3-oxomorpholin-2-yl)acetic acid or
2-((2R,5R,6R)-6-(3-Chlorophenyl)-5-(4-chlorophenyl)-4-((S)-1-(((R)-3-methylbutan-2-yl)sulfonyl)butan-2-yl)-3-oxomorpholin-2-yl)acetic acid or
2-((2R,5R,6R)-6-(3-Chlorophenyl)-5-(4-chlorophenyl)-4-((S)-1-(((S)-3-methylbutan-2-yl)sulfonyl)butan-2-yl)-3-oxomorpholin-2-yl)acetic acid

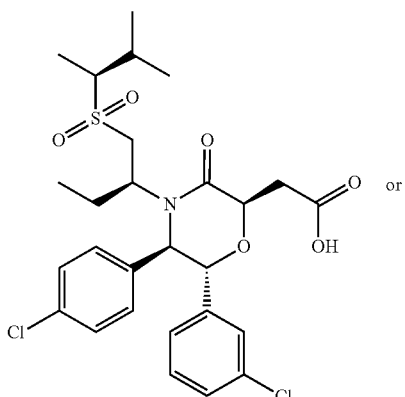

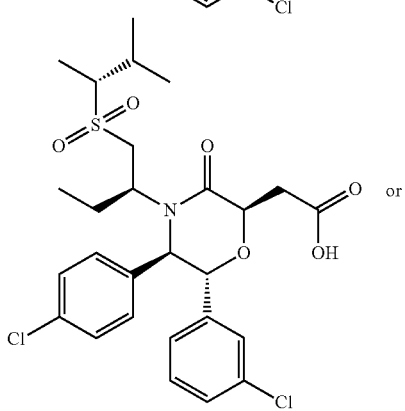

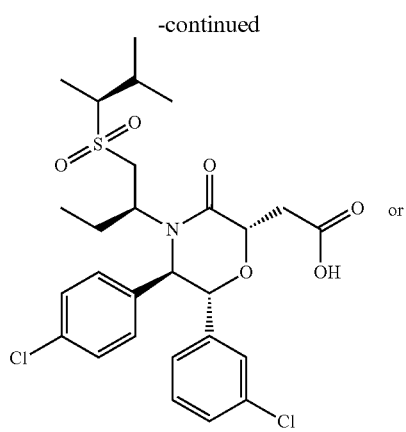

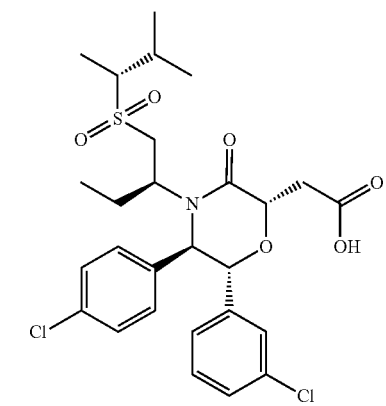

Step A. (5R,6R)-6-(3-Chlorophenyl)-5-(4-chlorophenyl)-4-((S)-1-(((S)-3-methylbutan-2-yl)thio)butan-2-yl)morpholin-3-one or (5R,6R)-6-(3-chlorophenyl)-5-(4-chlorophenyl)-4-((S)-1-(((R)-3-methylbutan-2-yl)thio)butan-2-yl)morpholin-3-one

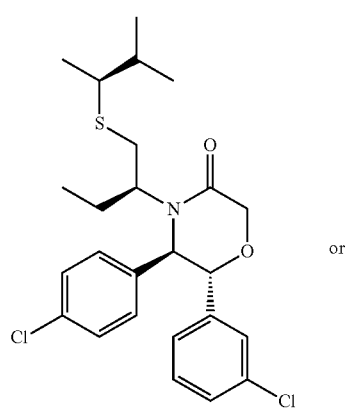

-continued

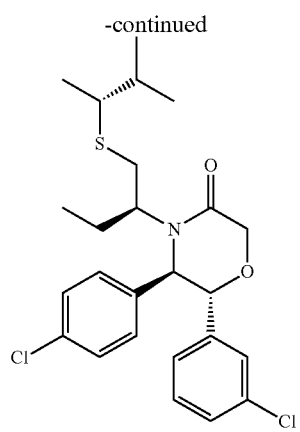

One of the title compounds was prepared from (5R,6R)-6-(3-chlorophenyl)-5-(4-chlorophenyl)-4-((S)-1-hydroxybutan-2-yl)morpholin-3-one (Example 112, Step C) by a procedure analogous to Example 112, Step D replacing ethanethiol with 3-methyl-2-butanethiol. The residue was purified by chiral SFC (150×21 mm Chiralpak® IC column (Chiral Technologies, Inc., West Chester, Pa., USA) with 5 g/min 0.1% NH₄OH in MeOH+60 g/min CO₂) to give one of the title compounds as the first (faster) eluting isomer.

Step B. 2-((2S,5R,6R)-6-(3-Chlorophenyl)-5-(4-chlorophenyl)-4-((S)-1-(((R)-3-methylbutan-2-yl)sulfonyl)butan-2-yl)-3-oxomorpholin-2-yl)acetic acid or 2-((2S,5R,6R)-6-(3-chlorophenyl)-5-(4-chlorophenyl)-4-((S)-1-(((S)-3-methylbutan-2-yl)sulfonyl)butan-2-yl)-3-oxomorpholin-2-yl)acetic acid or 2-((2R,5R,6R)-6-(3-chlorophenyl)-5-(4-chlorophenyl)-4-((S)-1-(((R)-3-methylbutan-2-yl)sulfonyl)butan-2-yl)-3-oxomorpholin-2-yl)acetic acid or 2-((2R,5R,6R)-6-(3-chlorophenyl)-5-(4-chlorophenyl)-4-((S)-1-(((S)-3-methylbutan-2-yl)sulfonyl)butan-2-yl)-3-oxomorpholin-2-yl)acetic acid One of the title compounds was obtained from (5R,6R)-6-(3-chlorophenyl)-5-(4-chlorophenyl)-4-((S)-1-(((S)-3-methylbutan-2-yl)thio)butan-2-yl)morpholin-3-one or (5R,6R)-6-(3-chlorophenyl)-5-(4-chlorophenyl)-4-((S)-1-(((R)-3-methylbutan-2-yl)thio)butan-2-yl)morpholin-3-one (Example 282, Step A) by procedures similar to those described in Example 112, Steps E and F. The residue was purified by reverse phase preparatory HPLC (Agilient 1100, column: Gemini® 5 μm C₁₈, 100 mm×30 mm (Phenomenex, Torrance, Calif.), gradient elution of 25% to 75% acetonitrile in water, where both solvents contain 0.1% TFA, 30 minutes) to give one of the compounds as the first (faster) eluting isomer. ¹H NMR (500 MHz, CDCl₃, δ ppm): 7.37-7.33 (m, 4H), 7.25-7.15 (m, 3H), 7.03 (d, J=7.6 Hz, 1H), 5.10-5.06 (m, 2H), 4.77 (dd, J=8.8, 4.4 Hz, 1H), 4.05 (t, J=11.5 Hz, 1H), 3.35 (br, 1H), 3.17 (dd, J=16.1, 9 Hz, 1H), 3.10-3.07 (m, 2H), 2.93 (dd, J=16.1, 3.4 Hz, 1H), 2.58-2.53 (m, 1H), 2.11-2.05 (m, 1H), 1.68-1.62 (m, 1H), 1.36-1.34 (m, 3H), 1.07-1.05 (m, 6H), 0.53-0.50 (m, 3H). MS (ESI) m/z=570 [M+1].

Example 283

2-((2S,5R,6R)-6-(3-Chlorophenyl)-5-(4-chlorophenyl)-4-((S)-1-(((R)-3-methylbutan-2-yl)sulfonyl)butan-2-yl)-3-oxomorpholin-2-yl)acetic acid or 2-((2S,5R,6R)-6-(3-chlorophenyl)-5-(4-chlorophenyl)-4-((S)-1-(((S)-3-methylbutan-2-yl)sulfonyl)butan-2-yl)-3-oxomorpholin-2-yl)acetic acid or 2-((2R,5R,6R)-6-(3-chlorophenyl)-5-(4-chlorophenyl)-4-((S)-1-(((R)-3-methylbutan-2-yl)sulfonyl)butan-2-yl)-3-oxomorpholin-2-yl)acetic acid or 2-((2R,5R,6R)-6-(3-chlorophenyl)-5-(4-chlorophenyl)-4-((S)-1-(((S)-3-methylbutan-2-yl)sulfonyl)butan-2-yl)-3-oxomorpholin-2-yl)acetic acid

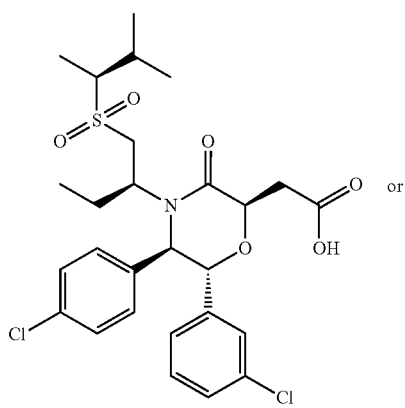

or

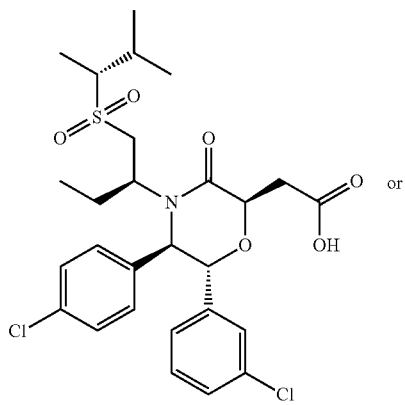

or

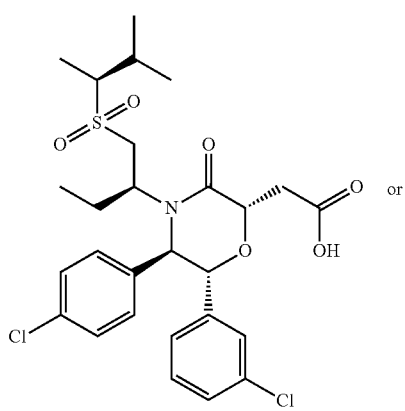

or

491

-continued

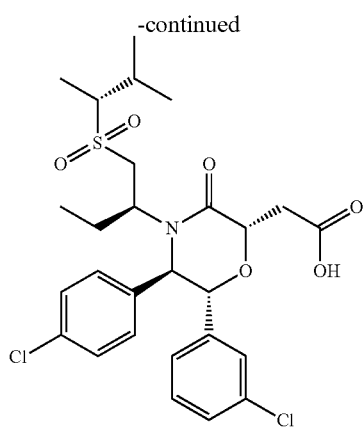

Further elution of the HPLC purification described in Example 282, Step A provided one of the title compounds as the second (slower) eluting isomer. $^1$H NMR (500 MHz, CDCl$_3$, δ ppm): 7.29 (s, 1H), 7.27 (s, 1H), 7.20 (d, J=7.8 Hz, 2H), 7.16-7.14 (m, 1H), 7.09-7.05 (m, 2H), 6.84 (d, J=7.6 Hz, 1H), 4.95-4.37 (m, 2H), 4.79-4.74 (m, 2H), 4.05-3.98 (m, 1H), 3.07-3.00 (m, 2H), 2.98-2.94 (m, 1H), 2.84 (dd, J=14.2, 11.5 Hz, 1H), 2.51-2.44 (m, 1H), 2.08-2.00 (m, 1H), 1.65-1.56 (m, 1H), 1.28 (d, J=26.9 Hz, 3H), 1.00 (dd, J=7, 4.5 Hz, 6H), 0.46 (t, J=7.5 Hz, 3H). MS (ESI) m/z=570 [M+1].

Example 284

2-((2S,5R,6R)-6-(3-chlorophenyl)-5-(4-Chlorophenyl)-4-((S)-1-(((R)-3-methylbutan-2-yl)sulfonyl)butan-2-yl)-3-oxomorpholin-2-yl)acetic acid or
2-((2S,5R,6R)-6-(3-chlorophenyl)-5-(4-chlorophenyl)-4-((S)-1-(((S)-3-methylbutan-2-yl)sulfonyl)butan-2-yl)-3-oxomorpholin-2-yl)acetic acid or
2-((2R,5R,6R)-6-(3-chlorophenyl)-5-(4-chlorophenyl)-4-((S)-1-(((R)-3-methylbutan-2-yl)sulfonyl)butan-2-yl)-3-oxomorpholin-2-yl)acetic acid or
2-((2R,5R,6R)-6-(3-chlorophenyl)-5-(4-chlorophenyl)-4-((S)-1-(((S)-3-methylbutan-2-yl)sulfonyl)butan-2-yl)-3-oxomorpholin-2-yl)acetic acid

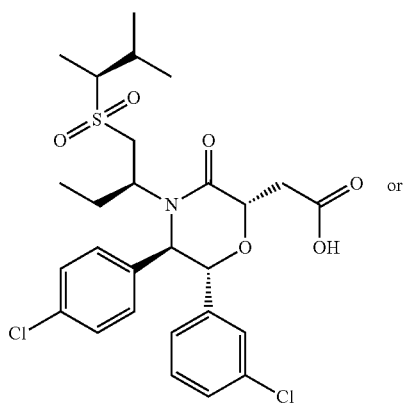

492

-continued

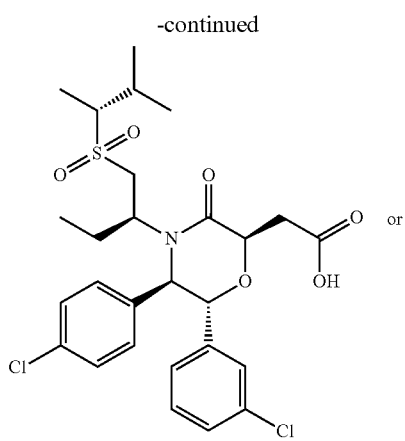

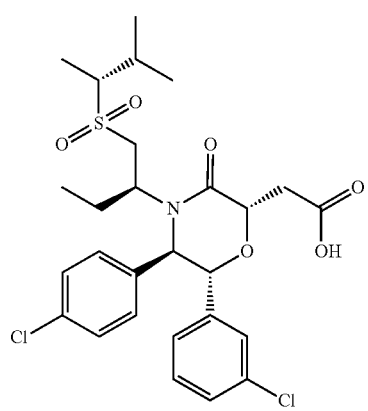

or or or

Step A. (5R,6R)-6-(3-Chlorophenyl)-5-(4-chlorophenyl)-4-((S)-1-(((S)-3-methylbutan-2-yl)thio)butan-2-yl)morpholin-3-one or (5R,6R)-6-(3-chlorophenyl)-5-(4-chlorophenyl)-4-((S)-1-(((R)-3-methylbutan-2-yl)thio)butan-2-yl)morpholin-3-one

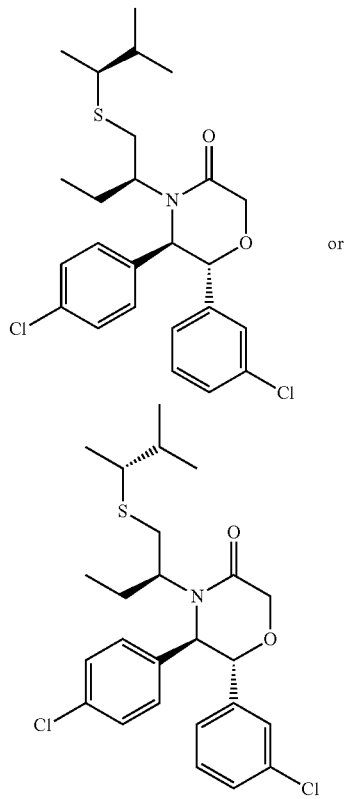

or

Further elution of the chromatographic separation described in Example 282, Step A provided one of the title compounds as the second (slower) eluting isomer.

Step B. 2-((2S,5R,6R)-6-(3-Chlorophenyl)-5-(4-chlorophenyl)-4-((S)-1-(((R)-3-methylbutan-2-yl)sulfonyl)butan-2-yl)-3-oxomorpholin-2-yl)acetic acid or 2-((2S,5R,6R)-6-(3-chlorophenyl)-5-(4-chlorophenyl)-4-((S)-1-(((S)-3-methylbutan-2-yl)sulfonyl)butan-2-yl)-3-oxomorpholin-2-yl)acetic acid or 2-((2R,5R,6R)-6-(3-chlorophenyl)-5-(4-chlorophenyl)-4-((S)-1-(((R)-3-methylbutan-2-yl)sulfonyl)butan-2-yl)-3-oxomorpholin-2-yl)acetic acid or 2-((2R,5R,6R)-6-(3-chlorophenyl)-5-(4-chlorophenyl)-4-((S)-1-(((S)-3-methylbutan-2-yl)sulfonyl)butan-2-yl)-3-oxomorpholin-2-yl)acetic acid One of the title compounds was obtained from (5R,6R)-6-(3-chlorophenyl)-5-(4-chlorophenyl)-4-((S)-1-(((S)-3-methylbutan-2-yl)thio)butan-2-yl)morpholin-3-one or (5R,6R)-6-(3-chlorophenyl)-5-(4-chlorophenyl)-4-((S)-1-(((R)-3-methylbutan-2-yl)thio)butan-2-yl)morpholin-3-one (Example 284, Step A) by procedures similar to those described in Example 112, Steps E and F. The residue was purified by reverse phase preparatory HPLC (Agilient 1100, column: Gemini® 5 μm $C_{18}$, 100 mm×30 mm (Phenomenex, Torrance, Calif.), gradient elution of 25% to 75% acetonitrile in water, where both solvents contain 0.1% TFA, 30 minutes) to give one of the compounds as the first (faster) eluting isomer. $^1$H NMR (500 MHz, CDCl$_3$, δ ppm): 7.36-7.33 (m, 4H), 7.25-7.17 (m, 3H), 7.02 (d, J=7.6 Hz, 1H), 5.11-5.05 (m, 2H), 4.77 (dd, J=9, 3.4 Hz, 1H), 4.00 (br, 1H), 3.35 (br, 1H), 3.21-3.01 (m, 3H), 2.96-2.93 (m, 1H), 2.60-2.54 (m, 1H), 2.14-2.05 (m, 1H), 1.70-1.60 (m, 1H), 1.31 (d, J=26.8 Hz, 3H), 1.07 (dd, J=7, 4.5 Hz, 6H), 0.52 (t, J=7.5 Hz, 3H). MS (ESI) m/z=570 [M+1].

Example 285

2-((2S,5R,6R)-6-(3-Chlorophenyl)-5-(4-chlorophenyl)-4-((S)-1-(((R)-3-methylbutan-2-yl)sulfonyl)butan-2-yl)-3-oxomorpholin-2-yl)acetic acid or 2-((2S,5R,6R)-6-(3-chlorophenyl)-5-(4-chlorophenyl)-4-((S)-1-(((S)-3-methylbutan-2-yl)sulfonyl)butan-2-yl)-3-oxomorpholin-2-yl)acetic acid or 2-((2R,5R,6R)-6-(3-chlorophenyl)-5-(4-chlorophenyl)-4-((S)-1-(((R)-3-methylbutan-2-yl)sulfonyl)butan-2-yl)-3-oxomorpholin-2-yl)acetic acid or 2-((2R,5R,6R)-6-(3-chlorophenyl)-5-(4-chlorophenyl)-4-((S)-1-(((S)-3-methylbutan-2-yl)sulfonyl)butan-2-yl)-3-oxomorpholin-2-yl)acetic acid

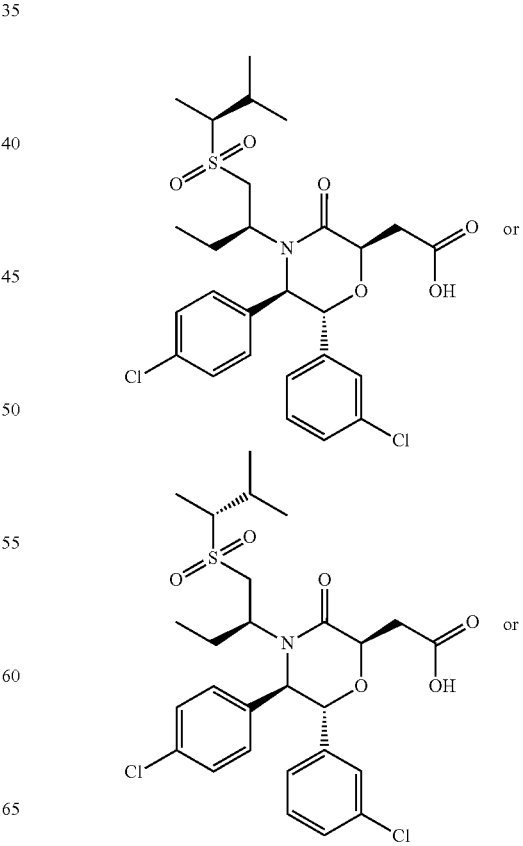

495
-continued

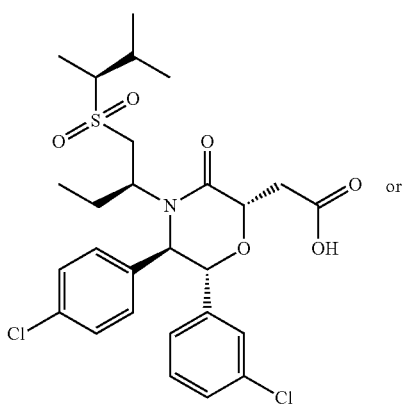

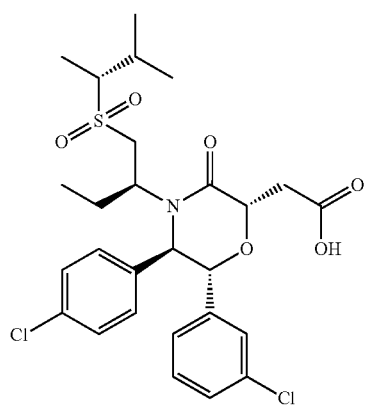

Further elution of the chromatographic purification described in Example 284, Step B provided one of the title compounds as the second (slower) eluting isomer.

$^1$H NMR (500 MHz, CDCl$_3$, δ ppm): 7.38-7.12 (7H), 6.90 (d, J=7.6 Hz, 1H), 5.03-4.95 (m, 2H), 4.07-4.00 (m, 1H), 3.29 (m, 1H), 3.19-3.06 (m 2H), 3.06-3.01 (m, 1H), 2.90-2.86 (m, 1H), 2.65-2.63 (m, 1H), 2.17-2.04 (m, 1H), 1.69-1.60 (m, 1H), 1.33 (d, J=26.8 Hz, 3H), 1.08 (dd, J=7, 4.5 Hz, 6H), 0.53 (t, J=7.5 Hz, 3H). MS (ESI) m/z=570 [M+1].

496

Example 286

2-((2R,5R,6R)-6-(3-Chlorophenyl)-5-(4-chlorophenyl)-4-((S)-1-cyclopropyl-2-(pyridin-4-ylsulfonyl)ethyl)-3-oxomorpholin-2-yl)acetic acid or 2-((2S,5R,6R)-6-(3-chlorophenyl)-5-(4-chlorophenyl)-4-((S)-1-cyclopropyl-2-(pyridin-4-ylsulfonyl)ethyl)-3-oxomorpholin-2-yl)acetic acid

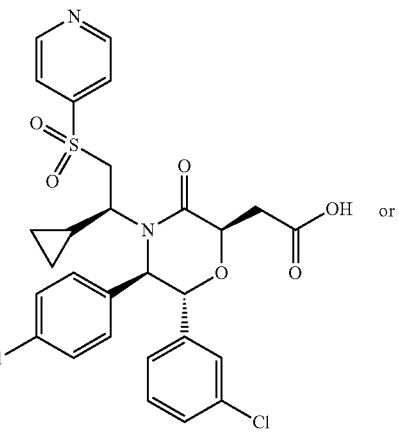

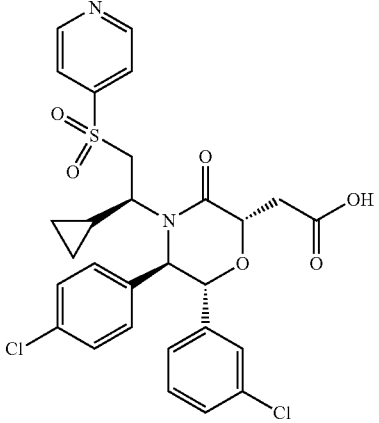

Step A. (2R,5R,6R)-2-Allyl-4-((S)-2-((tert-butyldimethylsilyl)oxy)-1-cyclopropylethyl)-6-(3-chlorophenyl)-5-(4-chlorophenyl)morpholin-3-one and (2S,5R,6R)-2-allyl-4-((S)-2-((tert-butyldimethylsilyl)oxy)-1-cyclopropylethyl)-6-(3-chlorophenyl)-5-(4-chlorophenyl)morpholin-3-one

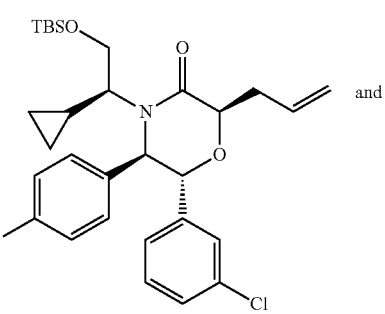

-continued

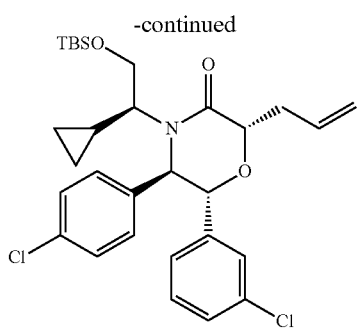

The title compounds were prepared from (5R,6R)-6-(3-chlorophenyl)-5-(4-chlorophenyl)-4-((S)-1-cyclopropyl-2-hydroxyethyl)morpholin-3-one (Example 154, Step B) by procedures analogous to those described in Example 214, Steps A and B.

Step B. (2R,5R,6R)-2-Allyl-6-(3-chlorophenyl)-5-(4-chlorophenyl)-4-((S)-1-cyclopropyl-2-hydroxyethyl)morpholin-3-one and (2S,5R,6R)-2-allyl-6-(3-chlorophenyl)-5-(4-chlorophenyl)-4-((S)-1-cyclopropyl-2-hydroxyethyl)morpholin-3-one

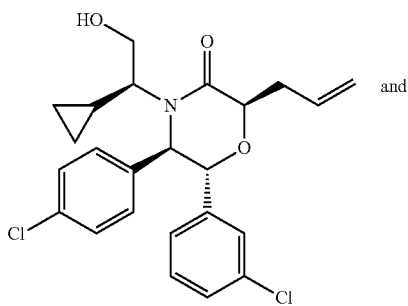

and

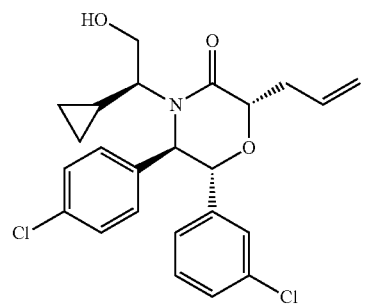

The title compounds were prepared from (2R,5R,6R)-2-allyl-4-((S)-2-((tert-butyldimethylsilyl)oxy)-1-cyclopropylethyl)-6-(3-chlorophenyl)-5-(4-chlorophenyl)morpholin-3-one and (2S,5R,6R)-2-allyl-4-((S)-2-((tert-butyldimethylsilyl)oxy)-1-cyclopropylethyl)-6-(3-chlorophenyl)-5-(4-chlorophenyl)morpholin-3-one (Example 286, Step A) by a procedure analogous to Example 214, Step D.

Step C. (2R,5R,6R)-2-Allyl-6-(3-chlorophenyl)-5-(4-chlorophenyl)-4-((S)-1-cyclopropyl-2-(pyridin-4-ylsulfonyl)ethyl)morpholin-3-one and (2S,5R,6R)-2-allyl-6-(3-chlorophenyl)-5-(4-chlorophenyl)-4-((S)-1-cyclopropyl-2-(pyridin-4-ylsulfonyl)ethyl)morpholin-3-one

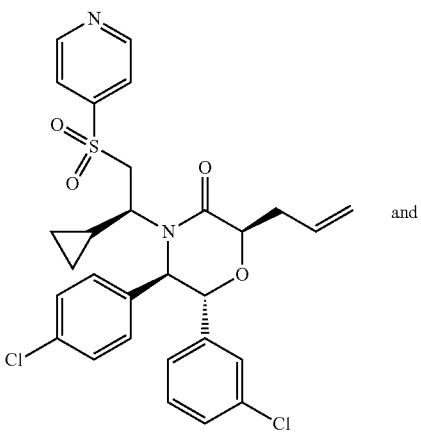

and

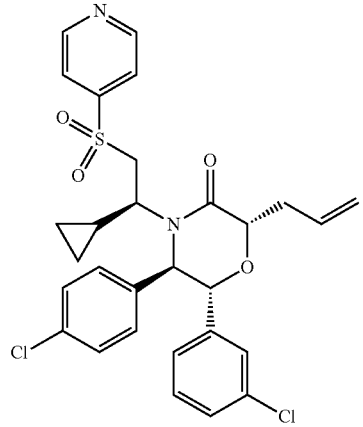

The title compounds were prepared from (2R,5R,6R)-2-allyl-6-(3-chlorophenyl)-5-(4-chlorophenyl)-4-((S)-1-cyclopropyl-2-hydroxyethyl)morpholin-3-one and (2S,5R,6R)-2-allyl-6-(3-chlorophenyl)-5-(4-chlorophenyl)-4-((S)-1-cyclopropyl-2-hydroxyethyl)morpholin-3-one (Example 286, Step B) by a procedure analogous to Example 112, Step D replacing ethanethiol with 4-mercaptopyridine Step D. 2-((2R,5R,6R)-6-(3-Chlorophenyl)-5-(4-chlorophenyl)-4-((S)-1-cyclopropyl-2-(pyridin-4-ylsulfonyl)ethyl)-3-oxomorpholin-2-yl)acetic acid or 2-((2S,5R,6R)-6-(3-chlorophenyl)-5-(4-chlorophenyl)-4-((S)-1-cyclopropyl-2-(pyridin-4-ylsulfonyl)ethyl)-3-oxomorpholin-2-yl)acetic acid

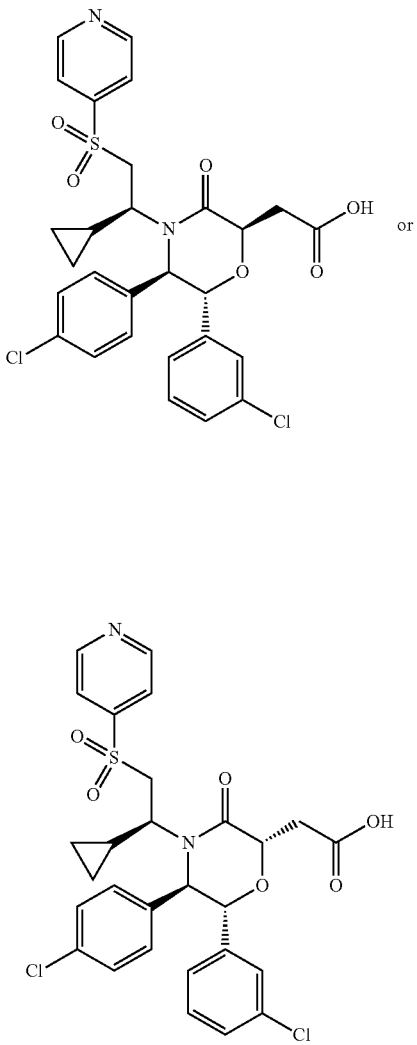

One of the title compounds was obtained from (2R,5R,6R)-2-allyl-6-(3-chlorophenyl)-5-(4-chlorophenyl)-4-((S)-1-cyclopropyl-2-(pyridin-4-ylsulfonyl)ethyl)morpholin-3-one and (2S,5R,6R)-2-allyl-6-(3-chlorophenyl)-5-(4-chlorophenyl)-4-((S)-1-cyclopropyl-2-(pyridin-4-ylsulfonyl)ethyl)morpholin-3-one (Example 286, Step C) by a procedure similar to that described in Example 112, Step F. The residue was purified by reverse phase preparatory HPLC (Agilient 1100, column: Gemini® 5 μm C$_{18}$, 100 mm×30 mm (Phenomenex, Torrance, Calif.), gradient elution of 25% to 100% acetonitrile in water, where both solvents contain 0.1% TFA, 30 minutes) to give one of the title compounds as the first (faster) eluting isomer. $^1$H NMR (400 MHz, CDCl$_3$, δ ppm): 8.95 (br. s., 2H), 7.90 (d, J=4.89 Hz, 1H), 7.39-7.42 (m, 4H), 7.25-7.33 (m, 4H), 7.17 (d, J=7.43 Hz, 1H), 5.11-5.24 (m, 1H), 4.97 (d, J=4.70 Hz, 1H), 4.52 (t, J=5.77 Hz, 1H), 4.03 (br. s., 1H), 3.21 (d, J=14.09 Hz, 1H), 3.09 (d, J=5.9 Hz, 2H), 1.63 (br. s., 1H), 0.53 (d, J=8.02 Hz, 2H), 0.14 (br. s., 1H), −0.40 (br. s., 1H). MS (ESI) m/z=589 [M+1].

Example 287

2-((2R,5R,6R)-6-(3-Chlorophenyl)-5-(4-chlorophenyl)-4-((S)-1-cyclopropyl-2-(pyridin-4-ylsulfonyl)ethyl)-3-oxomorpholin-2-yl)acetic acid or 2-((2S,5R,6R)-6-(3-chlorophenyl)-5-(4-chlorophenyl)-4-((S)-1-cyclopropyl-2-(pyridin-4-ylsulfonyl)ethyl)-3-oxomorpholin-2-yl)acetic acid

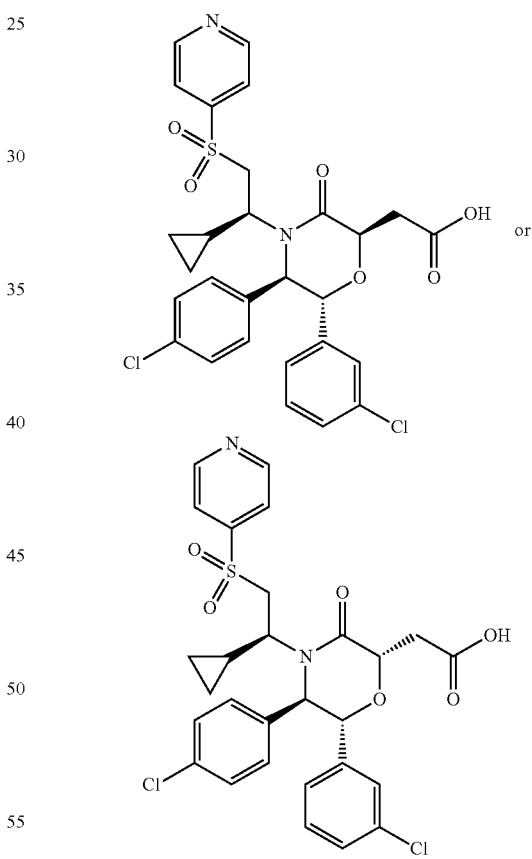

Further elution of the HPLC purification described in Example 286, Step D provided one of the title compounds as the second (slower) eluting isomer.

$^1$H NMR (400 MHz, CDCl$_3$, δ ppm): 8.98 (d, J=4.50 Hz, 2H), 7.98 (d, J=5.67 Hz, 2H), 7.35 (d, J=8.61 Hz, 2H), 7.15-7.25 (m, 3H), 7.06-7.15 (m, 2H), 6.83 (d, J=7.82 Hz, 1H), 5.03 (d, J=9.78 Hz, 1H), 4.67-4.85 (m, 2H), 3.01-3.40 (m, 5H), 1.86 (br. s., 1H), 0.40 (s, 2H), −0.12 (br. s., 1H), −0.67 (br. s., 1H). MS (ESI) m/z=589 [M+1].

Example 288

2-((2R,5R,6R)-6-(3-Chlorophenyl)-5-(4-chlorophenyl)-4-((S)-1-cyclopropyl-2-((2-hydroxy-2-methylpropyl)sulfonyl)ethyl)-3-oxomorpholin-2-yl)acetic acid or 2-((2S,5R,6R)-6-(3-chlorophenyl)-5-(4-chlorophenyl)-4-((S)-1-cyclopropyl-2-((2-hydroxy-2-methylpropyl)sulfonyl)ethyl)-3-oxomorpholin-2-yl)acetic acid

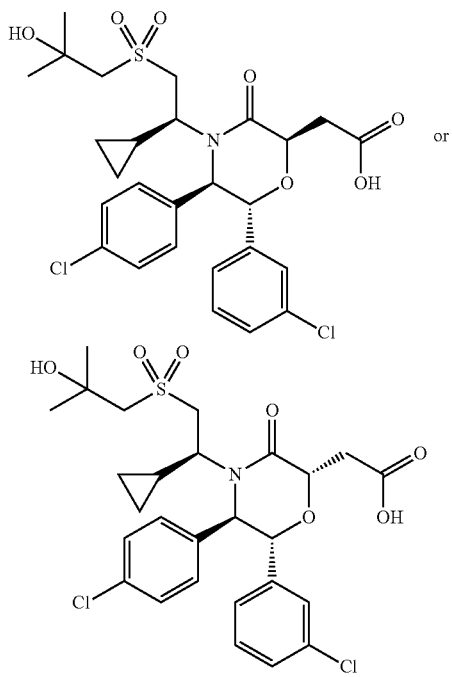

Step A. Methyl 2-((2R,5R,6R)-6-(3-chlorophenyl)-5-(4-chlorophenyl)-4-((S)-1-cyclopropyl-2-((2-hydroxy-2-methylpropyl)thio)ethyl)-3-oxomorpholin-2-yl)acetate and methyl 2-((2S,5R,6R)-6-(3-chlorophenyl)-5-(4-chlorophenyl)-4-((S)-1-cyclopropyl-2-((2-hydroxy-2-methylpropyl)thio)ethyl)-3-oxomorpholin-2-yl)acetate

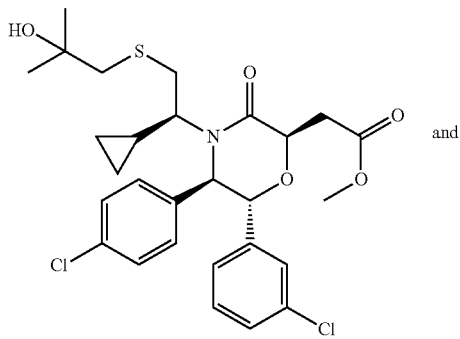

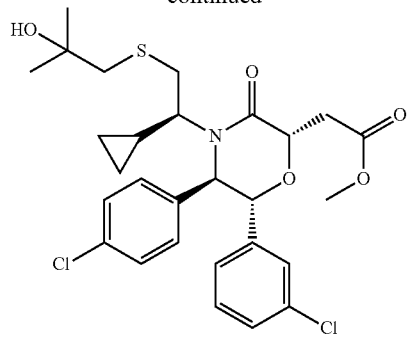

The title compounds were obtained from (2R,5R,6R)-2-Allyl-4-((S)-2-((tert-butyldimethylsilyl)oxy)-1-cyclopropylethyl)-6-(3-chlorophenyl)-5-(4-chlorophenyl)morpholin-3-one and (2S,5R,6R)-2-allyl-4-((S)-2-((tert-butyldimethylsilyl)oxy)-1-cyclopropylethyl)-6-(3-chlorophenyl)-5-(4-chlorophenyl)morpholin-3-one (Example 286, Step A) by procedures similar to that described in Example 214, Steps C through E, replacing phenylmethanethiol in Step E with 1-mercapto-2-methypropan-2-ol.

Step B. Methyl 2-((2R,5R,6R)-6-(3-chlorophenyl)-5-(4-chlorophenyl)-4-((S)-1-cyclopropyl-2-((2-hydroxy-2-methylpropyl)sulfonyl)ethyl)-3-oxomorpholin-2-yl)acetate and methyl 2-((2S,5R,6R)-6-(3-chlorophenyl)-5-(4-chlorophenyl)-4-((S)-1-cyclopropyl-2-((2-hydroxy-2-methylpropyl)sulfonyl)ethyl)-3-oxomorpholin-2-yl)acetate

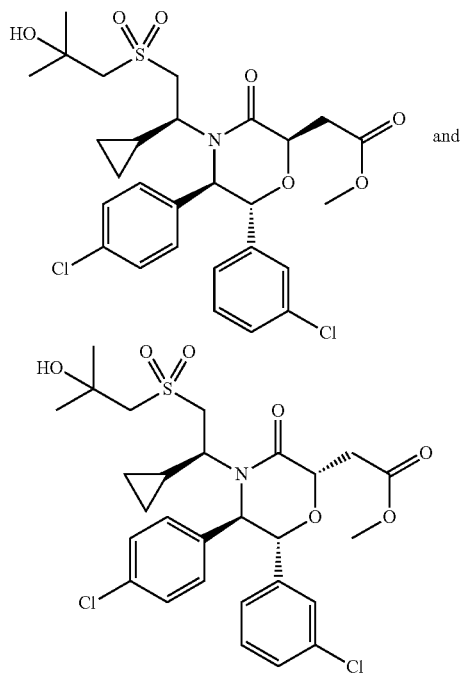

Methyl 2-((2R,5R,6R)-6-(3-chlorophenyl)-5-(4-chlorophenyl)-4-((S)-1-cyclopropyl-2-((2-hydroxy-2-methylpropyl)thio)ethyl)-3-oxomorpholin-2-yl)acetate and methyl 2-((2S,5R,6R)-6-(3-chlorophenyl)-5-(4-chlorophenyl)-4-

((S)-1-cyclopropyl-2-((2-hydroxy-2-methylpropyl)thio)ethyl)-3-oxomorpholin-2-yl)acetate (190 mg, 0.335 mmol, Example 288, Step A) were dissolved in a mixture of water (1.437 mL), acetonitrile (0.958 mL), and carbon tetrachloride (0.958 mL) and rapidly stirred. Sodium periodate (430 mg, 2.012 mmol) was added, followed by ruthenium(III) chloride hydrate (7.56 mg, 0.034 mmol). The mixture was stirred vigorously then acidified with 10% citric acid and diluted with ethyl acetate. The mixture was extracted with ethyl acetate (2×). The combined organic layers were washed with brine, dried over $Na_2SO_4$, filtered, and concentrated under reduced pressure.

Step C. 2-((2R,5R,6R)-6-(3-Chlorophenyl)-5-(4-chlorophenyl)-4-((S)-1-cyclopropyl-2-((2-hydroxy-2-methylpropyl)sulfonyl)ethyl)-3-oxomorpholin-2-yl)acetic acid or 2-((2S,5R,6R)-6-(3-chlorophenyl)-5-(4-chlorophenyl)-4-((S)-1-cyclopropyl-2-((2-hydroxy-2-methylpropyl)sulfonyl)ethyl)-3-oxomorpholin-2-yl)acetic acid

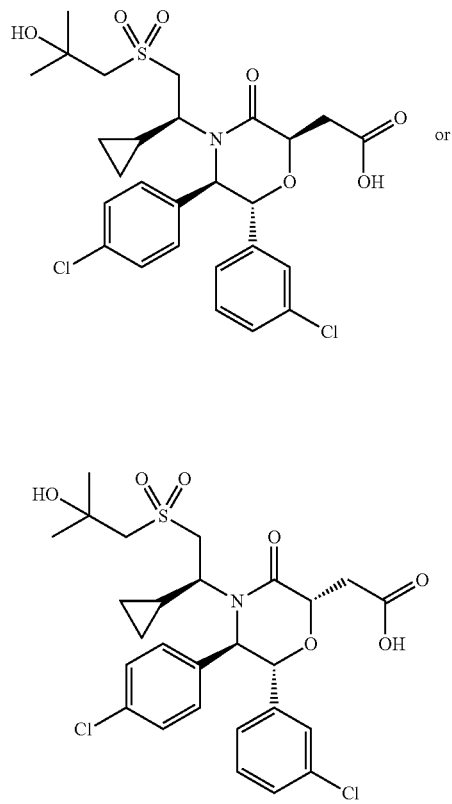

One of the title compounds was obtained from methyl 2-((2R,5R,6R)-6-(3-chlorophenyl)-5-(4-chlorophenyl)-4-((S)-1-cyclopropyl-2-((2-hydroxy-2-methylpropyl)sulfonyl)ethyl)-3-oxomorpholin-2-yl)acetate and methyl 2-((2S,5R,6R)-6-(3-chlorophenyl)-5-(4-chlorophenyl)-4-((S)-1-cyclopropyl-2-((2-hydroxy-2-methylpropyl)sulfonyl)ethyl)-3-oxomorpholin-2-yl)acetate (Example 288, Step B) by a procedure similar to that described in Example 214, Step G. The residue was purified by reverse phase preparatory HPLC (Agilient 1100, column: Gemini® 5 μm $C_{18}$, 100 mm×30 mm (Phenomenex, Torrance, Calif.), gradient elution of 25% to 75% acetonitrile in water, where both solvents contain 0.1% TFA, 30 minutes) to give one of the compounds as the first (faster) eluting isomer. $^1$H NMR (400 MHz, CDCl$_3$, δ ppm): 7.33-7.44 (m, 5H), 7.22-7.32 (m, 2H), 7.17 (d, J=7.43 Hz, 1H), 5.15 (d, J=4.50 Hz, 1H), 4.95 (d, J=4.70 Hz, 1H), 4.58 (t, J=5.77 Hz, 1H), 3.99 (br. s., 1H), 3.10-3.37 (m, 7H), 1.59 (br. s., 1H), 1.47 (d, J=1.76 Hz, 6H), 0.54 (br. s., 2H), 0.21 (br. s., 1H), −0.42 (br. s., 1H). MS (ESI) m/z=584 [M+1].

Example 289

2-((2R,5R,6R)-6-(3-Chlorophenyl)-5-(4-chlorophenyl)-4-((S)-1-cyclopropyl-2-((2-hydroxy-2-methylpropyl)sulfonyl)ethyl)-3-oxomorpholin-2-yl)acetic acid or 2-((2S,5R,6R)-6-(3-chlorophenyl)-5-(4-chlorophenyl)-4-((S)-1-cyclopropyl-2-((2-hydroxy-2-methylpropyl)sulfonyl)ethyl)-3-oxomorpholin-2-yl)acetic acid

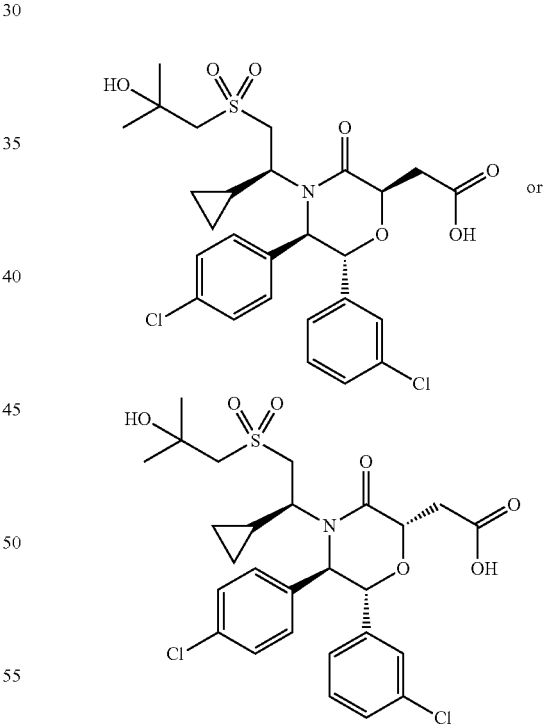

Further elution of the HPLC purification described in Example 288, Step C provided one of the title compounds as the second (slower) eluting isomer.

$^1$H NMR (400 MHz, CDCl$_3$, δ ppm): 7.31 (d, J=8.41 Hz, 2H), 7.18-7.24 (m, 1H), 7.04-7.18 (m, 4H), 6.81-6.83 (m, 1H), 4.99 (d, J=9.78 Hz, 1H), 4.68-4.82 (m, 2H), 3.86 (br. s., 3H), 3.03-3.39 (m, 4H), 1.82 (br. s., 1H), 1.51 (d, J=15.65 Hz, 6H), 0.42 (br. s., 2H), −0.11 (br. s., 1H), −0.74 (br. s., 1H). MS (ESI) m/z=584 [M+1].

Example 290

2-((2R,5R,6R)-6-(3-Chlorophenyl)-5-(4-chlorophenyl)-4-((S)-2-((2-cyanopropan-2-yl)sulfonyl)-1-cyclopropylethyl)-3-oxomorpholin-2-yl)acetic acid or 2-((2S,5R,6R)-6-(3-chlorophenyl)-5-(4-chlorophenyl)-4-((S)-2-((2-cyanopropan-2-yl)sulfonyl)-1-cyclopropylethyl)-3-oxomorpholin-2-yl)acetic acid

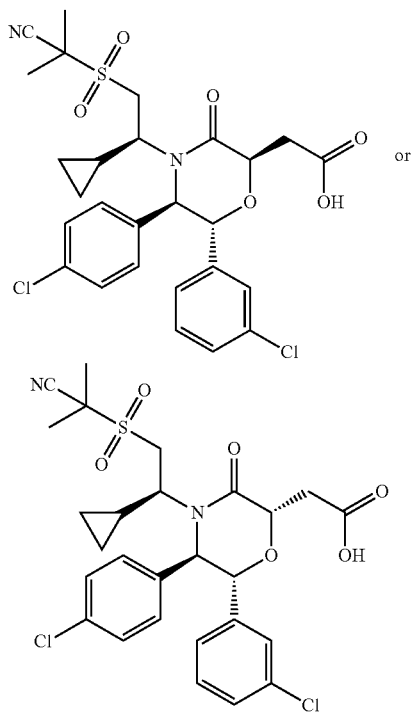

Step A. (S)-2-((2R,3R)-2-(3-Chlorophenyl)-3-(4-chlorophenyl)-5-oxomorpholino)-2-cyclopropylethyl methanesulfonate

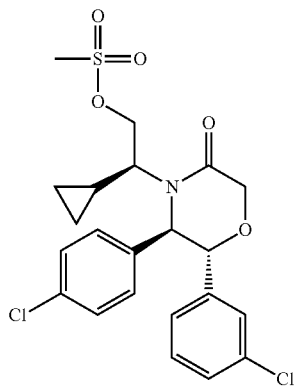 [SMILES: CS(=O)(=O)OC[C@H](C1CC1)N1C(=O)CO[C@H](c2cccc(Cl)c2)[C@H]1c1ccc(Cl)cc1]

Triethylamine (66.7 µL, 0.480 mmol) was added to a solution of (5R,6R)-6-(3-chlorophenyl)-5-(4-chlorophenyl)-4-((S)-1-cyclopropyl-2-hydroxyethyl)morpholin-3-one (Example 154, Step B) and methanesulfonic anhydride (62.7 mg, 0.360 mmol) in THF (800 µL) and stirred at room temperature. After 5 minutes, the mixture was diluted with dichloromethane and brine. The aqueous layer was extracted with dichloromethane (2×). The combined organic layers were dried over $Na_2SO_4$, filtered, and concentrated under reduced pressure to give the title compound.

Step B. S-((S)-2-((2R,3R)-2-(3-Chlorophenyl)-3-(4-chlorophenyl)-5-oxomorpholino)-2-cyclopropylethyl)ethanethioate

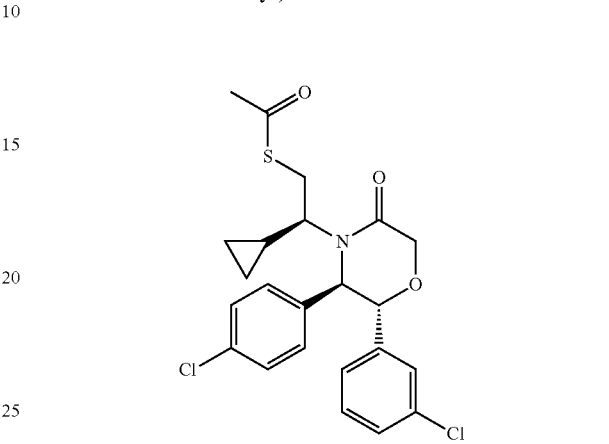

A solution of (S)-2-((2R,3R)-2-(3-chlorophenyl)-3-(4-chlorophenyl)-5-oxomorpholino)-2-cyclopropylethyl methanesulfonate (116 mg, 0.239 mmol, Example 290, Step A) in thioacetic acid (856 µL, 11.97 mmol) was stirred at 25° C. for 10 minutes and then heated to 90° C. overnight. The mixture was concentrated under reduced pressure and the residue was purified by flash chromatography on silica gel (12 g column; gradient elution of 0% to 20% ethyl acetate in hexanes) to give the title compound as a colorless film.

Step C. (5R,6R)-6-(3-Chlorophenyl)-5-(4-chlorophenyl)-4-((S)-1-cyclopropyl-2-mercaptoethyl)morpholin-3-one

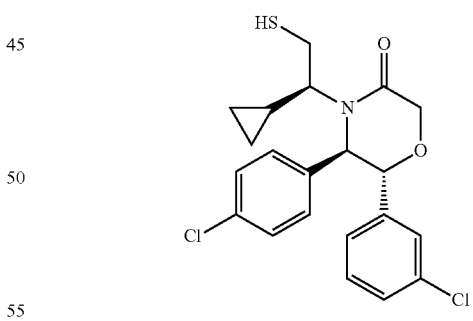

S-((S)-2-((2R,3R)-2-(3-Chlorophenyl)-3-(4-chlorophenyl)-5-oxomorpholino)-2-cyclopropylethyl)ethanethioate (66 mg, 0.142 mmol, Example 290, Step B) was dissolved in a mixture of THF (474 µL), MeOH (474 µL), and water (474 µL) at 25° C. under Ar(g). Lithium hydroxide (2 M in water, 85 µL, 0.171 mmol) was added, and the solution was stirred at 25° C. for 20 minutes. The mixture was quenched with 10% aqueous citric acid and extracted with ethyl acetate (2×). The combined organic layers were washed with brine (2×), dried over $Na_2SO_4$, filtered, and concentrated under reduced pressure.

Step D. 2-(((S)-2-((2R,3R)-2-(3-Chlorophenyl)-3-(4-chlorophenyl)-5-oxomorpholino)-2-cyclopropylethyl)thio)acetonitrile

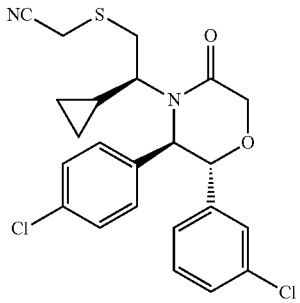 [SMILES: N#CCSC[C@H](C1CC1)N1C(=O)CO[C@H](c2cccc(Cl)c2)[C@H]1c1ccc(Cl)cc1]

Sodium hydride (60% dispersion in mineral oil, 10.23 mg, 0.256 mmol) was added to a solution of (5R,6R)-6-(3-chlorophenyl)-5-(4-chlorophenyl)-4-((S)-1-cyclopropyl-2-mercaptoethyl)morpholin-3-one (60 mg, 0.142 mmol, Example 290, Step C) and 2-bromoacetonitrile (37.9 µL, 0.568 mmol) in DMF (710 µL) at 0° C. The mixture was stirred at 0° C. for 20 minutes and warmed to room temperature. The mixture was stirred at room temperature for 20 minutes and quenched with saturated aqueous NH$_4$Cl. The mixture was extracted with ethyl acetate (2×), and the combined organic layers were washed with brine (3×), dried over Na$_2$SO$_4$, filtered, and concentrated under reduced pressure. The residue was purified by flash chromatography on silica gel (12 g column; stepwise gradient elution of 30% and 40% ethyl acetate in hexanes) to give the title compound.

Step E. 2-(((S)-2-((2R,3R)-2-(3-Chlorophenyl)-3-(4-chlorophenyl)-5-oxomorpholino)-2-cyclopropylethyl)thio)-2-methylpropanenitrile

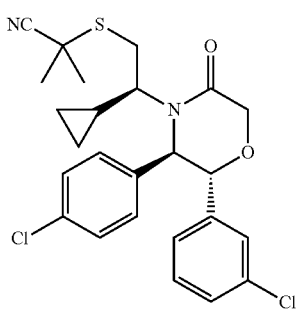 [SMILES: CC(C)(C#N)SC[C@H](C1CC1)N1C(=O)CO[C@H](c2cccc(Cl)c2)[C@H]1c1ccc(Cl)cc1]

Potassium hydroxide (50% aqueous solution, 79 µL, 0.988 mmol) was added to a solution of 2-(((S)-2-((2R,3R)-2-(3-chlorophenyl)-3-(4-chlorophenyl)-5-oxomorpholino)-2-cyclopropylethyl)thio)acetonitrile (57 mg, 0.124 mmol, Example 290, Step D) and iodomethane (30.9 µL, 0.494 mmol) in DMSO (618 µL) at 0° C. The mixture was warmed to room temperature and stirred for 45 minutes. The mixture was diluted with water and extracted with ethyl acetate (2×). The combined organic layers were washed with brine (3×), dried over Na$_2$SO$_4$, filtered, and concentrated under reduced pressure. The residue was purified by flash chromatography on silica gel (12 g column; gradient elution of 25% to 30% ethyl acetate in hexanes) to give the title compound.

Step F. 2-((2R,5R,6R)-6-(3-Chlorophenyl)-5-(4-chlorophenyl)-4-((S)-2-((2-cyanopropan-2-yl)sulfonyl)-1-cyclopropylethyl)-3-oxomorpholin-2-yl)acetic acid or 2-((2S,5R,6R)-6-(3-chlorophenyl)-5-(4-chlorophenyl)-4-((S)-2-((2-cyanopropan-2-yl)sulfonyl)-1-cyclopropylethyl)-3-oxomorpholin-2-yl)acetic acid

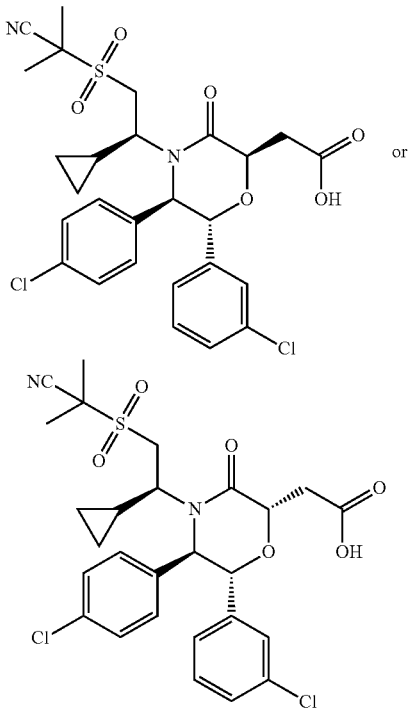

One of the title compounds was obtained from 2-(((S)-2-((2R,3R)-2-(3-chlorophenyl)-3-(4-chlorophenyl)-5-oxomorpholino)-2-cyclopropylethyl)thio)-2-methylpropanenitrile (Example 290, Step E) by procedures similar to those described in Example 112, Steps E and F. The residue was purified by reverse phase preparatory HPLC (Agilient 1100, column: Gemini® 5 µm C$_{18}$, 100 mm×30 mm (Phenomenex, Torrance, Calif.), gradient elution of 40% to 60% acetonitrile in water, where both solvents contain 0.1% TFA, 25 minutes) to give one of the compounds as the first (faster) eluting isomer. $^1$H NMR (400 MHz, CDCl$_3$, δ ppm): 7.31-7.41 (m, 5H), 7.21-7.29 (m, 2), 7.12 (d, J=7.2 Hz, 1H), 5.06 (d, J=4.9 Hz, 1H), 4.96 (d, J=5.1 Hz, 1H), 4.63-4.70 (m, 1H), 4.26-4.38 (m, 1H), 3.92-4.03 (m, 1H), 3.39-3.49 (m, 1H), 3.14 (d, J=5.5 Hz, 2H), 2.92-3.06 (m, 1H), 1.79 (s, 3H), 1.78 (s, 3H), 0.39-0.58 (m, 2H), 0.05-0.17 (m, 1H), −0.67 to −0.51 (m, 1H). MS (ESI) m/z=579 [M+H].

Example 291

2-((2R,5R,6R)-6-(3-Chlorophenyl)-5-(4-chlorophenyl)-4-((S)-2-((2-cyanopropan-2-yl)sulfonyl)-1-cyclopropylethyl)-3-oxomorpholin-2-yl)acetic acid or 2-((2S,5R,6R)-6-(3-Chlorophenyl)-5-(4-chlorophenyl)-4-((S)-2-((2-cyanopropan-2-yl)sulfonyl)-1-cyclopropylethyl)-3-oxomorpholin-2-yl)acetic acid

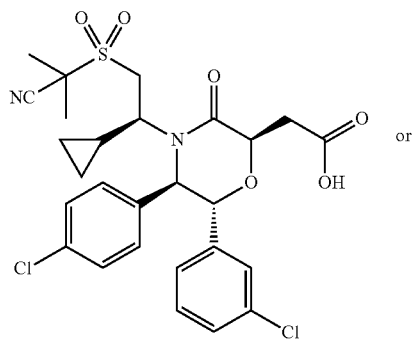

or

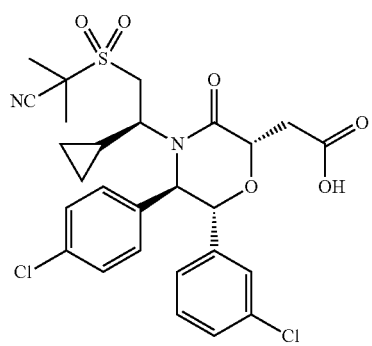

Further elution of the HPLC purification described in Example 290, Step F provided one of the title compounds as the second (slower) eluting isomer.

$^1$H NMR (400 MHz, CDCl$_3$, δ ppm): 7.33 (d, J=8.4 Hz, 2H), 7.05-7.23 (m, 5H), 6.82 (d, J=7.8 Hz, 1H), 4.92 (d, J=9.8 Hz, 1H), 4.71-4.82 (m, 2H), 4.48-4.63 (m, 1H), 3.40-3.50 (m, 1H), 3.17-3.25 (m, 1H), 3.01-3.15 (m, 1H), 2.64-2.75 (m, 1H), 2.33-2.41 (m, 1H), 1.82 (m, 3H), 1.79 (m, 3H), 0.34-0.53 (m, 2H), −0.15 to −0.01 (m, 1H), −0.86 to −0.68 (m, 1H). MS (ESI) m/z=579 [M+H].

Example 292

2-((2R,5R,6R)-4-((S)-2-(N-(tert-Butyl)sulfamoyl)-1-cyclopropylethyl)-6-(3-chlorophenyl)-5-(4-chlorophenyl)-3-oxomorpholin-2-yl)acetic acid or 2-((2S,5R,6R)-4-((S)-2-(N-(tert-butyl)sulfamoyl)-1-cyclopropylethyl)-6-(3-chlorophenyl)-5-(4-chlorophenyl)-3-oxomorpholin-2-yl)acetic acid

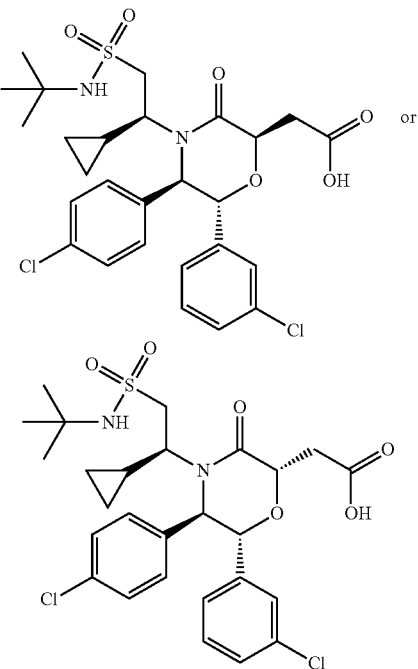

One of the title compounds was obtained from (2R,5R,6R)-2-allyl-4-((S)-2-((tert-butyldimethylsilyl)oxy)-1-cyclopropylethyl)-6-(3-chlorophenyl)-5-(4-chlorophenyl)morpholin-3-one and (2S,5R,6R)-2-allyl-4-((S)-2-((tert-butyldimethylsilyl)oxy)-1-cyclopropylethyl)-6-(3-chlorophenyl)-5-(4-chlorophenyl)morpholin-3-one (Example 286, Step A) by procedures similar to those described in Example 214, Steps B through G, replacing dimethylamine hydrochloride in Step F with 2-methylpropan-2-amine. The residue was purified by reverse phase preparatory HPLC (Agilent 1100, column: Gemini® 5 μm C$_{18}$, 100 mm×30 mm (Phenomenex, Torrance, Calif.), gradient elution of 25% to 75% acetonitrile in water, where both solvents contain 0.1% TFA, 30 minutes) to give one of the compounds as the first (faster) eluting isomer. $^1$H NMR (400 MHz, CDCl$_3$, δ ppm): 7.37 (s, 4H), 7.21-7.32 (m, 3H), 7.15 (d, J=7.63 Hz, 1H), 5.13 (d, J=4.70 Hz, 1H), 4.93 (d, J=4.69 Hz, 1H), 4.65 (dd, J=7.53, 5.18 Hz, 1H), 3.17-3.25 (m, 1H), 3.03-3.13 (m, 2H), 2.70 (br. s., 4H), 1.34 (s, 9H), 0.60 (br. s., 2H), 0.18 (br. s., 1H), −0.30 to −0.12 (m, 1H). MS (ESI) m/z=583 [M+1].

Example 293

2-((2R,5R,6R)-4-((S)-2-(N-(tert-Butyl)sulfamoyl)-1-cyclopropylethyl)-6-(3-chlorophenyl)-5-(4-chlorophenyl)-3-oxomorpholin-2-yl)acetic acid or
2-((2S,5R,6R)-4-((S)-2-(N-(tert-butyl)sulfamoyl)-1-cyclopropylethyl)-6-(3-chlorophenyl)-5-(4-chlorophenyl)-3-oxomorpholin-2-yl)acetic acid

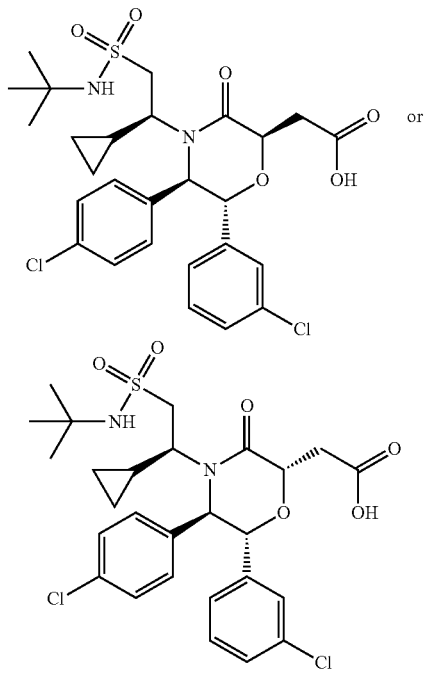

Further elution of the HPLC purification described in Example 292 provided one of the title compounds as the second (slower) eluting isomer.

$^1$H NMR (400 MHz, CDCl$_3$, δ ppm): 7.30 (d, J=8.61 Hz, 2H), 7.15-7.23 (m, 4H), 7.10 (t, J=7.83 Hz, 1H), 7.06 (t, J=1.66 Hz, 1H), 6.81 (br. s., 1H), 4.95 (d, J=9.78 Hz, 1H), 4.70-4.81 (m, 2H), 2.56-3.28 (m, 5H), 1.39 (s, 9H), 0.43 (+2H), −0.16 (br. s., 1H), −0.80 (br. s., 1H). MS (ESI) m/z=583 [M+1].

Examples 294-307

Examples 294 to 307 were also prepared from (2R,5R,6R)-2-allyl-4-((S)-2-((tert-butyldimethylsilyl)oxy)-1-cyclopropylethyl)-6-(3-chlorophenyl)-5-(4-chlorophenyl)morpholin-3-one and (2S,5R,6R)-2-allyl-4-((S)-2-((tert-butyldimethylsilyl)oxy)-1-cyclopropylethyl)-6-(3-chlorophenyl)-5-(4-chlorophenyl)morpholin-3-one (Example 286, Step A) by procedures similar to those described in Example 214, Steps B through G, substituting dimethylamine hydrochloride in Step F with an equivalent amount of the appropriate amine or aniline.

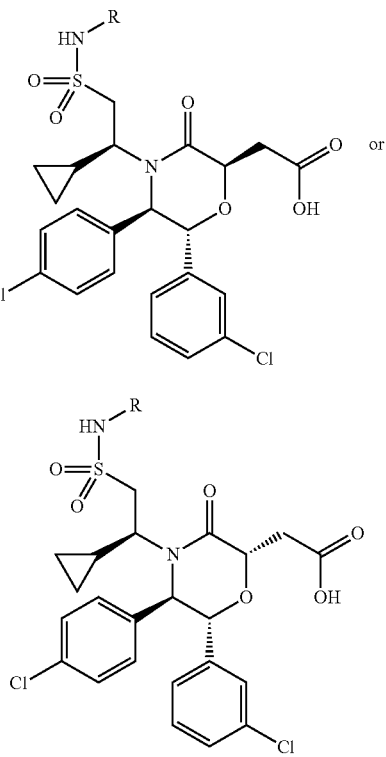

| Example | R | Reagent used |
|---|---|---|
| 294/295 | ![H2N-phenyl-F] | 4-fluoroaniline |
| 296/297 | ![methylpyrrolidine] | (s)-(+)-2-methylpyrrolidine |
| 298/299 | ![fluoroindoline] | 5-fluoroindoline |
| 300/301 | ![N-methyl-tert-butylamine] | N-methyl-tert-butylamine |
| 302/303 | ![morpholine] | morpholine |
| 304/305 | ![R-methylpyrrolidine] | (R)-(−)-2-methylpyrrolidine |
| 306/307 | ![dimethylpyrrolidine] | 2,2-dimethylpyrrolidine |

Example 294

2-((2R,5R,6R)-6-(3-Chlorophenyl)-5-(4-chlorophenyl)-4-((S)-1-cyclopropyl-2-(N-(2-fluorophenyl)sulfamoyl)ethyl)-3-oxomorpholin-2-yl)acetic acid or 2-((2S,5R,6R)-6-(3-chlorophenyl)-5-(4-chlorophenyl)-4-((S)-1-cyclopropyl-2-(N-(2-fluorophenyl)sulfamoyl)ethyl)-3-oxomorpholin-2-yl)acetic acid (faster eluting isomer)

$^1$H NMR (400 MHz, CDCl$_3$, δ ppm): 7.49-7.62 (m, 1H), 7.35-7.47 (m, 4H), 7.29-7.33 (m, 1H), 7.26 (br. s., 1H), 7.05-7.21 (m, 4H), 5.06-5.20 (m, 1H), 4.86-5.00 (m, 1H), 4.61-4.76 (m, 1H), 3.18-3.35 (m, 1H), 3.05-3.16 (m, 1H), 2.90-3.04 (m, 1H), 2.19-2.32 (m, 1H), 1.95-2.07 (m, 1H), 1.55-1.72 (m, 1H), 1.32-1.40 (m, 2H), 0.86-0.96 (m, 1H), 0.68-0.85 (m, 1H), 0.45-0.65 (m, 1H), 0.07-0.21 (m, 1H). MS (ESI) m/z=621 [M+1].

Example 295

2-((2R,5R,6R)-6-(3-Chlorophenyl)-5-(4-chlorophenyl)-4-((S)-1-cyclopropyl-2-(N-(2-fluorophenyl)sulfamoyl)ethyl)-3-oxomorpholin-2-yl)acetic acid or 2-((2S,5R,6R)-6-(3-chlorophenyl)-5-(4-chlorophenyl)-4-((S)-1-cyclopropyl-2-(N-(2-fluorophenyl)sulfamoyl)ethyl)-3-oxomorpholin-2-yl)acetic acid Further elution of the chromatographic separation in Example 294 provided one of the title compounds as the second (slower) eluting isomer. $^1$H NMR (400 MHz, CDCl$_3$, δ ppm): 7.45-7.60 (m, 1H), 7.28-7.34 (m, 1H), 7.03-7.24 (m, 8H), 4.94 (s, 1H), 4.76 (s, 2H), 3.90 (d, J=5.7 Hz, 1H), 3.65 (s, 1H), 3.11-3.24 (m, 3H), 1.27 (br. s., 3H), 0.80-0.94 (m, 1H), 0.33-0.57 (m, 1H). MS (ESI) m/z=621 [M+1].

Example 296

2-((2R,5R,6R)-6-(3-Chlorophenyl)-5-(4-chlorophenyl)-4-((S)-1-cyclopropyl-2-(((S)-2-methylpyrrolidin-1-yl)sulfonyl)ethyl)-3-oxomorpholin-2-yl)acetic acid or 2-((2S,5R,6R)-6-(3-chlorophenyl)-5-(4-chlorophenyl)-4-((S)-1-cyclopropyl-2-(((S)-2-methylpyrrolidin-1-yl)sulfonyl)ethyl)-3-oxomorpholin-2-yl)acetic acid (faster eluting isomer). $^1$H NMR (400 MHz, CDCl$_3$, δ ppm): 7.30-7.38 (m, 5H), 7.17-7.27 (m, 3H), 5.13 (d, J=5.1 Hz, 1H), 4.94 (d, J=5.1 Hz, 1H), 4.58-4.71 (m, 1H), 3.85-3.96 (m, 3H), 3.26-3.50 (m, 2H), 3.14 (dd, J=12.1, 6.1 Hz, 3H), 1.83-2.15 (m, 3H), 1.71-1.82 (m, 1H), 1.55-1.70 (m, 1H), 1.25-1.35 (m, 3H), 0.30-0.56 (m, 2H), −0.13-0.22 (m, 1H), −0.86 to −0.51 (m, 1H). MS (ESI) m/z=595 [M+1].

Example 297

2-((2R,5R,6R)-6-(3-Chlorophenyl)-5-(4-chlorophenyl)-4-((S)-1-cyclopropyl-2-(((S)-2-methylpyrrolidin-1-yl)sulfonyl)ethyl)-3-oxomorpholin-2-yl)acetic acid or 2-((2S,5R,6R)-6-(3-chlorophenyl)-5-(4-chlorophenyl)-4-((S)-1-cyclopropyl-2-(((S)-2-methylpyrrolidin-1-yl)sulfonyl)ethyl)-3-oxomorpholin-2-yl)acetic acid Further elution of the chromatographic separation in Example 296 provided one of the title compounds as the second (slower) eluting isomer. $^1$H NMR (400 MHz, CDCl$_3$, δ ppm): 7.30 (d, J=8.6 Hz, 2H), 7.18-7.23 (m, 1H), 7.15 (d, J=9.8 Hz, 2H), 7.08-7.12 (m, 1H), 7.06 (s, 1H), 6.88 (d, J=7.6 Hz, 1H), 4.98 (d, J=9.8 Hz, 1H), 4.76-4.84 (m, 1H), 4.72 (d, J=10.0 Hz, 1H), 4.11-4.31 (m, 1H), 3.85-4.00 (m, 1H), 3.38-3.49 (m, 1H), 3.24-3.36 (m, 2H), 2.87-3.03 (m, 3H), 1.76-2.17 (m, 4H), 1.58-1.72 (m, 1H), 1.30 (d, J=6.5 Hz, 3H), 0.25-0.50 (m, 2H), −0.31 to −0.08 (m, 1H), −1.04 to −0.75 (m, 1H). MS (ESI) m/z=595 [M+1].

Example 298

2-((2R,5R,6R)-6-(3-Chlorophenyl)-5-(4-chlorophenyl)-4-((S)-1-cyclopropyl-2-((5-fluoroindolin-1-yl)sulfonyl)ethyl)-3-oxomorpholin-2-yl)acetic acid or 2-((2S,5R,6R)-6-(3-chlorophenyl)-5-(4-chlorophenyl)-4-((S)-1-cyclopropyl-2-((5-fluoroindolin-1-yl)sulfonyl)ethyl)-3-oxomorpholin-2-yl)acetic acid (faster eluting isomer). $^1$H NMR (400 MHz, CDCl$_3$, δ ppm): 7.28-7.38 (m, 6H), 7.23 (d, J=7.8 Hz, 2H), 7.13 (d, J=7.6 Hz, 1H), 6.92-6.96 (m, 1H), 6.88 (td, J=8.8, 2.7 Hz, 1H), 5.00-5.16 (m, 1H), 4.94 (d, J=5.6 Hz, 1H), 4.57-4.79 (m, 1H), 4.02 (s, 3H), 3.13 (dd, J=7.6, 6.4 Hz, 5H), 2.94-3.05 (m, 1H), 1.54-1.79 (m, 1H), 0.30-0.57 (m, 2H), −0.14-0.21 (m, 1H), −0.86 to −0.42 (m, 1H). MS (ESI) m/z=669 [M+Na].

Example 299

2-((2R,5R,6R)-6-(3-Chlorophenyl)-5-(4-chlorophenyl)-4-((S)-1-cyclopropyl-2-((5-fluoroindolin-1-yl)sulfonyl)ethyl)-3-oxomorpholin-2-yl)acetic acid or 2-((2S,5R,6R)-6-(3-chlorophenyl)-5-(4-chlorophenyl)-4-((S)-1-cyclopropyl-2-((5-fluoroindolin-1-yl)sulfonyl)ethyl)-3-oxomorpholin-2-yl)acetic acid Further elution of the chromatographic separation in Example 298 provided one of the title compounds as the second (slower) eluting isomer. $^1$H NMR (400 MHz, CDCl$_3$, δ ppm): 7.32 (d, J=8.3 Hz, 2H), 7.23-7.26 (m, 1H), 7.19-7.23 (m, 1H), 7.13 (q, J=8.1 Hz, 3H), 7.07 (t, J=1.6 Hz, 1H), 6.82-6.97 (m, 3H), 4.94 (d, J=9.8 Hz, 1H), 4.79-4.87 (m, 1H), 4.74 (d, J=9.8 Hz, 1H), 4.18-4.44 (m, 1H), 4.04 (dd, J=9.3, 7.8 Hz, 2H), 3.25-3.36 (m, 1H), 3.16 (d, J=8.6 Hz, 2H), 2.99 (dd, J=16.4, 5.4 Hz, 2H), 2.41-2.69 (m, 1H), 1.67-1.90 (m, 1H), 0.25-0.47 (m, 2H), −0.34 to −0.13 (m, 1H), −0.95 to −0.74 (m, 1H). MS (ESI) m/z=669 [M+1].

Example 300

2-((2R,5R,6R)-4-((S)-2-(N-(tert-Butyl)-N-methylsulfamoyl)-1-cyclopropylethyl)-6-(3-chlorophenyl)-5-(4-chlorophenyl)-3-oxomorpholin-2-yl)acetic acid or 2-((2S,5R,6R)-4-((S)-2-(N-(tert-butyl)-N-methylsulfamoyl)-1-cyclopropylethyl)-6-(3-chlorophenyl)-5-(4-chlorophenyl)-3-oxomorpholin-2-yl)acetic acid (faster eluting isomer). $^1$H NMR (400 MHz, CDCl$_3$, δ ppm): 7.33 (d, J=9.2 Hz, 5H), 7.12-7.26 (m, 3H), 5.07-5.18 (m, 1H), 4.84-4.99 (m, 1H), 4.58-4.78 (m, 1H), 3.88-4.19 (m, 1H), 3.03-3.27 (m, 3H), 2.90 (s, 3H), 1.44 (s, 10H), 1.22-1.31 (m, 1H), 0.25-0.54 (m, 2H), −0.09-0.13 (m, 1H), −0.89 to −0.56 (m, 1H). MS (ESI) m/z=619 [M+22].

Example 301

2-((2R,5R,6R)-4-((S)-2-(N-(tert-Butyl)-N-methylsulfamoyl)-1-cyclopropylethyl)-6-(3-chlorophenyl)-5-(4-chlorophenyl)-3-oxomorpholin-2-yl)acetic acid or 2-((2S,5R,6R)-4-((S)-2-(N-(tert-butyl)-N-methylsulfamoyl)-1-cyclopropylethyl)-6-(3-chlorophenyl)-5-(4-chlorophenyl)-3-oxomorpholin-2-yl)acetic acid Further elution of the chromatographic separation in Example 300 provided one of the title compounds as the second (slower) eluting isomer. $^1$H NMR (400 MHz, $CDCl_3$, δ ppm): 7.30 (d, J=8.6 Hz, 2H), 7.09-7.23 (m, 4H), 7.06 (t, J=1.8 Hz, 1H), 6.88 (d, J=7.6 Hz, 1H), 4.98 (d, J=9.8 Hz, 1H), 4.78 (dd, J=7.8, 4.5 Hz, 1H), 4.71 (d, J=10.0 Hz, 1H), 4.19-4.39 (m, 1H), 3.24-3.41 (m, 1H), 2.94-3.01 (m, 2H), 2.84-2.93 (m, 4H), 2.41-2.62 (m, 1H), 1.46 (s, 9H), 1.13-1.34 (m, 1H), 0.25-0.50 (m, 2H), −0.31 to −0.12 (m, 1H), −0.96 to −0.79 (m, 1H). MS (ESI) m/z=619 [M+Na].

Example 302

2-((2R,5R,6R)-6-(3-Chlorophenyl)-5-(4-chlorophenyl)-4-((S)-1-cyclopropyl-2-(morpholinosulfonyl)ethyl)-3-oxomorpholin-2-yl)acetic acid or 2-((2S,5R,6R)-6-(3-chlorophenyl)-5-(4-chlorophenyl)-4-((S)-1-cyclopropyl-2-(morpholinosulfonyl)ethyl)-3-oxomorpholin-2-yl)acetic acid (faster eluting isomer). $^1$H NMR (400 MHz, $CDCl_3$, δ ppm): 7.34 (d, J=7.0 Hz, 6H), 7.18-7.25 (m, 1H), 7.13 (d, J=7.4 Hz, 1H), 5.02-5.19 (m, 1H), 4.88-5.00 (m, 1H), 4.56-4.73 (m, 1H), 3.78 (t, J=4.6 Hz, 5H), 3.05-3.34 (m, 7H), 2.78-3.02 (m, 2H), 0.36-0.65 (m, 2H), −0.04-0.19 (m, 1H), −0.74 to −0.41 (m, 1H). MS (ESI) m/z=597 [M+1].

Example 303

2-((2R,5R,6R)-6-(3-Chlorophenyl)-5-(4-chlorophenyl)-4-((S)-1-cyclopropyl-2-(morpholinosulfonyl)ethyl)-3-oxomorpholin-2-yl)acetic acid or 2-((2S,5R,6R)-6-(3-chlorophenyl)-5-(4-chlorophenyl)-4-((S)-1-cyclopropyl-2-(morpholinosulfonyl)ethyl)-3-oxomorpholin-2-yl)acetic acid Further elution of the chromatographic separation in Example 302 provided one of the title compounds as the second (slower) eluting isomer. $^1$H NMR (400 MHz, $CDCl_3$, δ ppm): 7.40-7.50 (m, 3H), 7.33-7.39 (m, 1H), 7.31 (s, 1H), 7.24-7.27 (m, 1H), 7.21 (t, J=1.8 Hz, 1H), 7.00 (d, J=7.6 Hz, 1H), 5.09 (d, J=9.8 Hz, 1H), 4.95 (d, J=11.7 Hz, 1H), 4.78-4.81 (m, 1H), 4.71-4.75 (m, 1H) 4.20-4.43 (m, 1H), 3.95 (t, J=4.4 Hz, 4H), 3.33-3.47 (m, 4H), 3.14 (dd, J=16.4, 5.3 Hz, 2H), 2.52-2.83 (m, 1H), 1.83-2.12 (m, 1H), 0.37-0.67 (m, 2H), −0.17-0.15 (m, 1H), −0.90 to −0.49 (m, 1H). MS (ESI) m/z=597 [M+1].

Example 304

2-((2R,5R,6R)-6-(3-Chlorophenyl)-5-(4-chlorophenyl)-4-((S)-1-cyclopropyl-2-(((R)-2-methylpyrrolidin-1-yl)sulfonyl)ethyl)-3-oxomorpholin-2-yl)acetic acid or 2-((2S,5R,6R)-6-(3-chlorophenyl)-5-(4-chlorophenyl)-4-((S)-1-cyclopropyl-2-(((R)-2-methylpyrrolidin-1-yl)sulfonyl)ethyl)-3-oxomorpholin-2-yl)acetic acid (faster eluting isomer). $^1$H NMR (400 MHz, $CDCl_3$, δ ppm): 7.33 (d, J=8.6 Hz, 5H), 7.24-7.26 (m, 1H), 7.20 (t, J=7.7 Hz, 1H), 7.10-7.16 (m, 1H), 5.04-5.16 (m, 1H), 4.87-4.99 (m, 1H), 4.60-4.76 (m, 1H), 3.71-4.02 (m, 1H), 3.30-3.51 (m, 2H), 2.94-3.26 (m, 3H), 1.94-2.03 (m, 6H), 1.55-1.71 (m, 1H), 1.29 (d, J=6.5 Hz, 3H), 0.29-0.53 (m, 2H), −0.09-0.16 (m, 1H), −0.81 to −0.55 (m, 1H). MS (ESI) m/z=595 [M+1].

Example 305

2-((2R,5R,6R)-6-(3-Chlorophenyl)-5-(4-chlorophenyl)-4-((S)-1-cyclopropyl-2-(((R)-2-methylpyrrolidin-1-yl)sulfonyl)ethyl)-3-oxomorpholin-2-yl)acetic acid or 2-((2S,5R,6R)-6-(3-chlorophenyl)-5-(4-chlorophenyl)-4-((S)-1-cyclopropyl-2-(((R)-2-methylpyrrolidin-1-yl)sulfonyl)ethyl)-3-oxomorpholin-2-yl) acetic acid Further elution of the chromatographic separation in Example 304 provided one of the title compounds as the second (slower) eluting isomer. $^1$H NMR (400 MHz, $CDCl_3$, δ ppm): 7.30 (d, J=8.61 Hz, 2H), 7.08-7.24 (m, 4H), 7.05 (t, J=1.76 Hz, 1H), 6.87 (d, J=7.63 Hz, 1H), 4.96 (d, J=9.78 Hz, 1H), 4.79 (dd, J=4.89, 7.24 Hz, 1H), 4.72 (d, J=9.78 Hz, 1H), 4.19 (br. s., 1H), 3.67-3.96 (m, 1H), 3.42 (t, J=6.55 Hz, 2H), 3.31 (dd, J=7.34, 16.14 Hz, 1H), 2.90-3.03 (m, 3H), 1.76-2.21 (m, 5H), 1.57-1.72 (m, 1H), 1.30 (d, J=6.26 Hz, 3H), 0.20-0.57 (m, 1H), −0.17 (br. s., 1H), −0.84 (br. s., 1H). MS (ESI) m/z=595 [M+1].

Example 306

2-((2R,5R,6R)-6-(3-Chlorophenyl)-5-(4-chlorophenyl)-4-((S)-1-cyclopropyl-2-((2,2-dimethylpyrrolidin-1-yl)sulfonyl)ethyl)-3-oxomorpholin-2-yl)acetic acid or 2-((2R,5R,6R)-6-(3-chlorophenyl)-5-(4-chlorophenyl)-4-((S)-1-cyclopropyl-2-((2,2-dimethylpyrrolidin-1-yl)sulfonyl) ethyl)-3-oxomorpholin-2-yl)acetic acid (faster eluting isomer). $^1$H NMR (400 MHz, $CDCl_3$, δ ppm): 7.29-7.38 (m, 5H), 7.14-7.26 (m, 3H), 5.12 (d, J=5.28 Hz, 1H), 4.92 (d, J=5.28 Hz, 1H), 4.67 (d, J=10.56 Hz, 1H), 3.84-4.10 (m, 1H), 3.44 (t, J=5.97 Hz, 2H), 2.97-3.32 (m, 3H), 2.50 (br. s., 1H), 1.80-1.96 (m, 4H), 1.68-1.80 (m, 1H), 1.47 (s, 3H), 1.44 (s, 3H), 0.25-0.60 (m, 2H), −0.17-0.15 (m, 1H), −0.99 to −0.58 (m, 1H). MS (ESI) m/z=609.0 [M+1].

Example 307

2-((2R,5R,6R)-6-(3-Chlorophenyl)-5-(4-chlorophenyl)-4-((S)-1-cyclopropyl-2-((2,2-dimethylpyrrolidin-1-yl)sulfonyl)ethyl)-3-oxomorpholin-2-yl)acetic acid or 2-((2R,5R,6R)-6-(3-chlorophenyl)-5-(4-chlorophenyl)-4-((S)-1-cyclopropyl-2-((2,2-dimethylpyrrolidin-1-yl)sulfonyl)ethyl)-3-oxomorpholin-2-yl) acetic acid Further elution of the chromatographic separation in Example 306 provided one of the title compounds as the second (slower) eluting isomer. $^1$H NMR (400 MHz, $CDCl_3$, δ ppm): 7.30 (d, J=8.61 Hz, 2H), 7.08-7.22 (m, 4H), 7.06 (t, J=1.76 Hz, 1H), 6.83-6.93 (m, 1H), 4.98 (d, J=9.78 Hz, 1H), 4.77 (dd, J=4.50, 7.83 Hz, 1H), 4.71 (d, J=9.98 Hz, 1H), 4.05-4.36 (m, 1H), 3.23-3.61 (m, 3H), 2.82-3.06 (m, 2H), 2.38-2.66 (m, 1H), 1.89 (d, J=3.33 Hz, 5H), 1.48 (d, J=12.52 Hz, 6H), 0.22-0.54 (m, 2H), −0.35 to −0.07 (m, 1H), −1.07 to −0.70 (m, 1H). MS (ESI) m/z=609.0 [M+1].

Example 308

2-((2R,5R,6R)-4-((S)-2-(tert-Butylsulfonyl)-1-cyclopropylethyl)-5-(4-chloro-3-fluorophenyl)-6-(3-chlorophenyl)-3-oxomorpholin-2-yl)acetic acid or 2-((2S,5R,6R)-4-((S)-2-(tert-butylsulfonyl)-1-cyclopropylethyl)-5-(4-chloro-3-fluorophenyl)-6-(3-chlorophenyl)-3-oxomorpholin-2-yl)acetic acid

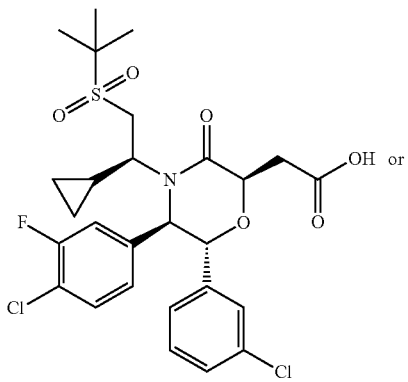

or

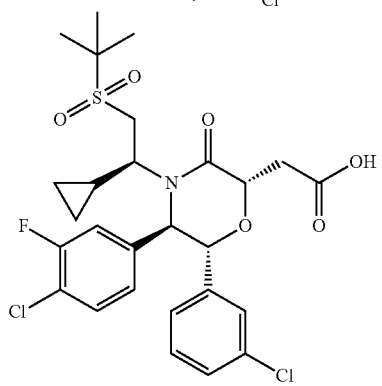

Step A. (S)-Ethyl 2-((2R,3R)-3-(4-chloro-3-fluorophenyl)-2-(3-chlorophenyl)-5-oxomorpholino)-2-cyclopropylacetate

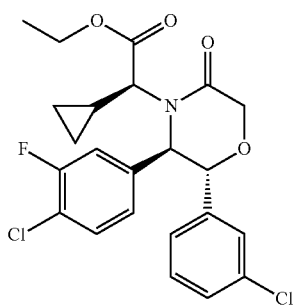 [SMILES: CCOC(=O)[C@H](C1CC1)N1C(=O)CO[C@H](c2cccc(Cl)c2)[C@H]1c1ccc(Cl)c(F)c1]

The title compound was prepared from (1R,2R)-2-amino-2-(4-chloro-3-fluorophenyl)-1-(3-chlorophenyl)ethanol (Intermediate D5 which was prepared by a method analogous to that described for Intermediate E1, Steps A through H) using the methods described in Example 112, Step A and Example 154, Step A. The residue was purified by flash chromatography on silica gel (80 g column; eluent: 5% ethyl acetate in dichloromethane) to give the title compound as the first (faster) eluting isomer.

Step B. (5R,6R)-5-(4-Chloro-3-fluorophenyl)-6-(3-chlorophenyl)-4-((S)-1-cyclopropyl-2-hydroxyethyl)morpholin-3-one

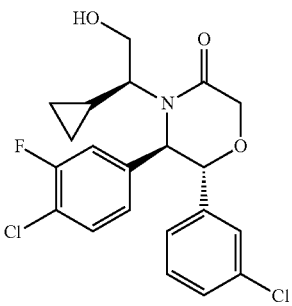 [SMILES: O=C1CO[C@H](c2cccc(Cl)c2)[C@@H](c2ccc(Cl)c(F)c2)N1[C@H](CO)C1CC1]

Lithium triethylborohydride (1.0 M in THF, 1.801 mL, 1.801 mmol) was added to a solution of (S)-ethyl 2-((2R,3R)-3-(4-chloro-3-fluorophenyl)-2-(3-chlorophenyl)-5-oxomorpholino)-2-cyclopropylacetate (0.4 g, 0.858 mmol, Example 308, Step A) in THF (0.858 mL) at −10° C. while maintaining an internal temperature between −5° C. and −1° C. Additional triethylborohydride (1.0 M in THF, 0.5 mL, 0.5 mmol) was added. The mixture was stirred at −10° C. for 15 minutes and then MeOH (1 mL) was added dropwise over 1 minute. Oxone® (potassium peroxymonosulfate, DuPont, Wilmington, Del.) (1.582 g, 2.57 mmol) in water (6 mL) was added dropwise over 10 minutes. The internal temperature increased from 0° C. to 25° C. The mixture was stirred at room temperature for 1 hour, then saturated aqueous NaHSO$_3$ (2 mL) was added. The mixture was stirred at room temperature for 15 minutes. The mixture was extracted with diethyl ether (2×30 mL). The combined organic layers were dried over MgSO$_4$, filtered and concentrated. The residue was purified by flash chromatography on silica gel (eluent: 20% acetone in hexanes) to give the title compound.

Step C. 2-((2R,5R,6R)-4-((S)-2-(tert-Butylsulfonyl)-1-cyclopropylethyl)-5-(4-chloro-3-fluorophenyl)-6-(3-chlorophenyl)-3-oxomorpholin-2-yl)acetic acid or 2-((2S,5R,6R)-4-((S)-2-(tert-butylsulfonyl)-1-cyclopropylethyl)-5-(4-chloro-3-fluorophenyl)-6-(3-chlorophenyl)-3-oxomorpholin-2-yl)acetic acid

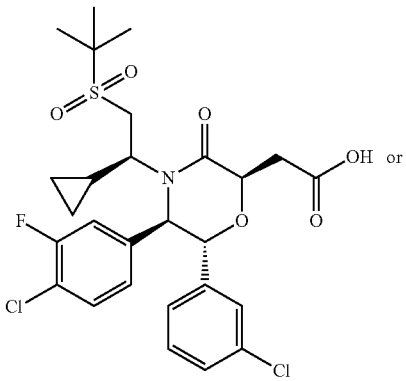

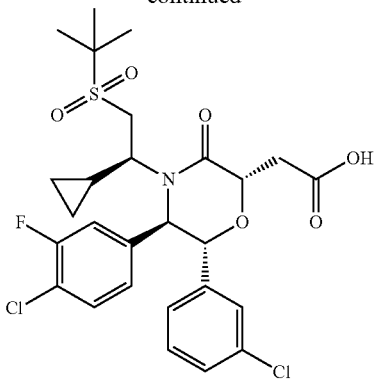

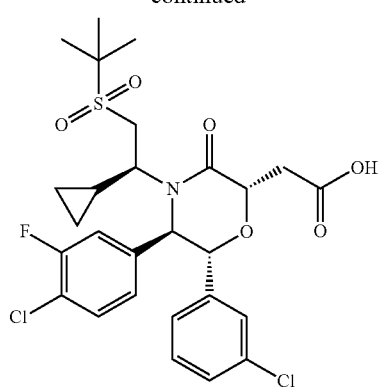

One of the title compounds was prepared from (5R,6R)-5-(4-chloro-3-fluorophenyl)-6-(3-chlorophenyl)-4-((S)-1-cyclopropyl-2-hydroxyethyl)morpholin-3-one (Example 308, Step B) by procedures similar to those described in Example 112, Steps D though F, replacing ethanethiol in Step D with tert-butylthiol. The residue was purified by reverse phase preparatory HPLC (Agilient 1100, column: Gemini® 5 μm $C_{18}$, 100 mm×30 mm (Phenomenex, Torrance, Calif.), gradient elution of 25% to 75% acetonitrile in water, where both solvents contain 0.1% TFA, 30 minutes) to give one of the compounds as the first (faster) eluting isomer. $^1$H NMR (400 MHz, CDCl$_3$, δ ppm): 7.35-7.44 (m, 3H), 7.28-7.32 (m, 1H), 7.21-7.26 (m, 2H), 7.15 (dd, J=1.17, 8.02 Hz, 1H), 5.21 (s, 1H), 4.96 (d, J=4.30 Hz, 1H), 4.54 (t, J=5.77 Hz, 1H), 3.85-4.08 (m, 1H), 3.20 (d, J=11.74 Hz, 1H), 3.12 (d, J=6.06 Hz, 3H), 1.73-1.99 (m, 1H), 1.44 (s, 9H), 0.34-0.57 (m, 2H), −0.01-0.19 (m, 1H), −0.81 to −0.53 (m, 1H). MS (ESI) m/z=586.1 [M+1].

Further elution of the HPLC purification described in Example 309 provided one of the title compounds as the second (slower) eluting isomer. $^1$H NMR (400 MHz, CDCl$_3$, δ ppm): 7.34 (t, J=7.83 Hz, 1H), 7.03-7.27 (m, 4H), 6.94 (d, J=6.26 Hz, 1H), 6.89 (d, J=7.63 Hz, 1H), 5.08 (d, J=9.59 Hz, 1H), 4.74-4.86 (m, J=6.26 Hz, 1H), 4.69 (d, J=9.78 Hz, 1H), 4.14-4.32 (m, 1H), 3.24 (dd, J=6.65, 16.43 Hz, 1H), 3.05 (d, J=12.72 Hz, 1H), 3.01 (d, J=5.28 Hz, 1H), 2.96 (d, J=5.09 Hz, 1H), 2.53-2.74 (m, 2H), 1.81-2.00 (m, 1H), 1.44 (s, 9H), 0.33-0.51 (m, J=7.83 Hz, 2H), −0.24 to −0.02 (m, 1H), −0.92 to −0.65 (m, 1H). MS (ESI) m/z=586.0 [M+1].

Example 310

2-((2R,5R,6R)-4-((S)-1-(tert-Butylsulfonyl)-3-methylbutan-2-yl)-5-(4-chloro-3-fluorophenyl)-6-(3-chlorophenyl)-3-oxomorpholin-2-yl)acetic acid or
2-((2S,5R,6R)-4-((S)-1-(tert-butylsulfonyl)-3-methylbutan-2-yl)-5-(4-chloro-3-fluorophenyl)-6-(3-chlorophenyl)-3-oxomorpholin-2-yl)acetic acid or
2-((2R,5R,6R)-4-((R)-1-(tert-butylsulfonyl)-3-methylbutan-2-yl)-5-(4-chloro-3-fluorophenyl)-6-(3-chlorophenyl)-3-oxomorpholin-2-yl)acetic acid or
2-((2S,5R,6R)-4-((R)-1-(tert-butylsulfonyl)-3-methylbutan-2-yl)-5-(4-chloro-3-fluorophenyl)-6-(3-chlorophenyl)-3-oxomorpholin-2-yl)acetic acid Example 309

2-((2R,5R,6R)-4-((S)-2-(tert-Butylsulfonyl)-1-cyclopropylethyl)-5-(4-chloro-3-fluorophenyl)-6-(3-chlorophenyl)-3-oxomorpholin-2-yl)acetic acid or
2-((2S,5R,6R)-4-((S)-2-(tert-butylsulfonyl)-1-cyclopropylethyl)-5-(4-chloro-3-fluorophenyl)-6-(3-chlorophenyl)-3-oxomorpholin-2-yl)acetic acid

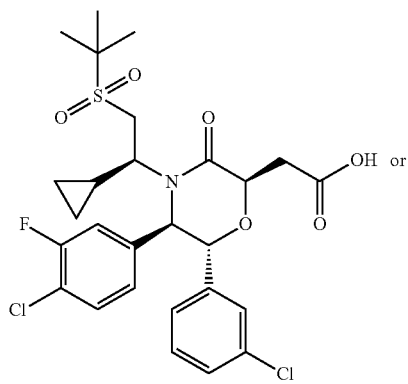

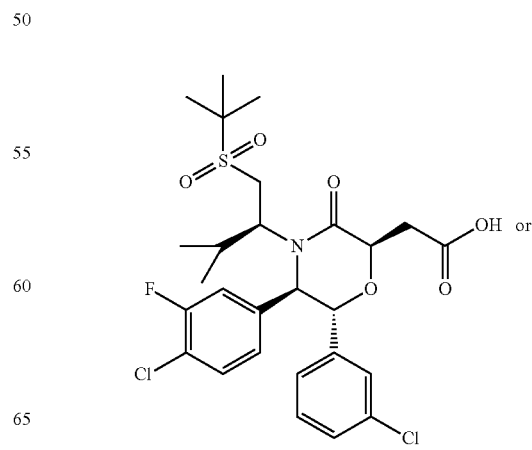

-continued

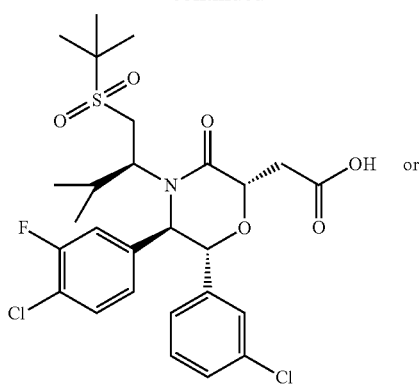

or

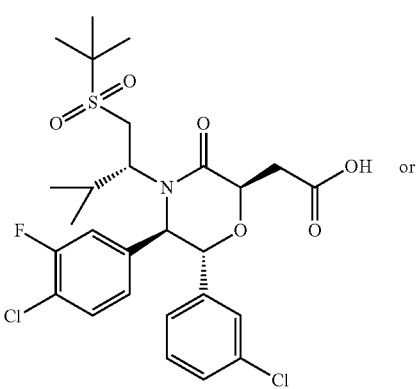

or

Step A. (S)-1-(((1R,2R)-2-((tert-Butyldimethylsilyl)oxy)-1-(4-chloro-3-fluorophenyl)-2-(3-chlorophenyl)ethyl)-2-isopropylaziridine or (R)-1-(((1R,2R)-2-((tert-butyldimethylsilyl)oxy)-1-(4-chloro-3-fluorophenyl)-2-(3-chlorophenyl)ethyl)-2-isopropylaziridine

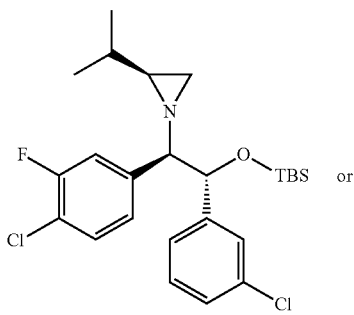

or

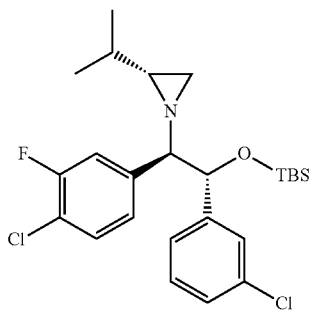

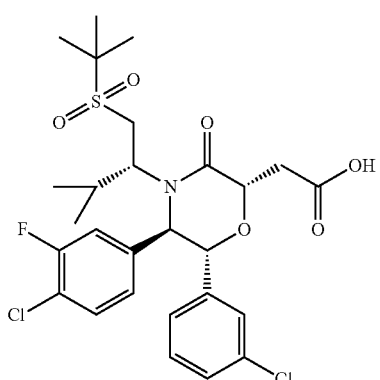

Diethyl azodicarboxylate (40 wt. % in toluene, 4.44 mL, 9.77 mmol) was added to a solution of triphenylphosphine (2.56 g, 9.77 mmol) and (S)-1-(((1R,2R)-2-((tert-butyldimethylsilyl)oxy)-1-(4-chloro-3-fluorophenyl)-2-(3-chlorophenyl)ethyl)amino)-3-methylbutan-2-ol and (R)-1-(((1R,2R)-2-((tert-butyldimethylsilyl)oxy)-1-(4-chloro-3-fluorophenyl)-2-(3-chlorophenyl)ethyl)amino)-3-methylbutan-2-ol (3.26 g, 6.51 mmol, prepared from Intermediate D5 by procedures similar to those described in Example 162, Steps A through C, replacing (R)-(+)-1,2-epoxybutane in Step B with 1,2-epoxy-3-methylbutane) in THF (6.51 mL). The mixture was stirred at room temperature overnight then concentrated. The residue was purified by flash chromatography on silica gel (120 g column; eluent: 5% acetone in hexanes) to give one of the title compounds as the second (slower) eluting isomer.

Step B. 2-((2R,5R,6R)-4-((S)-1-(tert-Butylsulfonyl)-3-methylbutan-2-yl)-5-(4-chloro-3-fluorophenyl)-6-(3-chlorophenyl)-3-oxomorpholin-2-yl)acetic acid or
2-((2S,5R,6R)-4-((S)-1-(tert-butylsulfonyl)-3-methylbutan-2-yl)-5-(4-chloro-3-fluorophenyl)-6-(3-chlorophenyl)-3-oxomorpholin-2-yl)acetic acid or
2-((2R,5R,6R)-4-((R)-1-(tert-butylsulfonyl)-3-methylbutan-2-yl)-5-(4-chloro-3-fluorophenyl)-6-(3-chlorophenyl)-3-oxomorpholin-2-yl)acetic acid or
2-((2S,5R,6R)-4-((R)-1-(tert-butylsulfonyl)-3-methylbutan-2-yl)-5-(4-chloro-3-fluorophenyl)-6-(3-chlorophenyl)-3-oxomorpholin-2-yl)acetic acid One of the title compounds was prepared from (S)-1-((1R,2R)-2-((tert-butyldimethylsilyl)oxy)-1-(4-chloro-3-fluorophenyl)-2-(3-chlorophenyl)ethyl)-2-isopropylaziridine or (R)-1-((1R,2R)-2-((tert-butyldimethylsilyl)oxy)-1-(4-chloro-3-fluorophenyl)-2-(3-chlorophenyl)ethyl)-2-isopropylaziridine (Example 310, Step A, second (slower) eluting isomer) by procedures similar to those described in Example 162, Steps D through H. The residue was purified by reverse phase preparatory HPLC (Agilient 1100, column: Gemini® 5 µm $C_{18}$, 100 mm×30 mm (Phenomenex, Torrance, Calif.), gradient elution of 25% to 75% acetonitrile in water, where both solvents contain 0.1% TFA, 30 minutes) to give one of the compounds as the first (faster) eluting isomer. $^1$H NMR (400 MHz, CDCl$_3$, δ ppm): 7.36 (t, J=7.63 Hz, 1H), 7.21-7.26 (m, J=1.47, 14.18 Hz, 3H), 7.16 (dd, J=7.04, 8.02 Hz, 1H), 6.99 (dd, J=7.63, 9.19 Hz, 1H), 6.91 (d, J=7.82 Hz, 1H), 4.98 (d, J=7.04 Hz, 1H), 4.82 (t, J=5.87 Hz, 1H), 4.74 (d, J=7.04 Hz, 1H), 3.87-3.99 (m, 1H), 3.47 (q, J=6.52 Hz, 1H), 3.31 (dd, J=5.67, 14.09 Hz, 1H), 3.13 (d, J=6.06 Hz, 2H), 2.39 (qd, J=6.76, 13.57 Hz, 1H), 1.34 (s, 9H), 1.02 (dd, J=6.85, 15.45 Hz, 6H). MS (ESI) m/z=588.1 [M+1].

Example 311

2-((2R,5R,6R)-4-((S)-1-(tert-Butylsulfonyl)-3-methylbutan-2-yl)-5-(4-chloro-3-fluorophenyl)-6-(3-chlorophenyl)-3-oxomorpholin-2-yl)acetic acid or
2-((2S,5R,6R)-4-((S)-1-(tert-butylsulfonyl)-3-methylbutan-2-yl)-5-(4-chloro-3-fluorophenyl)-6-(3-chlorophenyl)-3-oxomorpholin-2-yl)acetic acid or
2-((2R,5R,6R)-4-((R)-1-(tert-butylsulfonyl)-3-methylbutan-2-yl)-5-(4-chloro-3-fluorophenyl)-6-(3-chlorophenyl)-3-oxomorpholin-2-yl)acetic acid or
2-((2S,5R,6R)-4-((R)-1-(tert-butylsulfonyl)-3-methylbutan-2-yl)-5-(4-chloro-3-fluorophenyl)-6-(3-chlorophenyl)-3-oxomorpholin-2-yl)acetic acid

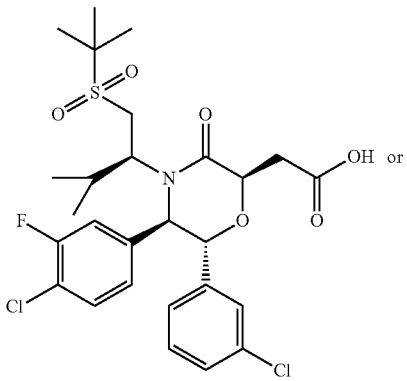 or

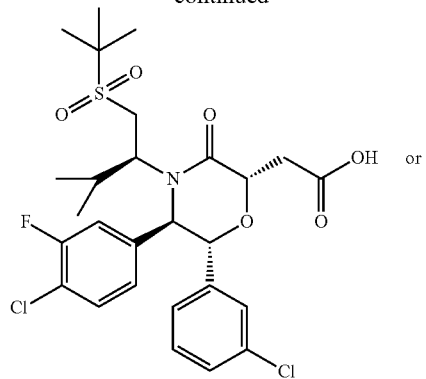 or

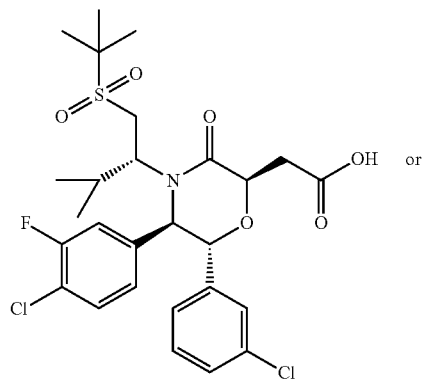 or

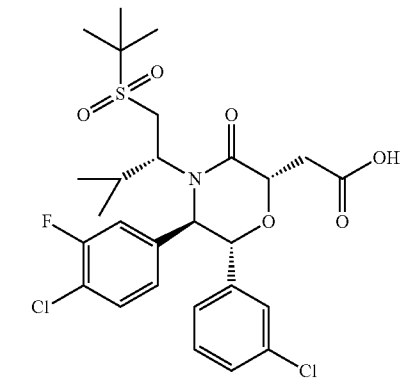

Further elution of the HPLC purification described in Example 310, Step B provided one of the title compounds as the second (slower) eluting isomer. $^1$H NMR (400 MHz, CDCl$_3$, δ ppm): 7.34 (t, J=7.82 Hz, 1H), 7.17-7.22 (m, 1H), 7.08-7.16 (m, 3H), 7.02 (d, J=8.02 Hz, 1H), 6.91 (d, J=7.83 Hz, 1H), 5.24 (d, J=9.78 Hz, 1H), 4.79 (d, J=9.98 Hz, 1H), 4.75 (t, J=5.38 Hz, 1H), 3.81-3.99 (m, J=8.41 Hz, 1H), 3.15 (s, 2H), 2.95-3.08 (m, 2H), 2.33-2.51 (m, 1H), 1.46 (s, 9H), 0.75 (d, J=6.85 Hz, 3H), 0.69 (d, J=6.85 Hz, 3H). MS (ESI) m/z=588.1 [M+1].

Example 312

2-((2R,5R,6R)-4-((S)-1-(tert-Butylsulfonyl)-3-methylbutan-2-yl)-5-(4-chloro-3-fluorophenyl)-6-(3-chlorophenyl)-3-oxomorpholin-2-yl)acetic acid or
2-((2S,5R,6R)-4-((S)-1-(tert-butylsulfonyl)-3-methylbutan-2-yl)-5-(4-chloro-3-fluorophenyl)-6-(3-chlorophenyl)-3-oxomorpholin-2-yl)acetic acid or
2-((2R,5R,6R)-4-((R)-1-(tert-butylsulfonyl)-3-methylbutan-2-yl)-5-(4-chloro-3-fluorophenyl)-6-(3-chlorophenyl)-3-oxomorpholin-2-yl)acetic acid or
2-((2S,5R,6R)-4-((R)-1-(tert-butylsulfonyl)-3-methylbutan-2-yl)-5-(4-chloro-3-fluorophenyl)-6-(3-chlorophenyl)-3-oxomorpholin-2-yl)acetic acid

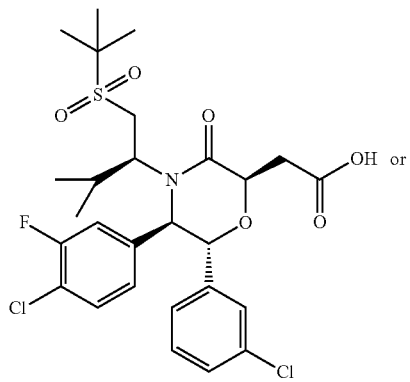 or

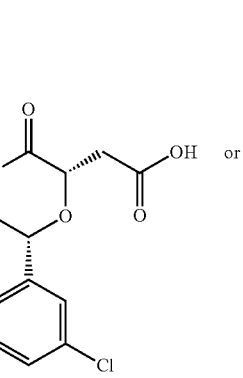 or

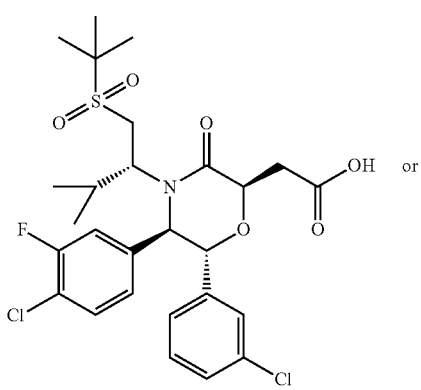

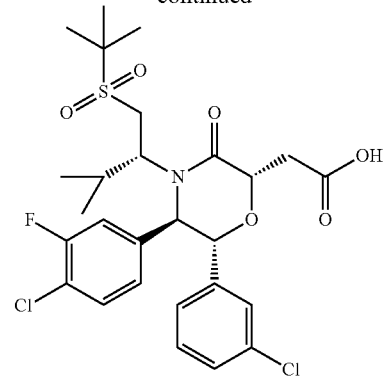

One of the title compounds was prepared from (S)-1-((1R,2R)-2-((tert-butyldimethylsilyl)oxy)-1-(4-chloro-3-fluorophenyl)-2-(3-chlorophenyl)ethyl)-2-isopropylaziridine or (R)-1-((1R,2R)-2-((tert-butyldimethylsilyl)oxy)-1-(4-chloro-3-fluorophenyl)-2-(3-chlorophenyl)ethyl)-2-isopropylaziridine (Example 310, Step A, first (faster) eluting isomer) by procedures similar to those described in Example 162, Steps D through H. The residue was purified by chiral SFC (150×20 mm Chiralpak® IC column (Chiral Technologies, Inc., West Chester, Pa., USA) with 10% ethanol in $CO_2$ at a flow rate of 60 mL/min) give one of the compounds as the first (faster) eluting isomer. $^1$H NMR (400 MHz, $CDCl_3$, δ ppm): 7.36 (t, J=7.63 Hz, 1H), 7.24 (d, J=1.17 Hz, 3H), 7.16 (dd, J=7.04, 8.02 Hz, 1H), 6.99 (d, J=7.63 Hz, 1H), 6.91 (d, J=7.82 Hz, 1H), 4.98 (d, J=7.04 Hz, 1H), 4.82 (t, J=5.87 Hz, 1H), 4.74 (d, J=7.04 Hz, 1H), 3.87-3.99 (m, 1H), 3.43-3.52 (m, 1H), 3.25-3.37 (m, 1H), 3.13 (d, J=6.06 Hz, 2H), 2.29-2.49 (m, 1H), 1.34 (s, 9H), 1.02 (dd, J=6.85, 15.45 Hz, 6H). MS (ESI) m/z=588.2 [M+1].

Example 313

2-((2R,5R,6R)-4-((S)-1-(tert-Butylsulfonyl)-3-methylbutan-2-yl)-5-(4-chloro-3-fluorophenyl)-6-(3-chlorophenyl)-3-oxomorpholin-2-yl)acetic acid or
2-((2S,5R,6R)-4-((S)-1-(tert-butylsulfonyl)-3-methylbutan-2-yl)-5-(4-chloro-3-fluorophenyl)-6-(3-chlorophenyl)-3-oxomorpholin-2-yl)acetic acid or
2-((2R,5R,6R)-4-((R)-1-(tert-butylsulfonyl)-3-methylbutan-2-yl)-5-(4-chloro-3-fluorophenyl)-6-(3-chlorophenyl)-3-oxomorpholin-2-yl)acetic acid or
2-((2S,5R,6R)-4-((R)-1-(tert-butylsulfonyl)-3-methylbutan-2-yl)-5-(4-chloro-3-fluorophenyl)-6-(3-chlorophenyl)-3-oxomorpholin-2-yl)acetic acid

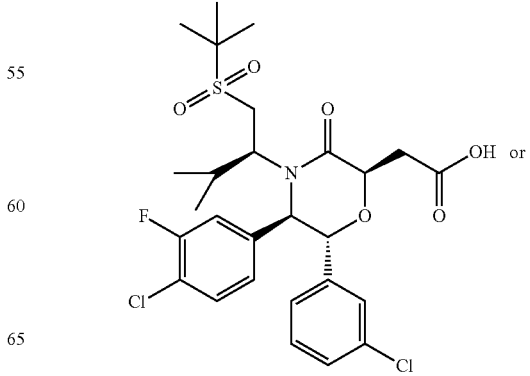 or

527
-continued

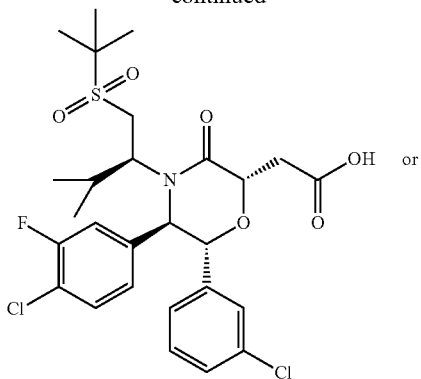

or

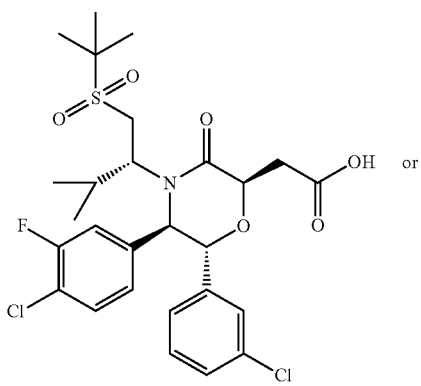

or

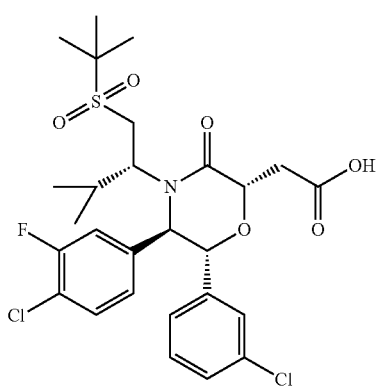

Further elution of the chromatographic purification described in Example 312 provided the title compound as the second (slower) eluting isomer. ¹H NMR (400 MHz, CDCl₃, δ ppm): 7.32 (t, J=7.83 Hz, 1H), 7.22 (d, J=8.02 Hz, 1H), 7.10 (s, 3H), 7.03 (d, J=8.02 Hz, 1H), 6.82 (d, J=7.63 Hz, 1H), 6.74 (d, J=7.63 Hz, 1H), 4.65-4.82 (m, 3H), 3.79-3.93 (m, 1H), 3.25-3.47 (m, 2H), 2.95-3.21 (m, 2H), 1.33 (s, 9H), 1.08 (d, J=6.85 Hz, 3H), 0.97 (d, J=6.65 Hz, 3H). MS (ESI) m/z=588.2 [M+1].

528
Example 314

2-((2R,5R,6R)-5-(4-Chloro-3-fluorophenyl)-6-(3-chlorophenyl)-4-((S)-1-cyclopropyl-2-(N-(2-fluorophenyl)cyclopropanesulfonamido)ethyl)-3-oxomorpholin-2-yl)acetic acid or 2-((2S,5R,6R)-5-(4-chloro-3-fluorophenyl)-6-(3-chlorophenyl)-4-((S)-1-cyclopropyl-2-(N-(2-fluorophenyl)cyclopropanesulfonamido)ethyl)-3-oxomorpholin-2-yl)acetic acid

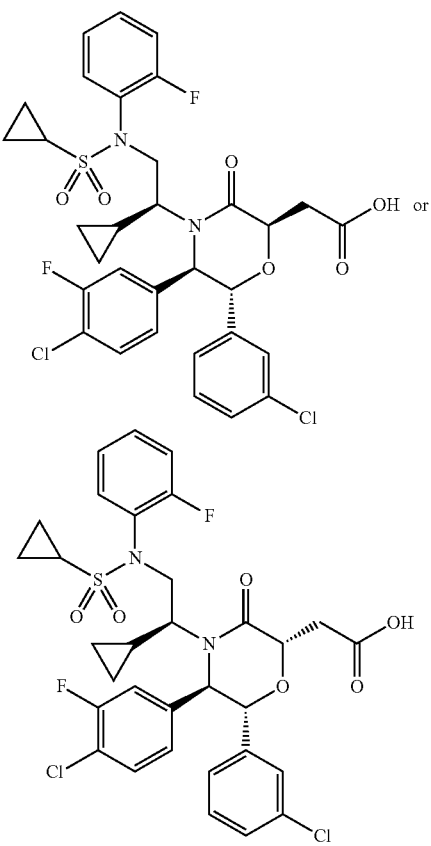

One of the title compounds was prepared from (5R,6R)-5-(4-chloro-3-fluorophenyl)-6-(3-chlorophenyl)-4-((S)-1-cyclopropyl-2-hydroxyethyl)morpholin-3-one (Example 308, Step B) by procedures similar to those described in Example 112, Steps D though F, replacing ethanethiol in Step D with N-(2-fluorophenyl)cyclopropanesulfonamide (Example 133). The residue was purified by reverse phase preparatory HPLC (Agilient 1100, column: Gemini® 5 µm C₁₈, 100 mm×30 mm (Phenomenex, Torrance, Calif.), gradient elution of 25% to 75% acetonitrile in water, where both solvents contain 0.1% TFA, 30 minutes) to give one of the compounds as the first (faster) eluting isomer. ¹H NMR (400 MHz, CDCl₃, δ ppm): 7.47 (dt, J=1.56, 7.92 Hz, 1H), 7.28-7.42 (m, 5H), 7.12-7.26 (m, 4H), 7.03 (d, J=7.83 Hz, 1H), 5.08 (d, J=4.69 Hz, 1H), 4.88 (d, J=5.48 Hz, 1H), 4.38 (t, J=6.16 Hz, 2H), 3.70-4.06 (m, 1H), 2.99-3.18 (m, 2H), 2.59-2.93 (m, 1H), 2.46 (quin, J=6.31 Hz, 1H), 1.35-1.60 (m, 1H), 0.81-1.06 (m, 4H), 0.45-0.59 (m, 1H), 0.29-0.43 (m, 1H), −0.09-0.22 (m, 1H), −0.99 to −0.44 (m, 1H). MS (ESI) m/z=679.0 [M+1].

Example 315

2-((2R,5R,6R)-5-(4-Chloro-3-fluorophenyl)-6-(3-chlorophenyl)-4-((S)-1-cyclopropyl-2-(N-(2-fluorophenyl)cyclopropanesulfonamido)ethyl)-3-oxomorpholin-2-yl)acetic acid or 2-((2S,5R,6R)-5-(4-chloro-3-fluorophenyl)-6-(3-chlorophenyl)-4-((S)-1-cyclopropyl-2-(N-(2-fluorophenyl)cyclopropanesulfonamido)ethyl)-3-oxomorpholin-2-yl)acetic acid

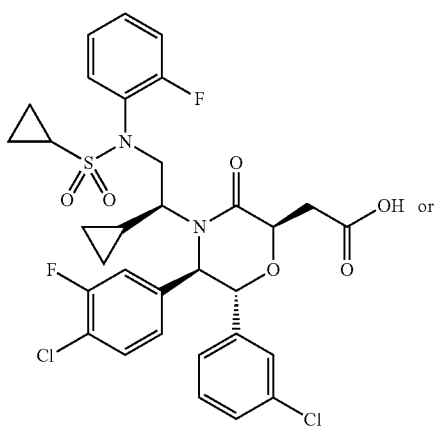

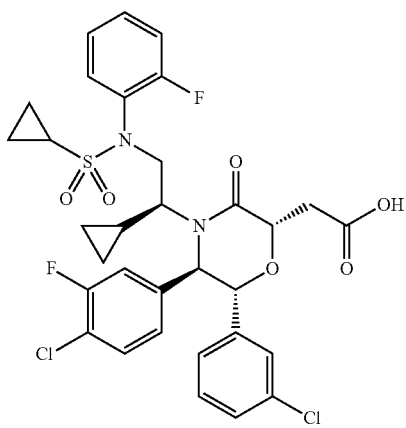

Further elution of the chromatographic purification described in Example 314 provided one of the title compounds as the second (slower) eluting isomer. $^1$H NMR (400 MHz, CDCl$_3$, δ ppm): 7.58 (t, J=7.63 Hz, 1H), 7.28-7.44 (m, 3H), 7.17-7.26 (m, 3H), 7.13 (s, 1H), 7.02 (d, J=9.39 Hz, 1H), 6.94 (d, J=7.04 Hz, 1H), 6.88 (d, J=7.63 Hz, 1H), 4.97 (d, J=9.78 Hz, 1H), 4.64-4.77 (m, 2H), 4.55 (br. s., 1H), 3.92 (br. s., 1H), 2.68-2.87 (m, J=8.61 Hz, 1H), 2.27-2.60 (m, 2H), 1.65 (br. s., 1H), 0.91 (d, J=6.65 Hz, 5H), 0.45 (br. s., 1H), 0.32 (br. s., 1H), −0.33 to −0.03 (m, 1H), −0.92 (br. s., 1H). MS (ESI) m/z=679.0 [M+1].

Example 316

2-((2R,5R,6R)-4-((S)-1-(tert-Butylsulfonyl)butan-2-yl)-5-(4-chloro-2-fluorophenyl)-6-(3-chlorophenyl)-3-oxomorpholin-2-yl)acetic acid or 2-((2S,5R,6R)-4-((S)-1-(tert-butylsulfonyl)butan-2-yl)-5-(4-chloro-2-fluorophenyl)-6-(3-chlorophenyl)-3-oxomorpholin-2-yl)acetic acid

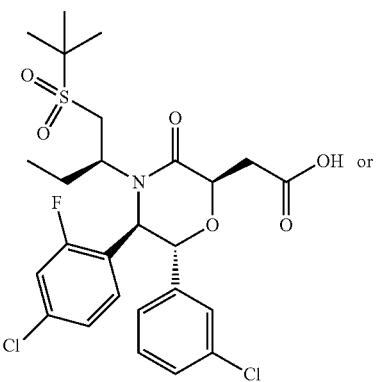

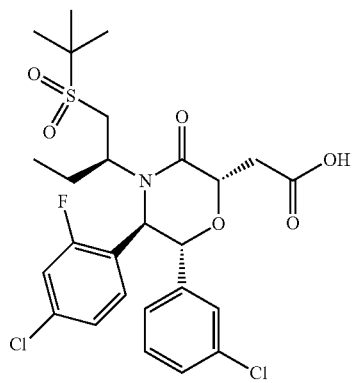

One of the title compounds was prepared from (1R,2R)-2-amino-2-(4-chloro-2-fluorophenyl)-1-(3-chlorophenyl)ethanol (Intermediate B1 which was prepared by a method analogous to that described for Intermediate E1, Steps A through H) by procedures similar to those described in Example 162, Steps A though H. The residue was purified by reverse phase preparatory HPLC (Agilient 1100, column: Gemini® 5 μm C$_{18}$, 100 mm×30 mm (Phenomenex, Torrance, Calif.), gradient elution of 40% to 70% acetonitrile in water, where both solvents contain 0.1% TFA) to give one of the compounds as the first (faster) eluting isomer. $^1$H NMR (500 MHz, CDCl$_3$, δ ppm): 7.40-7.22 (m, 3H), 7.22-7.09 (m, 4H), 5.36 (br. s., 1H), 5.06 (d, J=6.11 Hz, 1H), 4.80 (br. s., 1H), 3.96 (br. s., 1H), 3.39 (br. s., 1H), 3.15-3.02 (m, 2H), 2.96 (d, J=13.20 Hz, 1H), 2.19 (ddd, J=14.37, 9.60, 7.34 Hz, 1H), 1.65 (ddd, J=14.12, 7.64, 3.91 Hz, 1H), 1.44 (s, 9H), 0.60 (t, J=7.46 Hz, 3H). MS (ESI) m/z=574 [M+1].

Example 317

2-((2R,5R,6R)-4-((S)-1-(tert-Butylsulfonyl)butan-2-yl)-5-(4-chloro-2-fluorophenyl)-6-(3-chlorophenyl)-3-oxomorpholin-2-yl)acetic acid or 2-((2S,5R,6R)-4-((S)-1-(tert-butylsulfonyl)butan-2-yl)-5-(4-chloro-2-fluorophenyl)-6-(3-chlorophenyl)-3-oxomorpholin-2-yl)acetic acid

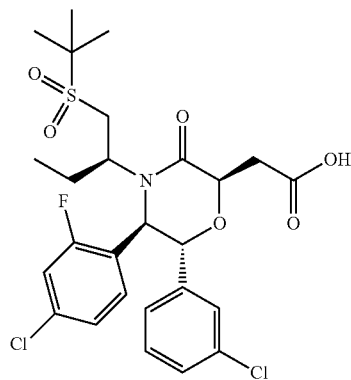

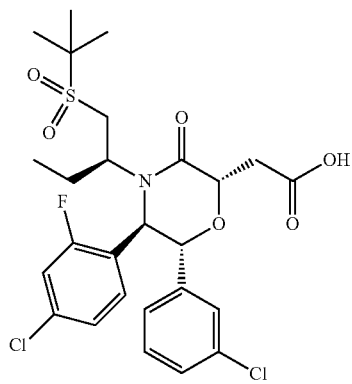

Further elution of the chromatographic purification in Example 316 provided one of the title compounds as the second (slower) eluting isomer. $^1$H NMR (500 MHz, CDCl$_3$, δ ppm): 7.23 (m, 2H), 7.20-7.10 (m, 3H), 7.07 (d, J=7.34 Hz, 1H), 6.97 (d, J=7.58 Hz, 1H), 5.19 (br. s., 1H), 4.94 (br. s., 1H), 4.72 (dd, J=6.97, 4.77 Hz, 1H), 4.12-3.98 (m, 1H), 3.32 (br. s., 1H), 3.24 (dd, J=16.38, 7.09 Hz, 1H), 3.03-2.88 (m, 2H), 2.24-2.13 (m, 1H), 1.65 (ddd, J=14.00, 7.52, 4.16 Hz, 1H), 1.44 (s, 9H), 0.58 (t, J=7.58 Hz, 3H). MS (ESI) m/z=574 [M+1].

Example 318

2-((2R,5R,6R)-4-((S)-2-(tert-Butylsulfonyl)-1-cyclopropylethyl)-5-(4-chlorophenyl)-6-(3,4-dichlorophenyl)-3-oxomorpholin-2-yl)acetic acid or 2-((2S,5R,6R)-4-((S)-2-(tert-butylsulfonyl)-1-cyclopropylethyl)-5-(4-chlorophenyl)-6-(3,4-dichlorophenyl)-3-oxomorpholin-2-yl)acetic acid

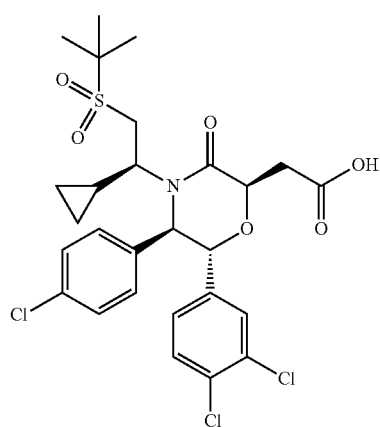

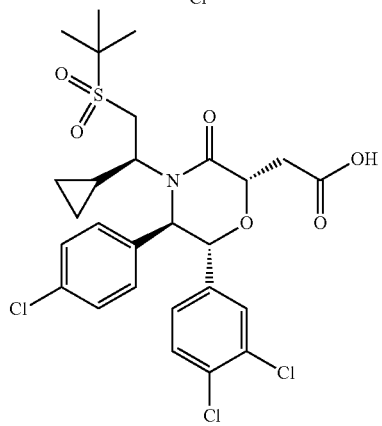

Step A. (R)-2-((tert-Butoxycarbonyl)amino)-2-(4-chlorophenyl)acetic acid

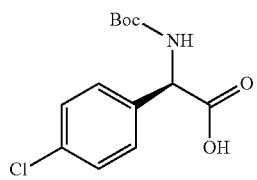 [SMILES: CC(C)(C)OC(=O)N[C@@H](C(=O)O)c1ccc(Cl)cc1]

Acetonitrile (150 mL), (R)-2-amino-2-(4-chlorophenyl)acetic acid (25 g, 135 mmol, 3B Pharmachem (Wuhan) International Co., Ltd; Hubei Province, China), and di-tert-butyl dicarbonate (28.8 mL, 135 mmol) were added to a solution of sodium hydroxide (5.31 mL, 283 mmol) in water (200 mL) at room temperature. After stirring at room temperature for 22 hours, the mixture was acidified to pH 4 with 2 M HCl and extracted with dichloromethane. The organic layer was washed with brine, dried over MgSO$_4$, filtered, and concentrated to provide the title compound.

Step B. (R)-tert-Butyl (1-(4-chlorophenyl)-2-hydroxyethyl)carbamate

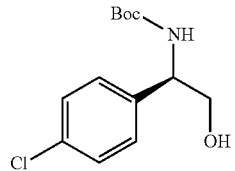 [SMILES: CC(C)(C)OC(=O)N[C@@H](CO)c1ccc(Cl)cc1]

Boranetetrahydrofuran complex (1 M in THF, 219 mL, 219 mmol) was added to a solution of (R)-2-((tert-butoxycarbonyl)amino)-2-(4-chlorophenyl)acetic acid (28.4 g, 99 mmol, Example 318, Step A) in THF (100 mL) at 0° C. The mixture was stirred at 0° C. for 45 minutes and then quenched by slow addition of water (100 mL). The mixture was diluted with ethyl acetate. The organic phase was separated and aqueous phase was extracted with ethyl acetate. The combined organic layers were washed with bring, dried over MgSO$_4$, filtered, and concentrated. The residue was purified by flash chromatography on silica gel (gradient elution of 0% to 70% ethyl acetate in hexanes) to give the title compound.

Step C. (2R,5R,6R)-2-Allyl-4-((S)-2-(tert-butylthio)-1-cyclopropylethyl)-5-(4-chlorophenyl)-6-(3,4-dichlorophenyl)morpholin-3-one and (2S,5R,6R)-2-allyl-4-((S)-2-(tert-butylthio)-1-cyclopropylethyl)-5-(4-chlorophenyl)-6-(3,4-dichlorophenyl)morpholin-3-one

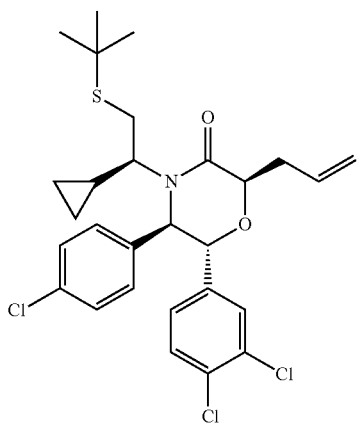

and

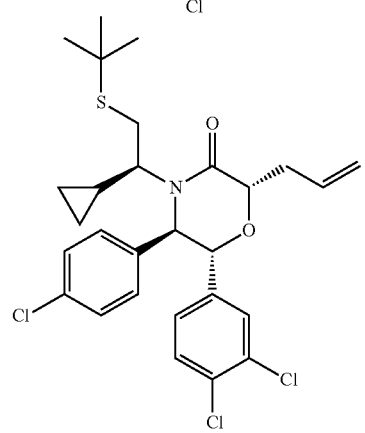

The title compounds were prepared from (R)-tert-butyl (1-(4-chlorophenyl)-2-hydroxyethyl)carbamate (Example 318, Step B) by procedures similar to those described in Intermediate C1, Steps C though E, Example 308, Steps A and B, and Example 112, Steps D and E, replacing ethanethiol in Step D with 2-methylpropane-2-thiol.

Step D. (2R,5R,6R)-2-Allyl-4-((S)-2-(tert-butylsulfonyl)-1-cyclopropylethyl)-5-(4-chlorophenyl)-6-(3,4-dichlorophenyl)morpholin-3-one and (2S,5R,6R)-2-allyl-4-((S)-2-(tert-butylsulfonyl)-1-cyclopropylethyl)-5-(4-chlorophenyl)-6-(3,4-dichlorophenyl)morpholin-3-one

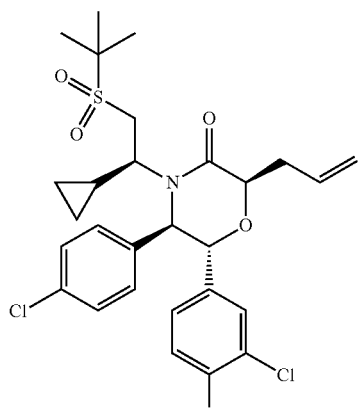

and

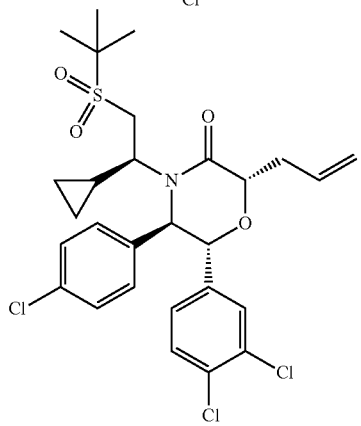

3-Chloroperoxybenzoic acid (14.59 mg, 0.065 mmol) was added to a solution of (2R,5R,6R)-2-allyl-4-((S)-2-(tert-butylthio)-1-cyclopropylethyl)-5-(4-chlorophenyl)-6-(3,4-dichlorophenyl)morpholin-3-one and (2S,5R,6R)-2-allyl-4-((S)-2-(tert-butylthio)-1-cyclopropylethyl)-5-(4-chlorophenyl)-6-(3,4-dichlorophenyl)morpholin-3-one (12 mg, 0.022 mmol, Example 318, Step C) in N,N-dimethylformamide (250 μL) at 0° C. The mixture was stirred at 0° C. for 1 hour and then quenched with 1 M aqueous Na$_2$S$_2$O$_3$ (0.25 mL). The mixture was extracted with ethyl acetate and the organic layer was washed with saturated NaHCO$_3$, water, and brine. The organic layer was dried over Na$_2$SO$_4$, filtered, and concentrated under the reduced pressure. The residue was purified by flash chromatography on silica gel (40 g column, gradient elution of 0% to 50% ethyl acetate in hexanes) to give the title compounds.

Step E. 2-((2R,5R,6R)-4-((S)-2-(tert-Butylsulfonyl)-1-cyclopropylethyl)-5-(4-chlorophenyl)-6-(3,4-dichlorophenyl)-3-oxomorpholin-2-yl)acetic acid or 2-((2S,5R,6R)-4-((S)-2-(tert-butylsulfonyl)-1-cyclopropylethyl)-5-(4-chlorophenyl)-6-(3,4-dichlorophenyl)-3-oxomorpholin-2-yl)acetic acid

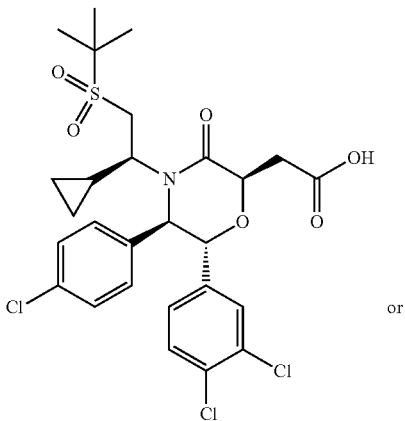

or

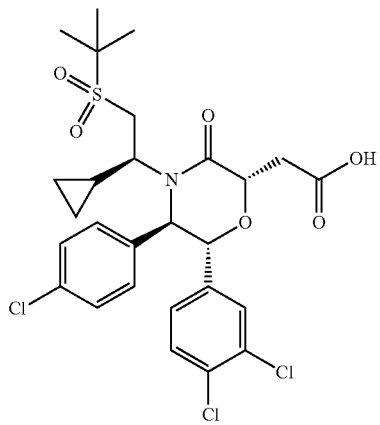

One of the title compounds was prepared from (2R,5R,6R)-2-allyl-4-((S)-2-(tert-butylsulfonyl)-1-cyclopropylethyl)-5-(4-chlorophenyl)-6-(3,4-dichlorophenyl)morpholin-3-one and (2S,5R,6R)-2-allyl-4-((S)-2-(tert-butylsulfonyl)-1-cyclopropylethyl)-5-(4-chlorophenyl)-6-(3,4-dichlorophenyl)morpholin-3-one (Example 318, Step D) by a procedure similar to that described in Example 112, Step F. The residue was purified by reverse phase preparatory HPLC (Agilient 1100, column: Gemini® 5 µm $C_{18}$, 100 mm×30 mm (Phenomenex, Torrance, Calif.), gradient elution of 45% to 65% acetonitrile in water, where both solvents contain 0.1% TFA, 20 minutes) to give one of the compounds as the first (faster) eluting isomer. $^1$H NMR (400 MHz, $CDCl_3$, δ ppm): 7.33 (d, J=8.0 Hz, 2H), 7.25-7.27 (d, J=8.0 Hz, 2H), 7.14-7.19 (m, 2H), 6.81-6.84 (dd, J=12.0, 4.0 Hz, 1H), 5.03 (d, J=8.0 Hz, 1H), 4.78 (t, J=8.0, 4 Hz, 1H), 4.73 (d, J=8.0 Hz, 1H), 4.24 (m, 1H), 3.23-3.28 (m, 1H), 2.95-3.05 (m, 2H), 2.50 (s, 1H), 1.90 (s, 1H), 1.44 (s, 9H), 0.36-0.42 (m, 2H), −0.18 (m, 1H), −0.82 (m, 1H). MS (ESI) m/z=604.0 [M+1].

Example 319

2-((2R,5R,6R)-4-((S)-2-(tert-Butylsulfonyl)-1-cyclopropylethyl)-5-(4-chlorophenyl)-6-(3,4-dichlorophenyl)-3-oxomorpholin-2-yl)acetic acid or 2-((2S,5R,6R)-4-((S)-2-(tert-butylsulfonyl)-1-cyclopropylethyl)-5-(4-chlorophenyl)-6-(3,4-dichlorophenyl)-3-oxomorpholin-2-yl)acetic acid

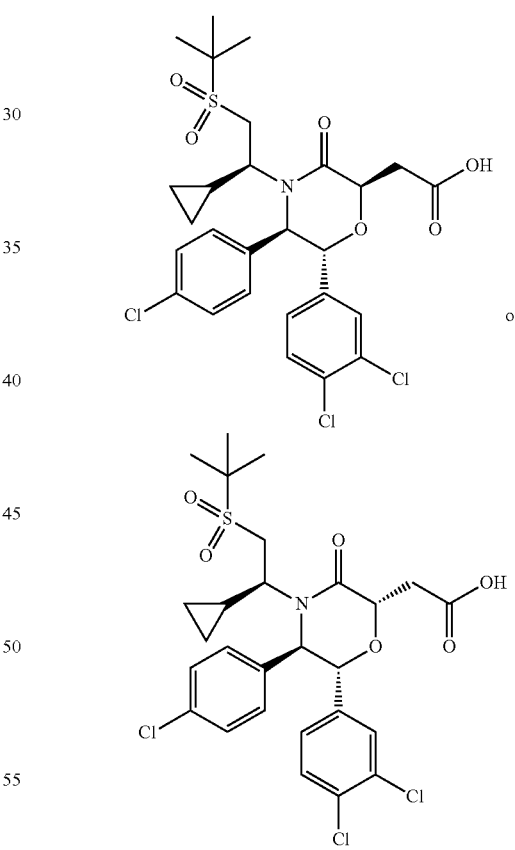

Further elution of the chromatographic purification described in Example 318, Step E provided one of the title compounds as the second (slower) eluting isomer. $^1$H NMR (400 MHz, $CDCl_3$, δ ppm): 7.22-7.33 (m, 4H), 7.16 (m, 1H), 7.04-7.06 (d, J=8.0 Hz, 1H), 6.68 (dd, J=8.3, 2.1 Hz, 1H), 4.66-4.80 (m, 3H), 3.52-3.64 (m, 2H), 3.03-3.19 (m, 3H), 1.34 (s, 9H), 1.18 (s, 1H), 0.56 (ddd, J=8.2, 2.6, 2.5 Hz, 2H), 0.45 (m, 1H), 0.32 (m, 1H). MS (ESI) m/z=604.0 [M+1].

Example 320

2-((2R,5R,6R)-4-((S)-2-(tert-Butylsulfonyl)-1-cyclopropylethyl)-6-(3-chloro-4-fluorophenyl)-5-(4-chlorophenyl)-3-oxomorpholin-2-yl)acetic acid or 2-((2S,5R,6R)-4-((S)-2-(tert-butylsulfonyl)-1-cyclopropylethyl)-6-(3-chloro-4-fluorophenyl)-5-(4-chlorophenyl)-3-oxomorpholin-2-yl)acetic acid

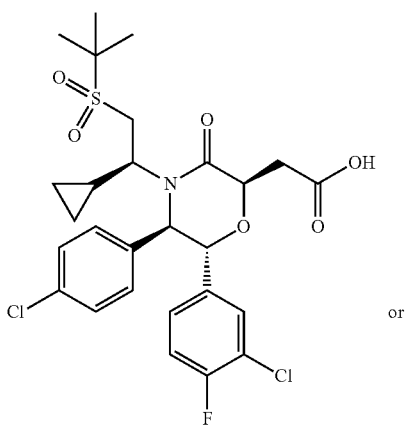

or

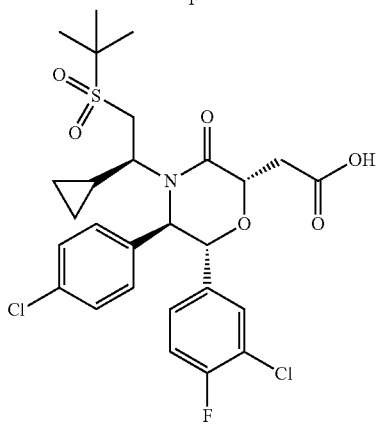

Step A. (5R,6R)-6-(3-Chloro-4-fluorophenyl)-5-(4-chlorophenyl)-4-((S)-1-cyclopropyl-2-hydroxyethyl)morpholin-3-one

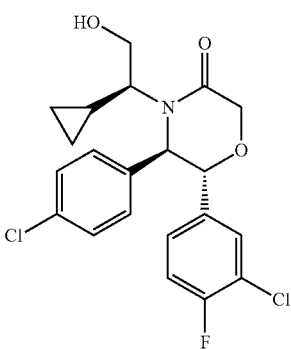 [SMILES: O=C1CO[C@H](c2ccc(F)c(Cl)c2)[C@@H](c2ccc(Cl)cc2)N1[C@H](CO)C1CC1]

The title compound was prepared from (1R,2R)-2-amino-1-(3-chloro-4-fluorophenyl)-2-(4-chlorophenyl)ethanol (Intermediate C8) by procedures similar to those described in Example 308, Steps A and B. The residue was purified by flash chromatography on silica gel (gradient elution of 10% to 30% ethyl acetate in dichloromethane) to give the title compound as the second (slower) eluting peak.

Step B. (2R,5R,6R)-2-Allyl-4-((S)-2-(tert-butylthio)-1-cyclopropylethyl)-6-(3-chloro-4-fluorophenyl)-5-(4-chlorophenyl)morpholin-3-one or (2S,5R,6R)-2-allyl-4-((S)-2-(tert-butylthio)-1-cyclopropylethyl)-6-(3-chloro-4-fluorophenyl)-5-(4-chlorophenyl)morpholin-3-one

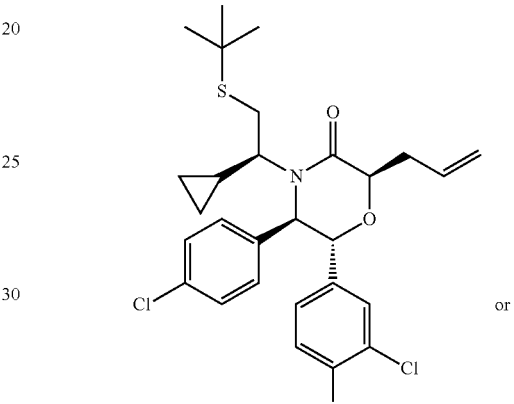

or

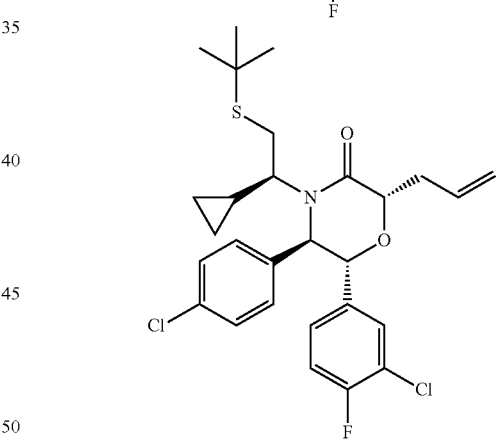

One of the title compounds was prepared from (5R,6R)-6-(3-chloro-4-fluorophenyl)-5-(4-chlorophenyl)-4-((S)-1-cyclopropyl-2-hydroxyethyl)morpholin-3-one (Example 320, Step A) by procedures similar to those described in Example 112, Steps C through E, replacing ethanethiol in Step D with 2-methylpropane-2-thiol. The residue was purified by flash chromatography on silica gel (2×40 g columns stacked, gradient elution of 0% to 40% ethyl acetate in hexanes) to give one of the title compounds as the first (faster) eluting isomer.

539

Step C. 2-((2R,5R,6R)-4-((S)-2-(tert-Butylsulfonyl)-1-cyclopropylethyl)-6-(3-chloro-4-fluorophenyl)-5-(4-chlorophenyl)-3-oxomorpholin-2-yl)acetic acid or 2-((2S,5R,6R)-4-((S)-2-(tert-butylsulfonyl)-1-cyclopropylethyl)-6-(3-chloro-4-fluorophenyl)-5-(4-chlorophenyl)-3-oxomorpholin-2-yl)acetic acid

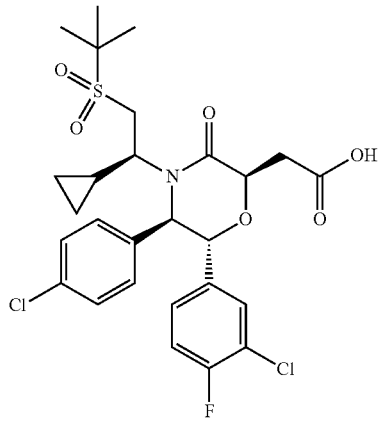

or

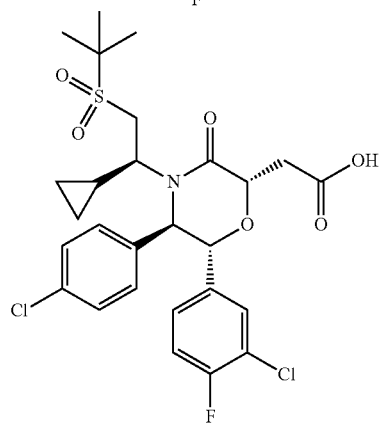

One of the title compounds was prepared from (2R,5R,6R)-2-allyl-4-((S)-2-(tert-butylthio)-1-cyclopropylethyl)-6-(3-chloro-4-fluorophenyl)-5-(4-chlorophenyl)morpholin-3-one or (2S,5R,6R)-2-allyl-4-((S)-2-(tert-butylthio)-1-cyclopropylethyl)-6-(3-chloro-4-fluorophenyl)-5-(4-chlorophenyl) morpholin-3-one (Example 320, Step B) by procedures similar to those described in Example 318, Steps D and E. The residue was purified by reverse phase preparatory HPLC (Agilent 1100, column: Gemini® 5 μm $C_{18}$, 100 mm×30 mm (Phenomenex, Torrance, Calif.), gradient elution of 45% to 70% acetonitrile in water, where both solvents contain 0.1% TFA, 30 minutes) to give one of the compounds. $^1$H NMR (400 MHz, CDCl$_3$, δ ppm): 7.44 (m, 1H), 7.36 (m, 4H), 7.16 (m, 1H), 7.04 (t, J=4.3 Hz, 1H), 5.14 (d, J=5.3 Hz, 1H), 4.95 (d, J=5.5 Hz, 1H), 4.62-4.68 (m, 1H), 4.03 (br. s., 1H), 3.13 (m, 3H), 2.83 (br. s., 1H), 1.83 (br. s., 1H), 1.44 (s, 9H), 0.44 (br. s., 1H), 0.36 (br. s., 1H), 0.01 (br. s., 1H), −0.75 (br. s., 1H). MS (ESI) m/z=586.0 [M+1].

540

Example 321

2-((2R,5R,6R)-4-((S)-2-(tert-Butylsulfonyl)-1-cyclopropylethyl)-6-(3-chloro-4-fluorophenyl)-5-(4-chlorophenyl)-3-oxomorpholin-2-yl)acetic acid or 2-((2S,5R,6R)-4-((S)-2-(tert-butylsulfonyl)-1-cyclopropylethyl)-6-(3-chloro-4-fluorophenyl)-5-(4-chlorophenyl)-3-oxomorpholin-2-yl)acetic acid

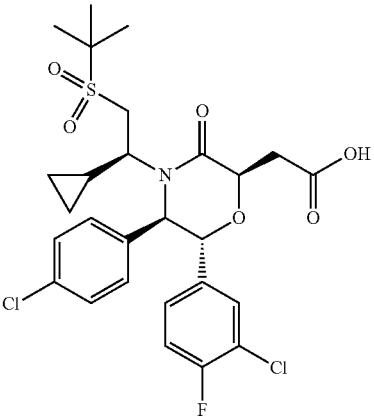

or

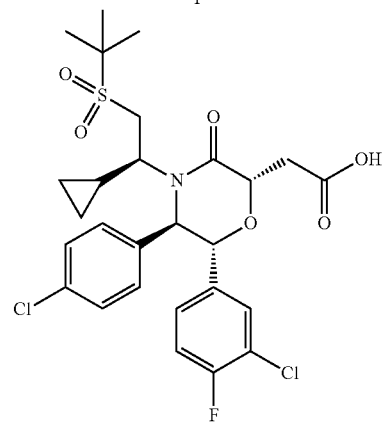

Step A. (2R,5R,6R)-2-Allyl-4-((S)-2-(tert-butylthio)-1-cyclopropylethyl)-6-(3-chloro-4-fluorophenyl)-5-(4-chlorophenyl)morpholin-3-one or (2S,5R,6R)-2-allyl-4-((S)-2-(tert-butylthio)-1-cyclopropylethyl)-6-(3-chloro-4-fluorophenyl)-5-(4-chlorophenyl) morpholin-3-one

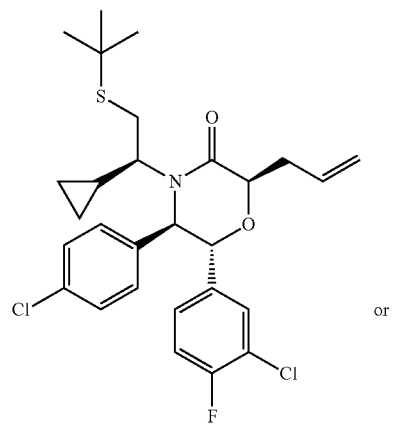

or

-continued

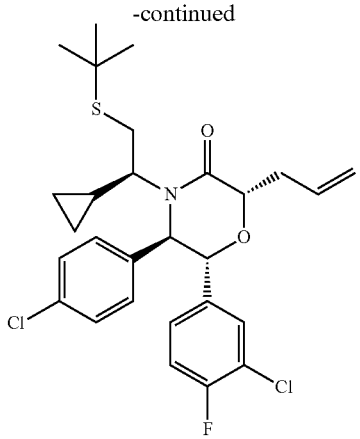

Further elution of the chromatographic purification described in Example 320, Step B provided one of the title compounds as the second (slower) eluting isomer.

Step B. 2-((2R,5R,6R)-4-((S)-2-(tert-Butylsulfonyl)-1-cyclopropylethyl)-6-(3-chloro-4-fluorophenyl)-5-(4-chlorophenyl)-3-oxomorpholin-2-yl)acetic acid or 2-((2S,5R,6R)-4-((S)-2-(tert-butylsulfonyl)-1-cyclopropylethyl)-6-(3-chloro-4-fluorophenyl)-5-(4-chlorophenyl)-3-oxomorpholin-2-yl)acetic acid

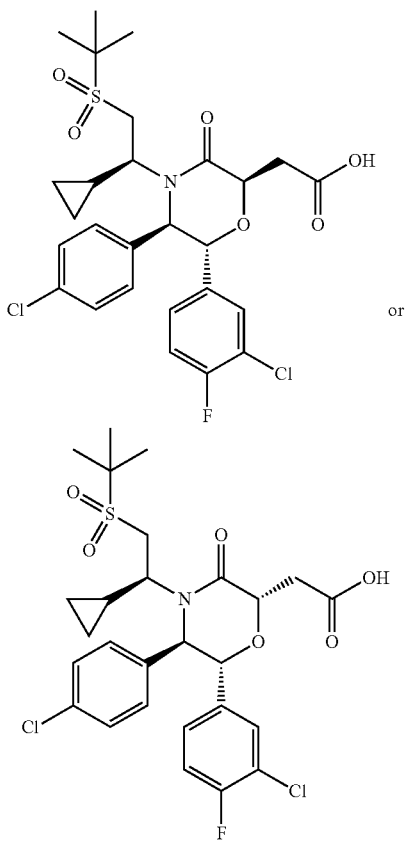

One of the title compounds was prepared from (2R,5R,6R)-2-allyl-4-((S)-2-(tert-butylthio)-1-cyclopropylethyl)-6-(3-chloro-4-fluorophenyl)-5-(4-chlorophenyl)morpholin-3-one or (2S,5R,6R)-2-allyl-4-((S)-2-(tert-butylthio)-1-cyclopropylethyl)-6-(3-chloro-4-fluorophenyl)-5-(4-chlorophenyl)morpholin-3-one (Example 320, Step B) by procedures similar to those described in Example 318, Steps D and E. The residue was purified by reverse phase preparatory HPLC (Agilient 1100, column: Gemini® 5 μm $C_{18}$, 100 mm×30 mm (Phenomenex, Torrance, Calif.), gradient elution of 45% to 70% acetonitrile in water, where both solvents contain 0.1% TFA, 30 minutes) to give one of the compounds. $^1$H NMR (400 MHz, CDCl$_3$, δ ppm): 7.31-7.33 (m, 2H), 7.13-7.18 (m, 3H), 6.92-6.99 (m, 1H), 6.87 (m, 1H), 5.03 (d, J=9.8 Hz, 1H), 4.78 (m, 1H), 4.73 (d, J=9.8 Hz, 1H), 4.25 (br. s., 1H), 3.23-3.29 (m, 1H), 2.99-3.05 (m, 2H), 2.65 (br. s., 1H), 1.88 (m, 1H), 1.44 (s, 9H), 0.36-0.43 (m, 2H), −0.18 (br. s., 1H), −0.82 (br. s., 1H). MS (ESI) m/z=586.0 [M+1].

Example 322

2-((2R,5R,6R)-6-(4-Bromo-3-chlorophenyl)-4-((S)-2-(tert-butylthio)-1-cyclopropylethyl)-5-(4-chlorophenyl)-3-oxomorpholin-2-yl)acetic acid or 2-((2S,5R,6R)-6-(4-bromo-3-chlorophenyl)-4-((S)-2-(tert-butylthio)-1-cyclopropylethyl)-5-(4-chlorophenyl)-3-oxomorpholin-2-yl)acetic acid

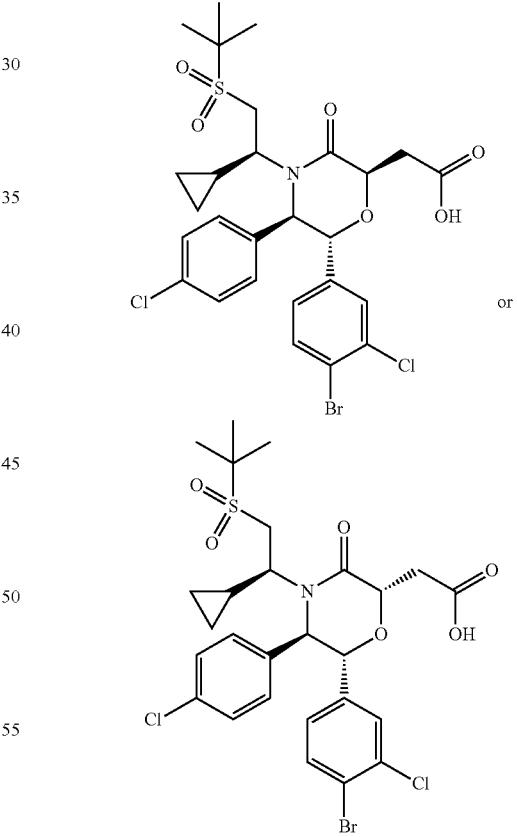

One of the title compounds was prepared from (1R,2R)-2-amino-1-(4-bromo-3-chlorophenyl)-2-(4-chlorophenyl)ethanol (prepared by methods similar to those described in Intermediate C1, Steps A through E, replacing 1-bromo-3-chloro-5-fluorobenzene in Step D with 1-bromo-2-chloro-4-iodobenzene) by procedures similar to those described in Example 320, Steps A through C. The residue was purified by reverse phase preparatory HPLC (Agilient 1100, column: Gemini® 5 µm C$_{18}$, 100 mm×30 mm (Phenomenex, Torrance, Calif.), gradient elution of 45% to 70% acetonitrile in water, where both solvents contain 0.1% TFA, 30 minutes) to give one of the compounds as the first (faster) eluting isomer. $^1$H NMR (400 MHz, CDCl$_3$, δ ppm): 7.51 (d, J=8.4 Hz, 1H), 7.42-7.48 (m, 1H), 7.36 (s, 4H), 7.03-7.05 (m, 1H), 5.13 (d, J=5.3 Hz, 1H), 4.92 (d, J=5.5 Hz, 1H), 4.69 (br. s., 2H), 4.00 (br. s., 1H), 3.13 (br. s., 3H), 1.81 (br. s., 1H), 1.43 (s, 9H), 0.36-0.44 (br. s., 2H), 0.00 (br. s., 1H), −0.74 (br. s., 1H). MS (ESI) m/z=648.0 [M+1].

Example 323

2-((2R,5R,6R)-6-(4-Bromo-3-chlorophenyl)-4-((S)-2-(tert-butylthio)-1-cyclopropylethyl)-5-(4-chlorophenyl)-3-oxomorpholin-2-yl)acetic acid or 2-((2S,5R,6R)-6-(4-bromo-3-chlorophenyl)-4-((S)-2-(tert-butylthio)-1-cyclopropylethyl)-5-(4-chlorophenyl)-3-oxomorpholin-2-yl)acetic acid

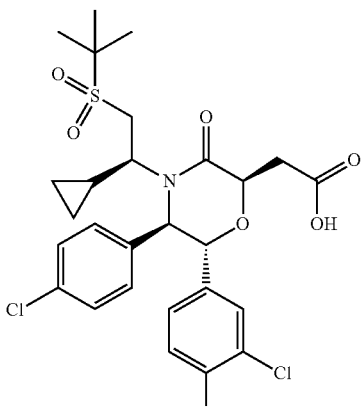

or

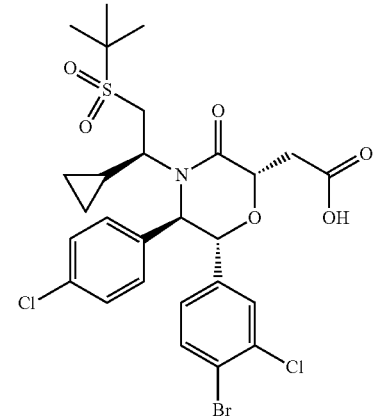

Further elution of the chromatographic separation described in Example 322 provided one of the title compounds as the second (slower) eluting isomer.

$^1$H NMR (400 MHz, CDCl$_3$, δ ppm): 7.43 (d, J=8.2 Hz, 1H), 7.30-7.38 (m, 2H), 7.13-7.23 (m, 3H), 6.75 (dd, J=1.8, 0.4 Hz, 1H), 5.02 (d, J=9.8 Hz, 1H), 4.75-4.80 (m, 1H), 4.71 (d, J=9.8 Hz, 1H), 4.25 (br. s., 1H), 3.24 (m, 1H), 2.99 (m, 2H), 2.64 (br. s., 1H), 1.89 (br. s., 1H), 1.44 (s, 9H), 0.35-0.43 (br. d., 2H), −0.18 (br. s., 1H), −0.83 (br. s., 1H). MS (ESI) m/z=648.0 [M+1].

Example 324

2-((2R,5R,6R)-4-((S)-2-(tert-Butylsulfonyl)-1-cyclopropylethyl)-6-(3-chloro-4-cyanophenyl)-5-(4-chlorophenyl)-3-oxomorpholin-2-yl)acetic acid or 2-((2S,5R,6R)-4-((S)-2-(tert-butylsulfonyl)-1-cyclopropylethyl)-6-(3-chloro-4-cyanophenyl)-5-(4-chlorophenyl)-3-oxomorpholin-2-yl)acetic acid

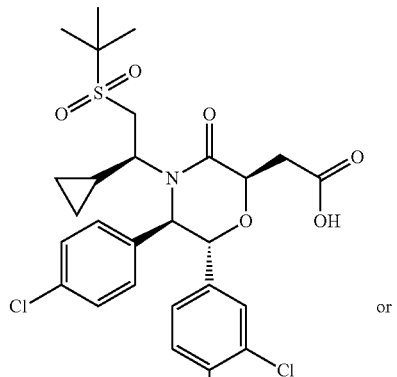

or

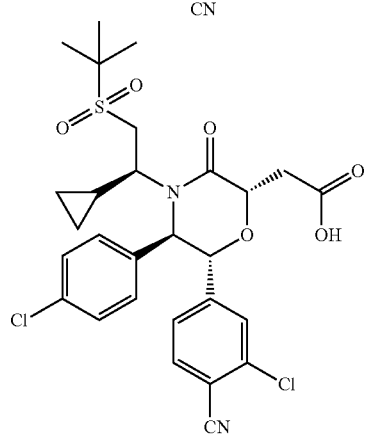

Step A. 4-((2R,3R,6S)-6-Allyl-4-((S)-2-(tert-butylsulfonyl)-1-cyclopropylethyl)-3-(4-chlorophenyl)-5-oxomorpholin-2-yl)-2-chlorobenzonitrile and 4-((2R,3R,6R)-6-allyl-4-((S)-2-(tert-butylsulfonyl)-1-cyclopropylethyl)-3-(4-chlorophenyl)-5-oxomorpholin-2-yl)-2-chlorobenzonitrile

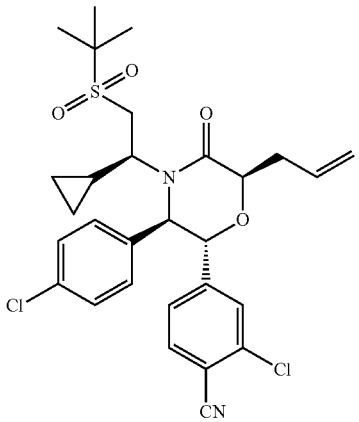

and

545
-continued

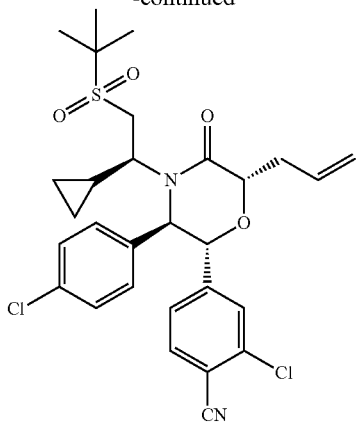

546
-continued

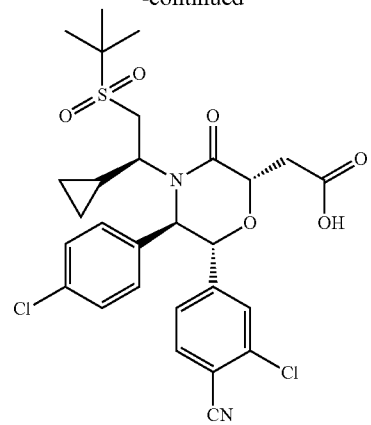

Cuprous cyanide (40 mg, 0.445 mmol), (2S,5R,6R)-2-Allyl-6-(4-bromo-3-chlorophenyl)-4-((S)-2-(tert-butylsulfonyl)-1-cyclopropylethyl)-5-(4-chlorophenyl)morpholin-3-one and (2S,5R,6R)-2-allyl-6-(4-bromo-3-chlorophenyl)-4-((S)-2-(tert-butylsulfonyl)-1-cyclopropylethyl)-5-(4-chlorophenyl)morpholin-3-one (56 mg, 0.089 mmol, prepared from (1R,2R)-2-amino-1-(4-bromo-3-chlorophenyl)-2-(4-chlorophenyl)ethanol by procedures similar to those described in Intermediate C1, Steps A through E and Example 318, Steps C and D), and DMF (1.2 mL) were added to an oven-dried 10 mL microwave tube. The mixture was purged with Ar(g) for 20 minutes then heated to 150° C. for 8 hours in a microwave reactor (CEM, Matthews, N.C.). After cooling, additional cuprous cyanide (32 mg, 0.356 mmol) was added. The mixture was again purged with Ar(g) for 20 minutes and heated to 150° C. for 4 hours in the microwave reactor. The mixture was diluted with ethyl acetate and water then filtered. The layers of the filtrate were separated, and the organic layer was washed with water, brine and dried over MgSO$_4$. After filtration, the mixture was concentrated to provide the title compounds.

Step B. 2-((2R,5R,6R)-4-((S)-2-(tert-Butylsulfonyl)-1-cyclopropylethyl)-6-(3-chloro-4-cyanophenyl)-5-(4-chlorophenyl)-3-oxomorpholin-2-yl)acetic acid or 2-((2S,5R,6R)-4-((S)-2-(tert-butylsulfonyl)-1-cyclopropylethyl)-6-(3-chloro-4-cyanophenyl)-5-(4-chlorophenyl)-3-oxomorpholin-2-yl)acetic acid One of the title compounds was prepared from 4-((2R,3R,6S)-6-allyl-4-((S)-2-(tert-butylsulfonyl)-1-cyclopropylethyl)-3-(4-chlorophenyl)-5-oxomorpholin-2-yl)-2-chlorobenzonitrile and 4-((2R,3R,6R)-6-allyl-4-((S)-2-(tert-butylsulfonyl)-1-cyclopropylethyl)-3-(4-chlorophenyl)-5-oxomorpholin-2-yl)-2-chlorobenzonitrile (Example 324, Step A) by a procedure similar to that described in Example 112, Step F. The residue was purified by reverse phase preparatory HPLC (Agilient 1200, column: ZORBAX Eclipse Plus 5 µm C$_{18}$, 150 mm×30 mm (Agilent Technologies, Santa Clara, Calif.), gradient elution of 30% to 70% acetonitrile in water, where both solvents contain 0.1% TFA, 30 minutes) to give one of the compounds as the first (faster) eluting isomer. $^1$H NMR (400 MHz, CDCl$_3$, δ ppm): 7.57 (d, J=8.0 Hz, 2H), 7.37 (m, 4H), 7.22 (m, 1H), 5.12 (d, J=4.0 Hz, 1H), 5.01 (d, J=4 Hz, 1H), 4.70-4.73 (m, 1H), 4.08-4.14 (m, 1H), 3.08-3.20 (m, 3H), 1.86 (br. s., 1H), 1.45 (s, 1H), 1.43 (s, 9H), 0.41-0.44 (br. d., 2H), −0.08 (br. s., 1H), −0.80 (br. s., 1H). MS (ESI) m/z=593.0 [M+1].

Example 325

2-((2R,5R,6R)-4-((S)-2-(tert-Butylsulfonyl)-1-cyclopropylethyl)-6-(3-chloro-4-cyanophenyl)-5-(4-chlorophenyl)-3-oxomorpholin-2-yl)acetic acid or 2-((2S,5R,6R)-4-((S)-2-(tert-butylsulfonyl)-1-cyclopropylethyl)-6-(3-chloro-4-cyanophenyl)-5-(4-chlorophenyl)-3-oxomorpholin-2-yl)acetic acid

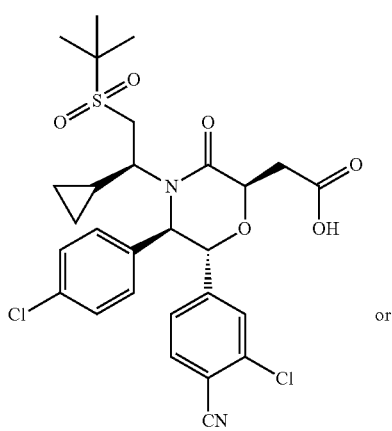

or

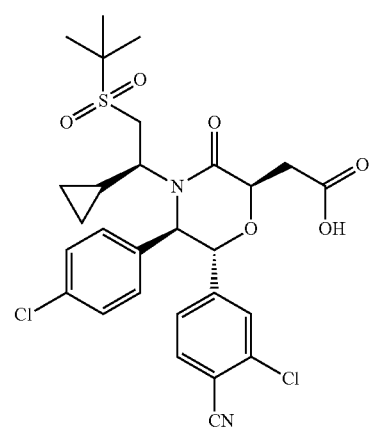

or

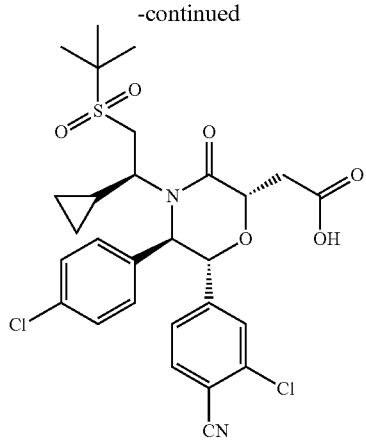

Further elution of the chromatographic purification described in Example 324, Step B provided one of the title compounds as the second (slower) eluting isomer.

$^1$H NMR (400 MHz, CDCl$_3$, δ ppm): 9.83 (s, 1H), 7.49 (d, J=8.0 Hz, 1H), 7.34 (m, 2H), 7.22 (m, 3H), 6.93 (d, J=8.0 Hz, 1H), 5.01 (d, J=8.0 Hz, 1H), 4.78 (d, J=8 Hz, 1H,), 4.25 (m, 1H), 3.25-3.31 (m, 1H), 3.01 (m, 2H), 2.96 (br. s., 1H), 1.91 (br. s., 2H), 1.44 (s, 9H), 0.41-0.44 (br. d., 2H), −0.19 (br. s., 1H), −0.83 (br. s., 1H). MS (ESI) m/z=593.0 [M+1].

Example 326

2-((2R,5R,6R)-4-((S)-2-(tert-Butylsulfonyl)-1-cyclopropylethyl)-6-(3-chloro-2-fluorophenyl)-5-(4-chlorophenyl)-3-oxomorpholin-2-yl)acetic acid and 2-((2S,5R,6R)-4-((S)-2-(tert-butylsulfonyl)-1-cyclopropylethyl)-6-(3-chloro-2-fluorophenyl)-5-(4-chlorophenyl)-3-oxomorpholin-2-yl)acetic acid

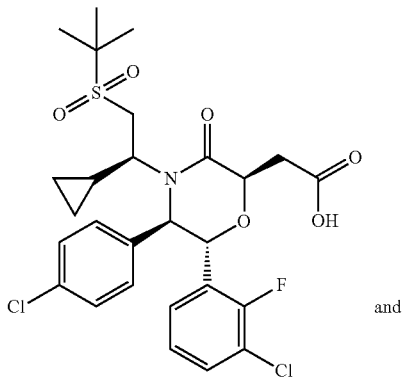

and

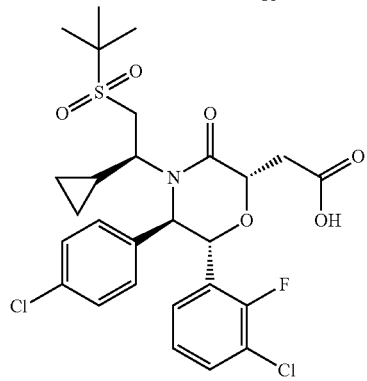

Step A. 2-(tert-Butylthio)-1-cyclopropylethanone

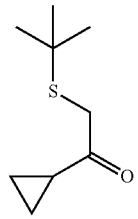

2-Bromo-1-cyclopropylethanone (24.65 mL, 151 mmol) was dissolved in acetonitrile (89 mL) and cooled to 0° C. N,N-Diisopropylethylamine (31.7 mL, 181 mmol) was added followed by tert-butylthiol (16.19 mL, 144 mmol). The mixture was gradually warmed to room temperature and stirred for 2 days. The mixture was poured into of 10% aqueous citric acid (300 mL). The mixture was extracted with ethyl acetate (2×). The organic layers were combined, dried over Na$_2$SO$_4$, filtered, and concentrated. The residue was purified by flash chromatography on silica gel (330 g GOLD column (Teledyne Isco, Lincoln, Nebr.); gradient elution of 0% to 100% ethyl acetate in hexanes) to give the title compound.

Step B. (1R,2R)-2-(((S)-2-(tert-Butylthio)-1-cyclopropylethyl)amino)-1-(3-chloro-2-fluorophenyl)-2-(4-chlorophenyl)ethanol

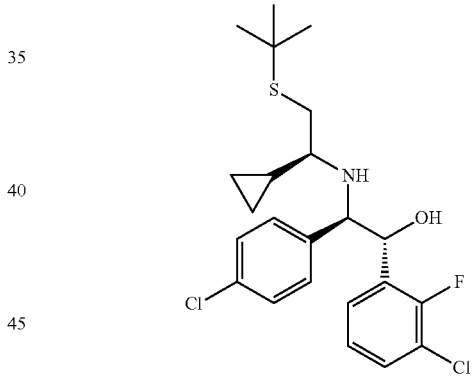

(1R,2R)-2-Amino-1-(3-chloro-2-fluorophenyl)-2-(4-chlorophenyl)ethanol (500 mg, 1.666 mmol, prepared by procedures similar to those described in Intermediate C1, Steps A through E, replacing 1-bromo-3-chloro-5-fluorobenzene in Step D with 1-bromo-3-chloro-2-fluorobenzene) and 4-methylbenzene sulfonic acid, monohydrate (15.84 mg, 0.083 mmol) were added to a single neck flask equipped with a stir bar. Toluene (16.7 mL) and 2-(tert-butylthio)-1-cyclopropylethanone (430 mg, 2.499 mmol, Example 326, Step A) were added. The flask was equipped with a Dean-Stark trap, condenser and N$_2$(g) inlet. The mixture was heated in an oil bath at reflux for 2.5 hours. A precipitate formed, and the mixture became light yellow. The mixture was concentrated. The residue was diluted with diethyl ether (8.3 mL) and cooled to 0° C. LAH (1.0 M in THF, 4150 μL, 4.15 mmol) was added and the mixture was stirred at 0° C. for 15 minutes. Methanol was added, and after stirring at 0° C. for 2 hours, disodium sulfate decahydrate (161 μL, 1.660 mmol) was added portionwise. The mixture was stirred at room temperature overnight.

A precipitate formed and the mixture was filtered. The filtrate was concentrated and the residue was purified by flash chromatography on silica gel (gradient elution of 0% to 10% (1% NH$_4$OH in MeOH), in dichloromethane). The residue was further purified by reverse phase preparatory HPLC (Agilient 1100, column: Gemini® 10 μm C$_{18}$, 110 Å, 250 mm×30 mm (Phenomenex, Torrance, Calif.), gradient elution of 10% to 90% acetonitrile in water, where both solvents contain 0.1% TFA). The fraction containing the desired mass was partitioned with ethyl acetate and saturated NaHCO$_3$. The organic layer was washed with brine, dried with sodium sulfate, filtered and concentrated. The residue still contained an impurity, so it was purified again by flash chromatography on silica gel (4 g column; gradient elution of 0 to 50% ethyl acetate in hexanes) to give the title compound.

Step C. 2-((2R,5R,6R)-4-((S)-2-(tert-Butylsulfonyl)-1-cyclopropylethyl)-6-(3-chloro-2-fluorophenyl)-5-(4-chlorophenyl)-3-oxomorpholin-2-yl)acetic acid and 2-((2S,5R,6R)-4-((S)-2-(tert-butylsulfonyl)-1-cyclopropylethyl)-6-(3-chloro-2-fluorophenyl)-5-(4-chlorophenyl)-3-oxomorpholin-2-yl)acetic acid

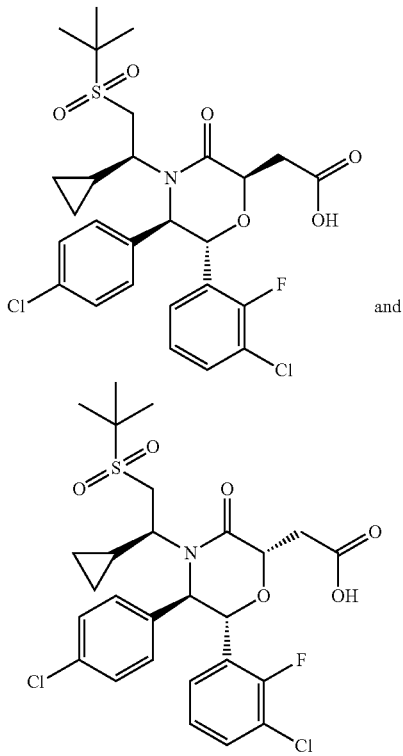

The title compound were prepared from (1R,2R)-2-(((S)-2-(tert-butylsulfonyl)-1-cyclopropylethyl)amino)-1-(3-chloro-2-fluorophenyl)-2-(4-chlorophenyl)ethanol (Example 326, Step B) by procedures similar to those described in Example 162, Steps F and G, followed by Example 112, Steps E and F. The residue was purified by preparative TLC (eluent: 20% IPA in hexanes) to give the titled compounds as a mixture of diastereomers. $^1$H NMR (400 MHz, CDCl$_3$, δ ppm): 10.07 (br. s., 1H), 7.50-7.43 (m, 1H), 7.37-7.29 (m, 4H), 7.22-7.20 (m, 1H), 7.13-7.09 (m, 1H), 5.30-5.29 (m), 5.20-5.15 (m, 2H), 4.80 (dd, J=4.9, 7.1 Hz), 4.64 (t, J=6.4 Hz, 1H), 4.22 (br. s), 4.08 (br. s., 1H), 3.25-2.66 (m, 4H), 1.87-1.75 (m, 1H), 1.41 (s, 9H), 0.44-0.35 (m, 2H), 0.05 (br. s.), −0.18 (br. s., 1H), −0.74 (br. s.), −0.81 (br. s., 1H). MS (ESI) m/z=586.1 [M+1].

Example 327

2-((2R,5R,6R)-4-((S)-2-(tert-Butylsulfonyl)-1-cyclopropylethyl)-6-(3-chloro-4-methylphenyl)-5-(4-chlorophenyl)-3-oxomorpholin-2-yl)acetic acid

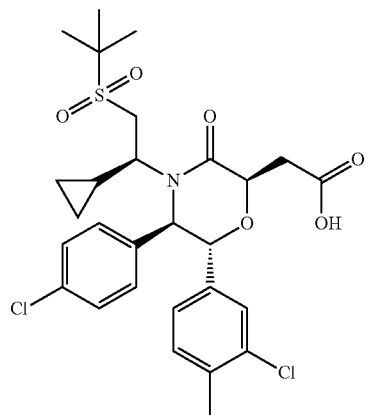 [SMILES: Cc1ccc([C@H]2O[C@H](CC(=O)O)C(=O)N([C@H](CS(=O)(=O)C(C)(C)C)C3CC3)[C@@H]2c2ccc(Cl)cc2)cc1Cl]

The title compound was prepared from (1R,2R)-2-amino-1-(3-chloro-4-methylphenyl)-2-(4-chlorophenyl)ethanol (prepared by methods similar to those described in Intermediate C1, Steps A through E, replacing 1-bromo-3-chloro-5-fluorobenzene in Step D with 4-bromo-2-chloro-1-methylbenzene) by procedures similar to those described in Example 320, Steps A through C. The residue was purified by flash chromatography on silica gel (eluent: 10% IPA in hexanes) to give the title compound. $^1$HNMR (500 MHz, CDCl$_3$, δ ppm): 7.44-7.31 (m, 5H), 7.17-7.12 (m, 2H), 5.19 (d, J=5.0 Hz, 1H), 4.94 (d, J=5.0 Hz, 1H), 4.54 (t, J=5.0 Hz, 1H), 3.95 (br. s., 1H), 3.20-3.06 (m, 3H), 2.89 (br. s., 1H), 2.34 (s, 3H), 1.82 (br. s., 1H), 1.44 (s, 9H), 0.46 (m, 1H), 0.37 (m, 1H,), 0.09 (m, 1H), −0.75 (m, 1H). MS (ESI) m/z=582 [M+1].

Example 328

2-((2R,5R,6R)-4-((S)-2-(tert-Butylthio)-1-cyclopropylethyl)-6-(3-chloro-4-methoxyphenyl)-5-(4-chlorophenyl)-3-oxomorpholin-2-yl)acetic acid or 2-((2S,5R,6R)-4-((S)-2-(tert-butylthio)-1-cyclopropylethyl)-6-(3-chloro-4-methoxyphenyl)-5-(4-chlorophenyl)-3-oxomorpholin-2-yl)acetic acid

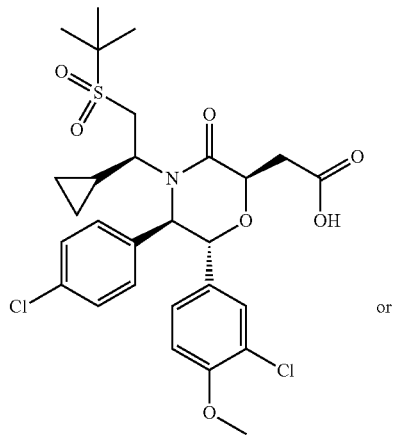

or

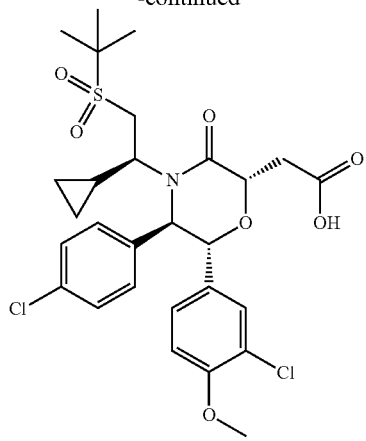

One of the title compounds was prepared from (1R,2R)-2-amino-1-(3-chloro-4-methoxyphenyl)-2-(4-chlorophenyl)ethanol (prepared by methods similar to those described in Intermediate C1, Steps A through E, replacing 1-bromo-3-chloro-5-fluorobenzene in Step D with 4-bromo-2-chloro-1-methoxybenzene) by procedures similar to those described in Example 320, Steps A through C. The residue was purified by reverse phase preparatory HPLC (Agilient 1200, column: ZORBAX Eclipse Plus 5 μm $C_{18}$, 150 mm×30 mm (Agilent Technologies, Santa Clara, Calif.), gradient elution of 5% to 45% acetonitrile in water, where both solvents contain 0.1% TFA, 35 minutes) to give one of the title compounds. $^1$HNMR (500 MHz, CDCl$_3$, δ ppm): 8.86 (br. s., 1H), 7.38-7.34 (m, 5H), 7.18 (d, J=10.0 Hz, 1H), 6.83 (d, J=10.0 Hz, 1H), 5.17 (d, J=5.0 Hz, 1H), 4.94 (d, J=5.0 Hz, 1H), 4.61 (t, J=5.0 Hz, 1H), 3.99 (br. s., 1H), 3.87 (s, 3H), 3.20-3.06 (m, 3H), 2.89 (br. s., 1H), 1.81 (br. s., 1H), 1.44 (s, 9H), 0.45 (m, 1H), 0.37 (m, 1H), 0.06 (m, 1H), −0.75 (m, 1H). MS (ESI) m/z=598 [M+1].

Example 329

2-((2R,5R,6R)-6-(3-Chlorophenyl)-5-(4-chlorophenyl)-4-((S)-1-(N-(2-fluorophenyl)cyclopropanesulfonamido)butan-2-yl)-2-methyl-3-oxomorpholin-2-yl)acetic acid or 2-((2S,5R,6R)-6-(3-chlorophenyl)-5-(4-chlorophenyl)-4-((S)-1-(N-(2-fluorophenyl)cyclopropanesulfonamido)butan-2-yl)-2-methyl-3-oxomorpholin-2-yl)acetic acid

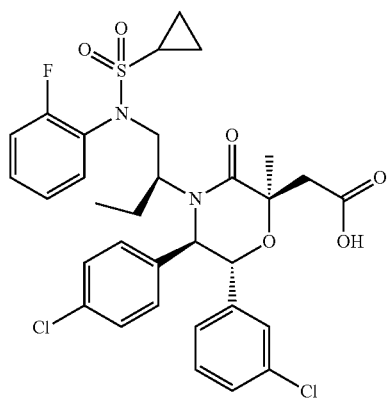

or

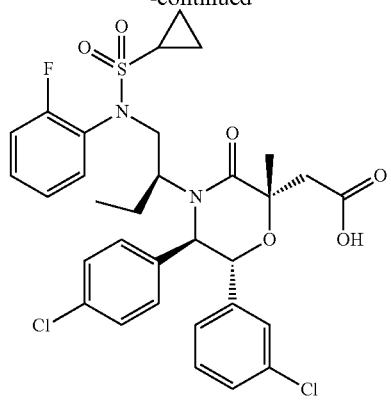

Step A. (2R,5R,6R)-6-(3-Chlorophenyl)-5-(4-chlorophenyl)-4-((S)-1-(((3,4-dimethoxybenzyl)oxy)butan-2-yl)-2-methylmorpholin-3-one and (2S,5R,6R)-6-(3-chlorophenyl)-5-(4-chlorophenyl)-4-((S)-1-((3,4-dimethoxybenzyl)oxy)butan-2-yl)-2-methylmorpholin-3-one

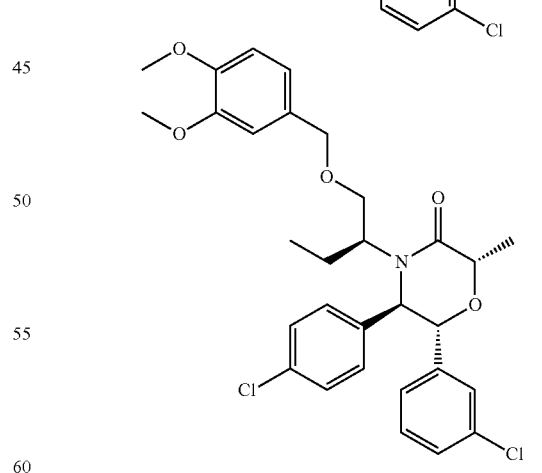

Lithium bis(trimethylsilyl)amide (1.0 M in THF, 1763 μL, 1.763 mmol) was added to a solution of (5R,6R)-6-(3-chlorophenyl)-5-(4-chlorophenyl)-4-(1-((3,4-dimethoxybenzyl)oxy)butan-2-yl)morpholin-3-one (800 mg, 1.469 mmol, Example 112, Step B) in THF (3673 μL) at −78° C. Iodomethane (100 μL, 1.616 mmol) was added and the mixture was stirred at −78° C. for 30 minutes. The mixture was warmed to −40° C. and stirred at −40° C. overnight. The mixture was diluted with saturated NH₄Cl (10 mL) and extracted with diethyl ether (3×30 mL). The organic layers werer combined, dried over MgSO₄, filtered, and concentrated to give a light-yellow oil. The residue was purified by flash chromatography on silica gel (120 g column; gradient elution of 10% to 30% acetone in hexanes) to give the title compounds as a white solid.

Step B. (2R,5R,6R)-2-Allyl-6-(3-chlorophenyl)-5-(4-chlorophenyl)-4-((S)-1-((3,4-dimethoxybenzyl)oxy)butan-2-yl)-2-methylmorpholin-3-one and (2S,5R,6R)-2-allyl-6-(3-chlorophenyl)-5-(4-chlorophenyl)-4-((S)-1-((3,4-dimethoxybenzyl)oxy)butan-2-yl)-2-methylmorpholin-3-one

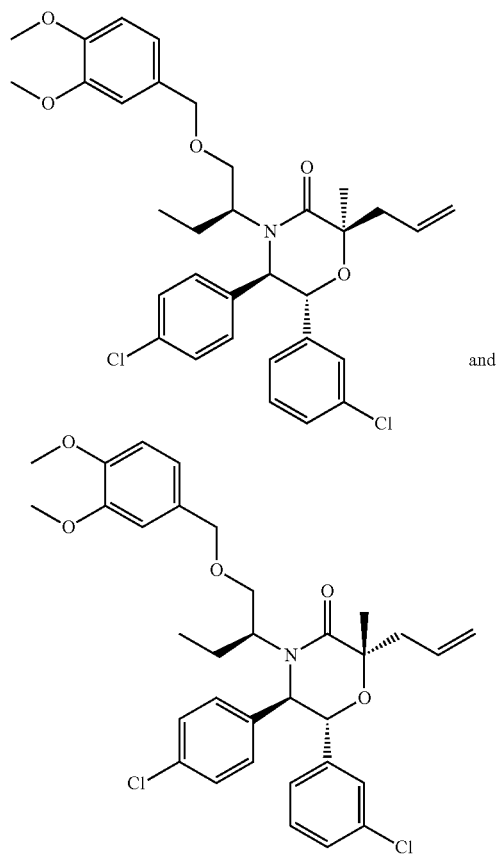

and

Lithium bis(trimethylsilyl)amide (1.0 M in THF, 1354 μL, 1.354 mmol) was added to a solution of (2R,5R,6R)-6-(3-chlorophenyl)-5-(4-chlorophenyl)-4-((S)-1-((3,4-dimethoxybenzyl)oxy)butan-2-yl)-2-methylmorpholin-3-one and (2S,5R,6R)-6-(3-chlorophenyl)-5-(4-chlorophenyl)-4-((S)-1-((3,4-dimethoxybenzyl)oxy)butan-2-yl)-2-methylmorpholin-3-one (630 mg, 1.128 mmol, Step 329, Step A) in THF (2820 μL) at −78° C. Allyl bromide (107 μL, 1.241 mmol) was added and the mixture was warmed to −40° C. After stirring overnight at −40° C., the mixture was diluted with water (5 mL) and extracted with diethyl ether (3×10 mL). The organic layer was dried over MgSO₄, filtered, and concentrated to give a light-yellow oil. The residue was purified by flash chromatography on silica gel (120 g column, gradient elution of 5% to 25% acetone in hexanes) to give the title compounds.

Step C. (2R,5R,6R)-2-Allyl-6-(3-chlorophenyl)-5-(4-chlorophenyl)-4-((S)-1-hydroxybutan-2-yl)-2-methylmorpholin-3-one or (2S,5R,6R)-2-allyl-6-(3-chlorophenyl)-5-(4-chlorophenyl)-4-((S)-1-hydroxybutan-2-yl)-2-methylmorpholin-3-one

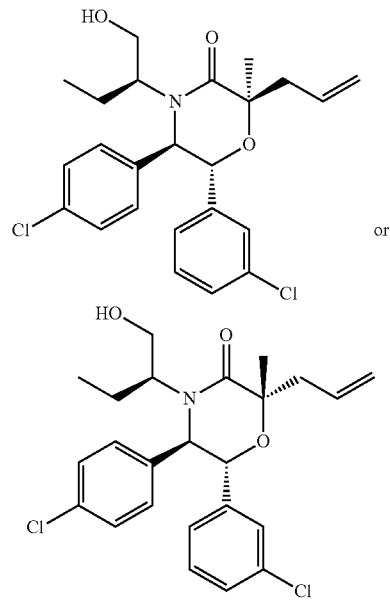

One of the title compounds was prepared from (2R,5R,6R)-2-allyl-6-(3-chlorophenyl)-5-(4-chlorophenyl)-4-((S)-1-((3,4-dimethoxybenzyl)oxy)butan-2-yl)-2-methylmorpholin-3-one and (2S,5R,6R)-2-allyl-6-(3-chlorophenyl)-5-(4-chlorophenyl)-4-((S)-1-((3,4-dimethoxybenzyl)oxy)butan-2-yl)-2-methylmorpholin-3-one (Example 329, Step B) by a procedure similar to that described in Example 112, Step C. The residue was purified by flash chromatography on silica gel (120 g column, gradient elution of 0% to 30% acetone in hexanes) to give one of the title compounds as the first (faster) eluting isomer as an off-white solid.

Step D. 2-((2R,5R,6R)-6-(3-Chlorophenyl)-5-(4-chlorophenyl)-4-((S)-1-(N-(2-fluorophenyl)cyclopropanesulfonamido)butan-2-yl)-2-methyl-3-oxomorpholin-2-yl)acetic acid or 2-((2S,5R,6R)-6-(3-chlorophenyl)-5-(4-chlorophenyl)-4-((S)-1-(N-(2-fluorophenyl)cyclopropanesulfonamido)butan-2-yl)-2-methyl-3-oxomorpholin-2-yl)acetic acid

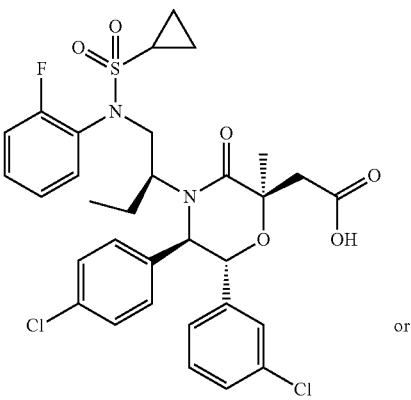

or

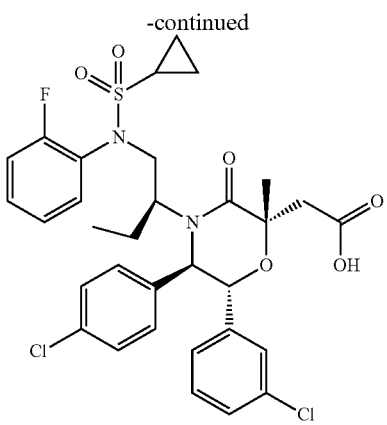

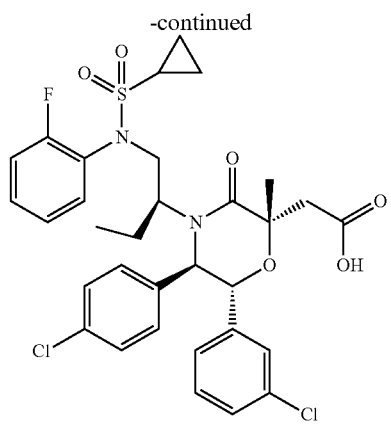

One of the title compounds was prepared from (2R,5R,6R)-2-allyl-6-(3-chlorophenyl)-5-(4-chlorophenyl)-4-((S)-1-hydroxybutan-2-yl)-2-methylmorpholin-3-one or (2S,5R,6R)-2-allyl-6-(3-chlorophenyl)-5-(4-chlorophenyl)-4-((S)-1-hydroxybutan-2-yl)-2-methylmorpholin-3-one (Example 329, Step C) by procedures similar to that described in Example 112, Steps D and F, replacing ethanethiol in Step D with N-(2-fluorophenyl)cyclopropanesulfonamide (Example 133). The residue was purified by reverse phase preparatory HPLC (Agilient 1100, column: Gemini® 5 μm C$_{18}$, 100 mm×30 mm (Phenomenex, Torrance, Calif.), gradient elution of 25% to 75% acetonitrile in water, where both solvents contain 0.1% TFA, 30 minutes) to give one of the title compounds. $^1$H NMR (400 MHz, CDCl$_3$, δ ppm): 7.45 (t, J=7.83 Hz, 1H), 7.32-7.41 (m, 1H), 7.28-7.32 (m, 1H), 7.11-7.26 (m, 6H), 7.05 (s, 1H), 6.96 (br. s., 1H), 6.83 (d, J=7.82 Hz, 1H), 4.68-4.95 (m, 2H), 4.44 (dd, J=7.43, 13.50 Hz, 1H), 3.80 (dd, J=3.81, 14.77 Hz, 1H), 2.63-2.86 (m, 2H), 2.31-2.52 (m, 1H), 1.86-2.07 (m, 1H), 1.72-1.80 (s, 3H), 1.45 (br. s., 1H), 1.57-1.69 (m, J=6.94, 12.23 Hz, 1H), 0.86-1.08 (m, 4H), 0.54 (dd, J=9.19, 10.96 Hz, 3H). MS (ESI) m/z=663.1 [M+1].

Example 330

2-((2R,5R,6R)-6-(3-Chlorophenyl)-5-(4-chlorophenyl)-4-((S)-1-(N-(2-fluorophenyl)cyclopropanesulfonamido)butan-2-yl)-2-methyl-3-oxomorpholin-2-yl)acetic acid or 2-((2S,5R,6R)-6-(3-chlorophenyl)-5-(4-chlorophenyl)-4-((S)-1-(N-(2-fluorophenyl)cyclopropanesulfonamido)butan-2-yl)-2-methyl-3-oxomorpholin-2-yl)acetic acid

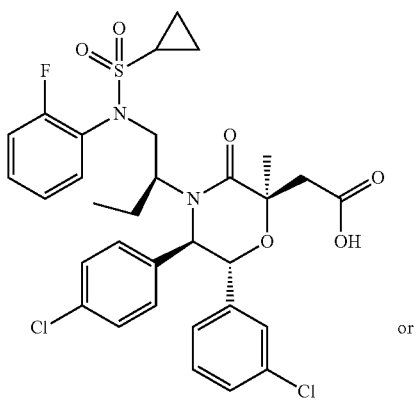

or

Step A. (2R,5R,6R)-2-Allyl-6-(3-chlorophenyl)-5-(4-chlorophenyl)-4-((S)-1-hydroxybutan-2-yl)-2-methylmorpholin-3-one or (2S,5R,6R)-2-allyl-6-(3-chlorophenyl)-5-(4-chlorophenyl)-4-((S)-1-hydroxybutan-2-yl)-2-methylmorpholin-3-one

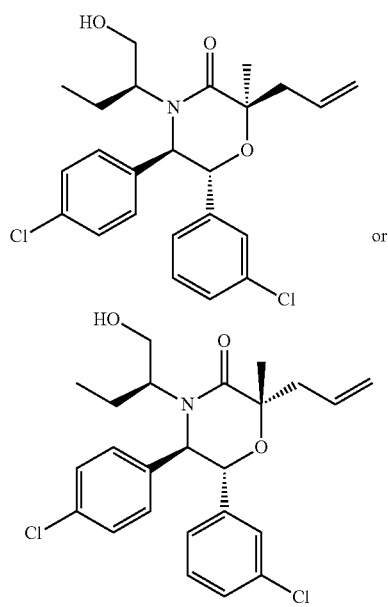

Further elution of the chromatographic separation described in Example 329, Step C provided one of the title compounds as the second (slower) eluting isomer.

Step B. 2-((2R,5R,6R)-6-(3-Chlorophenyl)-5-(4-chlorophenyl)-4-((S)-1-(N-(2-fluorophenyl)cyclopropanesulfonamido)butan-2-yl)-2-methyl-3-oxomorpholin-2-yl)acetic acid or 2-((2S,5R,6R)-6-(3-chlorophenyl)-5-(4-chlorophenyl)-4-((S)-1-(N-(2-fluorophenyl)cyclopropanesulfonamido)butan-2-yl)-2-methyl-3-oxomorpholin-2-yl)acetic acid One of the title compounds was prepared from (2R,5R,6R)-2-allyl-6-(3-chlorophenyl)-5-(4-chlorophenyl)-4-((S)-1-hydroxybutan-2-yl)-2-methylmorpholin-3-one or (2S,5R,6R)-2-allyl-6-(3-chlorophenyl)-5-(4-chlorophenyl)-4-((S)-1-hydroxybutan-2-yl)-2-methylmorpholin-3-one (Example 330, Step A) by procedures similar to that described in Example 112, Steps D and F, replacing ethanethiol in Step D with N-(2-fluorophenyl)cyclopropanesulfonamide (Example 133). The residue was purified by reverse phase preparatory HPLC (Agilient 1100, column: Gemini® 5 μm C$_{18}$, 100 mm×30 mm (Phenomenex, Torrance, Calif.), gradient elution of 25% to 75% acetonitrile in water, where both solvents contain 0.1% TFA, 30 minutes) to give one of the title compounds. $^1$H NMR (400 MHz, CDCl$_3$, δ ppm): 7.52 (t, J=7.73 Hz, 1H), 7.34-7.43 (m, J=4.70 Hz, 1H), 7.16-7.26 (m, 4H), 6.91-7.15 (m, 4H), 6.76 (d, J=7.63 Hz, 1H), 4.90 (d, J=10.17 Hz, 1H), 4.79 (d, J=9.59 Hz, 1H), 4.36 (dd, J=9.29, 14.77 Hz, 1H), 3.72 (dd, J=2.74, 14.87 Hz, 1H), 3.03 (td, J=15.45, 20.93 Hz, 3H), 2.40 (quin, J=6.41 Hz, 1H), 1.89-2.13 (m, 1H), 1.46-1.69 (m, J=3.42, 11.05 Hz, 1H), 1.33 (s, 3H), 1.26 (br. s., 1H) 0.81-1.12 (m, 4H), 0.49 (t, J=7.43 Hz, 3H). MS (ESI) m/z=663.0 [M+1].

Example 331

2-((2R,5R,6R)-6-(3-Chlorophenyl)-5-(4-chlorophenyl)-4-((S)-1-cyclopropyl-2-(N-(2-fluorophenyl)cyclopropanesulfonamido)ethyl)-2-methyl-3-oxomorpholin-2-yl)acetic acid or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-2-methyl-3-oxomorpholin-2-yl)acetic acid

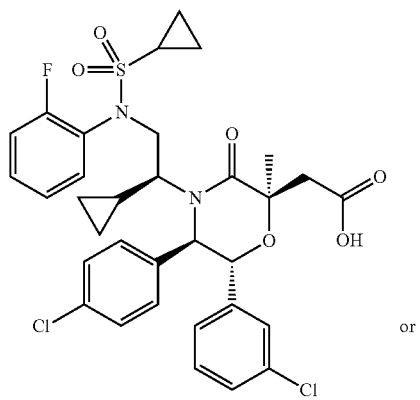

or

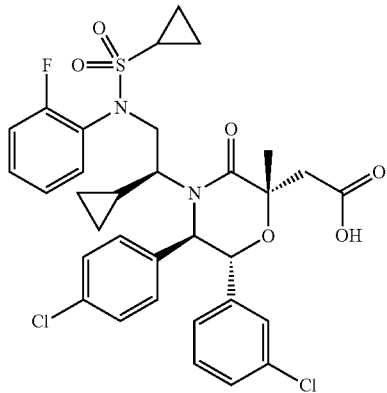

Step A. (5R,6R)-4-((S)-2-((tert-butyldiphenylsilyl)oxy)-1-cyclopropylethyl)-6-(3-chlorophenyl)-5-(4-chlorophenyl)morpholin-3-one

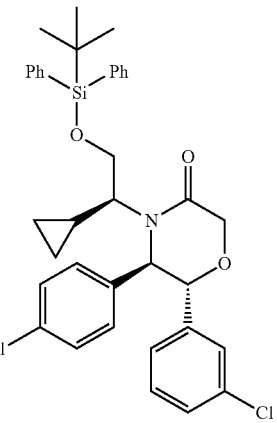

tert-Butylchlorodiphenylsilane (0.592 mL, 2.314 mmol) was added to a solution of (5R,6R)-6-(3-chlorophenyl)-5-(4-chlorophenyl)-4-((S)-1-cyclopropyl-2-hydroxyethyl)morpholin-3-one (470 mg, 1.157 mmol, Example 154, Step B) and 1H-imidazole (197 mg, 2.89 mmol) in DMF (3.889 mL). The yellow solution was stirred at room temperature overnight, under an N$_2$(g) atmosphere. The mixture was quenched with water (50 mL) and extracted with diethyl ether (3×50 mL). The combined the organic layers were dried over MgSO$_4$, filtered and concentrated to give a yellow oil. The yellow oil was purified by flash chromatography on silica gel (80 g column; gradient elution of 0% to 50% acetone in hexanes) to give the title compound as a white solid.

Step B. (2R,5R,6R)-2-Allyl-4-((S)-2-((tert-butyldiphenylsilyl)oxy)-1-cyclopropylethyl)-6-(3-chlorophenyl)-5-(4-chlorophenyl)-2-methylmorpholin-3-one and (2S,5R,6R)-2-allyl-4-((S)-2-((tert-butyldiphenylsilyl)oxy)-1-cyclopropylethyl)-6-(3-chlorophenyl)-5-(4-chlorophenyl)-2-methylmorpholin-3-one

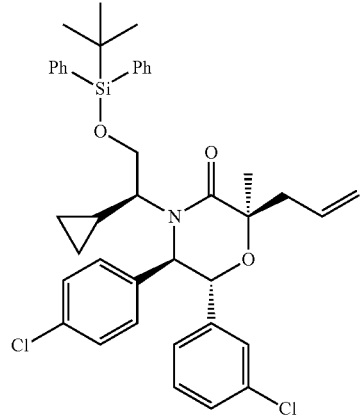

and

559
-continued

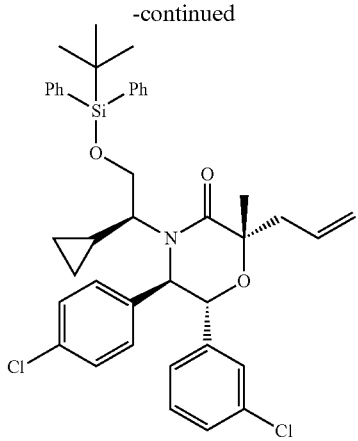

The title compounds were prepared from (5R,6R)-4-((S)-2-((tert-butyldiphenylsilyl)oxy)-1-cyclopropylethyl)-6-(3-chlorophenyl)-5-(4-chlorophenyl)morpholin-3-one by procedures similar to those described in Example 329, Steps A and B.

Step C. 2-((2R,5R,6R)-6-(3-Chlorophenyl)-5-(4-chlorophenyl)-4-((S)-1-cyclopropyl-2-(N-(2-fluorophenyl)cyclopropanesulfonamido)ethyl)-2-methyl-3-oxomorpholin-2-yl)acetic acid or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-2-methyl-3-oxomorpholin-2-yl)acetic acid

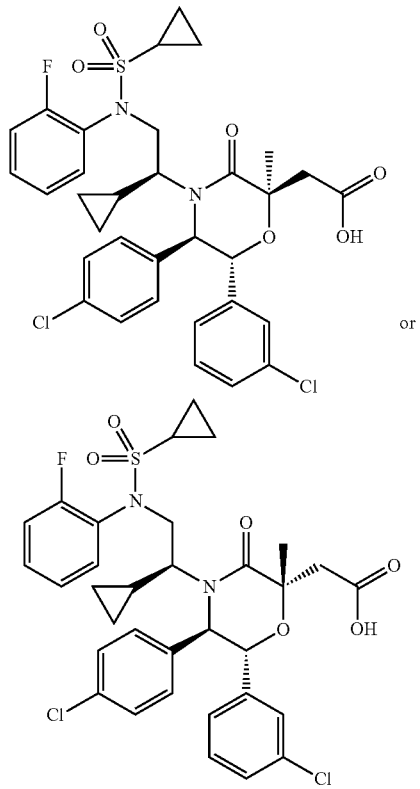

One of the title compounds was prepared from (2R,5R,6R)-2-allyl-4-((S)-2-((tert-butyldiphenylsilyl)oxy)-1-cyclopropylethyl)-6-(3-chlorophenyl)-5-(4-chlorophenyl)-2-me-

560 thylmorpholin-3-one and (2S,5R,6R)-2-allyl-4-((S)-2-((tert-butyldiphenylsilyl)oxy)-1-cyclopropylethyl)-6-(3-chlorophenyl)-5-(4-chlorophenyl)-2-methylmorpholin-3-one (Example 331, Step B) by procedures similar to those described in Example 214, Steps D and E, replacing phenylmethanethiol in Step E with N-(2-fluorophenyl)cyclopropanesulfonamide (Example 133) and Example 112, Step F. The residue was purified by reverse phase preparatory HPLC (Agilient 1100, column: Gemini® 5 µm $C_{18}$, 100 mm×30 mm (Phenomenex, Torrance, Calif.), gradient elution of 25% to 75% acetonitrile in water, where both solvents contain 0.1% TFA, 30 minutes) to give one of the compounds as the first (faster) eluting isomer. $^1$H NMR (400 MHz, CDCl$_3$, δ ppm): 7.72 (t, J=7.24 Hz, 1H), 7.47-7.59 (m, 1H), 7.31-7.47 (m, 6H), 7.13-7.30 (m, 3H), 6.93 (d, J=7.43 Hz, 1H), 5.14 (d, J=9.98 Hz, 1H), 5.00 (d, J=9.78 Hz, 1H), 3.87 (1q, J=6.26 Hz, H), 3.32 (d, J=14.08 Hz, 1H), 3.07 (d, J=13.89 Hz, 1H), 2.48-2.62 (m, 2H), 1.68-1.97 (m, 1H), 1.42 (br. s., 1H), 1.38 (t, J=6.94 Hz, 3H), 1.19 (br. s., 1H), 0.96-1.15 (m, 3H), 0.30-0.72 (m, 2H), −0.04 (br. s., 1H), −0.99 to −0.37 (m, 1H). MS (ESI) m/z=675.1 [M+1].

Example 332

2-((2R,5R,6R)-6-(3-Chlorophenyl)-5-(4-chlorophenyl)-4-((S)-1-cyclopropyl-2-(N-(2-fluorophenyl)cyclopropanesulfonamido)ethyl)-2-methyl-3-oxomorpholin-2-yl)acetic acid or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-2-methyl-3-oxomorpholin-2-yl)acetic acid

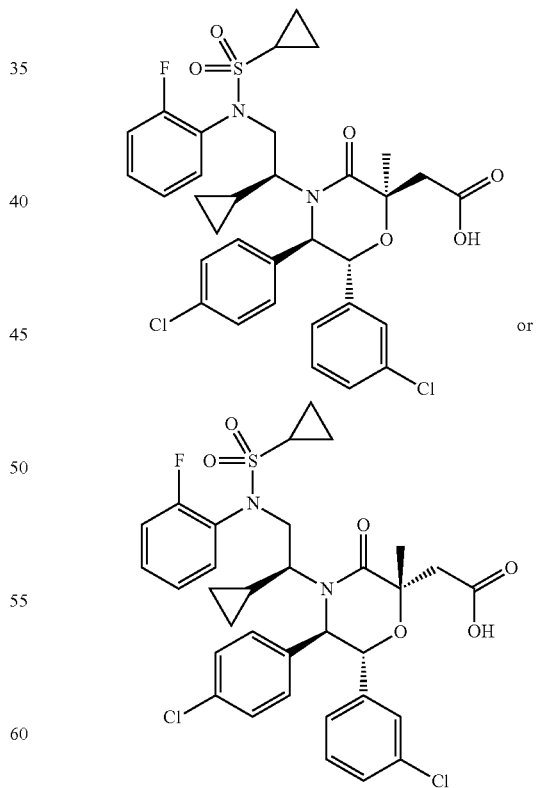

Further elution of the chromatographic purification described in Example 331, Step C provided one of the title compounds as the second (slower) eluting isomer. $^1$H NMR (400 MHz, CDCl$_3$, δ ppm): 7.49 (t, J=7.63 Hz, 1H), 7.32-7.40

(m, 1H), 7.27 (m, 10H), 4.86 (d, J=54.78 Hz, 2H), 4.54 (br. s., 1H), 4.07 (d, J=10.37 Hz, 1H), 2.21-3.02 (m, 4H), 1.77 (br. s., 3H), 1.67 (br. s., 1H), 1.27 (td, J=6.87, 18.14 Hz, 1H), 0.96 (br. s., 3H), 0.42 (br. s., 1H), 0.31 (br. s., 1H), −0.15 (br. s., 1H), −0.72 (br. s., 1H). MS (ESI) m/z=675.1 [M+1].

Example 333

2-((2S,5R,6R)-6-(3-Chlorophenyl)-5-(4-chlorophenyl)-4-((S)-1-cyclopropyl-2-(N-(2-fluorophenyl)cyclopropanesulfonamido)ethyl)-3-oxo-2-(2,2,2-trifluoroethyl)morpholin-2-yl)acetic acid or 2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxo-2-(2,2,2-trifluoroethyl)morpholin-2-yl)acetic acid

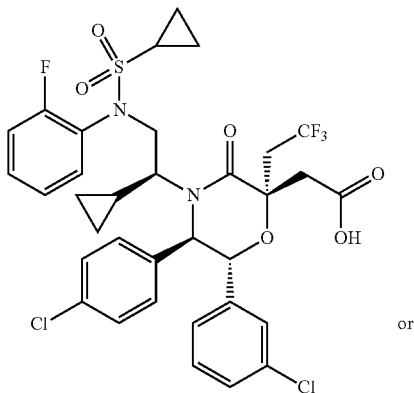

or

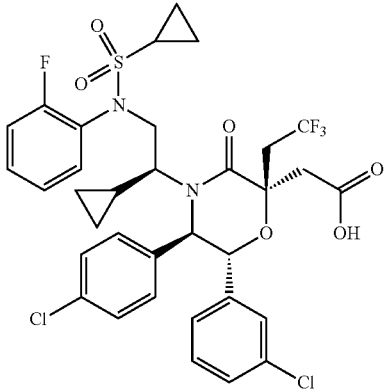

Step A. N-((S)-2-((2R,3R)-2-(3-Chlorophenyl)-3-(4-chlorophenyl)-5-oxomorpholino)-2-cyclopropylethyl)-N-(2-fluorophenyl)cyclopropanesulfonamide

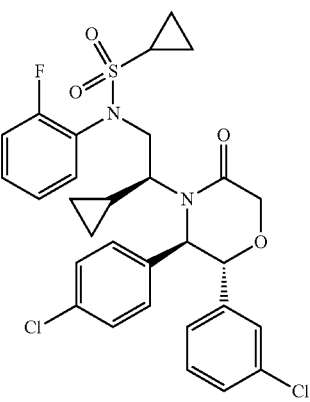 [SMILES: O=C1CO[C@H](c2cccc(Cl)c2)[C@@H](c2ccc(Cl)cc2)N1[C@H](CN(c1ccccc1F)S(=O)(=O)C1CC1)C1CC1]

The title compound was prepared from (5R,6R)-6-(3-chlorophenyl)-5-(4-chlorophenyl)-4-((S)-1-cyclopropyl-2-hydroxyethyl)morpholin-3-one (Example 154, Step B) by a procedure similar to that described in Example 133.

Step B. N-((S)-2-((2R,5R,6R)-2-Allyl-6-(3-chlorophenyl)-5-(4-chlorophenyl)-3-oxo-2-(2,2,2-trifluoroethyl)morpholino)-2-cyclopropylethyl)-N-(2-fluorophenyl)cyclopropanesulfonamide and N-((S)-2-((2S,5R,6R)-2-allyl-6-(3-chlorophenyl)-5-(4-chlorophenyl)-3-oxo-2-(2,2,2-trifluoroethyl)morpholino)-2-cyclopropylethyl)-N-(2-fluorophenyl)cyclopropanesulfonamide

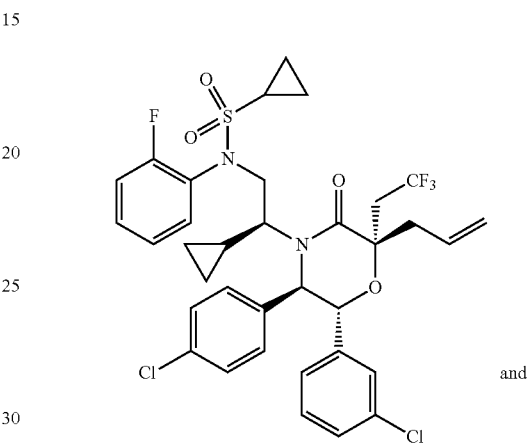

and

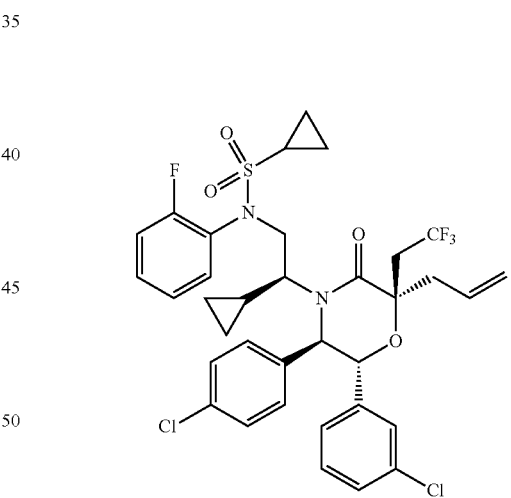

The title compounds were prepared from (Example 333, Step A) by procedures similar to those described in Example 329, Steps A and B, replacing iodomethane in Step A with 1-iodo-2,2,2-trifluoroethane.

563

Step C. 2-((2S,5R,6R)-6-(3-Chlorophenyl)-5-(4-chlorophenyl)-4-((S)-1-cyclopropyl-2-(N-(2-fluorophenyl)cyclopropanesulfonamido)ethyl)-3-oxo-2-(2,2,2-trifluoroethyl)morpholin-2-yl)acetic acid or 2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxo-2-(2,2,2-trifluoroethyl)morpholin-2-yl)acetic acid

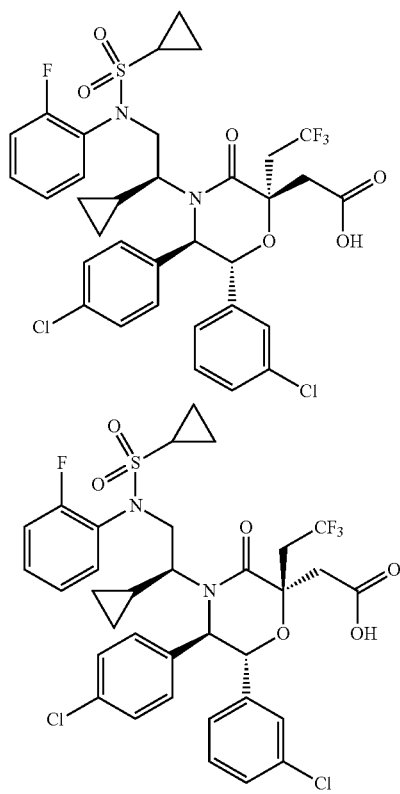

or

One of the title compounds was prepared from N-((S)-2-((2R,5R,6R)-2-allyl-6-(3-chlorophenyl)-5-(4-chlorophenyl)-3-oxo-2-(2,2,2-trifluoroethyl)morpholino)-2-cyclopropylethyl)-N-(2-fluorophenyl)cyclopropanesulfonamide and N-((S)-2-((2S,5R,6R)-2-allyl-6-(3-chlorophenyl)-5-(4-chlorophenyl)-3-oxo-2-(2,2,2-trifluoroethyl)morpholino)-2-cyclopropylethyl)-N-(2-fluorophenyl)cyclopropanesulfonamide (Example 333, Step B) by a procedure similar to that described in Example 112, Step F. The residue was purified by reverse phase preparatory HPLC (Agilient 1100, column: Gemini® 5 µm C$_{18}$, 100 mm×30 mm (Phenomenex, Torrance, Calif.), gradient elution of 30% to 70% acetonitrile in water, where both solvents contain 0.1% TFA, 30 minutes) to give one of the compounds as the first (faster) eluting isomer. MS (ESI) m/z=743.0 [M+1].

564

Example 334

2-((2R,5R,6R)-4-((S)-2-(tert-Butylsulfonyl)-1-cyclopropylethyl)-6-(3-chlorophenyl)-5-(4-chlorophenyl)-2-methyl-3-oxomorpholin-2-yl)acetic acid or 2-((2S,5R,6R)-4-((S)-2-(tert-butylsulfonyl)-1-cyclopropylethyl)-6-(3-chlorophenyl)-5-(4-chlorophenyl)-2-methyl-3-oxomorpholin-2-yl)acetic acid

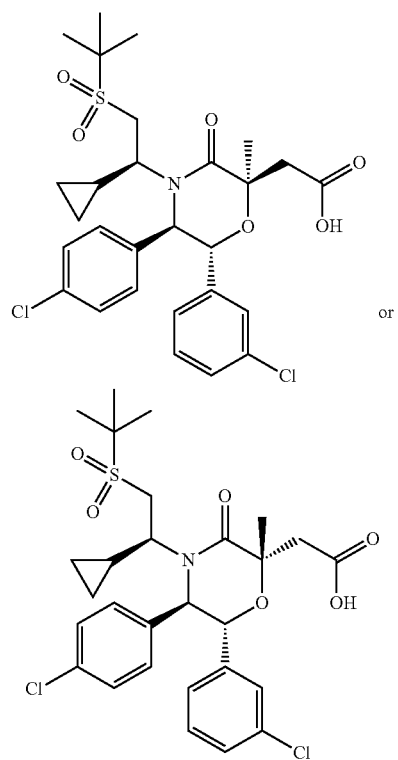

or

Step A. (2R,5R,6R)-2-Allyl-4-((S)-2-(tert-butylsulfonyl)-1-cyclopropylethyl)-6-(3-chlorophenyl)-5-(4-chlorophenyl)-2-methylmorpholin-3-one and (2S,5R,6R)-2-allyl-4-((S)-2-(tert-butylsulfonyl)-1-cyclopropylethyl)-6-(3-chlorophenyl)-5-(4-chlorophenyl)-2-methylmorpholin-3-one

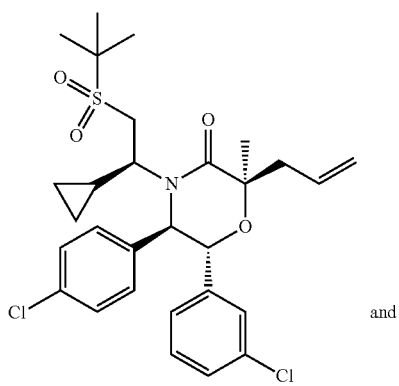

and

-continued

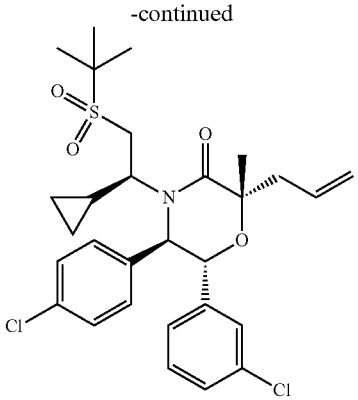

The title compounds were prepared from (2R,5R,6R)-2-allyl-4-((S)-2-((tert-butyldiphenylsilyl)oxy)-1-cyclopropylethyl)-6-(3-chlorophenyl)-5-(4-chlorophenyl)-2-methylmorpholin-3-one and (2S,5R,6R)-2-allyl-4-((S)-2-((tert-butyldiphenylsilyl)oxy)-1-cyclopropylethyl)-6-(3-chlorophenyl)-5-(4-chlorophenyl)-2-methylmorpholin-3-one (Example 331, Step B) by procedures similar to those described in Example 214, Steps D and E, replacing phenylmethanethiol in Step E with 2-methylpropane-2-thiol.

Step B. 2-((2R,5R,6R)-4-((S)-2-(tert-Butylsulfonyl)-1-cyclopropylethyl)-6-(3-chlorophenyl)-5-(4-chlorophenyl)-2-methyl-3-oxomorpholin-2-yl)acetic acid or 2-((2S,5R,6R)-4-((S)-2-(tert-butylsulfonyl)-1-cyclopropylethyl)-6-(3-chlorophenyl)-5-(4-chlorophenyl)-2-methyl-3-oxomorpholin-2-yl)acetic acid

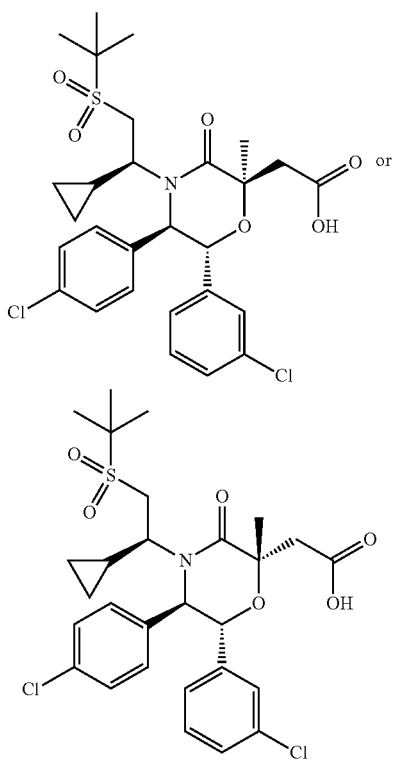

One of the title compounds was prepared from (2R,5R,6R)-2-allyl-4-((S)-2-(tert-butylsulfonyl)-1-cyclopropylethyl)-6-(3-chlorophenyl)-5-(4-chlorophenyl)-2-methylmorpholin-3-one and (2S,5R,6R)-2-allyl-4-((S)-2-(tert-butylsulfonyl)-1-cyclopropylethyl)-6-(3-chlorophenyl)-5-(4-chlorophenyl)-2-methylmorpholin-3-one (Example 334, Step B) by a procedure similar to that described in Example 112, Step F. The residue was purified by reverse phase preparatory HPLC (Agilient 1100, column: Gemini® 5 μm $C_{18}$, 100 mm×30 mm (Phenomenex, Torrance, Calif.), gradient elution of 25% to 75% acetonitrile in water, where both solvents contain 0.1% TFA, 30 minutes) to give one of the title compounds as the first (faster) eluting isomer. $^1$H NMR (500 MHz, $CDCl_3$, δ ppm): 7.28 (br, 3H), 7.18-7.16 (m, 1H), 7.10-7.05 (m, 3H), 6.85-6.83 (m, 1H), 5.09-5.02 (m, 2H), 4.23 (br, 1H), 3.22-3.07 (m, 2H), 2.97-2.94 (m, 1H), 2.75 (br, 1H), 1.96 (br, 1H), 1.76 (s, 3H), 1.43 (s, 9H), 0.43-0.41 (m, 2H), −0.23 (br, 1H), −0.67 (br, 1H). MS (ESI) m/z=582 [M+1].

Example 335

2-((2R,5R,6R)-4-((S)-2-(tert-Butylsulfonyl)-1-cyclopropylethyl)-6-(3-chlorophenyl)-5-(4-chlorophenyl)-2-methyl-3-oxomorpholin-2-yl)acetic acid or 2-((2S,5R,6R)-4-((S)-2-(tert-butylsulfonyl)-1-cyclopropylethyl)-6-(3-chlorophenyl)-5-(4-chlorophenyl)-2-methyl-3-oxomorpholin-2-yl)acetic acid

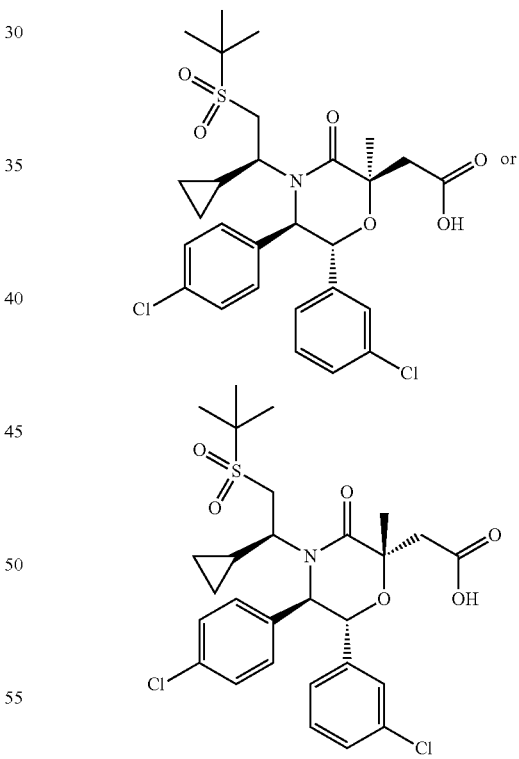

Further elution of the chromatographic purification described in Example 334, Step B provided one of the title compounds as the second (slower) eluting isomer.

$^1$HNMR (500 MHz, $CDCl_3$, δ ppm): 7.29 (br, 3H), 7.20-7.16 (m, 1H), 7.12-7.08 (m, 2H), 7.01 (s, 1H), 6.84 (d, J=7.6 Hz, 1H), 5.00-4.90 (m, 2H), 4.21-4.17 (m, 1H), 3.21-3.08 (m, 3H), 2.67 (br, 1H), 1.97 (br, 1H), 1.80 (s, 3H), 1.43 (s, 9H), 0.43 (d, J=7.8 Hz, 2H), −0.08 (br, 1H), −0.61 (br, 1H). MS (ESI) m/z=582 [M+1].

Example 336

2-((2R,5R,6R)-6-(3-Chlorophenyl)-5-(4-chlorophenyl)-4-((S)-1-cyclopropyl-2-(((S)-2-methylpyrrolidin-1-yl)sulfonyl)ethyl)-2-methyl-3-oxomorpholin-2-yl)acetic acid or 2-((2S,5R,6R)-6-(3-chlorophenyl)-5-(4-chlorophenyl)-4-((S)-1-cyclopropyl-2-(((S)-2-methylpyrrolidin-1-yl)sulfonyl)ethyl)-2-methyl-3-oxomorpholin-2-yl)acetic acid

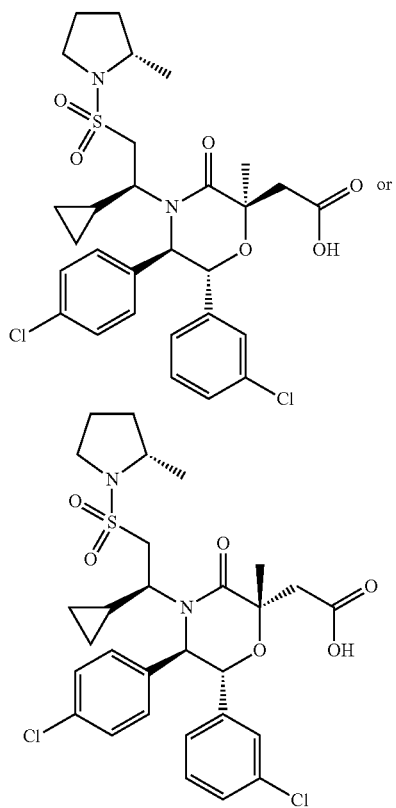

Step A. Methyl 2-((2R,5R,6R)-6-(3-chlorophenyl)-5-(4-chlorophenyl)-4-((S)-1-cyclopropyl-2-hydroxyethyl)-2-methyl-3-oxomorpholin-2-yl)acetate or methyl 2-((2S,5R,6R)-6-(3-chlorophenyl)-5-(4-chlorophenyl)-4-((S)-1-cyclopropyl-2-hydroxyethyl)-2-methyl-3-oxomorbholin-2-yl)acetate

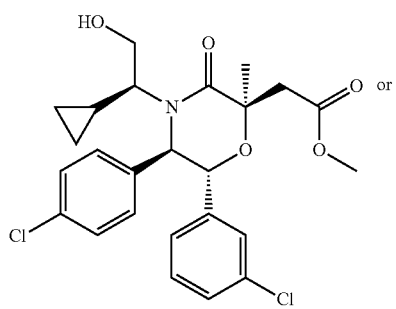

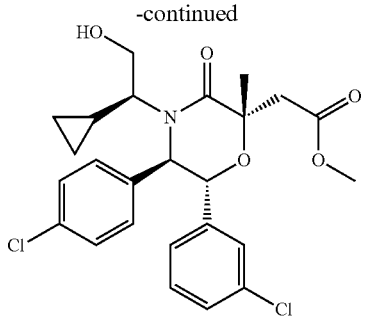

One of the title compounds was prepared from (2R,5R,6R)-2-allyl-4-((S)-2-((tert-butyldiphenylsilyl)oxy)-1-cyclopropylethyl)-6-(3-chlorophenyl)-5-(4-chlorophenyl)-2-methylmorpholin-3-one and (2S,5R,6R)-2-allyl-4-((S)-2-((tert-butyldiphenylsilyl)oxy)-1-cyclopropylethyl)-6-(3-chlorophenyl)-5-(4-chlorophenyl)-2-methylmorpholin-3-one (Example 331, Step B) by procedures similar to those described in Example 214, Steps C and D. The residue was purified by flash chromatography on silica gel (gradient elution of 10% to 50% ethyl acetate in hexanes) to give one of the compounds as the first (faster) eluting isomer.

Step B. 2-((2R,5R,6R)-6-(3-Chlorophenyl)-5-(4-chlorophenyl)-4-((S)-1-cyclopropyl-2-(((S)-2-methylpyrrolidin-1-yl)sulfonyl)ethyl)-2-methyl-3-oxomorpholin-2-yl)acetic acid or 2-((2S,5R,6R)-6-(3-chlorophenyl)-5-(4-chlorophenyl)-4-((S)-1-cyclopropyl-2-(((S)-2-methylpyrrolidin-1-yl)sulfonyl)ethyl)-2-methyl-3-oxomorpholin-2-yl)acetic acid

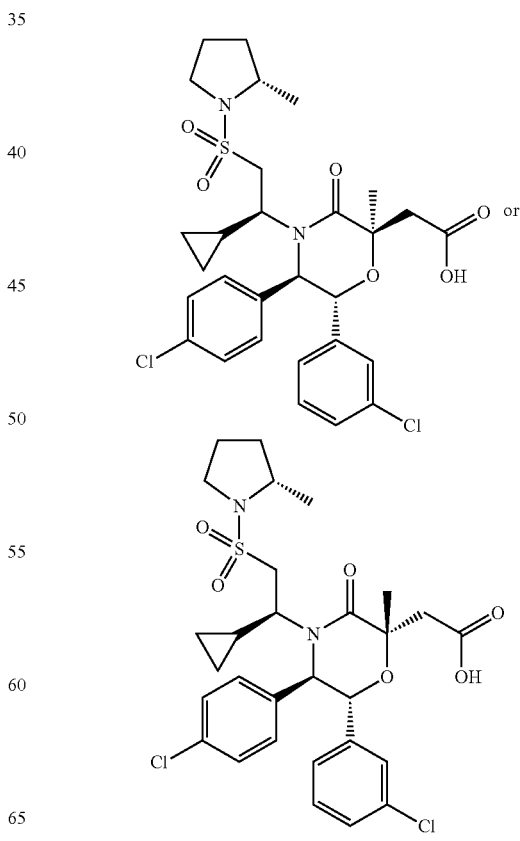

One of the title compounds was prepared from methyl 2-((2R,5R,6R)-6-(3-chlorophenyl)-5-(4-chlorophenyl)-4-((S)-1-cyclopropyl-2-hydroxyethyl)-2-methyl-3-oxomorpholin-2-yl)acetate or methyl 2-((2S,5R,6R)-6-(3-chlorophenyl)-4-((S)-1-cyclopropyl-2-hydroxyethyl)-2-methyl-3-oxomorpholin-2-yl)acetate (Example 336, Step A) by procedures similar to those described in Example 214, Steps E through G, replacing dimethylamine in Step F with (S)-(+)-2-methylpyrrolidine. The residue was purified by reverse phase preparatory HPLC (Agilient 1100, column: Gemini® 5 µm $C_{18}$, 100 mm×30 mm (Phenomenex, Torrance, Calif.), gradient elution of 25% to 75% acetonitrile in water, where both solvents contain 0.1% TFA, 30 minutes) to give one of the compounds as a white solid. $^1$H NMR (500 MHz, CDCl$_3$, δ ppm): 7.35-7.05 (m, 7H), 6.86-6.84 (m, 1H), 4.62-4.37 (m, 1H), 4.17 (br, 1H), 3.91-3.86 (m, 1H), 3.45-3.38 (m, 1H), 3.32-3.26 (m, 1H), 3.21-3.10 (m, 2H), 2.86-2.82 (m, 1H), 2.64 (br, 1H), 2.13-1.85 (m, 4H), 1.79 (s, 3H), 1.29 (d, J=6.3 Hz, 3H), 0.4 (d, J=7.8 Hz, 1H), −0.21 (br, 1H), −0.66 (br, 1H). MS (ESI) m/z=609 [M+1].

Example 337

2-((2R,5R,6R)-6-(3-Chlorophenyl)-6-(4-chlorophenyl)-4-((S)-1-cyclopropyl-2-(((S)-2-methylpyrrolidin-1-yl)sulfonyl)ethyl)-2-methyl-3-oxomorpholin-2-yl)acetic acid or 2-((2S,5R,6R)-6-(3-chlorophenyl)-5-(4-chlorophenyl)-4-((S)-1-cyclopropyl-2-(((S)-2-methylpyrrolidin-1-yl)sulfonyl)ethyl)-2-methyl-3-oxomorpholin-2-yl)acetic acid

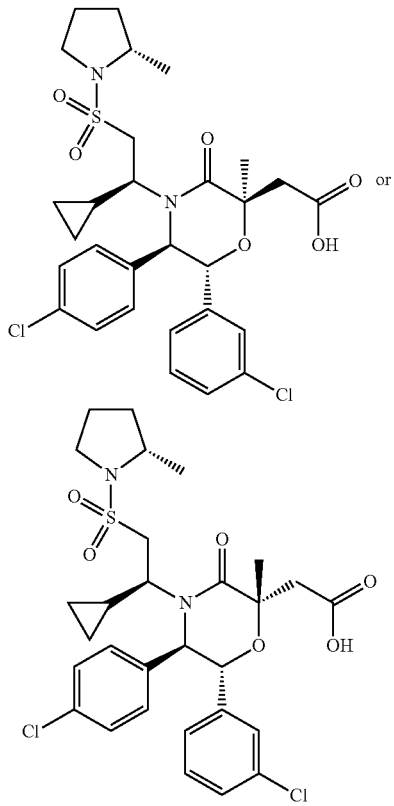

Step A. Methyl 2-((2R,5R,6R)-6-(3-chlorophenyl)-5-(4-chlorophenyl)-4-((S)-1-cyclopropyl-2-hydroxyethyl)-2-methyl-3-oxomorpholin-2-yl)acetate or methyl 2-((2S,5R,6R)-6-(3-chlorophenyl)-5-(4-chlorophenyl)-4-((S)-1-cyclopropyl-2-hydroxyethyl)-2-methyl-3-oxomorpholin-2-yl)acetate

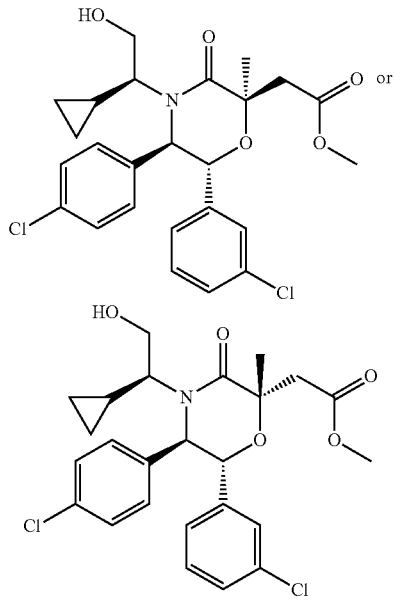

Further elution of the chromatographic separation described in Example 336, Step A provided one of the title compounds as the second (slower) eluting isomer.

Step B. 2-((2R,5R,6R)-6-(3-Chlorophenyl)-5-(4-chlorophenyl)-4-((S)-1-cyclopropyl-2-(((S)-2-methylpyrrolidin-1-yl)sulfonyl)ethyl)-2-methyl-3-oxomorpholin-2-yl)acetic acid or 2-((2S,5R,6R)-6-(3-chlorophenyl)-5-(4-chlorophenyl)-4-((S)-1-cyclopropyl-2-(((S)-2-methylpyrrolidin-1-yl)sulfonyl)ethyl)-2-methyl-3-oxomorpholin-2-yl)acetic acid One of the title compounds was prepared from methyl 2-((2R,5R,6R)-6-(3-chlorophenyl)-5-(4-chlorophenyl)-4-((S)-1-cyclopropyl-2-hydroxyethyl)-2-methyl-3-oxomorpholin-2-yl)acetate or methyl 2-((2S,5R,6R)-6-(3-chlorophenyl)-5-(4-chlorophenyl)-4-((S)-1-cyclopropyl-2-hydroxyethyl)-2-methyl-3-oxomorpholin-2-yl)acetate (Example 336, Step A) by procedures similar to those described in Example 214, Steps E through G, replacing dimethylamine in Step F with (S)-(+)-2-methylpyrrolidine. The residue was purified by reverse phase preparatory HPLC (Agilient 1100, column: Gemini® 5 µm $C_{18}$, 100 mm×30 mm (Phenomenex, Torrance, Calif.), gradient elution of 25% to 75% acetonitrile in water, where both solvents contain 0.1% TFA, 30 minutes) to give one of the compounds as a white solid. $^1$H NMR (500 MHz, CDCl$_3$, δ ppm): 7.30 (br, 3H), 7.19 (d, J=7.9 Hz, 1H), 7.11 (t, J=7.8 Hz, 2H), 7.02 (s, 1H), 6.86 (d, J=7.3 Hz, 1H), 5.00-4.90 (m, 2H), 4.22-4.15 (m, 1H), 3.95-3.92 (m, 1H), 3.40-3.20 (m, 4H), 3.08-3.00 (m, 1H), 2.55 (br, 1H), 2.16-1.86 (m, 5H), 1.82 (s, 3H), 1.26 (d, J=6.4 Hz, 3H), 0.42 (br, 2H), −0.13 (br, 1H), −0.67 (br, 1H). MS (ESI) m/z=609 [M+1].

Example 338

2-((2R,5R,6R)-4-((S)-1-(tert-Butylsulfonyl)butan-2-yl)-6-(3-chlorophenyl)-5-(4-chlorophenyl)-2-methyl-3-oxomorpholin-2-yl)acetic acid or 2-((2S,5R,6R)-4-((S)-1-(tert-butylsulfonyl)butan-2-yl)-6-(3-chlorophenyl)-5-(4-chlorophenyl)-2-methyl-3-oxomorpholin-2-yl)acetic acid

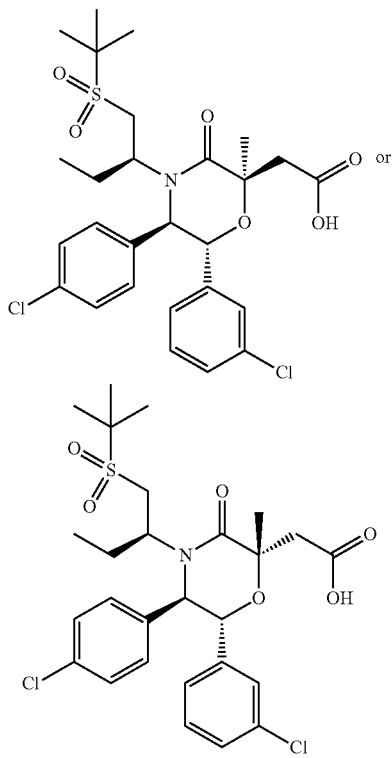

Step A. (5R,6R)-4-((S)-1-(tert-Butylsulfonyl)butan-2-yl)-6-(3-chlorophenyl)-5-(4-chlorophenyl)morpholin-3-one

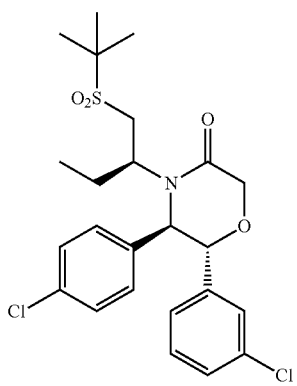 [SMILES: CC[C@@H](CS(=O)(=O)C(C)(C)C)N1C(=O)CO[C@H](c2cccc(Cl)c2)[C@H]1c1ccc(Cl)cc1]

The title compound was prepared from (5R,6R)-6-(3-chlorophenyl)-5-(4-chlorophenyl)-4-((S)-1-((3,4-dimethoxybenzyl)oxy)butan-2-yl)morpholin-3-one (Example 112, Step B) by procedures similar to those described in Example 112, Steps C and D, replacing ethanethiol in Step D with 2-methylpropane-2-thiol.

Step B. (2R,5R,6R)-2-Allyl-4-((S)-1-(tert-butylsulfonyl)butan-2-yl)-6-(3-chlorophenyl)-5-(4-chlorophenyl)-2-methylmorpholin-3-one and (2S,5R,6R)-2-allyl-4-((S)-1-(tert-butylsulfonyl)butan-2-yl)-6-(3-chlorophenyl)-5-(4-chlorophenyl)-2-methylmorpholin-3-one

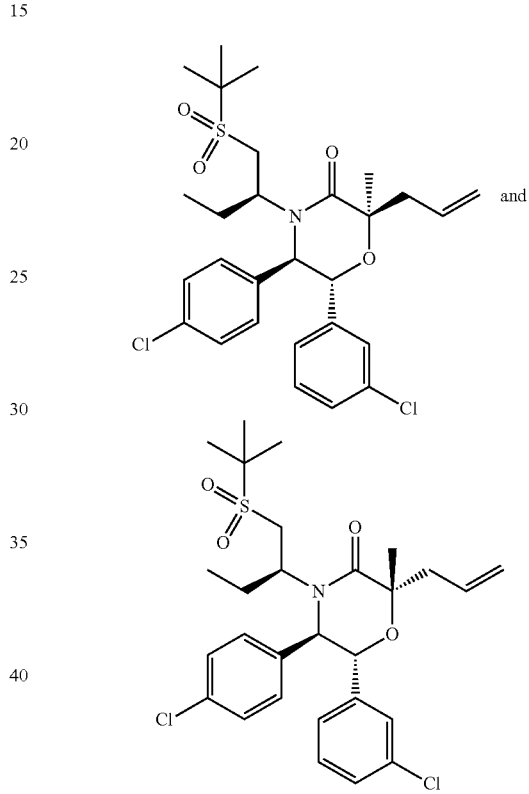

The title compound was prepared from (5R,6R)-4-((S)-1-(tert-butylsulfonyl)butan-2-yl)-6-(3-chlorophenyl)-5-(4-chlorophenyl)morpholin-3-one (Example 338, Step A) by procedures similar to those described in Example 324, Steps A and B.

Step C. 2-((2R,5R,6R)-4-((S)-1-(tert-Butylsulfonyl)butan-2-yl)-6-(3-chlorophenyl)-5-(4-chlorophenyl)-2-methyl-3-oxomorpholin-2-yl)acetic acid or 2-((2S,5R,6R)-4-((S)-1-(tert-butylsulfonyl)butan-2-yl)-6-(3-chlorophenyl)-5-(4-chlorophenyl)-2-methyl-3-oxomorpholin-2-yl)acetic acid One of the title compounds was prepared from (2R,5R,6R)-2-Allyl-4-((S)-1-(tert-butylsulfonyl)butan-2-yl)-6-(3-chlorophenyl)-5-(4-chlorophenyl)-2-methylmorpholin-3- one and (2S,5R,6R)-2-allyl-4-((S)-1-(tert-butylsulfonyl)butan-2-yl)-6-(3-chlorophenyl)-5-(4-chlorophenyl)-2-methylmorpholin-3-one (Example 338, Step B) by a procedure similar to that described in Example 112, Step F. The residue was purified by reverse phase preparatory HPLC (Agilent 1100, column: Gemini® 5 μm $C_{18}$, 100 mm×30 mm (Phenomenex, Torrance, Calif.), gradient elution of 25% to 75% acetonitrile in water, where both solvents contain 0.1% TFA, 30 minutes) to give one of the compounds as the first (faster) eluting isomer. $^1$H NMR (400 MHz, $CDCl_3$, δ ppm): 7.27-7.34 (m, 2H), 7.08 (d, J=16.43 Hz, 5H), 6.81 (d, J=7.83 Hz, 1H), 5.07 (q, J=9.59 Hz, 2H), 4.01 (dd, J=10.56, 13.30 Hz, 1H), 3.32 (dd, J=7.24, 9.39 Hz, 2H), 3.18 (d, J=15.85 Hz, 1H), 3.01 (d, J=15.65 Hz, 1H), 2.80 (d, J=12.32 Hz, 1H), 2.12-2.33 (m, 1H), 1.69-1.78 (m, 3H), 1.43 (s, 9H), 0.53 (t, J=7.43 Hz, 3H). MS (ESI) m/z=570.2 [M+1].

Example 339

2-((2R,5R,6R)-4-((S)-1-(tert-Butylsulfonyl)butan-2-yl)-6-(3-chlorophenyl)-5-(4-chlorophenyl)-2-methyl-3-oxomorpholin-2-yl)acetic acid and 2-((2S,5R,6R)-4-((S)-1-(tert-butylsulfonyl)butan-2-yl)-6-(3-chlorophenyl)-5-(4-chlorophenyl)-2-methyl-3-oxomorpholin-2-yl)acetic acid

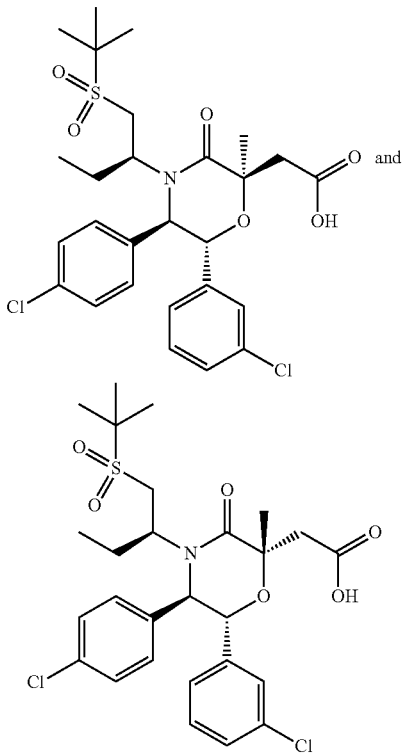

Further elution of the chromatographic separation described in Example 338, Step C provided the title compounds as a mixture of diastereomers. MS (ESI) m/z=570.2 [M+1].

Example 340

2-((2R,5R,6R)-4-((S)-1-(tert-Butylsulfonyl)-4,4,4-trifluorobutan-2-yl)-6-(3-chlorophenyl)-5-(4-chlorophenyl)-2-methyl-3-oxomorpholin-2-yl)acetic acid or 2-((2S,5R,6R)-4-((S)-1-(tert-butylsulfonyl)-4,4,4-trifluorobutan-2-yl)-6-(3-chlorophenyl)-5-(4-chlorophenyl)-2-methyl-3-oxomorpholin-2-yl)acetic acid

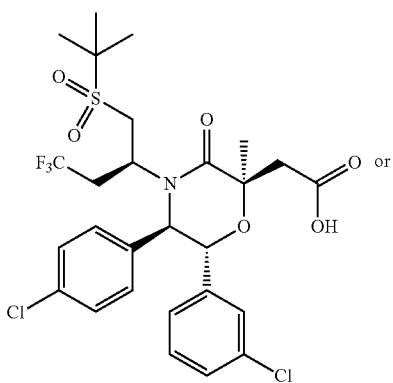

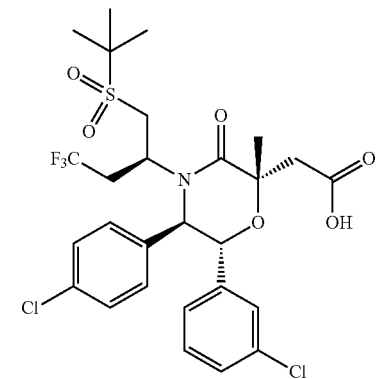

One of the title compounds was prepared from (5R,6R)-4-((S)-1-(tert-butylsulfonyl)-4,4,4-trifluorobutan-2-yl)-6-(3-chlorophenyl)-5-(4-chlorophenyl)morpholin-3-one (Example 266, Step B) by procedures similar to those described in Example 338, Steps B and C. The residue was purified by reverse phase preparatory HPLC (Agilent 1100, column: Gemini® 5 μm $C_{18}$, 100 mm×30 mm (Phenomenex, Torrance, Calif.), gradient elution of 45% to 70% acetonitrile in water, where both solvents contain 0.1% TFA, 30 minutes) to give one of the compounds as the first (faster) eluting isomer as a white foam. $^1$H NMR (400 MHz, $CDCl_3$, δ ppm): 7.33 (br. s., 2H), 7.17-7.23 (m, 2H), 7.09 (td, J=7.43, 8.41 Hz, 2H), 7.03 (t, J=1.76 Hz, 1H), 6.82 (d, J=7.82 Hz, 1H), 5.04 (d, J=9.59 Hz, 1H), 4.92 (d, J=9.59 Hz, 1H), 3.98 (dd, J=7.63, 13.89 Hz, 1H), 3.79-3.91 (m, 1H), 3.03-3.24 (m, 3H), 2.96 (d, J=15.85 Hz, 1H), 2.53-2.71 (m, 1H), 1.70 (br. s., 3H), 1.37-1.44 (m, 9H). MS (ESI) m/z=624.0 [M+1].

Example 341

2-((2R,5R,6R)-4-((S)-1-(tert-Butylsulfonyl)-4,4,4-trifluorobutan-2-yl)-6-(3-chlorophenyl)-5-(4-chlorophenyl)-2-methyl-3-oxomorpholin-2-yl)acetic acid or 2-((2S,5R,6R)-4-((S)-1-(tert-butylsulfonyl)-4,4,4-trifluorobutan-2-yl)-6-(3-chlorophenyl)-5-(4-chlorophenyl)-2-methyl-3-oxomorpholin-2-yl)acetic acid

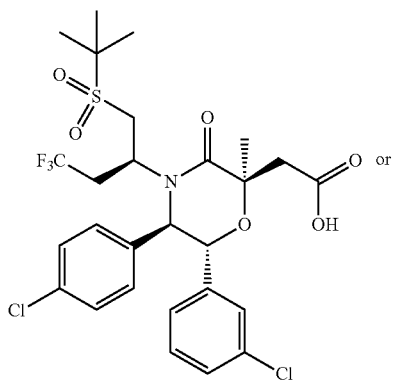

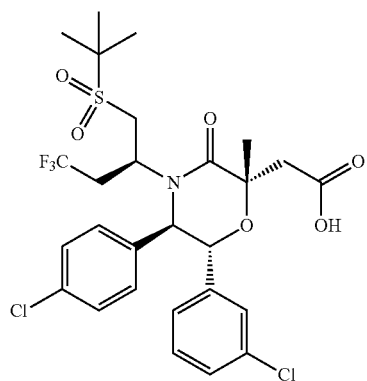

Further elution of the chromatographic separation described in Example 340 provided one of the title compounds as the second (slower) eluting isomer as a white foam. ¹H NMR (400 MHz, CDCl₃, δ ppm): 7.29-7.48 (m, 2H), 7.17 (ddd, J=1.08, 2.10, 7.97 Hz, 2H), 7.02-7.12 (m, 3H), 6.80 (d, J=7.83 Hz, 1H), 5.18 (d, J=9.19 Hz, 1H), 5.11 (d, J=9.59 Hz, 1H), 4.07 (dd, J=10.96, 13.50 Hz, 1H), 3.87 (t, J=10.27 Hz, 1H), 3.17-3.39 (m, 2H), 3.00 (dd, J=1.96, 13.50 Hz, 1H), 2.93 (d, J=16.43 Hz, 1H), 2.36-2.58 (m, 1H), 1.74 (br. s., 3H), 1.42 (s, 9H). MS (ESI) m/z=624.0 [M+1].

Example 342

2-((2R,5R,6R)-4-((S)-1-(tert-Butylsulfonyl)-4,4,4-trifluorobutan-2-yl)-6-(3-chlorophenyl)-5-(4-chlorophenyl)-2-ethyl-3-oxomorpholin-2-yl)acetic acid or 2-((2S,5R,6R)-4-((S)-1-(tert-butylsulfonyl)-4,4,4-trifluorobutan-2-yl)-6-(3-chlorophenyl)-5-(4-chlorophenyl)-2-ethyl-3-oxomorpholin-2-yl)acetic acid

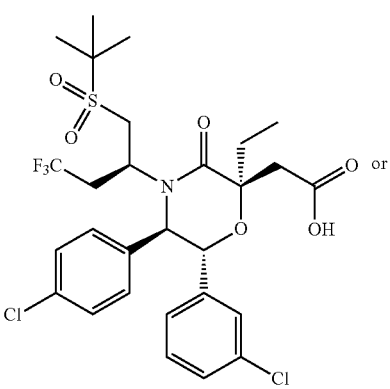

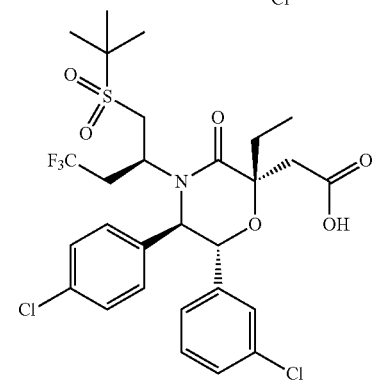

One of the title compounds was prepared from (5R,6R)-4-((S)-1-(tert-butylsulfonyl)-4,4,4-trifluorobutan-2-yl)-6-(3-chlorophenyl)-5-(4-chlorophenyl)morpholin-3-one (Example 266, Step B) by procedures similar to those described in Example 338, Steps B and C, replacing iodomethane in Step B with ethyl iodide. The residue was purified by reverse phase preparatory HPLC (Agilient 1100, column: Gemini® 5 μm C₁₈, 100 mm×30 mm (Phenomenex, Torrance, Calif.), gradient elution of 45% to 70% acetonitrile in water, where both solvents contain 0.1% TFA, 30 minutes) to give residue containing a mixture of diastereomers. The diastereomers were separated by chiral SFC (250×30 mm Chiralpak® OD-H column (Chiral Technologies, Inc., West Chester, Pa., USA) with 14 g/min ethanol+86 g/min CO₂ on a Thar 350 SFC (Thar Technologies, Inc., Pittsburg, Pa.)) to give one of the title compounds as the first (faster) eluting isomer. ¹H NMR (400 MHz, CDCl₃, δ ppm): 7.29-7.51 (m, 2H), 7.17-7.22 (m, 1H), 7.07 (d, J=19.37 Hz, 4H), 6.81 (d, J=7.63 Hz, 1H), 5.04 (d, J=9.78 Hz, 1H), 4.85 (d, J=9.78 Hz, 1H), 3.97 (dd, J=7.43, 13.89 Hz, 1H), 3.78-3.90 (m, 1H), 3.49 (q, J=7.04 Hz, 1H), 3.19 (dd, J=3.72, 13.89 Hz, 1H), 2.96-3.13 (m, J=11.74 Hz, 2H), 2.58-2.78 (m, 1H), 2.22-2.35 (m, 2H), 1.99-2.14 (m, 1H), 1.42 (s, 9H), 1.01 (t, J=7.53 Hz, 3H). MS (ESI) m/z=638.0 [M+1].

Example 343

2-((2R,5R,6R)-4-((S)-1-(tert-Butylsulfonyl)-4,4,4-trifluorobutan-2-yl)-6-(3-chlorophenyl)-5-(4-chlorophenyl)-2-ethyl-3-oxomorpholin-2-yl)acetic acid or 2-((2S,5R,6R)-4-((S)-1-(tert-butylsulfonyl)-4,4,4-trifluorobutan-2-yl)-6-(3-chlorophenyl)-5-(4-chlorophenyl)-2-ethyl-3-oxomorpholin-2-yl)acetic acid

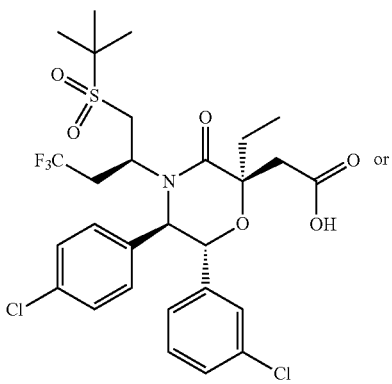

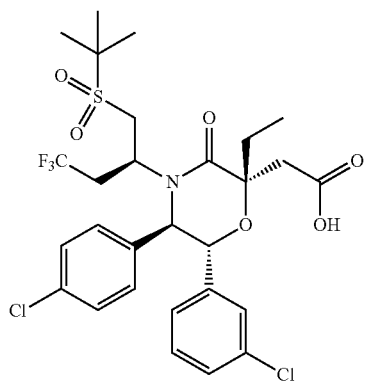

Further elution of the SFC purification described in Example 342 provided one of the title compounds as the second (slower) eluting isomer. $^1$H NMR (400 MHz, CDCl$_3$, δ ppm): 7.51-7.66 (m, 1H), 7.34-7.47 (m, 1H), 7.11-7.23 (m, 2H), 7.02-7.11 (m, 2H), 6.83-6.95 (m, 1H), 6.80 (d, J=7.63 Hz, 1H), 5.27 (d, J=9.78 Hz, 1H), 5.12 (d, J=9.78 Hz, 1H), 4.05 (dd, J=10.37, 13.89 Hz, 1H), 3.90 (t, J=10.17 Hz, 1H), 3.31-3.45 (m, 1H), 3.21 (d, J=17.02 Hz, 1H), 2.86-3.12 (m, 2H), 2.41-2.69 (m, 1H), 2.12-2.25 (m, 1H), 1.87-2.06 (m, 1H), 1.40 (s, 9H), 1.13 (t, J=7.43 Hz, 3H). MS (ESI) m/z=638.0 [M+1].

Example 344

2-((2S,5R,6R)-4-((S)-1-(tert-Butylsulfonyl)butan-2-yl)-6-(3-chlorophenyl)-5-(4-chlorophenyl)-3-oxomorpholin-2-yl)-N-cyanoacetamide

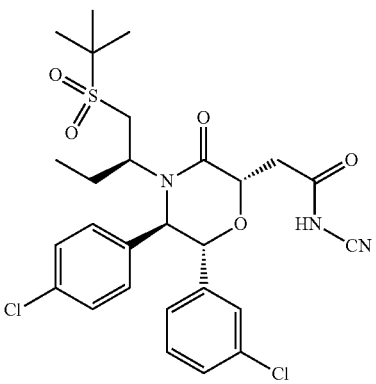 [SMILES: CC[C@@H](CS(=O)(=O)C(C)(C)C)N1C(=O)[C@H](CC(=O)NC#N)O[C@H](c2cccc(Cl)c2)[C@H]1c1ccc(Cl)cc1]

A mixture of 2-((2S,5R,6R)-4-((S)-1-(tert-butylsulfonyl)butan-2-yl)-6-(3-chlorophenyl)-5-(4-chlorophenyl)-3-oxomorpholin-2-yl)acetic acid (30 mg, 0.054 mmol, Example 121), carbodicyclohexylimide (11.12 mg, 0.054 mmol), and N-hydroxysuccinimide (6.20 mg, 0.054 mmol) was stirred in acetonitrile (0.270 mL) at room temperature for 4 hours. A precipitate formed. The mixture was filtered the filtrate was directly added to a solution of NaOH (10%, 0.043 mL, 0.108 mmol). Then sodium hydrogencyanamide (10.35 mg, 0.162 mmol) in water (0.5 mL) was added. The mixture was stirred at room temperature overnight and extracted with diethyl ether (2×30 mL) and water (30 mL). The aqueous layer was acidified with 10% HCl and the oil that formed was extracted with diethyl ether (2×30 mL). The combined organic layers were dried over MgSO$_4$, filtered, and concentrated. The residue was purified by reverse phase preparatory HPLC (Agilient 1100, column: Gemini® 5 µm C$_{18}$, 100 mm×30 mm (Phenomenex, Torrance, Calif.), gradient elution of 45% to 70% acetonitrile in water, where both solvents contain 0.1% TFA, 30 minutes) to give the title compound as a white foam. $^1$H NMR (400 MHz, CDCl$_3$, δ ppm): 7.35 (d, J=8.22 Hz, 2H), 7.24-7.28 (m, 1H), 7.13-7.21 (m, 3H), 7.08 (t, J=1.76 Hz, 1H), 6.91 (d, J=7.63 Hz, 1H), 5.17 (d, J=9.00 Hz, 1H), 4.72 (d, J=9.00 Hz, 1H), 4.05 (dt, J=2.74, 10.56 Hz, 1H), 3.23-3.39 (m, 1H), 3.02 (dt, J=3.91, 16.04 Hz, 1H), 2.91 (td, J=2.93, 10.95 Hz, 1H), 2.11-2.25 (m, 1H), 1.56-1.68 (m, 1H), 1.48 (s, 9H), 0.57 (t, J=7.83 Hz, 3H). MS (ESI) m/z=580.2 [M+1].

Example 345

2-((2R,5R,6R)-4-((S)-1-(tert-Butylsulfonyl)butan-2-yl)-6-(3-chlorophenyl)-5-(4-chlorophenyl)-3-oxomorpholin-2-yl)-N-cyanoacetamide

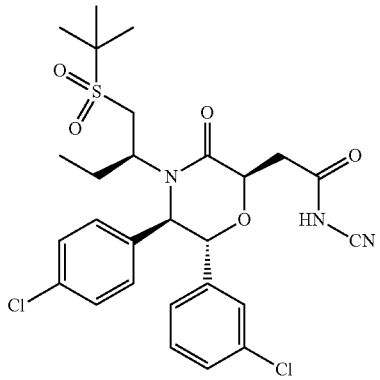 [SMILES: CC[C@@H](CS(=O)(=O)C(C)(C)C)N1C(=O)[C@@H](CC(=O)NC#N)O[C@H](c2cccc(Cl)c2)[C@H]1c1ccc(Cl)cc1]

The title compound was prepared from 2-((2R,5R,6R)-4-((S)-1-(tert-butylsulfonyl)butan-2-yl)-6-(3-chlorophenyl)-5-(4-chlorophenyl)-3-oxomorpholin-2-yl)acetic acid (Example 120) by a procedure similar to that described in Example 344. $^1$H NMR (400 MHz, CDCl$_3$, δ ppm): 7.35 (d, J=8.22 Hz, 2H), 7.24-7.28 (m, 1H), 7.13-7.21 (m, 3H), 7.08 (t, J=1.76 Hz, 1H), 6.91 (d, J=7.63 Hz, 1H), 5.17 (d, J=9.00 Hz, 1H), 4.72 (d, J=9.00 Hz, 1H), 4.05 (dt, J=2.74, 10.56 Hz, 1H), 3.23-3.39 (m, 1H), 3.02 (dt, J=3.91, 16.04 Hz, 1H), 2.91 (td, J=2.93, 10.95 Hz, 1H), 2.11-2.25 (m, 1H), 1.56-1.68 (m, 1H), 1.48 (s, 9H), 0.57 (t, J=7.83 Hz, 3H). MS (ESI) m/z=580.2 [M+1].

Example 346

2-((2R,5R,6R)-4-((S)-2-(tert-Butylsulfonyl)-1-cyclopropylethyl)-6-(3-chlorophenyl)-5-(4-chlorophenyl)-3-oxomorpholin-2-yl)-N-(2,2,2-trifluoroethyl)acetamide or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)-N-(2,2,2-trifluoro ethyl)acetamide

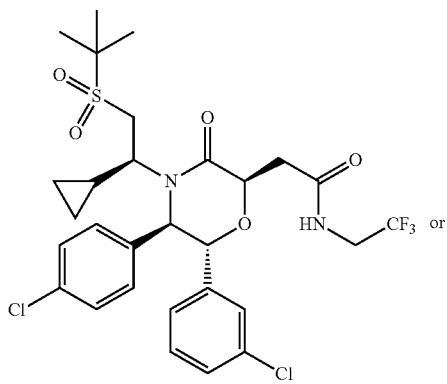

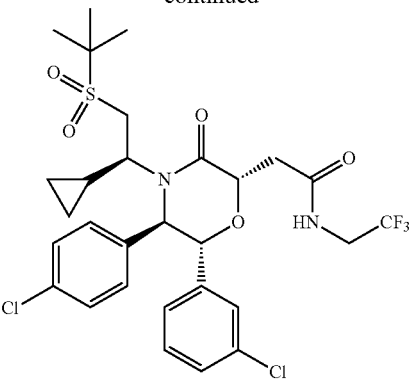

One of the title compounds was prepared from 2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid (Example 155) by a procedure similar to that described in Example 225, replacing triethylamine with N-ethyl-N-isopropylpropan-2-amine and ammonia with 2,2,2-trifluoroethanamine. The residue was purified by reverse phase preparatory HPLC (Agilient 1100, column: Gemini® 5 μm C$_{18}$, 100 mm×30 mm (Phenomenex, Torrance, Calif.), gradient elution of 40% to 60% acetonitrile in water, where both solvents contain 0.1% TFA, 20 minutes) to provide one of the title compounds. $^1$H NMR (400 MHz, CDCl$_3$, δ ppm): 7.14-7.36 (m, 6H), 7.06 (d, J=7.8 Hz, 1H), 6.85 (br. s., 1H), 6.30 (br. s., 1H), 5.13 (d, J=6.1 Hz, 1H), 4.96 (d, J=5.9 Hz, 1H), 4.60 (br. s., 1H), 3.88-3.99 (m, 3H), 2.98-3.11 (m, 4H), 1.72 (br. s., 1H), 1.39 (s, 9H), 0.42 (br. s., 2H), 0.00 (br. s., 1H), −0.66 (br. s., 1H). MS (ESI) m/z=649.0 [M+1].

Example 347

2-((2R,5R,6R)-4-((S)-2-(tert-Butylsulfonyl)-1-cyclopropylethyl)-6-(3-chlorophenyl)-5-(4-chlorophenyl)-3-oxomorpholin-2-yl)-N-(2,2,2-trifluoroethyl)acetamide or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)-N-(2,2,2-trifluoro ethyl)acetamide

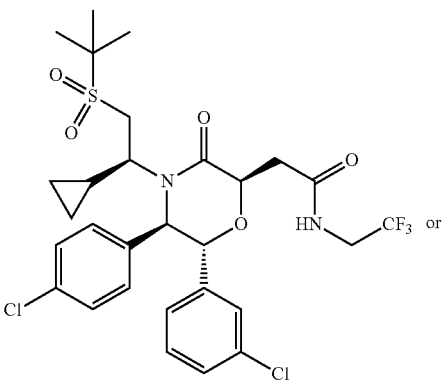

581

-continued

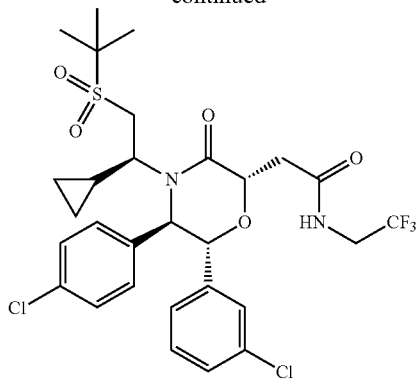

One of the title compounds was prepared from 2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl) acetic acid or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid (Example 154) by a procedure similar to that described in Example 346. The residue was purified by reverse phase preparatory HPLC (Agilient 1100, column: Gemini® 5 μm $C_{18}$, 100 mm×30 mm (Phenomenex, Torrance, Calif.), gradient elution of 30% to 70% acetonitrile in water, where both solvents contain 0.1% TFA, 30 minutes) to provide one of the title compounds. $^1$H NMR (400 MHz, CDCl$_3$, δ ppm): 7.50 (m, 2H), 7.35-7.40 (m, 2H), 7.26-7.31 (m, 2H), 7.03 (d, J=8.0 Hz, 1H), 6.87 (br. s., 1H), 5.81 (br. s., 1H), 5.24 (d, J=9.8 Hz, 1H), 4.94-5.00 (m, 2H), 4.49 (br. s., 1H), 4.01-4.22 (m, 2H), 3.33 (dd, J=15.4, 4.8 Hz, 1H), 3.23 (d, J=12 Hz, 1H), 3.12 (dd, J=15.3, 6.7 Hz, 1H), 2.08 (br. s., 2H), 1.63 (s, 9H), 0.53-0.64 (m, 2H), 0.00 (br. s., 1H), −0.63 (br. s., 1H). MS (ESI) m/z=649.0 [M+1].

Example 348

2-((2R,5R,6R)-4-((S)-2-(tert-Butylsulfonyl)-1-cyclopropylethyl)-6-(3-chlorophenyl)-5-(4-chlorophenyl)-3-oxomorpholin-2-yl)-N-(cyanomethyl)acetamide or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)-N-(cyanomethyl)acetamide

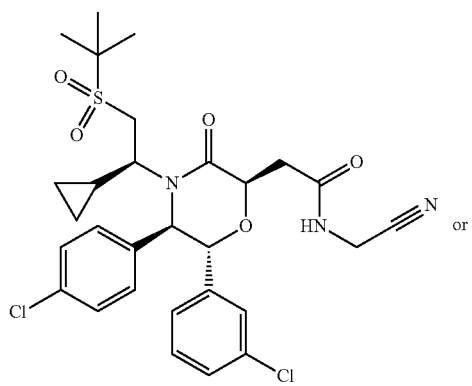

or

582

-continued

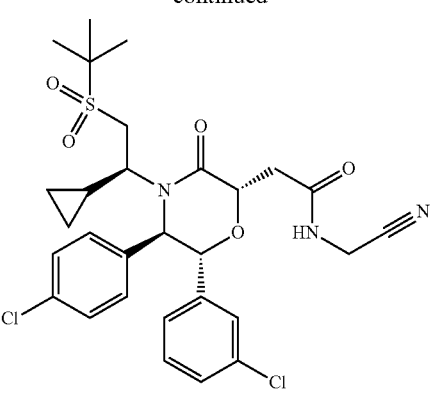

One of the title compounds was prepared from 2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl) acetic acid or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid (Example 155) by a procedure similar to that described in Example 346, replacing 2,2,2-trifluoroethanamine with 2-aminoacetonitrile. The residue was purified by reverse phase preparatory HPLC (Agilient 1100, column: Gemini® 5 μm $C_{18}$, 100 mm×30 mm (Phenomenex, Torrance, Calif.), gradient elution of 40% to 60% acetonitrile in water, where both solvents contain 0.1% TFA, 20 minutes) to provide one of the title compounds. $^1$H NMR (400 MHz, CDCl$_3$, δ ppm): 7.31-7.33 (m, 5H), 7.22 (m, 1H), 7.16 (m, 1H), 7.05 (d, J=4.0 Hz, 1H), 6.25 (br. s., 1H), 5.11 (d, J=4.0 Hz, 1H), 4.93-4.95 (d, J=8.0 Hz, 1H), 4.57 (br. s., 1H), 4.13 (m, 2H), 3.90 (br. s., 1H), 3.01 (m, 4H), 1.69 (br. s., 1H), 1.37 (s, 9H), 0.43 (m, 2H), 0.00 (br. s., 1H), −0.67 (br. s., 1H). MS (ESI) m/z=606.0 [M+1].

Example 349

2-((2R,5R,6R)-4-((S)-2-(tert-Butylsulfonyl)-1-cyclopropylethyl)-6-(3-chlorophenyl)-5-(4-chlorophenyl)-3-oxomorpholin-2-yl)-N-(cyanomethyl)acetamide or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)-N-(cyanomethyl)acetamide

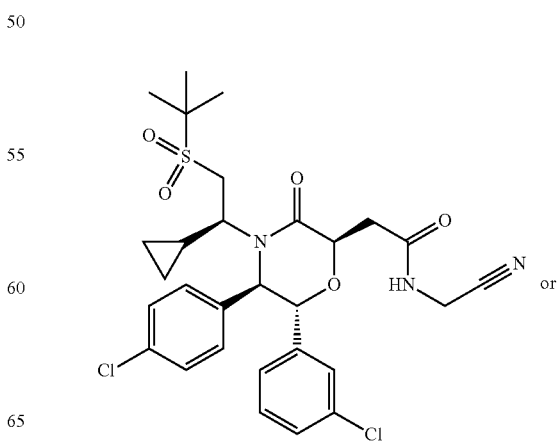

or

583

-continued

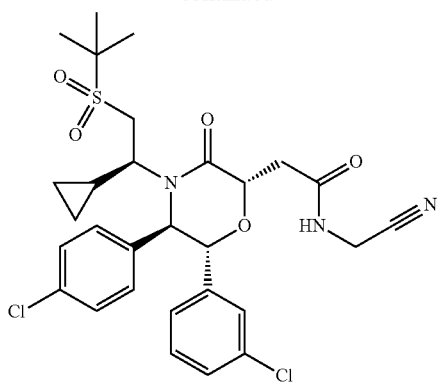

One of the title compounds was prepared from 2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid (Example 154) by a procedure similar to that described in Example 348. The residue was purified by reverse phase preparatory HPLC (Agilient 1100, column: Gemini® 5 μm $C_{18}$, 100 mm×30 mm (Phenomenex, Torrance, Calif.), gradient elution of 30% to 70% acetonitrile in water, where both solvents contain 0.1% TFA, 30 minutes) to provide one of the title compounds. $^1$H NMR (400 MHz, CDCl$_3$, δ ppm): 7.50-7.52 (m, 2H), 7.33 (m, 4H), 7.20 (m, 1H), 7.07 (d, J=8.0 Hz, 1H), 5.49 (br. s., 1H), 5.26 (d, J=12.0 Hz, 1H), 4.92-4.97 (m, 2H), 4.49 (br. s., 1H), 4.40 (d, J=8.0 Hz, 2H), 3.31-3.35 (m, 1H), 3.14-3.20 (m, 2H), 2.84 (br. s., 1H), 2.07 (s, 1H), 1.65 (s, 9H), 0.55-0.64 (m, 2H), 0.00 (br. s., 1H), −0.63 (br. s., 1H). MS (ESI) m/z=606.0 [M+1].

Example 350

2-((2R,5R,6R)-4-((S)-2-(tert-Butylsulfonyl)-1-cyclopropylethyl)-6-(3-chlorophenyl)-5-(4-chlorophenyl)-3-oxomorpholin-2-yl)-N-phenylacetamide or 2-42S,5R,6R)-4-((S)-2-(tert-butylsulfonyl)-1-cyclopropylethyl)-6-(3-chlorophenyl)-5-(4-chlorophenyl)-3-oxomorpholin-2-yl)-N-phenylacetamide

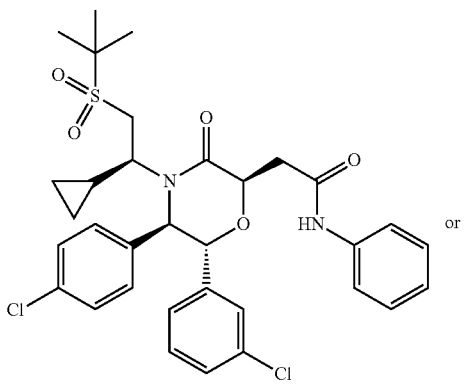

or

584

-continued

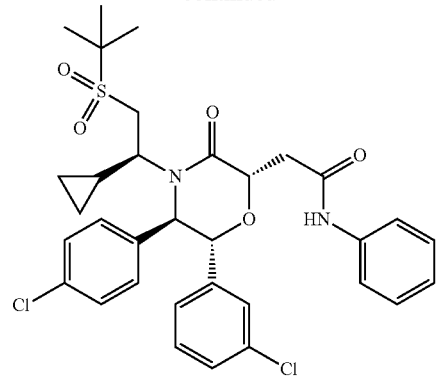

One of the title compounds was prepared from 2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid (Example 155) by a procedure similar to that described in Example 346, replacing 2,2,2-trifluoroethanamine with aniline. The residue was purified by reverse phase preparatory HPLC (Agilient 1100, column: Gemini® 5 μm $C_{18}$, 100 mm×30 mm (Phenomenex, Torrance, Calif.), gradient elution of 40% to 70% acetonitrile in water, where both solvents contain 0.1% TFA, 30 minutes) to provide one of the title compounds. $^1$H NMR (400 MHz, CDCl$_3$, δ ppm): 8.45 (s, 1H), 7.86 (br. s., 1H), 7.50 (m, 2H), 7.25-7.34 (m, 7H), 7.19 (m, 1H), 7.11 (m, 2H), 5.17 (d, J=4.0 Hz, 1H), 5.06 (d, J=8.0 Hz, 1H), 4.71 (m, 1H), 4.01 (br. s., 1H), 3.22-3.27 (m, 1H), 3.09-3.04 (m, 2H), 2.92 (br. s., 1H), 1.76 (br. s., 1H), 1.42 (s, 9H), 0.44 (br. s., 1H), 0.26 (br. s., 1H), 0.00 (br. s., 1H), −0.76 (br. s., 1H). MS (ESI) m/z=643.0 [M+1].

Example 351

2-((2R,5R,6R)-4-((S)-2-(tert-Butylsulfonyl)-1-cyclopropylethyl)-6-(3-chlorophenyl)-5-(4-chlorophenyl)-3-oxomorpholin-2-yl)-N-phenylacetamide or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)-N-phenylacetamide

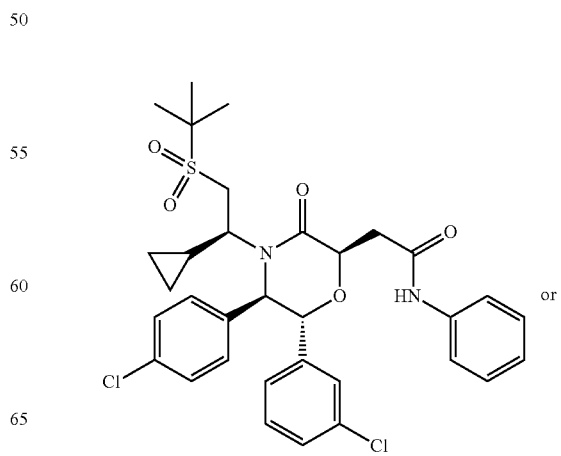

or

-continued

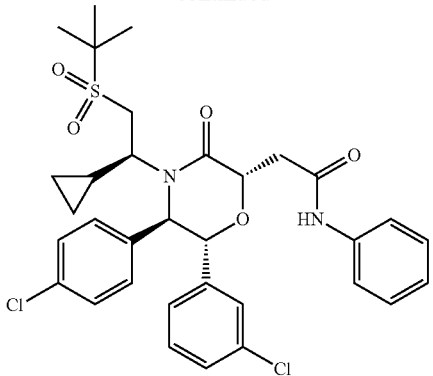

One of the title compounds was prepared from 2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid (Example 154) by a procedure similar to that described in Example 350. The residue was purified by reverse phase preparatory HPLC (Agilient 1100, column: Gemini® 5 μm C$_{18}$, 100 mm×30 mm (Phenomenex, Torrance, Calif.), gradient elution of 30% to 70% acetonitrile in water, where both solvents contain 0.1% TFA, 30 minutes) to provide one of the title compounds. $^1$H NMR (400 MHz, CDCl$_3$, δ ppm): 8.45 (s, 1H), 7.65 (d, J=8.0 Hz, 2H), 7.48 (m, 3H), 7.25-7.37 (m, 6H), 7.05 (d, J=8.0 Hz, 1H), 6.31 (br. s., 1H), 5.29 (d, J=8.0 Hz, 1H), 5.03 (m, 1H), 4.96 (d, J=12 Hz, 1H), 4.50 (br. s., 1H), 3.44 (dd, J=15.4, 4.8 Hz, 1H), 3.24 (d, J=6.5 Hz, 1H), 3.20 (d, J=6.7 Hz, 1H), 2.83 (br. s., 1H), 2.10 (br. s., 1H), 1.58 (s, 9H), 0.52 (br. s., 2H), 0.00 (br. s., 1H), −0.65 (br. s., 1H). MS (ESI) m/z=643.0 [M+1].

Example 352

2-((2R,5R,6R)-4-((S)-2-(tert-Butylsulfonyl)-1-cyclopropylethyl)-6-(3-chlorophenyl)-5-(4-chlorophenyl)-3-oxomorpholin-2-yl)-N-(2-fluorophenyl)acetamide or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)-N-(2-fluorophenyl)acetamide

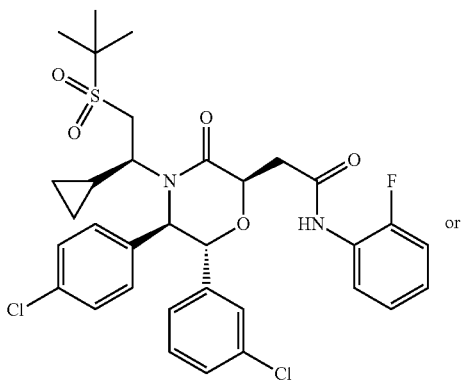

-continued

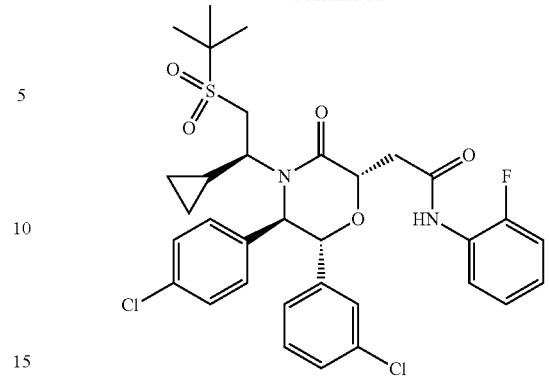

One of the title compounds was prepared from 2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid and 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid (Example 154, mixture of diastereomers at the C-2 position of the morpholinone ring) by a procedure similar to that described in Example 346, replacing 2,2,2-trifluoroethanamine with 2-fluoroaniline. The residue was purified by reverse phase preparatory HPLC (Agilient 1100, column: Gemini® 5 μm C$_{18}$, 100 mm×30 mm (Phenomenex, Torrance, Calif.), gradient elution of 30% to 70% acetonitrile in water, where both solvents contain 0.1% TFA, 30 minutes) to give one of the compounds as the first (faster) eluting isomer.

$^1$H NMR (400 MHz, CDCl$_3$, δ ppm): 8.34 (m, 1H), 8.30 (br, s, 1H), 7.23-7.33 (m, 5H), 7.15-7.23 (m, 4H), 7.00-7.03 (m, 2H), 5.15 (d, J=4.0 Hz, 1H), 5.01 (d, J=4.0 Hz, 1H), 4.64 (m, 2H), 3.97 (br. s., 1H), 3.19-3.25 (m, 1H), 3.06-3.11 (m, 2H), 1.79 (br. s., 1H), 1.40 (s, 9H), 0.40 (br. s., 1H), 0.22 (br. s., 1H), 0.00 (br. s., 1H), −0.79 (br. s., 1H). MS (ESI) m/z=661.0 [M+1].

Example 353

2-((2R,5R,6R)-4-((S)-2-(tert-Butylsulfonyl)-1-cyclopropylethyl)-6-(3-chlorophenyl)-5-(4-chlorophenyl)-3-oxomorpholin-2-yl)-N-(2-fluorophenyl)acetamide or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)-N-(2-fluorophenyl)acetamide

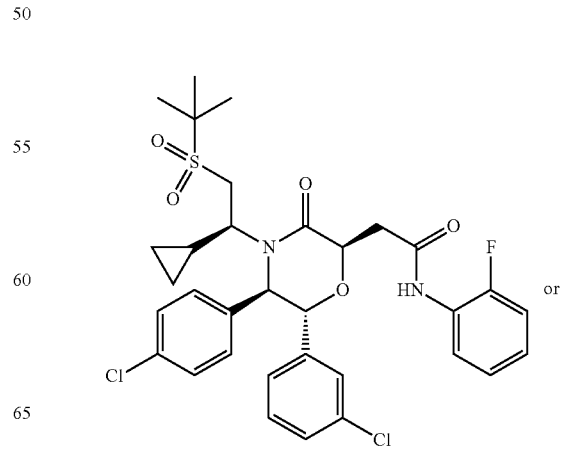

-continued

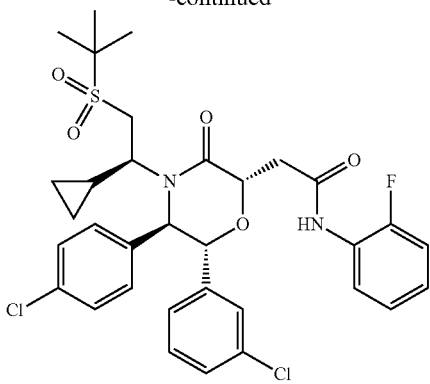

Further elution of chromatographic separation described in Example 352 provided one of the title compounds as the second (slower) eluting isomer.

$^1$H NMR (400 MHz, CDCl$_3$, δ ppm): 8.56 (s, 1H), 8.48 (m, 1H), 7.49 (m, 2H), 7.37 (m, 3H), 7.22-7.30 (m, 5H), 7.08 (m, 1H), 5.30 (d, J=12.0 Hz, 1H), 5.04 (m, 1H), 4.97 (d, J=12.0 Hz, 1H), 4.46 (br. s., 1H), 3.44-3.49 (m, 1H), 3.27-3.31 (m, 1H), 3.21-3.26 (m, 1H), 2.83 (br. s., 1H), 2.09 (br. s., 1H), 1.56 (s, 9H), 0.51-0.60 (m, 2H), 0.00 (br. s., 1H), −0.63 (br. s., 1H). MS (ESI) m/z=661.0 [M+1].

Example 354

2-((2R,5R,6R)-4-((S)-2-(tert-Butylsulfonyl)-1-cyclopropylethyl)-6-(3-chlorophenyl)-5-(4-chlorophenyl)-3-oxomorpholin-2-yl)-N-(pyridin-2-yl)acetamide or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)-N-(pyridin-2-yl)acetamide

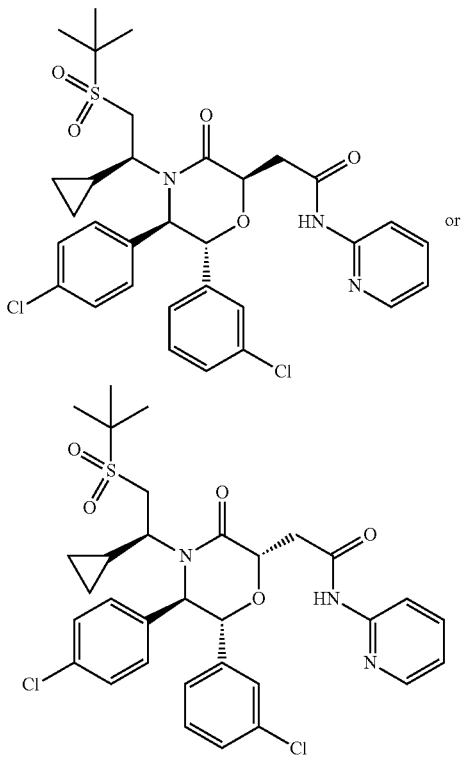

One of the title compounds was prepared from 2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl) acetic acid and 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid (Example 154, mixture of diastereomers) by a procedure similar to that described in Example 346, replacing 2,2,2-trifluoroethanamine with pyridin-2-amine. The residue was purified by reverse phase preparatory HPLC (Agilient 1100, column: Gemini® 5 μm C$_{18}$, 100 mm×30 mm (Phenomenex, Torrance, Calif.), gradient elution of 35% to 55% acetonitrile in water, where both solvents contain 0.1% TFA, 20 minutes) to give a mixture. The residue was further purified by reverse phase preparatory HPLC (Agilient 1100, column: Gemini® 5 μm C$_{18}$, 100 mm×30 mm (Phenomenex, Torrance, Calif.), gradient elution of 30% to 50% acetonitrile in water, where both solvents contain 0.1% TFA, 20 minutes) to give one of the title compounds as the first (faster) eluting isomer. $^1$H NMR (400 MHz, CDCl$_3$, δ ppm): 13.31 (br. s., 1H), 8.86-8.92 (m, 1H), 8.17-8.27 (m, 2H), 7.32-7.46 (m, 6H), 7.14-7.27 (m, 2H), 7.05-7.11 (m, 1H), 5.14-5.21 (m, 2H), 4.96-5.04 (m, 1H), 4.15 (br. s., 1H), 3.50 (m, 1H), 3.38 (s, 1H), 3.11 (m, 1H), 2.88 (br. s., 1H), 1.89 (br. s., 1H), 1.50 (s, 9H), 0.47 (d, J=7.8 Hz, 2H), 0.00 (br. s., 1H), −0.67 (br. s., 1H). MS (ESI) m/z=644.0 [M+1].

Example 355

2-((2R,5R,6R)-4-((S)-2-(tert-Butylsulfonyl)-1-cyclopropylethyl)-6-(3-chlorophenyl)-5-(4-chlorophenyl)-3-oxomorpholin-2-yl)-N-(pyridin-2-yl)acetamide or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)-N-(pyridin-2-yl)acetamide

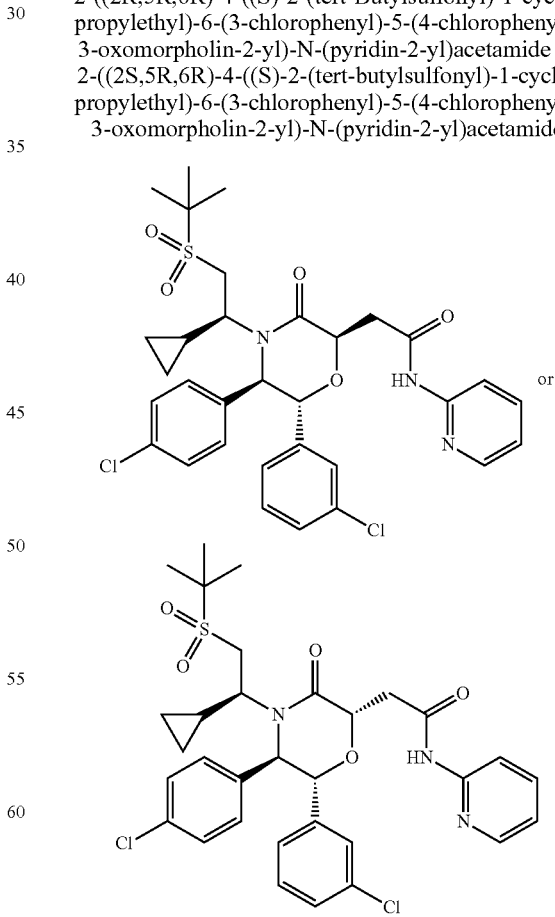

Further elution the second chromatographic separation described in Example 355 provided the title compound as the second (slower) eluting isomer. $^1$H NMR (400 MHz, CDCl$_3$, δ ppm): 13.31 (br. s., 1H), 8.86-8.92 (m, 1H), 8.17-8.27 (m, 2H), 7.32-7.46 (m, 6H), 7.14-7.27 (m, 2H), 7.05-7.11 (m, 1H), 5.14-5.21 (m, 2H), 4.96-5.04 (m, 1H), 4.15 (br. s., 1H), 3.50 (m, 1H), 3.38 (s, 1H), 3.11 (m, 1H), 2.88 (br. s., 1H), 1.89 (br. s., 1H), 1.50 (s, 9H), 0.47 (d, J=7.8 Hz, 2H), 0.00 (br. s., 1H), −0.67 (br. s., 1H). MS (ESI) m/z=644.0 [M+1].

Example 356

2-((2R,5R,6R)-4-((S)-2-(tert-Butylsulfonyl)-1-cyclopropylethyl)-6-(3-chlorophenyl)-5-(4-chlorophenyl)-3-oxomorpholin-2-yl)acetamide or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetamide

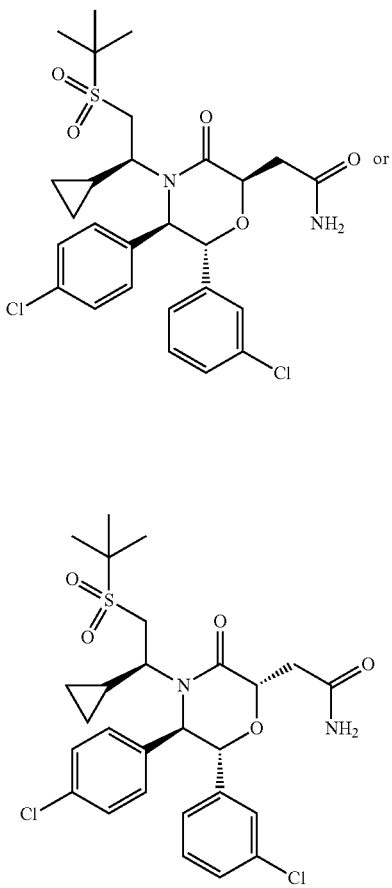

One of the title compounds was prepared from 2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid and 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid (Example 154, mixture of diastereomers) by a procedure similar to that described in Example 225. The residue was purified by reverse phase preparatory HPLC (Agilient 1100, column: Gemini® 5 μm C$_{18}$, 100 mm×30 mm (Phenomenex, Torrance, Calif.), gradient elution of 30% to 70% acetonitrile in water, where both solvents contain 0.1% TFA, 30 minutes) to give one of the compounds as the first (faster) eluting isomer. $^1$H NMR (400 MHz, CDCl$_3$, δ ppm): 7.31 (m, 2H), 7.24 (m, 4H), 7.19 (m, 1H), 7.10 (m, 1H), 6.43 (br. s., 1H), 6.40 (br. s., 1H), 5.14 (d, J=4.0 Hz, 1H), 4.97 (d, J=4.0 Hz, 1H), 4.58 (m, 1H), 4.00 (br. s., 1H), 2.96-3.08 (m, 3H), 2.85 (br. s., 1H), 1.79 (br. s., 1H), 1.41 (s, 9H), 0.43 (m, 2H), 0.00 (br. s., 1H), −0.71 (br. s., 1H). MS (ESI) m/z=567.0 [M+1].

Example 357

2-((2R,5R,6R)-4-((S)-2-(tert-Butylsulfonyl)-1-cyclopropylethyl)-6-(3-chlorophenyl)-5-(4-chlorophenyl)-3-oxomorpholin-2-yl)acetamide or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetamide

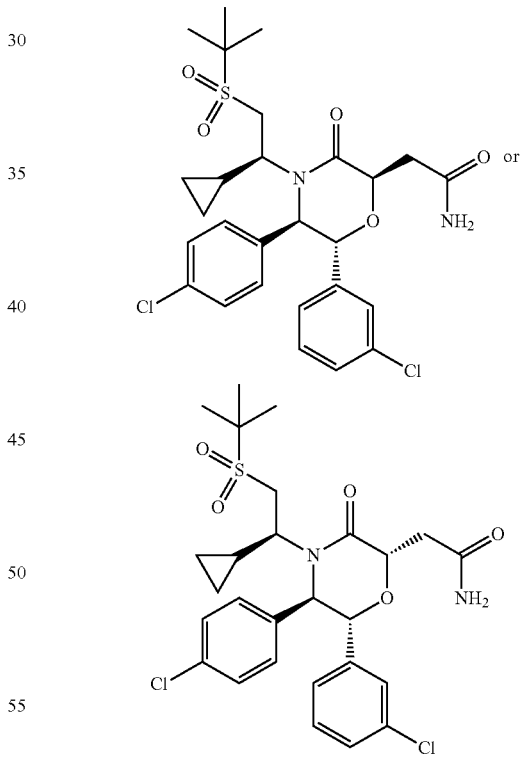

Further elution the chromatographic separation described in Example 356 provided one of the title compounds as the second (slower) eluting isomer. $^1$H NMR (400 MHz, CDCl$_3$, δ ppm): 7.51 (m, 2H), 7.39 (m, 4H), 7.30 (m, 1H), 7.09 (m, 1H), 6.60 (br. s., 1H), 6.54 (br. s., 1H), 5.30 (d, J=8.0 Hz, 1H), 4.99 (m, 1H), 4.93 (d, J=12.0 Hz, 1H), 4.49 (br. s., 1H), 3.30-3.35 (m, 1H), 3.23 (m, 1H), 3.10-3.15 (m, 1H), 2.80 (br. s., 1H), 2.10 (br. s., 1H), 1.64 (s, 9H), 0.54-0.63 (m, 2H), 0.00 (br. s., 1H), −0.63 (br. s., 1H). MS (ESI) m/z=567.0 [M+1].

Example 358

2-((2R,5R,6R)-6-(3-Chlorophenyl)-5-(4-chlorophenyl)-4-((S)-1-cyclopropyl-2-(N-(2,6-difluorophenyl)cyclopropanesulfonamido)ethyl)-3-oxomorpholin-2-yl)acetamide or 2-((2S,5R,6R)-6-(3-chlorophenyl)-5-(4-chlorophenyl)-4-((S)-1-cyclopropyl-2-(N-(2,6-difluorophenyl)cyclopropanesulfonamido)ethyl)-3-oxomorpholin-2-yl)acetamide

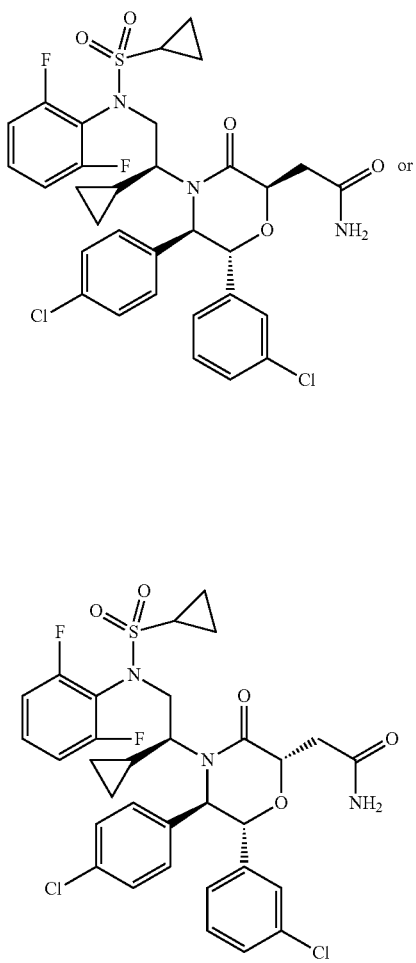

One of the title compounds was prepared from 2-((2R,5R,6R)-6-(3-chlorophenyl)-5-(4-chlorophenyl)-4-((S)-1-cyclopropyl-2-(N-(2,6-difluorophenyl)cyclopropanesulfonamido)ethyl)-3-oxomorpholin-2-yl)acetic acid and 2-((2S,5R,6R)-6-(3-chlorophenyl)-5-(4-chlorophenyl)-4-((S)-1-cyclopropyl-2-(N-(2,6-difluorophenyl)cyclopropanesulfonamido)ethyl)-3-oxomorpholin-2-yl)acetic acid (Example 250, mixture of diastereomers) by a procedure similar to that described in Example 225. The residue was purified by reverse phase preparatory HPLC (Waters DeltaPrep 4000, column: Gemini-NX® 10 μm $C_{18}$, 110 Å, 100 mm×50 mm (Phenomenex, Torrance, Calif.), gradient elution of 45% to 55% acetonitrile in water, where both solvents contain 0.1% TFA, 20 minutes) to give one of the compounds as the first (faster) eluting isomer. $^1$H NMR (400 MHz, CDCl$_3$, δ ppm): 8.19-8.47 (m, 2H), 7.16-7.43 (m, 6H), 6.97-7.14 (m, 4H), 6.89 (br. s., 1H), 5.13 (d, J=7.83 Hz, 1H), 4.97 (d, J=7.24 Hz, 1H), 4.59 (br. s., 1H), 3.66-3.85 (m, 1H), 3.07-3.21 (m, 2H), 2.96-3.07 (m, 2H), 2.47-2.58 (m, 2H), 1.43 (br. s., 1H), 0.94-1.15 (m, 3H), 0.54 (br. s., 1H), 0.38 (br. s., 1H), −0.09 (br. s., 1H), −0.82 (br. s., 1H). MS (ESI) m/z=678 [M+1].

Example 359

2-((2R,5R,6R)-6-(3-Chlorophenyl)-5-(4-chlorophenyl)-4-((S)-1-cyclopropyl-2-(N-(2,6-difluorophenyl)cyclopropanesulfonamido)ethyl)-3-oxomorpholin-2-yl)acetamide or 2-((2S,5R,6R)-6-(3-chlorophenyl)-5-(4-chlorophenyl)-4-((S)-1-cyclopropyl-2-(N-(2,6-difluorophenyl)cyclopropanesulfonamido)ethyl)-3-oxomorpholin-2-yl)acetamide

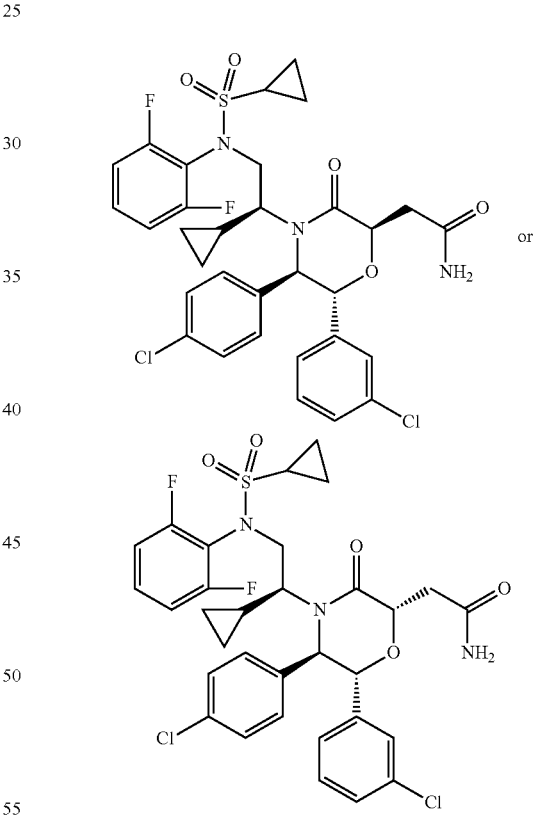

Further elution the chromatographic separation described in Example 358 provided one of the title compounds as the second (slower) eluting isomer. $^1$H NMR (400 MHz, CDCl$_3$, δ ppm): 9.01-9.31 (m, 2H), 7.32-7.49 (m, 1H), 7.21-7.30 (m, 4H), 7.16 (t, J=7.82 Hz, 1H), 6.94-7.12 (m, 3H), 6.88 (d, J=7.63 Hz, 1H), 6.69-6.82 (m, 1H), 4.91 (d, J=9.78 Hz, 1H), 4.80 (t, J=5.87 Hz, 1H), 4.70 (d, J=9.78 Hz, 1H), 3.78 (br. s., 1H), 2.97-3.24 (m, 1H), 2.66-2.78 (m, 1H), 2.43-2.61 (m, 1H), 1.66 (br. s., 1H), 0.96-1.16 (m, 6H), 0.41 (br. s., 1H), 0.24 (br. s., 1H), −0.40 (br. s., 1H), −1.05 (br. s., 1H).

MS (ESI) m/z=678 [M+1].

Example 360

2-((2R,5R,6R)-6-(3-Chlorophenyl)-5-(4-chlorophenyl)-4-((S)-1-cyclopropyl-2-(N-phenylcyclopropanesulfonamido)ethyl)-3-oxomorpholin-2-yl)acetamide or 2-((2S,5R,6R)-6-(3-chlorophenyl)-5-(4-chlorophenyl)-4-((S)-1-cyclopropyl-2-(N-phenylcyclopropanesulfonamido)ethyl)-3-oxomorpholin-2-yl)acetamide

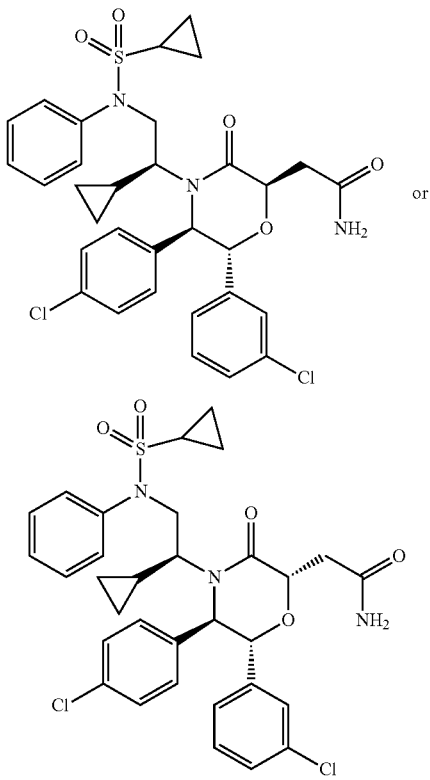

Step A. 2-((2R,5R,6R)-6-(3-Chlorophenyl)-5-(4-chlorophenyl)-4-((S)-1-cyclopropyl-2-(N-phenylcyclopropanesulfonamido)ethyl)-3-oxomorpholin-2-yl)acetic acid and 2-((2S,5R,6R)-6-(3-chlorophenyl)-5-(4-chlorophenyl)-4-((S)-1-cyclopropyl-2-(N-phenylcyclopropanesulfonamido)ethyl)-3-oxomorpholin-2-yl)acetic acid

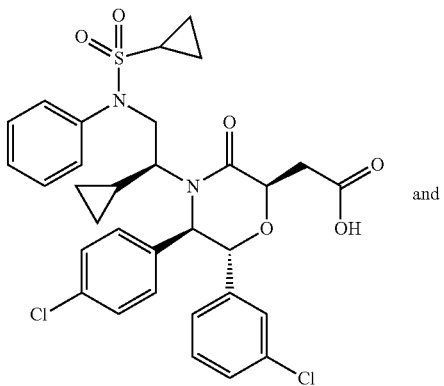

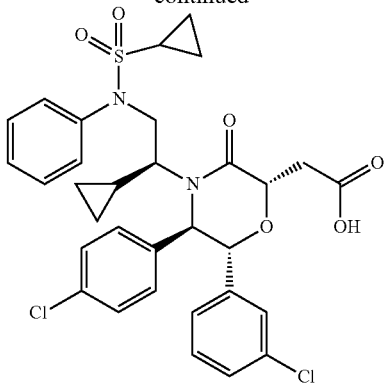

The title compounds were prepared from (5R,6R)-6-(3-chlorophenyl)-5-(4-chlorophenyl)-4-((S)-1-cyclopropyl-2-hydroxyethyl)morpholin-3-one (Example 154, Step B) by procedures similar to those described in Example 112, Steps D though F, replacing ethanethiol in Step D with N-phenylcyclopropanesulfonamide (prepared from aniline following a procedure similar to the one described in Example 133).

Step B. 2-((2R,5R,6R)-6-(3-Chlorophenyl)-5-(4-chlorophenyl)-4-((S)-1-cyclopropyl-2-(N-phenylcyclopropanesulfonamido)ethyl)-3-oxomorpholin-2-yl)acetamide or 2-((2S,5R,6R)-6-(3-chlorophenyl)-5-(4-chlorophenyl)-4-((S)-1-cyclopropyl-2-(N-phenylcyclopropanesulfonamido)ethyl)-3-oxomorpholin-2-yl)acetamide One of the title compounds was prepared from 2-((2R,5R,6R)-6-(3-chlorophenyl)-5-(4-chlorophenyl)-4-((S)-1-cyclopropyl-2-(N-phenylcyclopropanesulfonamido)ethyl)-3-oxomorpholin-2-yl)acetic acid and 2-((2S,5R,6R)-6-(3-chlorophenyl)-5-(4-chlorophenyl)-4-((S)-1-cyclopropyl-2-(N-phenylcyclopropanesulfonamido)ethyl)-3-oxomorpholin-2-yl)acetic acid (Example 360, Step A) by a procedure similar to that described in Example 225. The residue was purified by reverse phase preparatory HPLC (Waters DeltaPrep 4000, column: Gemini-NX® 10 μm $C_{18}$, 110 Å, 100 mm×50 mm (Phenomenex, Torrance, Calif.), gradient elution of 45% to 55% acetonitrile in water, where both solvents contain 0.1% TFA, 20 minutes) to give one of the compounds as the first (faster) eluting isomer. $^1$H NMR (400 MHz, CDCl$_3$, δ ppm): 7.38-7.50 (m, 3H), 7.18-7.36 (m, 8H), 7.03-7.16 (m, 2H), 6.81 (br. s., 2H), 4.75-5.14 (m, 2H), 4.35-4.52 (m, 1H), 3.71-3.91 (m, 1H), 3.03-3.23 (m, 1H), 2.89-3.03 (m, 1H), 2.35 (br. s., 1H), 1.32-1.51 (m, 1H), 0.76-1.15 (m, 6H), 0.54 (br. s., 1H), 0.28 (br. s., 1H), −0.10 (br. s., 1H), −0.84 (br. s., 1H). MS (ESI) m/z=642 [M+1].

Example 361

2-((2R,5R,6R)-6-(3-Chlorophenyl)-5-(4-chlorophenyl)-4-((S)-1-cyclopropyl-2-(N-phenylcyclopropanesulfonamido)ethyl)-3-oxomorpholin-2-yl)acetamide or 2-((2S,5R,6R)-6-(3-chlorophenyl)-5-(4-chlorophenyl)-4-((S)-1-cyclopropyl-2-(N-phenylcyclopropanesulfonamido)ethyl)-3-oxomorpholin-2-yl)acetamide

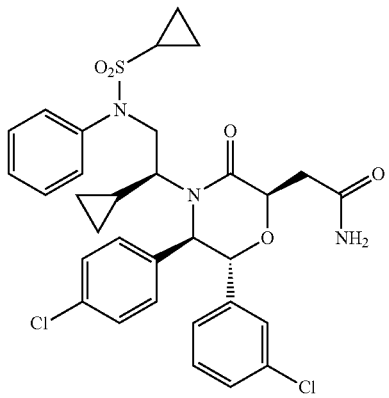

or

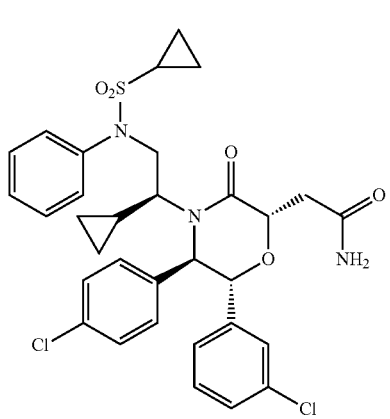

Further elution the chromatographic separation described in Example 360, Step B provided one of the title compounds as the second (slower) eluting isomer. $^1$H NMR (400 MHz, CDCl$_3$, δ ppm): 7.62 (br. s., 2H), 7.47 (br. s., 4H), 7.31-7.41 (m, 2H), 7.19-7.25 (m, 2H), 7.07-7.18 (m, 2H), 6.73-6.87 (m, 2H), 6.66 (br. s., 1H), 4.79 (br. s., 1H), 4.68 (d, J=9.78 Hz, 1H), 4.44-4.57 (m, 1H), 3.84 (d, J=17.80 Hz, 1H), 2.93 (dd, J=16.04, 4.30 Hz, 1H), 2.62 (br. s., 1H), 2.25-2.43 (m, 1H), 1.62 (br. s., 1H), 0.82-1.13 (m, 6H), 0.42 (br. s., 1H), 0.21 (br. s., 1H), −0.30 (br. s., 1H), −1.09 (br. s., 1H). MS (ESI) m/z=642 [M+1].

Example 362

2-((2R,5R,6R)-4-((S)-1-(tert-Butylsulfonyl)-4,4,4-trifluorobutan-2-yl)-6-(3-chlorophenyl)-5-(4-chlorophenyl)-3-oxomorpholin-2-yl)acetamide or 2-((2S,5R,6R)-4-((S)-1-(tert-butylsulfonyl)-4,4,4-trifluorobutan-2-yl)-6-(3-chlorophenyl)-5-(4-chlorophenyl)-3-oxomorpholin-2-yl)acetamide

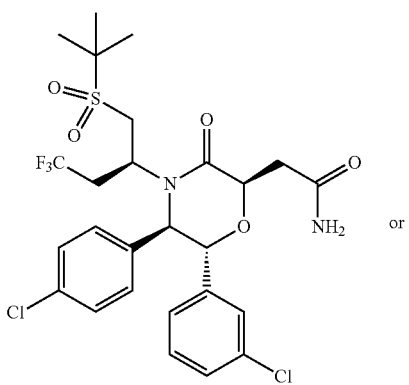

or

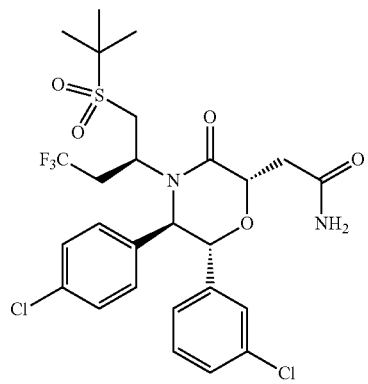

One of the title compounds was prepared from 2-((2R,5R,6R)-4-((S)-1-(tert-butylsulfonyl)-4,4,4-trifluorobutan-2-yl)-6-(3-chlorophenyl)-5-(4-chlorophenyl)-3-oxomorpholin-2-yl)acetic acid or 2-((2S,5R,6R)-4-((S)-1-(tert-butylsulfonyl)-4,4,4-trifluorobutan-2-yl)-6-(3-chlorophenyl)-5-(4-chlorophenyl)-3-oxomorpholin-2-yl)acetic acid (Example 266) by a procedure similar to that described in Example 225. The residue was purified by preparative TLC (eluent: 5% MeOH in dichloromethane) to give one of the compounds. $^1$H NMR (400 MHz, CDCl$_3$, δ ppm): 7.28-7.37 (m, 4H), 7.16-7.23 (m, 2H), 7.08-7.15 (m, 1H), 6.78-6.97 (m, 1H), 5.63-5.87 (m, 1H), 5.28-5.48 (m, 1H), 5.16 (d, J=5.09 Hz, 2H), 4.66-4.87 (m, 1H), 4.02-4.25 (m, 1H), 3.77-3.94 (m, 1H), 3.19 (dd, J=16.04, 6.26 Hz, 2H), 3.00-3.11 (m, 1H), 2.82 (dd, J=16.24, 3.72 Hz, 1H), 2.30-2.56 (m, 1H), 1.43 (s, 9H). MS (ESI) m/z=609 [M+1].

Example 363

22-((2R,5R,6R)-4-((S)-1-(tert-Butylsulfonyl)-4,4,4-trifluorobutan-2-yl)-6-(3-chlorophenyl)-5-(4-chlorophenyl)-3-oxomorpholin-2-yl)acetamide or 2-((2S,5R,6R)-4-((S)-1-(tert-butylsulfonyl)-4,4,4-trifluorobutan-2-yl)-6-(3-chlorophenyl)-5-(4-chlorophenyl)-3-oxomorpholin-2-yl)acetamide

Example 364

2-((2R,5R,6R)-6-(3-Chlorophenyl)-5-(4-chlorophenyl)-4-((S)-1-cyclopropyl-2-(N-(2-fluorophenyl)cyclopropanesulfonamido)ethyl)-3-oxomorpholin-2-yl)-N-methylacetamide or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)-N-methylacetamide

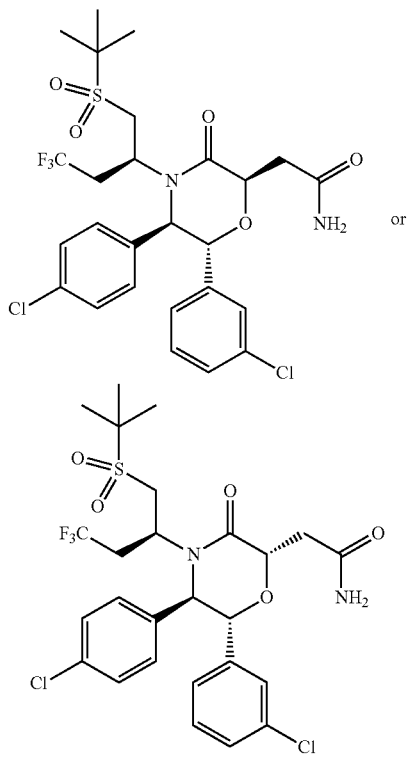

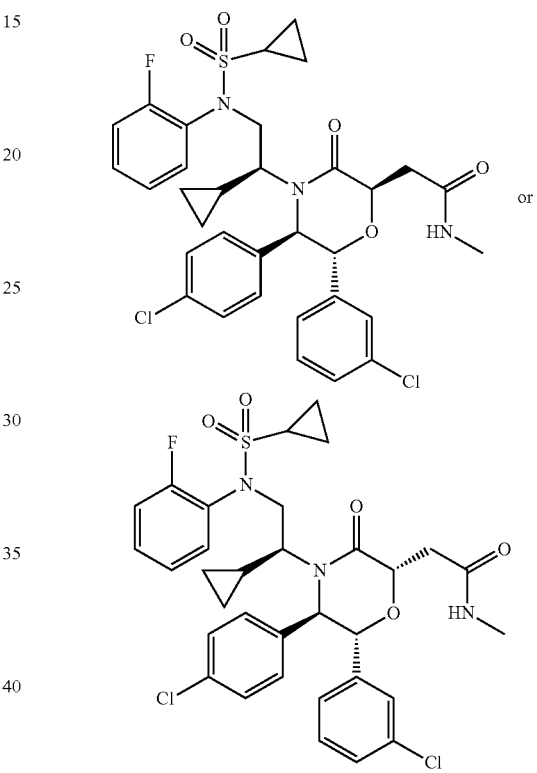

One of the title compounds was prepared from 2-((2R,5R,6R)-4-((S)-1-(tert-butylsulfonyl)-4,4,4-trifluorobutan-2-yl)-6-(3-chlorophenyl)-5-(4-chlorophenyl)-3-oxomorpholin-2-yl)acetic acid or 2-((2S,5R,6R)-4-((S)-1-(tert-butylsulfonyl)-4,4,4-trifluorobutan-2-yl)-6-(3-chlorophenyl)-5-(4-chlorophenyl)-3-oxomorpholin-2-yl)acetic acid (Example 267) by a procedure similar to that described in Example 225. The residue was purified by preparative TLC (eluent: 5% MeOH in dichloromethane) to give one of the compounds. $^1$H NMR (400 MHz, CDCl$_3$, δ ppm): 7.31-7.43 (m, 2H), 7.19-7.25 (m, 1H), 7.06-7.17 (m, 4H), 6.78-6.88 (m, 1H), 5.88 (br. s., 1H), 5.32 (br. s., 1H), 5.16 (d, J=9.78 Hz, 1H), 4.82 (dd, J=7.53, 4.21 Hz, 1H), 4.72 (d, J=9.98 Hz, 1H), 4.10 (d, J=13.50 Hz, 1H), 3.70-3.85 (m, 1H), 3.14-3.30 (m, 1H), 3.01-3.11 (m, 2H), 2.85 (dd, J=15.65, 7.43 Hz, 1H), 2.16-2.43 (m, 1H), 1.43 (s, 9H). MS (ESI) m/z=609 [M+1].

One of the title compounds was prepared from 2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid (Example 159) by a procedure similar to that described in Example 225, replacing ammonia with methylamine. The residue was purified by preparative TLC (eluent: 5% MeOH in dichloromethane) to give one of the title compounds. $^1$H NMR (400 MHz, CDCl$_3$, δ ppm): 7.54-7.67 (m, 1H), 7.32-7.43 (m, 1H), 7.12-7.30 (m, 7H), 7.06 (d, J=7.83 Hz, 2H), 6.80-6.96 (m, 1H), 5.93 (br. s., 1H), 4.81-4.94 (m, 1H), 4.77 (s, 1H), 4.70 (d, J=9.98 Hz, 1H), 2.81 (s, 2H), 2.79 (d, J=4.89 Hz, 3H), 2.68-2.75 (m, 1H), 2.40-2.50 (m, 1H), 2.21-2.37 (m, 1H), 0.85-1.10 (m, 6H), 0.40 (br. s., 1H), 0.22 (br. s., 1H), −0.24 (br. s., 1H), −1.04 (br. s., 1H). MS (ESI) m/z=674 [M+1].

Example 365

2-((2R,5R,6R)-6-(3-Chlorophenyl)-5-(4-chlorophenyl)-4-((S)-1-cyclopropyl-2-(N-(2-fluorophenyl)cyclopropanesulfonamido)ethyl)-3-oxomorpholin-2-yl)-N-methylacetamide or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)-N-methylacetamide

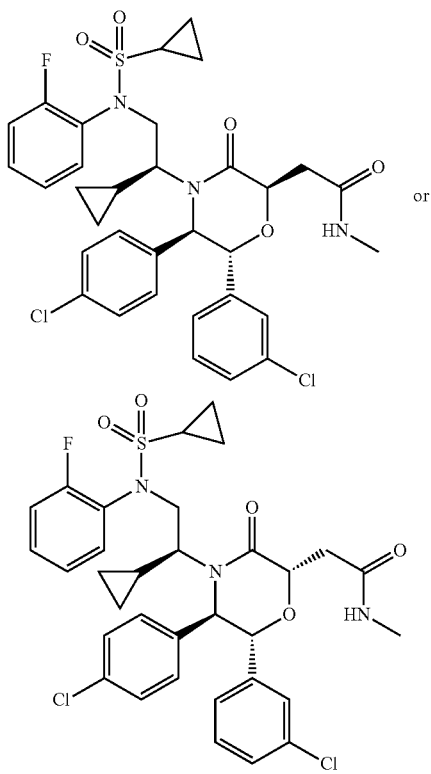

One of the title compounds was prepared from 2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid (Example 158) by a procedure similar to that described in Example 225, replacing ammonia with methylamine. The residue was purified by preparative TLC (eluent: 5% MeOH in dichloromethane) to give one of the title compounds. $^1$H NMR (400 MHz, CDCl$_3$, δ ppm): 7.46-7.62 (m, 1H), 7.08-7.42 (m, 11H), 4.98-5.12 (m, 1H), 4.95 (d, J=6.26 Hz, 1H), 4.33-4.36 (m, 2H), 2.76-3.03 (m, 7H), 2.33-2.53 (m, 1H), 0.82-1.09 (m, 6H), 0.51 (br. s., 1H), 0.35 (br. s., 1H), 0.04 (br. s., 1H), −0.77 (br. s., 1H). MS (ESI) m/z=674 [M+1].

Example 366

2-((2R,5R,6R)-6-(3-Chlorophenyl)-5-(4-chlorophenyl)-4-((S)-1-cyclopropyl-2-(N-(2-fluorophenyl)cyclopropanesulfonamido)ethyl)-3-oxomorpholin-2-yl)-N,N-dimethylacetamide or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)-N,N-dimethylacetamide

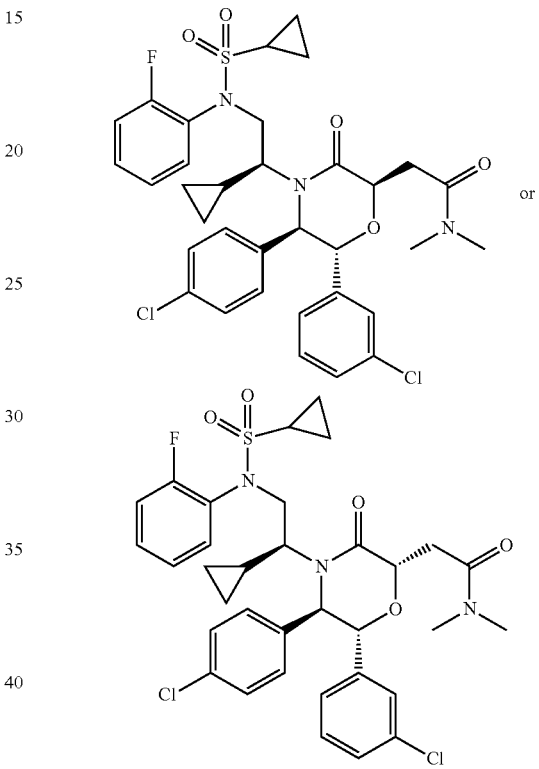

One of the title compounds was prepared from 2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid (Example 159) by a procedure similar to that described in Example 225, replacing ammonia with N,N-dimethylamine. The residue was purified by preparative TLC (eluent: 5% MeOH in dichloromethane) to give one of the title compounds.
$^1$H NMR (400 MHz, CDCl$_3$, δ ppm): 7.46-7.54 (m, 1H), 7.30-7.38 (m, 6H), 7.04-7.28 (m, 5H), 5.02 (s, 2H), 4.49-4.56 (m, 1H), 4.15-4.37 (m, 1H), 3.73-3.96 (m, 1H), 2.67-3.09 (m, 9H), 2.39-2.51 (m, 1H), 0.83-1.05 (m, 5H), 0.43-0.54 (m, 1H), 0.26-0.39 (m, 1H), −0.01-0.12 (m, 1H), −0.83 to −0.53 (m, 1H). MS (ESI) m/z=688 [M+1].

Example 367

2-((2R,5R,6R)-6-(3-Chlorophenyl)-5-(4-chlorophenyl)-4-((S)-1-cyclopropyl-2-(N-(2-fluorophenyl)cyclopropanesulfonamido)ethyl)-3-oxomorpholin-2-yl)-N,N-dimethylacetamide or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)-N,N-dimethylacetamide

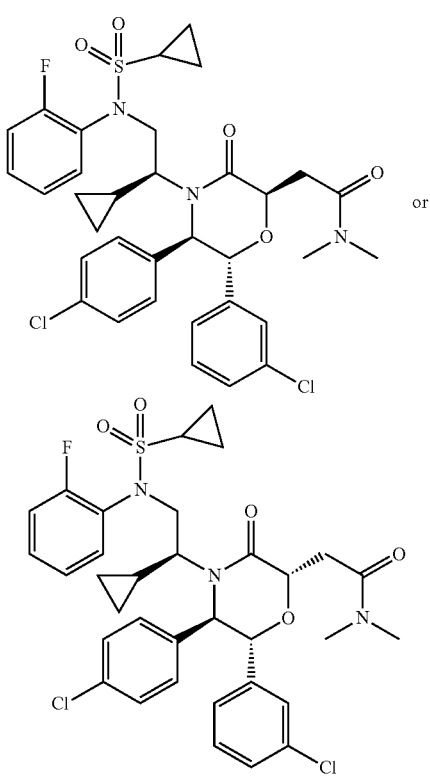

One of the title compounds was prepared 2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid (Example 158) by a procedure similar to that described in Example 225, replacing ammonia with N,N-dimethylamine. The residue was purified by preparative TLC (eluent: 5% MeOH in dichloromethane) to give one of the compounds. $^1$H NMR (400 MHz, CDCl$_3$, δ ppm): 7.30-7.41 (m, 1H), 7.24-7.29 (m, 2H), 7.05-7.25 (m, 8H), 6.83-6.92 (m, 1H), 4.93-5.06 (m, 1H), 4.88 (d, J=9.78 Hz, 1H), 4.76 (d, J=9.98 Hz, 1H), 2.75-3.12 (m, 9H), 2.21-2.58 (m, 3H), 0.74-1.13 (m, 5H), 0.43 (br. s., 1H), 0.21 (br. s., 1H), −0.15 (br. s., 1H), −1.02 (br. s., 1H). MS (ESI) m/z=688 [M+1].

Example 368

2-((2R,5R,6R)-6-(3-Chlorophenyl)-5-(4-chlorophenyl)-4-((S)-1-cyclopropyl-2-(N-(2-fluorophenyl)cyclopropanesulfonamido)ethyl)-3-oxomorpholin-2-yl)-N-(pyridin-2-yl)acetamide or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)-N-(pyridin-2-yl)acetamide

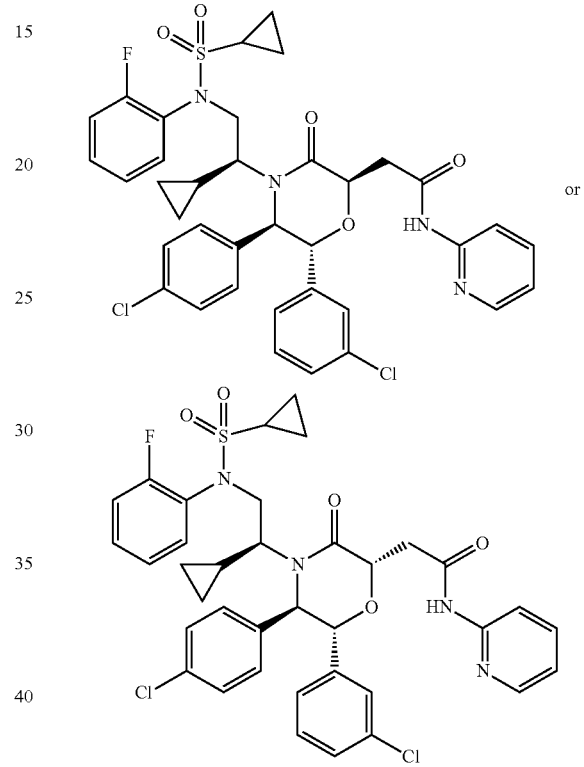

One of the title compounds was prepared from 2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid (Example 158, mixture of diastereomers) by a procedure similar to that described in Example 354. The residue was purified by reverse phase preparatory HPLC (Agilient 1100, column: Gemini® 5 μm C$_{18}$, 100 mm×30 mm (Phenomenex, Torrance, Calif.), gradient elution of 30% to 70% acetonitrile in water, where both solvents contain 0.1% TFA, 45 minutes) to give a mixture. The residue was further purified by chiral SFC (250×30 mm Chiralpak® OJ-H column (Chiral Technologies, Inc., West Chester, Pa., USA) with 17.6 g/min 20 mM NH$_3$ in ethanol+ 62.1 g/min CO$_2$ on a Thar 80 SFC (Thar Technologies, Inc., Pittsburg, Pa.)) to give one of the compounds as the first (faster) eluting isomer. $^1$H NMR (400 MHz, CDCl$_3$, δ ppm): 8.71 (br. s., 1H), 8.28 (m, 1H), 8.20 (d, J=8.4 Hz, 1H), 7.58-7.74 (m, 2H), 7.39-7.46 (m, 1H), 7.06-7.31 (m, 9H), 7.00-7.05 (m, 1H), 6.88-6.94 (m, 1H), 4.83-4.94 (m, 2H), 4.74 (d, J=10.0 Hz, 1H), 2.43-2.64 (m, 1H), 2.43 (br. s., 1H), 1.53-

1.83 (m, 2H), 1.16-1.39 (m, 1H), 0.89-0.95 (m, 6H), 0.39 (br. s., 1H), 0.23 (br. s., 1H), −0.21 (br. s., 1H), −1.05 (br. s., 1H). MS (ESI) m/z=737.0 [M+1].

Example 369

2-((2R,5R,6R)-6-(3-Chlorophenyl)-5-(4-chlorophenyl)-4-((S)-1-cyclopropyl-2-(N-(2-fluorophenyl)cyclopropanesulfonamido)ethyl)-3-oxomorpholin-2-yl)-N-(pyridin-2-yl)acetamide or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)-N-(pyridin-2-yl)acetamide

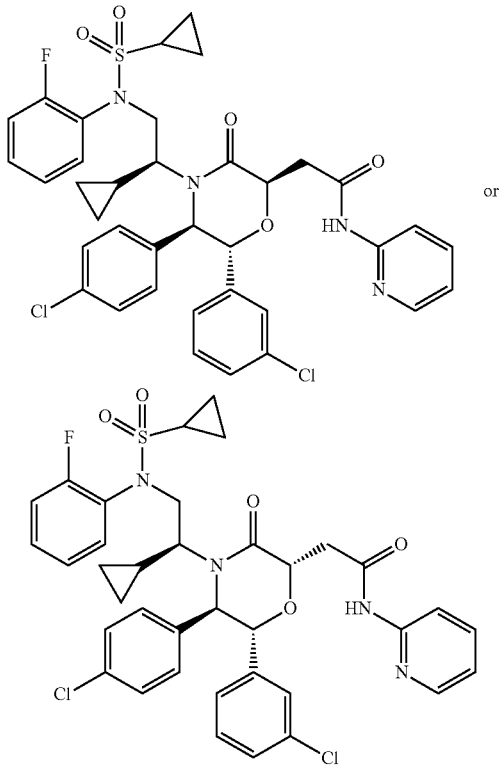

Further elution the SFC chromatographic separation described in Example 368 provided one of the title compounds as the second (slower) eluting isomer. ¹H NMR (400 MHz, CDCl₃, δ ppm): 8.75 (br. s., 1H), 8.08-8.38 (m, 2H), 7.62-7.80 (m, 1H), 7.43-7.62 (m, 1H), 7.12-7.40 (m, 11H), 6.87-7.09 (m, 1H), 5.07 (br. s., 1H), 4.98 (d, J=5.5 Hz, 1H), 4.43-4.49 (m, 1H), 3.07-3.16 (m, 2H), 2.42-2.54 (m, 1H), 1.55-1.72 (m, 2H), 1.23-1.53 (m, 1H), 0.81-1.10 (m, 5H), 0.48 (br. s., 1H), 0.10 (br. s., 1H), 0.06 (br. s., 1H), −0.75 (br. s., 1H). MS (ESI) m/z=737.0 [M+1].

Example 370

(2R,5R,6R)-4-((S)-2-(tert-Butylsulfonyl)-1-cyclopropylethyl)-6-(3-chlorophenyl)-5-(4-chlorophenyl)-2-(2-hydroxyethyl)morpholin-3-one or (2S,5R,6R)-4-((S)-2-(tert-butylsulfonyl)-1-cyclopropylethyl)-6-(3-chlorophenyl)-5-(4-chlorophenyl)-2-(2-hydroxyethyl)morpholin-3-one

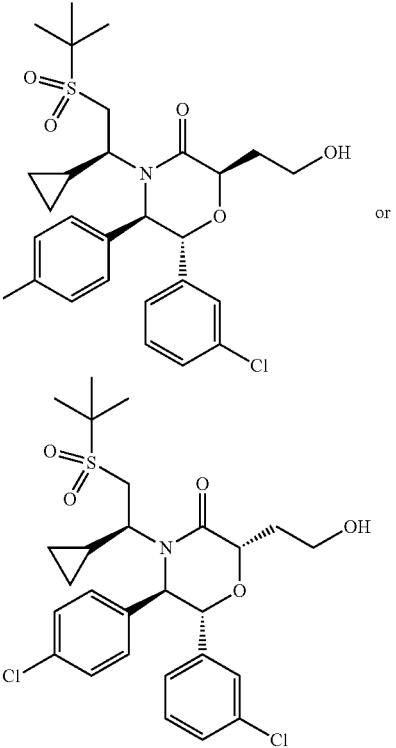

A solution of 2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid (Example 154) in methanol was allowed to stand at room temperature for 2 days. The solution was concentrated, and the redisue was purified by reverse phase preparatory HPLC (Agilient 1100, column: Gemini® 5 μm C₁₈, 100 mm×30 mm (Phenomenex, Torrance, Calif.) gradient elution of 25% to 75% acetonitrile in water, where both solvents contain 0.1% TFA, 30 minutes). The residue was dissolved in THF (0.154 mL) and lithium triethylborohydride (1.0 M in THF, 0.324 mL, 0.324 mmol) was added. The mixture was stirred at −10° C. for 15 minutes, then methanol (1 mL) was added dropwise over 1 minute. Then Oxone® (285 mg, 0.463 mmol) in water (20 mL) was added dropwise over 5 minutes. The mixture was stirred at room temperature for 1 hour. Saturated NaHSO₃ (3 mL) was added, and the mixture was extracted with diethyl ether (2×60 mL). The combined organic layers were dried over MgSO₄, filtered, and concentrated. The residue was purified by reverse phase preparatory HPLC (Agilient 1100, column: Gemini® 5 μm C₁₈, 100 mm×30 mm (Phenomenex, Torrance, Calif.), gradient elution of 25% to 75% acetonitrile in water, where both solvents contain 0.1% TFA, 30 minutes) to give one of the title compounds as a white foam. ¹H NMR (400 MHz, CDCl₃, δ ppm): 7.32-7.39 (m, 2H), 7.28-7.31 (m, 3H), 7.23-7.26 (m, 1H), 7.19 (t, J=7.73 Hz, 1H), 7.10 (d, J=7.43 Hz, 1H), 5.14 (d, J=6.26 Hz, 1H), 4.90 (d, J=6.26 Hz, 1H), 4.43 (t, J=6.75 Hz, 1H), 4.08 (dt, J=2.84, 11.59 Hz, 1H), 3.91 (t, J=5.48 Hz, 2H), 3.13 (d, J=11.74 Hz, 1H), 2.68-2.92 (m, 1H), 2.21-2.47 (m, 2H), 1.79-1.94 (m, 1H), 1.45 (s, 9H), 0.26-0.53 (m, 2H), −0.12-0.06 (m, 1H), −0.90 to −0.64 (m, 1H). MS (ESI) m/z=554.2 [M+1].

Example 371

(2R,5R,6R)-4-((S)-1-(tert-Butylsulfonyl)butan-2-yl)-6-(3-chlorophenyl)-5-(4-chlorophenyl)-2-((R)-2,3-dihydroxypropyl)morpholin-3-one or (2R,5R,6R)-4-((S)-1-(tert-butylsulfonyl)butan-2-yl)-6-(3-chlorophenyl)-5-(4-chlorophenyl)-2-((S)-2,3-dihydroxypropyl)morpholin-3-one or (2S,5R,6R)-4-((S)-1-(tert-butylsulfonyl)butan-2-yl)-6-(3-chlorophenyl)-5-(4-chlorophenyl)-2-((R)-2,3-dihydroxypropyl)morpholin-3-one or (2S,5R,6R)-4-((S)-1-(tert-butylsulfonyl)butan-2-yl)-6-(3-chlorophenyl)-5-(4-chlorophenyl)-2-((S)-2,3-dihydroxypropyl)morpholin-3-one

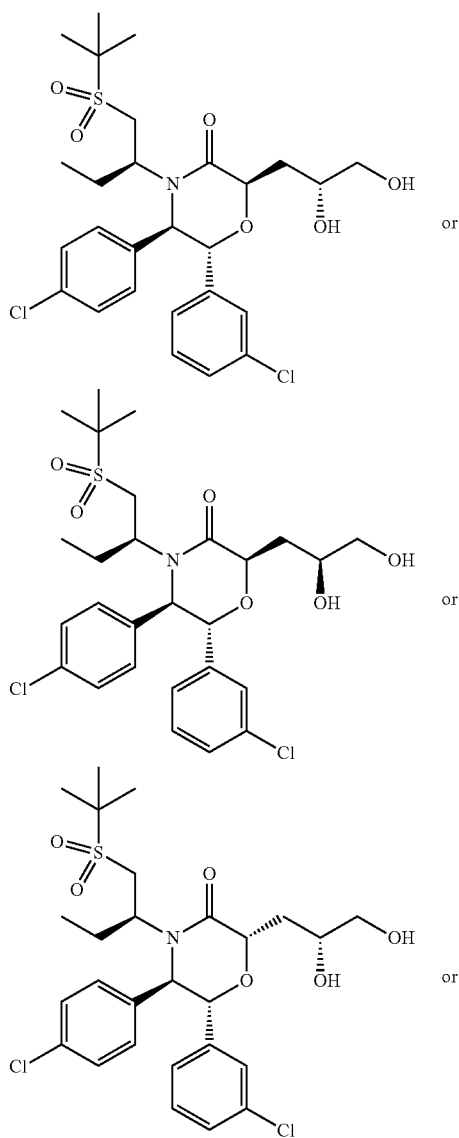

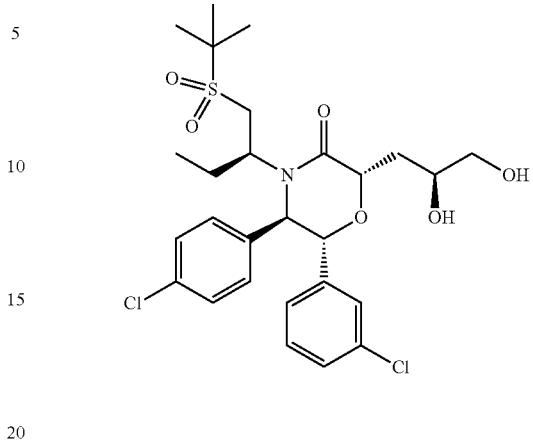

A solution of (2R,5R,6R)-2-allyl-4-((S)-1-(tert-butylsulfonyl)butan-2-yl)-6-(3-chlorophenyl)-5-(4-chlorophenyl)morpholin-3-one and (2S,5R,6R)-2-allyl-4-((S)-1-(tert-butylsulfonyl)butan-2-yl)-6-(3-chlorophenyl)-5-(4-chlorophenyl)morpholin-3-one (0.150 g, 0.279 mmol, prepared from (5R,6R)-6-(3-chlorophenyl)-5-(4-chlorophenyl)-4-((S)-1-hydroxybutan-2-yl)morpholin-3-one Example 112, Step C by procedures similar to Example 112 Steps D and E, replacing ethanethiol in Step D with 2-methylpropane-2-thiol) was dissolved in a mixture of THF (2.5 mL), water (1.5 mL) and t-butanol (1.5 mL). 4-Methylmorpholine 4-oxide (0.114 g, 0.975 mmol) followed by osmium tetroxide (2.5 wt. % in t-butanol, 0.068 mL, 6.96 µmol) were added at room temperature. The mixture was stirred for 16 hours, then diluted with water and extracted with dichloromethane (6×). The combined organic layers were washed with brine, dried over $Na_2SO_4$, filtered, and concentrated. The residue was purified by reversed phase preparatory HPLC (Agilient 1100, column: Gemini® 5 µm $C_{18}$, 100 mm×30 mm (Phenomenex, Torrance, Calif.), gradient elution of 40% to 60% acetonitrile in water, where both solvents contain 0.1% TFA) to provide two peaks that each contained a mixture of diastereomers. The first (faster) eluting peak was further purified by chiral SFC (250×30 mm Chiralpak® IC column (Chiral Technologies, Inc., West Chester, Pa., USA) with 16 g/min 20 mM $NH_3$ in MeOH+64 g/min $CO_2$ on a Thar 80 SFC (Thar Technologies, Inc., Pittsburg, Pa.)) to give one of the title compounds as the first (faster) eluting isomer. $^1$H NMR (500 MHz, $CDCl_3$, δ ppm): 0.54 (t, J=7.58 Hz, 3H), 1.44 (s, 9H), 1.58-1.69 (m, 1H), 2.09-2.33 (m, 3H), 2.88-2.95 (m, 1H), 3.35 (br. s., 1H), 3.55-3.64 (m, 1H), 3.70 (m, 1H), 3.94-4.12 (m, 2H), 4.62 (dd, J=8.31, 4.89 Hz, 1H), 4.91 (d, J=7.82 Hz, 1H), 5.13 (d, J=7.83 Hz, 1H), 6.98 (d, J=7.58 Hz, 1H), 7.12-7.18 (m, 1H), 7.18-7.25 (m, 4H), 7.29-7.36 (m, 2H); MS (ESI) m/z=572 [M+1].

Example 372

(2R,5R,6R)-4-((S)-1-(tert-Butylsulfonyl)butan-2-yl)-6-(3-chlorophenyl)-5-(4-chlorophenyl)-2-((R)-2,3-dihydroxypropyl)morpholin-3-one or (2R,5R,6R)-4-((S)-1-(tert-butylsulfonyl)butan-2-yl)-6-(3-chlorophenyl)-5-(4-chlorophenyl)-2-((S)-2,3-dihydroxypropyl)morpholin-3-one or (2S,5R,6R)-4-((S)-1-(tert-butylsulfonyl)butan-2-yl)-6-(3-chlorophenyl)-5-(4-chlorophenyl)-2-((R)-2,3-dihydroxypropyl)morpholin-3-one or (2S,5R,6R)-4-((S)-1-(tert-butylsulfonyl)butan-2-yl)-6-(3-chlorophenyl)-5-(4-chlorophenyl)-2-((S)-2,3-dihydroxypropyl)morpholin-3-one

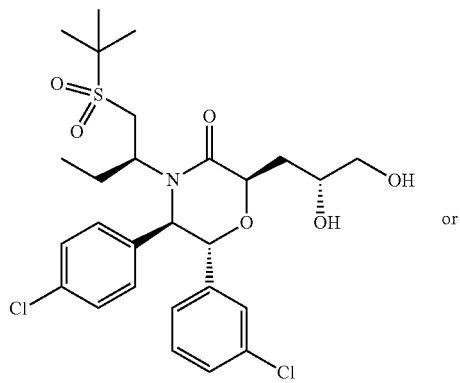 or

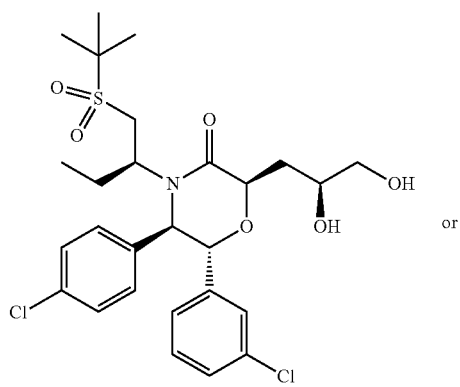

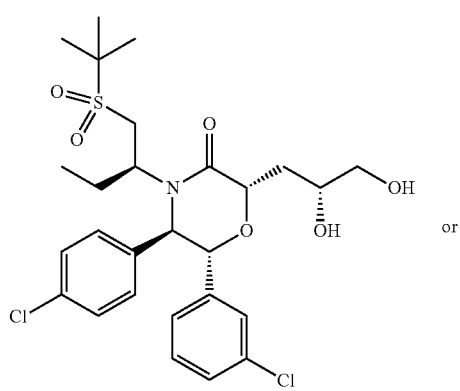 or

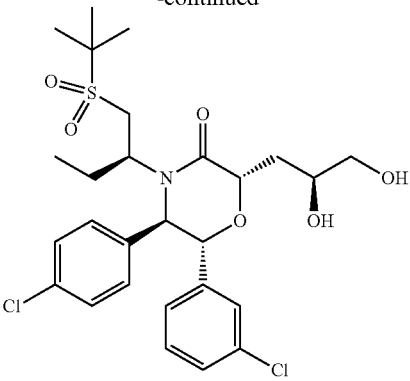

Further elution of the SFC chromatographic separation described in Example 371 provided one of the title compounds as the second (slower) eluting isomer. $^1$H NMR (500 MHz, CDCl$_3$, δ ppm): 0.54 (t, J=7.46 Hz, 3H), 1.37-1.51 (s, 9H), 1.60 (ddd, J=14.00, 7.64, 4.28 Hz, 1H), 2.02-2.25 (m, 2H), 2.25-2.42 (m, 1H), 2.81-3.02 (m, 1H), 3.37 (br. s., 1H), 3.51-3.63 (m, 1H), 3.63-3.80 (m, 1H), 3.97 (m, 2H), 4.55 (t, J=5.87 Hz, 1H), 4.81 (d, J=7.58 Hz, 1H), 5.05-5.18 (m, 1H), 6.98 (d, J=7.83 Hz, 1H), 7.12-7.19 (m, 1H), 7.19-7.26 (m, 4H), 7.31-7.37 (m, 2H). MS (ESI) m/z=572 [M+1].

Example 373

(2R,5R,6R)-4-((S)-1-(tert-Butylsulfonyl)butan-2-yl)-6-(3-chlorophenyl)-5-(4-chlorophenyl)-2-((R)-2,3-dihydroxypropyl)morpholin-3-one or (2R,5R,6R)-4-((S)-1-(tert-butylsulfonyl)butan-2-yl)-6-(3-chlorophenyl)-5-(4-chlorophenyl)-2-((S)-2,3-dihydroxypropyl)morpholin-3-one or (2S,5R,6R)-4-((S)-1-(tert-butylsulfonyl)butan-2-yl)-6-(3-chlorophenyl)-5-(4-chlorophenyl)-2-((R)-2,3-dihydroxypropyl)morpholin-3-one or (2S,5R,6R)-4-((S)-1-(tert-butylsulfonyl)butan-2-yl)-6-(3-chlorophenyl)-5-(4-chlorophenyl)-2-((S)-2,3-dihydroxypropyl)morpholin-3-one

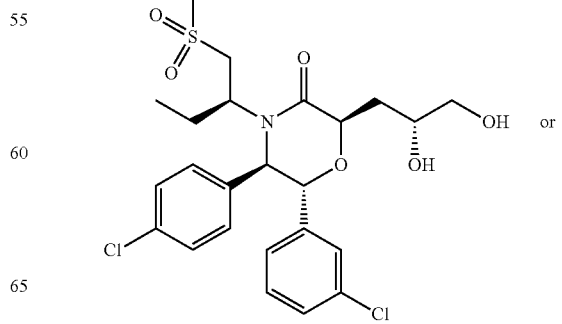

-continued

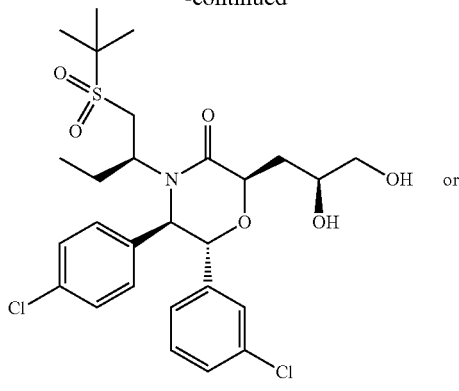 or

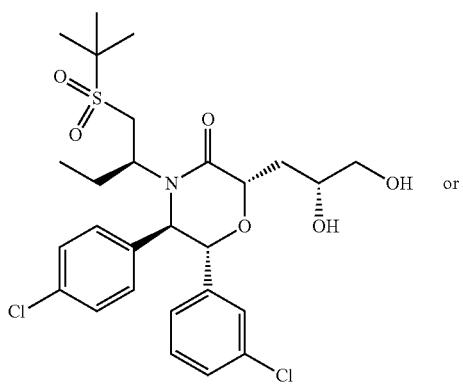 or

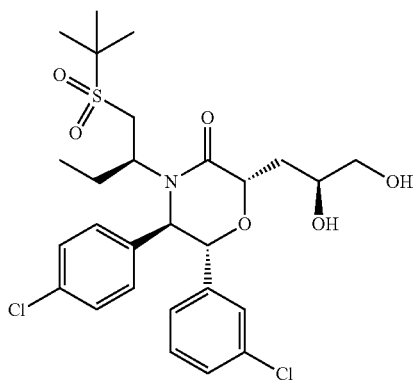

The second (slower) eluting peak (pair of diastereomers) from the reverse phase preparatory HPLC purification described in Example 371 was purified by chiral SFC (250× 30 mm Chiralpak® AD column (Chiral Technologies, Inc., West Chester, Pa., USA) with 16 g/min 20 mM NH$_3$ in MeOH+64 g/min CO$_2$ on a Thar 80 SFC (Thar Technologies, Inc., Pittsburg, Pa.)) to give one of the title compounds as the first (faster) eluting isomer. $^1$H NMR (400 MHz, CDCl$_3$, δ ppm): 0.52 (t, J=7.46 Hz, 3H), 1.42-1.44 (s, 9H), 1.65 (ddd, J=14.12, 7.76, 3.55 Hz, 1H), 2.13-2.27 (m, 2H), 2.29-2.40 (m, 1H), 2.84 (dd, J=13.45, 1.47 Hz, 1H), 3.30 (t, J=8.56 Hz, 1H), 3.55 (dd, J=11.25, 6.85 Hz, 1H), 3.67 (dd, J=11.25, 3.42 Hz, 1H), 4.05 (dd, J=13.33, 10.15 Hz, 1H), 4.14-4.20 (m, 1H), 4.58 (t, J=5.14 Hz, 1H), 4.68 (d, J=9.78 Hz, 1H), 5.11 (d, J=9.78 Hz, 1H), 6.88 (d, J=7.83 Hz, 1H), 7.06 (t, J=1.83 Hz, 1H), 7.13 (d, J=7.82 Hz, 2H), 7.19-7.25 (m, 2H), 7.29-7.33 (d, J=7.83 Hz, 2H). MS (ESI) m/z=572 [M+1].

Example 374

(2R,5R,6R)-4-((S)-1-(tert-Butylsulfonyl)butan-2-yl)-6-(3-chlorophenyl)-5-(4-chlorophenyl)-2-((R)-2,3-dihydroxypropyl)morpholin-3-one or (2R,5R,6R)-4-((S)-1-(tert-butylsulfonyl)butan-2-yl)-6-(3-chlorophenyl)-5-(4-chlorophenyl)-2-((S)-2,3-dihydroxypropyl)morpholin-3-one or (2S,5R,6R)-4-((S)-1-(tert-butylsulfonyl)butan-2-yl)-6-(3-chlorophenyl)-5-(4-chlorophenyl)-2-((R)-2,3-dihydroxypropyl)morpholin-3-one or (2S,5R,6R)-4-((S)-1-(tert-butylsulfonyl)butan-2-yl)-6-(3-chlorophenyl)-5-(4-chlorophenyl)-2-((S)-2,3-dihydroxypropyl)morpholin-3-one

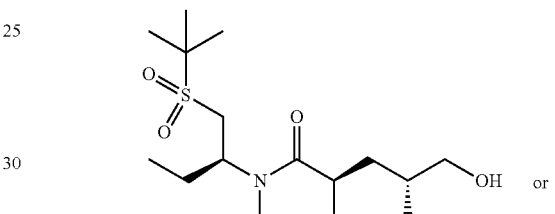 or

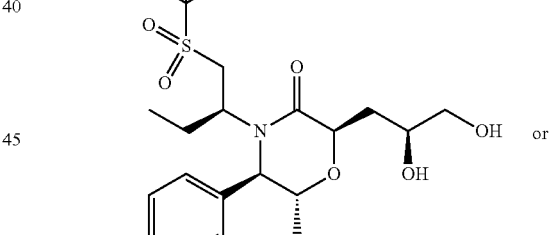 or

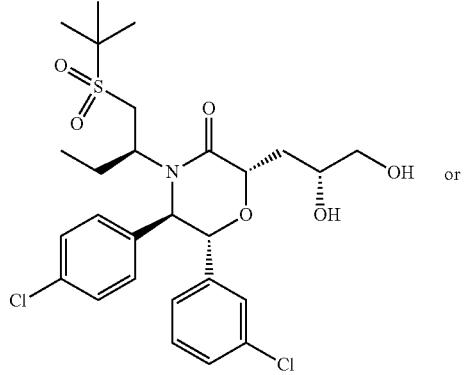 or

-continued

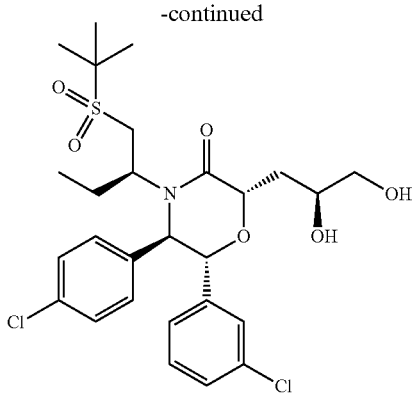

Further elution of the SFC purification described in Example 373 provided one of the title compounds as the second (slower) eluting isomer. $^1$H NMR (400 MHz, CDCl$_3$, δ ppm): 0.52 (t, J=7.46 Hz, 3H), 1.44 (s, 9H), 1.60 (ddd, J=14.06, 7.70, 3.67 Hz, 1H), 2.08 (ddd, J=14.67, 4.89, 2.69 Hz, 1H), 2.14-2.32 (m, 2H), 2.80-2.88 (m, 1H), 3.30 (br. s., 1H), 3.54 (dd, J=11.13, 6.72 Hz, 1H), 3.67 (dd, J=11.25, 3.67 Hz, 1H), 3.98-4.10 (m, 2H), 4.57 (t, J=5.50 Hz, 1H), 4.65 (d, J=9.78 Hz, 1H), 5.10 (d, J=10.03 Hz, 1H), 6.87 (d, J=7.83 Hz, 1H), 7.05-7.10 (m, 1H), 7.10-7.18 (m, 3H), 7.21 (m, 1H), 7.31 (d, J=8.56 Hz, 2H). MS (ESI) m/z=572 [M+1].

Example 375

3-(((2R,5R,6R)-4-((S)-1-(tert-Butylsulfonyl)butan-2-yl)-6-(3-chlorophenyl)-5-(4-chlorophenyl)-3-oxomorpholin-2-yl)methyl)-1,1-diethylurea or 3-(((2S,5R,6R)-4-((S)-1-(tert-butylsulfonyl)butan-2-yl)-6-(3-chlorophenyl)-5-(4-chlorophenyl)-3-oxomorpholin-2-yl)methyl)-1,1-diethylurea

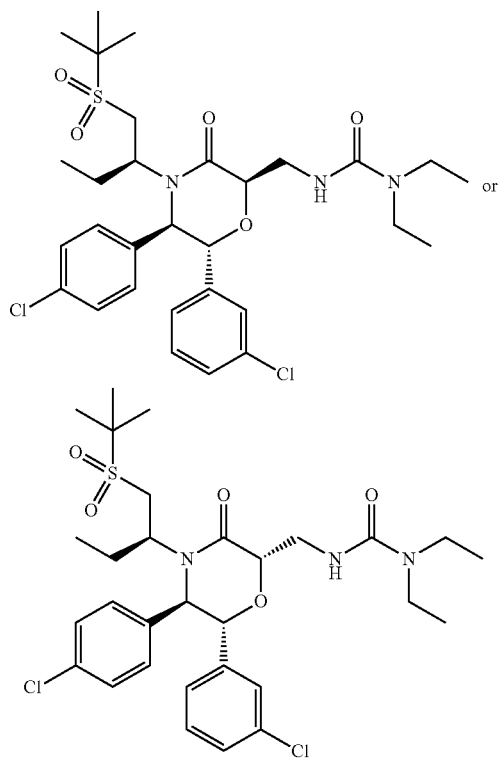

Triethylamine (0.132 mL, 0.949 mmol) and diphenylphosphoryl azide (0.205 mL, 0.948 mmol) were added to a solution of 2-((2R,5R,6R)-4-((S)-1-(tert-butylsulfonyl)butan-2-yl)-6-(3-chlorophenyl)-5-(4-chlorophenyl)-3-oxomorpholin-2-yl)acetic acid and 2-((2S,5R,6R)-4-((S)-1-(tert-butylsulfonyl)butan-2-yl)-6-(3-chlorophenyl)-5-(4-chlorophenyl)-3-oxomorpholin-2-yl)acetic acid (132 mg, 0.237 mmol, Example 121, mixture of diastereomers) in toluene (2.4 mL), and the mixture was heated to 95° C. After 3 hours, tert-butanol (0.27 mL, 2.85 mmol) was added. The mixture was heated at 110° C. for 5 hours, and additional tert-butanol (0.272 mL, 2.85 mmol) was added. After another 14 hours at 110° C., a final aliquot of tert-butanol (0.272 mL, 2.85 mmol) was added. The mixture was heated at 110° C. for 1 hour and concentrated. The residue was purified by flash chromatography on silica gel (12 g column; gradient elution of 50% to 100% ethyl acetate in hexanes) to give a mixture. The mixture was purified by reverse phase preparatory HPLC (Waters Delta 4000, column: Gemini-NX® 5 μm C$_{18}$, 110 Å, 100 mm×30 mm (Phenomenex, Torrance, Calif.), gradient elution of 10% to 90% acetonitrile in water, where both solvents contain 0.1% TFA) to give one of the title compounds as the first (faster) eluting isomer. $^1$H NMR (400 MHz, CDCl$_3$, δ ppm): 7.29-7.34 (m, 2H), 7.25-7.28 (m, 2H), 7.19-7.26 (m, 2H), 7.13 (t, J=7.82 Hz, 1H), 6.92-7.07 (m, 1H), 5.13 (d, J=7.63 Hz, 1H), 5.01 (d, J=7.83 Hz, 1H), 4.84 (br. s., 1H), 4.38 (dd, J=8.71, 5.77 Hz, 1H), 3.99 (dt, J=7.58, 1.39 Hz, 2H), 3.83 (s, 1H), 3.35 (br. s., 1H), 3.22 (q, J=7.04 Hz, 4H), 2.82-2.99 (m, 1H), 2.06-2.18 (m, 1H), 1.55-1.69 (m, 1H), 1.43 (s, 9H), 1.07 (t, J=7.14 Hz, 6H), 0.53 (t, J=7.53 Hz, 3H). MS (ESI) m/z=648 [M+Na].

Example 376

3-(((2R,5R,6R)-4-((S)-1-(tert-Butylsulfonyl)butan-2-yl)-6-(3-chlorophenyl)-5-(4-chlorophenyl)-3-oxomorpholin-2-yl)methyl)-1,1-diethylurea or 3-(((2S,5R,6R)-4-((S)-1-(tert-butylsulfonyl)butan-2-yl)-6-(3-chlorophenyl)-5-(4-chlorophenyl)-3-oxomorpholin-2-yl)methyl)-1,1-diethylurea

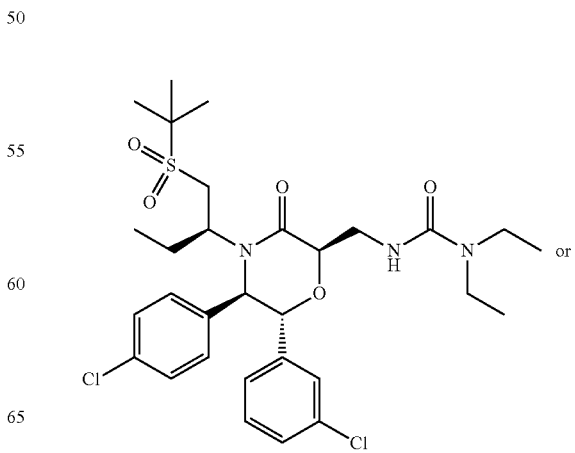

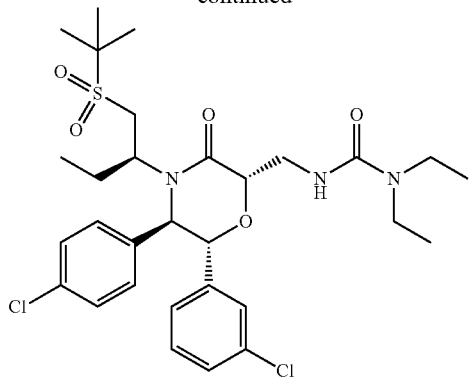

Further elution of the HPLC chromatographic purification described in Example 375 provided one of the title compounds as the second (slower) eluting isomer. ¹H NMR (400 MHz, CDCl₃, δ ppm): 7.22-7.41 (m, 2H), 6.97-7.22 (m, 5H), 6.80 (dt, J=7.78, 1.39 Hz, 1H), 5.10-5.21 (m, 1H), 5.05 (d, J=9.78 Hz, 1H), 4.67 (d, J=9.78 Hz, 1H), 4.44 (t, J=5.77 Hz, 1H), 4.09-4.14 (m, 1H), 3.94-4.00 (m, 1H), 3.69-3.75 (m, 1H), 3.17-3.44 (m, 4H), 2.77-2.91 (m, 1H), 2.11-2.26 (m, 1H), 1.54-1.68 (m, 1H), 1.44 (s, 9H), 1.06-1.21 (m, 7H), 0.38-0.63 (m, 3H). MS (ESI) m/z=626 [M+1].

Example 377 tert-Butyl (((2R,5R,6R)-4-((S)-1-(tert-utylsulfonyl)butan-2-yl)-6-(3-chlorophenyl)-5-(4-chlorophenyl)-3-oxomorpholin-2-yl)methyl)carbamate and tert-butyl (((2S,5R,6R)-4-((S)-1-(tert-butylsulfonyl)butan-2-yl)-6-(3-chlorophenyl)-5-(4-chlorophenyl)-3-oxomorpholin-2-yl)methyl)carbamate Triethylamine (0.018 mL, 0.127 mmol) and ethyl chloroformate (0.013 mL, 0.138 mmol) were added to a solution of 2-((2R,5R,6R)-4-((S)-1-(tert-butylsulfonyl)butan-2-yl)-6-(3-chlorophenyl)-5-(4-chlorophenyl)-3-oxomorpholin-2-yl)acetic acid and 2-((2S,5R,6R)-4-((S)-1-(tert-butylsulfonyl)butan-2-yl)-6-(3-chlorophenyl)-5-(4-chlorophenyl)-3-oxomorpholin-2-yl)acetic acid (59 mg, 0.106 mmol, Example 121, mixture of diastereomers)) in acetone (2 mL) and water (0.2 mL) at 0° C. After stirring at 0° C. for 35 minutes, sodium azide (10.34 mg, 0.159 mmol) in water (0.2 mL) was added. The mixture was stirred at 0° C. for 35 minutes, and cold water was added. The mixture was extracted with dichloromethane (3×). The combined organic layers were dried over Na₂SO₄, filtered, and concentrated to 2 mL. tert-Butanol (5 mL) was added and the mixture was heated to 90° C. for 19 hours. The mixture was cooled to room temperature and stirred at room temperature for 3 days. The mixture was concentrated and purified by preparative TLC (eluent: 5% MeOH in dichloromethane) to give the title compounds as a mixture of diastereomers. ¹H NMR (400 MHz, CDCl₃, δ ppm): 7.18-7.33 (m, 5H), 7.13 (t, J=7.83 Hz, 2H), 7.02-7.06 (m, 1H), 5.13 (d, J=7.43 Hz, 2H), 4.78-5.08 (m, 1H), 4.30 (s, 1H), 3.82-4.19 (m, 1H), 3.61-3.79 (m, 1H), 3.45-3.61 (m, 1H), 3.30-3.45 (m, 1H), 2.74-3.02 (m, 1H), 2.07-2.33 (m, 1H), 1.55-1.74 (m, 1H), 1.11-1.54 (m, 18H), 0.42-0.67 (m, 3H). MS (ESI) m/z=649 [M+Na].

Example 378

(2R,5R,6R)-2-(Aminomethyl)-4-((S)-1-(tert-butylsulfonyl)butan-2-yl)-6-(3-chlorophenyl)-5-(4-chlorophenyl)morpholin-3-one hydrochloride and (2S,5R,6R)-2-(aminomethyl)-4-((S)-1-(tert-butylsulfonyl)butan-2-yl)-6-(3-chlorophenyl)-5-(4-chlorophenyl)morpholin-3-one hydrochloride

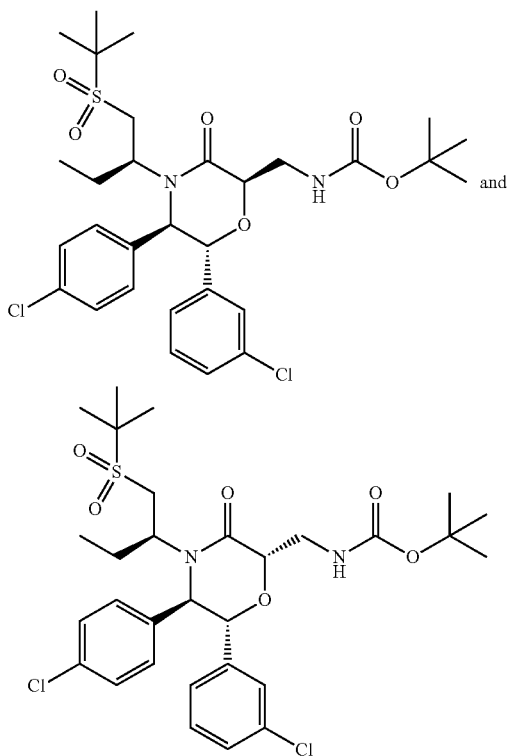

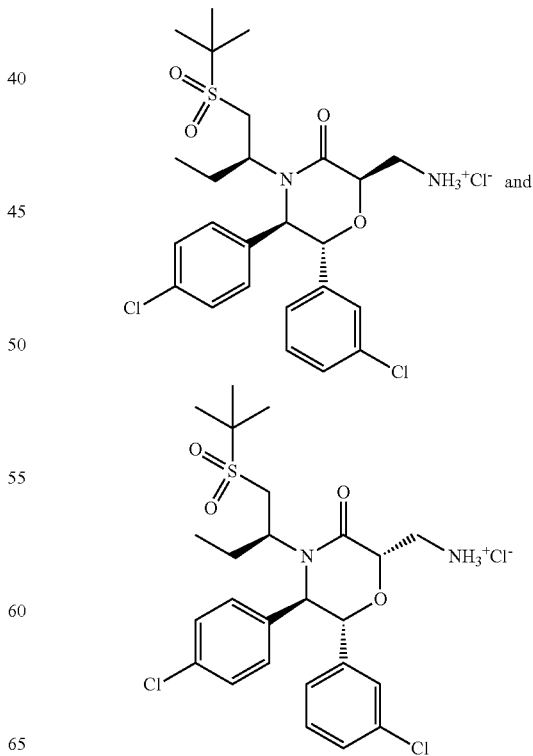

A solution of tert-butyl (((2R,5R,6R)-4-((S)-1-(tert-butylsulfonyl)butan-2-yl)-6-(3-chlorophenyl)-5-(4-chlorophenyl)-3-oxomorpholin-2-yl)methyl)carbamate and tert-butyl (((2S,5R,6R)-4-((S)-1-(tert-butylsulfonyl)butan-2-yl)-6-(3-chlorophenyl)-5-(4-chlorophenyl)-3-oxomorpholin-2-yl)methyl)carbamate (9 mg, 0.014 mmol, Example 377) in HCl (4 M in dioxane, 1 mL, 4.0 mmol) was stirred at room temperature for 1 hour. The mixture was concentrated to give the title compounds. $^1$H NMR (400 MHz, CD$_3$OD, δ ppm): 7.12-7.53 (m, 7H), 7.01-7.09 (m, 1H), 5.11 (d, J=3.13 Hz, 2H), 4.53-4.72 (m, 1H), 3.92-4.05 (m, 1H), 3.67 (d, J=5.28 Hz, 3H), 3.43-3.62 (m, 2H), 3.05-3.20 (m, 1H), 2.03-2.22 (m, 1H), 1.59-1.82 (m, 1H), 1.16-1.50 (m, 9H), 0.39-0.73 (m, 3H). MS (ESI) m/z=527 [M+1].

Example 379

N-(((2R,5R,6R)-4-((S)-1-(tert-Butylsulfonyl)butan-2-yl)-6-(3-chlorophenyl)-5-(4-chlorophenyl)-3-oxomorpholin-2-yl)methyl)acetamide or N-(42S,5R,6R)-4-((S)-1-(tert-butylsulfonyl)butan-2-yl)-6-(3-chlorophenyl)-5-(4-chlorophenyl)-3-oxomorpholin-2-yl)methyl)acetamide

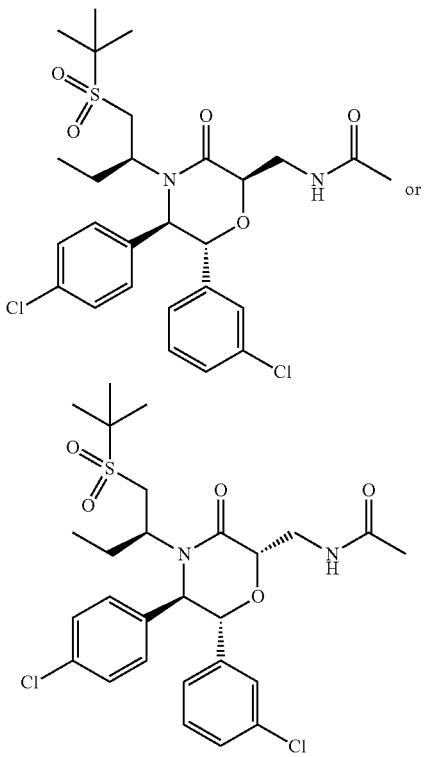

N,N-Diisopropylethylamine (0.136 mL, 0.779 mmol) and acetic acid N-hydroxy-succinimide ester (122 mg, 0.779 mmol) were added to a solution of (2R,5R,6R)-2-(aminomethyl)-4-((S)-1-(tert-butylsulfonyl)butan-2-yl)-6-(3-chlorophenyl)-5-(4-chlorophenyl)morpholin-3-one 2,2,2-trifluoroacetate and (2R,5R,6R)-2-(aminomethyl)-4-((S)-1-(tert-butylsulfonyl)butan-2-yl)-6-(3-chlorophenyl)-5-(4-chlorophenyl)morpholin-3-one 2,2,2-trifluoroacetate (50 mg, 0.078 mmol, prepared as in Example 378, replacing trifluoroacetic acid with HCl) in dichloromethane (2 mL). The mixture was stirred at room temperature for 2 hours, then diluted with water and extracted with ethyl acetate. The organic layer was washed with brine, dried over Na$_2$SO$_4$, filtered, and concentrated. The residue was purified by preparative TLC (eluent: 50% toluene in THF) to give a mixture. The mixture was further purified by preparative TLC (eluent: 8% ethanol in toluene with 0.5% triethylamine) to give a mixture. The mixture was finally purified by reverse phase preparatory HPLC (Waters Delta 4000, column: Gemini-NX® 5 μm C$_{18}$, 110 Å, 100 mm×30 mm (Phenomenex, Torrance, Calif.), gradient elution of 10% to 90% acetonitrile in water, where both solvents contain 0.1% TFA) to give one of the title compounds as the first (faster) eluting isomer. $^1$H NMR (400 MHz, CDCl$_3$, δ ppm): 7.27-7.39 (m, 2H), 7.20-7.31 (m, 4H), 7.13-7.17 (m, 1H), 6.98 (dt, J=7.92, 1.42 Hz, 1H), 6.11-6.29 (m, 1H), 5.13 (d, J=7.43 Hz, 1H), 4.93 (d, J=7.83 Hz, 1H), 4.34-4.51 (m, 1H), 3.93-4.05 (m, 1H), 3.83-3.89 (m, 1H), 3.27-3.52 (m, 1H), 2.81-2.99 (m, 1H), 1.94-2.19 (m, 4H), 1.55-1.70 (m, 1H), 1.34-1.52 (m, 10H), 0.39-0.65 (m, 3H). MS (ESI) m/z=569 [M+1].

Example 380

N-(((2R,5R,6R)-4-((S)-1-(tert-Butylsulfonyl)butan-2-yl)-6-(3-chlorophenyl)-5-(4-chlorophenyl)-3-oxomorpholin-2-yl)methyl)acetamide or N-(((2S,5R,6R)-4-((S)-1-(tert-butylsulfonyl)butan-2-yl)-6-(3-chlorophenyl)-5-(4-chlorophenyl)-3-oxomorpholin-2-yl)methyl)acetamide

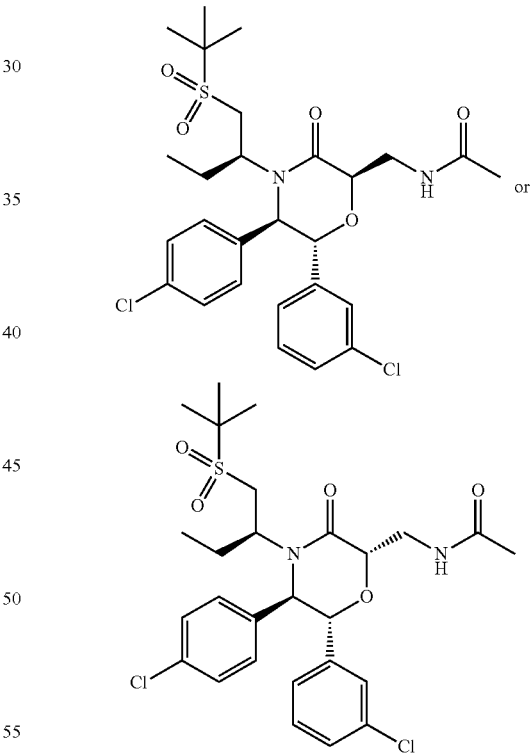

Further elution of the preparatory HPLC purification described in Example 379 provided one of the title compounds as the second (slower) eluting isomer. $^1$H NMR (400 MHz, CDCl$_3$, δ ppm): 7.19-7.38 (m, 3H), 7.09-7.18 (m, 3H), 7.03 (t, J=1.76 Hz, 1H), 6.91-6.98 (m, 1H), 6.80-6.89 (m, 1H), 5.07 (d, J=9.78 Hz, 1H), 4.69 (d, J=9.98 Hz, 1H), 4.51 (t, J=3.81 Hz, 1H), 4.07-4.19 (m, 1H), 3.85-3.97 (m, 2H), 3.22-3.35 (m, 1H), 2.84-2.94 (m, 1H), 2.17-2.28 (m, 1H), 2.12 (s, 3H), 1.56-1.66 (m, 1H), 1.44 (s, 9H), 0.53 (t, J=7.53 Hz, 3H). MS (ESI) m/z=569 [M+1].

Example 381

2-((2R,5R,6R)-4-((S)-1-(tert-Butylsulfonyl)butan-2-yl)-6-(3-chlorophenyl)-5-(4-chlorophenyl)-3-oxomorpholin-2-yl)acetonitrile

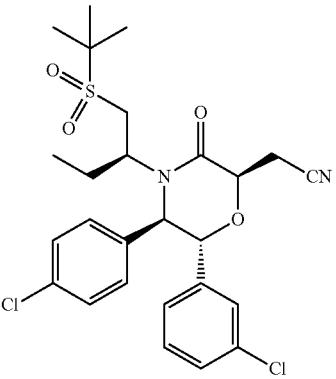 [SMILES: CC[C@@H](CS(=O)(=O)C(C)(C)C)N1C(=O)[C@@H](CC#N)O[C@H](c2cccc(Cl)c2)[C@H]1c1ccc(Cl)cc1]

The title compound was prepared from 2-((2R,5R,6R)-4-((S)-1-(tert-butylsulfonyl)butan-2-yl)-6-(3-chlorophenyl)-5-(4-chlorophenyl)-3-oxomorpholin-2-yl)acetamide (which was prepared from 2-((2R,5R,6R)-4-((S)-1-(tert-butylsulfonyl)butan-2-yl)-6-(3-chlorophenyl)-5-(4-chlorophenyl)-3-oxomorpholin-2-yl)acetic acid (Example 120) by the method described in Example 260) by a procedure similar to that described in Example 50, Step F. The residue was purified by reverse phase HPLC (Agilent 1100, column: Gemini® 5 μm $C_{18}$, 100 mm×30 mm (Phenomenex, Torrance, Calif.), gradient elution of 40% to 60% acetonitrile in water, where both solvents contain 0.1% TFA) to give the title compound. $^1$H NMR (500 MHz, CDCl$_3$, δ ppm): 0.57 (t, J=7.58 Hz, 3H), 1.45 (s, 9H), 1.69 (ddd, J=14.00, 7.64, 4.03 Hz, 1H), 2.13-2.24 (m, 1H), 2.86-2.99 (m, 2H), 3.19 (dd, J=16.99, 5.50 Hz, 1H), 3.41 (br. s., 1H), 4.00 (dd, J=13.69, 9.54 Hz, 1H), 4.57 (t, J=4.77 Hz, 1H), 5.17 (d, J=7.09 Hz, 1H), 5.23 (d, J=6.85 Hz, 1H), 7.02-7.06 (m, 1H), 7.17 (t, J=7.95 Hz, 1H), 7.23-7.26 (m, 1H), 7.29 (t, J=1.83 Hz, 1H), 7.35 (s, 4H). MS (ESI) m/z=537 [M+1].

Example 382

(2R,5R,6R)-2-((1H-Tetrazol-5-yl)methyl)-4-((S)-1-(tert-butylsulfonyl)butan-2-yl)-6-(3-chlorophenyl)-5-(4-chlorophenyl)morpholin-3-one

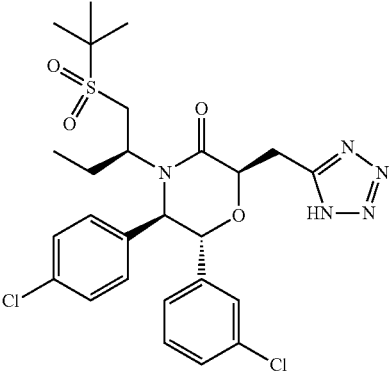 [SMILES: CC[C@@H](CS(=O)(=O)C(C)(C)C)N1C(=O)[C@@H](Cc2nnn[nH]2)O[C@H](c2cccc(Cl)c2)[C@H]1c1ccc(Cl)cc1]

Sodium azide (0.018 g, 0.275 mmol) and ammonium chloride (0.015 g, 0.275 mmol) were added to a solution of 2-((2R,5R,6R)-4-((S)-1-(tert-butylsulfonyl)butan-2-yl)-6-(3-chlorophenyl)-5-(4-chlorophenyl)-3-oxomorpholin-2-yl)acetonitrile (0.037 g, 0.069 mmol, Example 381) in DMF (0.5 mL). The mixture was stirred at 90° C. for 16 hours. Additional sodium azide (0.018 g, 0.275 mmol) and ammonium chloride (0.015 g, 0.275 mmol) were added. The mixture was stirred at 90° C. for 4 days. Then acidified with aqueous 10% citric acid and extracted with ethyl acetate (2×). The combined organic layers were washed with brine, dried over Na$_2$SO$_4$, filtered, and concentrated. The residue was purified by reverse phase HPLC (Agilient 1100, column: Gemini® 5 μm C$_{18}$, 100 mm×30 mm (Phenomenex, Torrance, Calif.), gradient elution of 40% to 60% acetonitrile in water, where both solvents contain 0.1% TFA) to give the title compound. $^1$H NMR (500 MHz, CDCl$_3$, δ ppm): 0.58 (t, J=7.46 Hz, 3H), 1.47 (s, 9H), 1.51-1.63 (m, 1H), 2.19 (ddd, J=14.24, 9.48, 7.34 Hz, 1H), 3.00 (d, J=13.20 Hz, 1H), 3.47 (br. s., 1H), 3.71-3.79 (m, 2H), 3.96 (br. s., 1H), 4.63 (t, J=6.24 Hz, 1H), 4.93 (d, J=6.60 Hz, 1H), 5.19 (d, J=6.60 Hz, 1H), 7.02-7.10 (m, 1H), 7.14-7.25 (m, 3H), 7.25-7.32 (m, 2H), 7.36 (d, J=8.31 Hz, 2H). MS (ESI) m/z=580 [M+1].

Example 383

(2S,5R,6R)-2-((1H-Tetrazol-5-yl)methyl)-4-((S)-1-(tert-butylsulfonyl)butan-2-yl)-6-(3-chlorophenyl)-5-(4-chlorophenyl)morpholin-3-one

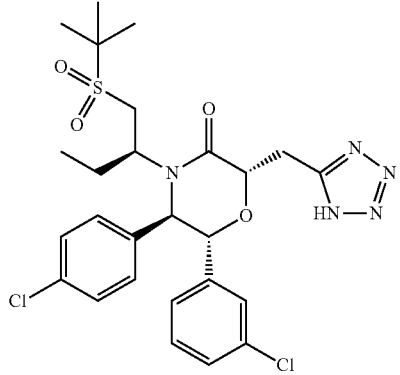 [SMILES: CC[C@@H](CS(=O)(=O)C(C)(C)C)N1C(=O)[C@H](Cc2nnn[nH]2)O[C@H](c2cccc(Cl)c2)[C@H]1c1ccc(Cl)cc1]

Step A. 2-((2S,5R,6R)-4-((S)-1-(tert-Butylsulfonyl)butan-2-yl)-6-(3-chlorophenyl)-5-(4-chlorophenyl)-3-oxomorpholin-2-yl)acetamide

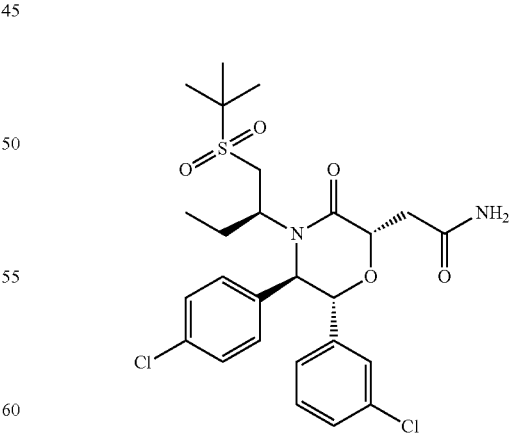

The title compound was prepared from a mixture of 2-((2S,5R,6R)-4-((S)-1-(tert-butylsulfonyl)butan-2-yl)-6-(3-chlorophenyl)-5-(4-chlorophenyl)-3-oxomorpholin-2-yl)acetamide and 2-((2R,5R,6R)-4-((S)-1-(tert-butylsulfonyl)butan-2-yl)-6-(3-chlorophenyl)-5-(4-chlorophenyl)-3- oxomorpholin-2-yl) (Example 260) by separating the diastereomers by reverse phase preparative HPLC (Agilient 1100, column: Gemini® 5 µm C₁₈, 100 mm×30 mm (Phenomenex, Torrance, Calif.), gradient elution of 40% to 60% acetonitrile in water, where both solvents contain 0.1% TFA). The title compound was isolated as the second (slower) eluting isomer.

Step B. (2S,5R,6R)-2-((1H-Tetrazol-5-yl)methyl)-4-((S)-1-(tert-butylsulfonyl)butan-2-yl)-6-(3-chlorophenyl)-5-(4-chlorophenyl)morpholin-3-one

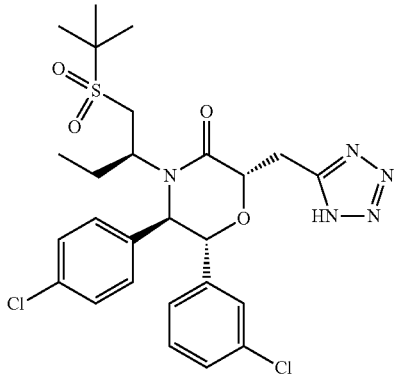 [SMILES: CC[C@@H](CS(=O)(=O)C(C)(C)C)N1C(=O)[C@H](Cc2nnn[nH]2)O[C@H](c2cccc(Cl)c2)[C@H]1c1ccc(Cl)cc1]

The title compound was prepared from 2-((2S,5R,6R)-4-((S)-1-(tert-butylsulfonyl)butan-2-yl)-6-(3-chlorophenyl)-5-(4-chlorophenyl)-3-oxomorpholin-2-yl)acetamide by procedures similar to those described in Example 381 and 382. The residue was purified by reverse phase HPLC (Agilient 1100, column: Gemini® 5 µm C₁₈, 100 mm×30 mm (Phenomenex, Torrance, Calif.), gradient elution of 40% to 60% acetonitrile in water, where both solvents contain 0.1% TFA) to give the title compound. ¹H NMR (500 MHz, CDCl₃, δ ppm): 0.55 (t, J=7.58 Hz, 3H), 1.39-1.52 (s, 9H), 1.65 (ddd, J=14.06, 7.70, 3.91 Hz, 1H), 2.17 (ddd, J=14.18, 9.78, 7.34 Hz, 1H), 2.88 (dd, J=13.20, 2.20 Hz, 1H), 3.38 (m, 1H), 3.74 (dd, J=16.63, 6.11 Hz, 1H), 3.90 (dd, J=16.63, 3.91 Hz, 1H), 4.05 (dd, J=12.96, 11.49 Hz, 1H), 4.67-4.79 (m, 2H), 5.24 (d, J=10.03 Hz, 1H), 6.92 (d, J=7.58 Hz, 1H), 7.03 (t, J=1.59 Hz, 1H), 7.13-7.21 (m, 3H), 7.22-7.26 (m, 1H), 7.34 (d, J=8.31 Hz, 2H). MS (ESI) m/z=580 [M+1].

Example 384

(2S,5R,6R)-4-((S)-2-(tert-Butylsulfonyl)-1-cyclopropylethyl)-6-(3-chlorophenyl)-5-(4-chlorophenyl)-2-(isoxazol-5-ylmethyl)morpholin-3-one

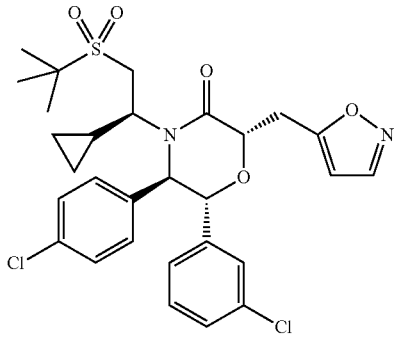 [SMILES: CC(C)(C)S(=O)(=O)C[C@H](C1CC1)N1C(=O)[C@H](Cc2ccno2)O[C@H](c2cccc(Cl)c2)[C@H]1c1ccc(Cl)cc1]

Step A. (2S,5R,6R)-4-((S)-2-(tert-Butylthio)-1-cyclopropylethyl)-6-(3-chlorophenyl)-5-(4-chlorophenyl)-2-(isoxazol-5-ylmethyl)morpholin-3-one

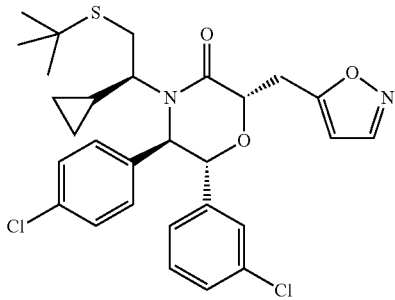 [SMILES: CC(C)(C)SC[C@H](C1CC1)N1C(=O)[C@H](Cc2ccno2)O[C@H](c2cccc(Cl)c2)[C@H]1c1ccc(Cl)cc1]

A solution of (5R,6R)-4-((S)-2-(tert-butylthio)-1-cyclopropylethyl)-6-(3-chlorophenyl)-5-(4-chlorophenyl)morpholin-3-one (107 mg, 0.224 mmol, Example 154, Step C) in THF (0.5 mL) was purged with N₂(g) for 5 minutes at room temperature. The mixture was cooled to −78° C. and then LiHMDS (1.0 M in THF, 0.895 mL, 0.895 mmol) was added dropwise. The mixture was stirred at −78° C. 10 minutes and 5-(bromomethyl)isoxazole (145 mg, 0.895 mmol) in THF (0.4 mL) was added dropwise. After 1.3 hours at −78° C., the mixture was diluted with water (0.5 mL) and extracted with ethyl acetate. The organic layer was washed with saturated NH₄Cl and brine. The organic layer was dried over MgSO₄, filtered, and concentrated. The residue was purified by flash chromatography on silica gel (gradient elution of 0% to 50% ethyl acetate in hexanes) to give the title compound.

Step B. (2S,5R,6R)-4-((S)-2-(tert-Butylsulfonyl)-1-cyclopropylethyl)-6-(3-chlorophenyl)-5-(4-chlorophenyl)-2-(isoxazol-5-ylmethyl)morpholin-3-one The title compound was prepared from (2S,5R,6R)-4-((S)-2-(tert-butylthio)-1-cyclopropylethyl)-6-(3-chlorophenyl)-5-(4-chlorophenyl)-2-(isoxazol-5-ylmethyl)morpholin-3-one (Example 384, Step A) by a procedure similar to that described in Example 318, Step D. The residue was purified by reverse phase HPLC (Agilient 1100, column: Gemini® 5 µm C₁₈, 100 mm×30 mm (Phenomenex, Torrance, Calif.), gradient elution of 30% to 60% acetonitrile in water, where both solvents contain 0.1% TFA, 30 minutes) to give the title compound. ¹H NMR (400 MHz, CDCl₃, δ ppm): 8.33 (d, J=1.8 Hz, 1H), 7.44-7.54 (m, 3H), 7.19-7.42 (m, 4H), 7.04 (dt, J=7.7, 1.4 Hz, 1H), 6.37-6.42 (m, 1H), 5.24 (d, J=9.8 Hz, 1H), 4.87-4.97 (m, 2H), 4.39 (br. s., 1H), 3.88 (dd, J=16.0, 3.7 Hz, 1H), 3.64 (dd, J=16.0, 8.2 Hz, 1H), 3.21 (br. d., 1H), 2.85 (br. s., 1H), 2.10 (br. s., 1H), 1.62 (s, 9H), 0.53-0.62 (m, 2H), 0.01 (br. s., 1H), −0.60 (br. s., 1H). MS (ESI) m/z=591.0 [M+1].

Example 385

(2R,5R,6R)-2-((1H-1,2,3-Triazol-5-yl)methyl)-4-((S)-2-(tert-butylsulfonyl)-1-cyclopropylethyl)-6-(3-chlorophenyl)-5-(4-chlorophenyl)morpholin-3-one or (2S,5R,6R)-2-((1H-1,2,3-triazol-5-yl)methyl)-4-((S)-2-(tert-butylsulfonyl)-1-cyclopropylethyl)-6-(3-chlorophenyl)-5-(4-chlorophenyl)morpholin-3-one

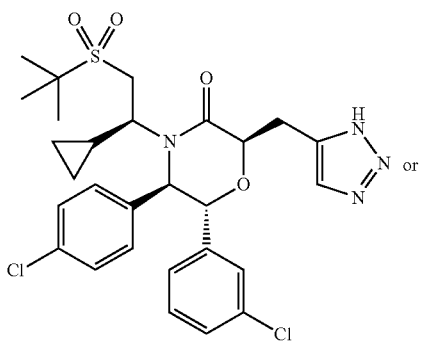 or

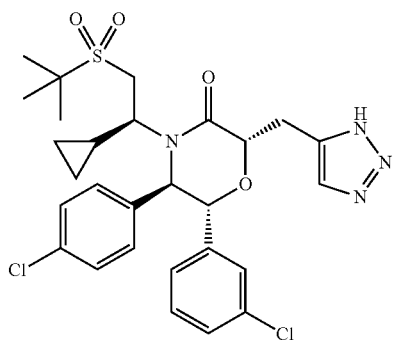

Step A. (2R,5R,6R)-4-((S)-2-(tert-Butylthio)-1-cyclopropylethyl)-6-(3-chlorophenyl)-5-(4-chlorophenyl)-2-(prop-2-yn-1-yl)morpholin-3-one or (2S,5R,6R)-4-((S)-2-(tert-butylthio)-1-cyclopropylethyl)-6-(3-chlorophenyl)-5-(4-chlorophenyl)-2-(prop-2-yn-1-yl)morpholin-3-one

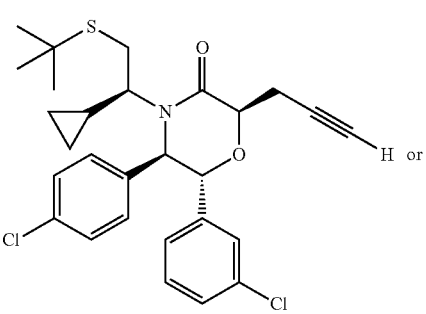 H or

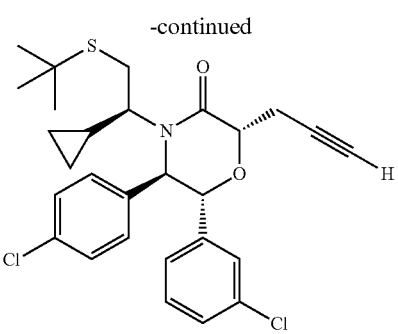

One of the title compounds was prepared from (5R,6R)-4-((S)-2-(tert-butylthio)-1-cyclopropylethyl)-6-(3-chlorophenyl)-5-(4-chlorophenyl)morpholin-3-one Example 154, Step C by a procedure similar to that described in Example 384, Step A, replacing 5-(bromomethyl)isoxazole with 3-bromoprop-1-yne.

Step B. (2R,5R,6R)-2-((1H-1,2,3-Triazol-5-yl)methyl)-4-((S)-2-(tert-butylthio)-1-cyclopropylethyl)-6-(3-chlorophenyl)-5-(4-chlorophenyl)morpholin-3-one or (2S,5R,6R)-2-((1H-1,2,3-triazol-5-yl)methyl)-4-((S)-2-(tert-butylthio)-1-cyclopropylethyl)-6-(3-chlorophenyl)-5-(4-chlorophenyl)morpholin-3-one

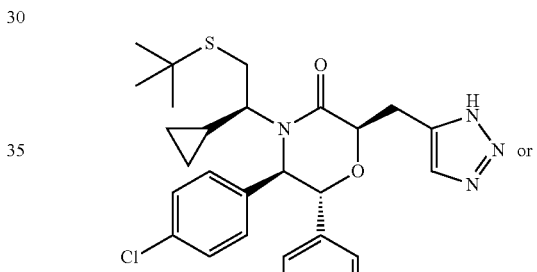 or

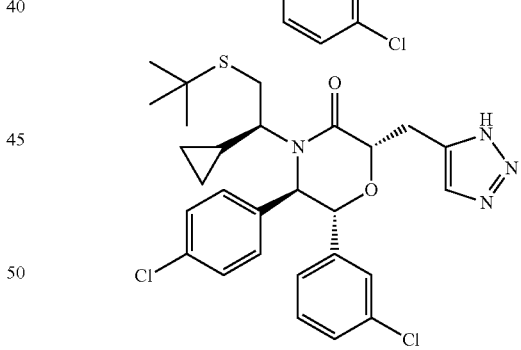

Copper(I) iodide (0.406 mg, 2.130 µmol) and azidotrimethylsilane (8.40 µL, 0.064 mmol) were added to a solution of (2R,5R,6R)-4-((S)-2-(tert-butylthio)-1-cyclopropylethyl)-6-(3-chlorophenyl)-5-(4-chlorophenyl)-2-(prop-2-yn-1-yl)morpholin-3-one or (2S,5R,6R)-4-((S)-2-(tert-butylthio)-1-cyclopropylethyl)-6-(3-chlorophenyl)-5-(4-chlorophenyl)-2-(prop-2-yn-1-yl)morpholin-3-one (22 mg, 0.043 mmol, Example 385, Step A) in DMF (0.1 mL) and water (0.022 mL). The mixture was purged with $N_2$(g) for 5 minutes, then heated at 100° C. for 21 hours. Additional copper(I) iodide (0.8 mg, 4.2 µmol) and DMF (0.1 mL) were added. The mixture was purged with $N_2$(g) for 5 minutes, then heated at 100° C. for 46 hours. The mixture was cooled, diluted with ethyl acetate, and washed with water and brine. The organic layer was dried over MgSO$_4$, filtered, and concentrated. The residue was purified by flash chromatography on silica gel (gradient elution of 0% to 100% ethyl acetate in hexanes) to give one of the title compounds.

Step C. (2R,5R,6R)-2-((1H-1,2,3-Triazol-5-yl)methyl)-4-((S)-2-(tert-butylsulfonyl)-1-cyclopropylethyl)-6-(3-chlorophenyl)-5-(4-chlorophenyl)morpholin-3-one or (2S,5R,6R)-2-((1H-1,2,3-triazol-5-yl)methyl)-4-((S)-2-(tert-butylsulfonyl)-1-cyclopropylethyl)-6-(3-chlorophenyl)-5-(4-chlorophenyl)morpholin-3-one

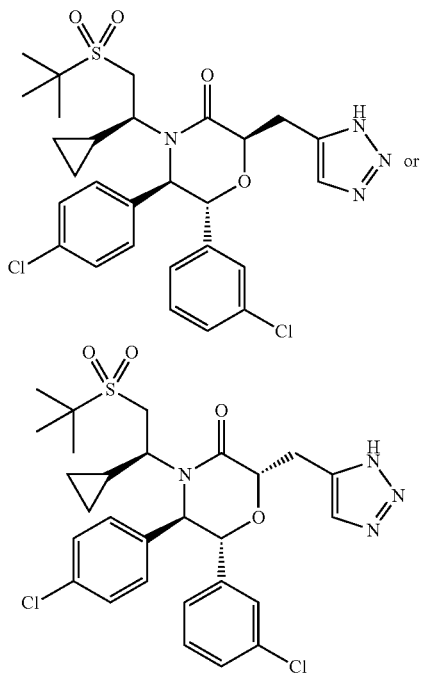

One of the title compounds was prepared from (2R,5R,6R)-2-((1H-1,2,3-triazol-5-yl)methyl)-4-((S)-2-(tert-butylthio)-1-cyclopropylethyl)-6-(3-chlorophenyl)-5-(4-chlorophenyl)morpholin-3-one or (2S,5R,6R)-2-((1H-1,2,3-triazol-5-yl)methyl)-4-((S)-2-(tert-butylthio)-1-cyclopropylethyl)-6-(3-chlorophenyl)-5-(4-chlorophenyl)morpholin-3-one (Example 385, Step B) by a procedure similar to that described in Example 318, Step D. The residue was purified by reverse phase HPLC (Agilient 1100, column: Gemini® 5 μm C$_{18}$, 100 mm×30 mm (Phenomenex, Torrance, Calif.), gradient elution of 30% to 70% acetonitrile in water, where both solvents contain 0.1% TFA, 30 minutes) to give one of the title compounds. $^1$H NMR (400 MHz, CDCl$_3$, δ ppm): 7.77 (br. s., 1H), 7.27-7.36 (m, 4H), 7.21 (m, 1H), 7.12 (m, 1H), 7.05 (m, 2H), 6.77 (s, 1H), 5.08 (d, J=5.1 Hz, 1H), 4.84 (d, J=4.9 Hz, 1H), 4.39-4.45 (m, 1H), 3.72 (br. s., 1H), 3.40-3.55 (m, 2H), 2.78-3.11 (m, 2H), 1.70 (br. s., 1H), 1.34 (s, 9H), 0.40 (br. s., 1H), 0.32 (br. s., 1H), 0.00 (br. s., 1H), −0.78 (br. s., 1H). MS (ESI) m/z=591.0 [M+1].

Example 386

(2R,5R,6R)-2-((1H-1,2,3-Triazol-5-yl)methyl)-4-((S)-2-(tert-butylsulfonyl)-1-cyclopropylethyl)-6-(3-chlorophenyl)-5-(4-chlorophenyl)morpholin-3-one or (2S,5R,6R)-2-((1H-1,2,3-triazol-5-yl)methyl)-4-((S)-2-(tert-butylsulfonyl)-1-cyclopropylethyl)-6-(3-chlorophenyl)-5-(4-chlorophenyl)morpholin-3-one

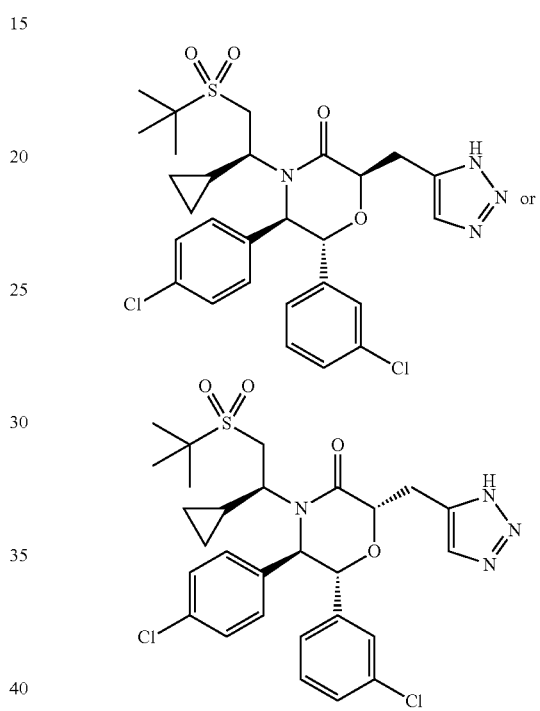

Step A. (2R,5R,6R)-4-((S)-2-(tert-Butylthio)-1-cyclopropylethyl)-6-(3-chlorophenyl)-5-(4-chlorophenyl)-2-(prop-2-yn-1-yl)morpholin-3-one or (2S,5R,6R)-4-((S)-2-(tert-butylthio)-1-cyclopropylethyl)-6-(3-chlorophenyl)-5-(4-chlorophenyl)-2-(prop-2-yn-1-yl)morpholin-3-one

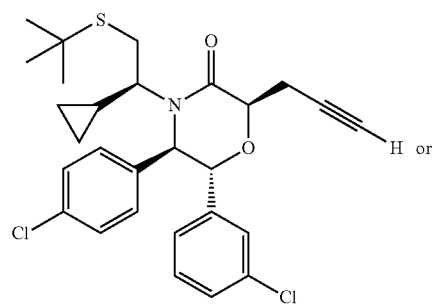

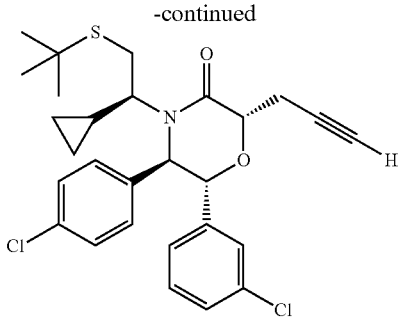

Further elution of the chromatographic separation described in Example 385, Step A provided one of the title compounds as the second (slower) eluting isomer.

Step B. (2R,5R,6R)-2-((1H-1,2,3-Triazol-5-yl)methyl)-4-((S)-2-(tert-butylsulfonyl)-1-cyclopropylethyl)-6-(3-chlorophenyl)-5-(4-chlorophenyl)morpholin-3-one or (2S,5R,6R)-2-((1H-1,2,3-triazol-5-yl)methyl)-4-((S)-2-(tert-butylsulfonyl)-1-cyclopropylethyl)-6-(3-chlorophenyl)-5-(4-chlorophenyl)morpholin-3-one One of the title compounds was prepared from (Example 386, Step A) by procedures similar to those described in Example 385, Steps B and C. The residue was purified by reverse phase HPLC (Agilient 1100, column: Gemini® 5 μm $C_{18}$, 100 mm×30 mm (Phenomenex, Torrance, Calif.), gradient elution of 30% to 70% acetonitrile in water, where both solvents contain 0.1% TFA, 30 minutes) to give one of the title compounds. $^1$H NMR (400 MHz, CDCl$_3$, δ ppm): 8.03 (s, 1H), 7.89 (br. s., 1H), 7.53 (m, 2H), 7.37 (m, 4H), 7.25 (s, 1H), 7.13 (d, J=8.0 Hz, 1H), 5.33 (d, J=12.0 Hz, 1H), 4.97 (d, J=12.0 Hz, 1H), 4.88 (m, 1H), 4.40 (br. s., 1H), 3.77 (d, J=4.0 Hz, 2H), 3.16-3.19 (br. s., 1H), 2.86 (br. s., 1H), 2.09 (br. s., 1H), 1.62 (s, 9H), 0.57-0.60 (br. s., 2H), 0.00 (br. s., 1H), −0.60 (br. s., 1H). MS (ESI) m/z=591.0 [M+1].

Example 387

2-((2R,5R,6R)-4-((S)-2-(tert-Butylsulfonyl)-1-cyclopropylethyl)-6-(3-chlorophenyl)-5-(4-chlorophenyl)-3-oxomorpholin-2-yl)acetonitrile or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetonitrile

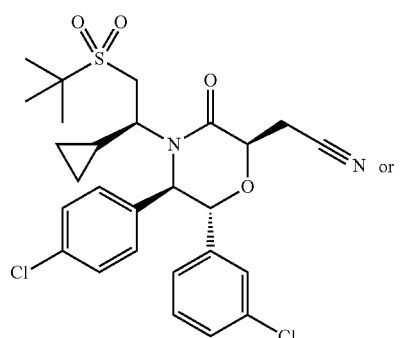

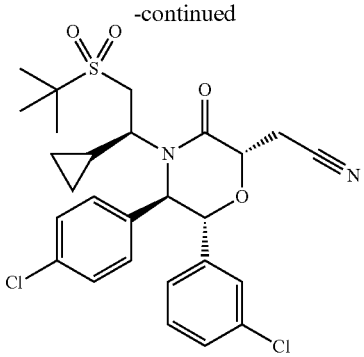

One of the title compounds was prepared from 2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)acetamide or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetamide (Example 356) by a procedure similar to that described in Example 50, Step F. The residue was purified by flash chromatography on silica gel (gradient elution of 0% to 50% ethyl acetate in hexanes) to give one of the title compounds. $^1$H NMR (400 MHz, CDCl$_3$, δ ppm): 7.43 (m, 2H), 7.36 (m, 3H), 7.25 (m, 1H), 7.14-7.20 (m, 2H), 5.15-5.19 (m, 2H), 4.42 (m, 1H), 4.02 (br. s., 1H), 3.12-3.20 (m, 2H), 2.88-2.94 (m, 2H), 1.83 (br. s., 1H), 1.42 (s, 9H), 0.42 (br. s., 2H), 0.00 (br. s., 1H), −0.69 (br. s., 1H). MS (ESI) m/z=571.0 [M+Na].

Example 388

2-((2R,5R,6R)-4-((S)-2-(tert-Butylsulfonyl)-1-cyclopropylethyl)-6-(3-chlorophenyl)-5-(4-chlorophenyl)-3-oxomorpholin-2-yl)acetonitrile or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetonitrile

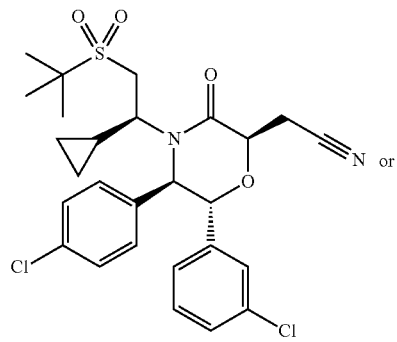

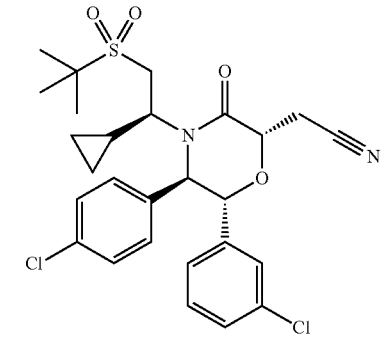

One of the title compounds was prepared from 2-((2R,5R,6R)-4-((S)-2-(tert-butylsulfonyl)-1-cyclopropylethyl)-6-(3- chlorophenyl)-5-(4-chlorophenyl)-3-oxomorpholin-2-yl)ac-etamide or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetamide (Example 357) by a procedure similar to that described in Example 50, Step F. The residue was purified by flash chromatography on silica gel (gradient elution of 0% to 50% ethyl acetate in hexanes) to give one of the title compounds. $^1$H NMR (400 MHz, CDCl$_3$, δ ppm): 7.45-7.50 (m, 2H), 7.31-7.35 (m, 4H), 7.25 (m, 1H), 7.07 (m, 1H), 5.27 (d, J=10.0 Hz, 1H), 4.91 (d, J=10.0 Hz, 1H), 4.82 (dd, J=7.7, 4.2 Hz, 1H), 4.40 (m, 1H), 3.41 (d, J=4.1 Hz, 1H), 3.18-3.26 (m, 2H), 2.83 (br. s., 1H), 2.05 (br. s., 1H), 1.62 (s, 9H), 0.52-00.62 (m, 2H), 0.00 (br. s., 1H), −0.63 (br. s., 1H). MS (ESI) m/z=571.0 [M+Na].

Example 389

(2R,5R,6R)-2-((1H-1,2,4-Triazol-5-yl)methyl)-4-((S)-2-(tert-butylsulfonyl)-1-cyclopropylethyl)-6-(3-chlorophenyl)-5-(4-chlorophenyl)morpholin-3-one or (2S,5R,6R)-2-((1H-1,2,4-triazol-5-yl)methyl)-4-((S)-2-(tert-butylsulfonyl)-1-cyclopropylethyl)-6-(3-chlorophenyl)-5-(4-chlorophenyl)morpholin-3-one

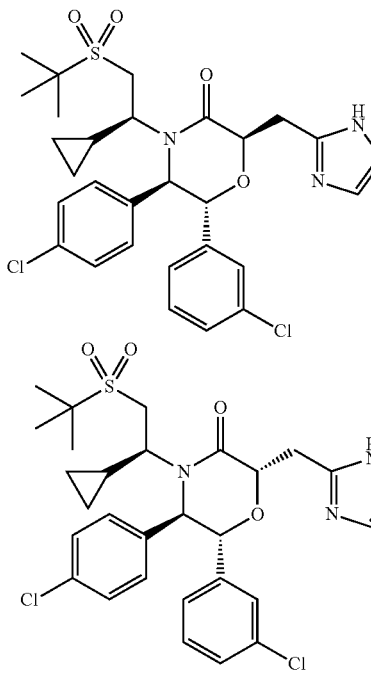

Sodium hydride (60% dispersion in mineral oil, 11 mg, 0.284 mmol) and formic hydrazide (28.4 mg, 0.473 mmol) were added to a solution of 2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)acetonitrile or 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetonitrile (52 mg, 0.095 mmol, Example 387) in methanol (2 mL). The mixture was stirred at room temperature for 30 minutes, then heated to 60° C. for 19 hours. The mixture was concentrated, and analysis of the crude residue revealed a number of products including two diastereomeric triazoles. The residue was purified by reverse phase HPLC (Agilient 1100, column: Gemini® 5 μm C$_{18}$, 100 mm×30 mm (Phenomenex, Torrance, Calif.), gradient elution of 30% to 70% acetonitrile in water, where both solvents contain 0.1% TFA, 30 minutes) to give one of the title compounds as the first (faster) eluting triazole isomer. $^1$H NMR (400 MHz, CDCl$_3$, δ ppm): 8.45 (s, 1H), 7.54-7.56 (d, J=8.0 Hz, 2H), 7.37-7.50 (m, 5H), 7.28 (s, 1H), 7.16 (d, J=8.0 Hz, 1H), 5.36 (d, J=12.0 Hz, 1H), 4.99-5.07 (m, 2H), 4.51 (br. s., 1H), 3.95-4.06 (m, 2H), 3.19-3.22 (d, J=12.0 Hz, 1H), 2.89 (br. s., 1H), 2.10 (br. s., 1H), 1.68 (s, 9H), 0.58-0.67 (m, 2H), 0.00 (br. s., 1H), −0.60 (br. s., 1H). MS (ESI) m/z=591.0 [M+1].

Example 390

(2R,5R,6R)-2-((1H-1,2,4-Triazol-5-yl)methyl)-4-((S)-2-(tert-butylsulfonyl)-1-cyclopropylethyl)-6-(3-chlorophenyl)-5-(4-chlorophenyl)morpholin-3-one or (2S,5R,6R)-2-((1H-1,2,4-triazol-5-yl)methyl)-4-((S)-2-(tert-butylsulfonyl)-1-cyclopropylethyl)-6-(3-chlorophenyl)-5-(4-chlorophenyl)morpholin-3-one

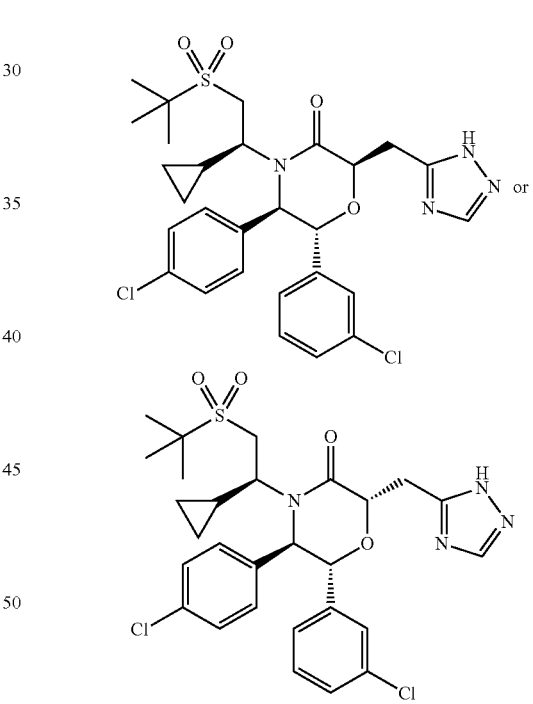

Further elution of the HPLC purification described in Example 389 provided one of the title compounds as the second (slower) eluting triazole isomer. $^1$H NMR (400 MHz, CDCl$_3$, δ ppm): 8.08 (s, 1H), 7.24-7.27 (m, 3H), 7.10-7.19 (m, 3H), 7.06-7.09 (m, 3H), 5.10 (d, J=8.0 Hz, 1H), 4.87 (d, J=4.0 Hz, 1H), 4.71 (m, 1H), 4.49 (m, 1H), 3.56-3.73 (m, 2H), 3.03 (br. s., 1H), 2.56 (br. s., 1H), 1.68 (br. s., 1H), 1.34 (s, 9H), 0.36-0.41 (m, 2H), 0.00 (br. s., 1H), −0.90 (br. s., 1H). MS (ESI) m/z=591.0 [M+1].

Example 391

(2R,5R,6R)-4-((S)-2-(tert-Butylsulfonyl)-1-cyclopropylethyl)-6-(3-chlorophenyl)-5-(4-chlorophenyl)-2-((3-methyl-1H-1,2,4-triazol-5-yl)methyl)morpholin-3-one and (2S,5R,6R)-4-((S)-2-(tert-butylsulfonyl)-1-cyclopropylethyl)-6-(3-chlorophenyl)-5-(4-chlorophenyl)-2-((3-methyl-1H-1,2,4-triazol-5-yl)methyl)morpholin-3-one

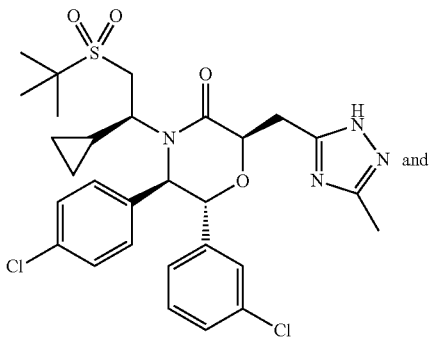 and

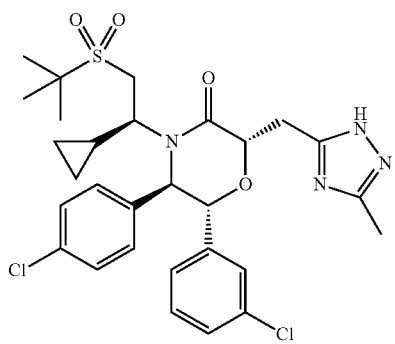

Sodium hydride (60% dispersion in mineral oil, 5.5 mg, 0.136 mmol) and acetohydrazide (16.85 mg, 0.227 mmol) were added to a solution of 2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)acetonitrile and 2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetonitrile (25 mg, 0.045 mmol, prepared as in Example 387 or 388, but as a mixture of diastereomers) in methanol (1 mL). The mixture was stirred at room temperature for 30 minutes, then heated at 70° C. for 3 days. The mixture was concentrated, and the residue was purified by reverse phase HPLC (Agilent 1100, column: Gemini® 5 µm $C_{18}$, 100 mm×30 mm (Phenomenex, Torrance, Calif.), gradient elution of 30% to 70% acetonitrile in water, where both solvents contain 0.1% TFA, 30 minutes) to give the title compounds as a mixture of diastereomers.

MS (ESI) m/z=605.2 [M+1].

Example 392

N-((S)-2-((2R,3R,6R)-2-(3-Chlorophenyl)-3-(4-chlorophenyl)-6-((3-methyl-1H-1,2,4-triazol-5-yl)methyl)-5-oxomorpholino)-2-cyclopropylethyl)-N-(2-fluorophenyl)cyclopropanesulfonamide or N-((S)-2-((2S,3R,6R)-2-(3-chlorophenyl)-3-(4-chlorophenyl)-6-((3-methyl-1H-1,2,4-triazol-5-yl)methyl)-5-oxomorpholino)-2-cyclopropylethyl)-N-(2-fluorophenyl)cyclopropanesulfonamide

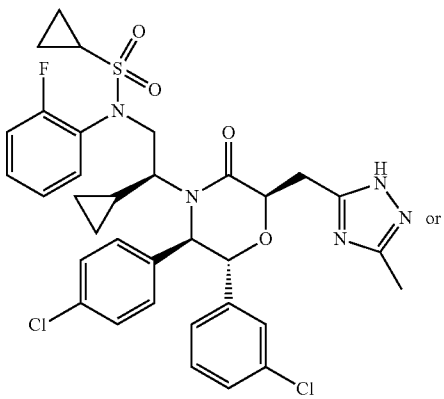 or

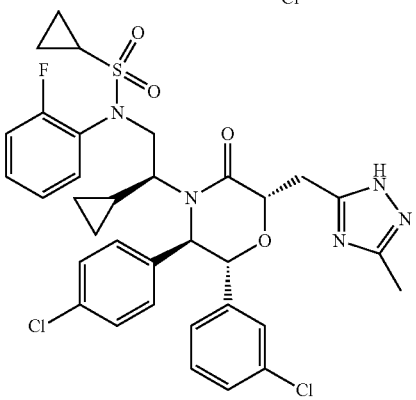

Step A. N-((S)-2-((2R,3R,6R)-2-(3-Chlorophenyl)-3-(4-chlorophenyl)-6-(cyanomethyl)-5-oxomorpholino)-2-cyclopropylethyl)-N-(2-fluorophenyl)cyclopropanesulfonamide and N-((S)-2-((2S,3R,6R)-2-(3-chlorophenyl)-3-(4-chlorophenyl)-6-(cyanomethyl)-5-oxomorpholino)-2-cyclopropylethyl)-N-(2-fluorophenyl)cyclopropanesulfonamide

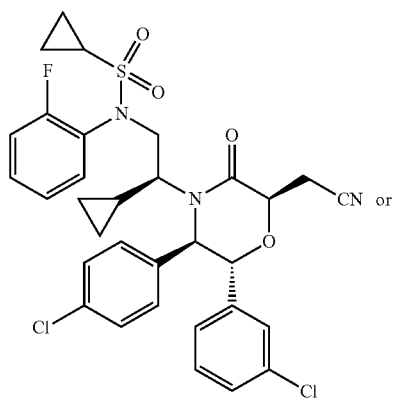 or

-continued

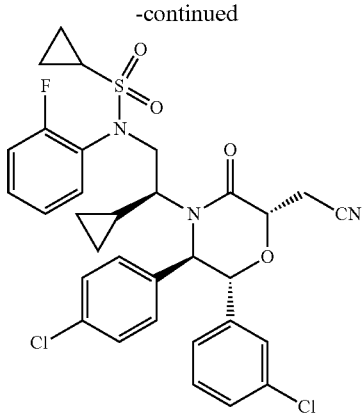

The title compounds were prepared from 2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetamide and 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetamide. (Example 256, mixture of diastereomers) by a procedure similar to that described in Example 50, Step F.

Step B. N-((S)-2-((2R,3R,6R)-2-(3-Chlorophenyl)-3-(4-chlorophenyl)-6-((3-methyl-1H-1,2,4-triazol-5-yl)methyl)-5-oxomorpholino)-2-cyclopropylethyl)-N-(2-fluorophenyl)cyclopropanesulfonamide or N-((S)-2-((2S,3R,6R)-2-(3-chlorophenyl)-3-(4-chlorophenyl)-6-((3-methyl-1H-1,2,4-triazol-5-yl)methyl)-5-oxomorpholino)-2-cyclopropylethyl)-N-(2-fluorophenyl)cyclopropanesulfonamide

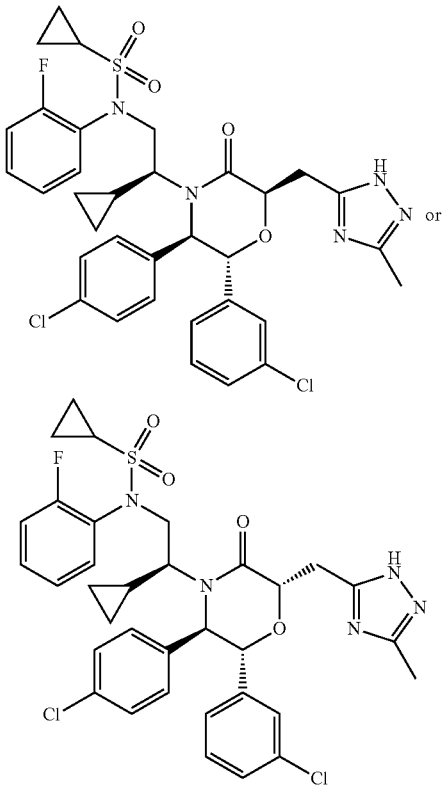

One of the title compounds was prepared from N-((S)-2-((2R,3R,6R)-2-(3-chlorophenyl)-3-(4-chlorophenyl)-6-(cyanomethyl)-5-oxomorpholino)-2-cyclopropylethyl)-N-(2-fluorophenyl)cyclopropanesulfonamide and N-((S)-2-((2S,3R,6R)-2-(3-chlorophenyl)-3-(4-chlorophenyl)-6-(cyanomethyl)-5-oxomorpholino)-2-cyclopropylethyl)-N-(2-fluorophenyl)cyclopropanesulfonamide (Example 392, Step A) by a procedure similar to that described in Example 391. The residue was purified by reverse phase preparatory HPLC (Agilient 1100, column: Gemini® 5 μm $C_{18}$, 100 mm×30 mm (Phenomenex, Torrance, Calif.), gradient elution of 30% to 70% acetonitrile in water, where both solvents contain 0.1% TFA, 30 minutes) to give a residue. The residue was purified by chiral SFC (250×30 mm Chiralpak® AD-H column (Chiral Technologies, Inc., West Chester, Pa., USA) with 36 g/min 20 mM $NH_3$ in IPA+84 g/min $CO_2$ on a Thar 200 SFC (Thar Technologies, Inc., Pittsburg, Pa.)) to give one of the title compounds as the first (faster) eluting triazole isomer. $^1$H NMR (400 MHz, CDCl$_3$, δ ppm): 10.86 (br. s., 1H), 7.46 (m, 1H), 7.08-7.43 (m, 9H), 6.93-6.97 (m, 2H), 4.97 (s, 1H), 4.86 (d, J=4.0 Hz, 1H), 4.24 (m, 2H), 3.32-3.46 (m, 2H), 2.37 (s, 3H), 1.53 (br. s., 1H), 1.19-1.25 (m, 2H), 0.82-0.88 (m, 5H), 0.42 (br. s., 1H), 0.26 (br. s., 1H), 0.00 (br. s., 1H), −0.85 (br. s., 1H). MS (ESI) m/z=698.0 [M+1].

Example 393

N-((S)-2-((2R,3R,6R)-2-(3-Chlorophenyl)-3-(4-chlorophenyl)-6-((3-methyl-1H-1,2,4-triazol-5-yl)methyl)-5-oxomorpholino)-2-cyclopropylethyl)-N-(2-fluorophenyl)cyclopropanesulfonamide or N-((S)-2-((2S,3R,6R)-2-(3-chlorophenyl)-3-(4-chlorophenyl)-6-((3-methyl-1H-1,2,4-triazol-5-yl)methyl)-5-oxomorpholino)-2-cyclopropylethyl)-N-(2-fluorophenyl)cyclopropanesulfonamide

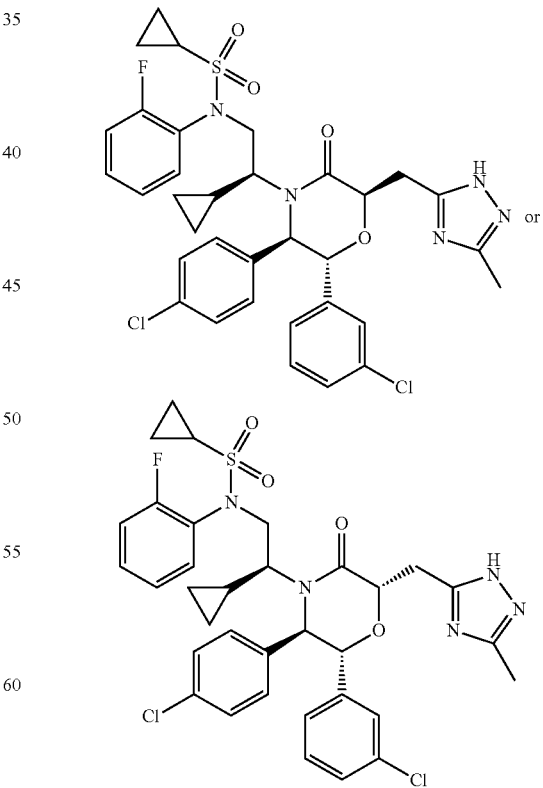

Further elution of the SFC chromatographic purification described in Example 392, Step B provided one of the title compounds as the second (slower) eluting triazole isomer. $^1$H NMR (400 MHz, CDCl$_3$, δ ppm): 7.63 (m, 1H), 7.37-7.39 (m, 1H), 7.20-7.30 (m, 6H), 7.08-7.18 (m, 3H), 6.93 (m, 1H), 4.93 (d, J=16.0 Hz, 1H), 4.70 (d, J=12.0 Hz, 1H), 4.67 (m, 1H), 3.93 (br. s., 1H), 3.25 (br. s., 1H), 2.98 (br. s., 1H), 2.47 (m, 1H), 2.40 (s, 3H), 1.68 (br. s., 1H), 1.35 (m, 1H), 0.86-1.08 (m, 5H), 0.43 (br. s., 1H), 0.25 (br. s., 1H), −0.20 (br. s., 1H), −0.97 (br. s., 1H). MS (ESI) m/z=698.0 [M+1].

Example 394

N-((S)-2-((2R,5R,6R)-2-((1H-1,2,3-Triazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide or N-((S)-2-((2S,5R,6R)-2-((1H-1,2,3-triazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide

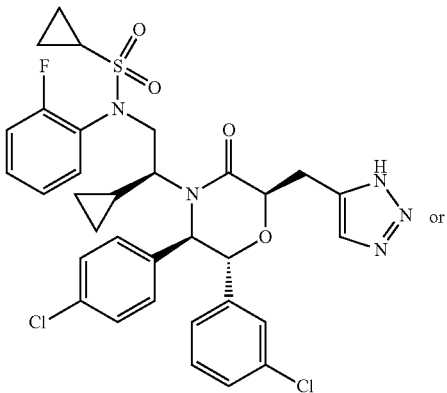

or

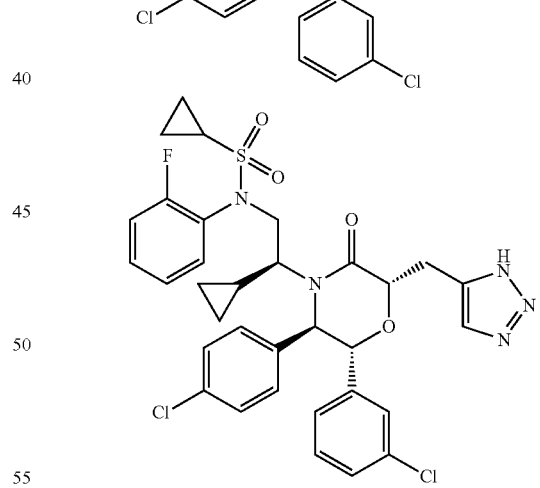

One of the title compounds was prepared from N-((S)-2-((2R,3R)-2-(3-chlorophenyl)-3-(4-chlorophenyl)-5-oxomorpholino)-2-cyclopropylethyl)-N-(2-fluorophenyl)cyclopropanesulfonamide (Example 333, Step A) by procedures similar to those described in Example 385, Steps A and B. The residue was purified by reverse phase preparatory HPLC (Agilient 1100, column: Gemini® 5 μm C$_{18}$, 100 mm×30 mm (Phenomenex, Torrance, Calif.), gradient elution of 30% to 70% acetonitrile in water, where both solvents contain 0.1% TFA, 30 minutes) to give a residue. The residue was purified by chiral SFC (250×30 mm Chiralpak® IC column (Chiral Technologies, Inc., West Chester, Pa., USA) with 48 g/min 20 mM NH$_3$ in IPA+72 g/min CO$_2$ on a Thar 350 SFC (Thar Technologies, Inc., Pittsburg, Pa.)) to give one of the title compounds as the first (faster) eluting isomer. $^1$H NMR (400 MHz, CDCl$_3$, δ ppm): 7.50 (s, 1H), 7.42 (m, 1H), 7.16-7.22 (m, 5H), 7.05-7.10 (m, 3H), 6.83 (m, 2H), 4.93 (br. s., 1H), 4.78 (d, J=8.0 Hz, 1H), 4.15 (m, 1H), 3.65 (m, 1H), 3.43 (m, 1H), 3.27 (m, 1H), 2.37 (m, 1H), 1.35 (s, 1H), 1.17 (m, 1H), 0.81-0.85 (m, 5H), 0.43 (br. s., 1H), 0.25 (br. s., 1H), 0.00 (br. s., 1H), −0.82 (br. s., 1H). MS (ESI) m/z=684.0 [M+1].

Example 395

N-((S)-2-((2R,5R,6R)-2-((1H-1,2,3-Triazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide or N-((S)-2-((2S,5R,6R)-2-((1H-1,2,3-triazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide

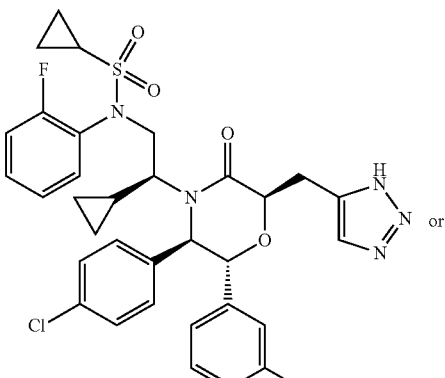

or

Further elution of the SFC chromatographic separation described in Example 394 provided one of the title compounds as the second (slower) eluting isomer.

$^1$H NMR (400 MHz, CDCl$_3$, δ ppm): 12.6 (br. S, 1 H), 7.61 (s, 1H), 7.56 (s, 1H), 7.37 (m, 1H), 7.18-7.30 (m, 6H), 7.08 (m, 3H), 6.90 (m, 1H), 4.88 (d, J=8.0 Hz, 1H), 4.69 (d, J=8.0 Hz, 1H), 4.52 (s, 1H), 3.90 (s, 1H), 3.76 (m, 1H), 3.30 (s, 1H), 2.85 (s, 1H), 2.47 (s, 1H), 1.71 (s, 1H), 1.27 (m, 1H), 0.89-1.04 (m, 5H), 0.43 (br. s., 1H), 0.26 (br. s., 1H), −0.15 (br. s., 1H), −0.92 (br. s., 1H). MS (ESI) m/z=684.0 [M+1].

Example 396

N-((S)-2-((2R,5R,6R)-2-((1H-1,2,4-Triazol-5-yl)
methyl)-6-(3-chlorophenyl)-5-(4-chlorophenyl)-3-
oxomorpholino)-2-cyclopropylethyl)-N-(2-fluo-
rophenyl)cyclopropanesulfonamide or N-((S)-2-((2S,
5R,6R)-2-((1H-1,2,4-triazol-5-yl)methyl)-6-(3-
chlorophenyl)-5-(4-chlorophenyl)-3-
oxomorpholino)-2-cyclopropylethyl)-N-(2-
fluorophenyl)cyclopropanesulfonamide

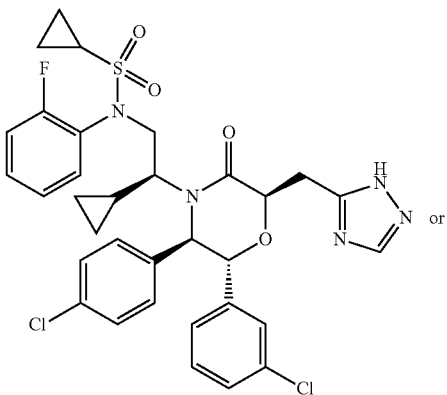

or

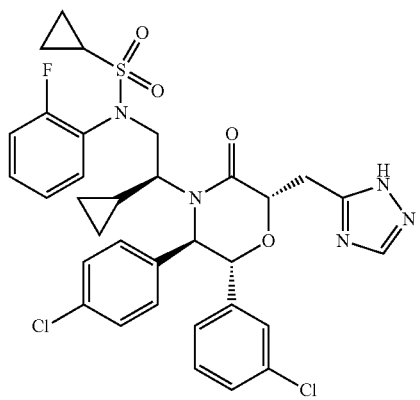

One of the title compounds was prepared from N-((S)-2-((2R,3R,6R)-2-(3-chlorophenyl)-3-(4-chlorophenyl)-6-(cyanomethyl)-5-oxomorpholino)-2-cyclopropylethyl)-N-(2-fluorophenyl)cyclopropanesulfonamide and N-((S)-2-((2S,3R,6R)-2-(3-chlorophenyl)-3-(4-chlorophenyl)-6-(cyanomethyl)-5-oxomorpholino)-2-cyclopropylethyl)-N-(2-fluorophenyl)cyclopropanesulfonamide (Example 392, Step A) by a procedure similar to that described in Example 389. The residue was purified by reverse phase preparatory HPLC (Agilient 1100, column: Gemini® 5 μm C$_{18}$, 100 mm×30 mm (Phenomenex, Torrance, Calif.), gradient elution of 30% to 70% acetonitrile in water, where both solvents contain 0.1% TFA, 30 minutes) to give one of the title compounds as the first (faster) eluting isomer. $^1$H NMR (400 MHz, CDCl$_3$, δ ppm): 11.51 (br. s., 1H), 8.32 (s, 1H), 7.34 (s, 1H), 7.16 (m, 1H), 6.91-7.06 (m, 6H), 6.77-6.84 (m, 3H), 6.67 (s, 1H), 4.66 (s, 1H), 4.57 (m, 3H), 3.63 (s, 1H), 3.37 (s, 1H), 3.14 (m, 1H), 2.24 (s, 1H), 1.96 (s, 1H), 1.40 (s, 1H), 0.74 (s, 4H), 0.18 (br. s., 1H), 0.00 (br. s., 1H), −0.45 (br. s., 1H), −1.27 (br. s., 1H). MS (ESI) m/z=684.0 [M+1].

Example 397

N-((S)-2-((2R,5R,6R)-2-((1H-1,2,4-Triazol-5-yl)
methyl)-6-(3-chlorophenyl)-5-(4-chlorophenyl)-3-
oxomorpholino)-2-cyclopropylethyl)-N-(2-fluo-
rophenyl)cyclopropanesulfonamide or N-((S)-2-((2S,
5R,6R)-2-((1H-1,2,4-triazol-5-yl)methyl)-6-(3-
chlorophenyl)-5-(4-chlorophenyl)-3-
oxomorpholino)-2-cyclopropylethyl)-N-(2-
fluorophenyl)cyclopropanesulfonamide

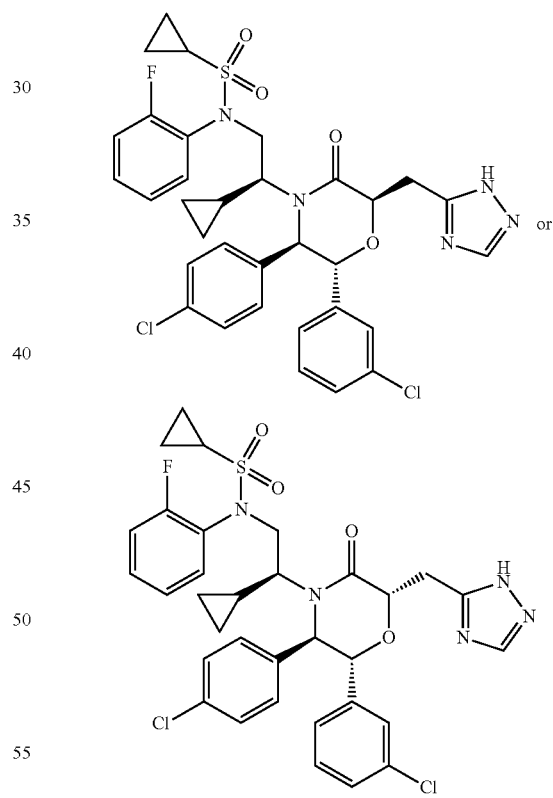

Further elution of the chromatographic separation described in Example 396 provided one of the title compounds as the second (slower) eluting isomer. $^1$H NMR (400 MHz, CDCl$_3$, δ ppm): 8.95 (br. s., 1H), 8.36 (s, 1H), 7.54 (m, 1H), 7.14-7.32 (m, 8H), 7.07 (m, 3H), 5.01 (m, 2H), 4.75-4.81 (m, 1H), 4.57 (br. s., 1H), 4.25 (br. s., 1H), 4.13 (m, 1H), 3.89 (m, 1H), 3.72 (m, 1H), 2.46 (m, 1H), 1.35 (s, 1H), 0.94 (br. s., 4H), 0.50 (s, 1H), 0.36 (br. s., 1H), 0.00 (br. s., 1H), −0.90 (br. s., 1H). MS (ESI) m/z=684.0 [M+1].

Example 398

N-((S)-2-((2R,5R,6R)-2-((1H-Tetrazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide or N-((S)-2-((2S,5R,6R)-2-((1H-tetrazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide

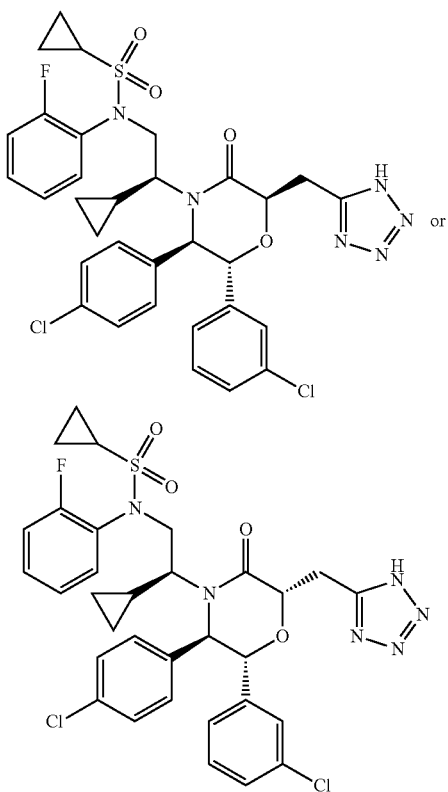

One of the title compounds was prepared from N-((S)-2-((2R,3R,6R)-2-(3-chlorophenyl)-3-(4-chlorophenyl)-6-(cyanomethyl)-5-oxomorpholino)-2-cyclopropylethyl)-N-(2-fluorophenyl)cyclopropanesulfonamide or N-((S)-2-((2S,3R,6R)-2-(3-chlorophenyl)-3-(4-chlorophenyl)-6-(cyanomethyl)-5-oxomorpholino)-2-cyclopropylethyl)-N-(2-fluorophenyl)cyclopropanesulfonamide (prepared from 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetamide or 2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetamide (Example 257) by the method in Example 392, Step A) by a procedure similar to that described in Example 382. The residue was purified by purified by reversed phase preparatory HPLC (Agilient 1100, column: Gemini® 5 µm $C_{18}$, 100 mm×30 mm (Phenomenex, Torrance, Calif.), gradient elution of 40% to 65% acetonitrile in water, where both solvents contain 0.1% TFA) to provide one of the title compounds as a white powder. $^1$H NMR (500 MHz, CDCl$_3$, δ ppm): 7.44-7.59 (m, 1H), 7.15-7.39 (m, 9H), 6.97-7.12 (m, 2H), 5.10 (br. s., 1H), 4.94 (d, J=5.13 Hz, 1H), 4.25 (t, J=5.99 Hz, 1H), 3.68-3.80 (m, 3H), 2.44 (br. s., 1H), 1.74 (m, 1H), 1.29-1.49 (m, 1H), 0.86-1.09 (m, 5H), 0.53 (br. s., 1H), 0.40 (br. s., 1H), −0.06-0.17 (m, 1H), −0.80 to −0.60 (m, 1H). MS (ESI) m/z=685 [M+1].

Example 399

N-((S)-2-((2R,5R,6R)-2-((1H-Tetrazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide or N-((S)-2-((2S,5R,6R)-2-((1H-tetrazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide

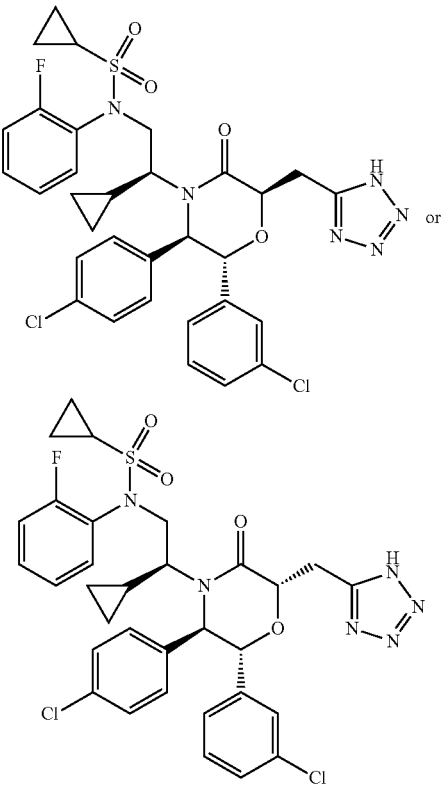

The title compound was prepared from N-((S)-2-((2R,3R,6R)-2-(3-chlorophenyl)-3-(4-chlorophenyl)-6-(cyanomethyl)-5-oxomorpholino)-2-cyclopropylethyl)-N-(2-fluorophenyl)cyclopropanesulfonamide or N-((S)-2-((2S,3R,6R)-2-(3-chlorophenyl)-3-(4-chlorophenyl)-6-(cyanomethyl)-5-oxomorpholino)-2-cyclopropylethyl)-N-(2-fluorophenyl)cyclopropanesulfonamide (prepared from 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetamide or 2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetamide (Example 256) by the method in Example 392, Step A) by a procedure similar to that described in Example 382. The residue was purified by purified by reversed phase preparatory HPLC (Agilient 1100, column: Gemini® 5 µm $C_{18}$, 100 mm×30 mm (Phenomenex, Torrance, Calif.), gradient elution of 40% to 65% acetonitrile in water, where both solvents contain 0.1% TFA) to provide one of the title compounds as a white powder. $^1$H NMR (500 MHz, CDCl$_3$, δ ppm): −0.99 (br. s., 1H), −0.26 (br. s., 1H), 0.25 (br. s., 1H), 0.44 (br. s., 1H), 0.91-1.12 (m, 5H), 1.58-1.72 (m, 1H), 2.30 (br. s., 1H), 2.47 (quin, J=6.24 Hz, 1H), 3.27 (m, 1H), 3.46 (dd, J=15.28, 3.55 Hz, 1H), 3.90 (m, 1H), 4.49 (dd, J=8.93, 3.79 Hz, 1H), 4.65-4.83 (m, 1H), 4.93 (d, J=10.03 Hz, 1H), 6.95 (d, J=7.58 Hz, 1H), 7.00-7.11 (m, 2H), 7.13 (s, 1H), 7.16-7.34 (m, 6H), 7.34-7.43 (m, 1H), 7.61 (t, J=7.58 Hz, 1H); MS (ESI) m/z=685 [M+1].

Example 400

(2R,5R,6R)-4-((S)-1-(tert-Butylsulfonyl)butan-2-yl)-6-(3-chlorophenyl)-5-(4-chlorophenyl)-2-((1-methyl-1H-tetrazol-5-yl)methyl)morpholin-3-one or (2R,5R,6R)-4-((S)-1-(tert-butylsulfonyl)butan-2-yl)-6-(3-chlorophenyl)-5-(4-chlorophenyl)-2-((2-methyl-2H-tetrazol-5-yl)methyl)morpholin-3-one

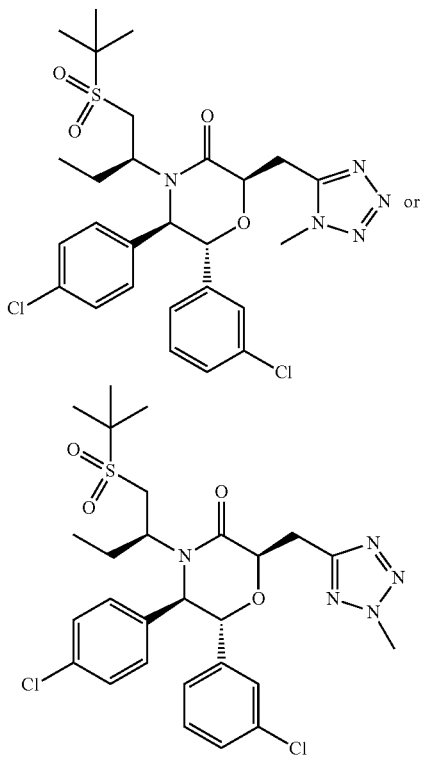

Potassium carbonate (4.68 μL, 0.078 mmol) and iodomethane (4.82 μL, 0.078 mmol) were added to a solution (2R,5R,6R)-2-((1H-tetrazol-5-yl)methyl)-4-((S)-1-(tert-butylsulfonyl)butan-2-yl)-6-(3-chlorophenyl)-5-(4-chlorophenyl)morpholin-3-one (0.009 g, 0.016 mmol, Example 382) in DMF (2.0 mL). The reaction was stirred at room temperature overnight. The mixture was diluted with saturated NH$_4$Cl (20 mL) and extracted with dichloromethane (3×20 mL). The organic layer was washed with water, dried over MgSO$_4$, filtered, and concentrated. The residue was purified by reverse phase preparatory HPLC (Agilient 1100, column: Gemini® 5 μm C$_{18}$, 100 mm×30 mm (Phenomenex, Torrance, Calif.), gradient elution of 40% to 70% acetonitrile in water, where both solvents contain 0.1% TFA, 30 minutes) to give one of the title compounds as the first (faster) eluting isomer as a white powder. $^1$H NMR (500 MHz, CDCl$_3$, δ ppm): 0.52 (t, J=7.46 Hz, 3H), 1.44 (s, 9H), 1.50-1.61 (m, 1H), 2.10-2.17 (m, 1H), 2.93 (dd, J=13.57, 2.32 Hz, 1H), 3.34 (br. s., 1H), 3.50 (dd, J=15.41, 4.40 Hz, 1H), 3.78 (dd, J=15.41, 6.60 Hz, 1H), 3.96 (dd, J=13.45, 9.54 Hz, 1H), 4.02 (s, 3H), 4.76-4.82 (m, 1H), 4.92 (d, J=7.09 Hz, 1H), 5.11 (d, J=7.09 Hz, 1H), 6.93-6.98 (m, 1H), 7.09-7.17 (m, 3H), 7.19-7.25 (m, 2H), 7.31 (d, J=8.31 Hz, 2H). MS (ESI) m/z=594 [M+1].

Example 401

(2R,5R,6R)-4-((S)-1-(tert-Butylsulfonyl)butan-2-yl)-6-(3-chlorophenyl)-5-(4-chlorophenyl)-2-((1-methyl-1H-tetrazol-5-yl)methyl)morpholin-3-one or (2R,5R,6R)-4-((S)-1-(tert-butylsulfonyl)butan-2-yl)-6-(3-chlorophenyl)-5-(4-chlorophenyl)-2-((2-methyl-2H-tetrazol-5-yl)methyl)morpholin-3-one

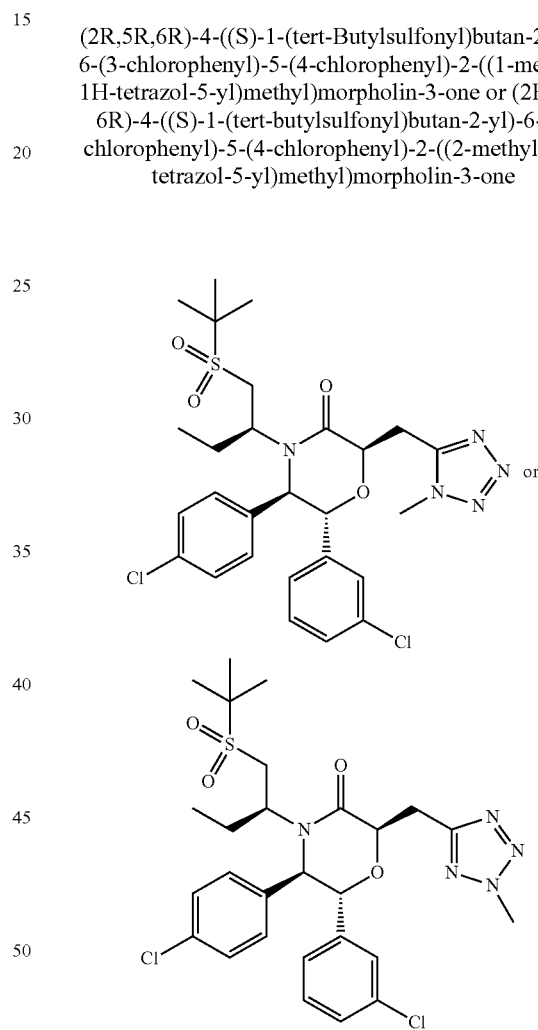

Further elution of the chromatographic separation described in Example 400 provided one of the title compounds as the second (slower) eluting isomer. $^1$H NMR (400 MHz, CDCl$_3$, δ ppm): 0.54 (t, J=7.58 Hz, 3H), 1.44 (s, 9H), 1.66 (ddd, J=13.94, 7.58, 4.40 Hz, 1H), 2.15 (ddd, J=14.18, 9.54, 7.34 Hz, 1H), 2.97 (dd, J=13.69, 2.45 Hz, 1H), 3.39 (br. s., 1H), 3.63 (dd, J=15.41, 4.65 Hz, 1H), 3.70 (dd, J=15.41, 8.80 Hz, 1H), 3.99 (dd, J=13.69, 9.05 Hz, 1H), 4.31 (s, 3H), 4.84 (dd, J=8.93, 4.52 Hz, 1H), 4.93 (d, J=7.09 Hz, 1H), 5.15 (d, J=6.85 Hz, 1H), 6.98-7.04 (m, 1H), 7.14 (t, J=7.70 Hz, 1H), 7.17-7.26 (m, 4H), 7.29-7.37 (m, 2H). MS (ESI) m/z=594 [M+1].

Example 402

(2R,5R,6R)-4-((S)-2-(tert-Butylsulfonyl)-1-cyclopropylethyl)-6-(3-chlorophenyl)-5-(4-chlorophenyl)-2-((1-methyl-1H-imidazol-2-yl)methyl)morpholin-3-one

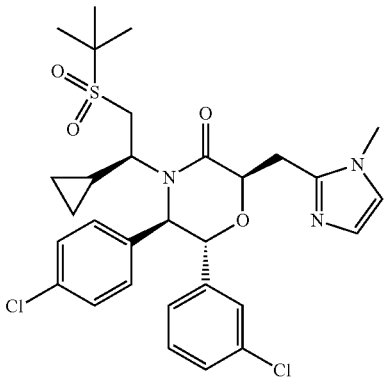 [SMILES: Cn1ccnc1C[C@H]1O[C@H](c2cccc(Cl)c2)[C@@H](c2ccc(Cl)cc2)N([C@H](CS(=O)(=O)C(C)(C)C)C2CC2)C1=O]

Step A. (2R,5R,6R)-4-((S)-2-(tert-Butylthio)-1-cyclopropylethyl)-6-(3-chlorophenyl)-5-(4-chlorophenyl)-2-((1-methyl-1H-imidazol-2-yl)methyl)morpholin-3-one

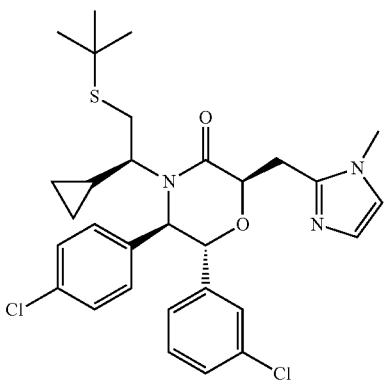 [SMILES: Cn1ccnc1C[C@H]1O[C@H](c2cccc(Cl)c2)[C@@H](c2ccc(Cl)cc2)N([C@H](CSC(C)(C)C)C2CC2)C1=O]

The title compound was prepared from (5R,6R)-4-((S)-2-(tert-butylthio)-1-cyclopropylethyl)-6-(3-chlorophenyl)-5-(4-chlorophenyl)morpholin-3-one Example 154, Step C by a procedure similar to that described in Example 384, Step A, replacing 5-(bromomethyl)isoxazole with 2-(chloromethyl)-1-methyl-1H-imidazole hydrochloride (Princeton BioMolecular, Monmouth Junction, N.J.). The residue was purified by flash chromatography on silica gel (4 g GOLD column (Teledyne Isco, Lincoln, Nebr.), gradient elution of 0% to 7% MeOH in dichloromethane) to give the title compound.

Step B. (2R,5R,6R)-4-((S)-2-(tert-Butylsulfonyl)-1-cyclopropylethyl)-6-(3-chlorophenyl)-5-(4-chlorophenyl)-2-((1-methyl-1H-imidazol-2-yl)methyl)morpholin-3-one

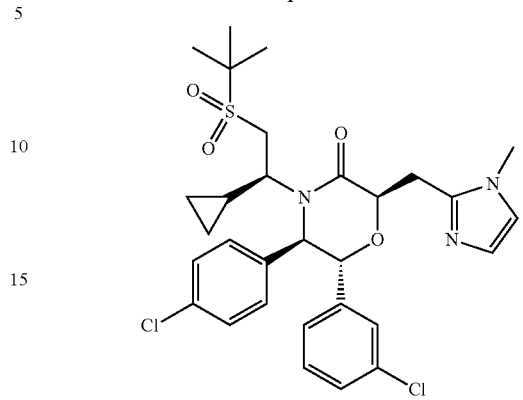

Sodium periodate (6.72 mg, 0.031 mmol) was added to a solution of (5R,6R)-4-((S)-2-(tert-butylthio)-1-cyclopropylethyl)-6-(3-chlorophenyl)-5-(4-chlorophenyl)-2-((1-methyl-1H-imidazol-2-yl)methyl)morpholin-3-one (9 mg, 0.016 mmol, Example 402, Step A) in MeOH (105 μL) and water (52.4 μL). After stirring at 45° C. for 90 minutes, more sodium periodate (6.72 mg, 0.031 mmol) was added. The mixture was heated to 50° C. for 2 hours, and then more sodium periodate (6.72 mg, 0.031 mmol) was added. After stirring at 55° C. for 2 hours, the mixture was cooled to room temperature and diluted with ethyl acetate and water. The organic layer was dried over $Na_2SO_4$, filtered, and concentrated. The residue was purified by flash chromatography on silica gel (4 g column; gradient elution of 0% to 10% MeOH in dichloromethane) to give the title compound. $^1$H NMR (500 MHz, acetone-$d_6$, δ ppm): 7.37 (m, 2H), 7.35-7.24 (m, 5H), 7.20 (br. s., 1H), 7.02 (s, 1H), 6.93 (s, 1H), 5.24 (br. s., 1H), 5.05 (d, J=6.1 Hz, 1H), 4.60 (br. s., 1H), 4.02 (br. s., 1H), 3.63 (s, 3H), 3.62-3.57 (m, 1H), 3.33 (dd, J=4.4, 15.2 Hz, 1H), 3.02 (br. s., 1H), 2.87 (br. s., 1H), 1.69 (br. s., 1H), 1.39 (s, 9H), 0.42 (br. s., 2H), 0.13 (br. s., 1H), −0.54 (br. s., 1H). MS (ESI) m/z=604.1 [M+1].

Example 403

N-((S)-2-((2R,3R,6R)-2-(3-Chlorophenyl)-3-(4-chlorophenyl)-6-((5-methyl-1,3,4-oxadiazol-2-yl)methyl)-5-oxomorpholino)-2-cyclopropylethyl)-N-(2-fluorophenyl)cyclopropanesulfonamide or N-((S)-2-((2S,3R,6R)-2-(3-chlorophenyl)-3-(4-chlorophenyl)-6-((5-methyl-1,3,4-oxadiazol-2-yl)methyl)-5-oxomorpholino)-2-cyclopropylethyl)-N-(2-fluorophenyl)cyclopropanesulfonamide

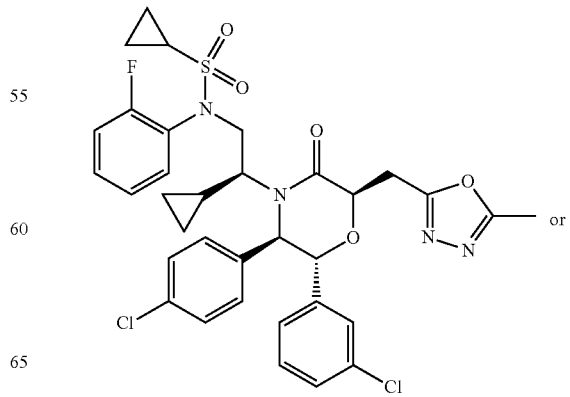

or

-continued

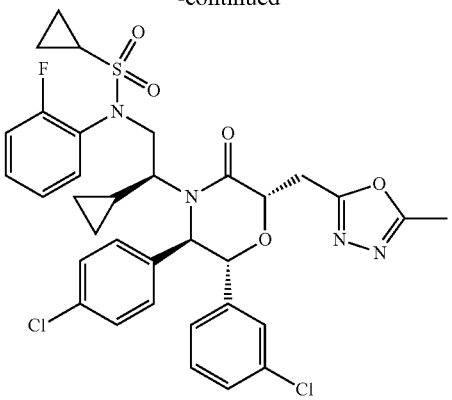

Step A. N-((S)-2-((2R,5R,6R)-2-(2-(2-Acetylhydrazinyl)-2-oxoethyl)-6-(3-chlorophenyl)-5-(4-chlorophenyl)-3-oxomorpholino)-2-cyclopropylethyl)-N-(2-fluorophenyl)cyclopropanesulfonamide or N-((S)-2-((2S,5R,6R)-2-(2-(2-acetylhydrazinyl)-2-oxoethyl)-6-(3-chlorophenyl)-5-(4-chlorophenyl)-3-oxomorpholino)-2-cyclopropylethyl)-N-(2-fluorophenyl)cyclopropanesulfonamide

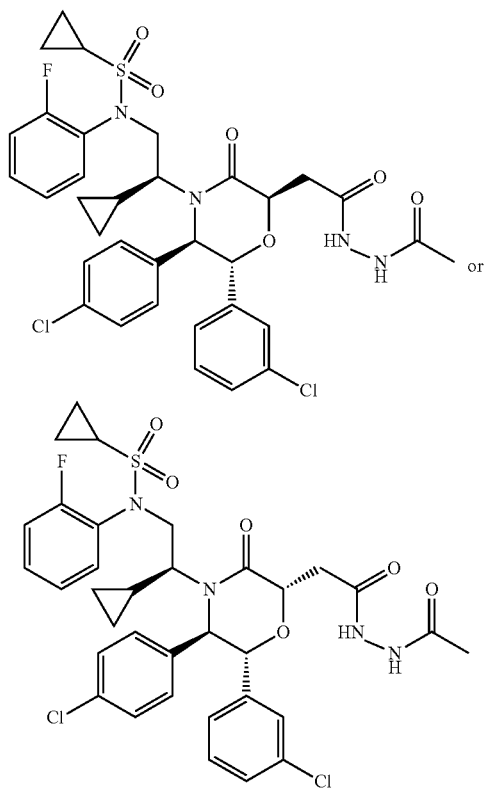

One of the title compounds was prepared from 2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid (Example 158) by a procedure similar to that described in Example 225, replacing triethylamine with N-ethyl-N-isopropylpropan-2-amine and ammonia with acetic acid hydrazide. The residue was purified by flash chromatography on silica gel (40 g column; gradient elution of 0% to 10% 2 M NH$_3$ in MeOH in dichloromethane) to give one of the title compounds as a light yellow oil.

Step B. N-((S)-2-((2R,3R,6R)-2-(3-Chlorophenyl)-3-(4-chlorophenyl)-6-((5-methyl-1,3,4-oxadiazol-2-yl)methyl)-5-oxomorpholino)-2-cyclopropylethyl)-N-(2-fluorophenyl)cyclopropanesulfonamide or N-((S)-2-((2S,3R,6R)-2-(3-chlorophenyl)-3-(4-chlorophenyl)-6-((5-methyl-1,3,4-oxadiazol-2-yl)methyl)-5-oxomorpholino)-2-cyclopropylethyl)-N-(2-fluorophenyl)cyclopropanesulfonamide

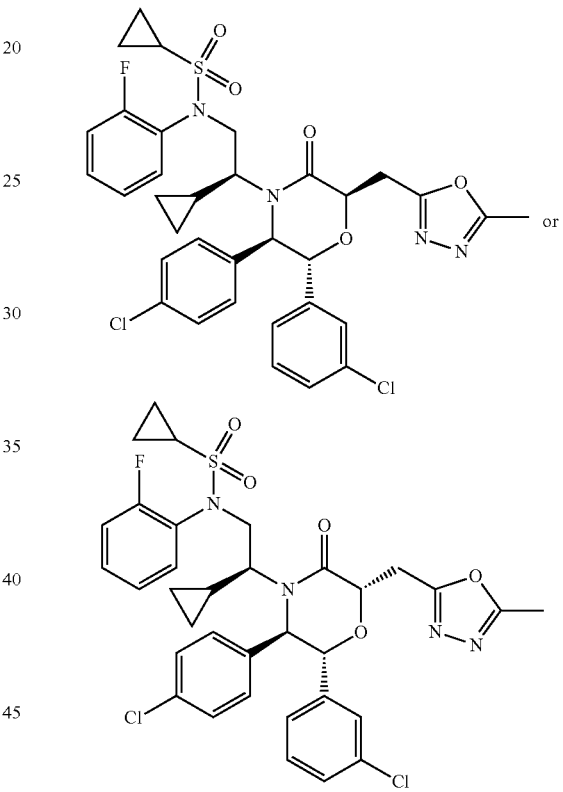

A solution of N-((S)-2-((2R,5R,6R)-2-(2-(2-acetylhydrazinyl)-2-oxoethyl)-6-(3-chlorophenyl)-5-(4-chlorophenyl)-3-oxomorpholino)-2-cyclopropylethyl)-N-(2-fluorophenyl)cyclopropanesulfonamide or N-((S)-2-((2S,5R,6R)-2-(2-(2-acetylhydrazinyl)-2-oxoethyl)-6-(3-chlorophenyl)-5-(4-chlorophenyl)-3-oxomorpholino)-2-cyclopropylethyl)-N-(2-fluorophenyl)cyclopropanesulfonamide (15 mg, 0.21 mmol, Example 402, Step A) and (methoxycarbonylsulfamoyl)triethylammonium hydroxide (19.92 mg, 0.084 mmol) in 1,2-dichloroethane (0.418 mL) was heated in a microwave reactor (CEM, Matthews, N.C.) for 30 minutes at 120° C. The mixture was cooled, diluted with water (20 mL), and extracted with dichloromethane (3×30 mL). The combined organic layers were combined, dried over MgSO$_4$, filtered, and concentrated. The residue was purified by reverse phase preparatory HPLC (Agilient 1100, column: Gemini® 5 µm C$_{18}$, 100 mm×30 mm (Phenomenex, Torrance, Calif.), gradient elution of 50% to 90% acetonitrile in water, where both solvents contain 0.1% TFA, 27 minutes) to give one of the title compounds as a white foam. $^1$H NMR (400 MHz, CDCl$_3$, δ ppm): 7.52 (dt, J=1.76, 7.92 Hz, 1H), 7.33-7.41 (m, 1H), 7.31 (d, J=8.41 Hz, 3H), 7.14-7.27 (m, 7H), 7.11 (d, J=7.43 Hz, 1H), 5.06 (d, J=6.85 Hz, 1H), 4.94 (d, J=7.04 Hz, 1H), 4.50 (dd, J=4.40, 9.68 Hz, 1H), 3.85 (br. s., 1H), 3.60-3.73 (m, 1H), 3.49-3.58 (m, J=4.50 Hz, 1H), 2.51 (s, 3H), 2.38-2.50 (m, 2H), 1.41-1.58 (m, 1H), 0.77-1.14 (m, 4H), 0.22-0.57 (m, 1H), −0.03 (br. s., 1H), −0.77 (br. s., 1H). MS (ESI) m/z=699.0 [M+1].

Example 404

N-((S)-2-((2S,3R,6R)-2-(3-Chlorophenyl)-3-(4-chlorophenyl)-6-((5-methyl-1,3,4-oxadiazol-2-yl)methyl)-5-oxomorpholino)-2-cyclopropylethyl)-N-(2-fluorophenyl)cyclopropanesulfonamide or N-((S)-2-((2R,3R,6R)-2-(3-chlorophenyl)-3-(4-chlorophenyl)-6-((5-methyl-1,3,4-oxadiazol-2-yl)methyl)-5-oxomorpholino)-2-cyclopropylethyl)-N-(2-fluorophenyl)cyclopropanesulfonamide

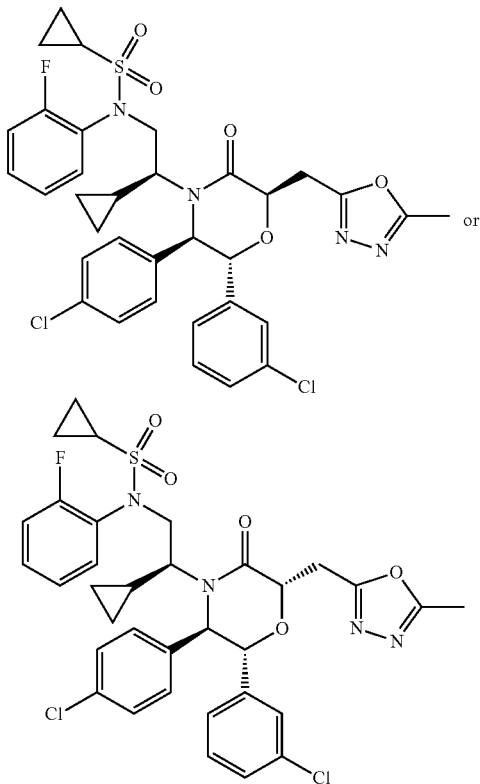

One of the title compounds was prepared from 2-((2R,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid or 2-((2S,5R,6R)-6-(3-chlorophenyl)-5-(4-chlorophenyl)-4-((S)-1-cyclopropyl-2-(N-(2-fluorophenyl)cyclopropanesulfonamido)ethyl)-3-oxomorpholin-2-yl)acetic acid (Example 159) by procedures similar to those described in Example 403, Steps A and B. The residue was purified by reverse phase preparatory HPLC (Agilent 1100, column: Gemini® 5 μm C$_{18}$, 100 mm×30 mm (Phenomenex, Torrance, Calif.), gradient elution of 25% to 75% acetonitrile in water, where both solvents contain 0.1% TFA, 30 minutes) to give one of the compounds as a white foam. $^1$H NMR (400 MHz, CDCl$_3$, δ ppm): 7.62 (t, J=7.34 Hz, 1H), 7.36-7.47 (m, 1H), 7.29 (d, J=8.41 Hz, 3H), 7.02-7.25 (m, 6H), 6.84 (d, J=7.63 Hz, 1H), 4.90 (d, J=9.98 Hz, 1H), 4.85 (dd, J=4.21, 8.71 Hz, 1H), 4.72 (d, J=9.98 Hz, 2H), 3.91 (br. s., 1H), 3.44 (td, J=4.30, 16.24 Hz, 1H), 2.83 (br. s., 1H), 2.51 (s, 3H), 2.41-2.49 (m, 1H), 1.63 (br. s., 1H), 0.93 (m, 5H), 0.41 (br. s., 1H), 0.25 (br. s., 1H), −0.20 (br. s., 1H), −0.94 (br. s., 1H). MS (ESI) m/z=699.2 [M+1].

Example 405

N-((S)-2-((2R,3R,6R)-2-(3-Chlorophenyl)-3-(4-chlorophenyl)-6-((1-methyl-1H-tetrazol-5-yl)methyl)-5-oxomorpholino)-2-cyclopropylethyl)-N-(2-fluorophenyl)cyclopropanesulfonamide or N-((S)-2-((2S,3R,6R)-2-(3-chlorophenyl)-3-(4-chlorophenyl)-6-((1-methyl-1H-tetrazol-5-yl)methyl)-5-oxomorpholino)-2-cyclopropylethyl)-N-(2-fluorophenyl)cyclopropanesulfonamide or N-((S)-2-((2R,3R,6R)-2-(3-chlorophenyl)-3-(4-chlorophenyl)-6-((2-methyl-2H-tetrazol-5-yl)methyl)-5-oxomorpholino)-2-cyclopropylethyl)-N-(2-fluorophenyl)cyclopropanesulfonamide or N-((S)-2-((2R,3R,6R)-2-(3-chlorophenyl)-3-(4-chlorophenyl)-6-((2-methyl-2H-tetrazol-5-yl)methyl)-5-oxomorpholino)-2-cyclopropylethyl)-N-(2-fluorophenyl)cyclopropanesulfonamide

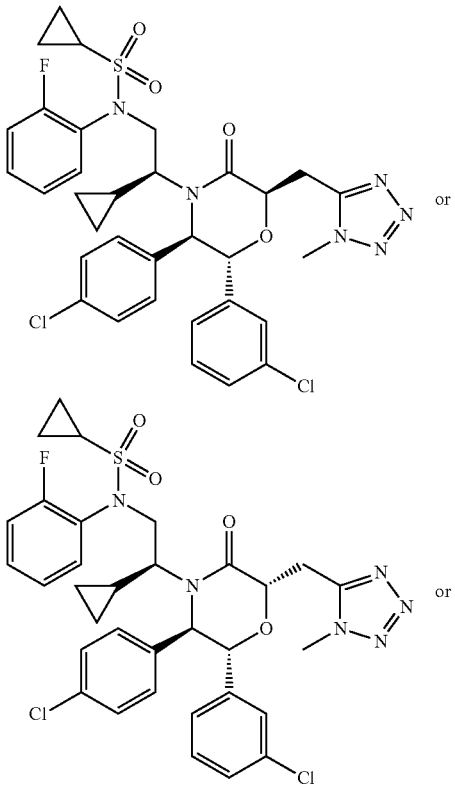

647
-continued

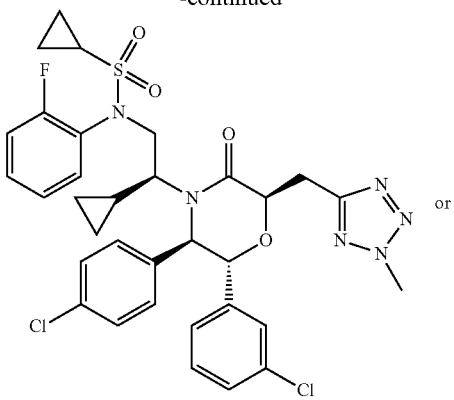

or

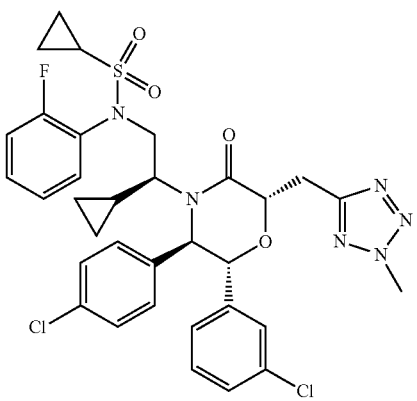

One of the title compounds was prepared from N-((S)-2-((2R,5R,6R)-2-((1H-tetrazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide or N-((S)-2-((2S,5R,6R)-2-((1H-tetrazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide (Example 398) by a procedure similar to that described in Example 400. The residue was purified by reverse phase preparatory HPLC (Agilient 1100, column: Gemini® 5 μm C$_{18}$, 100 mm×30 mm (Phenomenex, Torrance, Calif.), gradient elution of 45% to 70% acetonitrile in water, where both solvents contain 0.1% TFA, 25 minutes) to give one of the compounds as the first (faster) eluting isomer as a white powder. $^1$H NMR (500 MHz, CDCl$_3$, δ ppm): −0.67 (br. s., 1H), 0.06 (br. s., 1H), 0.35 (br. s., 1H), 0.50 (br. s., 1H), 0.84-1.04 (m, 4H), 1.35 (br. s., 1H), 2.37-2.50 (m, 1H), 2.75 (br. s., 1H), 3.52 (dd, J=15.28, 4.28 Hz, 1H), 3.76 (dd, J=15.16, 7.34 Hz, 2H), 4.01 (s, 3H), 4.28 (br. s., 1H), 4.44 (dd, J=6.85, 4.40 Hz, 1H), 4.95 (d, J=5.38 Hz, 1H), 5.04 (br. s., 1H), 6.96-7.10 (m, 2H), 7.10-7.22 (m, 3H), 7.22-7.42 (m, 6H), 7.42-7.53 (m, 1H). MS (ESI) m/z=699 [M+1].

648
Example 406

N-((S)-2-((2R,3R,6R)-2-(3-Chlorophenyl)-3-(4-chlorophenyl)-6-((1-methyl-1H-tetrazol-5-yl)methyl)-5-oxomorpholino)-2-cyclopropylethyl)-N-(2-fluorophenyl)cyclopropanesulfonamide or N-((S)-2-((2S,3R,6R)-2-(3-chlorophenyl)-3-(4-chlorophenyl)-6-((1-methyl-1H-tetrazol-5-yl)methyl)-5-oxomorpholino)-2-cyclopropylethyl)-N-(2-fluorophenyl)cyclopropanesulfonamide or N-((S)-2-((2R,3R,6R)-2-(3-chlorophenyl)-3-(4-chlorophenyl)-6-((2-methyl-2H-tetrazol-5-yl)methyl)-5-oxomorpholino)-2-cyclopropylethyl)-N-(2-fluorophenyl)cyclopropanesulfonamide or N-((S)-2-((2R,3R,6R)-2-(3-chlorophenyl)-3-(4-chlorophenyl)-6-((2-methyl-2H-tetrazol-5-yl)methyl)-5-oxomorpholino)-2-cyclopropylethyl)-N-(2-fluorophenyl)cyclopropanesulfonamide

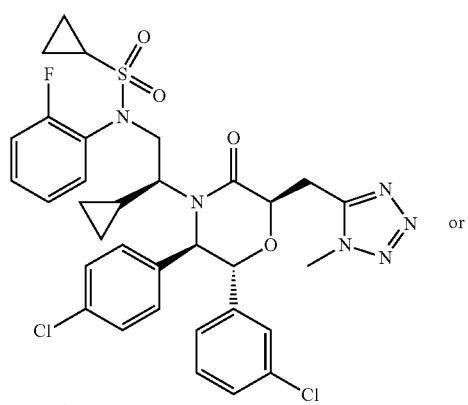

or

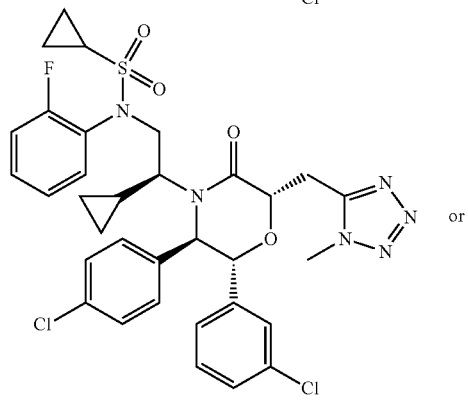

or

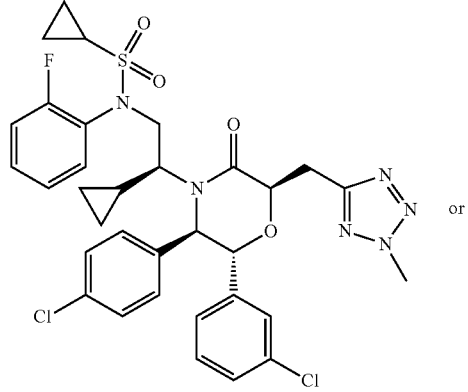

or

649

-continued

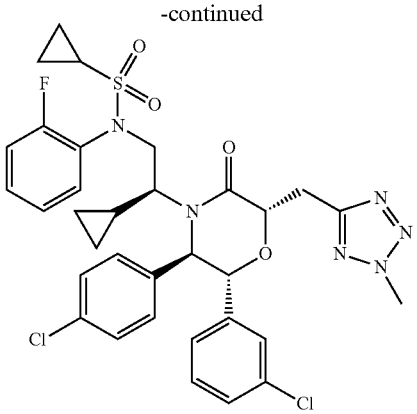

Further elution of the chromatographic separation described in Example 405 provided one of the title compounds as the second (slower) eluting isomer. ¹H NMR (500 MHz, CDCl₃, δ ppm): −0.81 (br. s., 1H), −0.01 (br. s., 1H), 0.31 (br. s., 1H), 0.48 (br. s., 1H), 0.86-1.00 (m, 3H), 1.04 (br. s., 1H), 1.50 (br. s., 1H), 2.41-2.51 (m, 2H), 3.60 (dd, J=15.16, 4.16 Hz, 1H), 3.71 (dd, J=15.28, 10.15 Hz, 1H), 3.90 (br. s., 1H), 4.30 (s, 3H), 4.38 (br. s., 1H), 4.53 (dd, J=10.15, 4.28 Hz, 1H), 4.97 (d, J=7.34 Hz, 1H), 5.07 (d, J=6.85 Hz, 1H), 7.12-7.20 (m, 5H), 7.20-7.33 (m, 12H), 7.33-7.39 (m, 1H), 7.54 (t, J=7.46 Hz, 1H). MS (ESI) m/z=699 [M+1].

Example 407

N-((S)-2-((2R,3R,6R)-2-(3-Chlorophenyl)-3-(4-chlorophenyl)-6-((1-methyl-1H-tetrazol-5-yl)methyl)-5-oxomorpholino)-2-cyclopropylethyl)-N-(2-fluorophenyl)cyclopropanesulfonamide or N-((S)-2-((2S,3R,6R)-2-(3-chlorophenyl)-3-(4-chlorophenyl)-6-((1-methyl-1H-tetrazol-5-yl)methyl)-5-oxomorpholino)-2-cyclopropylethyl)-N-(2-fluorophenyl)cyclopropanesulfonamide or N-((S)-2-((2R,3R,6R)-2-(3-chlorophenyl)-3-(4-chlorophenyl)-6-((2-methyl-2H-tetrazol-5-yl)methyl)-5-oxomorpholino)-2-cyclopropylethyl)-N-(2-fluorophenyl)cyclopropanesulfonamide or N-((S)-2-((2R,3R,6R)-2-(3-chlorophenyl)-3-(4-chlorophenyl)-6-((2-methyl-2H-tetrazol-5-yl)methyl)-5-oxomorpholino)-2-cyclopropylethyl)-N-(2-fluorophenyl)cyclopropanesulfonamide

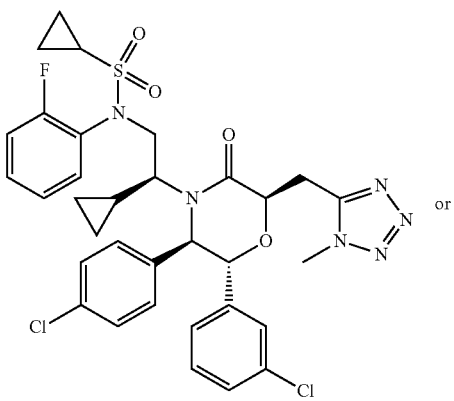

or

650

-continued

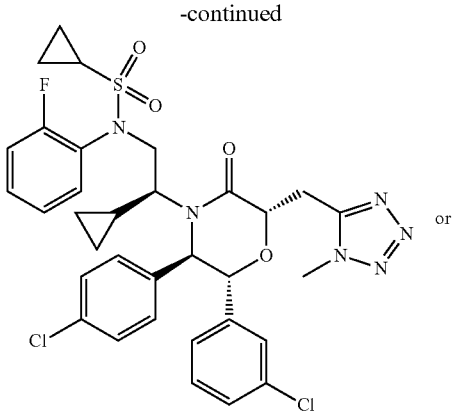

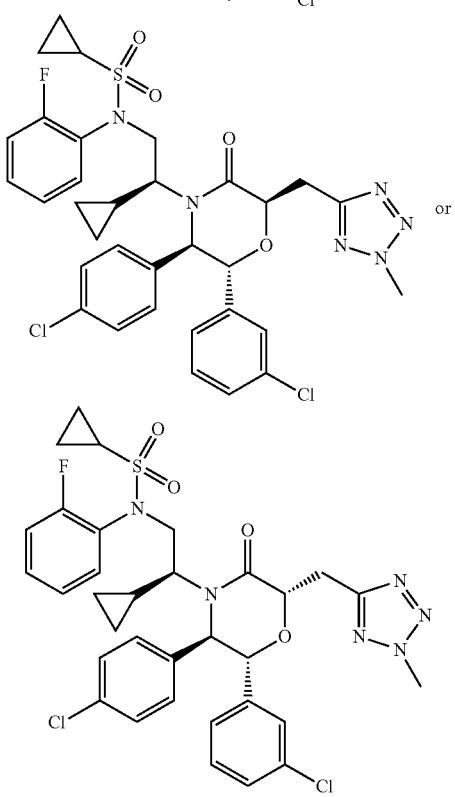

One of the title compounds was prepared from N-((S)-2-((2R,5R,6R)-2-((1H-tetrazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide or N-((S)-2-((2S,5R,6R)-2-((1H-tetrazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide (Example 399) by a procedure similar to that described in Example 400. The residue was purified by reverse phase preparatory HPLC (Agilient 1100, column: Gemini® 5 µm C₁₈, 100 mm×30 mm (Phenomenex, Torrance, Calif.), gradient elution of 45% to 70% acetonitrile in water, where both solvents contain 0.1% TFA, 25 minutes) to give one of the compounds as the first (faster) eluting isomer as a white powder. ¹H NMR (500 MHz, CDCl₃, δ ppm): −1.03 (br. s., 1H), −0.41 (br. s., 1H), 0.24 (br. s., 1H), 0.38 (br. s., 1H), 0.99 (d, J=3.91 Hz, 3H), 1.07 (br. s., 1H), 1.68 (br. s., 1H), 2.05 (br. s., 1H), 2.41-2.53 (m, 1H), 3.35 (dd, J=14.92, 8.31 Hz, 2H), 3.70 (dd, J=15.16, 4.89 Hz, 1H), 3.79 (d, J=12.23 Hz, 1H), 3.99 (s, 3H), 4.61 (d, J=10.03 Hz, 1H), 4.85 (dd, J=8.07, 5.14 Hz, 2H), 4.91 (d, J=9.78 Hz, 1H), 6.90 (d, J=7.34 Hz, 1H), 7.00 (d, J=6.85 Hz, 2H), 7.11 (s, 1H), 7.14-7.20 (m, 1H), 7.20-7.30 (m, 9H), 7.35-7.43 (m, 1H), 7.56 (t, J=7.58 Hz, 1H). MS (ESI) m/z=699 [M+1].

Example 408

N-((S)-2-((2R,3R,6R)-2-(3-Chlorophenyl)-3-(4-chlorophenyl)-6-((1-methyl-1H-tetrazol-5-yl)methyl)-5-oxomorpholino)-2-cyclopropylethyl)-N-(2-fluorophenyl)cyclopropanesulfonamide or N-((S)-2-((2S,3R,6R)-2-(3-chlorophenyl)-3-(4-chlorophenyl)-6-((1-methyl-1H-tetrazol-5-yl)methyl)-5-oxomorpholino)-2-cyclopropylethyl)-N-(2-fluorophenyl)cyclopropanesulfonamide or N-((S)-2-((2R,3R,6R)-2-(3-chlorophenyl)-3-(4-chlorophenyl)-6-((2-methyl-2H-tetrazol-5-yl)methyl)-5-oxomorpholino)-2-cyclopropylethyl)-N-(2-fluorophenyl)cyclopropanesulfonamide or N-((S)-2-((2R,3R,6R)-2-(3-chlorophenyl)-3-(4-chlorophenyl)-6-((2-methyl-2H-tetrazol-5-yl)methyl)-5-oxomorpholino)-2-cyclopropylethyl)-N-(2-fluorophenyl)cyclopropanesulfonamide

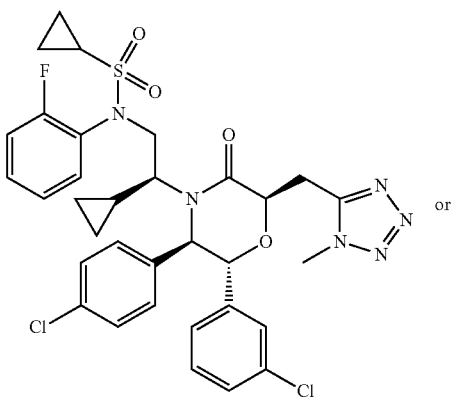

or

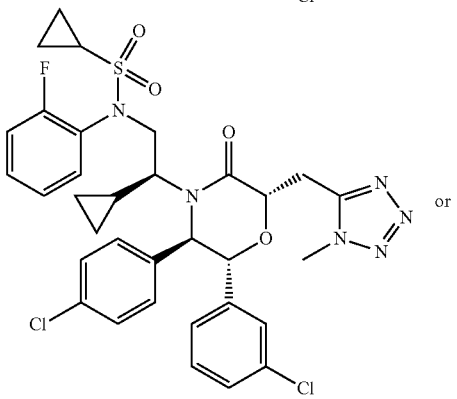

or

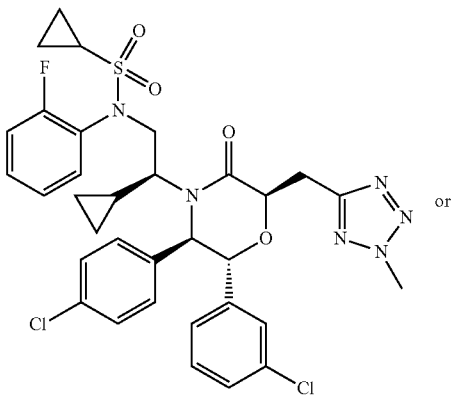

or

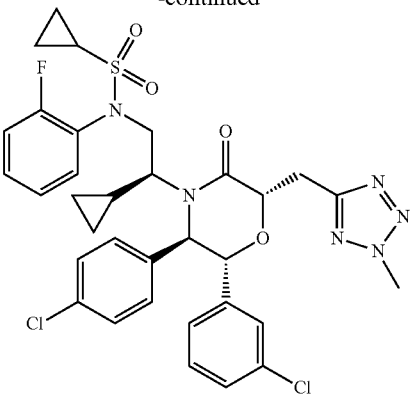

Further elution of the chromatographic separation described in Example 407 provided one of the title compounds as the second (slower) eluting isomer. $^1$H NMR (500 MHz, CDCl$_3$, δ ppm): −0.96 (br. s., 1H), −0.17 (br. s., 1H), 0.24 (br. s., 1H), 0.42 (br. s., 1H), 0.81-1.03 (m, 4H), 1.07 (br. s., 1H), 1.66 (br. s., 1H), 2.46 (br. s., 1H), 2.86 (br. s., 1H), 3.48 (d, J=14.18 Hz, 1H), 3.98 (s, 1H), 4.29 (s, 3H), 4.47-4.64 (m, 1H), 4.70 (d, J=10.03 Hz, 1H), 4.81-4.98 (m, 2H), 6.85 (br. s., 1H), 6.98-7.07 (m, 1H), 7.07-7.18 (m, 3H), 7.18-7.36 (m, 5H), 7.36-7.47 (m, 1H), 7.65 (br. s., 1H). MS (ESI) m/z=699 [M+1].

Example 409

N-((S)-2-((2R,3R,6S)-2-(3-Chlorophenyl)-3-(4-chlorophenyl)-5-oxo-6-(sulfamoylmethyl)morpholino)-2-cyclopropylethyl)-N-(2-fluorophenyl)cyclopropanesulfonamide or N-((S)-2-((2S,3R,6S)-2-(3-chlorophenyl)-3-(4-chlorophenyl)-5-oxo-6-(sulfamoylmethyl)morpholino)-2-cyclopropylethyl)-N-(2-fluorophenyl)cyclopropanesulfonamide

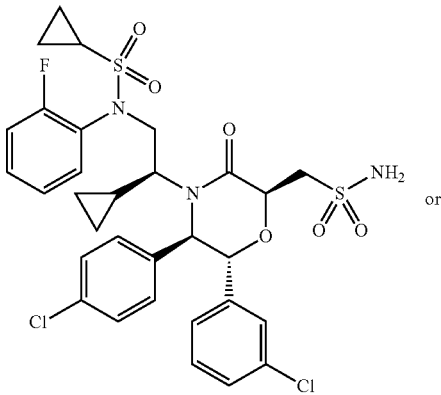

or

-continued

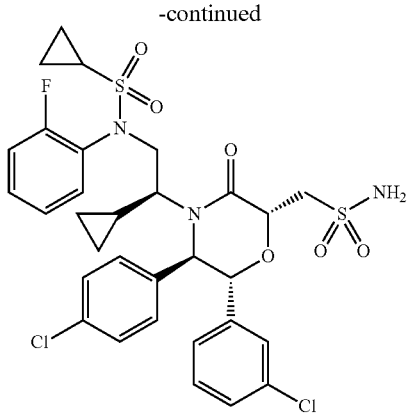

Step A. (2S,5R,6R)-Ethyl 6-(3-chlorophenyl)-5-(4-chlorophenyl)-4-((S)-1-cyclopropyl-2-(N-(2-fluorophenyl)cyclopropanesulfonamido)ethyl)-3-oxomorpholine-2-carboxylate and (2R,5R,6R)-ethyl 6-(3-chlorophenyl)-5-(4-chlorophenyl)-4-((S)-1-cyclopropyl-2-(N-(2-fluorophenyl)cyclopropanesulfonamido)ethyl)-3-oxomorpholine-2-carboxylate

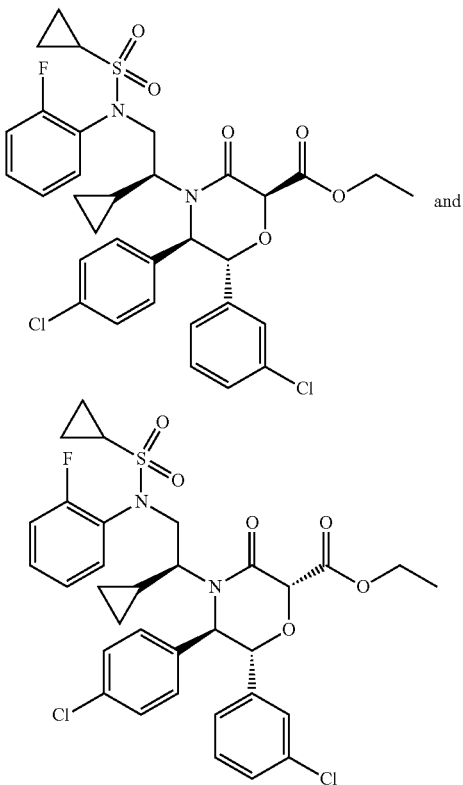

Lithium bis(trimethylsilyl)amide (1.0 M in THF, 1.471 mL, 1.471 mmol) was added to a solution of N-((S)-2-((2R,3R)-2-(3-chlorophenyl)-3-(4-chlorophenyl)-5-oxomorpholino)-2-cyclopropylethyl)-N-(2-fluorophenyl)cyclopropanesulfonamide (0.740 g, 1.226 mmol, Example 333, Step A) in THF (7.0 mL)-78° C. Ethyl chloroformate (0.152 mL, 1.594 mmol) was added, and the mixture was stirred at −78° C. for 3 hours. The mixture was quenched with saturated NH₄Cl and extracted with ethyl acetate. The organic layer was dried over MgSO₄, filtered, and concentrated. The residue was purified by flash chromatography on silica gel (gradient elution of 20% to 45% ethyl acetate in hexanes) to give the title compounds.

Step B. N-((S)-2-((2R,3R,6S)-2-(3-Chlorophenyl)-3-(4-chlorophenyl)-6-(hydroxymethyl)-5-oxomorpholino)-2-cyclopropylethyl)-N-(2-fluorophenyl)cyclopropanesulfonamide and N-((S)-2-((2S,3R,6S)-2-(3-chlorophenyl)-3-(4-chlorophenyl)-6-(hydroxymethyl)-5-oxomorpholino)-2-cyclopropylethyl)-N-(2-fluorophenyl)cyclopropanesulfonamide

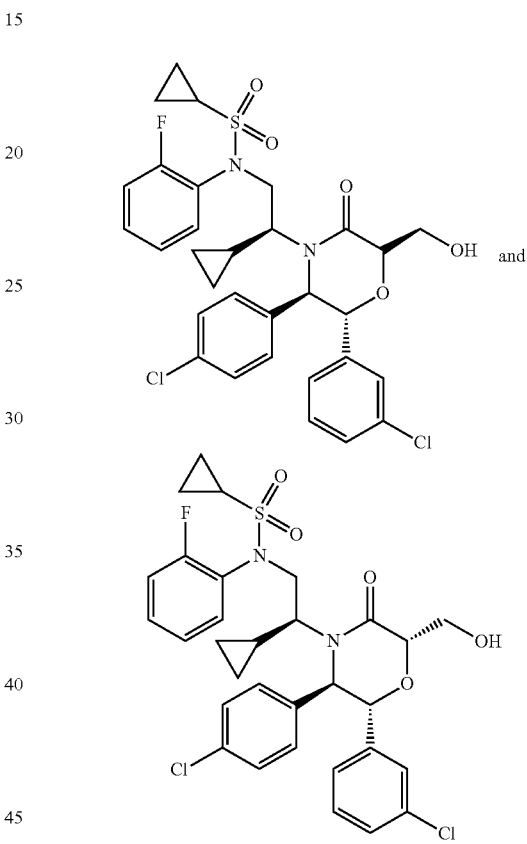

Sodium borohydride (0.028 g, 0.740 mmol) and calcium chloride hydrate (0.048 g, 0.370 mmol) were added to a solution of (2S,5R,6R)-ethyl 6-(3-chlorophenyl)-5-(4-chlorophenyl)-4-((S)-1-cyclopropyl-2-(N-(2-fluorophenyl)cyclopropanesulfonamido)ethyl)-3-oxomorpholine-2-carboxylate and (2R,5R,6R)-ethyl 6-(3-chlorophenyl)-4-((S)-1-cyclopropyl-2-(N-(2-fluorophenyl)cyclopropanesulfonamido)ethyl)-3-oxomorpholine-2-carboxylate (0.250 g, 0.370 mmol, Example 409, Step A) in methanol (5 mL) at 0° C. under Ar(g). After stirring at 0° C. for 1 hour, the mixture was quenched with saturated aqueous NH₄Cl and diluted with ethyl acetate. The mixture was stirred at room temperature for 30 minutes. The layers were separated, and the aqueous layer was extracted with ethyl acetate (2×). The combined organic layers were washed with brine, dried over MgSO₄, filtered, and concentrated The residue was purified by flash chromatography on silica gel (12 g column; gradient elution of 35% to 50% ethyl acetate in hexanes) to give the title compounds.

Step C. N-((S)-2-((2R,3R,6S)-2-(3-Chlorophenyl)-3-(4-chlorophenyl)-5-oxo-6-(sulfamoylmethyl)morpholino)-2-cyclopropylethyl)-N-(2-fluorophenyl)cyclopropanesulfonamide or N-((S)-2-((2S,3R,6S)-2-(3-chlorophenyl)-3-(4-chlorophenyl)-5-oxo-6-(sulfamoylmethyl)morpholino)-2-cyclopropylethyl)-N-(2-fluorophenyl)cyclopropanesulfonamide

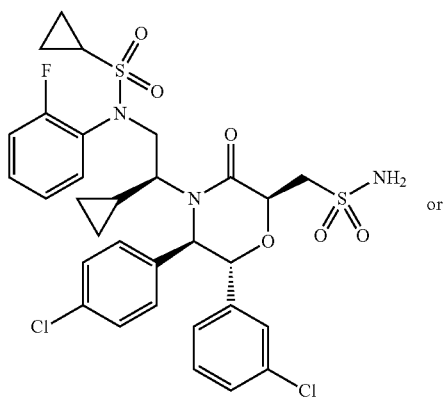

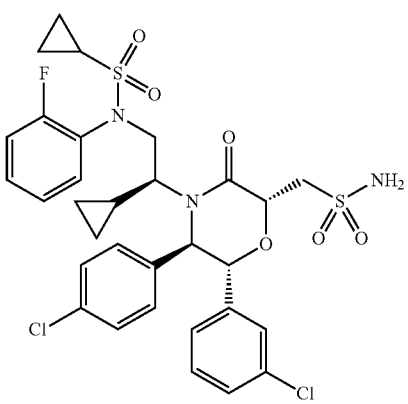

One of the title compounds was prepared from N-((S)-2-((2R,3R,6S)-2-(3-chlorophenyl)-3-(4-chlorophenyl)-6-(hydroxymethyl)-5-oxomorpholino)-2-cyclopropylethyl)-N-(2-fluorophenyl)cyclopropanesulfonamide and N-((S)-2-((2S,3R,6S)-2-(3-chlorophenyl)-3-(4-chlorophenyl)-6-(hydroxymethyl)-5-oxomorpholino)-2-cyclopropylethyl)-N-(2-fluorophenyl)cyclopropanesulfonamide (Example 409, Step B) by procedures similar to those described in Example 214, Steps E and F, replacing dimethylamine hydrochloride in Step F with ammonia. The residue was purified by reverse phase preparatory HPLC (Agilient 1100, column: Gemini® 5 µm $C_{18}$, 100 mm×30 mm (Phenomenex, Torrance, Calif.), gradient elution of 40% to 60% acetonitrile in water, where both solvents contain 0.1% TFA, 25 minutes) to give one of the compounds as the first (faster) eluting isomer. $^1$H NMR (500 MHz, CDCl$_3$, δ ppm): −1.01 (br. s., 1H), −0.35 (br. s., 1H), 0.25 (br. s., 1H), 0.39 (br. s., 1H), 0.84-1.07 (m, 5H), 1.67 (br. s., 1H), 2.30-2.49 (m, 1H), 3.83 (m, 3H), 4.74 (d, J=10.03 Hz, 2H), 4.80-5.04 (m, 2H), 6.85-6.98 (m, 1H), 7.02-7.13 (m, 4H), 7.18-7.42 (m, 6H), 7.50-7.60 (m, 1H). MS (ESI) m/z=696 [M+1].

Example 410

N-((S)-2-((2R,3R,6S)-2-(3-Chlorophenyl)-3-(4-chlorophenyl)-5-oxo-6-(sulfamoylmethyl)morpholino)-2-cyclopropylethyl)-N-(2-fluorophenyl)cyclopropanesulfonamide or N-((S)-2-((2S,3R,6S)-2-(3-chlorophenyl)-3-(4-chlorophenyl)-5-oxo-6-(sulfamoylmethyl)morpholino)-2-cyclopropylethyl)-N-(2-fluorophenyl)cyclopropanesulfonamide

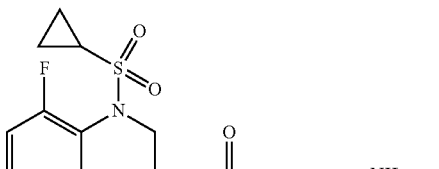

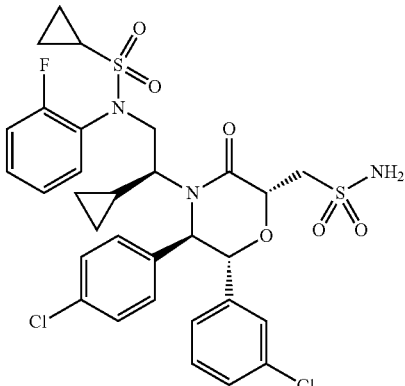

Further elution of the chromatographic separation described in Example 409, Step C provided one of the title compounds as the second (slower) eluting isomer. $^1$H NMR (500 MHz, CDCl$_3$, δ ppm): −0.71 (br. s., 1H), −0.04 (br. s., 1H), 0.35 (br. s., 1H), 0.48 (br. s., 1H), 0.87-1.11 (m, 5H), 1.43 (br. s., 1H), 2.35-2.52 (m, 1H), 3.73-3.95 (m, 3H), 4.64 (dd, J=8.44, 4.77 Hz, 1H), 4.83 (br. s., 1H), 4.90 (d, J=7.34 Hz, 1H), 5.08 (d, J=6.60 Hz, 1H), 7.01-7.14 (m, 1H), 7.16-7.35 (m, 9H), 7.36-7.40 (m, 1H), 7.54 (t, J=7.46 Hz, 1H). MS (ESI) m/z=696 [M+1].

Example 411

2-((2R,5R,6R)-4-((S)-2-(tert-Butylsulfonyl)-1-cyclopropylethyl)-5-(4-chloro-3-fluorophenyl)-6-(3-chlorophenyl)-2-methyl-3-oxomorpholin-2-yl)acetic acid or 2-((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)acetic acid

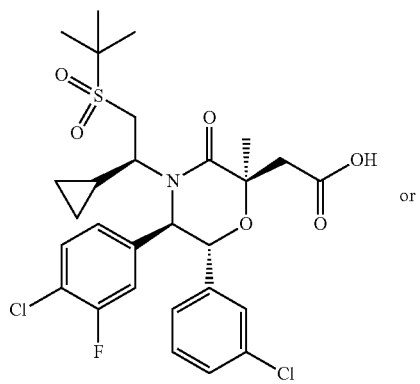

or

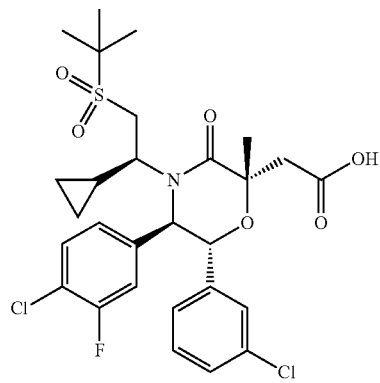

Step A. (2R,5R,6R)-2-Allyl-4-((S)-2-((tert-butyldimethylsilyl)oxy)-1-cyclopropylethyl)-5-(4-chloro-3-fluorophenyl)-6-(3-chlorophenyl)-2-methylmorpholin-3-one or (2S,5R,6R)-2-allyl-4-((S)-2-((tert-butyldimethylsilyl)oxy)-1-cyclopropylethyl)-5-(4-chloro-3-fluorophenyl)-6-(3-chlorophenyl)-2-methylmorpholin-3-one

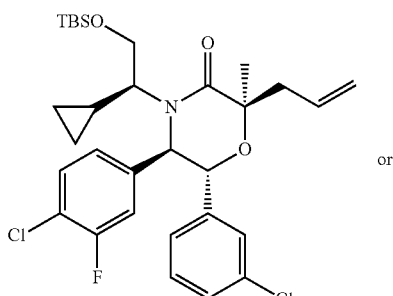

or

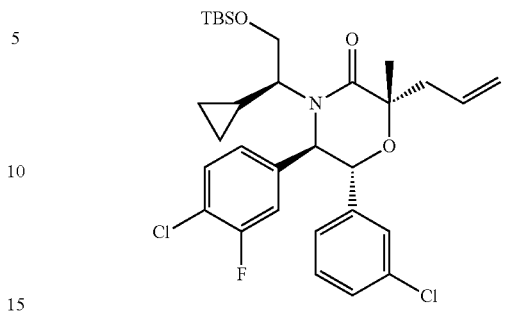

One of the title compounds was prepared from (5R,6R)-5-(4-chloro-3-fluorophenyl)-6-(3-chlorophenyl)-4-((S)-1-cyclopropyl-2-hydroxyethyl)morpholin-3-one (Example 308, Step B) by procedures similar to those described in Example 329, Steps A and B. The residue was purified by flash chromatography on silica gel (gradient elution of 5% to 10% ethyl acetate in hexanes) to give one of the title compounds as the first (faster) eluting isomer.

Step B. 2-((2R,5R,6R)-4-((S)-2-(tert-Butylsulfonyl)-1-cyclopropylethyl)-5-(4-chloro-3-fluorophenyl)-6-(3-chlorophenyl)-2-methyl-3-oxomorpholin-2-yl) acetic acid or 2-((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)acetic acid One of the title compounds was prepared from (2R,5R,6R)-2-allyl-4-((S)-2-((tert-butyldimethylsilyl)oxy)-1-cyclopropylethyl)-5-(4-chloro-3-fluorophenyl)-6-(3-chlorophenyl)-2-methylmorpholin-3-one or (2S,5R,6R)-2-allyl-4-((S)-2-((tert-butyldimethylsilyl)oxy)-1-cyclopropylethyl)-5-(4-chloro-3-fluorophenyl)-6-(3-chlorophenyl)-2-methylmorpholin-3-one (Example 411, Step A) by procedures similar to those described in Example 286, Steps B through D, replacing 4-mercaptopyridine in Step C with 2-methylpropane-2-thiol. The residue was purified by reverse phase preparatory HPLC (Agilient 1100, column: Gemini® 5 μm $C_{18}$, 100 mm×30 mm (Phenomenex, Torrance, Calif.), gradient elution of 25% to 75% acetonitrile in water, where both solvents contain 0.1% TFA, 30 minutes) to give one of the compounds. $^1$H NMR (400 MHz, CDCl$_3$, δ ppm): 7.31 (br, 3H), 7.20-7.17 (m, 1H), 7.12-7.02 (m, 2H), 6.86 (d, J=7.6, 1H), 5.11-5.01 (m, 2H), 4.22 (t, J=12.3 Hz, 1H), 3.23 (d, J=15.5 Hz, 1H), 3.07-2.94 (m, 2H), 2.73 (br, 1H), 2.00 (br, 1H), 1.75 (s, 3H), 1.43 (s, 9H), 0.54-0.40 (m, 2H), −0.19 (br, 1H), −0.63 (br, 1H). MS (ESI) m/z=600 [M+1].

Example 412

2-((2R,5R,6R)-4-((S)-2-(tert-Butylsulfonyl)-1-cyclopropylethyl)-5-(4-chloro-3-fluorophenyl)-6-(3-chlorophenyl)-2-methyl-3-oxomorpholin-2-yl)acetic acid or 2-((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)acetic acid

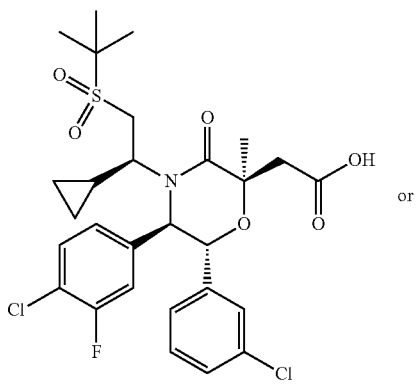

or

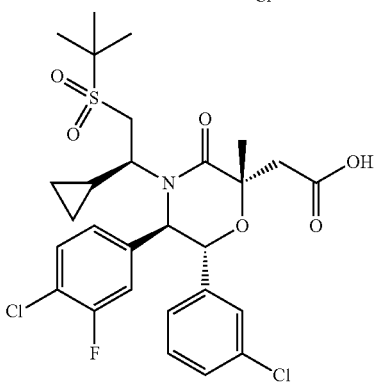

Step A. (2R,5R,6R)-2-Allyl-4-((S)-2-((tert-butyldimethylsilyl)oxy)-1-cyclopropylethyl)-5-(4-chloro-3-fluorophenyl)-6-(3-chlorophenyl)-2-methylmorpholin-3-one or (2S,5R,6R)-2-allyl-4-((S)-2-((tert-butyldimethylsilyl)oxy)-1-cyclopropylethyl)-5-(4-chloro-3-fluorophenyl)-6-(3-chlorophenyl)-2-methylmorpholin-3-one

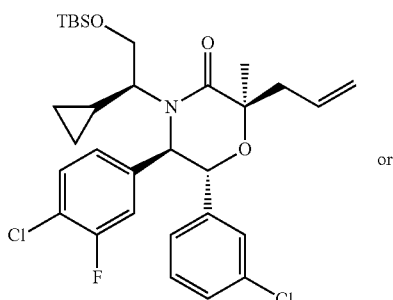

or

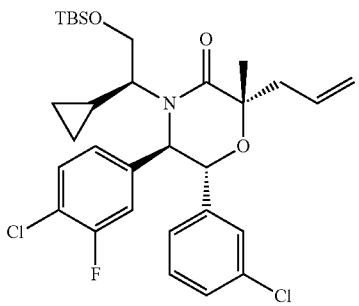

Further elution of the chromatographic separation described in Example 411, Step A provided one of the title compounds as the second (slower) eluting isomer.

Step B. 2-((2R,5R,6R)-4-((S)-2-(tert-Butylsulfonyl)-1-cyclopropylethyl)-5-(4-chloro-3-fluorophenyl)-6-(3-chlorophenyl)-2-methyl-3-oxomorpholin-2-yl) acetic acid or 2-((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)acetic acid One of the title compounds was prepared from (2R,5R,6R)-2-allyl-4-((S)-2-((tert-butyldimethylsilyl)oxy)-1-cyclopropylethyl)-5-(4-chloro-3-fluorophenyl)-6-(3-chlorophenyl)-2-methylmorpholin-3-one or (2S,5R,6R)-2-allyl-4-((S)-2-((tert-butyldimethylsilyl)oxy)-1-cyclopropylethyl)-5-(4-chloro-3-fluorophenyl)-6-(3-chlorophenyl)-2-methylmorpholin-3-one (Example 412, Step A) by procedures similar to those described in Example 286, B through D, replacing 4-mercaptopyridine in Step C with 2-methylpropane-2-thiol. The residue was purified by reverse phase preparatory HPLC (Agilient 1100, column: Gemini® 5 μm $C_{18}$, 100 mm×30 mm (Phenomenex, Torrance, Calif.), gradient elution of 25% to 75% acetonitrile in water, where both solvents contain 0.1% TFA, 30 minutes) to give one of the compounds. $^1$H NMR (500 MHz, CDCl$_3$, δ ppm): 7.31 (br, 3H), 7.21 (d, J=7.6 Hz, 1H), 7.12 (t, J=7.8 Hz, 1H), 7.04 (s, 1H), 6.84 (d, J=7.8 Hz, 1H), 5.02-4.87 (m, 2H), 4.17 (br, 1H), 3.21-3.15 (m, 2H), 3.07-3.03 (m, 1H), 2.64 (br, 1H), 2.01 (br, 1H), 1.79 (s, 3H), 1.43 (s, 9H), 0.51-0.45 (m, 2H), −0.02 (br, 1H), −0.54 (br, 1H). MS (ESI) m/z=600 [M+1].

Example 413

2-((2R,5R,6R)-6-(3-Chlorophenyl)-5-(4-chlorophenyl)-4-((2S,3S)-2-(isopropylsulfonyl)pentan-3-yl)-3-oxomorpholin-2-yl)acetic acid or 2-((2S,5R,6R)-6-(3-chlorophenyl)-5-(4-chlorophenyl)-4-((2S,3S)-2-(isopropylsulfonyl)pentan-3-yl)-3-oxomorpholin-2-yl)acetic acid or 2-((2R,5R,6R)-6-(3-chlorophenyl)-5-(4-chlorophenyl)-4-((2R,3S)-2-(isopropylsulfonyl)pentan-3-yl)-3-oxomorpholin-2-yl)acetic acid or 2-((2S,5R,6R)-6-(3-chlorophenyl)-5-(4-chlorophenyl)-4-((2R,3S)-2-(isopropylsulfonyl)pentan-3-yl)-3-oxomorpholin-2-yl)acetic acid

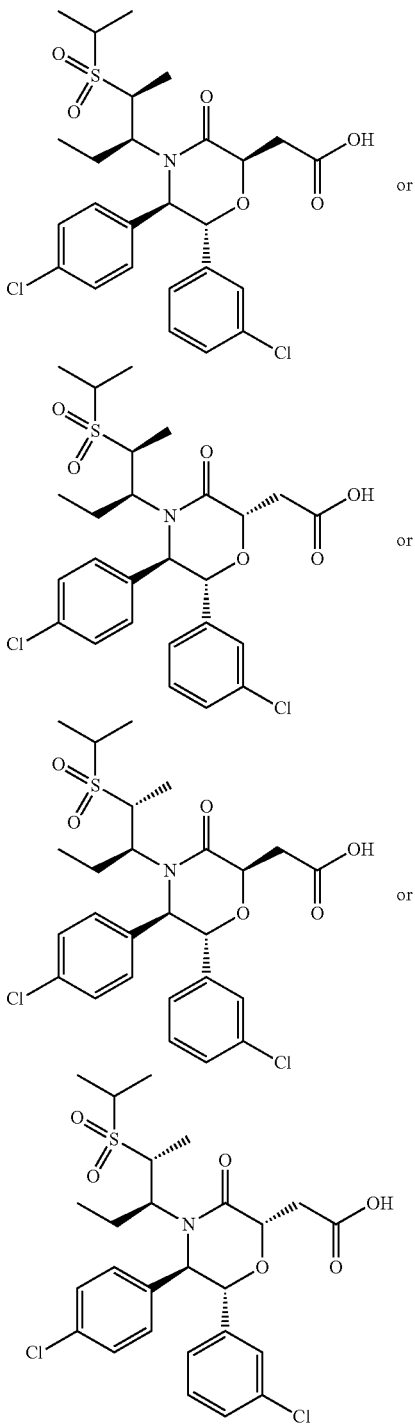

Step A. (S)-2-((2R,3R)-2-(3-Chlorophenyl)-3-(4-chlorophenyl)-5-oxomorpholino)butanal

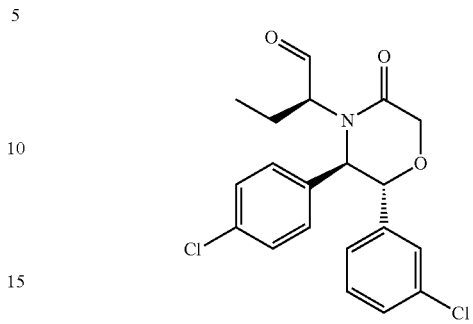

The title compound was prepared from (5R,6R)-6-(3-Chlorophenyl)-5-(4-chlorophenyl)-4-((S)-1-hydroxybutan-2-yl)morpholin-3-one (Example 112, Step C) by a procedure similar to that described in Example 243, Step B.

Step B. (5R,6R)-6-(3-Chlorophenyl)-5-(4-chlorophenyl)-4-((2S,3S)-2-hydroxypentan-3-yl)morpholin-3-one and (5R,6R)-6-(3-chlorophenyl)-5-(4-chlorophenyl)-4-((2R,3S)-2-hydroxypentan-3-yl)morpholin-3-one

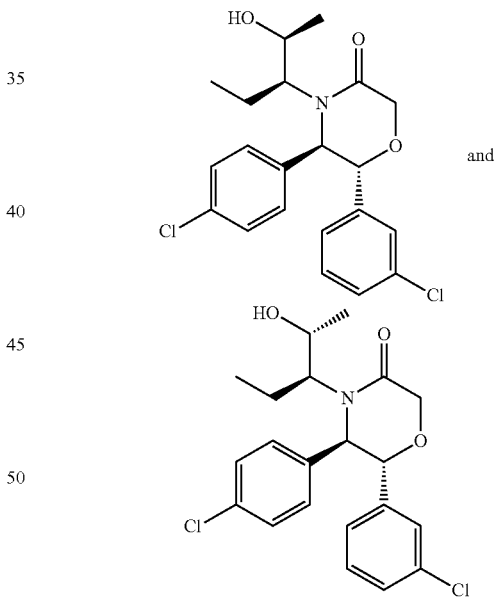

Methylmagnesium chloride (22 wt % in THF, 0.610 mL, 1.816 mmol) was added to a solution of (S)-2-((2R,3R)-2-(3-chlorophenyl)-3-(4-chlorophenyl)-5-oxomorpholino)butanal (475 mg, 1.211 mmol, Example 413, Step A) in THF (2.422 mL) at 0° C. After stirring at 0° C. for 1 hour, the mixture was diluted with water (30 mL) and extracted with diethyl ether (3×30 mL). The combined organic layers were dried over MgSO₄, filtered, and concentrated. The residue was purified by flash chromatography on silica gel (80 g column; gradient elution of 5% to 25% acetone in hexanes) to give the title compounds as light-yellow oil.

663

Step C. S-((2S,3S)-3-((2R,3R)-2-(3-Chlorophenyl)-3-(4-chlorophenyl)-5-oxomorpholino)pentan-2-yl)ethanethioate and S-42R,3S)-3-((2R,3R)-2-(3-chlorophenyl)-3-(4-chlorophenyl)-5-oxomorpholino)pentan-2-yl)ethanethioate

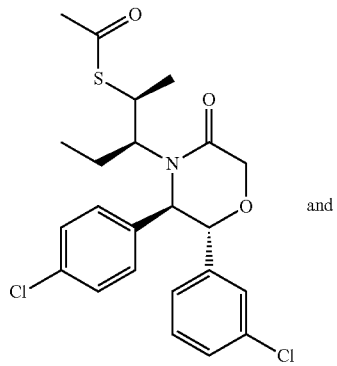

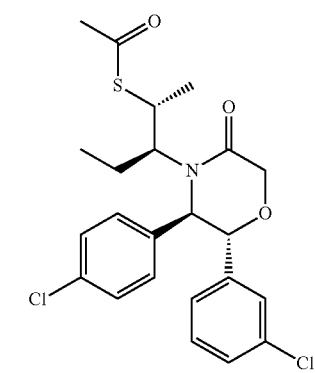

Methanesulfonyl chloride (0.0709 mL, 0.916 mmol) and triethylamine (0.127 mL, 0.916 mmol) were added to a solution of (5R,6R)-6-(3-chlorophenyl)-5-(4-chlorophenyl)-4-((2S,3S)-2-hydroxypentan-3-yl)morpholin-3-one and (5R,6R)-6-(3-chlorophenyl)-5-(4-chlorophenyl)-4-((2R,3S)-2-hydroxypentan-3-yl)morpholin-3-one (0.127 mL, 0.916 mmol, Example 413, Step B) in dichloromethane (0.833 mL) at 0° C. After stirring at 0° C. for 1 hour, the mixture was diluted with water. The layers were separated, and the aqueous layer was extracted with dichloromethane (3×10 mL). The combined organic layers were dried over MgSO$_4$, filtered, and concentrated. Thioacetic acid (2.381 mL, 33.3 mmol) was added and the neat mixture was heated to 90° C. for 5 days. The residue was purified by flash chromatography on silica gel (40 g column; gradient elution of 0% to 10% acetone in hexanes) to give the title compounds.

664

Step D. (5R,6R)-6-(3-Chlorophenyl)-5-(4-chlorophenyl)-4-((2S,3S)-2-mercaptopentan-3-yl)morpholin-3-one and (5R,6R)-6-(3-chlorophenyl)-5-(4-chlorophenyl)-4-((2R,3S)-2-mercaptopentan-3-yl)morpholin-3-one

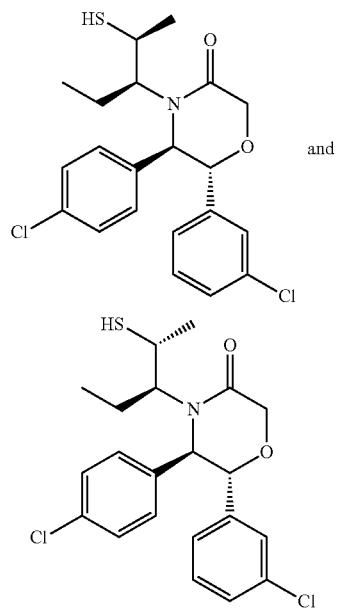

Lithium hydroxide (2.0 M in water, 0.489 mL, 0.489 mmol) was added to a solution of S-((2S,3S)-3-((2R,3R)-2-(3-chlorophenyl)-3-(4-chlorophenyl)-5-oxomorpholino)pentan-2-yl)ethanethioate and S-42R,3S)-3-((2R,3R)-2-(3-chlorophenyl)-3-(4-chlorophenyl)-5-oxomorpholino)pentan-2-yl)ethanethioate (190 mg, 0.407 mmol, Example 413, Step C) in THF (1.400 mL), MeOH (1.400 mL), and water (1.400 mL) at room temperature. After stirring at room temperature for 2.25 hours, the mixture was quenched with citric acid (10% aqueous, 2 mL). The mixture was extracted with diethyl ether (3×20 mL). The combined organic layers were dried over MgSO$_4$, filtered, and concentrated to give the title compounds as a colorless foam.

Step E. (5R,6R)-6-(3-Chlorophenyl)-5-(4-chlorophenyl)-4-((2S,3S)-2-(isopropylthio)pentan-3-yl)morpholin-3-one or (5R,6R)-6-(3-chlorophenyl)-5-(4-chlorophenyl)-4-((2R,3S)-2-(isopropylthio)pentan-3-yl)morpholin-3-one

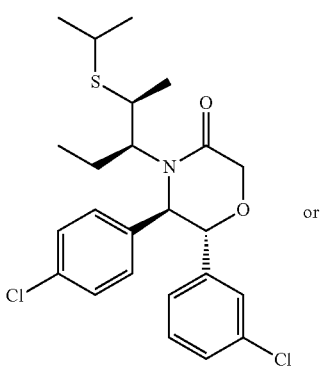

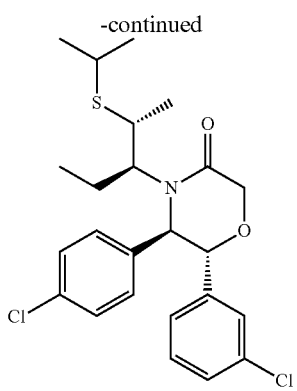

2-Iodopropane (0.0454 mL, 0.454 mmol) and DBU (0.077 mL, 0.510 mmol) were added to a solution of (5R,6R)-6-(3-chlorophenyl)-5-(4-chlorophenyl)-4-((2S,3S)-2-mercaptopentan-3-yl)morpholin-3-one and (5R,6R)-6-(3-chlorophenyl)-5-(4-chlorophenyl)-4-((2R,3S)-2-mercaptopentan-3-yl)morpholin-3-one (173 mg, 0.408 mmol, Example 413, Step D) in THF (2 mL) under Ar(g). The mixture was stirred at room temperature overnight. Additional DBU (0.077 mL, 0.510 mmol) and 2-iodopropane (0.0454 mL, 0.454 mmol) were added and the mixture was stirred at room temperature for 6 hours. The mixture was concentrated, and the residue was purified by reverse phase preparatory HPLC (Agilient 1100, column: Gemini® 5 µm C$_{18}$, 100 mm×30 mm (Phenomenex, Torrance, Calif.), gradient elution of 50% to 90% acetonitrile in water, where both solvents contain 0.1% TFA, 30 minutes) to give one of the title compounds as the first (faster) eluting isomer.

Step F. 2-((2R,5R,6R)-6-(3-Chlorophenyl)-5-(4-chlorophenyl)-4-((2S,3S)-2-(isopropylsulfonyl)pentan-3-yl)-3-oxomorpholin-2-yl)acetic acid or 2-((2S,5R,6R)-6-(3-chlorophenyl)-5-(4-chlorophenyl)-4-((2S,3S)-2-(isopropylsulfonyl)pentan-3-yl)-3-oxomorpholin-2-yl)acetic acid or 2-((2R,5R,6R)-6-(3-chlorophenyl)-5-(4-chlorophenyl)-4-((2R,3S)-2-(isopropylsulfonyl)pentan-3-yl)-3-oxomorpholin-2-yl)acetic acid or 2-((2S,5R,6R)-6-(3-chlorophenyl)-5-(4-chlorophenyl)-4-((2R,3S)-2-(isopropylsulfonyl)pentan-3-yl)-3-oxomorpholin-2-yl)acetic acid

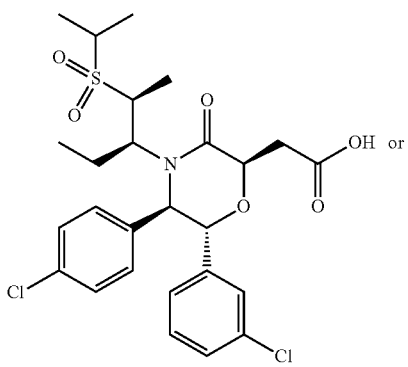

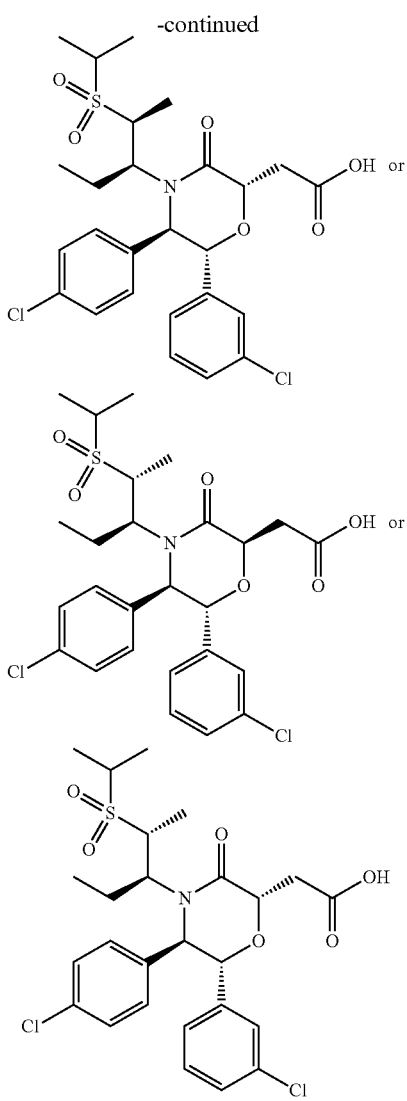

One of the title compounds was prepared from (5R,6R)-6-(3-chlorophenyl)-5-(4-chlorophenyl)-4-((2S,3S)-2-(isopropylthio)pentan-3-yl)morpholin-3-one or (5R,6R)-6-(3-chlorophenyl)-5-(4-chlorophenyl)-4-((2R,3S)-2-(isopropylthio)pentan-3-yl)morpholin-3-one (Example 413, Step E) by procedures similar to those described in Example 112, Steps E and F. The residue was purified by reverse phase preparatory HPLC (Agilient 1100, column: Gemini® 5 µm C$_{18}$, 100 mm×30 mm (Phenomenex, Torrance, Calif.), gradient elution of 25% to 75% acetonitrile in water, where both solvents contain 0.1% TFA, 30 minutes) to give one of the compounds as the first (faster) eluting isomer as a white foam. $^1$H NMR (400 MHz, CDCl$_3$, δ ppm): 7.46 (s, 1H), 7.39 (s, 5H), 7.19-7.28 (m, 2H), 5.22 (d, J=5.09 Hz, 1H), 4.99 (d, J=5.09 Hz, 1H), 4.75 (dd, J=5.09, 7.24 Hz, 1H), 3.63 (br. s., 1H), 3.33 (quin, J=6.75 Hz, 2H), 3.04-3.25 (m, 2H), 2.10 (quin, J=7.29 Hz, 2H), 1.47 (dd, J=7.04, 10.96 Hz, 6H), 1.34 (d, J=6.65 Hz, 3H), 0.59 (t, J=7.43 Hz, 3H). MS (ESI) m/z=556.7 [M+1].

Example 414

2-((2R,5R,6R)-6-(3-Chlorophenyl)-5-(4-chlorophenyl)-4-((2S,3S)-2-(isopropylsulfonyl)pentan-3-yl)-3-oxomorpholin-2-yl)acetic acid or 2-((2S,5R,6R)-6-(3-chlorophenyl)-5-(4-chlorophenyl)-4-((2S,3S)-2-(isopropylsulfonyl)pentan-3-yl)-3-oxomorpholin-2-yl)acetic acid or 2-((2R,5R,6R)-6-(3-chlorophenyl)-5-(4-chlorophenyl)-4-((2R,3S)-2-(isopropylsulfonyl)pentan-3-yl)-3-oxomorpholin-2-yl)acetic acid or 2-((2S,5R,6R)-6-(3-chlorophenyl)-5-(4-chlorophenyl)-4-((2R,3S)-2-(isopropylsulfonyl)pentan-3-yl)-3-oxomorpholin-2-yl)acetic acid

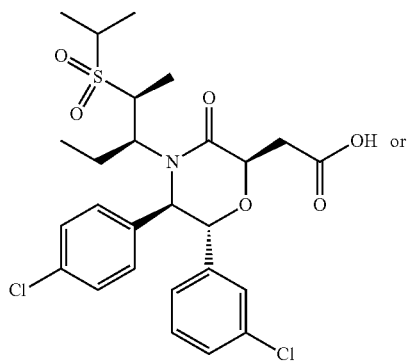 or

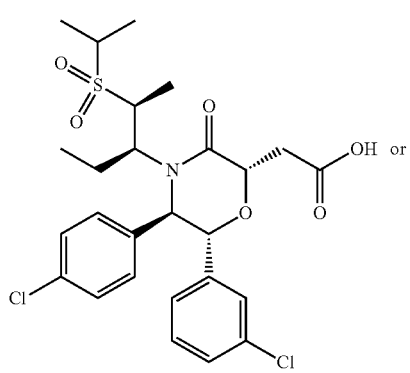 or

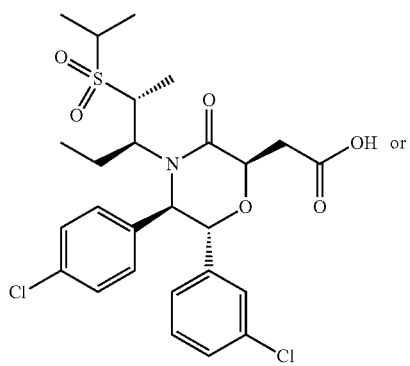 or

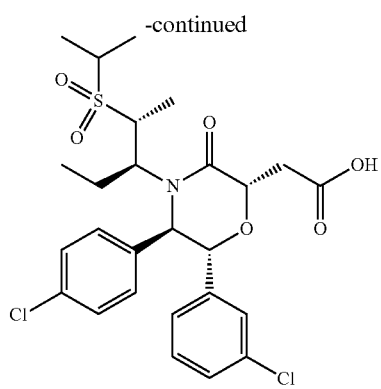

Further elution of the chromatographic separation described in Example 413, Step F provided one of the title compounds as the second (slower) eluting isomer as a white foam. ¹H NMR (400 MHz, CDCl₃, δ ppm): 7.29-7.38 (m, 2H), 7.20-7.25 (m, 1H), 7.05-7.18 (m 4H), 6.80 (d, J=7.63 Hz, 1H), 4.94 (d, J=9.59 Hz, 1H), 4.79 (t, J=6.06 Hz, 1H), 4.70 (d, J=9.98 Hz, 1H), 3.05-3.35 (m, J=6.65 Hz, 4H), 2.93 (dd, J=5.67, 16.24 Hz, 1H), 2.03-2.23 (m, 2H), 1.52 (d, J=7.04 Hz, 3H), 1.40 (d, J=6.85 Hz, 3H), 1.30 (d, J=6.85 Hz, 3H), 0.60 (t, J=7.24 Hz, 3H). MS (ESI) m/z=556.2 [M+1].

Example 415

2-((2R,5R,6R)-6-(3-Chlorophenyl)-5-(4-chlorophenyl)-4-((2S,3S)-2-(isopropylsulfonyl)pentan-3-yl)-3-oxomorpholin-2-yl)acetic acid or 2-((2S,5R,6R)-6-(3-chlorophenyl)-5-(4-chlorophenyl)-4-((2S,3S)-2-(isopropylsulfonyl)pentan-3-yl)-3-oxomorpholin-2-yl)acetic acid or 2-((2R,5R,6R)-6-(3-chlorophenyl)-5-(4-chlorophenyl)-4-((2R,3S)-2-(isopropylsulfonyl)pentan-3-yl)-3-oxomorpholin-2-yl)acetic acid or 2-((2S,5R,6R)-6-(3-chlorophenyl)-5-(4-chlorophenyl)-4-((2R,3S)-2-(isopropylsulfonyl)pentan-3-yl)-3-oxomorpholin-2-yl)acetic acid

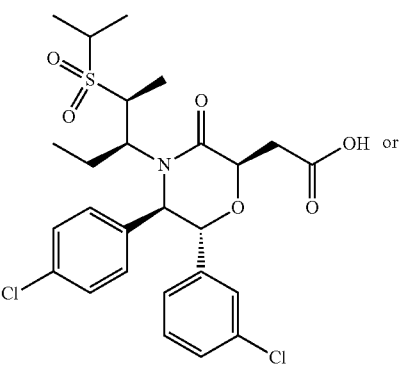 or

-continued

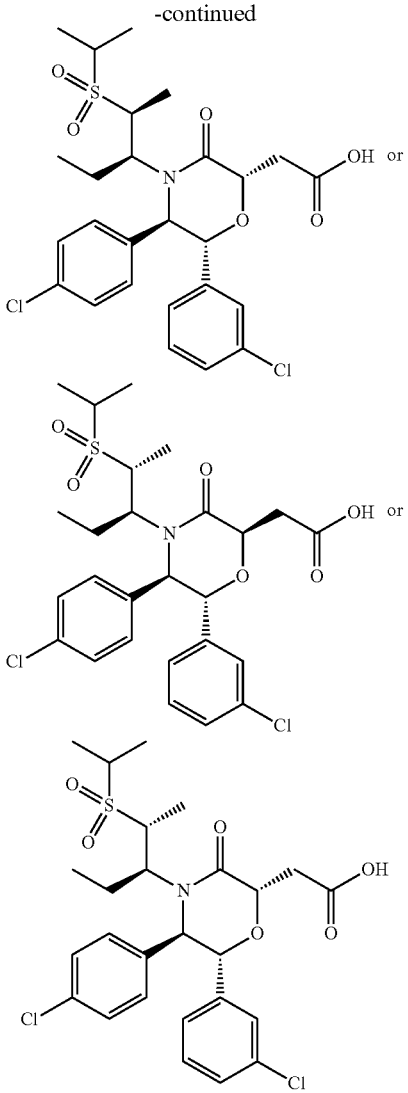

Step A. (5R,6R)-6-(3-Chlorophenyl)-5-(4-chlorophenyl)-4-((2S,3S)-2-(isopropylthio)pentan-3-yl)morpholin-3-one or (5R,6R)-6-(3-chlorophenyl)-5-(4-chlorophenyl)-4-((2R,3S)-2-(isopropylthio)pentan-3-yl)morpholin-3-one

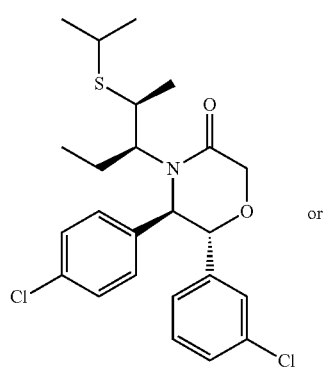

-continued

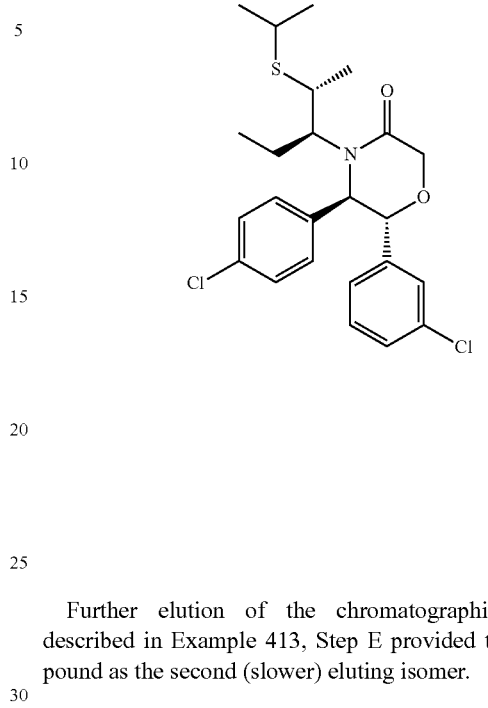

Further elution of the chromatographic separation described in Example 413, Step E provided the title compound as the second (slower) eluting isomer.

Step B. 2-((2R,5R,6R)-6-(3-Chlorophenyl)-5-(4-chlorophenyl)-4-((2S,3S)-2-(isopropylsulfonyl)pentan-3-yl)-3-oxomorpholin-2-yl)acetic acid or 2-((2S, 5R,6R)-6-(3-chlorophenyl)-5-(4-chlorophenyl)-4-((2S,3S)-2-(isopropylsulfonyl)pentan-3-yl)-3-oxomorpholin-2-yl)acetic acid or 2-((2R,5R,6R)-6-(3-chlorophenyl)-5-(4-chlorophenyl)-4-((2R,3S)-2-(isopropylsulfonyl)pentan-3-yl)-3-oxomorpholin-2-yl)acetic acid or 2-((2S,5R,6R)-6-(3-chlorophenyl)-5-(4-chlorophenyl)-4-((2R,3S)-2-(isopropylsulfonyl)pentan-3-yl)-3-oxomorpholin-2-yl)acetic acid One of title compounds was prepared from (5R,6R)-6-(3-chlorophenyl)-5-(4-chlorophenyl)-4-((2S,3S)-2-(isopropylthio)pentan-3-yl)morpholin-3-one or (5R,6R)-6-(3-chlorophenyl)-5-(4-chlorophenyl)-4-((2R,3S)-2-(isopropylthio) pentan-3-yl)morpholin-3-one (Example 415, Step A) by procedures similar to those described in Example 112, Steps E and F. The residue was purified by reverse phase preparatory HPLC (Agilent 1100, column: Gemini® 5 μm $C_{18}$, 100 mm×30 mm (Phenomenex, Torrance, Calif.), gradient elution of 25% to 75% acetonitrile in water, where both solvents contain 0.1% TFA, 30 minutes) to give one of the compounds as the first (faster) eluting isomer as a white foam. $^1$H NMR (400 MHz, $CDCl_3$, δ ppm): 7.43 (d, J=8.41 Hz, 2H), 7.32-7.40 (m, 3H), 7.27-7.30 (m, 1H), 7.21 (d, J=14.87 Hz, 2H), 5.22 (d, J=4.69 Hz, 1H), 5.03 (d, J=4.50 Hz, 1H), 4.59 (t, J=5.97 Hz, 1H), 3.83 (quin, J=6.55 Hz, 1H), 3.37-3.45 (m, J=5.87 Hz, 1H), 3.33 (td, J=6.70, 13.60 Hz, 1H), 3.11 (dd, J=2.64, 5.97 Hz, 2H), 1.76-1.98 (m, 2H), 1.46 (d, J=6.85 Hz, 3H), 1.37-1.44 (m, 6H), 0.43 (t, J=7.53 Hz, 3H). MS (ESI) m/z=556.2 [M+1].

Example 416

2-((2R,5R,6R)-6-(3-Chlorophenyl)-5-(4-chlorophenyl)-4-((2S,3S)-2-(isopropylsulfonyl)pentan-3-yl)-3-oxomorpholin-2-yl)acetic acid or 2-((2S,5R,6R)-6-(3-chlorophenyl)-5-(4-chlorophenyl)-4-((2S,3S)-2-(isopropylsulfonyl)pentan-3-yl)-3-oxomorpholin-2-yl)acetic acid or 2-((2R,5R,6R)-6-(3-chlorophenyl)-5-(4-chlorophenyl)-4-((2R,3S)-2-(isopropylsulfonyl)pentan-3-yl)-3-oxomorpholin-2-yl)acetic acid or 2-((2S,5R,6R)-6-(3-chlorophenyl)-5-(4-chlorophenyl)-4-((2R,3S)-2-(isopropylsulfonyl)pentan-3-yl)-3-oxomorpholin-2-yl)acetic acid

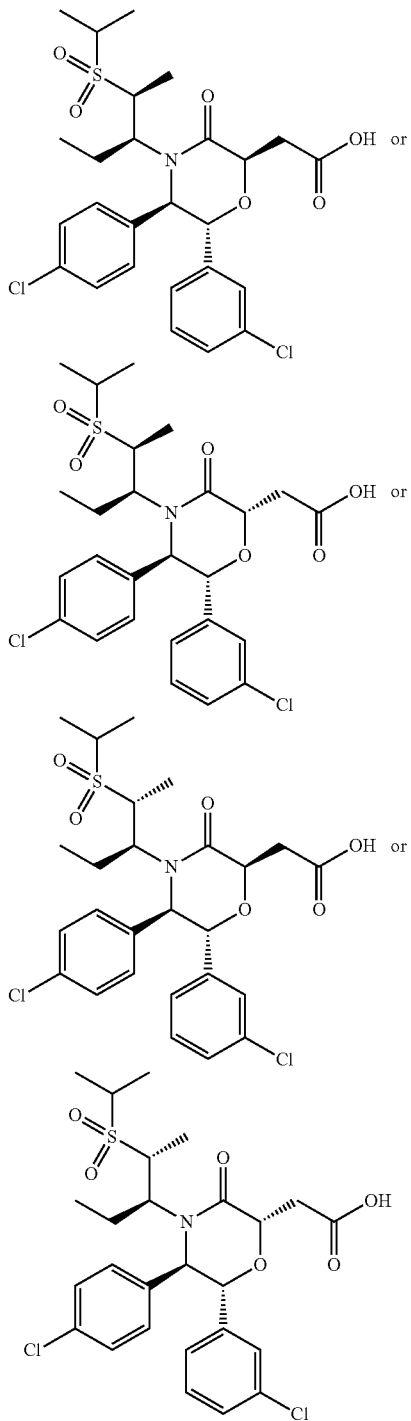

Further elution of the chromatographic separation described in Example 415, Step B provided one of the title compounds as the second (slower) eluting isomer as a white foam. $^1$H NMR (400 MHz, CDCl$_3$, δ ppm): 7.29-7.37 (m, 2H), 7.02-7.23 (m, 5H), 6.82 (d, J=7.83 Hz, 1H), 5.05 (d, J=9.78 Hz, 1H), 4.67-4.82 (m, 2H), 4.16 (s, 1H), 3.08-3.41 (m, 3H), 2.99 (dd, J=5.09, 16.43 Hz, 1H), 1.89-2.05 (m, 1H), 1.78 (s, 1H), 1.24-1.51 (m, 9H), 0.47 (t, J=7.63 Hz, 3H). MS (ESI) m/z=556.2 [M+1].

Example 417

2-((2R,5R,6R)-6-(3-Chlorophenyl)-5-(4-chlorophenyl)-4-((1S,2S)-1-cyclopropyl-2-(isopropylsulfonyl)propyl)-3-oxomorpholin-2-yl)acetic acid or 2-((2S,5R,6R)-6-(3-chlorophenyl)-5-(4-chlorophenyl)-4-((1S,2S)-1-cyclopropyl-2-(isopropylsulfonyl)propyl)-3-oxomorpholin-2-yl)acetic acid or 2-((2R,5R,6R)-6-(3-chlorophenyl)-5-(4-chlorophenyl)-4-((1S,2R)-1-cyclopropyl-2-(isopropylsulfonyl)propyl)-3-oxomorpholin-2-yl)acetic acid or 2-((2S,5R,6R)-6-(3-chlorophenyl)-5-(4-chlorophenyl)-4-((1S,2R)-1-cyclopropyl-2-(isopropylsulfonyl)propyl)-3-oxomorpholin-2-yl)acetic acid

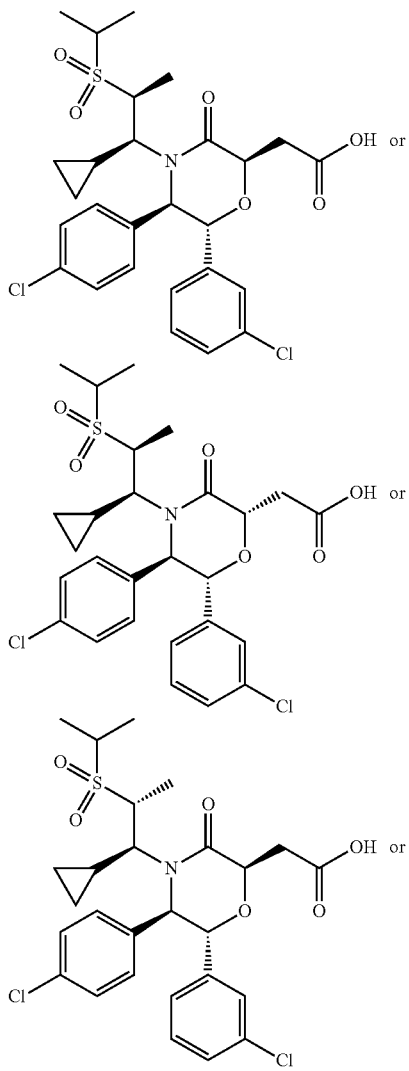

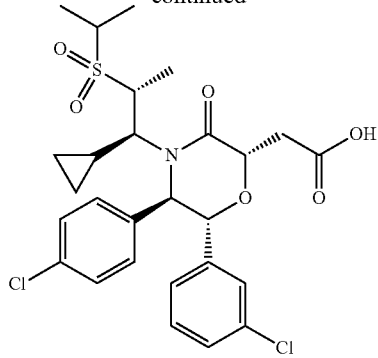

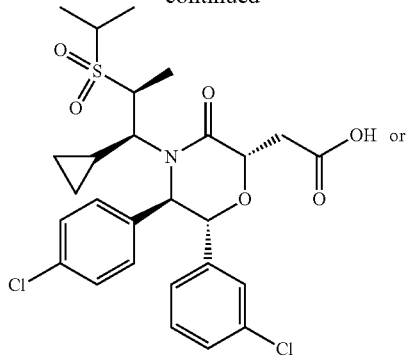

One of the title compounds was prepared from (5R,6R)-6-(3-chlorophenyl)-5-(4-chlorophenyl)-4-((S)-1-cyclopropyl-2-hydroxyethyl)morpholin-3-one (Example 154, Step B) by procedures similar to those described in Example 413, Steps A and F. The residue was purified by reverse phase preparatory HPLC (Agilient 1100, column: Gemini® 5 μm $C_{18}$, 100 mm×30 mm (Phenomenex, Torrance, Calif.), gradient elution of 25% to 75% acetonitrile in water, where both solvents contain 0.1% TFA, 30 minutes) to give one of the compounds as the first (faster) eluting isomer as a white foam. $^1$H NMR (400 MHz, CDCl$_3$, δ ppm): 7.50-7.59 (m, 3H), 7.37-7.48 (m, 3H), 7.28-7.36 (m, 2H), 5.35 (s, 1H), 5.04 (s, 1H), 4.32 (t, J=5.77 Hz, 1H), 3.59 (dq, J=3.72, 7.04 Hz, 1H), 3.30-3.44 (m, 1H), 3.01-3.24 (m, J=5.87, 11.74 Hz, 2H), 2.83 (d, J=11.15 Hz, 1H), 1.65 (br. s., 1H), 1.64 (d, J=7.04 Hz, 3H), 1.49 (d, J=6.85 Hz, 3H), 1.45 (d, J=6.65 Hz, 3H), 0.39-0.56 (m, 1H), 0.03-0.36 (m, 2H), −1.17 to −0.92 (m, 1H). MS (ESI) m/z=568.5 [M+1].

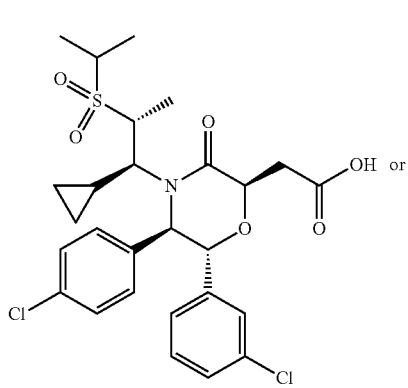

Example 418

2-((2R,5R,6R)-6-(3-Chlorophenyl)-5-(4-chlorophenyl)-4-((1S,2S)-1-cyclopropyl-2-(isopropylsulfonyl)propyl)-3-oxomorpholin-2-yl)acetic acid or 2-((2S,5R,6R)-6-(3-chlorophenyl)-5-(4-chlorophenyl)-4-(1S,2S)-1-cyclopropyl-2-(isopropylsulfonyl)propyl)-3-oxomorpholin-2-yl)acetic acid or 2-((2R,5R,6R)-6-(3-chlorophenyl)-5-(4-chlorophenyl)-4-((1S,2R)-1-cyclopropyl-2-(isopropylsulfonyl)propyl)-3-oxomorpholin-2-yl)acetic acid or 2-((2S,5R,6R)-6-(3-chlorophenyl)-5-(4-chlorophenyl)-4-((1S,2R)-1-cyclopropyl-2-(isopropylsulfonyl)propyl)-3-oxomorpholin-2-yl)acetic acid

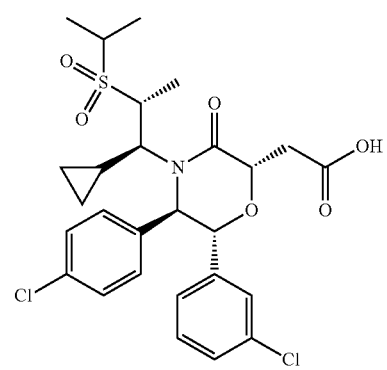

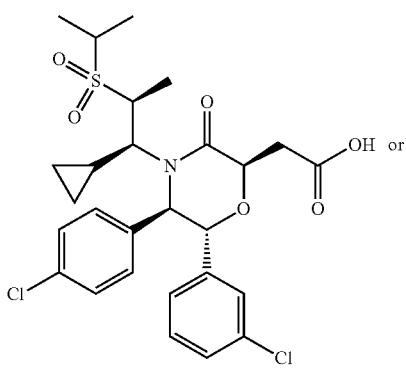

Further elution of the chromatographic separation described in Example 417 provided one of the title compounds as the second (slower) eluting isomer as a white foam. $^1$H NMR (400 MHz, CDCl$_3$, δ ppm): 7.28-7.35 (m, 2H), 7.22 (d, J=8.41 Hz, 3H), 7.09 (d, J=9.00 Hz, 2H), 6.81 (d, J=7.83 Hz, 1H), 5.07 (d, J=9.78 Hz, 1H), 4.78 (d, J=10.17 Hz, 1H), 4.72 (t, J=5.28 Hz, 1H), 3.97-4.14 (m, 1H), 3.26-3.42 (m, 1H), 3.12 (dd, J=5.28, 8.02 Hz, 3H), 1.69-1.81 (m, 1H), 1.56 (d, J=7.04 Hz, 3H), 1.44 (d, J=6.85 Hz, 6H), 0.45-0.58 (m, 1H), 0.30 (br. s., 1H), 0.05 (br. s., 1H), −0.76 (br. s., 1H). MS (ESI) m/z=568.5 [M+1].

Example 419

2-((2R,5R,6R)-4-((2S,3S)-2-(tert-Butylsulfonyl)
pentan-3-yl)-6-(3-chlorophenyl)-5-(4-chlorophenyl)-
3-oxomorpholin-2-yl)acetic acid or 2-((2S,5R,6R)-4-
((2S,3S)-2-(tert-butylsulfonyl)pentan-3-yl)-6-(3-
chlorophenyl)-5-(4-chlorophenyl)-3-oxomorpholin-
2-yl)acetic acid or 2-((2R,5R,6R)-4-((2R,3S)-2-(tert-
butylsulfonyl)pentan-3-yl)-6-(3-chlorophenyl)-5-(4-
chlorophenyl)-3-oxomorpholin-2-yl)acetic acid or
2-((2S,5R,6R)-4-((2R,3S)-2-(tert-butylsulfonyl)pen-
tan-3-yl)-6-(3-chlorophenyl)-5-(4-chlorophenyl)-3-
oxomorpholin-2-yl)acetic acid or 2-((2R,5R,6R)-4-
((2S,3R)-2-(tert-butylsulfonyl)pentan-3-yl)-6-(3-
chlorophenyl)-5-(4-chlorophenyl)-3-oxomorpholin-
2-yl)acetic acid or 2-((2S,5R,6R)-4-((2S,3R)-2-(tert-
butylsulfonyl)pentan-3-yl)-6-(3-chlorophenyl)-5-(4-
chlorophenyl)-3-oxomorpholin-2-yl)acetic acid or
2-((2R,5R,6R)-4-((2R,3R)-2-(tert-butylsulfonyl)
pentan-3-yl)-6-(3-chlorophenyl)-5-(4-chlorophenyl)-
3-oxamorpholin-2-yl)acetic acid or 2-((2S,5R,6R)-
442R,3R)-2-(tert-butylsulfonyl)pentan-3-yl)-6-(3-
chlorophenyl)-5-(4-chlorophenyl)-3-oxomorpholin-
2-yl)acetic acid

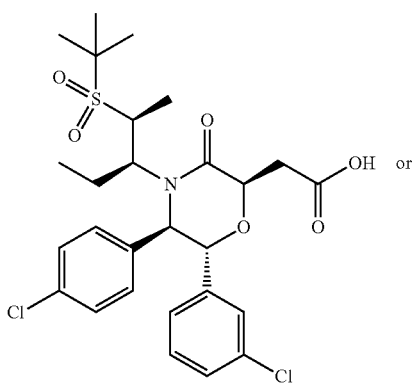

or

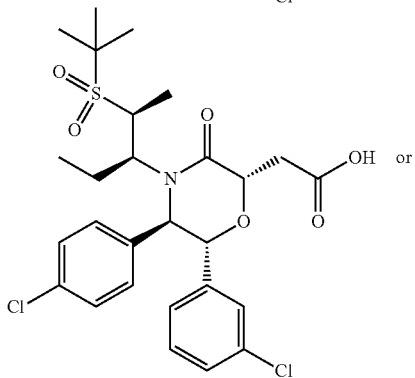

or

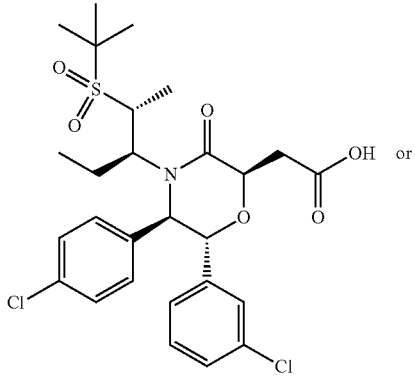

or

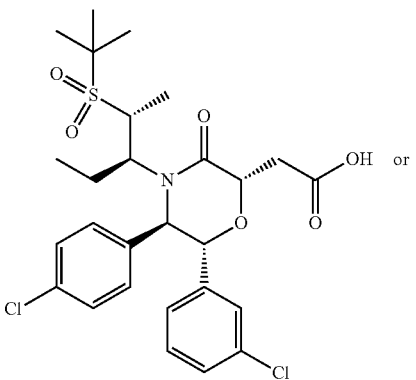

or

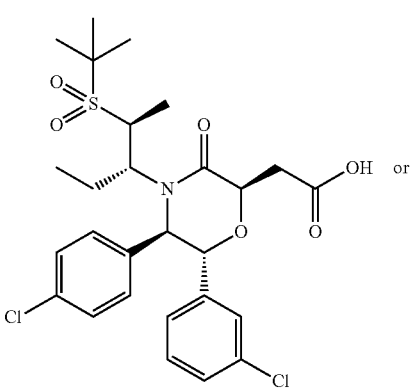

or

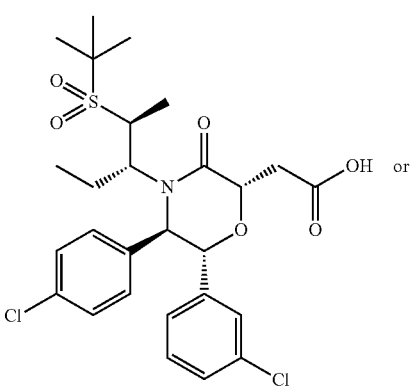

or

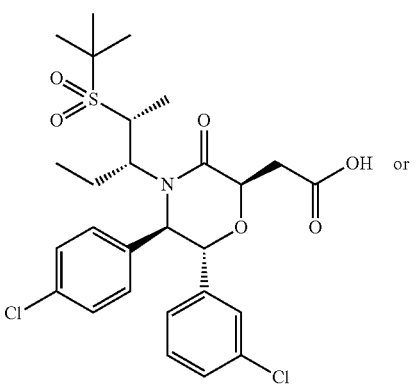

or

-continued

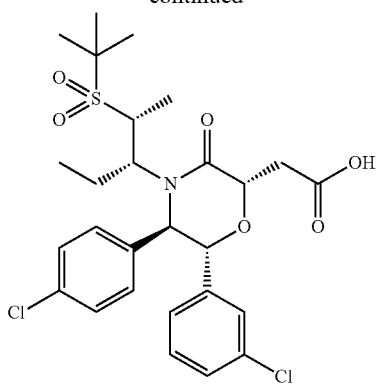

Step A. (R)-2-(tert-Butylthio)pentan-3-one and (S)-2-(tert-butylthio)pentan-3-one

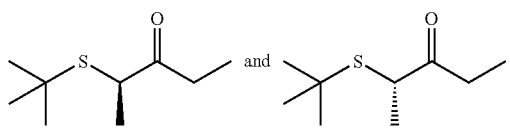

Bromine (1.989 mL, 38.6 mmol) was added to a solution of pentan-3-one (4.31 mL, 40.6 mmol) in diethyl ether (102 mL). The dark-red mixture was stirred at room temperature for 30 minutes. The mixture became light-yellow and was quenched with water (40 mL) and diluted with diethylether (100 mL). The organic layer was washed with saturated NaHCO$_3$ (120 mL), saturated aqueous Na$_2$S$_2$O$_3$ (120 mL), and brine (120 mL). The organic layer was dried over Na$_2$SO$_4$. The residue was purified by flash chromatography on silica gel (gradient elution of 10% to 20% dichloromethane in hexanes) to give a residue. The residue was dissolved in acetonitrile (10.48 mL) and 2-methyl-2-propanethiol (1.908 mL, 16.92 mmol) and N,N-diisopropylethylamine (3.73 mL, 21.38 mmol) were added at room temperature. After stirring at room temperature for 5 days, the mixture was diluted with 10% aqueous citric acid, extracted with ethyl acetate (2×), and the combined organic layers were washed with brine. The organic layer was dried over Na$_2$SO$_4$, filtered and concentrated under reduced pressure. The residue was purified by flash chromatography on silica gel (gradient elution of 5% to 10% ethyl acetate in hexanes) to give the titled compounds as a colorless liquid.

Step B. (2S,3S)-N-((1R,2R)-2-((tert-Butyldimethylsilyl)oxy)-2-(3-chlorophenyl)-1-(4-chlorophenyl)ethyl)-2-(tert-butylthio)pentan-3-amine and (2R,3S)-N-((1R,2R)-2-((tert-butyldimethylsilyl)oxy)-2-(3-chlorophenyl)-1-(4-chlorophenyl)ethyl)-2-(tert-butylthio)pentan-3-amine and (2S,3R)-N-((1R,2R)-2-((tert-butyldimethylsilyl)oxy)-2-(3-chlorophenyl)-1-(4-chlorophenyl)ethyl)-2-(tert-butylthio)pentan-3-amine and (2R,3R)-N-((1R,2R)-2-((tert-butyldimethylsilyl)oxy)-2-(3-chlorophenyl)-1-(4-chlorophenyl)ethyl)-2-(tert-butylthio)pentan-3-amine

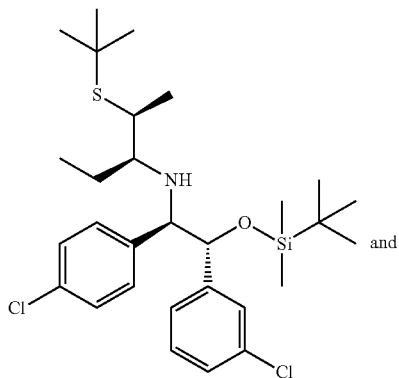
and

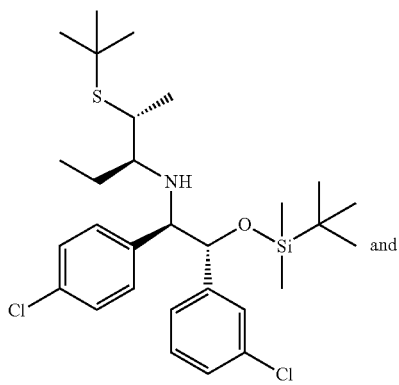
and

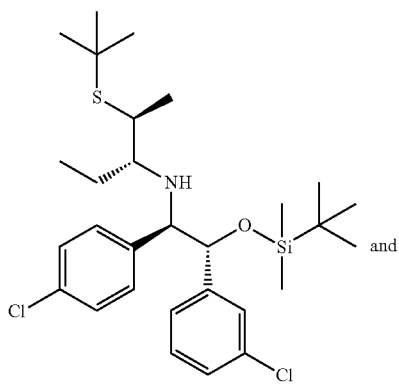
and

-continued

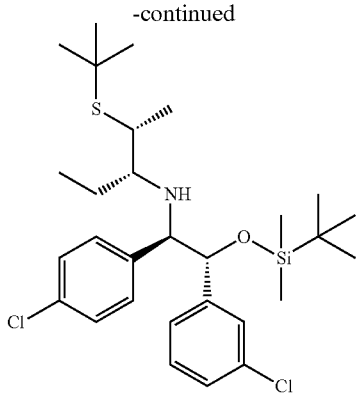

(R)-2-(tert-Butylthio)pentan-3-one and (S)-2-(tert-butylthio)pentan-3-one (2.75 g, 15.77 mmol, Example 419, Step A) and (1R,2R)-2-((tert-butyldimethylsilyl)oxy)-2-(3-chlorophenyl)-1-(4-chlorophenyl)ethanamine (2.50 g, 6.31 mmol, prepared from Intermediate A2 following a procedure similar to the one described in Example 162, Step A) were added to neat titanium isopropoxide (5.38 g, 18.92 mmol) and stirred at 40° C. for 4 days. Methanol (10 mL) was added, followed by careful addition of sodium borohydride (0.716 g, 18.92 mmol). The mixture was stirred at room temperature for 2 hours. Then the mixture was quenched with NaOH (1 M) and filtered through celite. The solid was washed with ethyl acetate, and the filtrate was washed with brine, dried over $Na_2SO_4$, filtered, and concentrated.

Step C. (5R,6R)-4-((2S,3S)-2-(tert-Butylsulfonyl)pentan-3-yl)-6-(3-chlorophenyl)-5-(4-chlorophenyl)morpholin-3-one or (5R,6R)-4-((2R,3S)-2-(tert-butylsulfonyl)pentan-3-yl)-6-(3-chlorophenyl)-5-(4-chlorophenyl)morpholin-3-one or (5R,6R)-4-((2S,3R)-2-(tert-Butylsulfonyl)pentan-3-yl)-6-(3-chlorophenyl)-5-(4-chlorophenyl)morpholin-3-one or (5R,6R)-4-((2R,3R)-2-(tert-butylsulfonyl)pentan-3-yl)-6-(3-chlorophenyl)-5-(4-chlorophenyl)morpholin-3-one

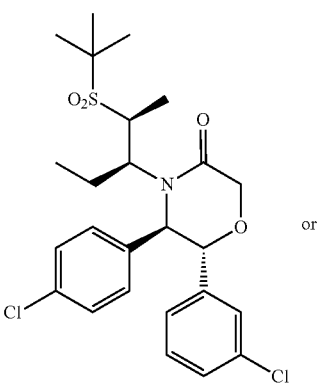

or

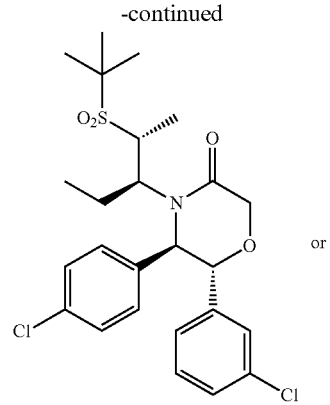

or

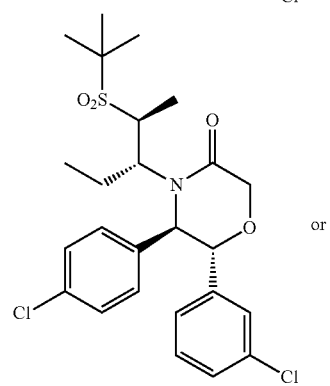

or

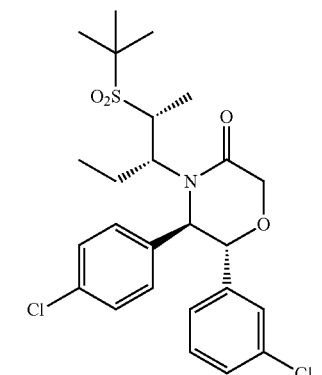

One of the title compounds was prepared from (2S,3S)-N-((1R,2R)-2-((tert-butyldimethylsilyl)oxy)-2-(3-chlorophenyl)-1-(4-chlorophenyl)ethyl)-2-(tert-butylthio)pentan-3-amine and (2R,3S)-N-((1R,2R)-2-((tert-butyldimethylsilyl)oxy)-2-(3-chlorophenyl)-1-(4-chlorophenyl)ethyl)-2-(tert-butylthio)pentan-3-amine and (2S,3R)-N-((1R,2R)-2-((tert-butyldimethylsilyl)oxy)-2-(3-chlorophenyl)-1-(4-chlorophenyl)ethyl)-2-(tert-butylthio)pentan-3-amine and (2R,3R)-N-((1R,2R)-2-((tert-butyldimethylsilyl)oxy)-2-(3-chlorophenyl)-1-(4-chlorophenyl)ethyl)-2-(tert-butylthio)pentan-3-amine (Example 419, Step B) by procedures similar to those described in Example 162, Steps E through H. The residue was purified by reverse phase preparatory HPLC (Agilent 1100, column: Gemini® 5 µm $C_{18}$, 100 mm×30 mm (Phenomenex, Torrance, Calif.), gradient elution of 60% to 80% acetonitrile in water, where both solvents contain 0.1% TFA). The first eluting peak was impure, whereas the second (slower) eluting peak appeared to contain a single diastereomer which was one of the title compounds. The second eluting peak was used in Example 291, Step D.

Step D. 2-((2R,5R,6R)-4-((2S,3S)-2-(tert-Butylsulfonyl)pentan-3-yl)-6-(3-chlorophenyl)-5-(4-chlorophenyl)-3-oxomorpholin-2-yl)acetic acid or 2-((2S,5R,6R)-4-((2S,3S)-2-(tert-butylsulfonyl)pentan-3-yl)-6-(3-chlorophenyl)-5-(4-chlorophenyl)-3-oxomorpholin-2-yl)acetic acid or 2-((2R,5R,6R)-4-((2R,3S)-2-(tert-butylsulfonyl)pentan-3-yl)-6-(3-chlorophenyl)-5-(4-chlorophenyl)-3-oxomorpholin-2-yl)acetic acid or 2-((2S,5R,6R)-4-42R,3S)-2-(tert-butylsulfonyl)pentan-3-yl)-6-(3-chlorophenyl)-5-(4-chlorophenyl)-3-oxomorpholin-2-yl)acetic acid or 2-((2R,5R,6R)-4-((2S,3R)-2-(tert-butylsulfonyl)pentan-3-yl)-6-(3-chlorophenyl)-5-(4-chlorophenyl)-3-oxomorpholin-2-yl)acetic acid or 2-((2S,5R,6R)-4-((2S,3R)-2-(tert-butylsulfonyl)pentan-3-yl)-6-(3-chlorophenyl)-5-(4-chlorophenyl)-3-oxomorpholin-2-yl)acetic acid or 2-((2R,5R,6R)-4-((2R,3R)-2-(tert-butylsulfonyl)pentan-3-yl)-6-(3-chlorophenyl)-5-(4-chlorophenyl)-3-oxomorpholin-2-yl)acetic acid or 2-((2S,5R,6R)-4-((2R,3R)-2-(tert-butylsulfonyl)pentan-3-yl)-6-(3-chlorophenyl)-5-(4-chlorophenyl)-3-oxomorpholin-2-yl)acetic acid -continued

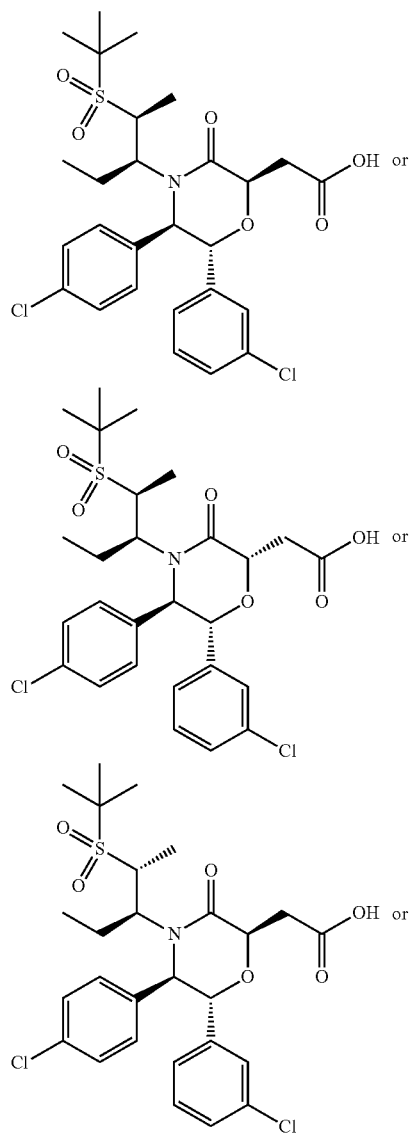

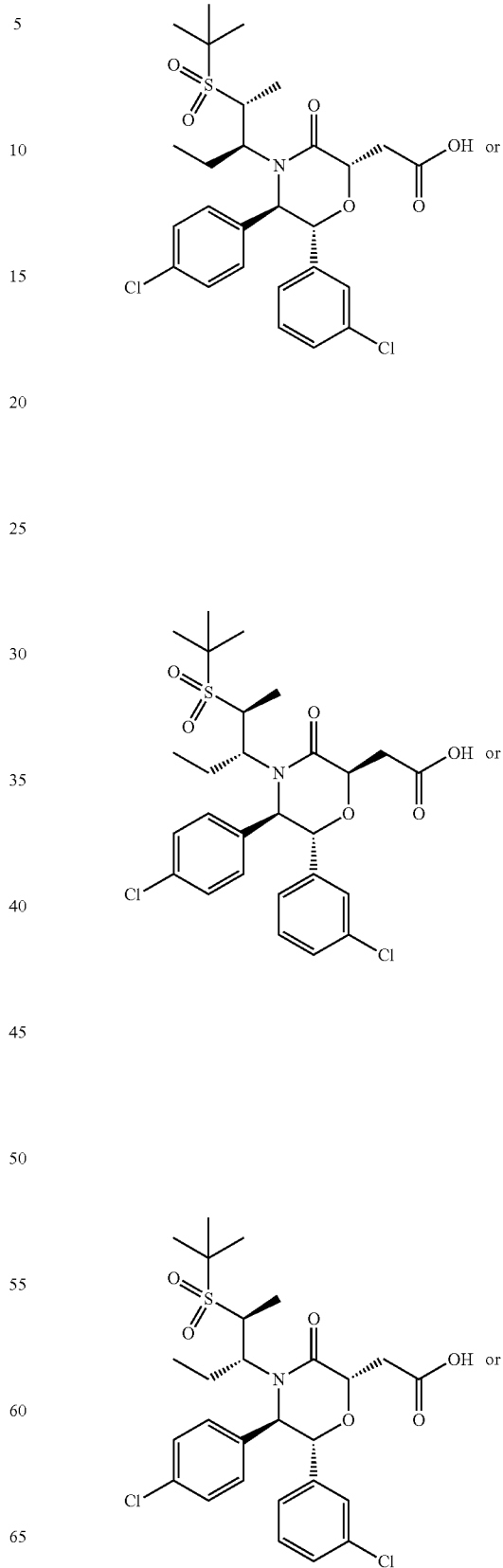

683
-continued

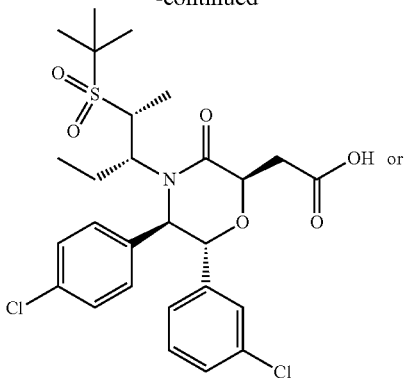

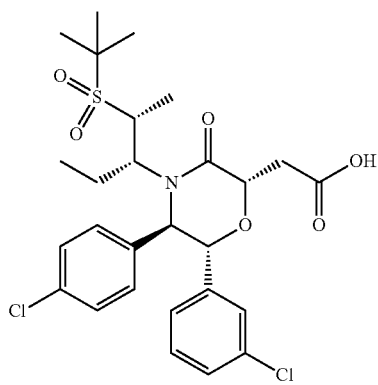

One of the title compounds was prepared from (5R,6R)-4-((2S,3S)-2-(tert-Butylsulfonyl)pentan-3-yl)-6-(3-chlorophenyl)-5-(4-chlorophenyl)morpholin-3-one or (5R,6R)-4-((2R,3S)-2-(tert-butylsulfonyl)pentan-3-yl)-6-(3-chlorophenyl)-5-(4-chlorophenyl)morpholin-3-one or (5R,6R)-4-((2S,3R)-2-(tert-Butylsulfonyl)pentan-3-yl)-6-(3-chlorophenyl)-5-(4-chlorophenyl)morpholin-3-one or (5R,6R)-4-((2R,3R)-2-(tert-butylsulfonyl)pentan-3-yl)-6-(3-chlorophenyl)-5-(4-chlorophenyl)morpholin-3-one (Example 419, Step C, second eluting isomer) by a procedure similar to that described in Example 112, Step F. The residue was purified by reverse phase preparatory HPLC (Agilient 1100, column: Gemini® 5 μm $C_{18}$, 100 mm×30 mm (Phenomenex, Torrance, Calif.), gradient elution of 40% to 70% acetonitrile in water, where both solvents contain 0.1% TFA) to give one of the compounds as the first (faster) eluting isomer. $^1$H NMR (500 MHz, CDCl$_3$, δ ppm): 0.41 (t, J=7.46 Hz, 3H), 1.50 (s, 9H), 1.53 (d, J=7.09 Hz, 3H), 1.70 (ddd, J=14.73, 7.64, 5.50 Hz, 1H), 1.93 (dt, J=14.86, 7.37 Hz, 1H), 3.04-3.18 (m, 2H), 3.57 (d, J=6.85 Hz, 1H), 3.91 (dd, J=7.21, 5.01 Hz, 1H), 4.52 (t, J=6.11 Hz, 1H), 5.03 (d, J=3.91 Hz, 1H), 5.28 (d, J=3.91 Hz, 1H), 7.21-7.29 (m, 2H), 7.29-7.33 (m, 1H), 7.35-7.41 (m, 2H), 7.42 (s, 1H), 7.46-7.51 (m, 2H). MS (ESI) m/z=570 [M+1].

Example 420

2-((2R,5R,6R)-4-((2S,3S)-2-(tert-Butylsulfonyl)pentan-3-yl)-6-(3-chlorophenyl)-5-(4-chlorophenyl)-3-oxomorpholin-2-yl)acetic acid or 2-((2S,5R,6R)-4-((2S,3S)-2-(tert-butylsulfonyl)pentan-3-yl)-6-(3-chlorophenyl)-5-(4-chlorophenyl)-3-oxomorpholin-2-yl)acetic acid or 2-((2R,5R,6R)-4-((2R,3S)-2-(tert-butylsulfonyl)pentan-3-yl)-6-(3-chlorophenyl)-5-(4-chlorophenyl)-3-oxomorpholin-2-yl)acetic acid or 2-((2S,5R,6R)-4-42R,3S)-2-(tert-butylsulfonyl)pentan-3-yl)-6-(3-chlorophenyl)-5-(4-chlorophenyl)-3-oxomorpholin-2-yl)acetic acid or 2-((2R,5R,6R)-4-((2S,3R)-2-(tert-butylsulfonyl)pentan-3-yl)-6-(3-chlorophenyl)-5-(4-chlorophenyl)-3-oxomorpholin-2-yl)acetic acid or 2-((2S,5R,6R)-4-((2S,3R)-2-(tert-butylsulfonyl)pentan-3-yl)-6-(3-chlorophenyl)-5-(4-chlorophenyl)-3-oxomorpholin-2-yl)acetic acid or 2-((2R,5R,6R)-4-((2R,3R)-2-(tert-butylsulfonyl)pentan-3-yl)-6-(3-chlorophenyl)-5-(4-chlorophenyl)-3-oxomorpholin-2-yl)acetic acid or 2-((2S,5R,6R)-4-((2R,3R)-2-(tert-butylsulfonyl)pentan-3-yl)-6-(3-chlorophenyl)-5-(4-chlorophenyl)-3-oxomorpholin-2-yl)acetic acid

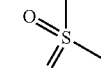

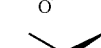

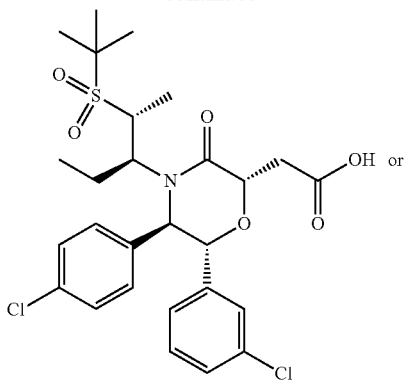

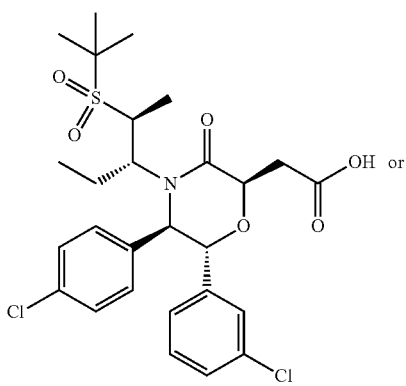

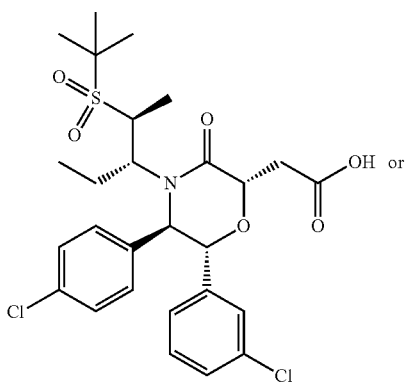

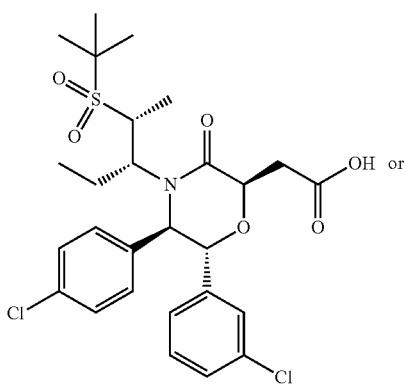

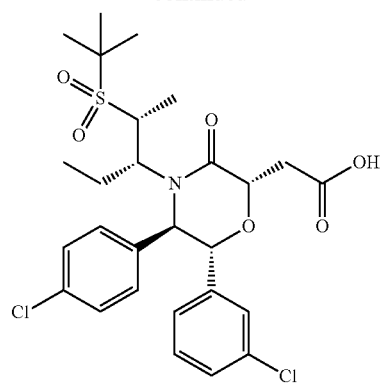

Further elution of the chromatographic separation described in Example 419, Step D provided one of the title compounds as the second (slower) eluting isomer. $^1$H NMR (500 MHz, CDCl$_3$, δ ppm): 0.46 (t, J=7.46 Hz, 3H), 1.37-1.55 (m, 12H), 1.70 (m, 1H), 2.00-2.11 (m, 1H), 3.03-3.14 (m, 2H), 3.34 (m, 1H), 4.13-4.25 (m, 1H), 4.63-4.79 (m, 2H), 4.96-5.08 (m, 1H), 6.77 (d, J=7.58 Hz, 1H), 7.05-7.19 (m, 4H), 7.19-7.29 (m, 2H), 7.29-7.37 (m, 3H), 7.37-7.53 (m, 2H). MS (ESI) m/z=570 [M+1].

Example 421

2-((2R,5R,6R)-6-(3-Chlorophenyl)-5-(4-chlorophenyl)-4-((1S,2S)-2-(isopropylsulfonyl)cyclopentyl)-3-oxomorpholin-2-yl)acetic acid or 2-((2S,5R,6R)-6-(3-chlorophenyl)-5-(4-chlorophenyl)-4-((1S,2S)-2-(isopropylsulfonyl)cyclopentyl)-3-oxomorpholin-2-yl)acetic acid or 2-((2R,5R,6R)-6-(3-chlorophenyl)-5-(4-chlorophenyl)-4-((1R,2R)-2-(isopropylsulfonyl)cyclopentyl)-3-oxomorpholin-2-yl)acetic acid or 2-((2S,5R,6R)-6-(3-chlorophenyl)-5-(4-chlorophenyl)-4-((1R,2R)-2-(isopropylsulfonyl)cyclopentyl)-3-oxomorpholin-2-yl)acetic acid

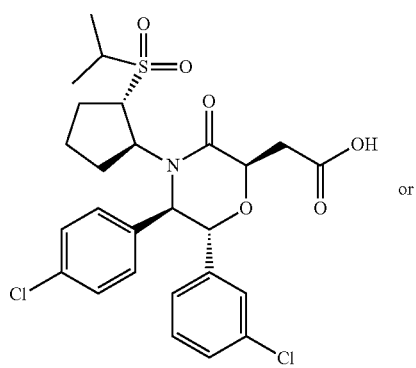

687

-continued

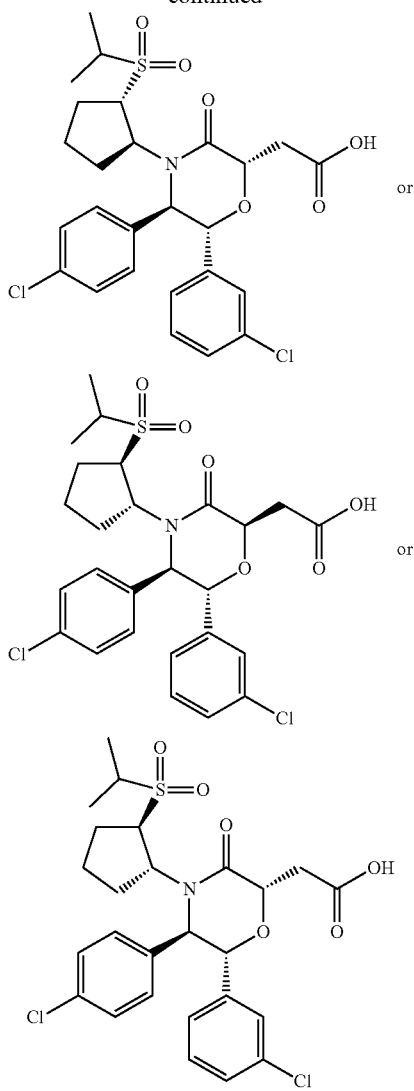

Step A. (1S,2S)-N-((1R,2R)-2-((tert-Butyldimethyl-silyl)oxy)-2-(3-chlorophenyl)-1-(4-chlorophenyl)ethyl)-2-(isopropylthio)cyclopentanamine or (1R,2R)-N-((1R,2R)-2-((tert-butyldimethylsilyl)oxy)-2-(3-chlorophenyl)-1-(4-chlorophenyl)ethyl)-2-(isopropylthio)cyclopentanamine

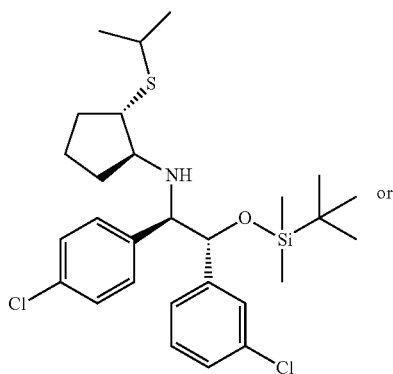

688

-continued

One of the title compounds was obtained from (1R,2R)-2-((tert-butyldimethylsilyl)oxy)-2-(3-chlorophenyl)-1-(4-chlorophenyl)ethanamine (1.27 g, 3.20 mmol, prepared from Intermediate A2 following a method similar to the one described in Example 162, Step A) by procedures similar to those described in Example 162, Steps B through D, replacing (R)-(+)-1,2-epoxybutane in Step B with 1,2-epoxycyclopentane and replacing tert-butanethiol in Step D with 2-propanethiol. The crude residue was purified by flash chromatography on silica gel (gradient elution of 0% to 10% ethyl acetate in hexanes) to provide one of the title compounds as the first eluting isomer.

Step B. (2R,5R,6R)-2-Allyl-6-(3-chlorophenyl)-5-(4-chlorophenyl)-4-((1S,2S)-2-(isopropylthio)cyclopentyl)morpholin-3-one or (2S,5R,6R)-2-allyl-6-(3-chlorophenyl)-5-(4-chlorophenyl)-4-((1S,2S)-2-(isopropylthio)cyclopentyl)morpholin-3-one or (2R,5R,6R)-2-allyl-6-(3-chlorophenyl)-5-(4-chlorophenyl)-4-((1R,2R)-2-(isopropylthio)cyclopentyl)morpholin-3-one or (2S,5R,6R)-2-allyl-6-(3-chlorophenyl)-5-(4-chlorophenyl)-4-((1R,2R)-2-(isopropylthio)cyclopentyl)morpholin-3-one

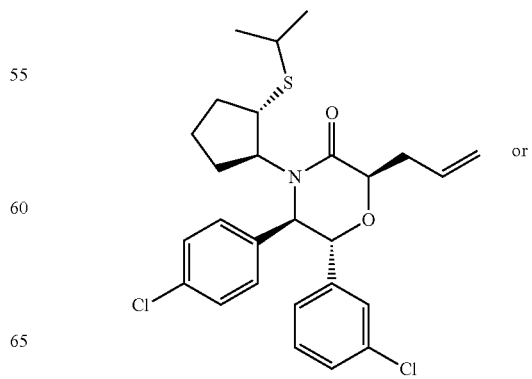

689
-continued

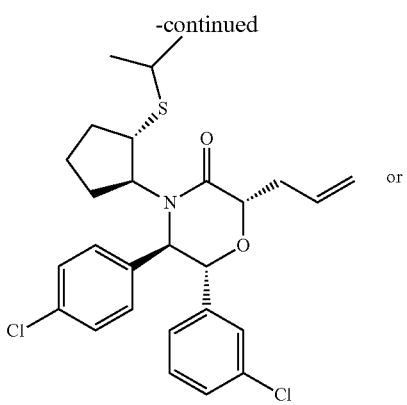

or

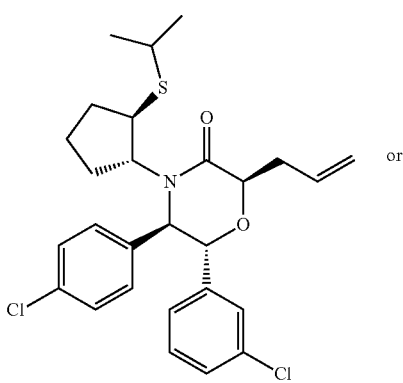

or

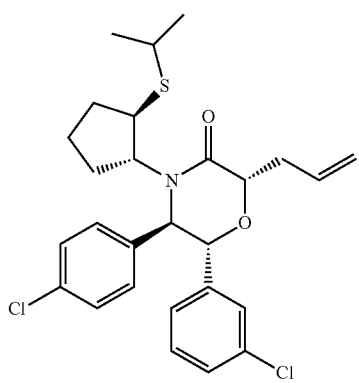

One of the title compounds was prepared from (1S,2S)-N-((1R,2R)-2-((tert-butyldimethylsilyl)oxy)-2-(3-chlorophenyl)-1-(4-chlorophenyl)ethyl)-2-(isopropylthio)cyclopentanamine or (1R,2R)-N-((1R,2R)-2-((tert-butyldimethylsilyl)oxy)-2-(3-chlorophenyl)-1-(4-chlorophenyl)ethyl)-2-(isopropylthio)cyclopentanamine (Example 421, Step A) by procedures similar to those described in Example 162, Steps E through G and Example 112, Step E. The crude residue was purified by flash chromatography on silica gel (gradient elution of 5% to 15% ethyl acetate in hexanes) to provide one of the title compounds as the first eluting isomer.

690

Step C. 2-((2R,5R,6R)-6-(3-Chlorophenyl)-5-(4-chlorophenyl)-4-((1S,2S)-2-(isopropylsulfonyl)cyclopentyl)-3-oxomorpholin-2-yl)acetic acid or 2-((2S,5R,6R)-6-(3-chlorophenyl)-5-(4-chlorophenyl)-4-((1S,2S)-2-(isopropylsulfonyl)cyclopentyl)-3-oxomorpholin-2-yl)acetic acid or 2-((2R,5R,6R)-6-(3-chlorophenyl)-5-(4-chlorophenyl)-4-((1R,2R)-2-(isopropylsulfonyl)cyclopentyl)-3-oxomorpholin-2-yl)acetic acid or 2-((2S,5R,6R)-6-(3-chlorophenyl)-5-(4-chlorophenyl)-4-((1R,2R)-2-(isopropylsulfonyl)cyclopentyl)-3-oxomorpholin-2-yl)acetic acid

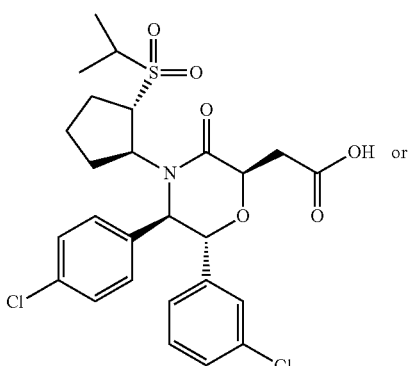

or

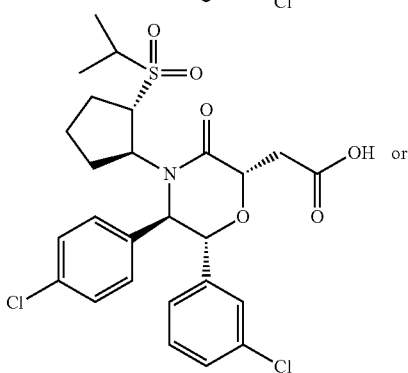

or

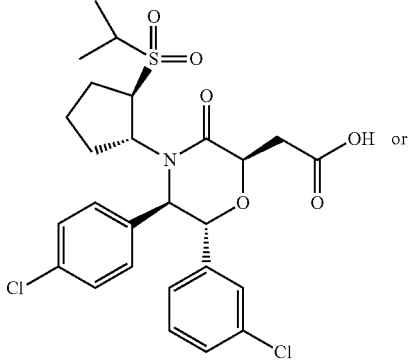

or

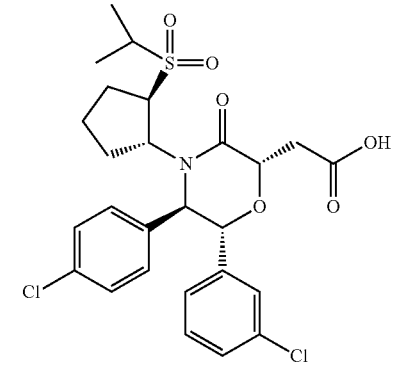

One of the title compounds was prepared from (2R,5R,6R)-2-allyl-6-(3-chlorophenyl)-5-(4-chlorophenyl)-4-((1S,2S)-2-(isopropylthio)cyclopentyl)morpholin-3-one or (2S,5R,6R)-2-allyl-6-(3-chlorophenyl)-5-(4-chlorophenyl)-4-((1S,2S)-2-(isopropylthio)cyclopentyl)morpholin-3-one or (2R,5R,6R)-2-allyl-6-(3-chlorophenyl)-5-(4-chlorophenyl)-4-((1R,2R)-2-(isopropylthio)cyclopentyl)morpholin-3-one or (2S,5R,6R)-2-allyl-6-(3-chlorophenyl)-5-(4-chlorophenyl)-4-((1R,2R)-2-(isopropylthio)cyclopentyl)morpholin-3-one (Example 421, Step B) by a similar procedure as that described for Example 112, Step F. The residue was purified by reverse phase preparatory HPLC (Agilient 1100, column: Gemini® 5 μm $C_{18}$, 100 mm×30 mm (Phenomenex, Torrance, Calif.), gradient elution of 25% to 75% acetonitrile in water, where both solvents contain 0.1% TFA, 30 minutes) to give one of the compounds. $^1$H NMR (500 MHz, CDCl$_3$, δ ppm): 7.54 (s, 1H), 7.38-7.25 (m, 7H), 5.27 (d, J=3.3 Hz, 1H), 4.93 (d, J=3.1 Hz, 1H), 4.33 (t. J=5.7 Hz, 1H), 4.20-4.15 (m, 1H), 3.88-3.82 (m, 1H), 3.28-3.18 (m, 1H), 3.12-2.98 (m, 2H), 2.34-2.20 (m, 2H), 1.96-1.85 (m, 2H), 1.64-1.60 (m, 2H), 1.41 (d, J=6.7 Hz, 6H). MS (ESI) m/z=554 [M+1].

Example 422

2-((2R,5R,6R)-6-(3-Chlorophenyl)-5-(4-chlorophenyl)-4-((1S,2S)-2-(isopropylsulfonyl)cyclopentyl)-3-oxomorpholin-2-yl)acetic acid or 2-((2S,5R,6R)-6-(3-chlorophenyl)-5-(4-chlorophenyl)-4-((1S,2S)-2-(isopropylsulfonyl)cyclopentyl)-3-oxomorpholin-2-yl)acetic acid or 2-((2R,5R,6R)-6-(3-chlorophenyl)-5-(4-chlorophenyl)-4-((1R,2R)-2-(isopropylsulfonyl)cyclopentyl)-3-oxomorpholin-2-yl)acetic acid or 2-((2S,5R,6R)-6-(3-chlorophenyl)-5-(4-chlorophenyl)-4-((1R,2R)-2-(isopropylsulfonyl)cyclopentyl)-3-oxomorpholin-2-yl)acetic acid

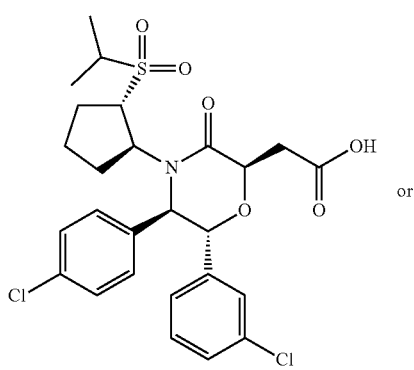

or

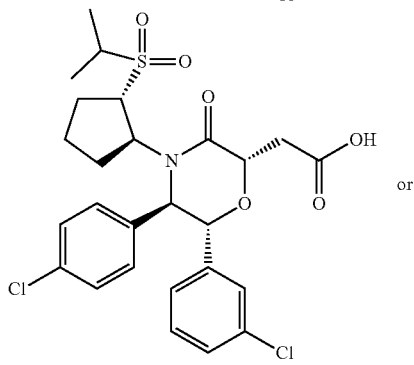

or

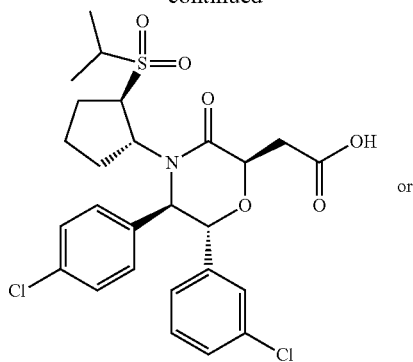

or

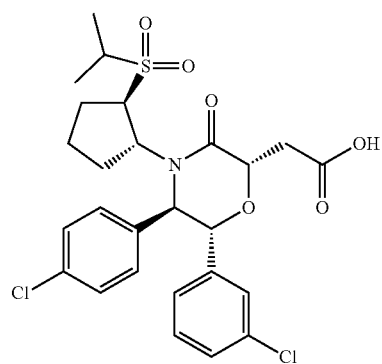

Step A. (2R,5R,6R)-2-Allyl-6-(3-chlorophenyl)-5-(4-chlorophenyl)-4-((1S,2S)-2-(isopropylthio)cyclopentyl)morpholin-3-one or (2S,5R,6R)-2-allyl-6-(3-chlorophenyl)-5-(4-chlorophenyl)-4-((1S,2S)-2-(isopropylthio)cyclopentyl)morpholin-3-one or (2R,5R,6R)-2-allyl-6-(3-chlorophenyl)-5-(4-chlorophenyl)-4-((1R,2R)-2-(isopropylthio)cyclopentyl)morpholin-3-one or (2S,5R,6R)-2-allyl-6-(3-chlorophenyl)-5-(4-chlorophenyl)-4-((1R,2R)-2-(isopropylthio)cyclopentyl)morpholin-3-one

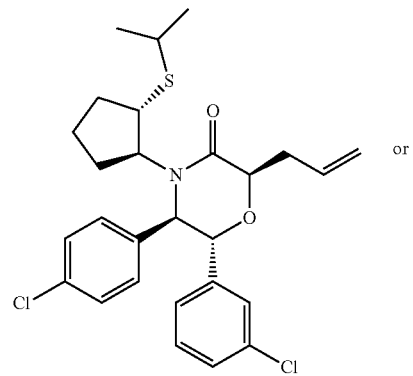

or

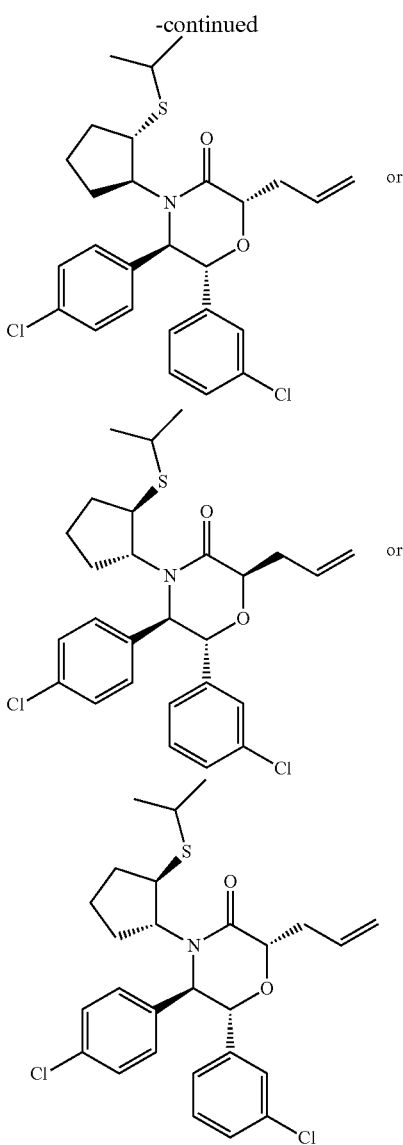

Further elution of the chromatographic separation described in Example 421, Step B provided one of the title compounds as the second (slower) eluting isomer.

Step B. 2-((2R,5R,6R)-6-(3-Chlorophenyl)-5-(4-chlorophenyl)-4-((1S,2S)-2-(isopropylsulfonyl)cyclopentyl)-3-oxomorpholin-2-yl)acetic acid or 2-((2S,5R,6R)-6-(3-chlorophenyl)-5-(4-chlorophenyl)-4-((1S,2S)-2-(isopropylsulfonyl)cyclopentyl)-3-oxomorpholin-2-yl)acetic acid or 2-((2R,5R,6R)-6-(3-chlorophenyl)-5-(4-chlorophenyl)-4-((1R,2R)-2-(isopropylsulfonyl)cyclopentyl)-3-oxomorpholin-2-yl)acetic acid or 2-((2S,5R,6R)-6-(3-chlorophenyl)-5-(4-chlorophenyl)-4-((1R,2R)-2-(isopropylsulfonyl)cyclopentyl)-3-oxomorpholin-2-yl)acetic acid One of the title compounds was prepared from (2R,5R,6R)-2-allyl-6-(3-chlorophenyl)-5-(4-chlorophenyl)-4-((1S,2S)-2-(isopropylthio)cyclopentyl)morpholin-3-one or (2S,5R,6R)-2-allyl-6-(3-chlorophenyl)-5-(4-chlorophenyl)-4-((1S,2S)-2-(isopropylthio)cyclopentyl)morpholin-3-one or (2R,5R,6R)-2-allyl-6-(3-chlorophenyl)-5-(4-chlorophenyl)-4-((1R,2R)-2-(isopropylthio)cyclopentyl)morpholin-3-one or (2S,5R,6R)-2-allyl-6-(3-chlorophenyl)-5-(4-chlorophenyl)-4-((1R,2R)-2-(isopropylthio)cyclopentyl)morpholin-3-one (Example 422, Step A) by a similar procedure as that described for Example 112, Step F. The residue was purified by reverse phase preparatory HPLC (Agilient 1100, column: Gemini® 5 μm $C_{18}$, 100 mm×30 mm (Phenomenex, Torrance, Calif.), gradient elution of 25% to 75% acetonitrile in water, where both solvents contain 0.1% TFA, 30 minutes) to give one of the compounds. $^1$H NMR (500 MHz, CDCl$_3$, δ ppm): 7.31-7.25 (m, 2H), 7.22-7.20 (m, 1H), 7.10 (t, J=7.3 Hz, 1H), 7.06-7.01 (m, 3H), 6.78 (d, J=7.8 Hz, 1H), 5.04 (d, J=9.8 Hz, 1H), 4.70 (t, J=10.6 Hz 1H), 4.60 (d, J=10 Hz, 1H), 4.29-4.23 (m, 1H), 3.73-3.67 (m, 1H), 3.19-3.12 (m, 1H), 3.10-3.08 (m, 2H), 3.35-3.15 (m, 2H), 1.96-1.78 (m, 2H), 1.62-1.50 (m, 2H), 1.40 (d, J=6.7 Hz, 6H). MS (ESI) m/z=554 [M+1].

Example 423

2-((2R,5R,6R)-4-((S)-1-(tert-Butylsulfonyl)propan-2-yl)-5-(4-chloro-3-fluorophenyl)-6-(3-chloro-5-fluorophenyl)-3-oxomorpholin-2-yl)acetic acid or 2-((2S,5R,6R)-4-((S)-1-(tert-butylsulfonyl)propan-2-yl)-5-(4-chloro-3-fluorophenyl)-6-(3-chloro-5-fluorophenyl)-3-oxomorpholin-2-yl)acetic acid

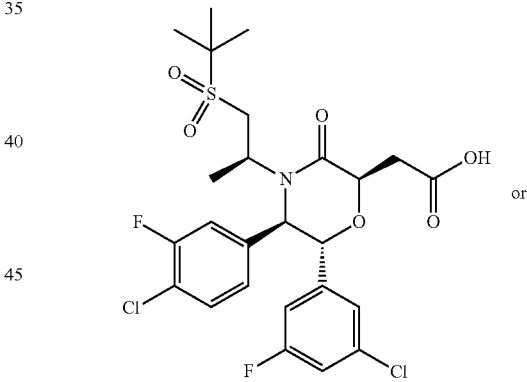

or

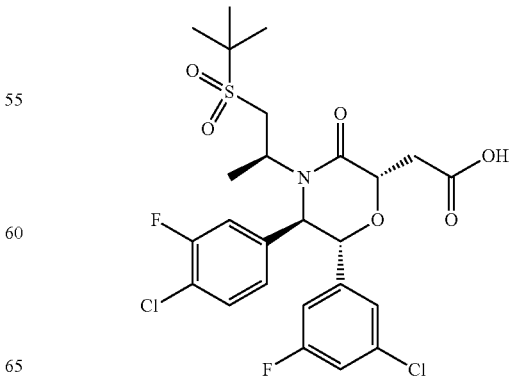

Step A. (1R,2R)-2-Amino-2-(4-chloro-3-fluorophenyl)-1-(3-chloro-5-fluorophenyl)ethanol

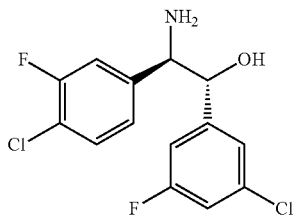 [SMILES: N[C@H](c1ccc(Cl)c(F)c1)[C@H](O)c1cc(F)cc(Cl)c1]

The title compound was prepared from 4-chloro-3-fluorobenzyaldehyde by similar procedures as those described for Intermediate E1, Steps B through H replacing 3-chlorophenylmagnesium bromide in Step G with (3-chloro-5-fluorophenyl)magnesium bromide (prepared from 1-bromo-3-chloro-5-fluorobenzene by a similar procedure as that described in Intermediate C1, Step D).

Step B. (2R,5R,6R)-2-Allyl-4-((S)-1-(tert-butylthio)propan-2-yl)-5-(4-chloro-3-fluorophenyl)-6-(3-chloro-5-fluorophenyl)morpholin-3-one or (2S,5R,6R)-2-allyl-4-((S)-1-(tert-butylthio)propan-2-yl)-5-(4-chloro-3-fluorophenyl)-6-(3-chloro-5-fluorophenyl)morpholin-3-one

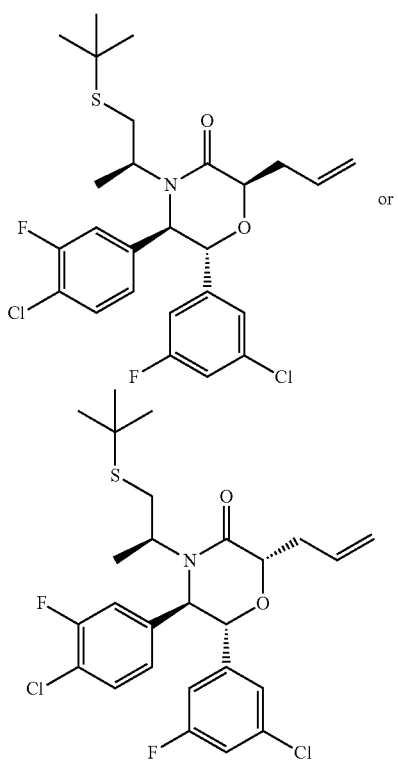

One of the title compounds was prepared from (1R,2R)-2-amino-2-(4-chloro-3-fluorophenyl)-1-(3-chloro-5-fluorophenyl)ethanol (Example 423, Step A) by procedures similar to those described in Example 162, Steps A through G, replacing (R)-(+)-1,2-epoxybutane in Step B with (R)-(+)-1,2-epoxypropane and Example 112, Step E. The crude residue was purified by flash chromatography on silica gel (gradient elution of 0% to 10% acetone in hexanes) to provide one of the title compounds as the first eluting isomer.

Step C. 2-((2R,5R,6R)-4-((S)-1-(tert-Butylsulfonyl)propan-2-yl)-5-(4-chloro-3-fluorophenyl)-6-(3-chloro-5-fluorophenyl)-3-oxomorpholin-2-yl)acetic acid or 2-((2S,5R,6R)-4-((S)-1-(tert-butylsulfonyl)propan-2-yl)-5-(4-chloro-3-fluorophenyl)-6-(3-chloro-5-fluorophenyl)-3-oxomorpholin-2-yl)acetic acid

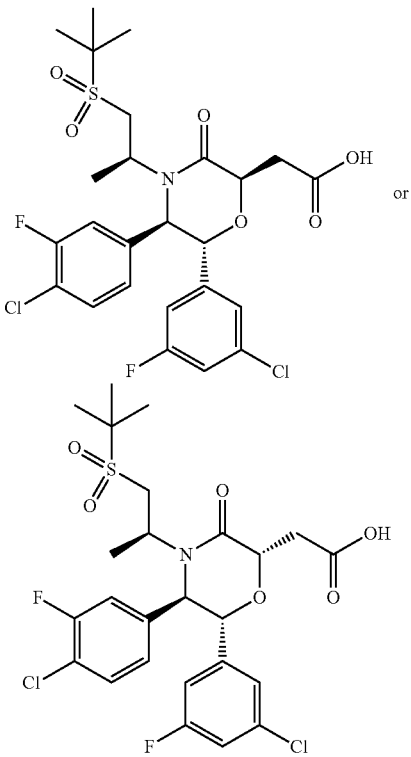

One of the title compounds was prepared (2R,5R,6R)-2-allyl-4-((S)-1-(tert-butylthio)propan-2-yl)-5-(4-chloro-3-fluorophenyl)-6-(3-chloro-5-fluorophenyl)morpholin-3-one or (2S,5R,6R)-2-allyl-4-((S)-1-(tert-butylthio)propan-2-yl)-5-(4-chloro-3-fluorophenyl)-6-(3-chloro-5-fluorophenyl)morpholin-3-one (Example 423, Step B) by a similar procedure as that described for Example 112, Step F. The residue was purified by reverse phase preparatory HPLC (Agilient 1100, column: Gemini® 5 μm $C_{18}$, 100 mm×30 mm (Phenomenex, Torrance, Calif.), gradient elution of 25% to 75% acetonitrile in water, where both solvents contain 0.1% TFA, 30 minutes) to give one of the compounds. $^1$H NMR (400 MHz, CDCl$_3$, δ ppm): 7.41 (t, J=7.73 Hz, 1H), 7.27 (td, J=1.57, 9.00 Hz, 1H), 7.04-7.12 (m, 2H), 7.01 (td, J=1.86, 8.22 Hz, 1H), 6.91 (d, J=8.80 Hz, 1H), 5.10 (d, J=6.06 Hz, 1H), 4.90 (d, J=6.06 Hz, 1H), 4.65 (dddd, J=2.15, 4.11, 4.89, 11.35 Hz, 1H), 4.07 (dd, J=8.90, 13.60 Hz, 1H), 3.64-3.78 (m, 1H), 3.01-3.21 (m, 2H), 2.89 (dd, J=3.23, 13.60 Hz, 1H), 1.43 (s, 9H), 1.38 (d, J=6.85 Hz, 3H). MS (ESI) m/z=578.0 [M+1].

Example 424

2-((2R,5R,6R)-4-((S)-1-(tert-Butylsulfonyl)propan-2-yl)-5-(4-chloro-3-fluorophenyl)-6-(3-chloro-5-fluorophenyl)-3-oxomorpholin-2-yl)acetic acid or 2-((2S,5R,6R)-4-((S)-1-(tert-butylsulfonyl)propan-2-yl)-5-(4-chloro-3-fluorophenyl)-6-(3-chloro-5-fluorophenyl)-3-oxomorpholin-2-yl)acetic acid

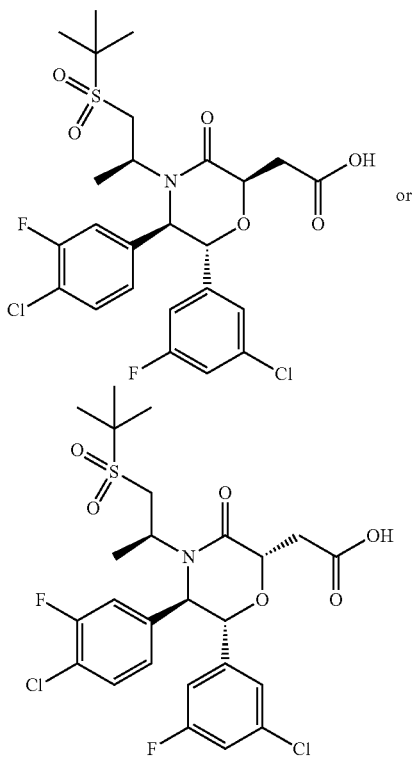

Step A. (2R,5R,6R)-2-Allyl-4-((S)-1-(tert-butylthio)propan-2-yl)-5-(4-chloro-3-fluorophenyl)-6-(3-chloro-5-fluorophenyl)morpholin-3-one or (2S,5R,6R)-2-allyl-4-((S)-1-(tert-butylthio)propan-2-yl)-5-(4-chloro-3-fluorophenyl)-6-(3-chloro-5-fluorophenyl)morpholin-3-one

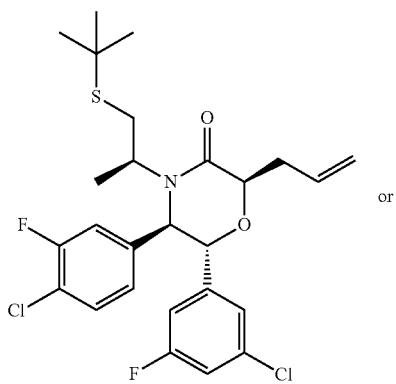

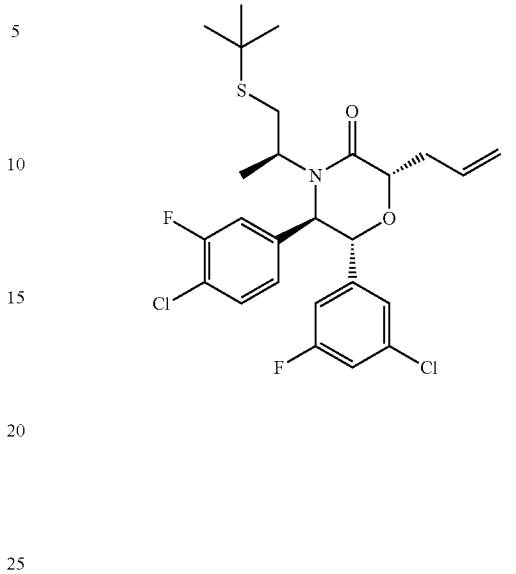

Further elution from the chromatographic separation described in Example 423, Step B provided one of the title compounds as the second (slower) eluting isomer.

Step B. 2-((2R,5R,6R)-4-((S)-1-(tert-Butylsulfonyl)propan-2-yl)-5-(4-chloro-3-fluorophenyl)-6-(3-chloro-5-fluorophenyl)-3-oxomorpholin-2-yl)acetic acid or 2-((2S,5R,6R)-4-((S)-1-(tert-butylsulfonyl)propan-2-yl)-5-(4-chloro-3-fluorophenyl)-6-(3-chloro-5-fluorophenyl)-3-oxomorpholin-2-yl)acetic acid One of the title compounds was prepared (2R,5R,6R)-2-allyl-4-((S)-1-(tert-butylthio)propan-2-yl)-5-(4-chloro-3-fluorophenyl)-6-(3-chloro-5-fluorophenyl)morpholin-3-one or (2S,5R,6R)-2-allyl-4-((S)-1-(tert-butylthio)propan-2-yl)-5-(4-chloro-3-fluorophenyl)-6-(3-chloro-5-fluorophenyl) morpholin-3-one (Example 424, Step A) by a similar procedure as that described for Example 112, Step F. The residue was purified by reverse phase preparatory HPLC (Agilient 1100, column: Gemini® 5 μm $C_{18}$, 100 mm×30 mm (Phenomenex, Torrance, Calif.), gradient elution of 25% to 75% acetonitrile in water, where both solvents contain 0.1% TFA, 30 minutes) to give one of the compounds. $^1$H NMR (400 MHz, CDCl$_3$, δ ppm): 7.38 (t, J=7.83 Hz, 1H), 7.03 (dd, J=1.76, 9.19 Hz, 1H), 6.98 (td, J=2.05, 8.41 Hz, 1H), 6.92 (d, J=8.22 Hz, 1H), 6.78 (s, 1H), 6.67 (d, J=8.41 Hz, 1H), 5.00 (d, J=9.59 Hz, 1H), 4.78 (t, J=5.87 Hz, 1H), 4.62 (d, J=9.78 Hz, 1H), 4.12 (dd, J=9.68, 13.40 Hz, 1H), 3.55-3.68 (m, 1H), 3.21 (dd, J=5.48, 16.63 Hz, 1H), 2.98 (dd, J=6.16, 16.73 Hz, 1H), 2.83 (d, J=3.33 Hz, 1H), 1.41 (s, 9H), 1.37 (d, J=6.85 Hz, 3H). MS (ESI) m/z=578.1 [M+1].

Example 425

2-((2R,5R,6R)-4-((S)-1-(tert-Butylsulfonyl)butan-2-yl)-5-(4-chloro-3-fluorophenyl)-6-(3-chloro-5-fluorophenyl)-3-oxomorpholin-2-yl)acetic acid or 2-((2S,5R,6R)-4-((S)-1-(tert-butylsulfonyl)butan-2-yl)-5-(4-chloro-3-fluorophenyl)-6-(3-chloro-5-fluorophenyl)-3-oxomorpholin-2-yl)acetic acid

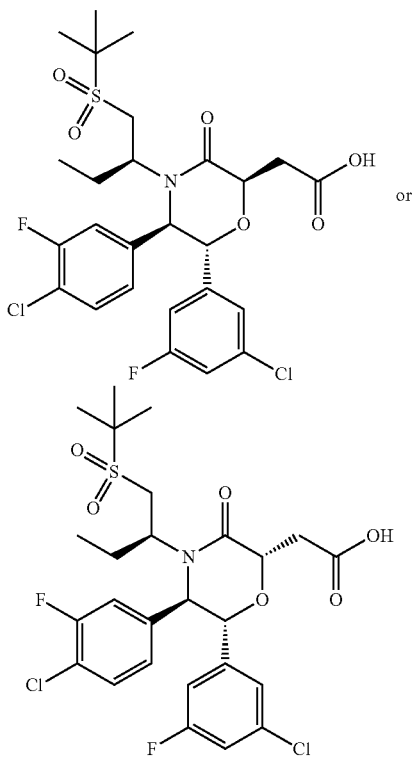

Step A. (2R,5R,6R)-2-Allyl-4-((S)-1-(tert-butylthio)butan-2-yl)-5-(4-chloro-3-fluorophenyl)-6-(3-chloro-5-fluorophenyl)morpholin-3-one or (2S,5R,6R)-2-allyl-4-((S)-1-(tert-butylthio)butan-2-yl)-5-(4-chloro-3-fluorophenyl)-6-(3-chloro-5-fluorophenyl)morpholin-3-one

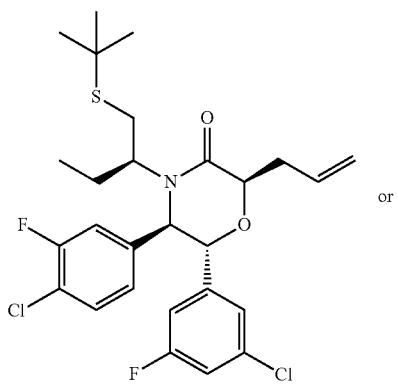

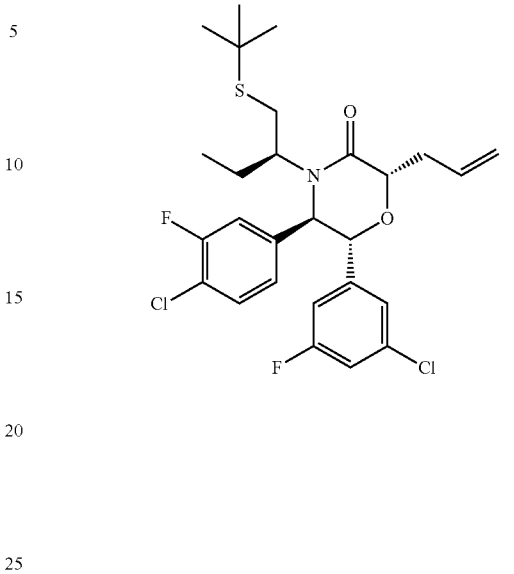

One of the title compounds was prepared from (1R,2R)-2-amino-2-(4-chloro-3-fluorophenyl)-1-(3-chloro-5-fluorophenyl)ethanol (Example 423, Step A) by procedures similar to those described in Example 162, Steps A through G and Example 112, Step E. The residue was purified by flash chromatography on silica gel (40 g column; gradient elution of 0% to 10% acetone in hexanes) to give one of the title compounds as the first (faster) eluting isomer.

Step B. 2-((2R,5R,6R)-4-((S)-1-(tert-Butylsulfonyl)butan-2-yl)-5-(4-chloro-3-fluorophenyl)-6-(3-chloro-5-fluorophenyl)-3-oxomorpholin-2-yl)acetic acid or 2-((2S,5R,6R)-4-((S)-1-(tert-butylsulfonyl)butan-2-yl)-5-(4-chloro-3-fluorophenyl)-6-(3-chloro-5-fluorophenyl)-3-oxomorpholin-2-yl)acetic acid One of the title compounds was prepared (2R,5R,6R)-2-allyl-4-((S)-1-(tert-butylthio)butan-2-yl)-5-(4-chloro-3-fluorophenyl)-6-(3-chloro-5-fluorophenyl)morpholin-3-one or (2S,5R,6R)-2-allyl-4-((S)-1-(tert-butylthio)butan-2-yl)-5-(4-chloro-3-fluorophenyl)-6-(3-chloro-5-fluorophenyl)morpholin-3-one (Example 425, Step A) by a similar procedure as that described for Example 112, Step F. The residue was purified by reverse phase preparatory HPLC (Agilient 1100, column: Gemini® 5 μm $C_{18}$, 100 mm×30 mm (Phenomenex, Torrance, Calif.), gradient elution of 25% to 75% acetonitrile in water, where both solvents contain 0.1% TFA, 30 minutes) to give one of the title compounds. $^1$H NMR (400 MHz, CDCl$_3$, δ ppm): 7.41 (t, J=7.83 Hz, 1H), 7.31 (d, J=7.83 Hz, 1H), 7.08-7.18 (m, 2H), 6.90-7.05 (m, 2H), 5.16 (d, J=5.48 Hz, 1H), 4.95 (d, J=5.48 Hz, 1H), 4.61 (dd, J=4.50, 6.65 Hz, 1H), 3.92 (dd, J=8.80, 13.69 Hz, 1H), 3.31-3.46 (m, 1H), 2.87-3.22 (m, 3H), 2.04-2.26 (m, 1H), 1.56-1.71 (m, 1H), 1.44 (s, 9H), 0.58 (t, J=7.43 Hz, 3H). MS (ESI) m/z=592.0 [M+1].

Example 426

2-((2R,5R,6R)-4-((S)-1-(tert-Butylsulfonyl)butan-2-yl)-5-(4-chloro-3-fluorophenyl)-6-(3-chloro-5-fluorophenyl)-3-oxomorpholin-2-yl)acetic acid or 2-((2S,5R,6R)-4-((S)-1-(tert-butylsulfonyl)butan-2-yl)-5-(4-chloro-3-fluorophenyl)-6-(3-chloro-5-fluorophenyl)-3-oxomorpholin-2-yl)acetic acid

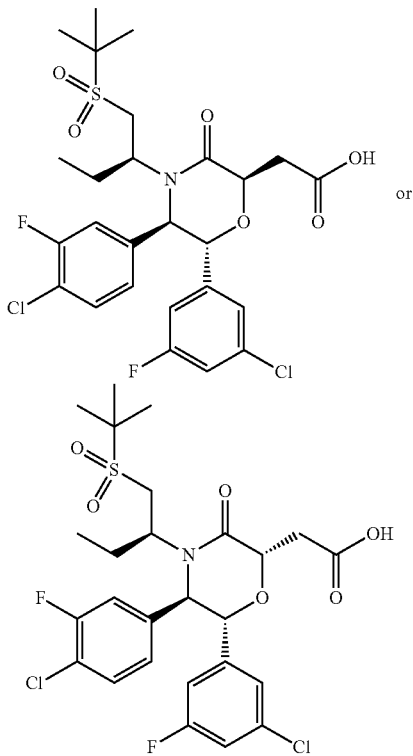

Step A. (2R,5R,6R)-2-Allyl-4-((S)-1-(tert-butylthio)butan-2-yl)-5-(4-chloro-3-fluorophenyl)-6-(3-chloro-5-fluorophenyl)morpholin-3-one or (2S,5R,6R)-2-allyl-4-((S)-1-(tert-butylthio)butan-2-yl)-5-(4-chloro-3-fluorophenyl)-6-(3-chloro-5-fluorophenyl)morpholin-3-one

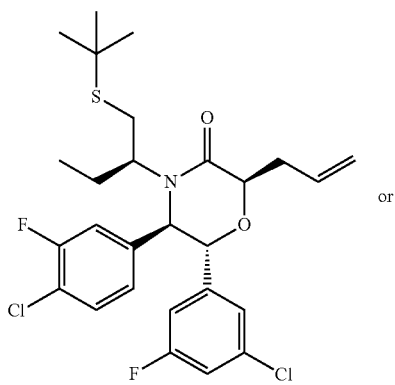

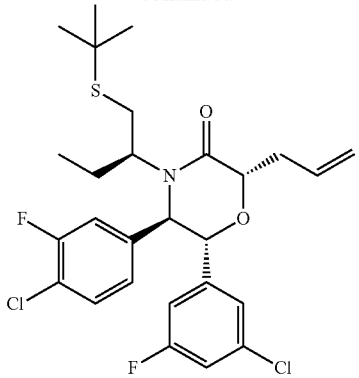

Further elution of the chromatographic separation described in Example 425, Step A provided one of the title compounds as the second (slower) eluting isomer.

Step B. 2-((2R,5R,6R)-4-((S)-1-(tert-Butylsulfonyl)butan-2-yl)-5-(4-chloro-3-fluorophenyl)-6-(3-chloro-5-fluorophenyl)-3-oxomorpholin-2-yl)acetic acid or 2-((2S,5R,6R)-4-((S)-1-(tert-butylsulfonyl)butan-2-yl)-5-(4-chloro-3-fluorophenyl)-6-(3-chloro-5-fluorophenyl)-3-oxomorpholin-2-yl)acetic acid One of the title compounds was prepared (2R,5R,6R)-2-allyl-4-((S)-1-(tert-butylthio)butan-2-yl)-5-(4-chloro-3-fluorophenyl)-6-(3-chloro-5-fluorophenyl)morpholin-3-one or (2S,5R,6R)-2-allyl-4-((S)-1-(tert-butylthio)butan-2-yl)-5-(4-chloro-3-fluorophenyl)-6-(3-chloro-5-fluorophenyl)morpholin-3-one (Example 426, Step A) by a similar procedure as that described for Example 112, Step F. The residue was purified by reverse phase preparatory HPLC (Agilent 1100, column: Gemini® 5 μm $C_{18}$, 100 mm×30 mm (Phenomenex, Torrance, Calif.), gradient elution of 25% to 75% acetonitrile in water, where both solvents contain 0.1% TFA, 30 minutes) to give one of the title compounds. $^1$H NMR (400 MHz, CDCl$_3$, δ ppm): 8.65 (br. s., 1H), 7.65-7.85 (m, 1H), 7.52 (s, 1H), 7.15-7.37 (m, 7H), 7.08-7.14 (m, 1H), 6.83 (dd, J=1.76, 8.61 Hz, 1H), 5.15 (d, J=5.48 Hz, 1H), 4.96 (d, J=5.48 Hz, 1H), 4.62 (t, J=4.79 Hz, 1H), 3.94-4.09 (m, 1H), 3.80-3.90 (m, 7H), 3.01-3.19 (m, 3H), 1.40 (s, 9H), 0.41 (br. s., 1H), 0.25 (br. s., 1H), −0.01 (br. s., 1H), −0.77 (br. s., 1H).

Biological Assays

Compounds of the present invention display inhibition of the interaction between HDM2 and p53 in the following assays.

Homogenous Time-Resolved Fluorescence Assay (HTRF1 Assay)

The standard assay conditions for the in vitro HTRF assay consisted of a 50 ul total reaction volume in black 384-well Costar polypropylene plates in 1X PBS buffer pH 7.4, 1 mM DTT, 0.1% BSA, 2.5 nM GST-hMDM2 (aa 1-188), 5 nM biotinylated-p53 (aa 1-83), 1.8 nM SA-XLent (Cisbio; Bedford, Mass.), 0.6 nM anti-GST cryptate monoclonal antibody (Cisbio; Bedford, Mass.) and 200 mM KF. Amino acid residues 1-188 of human MDM2 were expressed as an amino-terminal glutathione-S-transferase (GST) fusion protein (GST-hMDM2) in *Escherichia coli*. Residues 1-83 of human p53 were expressed as an amino-terminal AviTag™-TrxA-6xHis fusion protein (biotinylated p53) in *E. coli*. Each protein was purified from cell paste by affinity chromatography.

Specifically, 10 uL of GST-hMDM2 was incubated with 10 ul of diluted compound (various concentrations, serially diluted) in 10% DMSO for 20 minutes at room temperature. 20 uL of biotinylated-p53 was added to the GST-hMDM2+ compound mixture, and then incubated at room temperature for 60 min. 10 uL of detection buffer consisting of SA-XLent, anti-GST cryptate antibody and KF was added to GST-hMDM2, biotinylated-p53 and compound reaction and left at room temperature to reach equilibrium for >4 hrs. The final concentration of DMSO in the reaction was 2%. Time-resolved fluorescence readings were measured on a microplate multilabel reader. Percentage of inhibition was calculated relative to nutlin-3.

As the potencies of the HDM2 inhibitors increased, an improved HTRF assay (HTRF2 assay) was developed. All assay conditions remained the same as described above, with the exception of the following changes in reagent concentrations: 0.2 nM GST-hMDM2 (1-188), 0.5 nM biotinylated-p53 (1-83), 0.18 nM SA-XLent, and 100 mM KF.

Results are provided in the table below.

| Example No. | HTRF1 IC$_{50}$ (µM) | HTRF2 IC$_{50}$ (µM) |
| --- | --- | --- |
| 1 | 33.4 | |
| 2 | 31.4 | |
| 3 | 23.5 | |
| 4 | 25 | |
| 5 | 39.5 | |
| 6 | 46.7 | |
| 7 | 1.1 | |
| 8 | 1.6 | |
| 9 | 0.5 | |
| 10 | 0.8 | |
| 11 | 0.6 | |
| 12 | 0.9 | |
| 13 | 0.7 | |
| 14 | 0.3 | |
| 15 | 0.3 | |
| 16 | 0.3 | |
| 17 | 0.2 | |
| 18 | 0.1 | |
| 19 | 0.6 | |
| 20 | 0.3 | |
| 21 | 0.3 | |
| 22 | 0.5 | |
| 23 | 0.3 | |
| 24 | 1.0 | |
| 25 | 0.6 | |
| 26 | 1.5 | |
| 27 | 0.6 | |
| 28 | 0.5 | |
| 29 | 0.3 | |
| 30 | 1.8 | |
| 31 | 0.1 | |
| 32 | 0.1 | |
| 33 | 1.1 | |
| 34 | 25.0 | |
| 35 | 13.0 | |
| 36 | 0.2 | |
| 37 | 0.3 | |
| 38 | 0.3 | |
| 39 | 0.3 | |
| 40 | 0.7 | |
| 41 | 0.5 | |
| 42 | 0.2 | |
| 43 | 1.1 | |
| 44 | 0.9 | |
| 45 | 0.8 | |
| 46 | 0.8 | |
| 47 | 0.8 | |
| 48 | 0.5 | |
| 49 | 0.6 | |
| 50 | 0.7 | |
| 51 | 0.6 | |
| 52 | 19.7 | |
| 53 | 0.1 | |
| 54 | 0.6 | |
| 55 | 3.3 | |
| 56 | 0.7 | |
| 57 | 0.8 | |
| 58 | 0.9 | |
| 59 | 0.7 | |
| 60 | 0.7 | |
| 61 | 0.6 | |
| 62 | 0.9 | |
| 63 | 9.1 | |
| 64 | 1.5 | |
| 65 | 1.1 | |
| 66 | 13.5 | |
| 67 | 17.5 | |
| 68 | 14.2 | |
| 69 | 3.91 | |
| 70 | 0.1 | |
| 71 | 3.1 | |
| 72 | 1.5 | |
| 73 | 11.6 | |
| 74 | 4.5 | |
| 75 | 3.7 | |
| 76 | 1.4 | |
| 77 | 0.3 | |
| 78 | 0.8 | |
| 79 | 70.2 | |
| 80 | 14.8 | |
| 81 | 15.7 | |
| 82 | 30.0 | |
| 83 | 0.3 | |
| 84 | 0.3 | |
| 85 | 1.6 | |
| 86 | 0.8 | |
| 87 | 1.8 | |
| 88 | 2.1 | |
| 89 | 6.1 | |
| 90 | 3.5 | |
| 91 | 0.6 | |
| 92 | 19.5 | |
| 93 | 0.3 | |
| 94 | 0.6 | |
| 95 | 33.5 | |
| 96 | 1.1 | |
| 97 | 0.5 | |
| 98 | 1.8 | |
| 99 | 1.1 | |
| 100 | 1.1 | |
| 101 | 0.6 | |
| 102 | 6.5 | |
| 103 | 3.4 | |
| 104 | 0.5 | |
| 105 | 0.3 | |
| 106 | 5.2 | |
| 107 | 3.8 | |
| 108 | 4.3 | |
| 109 | 2.8 | |
| 110 | 3.7 | |
| 111 | 2.3 | |
| 112 | | 0.004 |
| 113 | | 0.004 |
| 114 | | 0.053 |
| 115 | | 0.063 |
| 116 | | 0.013 |
| 117 | | 0.022 |
| 118 | | 0.002 |
| 119 | | 0.005 |
| 120 | | <0.001 |
| 121 | | 0.002 |
| 122 | | <0.001 |
| 123 | | 0.001 |
| 124 | | 0.002 |
| 125 | | 0.011 |
| 126 | | 0.061 |

-continued

| Example No. | HTRF1 IC$_{50}$ (μM) | HTRF2 IC$_{50}$ (μM) |
|---|---|---|
| 127 | | 0.034 |
| 128 | | <0.001 |
| 129 | | <0.001 |
| 130 | | 0.024 |
| 131 | | 0.020 |
| 132 | | 0.709 |
| 133 | | <0.001 |
| 134 | | <0.001 |
| 135 | | 0.001 |
| 136 | | 0.001 |
| 137 | | 0.005 |
| 138 | | 0.029 |
| 139 | | 0.005 |
| 140 | | 0.003 |
| 141 | | 0.001 |
| 142 | | 0.007 |
| 143 | | 0.001 |
| 144 | | 0.004 |
| 145 | | 0.008 |
| 146 | | 0.015 |
| 147 | | 0.006 |
| 148 | | 0.007 |
| 149 | | 0.030 |
| 150 | | 0.021 |
| 151 | | 0.022 |
| 152 | | 0.037 |
| 153 | | 0.059 |
| 154 | | <0.001 |
| 155 | | 0.001 |
| 156 | | 0.001 |
| 157 | | 0.001 |
| 158 | | <0.001 |
| 159 | | <0.001 |
| 160 | | 0.002 |
| 161 | | <0.001 |
| 162 | | 6.250 |
| 163 | | 6.620 |
| 164 | | 0.002 |
| 165 | | 0.008 |
| 166 | | 0.101 |
| 167 | | 0.064 |
| 168 | | 0.004 |
| 169 | | 0.004 |
| 170 | | <0.001 |
| 171 | | <0.001 |
| 172 | | <0.001 |
| 173 | | <0.001 |
| 174 | | <0.001 |
| 175 | | <0.001 |
| 176 | | <0.001 |
| 177 | | <0.001 |
| 178 | | 0.182 |
| 179 | | 0.141 |
| 180 | | <0.001 |
| 181 | | 0.001 |
| 182 | | 0.004 |
| 183 | | 0.178 |
| 184 | | 0.005 |
| 185 | | 0.006 |
| 186 | | 0.002 |
| 187 | | 0.002 |
| 188 | | <0.001 |
| 189 | | <0.001 |
| 190 | | 0.003 |
| 191 | | 0.005 |
| 192 | | 0.001 |
| 193 | | 0.032 |
| 194 | | 0.003 |
| 195 | | 0.003 |
| 196 | | 0.001 |
| 197 | | 0.001 |
| 198 | | 0.001 |
| 199 | | 0.001 |
| 200 | | 0.001 |
| 201 | | 0.002 |

-continued

| Example No. | HTRF1 IC$_{50}$ (μM) | HTRF2 IC$_{50}$ (μM) |
|---|---|---|
| 202 | | 0.004 |
| 203 | | 0.020 |
| 204 | | 0.001 |
| 205 | | 0.047 |
| 206 | | 0.145 |
| 207 | | <0.001 |
| 208 | | 0.002 |
| 209 | | 0.007 |
| 210 | | 0.001 |
| 211 | | 0.004 |
| 212 | | 0.002 |
| 213 | | 0.005 |
| 214 | | 0.001 |
| 215 | | 0.004 |
| 216 | | <0.001 |
| 217 | | <0.001 |
| 218 | | 0.001 |
| 219 | | 0.001 |
| 220 | | 0.009 |
| 221 | | 0.012 |
| 222 | | 0.170 |
| 223 | | 0.001 |
| 224 | | 0.002 |
| 225 | | 0.006 |
| 226 | | 0.011 |
| 227 | | 0.011 |
| 228 | | 0.014 |
| 229 | | 0.008 |
| 230 | | 0.007 |
| 231 | | 0.016 |
| 232 | | 0.031 |
| 233 | | 0.006 |
| 234 | | 0.015 |
| 235 | | 0.011 |
| 236 | | 0.022 |
| 237 | | 0.003 |
| 238 | | 0.001 |
| 239 | | <0.001 |
| 240 | | 0.011 |
| 241 | | 0.001 |
| 242 | | 0.002 |
| 243 | | 0.001 |
| 244 | | 0.001 |
| 245 | | 0.009 |
| 246 | | 0.006 |
| 247 | | 0.003 |
| 248 | | 0.008 |
| 249 | | 0.004 |
| 250 | | <0.001 |
| 251 | | <0.001 |
| 252 | | 0.001 |
| 253 | | 0.018 |
| 254 | | 0.001 |
| 255 | | 0.004 |
| 256 | | <0.001 |
| 257 | | <0.001 |
| 258 | | 0.001 |
| 259 | | 0.001 |
| 260 | | 0.008 |
| 261 | | 0.006 |
| 262 | | 0.002 |
| 263 | | 0.002 |
| 264 | | 0.019 |
| 265 | | 0.001 |
| 266 | | <0.001 |
| 267 | | 0.001 |
| 268 | | 0.157 |
| 269 | | 0.067 |
| 270 | | 0.002 |
| 271 | | 0.005 |
| 272 | | 0.154 |
| 273 | | 0.095 |
| 274 | | 0.004 |
| 275 | | <0.001 |
| 276 | | <0.001 |

| Example No. | HTRF1 IC$_{50}$ (μM) | HTRF2 IC$_{50}$ (μM) |
|---|---|---|
| 277 | | 0.106 |
| 278 | | 0.084 |
| 279 | | 0.039 |
| 280 | | 0.002 |
| 281 | | 0.004 |
| 282 | | 0.002 |
| 283 | | 0.003 |
| 284 | | 0.005 |
| 285 | | 0.009 |
| 286 | | 0.002 |
| 287 | | 0.005 |
| 288 | | <0.001 |
| 289 | | 0.002 |
| 290 | | <0.001 |
| 291 | | <0.001 |
| 292 | | <0.001 |
| 293 | | 0.001 |
| 294 | | <0.001 |
| 295 | | 0.002 |
| 296 | | <0.001 |
| 297 | | <0.001 |
| 298 | | 0.026 |
| 299 | | 0.011 |
| 300 | | <0.001 |
| 301 | | <0.001 |
| 302 | | <0.001 |
| 303 | | 0.001 |
| 304 | | <0.001 |
| 305 | | <0.001 |
| 306 | | <0.001 |
| 307 | | <0.001 |
| 308 | | <0.001 |
| 309 | | 0.001 |
| 310 | | 0.001 |
| 311 | | 0.005 |
| 312 | | 0.279 |
| 313 | | 0.038 |
| 314 | | <0.001 |
| 315 | | <0.001 |
| 316 | | 0.002 |
| 317 | | 0.003 |
| 318 | | 0.008 |
| 319 | | 0.113 |
| 320 | | 0.003 |
| 321 | | 0.002 |
| 322 | | 0.051 |
| 323 | | 0.016 |
| 324 | | 0.007 |
| 325 | | 0.004 |
| 326 | | <0.001 |
| 327 | | 0.051 |
| 328 | | 0.012 |
| 329 | | 0.138 |
| 330 | | 0.001 |
| 331 | | <0.001 |
| 332 | | 0.027 |
| 333 | | 0.199 |
| 334 | | <0.001 |
| 335 | | 0.003 |
| 336 | | <0.001 |
| 337 | | 0.050 |
| 338 | | 0.024 |
| 339 | | <0.001 |
| 340 | | 0.028 |
| 341 | | <0.001 |
| 342 | | 0.104 |
| 343 | | 0.001 |
| 344 | | <0.001 |
| 345 | | <0.001 |
| 346 | | 0.021 |
| 347 | | 0.004 |
| 348 | | 0.005 |
| 349 | | 0.001 |
| 350 | | 0.016 |
| 351 | | 0.004 |
| 352 | | 0.025 |
| 353 | | 0.009 |
| 354 | | 0.002 |
| 355 | | 0.004 |
| 356 | | 0.010 |
| 357 | | 0.006 |
| 358 | | <0.001 |
| 359 | | <0.001 |
| 360 | | 0.001 |
| 361 | | <0.001 |
| 362 | | 0.020 |
| 363 | | 0.023 |
| 364 | | <0.001 |
| 365 | | 0.002 |
| 366 | | <0.001 |
| 367 | | 0.004 |
| 368 | | <0.001 |
| 369 | | 0.008 |
| 370 | | 0.028 |
| 371 | | 0.015 |
| 372 | | 0.067 |
| 373 | | 0.045 |
| 374 | | 0.019 |
| 375 | | 0.055 |
| 376 | | 0.048 |
| 377 | | 0.086 |
| 378 | | 0.142 |
| 379 | | 0.082 |
| 380 | | 0.048 |
| 381 | | 0.066 |
| 382 | | <0.001 |
| 383 | | <0.001 |
| 384 | | 0.013 |
| 385 | | 0.004 |
| 386 | | 0.013 |
| 387 | | 0.062 |
| 388 | | 0.028 |
| 389 | | 0.019 |
| 390 | | 0.011 |
| 391 | | 0.004 |
| 392 | | <0.001 |
| 393 | | <0.001 |
| 394 | | 0.001 |
| 395 | | 0.001 |
| 396 | | 0.002 |
| 397 | | 0.001 |
| 398 | | <0.001 |
| 399 | | <0.001 |
| 400 | | 0.037 |
| 401 | | 0.038 |
| 402 | | 0.029 |
| 403 | | 0.002 |
| 404 | | 0.134 |
| 405 | | 0.003 |
| 406 | | 0.004 |
| 407 | | <0.001 |
| 408 | | 0.001 |
| 409 | | <0.001 |
| 410 | | <0.001 |
| 411 | | <0.001 |
| 412 | | 0.011 |
| 413 | | <0.001 |
| 414 | | 0.001 |
| 415 | | 0.001 |
| 416 | | 0.004 |
| 417 | | 0.003 |
| 418 | | 0.003 |
| 419 | | 0.004 |
| 420 | | 0.012 |
| 421 | | 13.6 |
| 422 | | 0.003 |
| 423 | | 0.001 |
| 424 | | 0.003 |

-continued

| Example No. | HTRF1 IC$_{50}$ (μM) | HTRF2 IC$_{50}$ (μM) |
|---|---|---|
| 425 |  | <0.001 |
| 426 |  | 0.001 |

What is claimed is:
1. A compound of Formula I or II, or a pharmaceutically acceptable salt thereof,

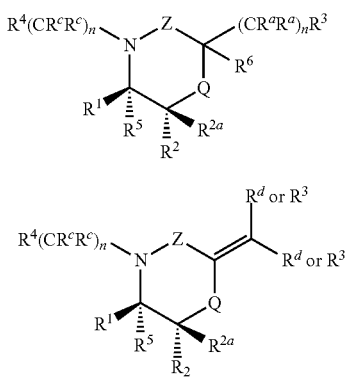

wherein:
Q is O;
Z is —C(=O)—;
$R^1$ is a phenyl group, and the phenyl group can be unsubstituted or substituted with from one to three substituents independently selected from halo, —C$_{1-6}$alkyl, —OH, —NO$_2$, —NHC(=O)C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, —(CH$_2$)$_n$C(=O)R$^f$, —(CH$_2$)$_n$C(=O)NR$^f$R$^f$, —CN, —NR$^g$R$^g$ or A,
each A is independently a 5 or 6 membered aryl or heteroaryl group, which heteroaryl group can contain from one to three heteroatoms independently selected from O, N or S, and the aryl or heteroaryl group can be unsubstituted or substituted with from one to three substituents independently selected from halo, —C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, or —CN;
$R^2$ is a phenyl group, and the phenyl group can be unsubstituted or substituted with from one to three substituents independently selected from halo, —C$_{1-6}$alkyl, —OH, —NO$_2$, —NHC(=O)C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, —(CH$_2$)$_n$C(=O)R$^f$, —(CH$_2$)$_n$C(=O)NR$^f$R$^f$, —CN, —NR$^g$R$^g$ or B,
each B is independently a 5 or 6 membered aryl or heteroaryl group, which heteroaryl group can contain from one to three heteroatoms independently selected from O, N or S, and the aryl or heteroaryl group can be unsubstituted or substituted with from one to three substituents independently selected from halo, —C$_{1-6}$alkyl, —S(=O)C$_{1-6}$alkyl, —S(=O)C$_{1-6}$alkyl, —OC$_{1-6}$alkyl, —CF$_3$, —OCF$_3$, —OCHF$_2$, —OCH$_2$F, or —CN;
$R^{2a}$ is hydrogen or —C$_{1-3}$alkyl;
$R^3$ is hydrogen, —C$_{1-6}$alkyl, —C(=O)OR$^f$, —C(=O)C$_{1-6}$alkyl, —S(=O)$_2$R$^f$, —S(=O)R$^f$, —OR$^f$, —C(=O)NR$^f$N(R$^f$)$_2$, —C(=O)NR$^f$S(=O)$_2$R$^f$, —S(=O)$_2$NR$^f$C(=O)R$^f$, —S(=O)$_2$NR$^f$R$^f$, —N(R$^f$)C(=O)NR$^f$R$^f$, —NR$^f$CO$_2$R$^f$, —C(=O)NR$^f$R$^f$, —NR$^f$S(=O)$_2$R$^f$, —CN, —NR$^f$R$^f$, —C(=O)NOH, —NR$^f$C(=O)OR$^f$, —NR$^f$C(=O)R$^f$, —C$_{1-6}$alkyl substituted with from 1 to 3 hydroyl groups, —C$_{1-6}$alkenyl, or a 5 or 6 membered aryl or heteroaryl group, which heteroaryl group can contain from one to four heteroatoms independently selected from O, N or S, and the aryl or heteroaryl group can be unsubstituted or substituted with from one to three substituents independently selected from halo, —C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, or —CN, and any C$_{1-6}$alkyl group can be unsubstituted or substituted with from one to three substituents independently selected from halo, —OH, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, or —CN;
$R^4$ is —C$_{2-6}$alkenyl, —CF$_3$, —CH$_2$F, —CHF$_2$, —S(=O)$_2$R$^f$, —SR$^f$, —S(=O)R$^f$, —S(=O)$_2$NR$^f$R$^f$, —NR$^f$S(=O)$_2$NR$^f$R$^f$, —C(=O)NR$^f$R$^f$, —NR$^f$S(=O)$_2$R$^f$, —CO$_2$R$^f$, —OR$^f$, a 3 to 7 membered cycloalkyl or heterocycloalkyl, optionally containing a —(C=O)— group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halo, —C$_{1-6}$alkyl —OH, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, or —CN, and the —C$_{1-6}$alkyl or —C$_{2-6}$alkenyl group can be unsubstituted or substituted with from one to three substituents independently selected from halo, —NR$^f$R$^f$, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, or —CN;
$R^5$ is hydrogen or —C$_{1-6}$alkyl;
$R^6$ is hydrogen, —C$_{1-6}$alkyl, —(CH$_2$)$_n$—NR$^f$R$^f$, or —(CH$_2$)$_n$C(=O)NR$^f$R$^f$;
each $R^a$ is independently hydrogen, halo or —C$_{1-6}$alkyl, or two $R^a$ groups that are attached to the same carbon atom can form an (=O) group or a 3 to 6 membered cycloalkyl or heterocycloalkyl group, or an $R^a$ group and $R^6$ along with the atoms to which they are attached can form a 3 to 6 membered cycloalkyl or heterocycloalkyl group, which heterocycloalkyl group can contain from one to two heteroatoms independently selected from O, N or S, and the cycloalkyl or heterocycloalkyl group can be unsubstituted or substituted with from one to three substituents independently selected from halo, —C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, or —CN;
each $R^c$ is independently hydrogen, —C$_{1-6}$alkyl, —C$_{1-6}$alkyl-CF$_3$, —CF$_3$, a 3 to 6 membered cycloalkyl or heterocycloalkyl group, which heterocycloalkyl group can contain from one to two heteroatoms independently selected from O, N or S, and the cycloalkyl or heterocycloalkyl group can be unsubstituted or substituted with from one to three substituents independently selected from halo, C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, or —CN;
or two $R^c$ groups that are attached to the same or adjacent carbon atoms can together with the carbon atom or atoms to which they are attached form or a 3 to 6 membered cycloalkyl or heterocycloalkyl group, which heterocycloalkyl group can contain from one to two heteroatoms independently selected from O, N or S, and the cycloalkyl or heterocycloalkyl group can be unsubstituted or substituted with from one to three substituents independently selected from halo, —$C_{1-6}$alkyl, —S(=O)$_2$$C_{1-6}$alkyl, —S(=O)$C_{1-6}$alkyl, —O$C_{1-6}$alkyl, —$CF_3$, —$OCF_3$, —$OCHF_2$, —$OCH_2F$, or —CN;

each $R^d$ is independently hydrogen or —$C_{1-6}$alkyl;

each $R^e$ is independently hydrogen or —$C_{1-6}$alkyl;

each $R^f$ is independently hydrogen, —CN, —$C_{1-6}$alkyl, —$C_{1-6}$alkyl-CN, —$C_{1-6}$alkyl-$CF_3$, hydroxy$C_{1-6}$alkyl, —$C_{1-6}$alkylN$R^eR^e$, or a 5 to 6 membered aryl, —$C_{1-6}$alkylaryl, heteroaryl, or —$C_{1-6}$alkylheteroaryl, or a 3 to 9 membered cycloalkyl, —$C_{1-6}$alkylcycloalkyl, heterocycloalkyl or —$C_{1-6}$alkylheterocycloalkyl group, which heteroaryl, alkylheteroaryl, heterocycloalkyl, or alkylheterocycloalkyl group can contain from one to three heteroatoms independently selected from O, N or S, and the alkyl, aryl, alkylaryl, heteroaryl, alkylheteroaryl, cycloalkyl, alkylcycloalkyl, heterocycloalkyl, or alkylheterocycloalkyl group can be unsubstituted or substituted with from one to three substituents independently selected from halo, —$C_{1-6}$alkyl, —S(=O)$_2$$C_{1-6}$alkyl, —S(=O)$C_{1-6}$alkyl, —O$C_{1-6}$alkyl, —$CF_3$, —$OCF_3$, —$OCHF_2$, —$OCH_2F$, or —CN;

or when $R^f$ and $R^f$ are part of an N$R^fR^f$ or C$R^fR^f$ moiety in a group, then $R^f$ and $R^f$ together with the nitrogen or carbon atom to which they are attached can form a 3 to 7 membered heterocycloalkyl or cycloalkyl group, which heterocycloalkyl group can contain from one to two additional heteroatoms independently selected from O, N or S, and the heterocycloalkyl or cycloalkyl group can be unsubstituted or substituted with from one to three substituents independently selected from halo, —$C_{1-6}$alkyl, —S(=O)$_2$$C_{1-6}$alkyl, —S(=O)$C_{1-6}$alkyl, —O$C_{1-6}$alkyl, —$CF_3$, —$OCF_3$, —$OCHF_2$, —$OCH_2F$, or —CN;

each $R^g$ is independently hydrogen, or —$C_{1-6}$alkyl; and each n is independently 0, 1, 2, 3 or 4, provided that the compound is not 2-((2R,5R,6R)-6-(3-chlorophenyl)-5-(4-chlorophenyl)-4-((1S,2S)-2-(isopropylsulfonyl)cyclopentyl)-3-oxomorpholin-2-yl)acetic acid; 2-((2S,5R,6R)-6-(3-chlorophenyl)-5-(4-chlorophenyl)-4-((1S,2S)-2-(isopropylsulfonyl)cyclopentyl)-3-oxomorpholin-2-yl)acetic acid; 2-((2R,5R,6R)-6-(3-chlorophenyl)-5-(4-chlorophenyl)-4-((1R,2R)-2-(isopropylsulfonyl)cyclopentyl)-3-oxomorpholin-2-yl)acetic acid; or 2-((2S,5R,6R)-6-(3-chlorophenyl)-5-(4-chlorophenyl)-4-((1R,2R)-2-(isopropylsulfonyl)cyclopentyl)-3-oxomorpholin-2-yl)acetic acid.

2. A compound in accordance with claim 1, or a pharmaceutically acceptable salt thereof,

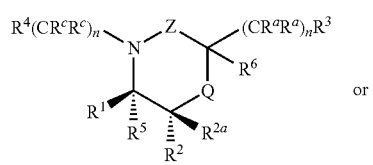

or

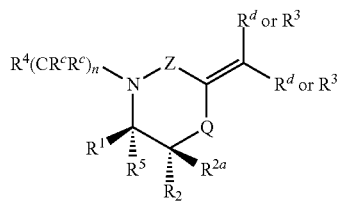

wherein:
Q is O;
Z is —C(=O)—;
$R^1$ is a phenyl group, and the phenyl group can be unsubstituted or substituted with from one to three substituents independently selected from halo, —$C_{1-6}$alkyl, —OH, —$NO_2$, —NHC(=O)$C_{1-6}$alkyl, —S(=O)$_2$$C_{1-6}$alkyl, —S(=O)$C_{1-6}$alkyl, —O$C_{1-6}$alkyl, —$CF_3$, —$OCF_3$, —$OCHF_2$, —$OCH_2F$, —$(CH_2)_n$C(=O)$R^f$, —$(CH_2)_n$C(=O)—N$R^fR^f$, —CN, —N$R^gR^g$ or A, each A is independently a 5 or 6 membered aryl or heteroaryl group, which heteroaryl group can contain from one to three heteroatoms independently selected from O, N or S, and the aryl or heteroaryl group can be unsubstituted or substituted with from one to three substituents independently selected from halo, —$C_{1-6}$alkyl, —S(=O)$_2$$C_{1-6}$alkyl, —S(=O)$C_{1-6}$alkyl, —O$C_{1-6}$alkyl, —$CF_3$, —$OCF_3$, —$OCHF_2$, —$OCH_2F$, or —CN;

$R^2$ is a phenyl group, and the phenyl group can be unsubstituted or substituted with from one to three substituents independently selected from halo, —$C_{1-6}$alkyl, —OH, —$NO_2$, —NHC(=O)$C_{1-6}$alkyl, —S(=O)$_2$$C_{1-6}$alkyl, —S(=O)$C_{1-6}$alkyl, —O$C_{1-6}$alkyl, —$CF_3$, —$OCF_3$, —$OCHF_2$, —$OCH_2F$, —$(CH_2)_n$C(=O)$R^f$, —$(CH_2)_n$C(=O)N$R^fR^f$, —CN, —N$R^gR^g$ or B, each B is independently a 5 or 6 membered aryl or heteroaryl group, which heteroaryl group can contain from one to three heteroatoms independently selected from O, N or S, and the aryl or heteroaryl group can be unsubstituted or substituted with from one to three substituents independently selected from halo, —$C_{1-6}$alkyl, —S(=O)$_2$$C_{1-6}$alkyl, —S(=O)$C_{1-6}$alkyl, —O$C_{1-6}$alkyl, —$CF_3$, —$OCF_3$, —$OCHF_2$, —$OCH_2F$, or —CN;

$R^{2a}$ is hydrogen or —$C_{1-3}$alkyl;

$R^3$ is hydrogen, —$C_{1-6}$alkyl, —C(=O)O$R^f$, —C(=O)$C_{1-6}$alkyl, —S(=O)$_2$$R^f$, —S(=O)$R^f$, —O$R^f$, —C(=O)N$R^f$N($R^f$)$_2$, —C(=O)N$R^f$S(=O)$_2$$R^f$, —S(=O)$_2$N$R^f$C(=O)$R^f$, —S(=O)$_2$N$R^fR^f$, —N($R^f$)C(=O)N$R^fR^f$, —N$R^f$CO$_2$$R^f$, —C(=O)N$R^fR^f$, —N$R^f$S(=O)$_2$$R^f$, —CN, —N$R^fR^f$, or a 5 or 6 membered aryl or heteroaryl group, which heteroaryl group can contain from one to four heteroatoms independently selected from O, N or S, and the aryl or heteroaryl group can be unsubstituted or substituted with from one to three substituents independently selected from halo, —$C_{1-6}$alkyl, —S(=O)$_2$$C_{1-6}$alkyl, —S(=O)$C_{1-6}$alkyl, —O$C_{1-6}$alkyl, —$CF_3$, —$OCF_3$, —$OCHF_2$, —$OCH_2F$, or —CN, and any $C_{1-6}$alkyl group can be unsubstituted or substituted with from one to three substituents independently selected from halo, —OH, —S(=O)$_2$$C_{1-6}$alkyl, —S(=O)$C_{1-6}$alkyl, —O$C_{1-6}$alkyl, —$CF_3$, —$OCF_3$, —$OCHF_2$, —$OCH_2F$, or —CN;

$R^4$ is —$C_{2-6}$alkenyl, —$CF_3$, —$CH_2F$, —$CHF_2$, —S(=O)$_2$$R^f$, —S$R^f$, —S(=O)$R^f$, —S(=O)$_2$N$R^fR^f$, —N$R^f$S(=O)$_2$N$R^fR^f$, —C(=O)N$R^fR^f$, —N$R^f$S(=O)$_2$$R^f$, —CO$_2$$R^f$, —O$R^f$, a 3 to 7 membered cycloalkyl or heterocycloalkyl, optionally containing a —(C=O)— group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halo, —$C_{1-6}$alkyl —OH, —S(=O)$_2$$C_{1-6}$alkyl, —S(=O)$C_{1-6}$alkyl, —O$C_{1-6}$alkyl, —CF$_3$, —OCF$_3$, —OCHF$_2$, —OCH$_2$F, or —CN, and the —$C_{1-6}$alkyl or —$C_{2-6}$alkenyl group can be unsubstituted or substituted with from one to three substituents independently selected from halo, —NR$^f$R$^f$, —S(=O)$_2$$C_{1-6}$alkyl, —S(=O)$C_{1-6}$alkyl, —O$C_{1-6}$alkyl, —CF$_3$, —OCF$_3$, —OCHF$_2$, —OCH$_2$F, or —CN;

$R^5$ is hydrogen or —$C_{1-6}$alkyl;

$R^6$ is hydrogen, —$C_{1-6}$alkyl, —(CH$_2$)$_n$NR$^f$R$^f$, or —(CH$_2$)$_n$C(=O)NR$^f$R$^f$;

each $R^a$ is independently hydrogen, halo or —$C_{1-6}$alkyl, or two $R^a$ groups that are attached to the same carbon atom can form an (=O) group or a 3 to 6 membered cycloalkyl or heterocycloalkyl group, or an $R^a$ group and $R^6$ along with the atoms to which they are attached can form a 3 to 6 membered cycloalkyl or heterocycloalkyl group, which heterocycloalkyl group can contain from one to two heteroatoms independently selected from O, N or S, and the cycloalkyl or heterocycloalkyl group can be unsubstituted or substituted with from one to three substituents independently selected from halo, —$C_{1-6}$alkyl, —S(=O)$_2$$C_{1-6}$alkyl, —S(=O)$C_{1-6}$alkyl, —O$C_{1-6}$alkyl, —CF$_3$, —OCF$_3$, —OCHF$_2$, —OCH$_2$F, or —CN;

each $R^c$ is independently hydrogen, —$C_{1-6}$alkyl, a 3 to 6 membered cycloalkyl or heterocycloalkyl group, which heterocycloalkyl group can contain from one to two heteroatoms independently selected from O, N or S, and the cycloalkyl or heterocycloalkyl group can be unsubstituted or substituted with from one to three substituents independently selected from halo, $C_{1-6}$alkyl, —S(=O)$_2$$C_{1-6}$alkyl, —S(=O)$C_{1-6}$alkyl, —O$C_{1-6}$alkyl, —CF$_3$, —OCF$_3$, —OCHF$_2$, —OCH$_2$F, or —CN; or two $R^c$ groups that are attached to the same or adjacent carbon atoms can together with the carbon atom or atoms to which they are attached form or a 3 to 6 membered cycloalkyl or heterocycloalkyl group, which heterocycloalkyl group can contain from one to two heteroatoms independently selected from O, N or S, and the cycloalkyl or heterocycloalkyl group can be unsubstituted or substituted with from one to three substituents independently selected from halo, —$C_{1-6}$alkyl, —S(=O)$_2$$C_{1-6}$alkyl, —S(=O)$C_{1-6}$alkyl, —O$C_{1-6}$alkyl, —CF$_3$, —OCF$_3$, —OCHF$_2$, —OCH$_2$F, or —CN;

each $R^d$ is independently hydrogen or —$C_{1-6}$alkyl;

each $R^e$ is independently hydrogen or —$C_{1-6}$alkyl;

each $R^f$ is independently hydrogen, —$C_{1-6}$alkyl or a 5 to 6 membered aryl, —$C_{1-6}$alkylaryl, heteroaryl, or —$C_{1-6}$alkylheteroaryl, or a 3 to 7 membered cycloalkyl, —$C_{1-6}$alkylcycloalkyl, heterocycloalkyl or —$C_{1-6}$alkylheterocycloalkyl group, which heteroaryl, alkylheteroaryl, heterocycloalkyl, or alkylheterocycloalkyl group can contain from one to three heteroatoms independently selected from O, N or S, and the aryl, alkylaryl, heteroaryl, alkylheteroaryl, cycloalkyl, alkylcycloalkyl, heterocycloalkyl, or alkylheterocycloalkyl group can be unsubstituted or substituted with from one to three substituents independently selected from halo, —$C_{1-6}$alkyl, —S(=O)$_2$$C_{1-6}$alkyl, —S(=O)$C_{1-6}$alkyl, —O$C_{1-6}$alkyl, —CF$_3$, —OCF$_3$, —OCHF$_2$, —OCH$_2$F, or —CN;

or when $R^f$ and $R^f$ are part of an NR$^f$R$^f$ or CR$^f$R$^f$ moiety in a group, then $R^f$ and $R^f$ together with the nitrogen or carbon atom to which they are attached can form a 3 to 7 membered heterocycloalkyl or cycloalkyl group, which heterocycloalkyl group can contain from one to two additional heteroatoms independently selected from O, N or S, and the heterocycloalkyl or cycloalkyl group can be unsubstituted or substituted with from one to three substituents independently selected from halo, —$C_{1-6}$alkyl, —S(=O)$_2$$C_{1-6}$alkyl, —S(=O)$C_{1-6}$alkyl, —O$C_{1-6}$alkyl, —CF$_3$, —OCF$_3$, —OCHF$_2$, —OCH$_2$F, or —CN;

each $R^g$ is independently hydrogen, or —$C_{1-6}$alkyl; and each n is independently 0, 1, 2, 3 or 4.

3. A compound in accordance with claim 1, or a pharmaceutically acceptable salt thereof, wherein:

Q is O;

Z is —C(=O)—;

$R^1$ is a phenyl group, and the phenyl group can be unsubstituted or substituted with from one to three substituents independently selected from halo, —$C_{1-6}$alkyl, —S(=O)$_2$$C_{1-6}$alkyl, —S(=O)$C_{1-6}$alkyl, —O$C_{1-6}$alkyl, —CF$_3$ —OCF$_3$, —OCHF$_2$, —OCH$_2$F, —CN, or A;

each A is independently a 5 or 6 membered aryl or heteroaryl group, which heteroaryl group can contain from one to three heteroatoms independently selected from O, N or S, and the aryl or heteroaryl group can be unsubstituted or substituted with from one to three substituents independently selected from halo, —$C_{1-6}$alkyl, —S(=O)$_2$$C_{1-6}$alkyl, —S(=O)$C_{1-6}$alkyl, —O$C_{1-6}$alkyl, —CF$_3$, —OCF$_3$, —OCHF$_2$, —OCH$_2$F, or —CN;

$R^2$ is a phenyl group, and the phenyl group can be unsubstituted or substituted with from one to three substituents independently selected from halo, —$C_{1-6}$alkyl, —S(=O)$_2$$C_{1-6}$alkyl, —S(=O)$C_{1-6}$alkyl, —O$C_{1-6}$alkyl, —CF$_3$, —OCF$_3$, —OCHF$_2$, —OCH$_2$F, —CN, or B;

each B is independently a 5 or 6 membered aryl or heteroaryl group, which heteroaryl group can contain from one to three heteroatoms independently selected from O, N or S, and the aryl or heteroaryl group can be unsubstituted or substituted with from one to three substituents independently selected from halo, —$C_{1-6}$alkyl, —S(=O)$_2$$C_{1-6}$alkyl, —S(=O)$C_{1-6}$alkyl, —O$C_{1-6}$alkyl, —CF$_3$, —OCF$_3$, —OCHF$_2$, —OCH$_2$F, or —CN;

$R^3$ is hydrogen, —$C_{1-6}$alkyl, —C(=O)OR$^f$, —C(=O)$C_{1-6}$alkyl, —S(=O)$_2$R$^f$, —S(=O)R$^f$, —OR$^f$, —C(=O)NR$^f$N(R$^f$)$_2$, —C(=O)NR$^f$S(=O)$_2$R$^f$, —S(=O)$_2$NR$^f$C(=O)R$^f$, —S(=O)$_2$NR$^f$R$^f$, —N(R$^f$)C(=O)NR$^f$R$^f$, —NR$^f$CO$_2$R$^f$, —C(=O)NR$^f$R$^f$, —NR$^f$S(=O)$_2$R$^f$, —CN, —NR$^f$R$^f$, or a 5 or 6 membered aryl or heteroaryl group, which heteroaryl group can contain from one to four heteroatoms independently selected from O, N or S, and the aryl or heteroaryl group can be unsubstituted or substituted with from one to three substituents independently selected from halo, —$C_{1-6}$alkyl, —S(=O)$_2$$C_{1-6}$alkyl, —S(=O)$C_{1-6}$alkyl, —O$C_{1-6}$alkyl, —CF$_3$, —OCF$_3$, —OCHF$_2$, —OCH$_2$F, or —CN, and any $C_{1-6}$alkyl group can be unsubstituted or substituted with from one to three substituents independently selected from halo, —OH, —S(=O)$_2$$C_{1-6}$alkyl, —S(=O)$C_{1-6}$alkyl, —O$C_{1-6}$alkyl, —CF$_3$, —OCF$_3$, —OCHF$_2$, —OCH$_2$F, or —CN;

R$^4$ is —C$_{2-6}$alkenyl, —CF$_3$, —CH$_2$F, —CHF$_2$, —S(=O)$_2$R$^f$, —SR$^f$, —S(=O)R$^f$, —S(=O)$_2$NR$^f$R$^f$, —NR$^f$S(=O)$_2$NR$^f$R$^f$, —C(=O)NR$^f$R$^f$, —NR$^f$S(=O)$_2$R$^f$, —CO$_2$R$^f$, —OR$^f$, a 3 to 7 membered cycloalkyl or heterocycloalkyl, optionally containing a —(C=O)— group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halo, —C$_{1-6}$alkyl —OH, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, or —CN, and the —C$_{1-6}$alkyl or —C$_{2-6}$alkenyl group can be unsubstituted or substituted with from one to three substituents independently selected from halo, —NR$^f$R$^f$, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, or —CN;

R$^6$ is hydrogen or —C$_{1-6}$alkyl;

each R$^a$ is independently hydrogen or —C$_{1-6}$alkyl; and each R$^c$ is independently hydrogen or —C$_{1-6}$alkyl.

4. A compound in accordance with claim 1, or a pharmaceutically acceptable salt thereof, wherein:

Q is O;

Z is —C(=O)—;

R$^1$ is a phenyl group, and the phenyl group can be unsubstituted or substituted with from one to three substituents independently selected from halo, —C$_{1-6}$alkyl, —S(=O)$_2$C$_{1-6}$alkyl, —S(=O)C$_{1-6}$alkyl, —OC$_{1-6}$alkyl, —CF$_3$ —OCF$_3$, —OCHF$_2$, —OCH$_2$F, —CN, or A;

each A is independently a 5 or 6 membered aryl or heteroaryl group, which heteroaryl group can contain from one to three heteroatoms independently selected from O, N or S, and the aryl or heteroaryl group can be unsubstituted or substituted with from one to three substituents independently selected from halo, —C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, or —CN;

R$^2$ is a phenyl group, and the phenyl group can be unsubstituted or substituted with from one to three substituents independently selected from halo, —C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, —CN, or B;

each B is independently a 5 or 6 membered aryl or heteroaryl group, which heteroaryl group can contain from one to three heteroatoms independently selected from O, N or S, and the aryl or heteroaryl group group can be unsubstituted or substituted with from one to three substituents independently selected from halo, —C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, or —CN;

R$^3$ is hydrogen, —C(=O)OH, —C(=O)OC$_{1-6}$alkyl, —S(=O)$_2$C$_{1-6}$alkyl, —S(=O)C$_{1-6}$alkyl, —OH, or a 5 or 6 membered aryl or heteroaryl group, which heteroaryl group can contain from one to four heteroatoms independently selected from O, N or S, and the aryl or heteroaryl group can be unsubstituted or substituted with from one to three substituents independently selected from halo, —C$_{1-6}$alkyl, —S(=O)$_2$C$_{1-6}$alkyl, —S(=O)C$_{1-6}$alkyl, —OC$_{1-6}$alkyl, —CF$_3$, —OCF$_3$, —OCHF$_2$, —OCH$_2$F, or —CN;

R$^4$ is —C$_{2-6}$alkenyl, —CF$_3$, —CH$_2$F, —CHF$_2$, —S(=O)$_2$C$_{1-6}$alkyl, —S(=O)C$_{1-6}$alkyl, —C(=O)OC$_{1-6}$alkyl, —OR$^f$, —S(=O)$_2$R$^f$, —NR$^f$S(=O)$_2$R$^f$, a 3 to 6 membered cycloalkyl or heterocycloalkyl, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halo, —C$_{1-6}$alkyl, —S(=O)$_2$C$_{1-6}$alkyl, —S(=O)C$_{1-6}$alkyl, —CF$_3$, —OCF$_3$, —OCHF$_2$, —OCH$_2$F, or —CN;

R$^6$ is hydrogen or —C$_{1-6}$alkyl;

each R$^a$ is independently hydrogen or —C$_{1-6}$alkyl; and each R$^c$ is independently hydrogen or —C$_{1-6}$alkyl.

5. A compound in accordance with claim 1, or a pharmaceutically acceptable salt thereof, wherein —(CR$^a$R$^a$)$_n$— is —CH$_2$—.

6. A compound in accordance with claim 1, or a pharmaceutically acceptable salt thereof, wherein R$^3$ is —CO$_2$R$^f$ or tetrazolyl.

7. A compound in accordance with claim 1, or a pharmaceutically acceptable salt thereof, wherein R$^3$ is —CO$_2$H or tetrazolyl.

8. A compound in accordance with claim 1, or a pharmaceutically acceptable salt thereof, wherein —(CR$^a$R$^a$)$_n$— is —CH$_2$— and R$^3$ is —CO$_2$H or tetrazolyl.

9. A compound in accordance with claim 1, or a pharmaceutically acceptable salt thereof, wherein —(CR$^c$R$^c$)$_n$— is absent, —CH$_2$—, —CH(CH$_2$CH$_3$)—, —CH$_2$CH$_2$—, —CH$_2$CH$_2$CH$_2$—, —CH(CH$_3$)—, —CH(CH$_2$CH$_3$)CH$_2$—, —CH(CHCH$_3$CH$_3$)CH$_2$—, or —C(CCH$_3$CH$_3$CH$_3$)CH$_2$—.

10. A compound in accordance with claim 9, or a pharmaceutically acceptable salt thereof, wherein —(CR$^c$R$^c$)$_n$— is absent.

11. A compound in accordance with claim 9, or a pharmaceutically acceptable salt thereof, wherein —(CR$^c$R$^c$)$_n$— is —CH$_2$—.

12. A compound in accordance with claim 9, or a pharmaceutically acceptable salt thereof, wherein —(CR$^c$R$^c$)$_n$— is —CH(CH$_2$CH$_3$)—.

13. A compound in accordance with claim 9, or a pharmaceutically acceptable salt thereof, wherein —(CR$^c$R$^c$)$_n$— is —CH(CH$_3$)—.

14. A compound in accordance with claim 9, or a pharmaceutically acceptable salt thereof, wherein —(CR$^c$R$^c$)$_n$— is —CH(CH$_2$CH$_3$)CH$_2$—.

15. A compound in accordance with claim 1, or a pharmaceutically acceptable salt thereof, wherein R$^4$ is cyclopropyl, —CO$_2$C$_{1-6}$alkyl, cyclopentyl, cyclobutyl, cyclohexyl, phenyl, oxazolyl, —CF$_3$, —C$_{2-6}$alkenyl, —S(=O)$_2$C$_{1-6}$alkyl, —OH, —S(=O)$_2$phenyl, or —N(phenyl)S(=O)$_2$-cyclopropyl.

16. A compound in accordance with claim 15, or a pharmaceutically acceptable salt thereof, wherein R$^4$ is cyclopropyl.

17. A compound in accordance with claim 15, or a pharmaceutically acceptable salt thereof, wherein R$^4$ is —CO$_2$C$_{1-6}$alkyl.

18. A compound in accordance with claim 15, or a pharmaceutically acceptable salt thereof, wherein R$^4$ is —S(=O)$_2$C$_{1-6}$alkyl.

19. A compound in accordance with claim 15, or a pharmaceutically acceptable salt thereof, wherein R$^4$ is —OH.

20. A compound in accordance with claim 15, or a pharmaceutically acceptable salt thereof, wherein R$^4$ is —S(=O)$_2$phenyl.

21. A compound in accordance with claim 15, or a pharmaceutically acceptable salt thereof, wherein $R^4$ is —N(phenyl)S(=O)$_2$-cyclopropyl.

22. A compound in accordance with claim 1, or a pharmaceutically acceptable salt thereof, wherein $R^4(CR^cR^c)_n$— is —CH$_2$-cyclopropyl, —CH(CH$_2$CH$_3$)CH$_2$S(=O)$_2$C$_{1-6}$alkyl, —CH$_2$-cyclopentyl, —CH$_2$-cyclobutyl, —CH$_2$-cyclohexyl, cyclopropyl, cyclobutyl, or cyclohexyl.

23. A compound in accordance with claim 1, or a pharmaceutically acceptable salt thereof, wherein $R^1$ is substituted phenyl.

24. A compound in accordance with claim 23, or a pharmaceutically acceptable salt thereof, wherein $R^1$ is 4-chlorophenyl.

25. A compound in accordance with claim 23, or a pharmaceutically acceptable salt thereof, wherein $R^1$ is 3-chlorophenyl.

26. A compound in accordance with claim 1, or a pharmaceutically acceptable salt thereof, wherein $R^2$ is substituted phenyl.

27. A compound in accordance with claim 26, or a pharmaceutically acceptable salt thereof, wherein $R^2$ is 3-chlorophenyl.

28. A compound in accordance with claim 1, or a pharmaceutically acceptable salt thereof, wherein $R^6$ is hydrogen or —CH$_3$.

29. A compound in accordance with claim 28, or a pharmaceutically acceptable salt thereof, wherein $R^6$ is hydrogen.

30. A compound in accordance with claim 1, or a pharmaceutically acceptable salt thereof, wherein $R^5$ is hydrogen or —CH$_3$.

31. A compound in accordance with claim 30, or a pharmaceutically acceptable salt thereof, wherein $R^5$ is hydrogen.

32. A compound in accordance with claims 1, or a pharmaceutically acceptable salt thereof, wherein $R^d$ is hydrogen.

33. A compound in accordance with claim 1, or a pharmaceutically acceptable salt thereof, wherein:
Q is O;
Z is —C(=O)—;
—(CR$^a$R$^a$)$_n$— is —CH$_2$—;
$R^3$ is —CO$_2$H or tetrazolyl;
—(CR$^c$R$^c$)$_n$— is absent, —CH$_2$—, —CH(CH$_2$CH$_3$)—, —CH$_2$CH$_2$—, —CH$_2$CH$_2$CH$_2$—, —CH(CH$_3$)—, —CH(CH$_2$CH$_3$)CH$_2$—, —CH(CHCH$_3$CH$_3$)CH$_2$—, or —C(CCH$_3$CH$_3$CH$_3$)CH$_2$—;
$R^4$ is cyclopropyl, —CO$_2$C$_{1-6}$alkyl, cyclopentyl, cyclobutyl, cyclohexyl, phenyl, oxazolyl, —CF$_3$, —C$_{2-6}$alkenyl, —S(=O)$_2$C$_{1-6}$alkyl, —OH, —S(=O)$_2$phenyl, or —N(phenyl)S(=O)$_2$-cyclopropyl;
$R^1$ is substituted phenyl; and
$R^2$ is substituted phenyl.

34. A pharmaceutical composition comprising a compound of claim 1, or a pharmaceutically acceptable salt thereof, and a pharmaceutically acceptable excipient.

35. A method of treating myelogenous leukemia in a subject in need thereof, the method comprising administering to the subject an effective dosage amount of a compound according to claim 1, or a pharmaceutically acceptable salt thereof.

36. The compound in accordance with claim 1, or a pharmaceutically acceptable salt thereof, selected from:
2-((2R,5R,6R)-4-((S)-1-(tert-Butylsulfonyl)butan-2-yl)-6-(3-chlorophenyl)-5-(4-chlorophenyl)-3-oxomorpholin-2-yl)acetic acid;
2-((2R,5R,6R)-6-(3-Chlorophenyl)-5-(4-chlorophenyl)-3-oxo-4-((S)-1-(tert-pentylsulfonyl)butan-2-yl)morpholin-2-yl)acetic acid;
2-((2S,5R,6R)-6-(3-Chlorophenyl)-5-(4-chlorophenyl)-3-oxo-4-((S)-1-(tert-pentylsulfonyl)butan-2-yl)morpholin-2-yl)acetic acid;
2-((2R,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid;
2-((2S,5R,6R)-4-((S)-2-(tert-butylsulfonyl)-1-cyclopropylethyl)-6-(3-chlorophenyl)-5-(4-chlorophenyl)-3-oxomorpholin-2-yl)acetic acid;
2-((2R,5R,6R)-6-(3-chlorophenyl)-5-(4-chlorophenyl)-4-((S)-1-(N-methylcyclopropanesulfonamido)butan-2-yl)-3-oxomorpholin-2-yl)acetic acid;
2-((2S,5R,6R)-6-(3-chlorophenyl)-5-(4-chlorophenyl)-4-((S)-1-(N-methylcyclopropanesulfonamido)butan-2-yl)-3-oxomorpholin-2-yl)acetic acid;
2-((2R,5R,6R)-6-(3-chlorophenyl)-5-(4-chlorophenyl)-4-((S)-1-(N-(2-fluorophenyl)methylsulfonamido)butan-2-yl)-3-oxomorpholin-2-yl)acetic acid;
2-((2S,5R,6R)-6-(3-chlorophenyl)-5-(4-chlorophenyl)-4-((S)-1-(N-(2-fluorophenyl)methylsulfonamido)butan-2-yl)-3-oxomorpholin-2-yl)acetic acid;
2-((2R,5R,6R)-6-(3-chlorophenyl)-5-(4-chlorophenyl)-4-((S)-1-(N-(2-fluorophenyl)propan-2-ylsulfonamido)butan-2-yl)-3-oxomorpholin-2-yl)acetic acid;
2-((2S,5R,6R)-6-(3-chlorophenyl)-5-(4-chlorophenyl)-4-((S)-1-(N-(2-fluorophenyl)propan-2-ylsulfonamido)butan-2-yl)-3-oxomorpholin-2-yl)acetic acid;
2-((2R,5R,6R)-6-(3-chlorophenyl)-5-(4-chlorophenyl)-4-((S)-1-(N-(2-fluorophenyl)-1-methylcyclopropanesulfonamido)butan-2-yl)-3-oxomorpholin-2-yl)acetic acid;
2-((2S,5R,6R)-6-(3-chlorophenyl)-5-(4-chlorophenyl)-4-((S)-1-(N-(2-fluorophenyl)-1-methylcyclopropanesulfonamido)butan-2-yl)-3-oxomorpholin-2-yl)acetic acid;
2-((2R,5R,6R)-6-(3-chlorophenyl)-5-(4-chlorophenyl)-4-((S)-1-(N-(2-fluorophenyl)-1-methylcyclopropanesulfonamido)butan-2-yl)-3-oxomorpholin-2-yl)acetic acid;
2-((2S,5R,6R)-6-(3-chlorophenyl)-5-(4-chlorophenyl)-4-((S)-1-(N-(2-fluorophenyl)-1-methylcyclopropanesulfonamido)butan-2-yl)-3-oxomorpholin-2-yl)acetic acid;
2-((2R,5R,6R)-4-((S)-1-(tert-butylsulfonyl)-4,4,4-trifluorobutan-2-yl)-6-(3-chlorophenyl)-5-(4-chlorophenyl)-3-oxomorpholin-2-yl)acetic acid;
2-((2S,5R,6R)-4-((S)-1-(tert-butylsulfonyl)-4,4,4-trifluorobutan-2-yl)-6-(3-chlorophenyl)-5-(4-chlorophenyl)-3-oxomorpholin-2-yl)acetic acid
2-((2R,5R,6R)-6-(3-Chlorophenyl)-5-(4-chlorophenyl)-4-((S)-1-cyclopropyl-2-((2-hydroxy-2-methylpropyl)sulfonyl)ethyl)-3-oxomorpholin-2-yl)acetic acid;
2-((2S,5R,6R)-6-(3-chlorophenyl)-5-(4-chlorophenyl)-4-((S)-1-cyclopropyl-2-((2-hydroxy-2-methylpropyl)sulfonyl)ethyl)-3-oxomorpholin-2-yl)acetic acid;
2-((2R,5R,6R)-6-(3-Chlorophenyl)-5-(4-chlorophenyl)-4-((S)-2-((2-cyanopropan-2-yl)sulfonyl)-1-cyclopropylethyl)-3-oxomorpholin-2-yl)acetic acid;
2-((2S,5R,6R)-6-(3-chlorophenyl)-5-(4-chlorophenyl)-4-((S)-2-((2-cyanopropan-2-yl)sulfonyl)-1-cyclopropylethyl)-3-oxomorpholin-2-yl)acetic acid;
2-((2R,5R,6R)-6-(3-Chlorophenyl)-5-(4-chlorophenyl)-4-((S)-2-((2-cyanopropan-2-yl)sulfonyl)-1-cyclopropylethyl)-3-oxomorpholin-2-yl)acetic acid;
2-((2S,5R,6R)-6-(3-chlorophenyl)-5-(4-chlorophenyl)-4-((S)-2-((2-cyanopropan-2-yl)sulfonyl)-1-cyclopropylethyl)-3-oxomorpholin-2-yl)acetic acid;

2-((2R,5R,6R)-4-((S)-2-(N-(tert-Butyl)sulfamoyl)-1-cyclopropylethyl)-6-(3-chlorophenyl)-5-(4-chlorophenyl)-3-oxomorpholin-2-yl)acetic acid;

2-((2S,5R,6R)-4-((S)-2-(N-(tert-butyl)sulfamoyl)-1-cyclopropylethyl)-6-(3-chlorophenyl)-5-(4-chlorophenyl)-3-oxomorpholin-2-yl)acetic acid;

2-((2R,5R,6R)-6-(3-Chlorophenyl)-5-(4-chlorophenyl)-4-((S)-1-cyclopropyl-2-(N-(2-fluorophenyl)sulfamoyl)ethyl)-3-oxomorpholin-2-yl)acetic acid;

2-((2S,5R,6R)-6-(3-chlorophenyl)-5-(4-chlorophenyl)-4-((S)-1-cyclopropyl-2-(N-(2-fluorophenyl)sulfamoyl)ethyl)-3-oxomorpholin-2-yl)acetic acid;

2-((2R,5R,6R)-6-(3-Chlorophenyl)-5-(4-chlorophenyl)-4-((S)-1-cyclopropyl-2-(((S)-2-methylpyrrolidin-1-yl)sulfonyl)ethyl)-3-oxomorpholin-2-yl)acetic acid;

2-((2S,5R,6R)-6-(3-chlorophenyl)-5-(4-chlorophenyl)-4-((S)-1-cyclopropyl-2-(((S)-2-methylpyrrolidin-1-yl)sulfonyl)ethyl)-3-oxomorpholin-2-yl)acetic acid;

2-((2R,5R,6R)-6-(3-Chlorophenyl)-5-(4-chlorophenyl)-4-((S)-1-cyclopropyl-2-(((S)-2-methylpyrrolidin-1-yl)sulfonyl)ethyl)-3-oxomorpholin-2-yl)acetic acid;

2-((2S,5R,6R)-6-(3-chlorophenyl)-5-(4-chlorophenyl)-4-((S)-1-cyclopropyl-2-(((S)-2-methylpyrrolidin-1-yl)sulfonyl)ethyl)-3-oxomorpholin-2-yl)acetic acid;

2-((2R,5R,6R)-4-((S)-2-(N-(tert-Butyl)-N-methylsulfamoyl)-1-cyclopropylethyl)-6-(3-chlorophenyl)-5-(4-chlorophenyl)-3-oxomorpholin-2-yl)acetic acid;

2-((2S,5R,6R)-4-((S)-2-(N-(tert-butyl)-N-methylsulfamoyl)-1-cyclopropylethyl)-6-(3-chlorophenyl)-5-(4-chlorophenyl)-3-oxomorpholin-2-yl)acetic acid;

2-((2R,5R,6R)-4-((S)-2-(N-(tert-Butyl)-N-methylsulfamoyl)-1-cyclopropylethyl)-6-(3-chlorophenyl)-5-(4-chlorophenyl)-3-oxomorpholin-2-yl)acetic acid;

2-((2S,5R,6R)-4-((S)-2-(N-(tert-butyl)-N-methylsulfamoyl)-1-cyclopropylethyl)-6-(3-chlorophenyl)-5-(4-chlorophenyl)-3-oxomorpholin-2-yl)acetic acid;

2-((2R,5R,6R)-6-(3-Chlorophenyl)-5-(4-chlorophenyl)-4-((S)-1-cyclopropyl-2-(morpholinosulfonyl)ethyl)-3-oxomorpholin-2-yl)acetic acid;

2-((2S,5R,6R)-6-(3-chlorophenyl)-5-(4-chlorophenyl)-4-((S)-1-cyclopropyl-2-(morpholinosulfonyl)ethyl)-3-oxomorpholin-2-yl)acetic acid;

2-((2R,5R,6R)-6-(3-Chlorophenyl)-5-(4-chlorophenyl)-4-((S)-1-cyclopropyl-2-(((R)-2-methylpyrrolidin-1-yl)sulfonyl)ethyl)-3-oxomorpholin-2-yl)acetic acid;

2-((2S,5R,6R)-6-(3-chlorophenyl)-5-(4-chlorophenyl)-4-((S)-1-cyclopropyl-2-(((R)-2-methylpyrrolidin-1-yl)sulfonyl)ethyl)-3-oxomorpholin-2-yl)acetic acid;

2-((2R,5R,6R)-6-(3-Chlorophenyl)-5-(4-chlorophenyl)-4-((S)-1-cyclopropyl-2-((2,2-dimethylpyrrolidin-1-yl)sulfonyl)ethyl)-3-oxomorpholin-2-yl)acetic acid;

2-((2R,5R,6R)-4-((S)-2-(tert-Butylsulfonyl)-1-cyclopropylethyl)-5-(4-chloro-3-fluorophenyl)-6-(3-chlorophenyl)-3-oxomorpholin-2-yl)acetic acid;

2-((2S,5R,6R)-4-((S)-2-(tert-butylsulfonyl)-1-cyclopropylethyl)-5-(4-chloro-3-fluorophenyl)-6-(3-chlorophenyl)-3-oxomorpholin-2-yl)acetic acid;

2-((2R,5R,6R)-4-((S)-2-(tert-Butylsulfonyl)-1-cyclopropylethyl)-6-(3-chloro-2-fluorophenyl)-5-(4-chlorophenyl)-3-oxomorpholin-2-yl)acetic acid;

2-((2S,5R,6R)-4-((S)-2-(tert-butylsulfonyl)-1-cyclopropylethyl)-6-(3-chloro-2-fluorophenyl)-5-(4-chlorophenyl)-3-oxomorpholin-2-yl)acetic acid;

2-((2R,5R,6R)-4-((S)-2-(tert-Butylsulfonyl)-1-cyclopropylethyl)-6-(3-chlorophenyl)-5-(4-chlorophenyl)-2-methyl-3-oxomorpholin-2-yl)acetic acid;

2-((2S,5R,6R)-4-((S)-2-(tert-butylsulfonyl)-1-cyclopropylethyl)-6-(3-chlorophenyl)-5-(4-chlorophenyl)-2-methyl-3-oxomorpholin-2-yl)acetic acid;

2-((2R,5R,6R)-6-(3-Chlorophenyl)-5-(4-chlorophenyl)-4-((S)-1-cyclopropyl-2-(((S)-2-methylpyrrolidin-1-yl)sulfonyl)ethyl)-2-methyl-3-oxomorpholin-2-yl)acetic acid;

2-((2S,5R,6R)-6-(3-chlorophenyl)-5-(4-chlorophenyl)-4-((S)-1-cyclopropyl-2-(((S)-2-methylpyrrolidin-1-yl)sulfonyl)ethyl)-2-methyl-3-oxomorpholin-2-yl)acetic acid;

2-((2R,5R,6R)-4-((S)-1-(tert-Butylsulfonyl)butan-2-yl)-6-(3-chlorophenyl)-5-(4-chlorophenyl)-2-methyl-3-oxomorpholin-2-yl)acetic acid;

2-((2S,5R,6R)-4-((S)-1-(tert-butylsulfonyl)butan-2-yl)-6-(3-chlorophenyl)-5-(4-chlorophenyl)-2-methyl-3-oxomorpholin-2-yl)acetic acid;

2-((2R,5R,6R)-4-((S)-1-(tert-Butylsulfonyl)-4,4,4-trifluorobutan-2-yl)-6-(3-chlorophenyl)-5-(4-chlorophenyl)-2-methyl-3-oxomorpholin-2-yl)acetic acid;

2-((2S,5R,6R)-4-((S)-1-(tert-butylsulfonyl)-4,4,4-trifluorobutan-2-yl)-6-(3-chlorophenyl)-5-(4-chlorophenyl)-2-methyl-3-oxomorpholin-2-yl)acetic acid;

2-((2R,5R,6R)-4-((S)-1-(tert-Butylsulfonyl)butan-2-yl)-6-(3-chlorophenyl)-5-(4-chlorophenyl)-3-oxomorpholin-2-yl)-N-cyanoacetamide;

2-((2R,5R,6R)-4-((S)-1-(tert-Butylsulfonyl)butan-2-yl)-6-(3-chlorophenyl)-5-(4-chlorophenyl)-3-oxomorpholin-2-yl)-N-cyanoacetamide;

(2R,5R,6R)-2-((1H-Tetrazol-5-yl)methyl)-4-((S)-1-(tert-butylsulfonyl)butan-2-yl)-6-(3-chlorophenyl)-5-(4-chlorophenyl)morpholin-3-one;

N-((S)-2-((2R,3R,6R)-2-(3-Chlorophenyl)-3-(4-chlorophenyl)-6-((3-methyl-1H-1,2,4-triazol-5-yl)methyl)-5-oxomorpholino)-2-cyclopropylethyl)-N-(2-fluorophenyl)cyclopropanesulfonamide;

N-((S)-2-((2R,3R,6R)-2-(3-Chlorophenyl)-3-(4-chlorophenyl)-6-((3-methyl-1H-1,2,4-triazol-5-yl)methyl)-5-oxomorpholino)-2-cyclopropylethyl)-N-(2-fluorophenyl)cyclopropanesulfonamide;

N-((S)-2-((2R,5R,6R)-2-((1H-Tetrazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide;

N-((S)-2-((2S,5R,6R)-2-((1H-tetrazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide;

N-((S)-2-((2R,5R,6R)-2-((1H-Tetrazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide;

N-((S)-2-((2S,5R,6R)-2-((1H-tetrazol-5-yl)methyl)-6-(3-chlorophenyl)-5-(4-chlorophenyl)-3-oxomorpholino)-2-cyclopropylethyl)-N-(2-fluorophenyl)cyclopropanesulfonamide;

N-((S)-2-((2S,3R,6R)-2-(3-chlorophenyl)-3-(4-chlorophenyl)-6-((1-methyl-1H-tetrazol-5-yl)methyl)-5-oxomorpholino)-2-cyclopropylethyl)-N-(2-fluorophenyl)cyclopropanesulfonamide;

N-((S)-2-((2R,3R,6R)-2-(3-chlorophenyl)-3-(4-chlorophenyl)-6-((2-methyl-2H-tetrazol-5-yl)methyl)-5-oxomorpholino)-2-cyclopropylethyl)-N-(2-fluorophenyl)cyclopropanesulfonamide;

N-((S)-2-((2R,3R,6R)-2-(3-chlorophenyl)-3-(4-chlorophenyl)-6-((2-methyl-2H-tetrazol-5-yl)methyl)-5- oxomorpholino)-2-cyclopropylethyl)-N-(2-fluorophenyl)cyclopropanesulfonamide;

N-((S)-2-((2S,3R,6S)-2-(3-chlorophenyl)-3-(4-chlorophenyl)-5-oxo-6-(sulfamoylmethyl)morpholino)-2-cyclopropylethyl)-N-(2-fluorophenyl)cyclopropanesulfonamide;

N-((S)-2-((2S,3R,6S)-2-(3-chlorophenyl)-3-(4-chlorophenyl)-5-oxo-6-(sulfamoylmethyl)morpholino)-2-cyclopropylethyl)-N-(2-fluorophenyl)cyclopropanesulfonamide;

2-((2R,5R,6R)-4-((S)-2-(tert-Butylsulfonyl)-1-cyclopropylethyl)-5-(4-chloro-3-fluorophenyl)-6-(3-chlorophenyl)-2-methyl-3-oxomorpholin-2-yl)acetic acid;

2-((2S,5R,6R)-4-((S)-2-(tert-butylsulfonyl)-1-cyclopropylethyl)-5-(4-chloro-3-fluorophenyl)-6-(3-chlorophenyl)-2-methyl-3-oxomorpholin-2-yl)acetic acid;

2-((2R,5R,6R)-6-(3-Chlorophenyl)-5-(4-chlorophenyl)-4-((2S,3S)-2-(isopropylsulfonyl)pentan-3-yl)-3-oxomorpholin-2-yl)acetic acid;

2-((2S,5R,6R)-6-(3-chlorophenyl)-5-(4-chlorophenyl)-4-((2S,3S)-2-(isopropylsulfonyl)pentan-3-yl)-3-oxomorpholin-2-yl)acetic acid;

2-((2R,5R,6R)-6-(3-chlorophenyl)-5-(4-chlorophenyl)-4-((2R,3S)-2-(isopropylsulfonyl)pentan-3-yl)-3-oxomorpholin-2-yl)acetic acid;

2-((2S,5R,6R)-6-(3-chlorophenyl)-5-(4-chlorophenyl)-4-((2R,3S)-2-(isopropylsulfonyl)pentan-3-yl)-3-oxomorpholin-2-yl)acetic acid;

2-((2R,5R,6R)-4-((S)-1-(tert-Butylsulfonyl)butan-2-yl)-5-(4-chloro-3-fluorophenyl)-6-(3-chloro-5-fluorophenyl)-3-oxomorpholin-2-yl)acetic acid; and 2-((2S,5R,6R)-4-((S)-1-(tert-butylsulfonyl)butan-2-yl)-5-(4-chloro-3-fluorophenyl)-6-(3-chloro-5-fluorophenyl)-3-oxomorpholin-2-yl)acetic acid.

37. A pharmaceutical composition comprising a compound of claim 36, or a pharmaceutically acceptable salt thereof, and a pharmaceutically acceptable excipient.

\* \* \* \* \*